United States Patent
Kim et al.

(10) Patent No.: US 10,347,845 B2
(45) Date of Patent: Jul. 9, 2019

(54) NITROGEN-CONTAINING CONDENSED CYCLIC COMPOUND AND ORGANIC LIGHT EMITTING DEVICE USING SAME

(71) Applicant: LG CHEM, LTD., Seoul (KR)

(72) Inventors: Minjun Kim, Daejeon (KR); Hyok Joon Kwon, Daejeon (KR); Wanpyo Hong, Daejeon (KR); Kongkyeom Kim, Daejeon (KR); Jungha Lee, Daejeon (KR)

(73) Assignee: LG CHEM, LTD., Seoul (KR)

( * ) Notice: Subject to any disclaimer, the term of this patent is extended or adjusted under 35 U.S.C. 154(b) by 0 days.

(21) Appl. No.: 15/324,947

(22) PCT Filed: Jun. 3, 2016

(86) PCT No.: PCT/KR2016/005954
§ 371 (c)(1),
(2) Date: Jan. 9, 2017

(87) PCT Pub. No.: WO2016/195441
PCT Pub. Date: Dec. 8, 2016

(65) Prior Publication Data
US 2017/0213984 A1    Jul. 27, 2017

(30) Foreign Application Priority Data
Jun. 3, 2015 (KR) .................. 10-2015-0078801

(51) Int. Cl.
*H01L 51/00* (2006.01)
*C07D 519/00* (2006.01)
(Continued)

(52) U.S. Cl.
CPC ........ *H01L 51/0072* (2013.01); *C07D 487/16* (2013.01); *C07D 519/00* (2013.01); *C09K 11/025* (2013.01); *C09K 11/06* (2013.01); *H01L 51/0052* (2013.01); *H01L 51/0054* (2013.01); *H01L 51/0071* (2013.01); *H01L 51/50* (2013.01); *C09K 2211/1007* (2013.01); *C09K 2211/1044* (2013.01);
(Continued)

(58) Field of Classification Search
None
See application file for complete search history.

(56) References Cited

U.S. PATENT DOCUMENTS

2013/0026422 A1   1/2013  Parham et al.
2014/0319507 A1  10/2014  Yamanoto et al.
2016/0293853 A1* 10/2016  Zeng .................. H01L 51/0073

FOREIGN PATENT DOCUMENTS

KR   10-2000-0051826 A1    8/2000
KR   10-2014-0034710    *   3/2014
(Continued)

OTHER PUBLICATIONS

Machine English translation of Yu et al. (KR 10-2014-0034710). Jun. 12, 2018.*

(Continued)

*Primary Examiner* — Jay Yang
(74) *Attorney, Agent, or Firm* — Dentons US LLP

(57) ABSTRACT

The present specification provides a nitrogen-containing condensed cyclic compound of chemical formula 1 and an organic light emitting device comprising the same.

11 Claims, 4 Drawing Sheets

(51) Int. Cl.
      *C09K 11/02*       (2006.01)
      *C07D 487/16*     (2006.01)
      *C09K 11/06*       (2006.01)
      *H01L 51/50*       (2006.01)

(52) U.S. Cl.
      CPC ............... *C09K 2211/1048* (2013.01); *C09K 2211/1051* (2013.01); *C09K 2211/1059* (2013.01); *H01L 51/0085* (2013.01); *H01L 51/5016* (2013.01)

(56) References Cited

FOREIGN PATENT DOCUMENTS

| KR | 10-2014-0034710 A | 3/2014 |
| KR | 10-2014-0101411 A | 8/2014 |
| KR | 10-2014-0101807 A | 8/2014 |
| WO | 2011-128017 A1 | 10/2011 |

OTHER PUBLICATIONS

Rivoal, Morgane et al., "Substituted dibenzo[2,3:5,6]-pyrrolizino[1,7-bc]indolo[1,2,3-lm]carbazoles: a series of new electron donors," Tetrahedron 2013, vol. 69, pp. 3302-3307.

\* cited by examiner

[Figure 1]
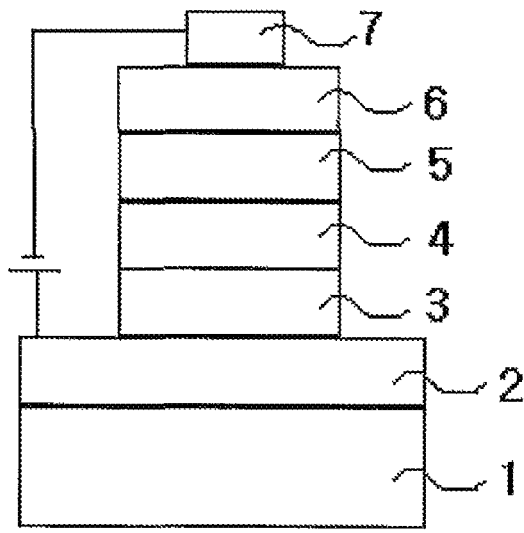
[Figure 2]
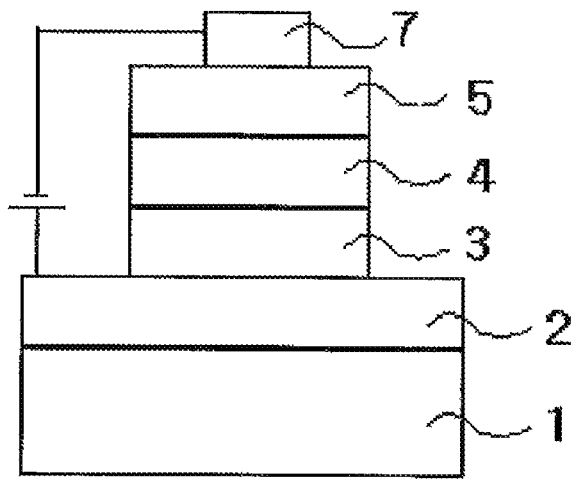

[Figure 3]
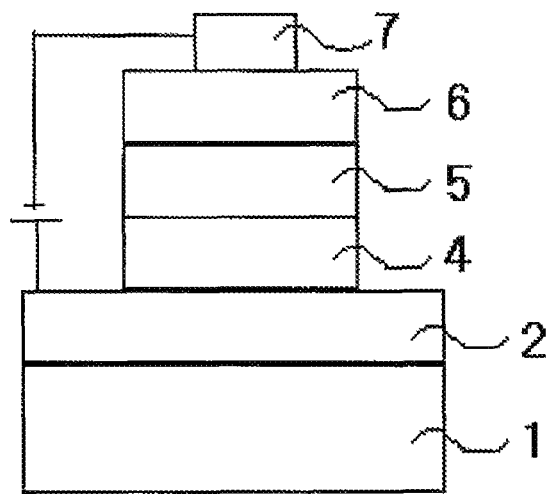
[Figure 4]
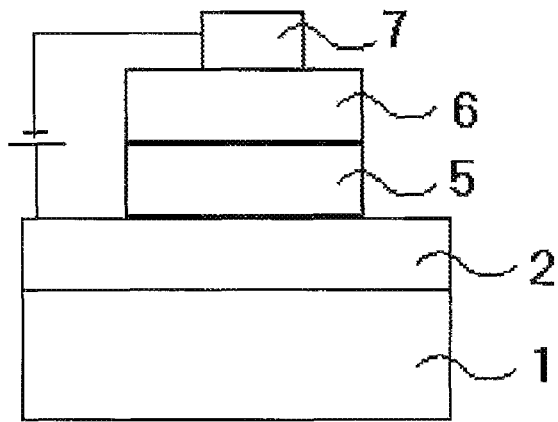

[Figure 5]
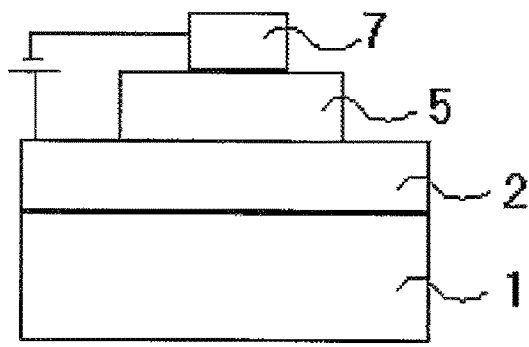
[Figure 6]
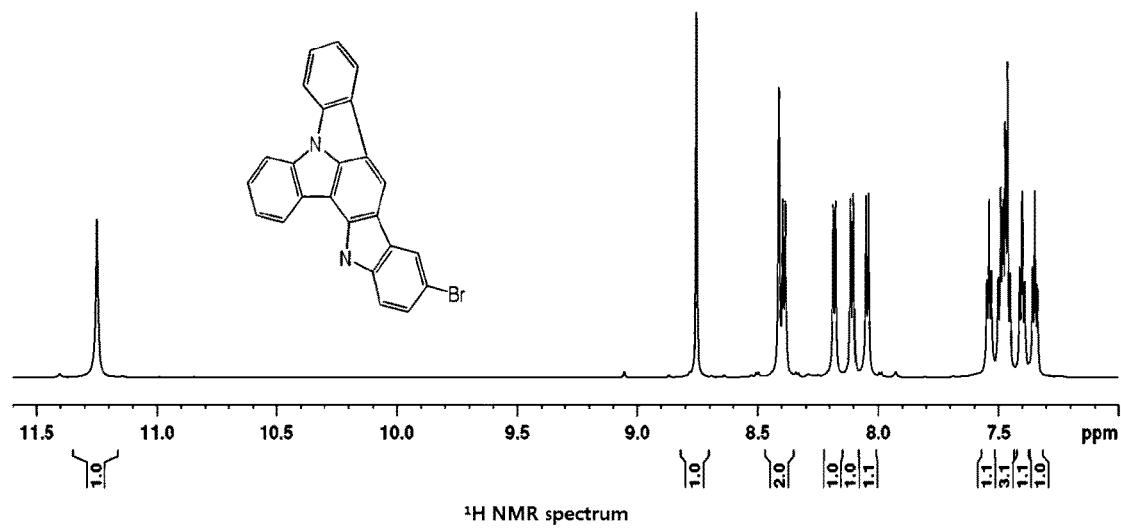
¹H NMR spectrum

[Figure 7]
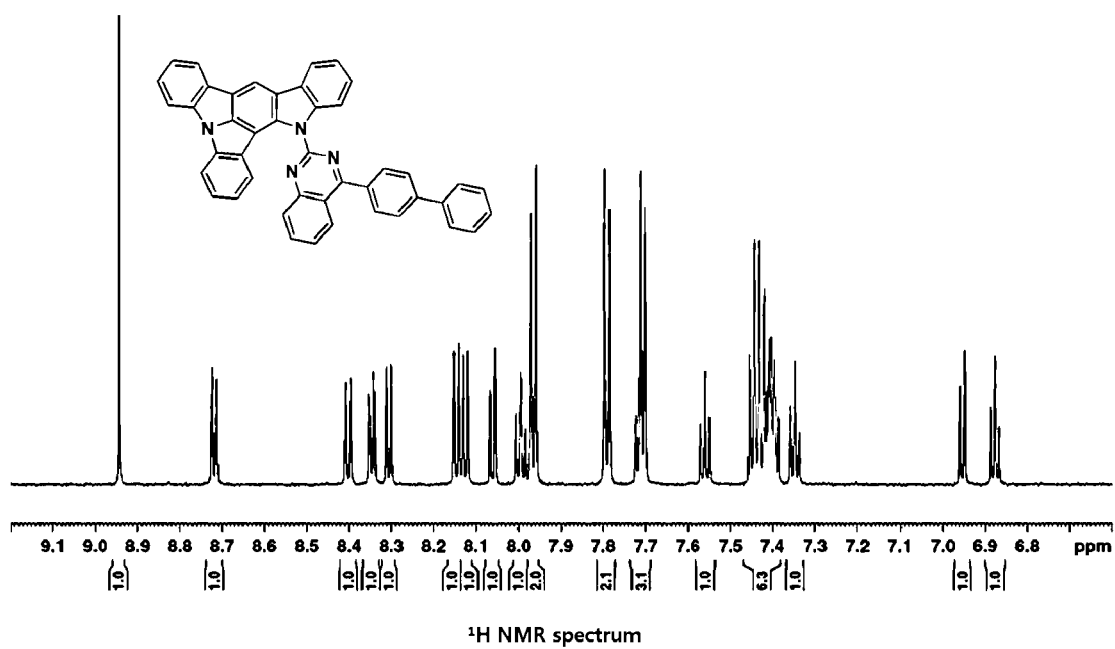
¹H NMR spectrum

NITROGEN-CONTAINING CONDENSED CYCLIC COMPOUND AND ORGANIC LIGHT EMITTING DEVICE USING SAME

TECHNICAL FIELD

This application is a National Stage Entry of International Application No. PCT/KR2016/005954, filed Jun. 3, 2016, and claims the benefit of and priority to Korean Application No. KR 10-2015-0078801, filed on Jun. 3, 2015, all of which are hereby incorporated by reference in their entirety for all purposes as if fully set forth herein.

The present specification relates to a fused cyclic compound including nitrogen and an organic light emitting device using the same.

BACKGROUND ART

An organic light emission phenomenon is one of the examples of converting current into visible rays through an internal process of a specific organic molecule. The principle of the organic light emission phenomenon is as follows.

When an organic material layer is disposed between a positive electrode and a negative electrode, if voltage is applied between the two electrodes, electrons and holes are injected from the negative electrode and the positive electrode, respectively, into the organic material layer. The electrons and the holes which are injected into the organic material layer are recombined to form an exciton, and the exciton falls down again to the ground state to emit light. An organic light emitting device using this principle may be composed of a negative electrode, a positive electrode, and an organic material layer disposed therebetween, for example, an organic material layer including a hole injection layer, a hole transporting layer, a light emitting layer, and an electron transporting layer.

The materials used in the organic light emitting device are mostly pure organic materials or complex compounds in which organic materials and metals form a complex compound, and may be classified into a hole injection material, a hole transporting material, a light emitting material, an electron transporting material, an electron injection material, and the like according to the use thereof. Here, an organic material having a p-type property, that is, an organic material, which is easily oxidized and electrochemically stable when the material is oxidized, is usually used as the hole injection material or the hole transporting material. Meanwhile, an organic material having an n-type property, that is, an organic material, which is easily reduced and electrochemically stable when the material is reduced, is usually used as the electron injection material or the electron transporting material. As the light emitting layer material, a material having both p-type and n-type properties, that is, a material, which is stable during both the oxidation and reduction states, is preferred, and when an exciton is formed, a material having high light emitting efficiency for converting the exciton into light is preferred.

Therefore, there is a need for developing a new organic material in the art.

DISCLOSURE

Technical Problem

The present specification provides a fused cyclic compound and an organic light emitting device using the same.

Technical Solution

An exemplary embodiment of the present specification provides a compound represented by the following Chemical Formula 1:

[Chemical Formula 1]

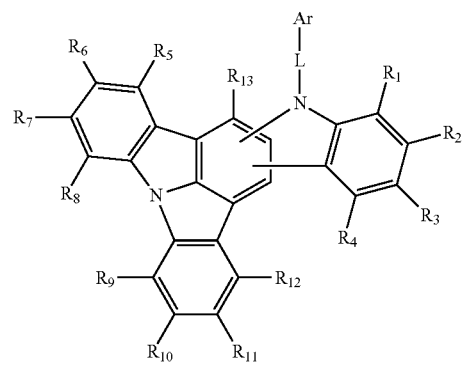

In Chemical Formula 1,

Ar is a substituted or unsubstituted bicyclic or more heterocyclic group,

L is a direct bond; a substituted or unsubstituted arylene group; or a substituted or unsubstituted heteroarylene group, $R_1$ to $R_{13}$ are the same as or different from each other, and each independently hydrogen; deuterium; a nitrile group; a substituted or unsubstituted alkyl group; a substituted or unsubstituted alkenyl group; a substituted or unsubstituted cycloalkyl group; a substituted or unsubstituted aryl group; a substituted or unsubstituted aromatic or aliphatic heterocyclic group; a substituted or unsubstituted alkoxy group; a substituted or unsubstituted aryloxy group; a substituted or unsubstituted alkylamine group; a substituted or unsubstituted arylamine group; a substituted or unsubstituted aralkylamine group; a substituted or unsubstituted alkylarylamine group; or a substituted or unsubstituted heteroarylamine group, or combine with an adjacent substituent to form a ring. Another exemplary embodiment of the present specification provides an organic light emitting device including: a first electrode; a second electrode provided to face the first electrode; and one or more organic material layers including a light emitting layer provided between the first electrode and the second electrode, in which one or more layers of the organic material layers include the compound represented by Chemical Formula 1.

Advantageous Effects

A novel fused cyclic compound according to exemplary embodiments of the present specification has an appropriate energy level, and is excellent in electrochemical stability and thermal stability. Therefore, an organic light emitting device including the compound provides high efficiency and/or high driving stability and long service life effects.

DESCRIPTION OF DRAWINGS

FIGS. 1 to 5 are cross-sectional views illustrating the structure of an organic light emitting device according to an exemplary embodiment of the present specification.

FIGS. 6 and 7 illustrate 1H NMR spectra of the materials used and prepared in the Synthesis Examples.

MODE FOR INVENTION

Hereinafter, the present specification will be described in more detail.

An exemplary embodiment of the present specification provides the compound represented by Chemical Formula 1. A novel core structure represented by Chemical Formula 1 has flat structural characteristics and thus is excellent in thermal stability due to a higher glass transition temperature than the existing known structures, and the novel compounds may be used as a host material and/or a hole transporting material of an organic material layer, particularly, a light emitting layer of an organic light emitting device. Further, the novel compounds may serve as a hole injection material, an electron transporting material, an electron injection material, and the like.

Examples of the substituents will be described below, but are not limited thereto.

In the present specification,

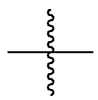

means a moiety linked to another substituent.

In the present specification, the term "substituted or unsubstituted" means being unsubstituted or substituted with one or more substituents selected from the group consisting of deuterium; a nitrile group; an alkyl group; an alkenyl group; a cycloalkyl group; an aryl group; a heterocyclic group; an aralkyl group; an aralkenyl group; an alkylaryl group; an alkenylaryl group; an alkoxy group; an aryloxy group; an alkyl amine group; an aralkylamine group; an arylamine group; an alkylarylamine group; or a heteroarylamine group, or being unsubstituted or substituted with a substituent to which two or more substituents among the substituents exemplified above are linked. For example, "the substituent to which two or more substituents are linked" may be a biphenyl group. That is, the biphenyl group may also be an aryl group, and may be interpreted as a substituent to which two phenyl groups are linked.

In the present specification, the alkyl group may be straight-chained or branched, and the number of carbon atoms thereof is not particularly limited, but is preferably 1 to 50. Specific examples thereof include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethyl-propyl, isohexyl, 2-methylpentyl, 4-methylhexyl, 5-methylhexyl, and the like, but are not limited thereto.

In the present specification, the alkenyl group may be straight-chained or branched, and the number of carbon atoms thereof is not particularly limited, but is preferably 2 to 50. Specific examples thereof include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl, a stilbenyl group, a styrenyl group, and the like, but are not limited thereto.

In the present specification, a cycloalkyl group is not particularly limited, but the number of carbon atoms thereof is preferably 3 to 60, and specific examples thereof include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl, and the like, but are not limited thereto.

In the present specification, an aryl group may be a monocyclic aryl group or a polycyclic aryl group. When the aryl group is a monocyclic aryl group, the number of carbon atoms thereof is not particularly limited, but is preferably 6 to 60. Specific examples of the monocyclic aryl group include a phenyl group, a biphenyl group, a terphenyl group, and the like, but are not limited thereto. Specific examples of the polycyclic aryl group include a naphthyl group, an anthracenyl group, a phenanthryl group, a pyrenyl group, a perylenyl group, a chrysenyl group, a fluorenyl group, and the like, but are not limited thereto. In the present specification, the fluorenyl group may be substituted, and two substituents may combine with each other to form a spiro structure.

When the fluorenyl group is substituted, the group may be

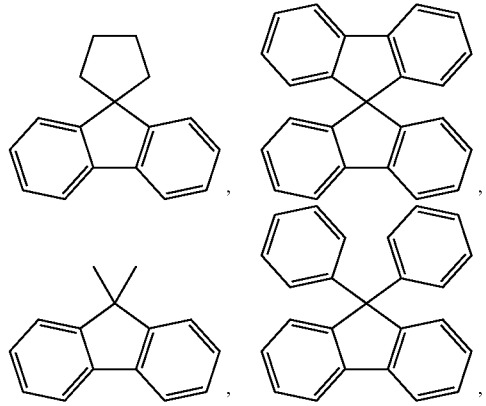

and the like. However, the group is not limited thereto.

In the present specification, a heterocyclic group is an aromatic or aliphatic heterocyclic group including one or more of O, N, and S as a hetero element, and the number of carbon atoms thereof is not particularly limited, but is preferably 2 to 60. Examples of the heterocyclic group include a thiophene group, a furan group, a pyrrole group, an imidazole group, a thiazole group, an oxazole group, an oxadiazole group, a triazole group, a pyridine group, a bipyridine group, a pyrimidine group, a triazine group, a triazole group, an acridine group, a pyridazine group, a pyrazine group, a qinoline group, a quinazoline group, a quinoxaline group, a phthalazine group, a pyridopyrimidinyl group, a pyridopyrazinyl group, a pyrazinopyrazinyl group, an isoquinoline group, an indole group, a carbazole group, a carboline group, a benzoxazole group, a benzoimidazole group, a benzothiazole group, a benzocarbazole group, a benzothiophene group, a dibenzothiophene group, a benzofuranyl group, a phenanthroline group, a thiazolyl group, an isoxazolyl group, an oxadiazolyl group, a thiadiazolyl group, a benzothiazolyl group, a phenothiazinyl group, a dibenzofuranyl group, and the like, but are not limited thereto.

In the present specification, the alkoxy group may be straight-chained, branched, or cyclic. The number of carbon atoms of the alkoxy group is not particularly limited, but is preferably 1 to 20. Specific examples thereof include methoxy, ethoxy, n-propoxy, isopropoxy, i-propyloxy, n-butoxy, isobutoxy, tert-butoxy, sec-butoxy, n-pentyloxy, neopentyloxy, isopentyloxy, n-hexyloxy, 3,3-dimethylbutyloxy, 2-ethylbutyloxy, n-octyloxy, n-nonyloxy, n-decyloxy, benzyloxy, p-methylbenzyloxy, and the like, but are not limited thereto.

In the present specification, the aryl group in the aryloxy group is the same as the above-described examples of the aryl group. Specifically, examples of the aryloxy group include phenoxy, p-tolyloxy, m-tolyloxy, 3,5-dimethyl-phenoxy, 2,4,6-trimethylphenoxy, p-tert-butylphenoxy, 3-biphenyloxy, 4-biphenyloxy, 1-naphthyloxy, 2-naphthyloxy, 4-methyl-1-naphthyloxy, 5-methyl-2-naphthyloxy, 1-anthryloxy, 2-anthryloxy, 9-anthryloxy, 1-phenanthryloxy, 3-phenanthryloxy, 9-phenanthryloxy, and the like, examples of the arylthioxy group include a phenylthioxy group, a 2-methylphenylthioxy group, a 4-tert-butylphenylthioxy group, and the like, but are not limited thereto.

In the present specification, the alkylamine group, the aralkylamine group, the arylamine group, the alkylarylamine group, and the heteroarylamine group are amine groups substituted with an alkyl group, an aralkyl group, an aryl group, an alkylaryl group, and a heteroaryl group, respectively, and here, the above-described description on the alkyl group and the aryl group may be applied to alkyl and aryl, and the above-described description on the aromatic heterocyclic group in the heterocyclic group may be applied to the heteroaryl group. Specific examples of the amine group include a methylamine group, a dimethylamine group, an ethylamine group, a diethylamine group, a phenylamine group, a naphthylamine group, a biphenylamine group, an anthracenylamine group, 3-methyl-phenylamine, 4-methyl-naphthylamine, 2-methyl-biphenylamine, a 9-methyl-anthracenylamine group, a diphenylamine group, a phenyl-naphthylamine group, a ditolylamine group, a phenyltolylamine group, a triphenylamine group, and the like, but are not limited thereto.

In the present specification, the arylene group means that there are two bonding positions in an aryl group, that is, a divalent group. The above-described description on the aryl group may be applied, except that the arylene groups are each a divalent group.

In the present specification, the heteroarylene group means that there are two bonding positions in a heteroaryl group, that is, a divalent group. The above-described description on the aromatic heterocyclic group may be applied, except that the heteroarylene groups are each a divalent group.

In the present specification, the meaning of combining with an adjacent group to form a ring means combining with an adjacent group to form a substituted or unsubstituted aliphatic hydrocarbon ring; a substituted or unsubstituted aromatic hydrocarbon ring; a substituted or unsubstituted aliphatic hetero ring; or a substituted or unsubstituted aromatic hetero ring.

In the present specification, the "adjacent group" may mean a substituent substituted with an atom directly linked to an atom in which the corresponding substituent is substituted, a substituent disposed sterically closest to the corresponding substituent, or another substituent substituted with an atom in which the corresponding substituent is substituted. For example, two substituents substituted at the ortho position in a benzene ring and two substituents substituted with the same carbon in an aliphatic ring may be interpreted as "an adjacent group" to each other.

In the present specification, the aliphatic hydrocarbon ring means a ring composed only of carbon and hydrogen atoms as a ring which is not an aromatic group. In the present specification, examples of the aromatic hydrocarbon ring include a phenyl group, a naphthyl group, an anthracenyl group, and the like, but are not limited thereto.

In the present specification, the aliphatic hetero ring means an aliphatic ring including one or more of N, O, or S atoms as a hetero atom.

In the present specification, the aromatic hetero ring means an aromatic ring including one or more of N, O, or S atoms as a hetero atom.

In the present specification, the aliphatic ring, the aromatic ring, the aliphatic hetero ring, and the aromatic hetero ring may be monocyclic or polycyclic.

In an exemplary embodiment of the present specification, the compound represented by Chemical Formula 1 may be represented by the following Chemical Formula 2 or 3.

[Chemical Formula 2]

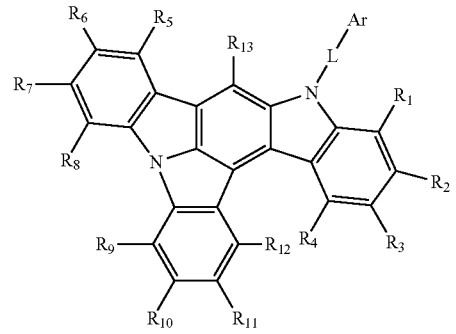

[Chemical Formula 3]

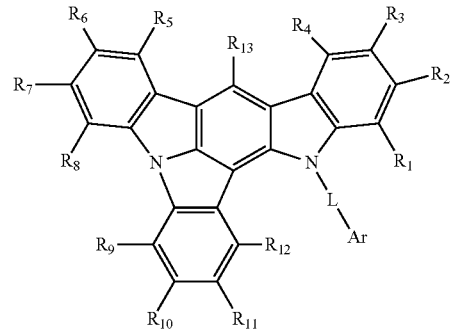

In Chemical Formulae 2 and 3, $R_1$ to $R_{13}$, Ar, and L are the same as those defined in Chemical Formula 1.

According to an exemplary embodiment of the present specification, Ar in Chemical Formulae 1 to 3 is a substituted or unsubstituted bicyclic or more heterocyclic group including N.

According to an exemplary embodiment of the present specification, Ar in Chemical Formulae 1 to 3 is a substituted or unsubstituted bicyclic or more heterocyclic group including two or more N's.

According to an exemplary embodiment of the present specification, Ar in Chemical Formulae 1 to 3 is an unsubstituted bicyclic or more heterocyclic group including two or more N's, which are unsubstituted or substituted with a nitrile group, an alkyl group, an aryl group, a heteroaryl group, an arylheteroaryl group, a heteroarylaryl group, and an aryl group which is substituted with a nitrile group.

According to an exemplary embodiment of the present specification, L in Chemical Formulae 1 to 3 is a direct bond; a substituted or unsubstituted phenylene group; or a substituted or unsubstituted monocyclic heteroarylene group.

According to an exemplary embodiment of the present specification, L in Chemical Formulae 1 to 3 is a direct bond; a substituted or unsubstituted phenylene group; or a substituted or unsubstituted monocyclic heteroarylene group.

According to an exemplary embodiment of the present specification, L in Chemical Formulae 1 to 3 is a direct bond; a substituted or unsubstituted phenylene group; or a substituted or unsubstituted monocyclic heteroarylene group including N.

According to an exemplary embodiment of the present specification, L in Chemical Formulae 1 to 3 is a direct bond; a substituted or unsubstituted phenylene group; a substituted or unsubstituted pyridine group; a substituted or unsubstituted pyrimidine group; or a substituted or unsubstituted triazine group.

According to an exemplary embodiment of the present specification, L in Chemical Formulae 1 to 3 is a direct bond; a phenylene group; a pyridine group; a pyrimidine group; or a triazine group.

According to an exemplary embodiment of the present specification, L in Chemical Formulae 1 to 3 is a direct bond; a phenylene group; or a pyridine group.

According to an exemplary embodiment of the present specification, the phenylene group may be represented by the following structure.

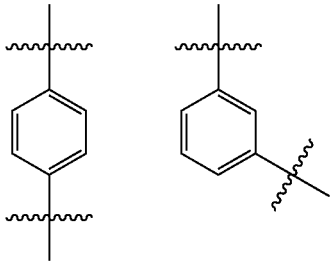 [SMILES: *c1ccc(*)cc1 ; *c1cccc(*)c1]

According to an exemplary embodiment of the present specification, Ar in Chemical Formulae 1 to 3 is represented by any one of the following Chemical Formulae A to F.

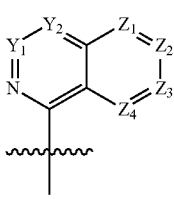

[Chemical Formula A]

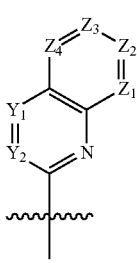

[Chemical Formula B]

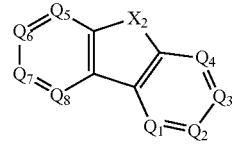

[Chemical Formula C]

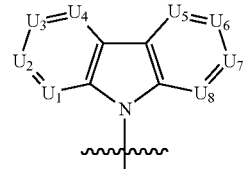

[Chemical Formula D]

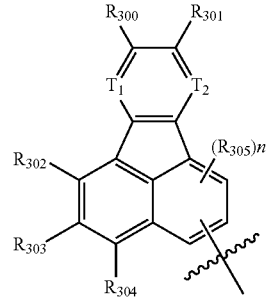

[Chemical Formula E]

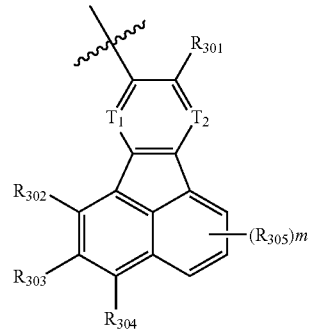

[Chemical Formula F]

In Chemical Formulae A to F, $Y_1$, $Y_2$, $Z_1$ to $Z_4$, $Q_1$ to $Q_8$, $T_1$, $T_2$ and $U_1$ to $U_8$ are the same as or different from each other, and each independently N or CRd, provided that one of $Q_1$ to $Q_4$ is C linked to L, $X_2$ is $NAr_1$, S, or O, and $Ar_1$, Rd, and $R_{300}$ to $R_{305}$ are the same as or different from each other, and each independently hydrogen; deuterium; a nitrile group; a substituted or unsubstituted alkyl group; a substituted or unsubstituted alkenyl group; a substituted or unsubstituted cycloalkyl group; a substituted or unsubstituted aryl group; a substituted or unsubstituted aromatic or aliphatic heterocyclic group; a substituted or unsubstituted alkoxy group; a substituted or unsubstituted aryloxy group; a substituted or unsubstituted alkylamine group; a substituted or unsubstituted arylamine group; a substituted or unsubstituted aralkylamine group; a substituted or unsubstituted alkylarylamine group; or a substituted or unsubstituted heteroarylamine group, or combine with an adjacent substituent to form a ring, and when n is an integer of 0 to 2, m is an integer of 0 to 3, and n or m is 2, $R_{305}$'s are the same as or different from each other.

According to an exemplary embodiment of the present specification, Chemical Formula A may be represented by the following Chemical Formula A-1.

[Chemical Formula A-1]

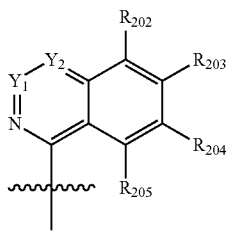

In Chemical Formula A-1, the definitins of $Y_1$ and $Y_2$ are the same as those described above, $R_{202}$ to $R_{205}$ are the same as or different from each other, and each independently hydrogen; deuterium; a nitrile group; a substituted or unsubstituted alkyl group; a substituted or unsubstituted alkenyl group; a substituted or unsubstituted cycloalkyl group; a substituted or unsubstituted aryl group; a substituted or unsubstituted aromatic or aliphatic heterocyclic group; a substituted or unsubstituted alkoxy group; a substituted or unsubstituted aryloxy group; a substituted or unsubstituted alkylamine group; a substituted or unsubstituted arylamine group; a substituted or unsubstituted aralkylamine group; a substituted or unsubstituted alkylarylamine group; or a substituted or unsubstituted heteroarylamine group, or combine with an adjacent substituent to form a ring.

According to an exemplary embodiment of the present specification, Chemical Formula B is represented by any one of the following Chemical Formulae B-1 to B-6-2.

[Chemical Formula B-1]

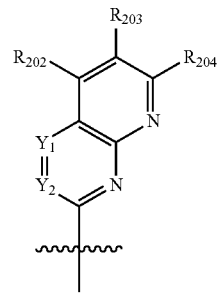

[Chemical Formula B-2]

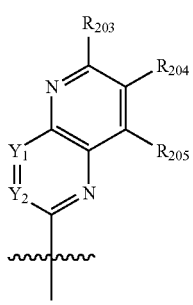

[Chemical Formula B-3]

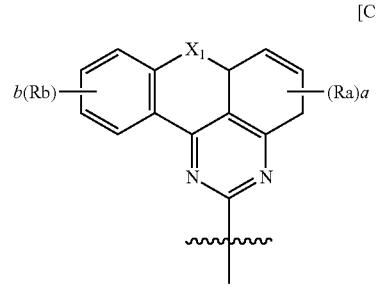

[Chemical Formula B-4]

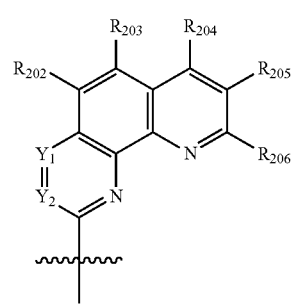

[Chemical Formula B-5]

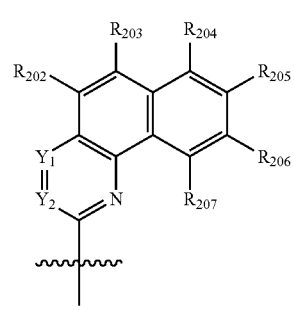

[Chemical Formula B-6-1]

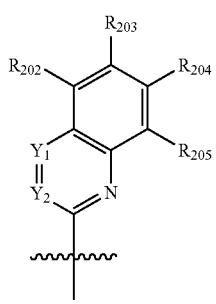

[Chemical Formula B-6-2]

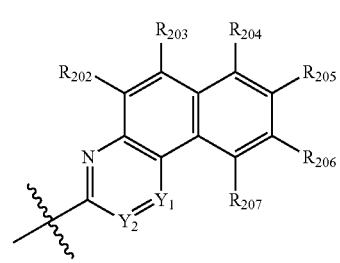

In Chemical Formulae B-1 to B-6-2,
the definitions of $Y_1$ and $Y_2$ are the same as those described above,
$X_1$ is a direct bond, C(=O), or CRR', and
$R_{202}$ to $R_{207}$, R, R', Ra, and Rb are the same as or different from each other, and each independently hydrogen; deuterium; a nitrile group; a substituted or unsubstituted alkyl group; a substituted or unsubstituted alkenyl group; a substituted or unsubstituted cycloalkyl group; a substituted or unsubstituted aryl group; a substituted or unsubstituted aromatic or aliphatic heterocyclic group; a substituted or unsubstituted alkoxy group; a substituted or unsubstituted aryloxy group; a substituted or unsubstituted alkylamine group; a substituted or unsubstituted arylamine group; a substituted or unsubstituted aralkylamine group; a substituted or unsubstituted alkylarylamine group; or a substituted or unsubstituted heteroarylamine group, or combine with an adjacent substituent to form a ring, and a is an integer of 0 to 3, and when a is 2 or more, Ra's are the same as or different from each other, and b is an integer of 0 to 4, and when b is 2 or more, Rb's are the same as or different from each other.

According to an exemplary embodiment of the present specification, in Chemical Formulae A-1, B-1, B-2, B-5, B-6-1, and B-6-2, at least one of $Y_1$ and $Y_2$ is N.

According to an exemplary embodiment of the present specification, in Chemical Formulae A-1, B-1, B-2, B-5, B-6-1, and B-6-2, one of $Y_1$ and $Y_2$ is N.

According to an exemplary embodiment of the present specification, at least one of $U_1$ to $U_8$ of Chemical Formula D is N.

According to an exemplary embodiment of the present specification, at least one of $Q_1$ to $Q_8$ of Chemical Formula C is N.

According to an exemplary embodiment of the present specification, at least one of $Q_1$ to $Q_4$ of Chemical Formula C is N.

According to an exemplary embodiment of the present specification, one of $Q_3$ and $Q_4$ of Chemical Formula C is N.

According to an exemplary embodiment of the present specification, one of $Q_3$ and $Q_4$ of Chemical Formula C is N, and $X_2$ is $NAr_1$.

According to an exemplary embodiment of the present specification, $Q_1$ and $Q_3$ of Chemical Formula C are N.

According to an exemplary embodiment of the present specification, Q1 and Q3 of Chemical Formula C are N, and $X_2$ is O or S.

According to an exemplary embodiment of the present specification, at least one of $U_1$ to $U_8$ of Chemical Formula D is N.

According to an exemplary embodiment of the present specification, Chemical Formula B-1 may be represented by the following Chemical Formula B-7 or B-8.

[Chemical Formula B-7]

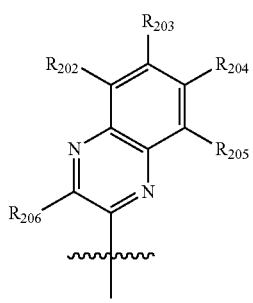

[Chemical Formula B-8]

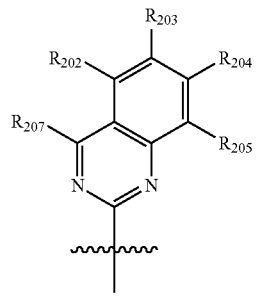

In Chemical Formulae B-7 and B-8, $R_{202}$ to $R_{207}$ are the same as or different from each other, and each independently hydrogen; deuterium; a nitrile group; a substituted or unsubstituted alkyl group; a substituted or unsubstituted alkenyl group; a substituted or unsubstituted cycloalkyl group; a substituted or unsubstituted aryl group; a substituted or unsubstituted aromatic or aliphatic heterocyclic group; a substituted or unsubstituted alkoxy group; a substituted or unsubstituted aryloxy group; a substituted or unsubstituted alkylamine group; a substituted or unsubstituted arylamine group; a substituted or unsubstituted aralkylamine group; a substituted or unsubstituted alkylarylamine group; or a substituted or unsubstituted heteroarylamine group, or combine with an adjacent substituent to form a ring. According to an exemplary embodiment of the present specification, Chemical Formulae B-2 and B-3 may be represented by the following Chemical Formula B-9 and B-10, respectively.

[Chemical Formula B-9]

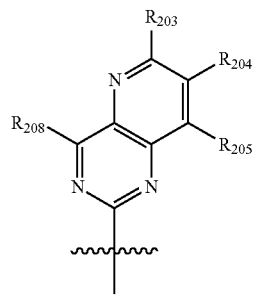

[Chemical Formula B-10]

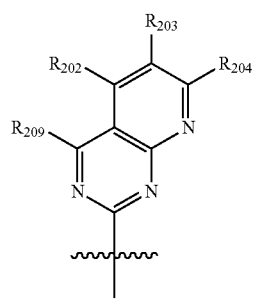

In Chemical Formulae B-9 and B-10, $R_{202}$ to $R_{205}$, $R_{208}$, and $R_{209}$ are the same as or different from each other, and each independently hydrogen; deuterium; a nitrile group; a substituted or unsubstituted alkyl group; a substituted or unsubstituted alkenyl group; a substituted or unsubstituted cycloalkyl group; a substituted or unsubstituted aryl group; a substituted or unsubstituted aromatic or aliphatic heterocyclic group; a substituted or unsubstituted alkoxy group; a substituted or unsubstituted aryloxy group; a substituted or unsubstituted alkylamine group; a substituted or unsubstituted arylamine group; a substituted or unsubstituted aralkylamine group; a substituted or unsubstituted alkylarylamine group; or a substituted or unsubstituted heteroarylamine group, or combine with an adjacent substituent to form a ring.

According to an exemplary embodiment of the present specification, Chemical Formula B-4 may be represented by any one of the following Chemical Formulae B-11 to B-13.

[Chemical Formula B-11]

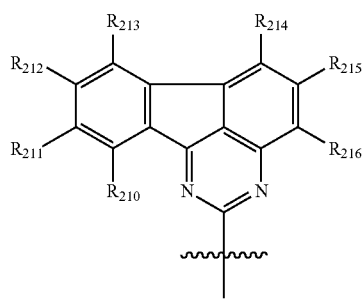

[Chemical Formula B-12]

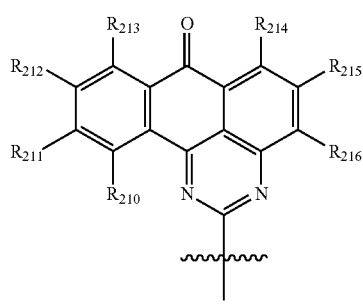

[Chemical Formula B-13]

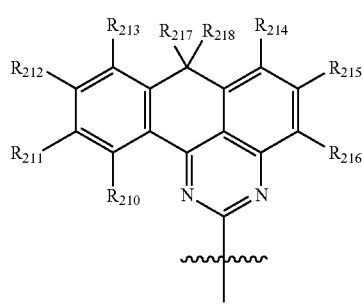

In Chemical Formulae B-11 to B-13, $R_{210}$ to $R_{218}$ are the same as or different from each other, and each independently hydrogen; deuterium; a nitrile group; a substituted or unsubstituted alkyl group; a substituted or unsubstituted alkenyl group; a substituted or unsubstituted cycloalkyl group; a substituted or unsubstituted aryl group; a substituted or unsubstituted aromatic or aliphatic heterocyclic group; a substituted or unsubstituted alkoxy group; a substituted or unsubstituted aryloxy group; a substituted or unsubstituted alkylamine group; a substituted or unsubstituted arylamine group; a substituted or unsubstituted aralkylamine group; a substituted or unsubstituted alkylarylamine group; or a substituted or unsubstituted heteroarylamine group, or combine with an adjacent substituent to form a ring.

According to an exemplary embodiment of the present specification, Chemical Formula C may be represented by any one of the following Chemical Formulae C-1 to C-6.

[Chemical Formula C-1]

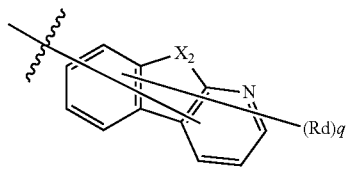

[Chemical Formula C-2]

[Chemical Formula C-3]

[Chemical Formula C-4]

[Chemical Formula C-5]

[Chemical Formula C-6]

In the chemical formulae, the definitions of X2 and Rd are the same as those described above, and q is an integer of 0 to 6, and when q is 2 or more, Rd's are the same as or different from each other.

According to an exemplary embodiment of the present specification, Chemical Formula C may be represented by any one of the following chemical formulae.

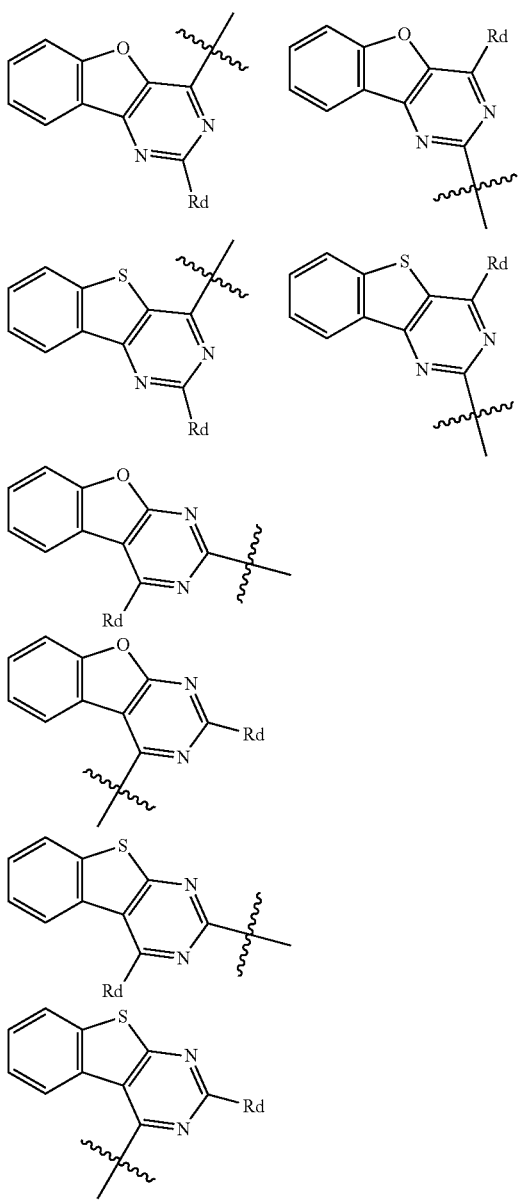

In the structural formulae, the definition of Rd is the same as that described above.

According to an exemplary embodiment of the present specification, Chemical Formula D may be represented by the following Chemical Formula D-1.

[Chemical Formula D-1]

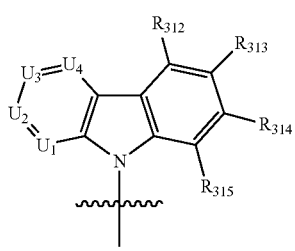

In Chemical Formula D-1, $U_1$ to $U_4$ are the same as those defined in Chemical Formula D, and $R_{312}$ to $R_{315}$ are the same as or different from each other, and each independently hydrogen; deuterium; a nitrile group; a substituted or unsubstituted alkyl group; a substituted or unsubstituted alkenyl group; a substituted or unsubstituted cycloalkyl group; a substituted or unsubstituted aryl group; a substituted or unsubstituted aromatic or aliphatic heterocyclic group; a substituted or unsubstituted alkoxy group; a substituted or unsubstituted aryloxy group; a substituted or unsubstituted alkylamine group; a substituted or unsubstituted arylamine group; a substituted or unsubstituted aralkylamine group; a substituted or unsubstituted alkylarylamine group; or a substituted or unsubstituted heteroarylamine group, or combine with an adjacent substituent to form a ring.

According to an exemplary embodiment of the present specification, one or two or more of $U_1$ to $U_4$ of Chemical Formula D-1 is/are N.

According to an exemplary embodiment of the present specification, Chemical Formula D may be represented by the following Chemical Formula D-2 or D-3.

[Chemical Formula D-2]

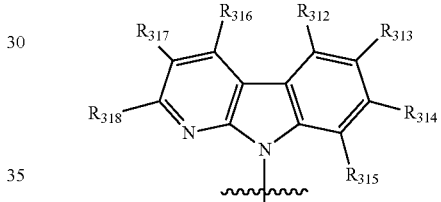

[Chemical Formula D-3]

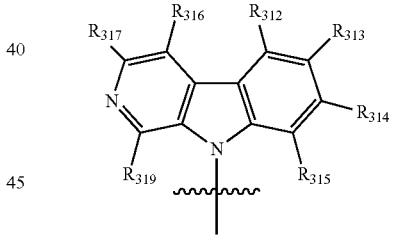

In Chemical Formulae D-2 and D-3, $R_{312}$ to $R_{319}$ are the same as or different from each other, and each independently hydrogen; deuterium; a nitrile group; a substituted or unsubstituted alkyl group; a substituted or unsubstituted alkenyl group; a substituted or unsubstituted cycloalkyl group; a substituted or unsubstituted aryl group; a substituted or unsubstituted aromatic or aliphatic heterocyclic group; a substituted or unsubstituted alkoxy group; a substituted or unsubstituted aryloxy group; a substituted or unsubstituted alkylamine group; a substituted or unsubstituted arylamine group; a substituted or unsubstituted aralkylamine group; a substituted or unsubstituted alkylarylamine group; or a substituted or unsubstituted heteroarylamine group, or combine with an adjacent substituent to form a ring.

According to an exemplary embodiment of the present specification, Chemical Formula E may be represented by the following Chemical Formula E-1.

[Chemical Formula E-1]

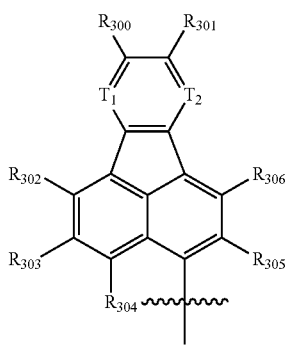

In Chemical Formula E-1, $T_1$ and $T_2$ are the same as those defined in Chemical Formula E, $R_{300}$ to $R_{306}$ are the same as or different from each other, and each independently hydrogen; deuterium; a nitrile group; a substituted or unsubstituted alkyl group; a substituted or unsubstituted alkenyl group; a substituted or unsubstituted cycloalkyl group; a substituted or unsubstituted aryl group; a substituted or unsubstituted aromatic or aliphatic heterocyclic group; a substituted or unsubstituted alkoxy group; a substituted or unsubstituted aryloxy group; a substituted or unsubstituted alkylamine group; a substituted or unsubstituted arylamine group; a substituted or unsubstituted aralkylamine group; a substituted or unsubstituted alkylarylamine group; or a substituted or unsubstituted heteroarylamine group, or combine with an adjacent substituent to form a ring.

According to an exemplary embodiment of the present specification, Chemical Formula E may be represented by any one of the following Chemical Formulae E-2 to E-4.

[Chemical Formula E-2]

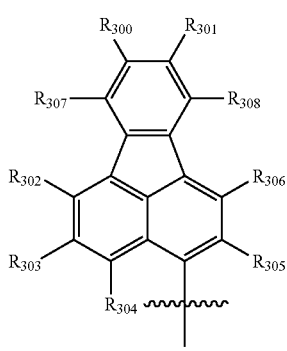

[Chemical Formula E-3]

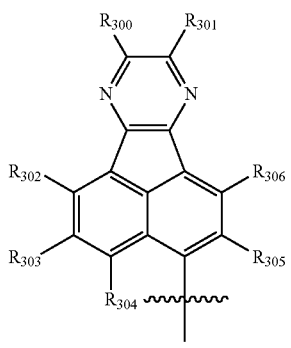

[Chemical Formula E-4]

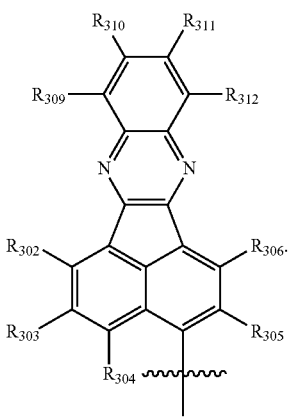

In Chemical Formulae E-2 to E-4, $R_{300}$ to $R_{312}$ are the same as or different from each other, and each independently hydrogen; deuterium; a nitrile group; a substituted or unsubstituted alkyl group; a substituted or unsubstituted alkenyl group; a substituted or unsubstituted cycloalkyl group; a substituted or unsubstituted aryl group; a substituted or unsubstituted aromatic or aliphatic heterocyclic group; a substituted or unsubstituted alkoxy group; a substituted or unsubstituted aryloxy group; a substituted or unsubstituted alkylamine group; a substituted or unsubstituted arylamine group; a substituted or unsubstituted aralkylamine group; a substituted or unsubstituted alkylarylamine group; or a substituted or unsubstituted heteroarylamine group, or combine with an adjacent substituent to form a ring.

In an exemplary embodiment of the present specification, adjacent two of $R_1$ to $R_4$ in Chemical Formulae 1 to 3 combine with each other to form a ring, for example, an aromatic ring.

According to an exemplary embodiment of the present specification, Chemical Formula 2 may be represented by any one of the following Chemical Formulae 6 to 8.

[Chemical Formula 6]

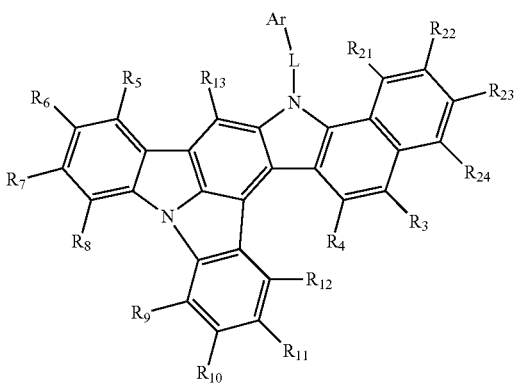

[Chemical Formula 7]

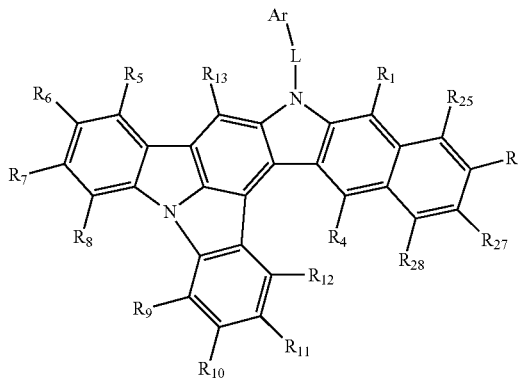

[Chemical Formula 8]

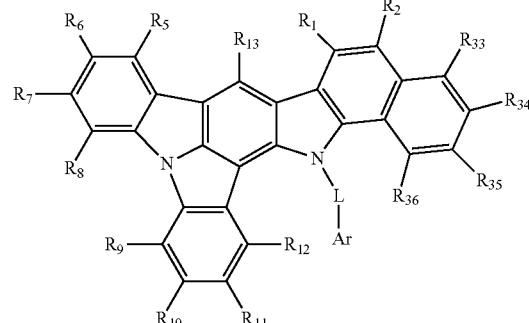

In Chemical Formulae 6 to 8, $R_1$ to $R_{13}$, L, and Ar are the same as those defined in Chemical Formula 1, and $R_{21}$ to $R_{32}$ are the same as or different from each other, and each independently hydrogen; deuterium; a nitrile group; a substituted or unsubstituted alkyl group; a substituted or unsubstituted alkenyl group; a substituted or unsubstituted cycloalkyl group; a substituted or unsubstituted aryl group; a substituted or unsubstituted aromatic or aliphatic heterocyclic group; a substituted or unsubstituted alkoxy group; a substituted or unsubstituted aryloxy group; a substituted or unsubstituted alkylamine group; a substituted or unsubstituted arylamine group; a substituted or unsubstituted aralkylamine group; a substituted or unsubstituted alkylarylamine group; or a substituted or unsubstituted heteroarylamine group, or combine with an adjacent substituent to form a ring.

In an exemplary embodiment of the present specification, Chemical Formula 3 may be represented by any one of the following Chemical Formulae 9 to 11.

[Chemical Formula 9]

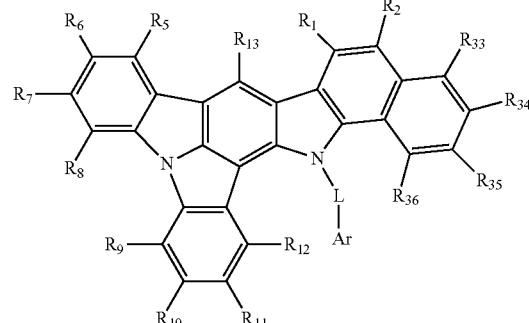

[Chemical Formula 10]

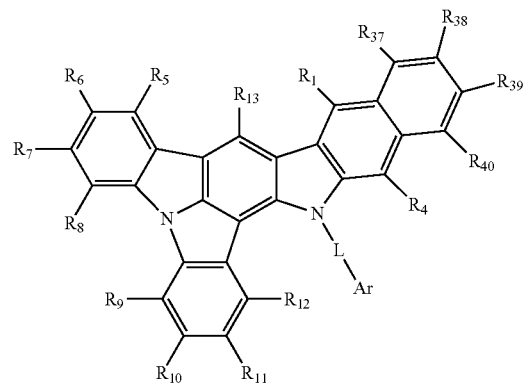

[Chemical Formula 11]

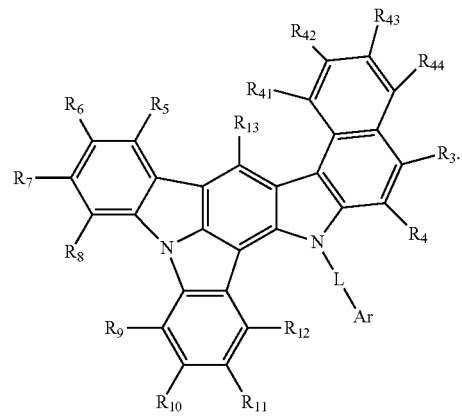

In Chemical Formulae 9 to 11, $R_1$ to $R_{13}$, L, and Ar are the same as those defined in Chemical Formula 1, and $R_{33}$ to $R_{44}$ are the same as or different from each other, and each independently hydrogen; deuterium; a nitrile group; a substituted or unsubstituted alkyl group; a substituted or unsubstituted alkenyl group; a substituted or unsubstituted cycloalkyl group; a substituted or unsubstituted aryl group; a substituted or unsubstituted aromatic or aliphatic heterocyclic group; a substituted or unsubstituted alkoxy group; a substituted or unsubstituted aryloxy group; a substituted or unsubstituted alkylamine group; a substituted or unsubstituted arylamine group; a substituted or unsubstituted aralkylamine group; a substituted or unsubstituted alkylarylamine group; or a substituted or unsubstituted heteroarylamine group, or combine with an adjacent substituent to form a ring.

In an exemplary embodiment of the present specification, at least one of $R_3$, $R_6$, and $R_7$ of Chemical Formulae 1 to 3 is a substituted or unsubstituted phenyl group, a substituted or unsubstituted naphthyl group, or a substituted or unsubstituted biphenyl group.

In an exemplary embodiment of the present specification, Chemical Formula 1 is represented by the following Chemical Formula 12 or 13.

[Chemical Formula 12]

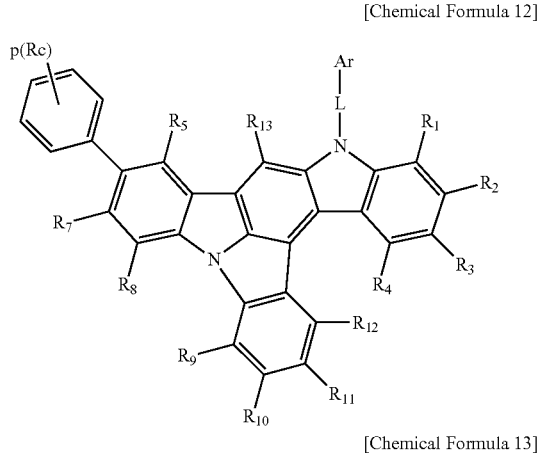

[Chemical Formula 13]

[Chemical Formula 14]

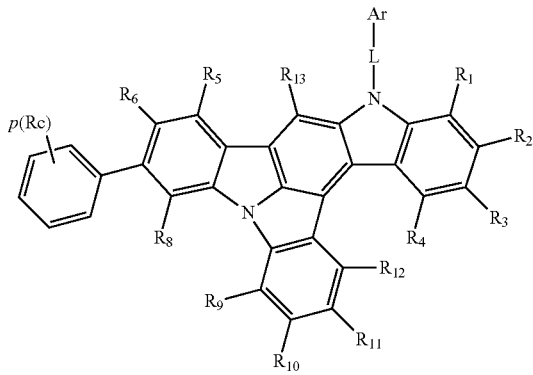

[Chemical Formula 15]

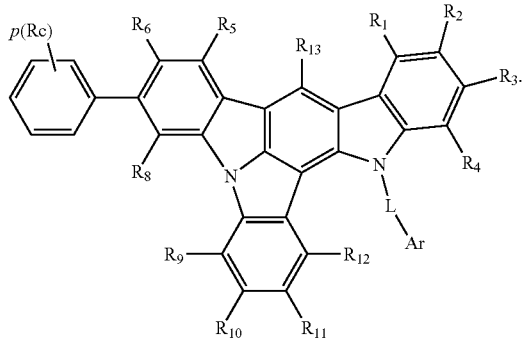

In Chemical Formulae 12 and 13, $R_1$ to $R_5$, $R_7$ to $R_{13}$, L, and Ar are the same as those defined in Chemical Formula 1, Rc is hydrogen; deuterium; a nitrile group; a substituted or unsubstituted alkyl group; a substituted or unsubstituted alkenyl group; a substituted or unsubstituted cycloalkyl group; a substituted or unsubstituted aryl group; a substituted or unsubstituted aromatic or aliphatic heterocyclic group; a substituted or unsubstituted alkoxy group; a substituted or unsubstituted aryloxy group; a substituted or unsubstituted alkylamine group; a substituted or unsubstituted arylamine group; a substituted or unsubstituted aralkylamine group; a substituted or unsubstituted alkylarylamine group; or a substituted or unsubstituted heteroarylamine group, or combine with an adjacent substituent to form a ring, and p is an integer of 1 to 5.

In an exemplary embodiment of the present specification, Chemical Formula 1 is represented by any one of the following Chemical Formulae 14 and 15.

In Chemical Formulae 14 and 15, $R_1$ to $R_6$, $R_8$ to $R_{13}$, L, and Ar are the same as those defined in Chemical Formula 1, Rc is hydrogen; deuterium; a nitrile group; a substituted or unsubstituted alkyl group; a substituted or unsubstituted alkenyl group; a substituted or unsubstituted cycloalkyl group; a substituted or unsubstituted aryl group; a substituted or unsubstituted aromatic or aliphatic heterocyclic group; a substituted or unsubstituted alkoxy group; a substituted or unsubstituted aryloxy group; a substituted or unsubstituted alkylamine group; a substituted or unsubstituted arylamine group; a substituted or unsubstituted aralkylamine group; a substituted or unsubstituted alkylarylamine group; or a substituted or unsubstituted heteroarylamine group, or combine with an adjacent substituent to form a ring, and p is an integer of 1 to 5.

According to an exemplary embodiment of the present specification, adjacent two of $R_5$ to $R_8$ in Chemical Formulae 1 to 3 combine with each other to form a ring, for example, an aromatic ring.

According to an exemplary embodiment of the present specification, Chemical Formula 1 is represented by any one of the following Chemical Formulae 16 and 17.

[Chemical Formula 16]

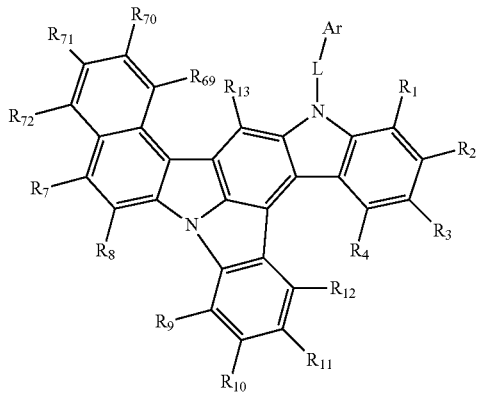

[Chemical Formula 17]

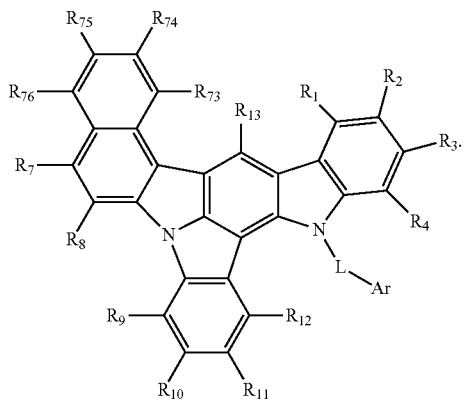

[Chemical Formula 18]

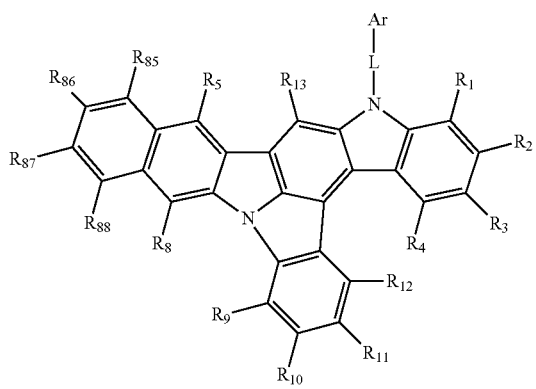

[Chemical Formula 19]

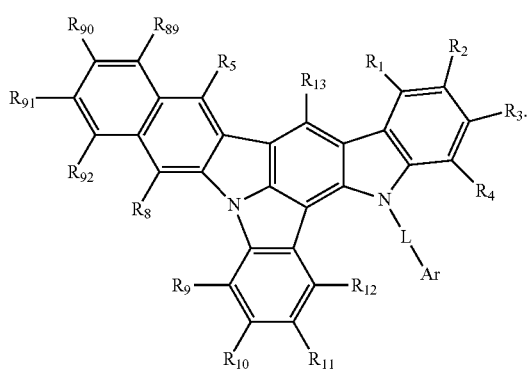

In Chemical Formulae 16 and 17, $R_1$ to R4, $R_7$ to $R_{13}$, L, and Ar are the same as those defined in Chemical Formula 1, and $R_{69}$ to $R_{76}$ are the same as or different from each other, and each independently hydrogen; deuterium; a nitrile group; a substituted or unsubstituted alkyl group; a substituted or unsubstituted alkenyl group; a substituted or unsubstituted cycloalkyl group; a substituted or unsubstituted aryl group; a substituted or unsubstituted aromatic or aliphatic heterocyclic group; a substituted or unsubstituted alkoxy group; a substituted or unsubstituted aryloxy group; a substituted or unsubstituted alkylamine group; a substituted or unsubstituted arylamine group; a substituted or unsubstituted aralkylamine group; a substituted or unsubstituted alkylarylamine group; or a substituted or unsubstituted heteroarylamine group, or combine with an adjacent substituent to form a ring.

According to an exemplary embodiment of the present specification, Chemical Formula 1 is represented by any one of the following Chemical Formulae 18 and 19.

In Chemical Formulae 18 and 19, $R_1$ to $R_5$, $R_8$ to $R_{13}$, L, and Ar are the same as those defined in Chemical Formula 1, and $R_{85}$ to $R_{92}$ are the same as or different from each other, and each independently hydrogen; deuterium; a nitrile group; a substituted or unsubstituted alkyl group; a substituted or unsubstituted alkenyl group; a substituted or unsubstituted cycloalkyl group; a substituted or unsubstituted aryl group; a substituted or unsubstituted aromatic or aliphatic heterocyclic group; a substituted or unsubstituted alkoxy group; a substituted or unsubstituted aryloxy group; a substituted or unsubstituted alkylamine group; a substituted or unsubstituted arylamine group; a substituted or unsubstituted aralkylamine group; a substituted or unsubstituted alkylarylamine group; or a substituted or unsubstituted heteroarylamine group, or combine with an adjacent substituent to form a ring.

According to an exemplary embodiment of the present specification, Chemical Formula 1 is represented by any one of the following Chemical Formulae 20 and 21.

[Chemical Formula 20]

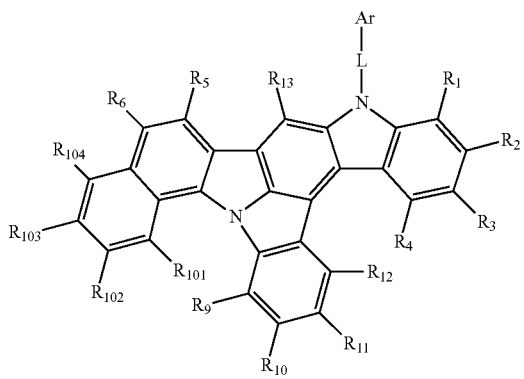

[Chemical Formula 21]

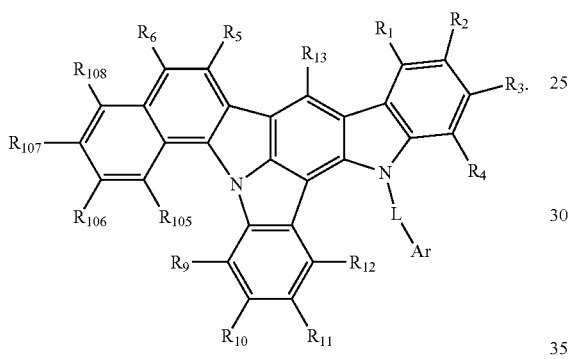

In Chemical Formulae 20 and 21, $R_1$ to $R_6$, $R_9$ to $R_{13}$, L, and Ar are the same as those defined in Chemical Formula 1, and $R_{101}$ to $R_{108}$ are the same as or different from each other, and each independently hydrogen; deuterium; a nitrile group; a substituted or unsubstituted alkyl group; a substituted or unsubstituted alkenyl group; a substituted or unsubstituted cycloalkyl group; a substituted or unsubstituted aryl group; a substituted or unsubstituted aromatic or aliphatic heterocyclic group; a substituted or unsubstituted alkoxy group; a substituted or unsubstituted aryloxy group; a substituted or unsubstituted alkylamine group; a substituted or unsubstituted arylamine group; a substituted or unsubstituted aralkylamine group; a substituted or unsubstituted alkylarylamine group; or a substituted or unsubstituted heteroarylamine group, or combine with an adjacent substituent to form a ring.

According to an exemplary embodiment of the present specification, adjacent two of $R_9$ to $R_{12}$ in Chemical Formulae 1 to 3 combine with each other to form a ring, for example, an aromatic ring.

According to an exemplary embodiment of the present specification, Chemical Formula 1 is represented by any one of the following Chemical Formulae 22 and 23.

[Chemical Formula 22]

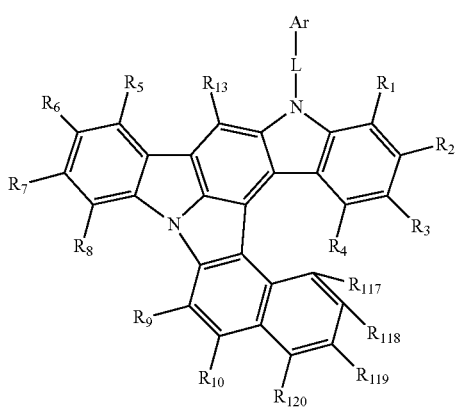

[Chemical Formula 23]

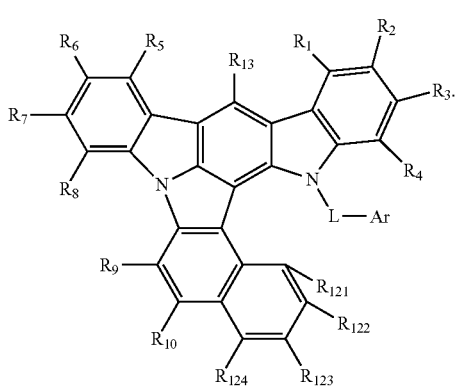

In Chemical Formulae 22 and 23, $R_1$ to $R_{10}$, $R_{13}$, L, and Ar are the same as those defined in Chemical Formula 1, and $R_{117}$ to $R_{124}$ are the same as or different from each other, and each independently hydrogen; deuterium; a nitrile group; a substituted or unsubstituted alkyl group; a substituted or unsubstituted alkenyl group; a substituted or unsubstituted cycloalkyl group; a substituted or unsubstituted aryl group; a substituted or unsubstituted aromatic or aliphatic heterocyclic group; a substituted or unsubstituted alkoxy group; a substituted or unsubstituted aryloxy group; a substituted or unsubstituted alkylamine group; a substituted or unsubstituted arylamine group; a substituted or unsubstituted aralkylamine group; a substituted or unsubstituted alkylarylamine group; or a substituted or unsubstituted heteroarylamine group, or combine with an adjacent substituent to form a ring.

According to an exemplary embodiment of the present specification, Chemical Formula 1 is represented by any one of the following Chemical Formulae 24 and 25.

[Chemical Formula 24]

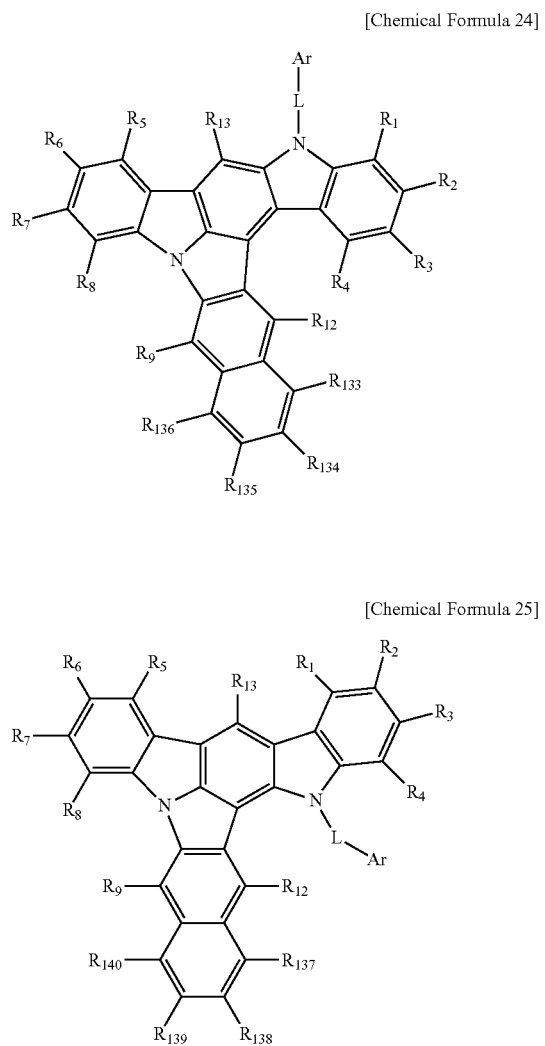

[Chemical Formula 25]

[Chemical Formula 26]

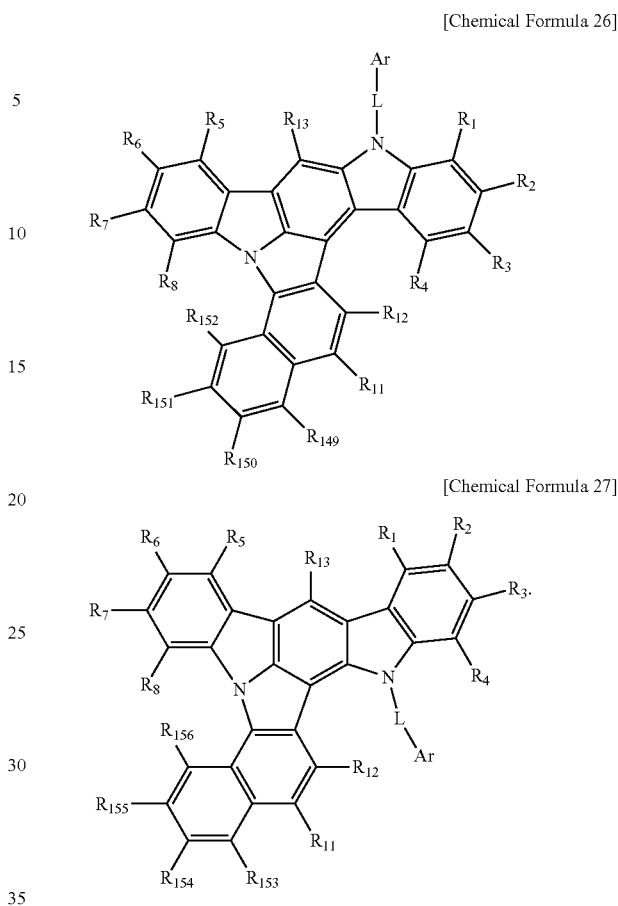

[Chemical Formula 27]

In Chemical Formulae 24 and 25, $R_1$ to $R_9$, $R_{12}$, $R_{13}$, L, and Ar are the same as those defined in Chemical Formula 1, and $R_{133}$ to $R_{140}$ are the same as or different from each other, and each independently hydrogen; deuterium; a nitrile group; a substituted or unsubstituted alkyl group; a substituted or unsubstituted alkenyl group; a substituted or unsubstituted cycloalkyl group; a substituted or unsubstituted aryl group; a substituted or unsubstituted aromatic or aliphatic heterocyclic group; a substituted or unsubstituted alkoxy group; a substituted or unsubstituted aryloxy group; a substituted or unsubstituted alkylamine group; a substituted or unsubstituted arylamine group; a substituted or unsubstituted aralkylamine group; a substituted or unsubstituted alkylarylamine group; or a substituted or unsubstituted heteroarylamine group, or combine with an adjacent substituent to form a ring.

According to an exemplary embodiment of the present specification, Chemical Formula 1 is represented by any one of the following Chemical Formulae 26 and 27.

In Chemical Formulae 26 and 27, $R_1$ to $R_8$, $R_{11}$ to $R_{13}$, L, and Ar are the same as those defined in Chemical Formula 1, and $R_{149}$ to $R_{156}$ are the same as or different from each other, and each independently hydrogen; deuterium; a nitrile group; a substituted or unsubstituted alkyl group; a substituted or unsubstituted alkenyl group; a substituted or unsubstituted cycloalkyl group; a substituted or unsubstituted aryl group; a substituted or unsubstituted aromatic or aliphatic heterocyclic group; a substituted or unsubstituted alkoxy group; a substituted or unsubstituted aryloxy group; a substituted or unsubstituted alkylamine group; a substituted or unsubstituted arylamine group; a substituted or unsubstituted aralkylamine group; a substituted or unsubstituted alkylarylamine group; or a substituted or unsubstituted heteroarylamine group, or combine with an adjacent substituent to form a ring.

According to an exemplary embodiment of the present specification, in Chemical Formula B-7, $R_{206}$ is hydrogen, a substituted or unsubstituted alkyl group, for example, a methyl group, or a substituted or unsubstituted aryl group, for example, a phenyl group, a biphenylyl group, or a naphthyl group.

According to an exemplary embodiment of the present specification, in Chemical Formula B-8, $R_{207}$ is hydrogen, a substituted or unsubstituted alkyl group, for example, a methyl group, or a substituted or unsubstituted aryl group, for example, a phenyl group, a biphenylyl group, or a naphthyl group.

According to an exemplary embodiment of the present specification, in Chemical Formula B-9, $R_{208}$ is hydrogen, a substituted or unsubstituted alkyl group, for example, a methyl group, or a substituted or unsubstituted aryl group, for example, a phenyl group, a biphenylyl group, or a naphthyl group.

According to an exemplary embodiment of the present specification, in Chemical Formula B-10, $R_{209}$ is hydrogen, a substituted or unsubstituted alkyl group, for example, a methyl group, or a substituted or unsubstituted aryl group, for example, a phenyl group, a biphenylyl group, or a naphthyl group.

According to an exemplary embodiment of the present specification, in Chemical Formula B, $Y_1$ is $CR_{219}$, $Y_2$ is N or $CR_{220}$, $R_{219}$ is hydrogen, a substituted or unsubstituted alkyl group, for example, a methyl group, or a substituted or unsubstituted aryl group, for example, a phenyl group, a biphenylyl group, or a naphthyl group, and $R_{220}$ is hydrogen; deuterium; a nitrile group; a substituted or unsubstituted alkyl group; a substituted or unsubstituted alkenyl group; a substituted or unsubstituted cycloalkyl group; a substituted or unsubstituted aryl group; a substituted or unsubstituted aromatic or aliphatic heterocyclic group; a substituted or unsubstituted alkoxy group; a substituted or unsubstituted aryloxy group; a substituted or unsubstituted alkylamine group; a substituted or unsubstituted arylamine group; a substituted or unsubstituted aralkylamine group; a substituted or unsubstituted alkylarylamine group; or a substituted or unsubstituted heteroarylamine group.

According to an exemplary embodiment of the present specification, in Chemical Formula B, $Y_1$ is $CR_{219}$, $Y_2$ is N, and $R_{219}$ is hydrogen, a substituted or unsubstituted alkyl group, for example, a methyl group, or a substituted or unsubstituted aryl group, for example, a phenyl group, a biphenylyl group, or a naphthyl group.

According to an exemplary embodiment of the present specification, in Chemical Formula B, $Y_1$ is $CR_{219}$, $Y_2$ is N, and $R_{219}$ is a substituted or unsubstituted aryl group, for example, a phenyl group, a biphenylyl group, or a naphthyl group.

According to an exemplary embodiment of the present specification, Ar may be a group represented by the following chemical formulae.

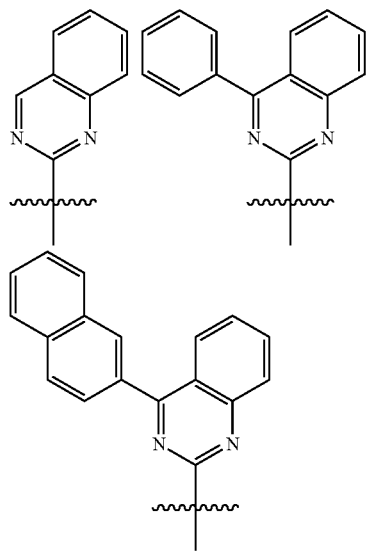

-continued

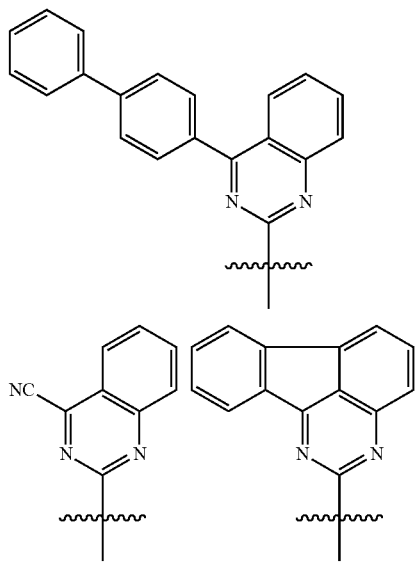

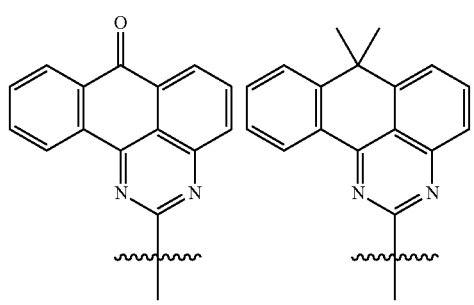

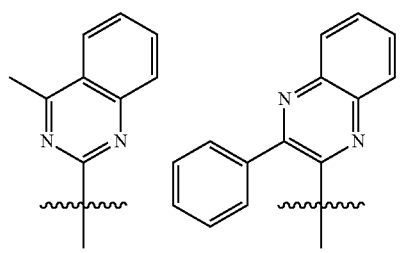

-continued
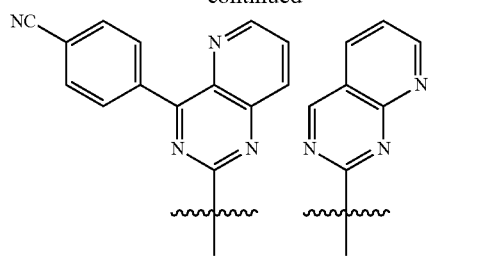
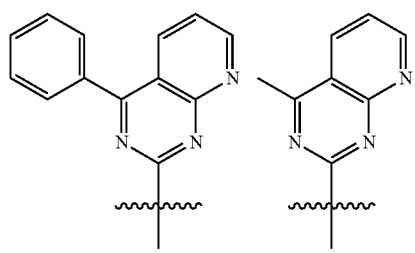
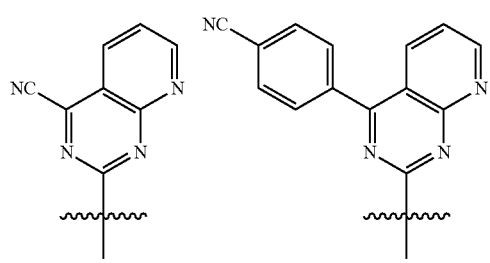
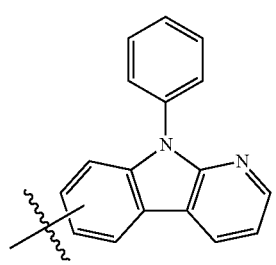
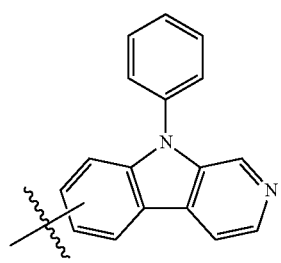
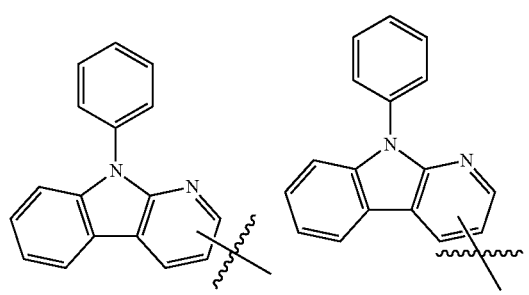
-continued
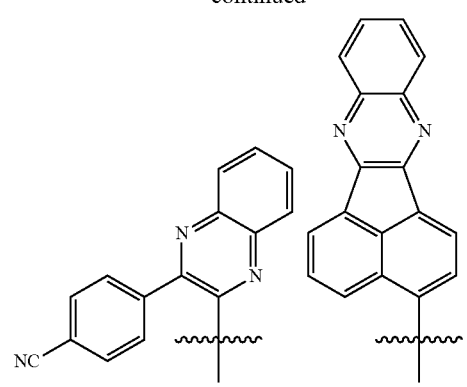
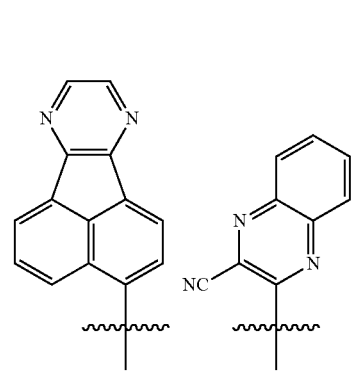
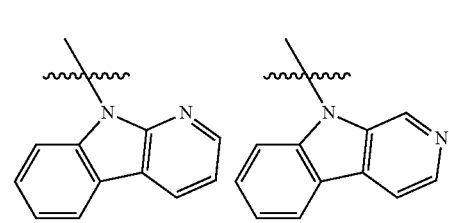
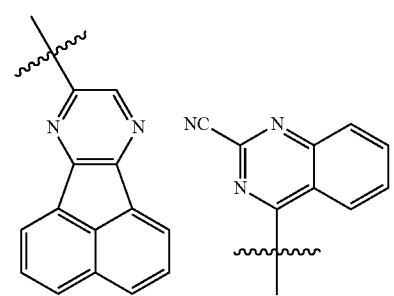
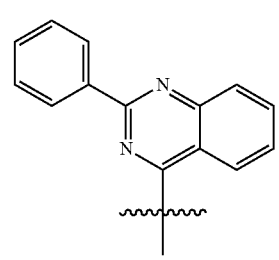

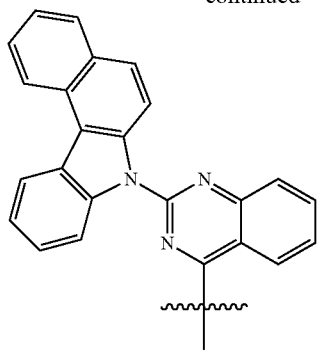
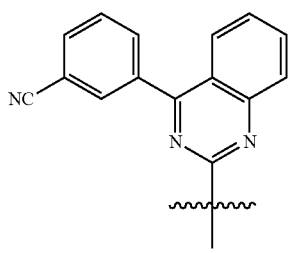
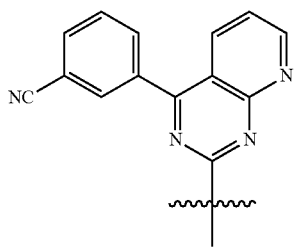
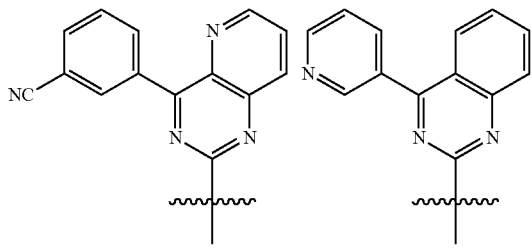
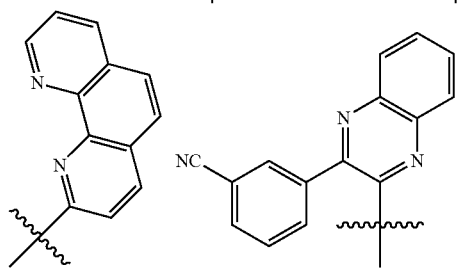
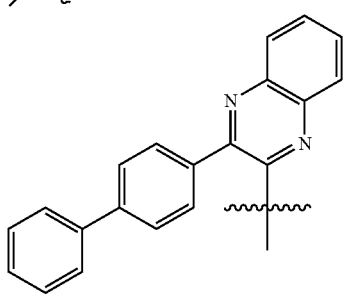
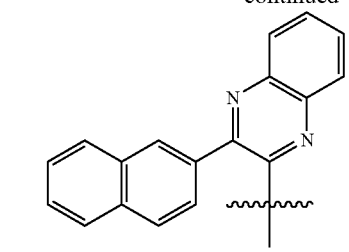
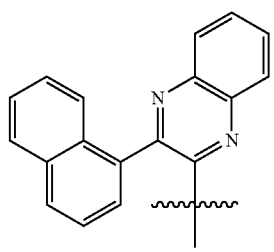
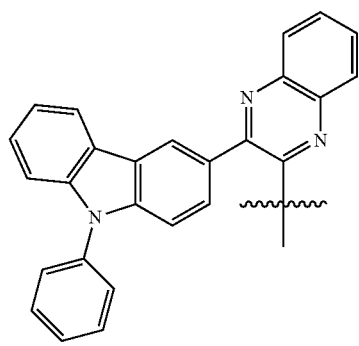
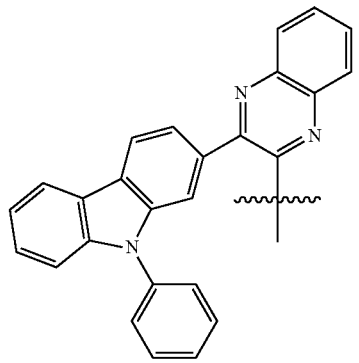
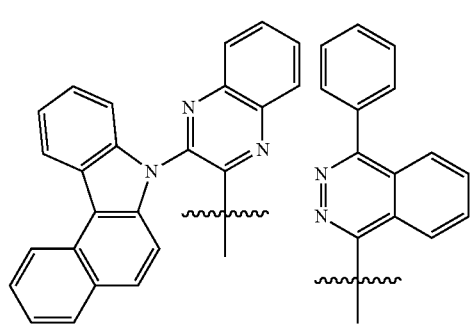

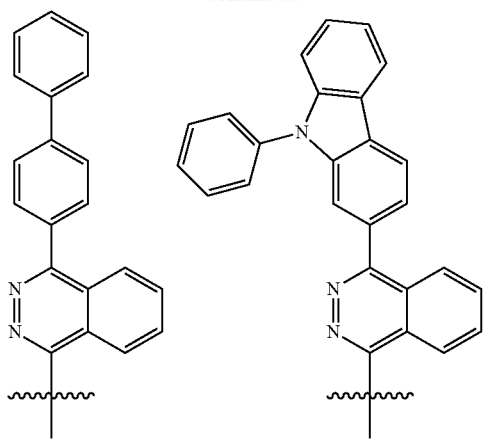
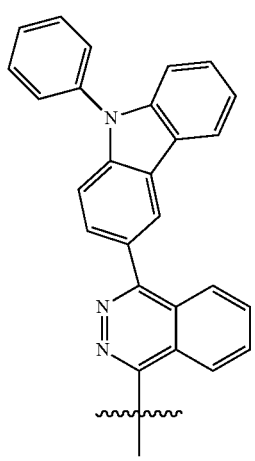
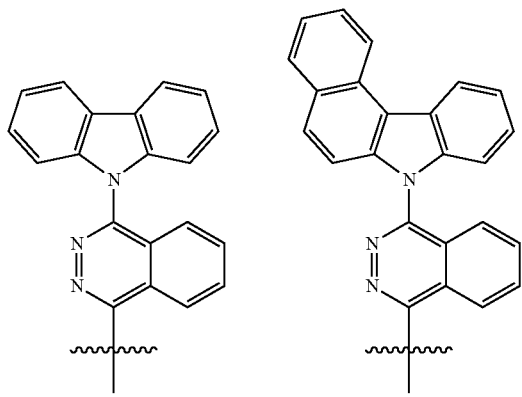
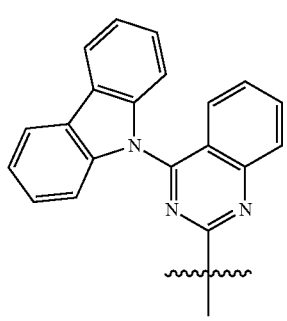
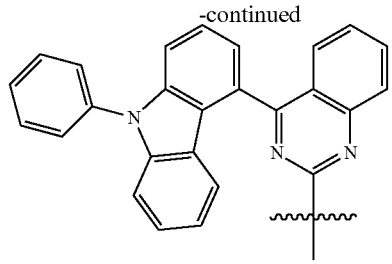
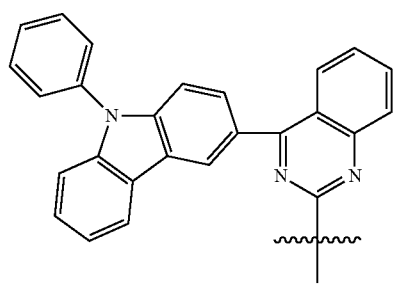
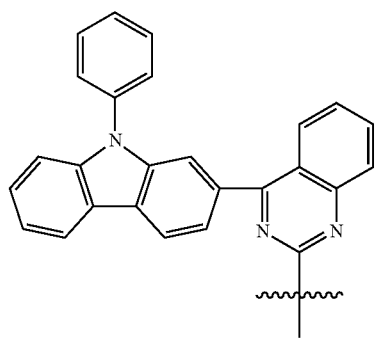
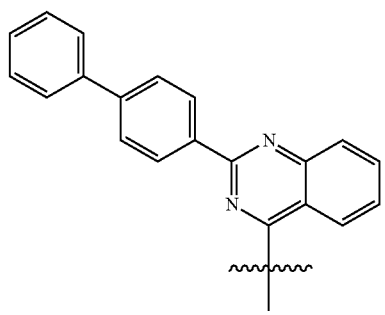
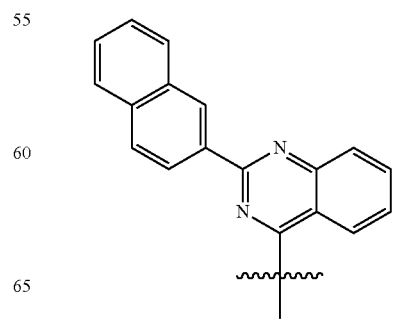

-continued
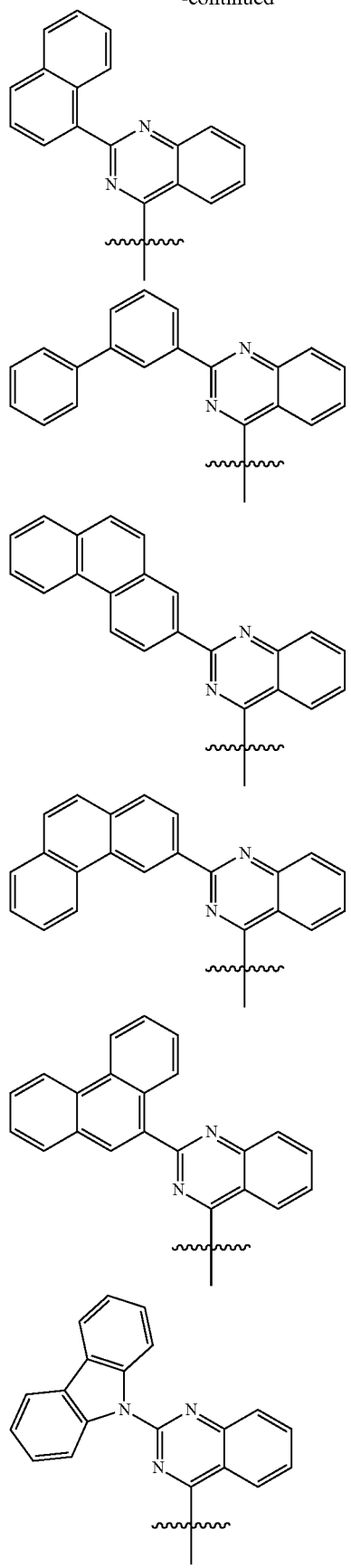
-continued
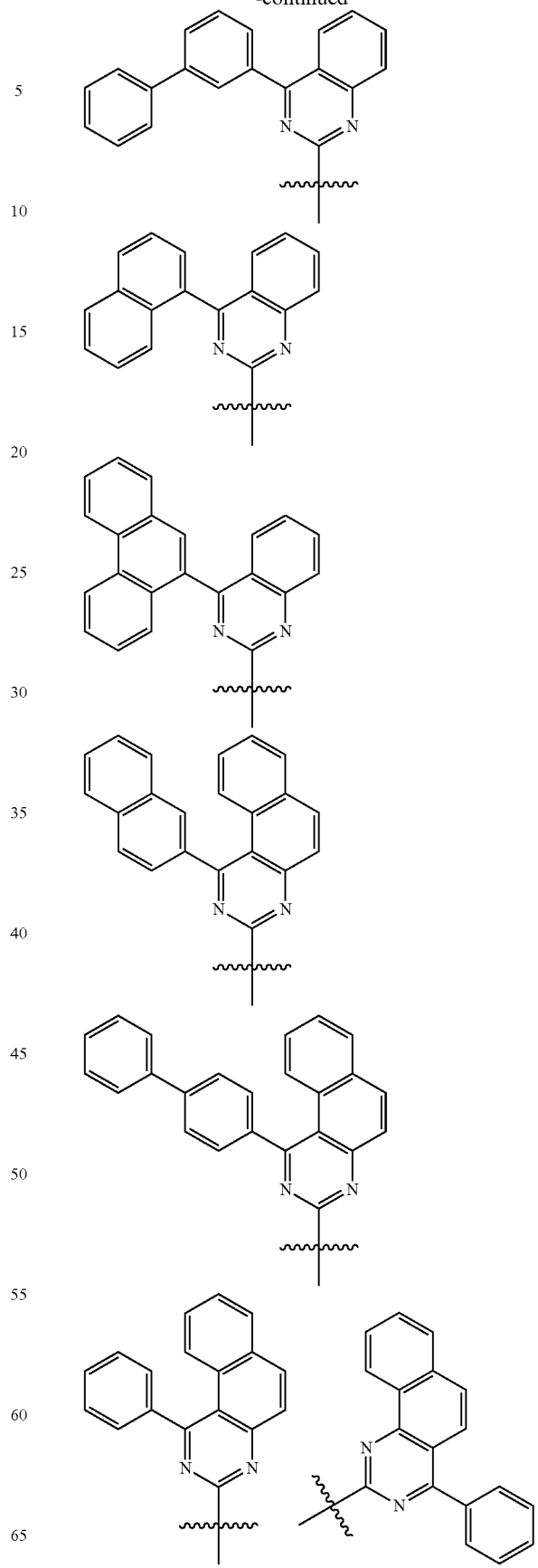

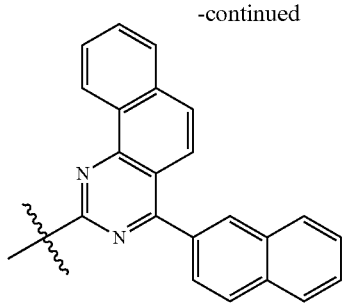
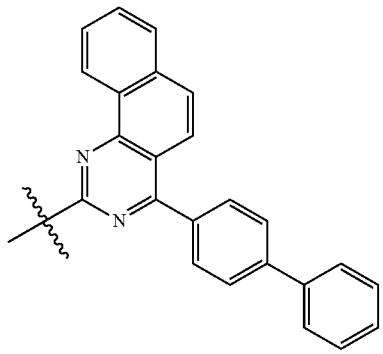
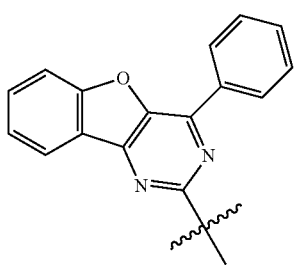
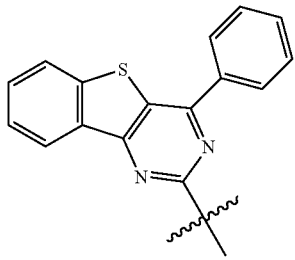
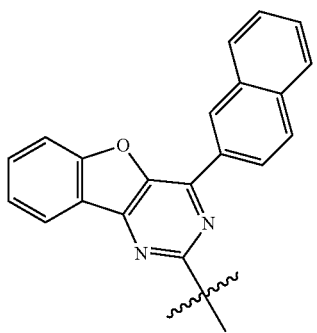
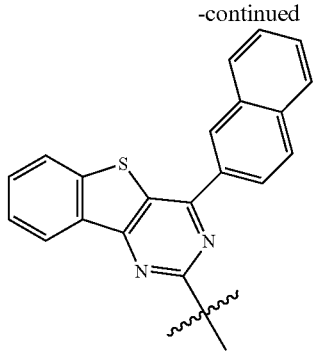
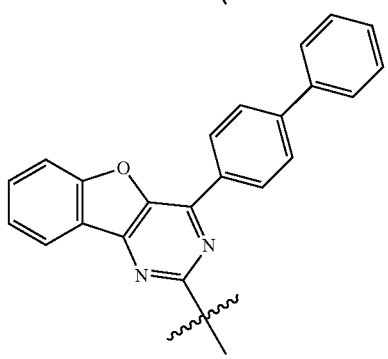
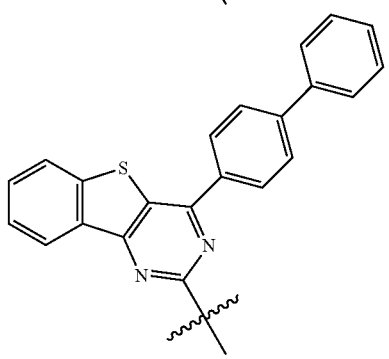
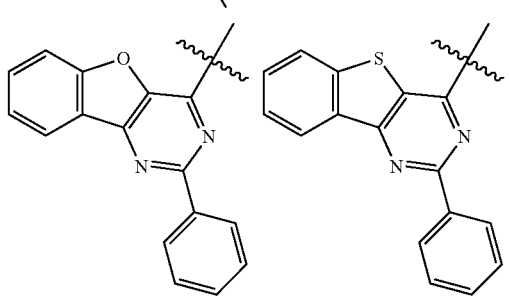
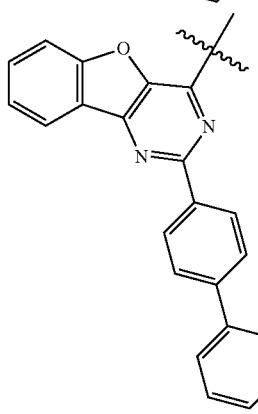

41
-continued
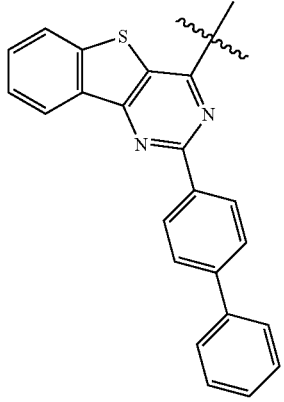
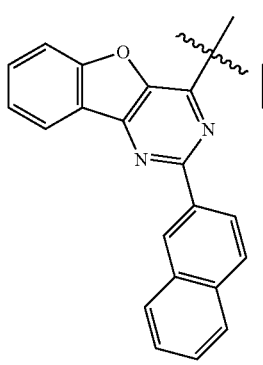 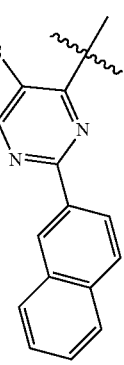
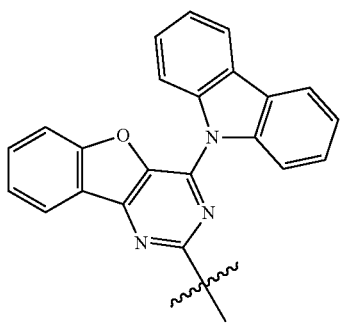
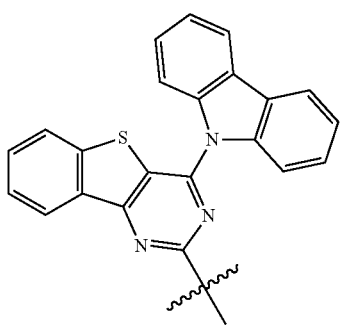
42
-continued
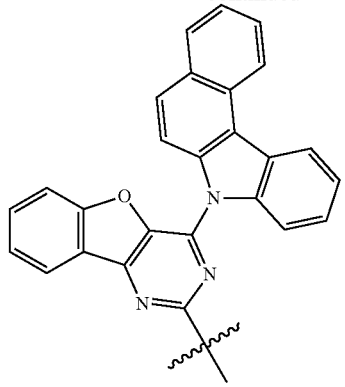
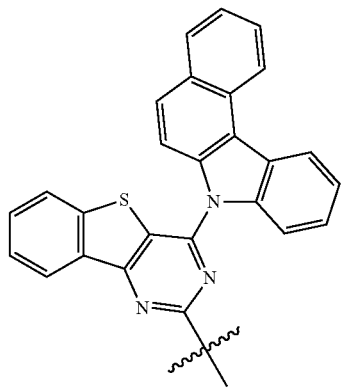
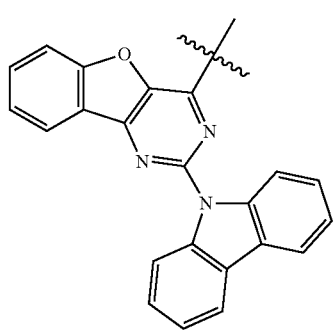
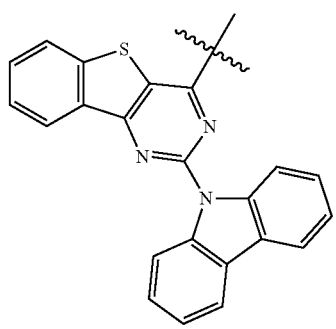

-continued
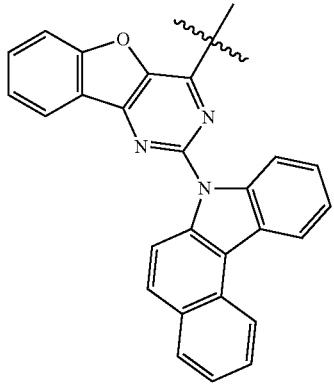
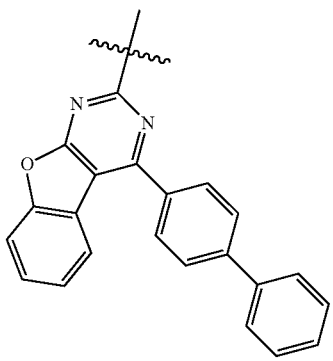
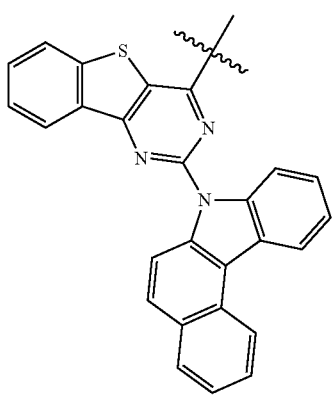
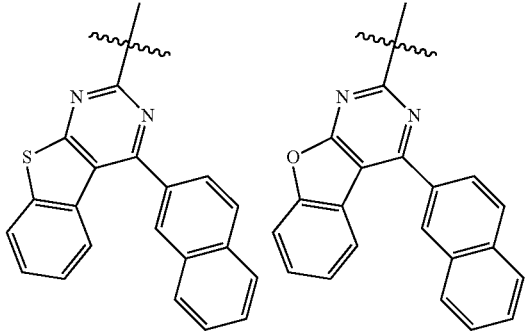
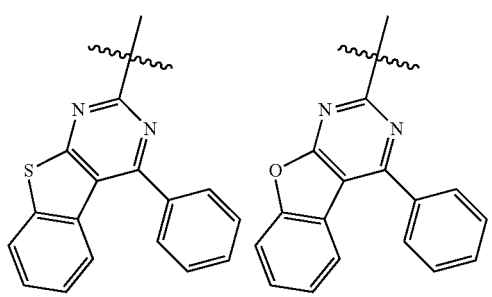
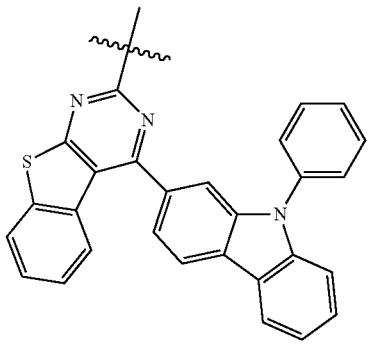
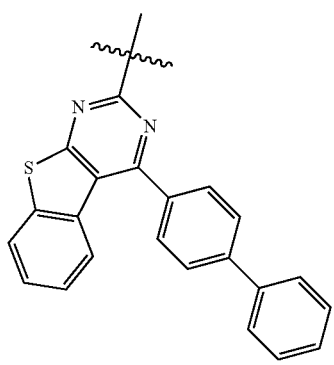
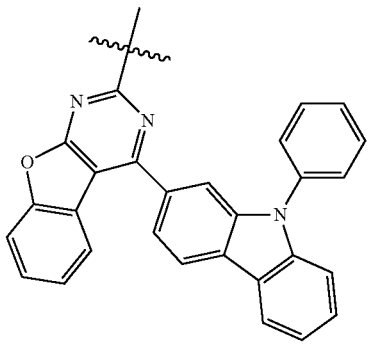

-continued
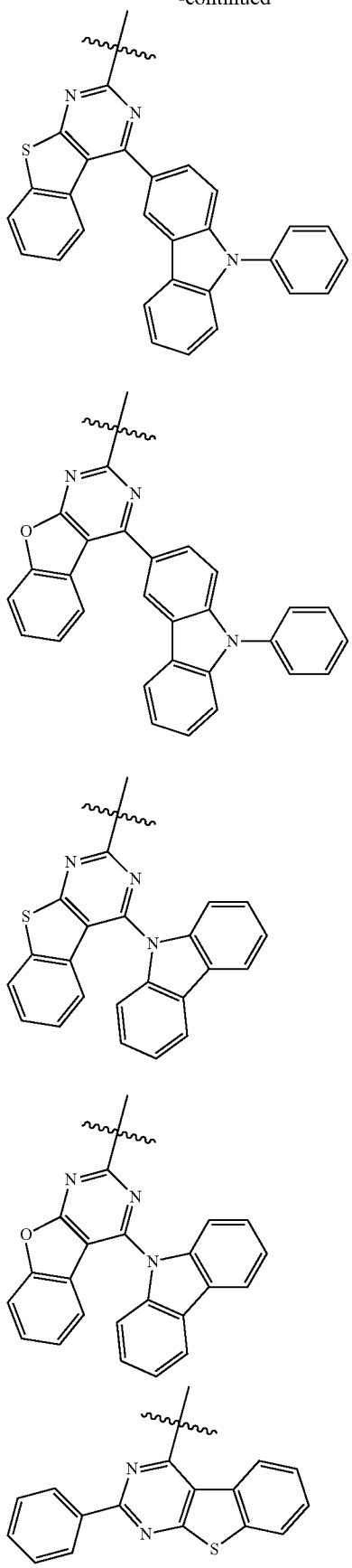
-continued
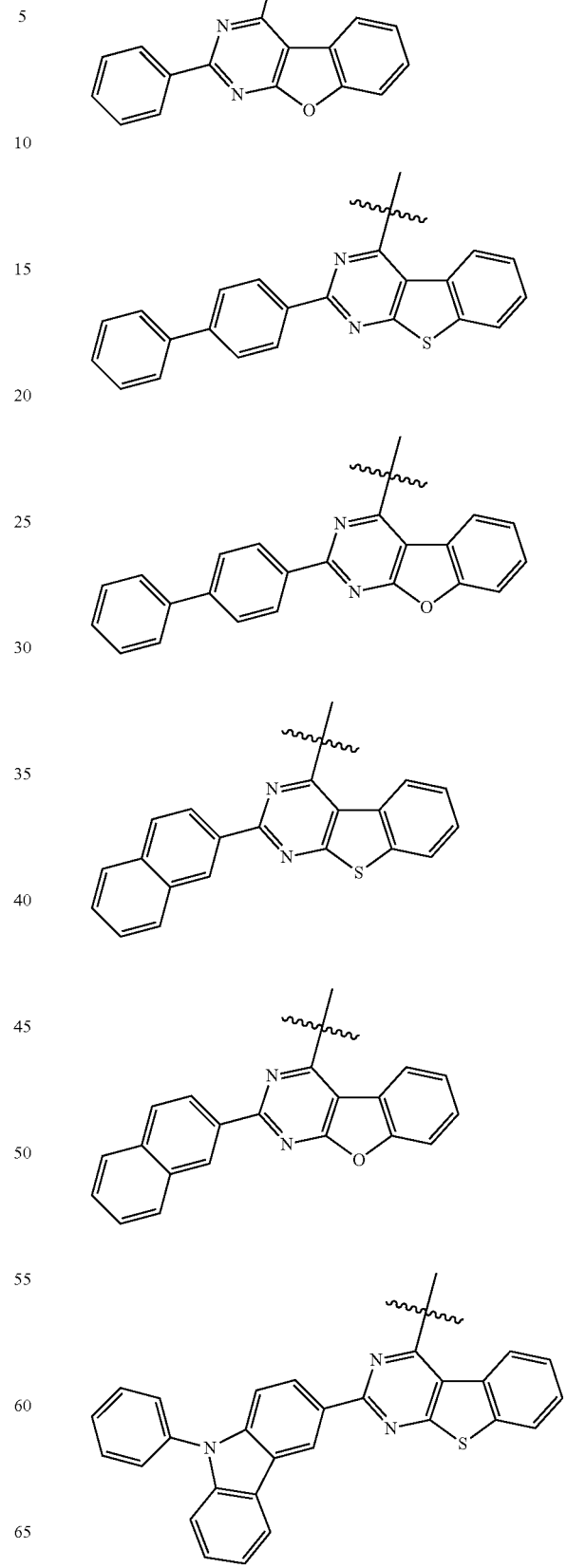

47
-continued
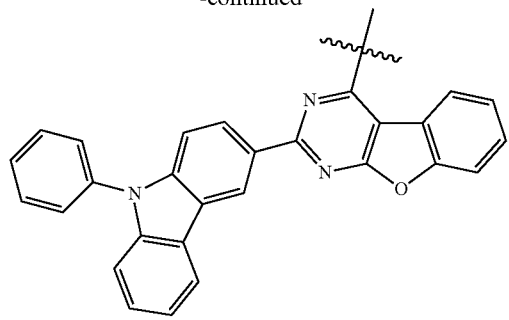
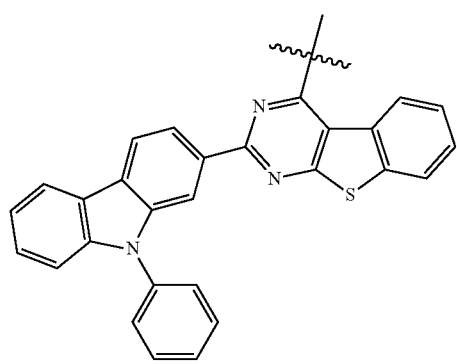
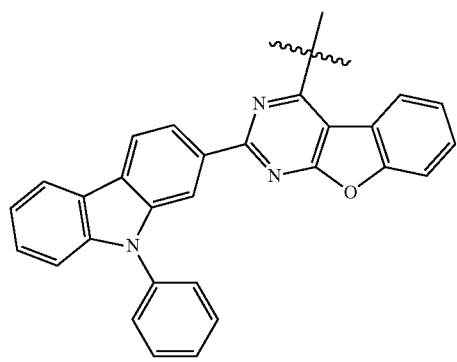
48
-continued
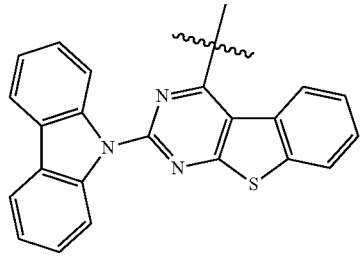
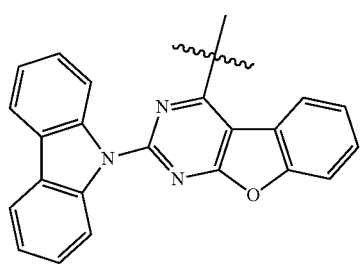 [SMILES: *c1nc(-n2c3ccccc3c3ccccc32)nc2oc3ccccc3c12]
According to an exemplary embodiment of the present specification, Chemical Formula 1 is represented by any one of the following compounds.
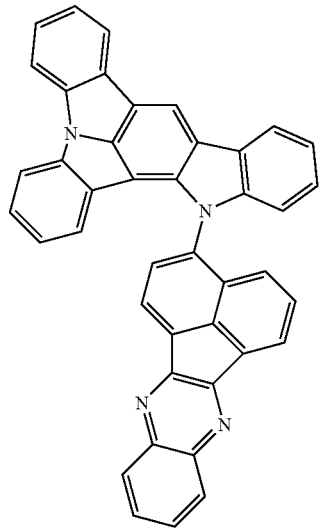
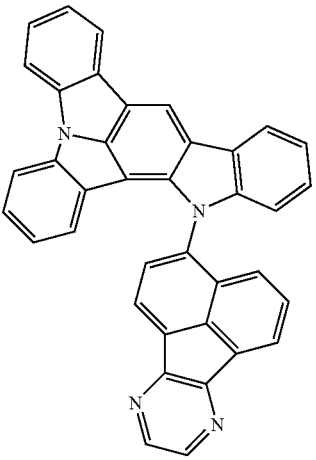

-continued
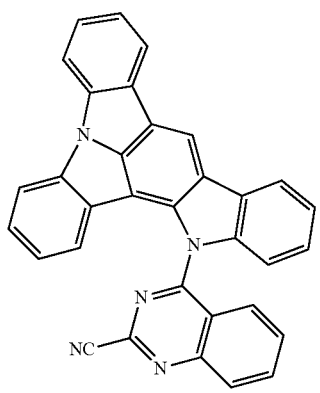
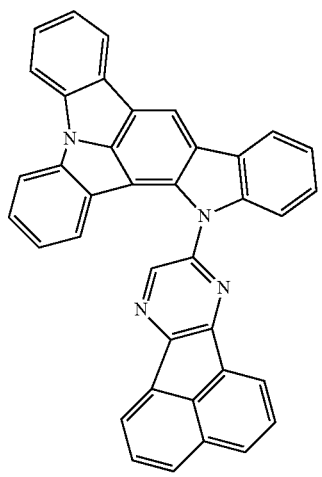
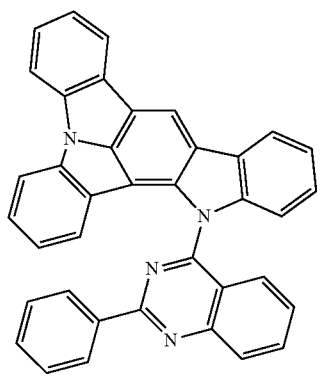
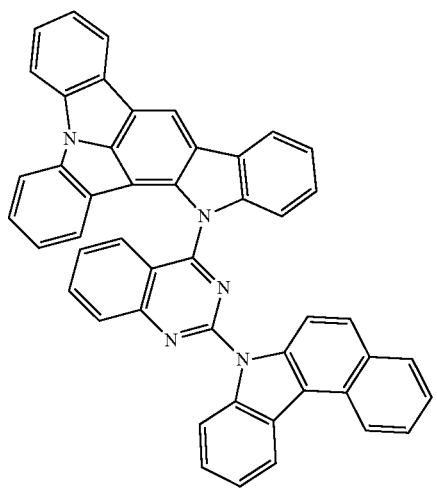
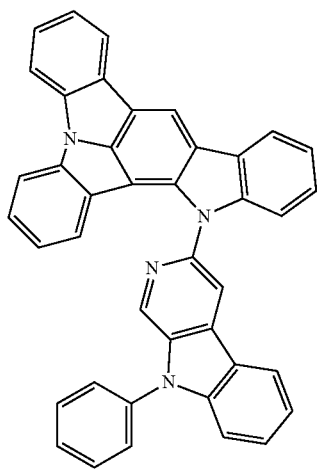
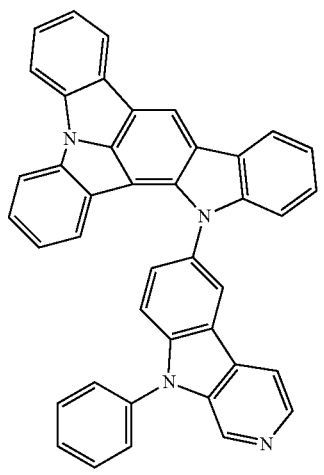

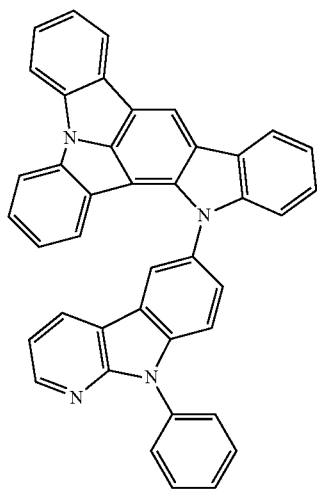
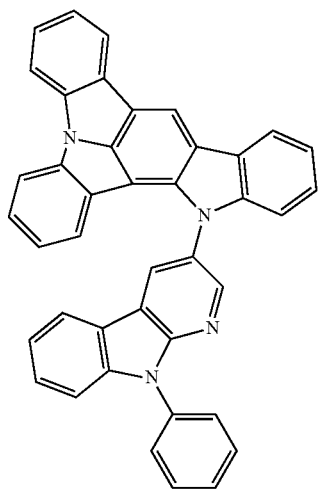
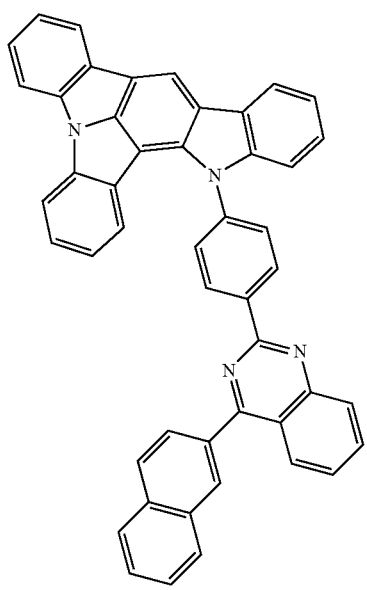
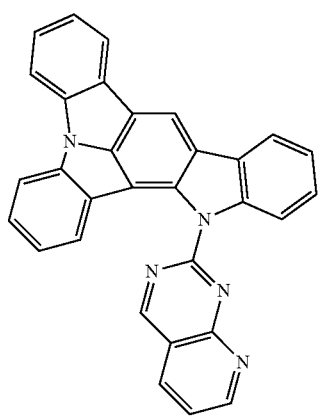
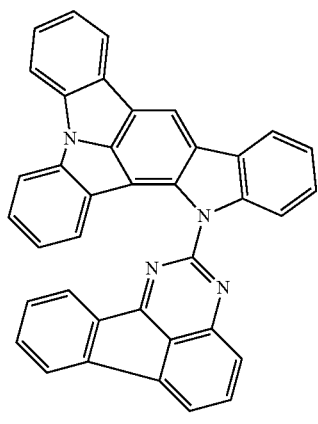
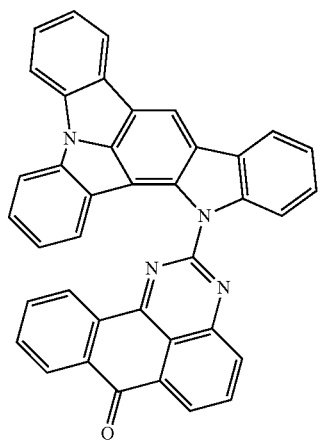

-continued
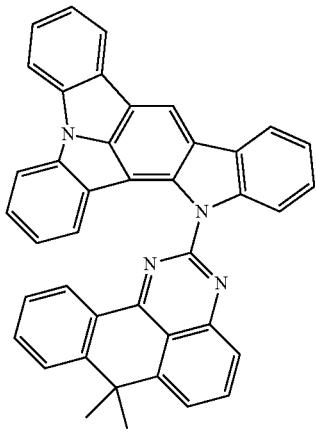 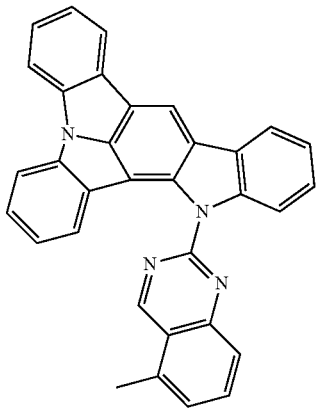
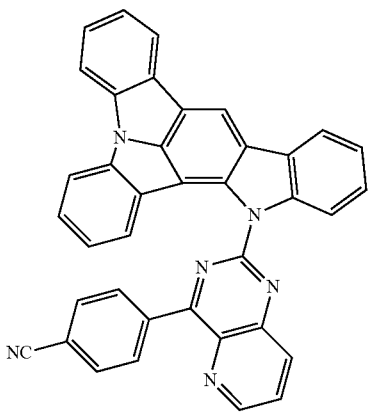 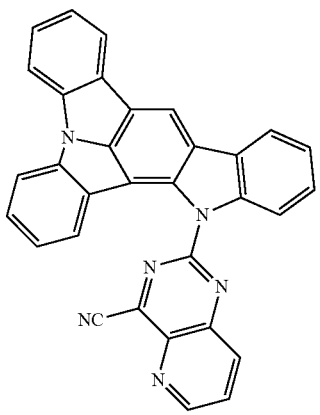
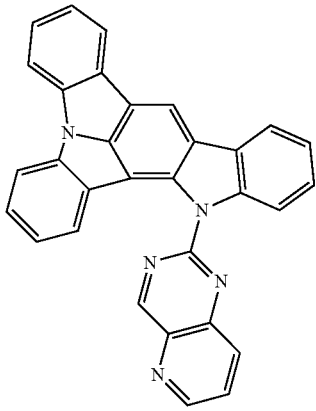 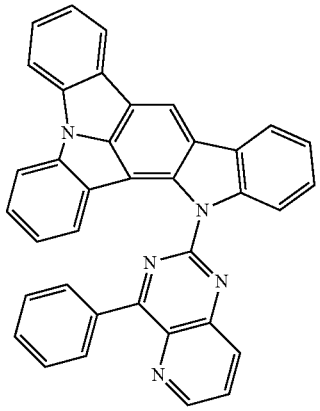
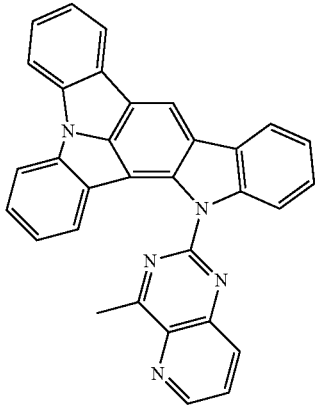 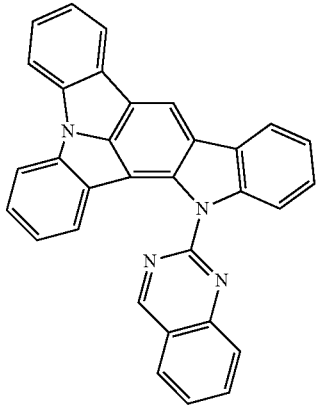

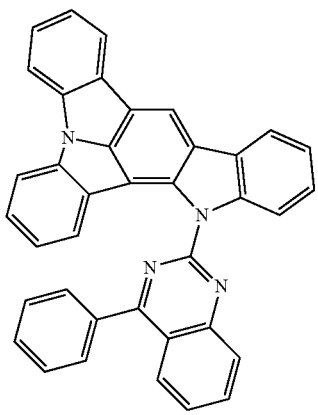
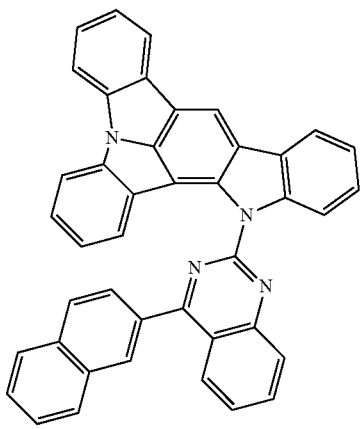
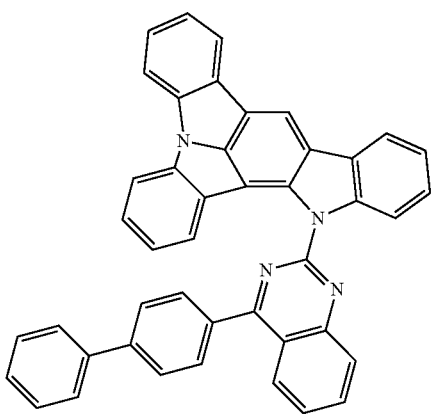
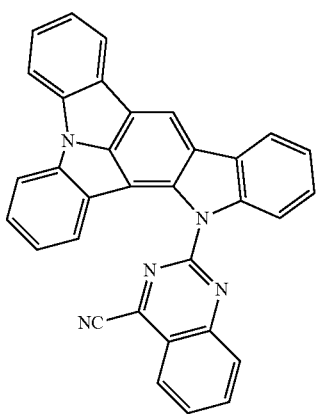
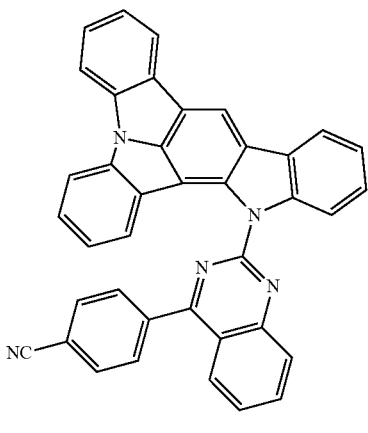
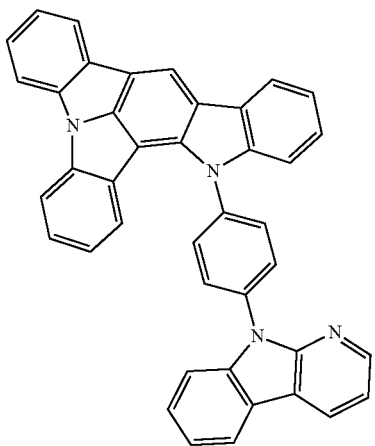

-continued
| 57 | 58 |
|---|---|
| 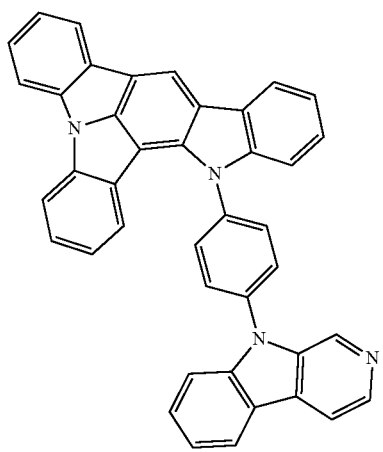 | 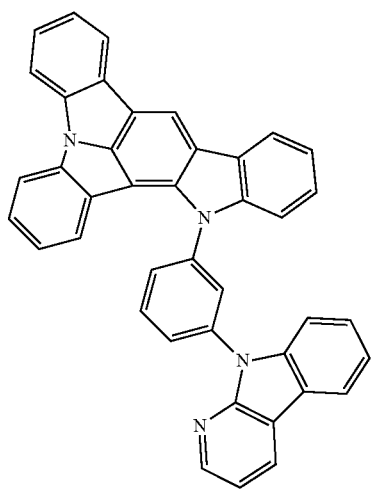 |
| 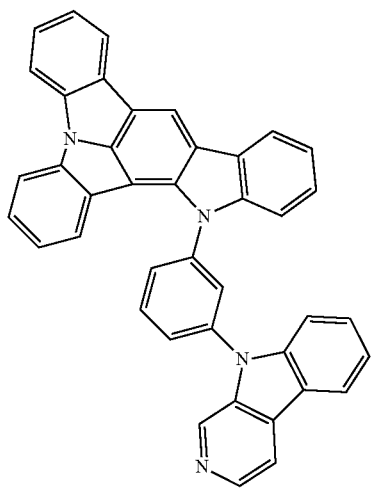 | 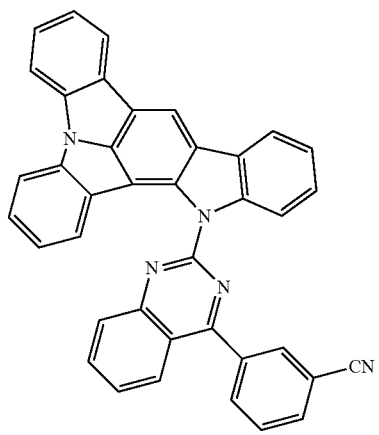 |
| 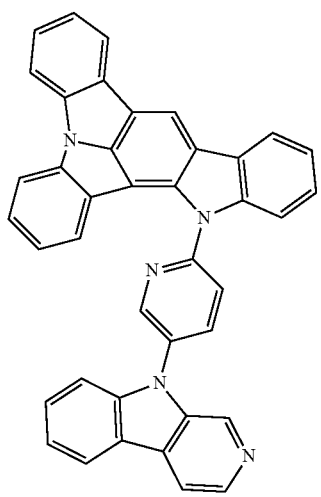 | 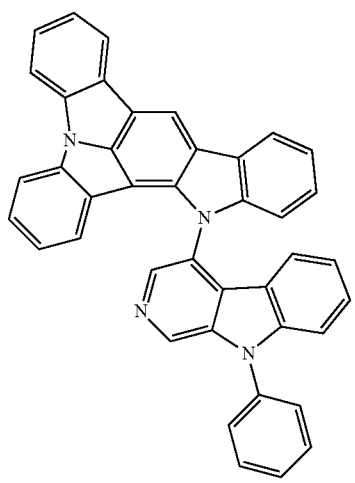 |

-continued
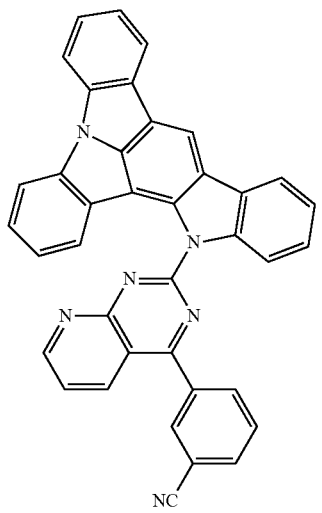
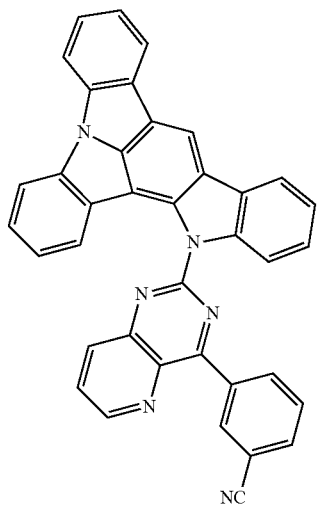
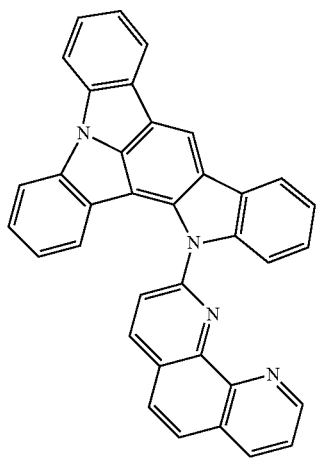
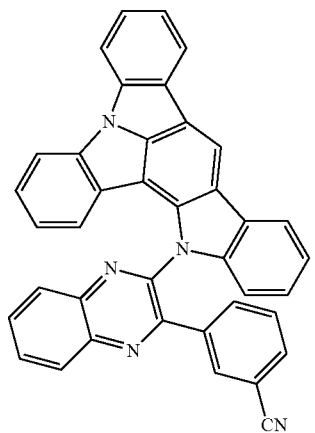
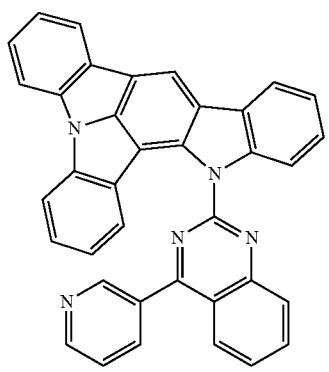
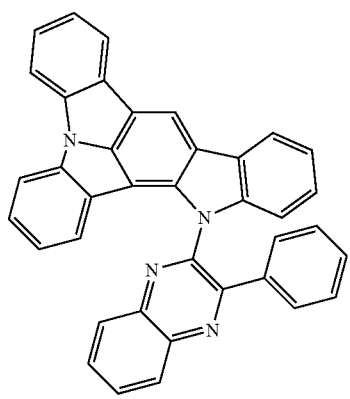

61
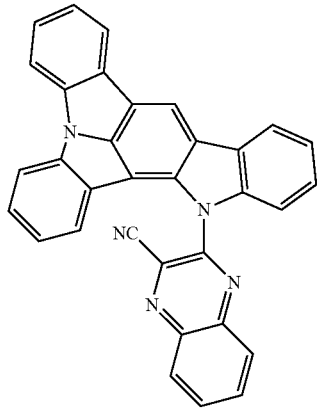
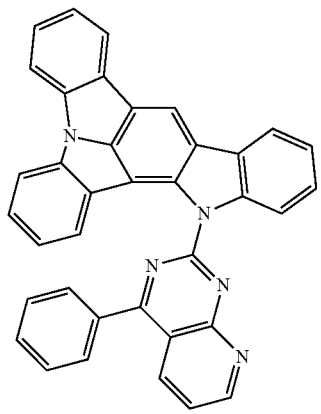
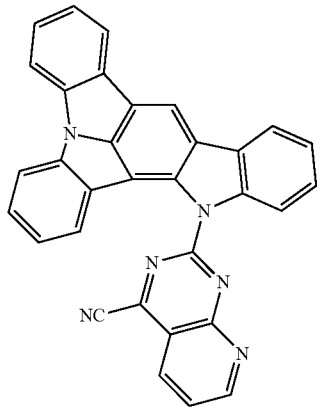
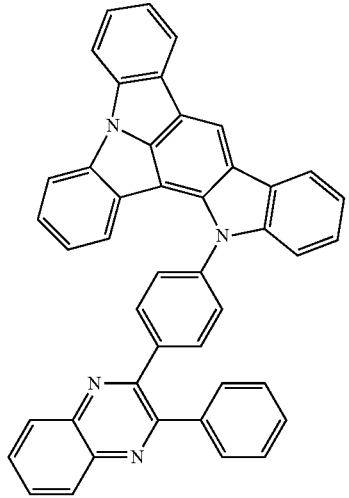
62
-continued
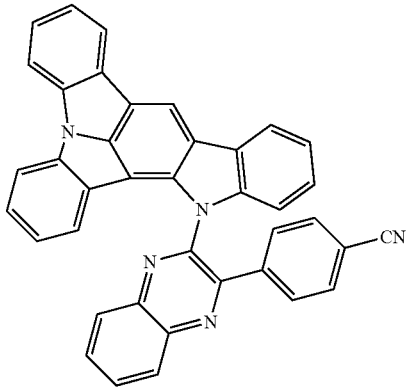
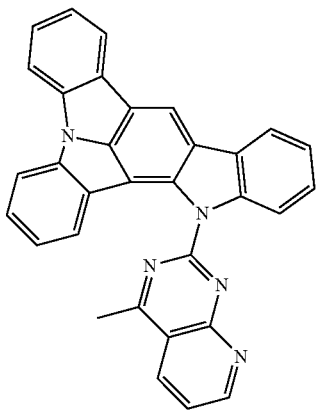
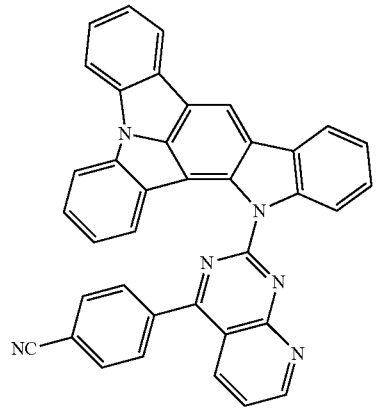
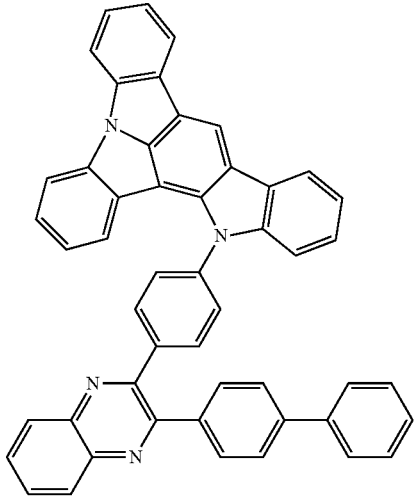

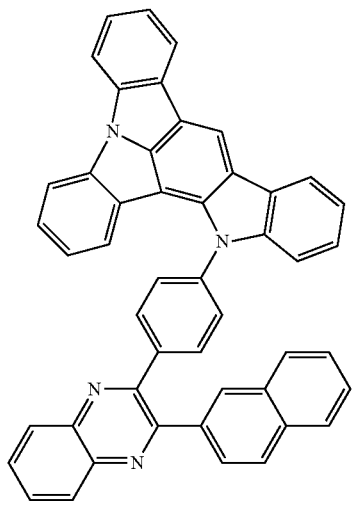
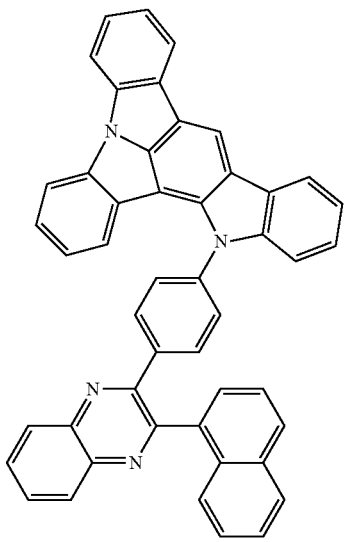
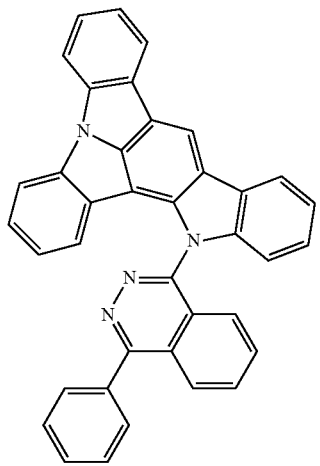
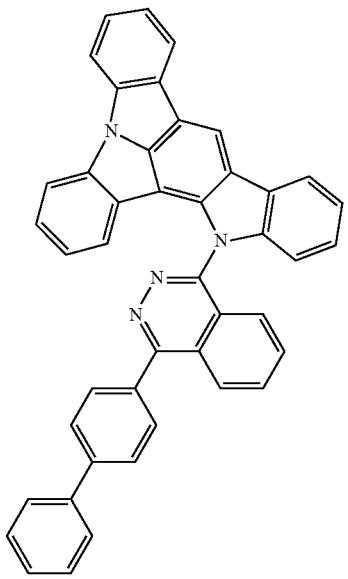
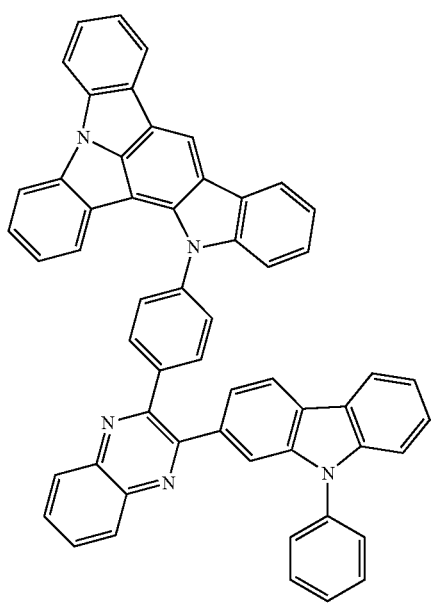
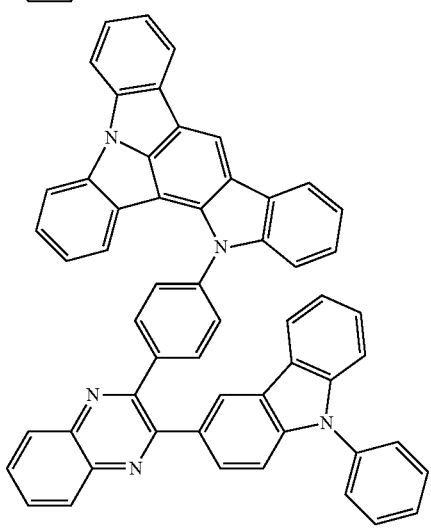

65
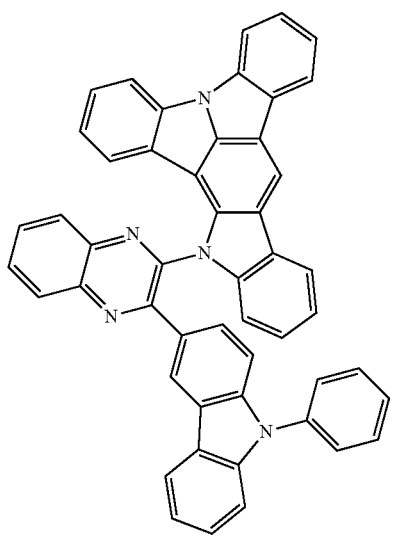
66
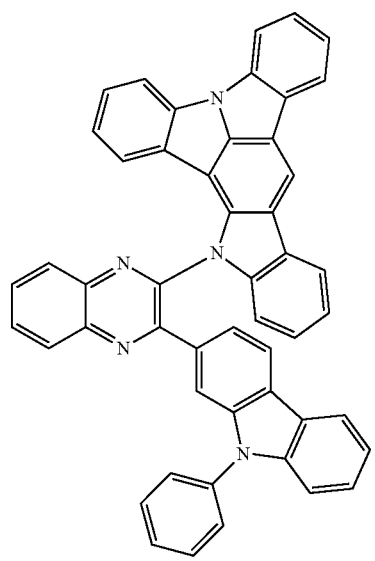
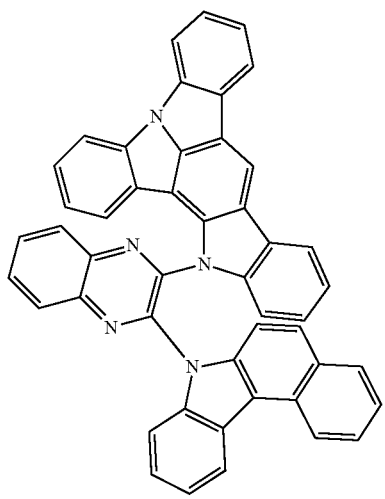
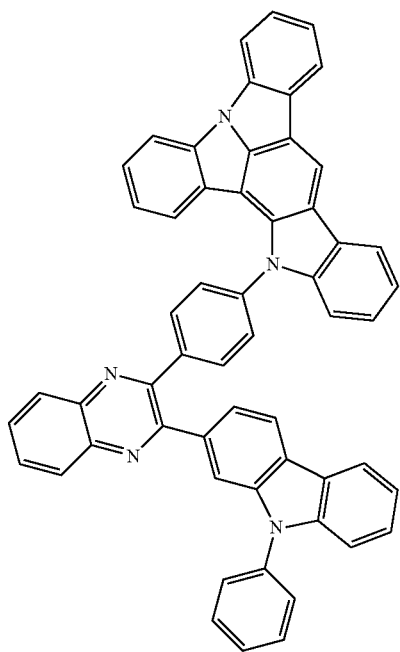

-continued
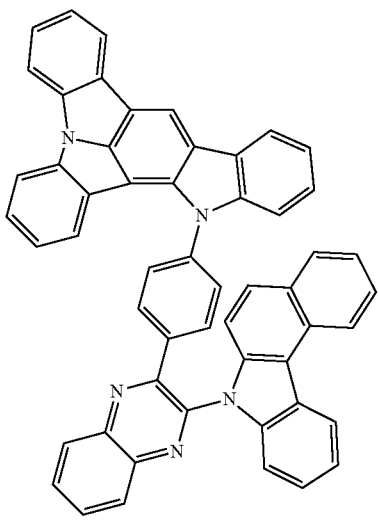
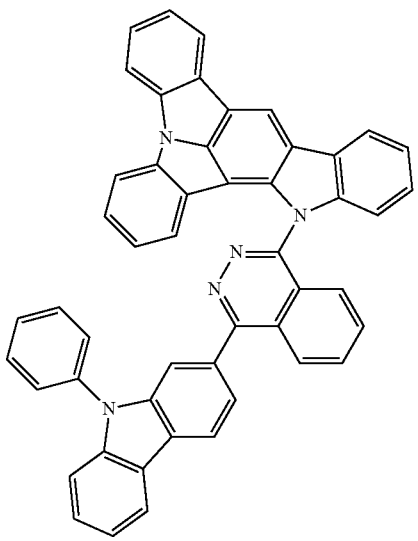
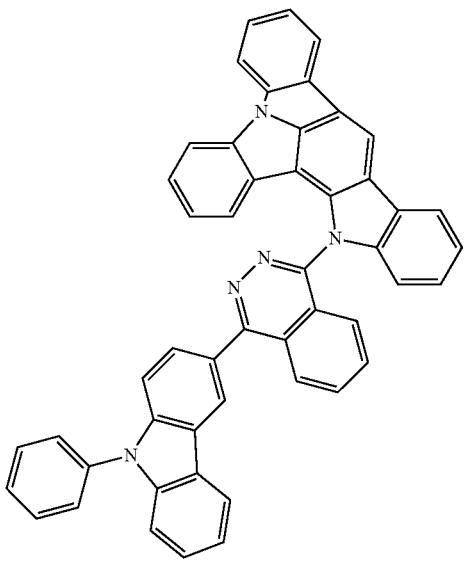
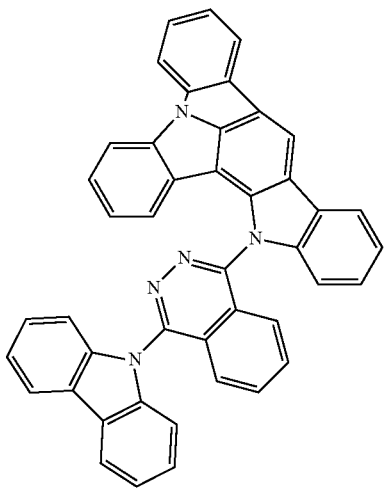
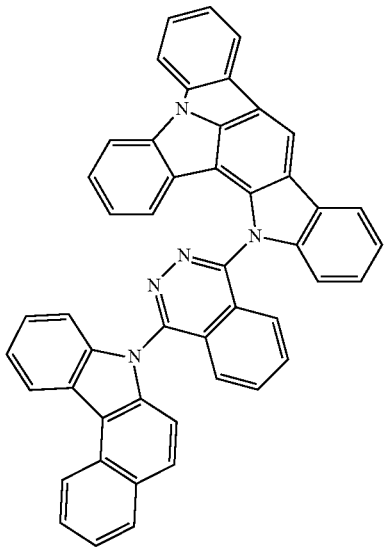
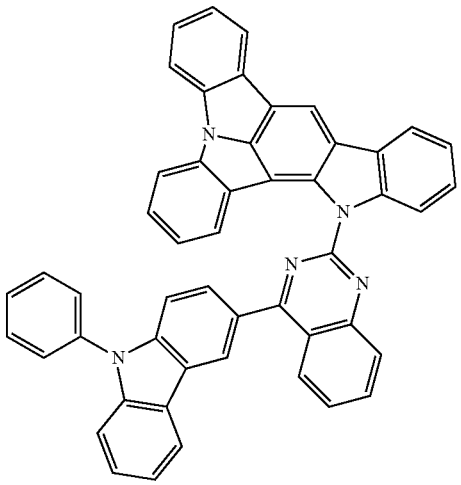

-continued
69
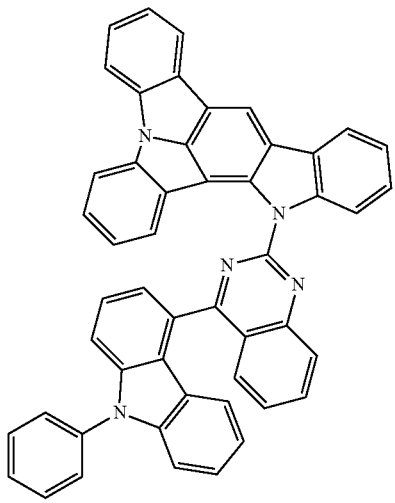
70
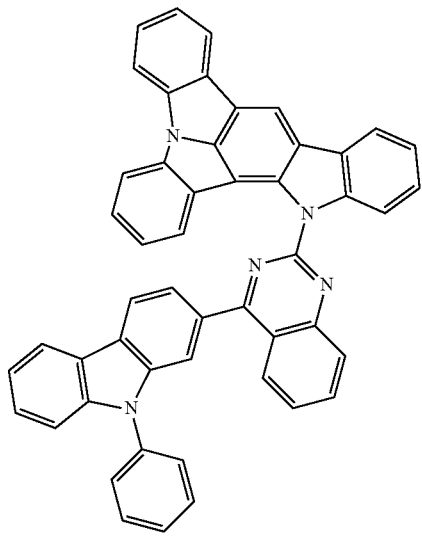
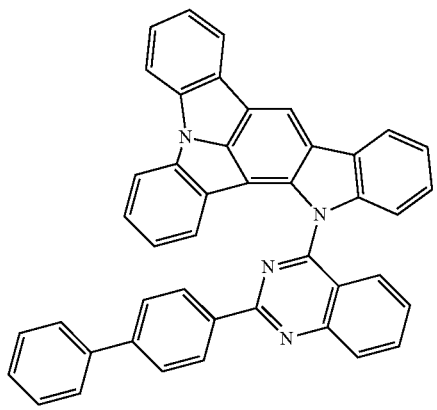
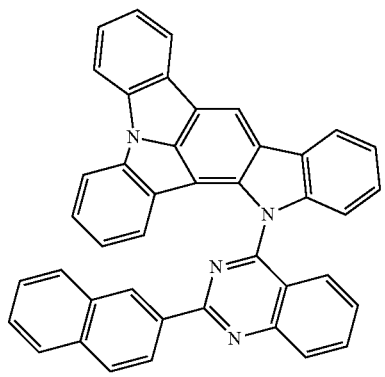
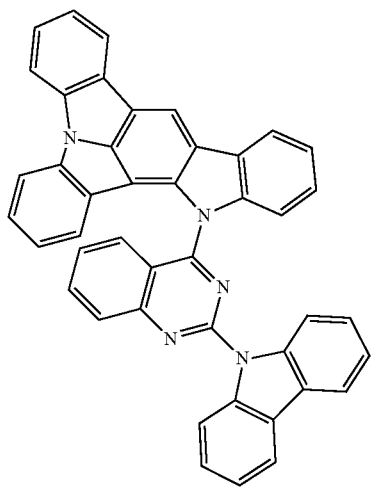
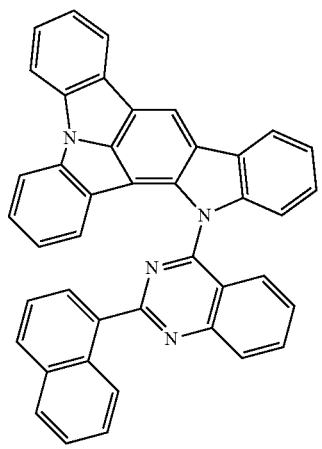

-continued
71
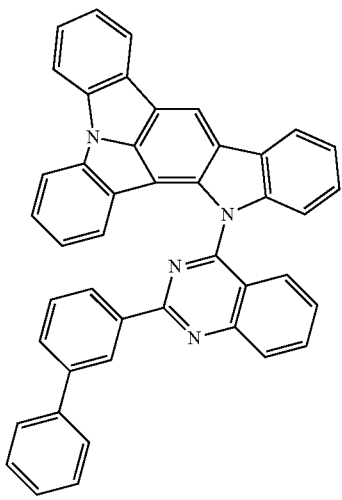
72
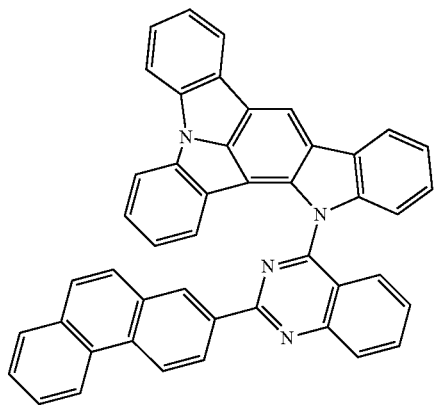
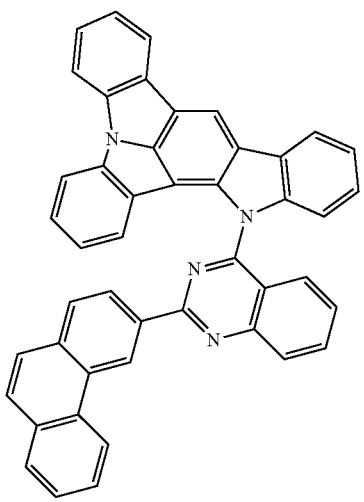
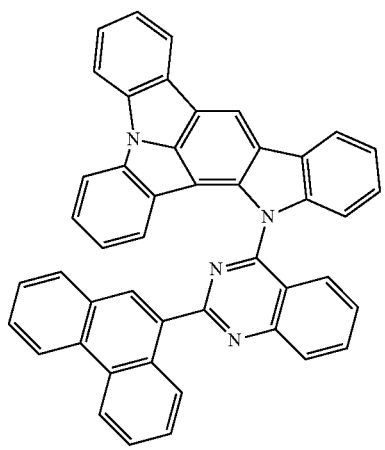
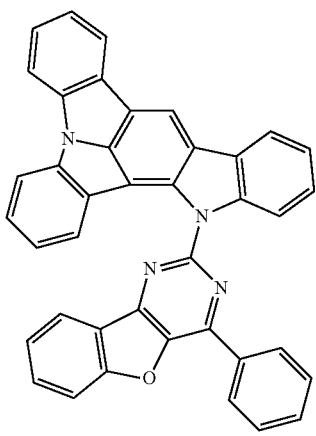
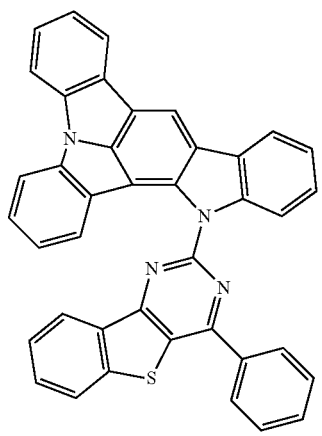

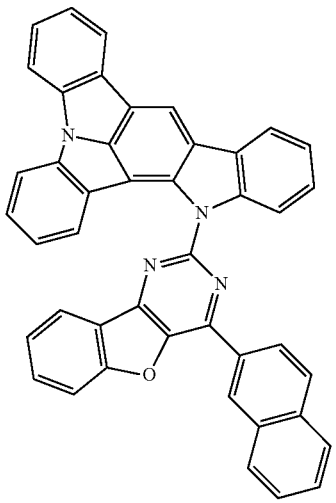
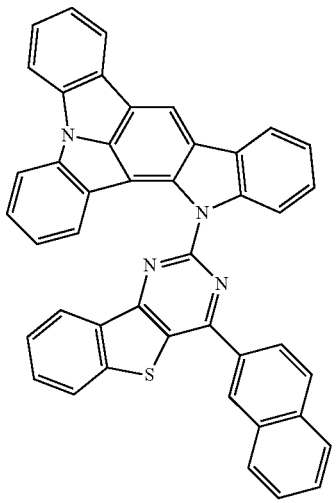
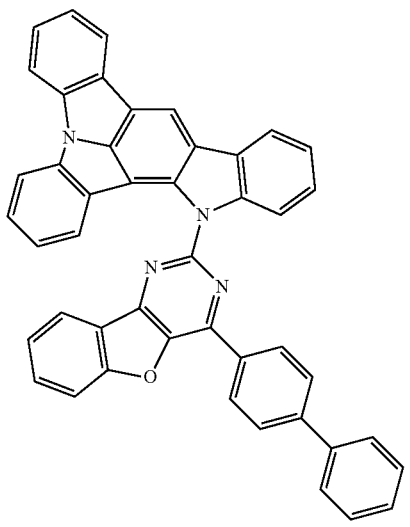
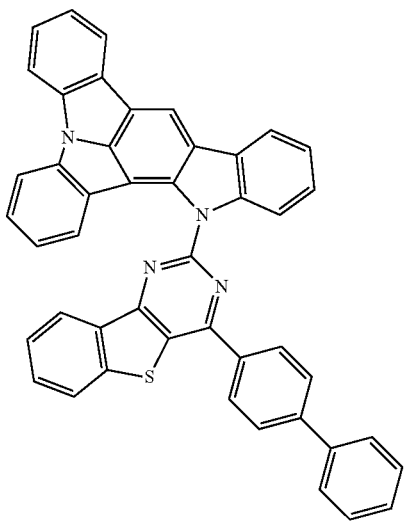
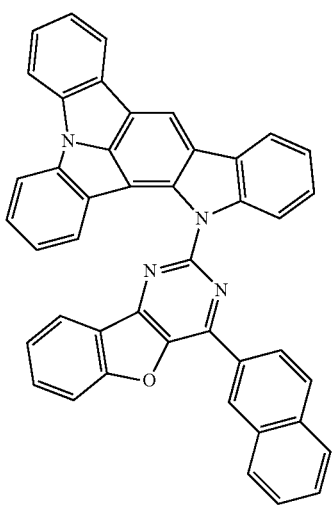
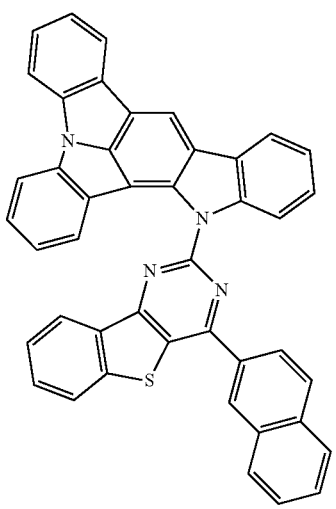

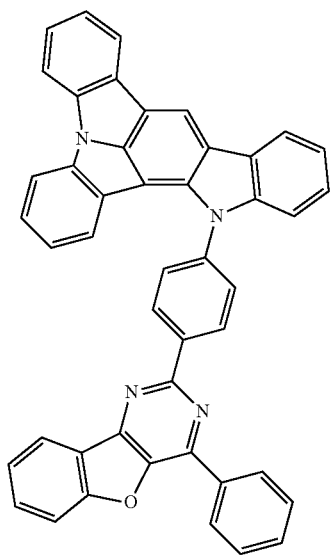
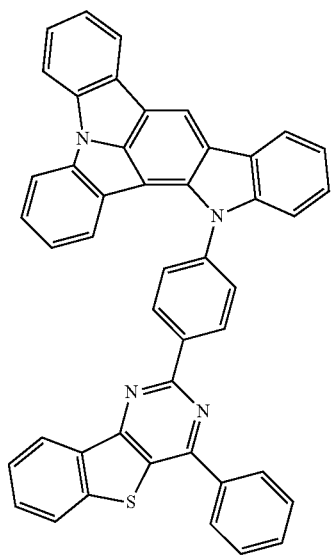
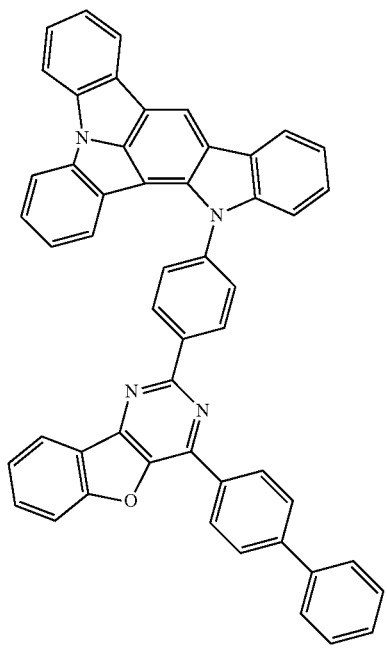
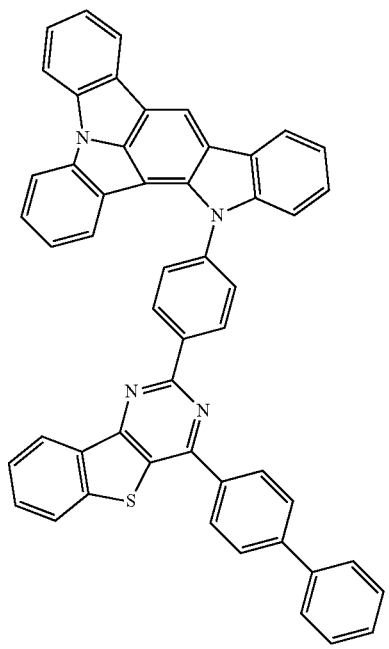
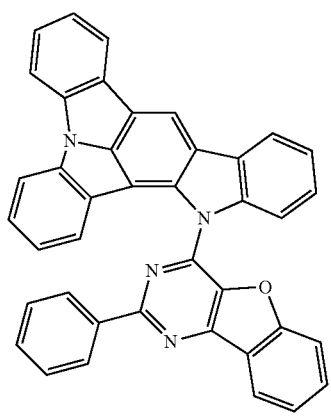
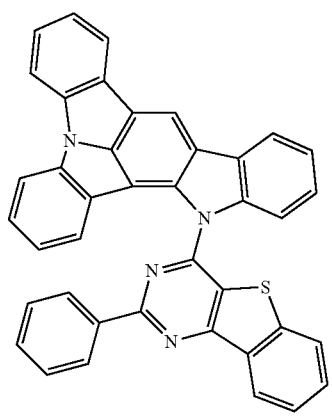

77
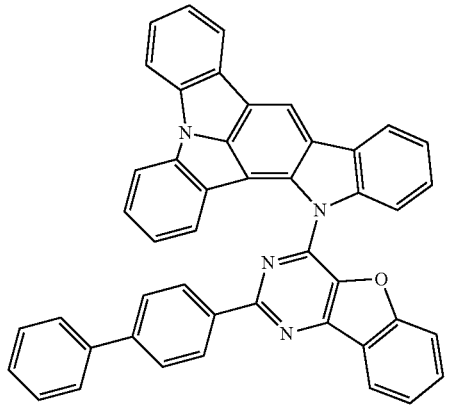
78
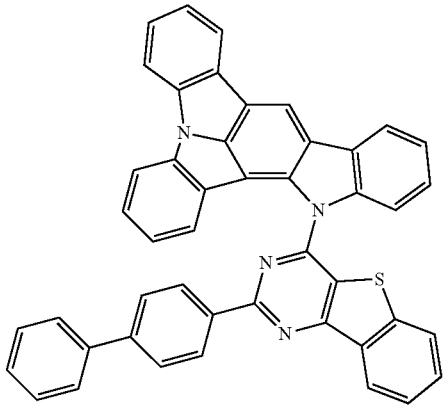
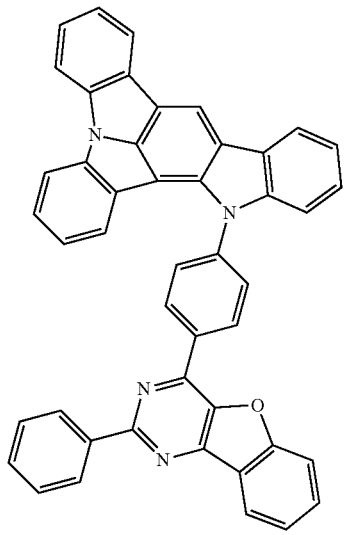
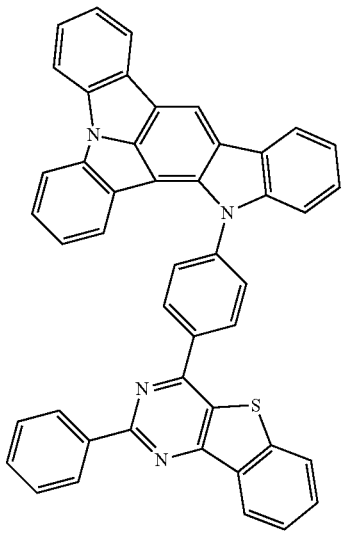
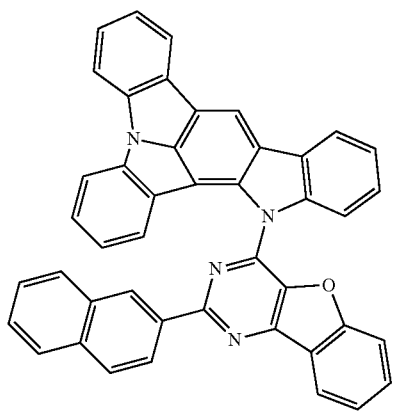
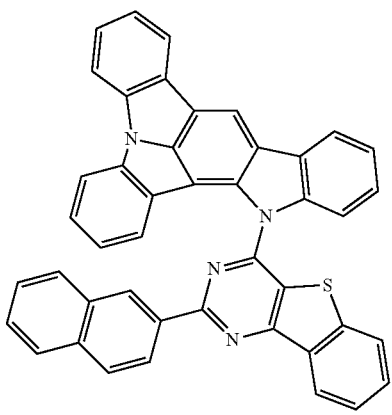

-continued
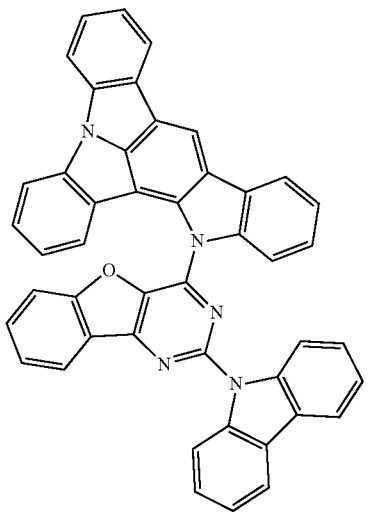
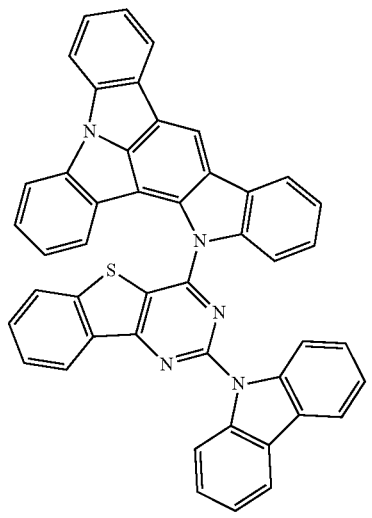
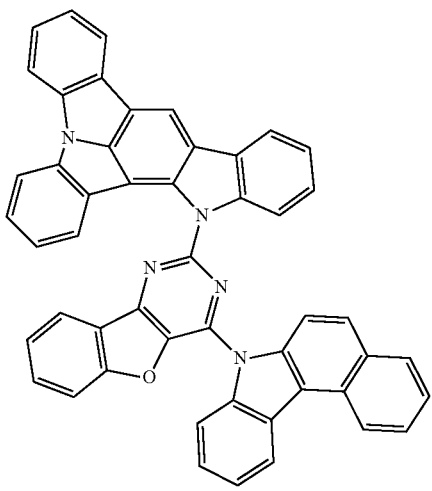
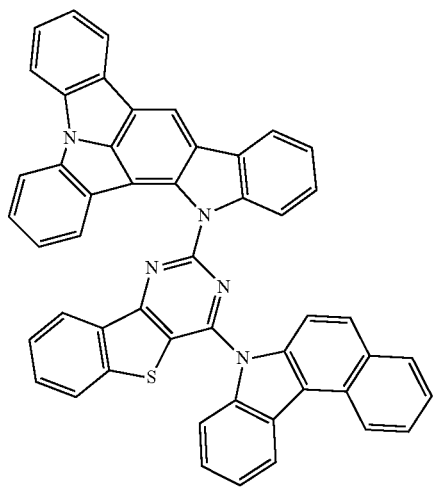
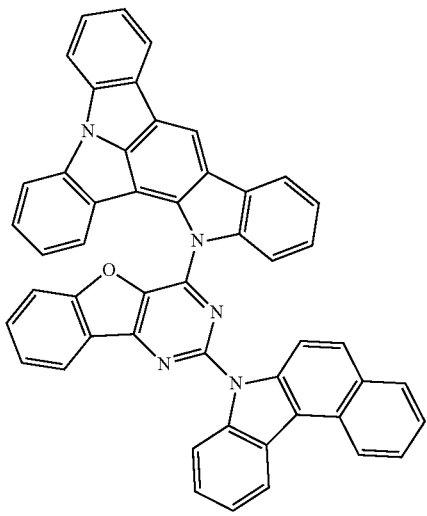
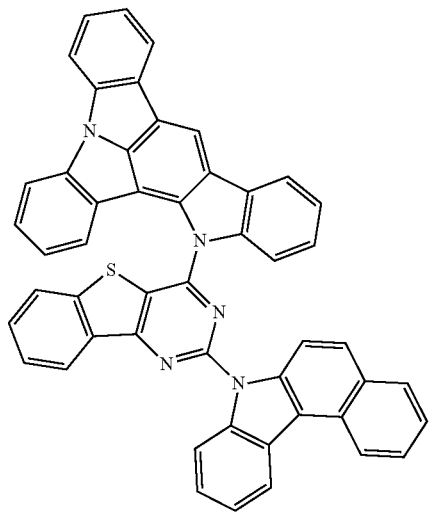

-continued
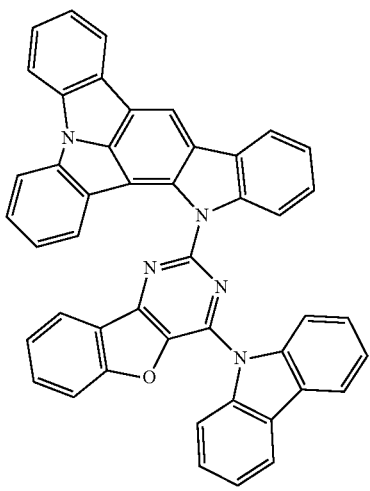
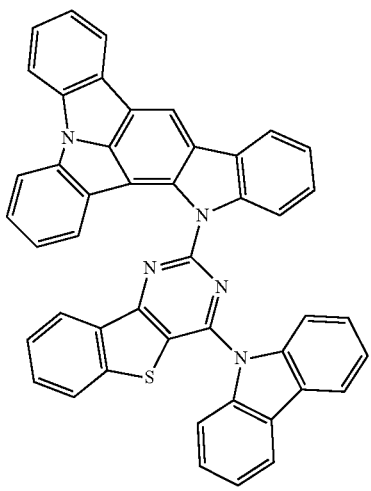
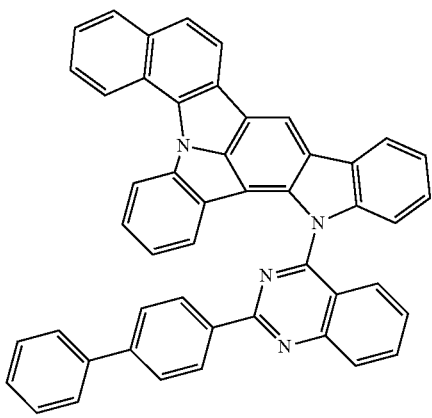
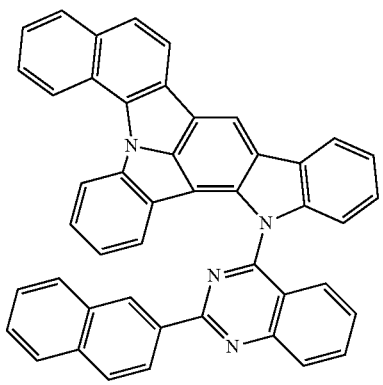
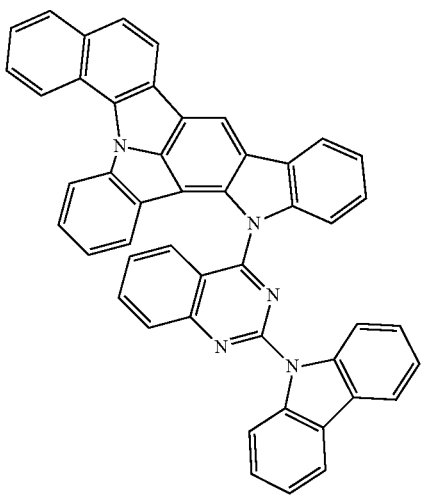
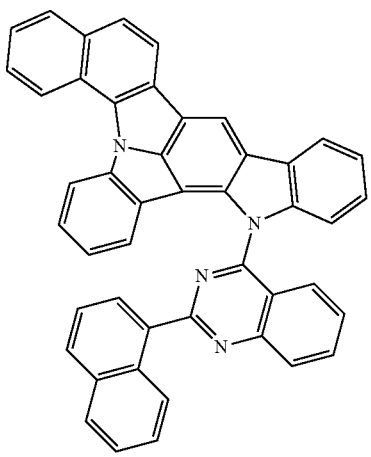

-continued
83
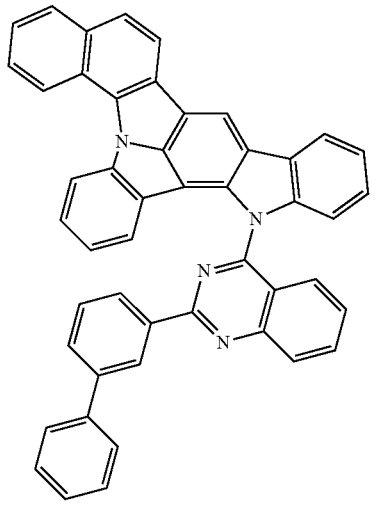
84
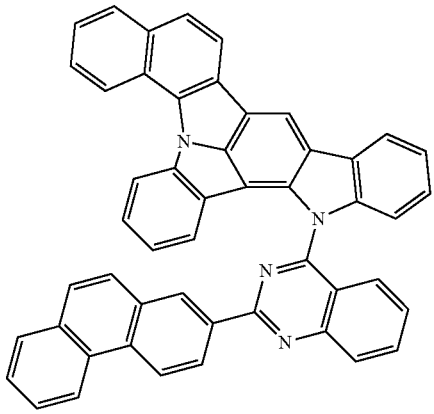
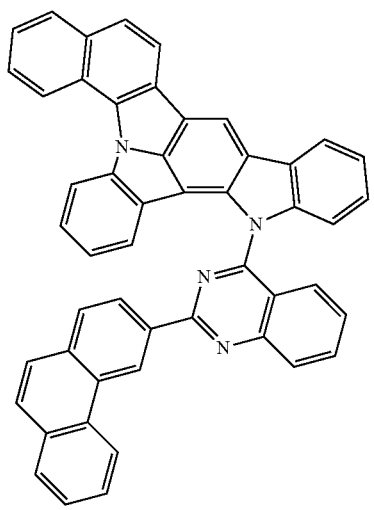
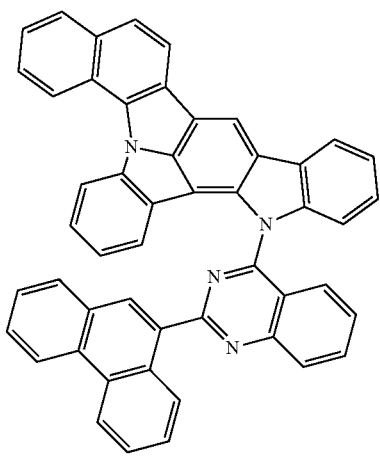
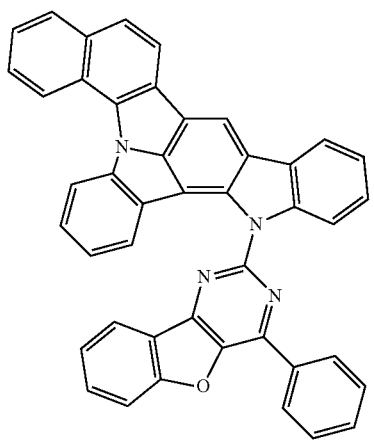
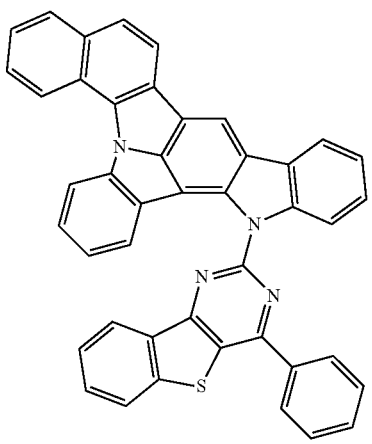

85
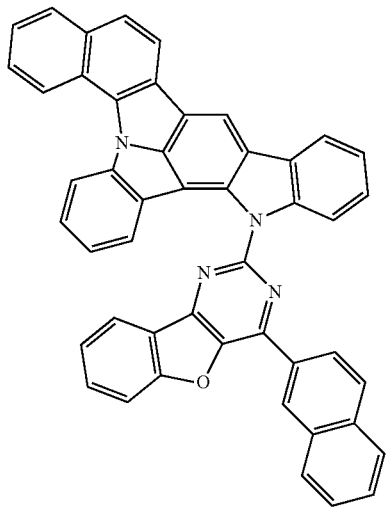
86
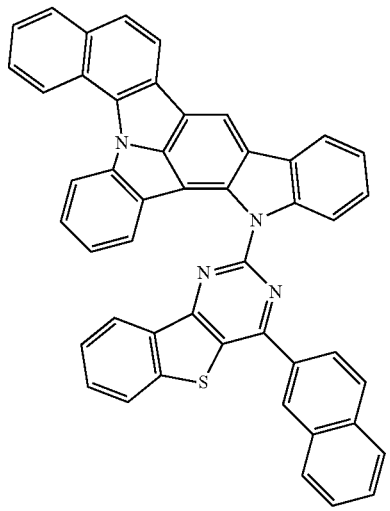
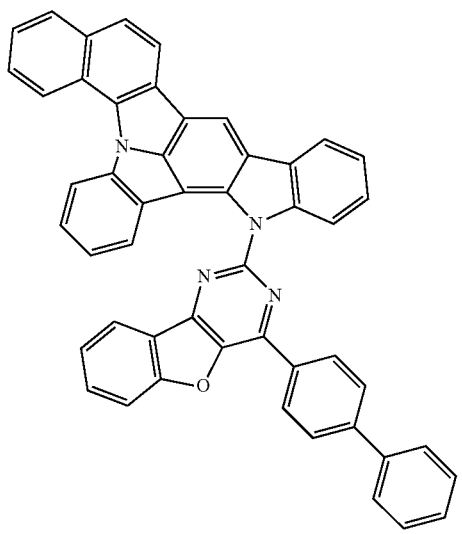
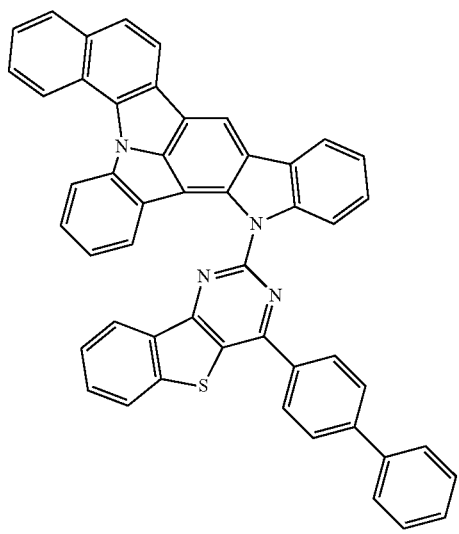
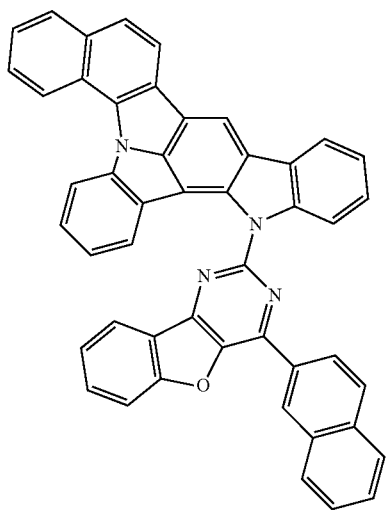
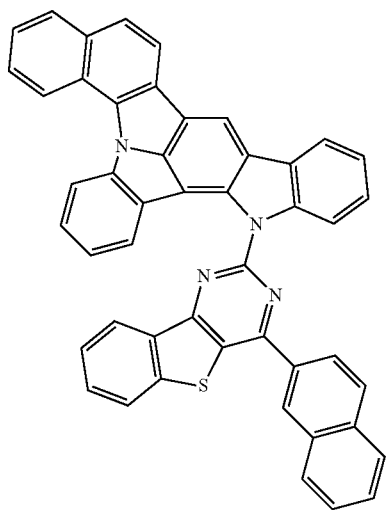

-continued
87
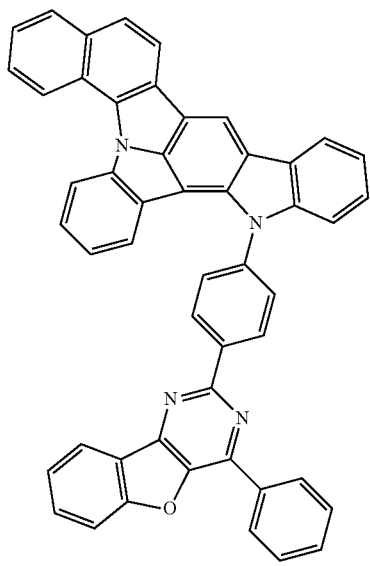
88
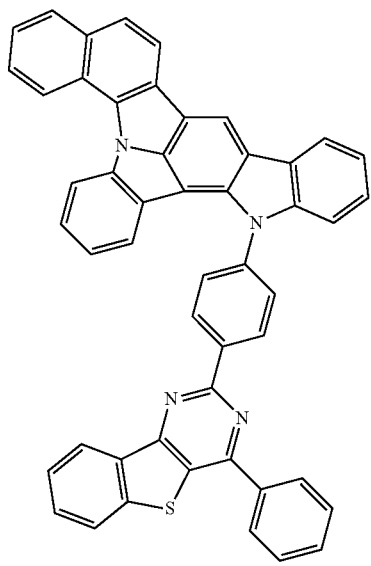
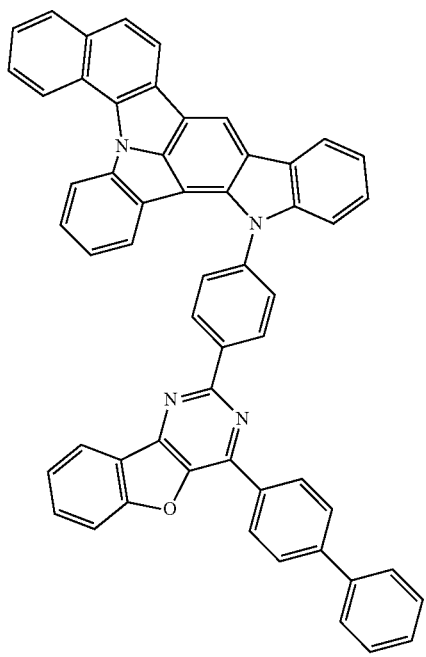
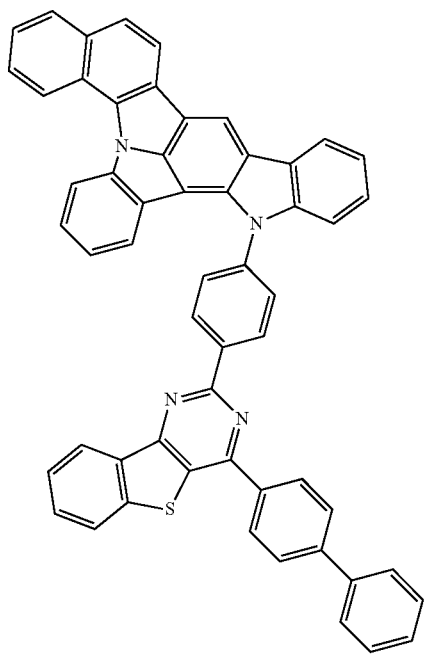
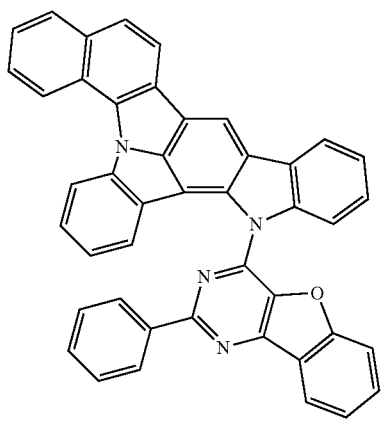
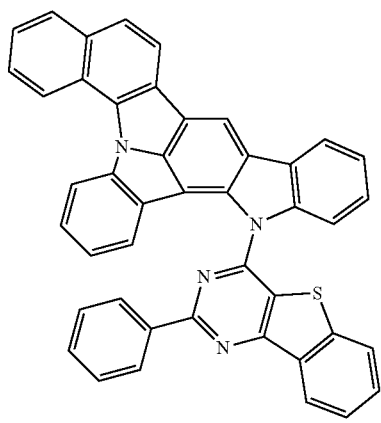

89
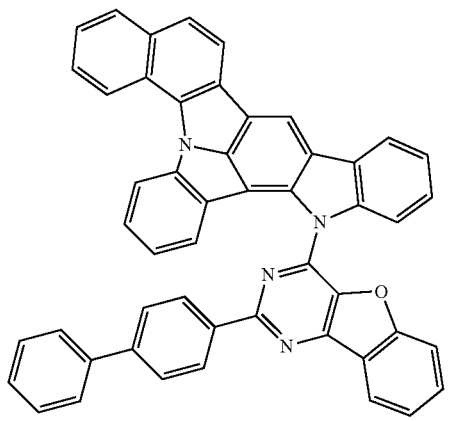
90
-continued
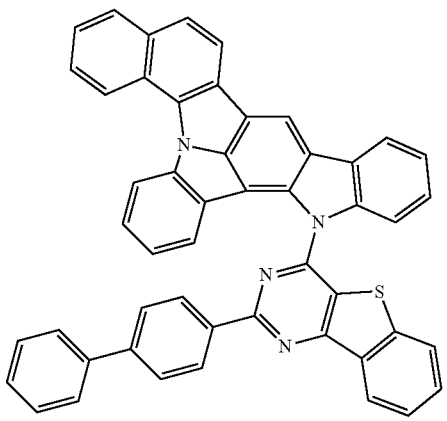
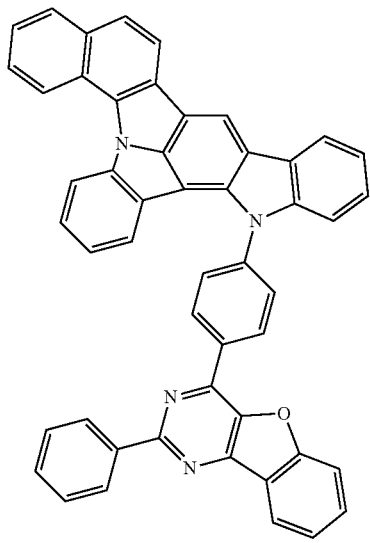
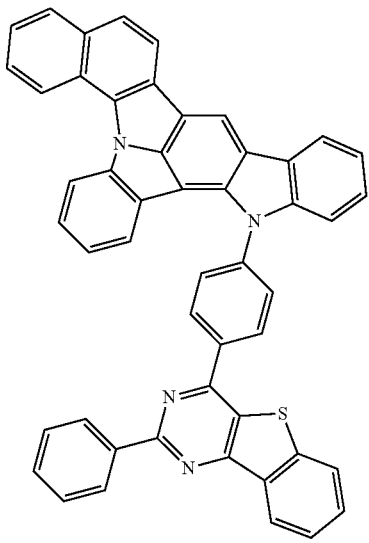
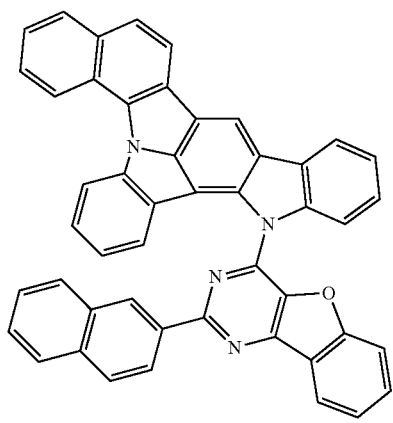
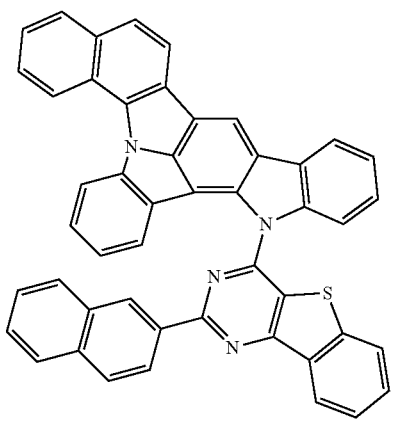

-continued
91
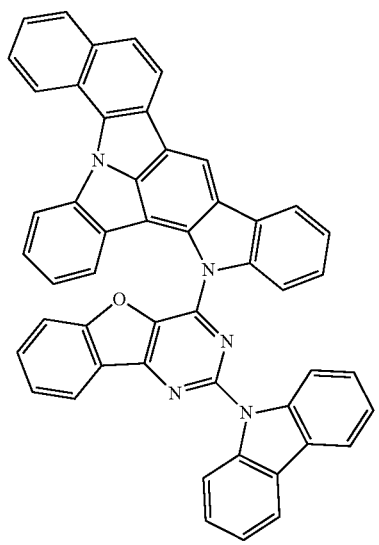
92
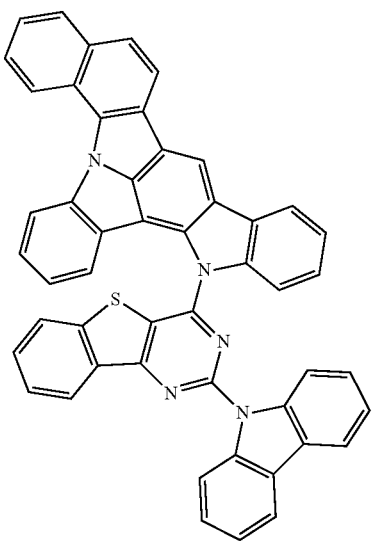
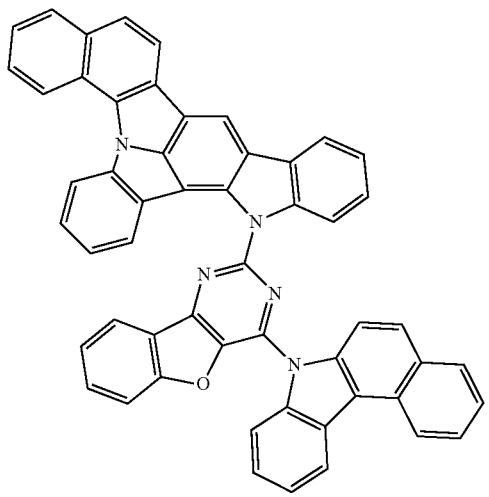
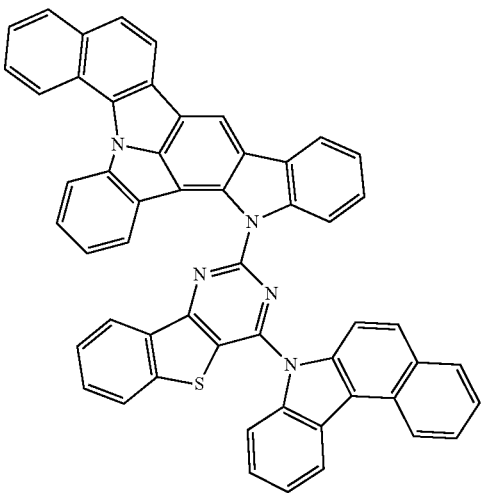
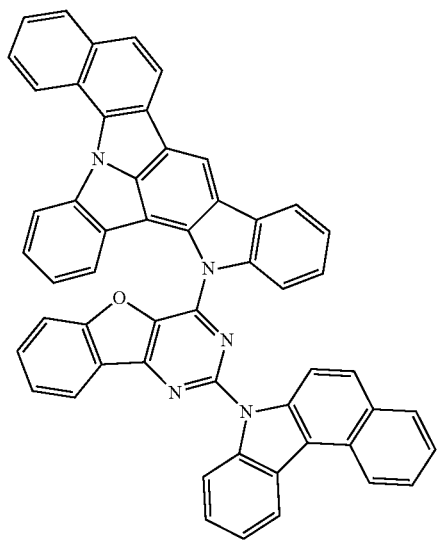
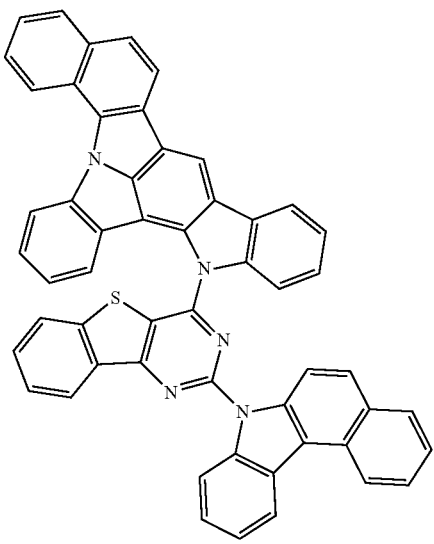

-continued
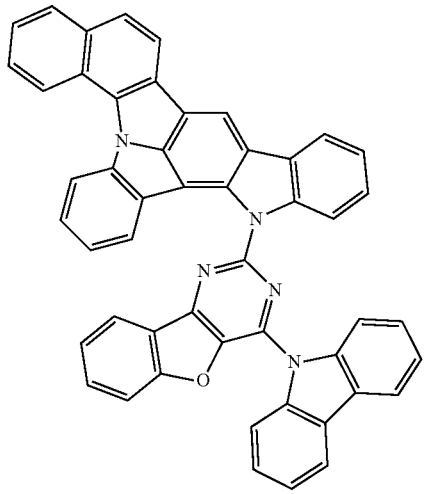
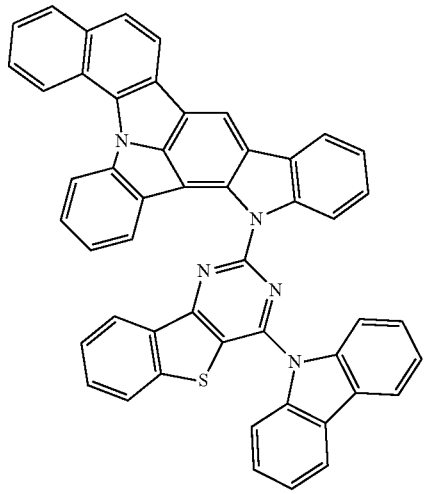
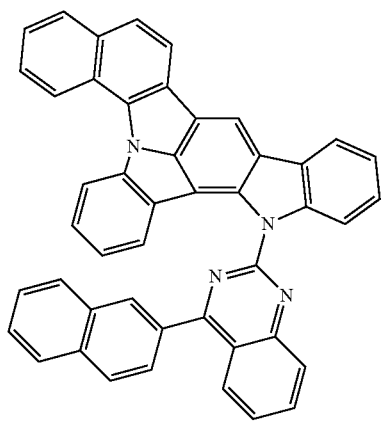
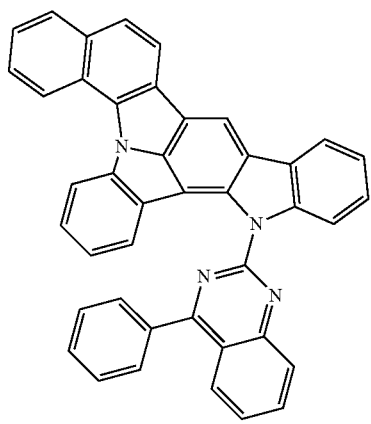
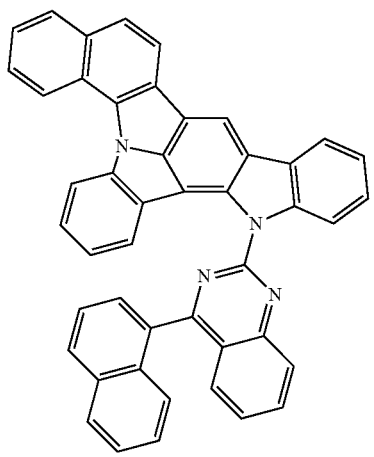
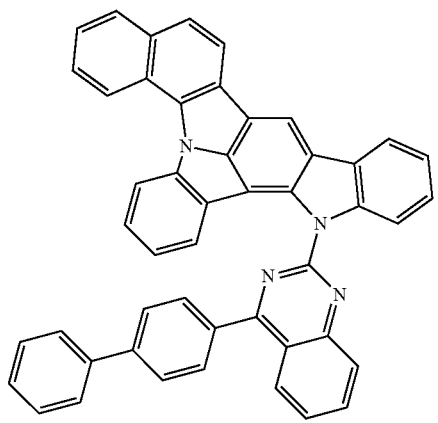

95
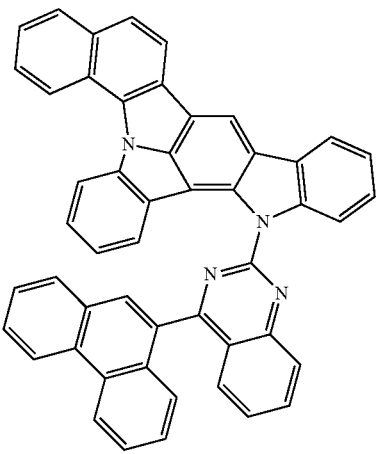
96
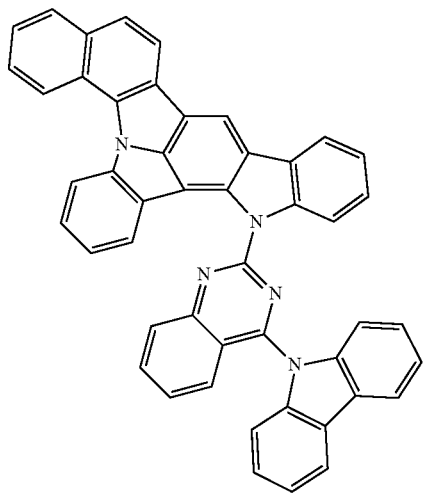
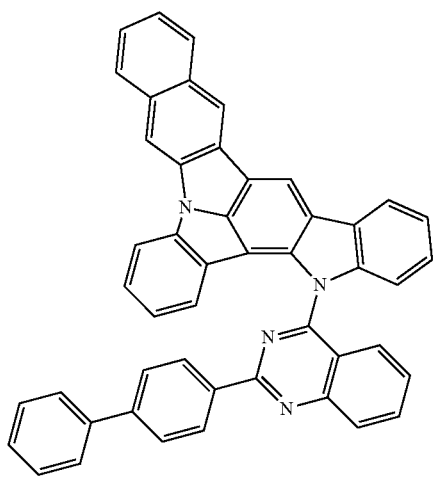
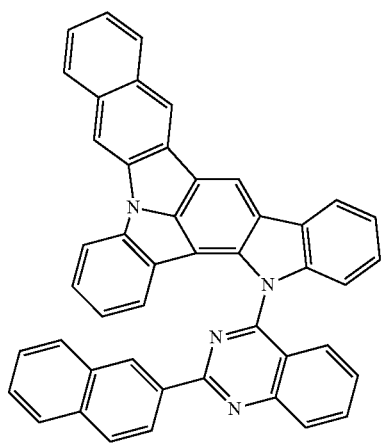
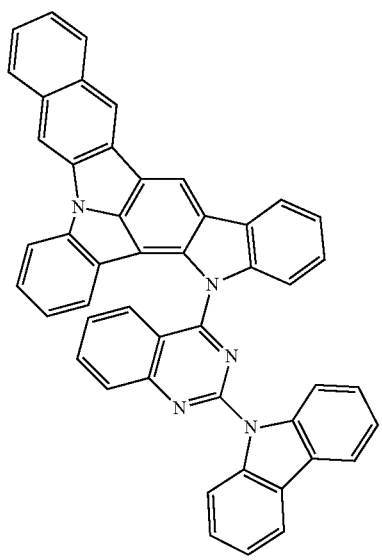
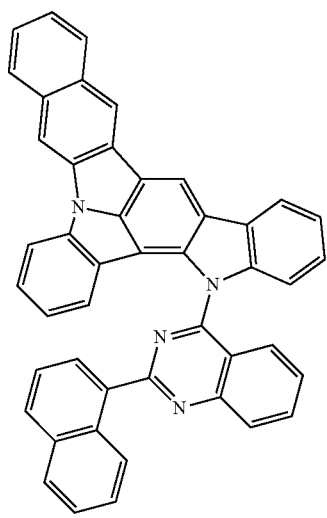

-continued
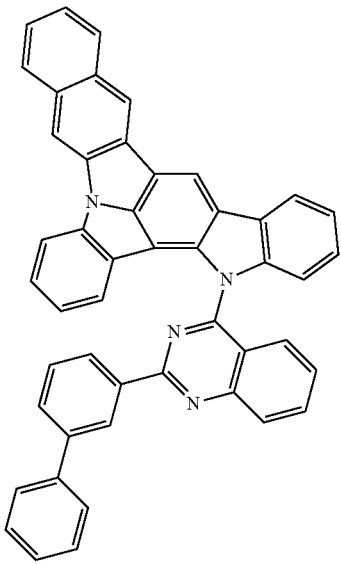
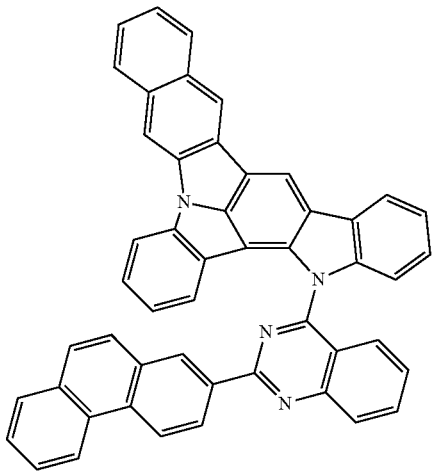
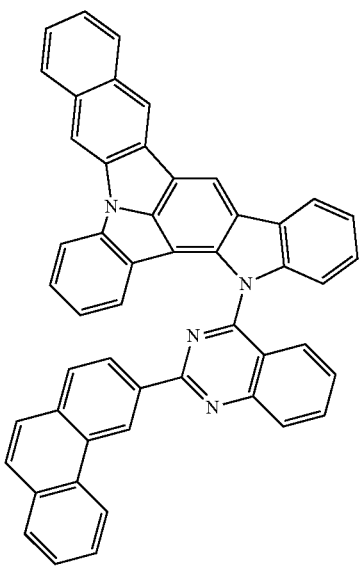
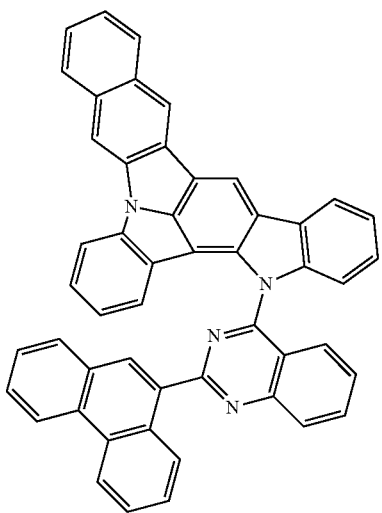
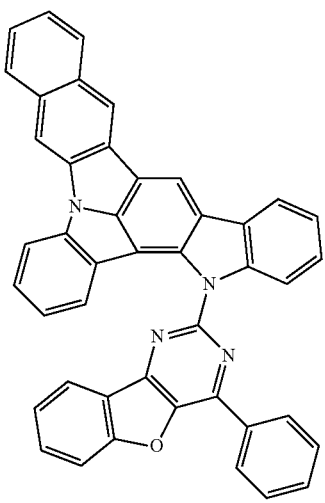
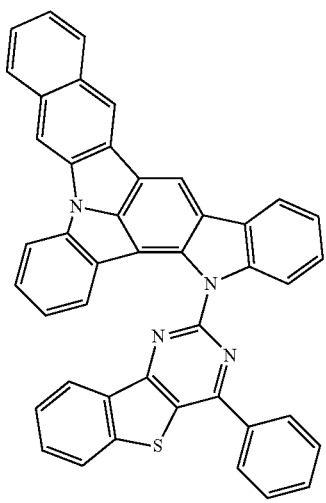

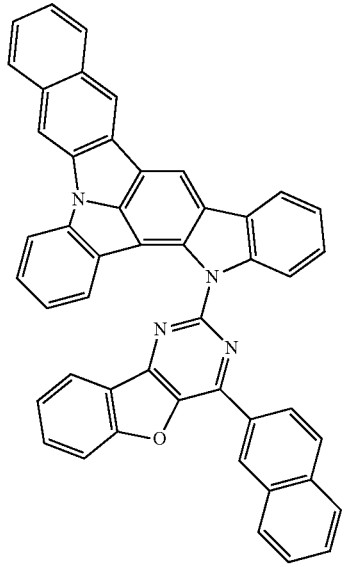
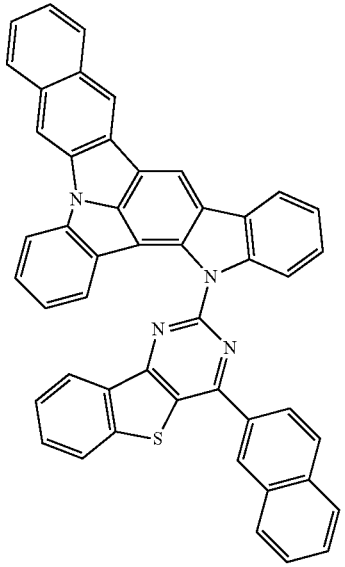
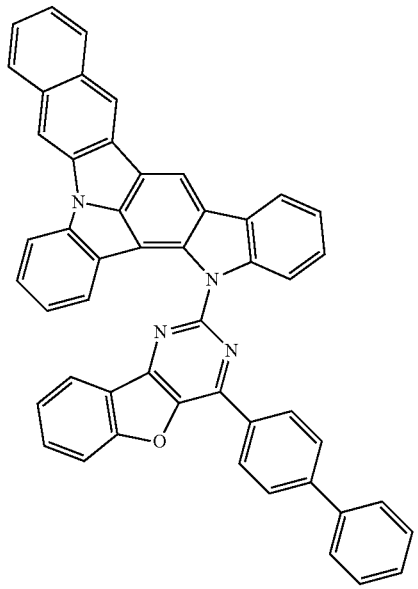
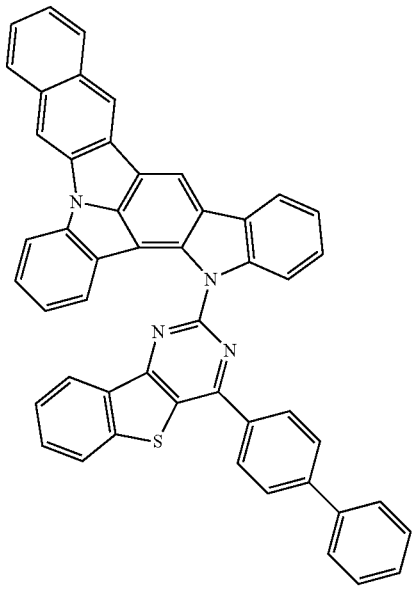
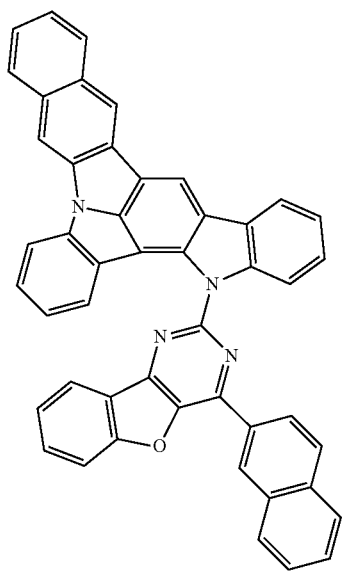
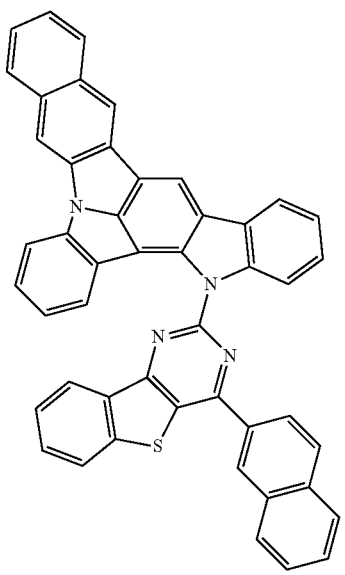

101
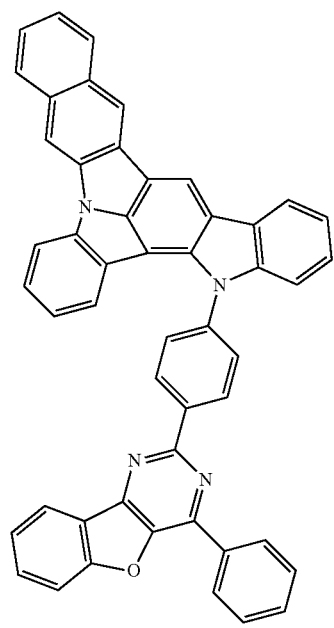
102
-continued
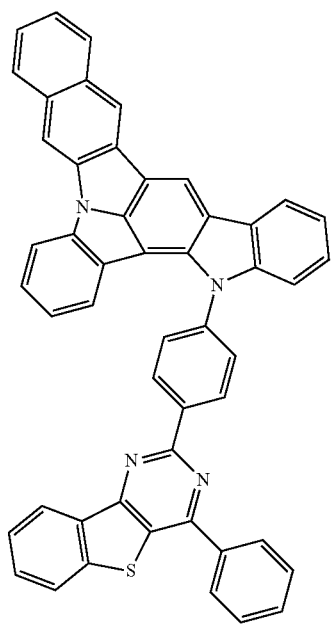
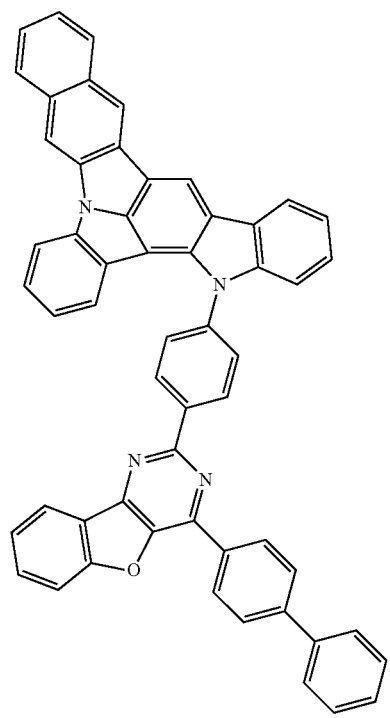
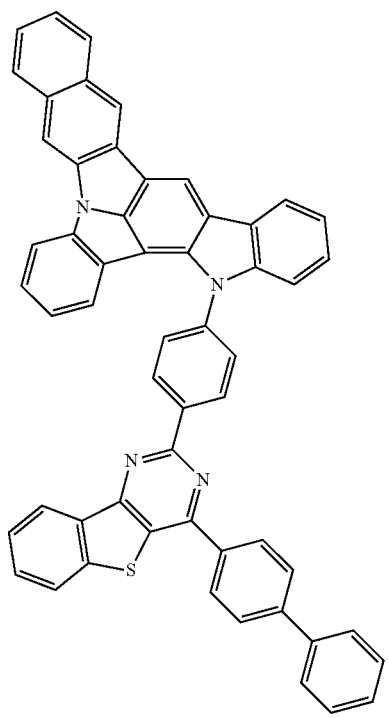

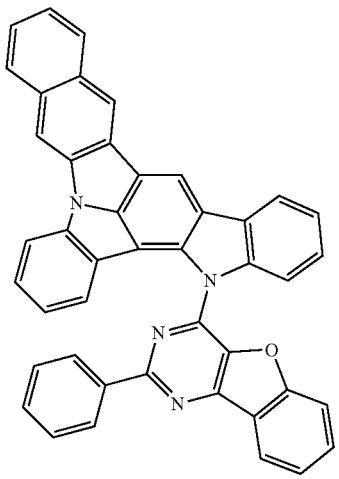
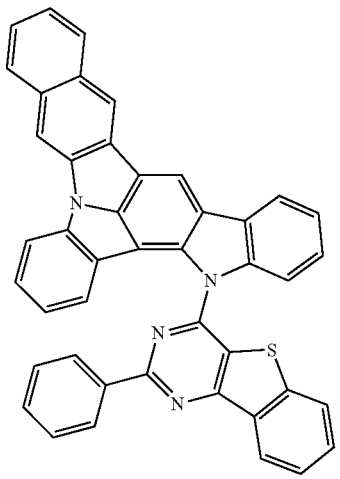
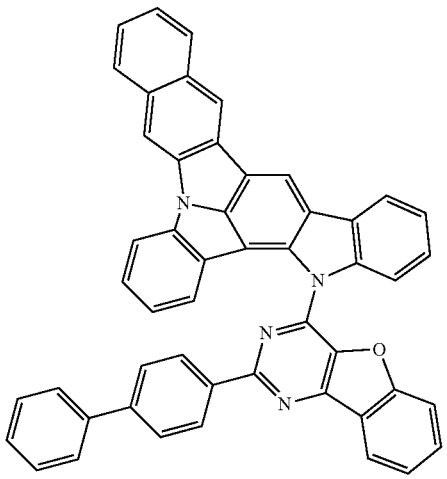
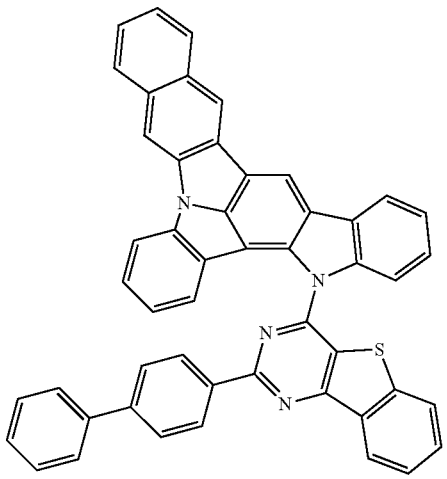
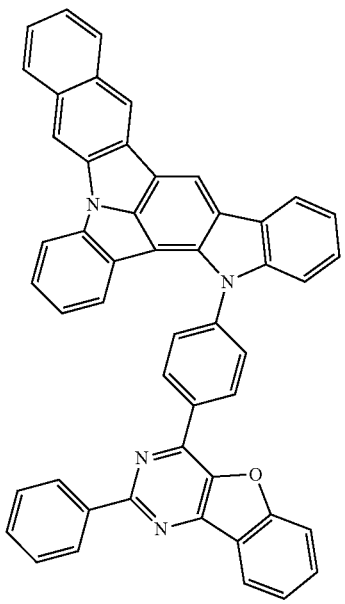
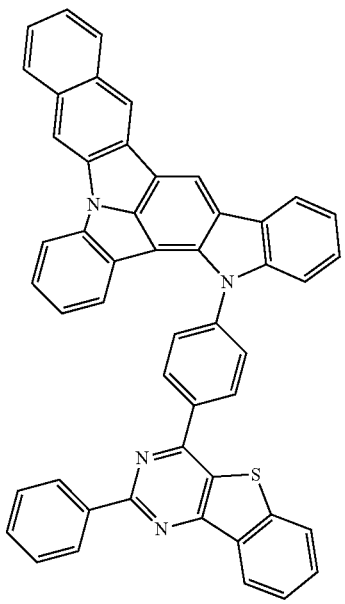

-continued
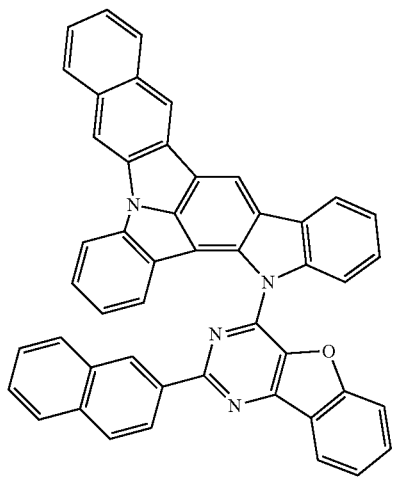
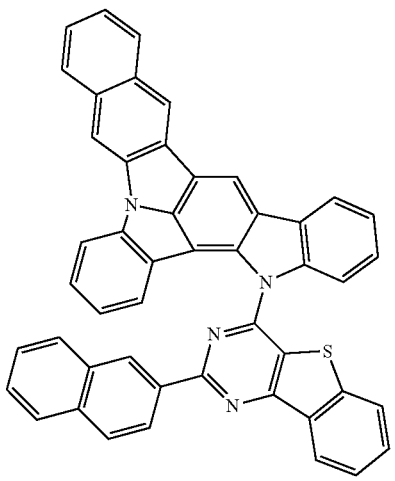
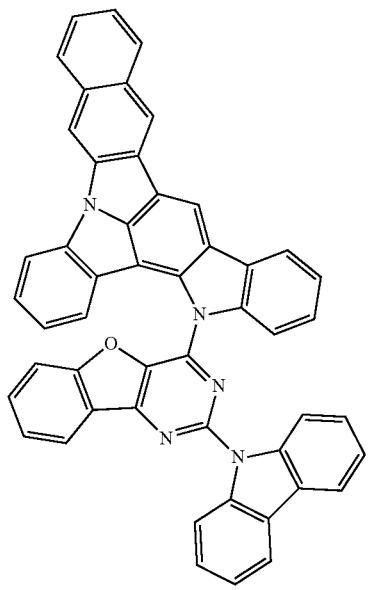
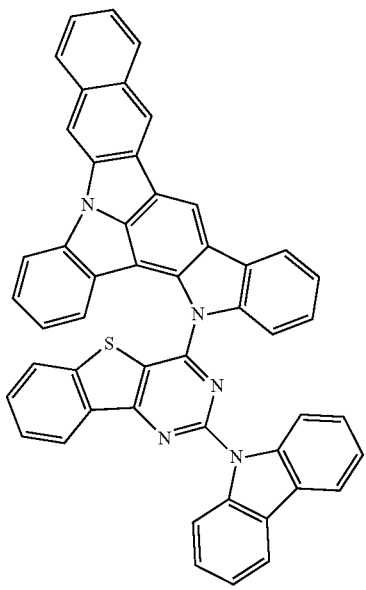
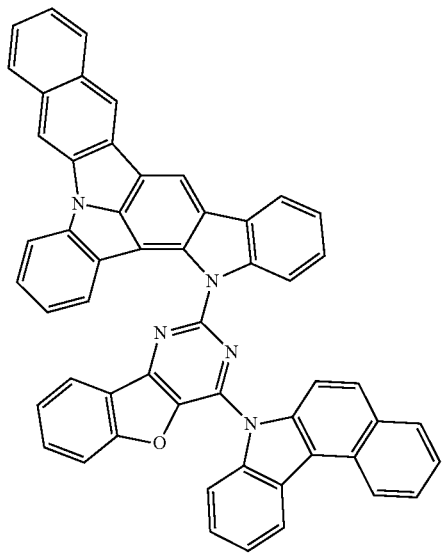
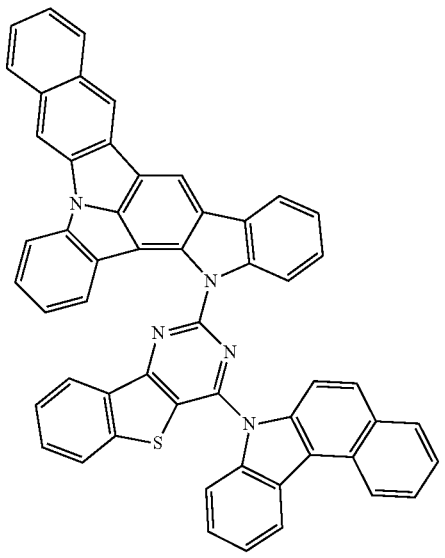

-continued
107
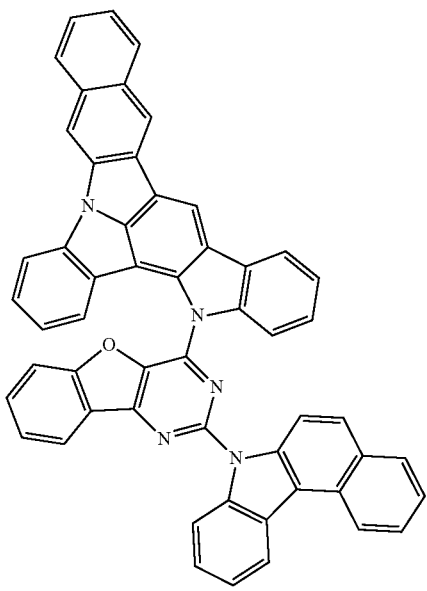
108
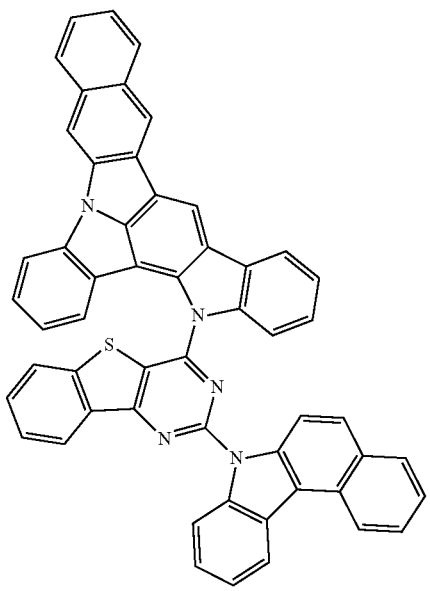
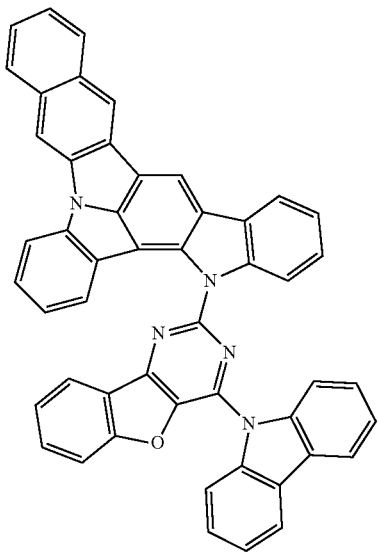
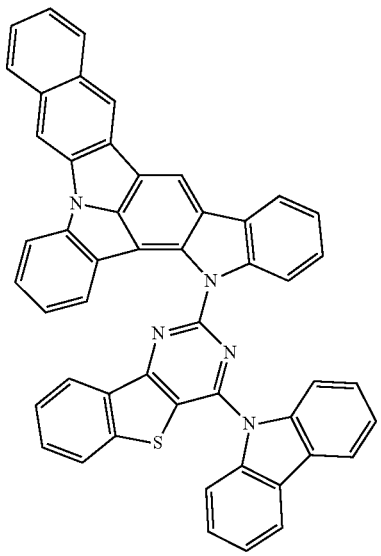
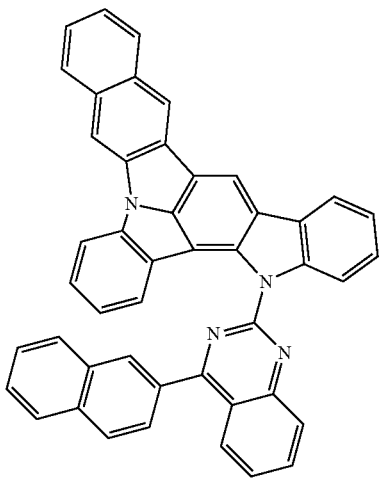
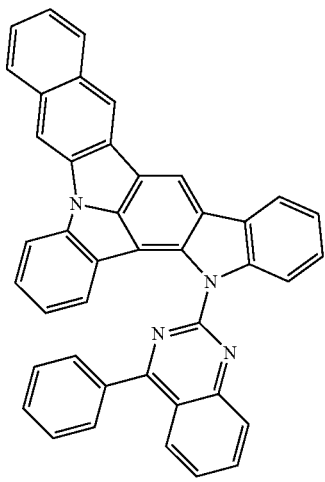

109
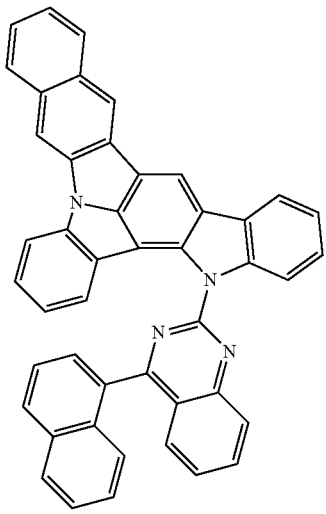
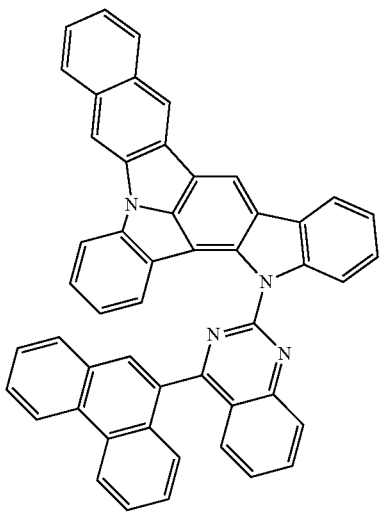
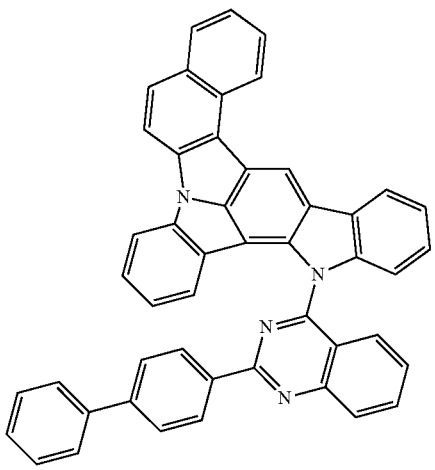
-continued
110
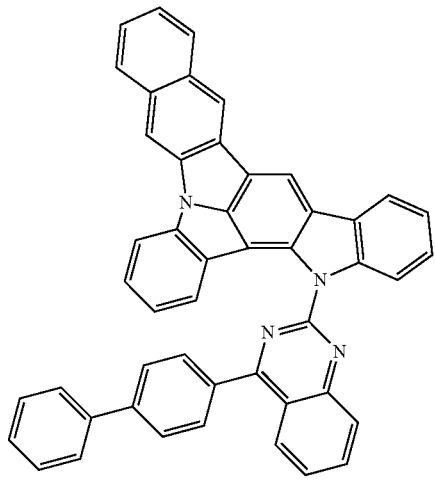
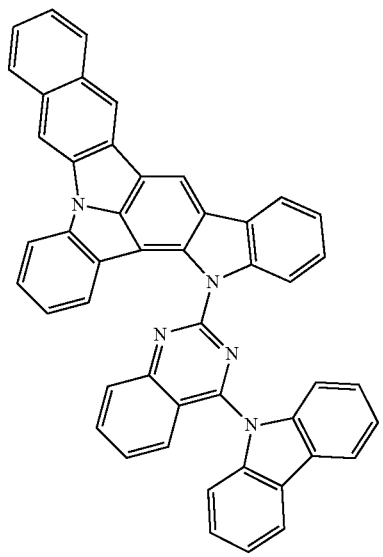
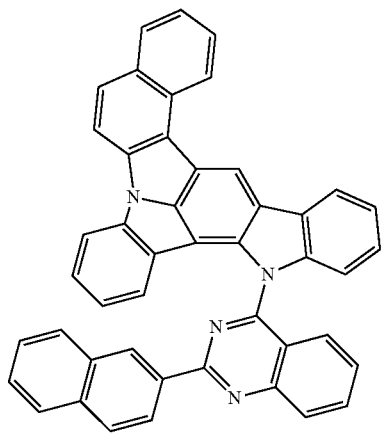

-continued
111
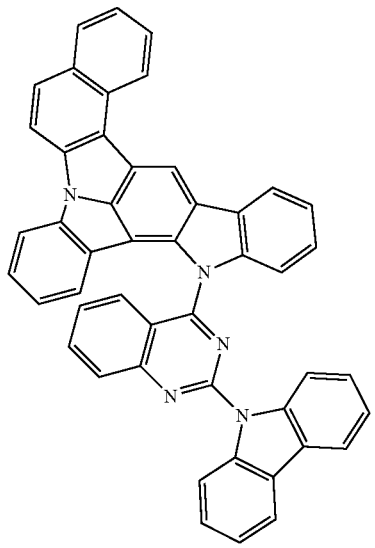
112
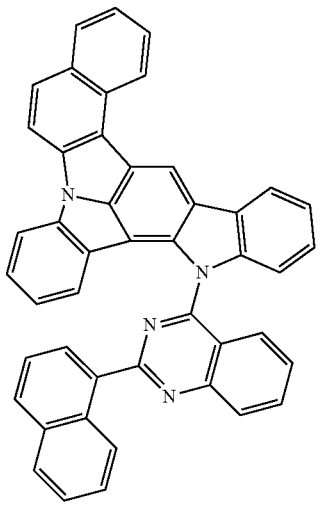
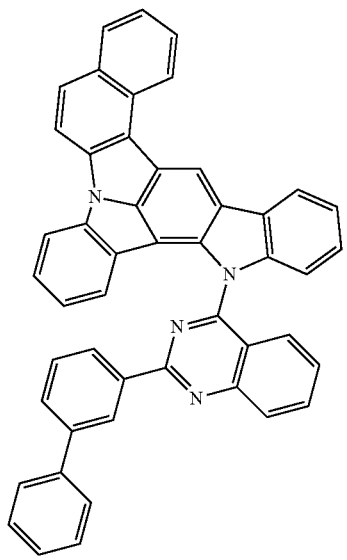
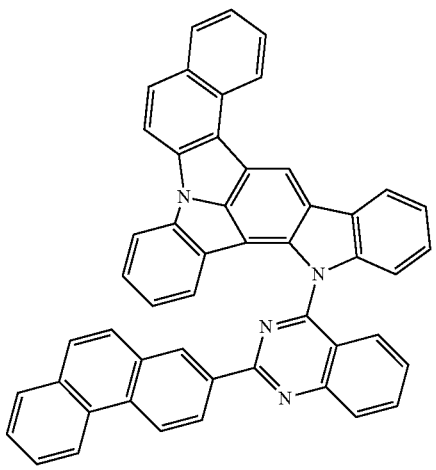
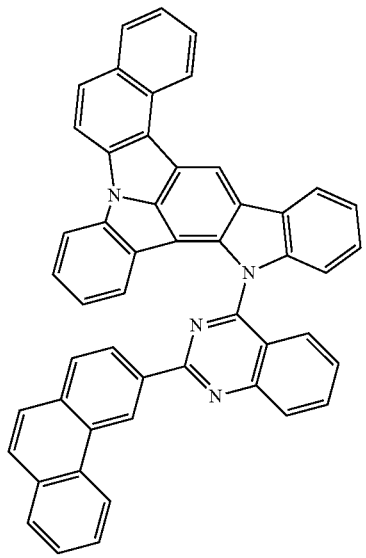
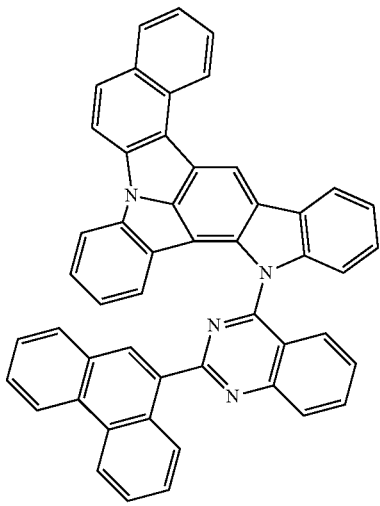

-continued
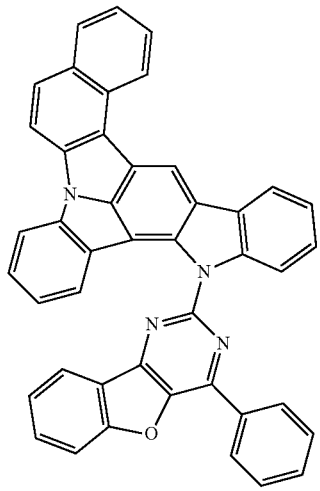
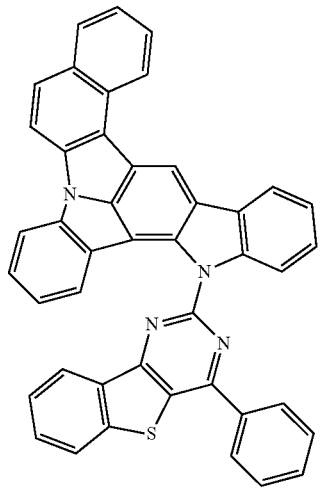
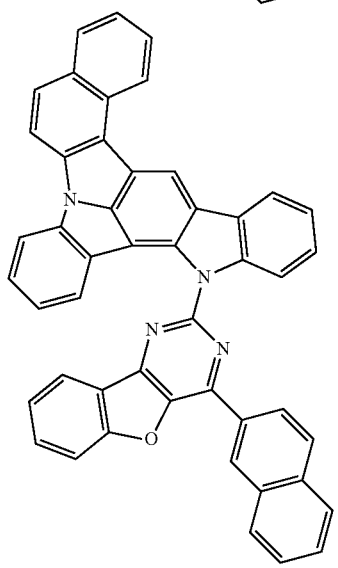
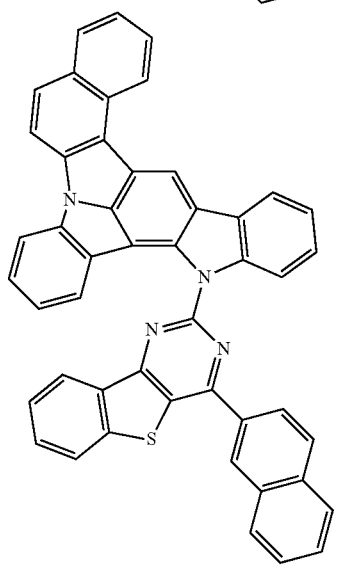
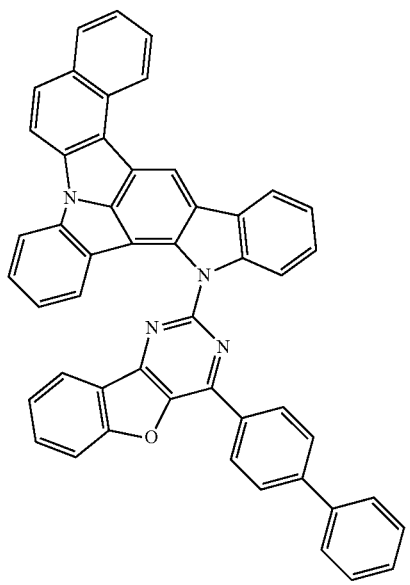
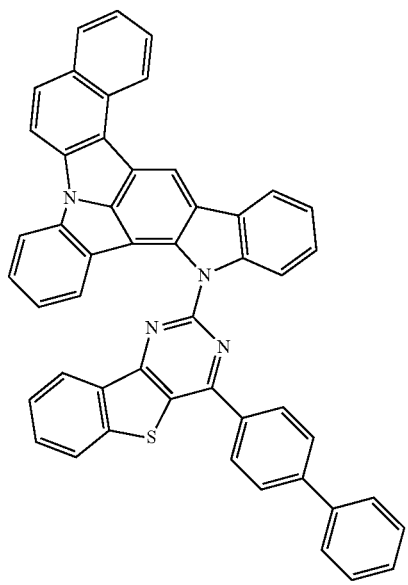

-continued
115
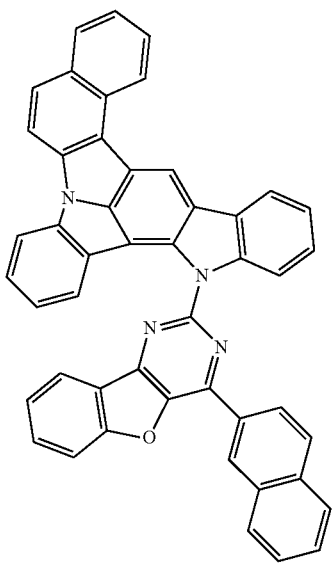
116
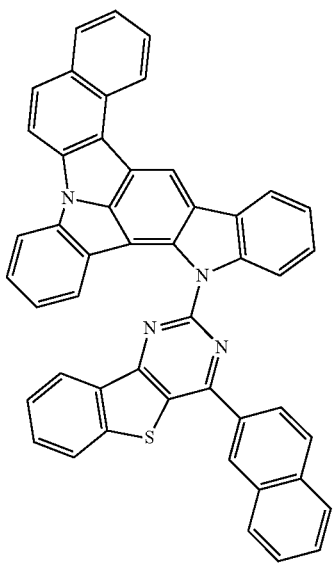
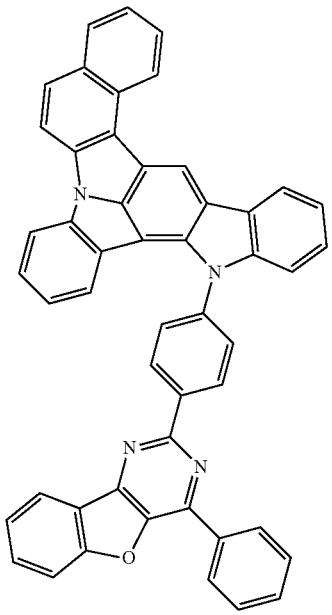
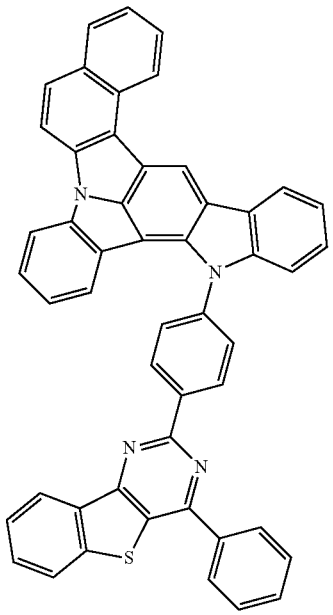

-continued
117
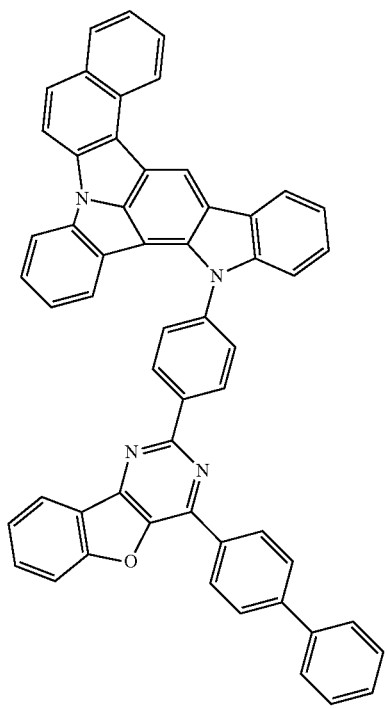
118
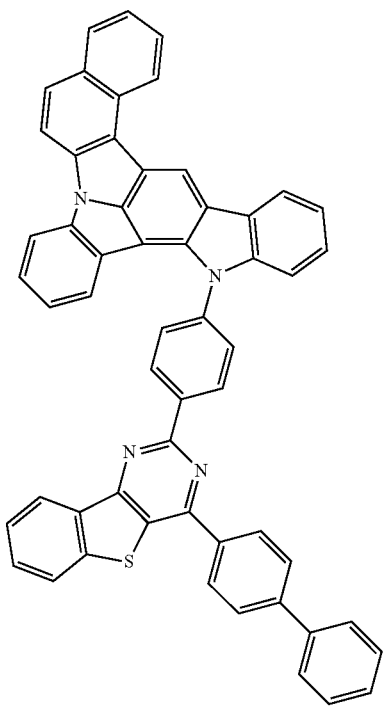
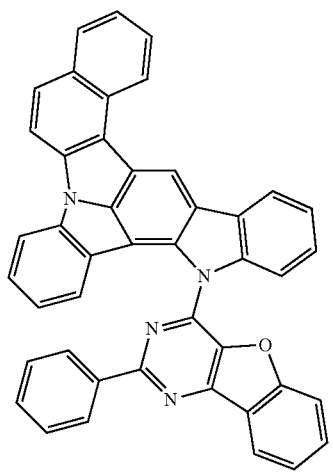
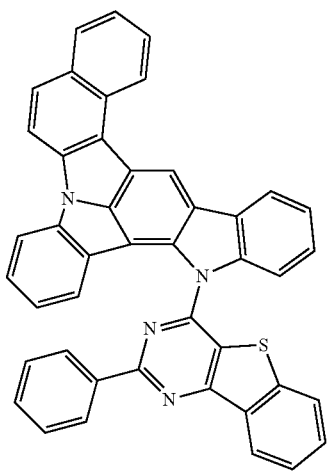
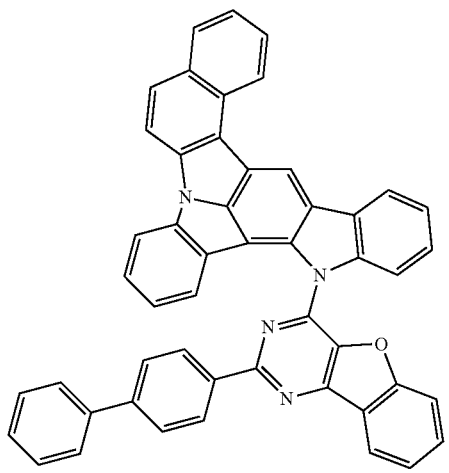
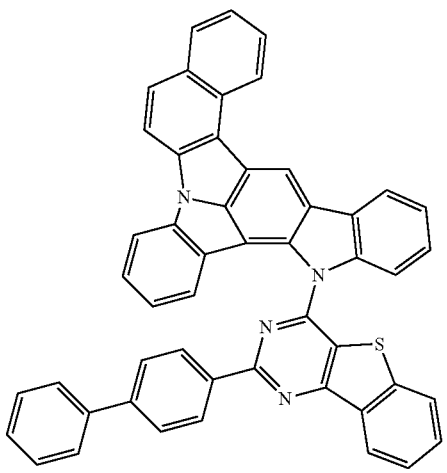

-continued
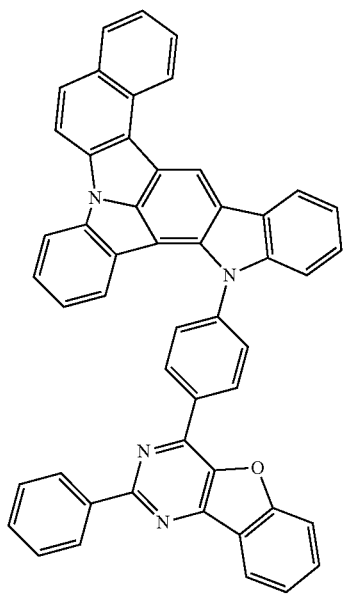
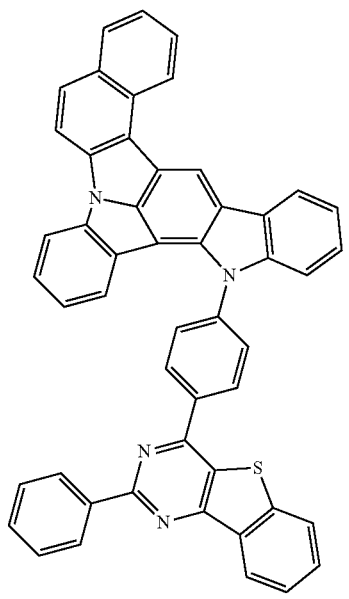
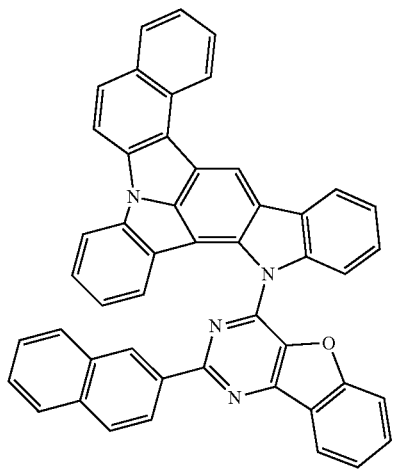
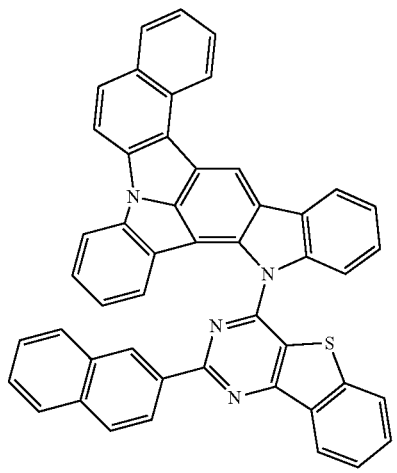
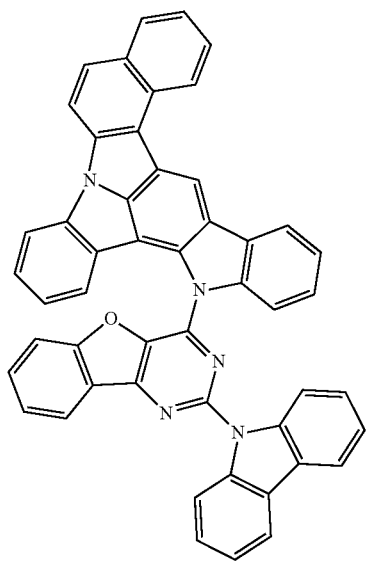
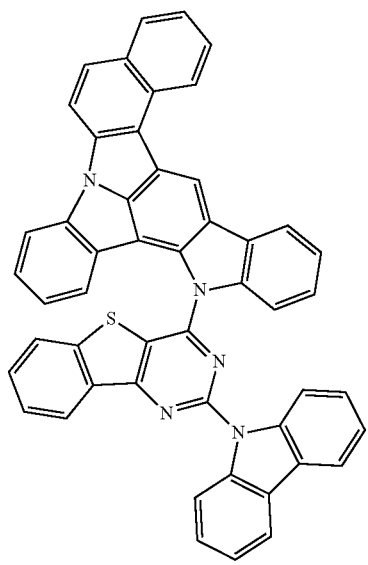

-continued
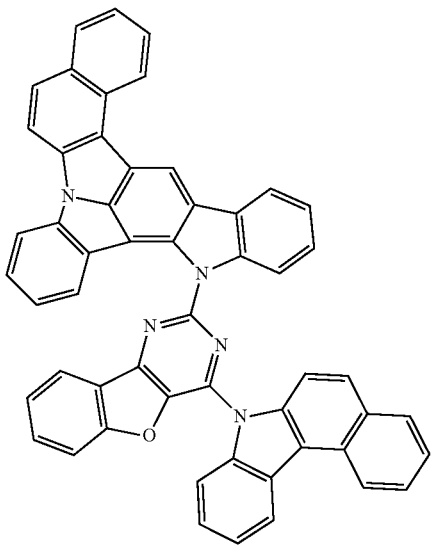
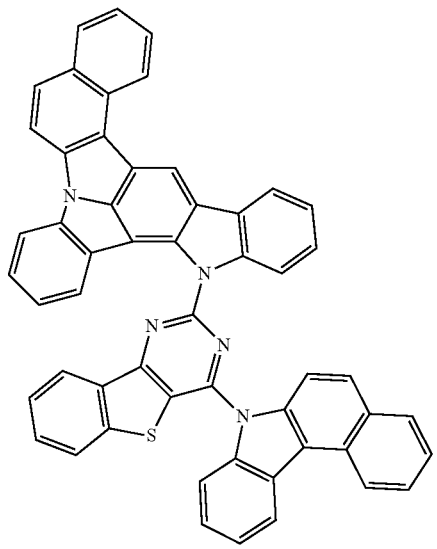
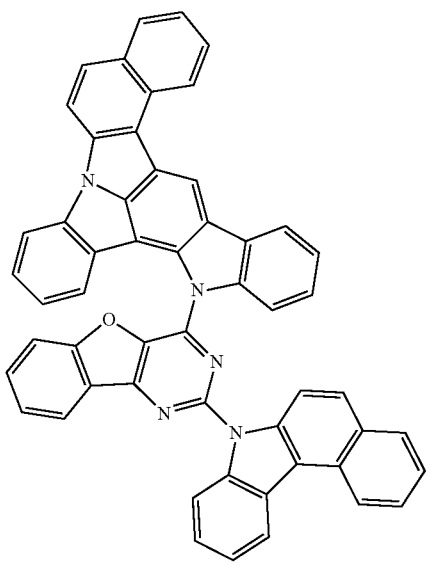
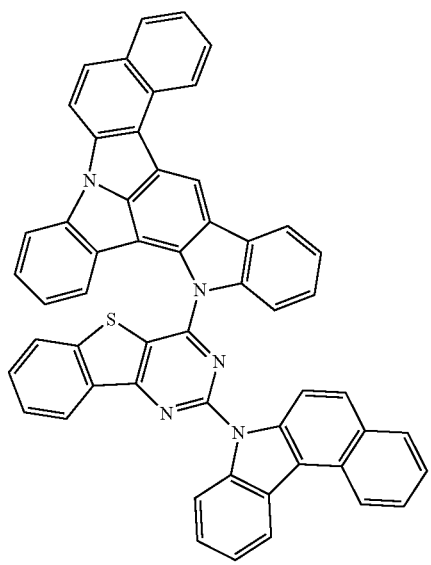
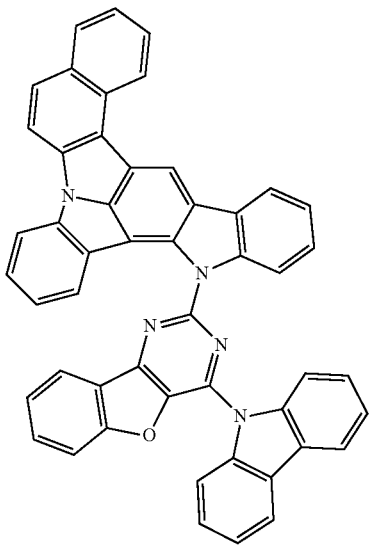
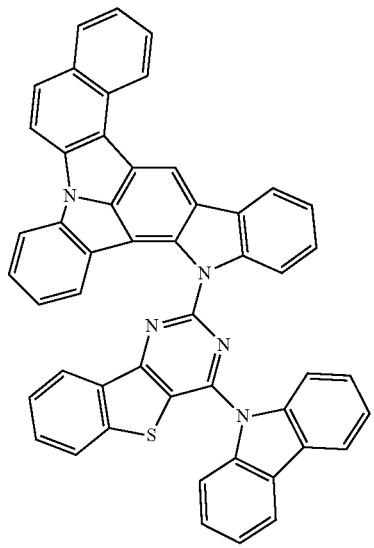

123
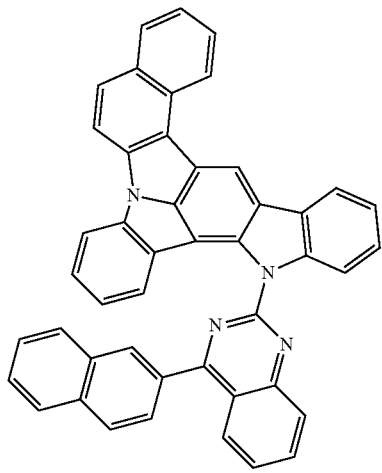
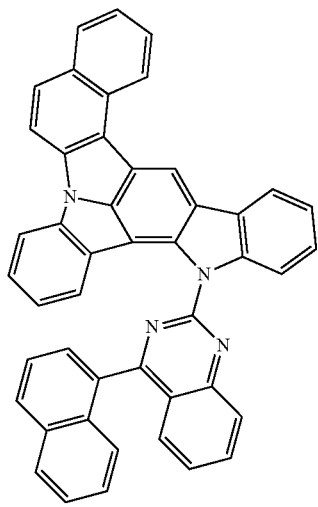
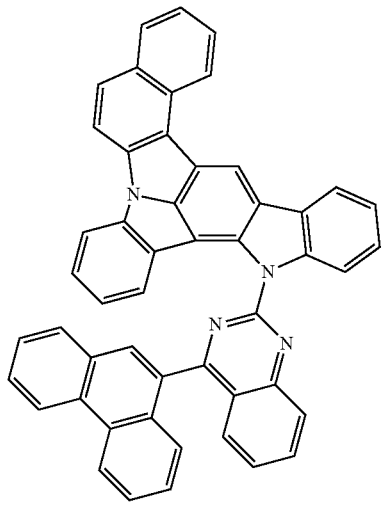
-continued
124
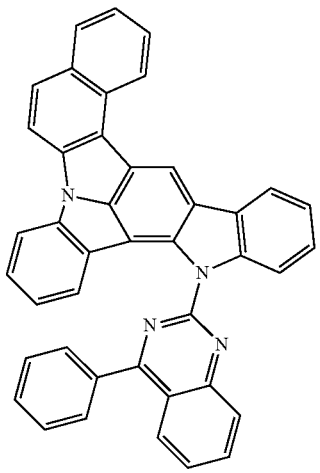
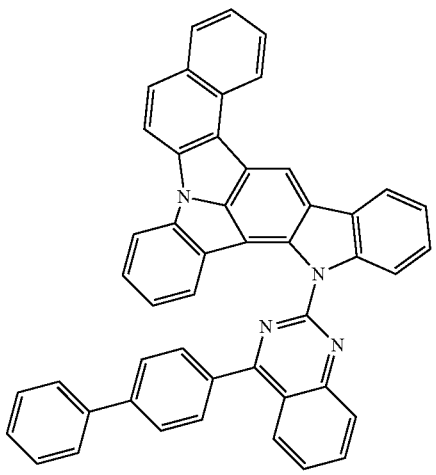
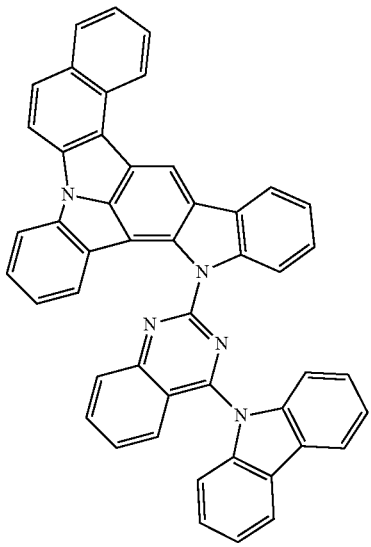

125
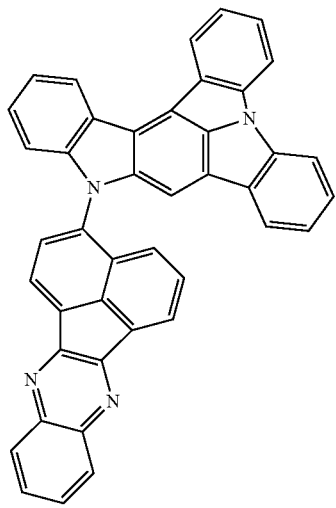
126
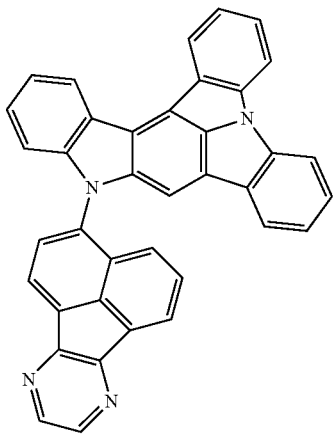
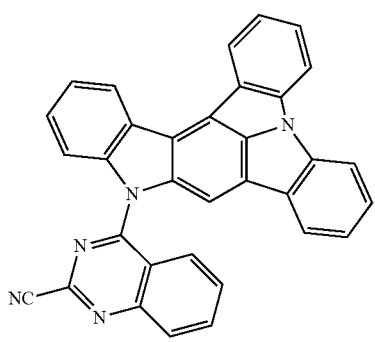
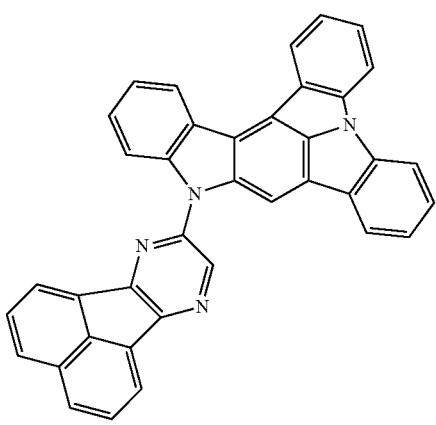
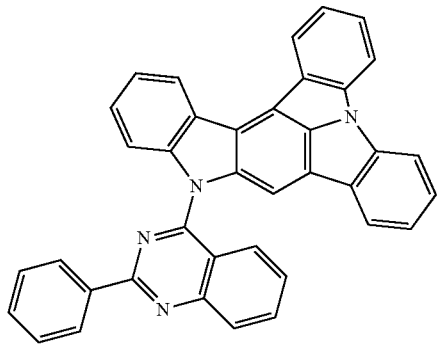
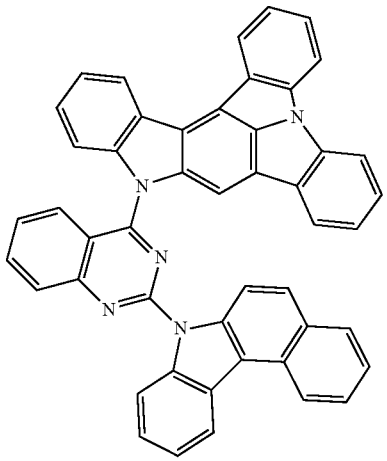

-continued
127
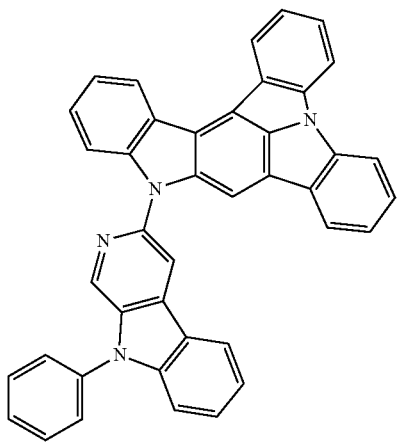
128
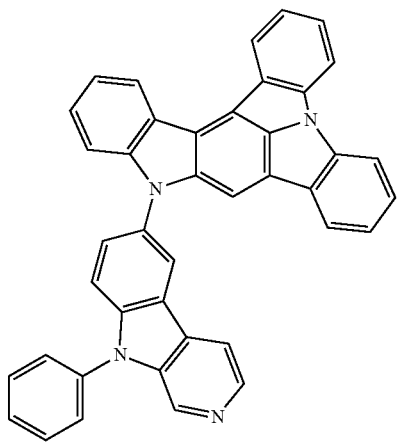
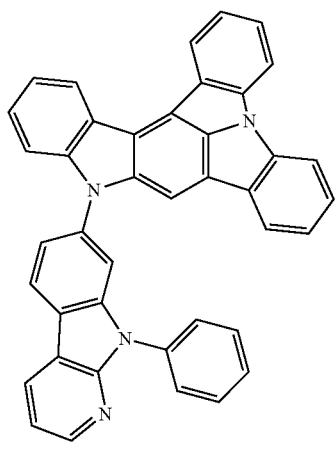
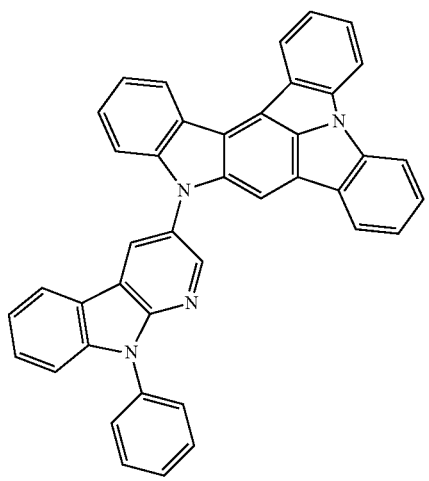
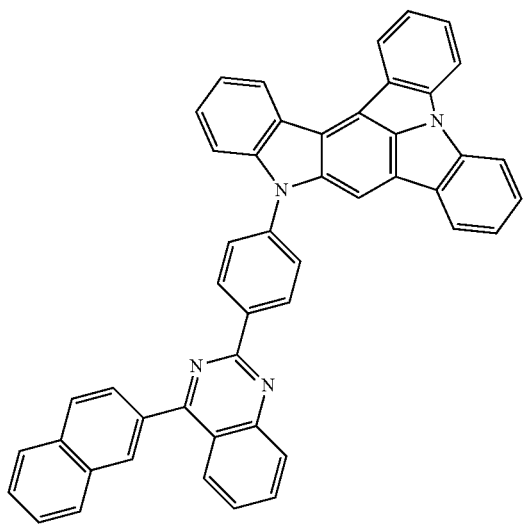
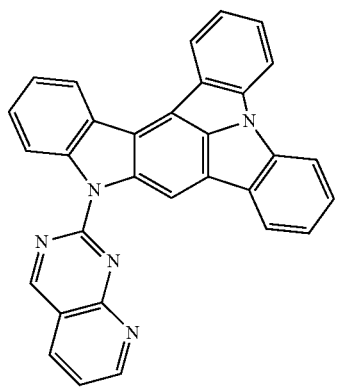

129 130
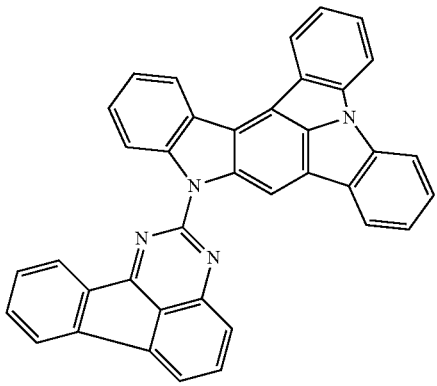 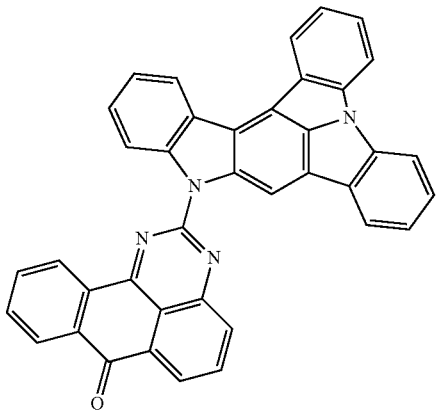
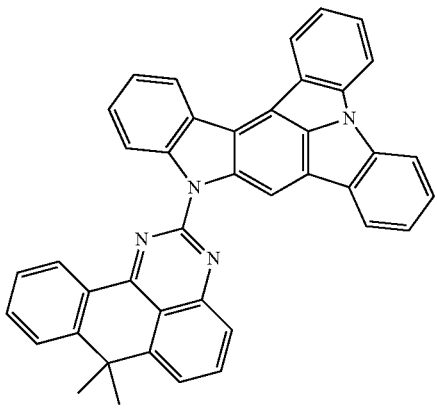 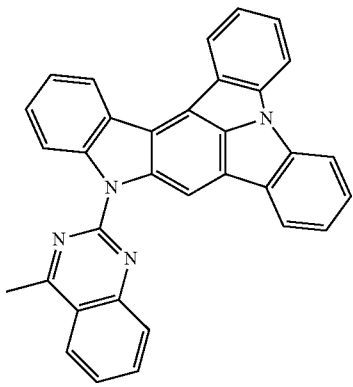
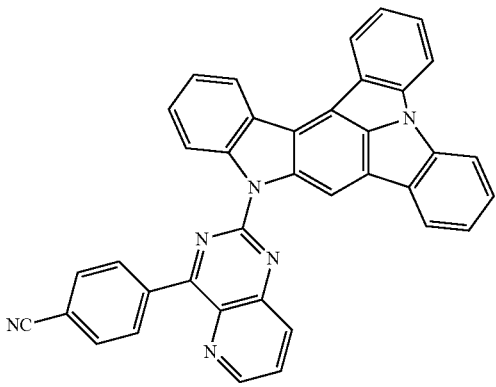 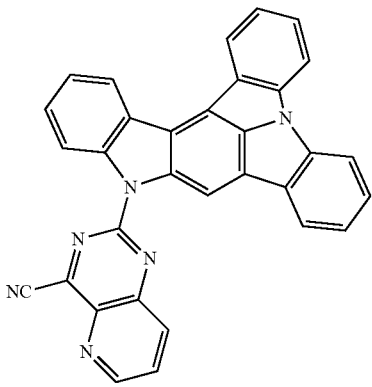
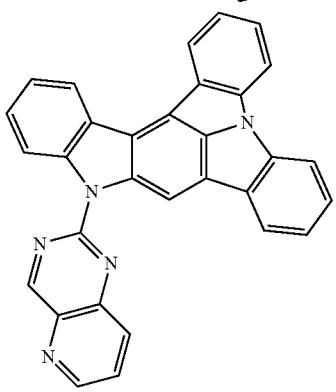 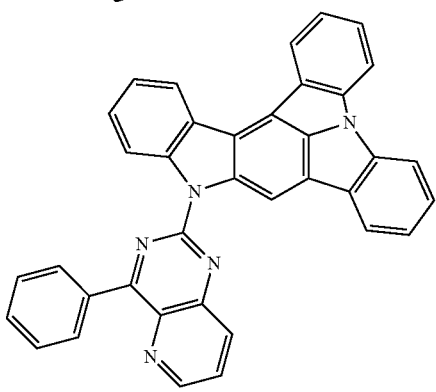

-continued
| 131 | 132 |
|---|---|
| 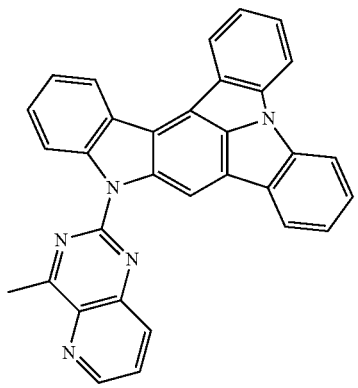 | 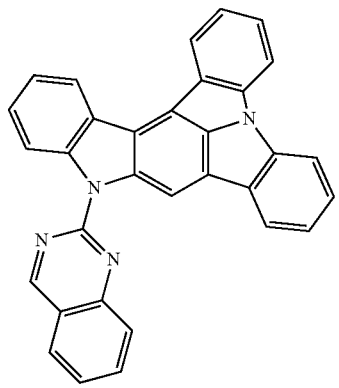 |
| 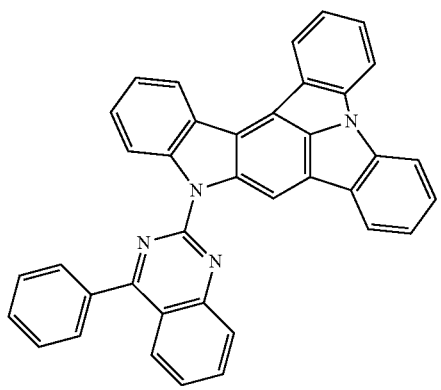 | 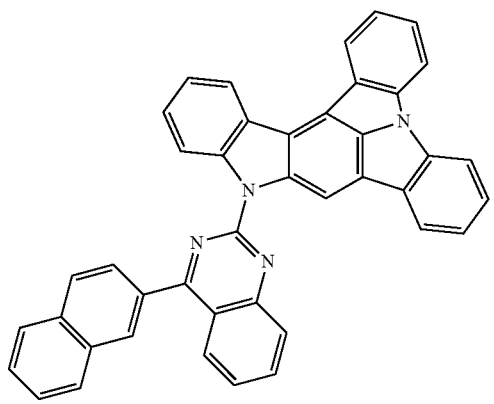 |
| 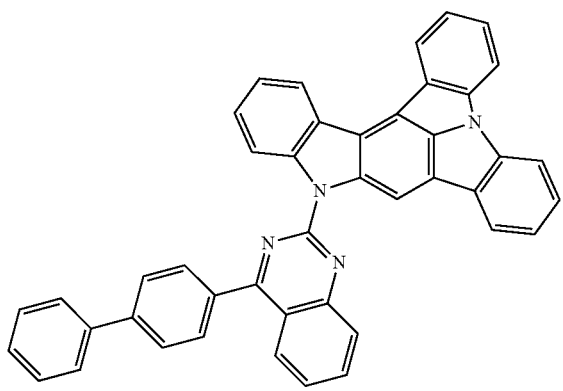 | 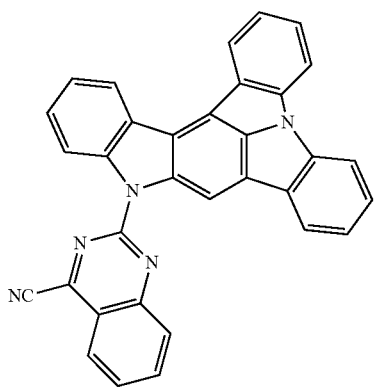 |
| 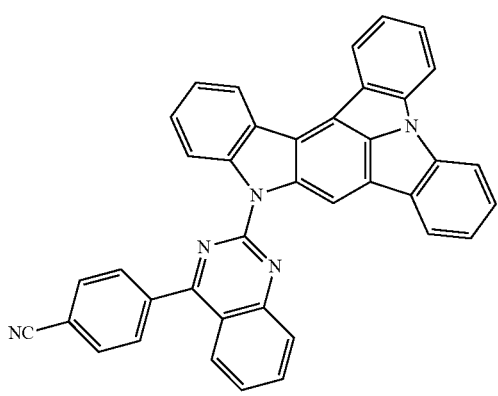 | 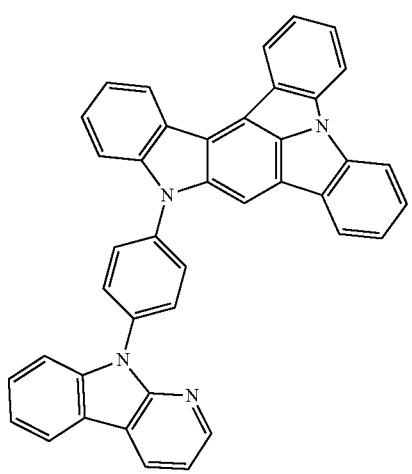 |

-continued
133
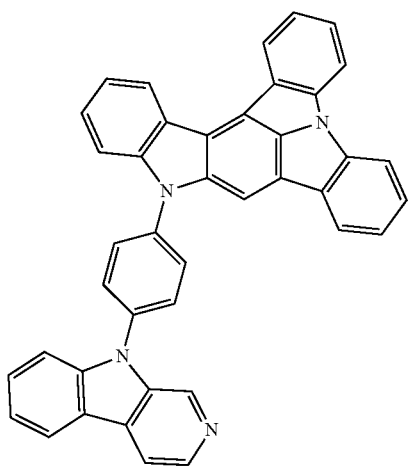
134
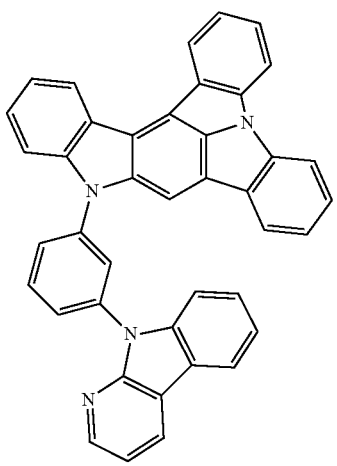
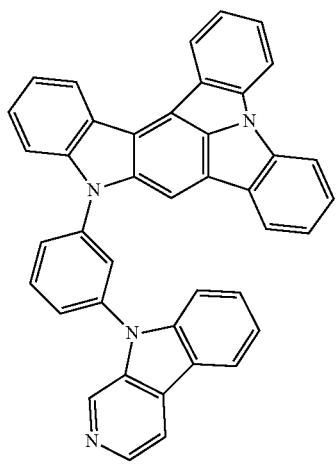
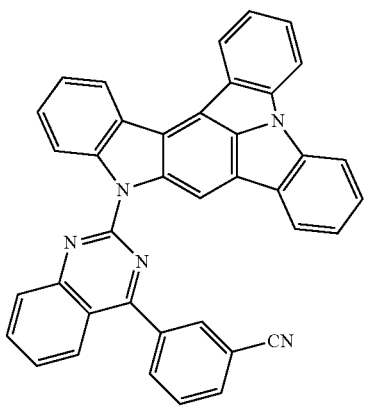
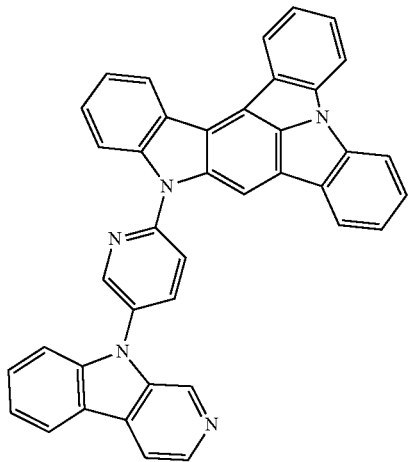
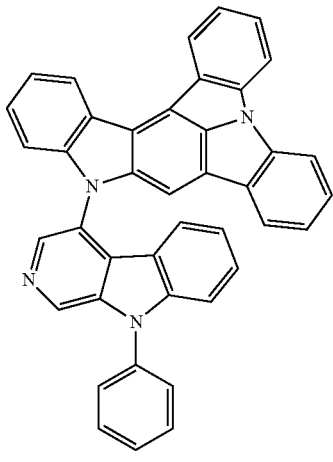

-continued
135
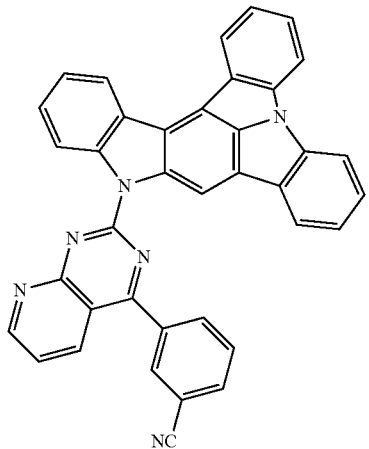
136
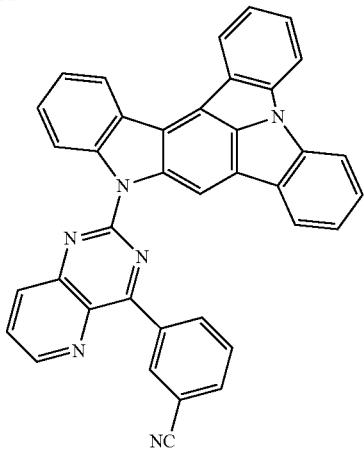
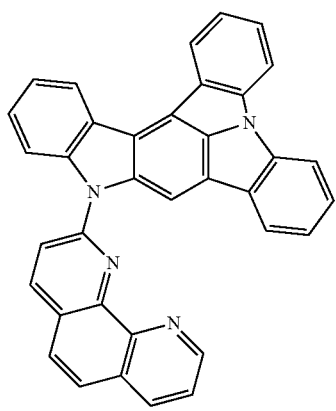
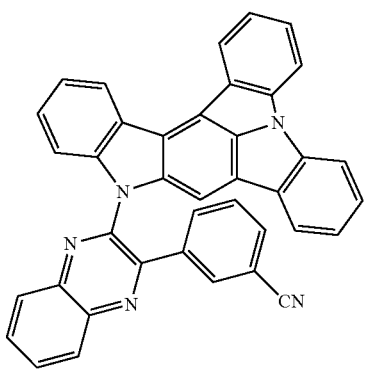
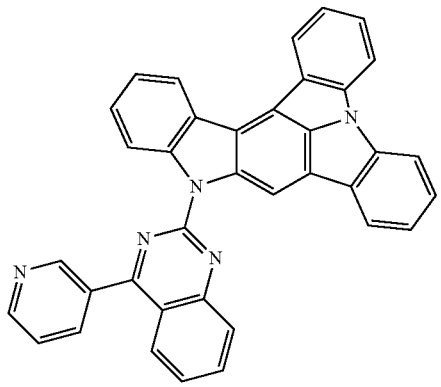
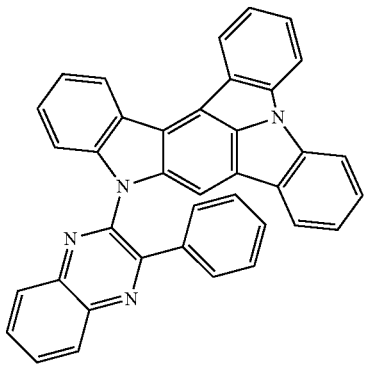
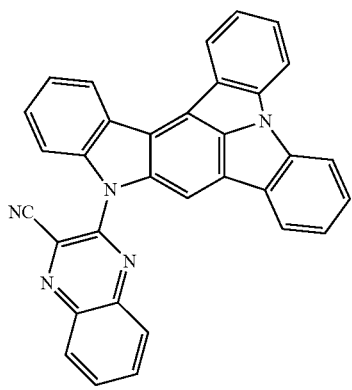
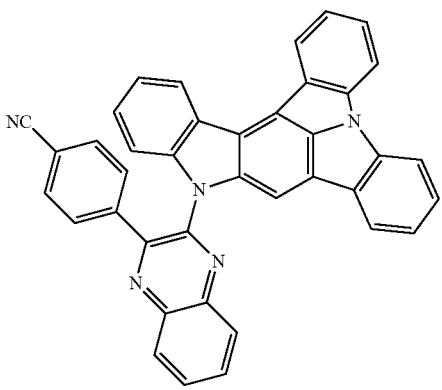

137
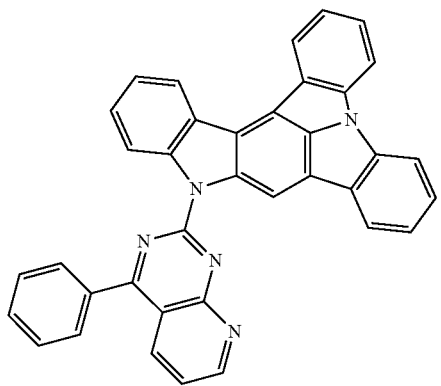
138
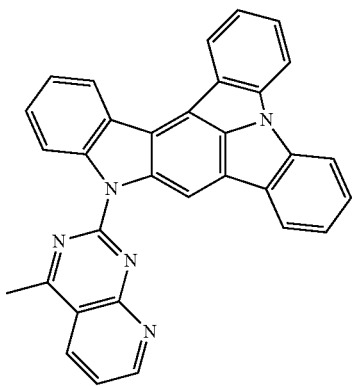
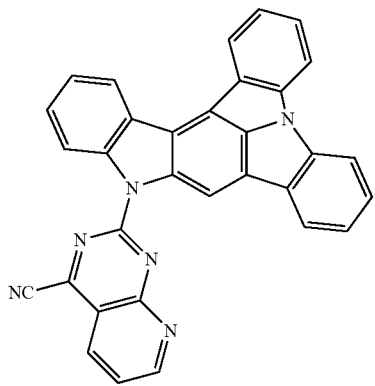
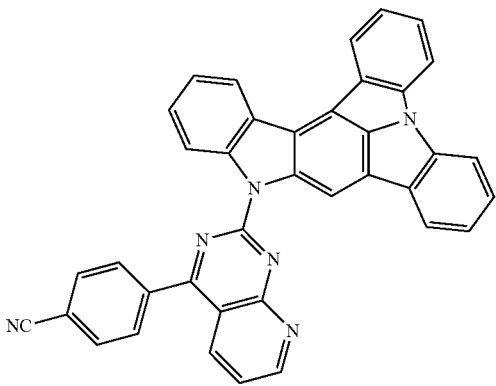
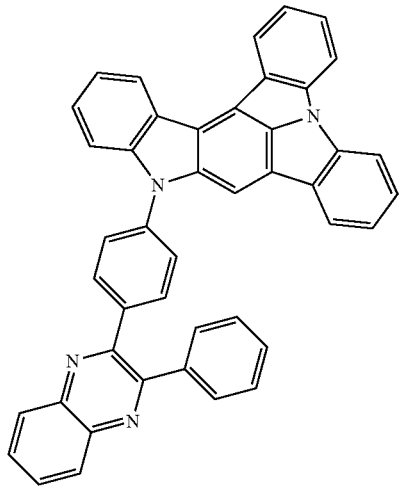
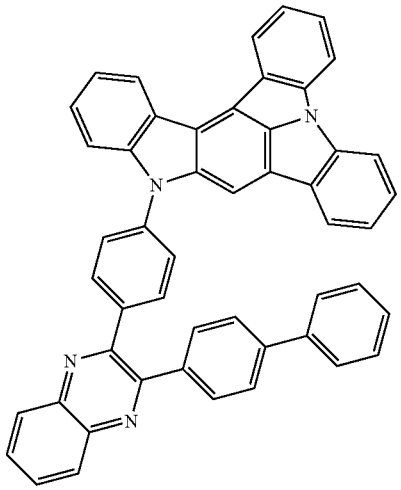

-continued
139
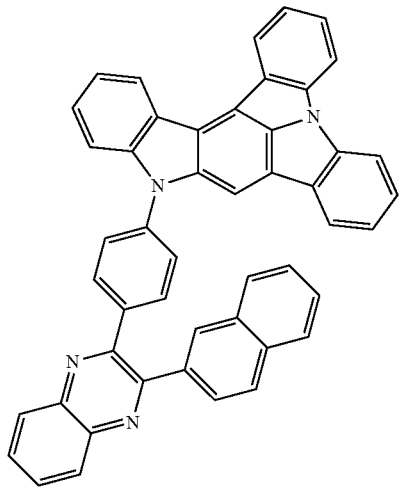
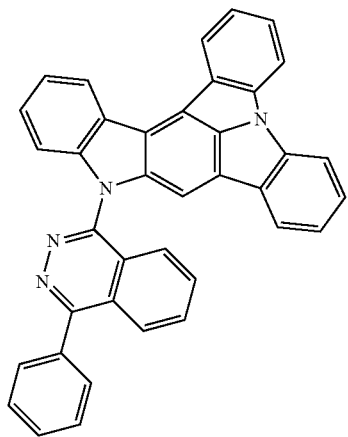
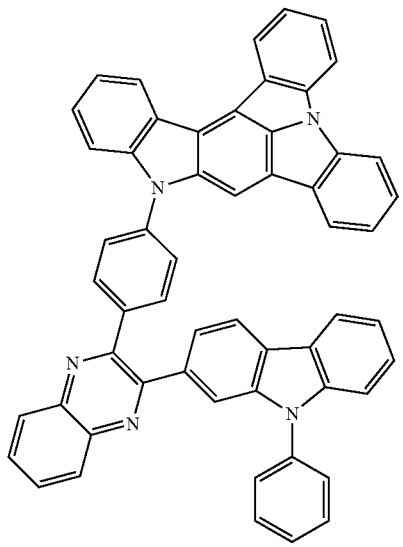
140
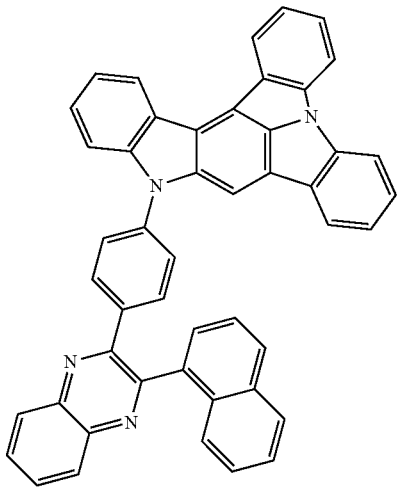
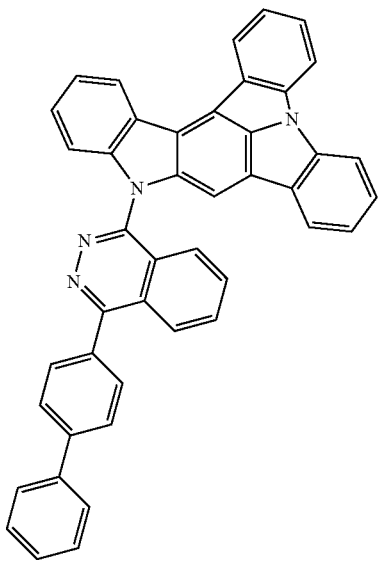
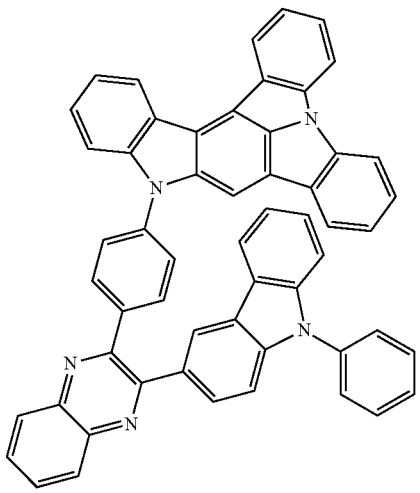

-continued
141
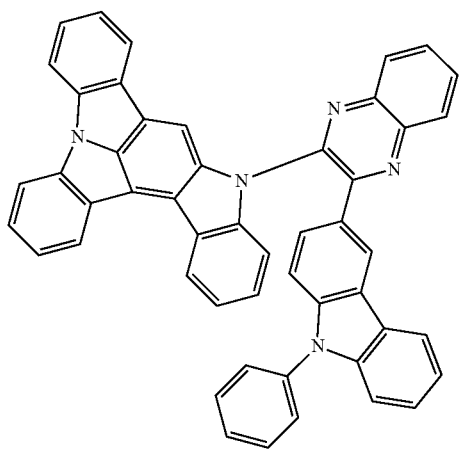
142
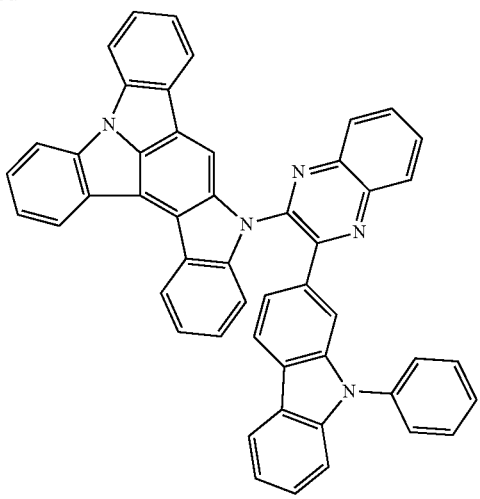
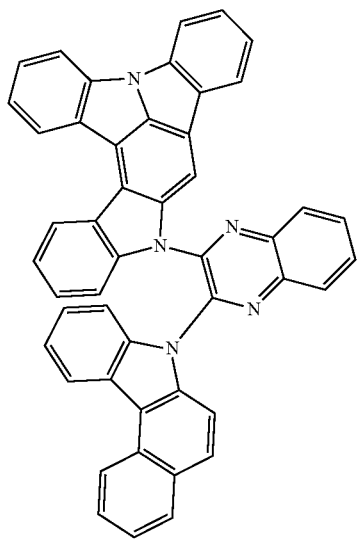
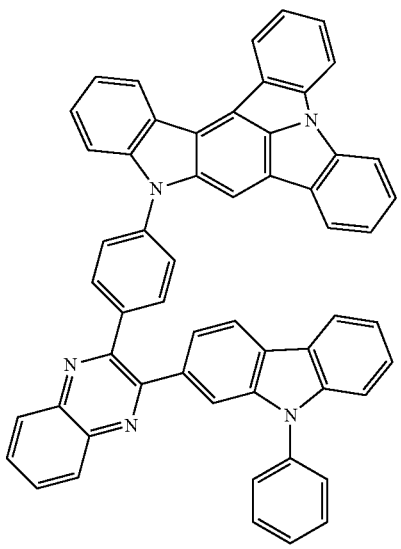
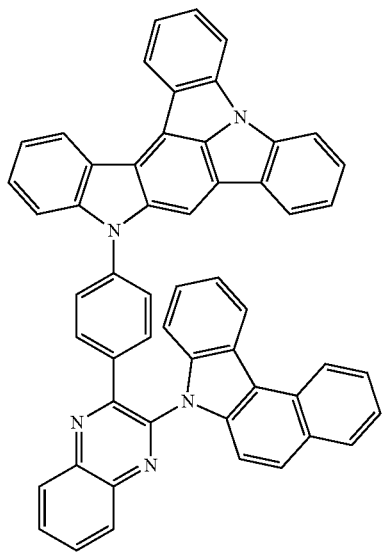
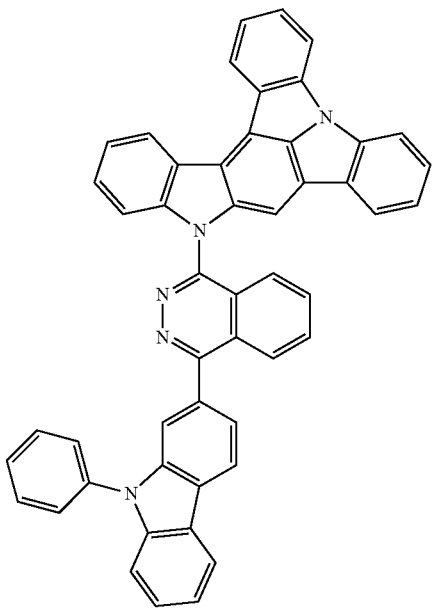

-continued
143
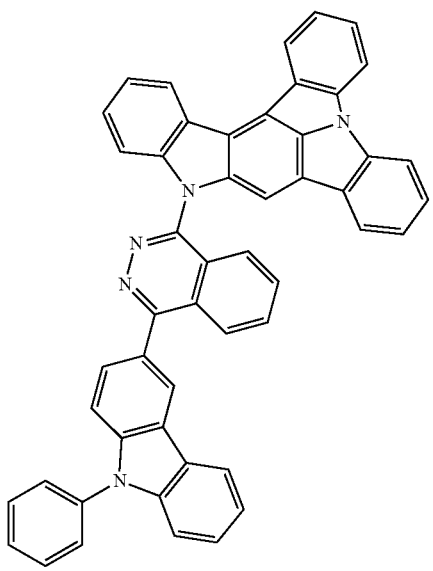
144
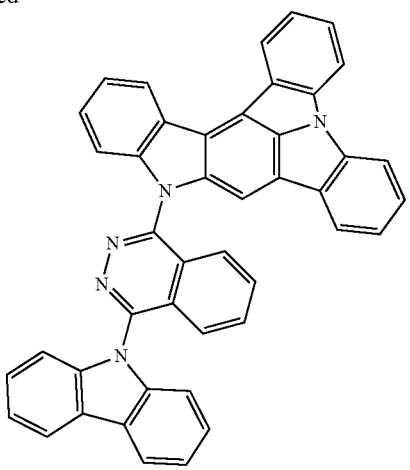
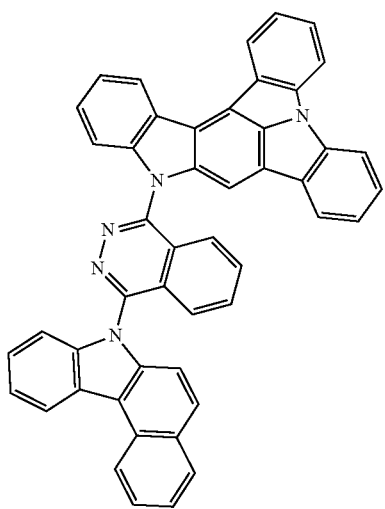
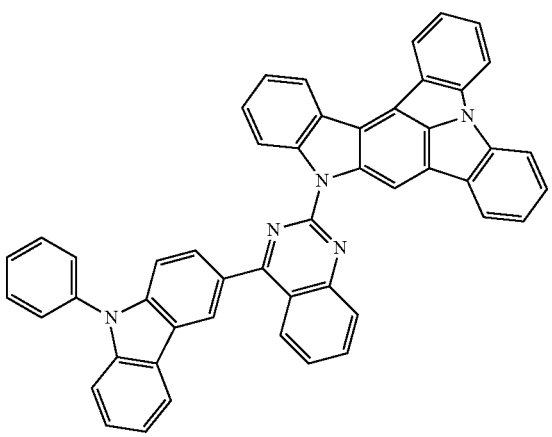
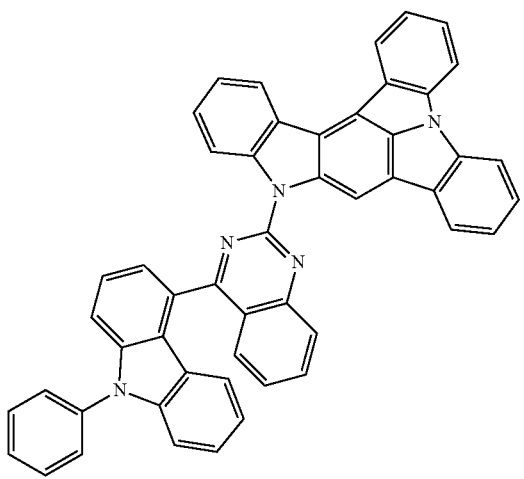
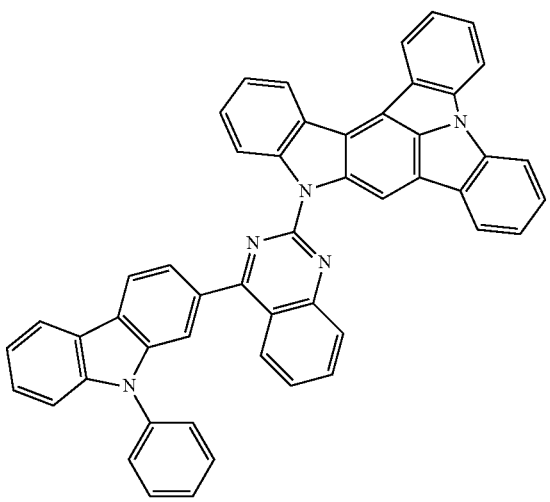

145
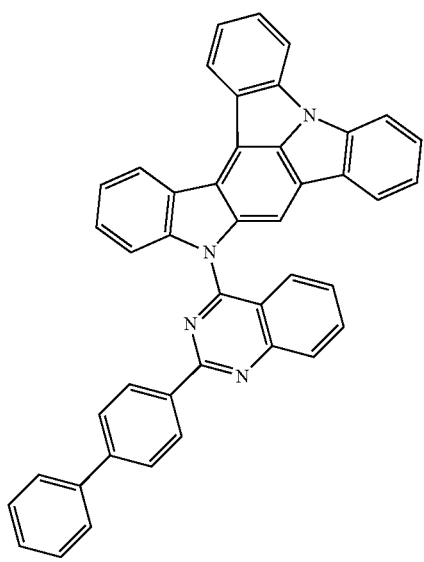
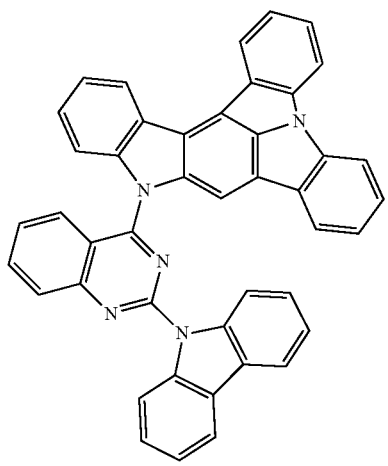
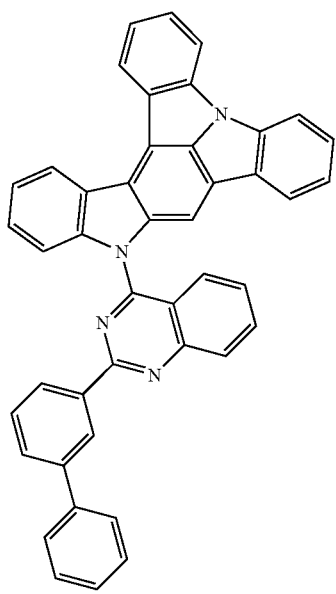
146
-continued
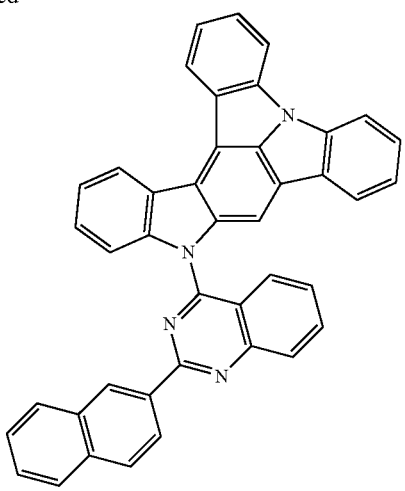
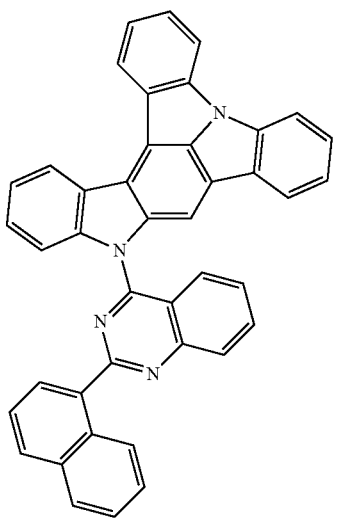
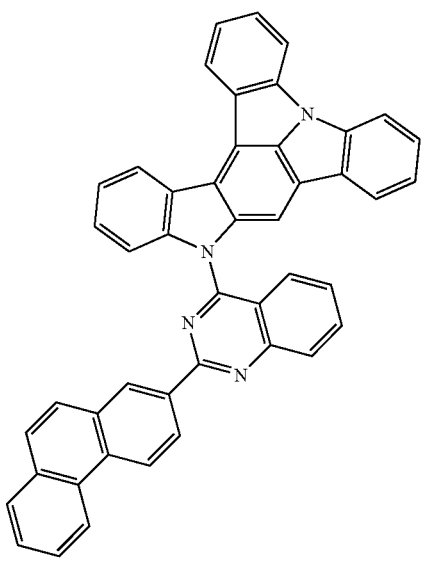

147
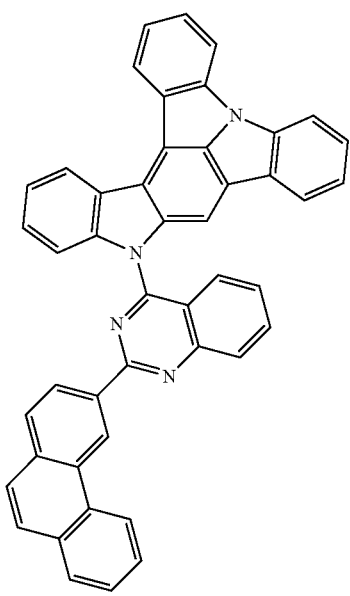
148
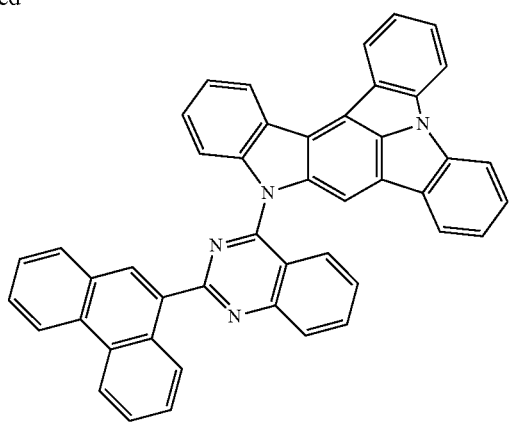
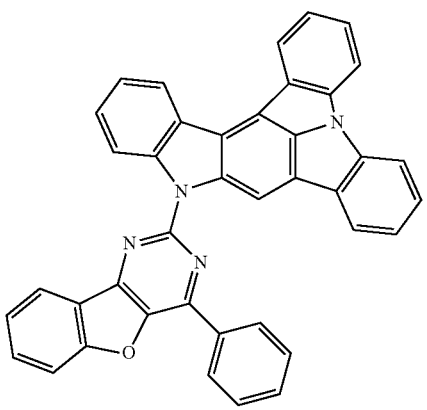
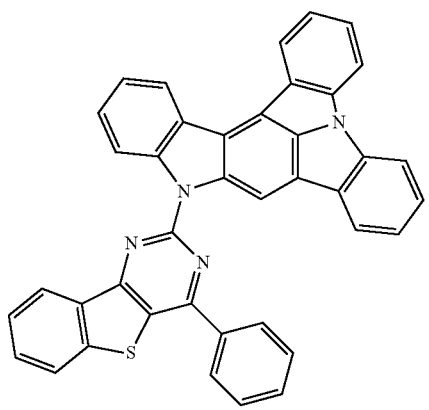
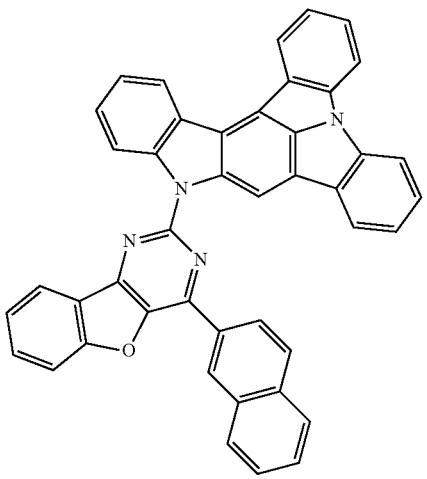
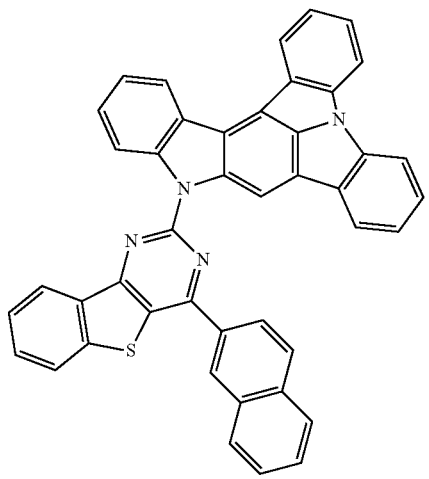

-continued
149
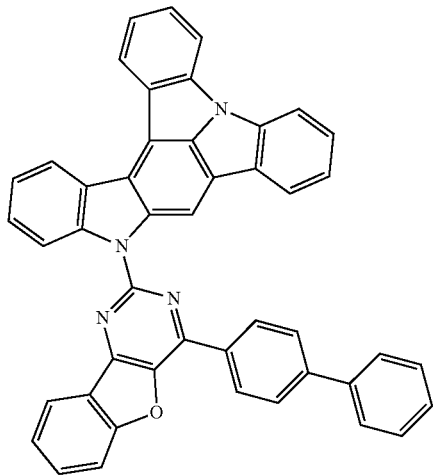
150
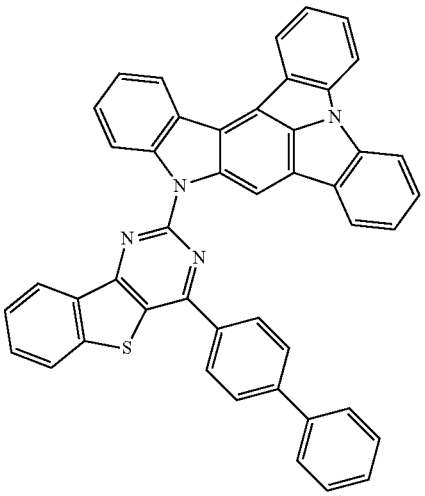
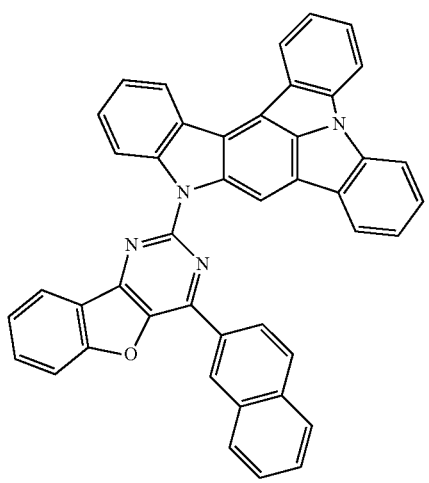
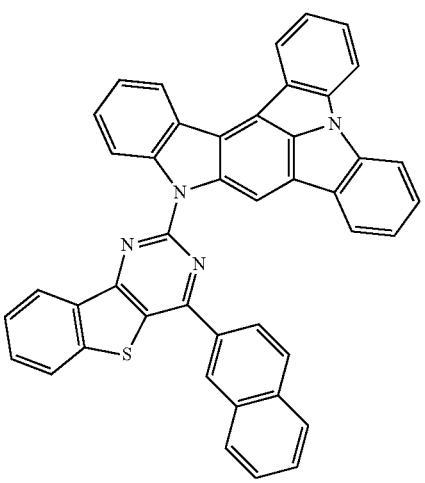
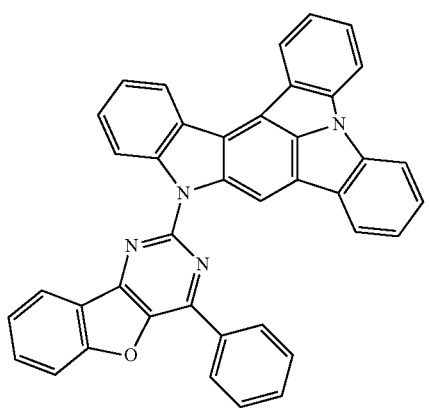
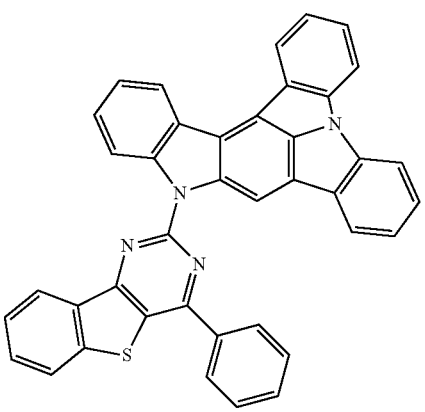

| 151 | 152 |
|---|---|
| 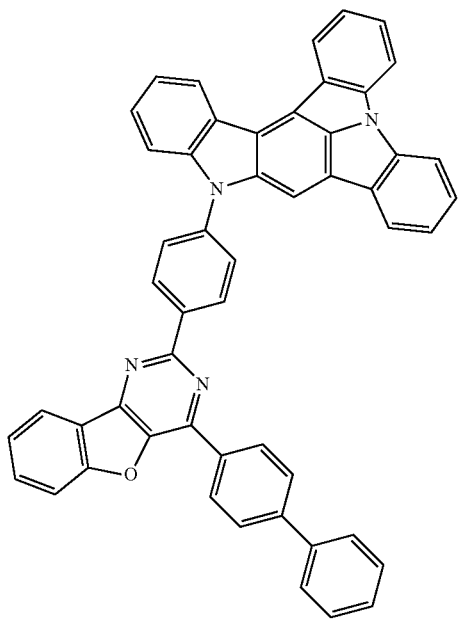 | 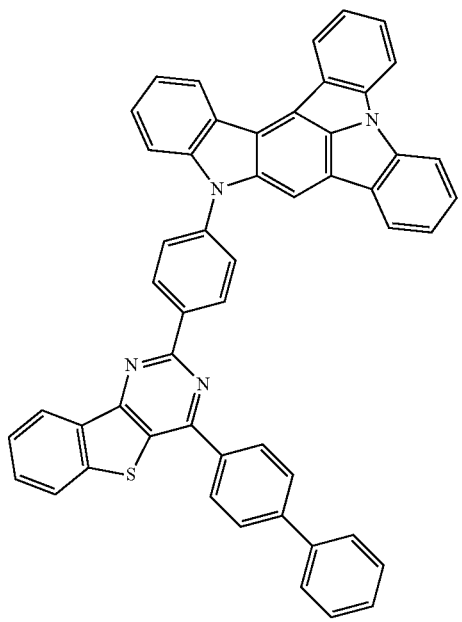 |
| 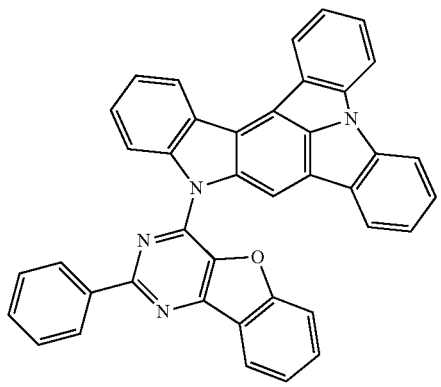 | 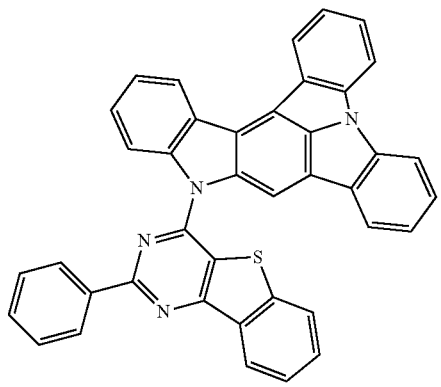 |
| 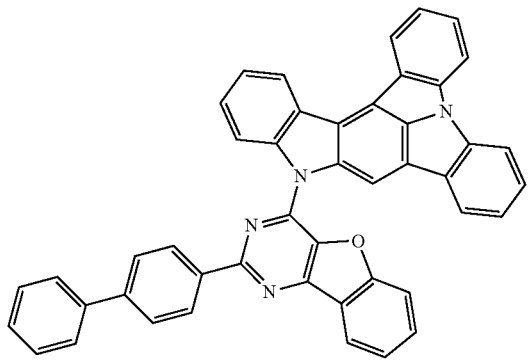 | 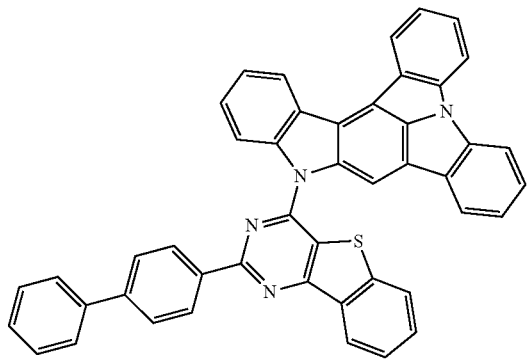 |

-continued
153
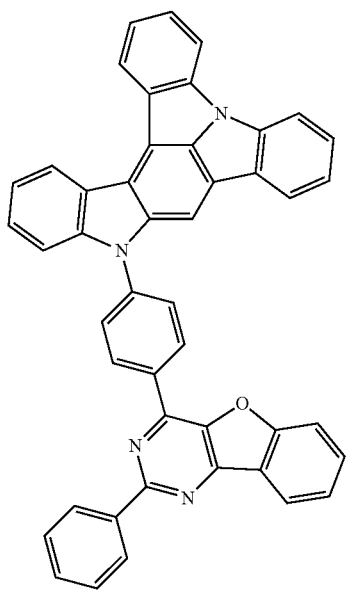
154
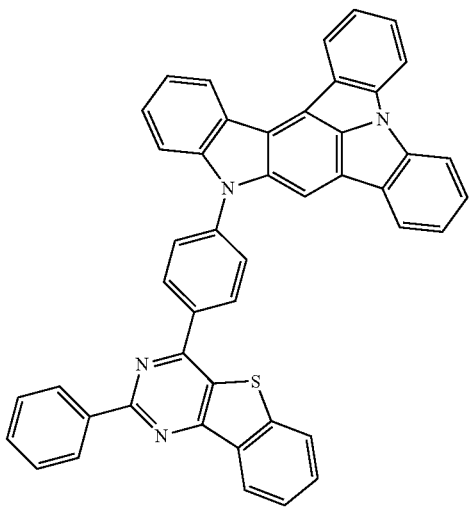
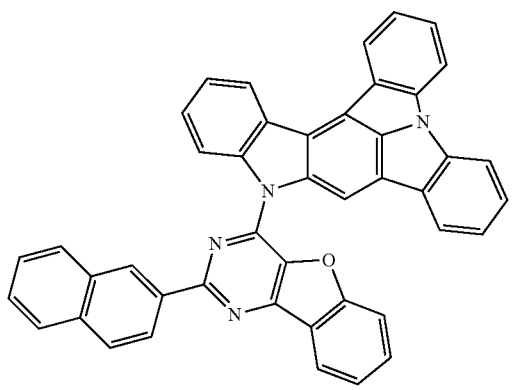
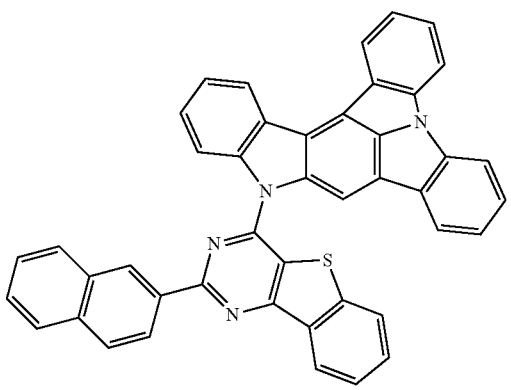
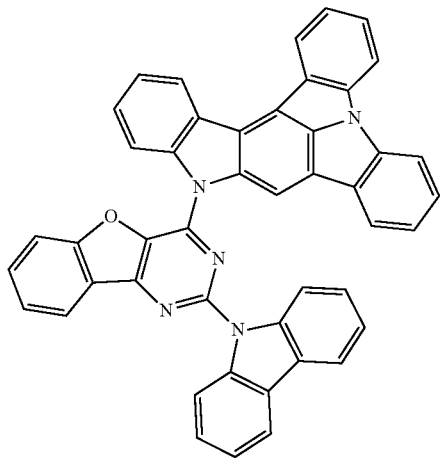
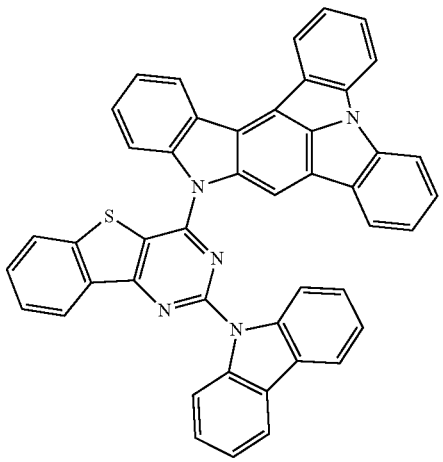

-continued
155
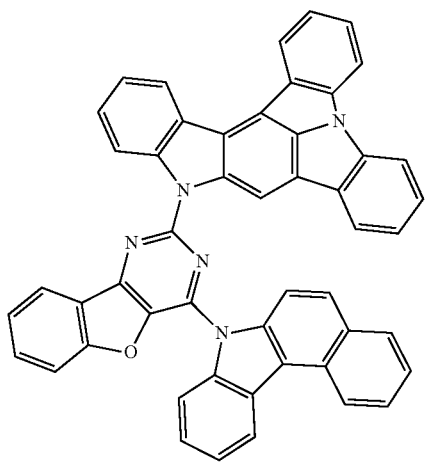
156
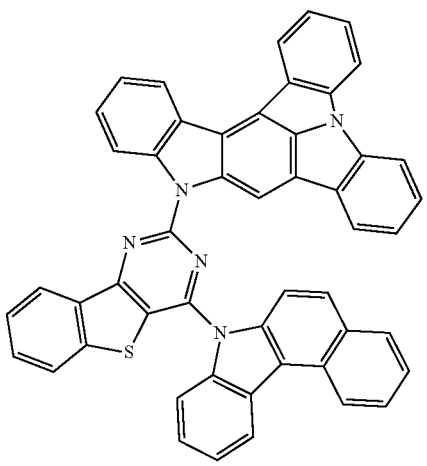
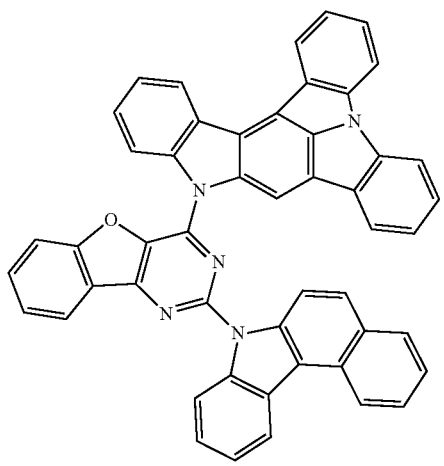
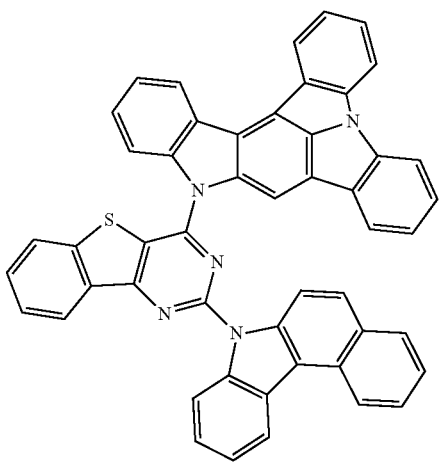
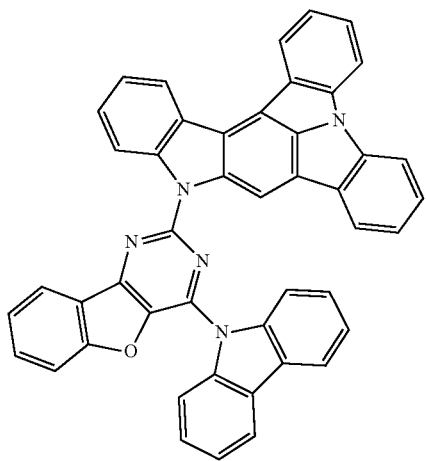
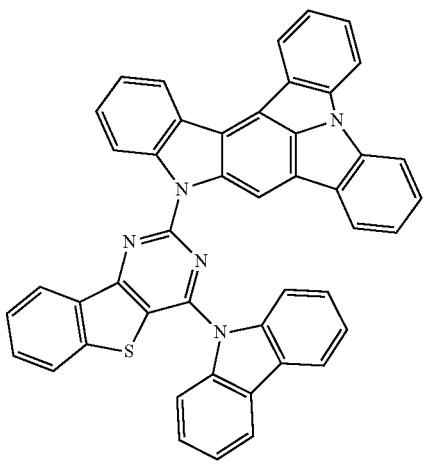

-continued
157
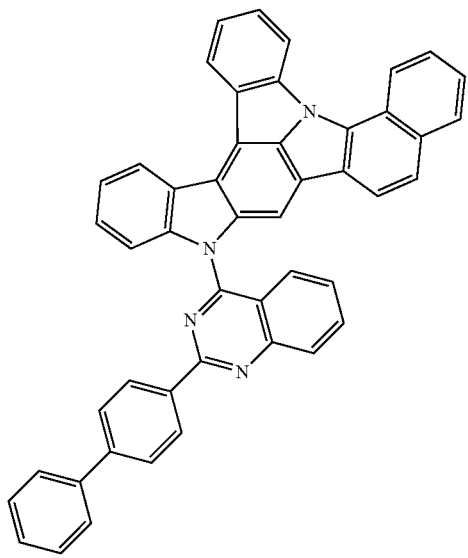
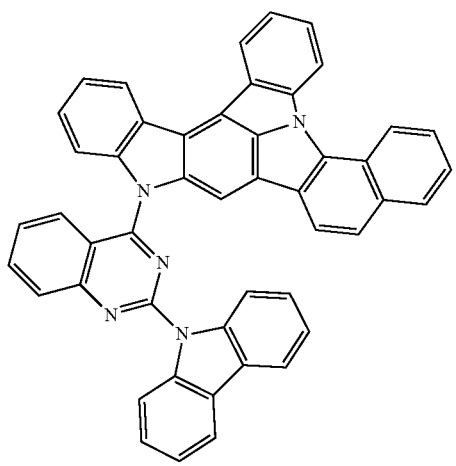
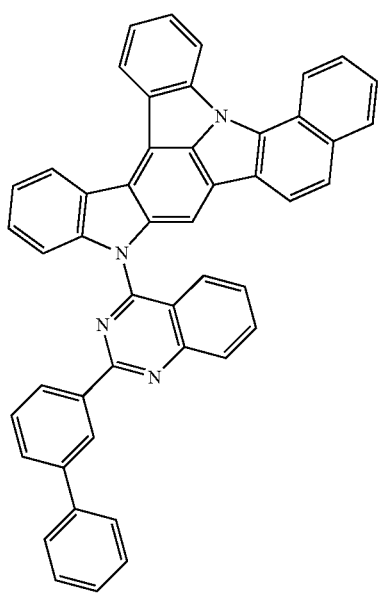
158
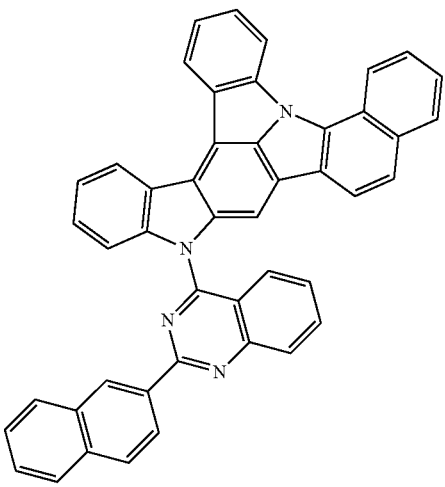
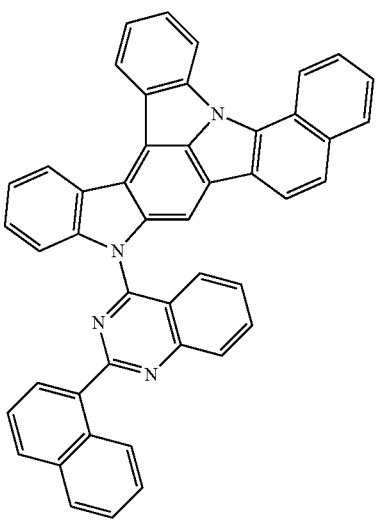
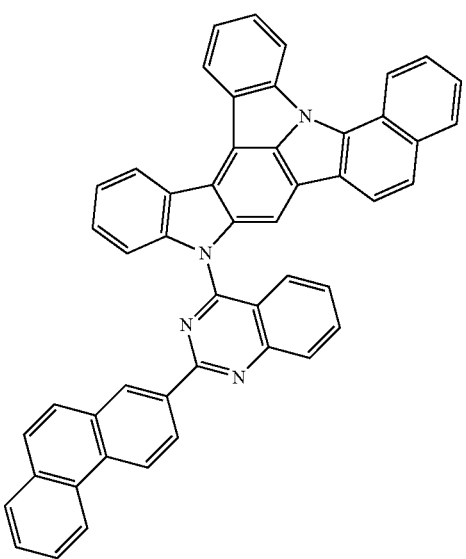

-continued
159
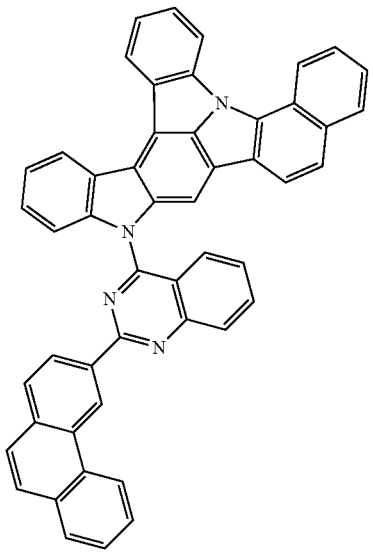
160
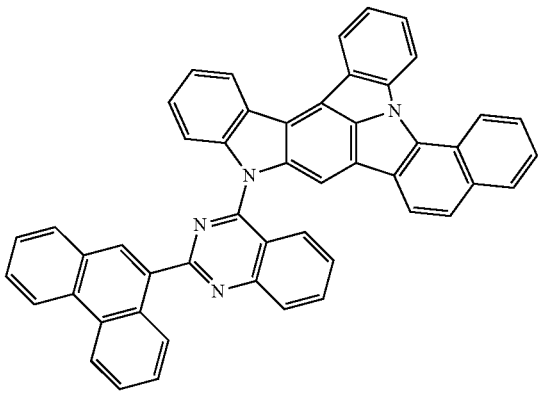
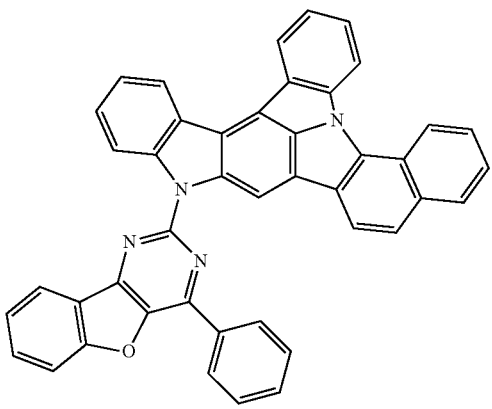
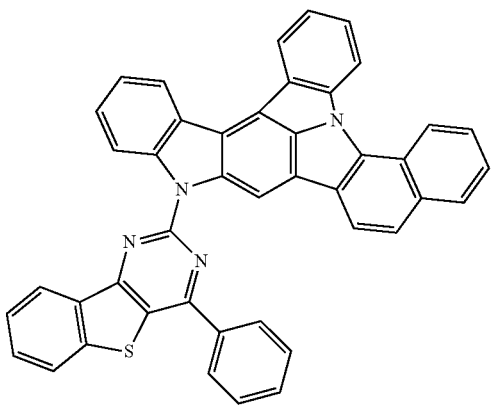
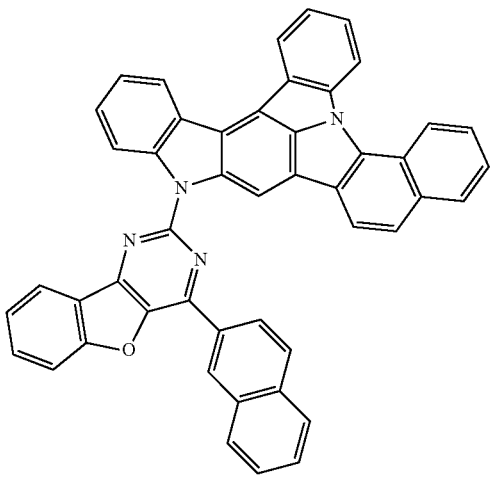
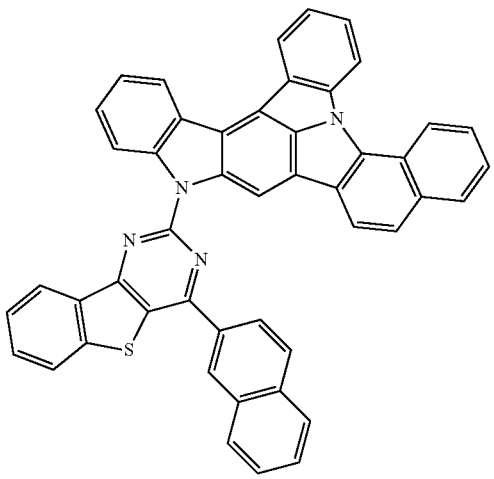

161
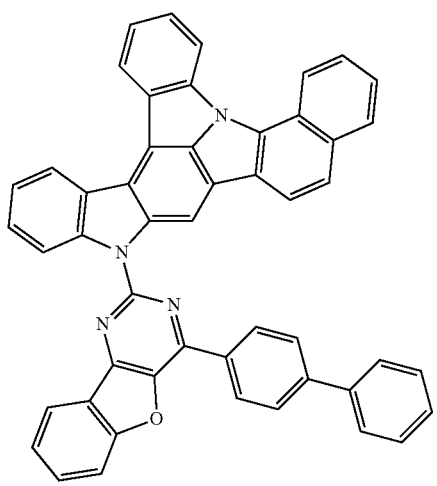
162
-continued
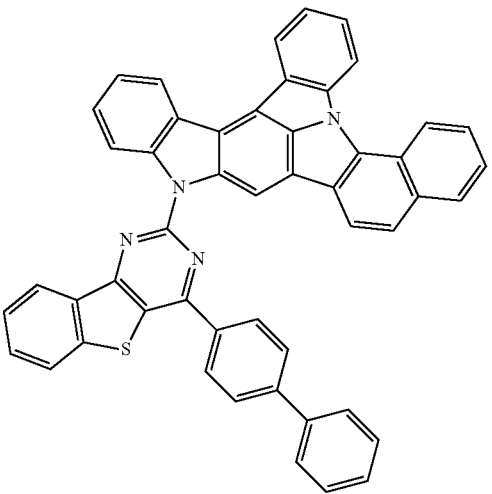
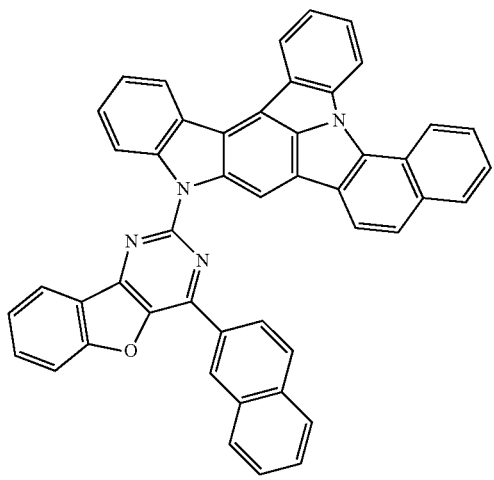
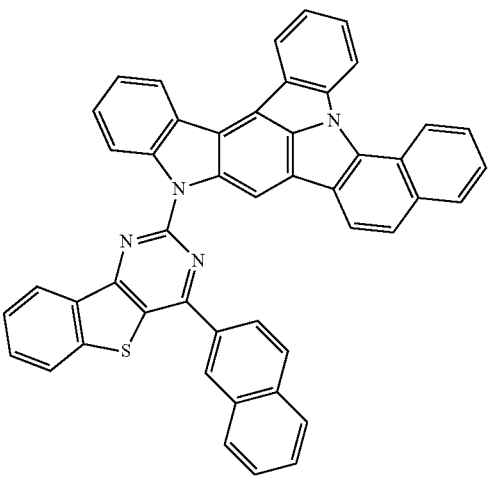
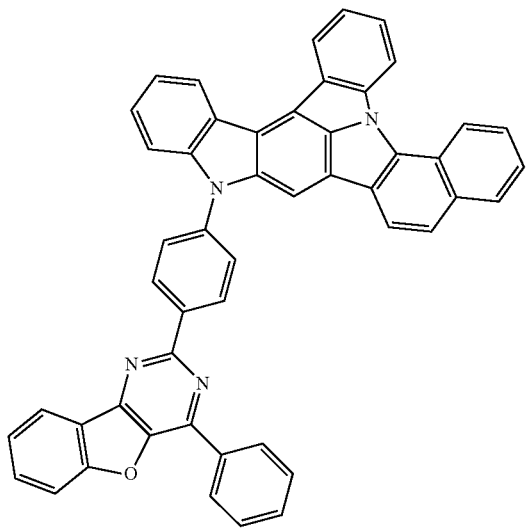
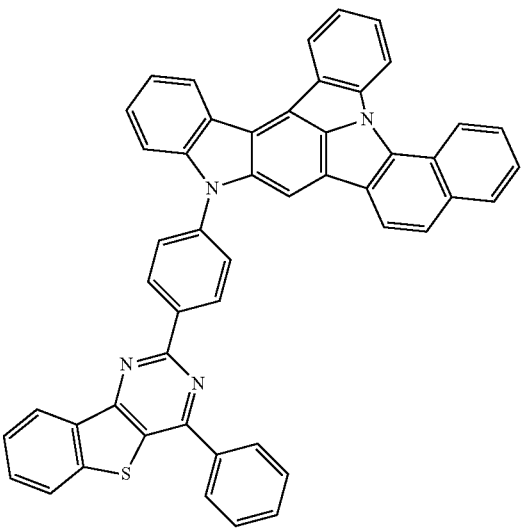

-continued
| 163 | 164 |
|---|---|
| 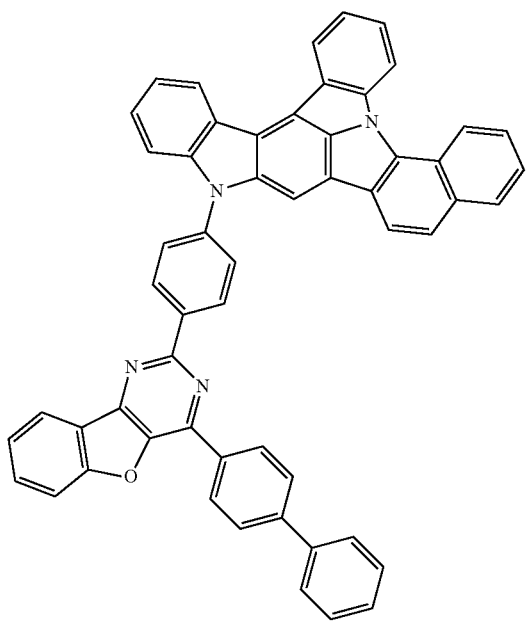 | 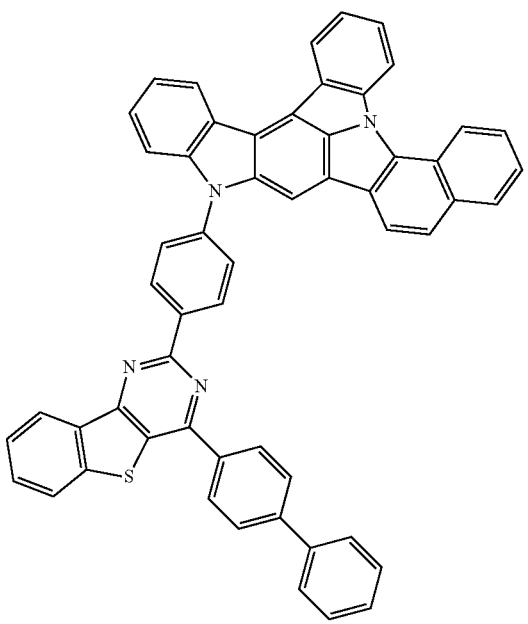 |
| 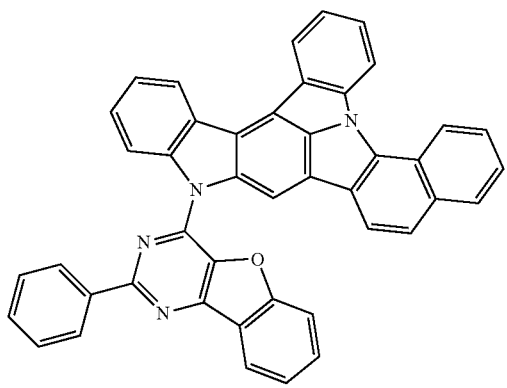 | 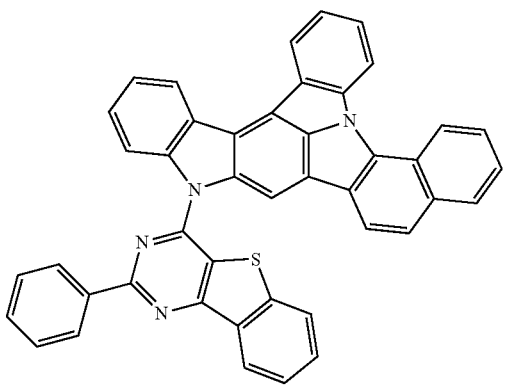 |
| 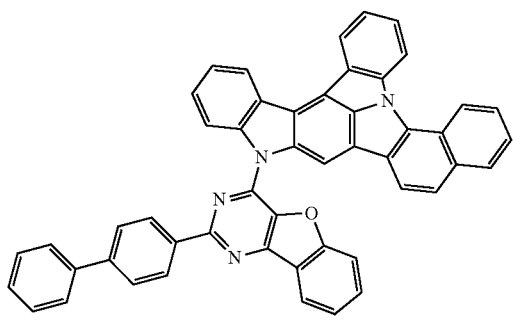 | 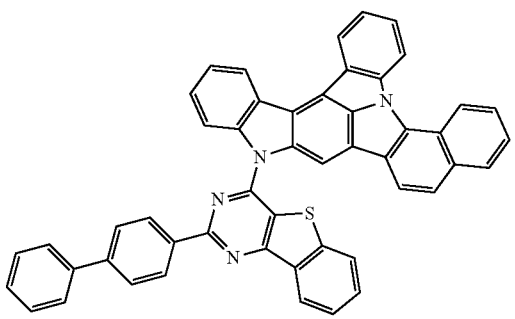 |

-continued
| 165 | 166 |
|---|---|
| 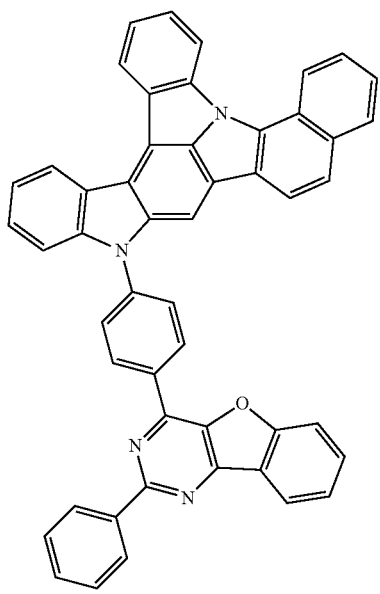 | 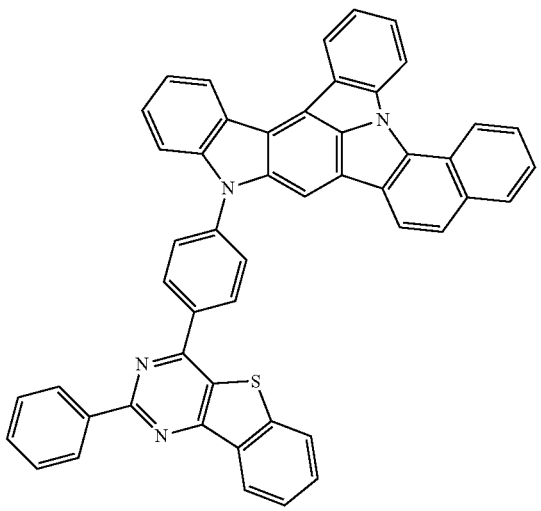 |
| 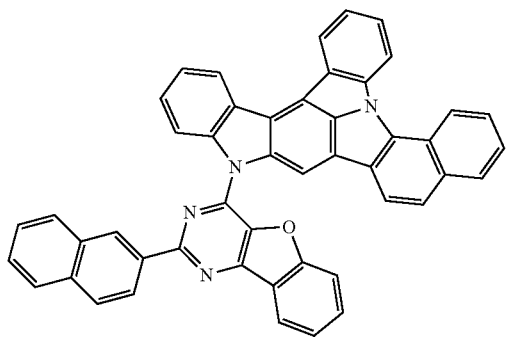 | 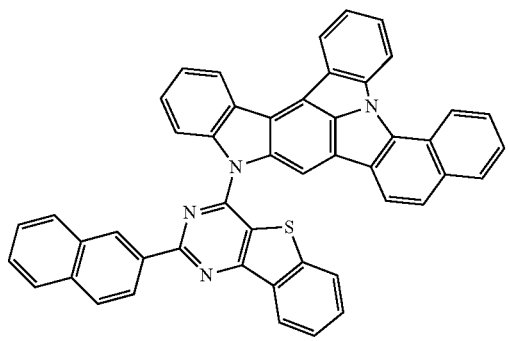 |
| 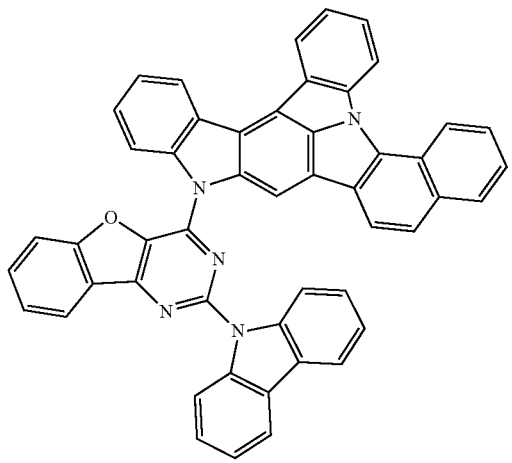 | 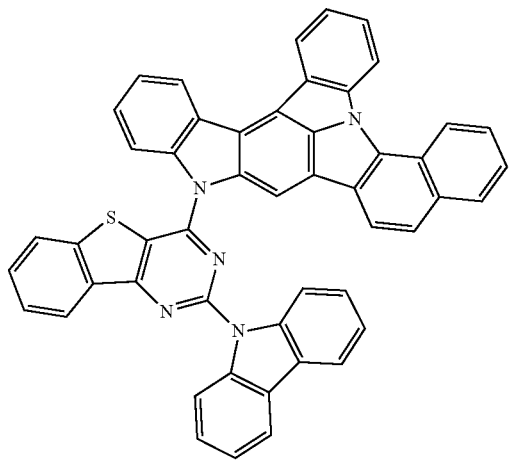 |

-continued
167
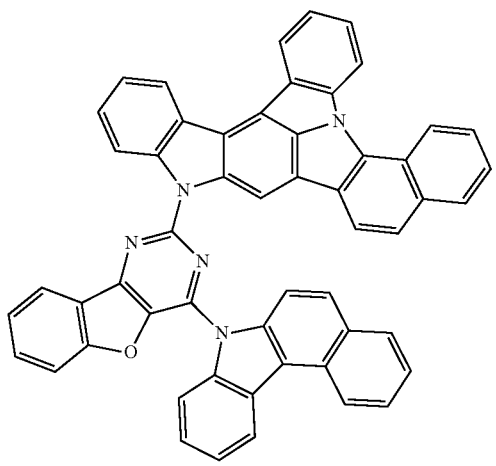
168
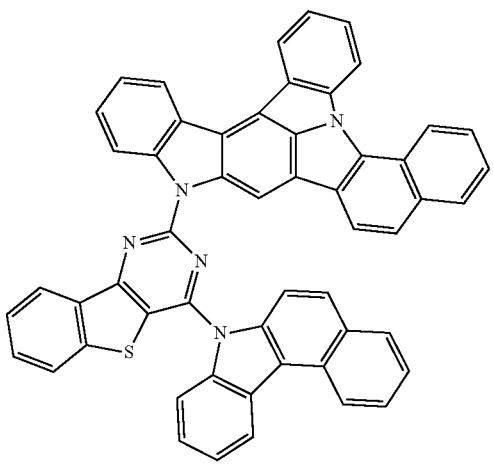
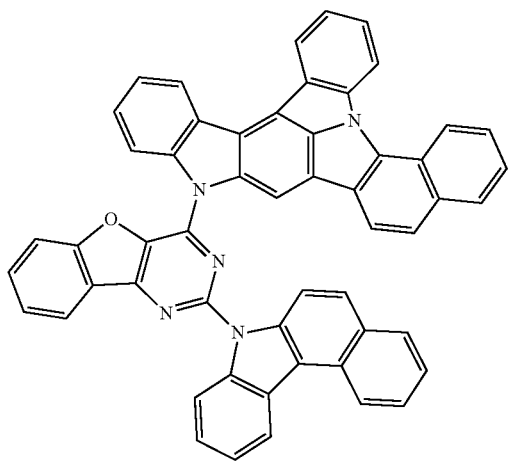
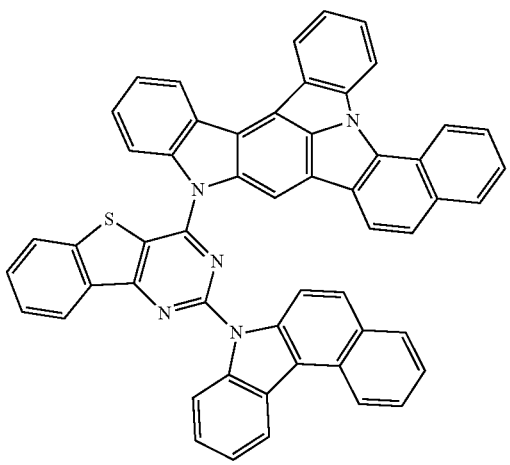
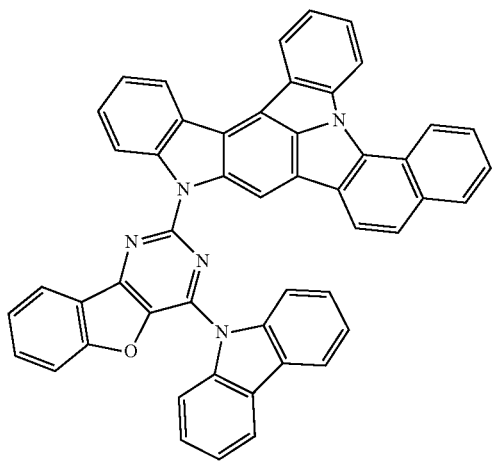
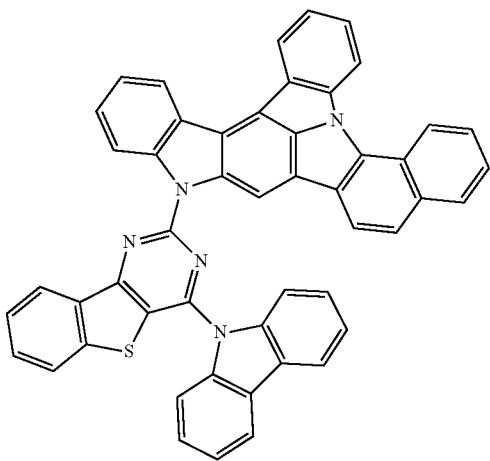

169
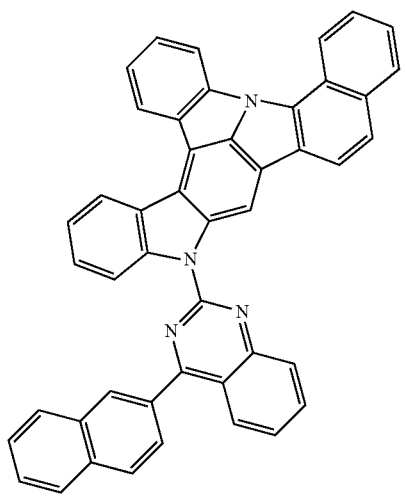
170
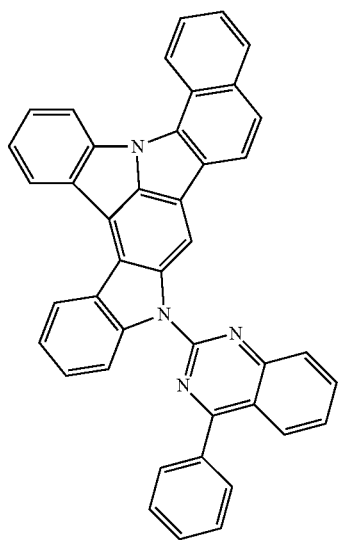
-continued
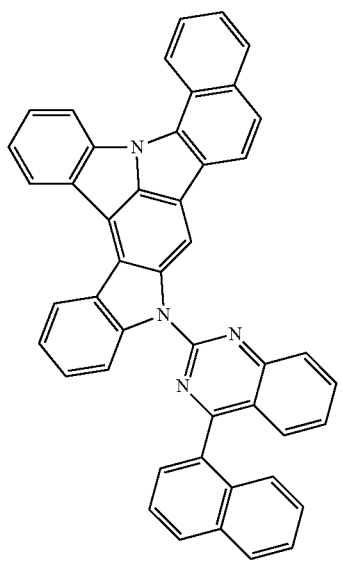
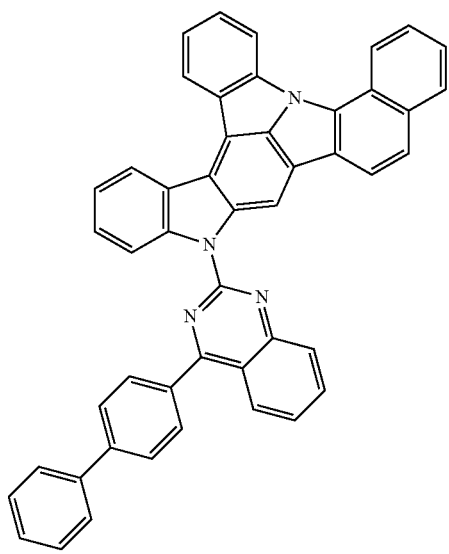
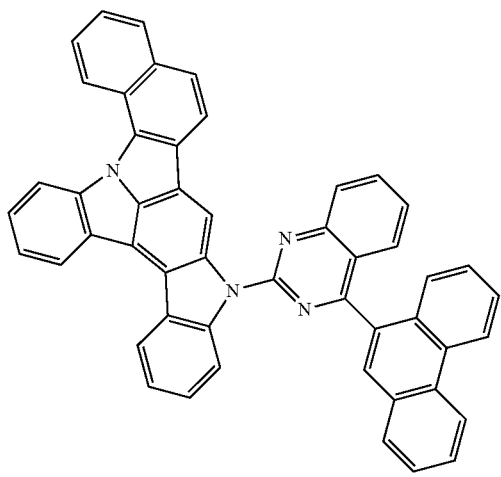
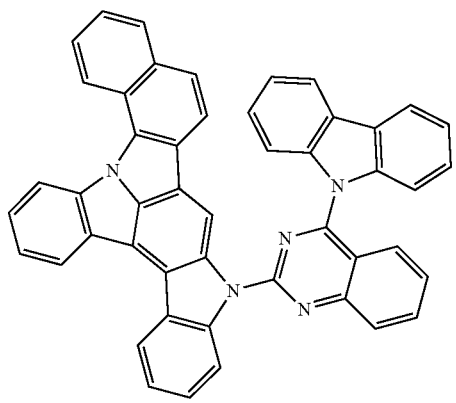

-continued
171
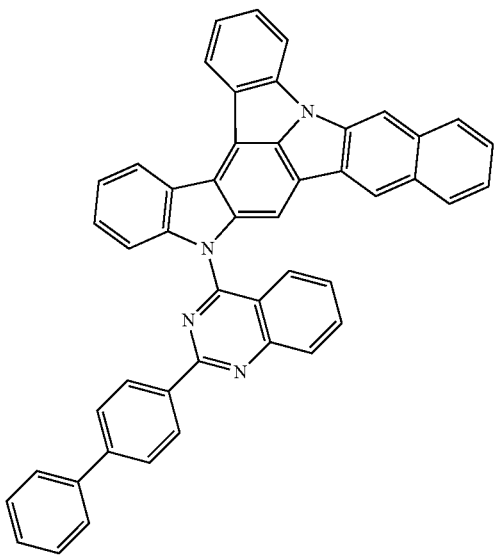
172
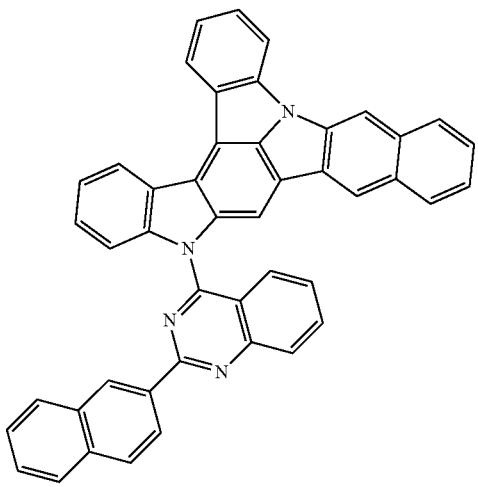
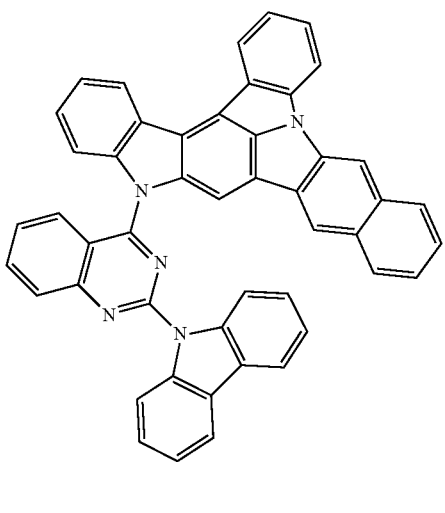
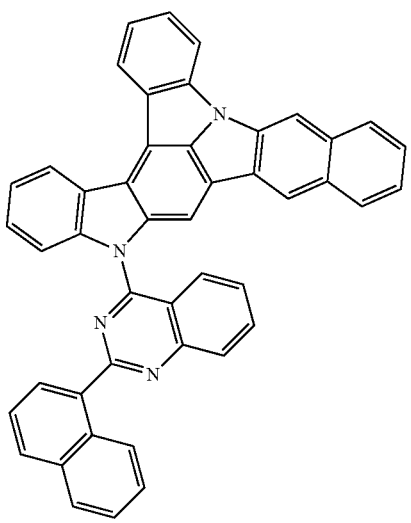
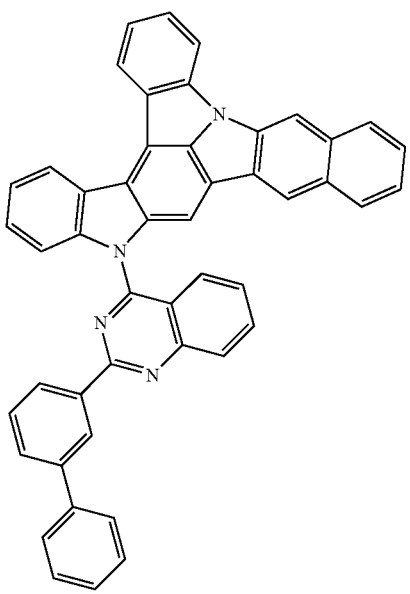
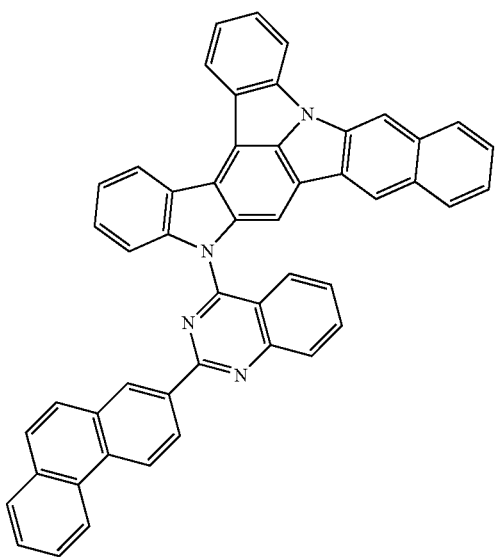

-continued
173
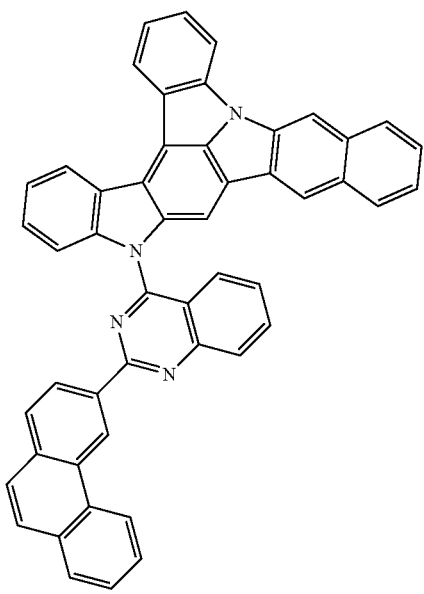
174
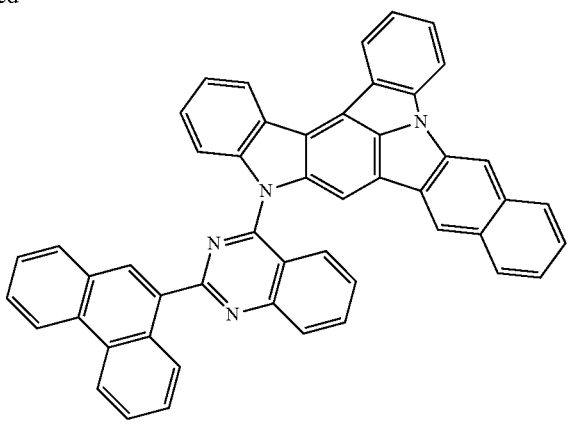
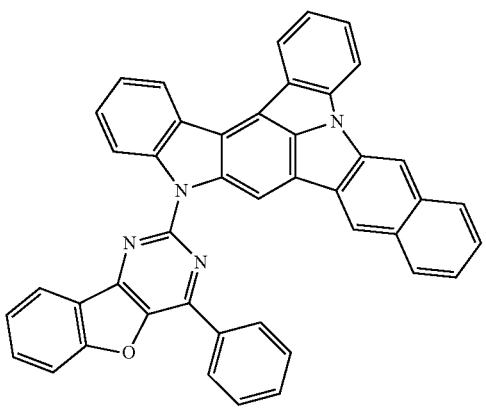
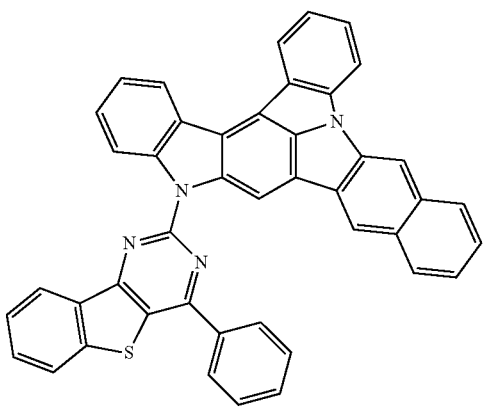
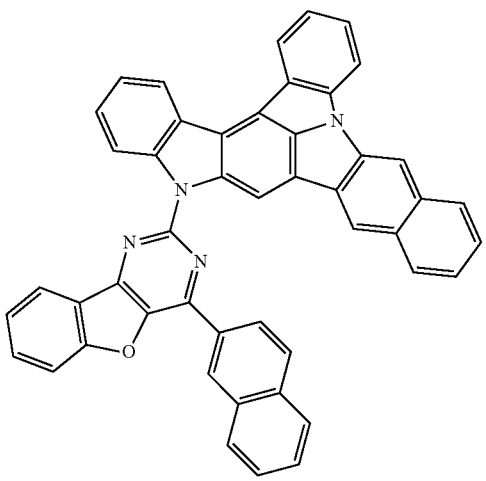
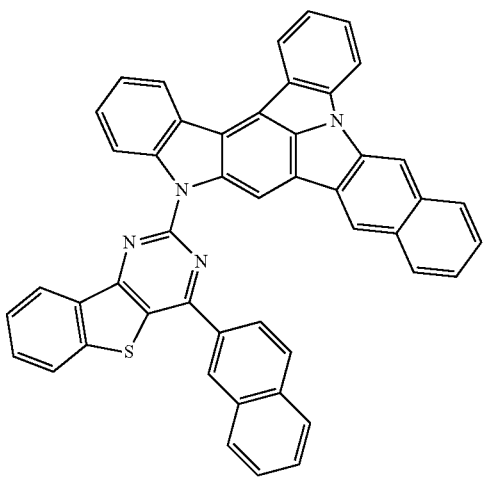

-continued
| 175 | 176 |
|---|---|
| 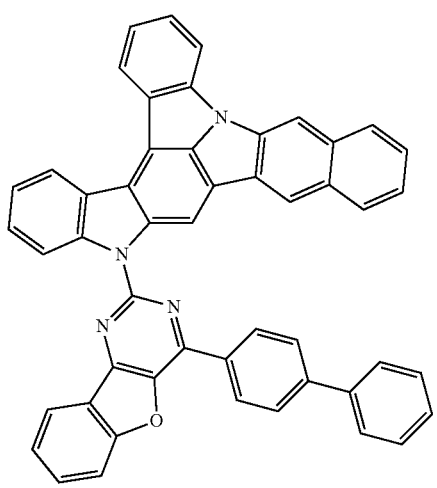 | 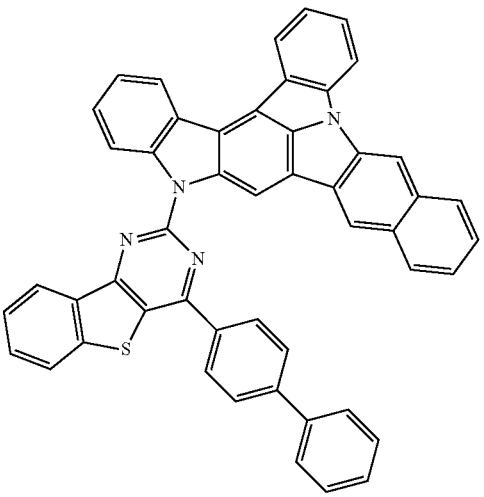 |
| 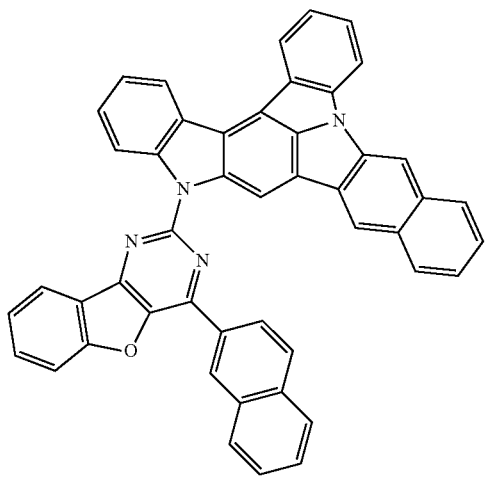 | 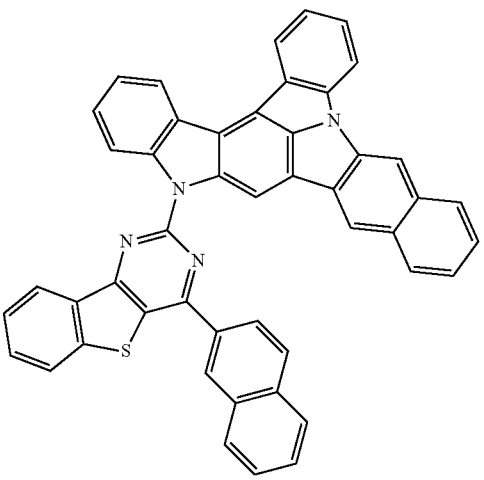 |
| 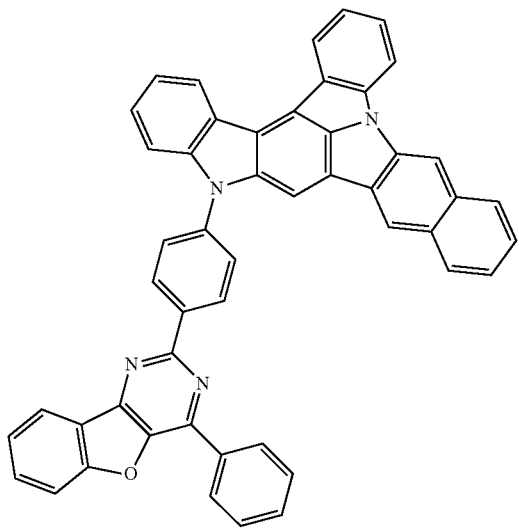 | 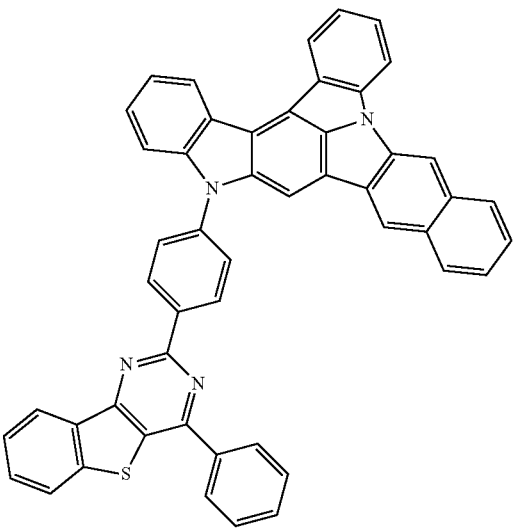 |

-continued
| 177 | 178 |
|---|---|
| 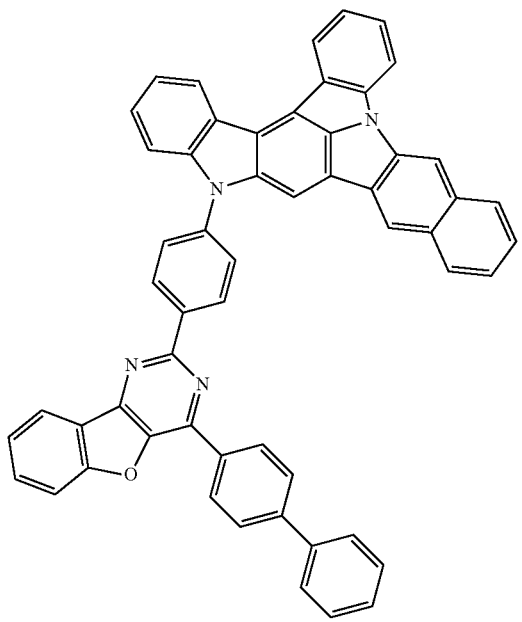 | 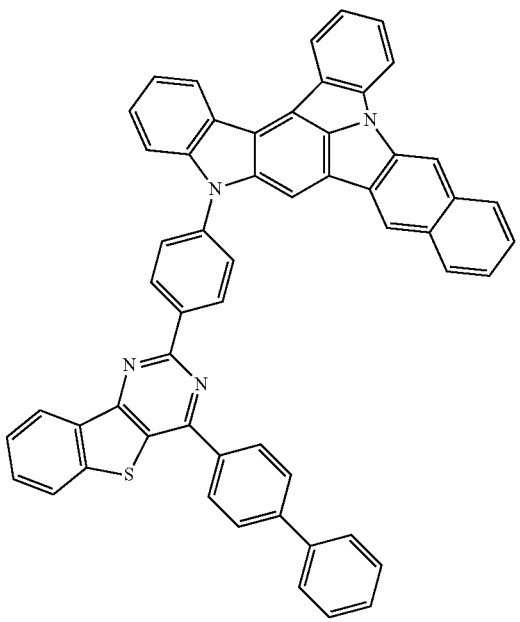 |
| 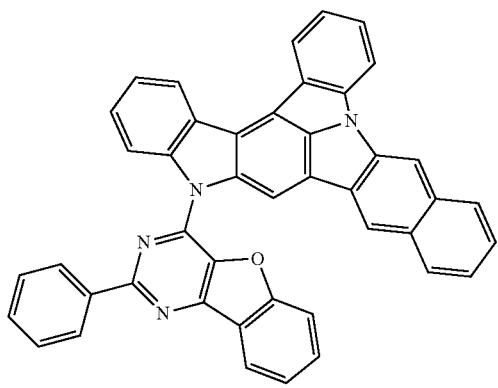 | 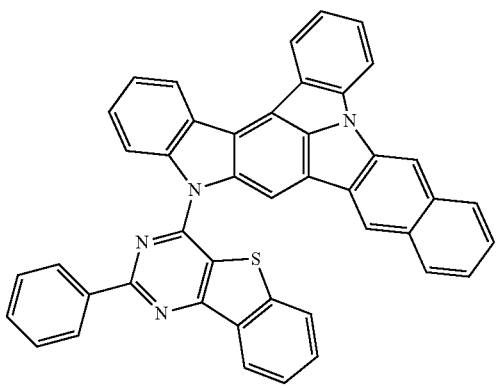 |
| 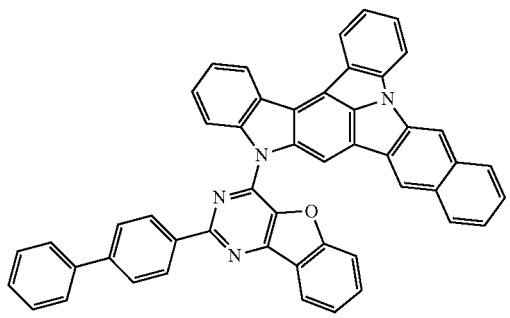 | 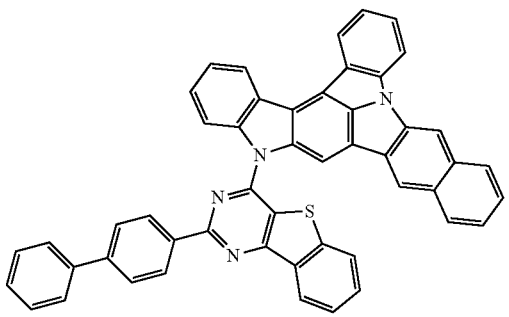 |

-continued
179
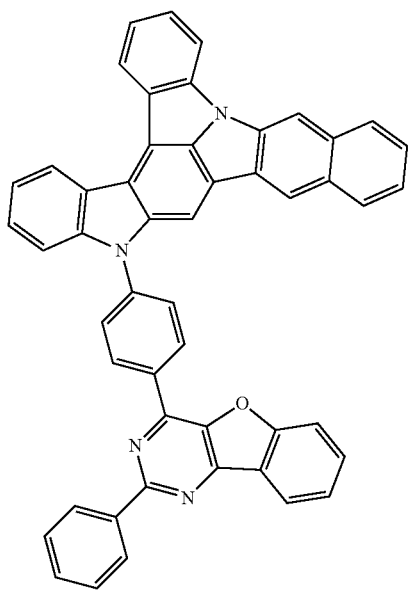
180
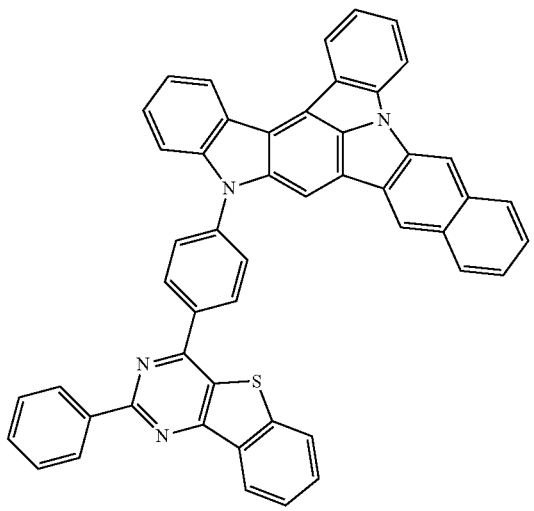
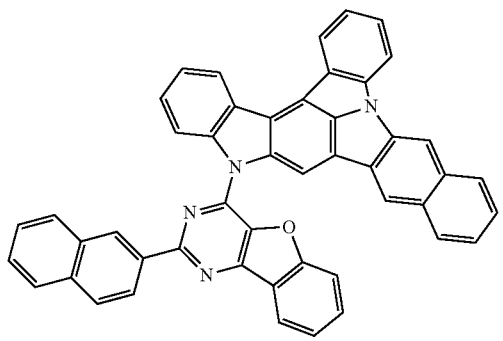
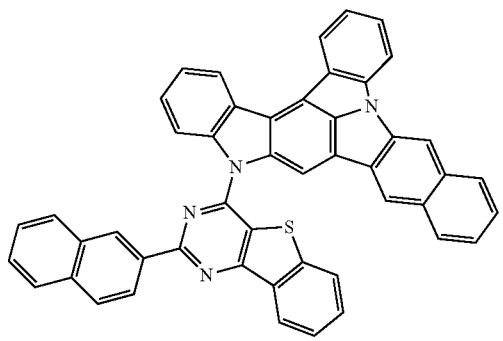
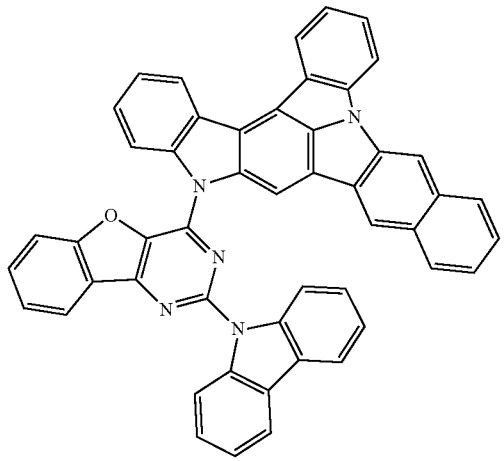
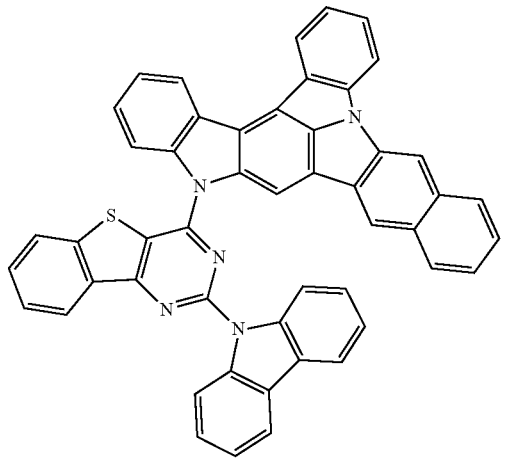

-continued
181
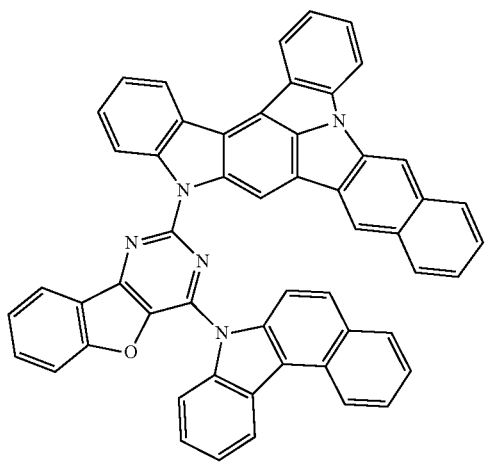
182
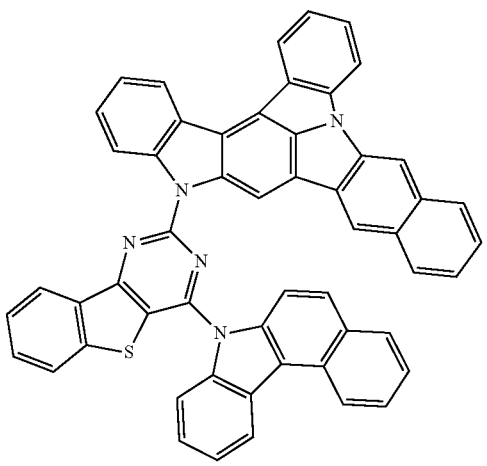
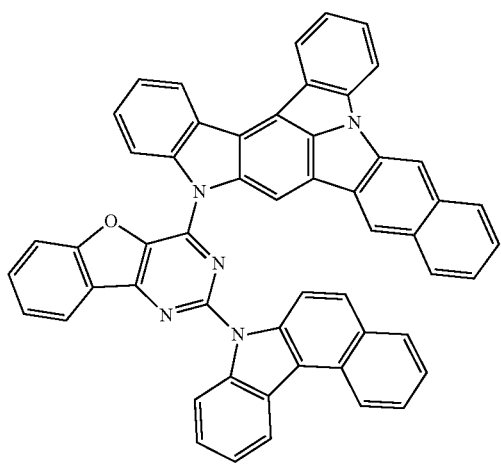
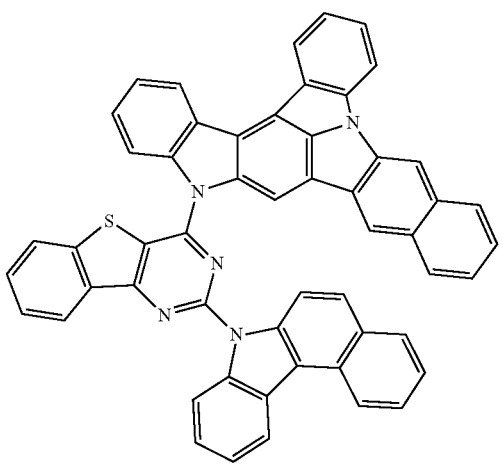
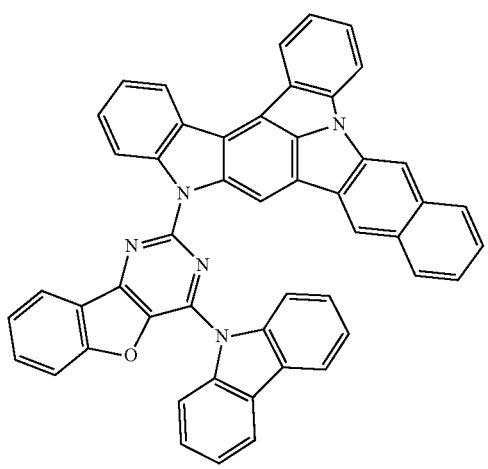
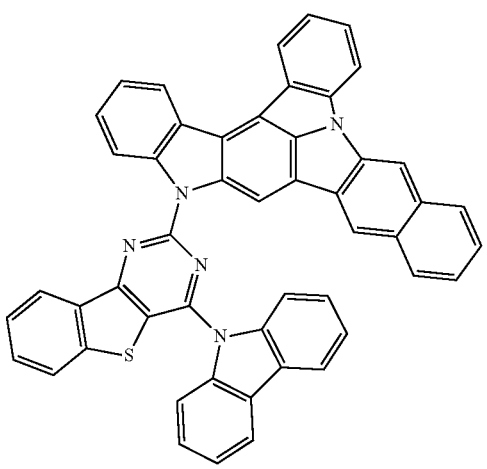

-continued
183
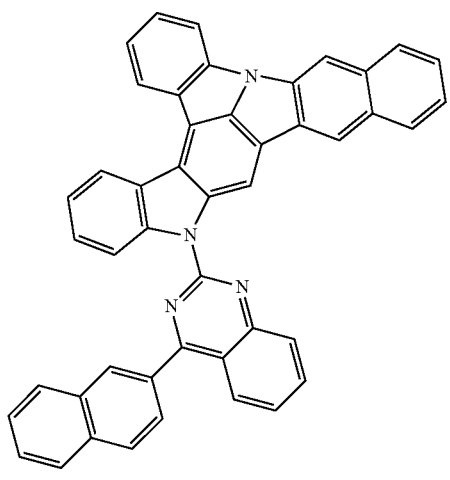
184
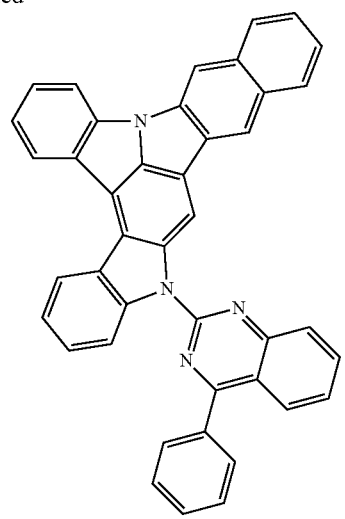
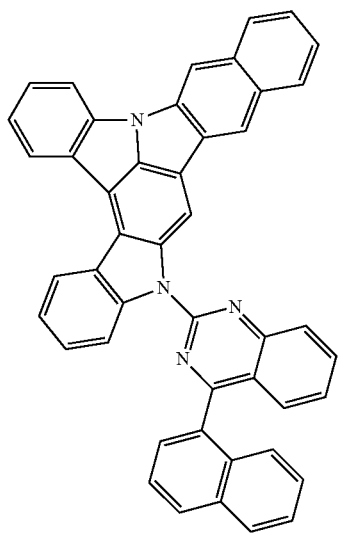
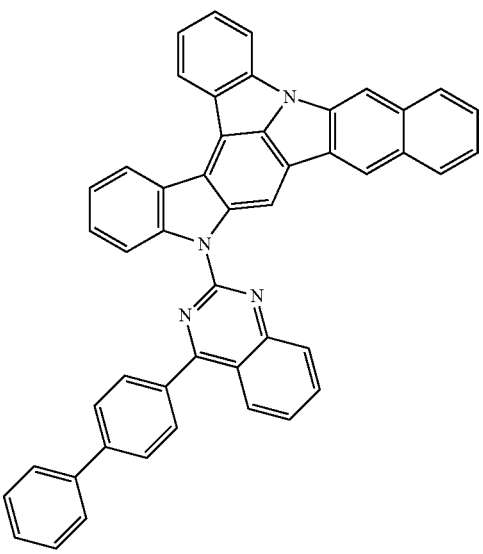
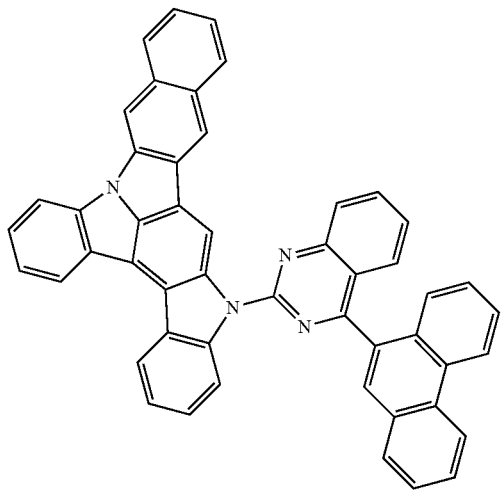
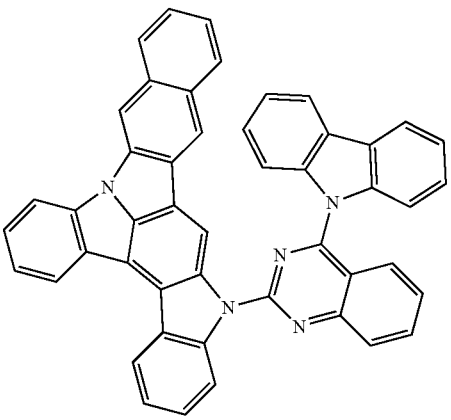

185 186
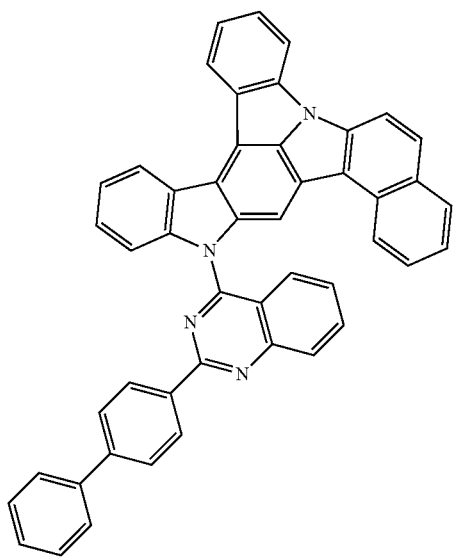
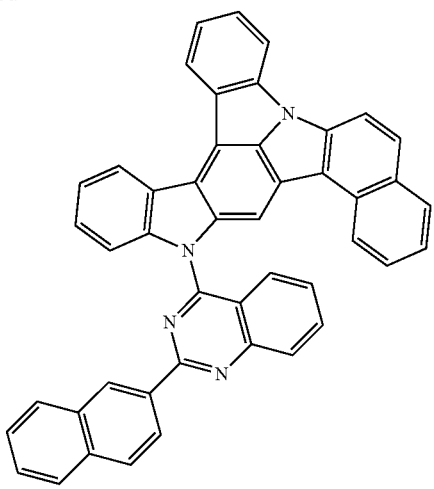
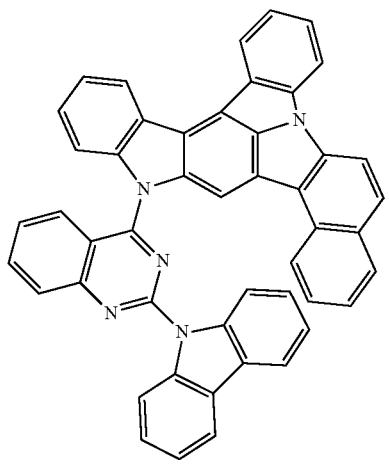
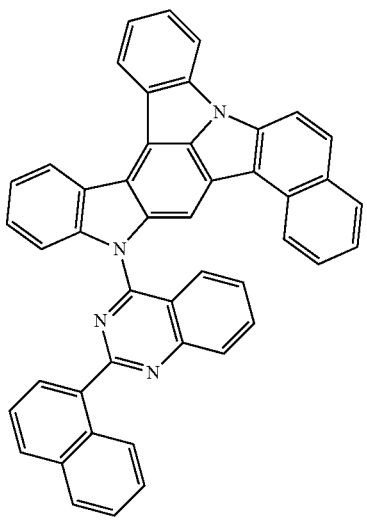
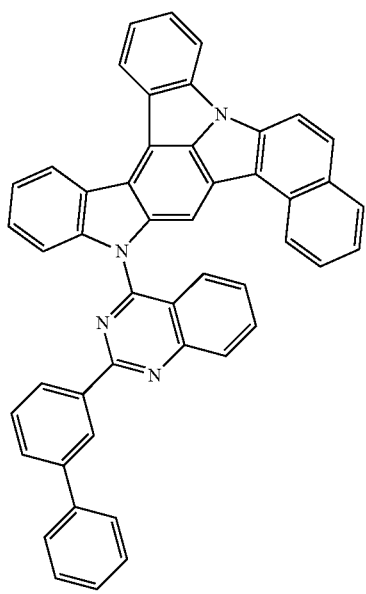
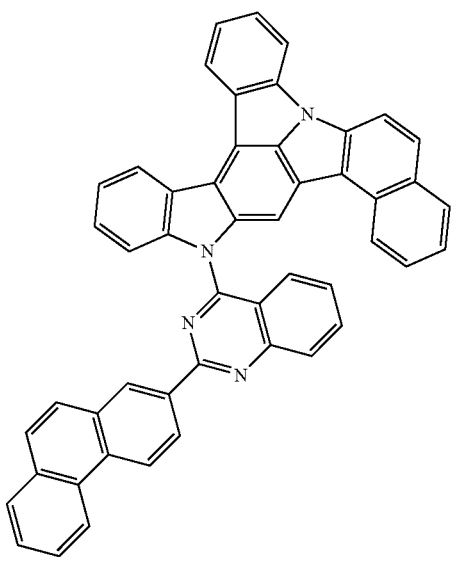

-continued
187
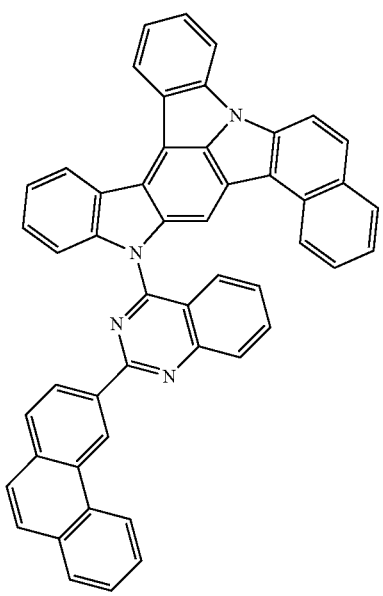
188
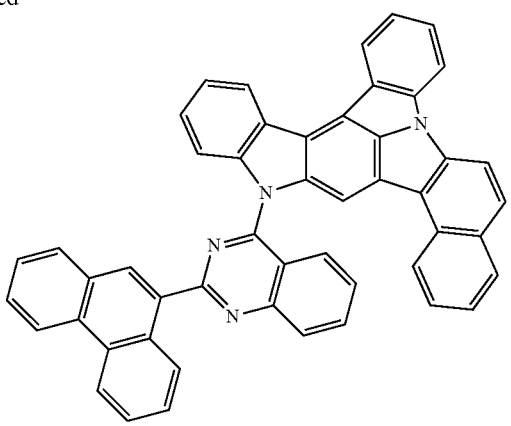
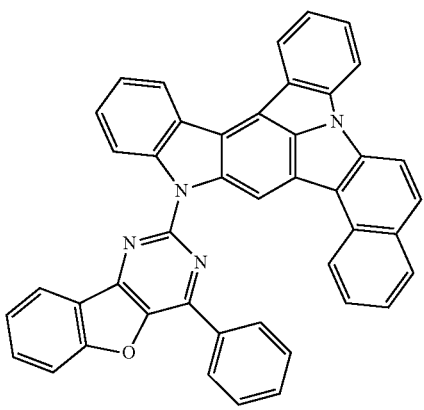
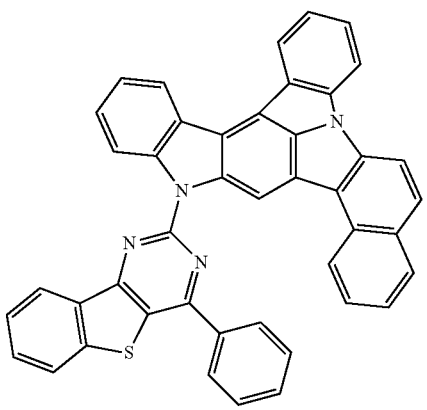
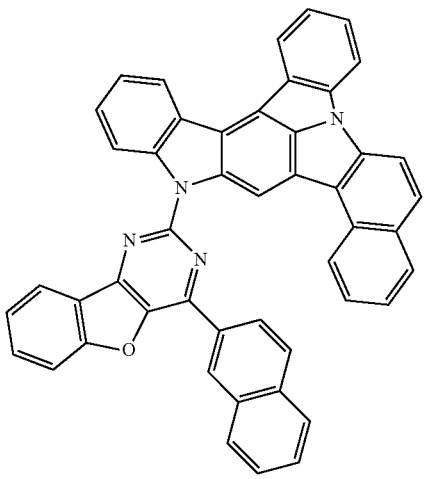
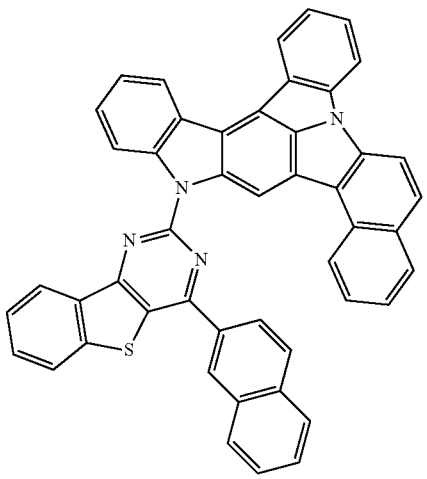

-continued
189
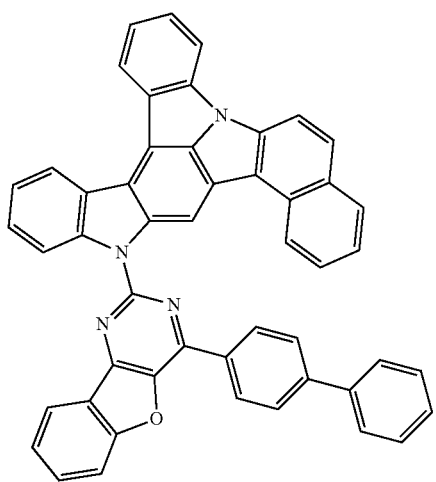
190
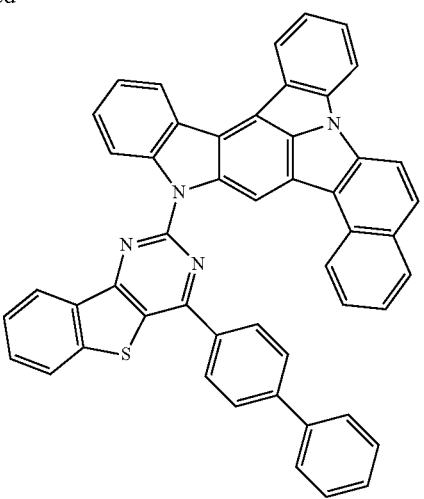
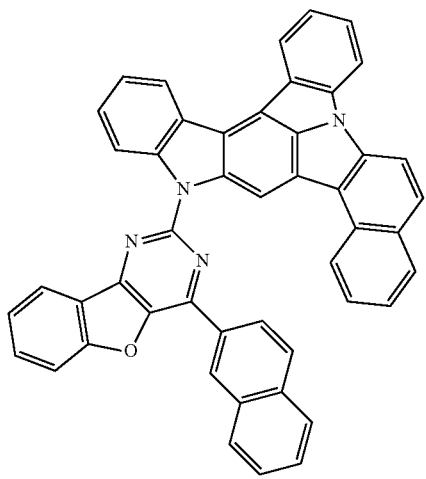
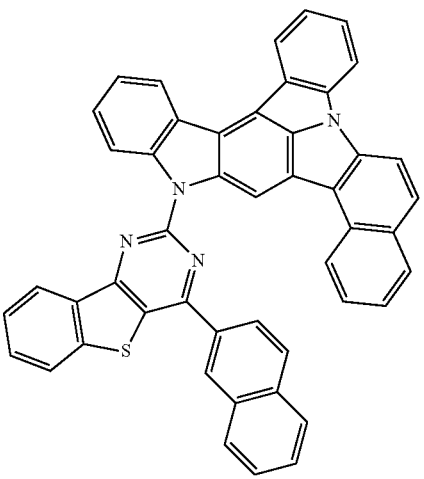
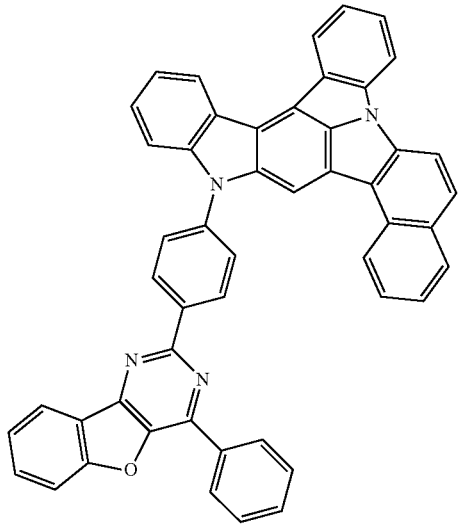
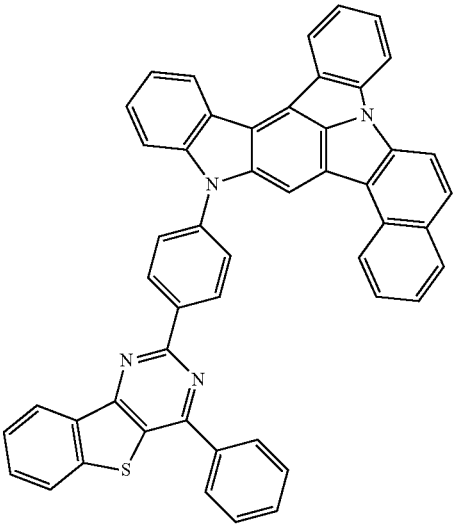

-continued
191
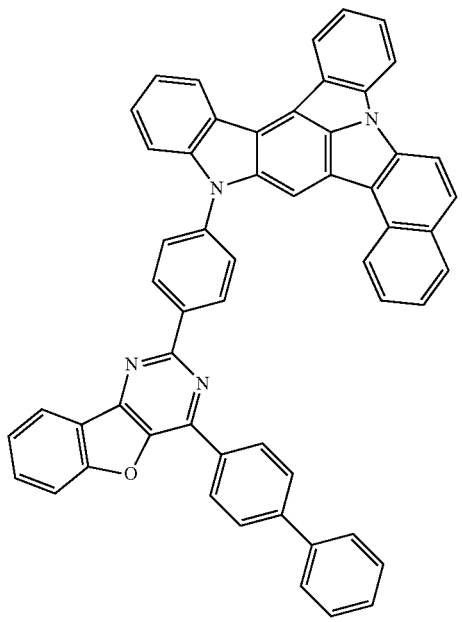
192
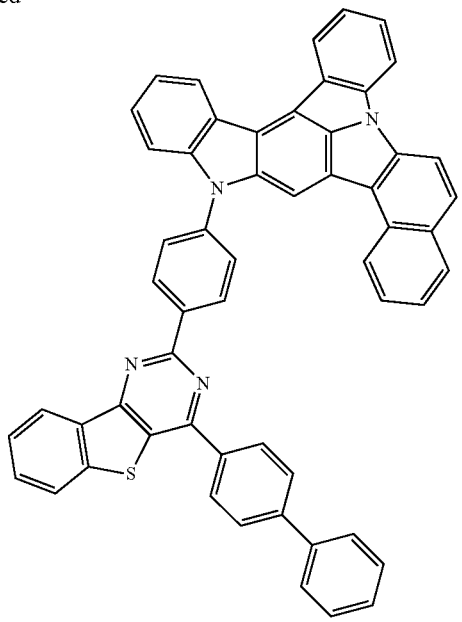
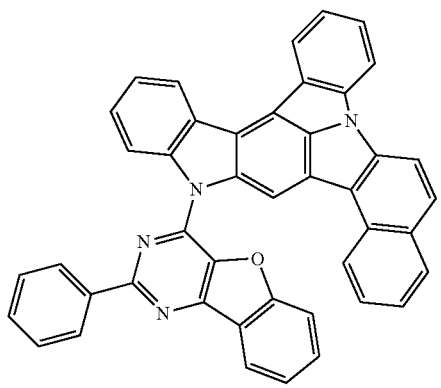
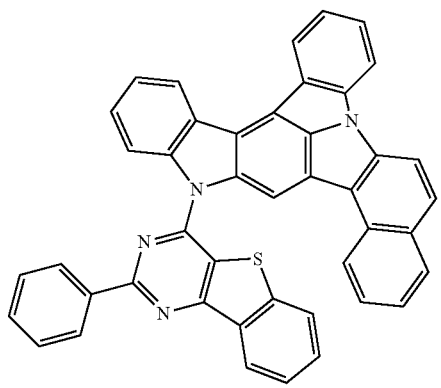
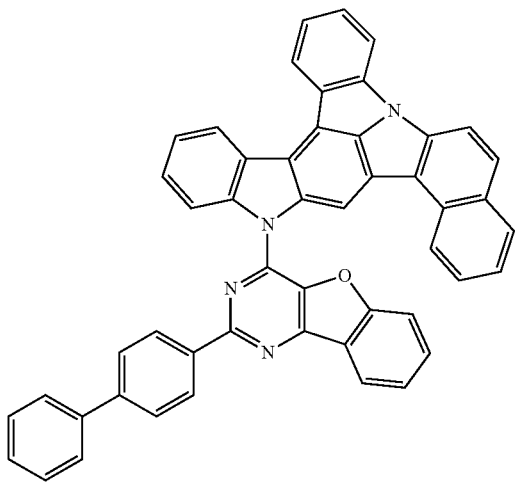
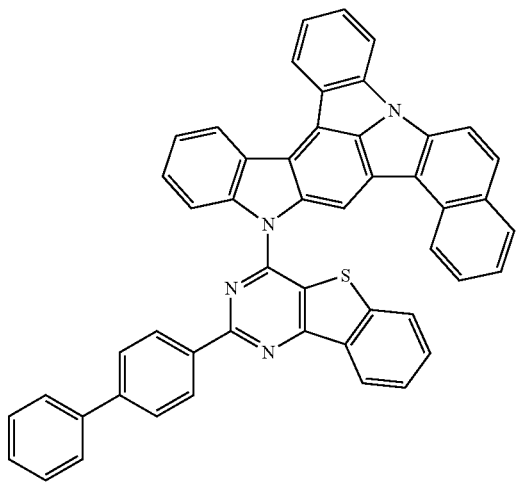

-continued
193
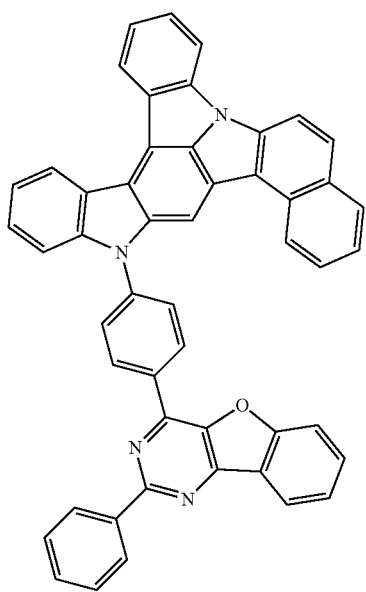
194
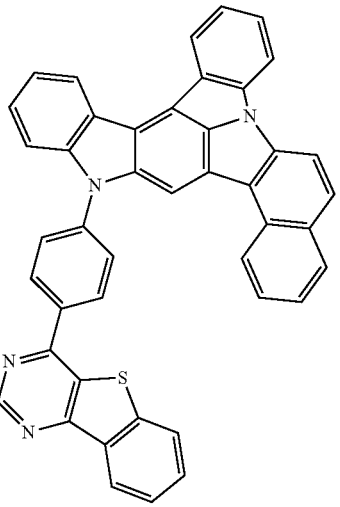
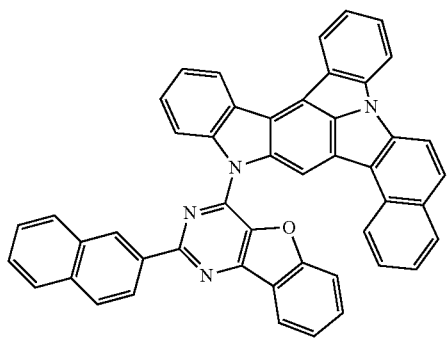
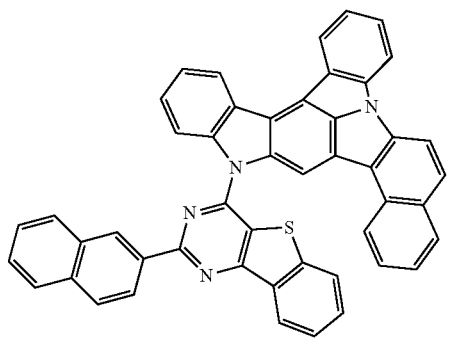
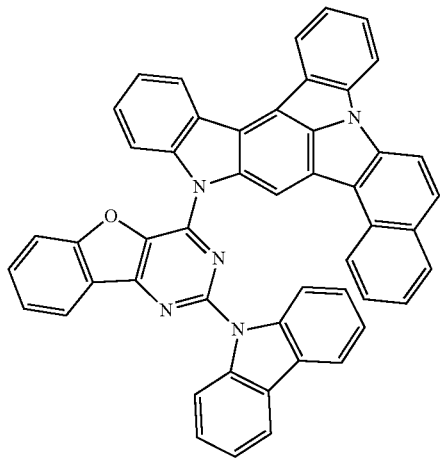
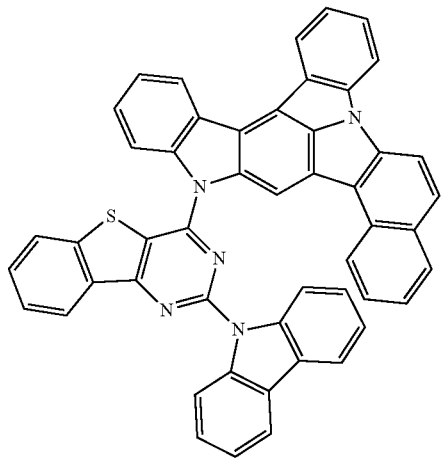

-continued
195
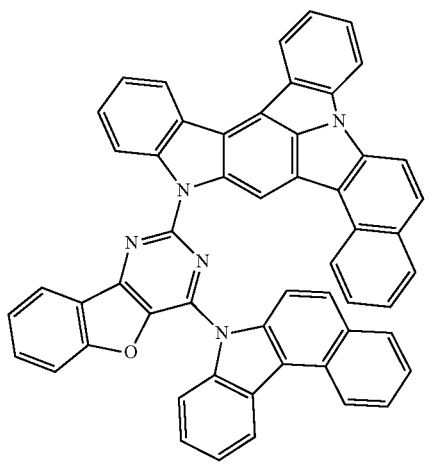
196
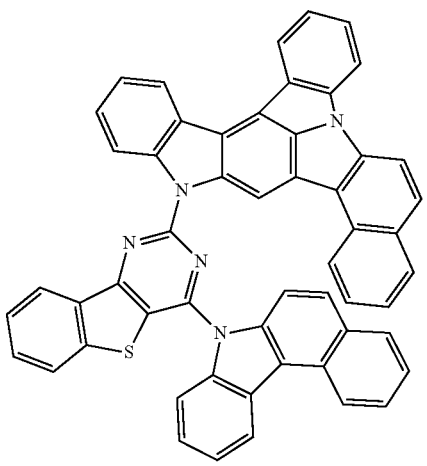
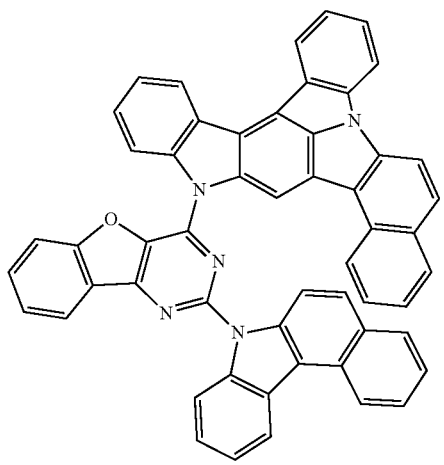
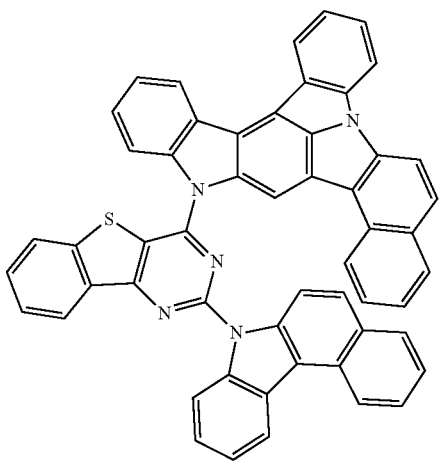
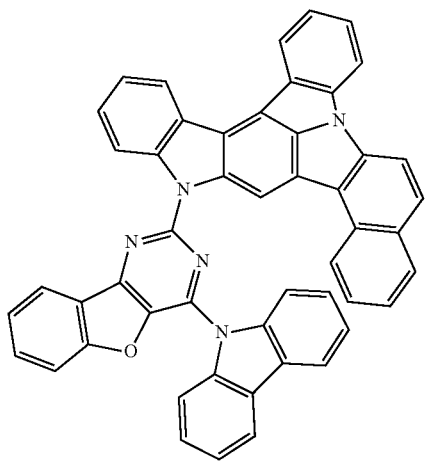
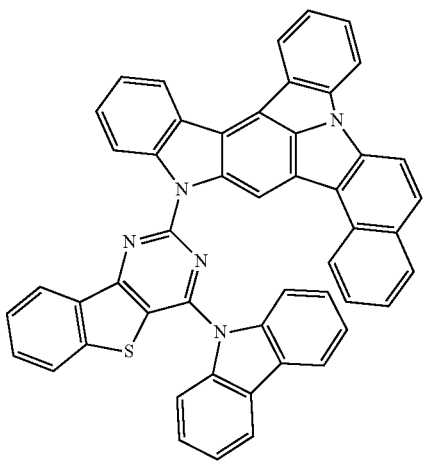

-continued
197
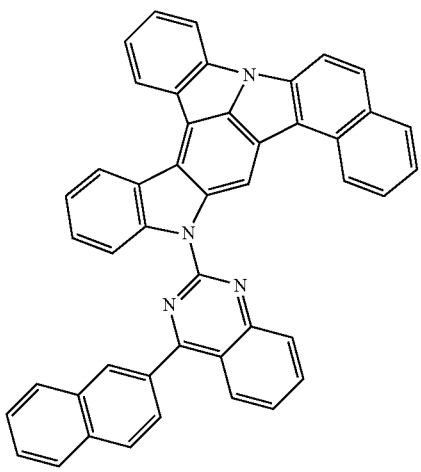
198
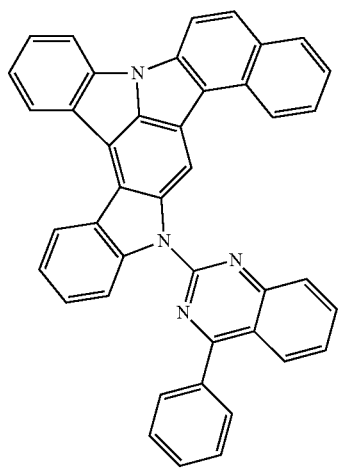
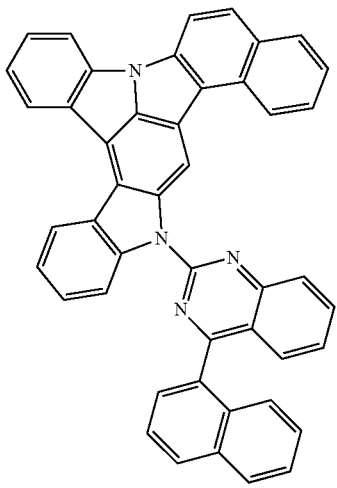
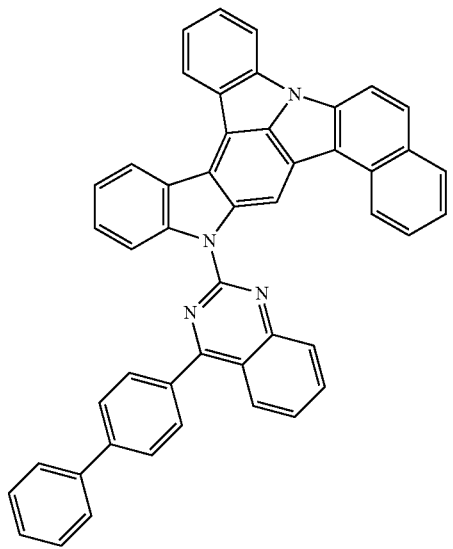
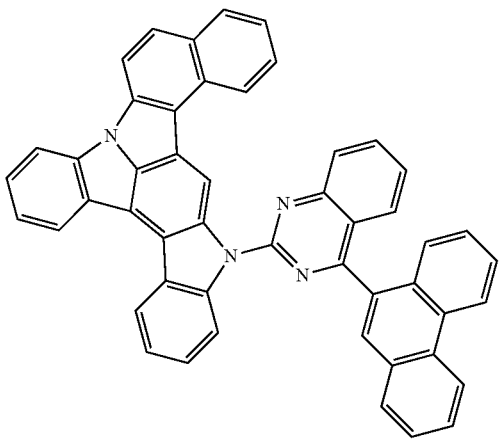
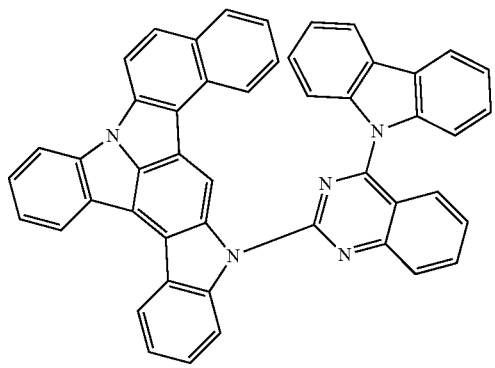

199
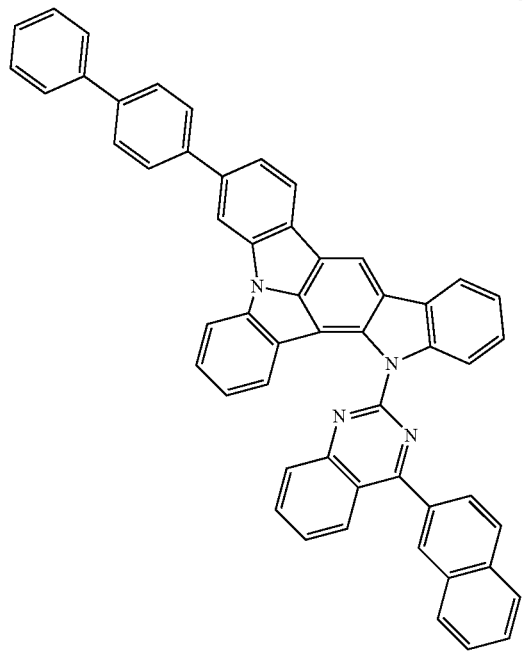
200
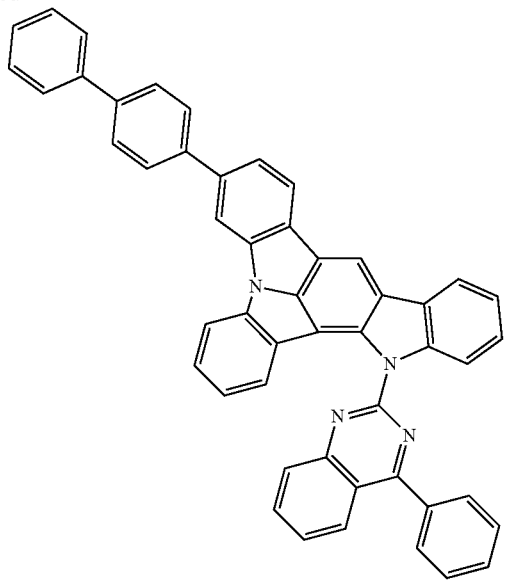
-continued
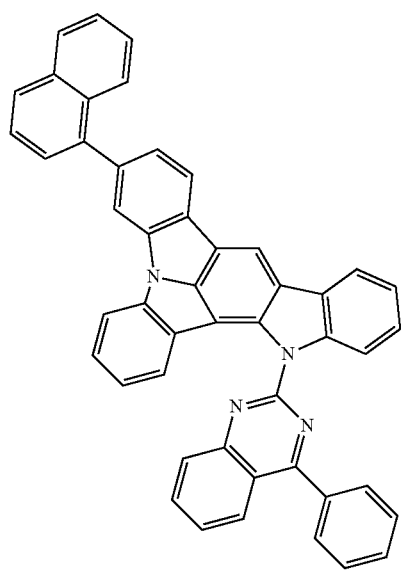
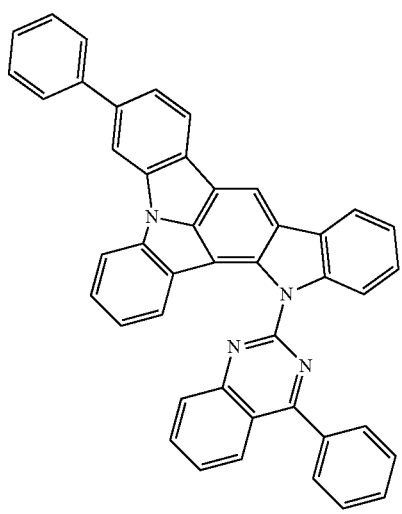

-continued
201
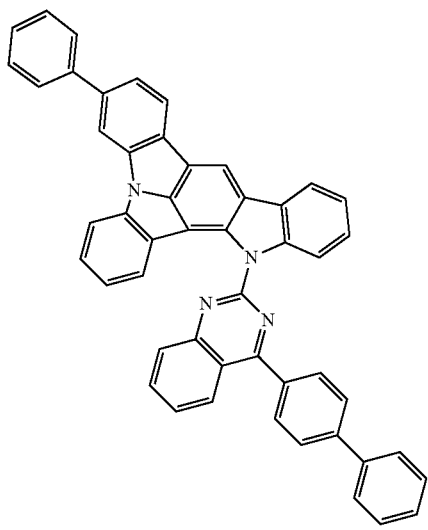
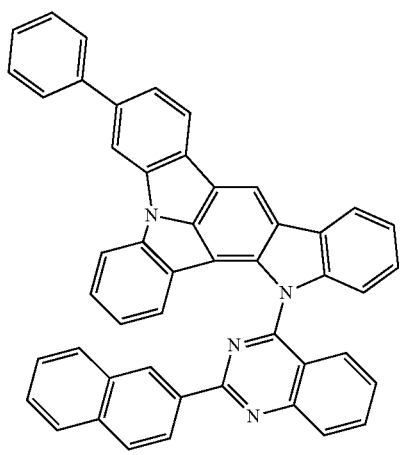
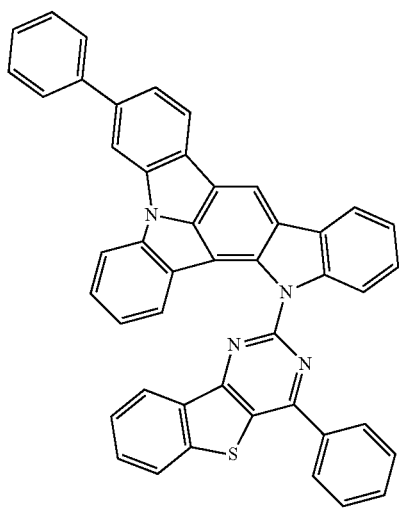
202
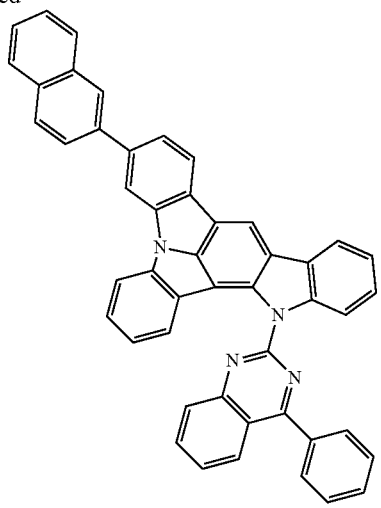
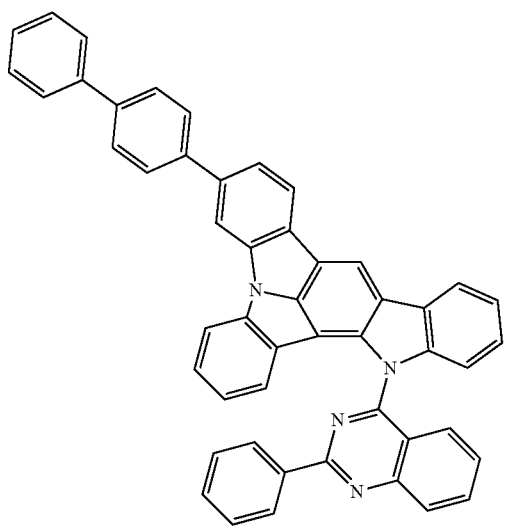
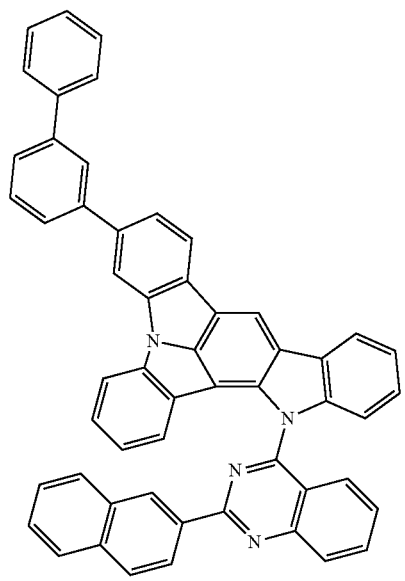

203
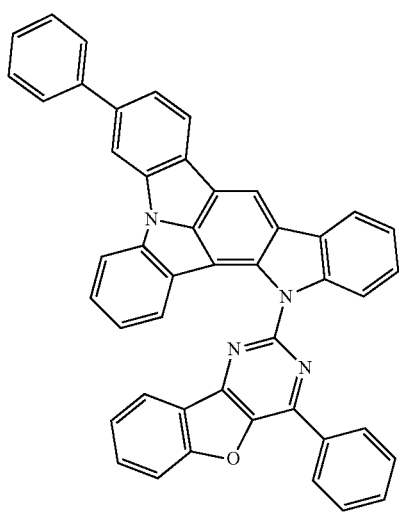
-continued
204
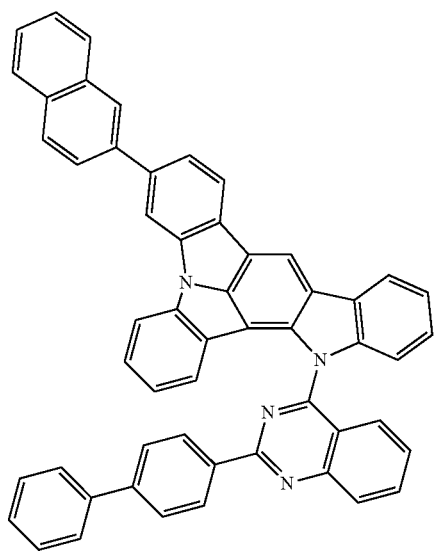
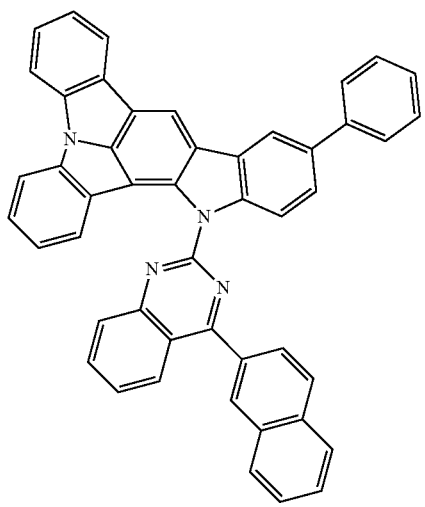
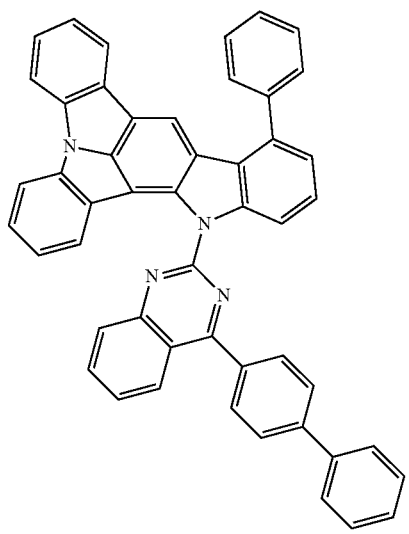
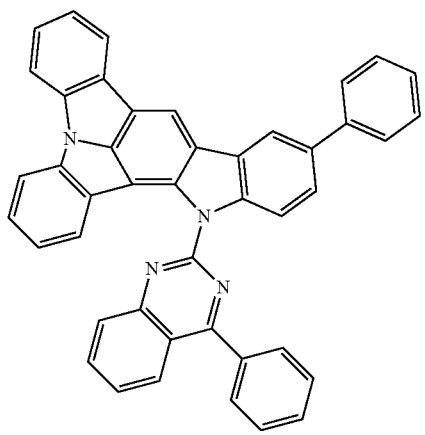
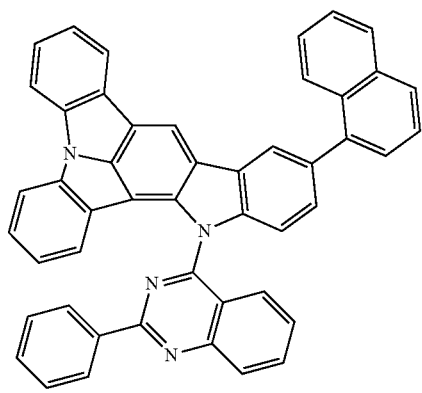

-continued
205
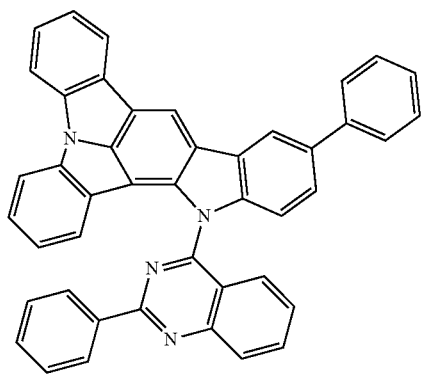
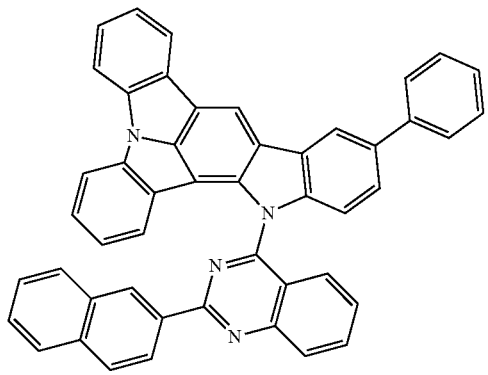
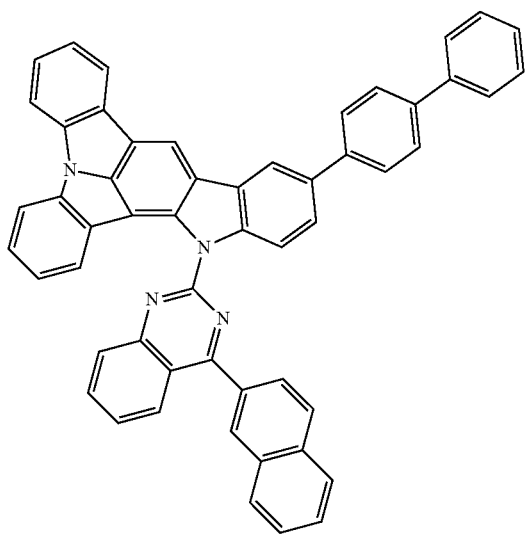
206
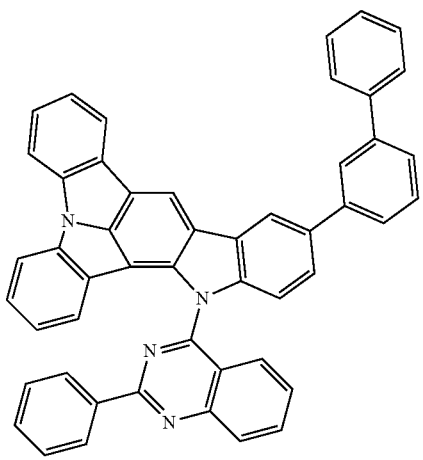
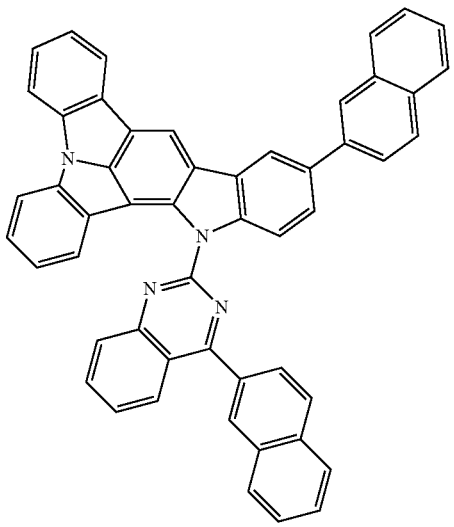
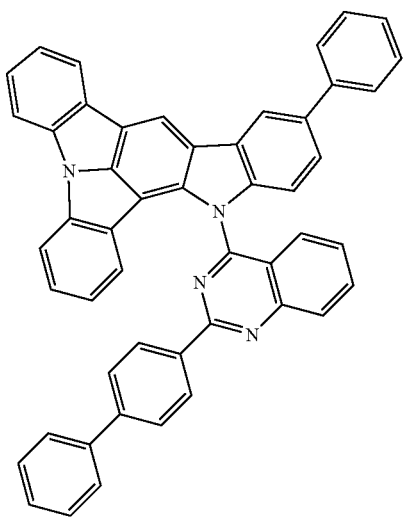

-continued
| 207 | 208 |
|---|---|
| 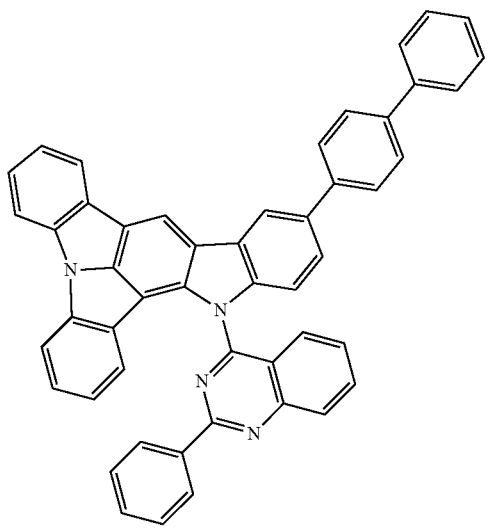 | 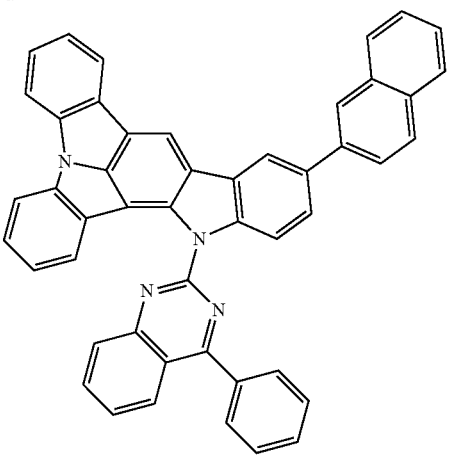 |
| 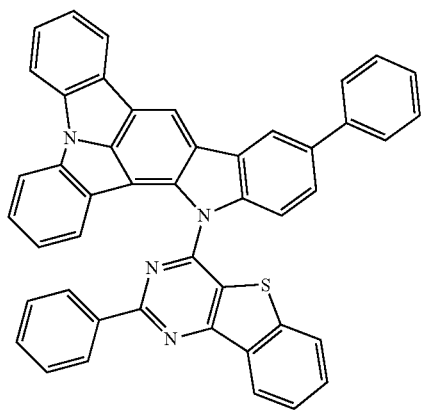 | 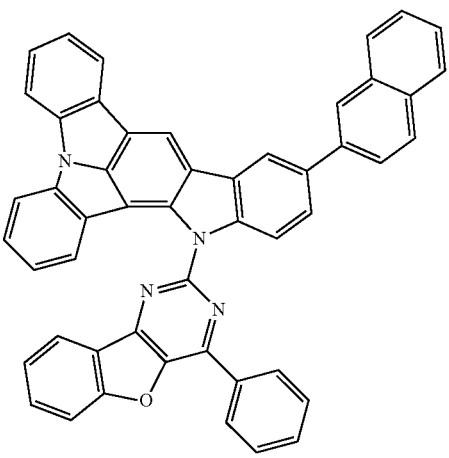 |
| 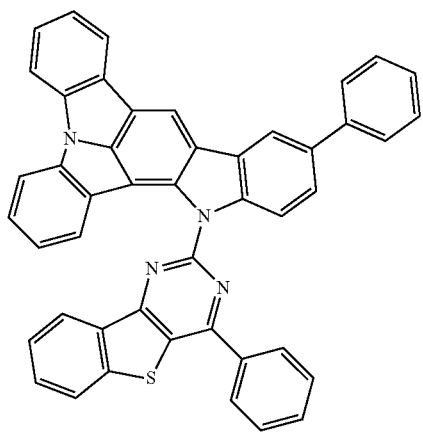 | 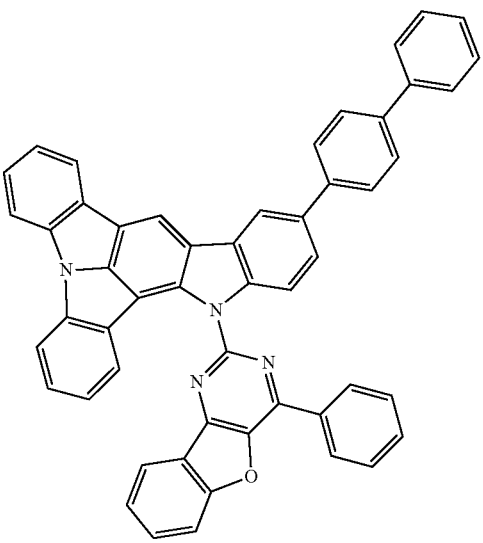 |

-continued
| 209 | 210 |
|---|---|
| 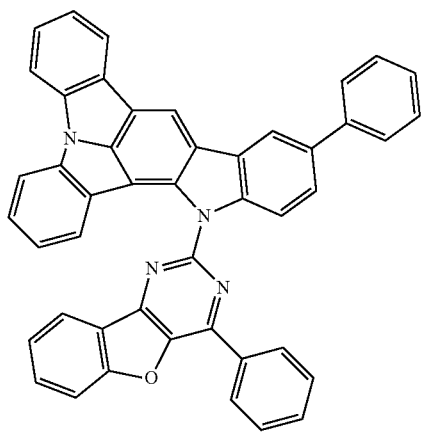 | 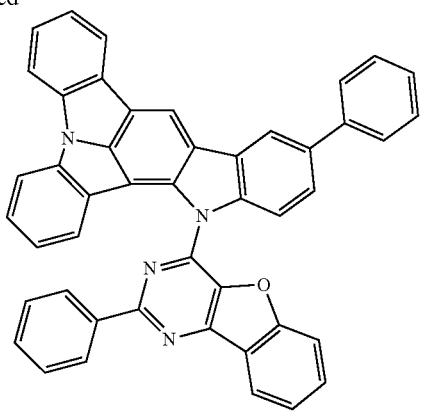 |
| 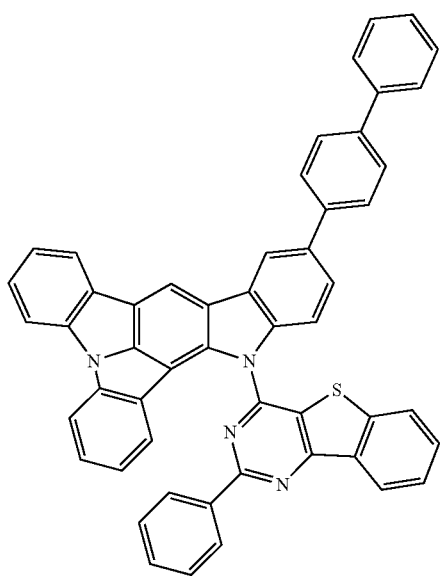 | 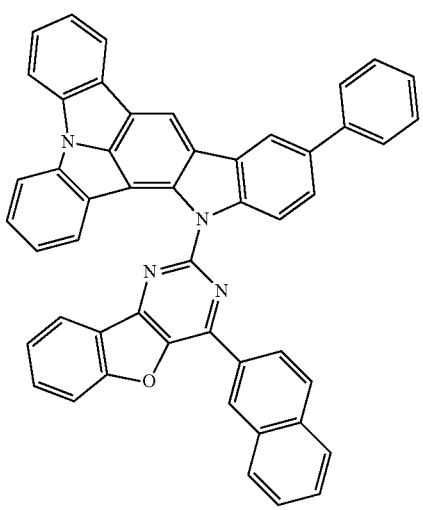 |
| 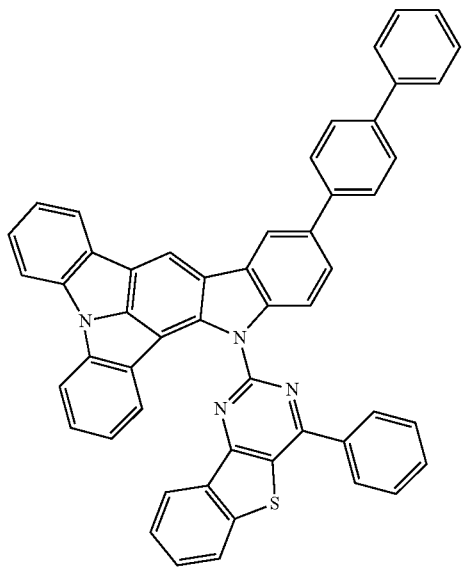 | 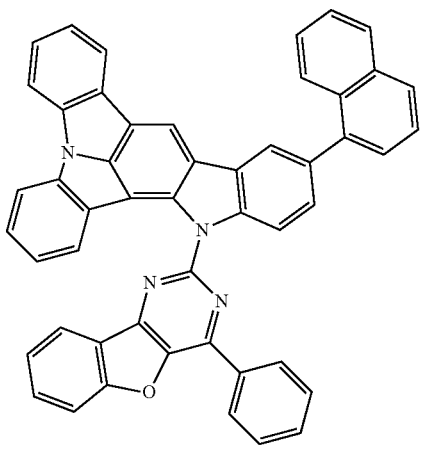 |

-continued
211
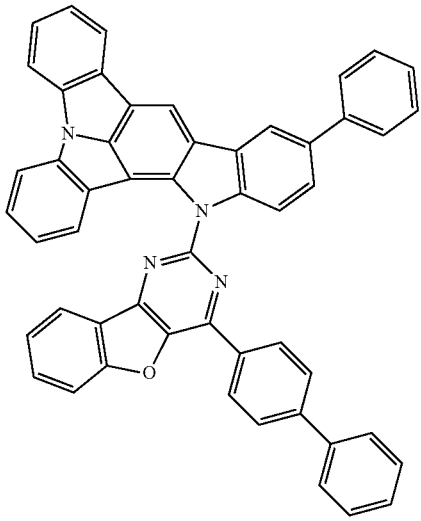
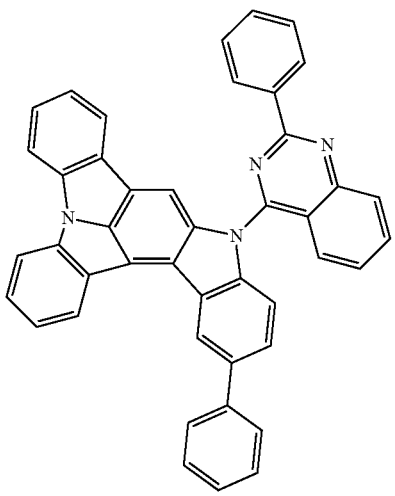
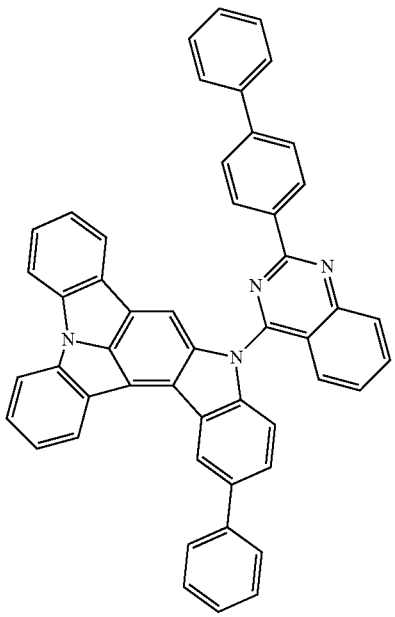
212
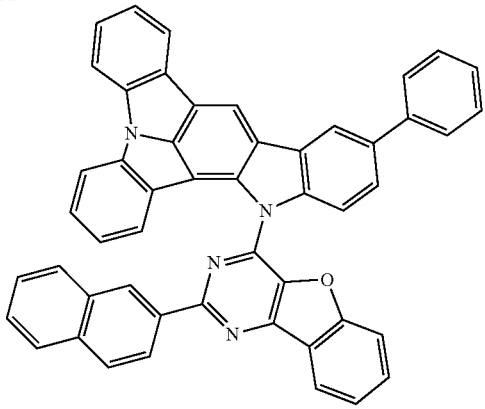
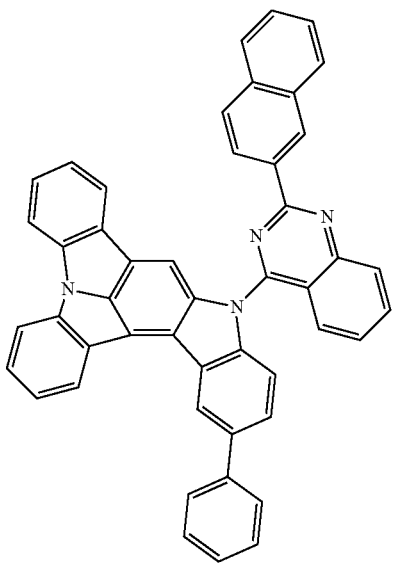
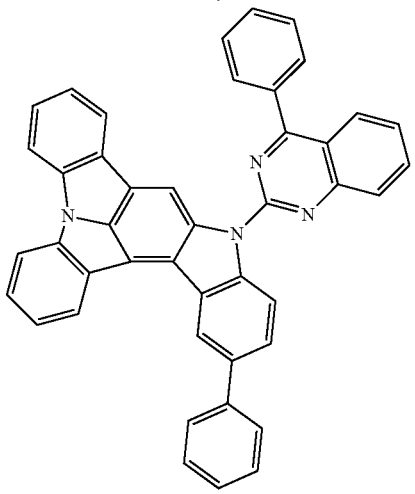

213 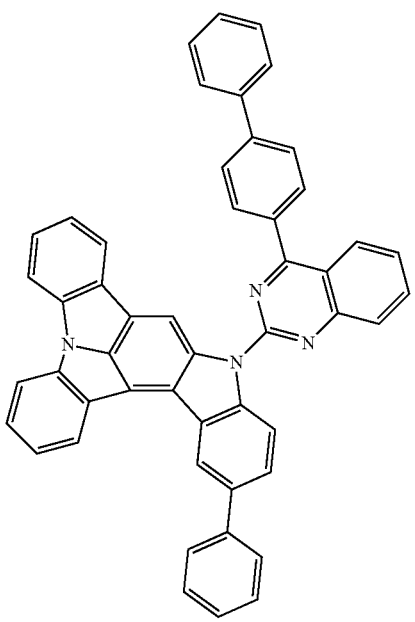
214 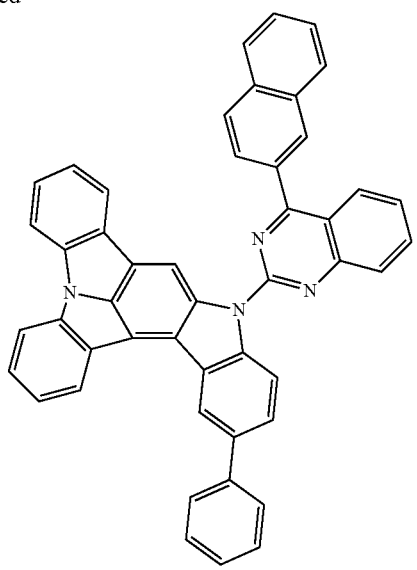
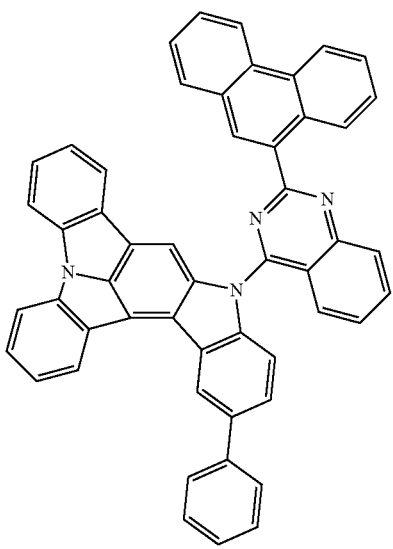
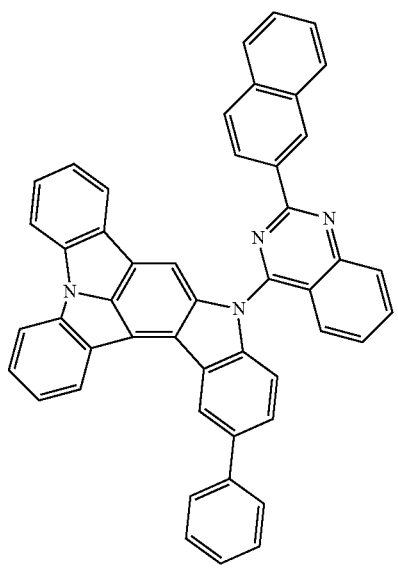

215
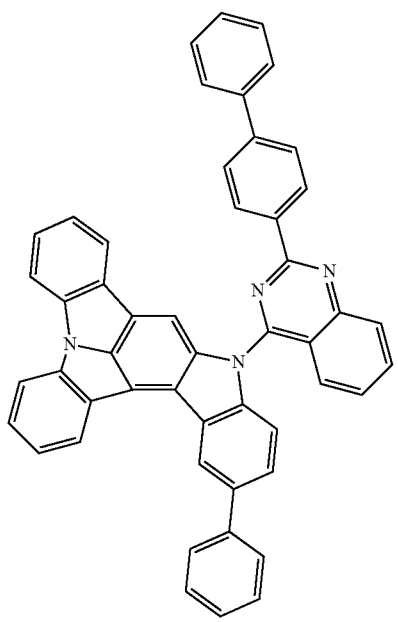
216
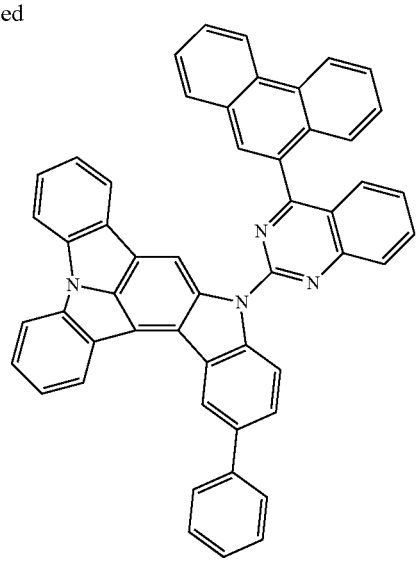
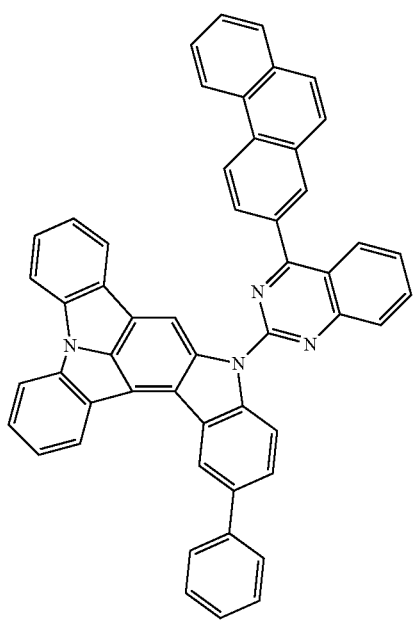
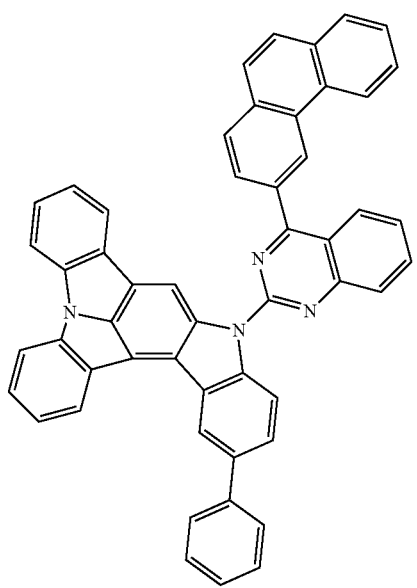

217
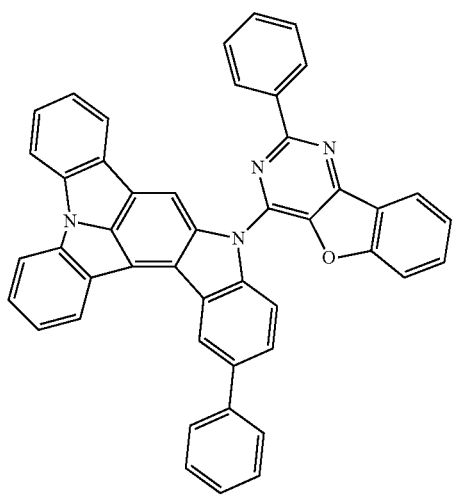
218
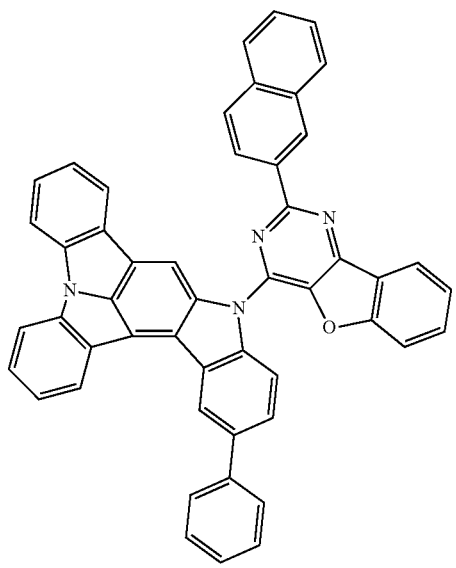
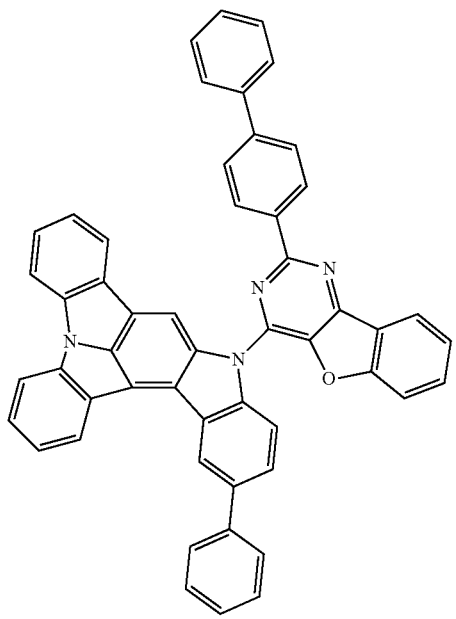
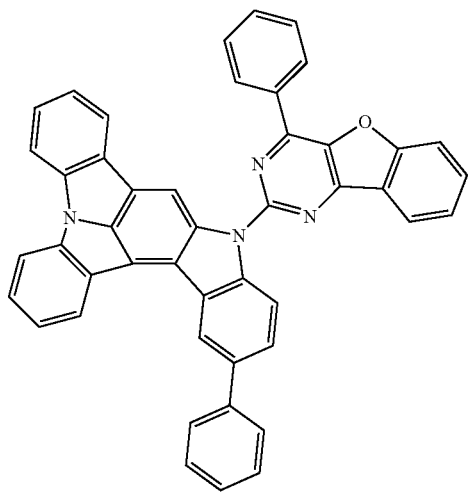

-continued
219
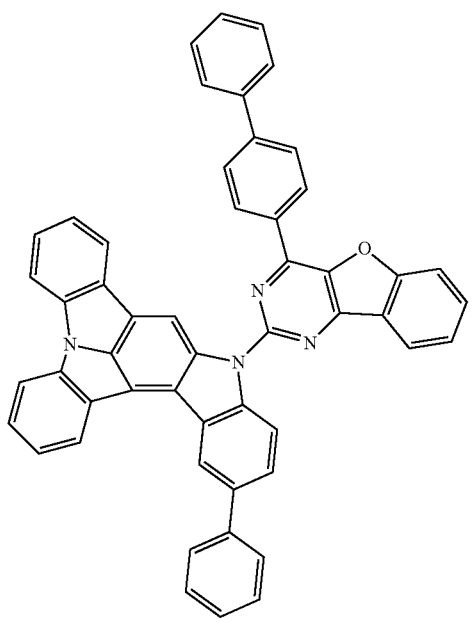
220
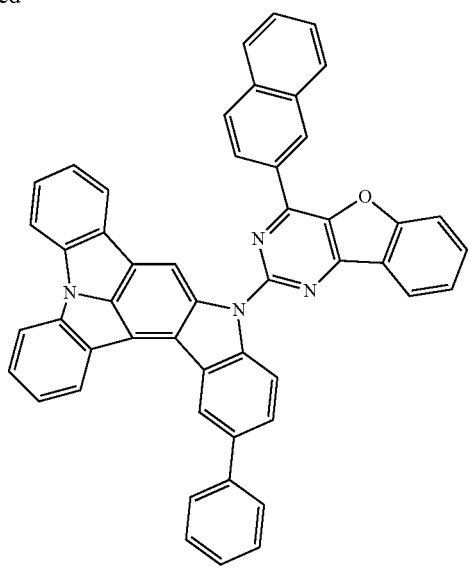
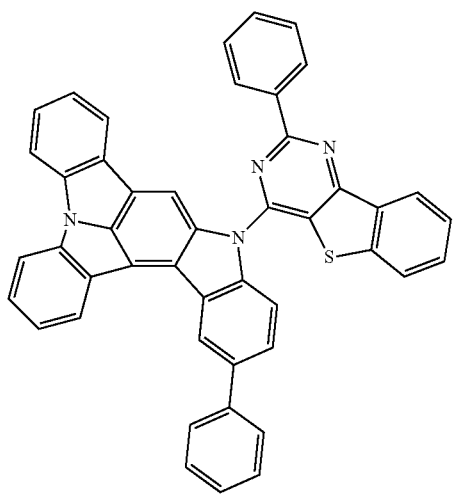
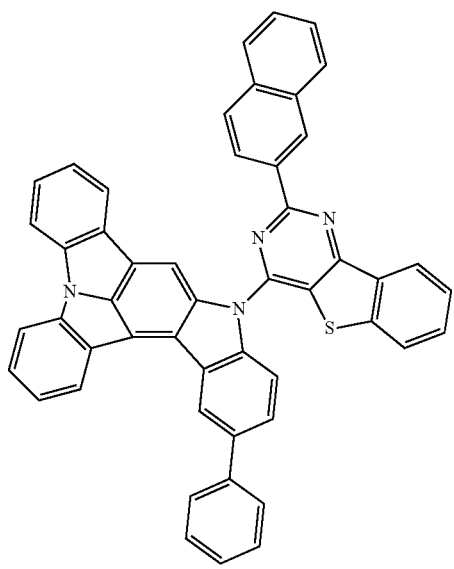

221
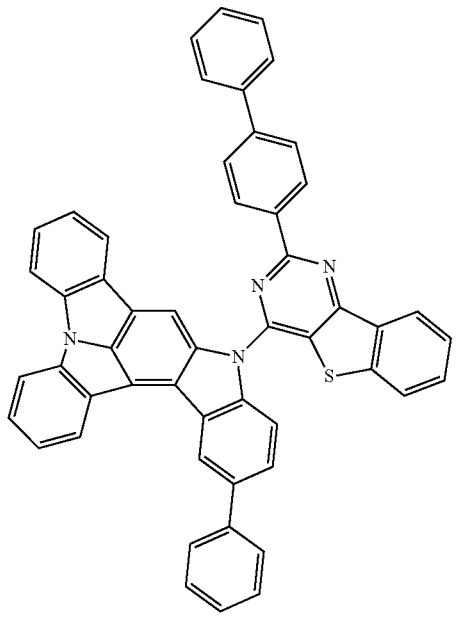
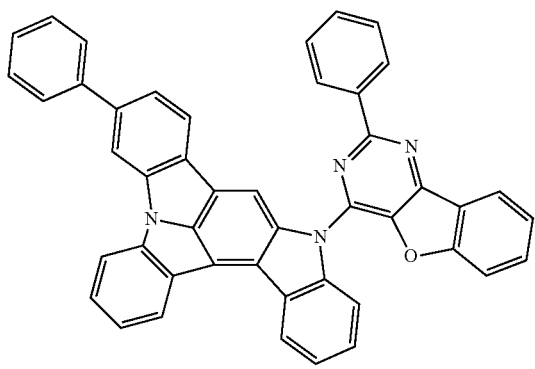
222
-continued
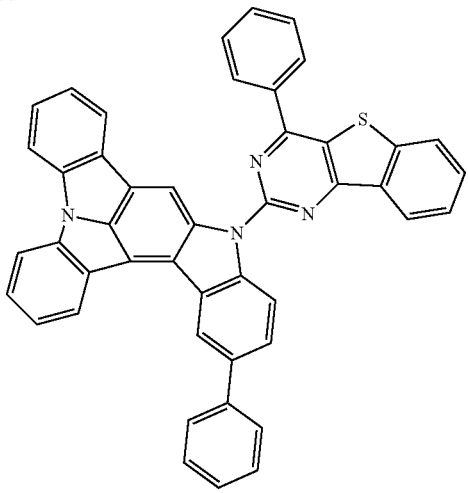
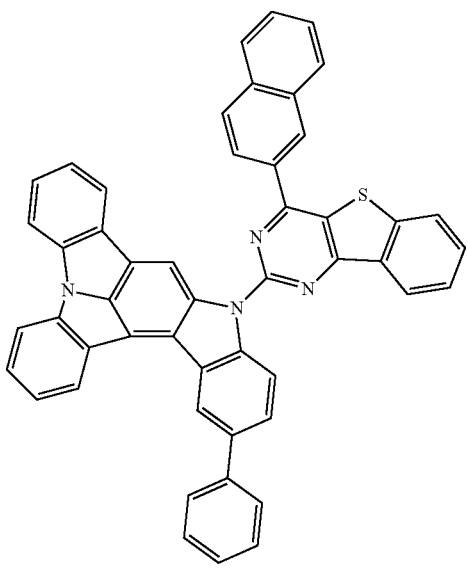
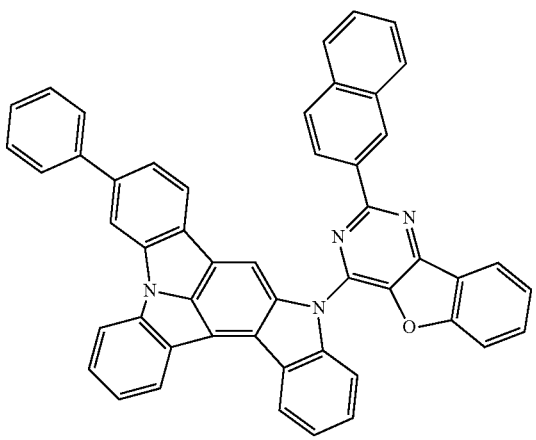

223
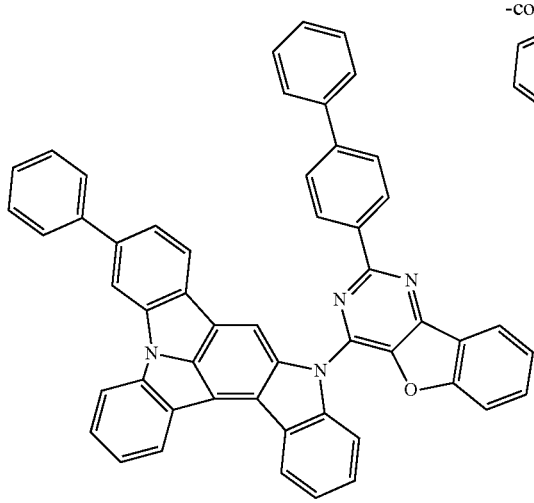
224
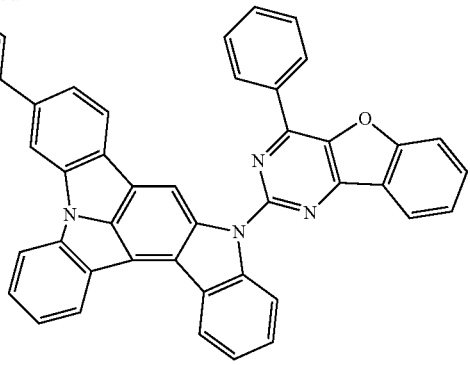
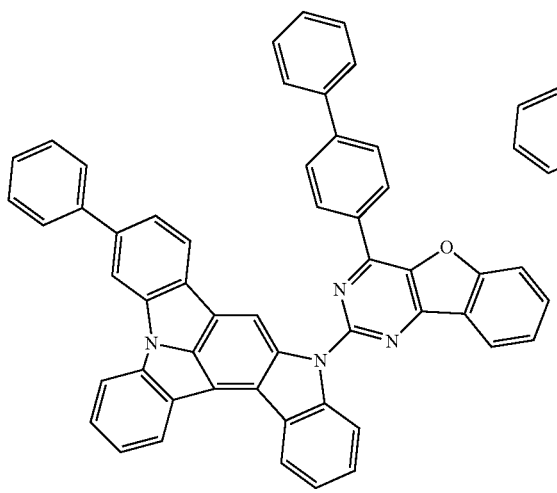
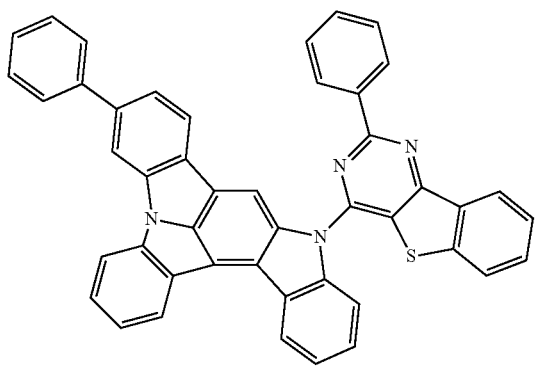
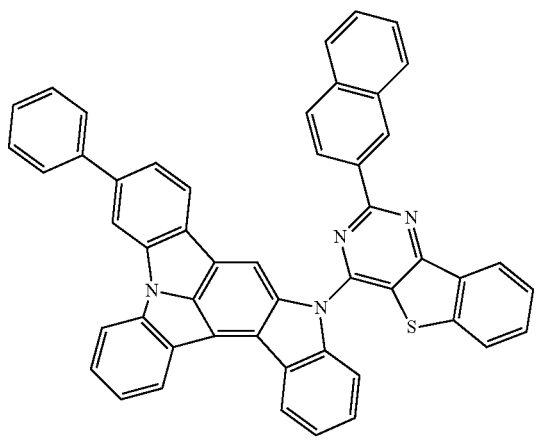

-continued
225
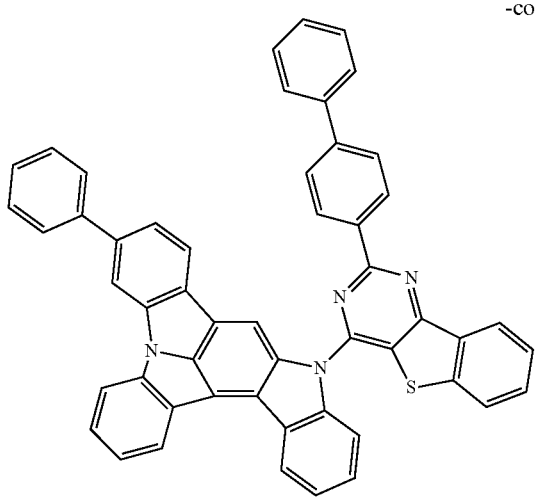
226
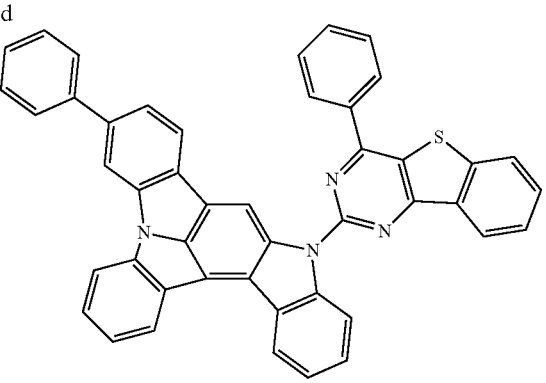
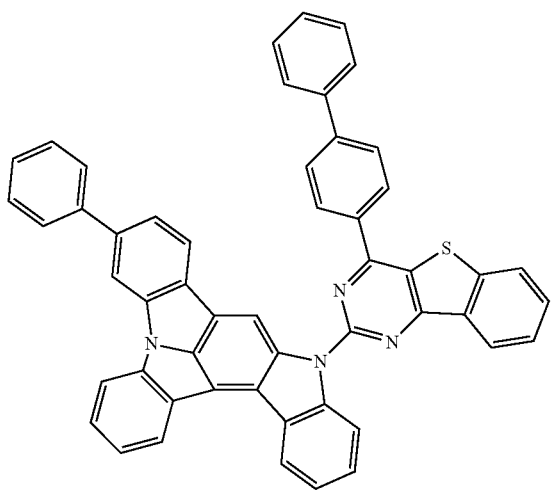
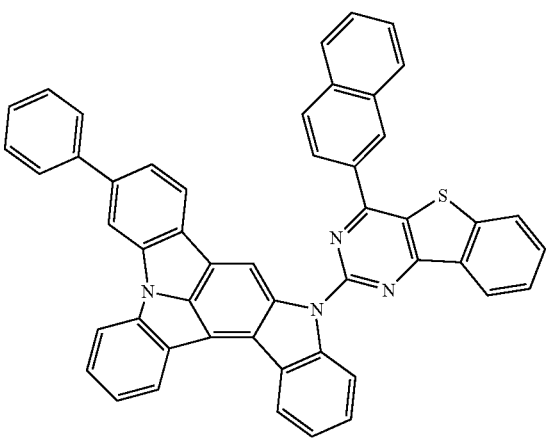
-continued
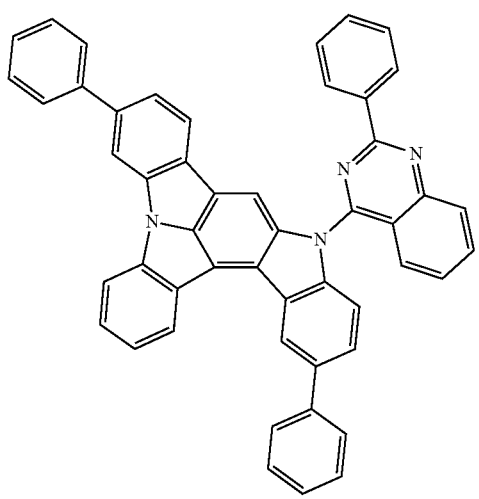
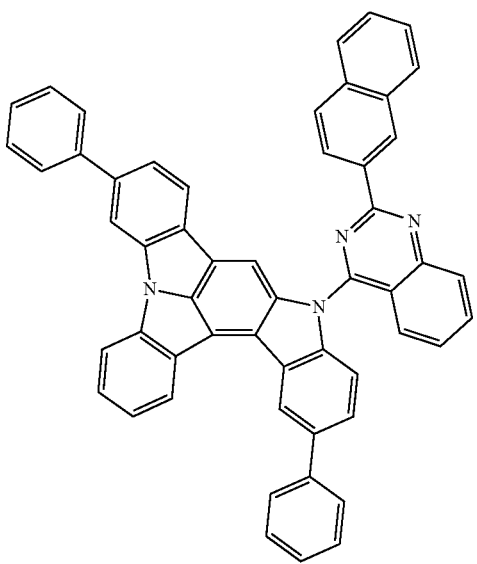

227
-continued
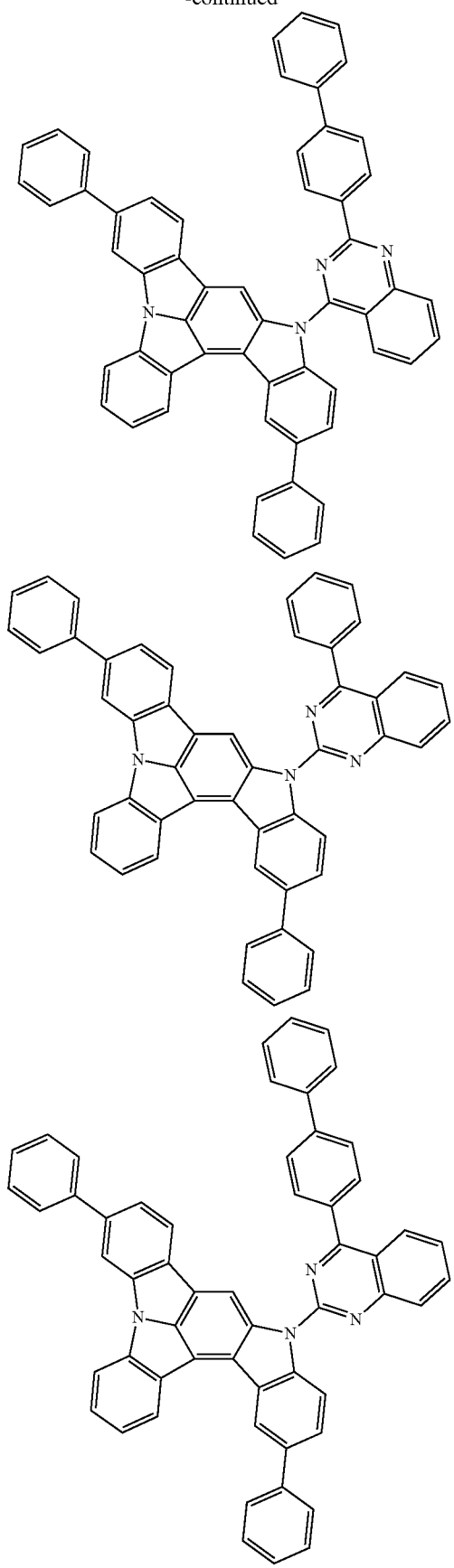
228
-continued
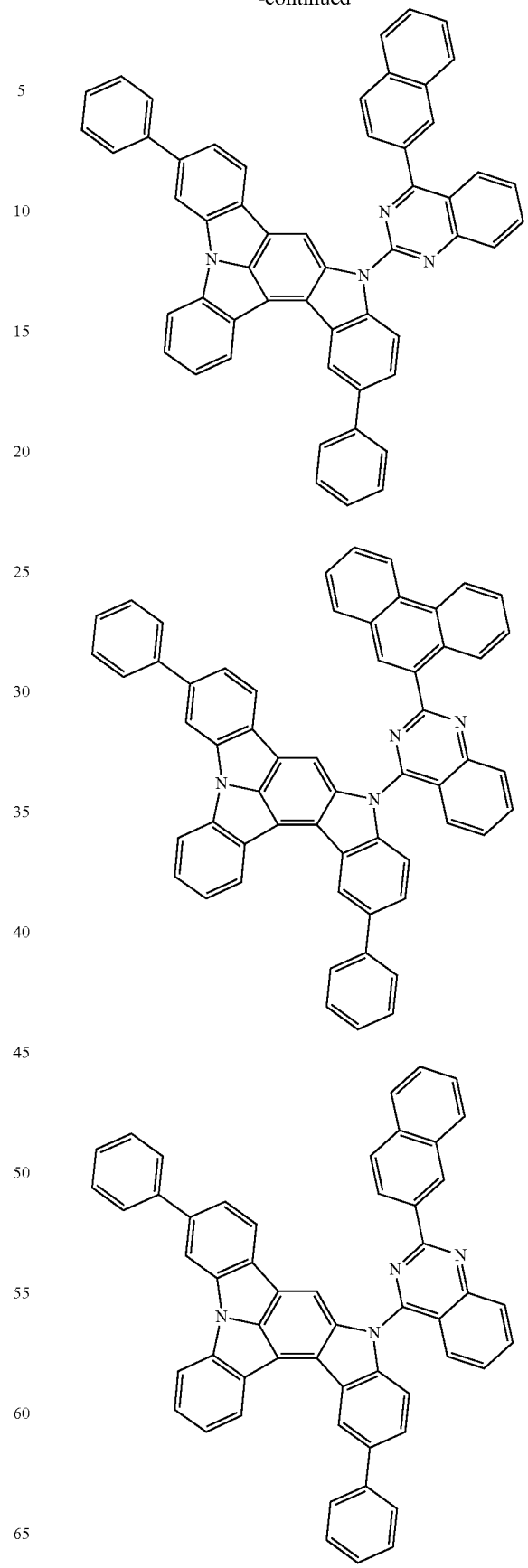

229
-continued
230
-continued
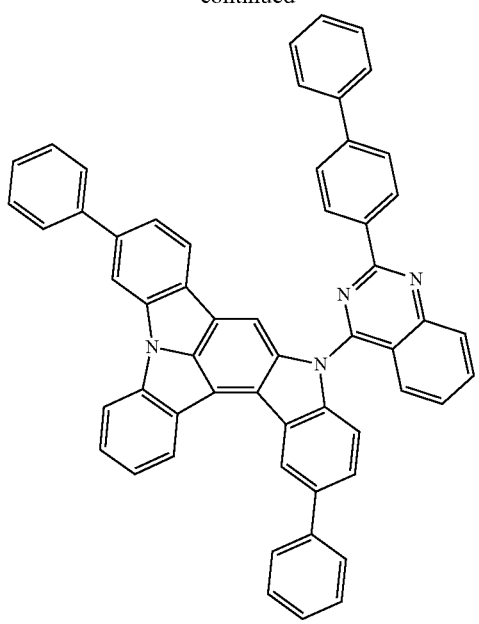

231
-continued
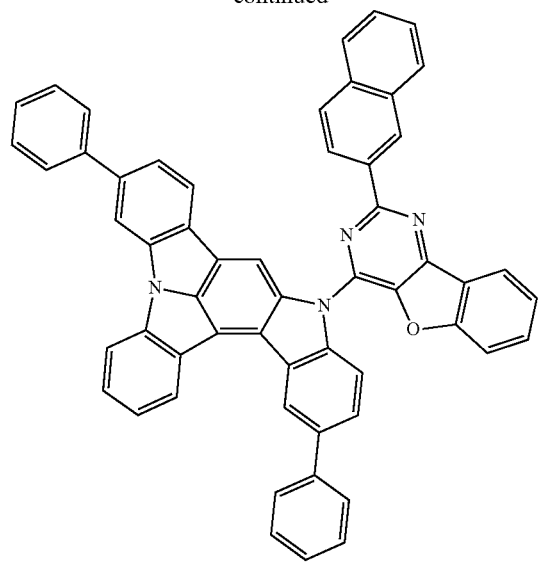
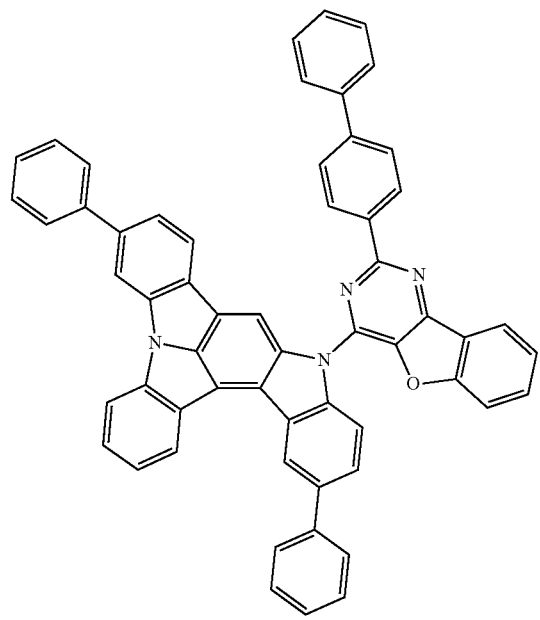
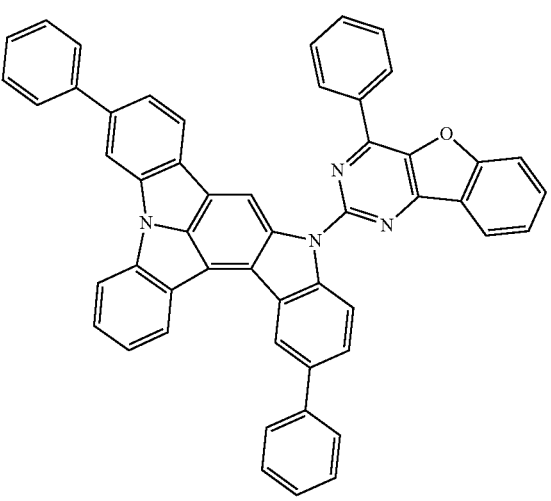
232
-continued
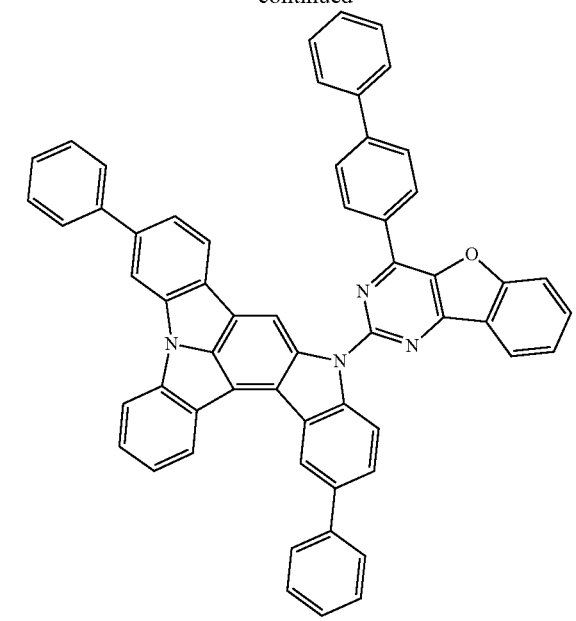
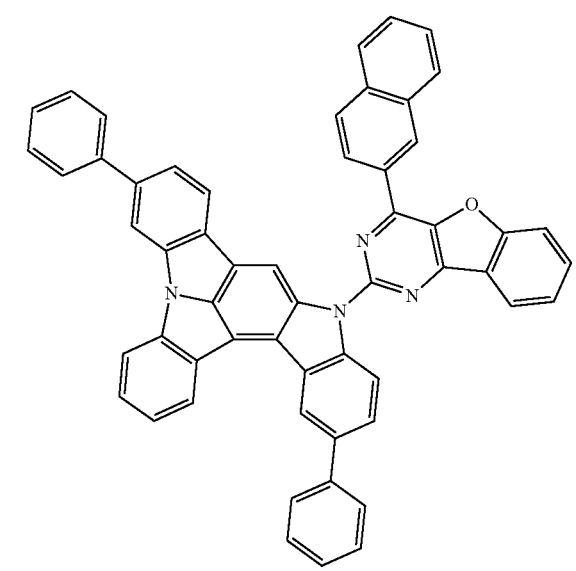
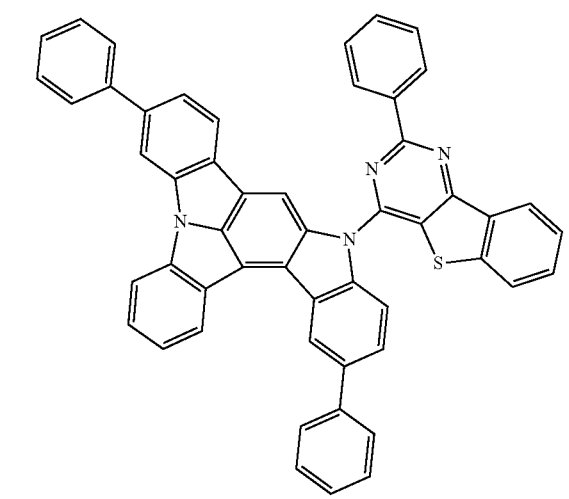

233
-continued
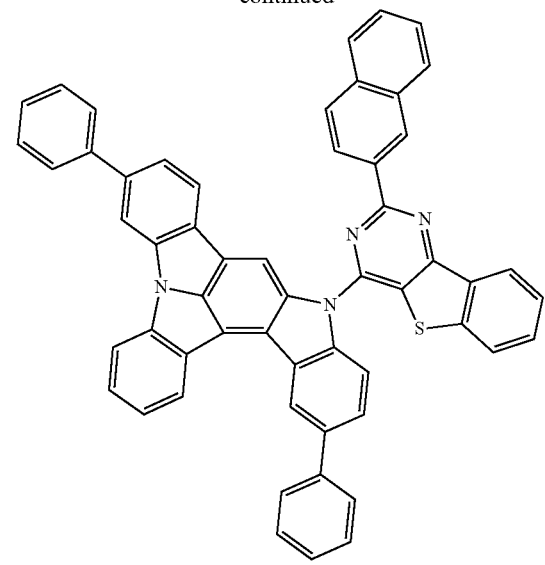
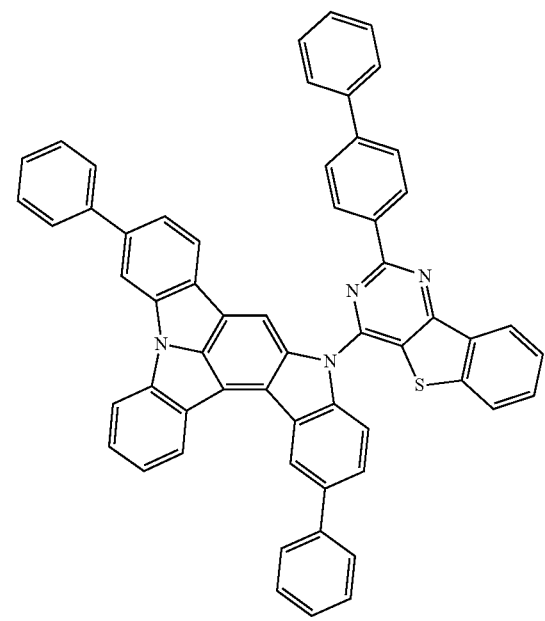
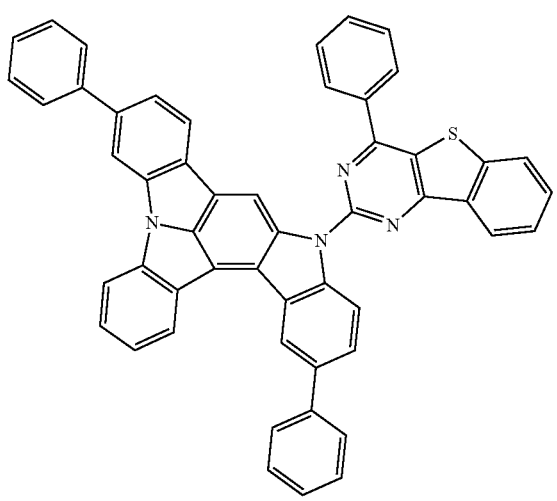
234
-continued
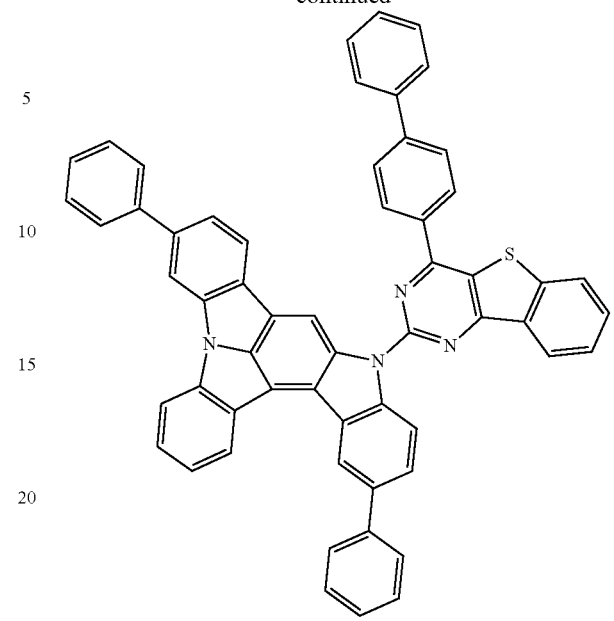
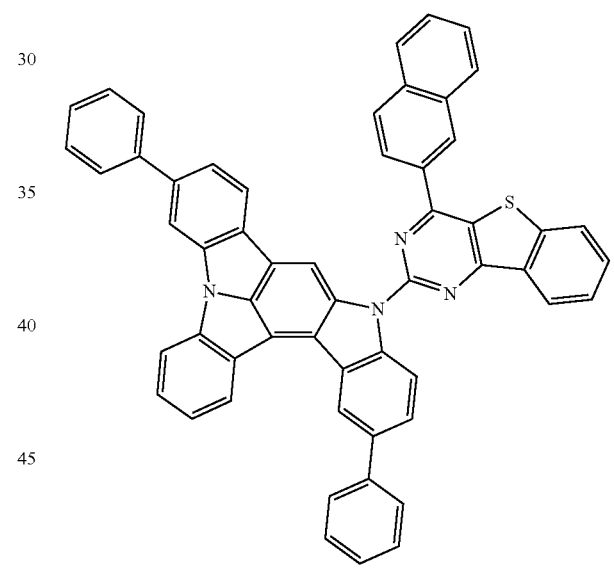
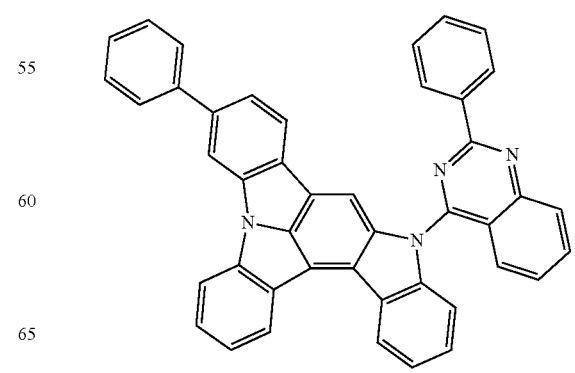

235
-continued
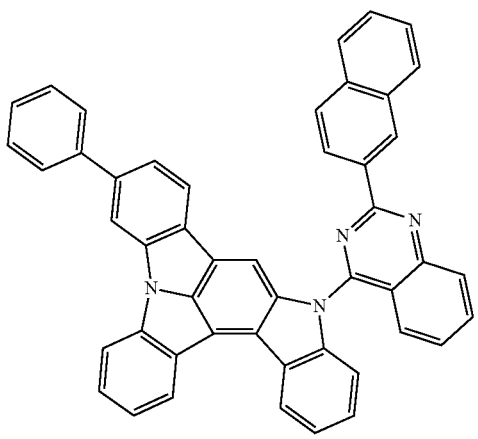
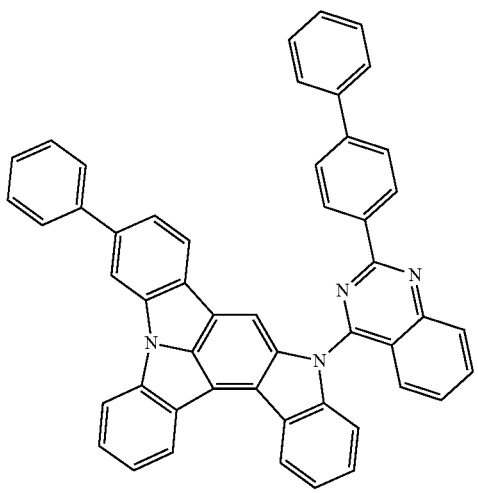
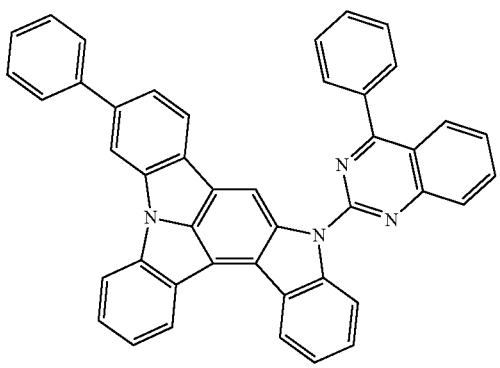
236
-continued
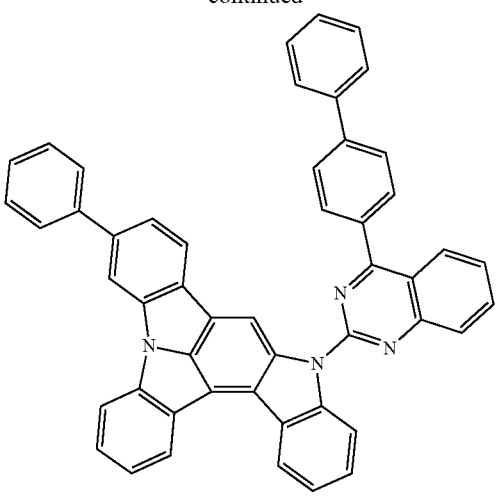
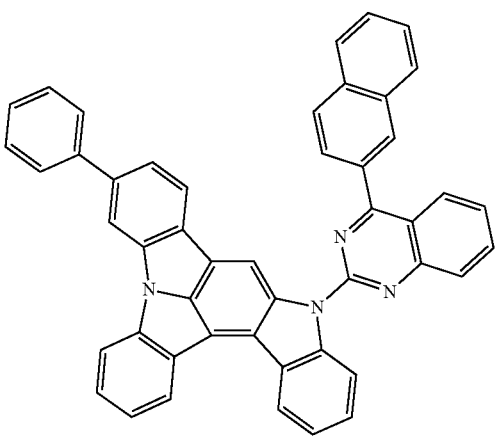
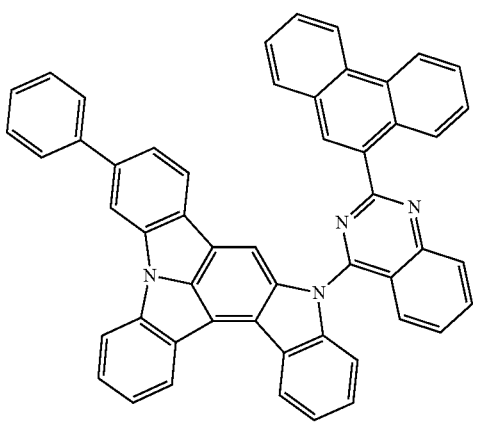

237
-continued
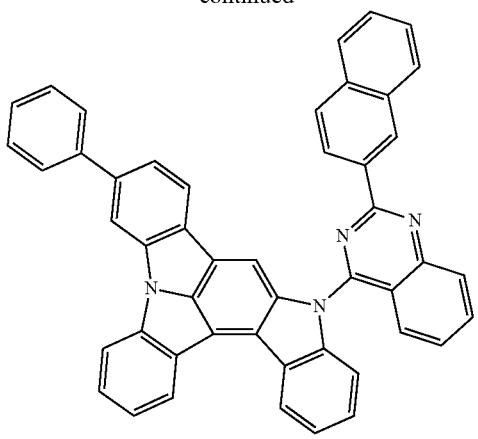
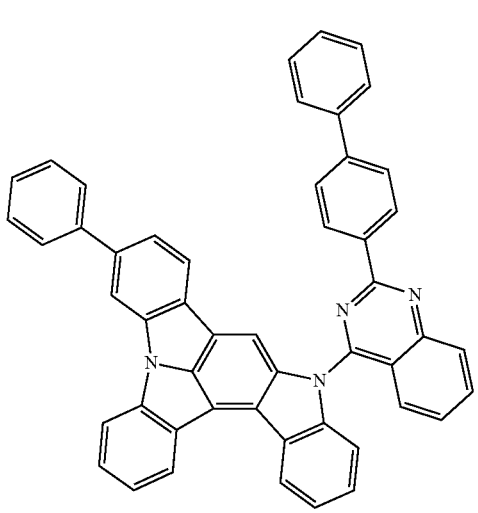
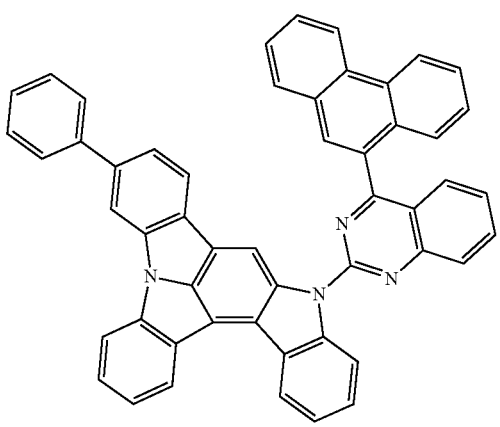
238
-continued
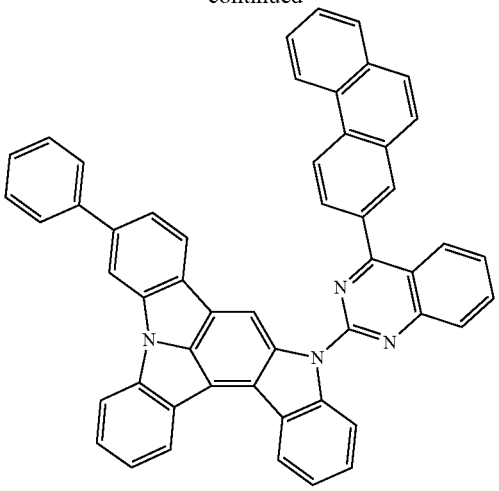
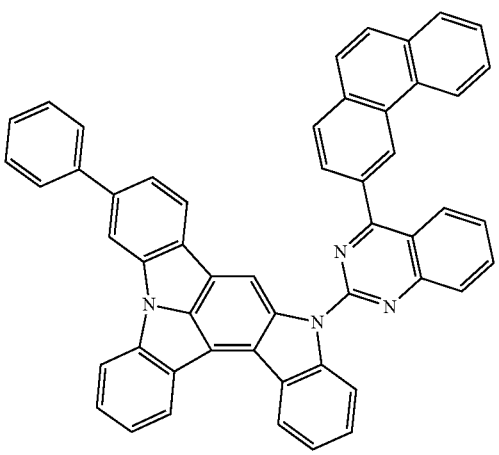
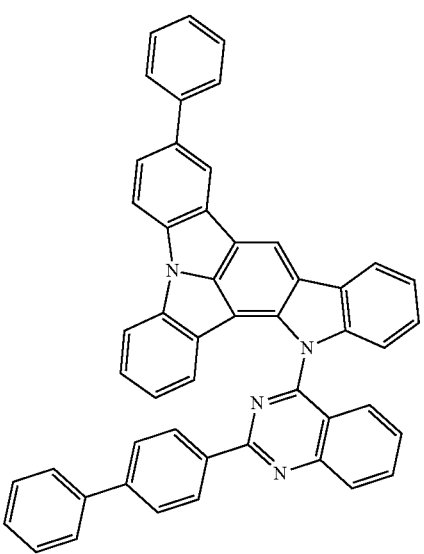

239
-continued
240
-continued
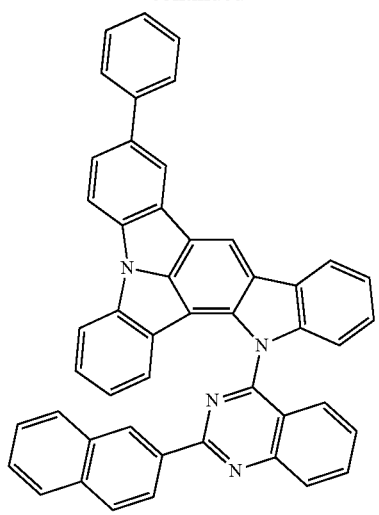
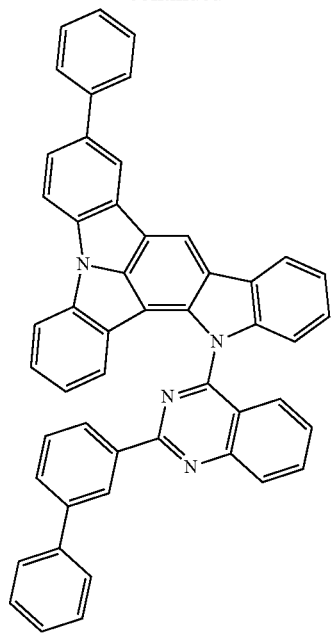

-continued
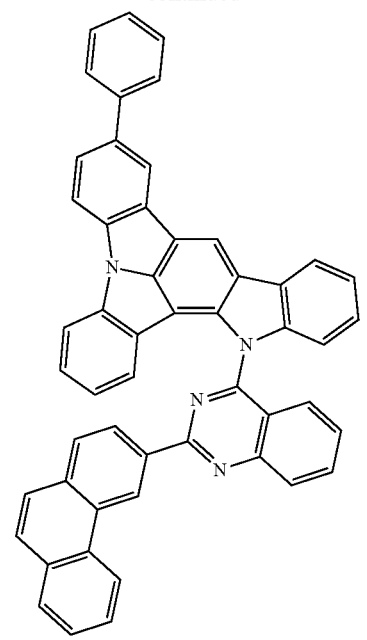
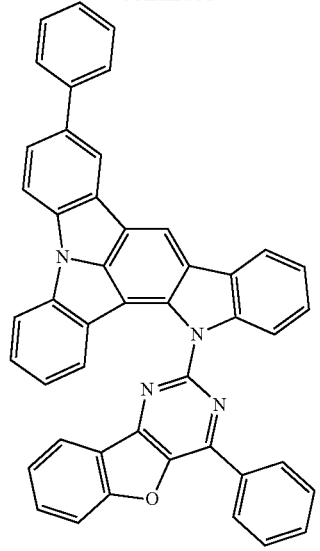
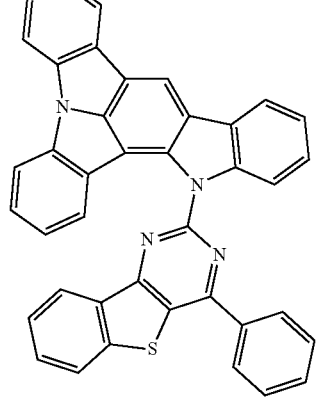
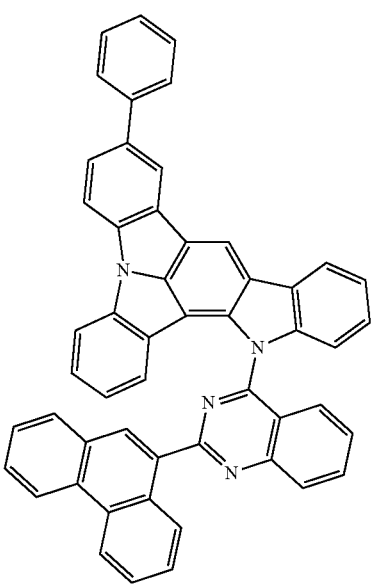
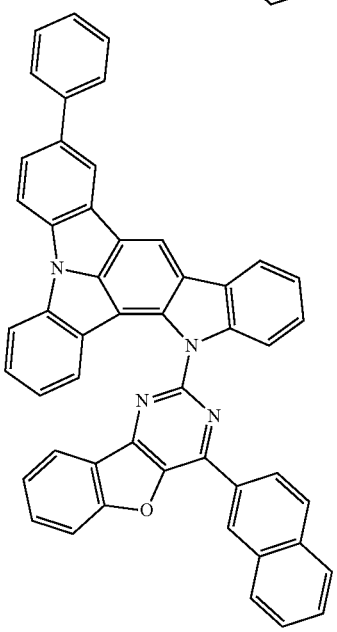

243
-continued
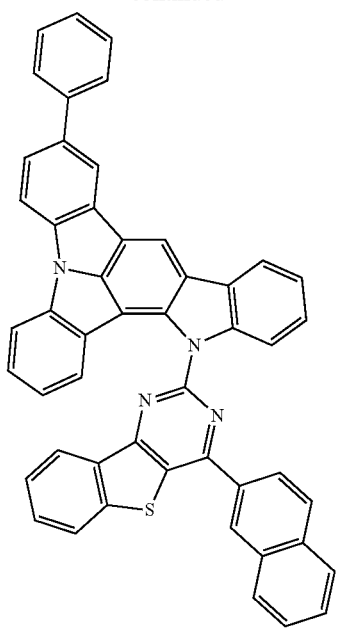
244
-continued
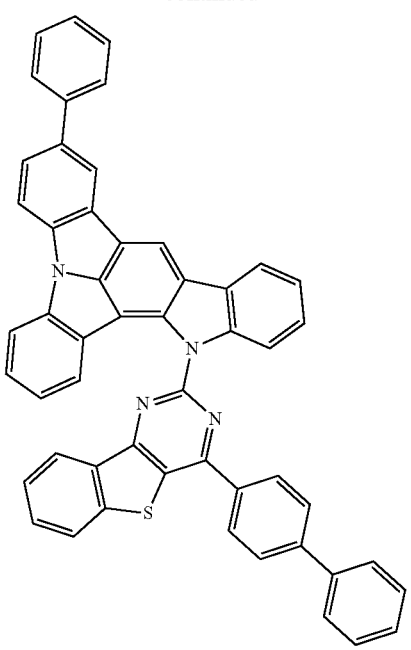
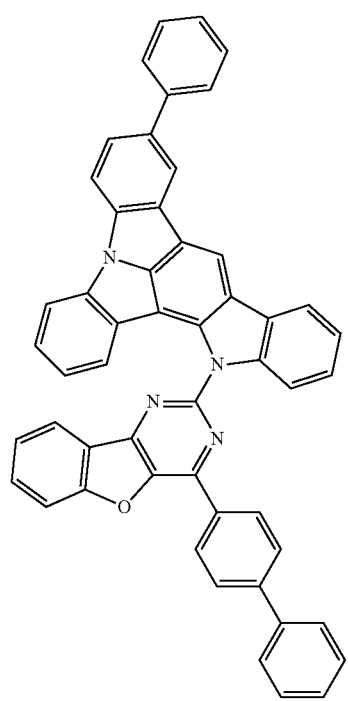
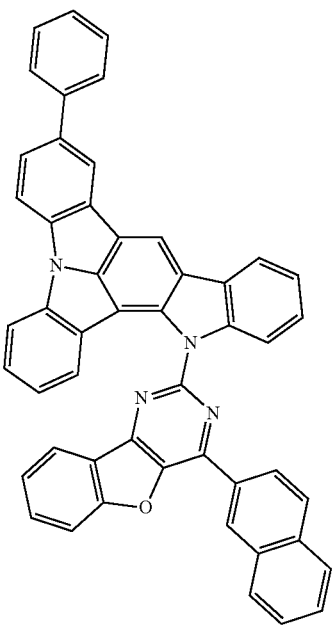

245
-continued
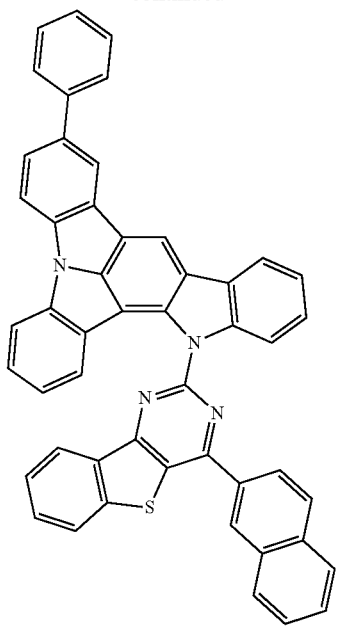
246
-continued
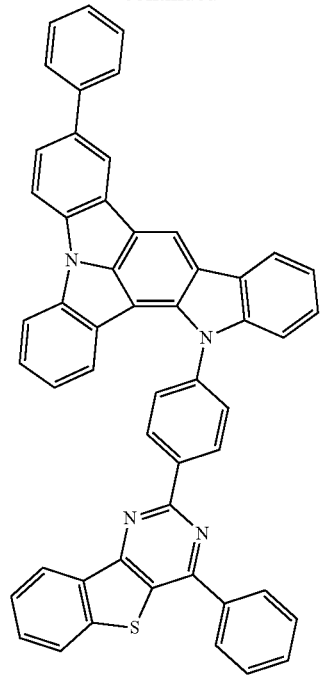
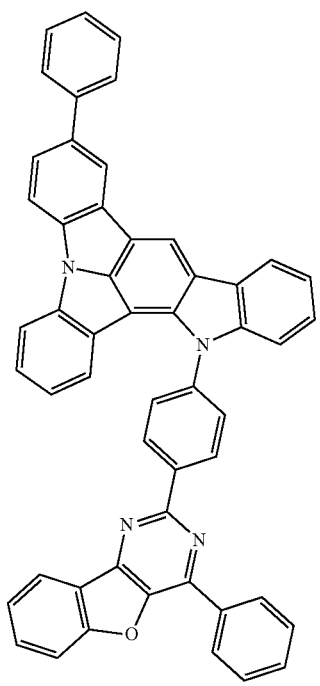

247
-continued
248
-continued
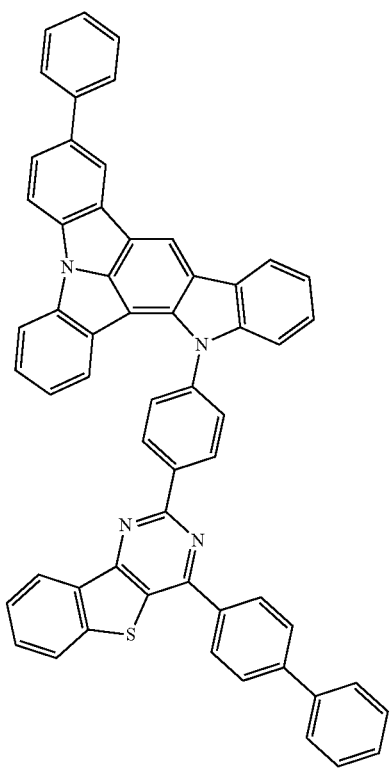
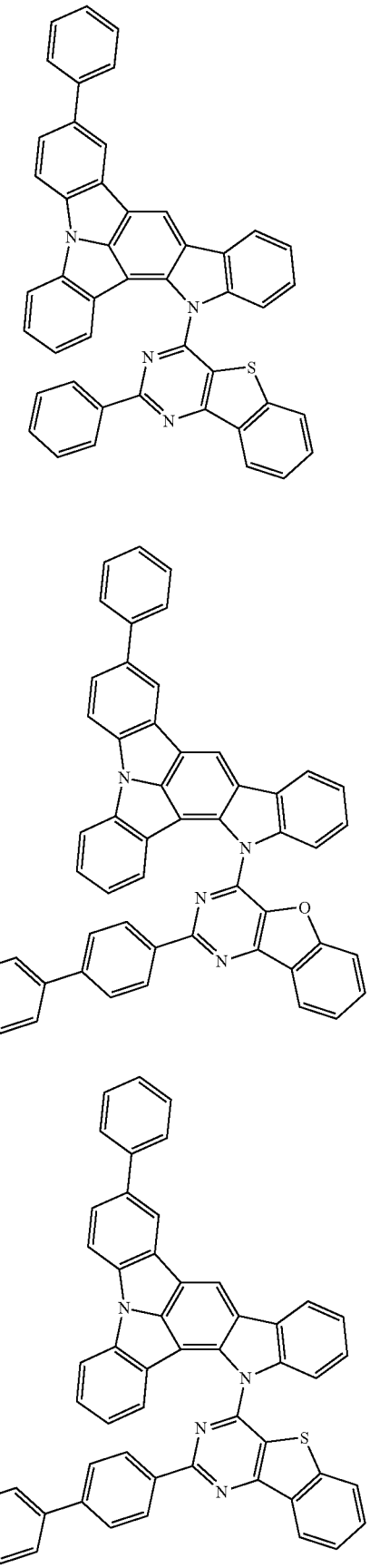

249
-continued
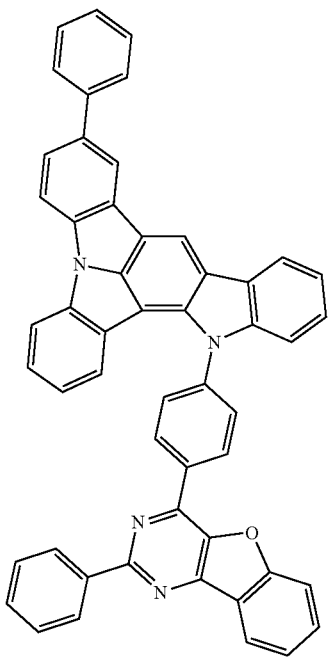
250
-continued
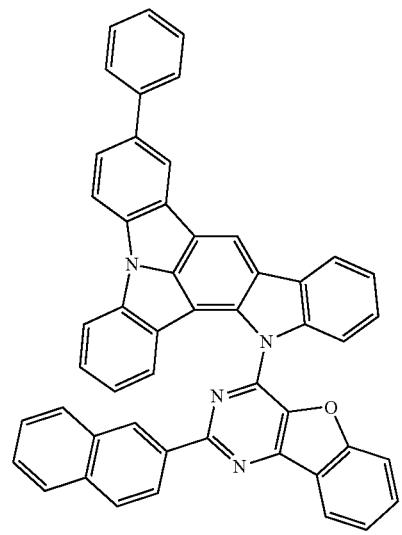
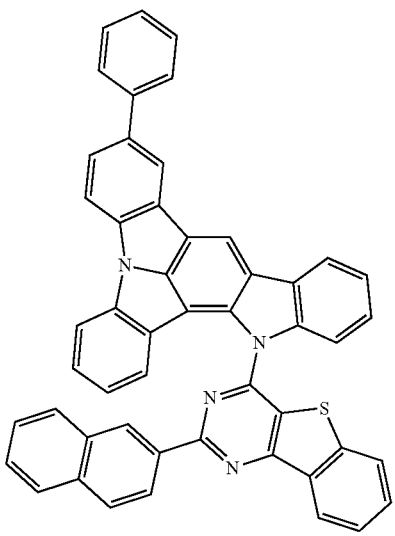
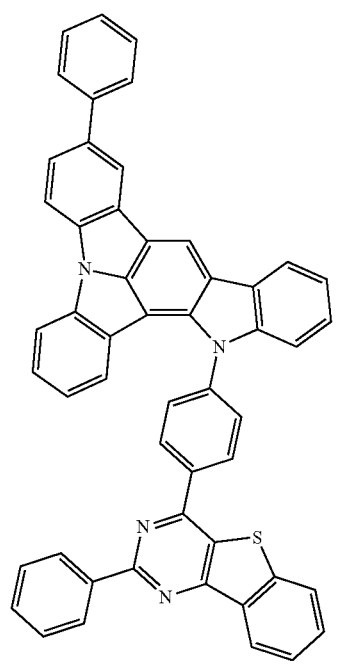

251
-continued
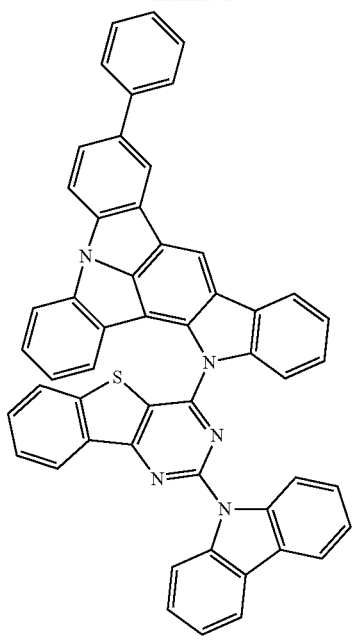
252
-continued
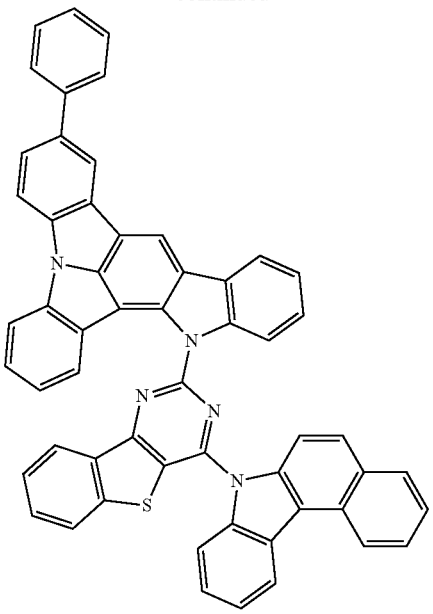
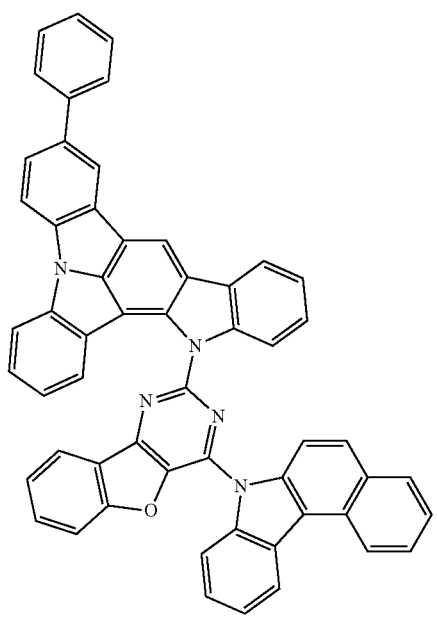
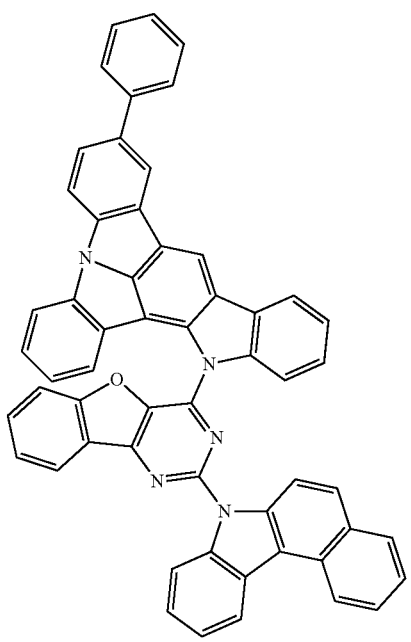

253
-continued
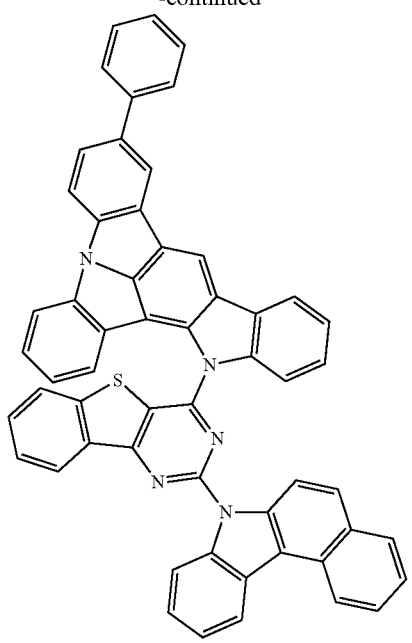
254
-continued
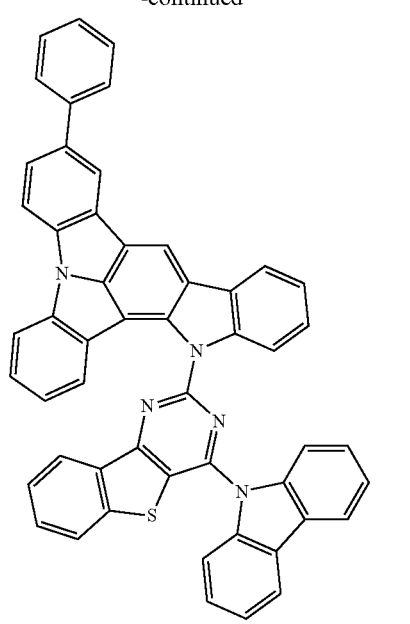
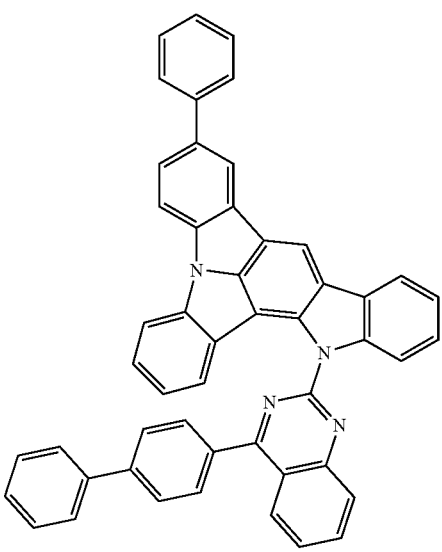
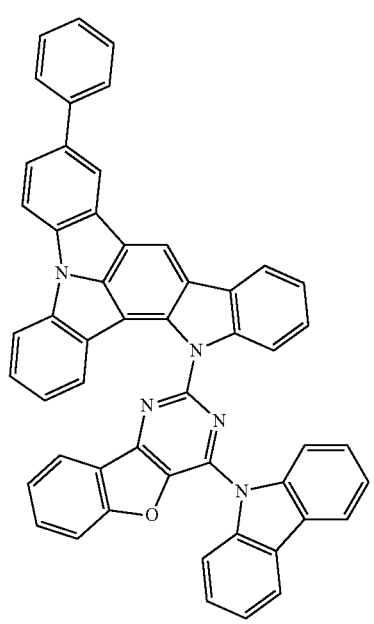
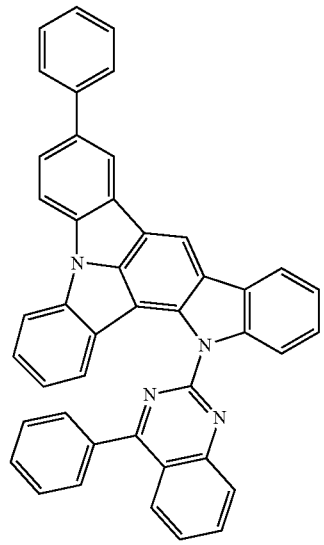

255
-continued
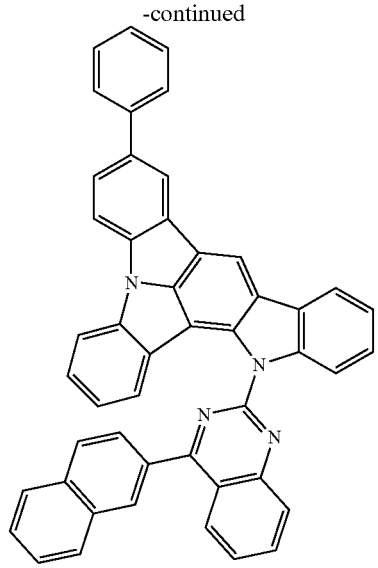
256
-continued
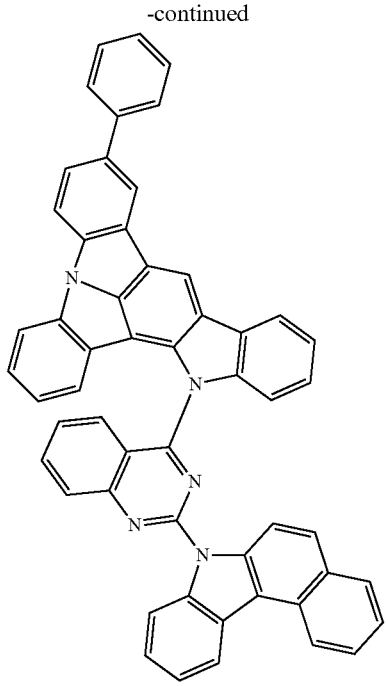
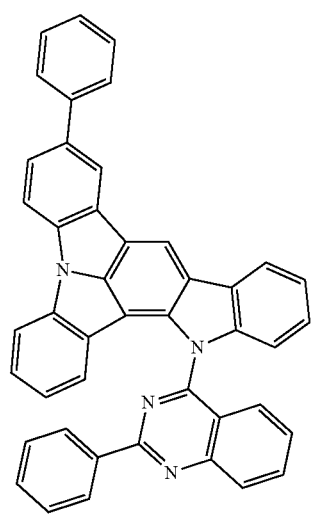
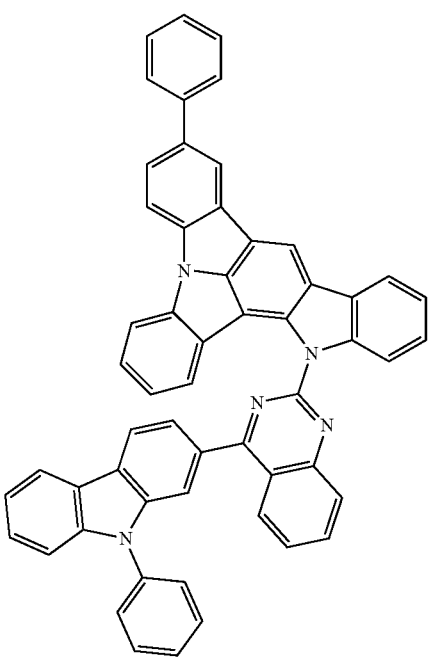 [SMILES: c1ccc(-c2ccc3c(c2)c2cc4c5ccccc5n(-c5nc(-c6ccc7c8ccccc8n(-c8ccccc8)c7c6)c6ccccc6n5)c4c4c5ccccc5n3c24)cc1]

257 258
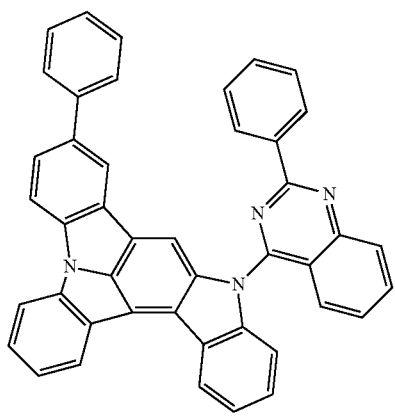
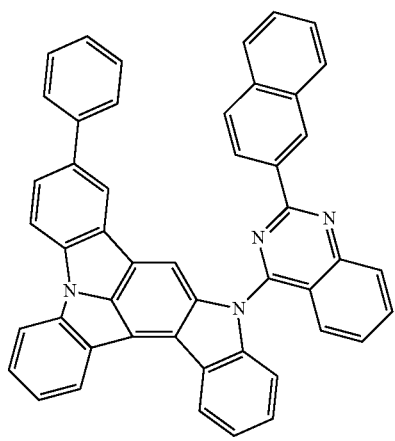
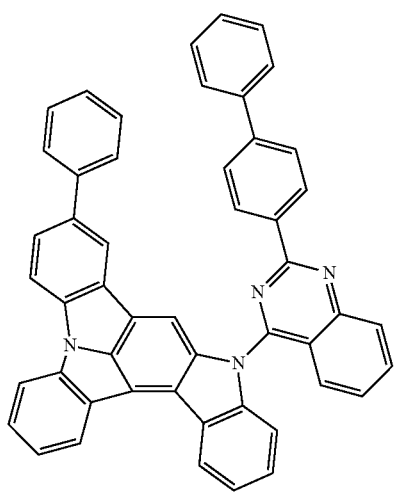
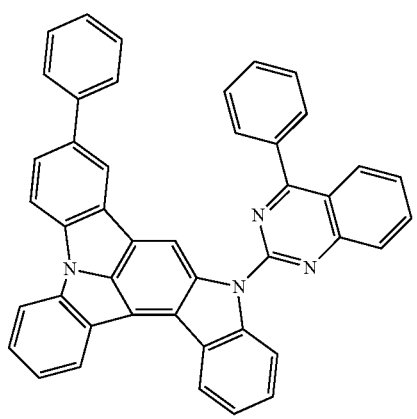
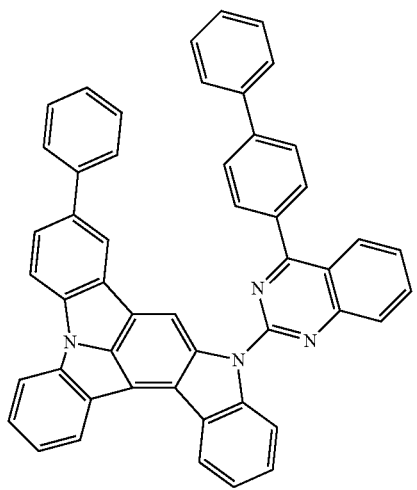
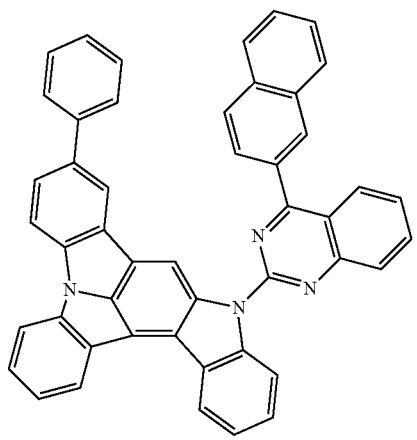

-continued
259
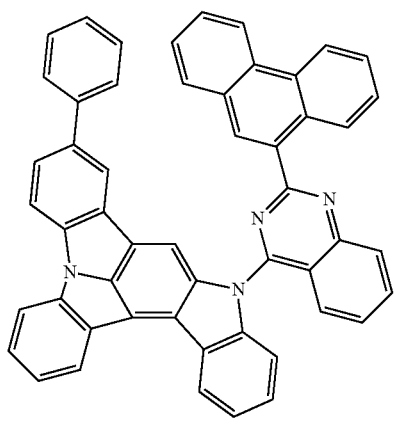
260
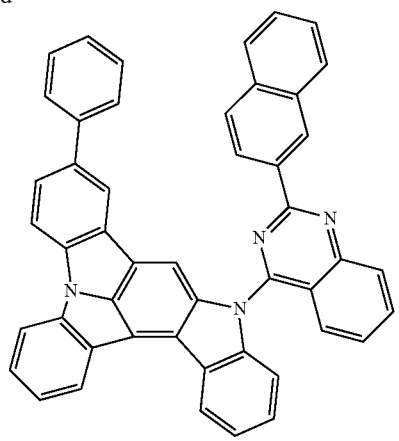
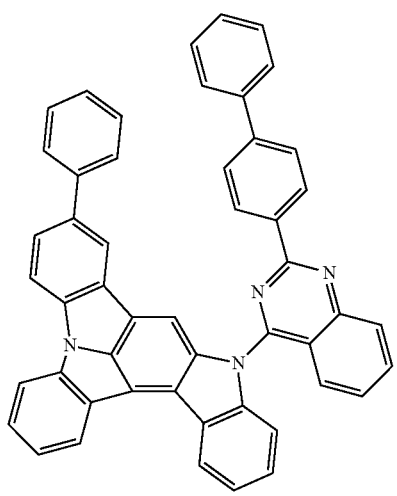
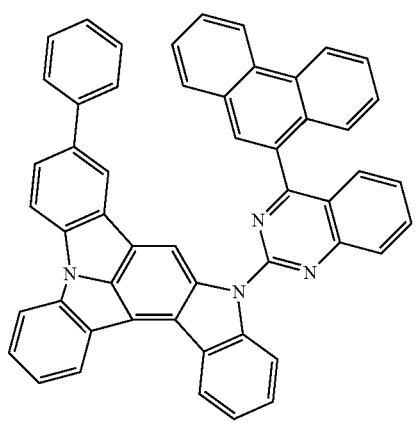
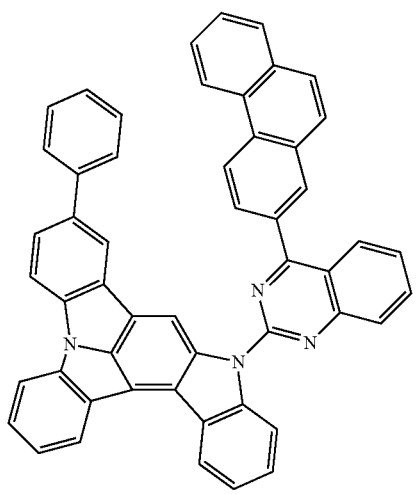
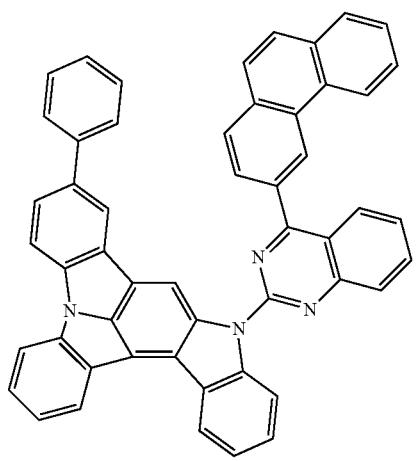

261
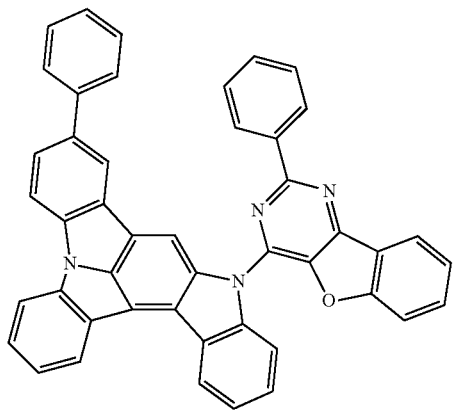
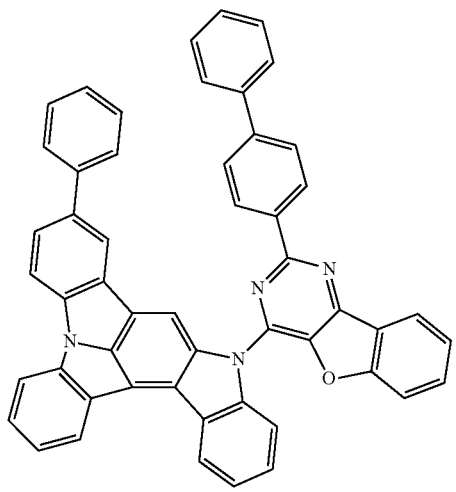
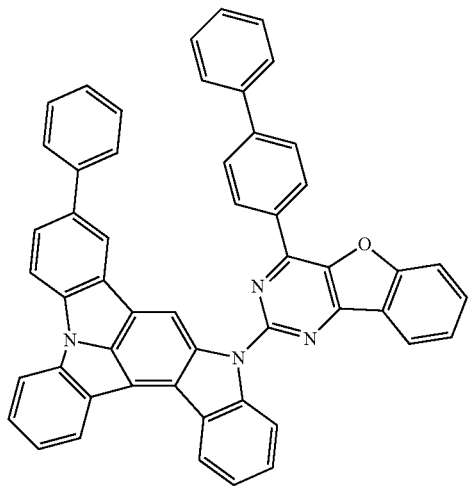
262
-continued
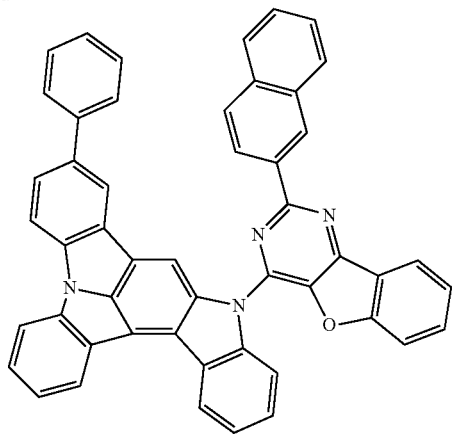
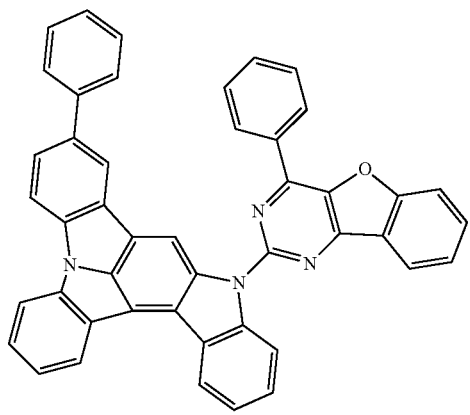
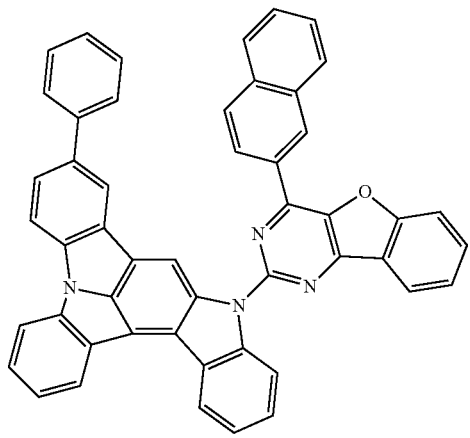

-continued
263
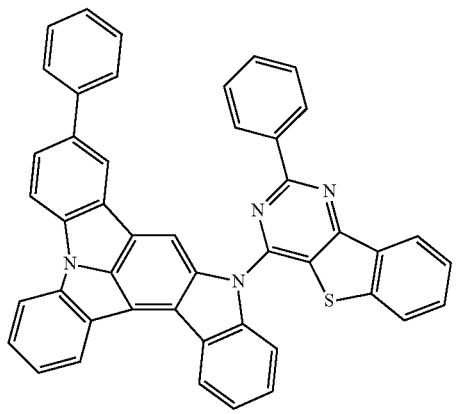
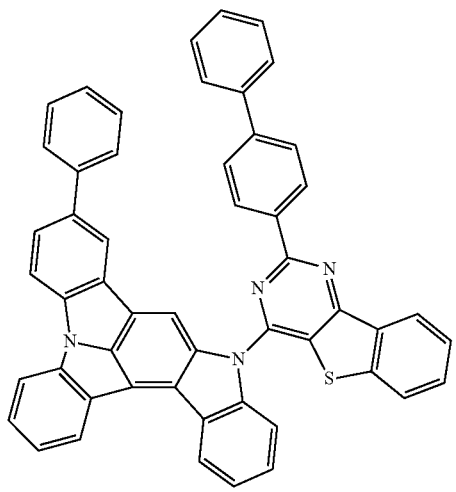
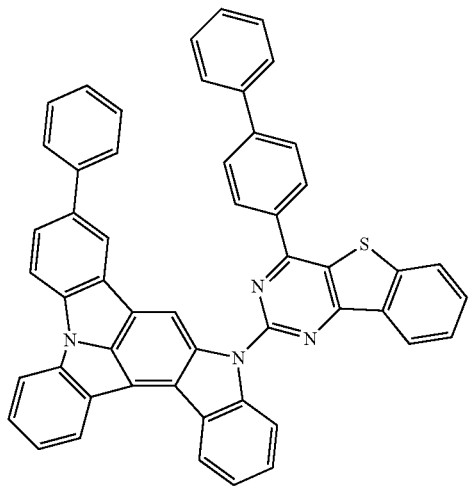
264
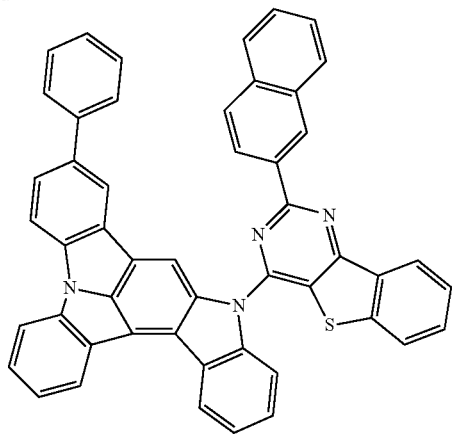
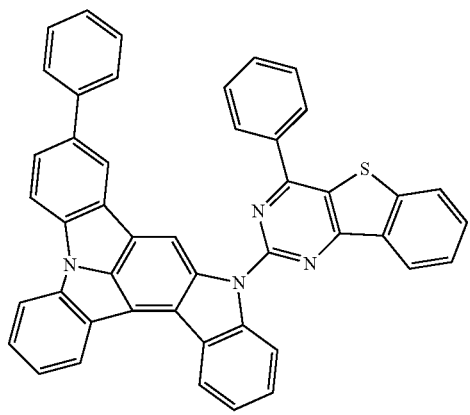
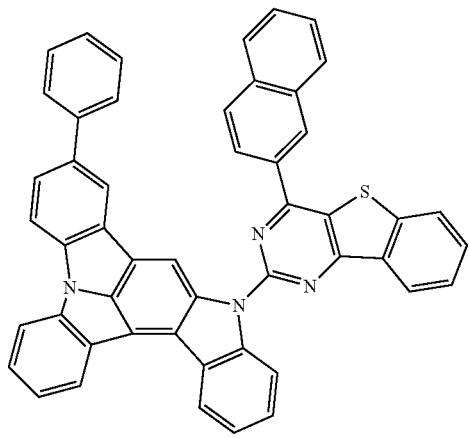

265
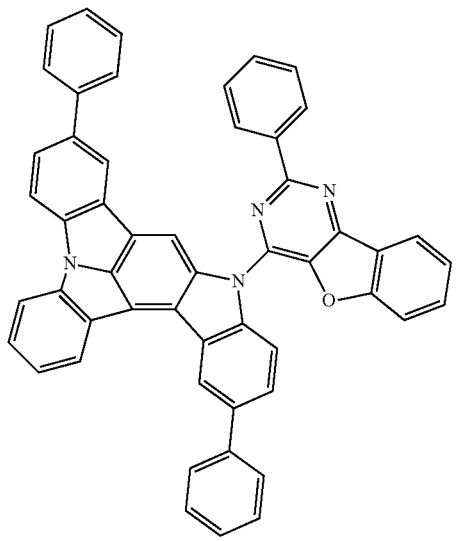
266
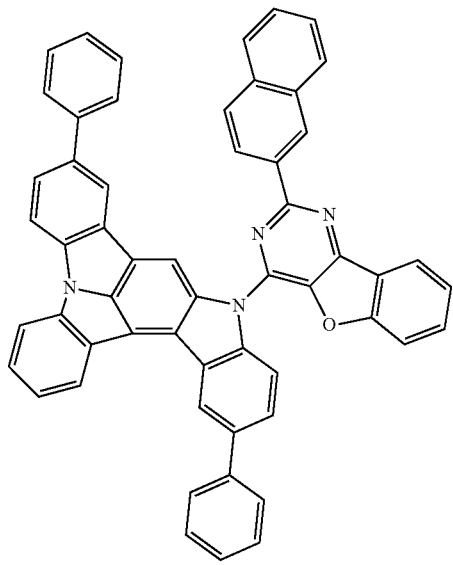
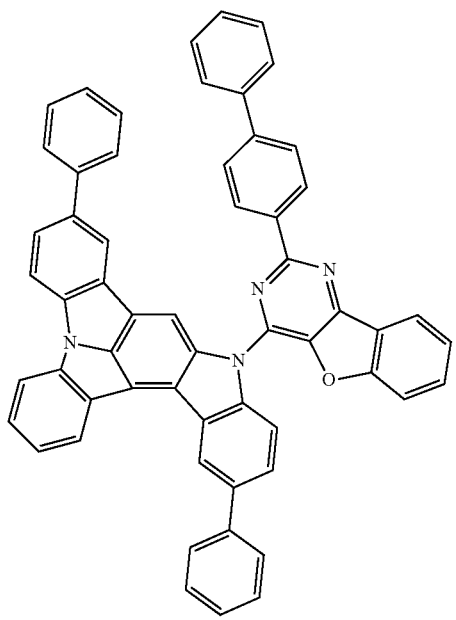
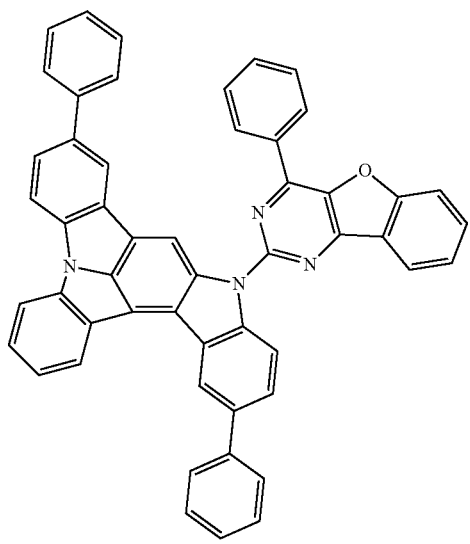

267
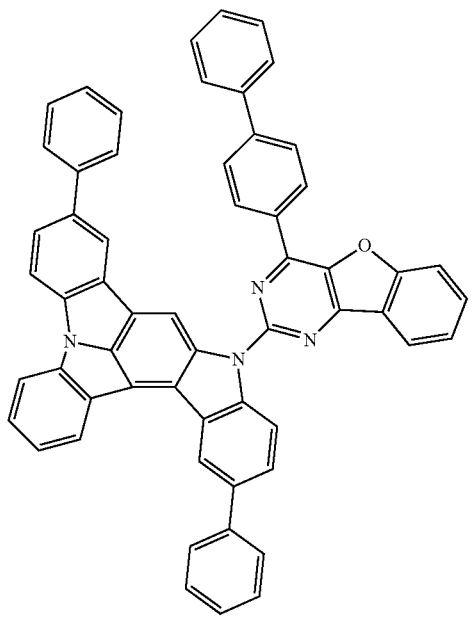
268
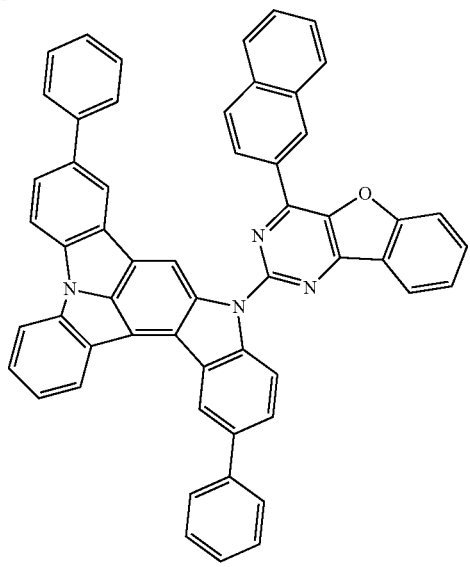
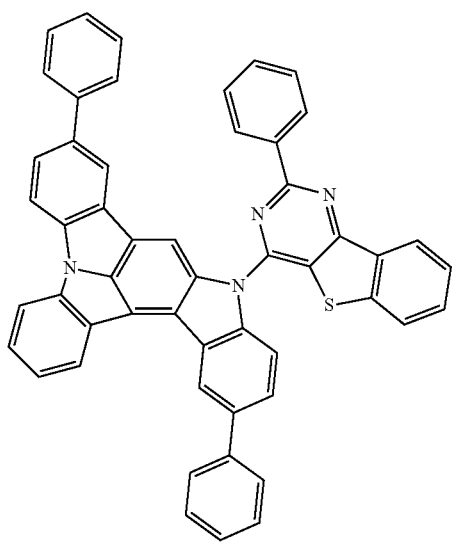
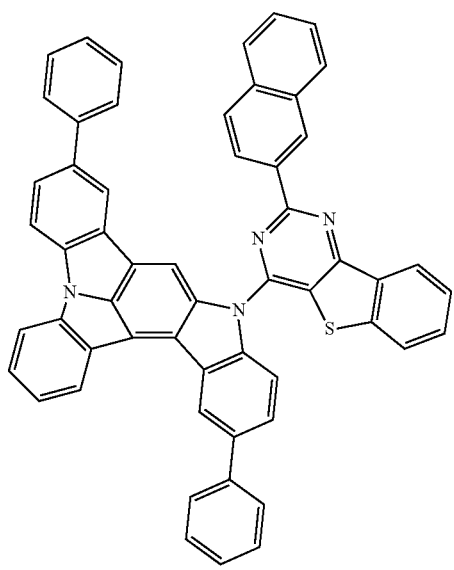

269
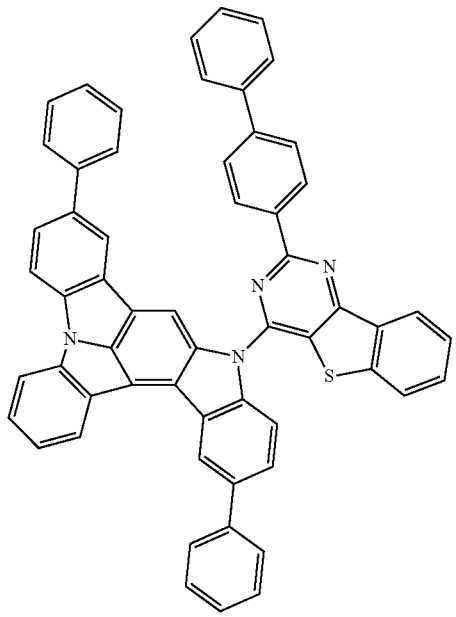
270
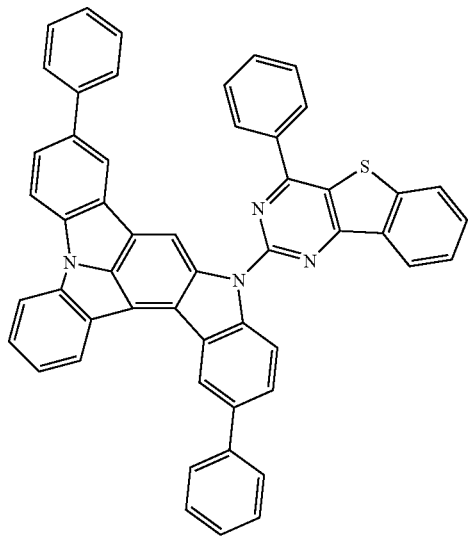
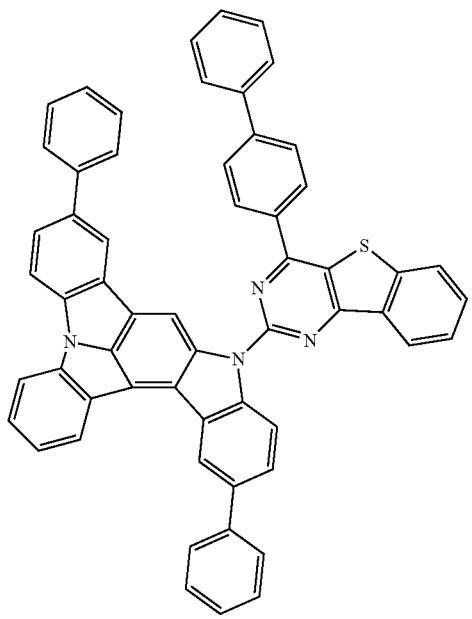
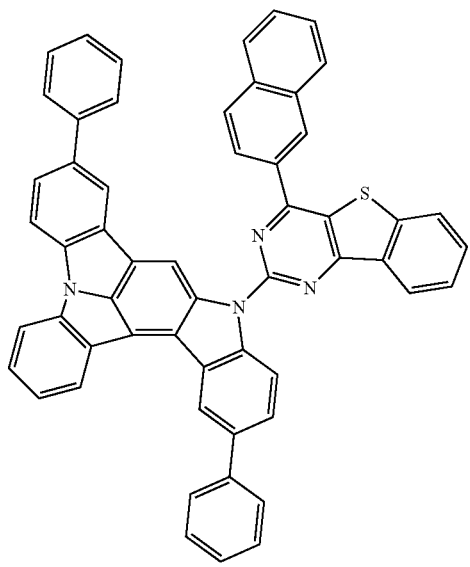

-continued
271
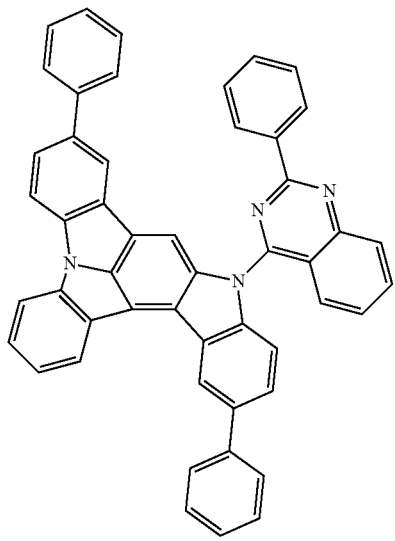
272
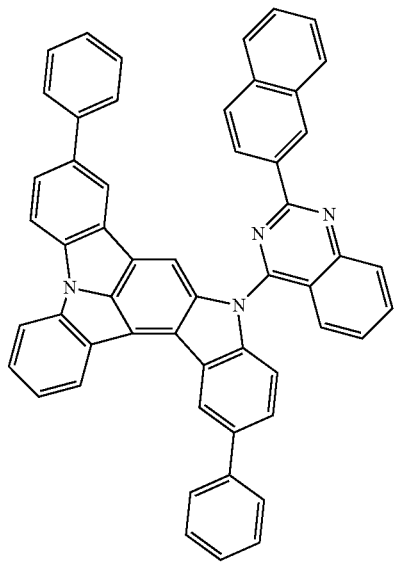
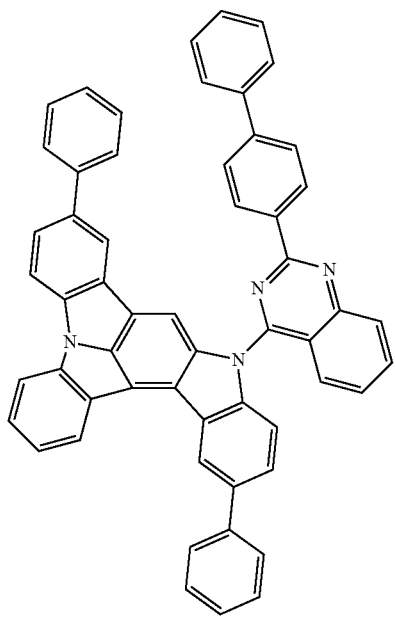
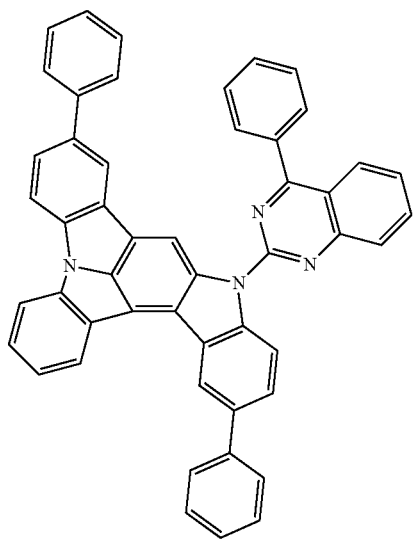

-continued
| 273 | 274 |
|---|---|
| 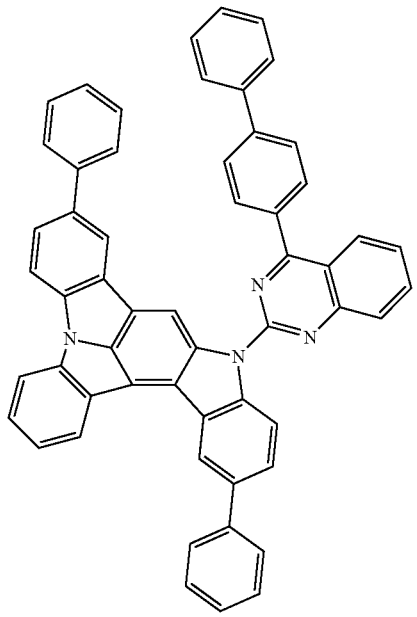 | 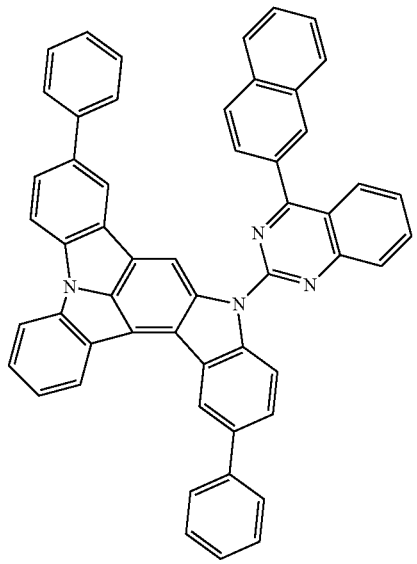 |
| 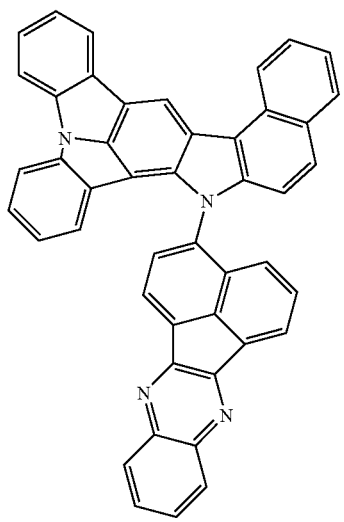 | 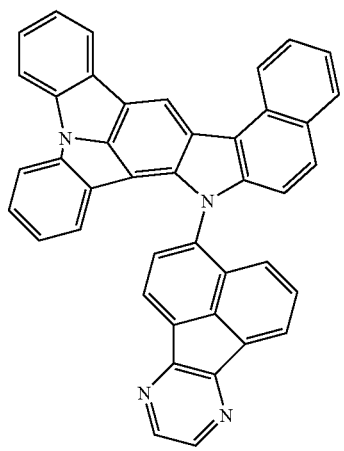 |
| 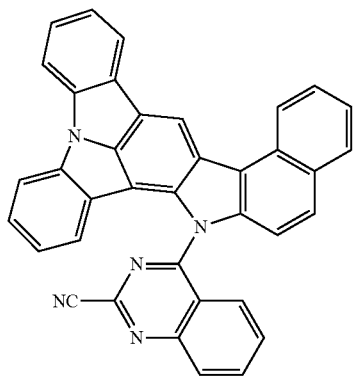 | 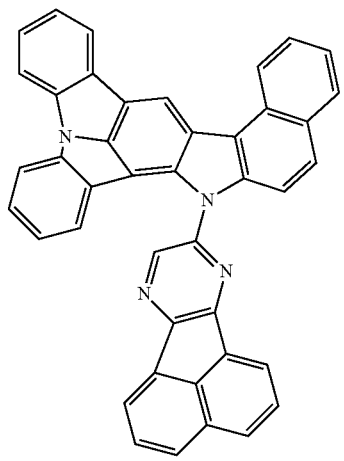 |

275
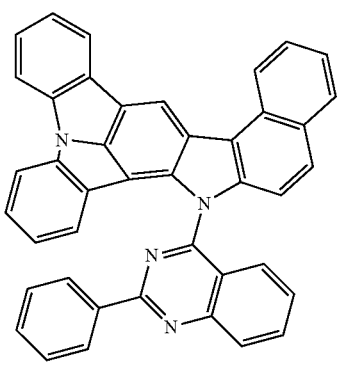
276
-continued
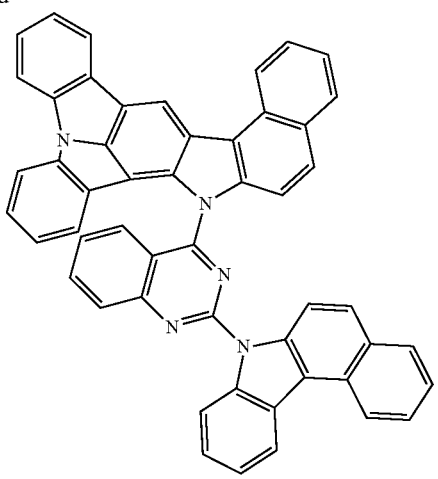
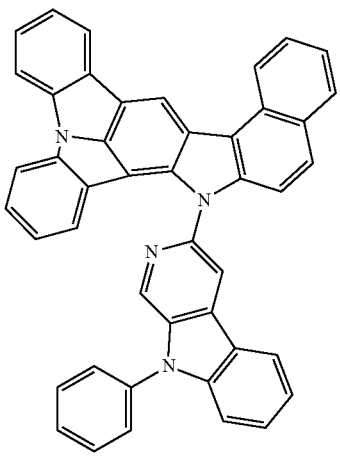
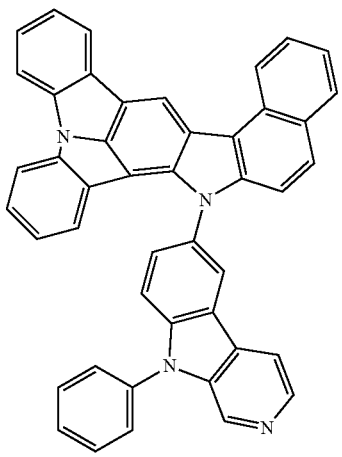
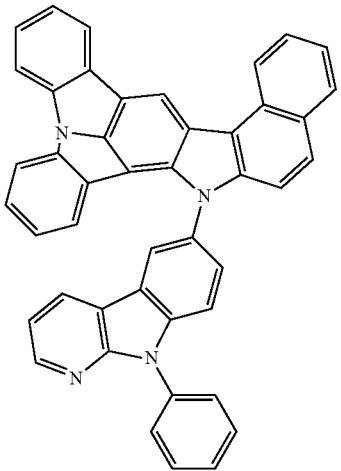
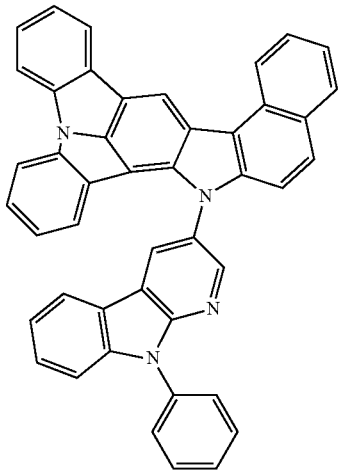

277
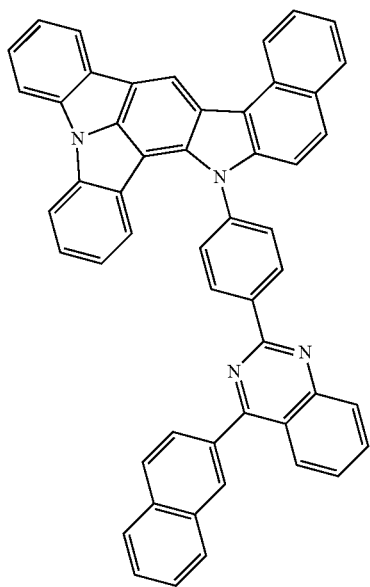
278
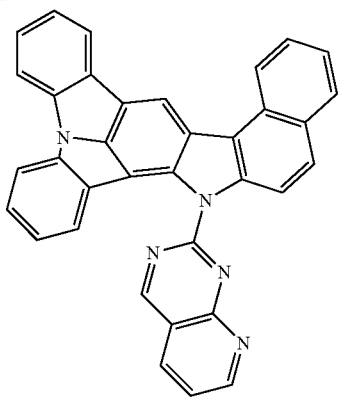
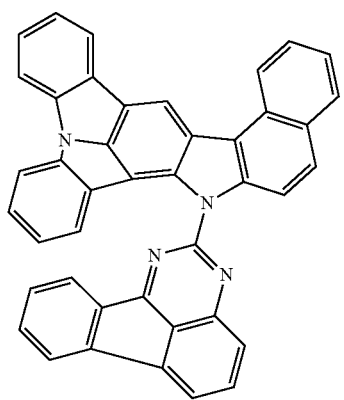
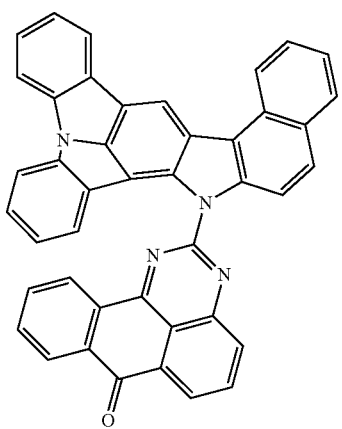
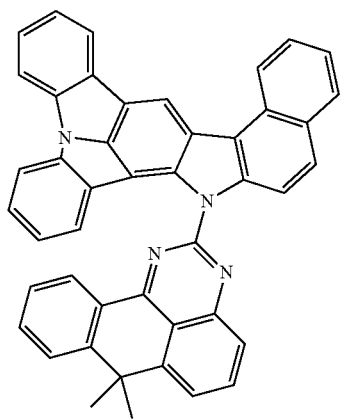
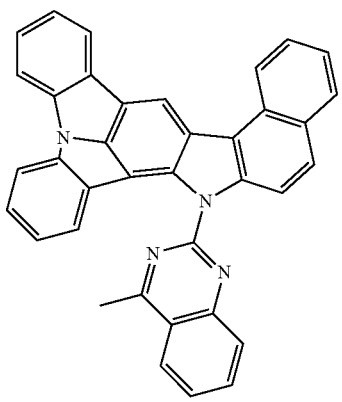

-continued
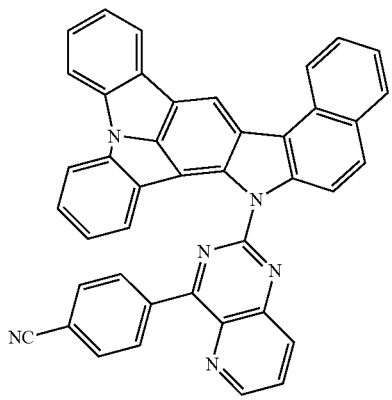
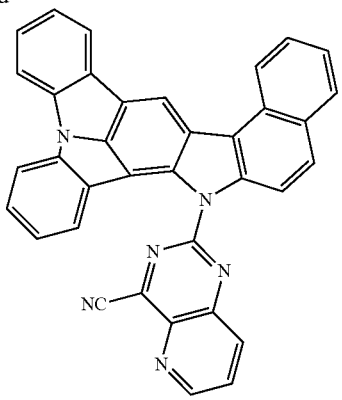
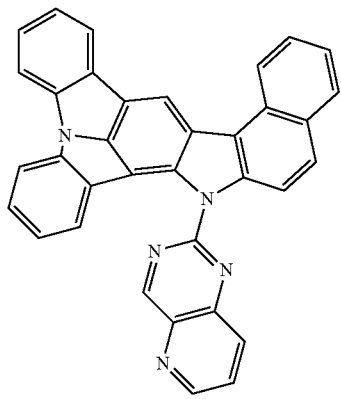
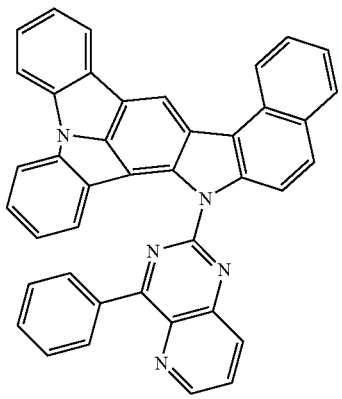
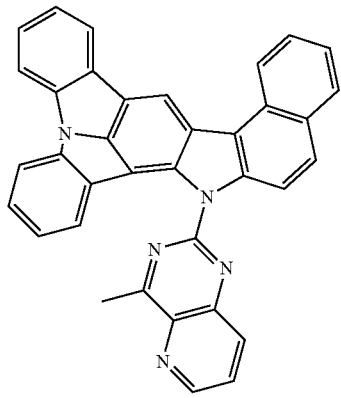
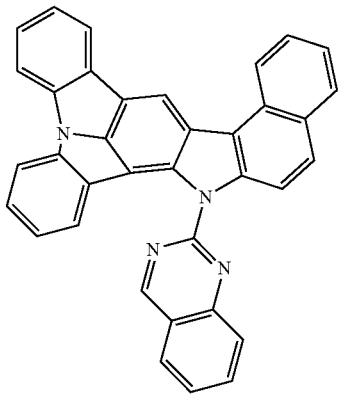
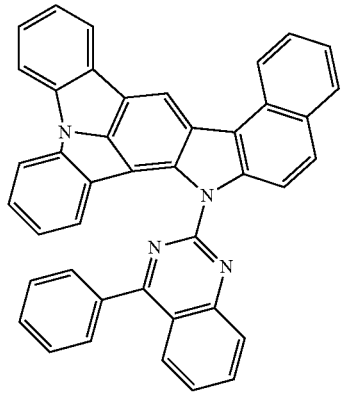
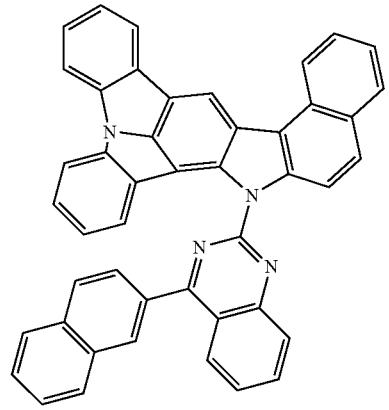

281
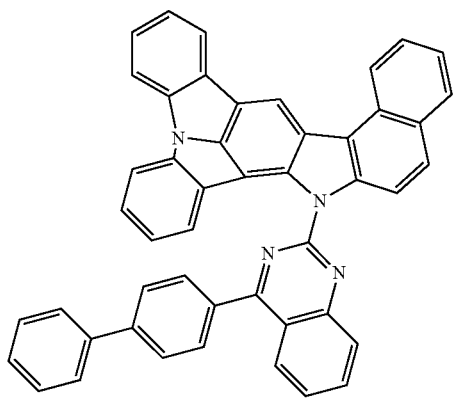
282
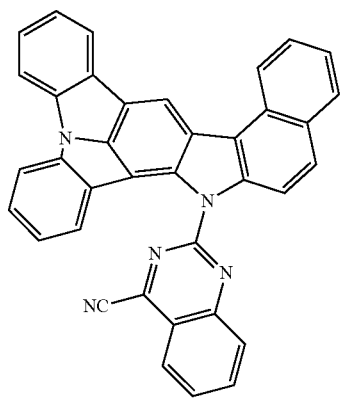
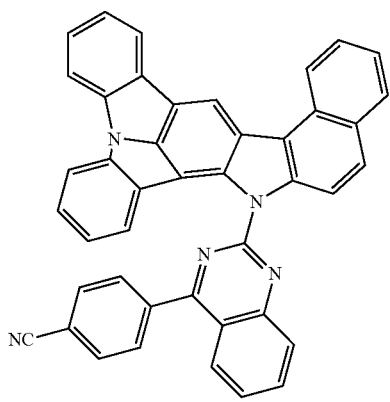
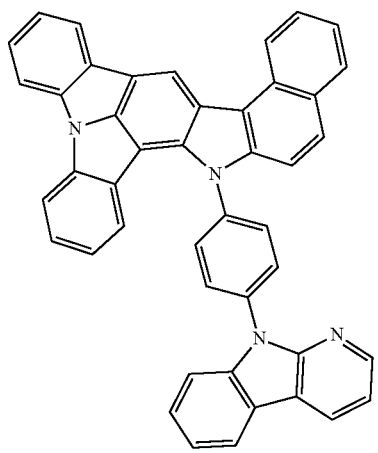
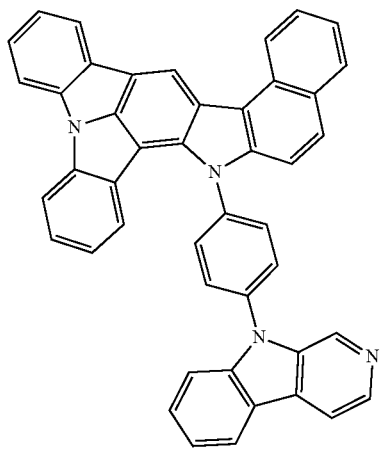
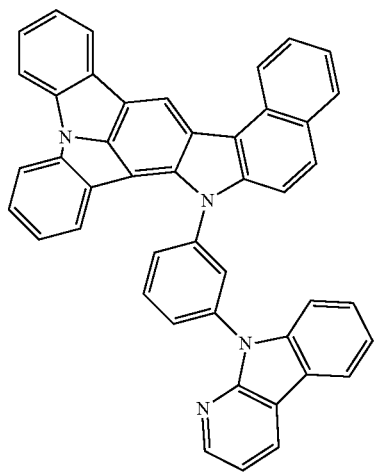

283
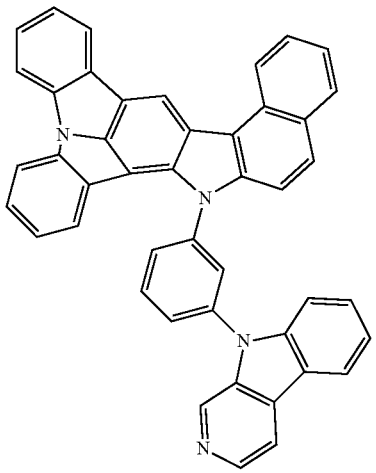
284
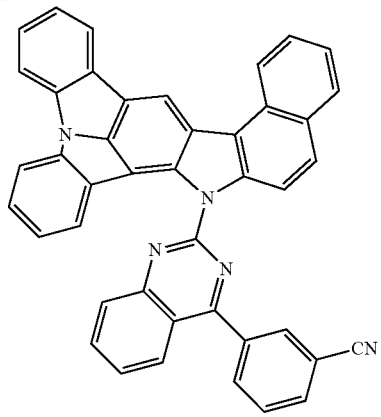
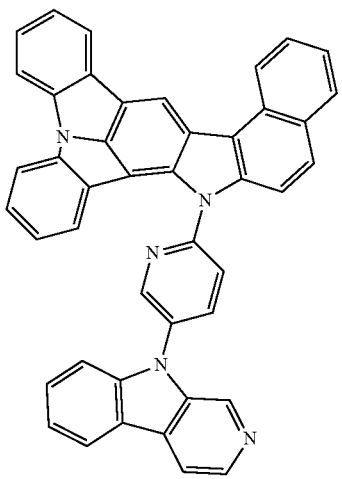
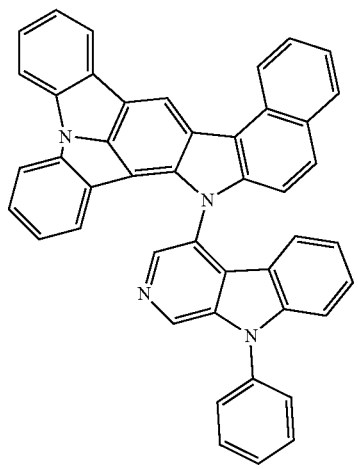
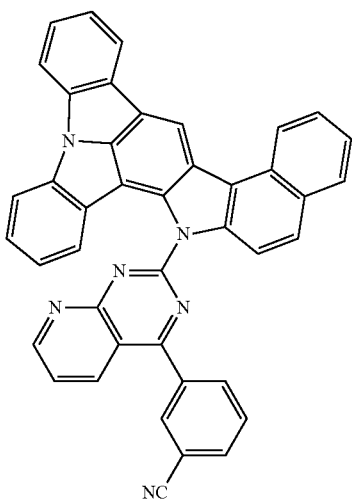
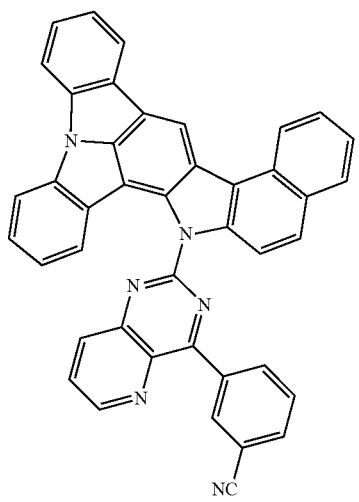

285 286
-continued
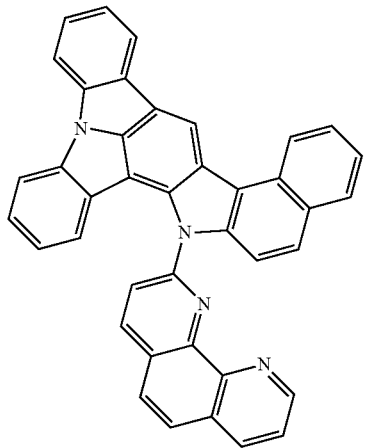
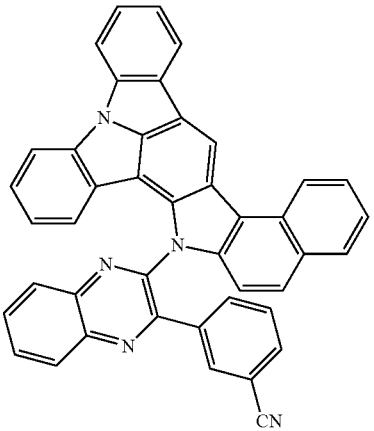
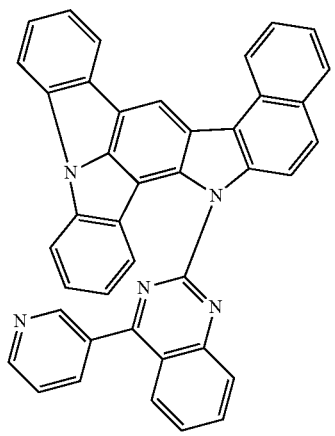
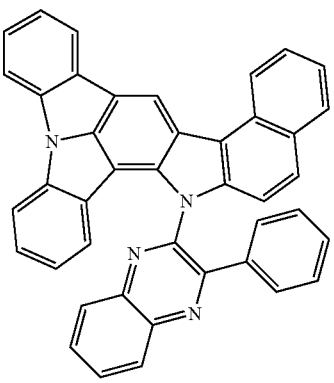
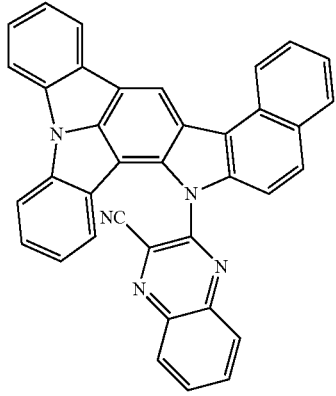
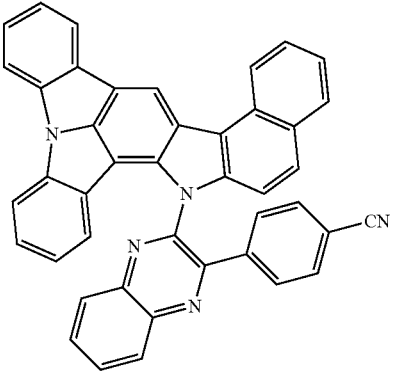
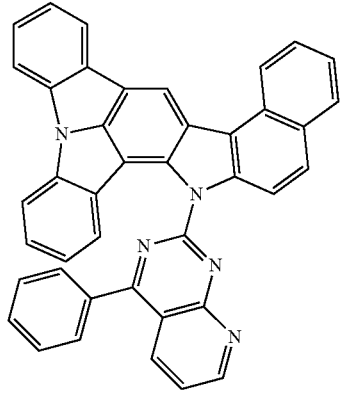
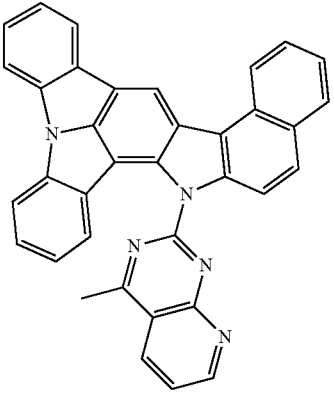

287            288
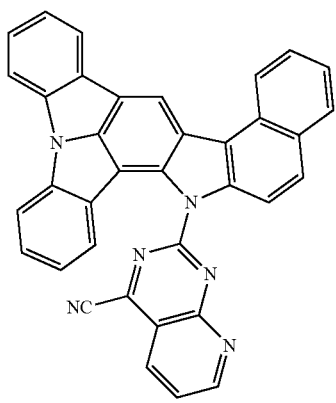 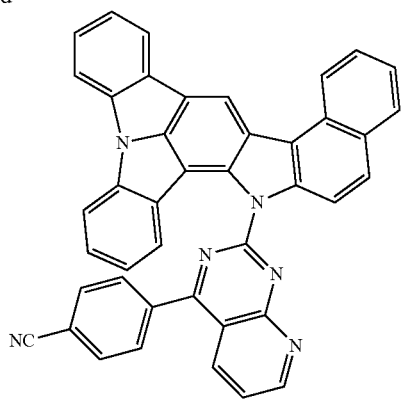
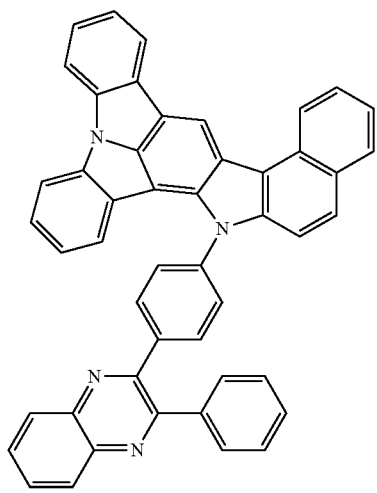 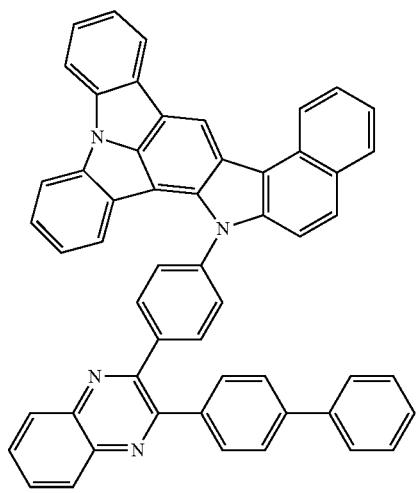
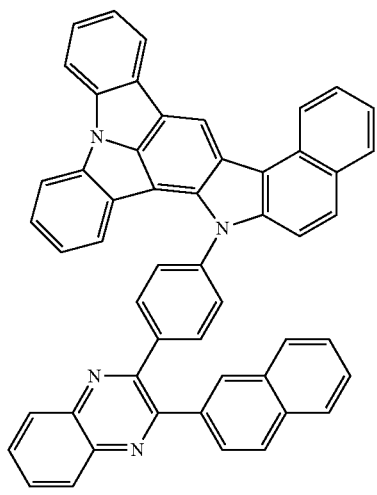 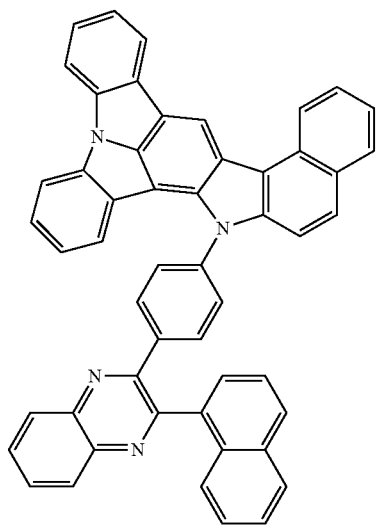

-continued
289
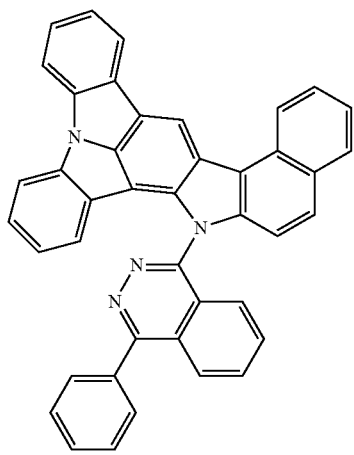
290
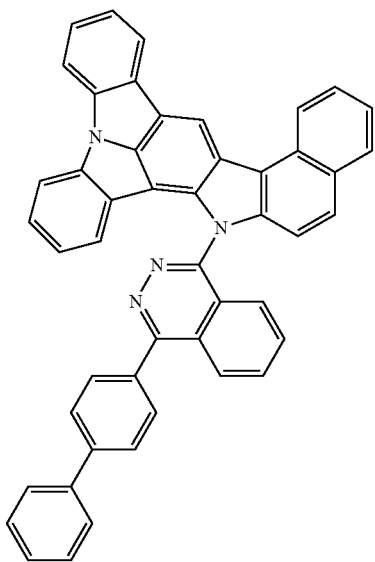
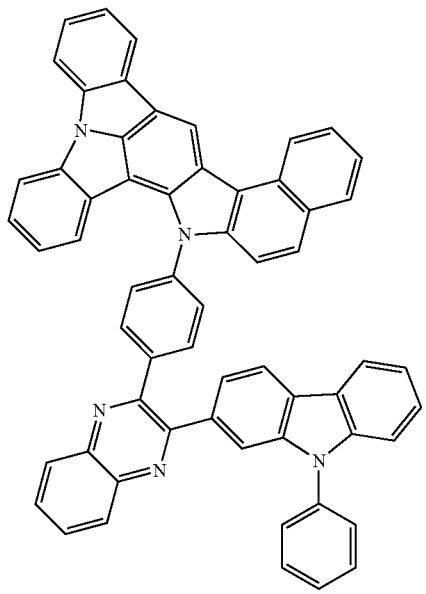
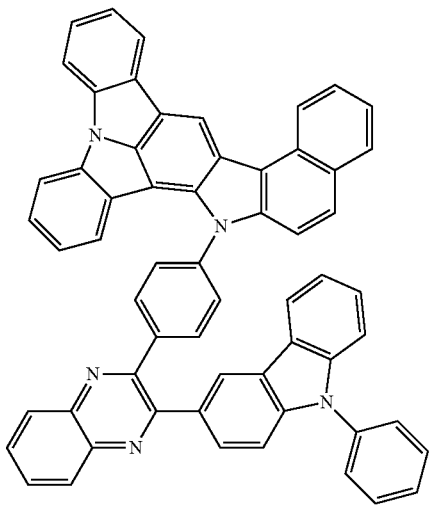
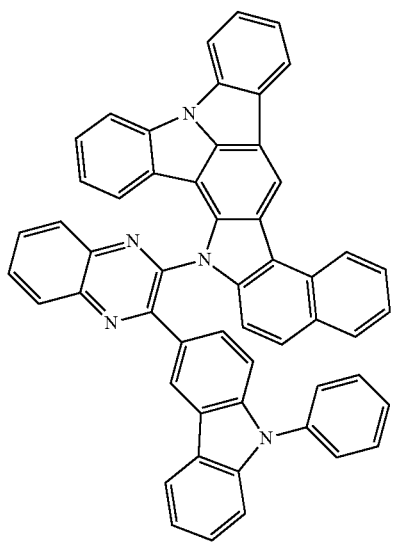
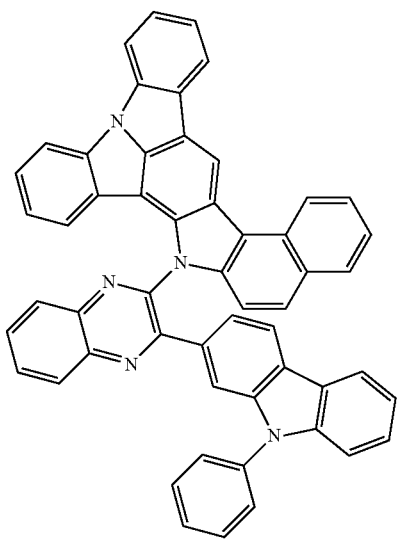

-continued
| 291 | 292 |
|---|---|
| 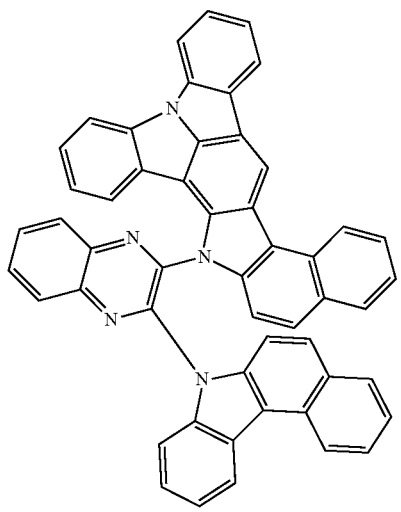 | 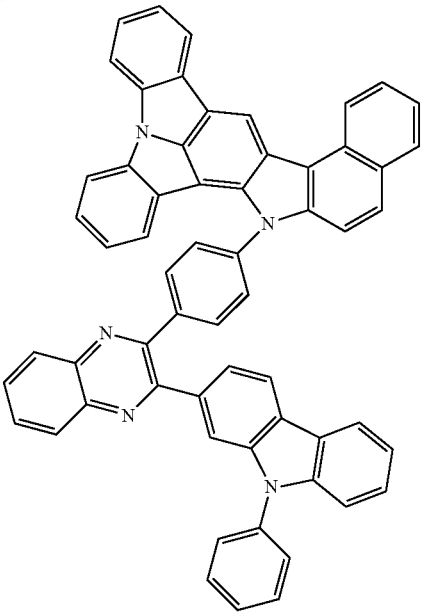 |
| 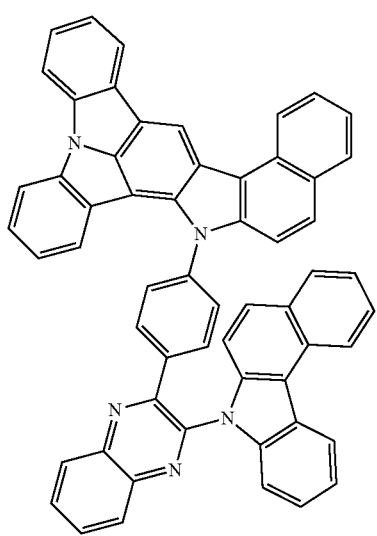 | 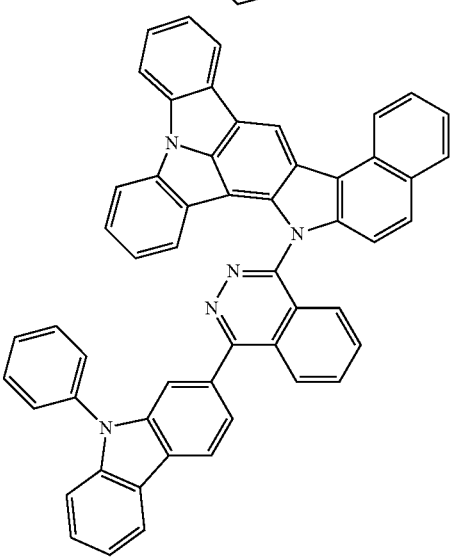 |
| 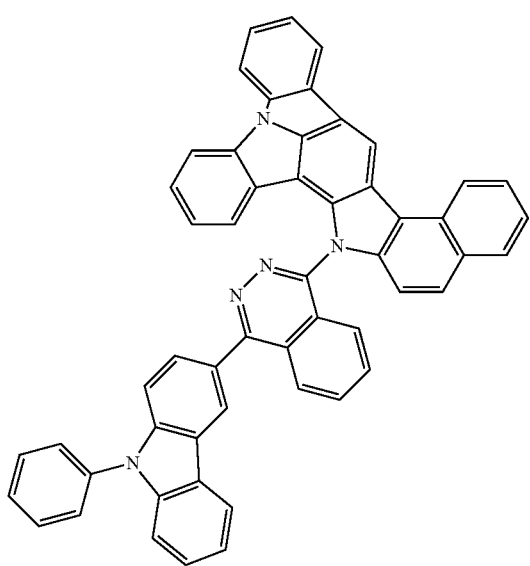 | 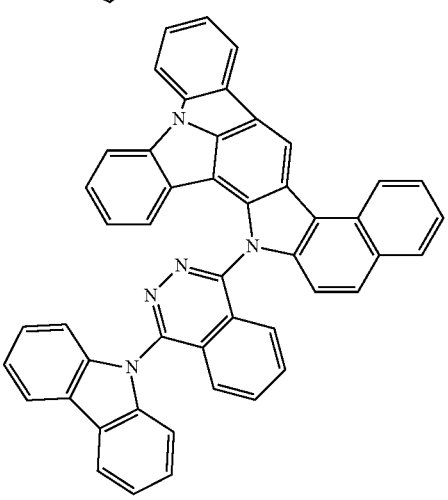 |

293
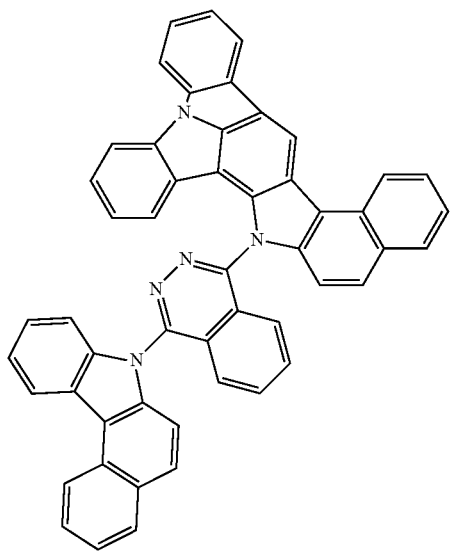
294
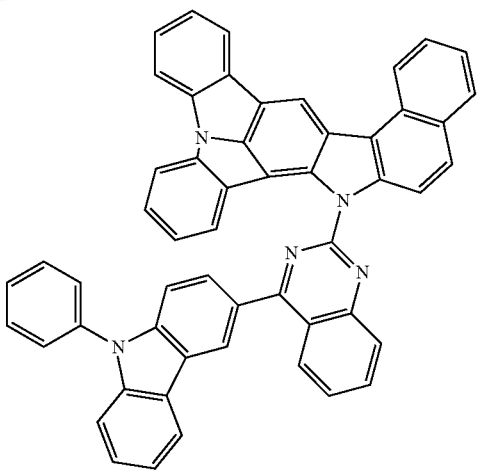
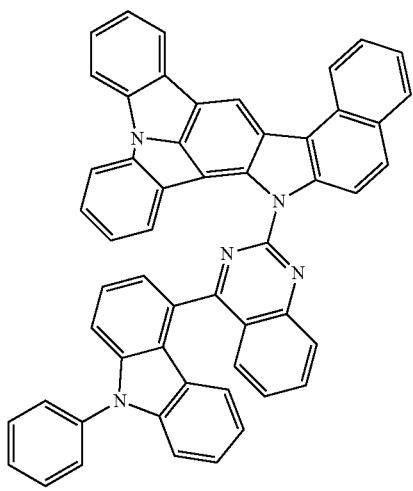
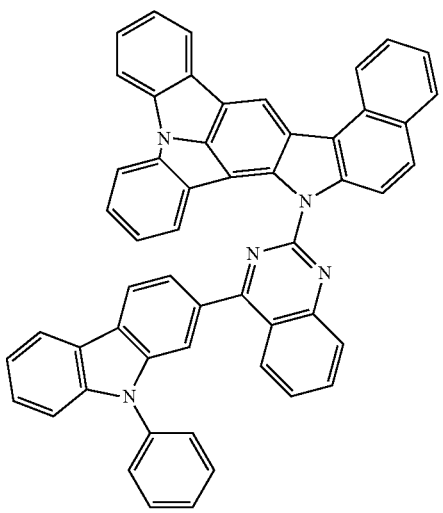
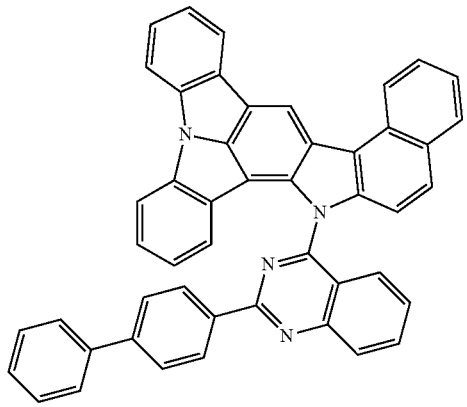
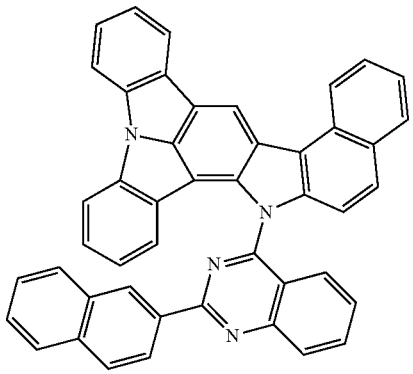

295
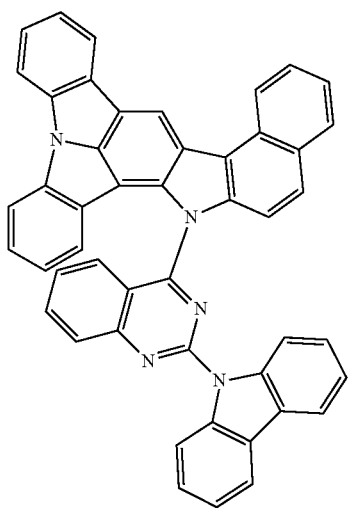
296
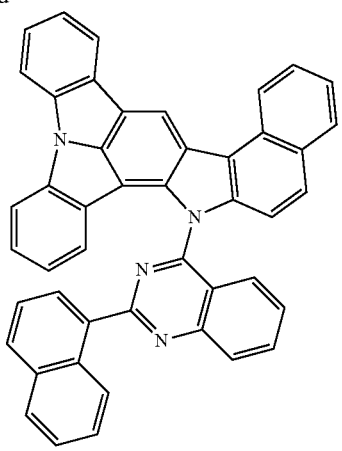
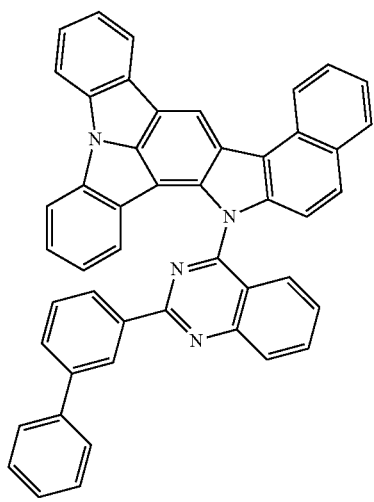
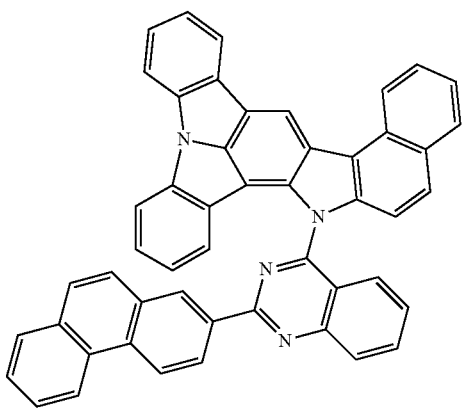
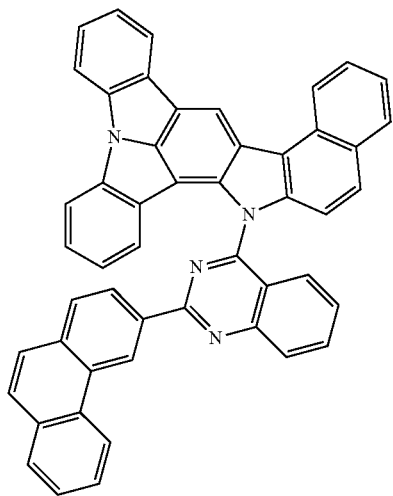
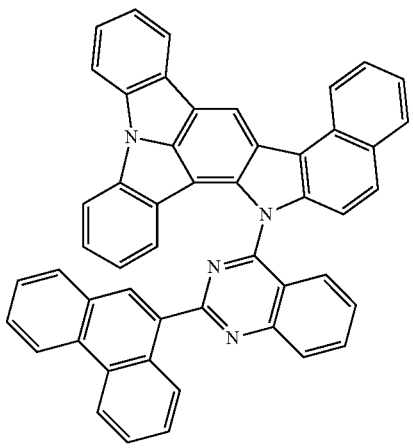

297
298
-continued
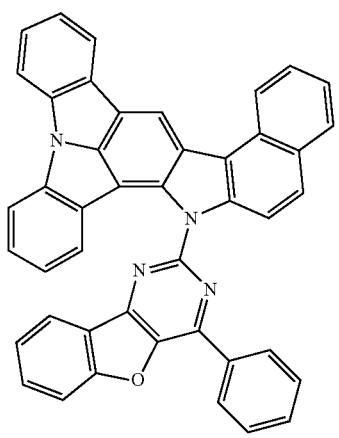
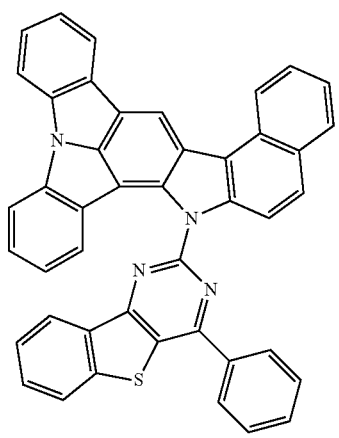
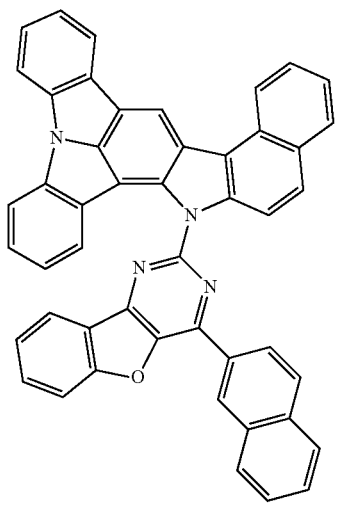
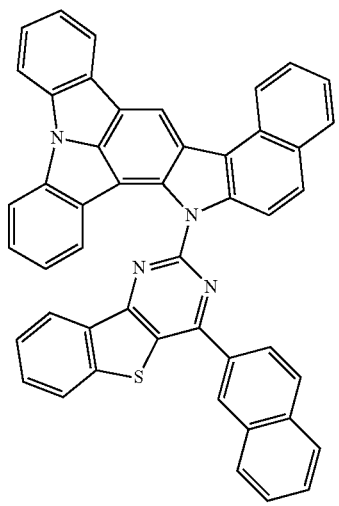
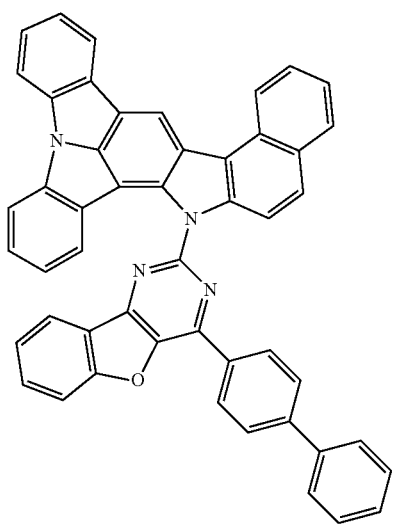
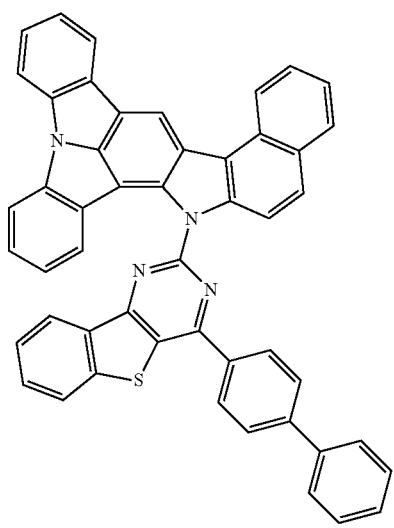

299 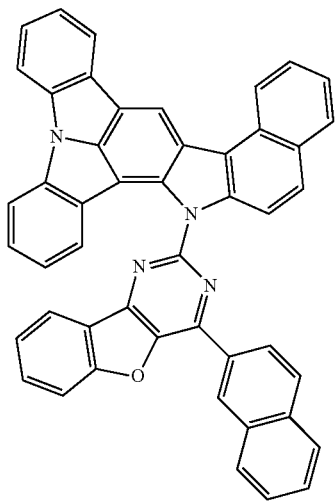 300 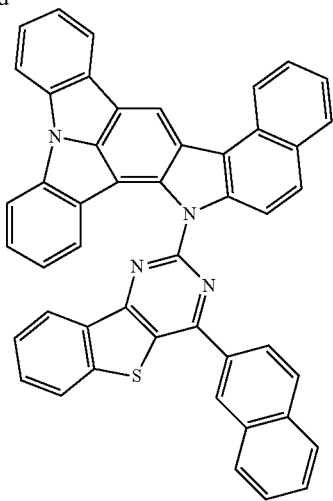
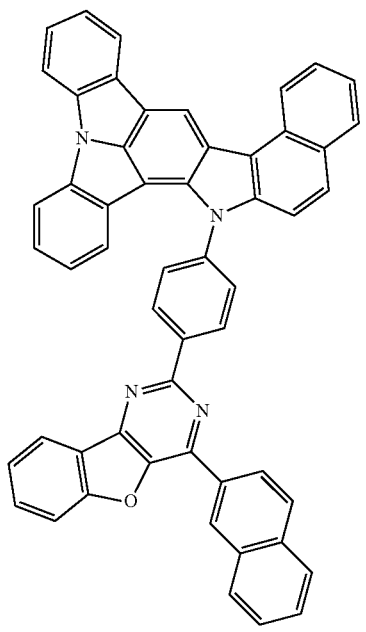 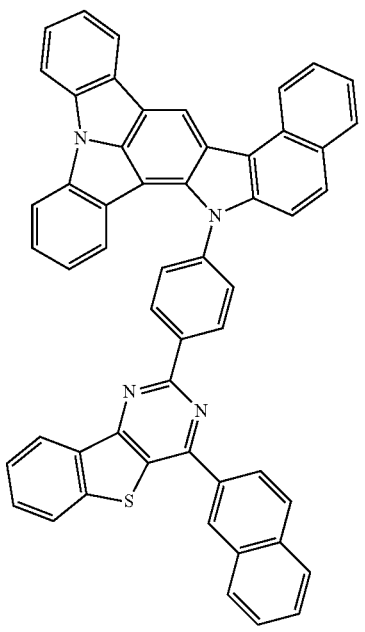

301
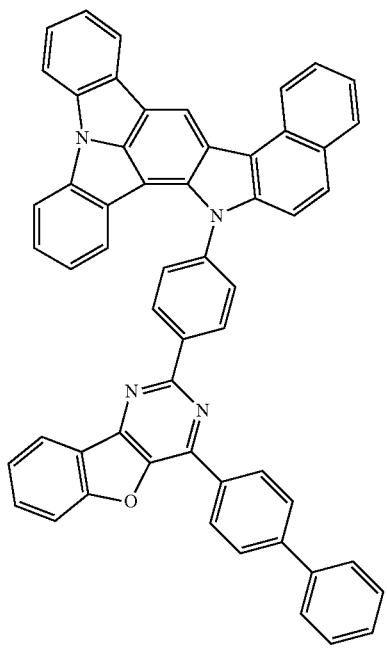
302
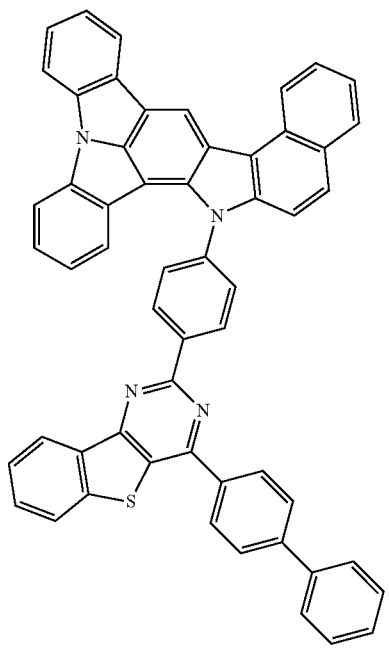
-continued
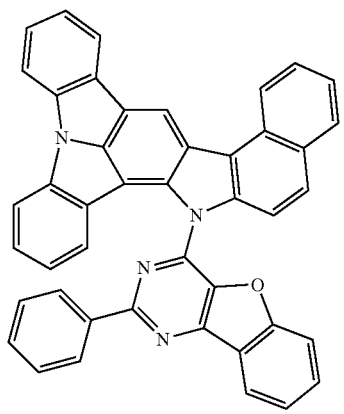
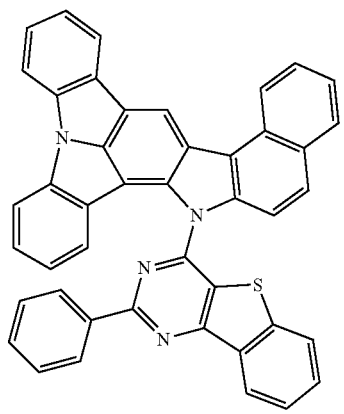
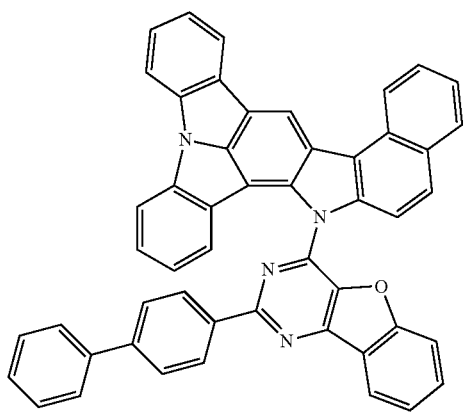
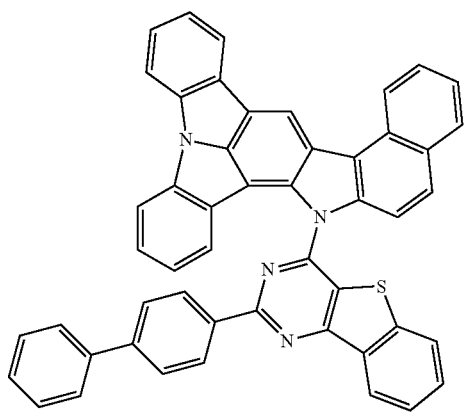

303
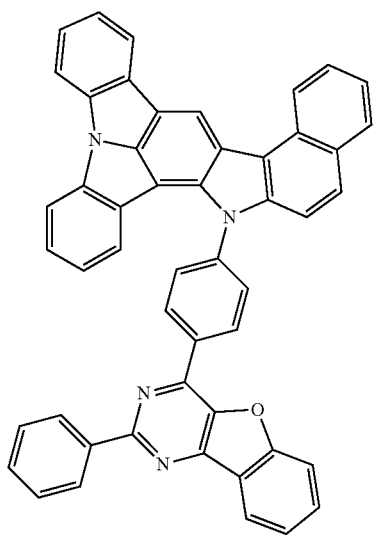
304
-continued
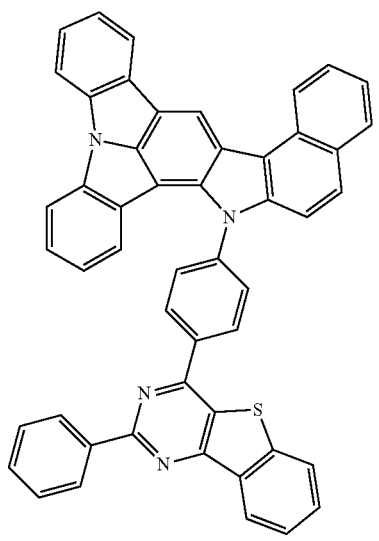
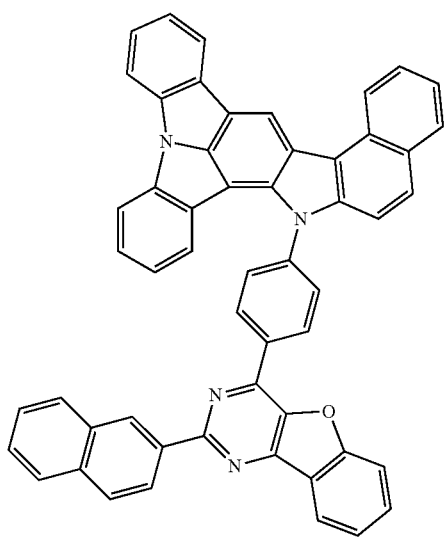
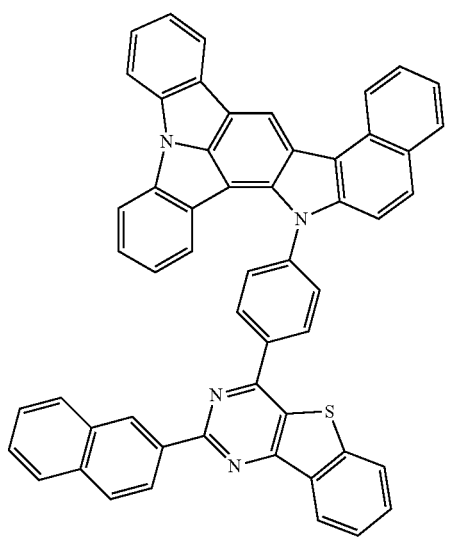
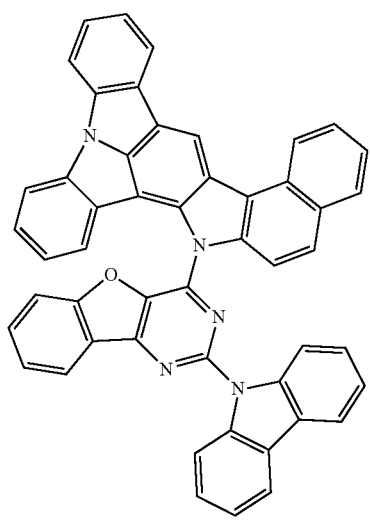
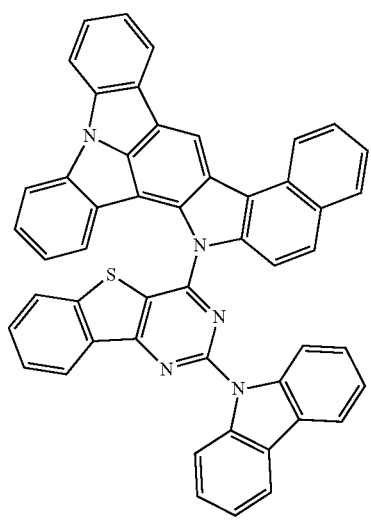

305
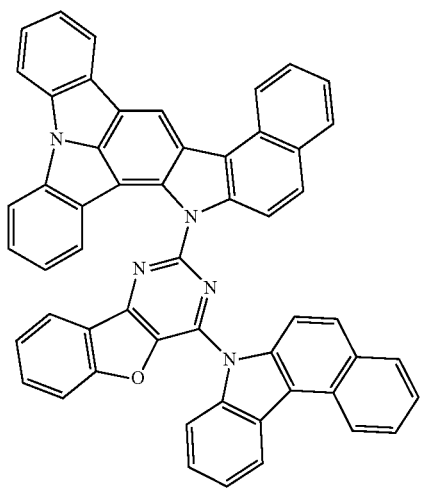
306
-continued
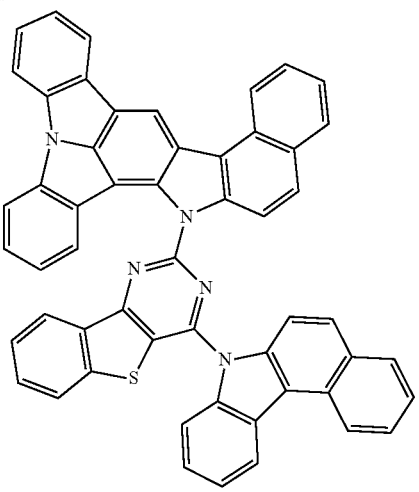
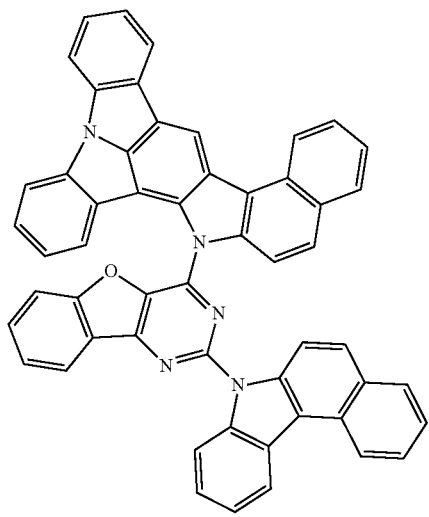
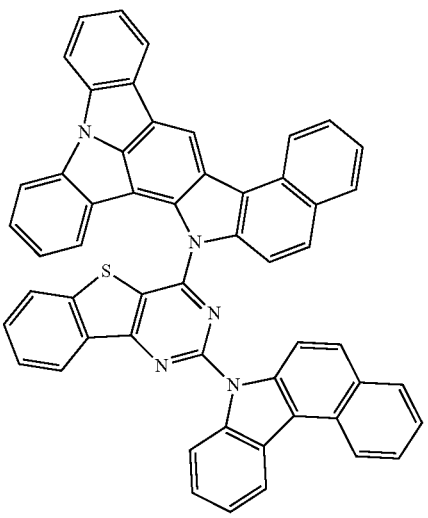
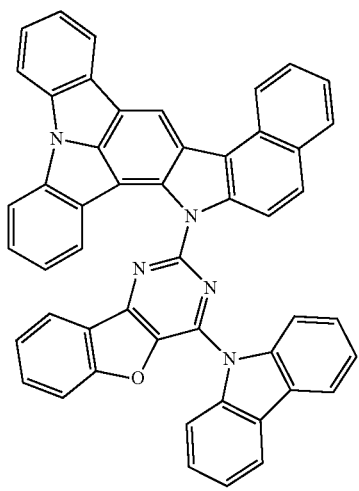
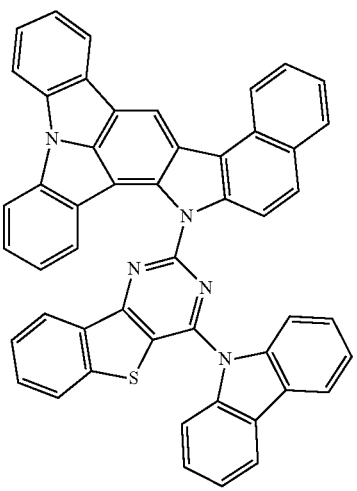

307
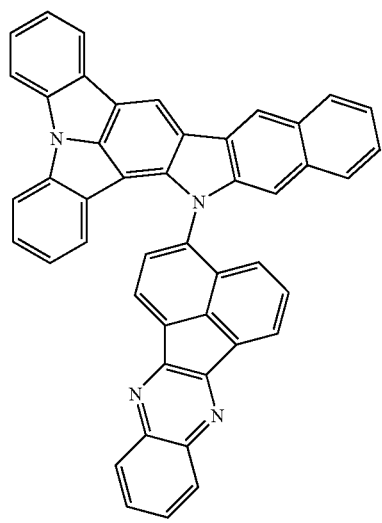
308
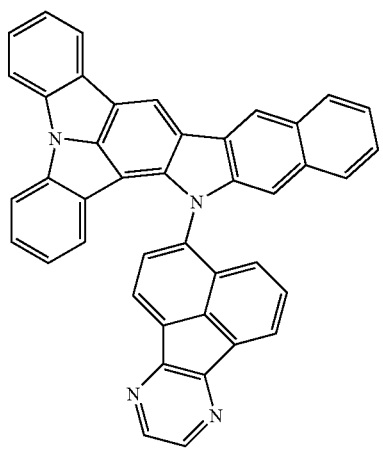
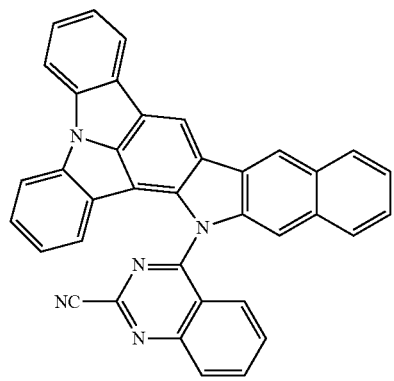
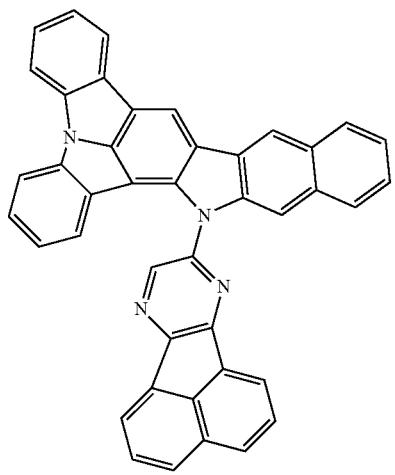
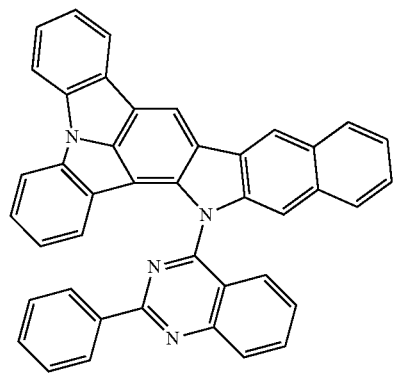
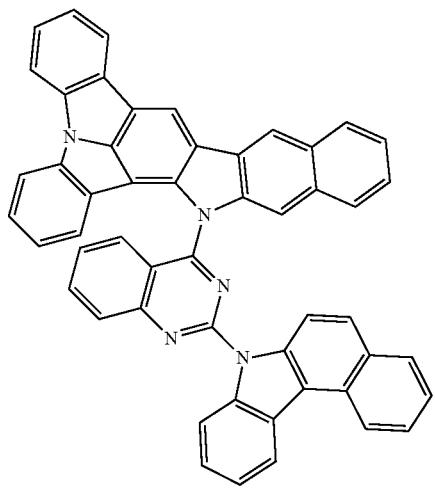

-continued
309
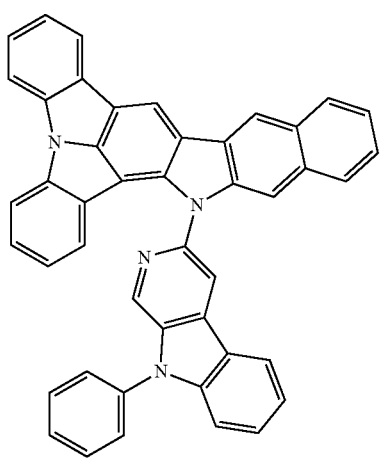
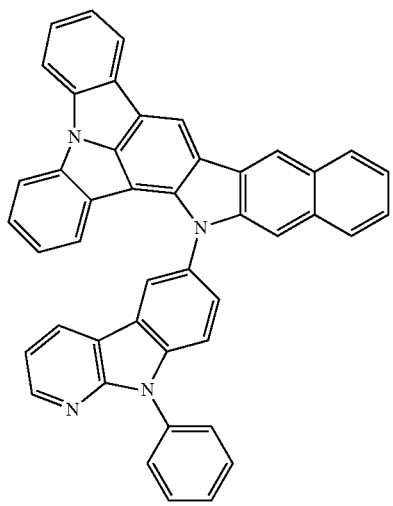
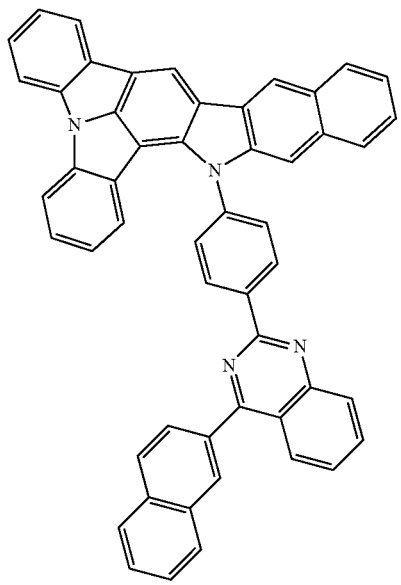
310
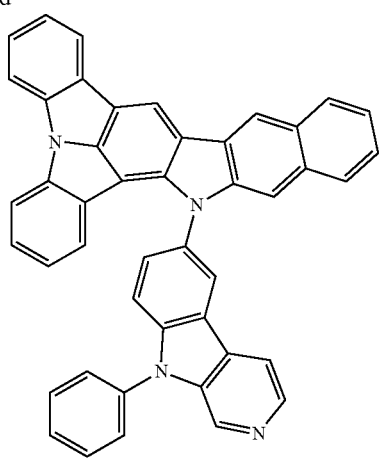
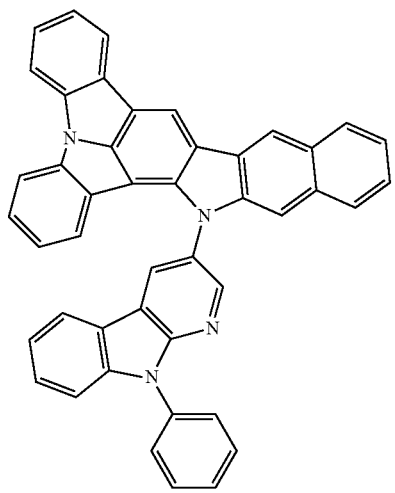
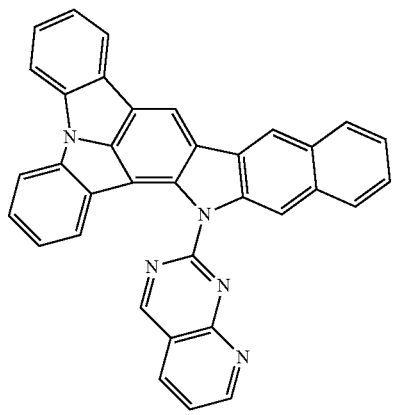

-continued
| 311 | 312 |
|---|---|
| 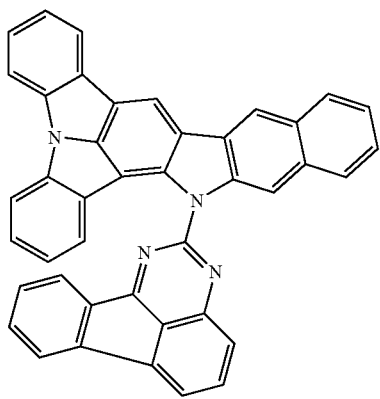 | 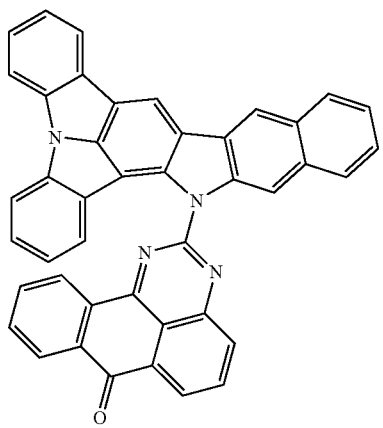 |
| 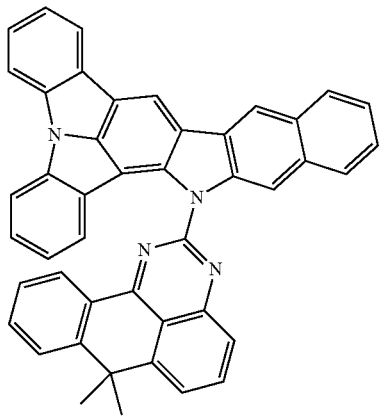 | 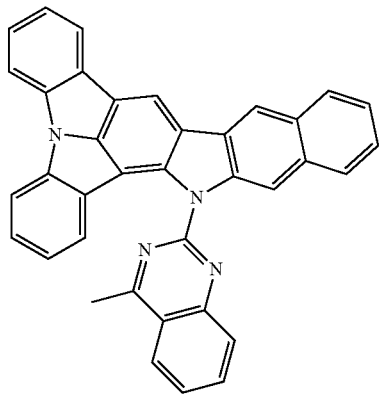 |
| 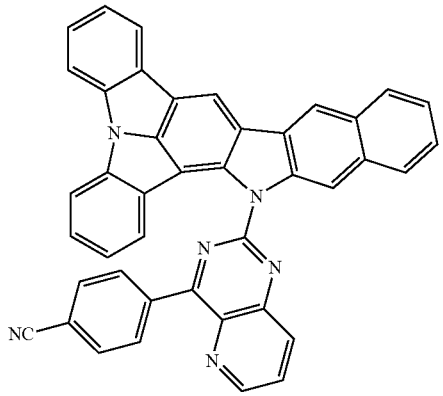 | 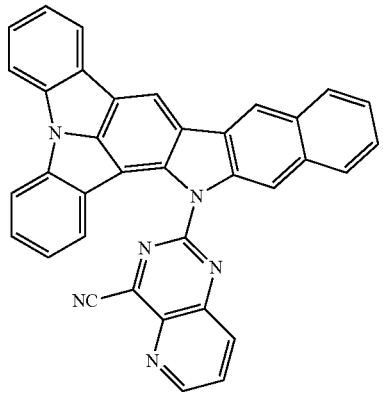 |
| 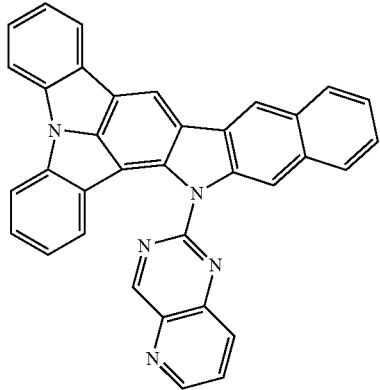 | 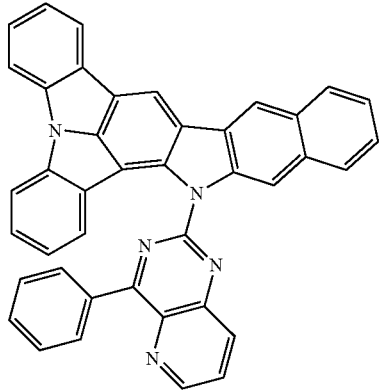 |

-continued
| 313 | 314 |
|---|---|
| 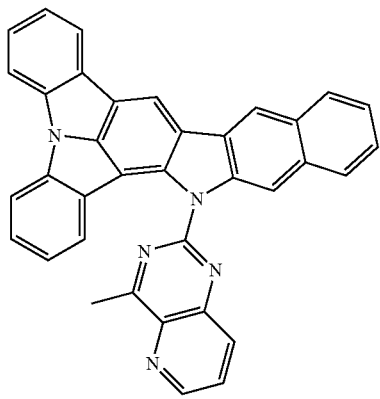 | 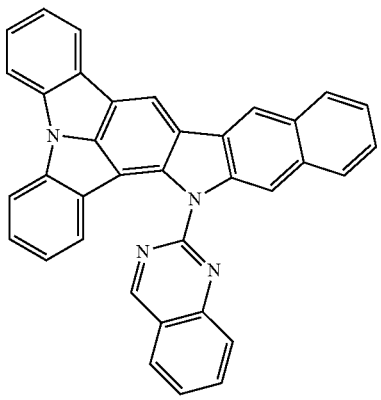 |
| 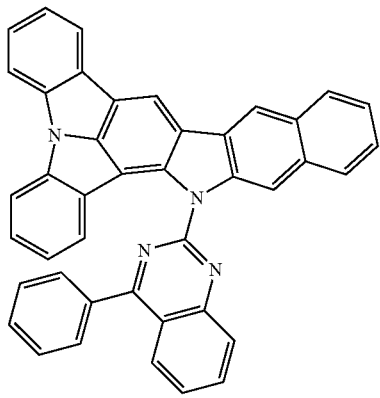 | 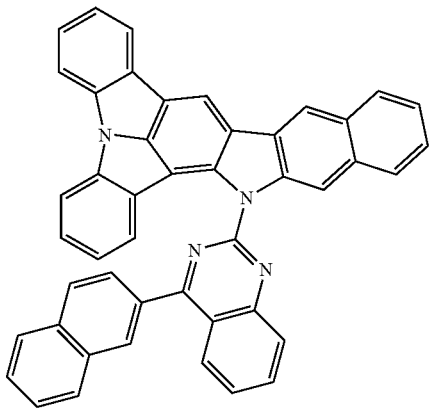 |
| 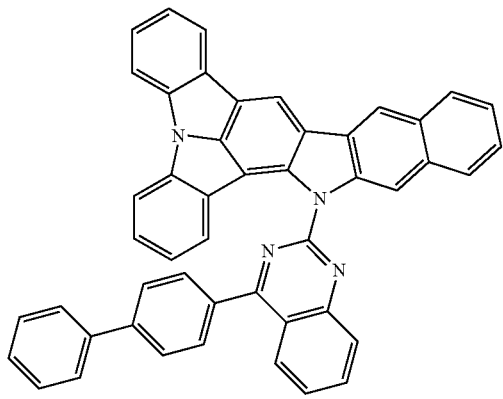 | 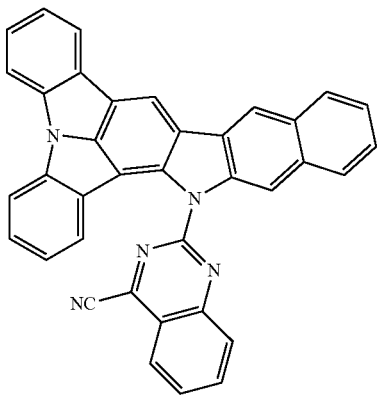 |
| 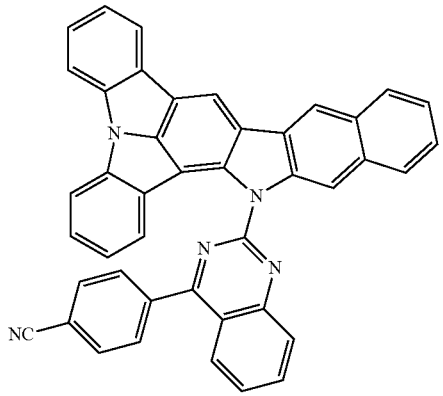 | 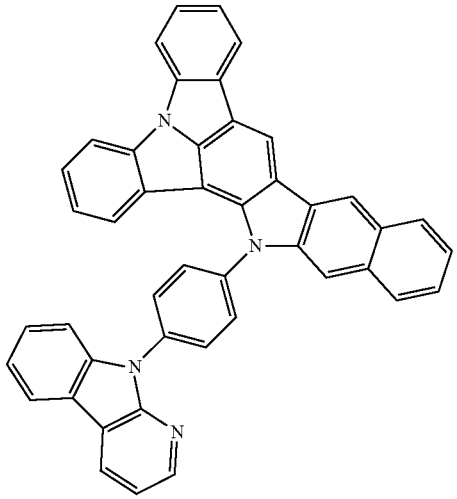 |

315
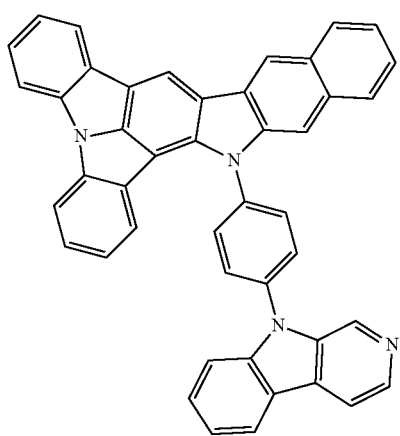
316
-continued
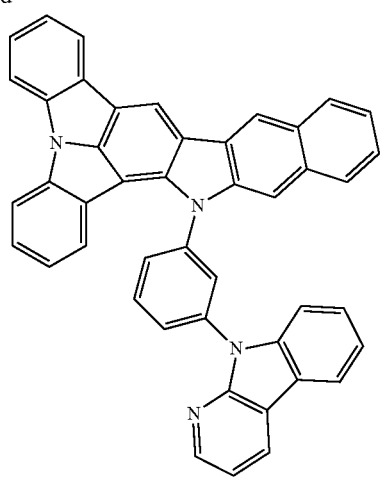
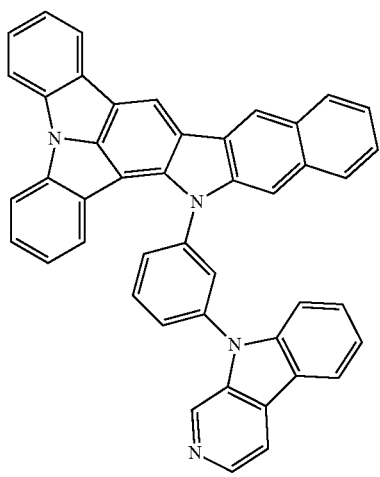
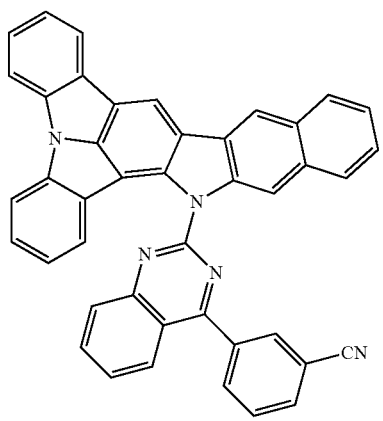
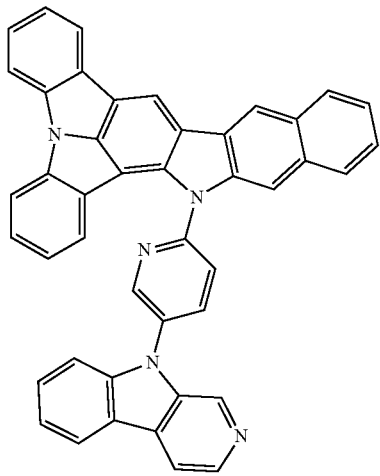
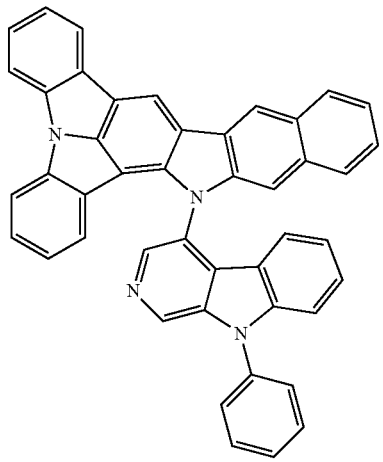

317 318
-continued
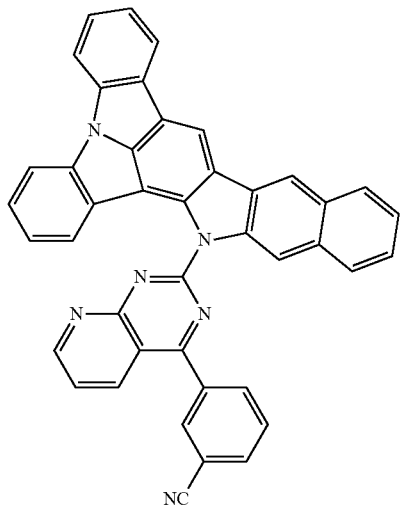
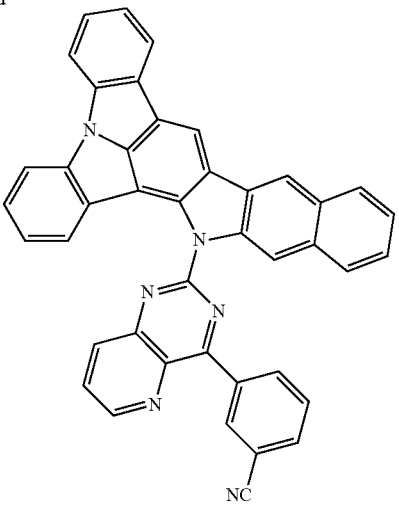
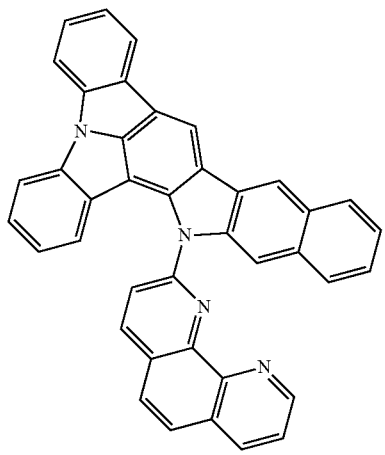
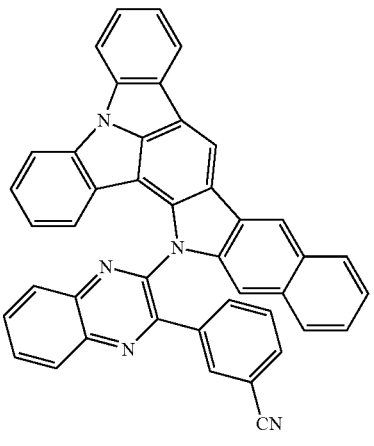
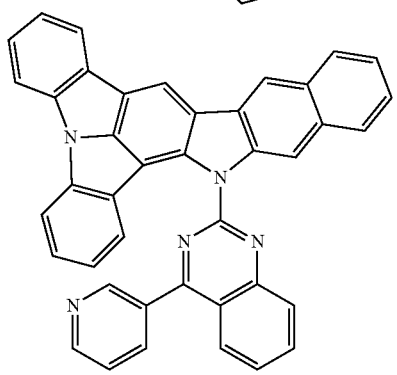
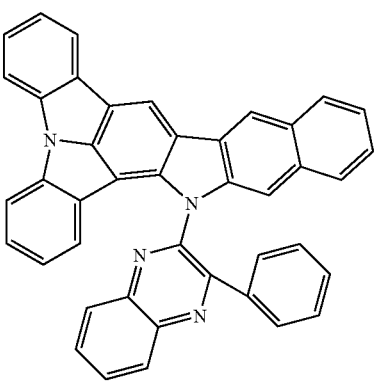
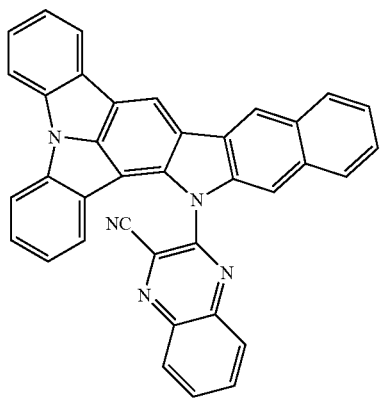
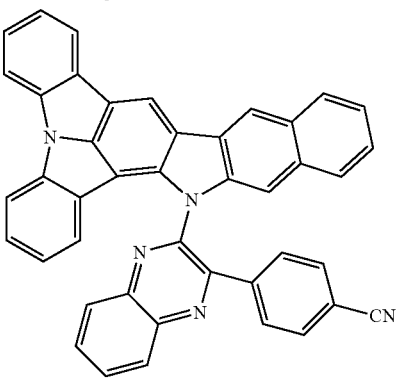

-continued
| 319 | 320 |
|---|---|
| 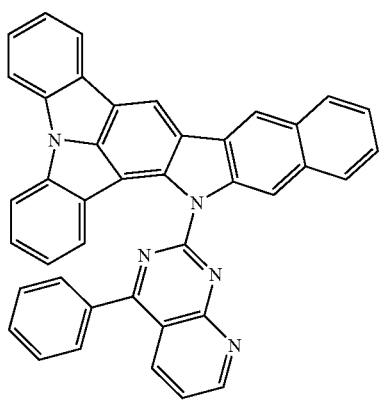 | 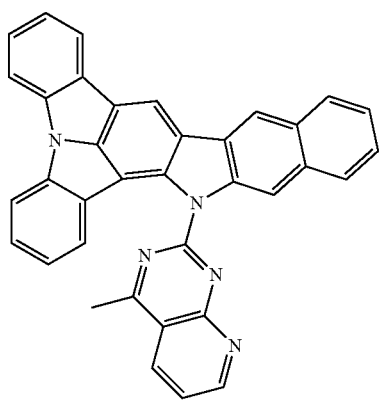 |
| 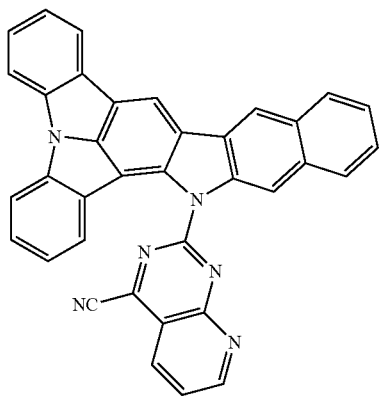 | 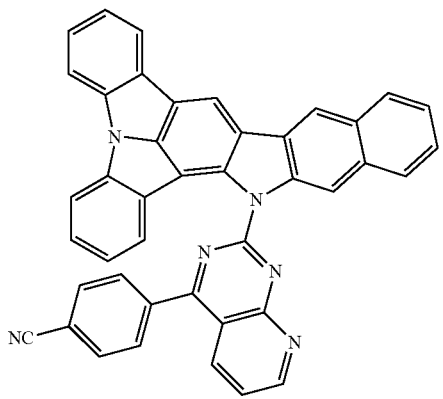 |
| 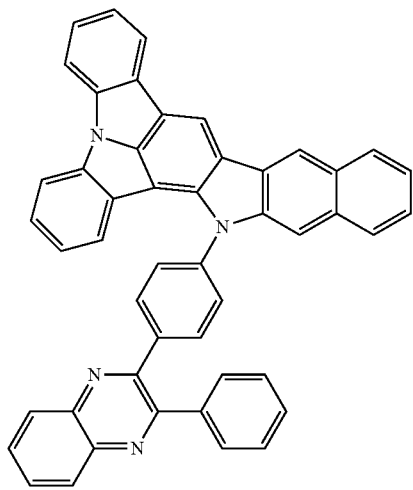 | 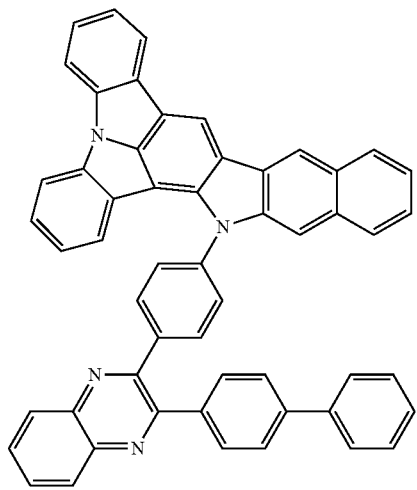 |

321 322
-continued
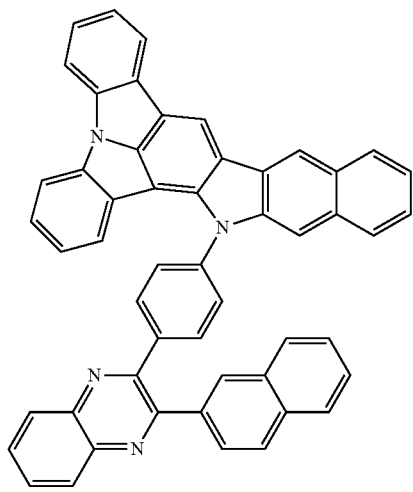
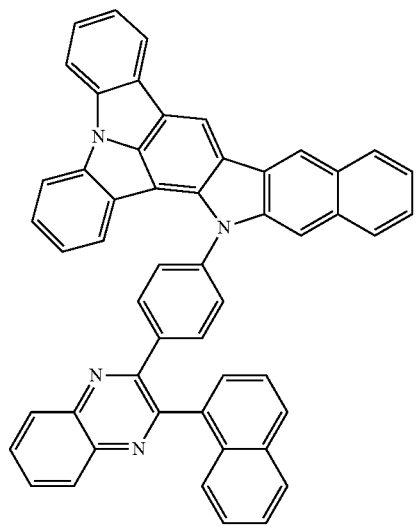
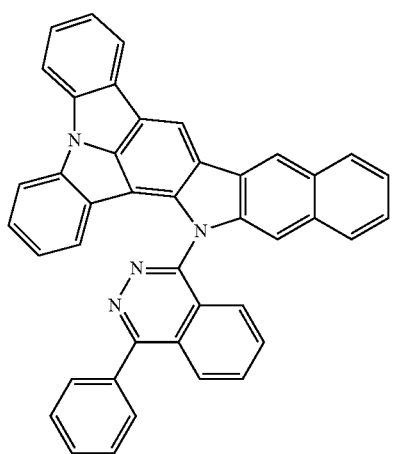
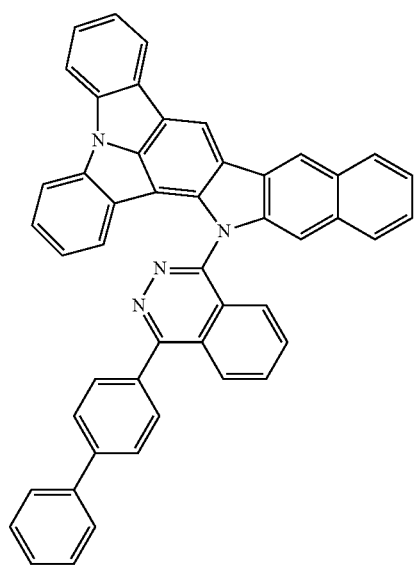
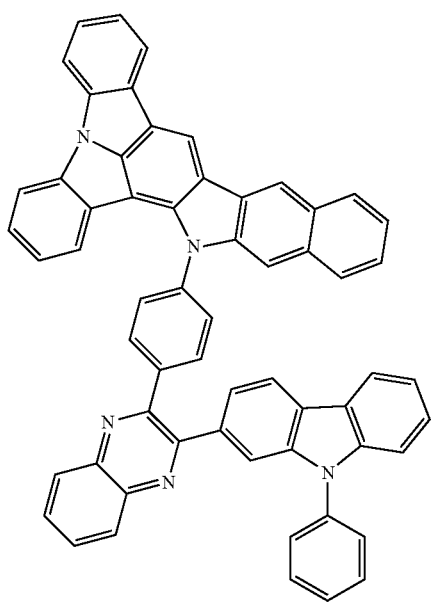
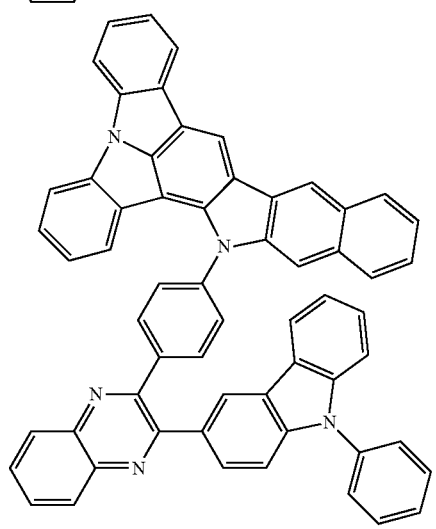

323
324
-continued
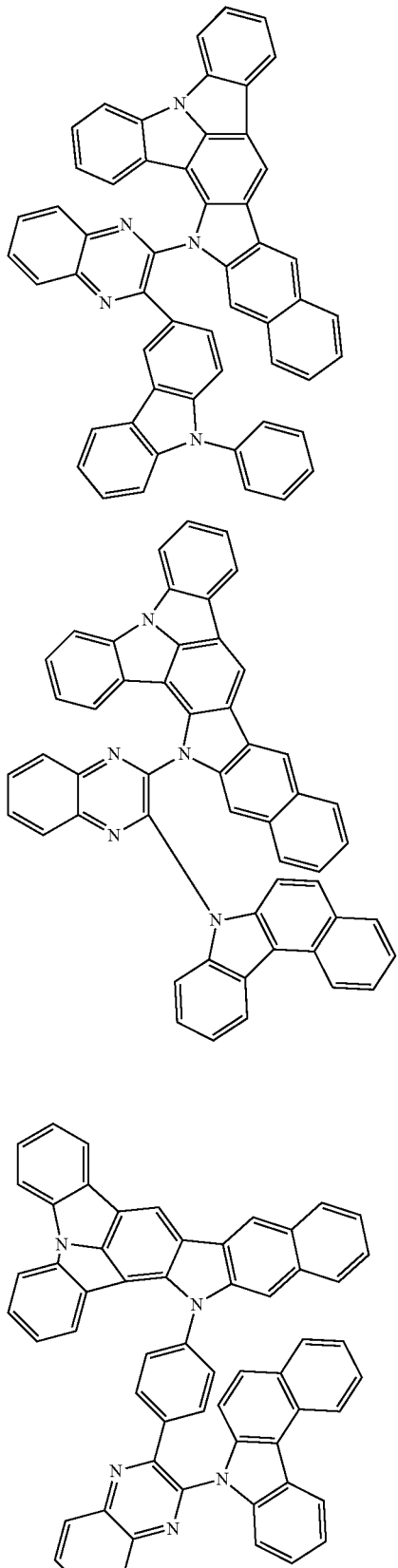
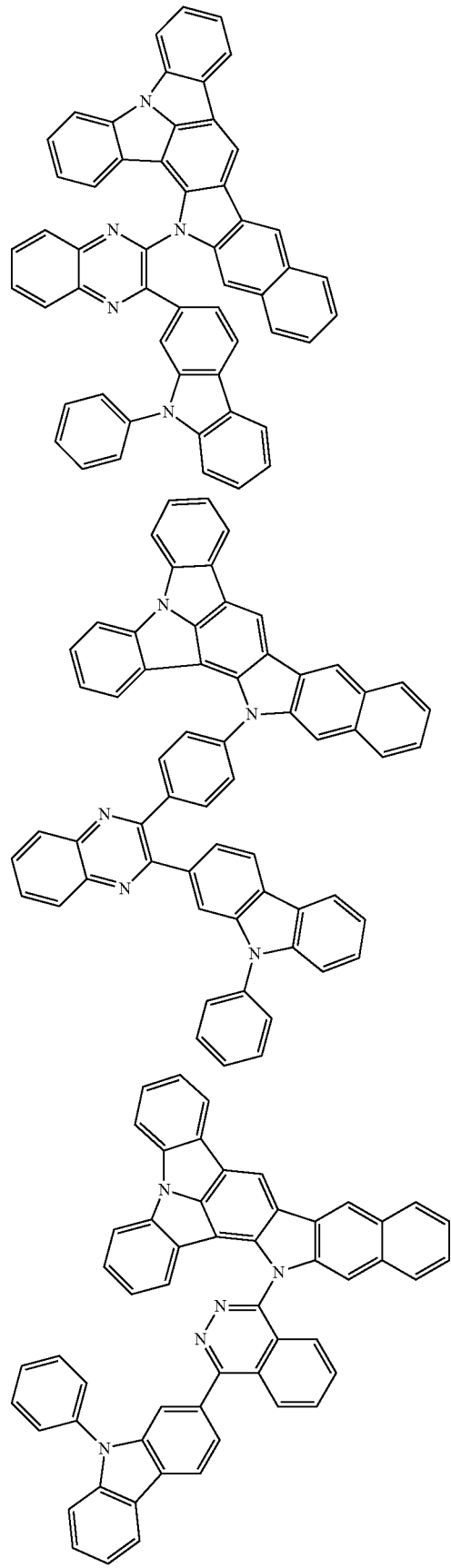

325
326
-continued
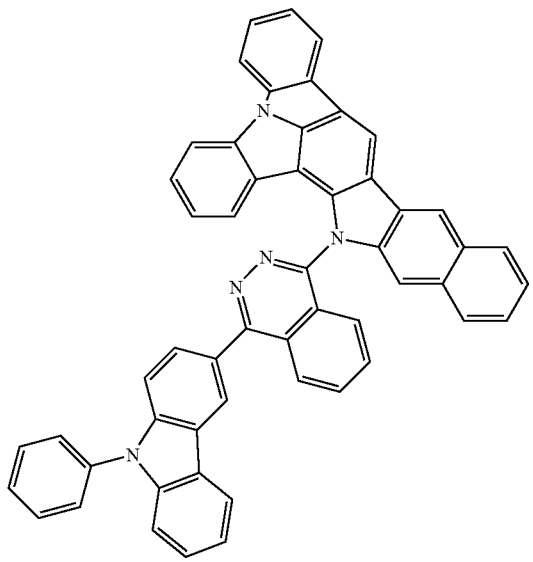
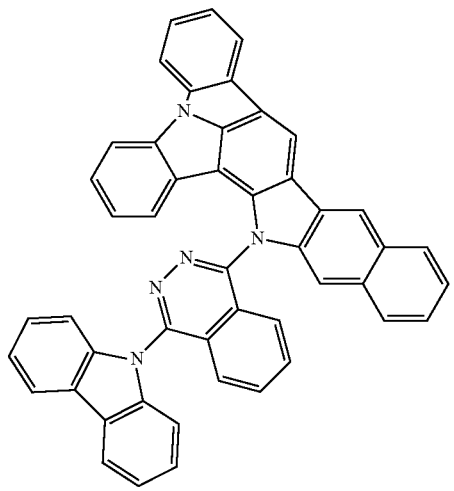
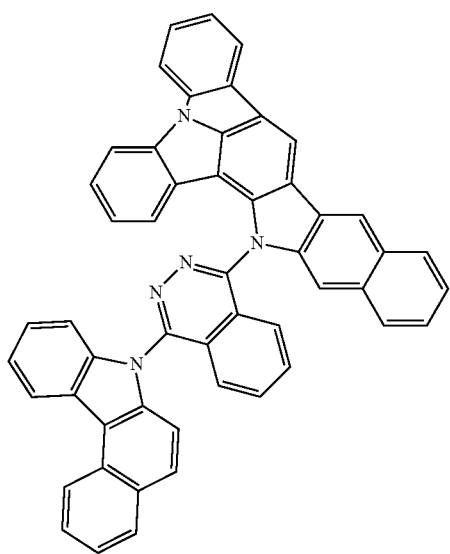
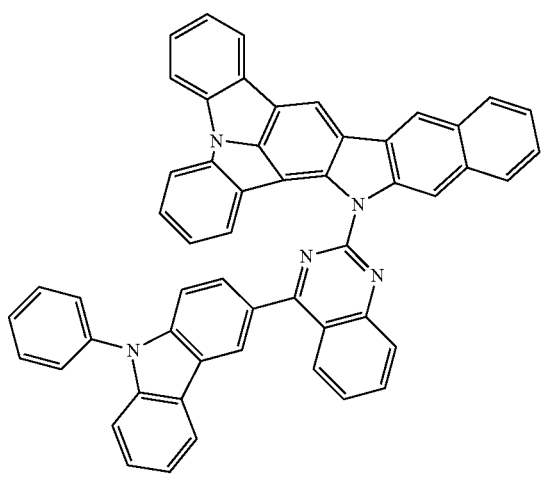
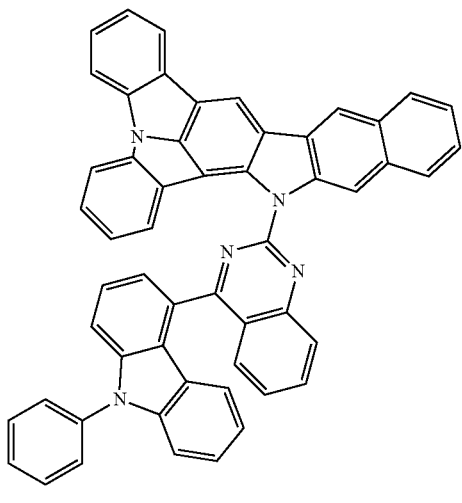
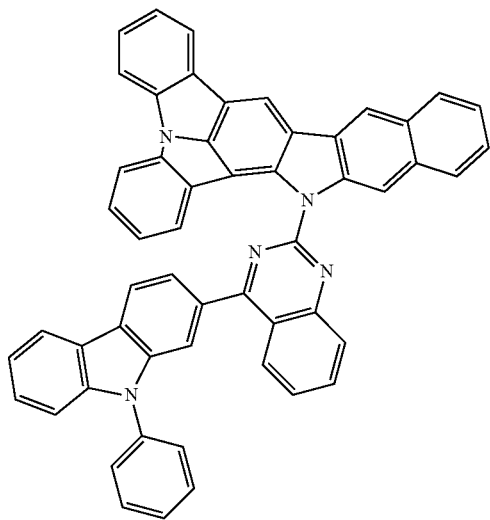

-continued
327
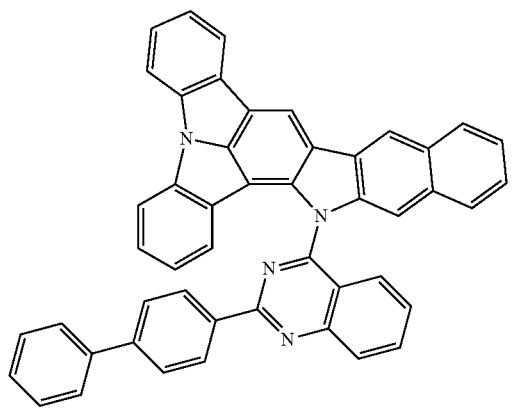
328
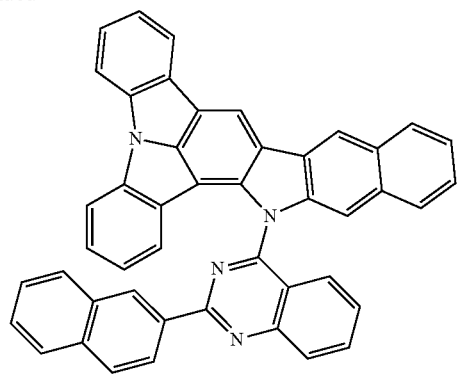
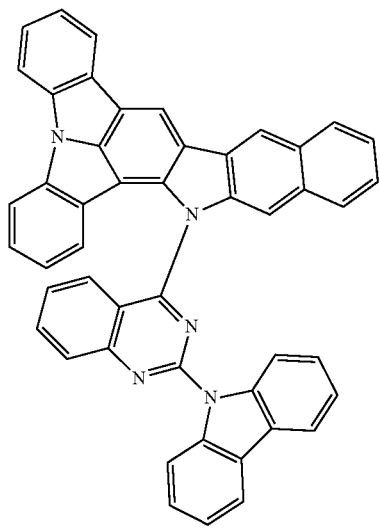
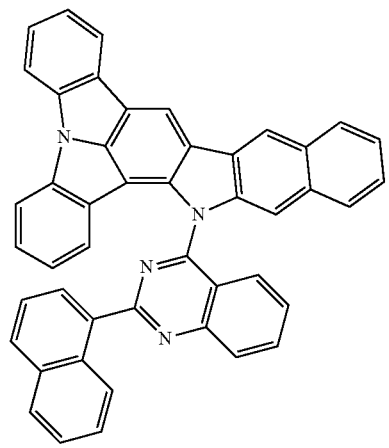
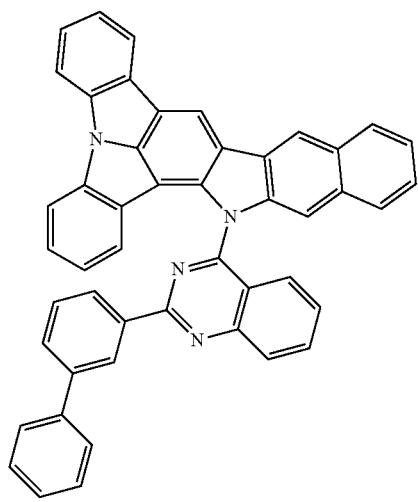
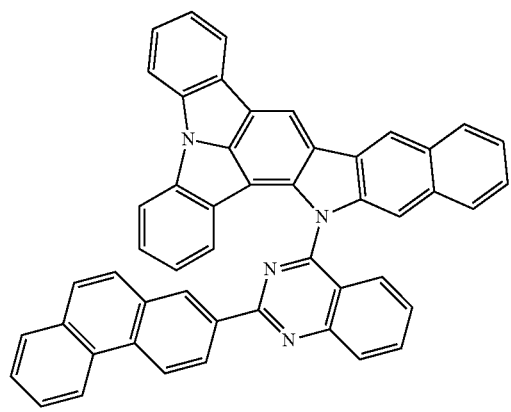

-continued
| 329 | 330 |
|---|---|
| 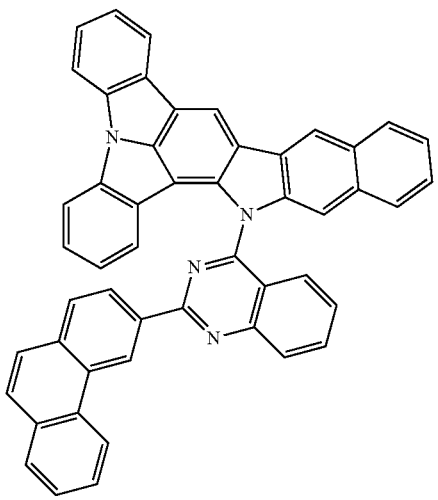 | 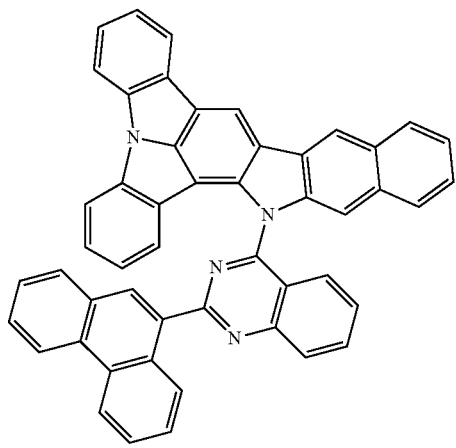 |
| 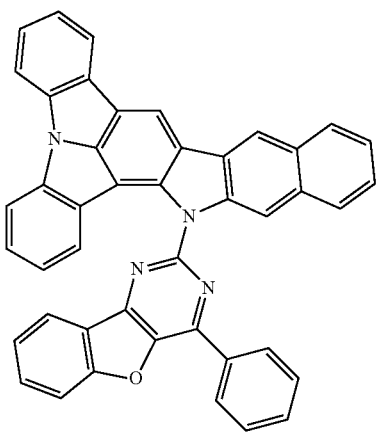 | 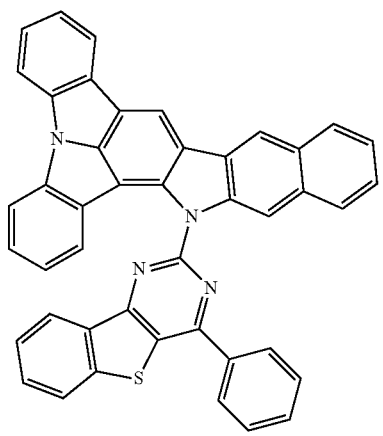 |
| 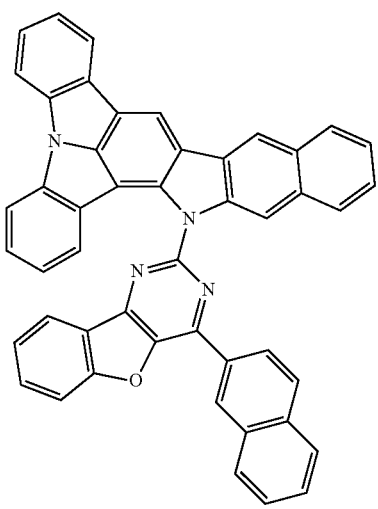 | 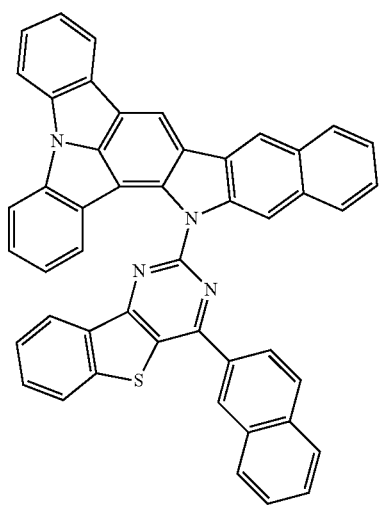 |

-continued
| 331 | 332 |
|---|---|
| 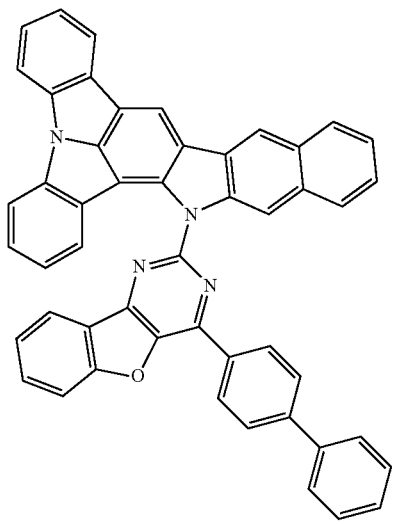 | 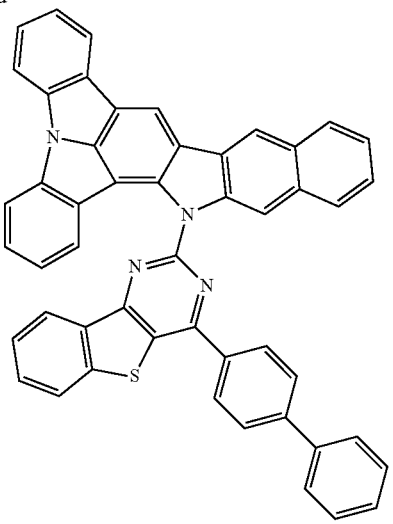 |
| 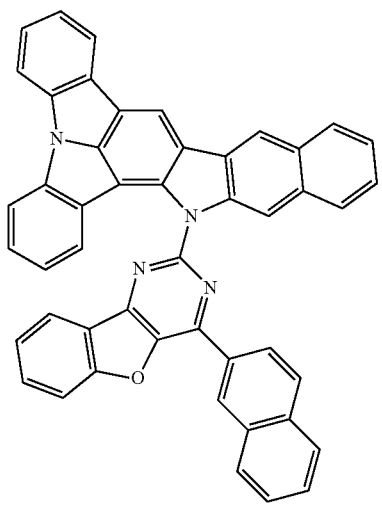 | 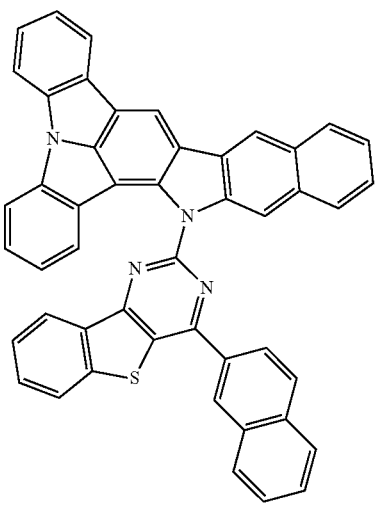 |
| 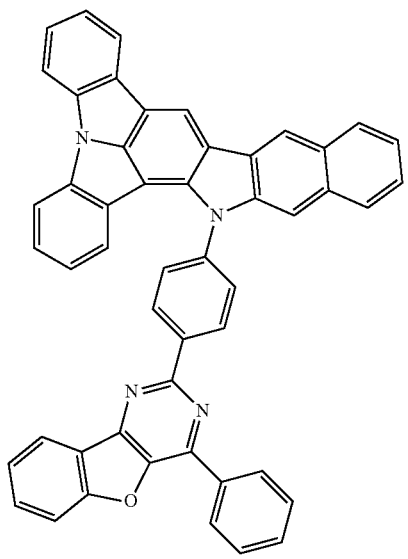 | 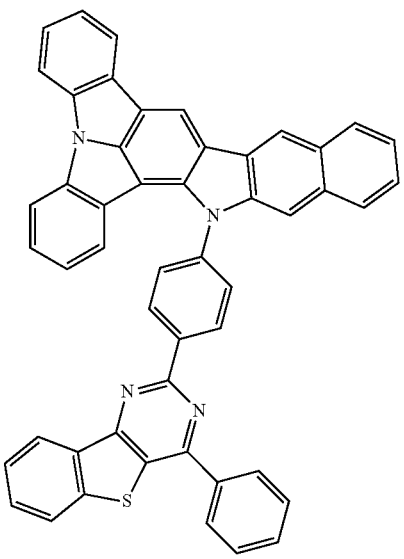 |

333                                      334
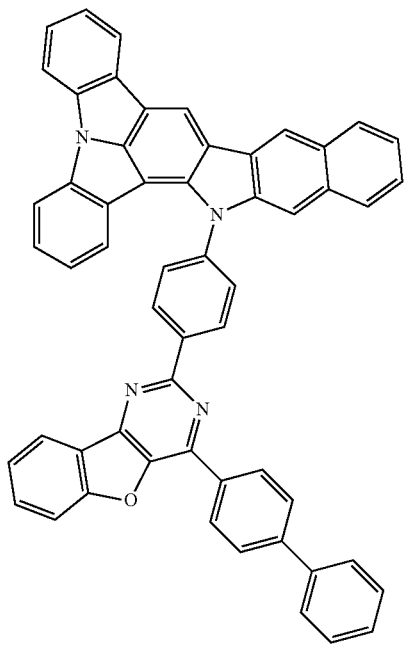          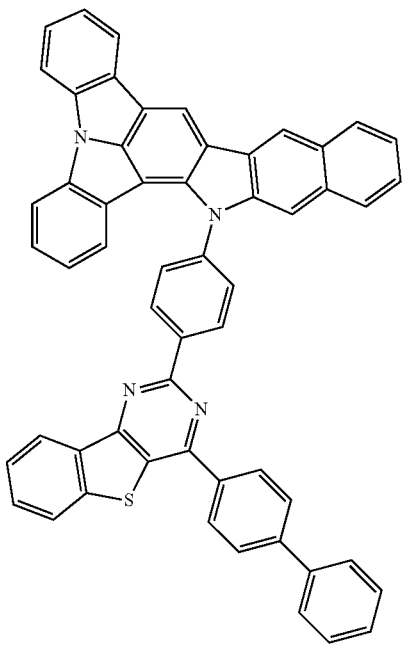
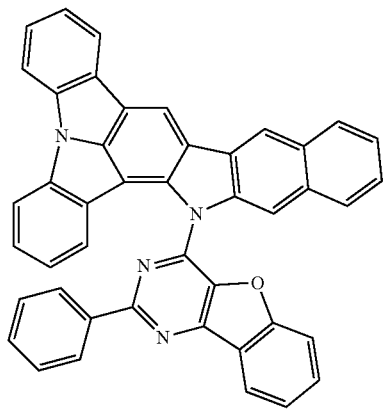          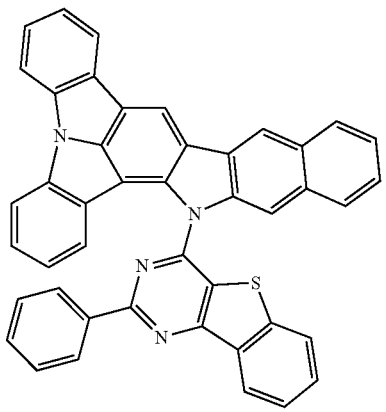
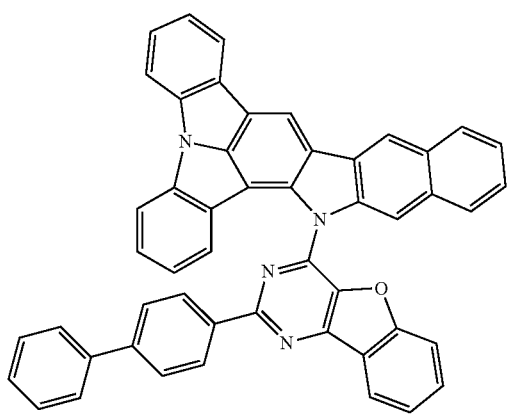          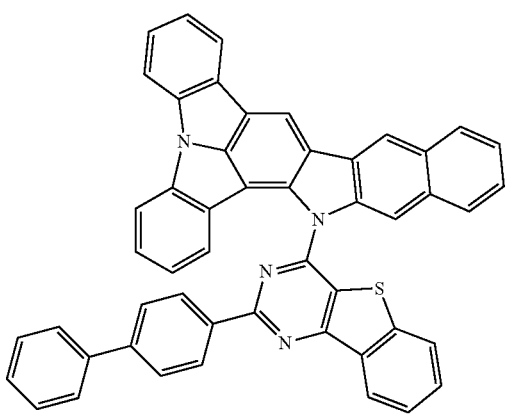

335 336
-continued
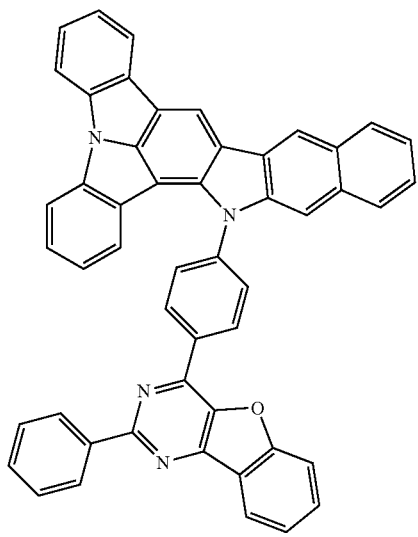
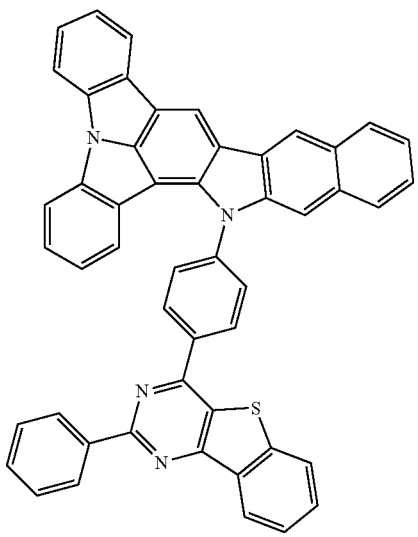
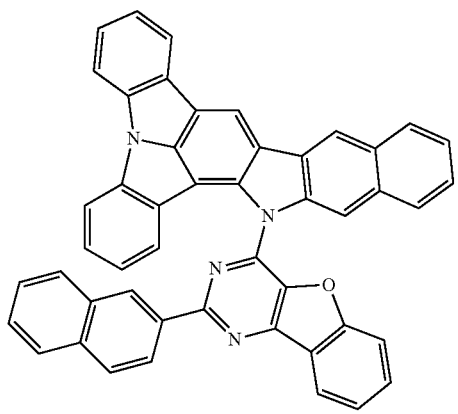
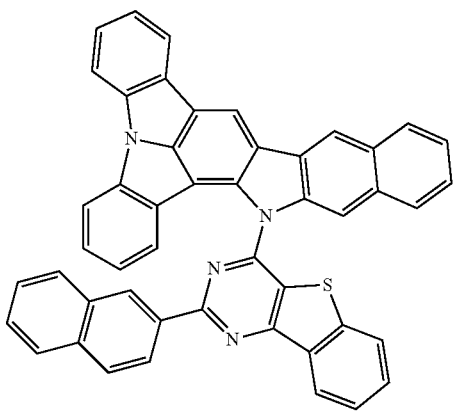
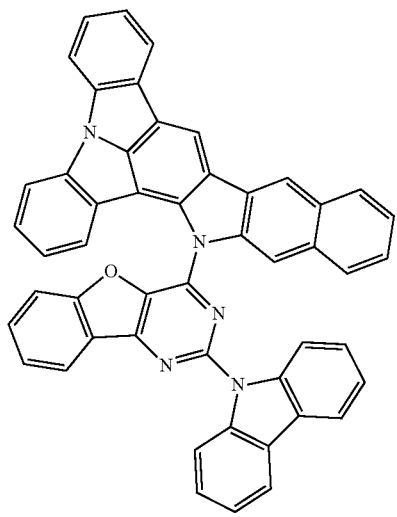
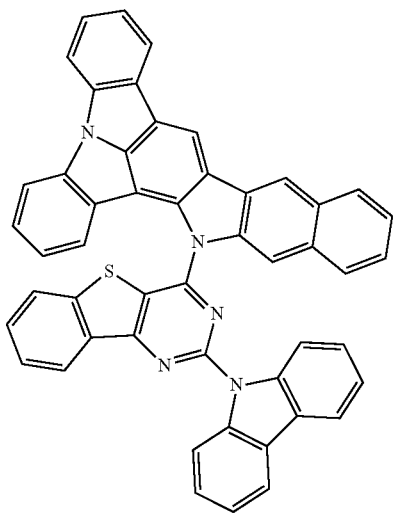

337 338
-continued
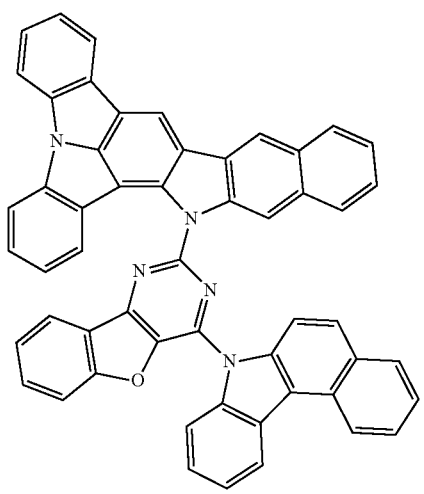
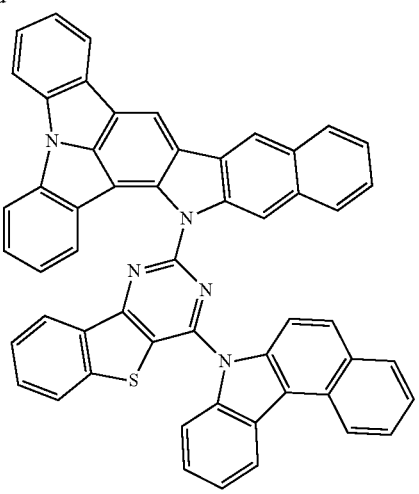
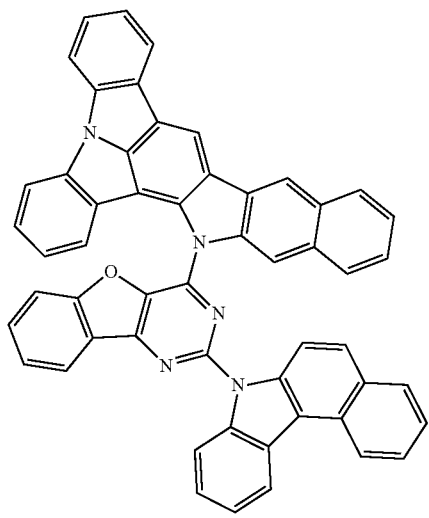
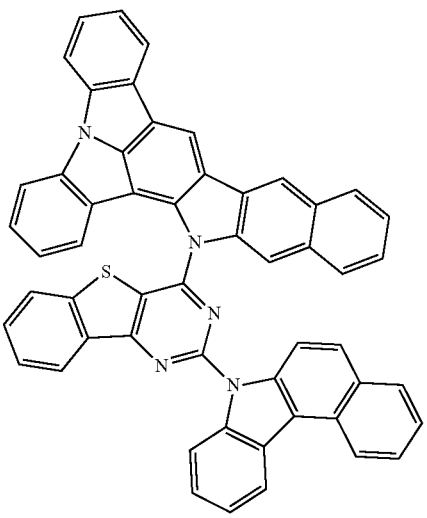
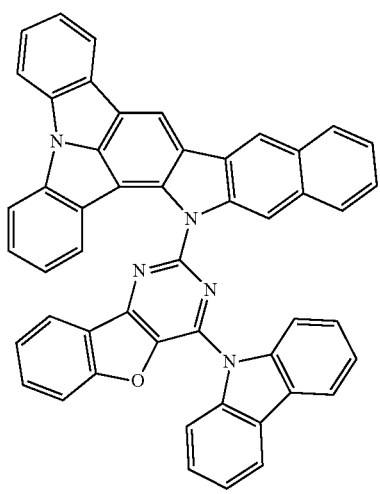
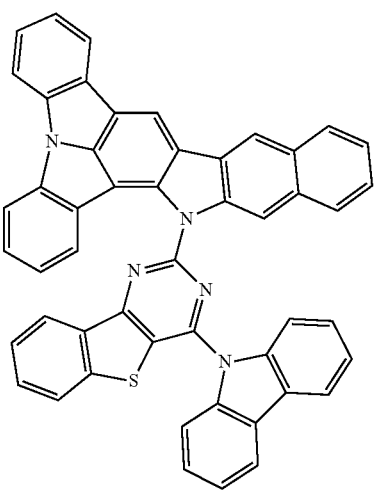

339
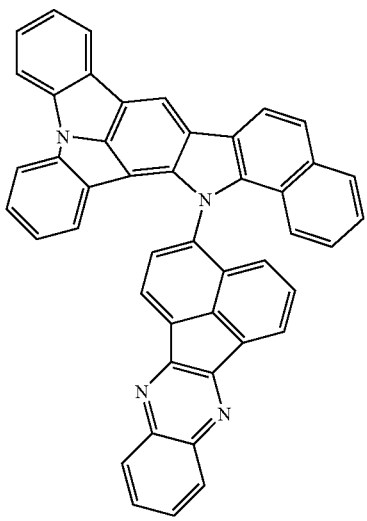
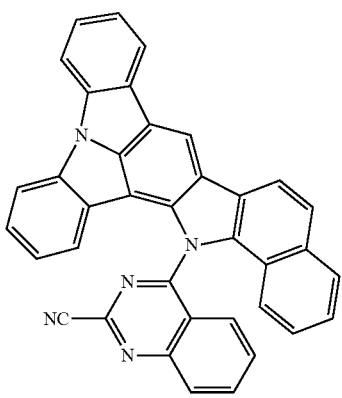
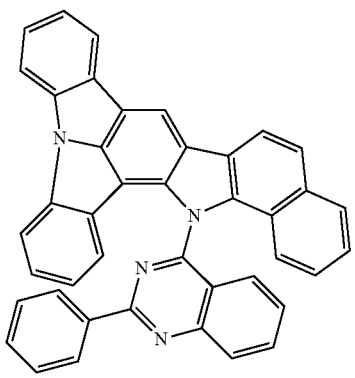
340
-continued
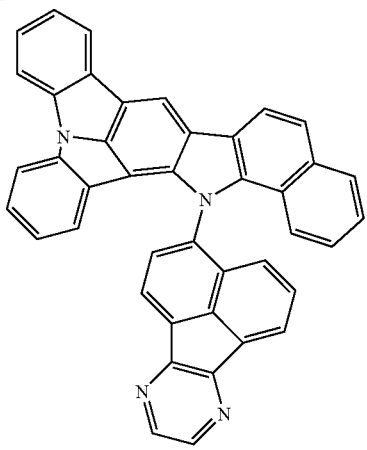
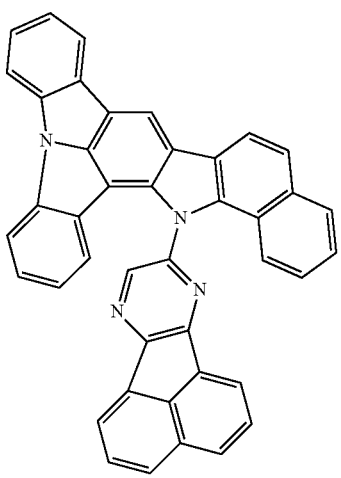
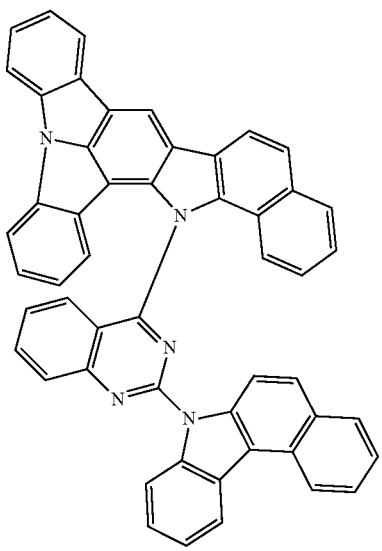

-continued
| 341 | 342 |
|---|---|
| 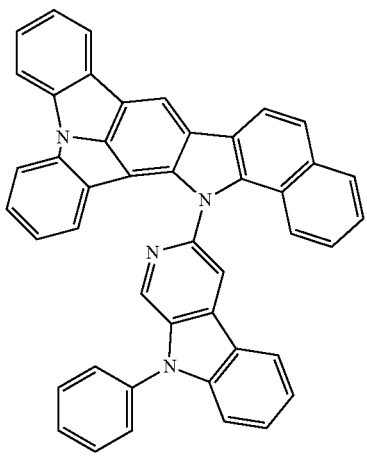 | 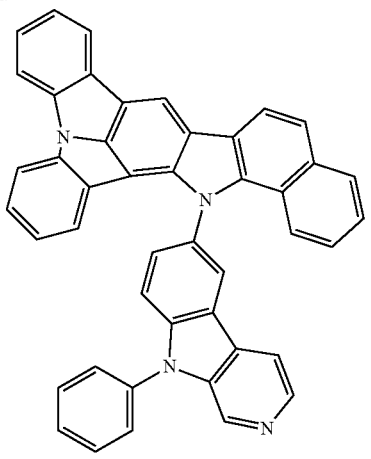 |
| 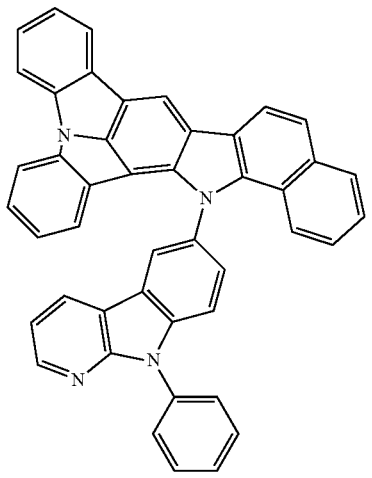 | 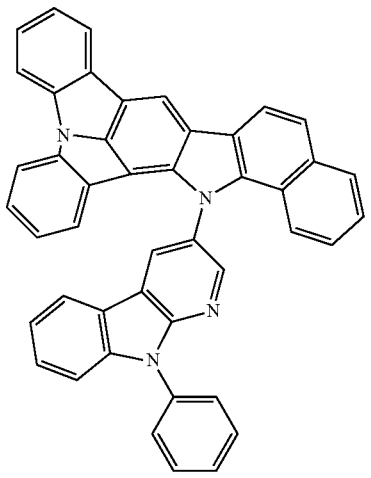 |
| 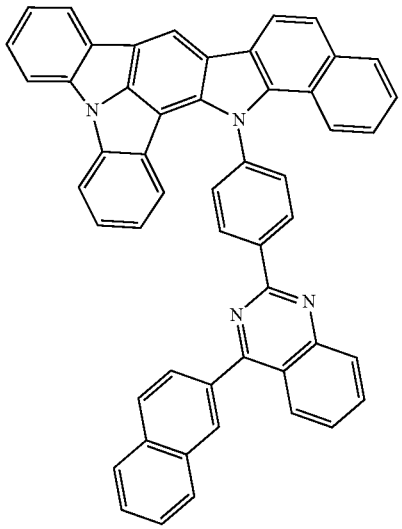 | 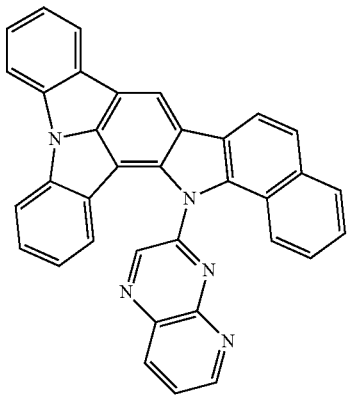 |

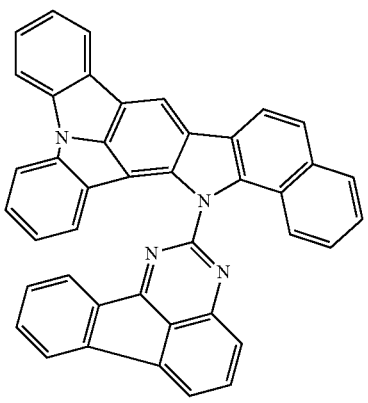
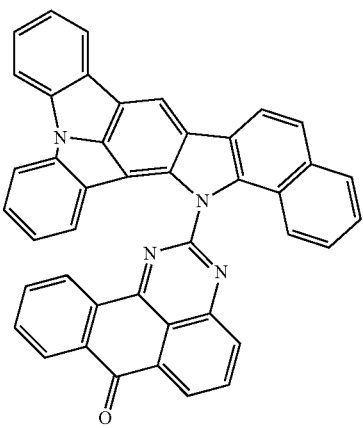
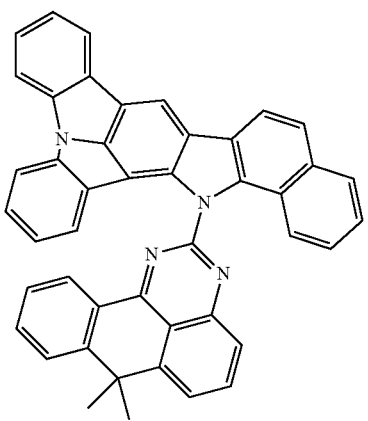
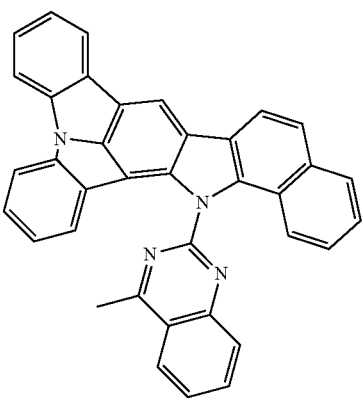
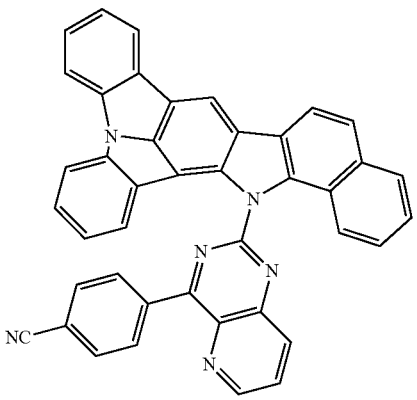
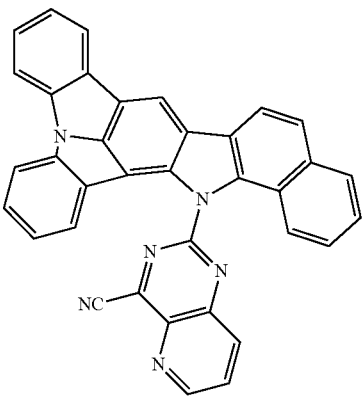
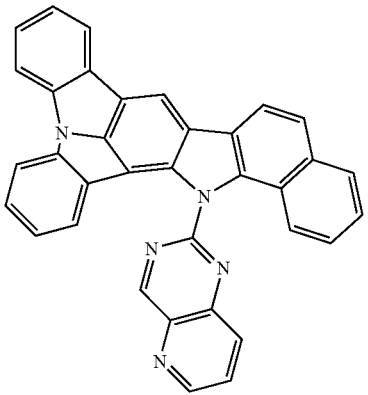
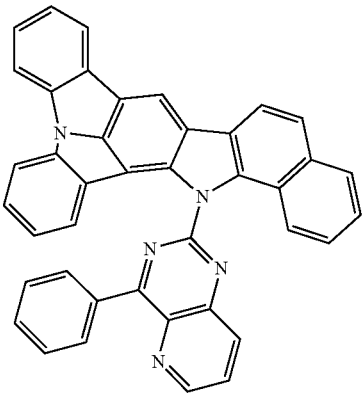

345 346
-continued
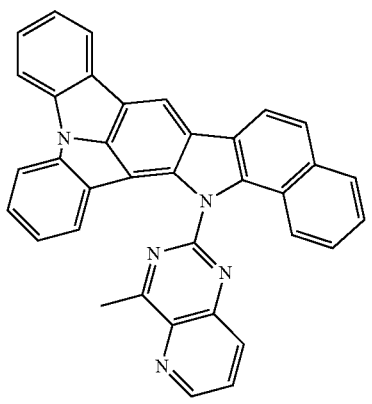
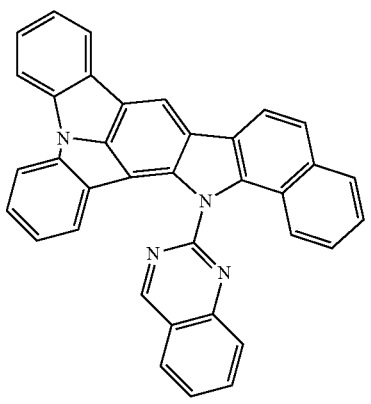
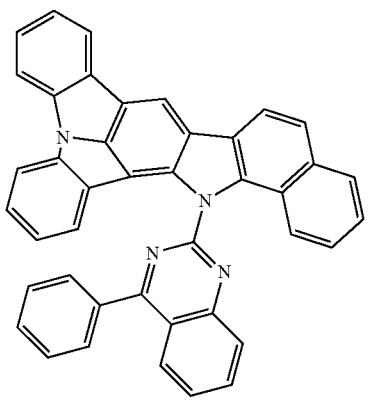
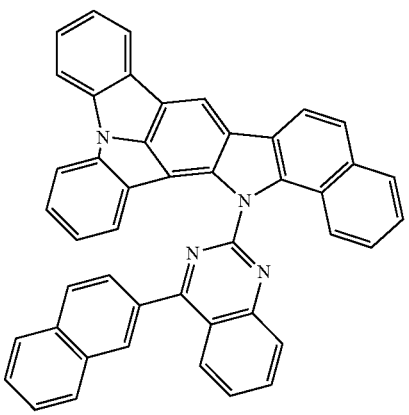
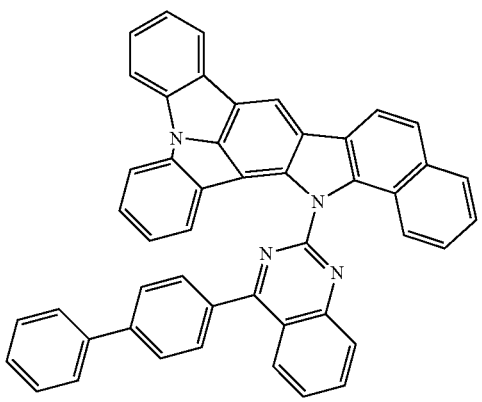
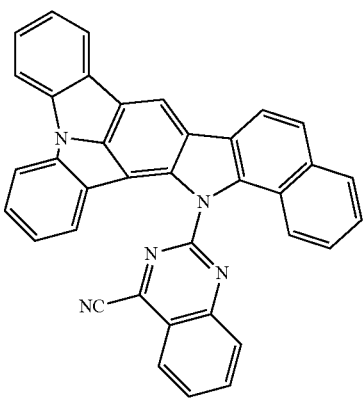
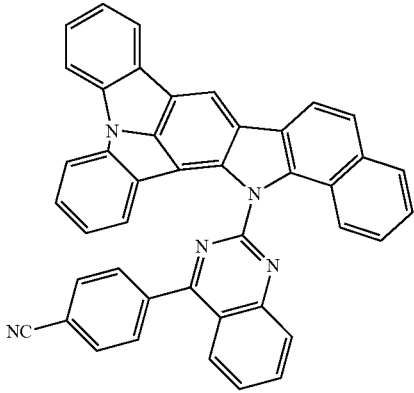
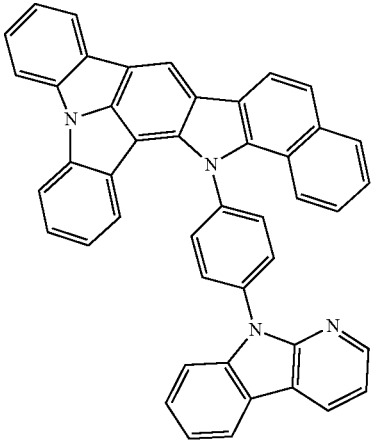

347
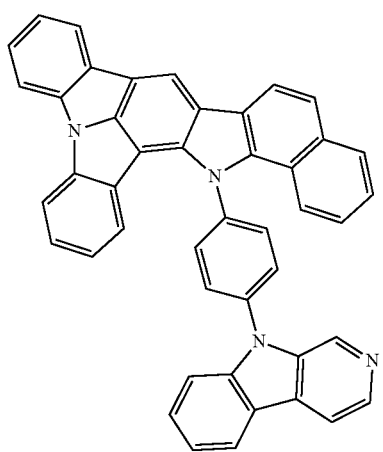
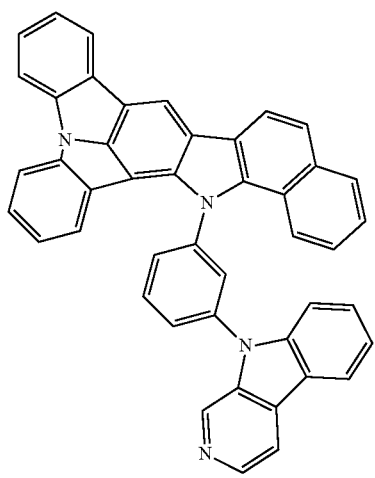
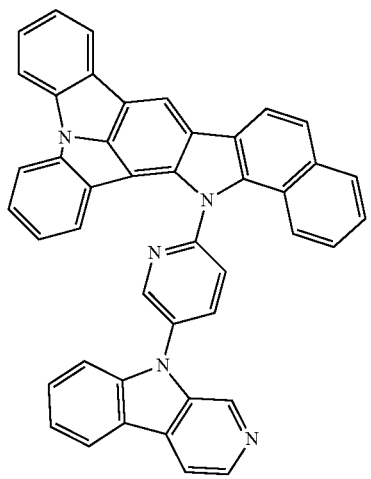
-continued
348
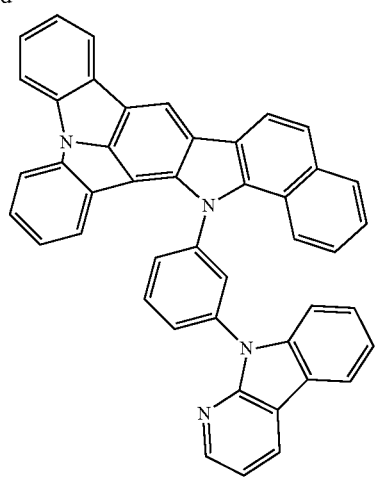
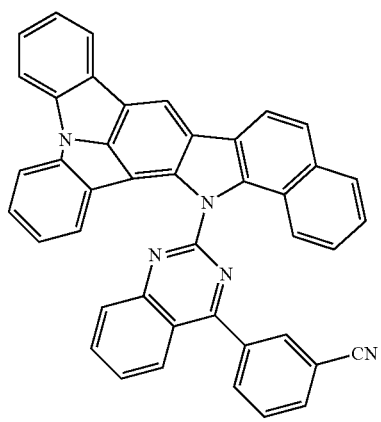
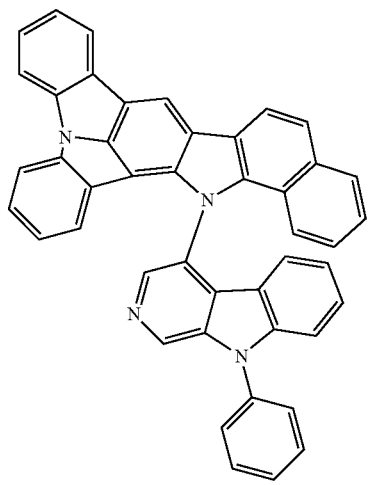

-continued
| 349 | 350 |
|---|---|
| 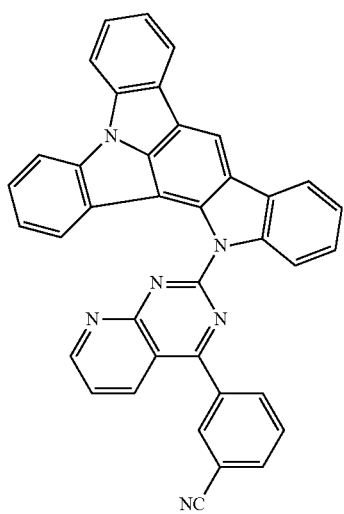 | 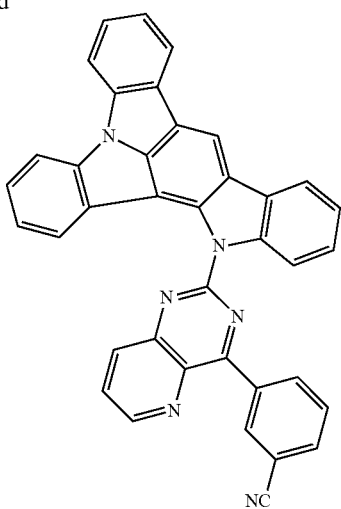 |
| 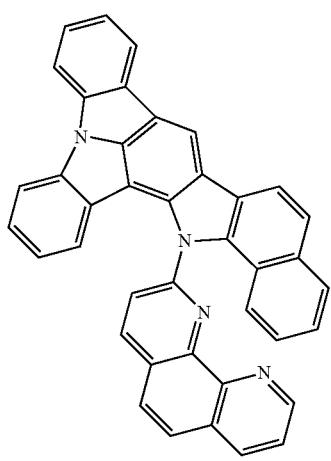 | 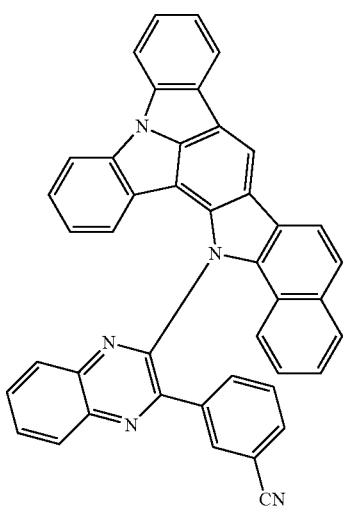 |
| 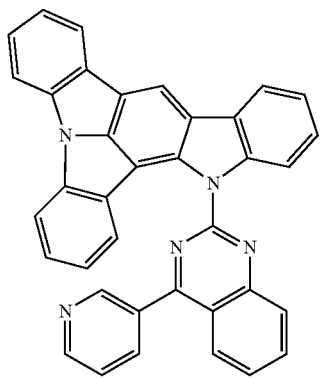 | 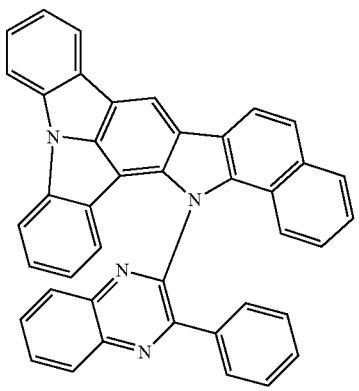 |

351
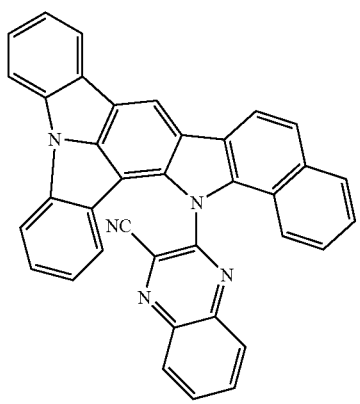
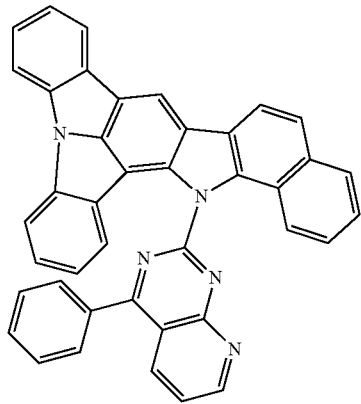
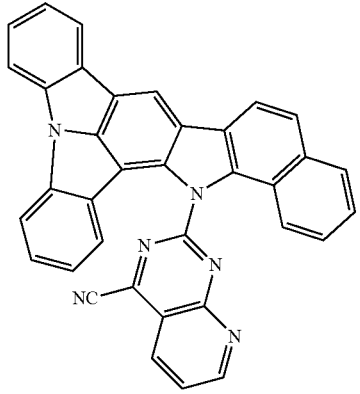
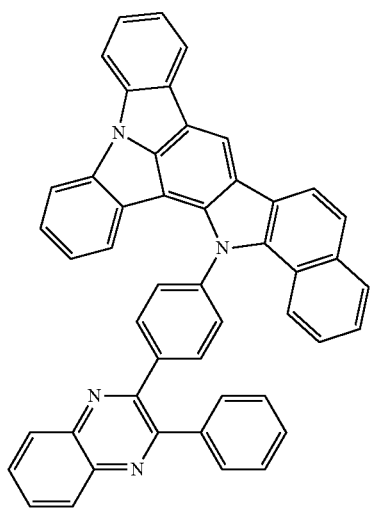
-continued
352
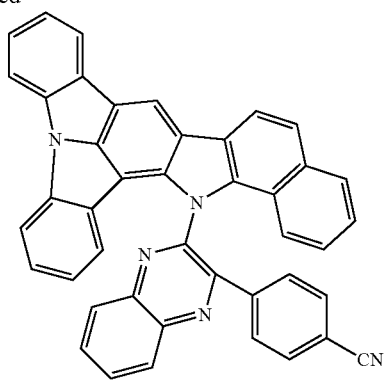
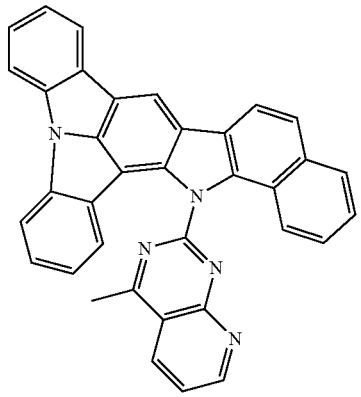
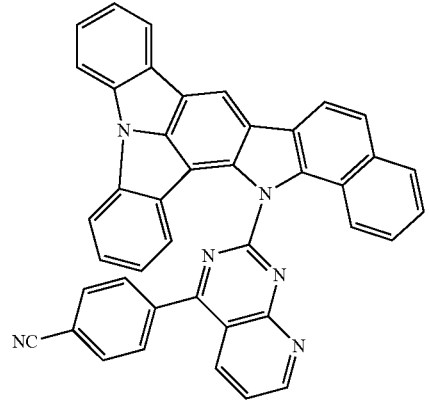
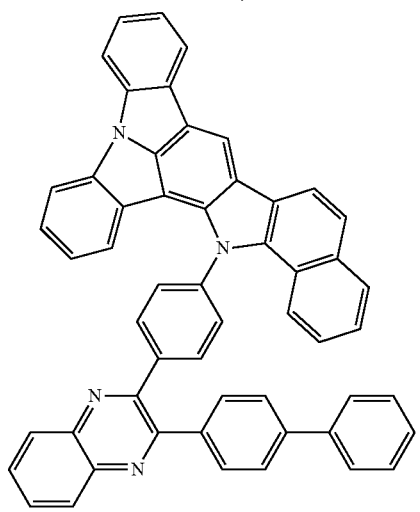

353 354
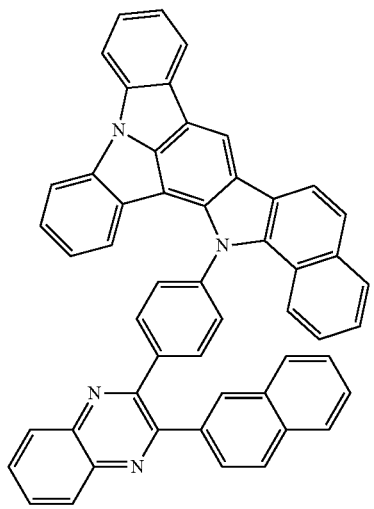 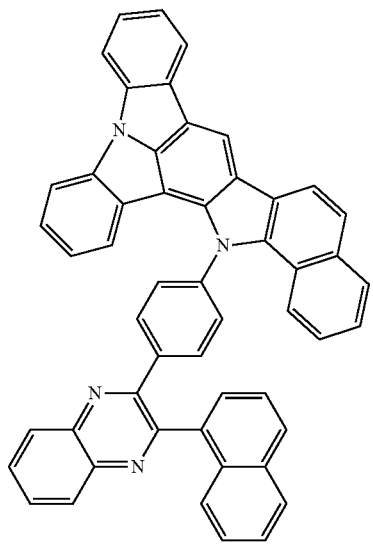
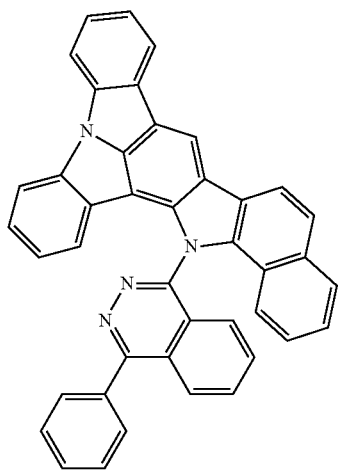 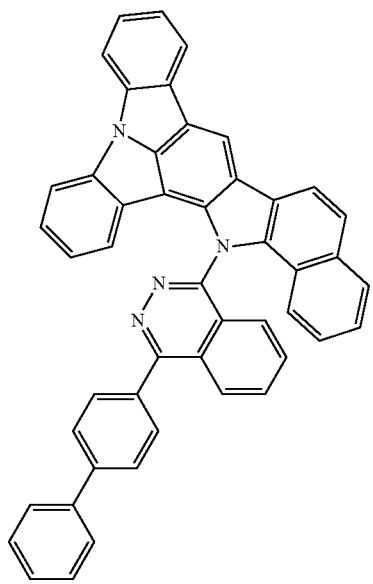
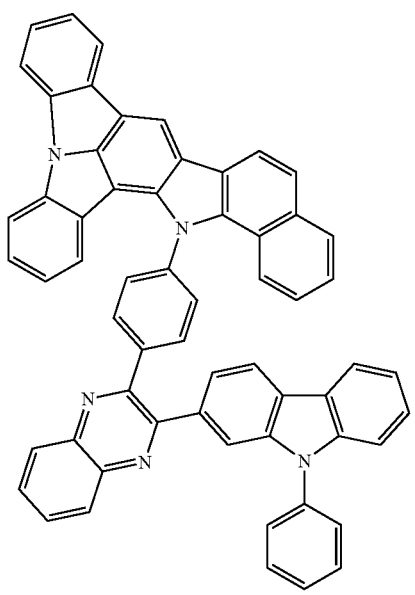 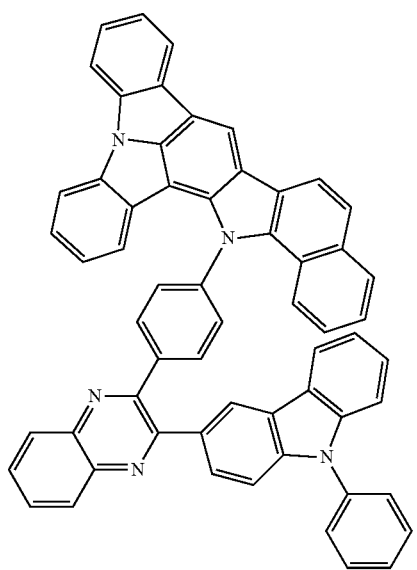

355
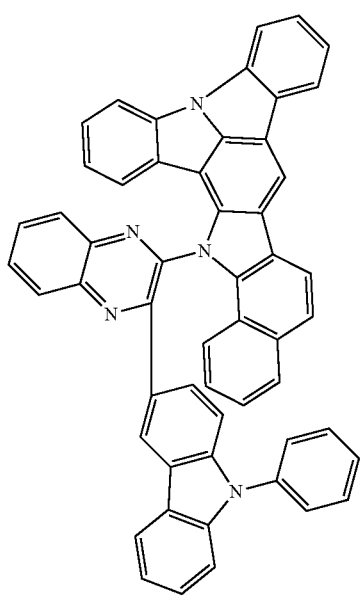
356
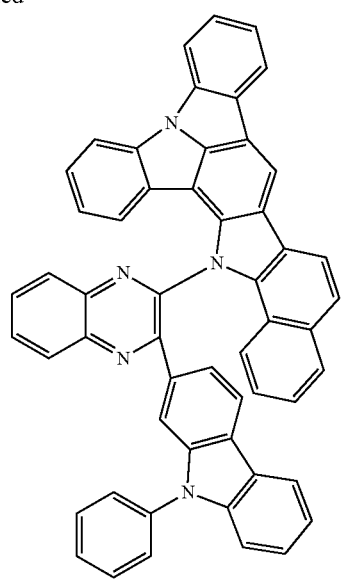
-continued
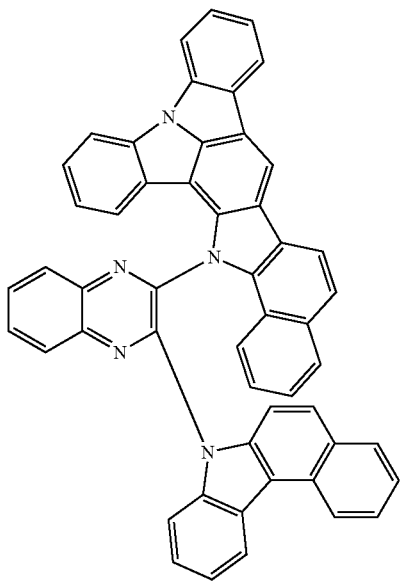
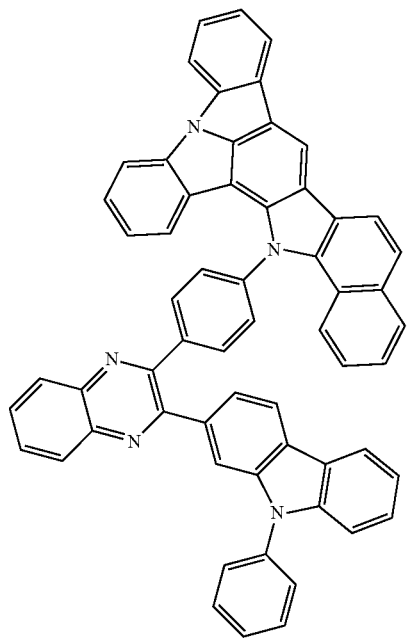

357
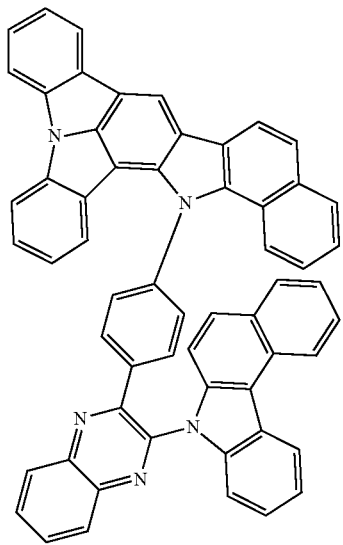
358
-continued
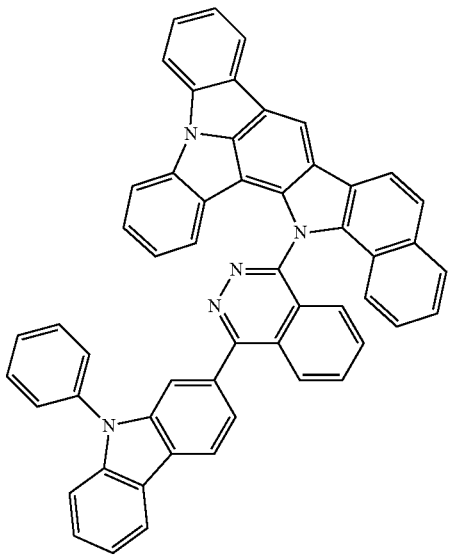
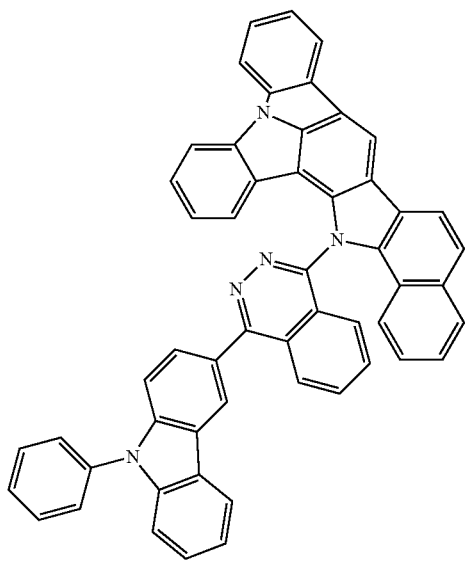
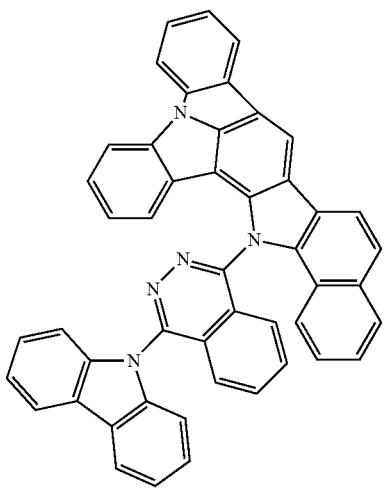
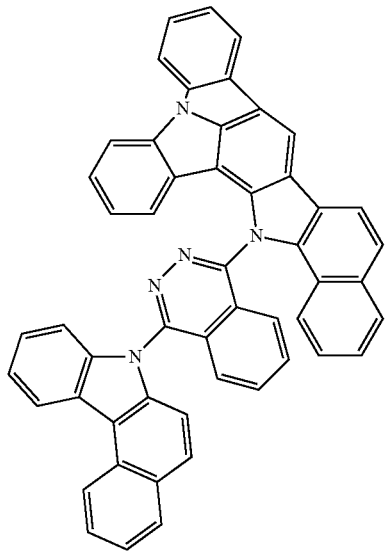
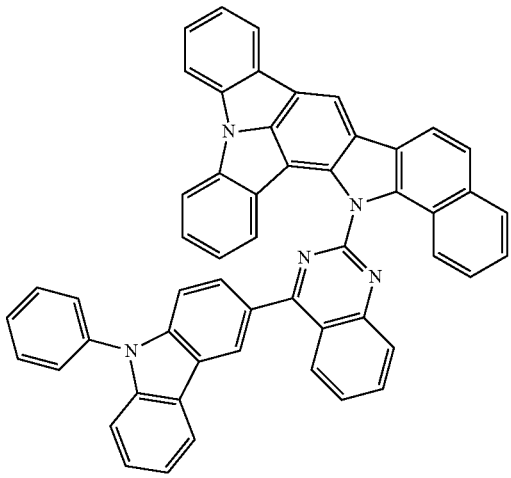

-continued
359
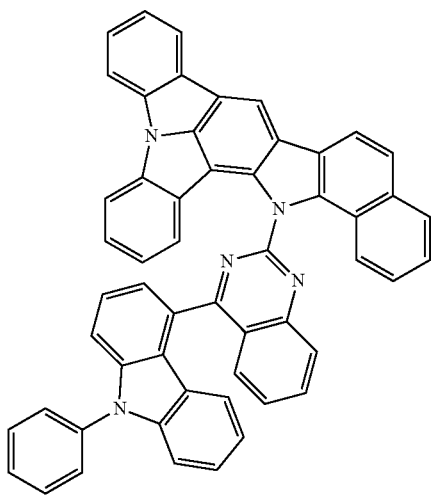
360
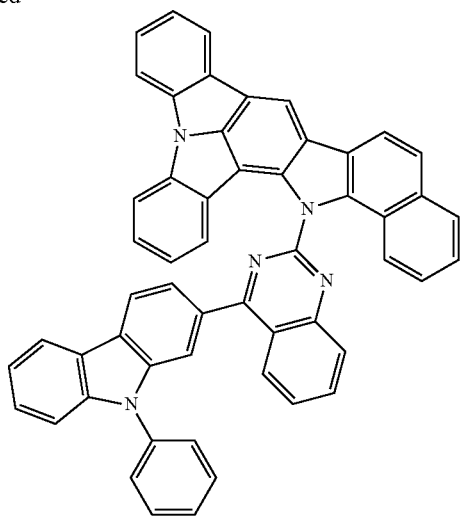
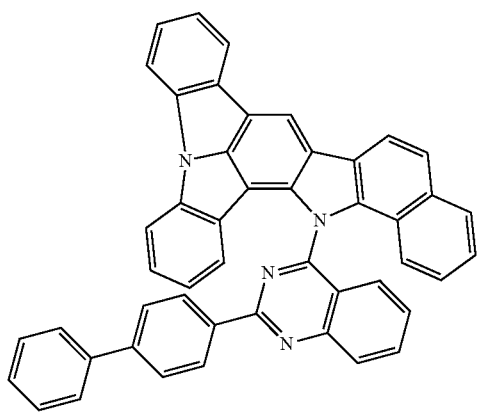
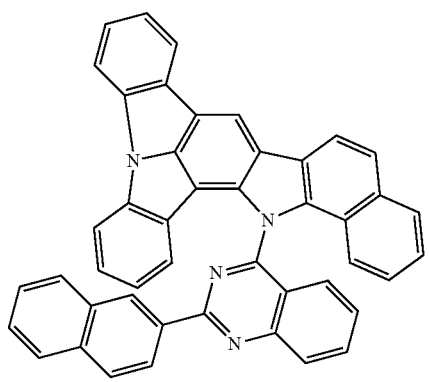
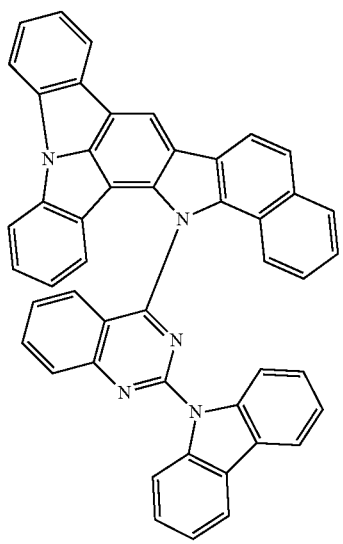
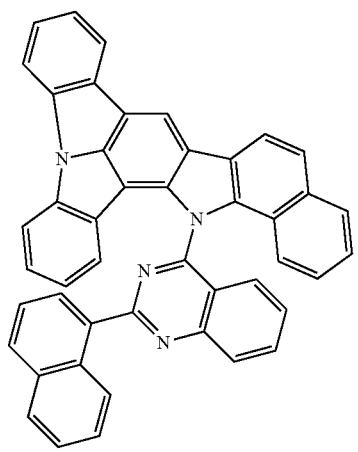

361
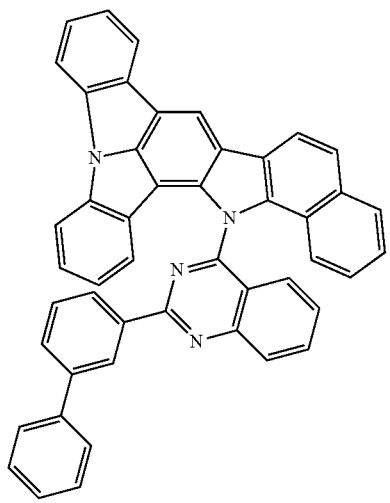
362
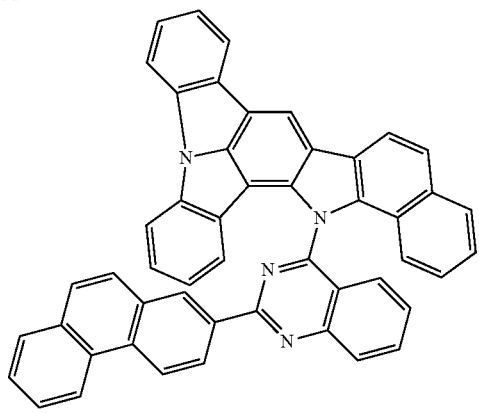
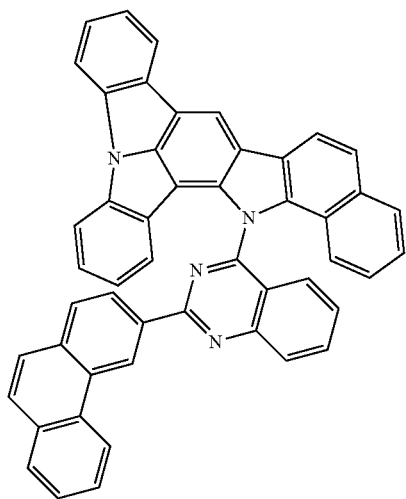
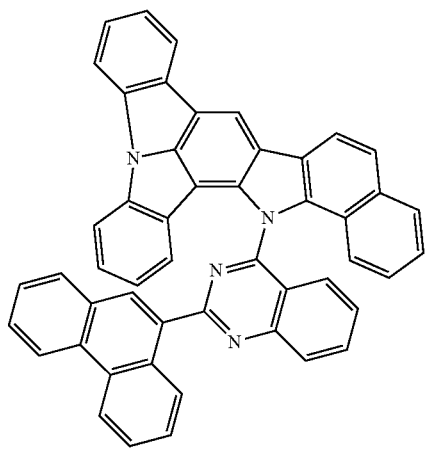
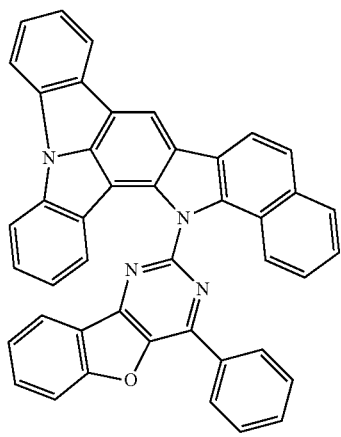
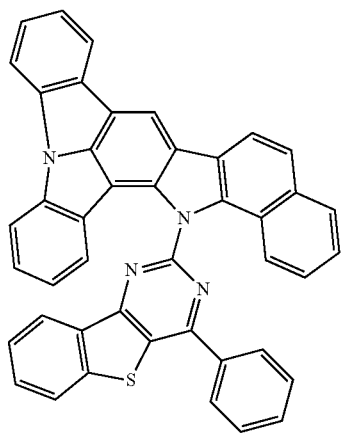

-continued
| 363 | 364 |
|---|---|
| 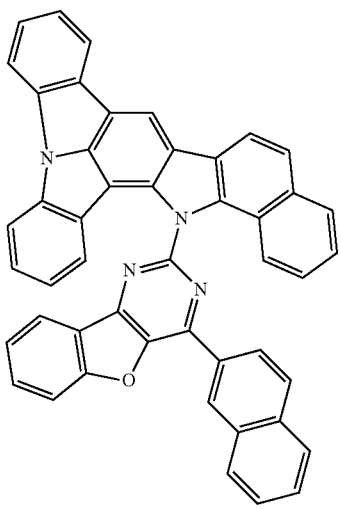 | 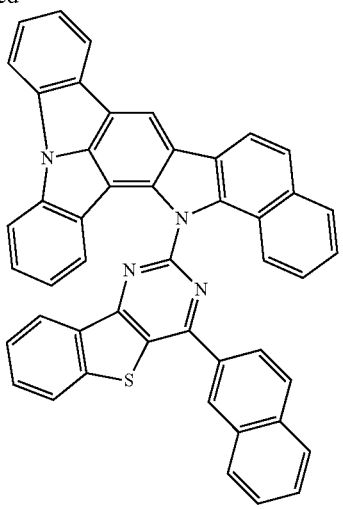 |
| 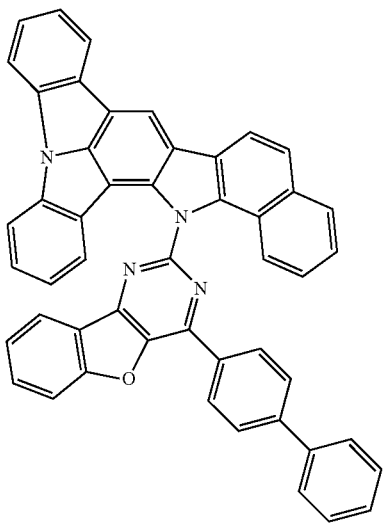 | 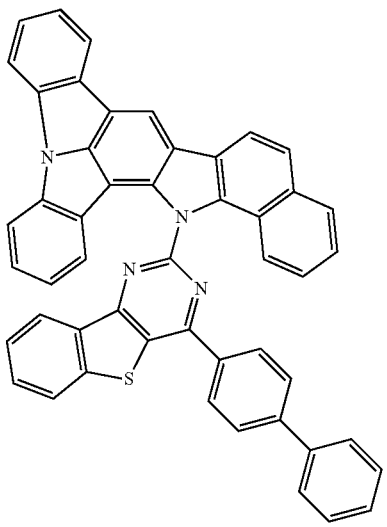 |
| 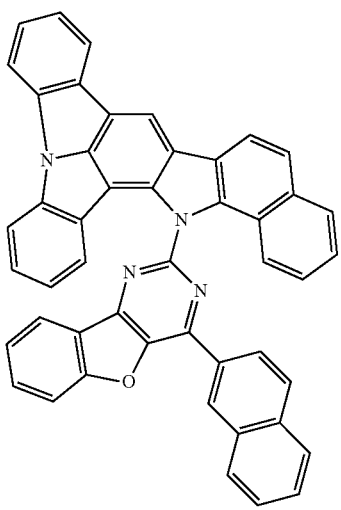 | 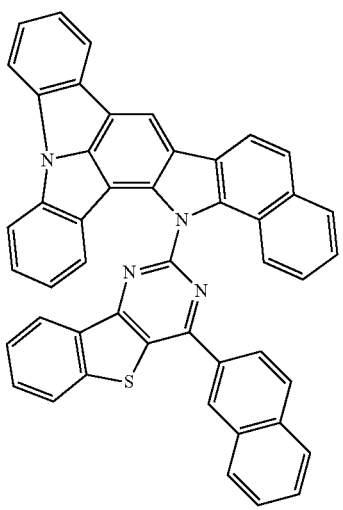 |

365 366
-continued
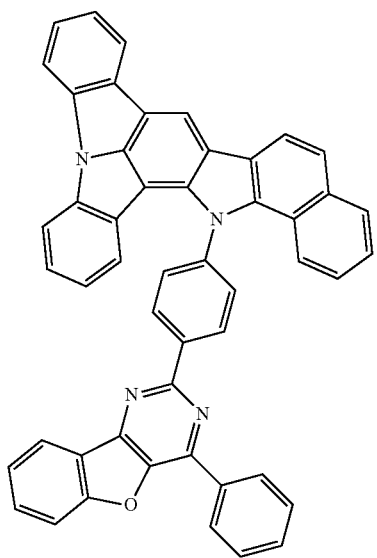
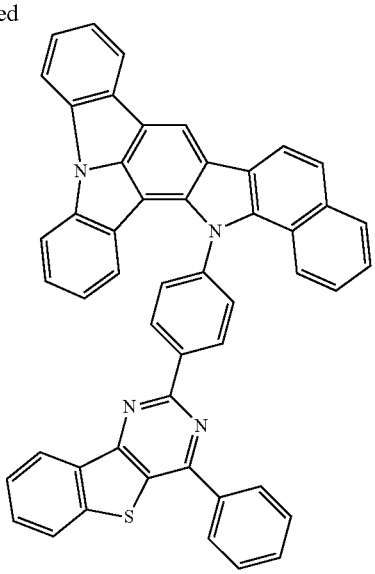
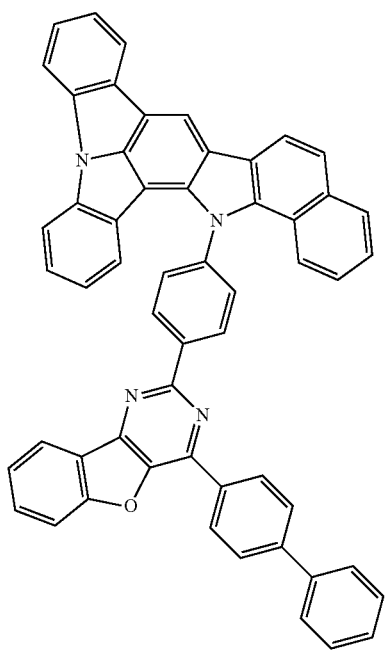
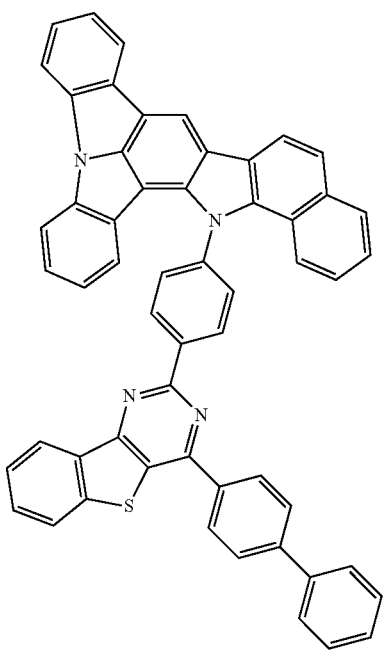
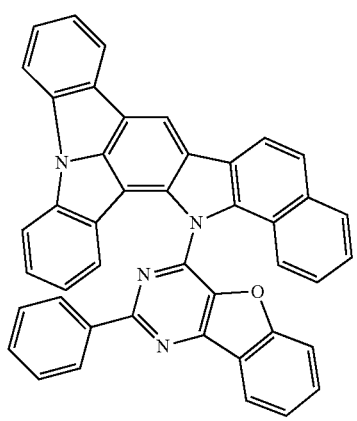
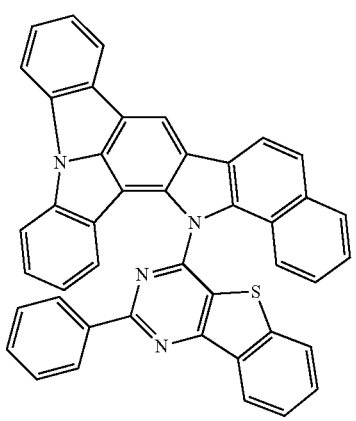

367
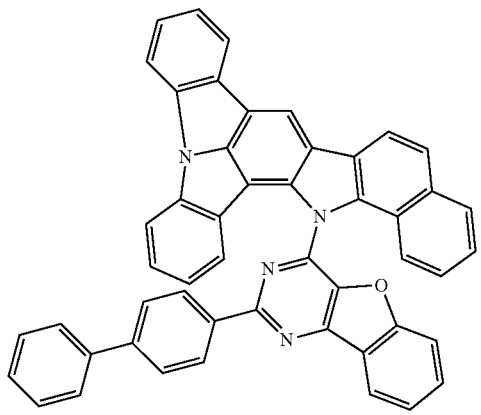
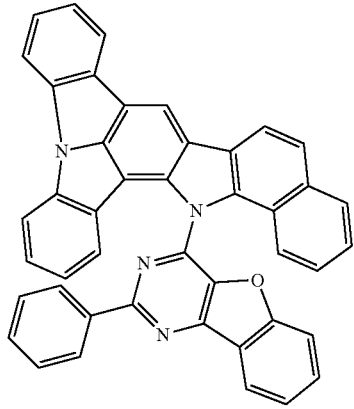
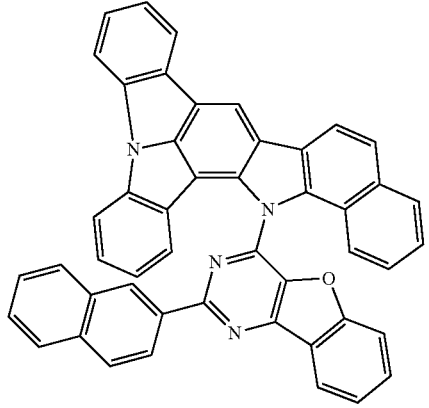
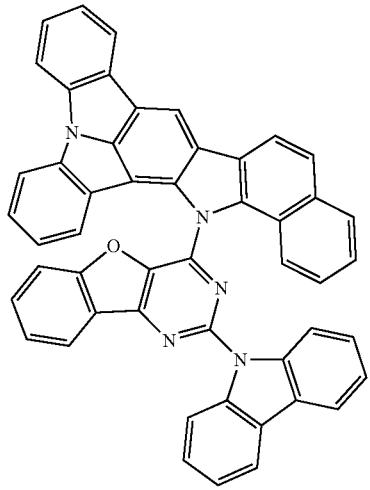
368
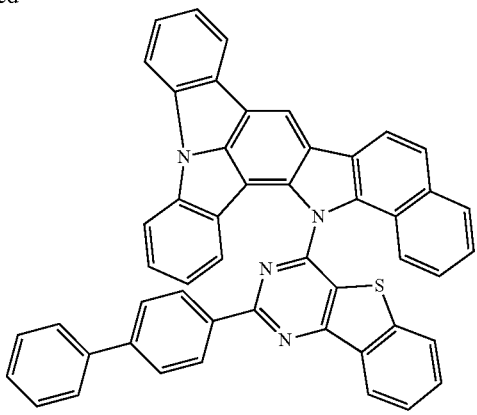
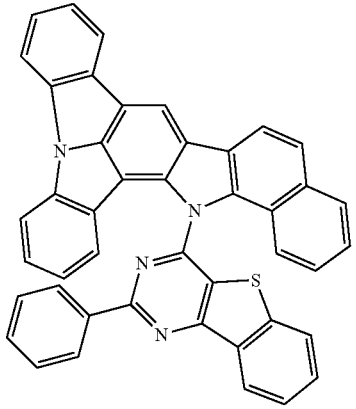
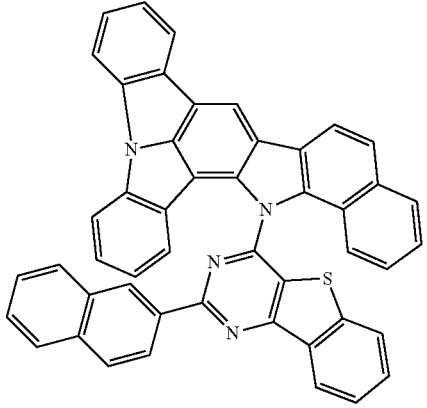
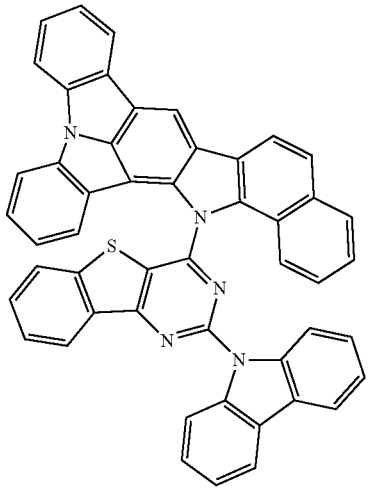

-continued
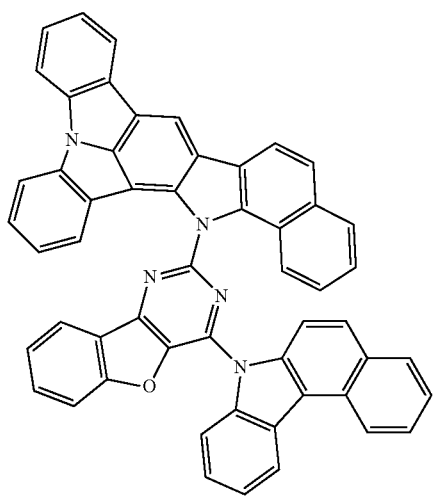
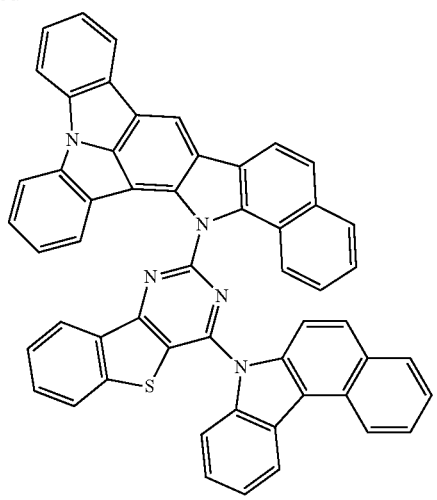
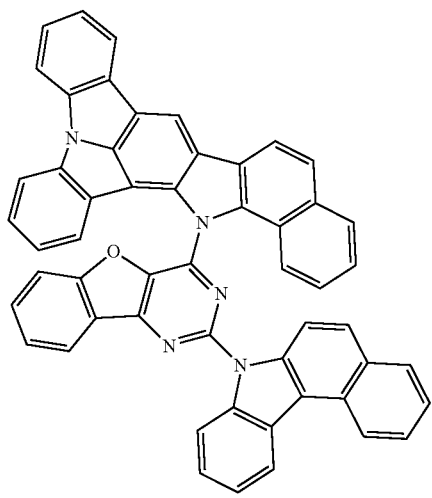
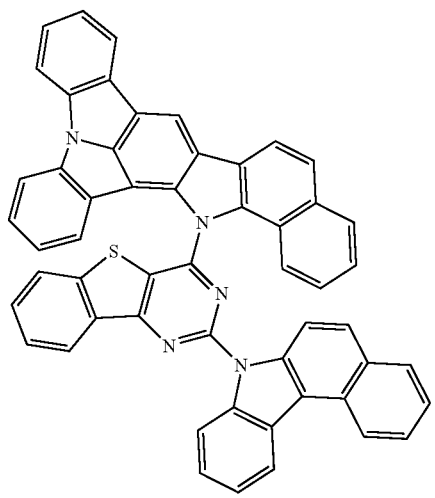
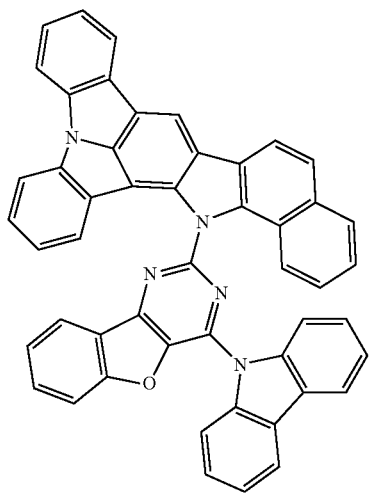
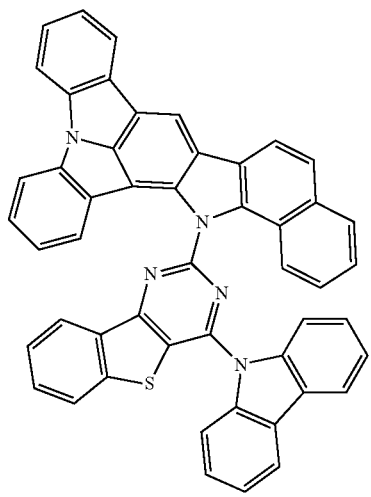

371
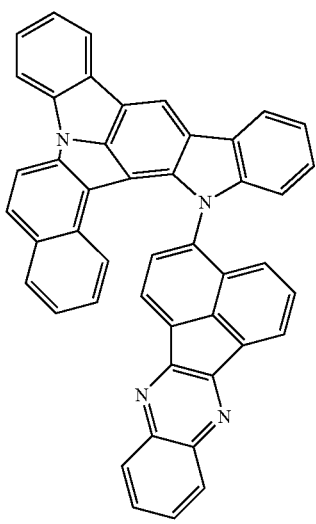
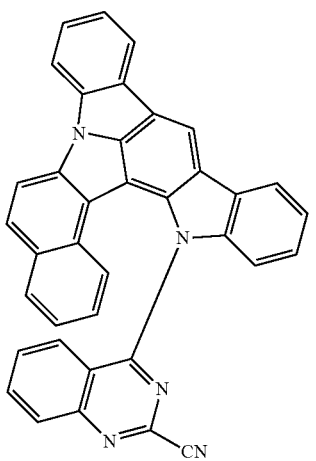
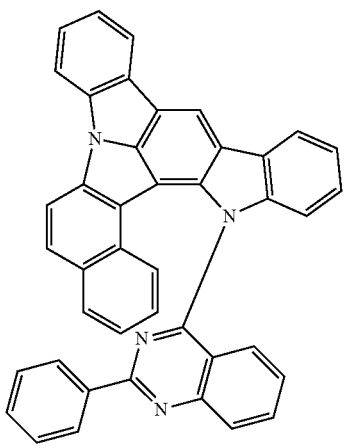
372
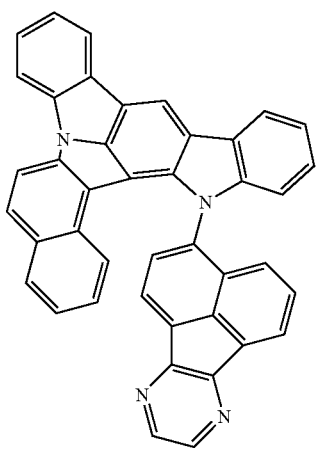
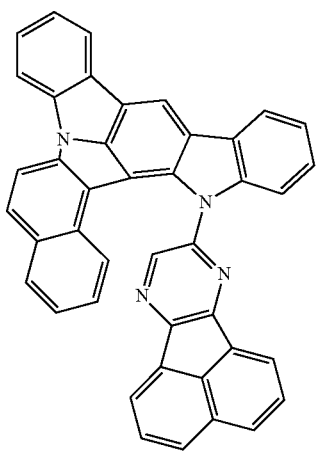
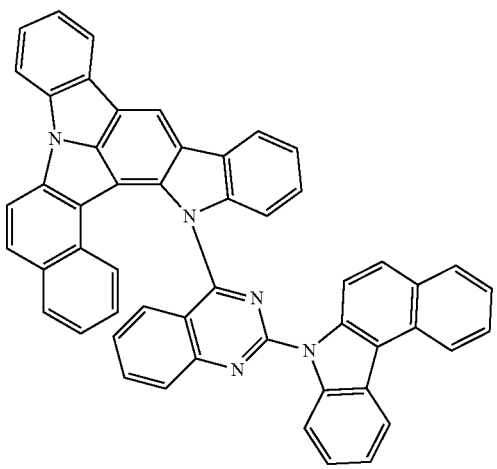

373
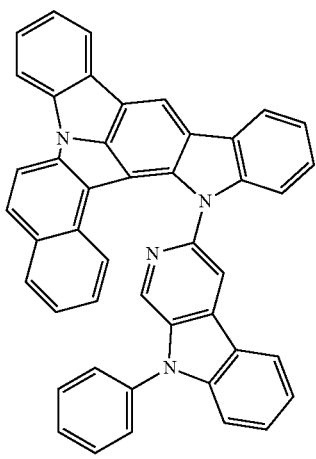
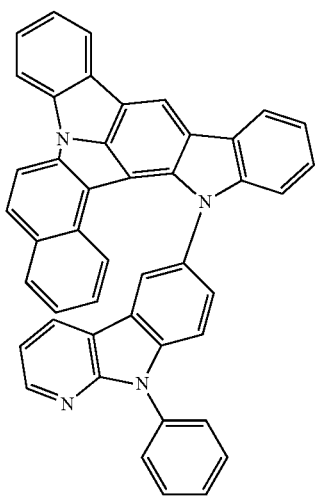
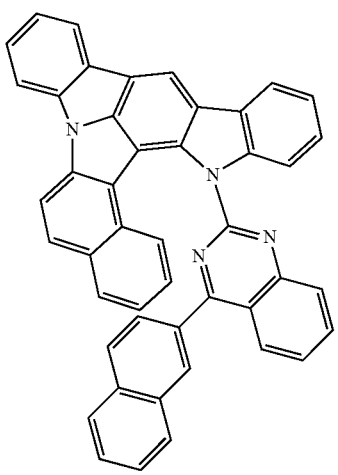
-continued
374
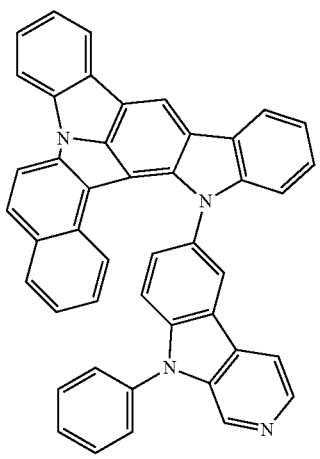
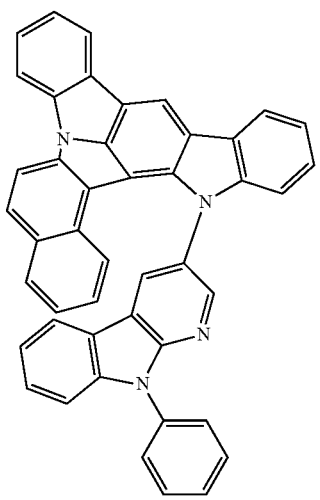
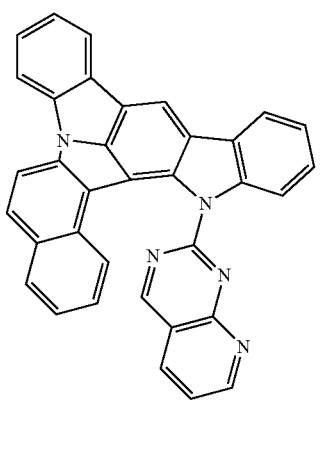

375
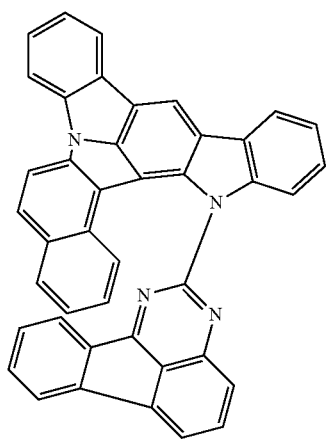
376
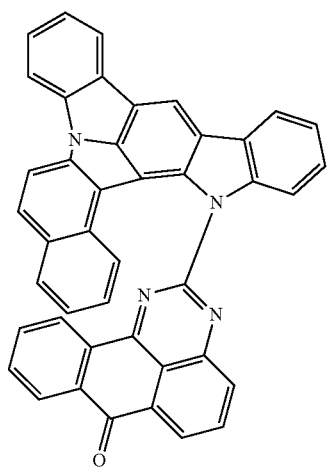
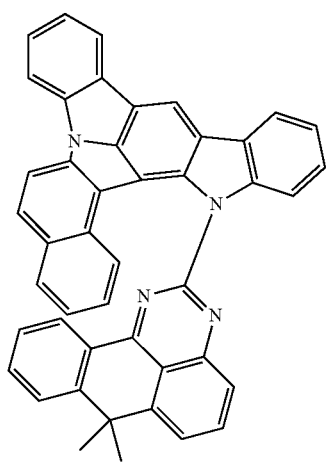
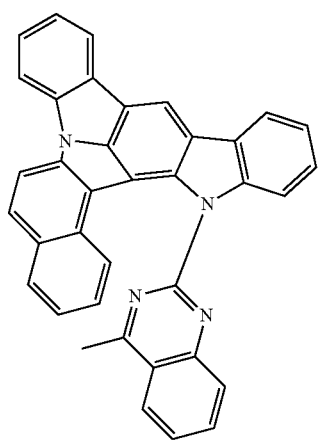
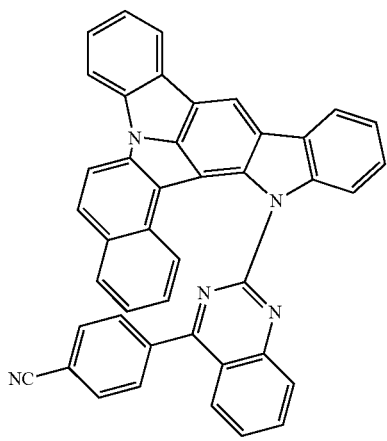
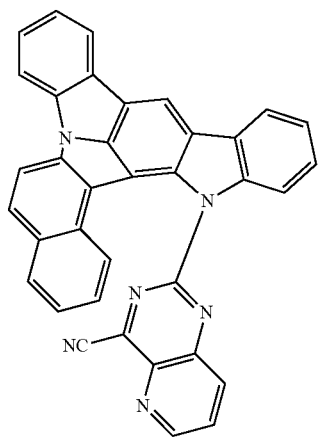

-continued
| 377 | 378 |
|---|---|
| 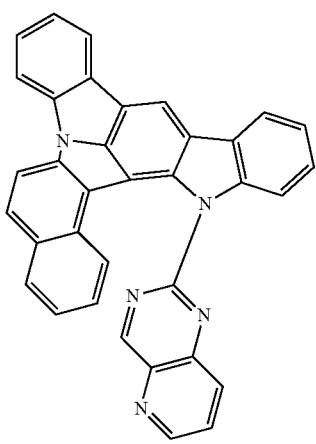 | 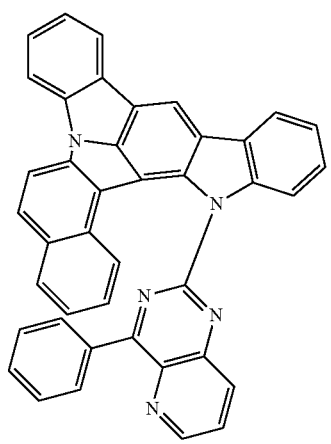 |
| 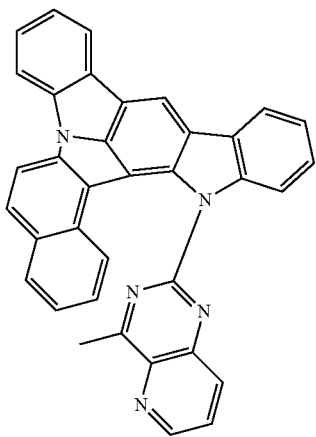 | 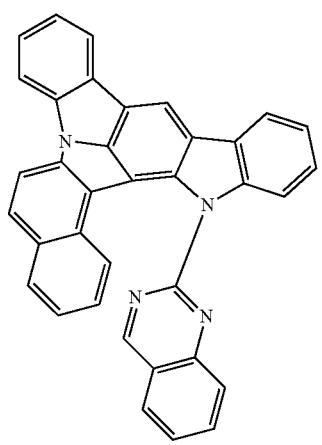 |
| 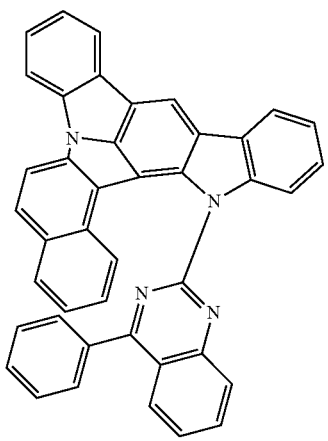 | 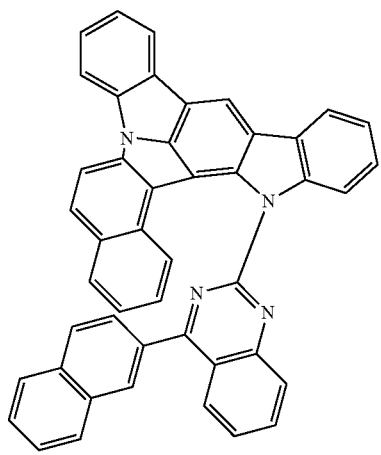 |

379
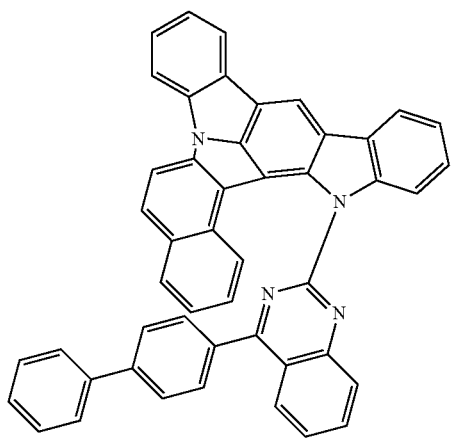
380
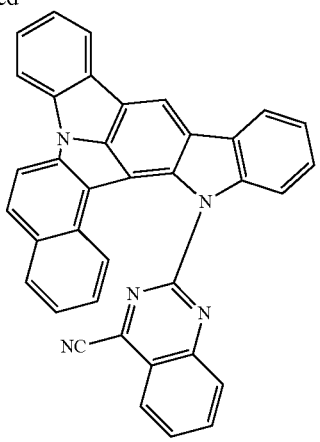
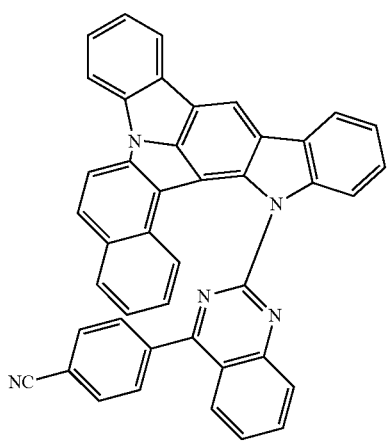
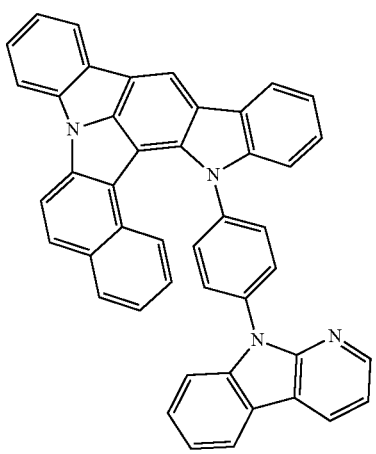
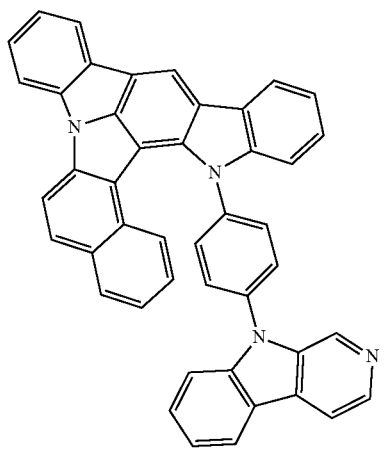
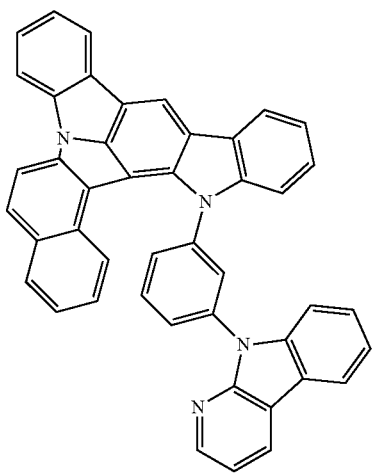

381
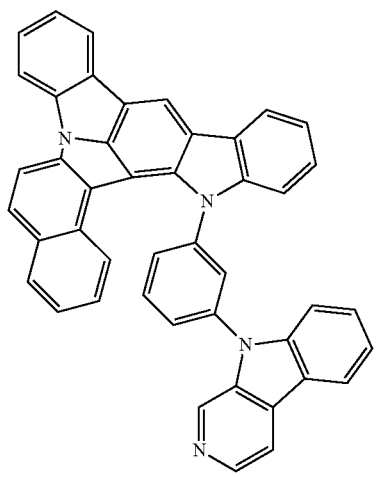
382
-continued
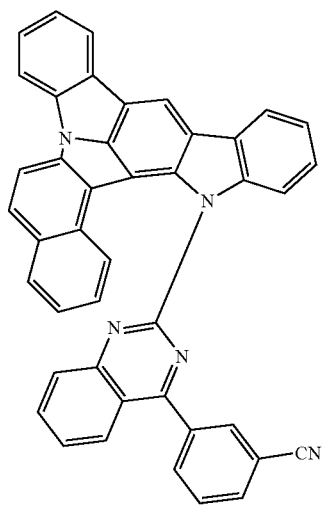
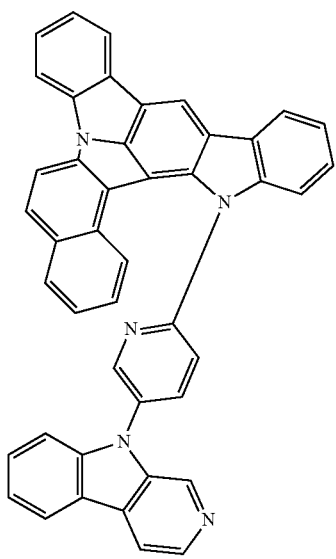
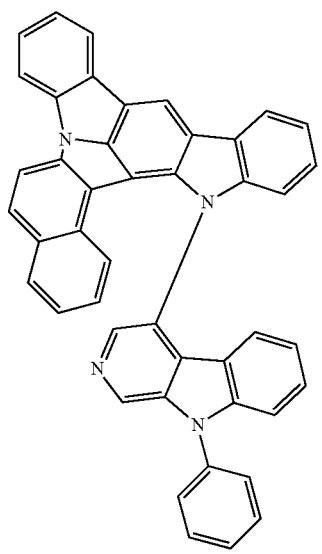
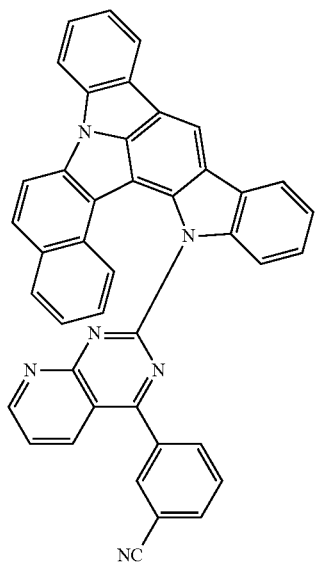
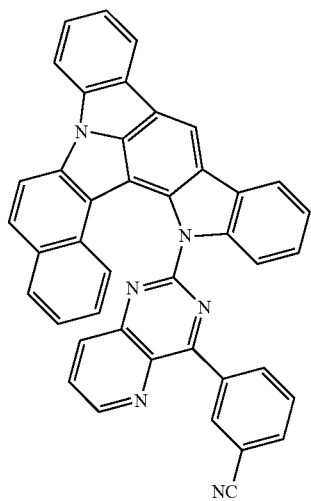

-continued
| 383 | 384 |
|---|---|
| 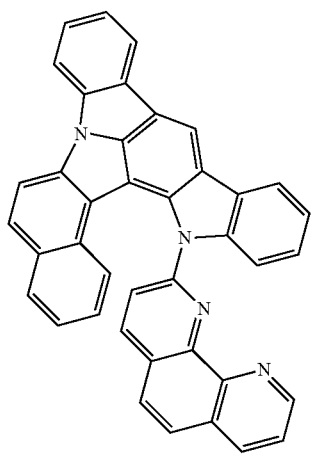 | 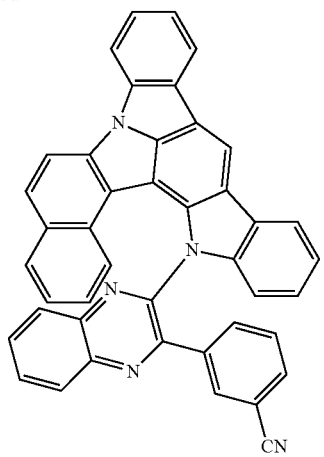 |
| 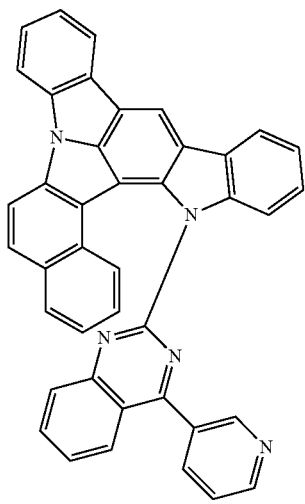 | 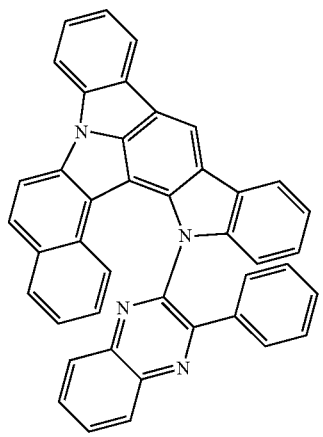 |
| 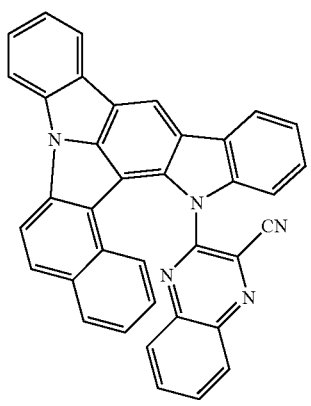 | 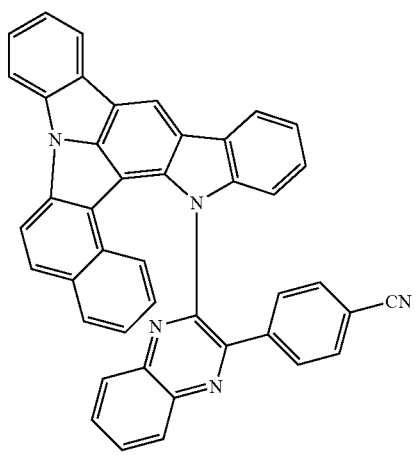 |

385
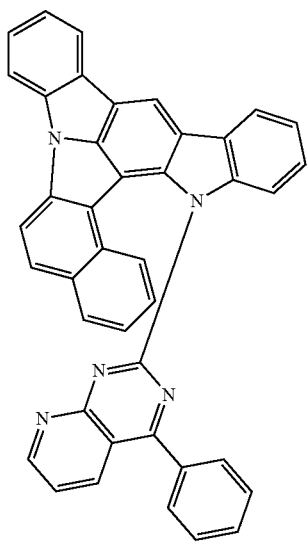
386
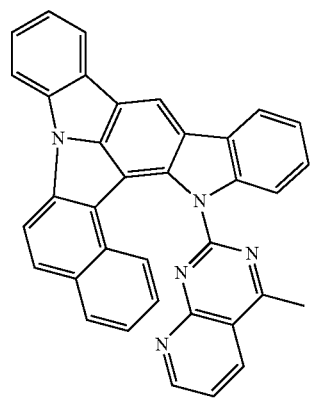
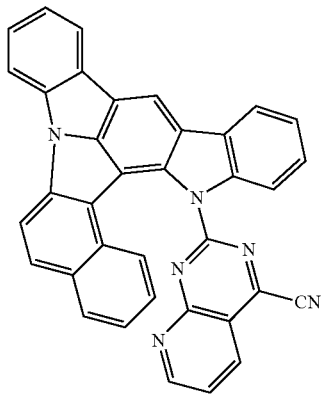
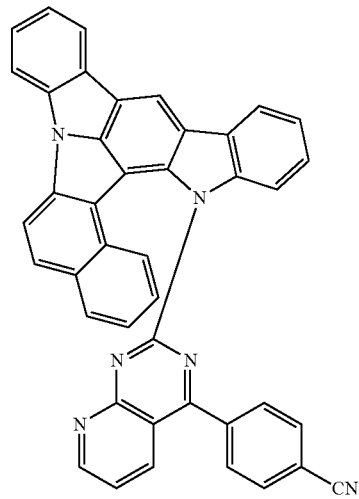
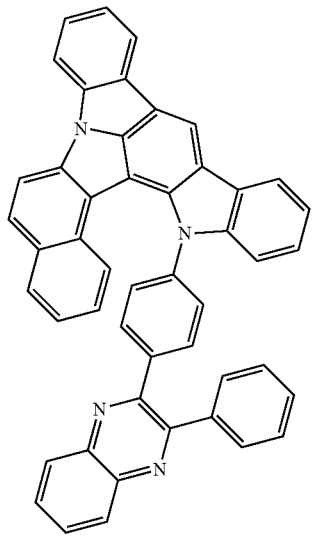
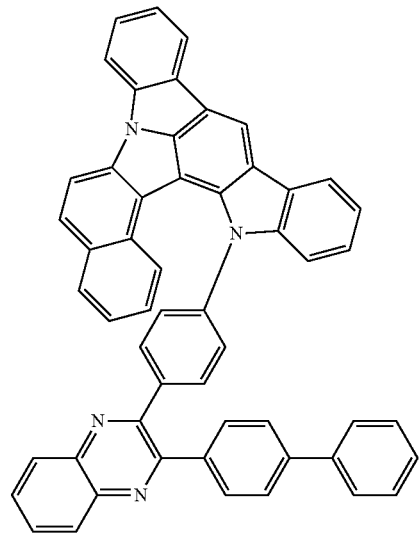

-continued
387
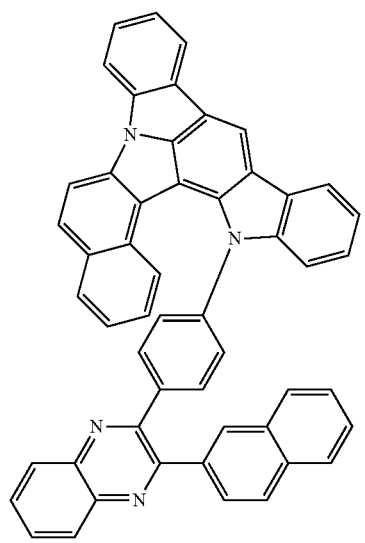
388
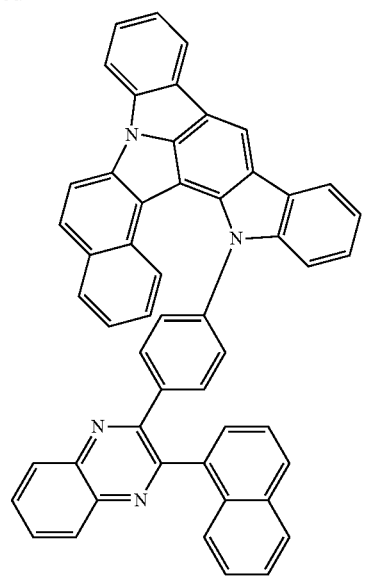
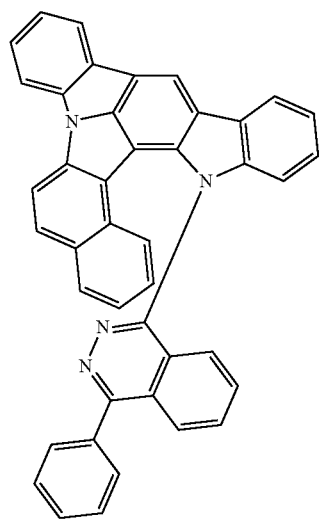
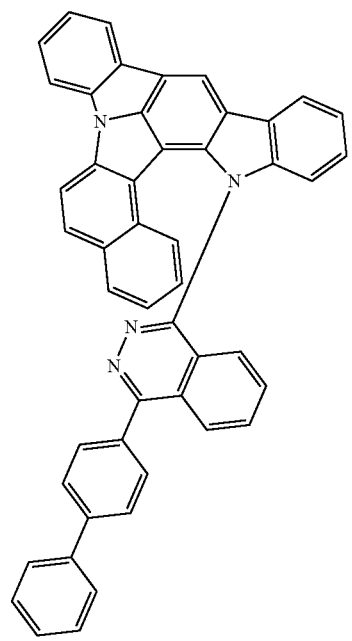

-continued
389
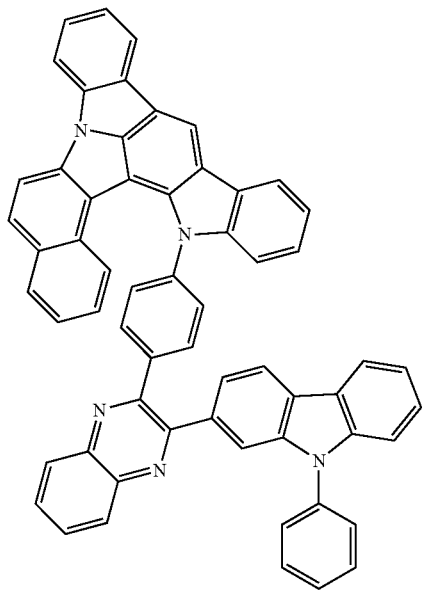
390
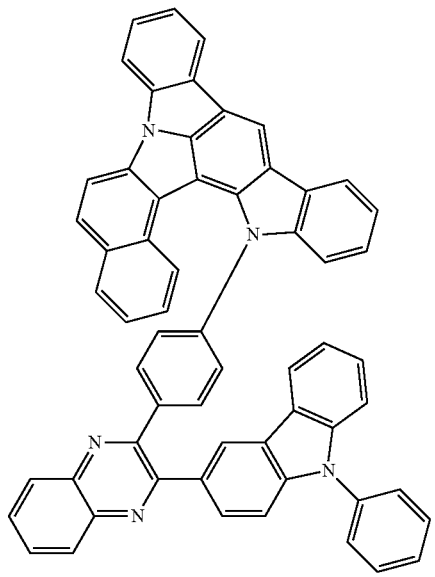
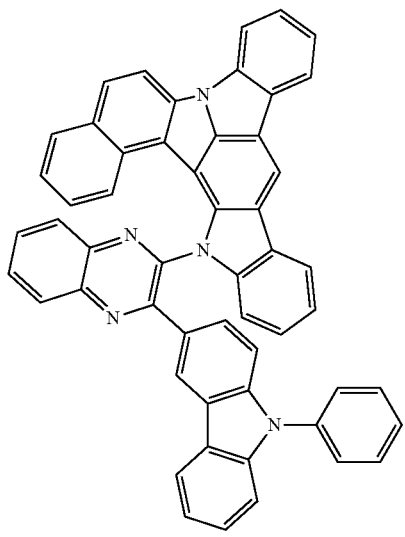
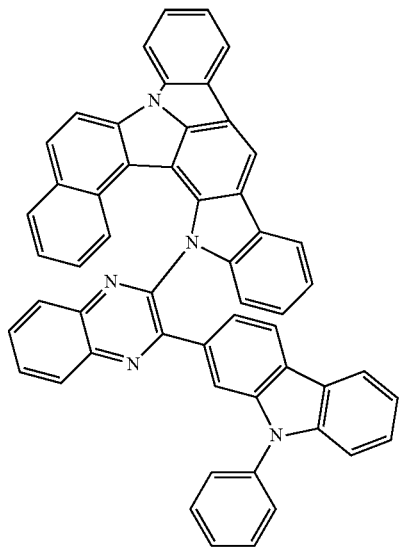

391
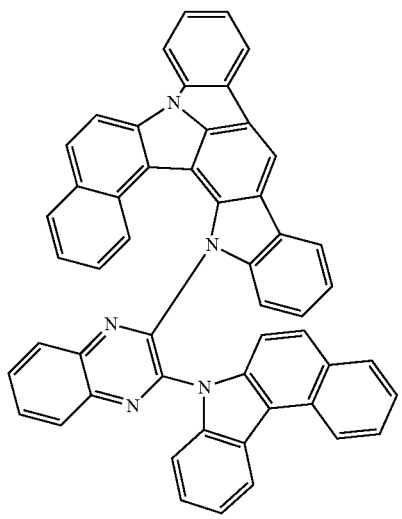
392
-continued
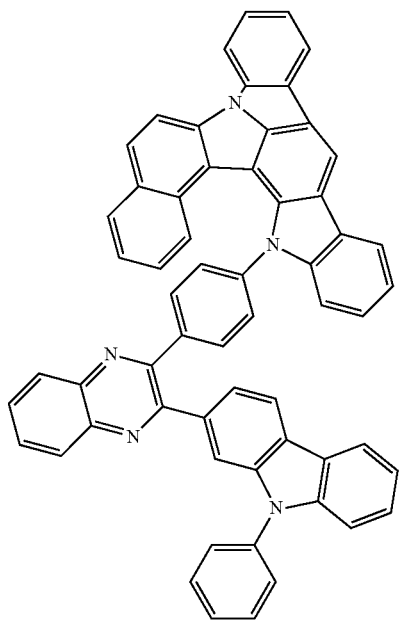
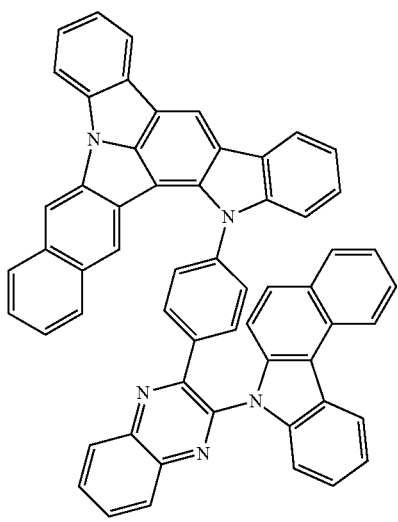
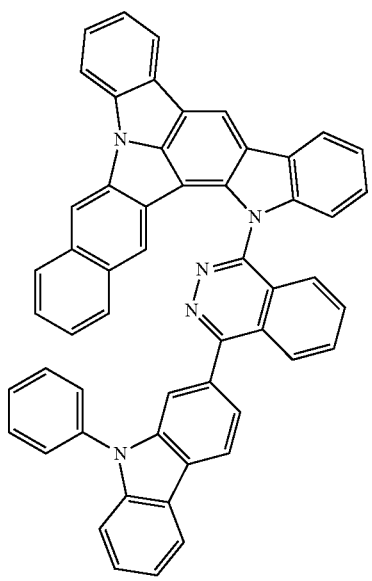

393
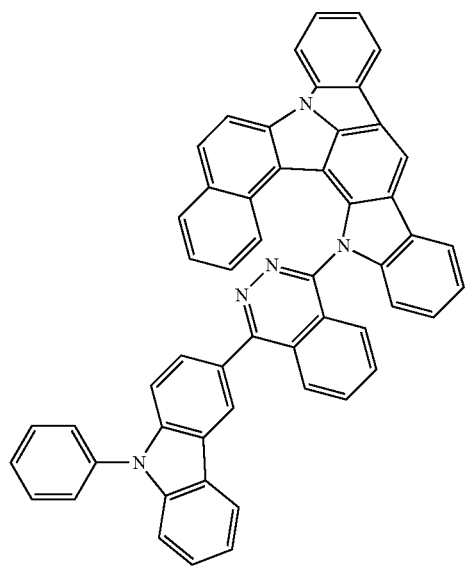
394
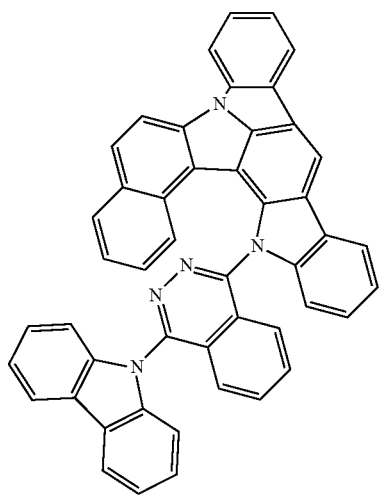
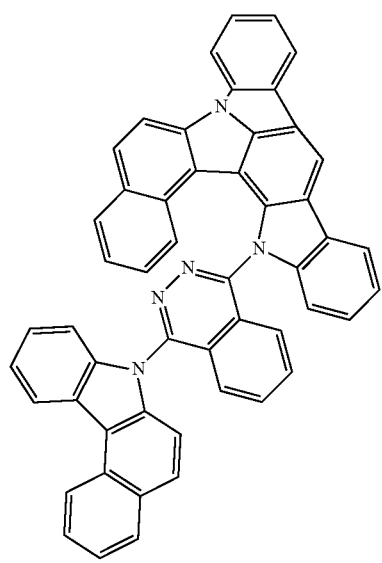
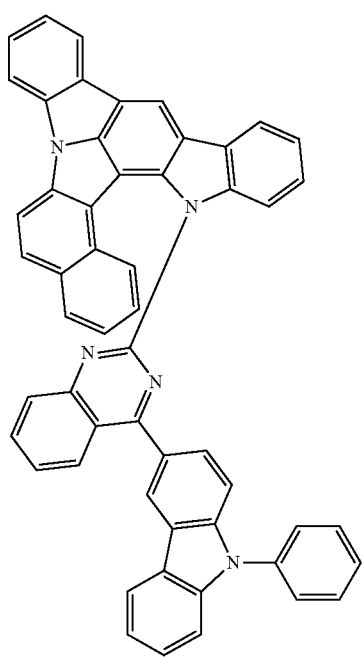

395
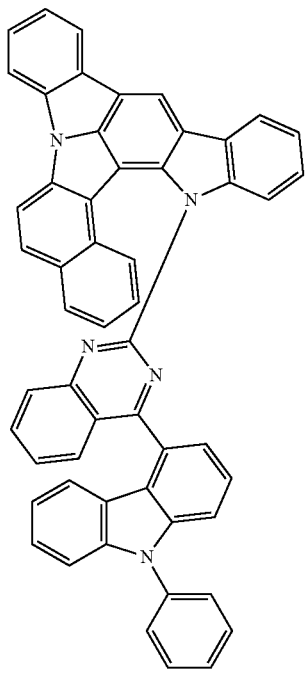
396
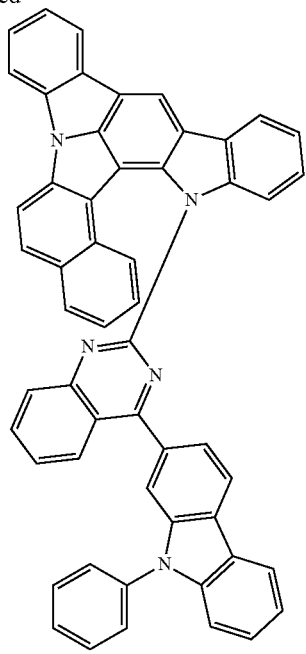
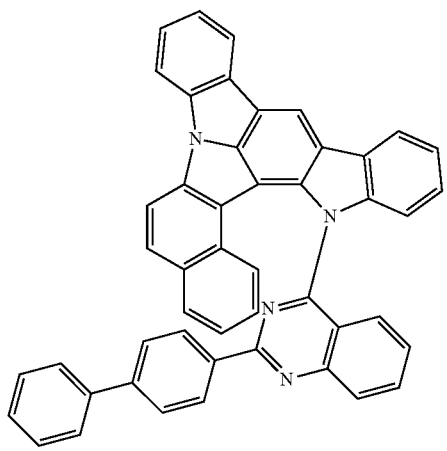
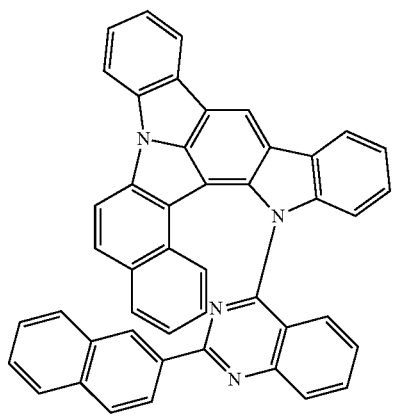
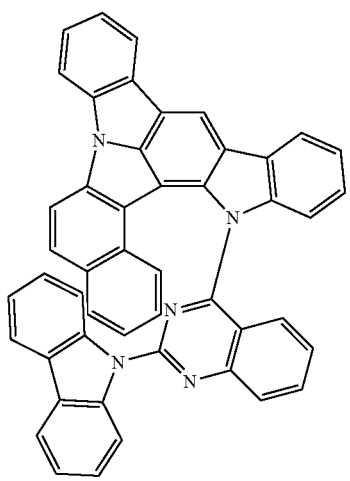
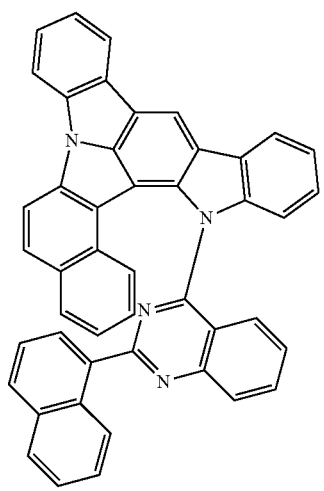

397
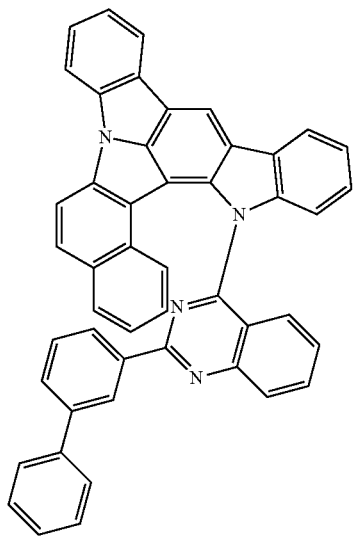
398
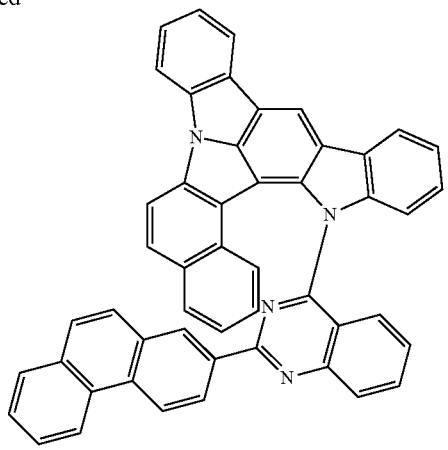
-continued
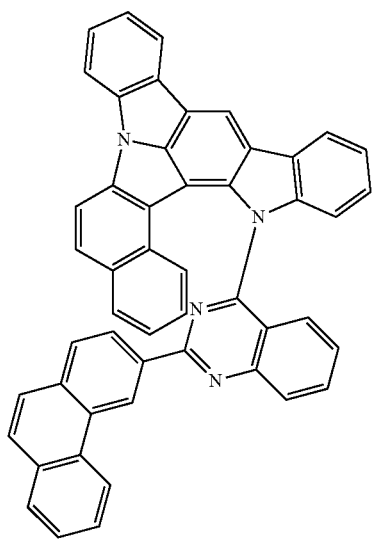
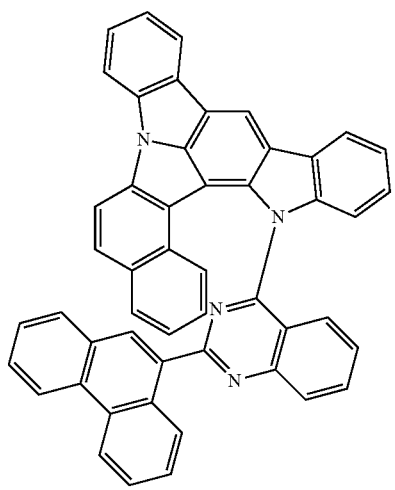
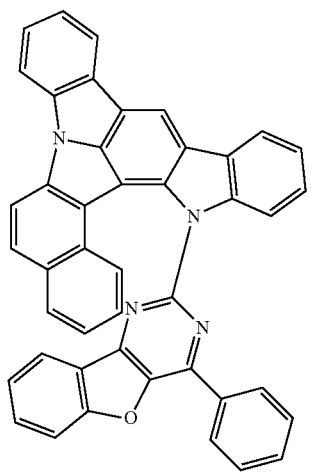
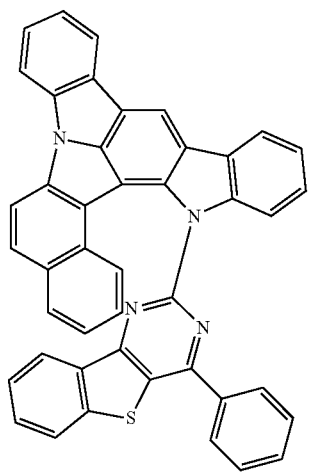

-continued
| 399 | 400 |
|---|---|
| 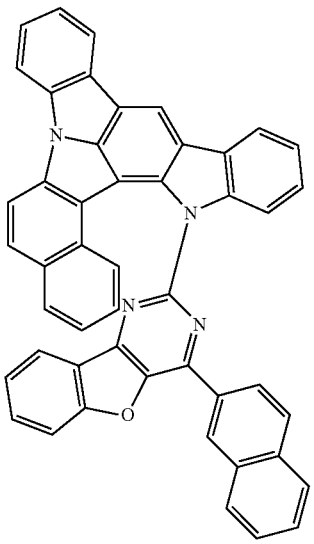 | 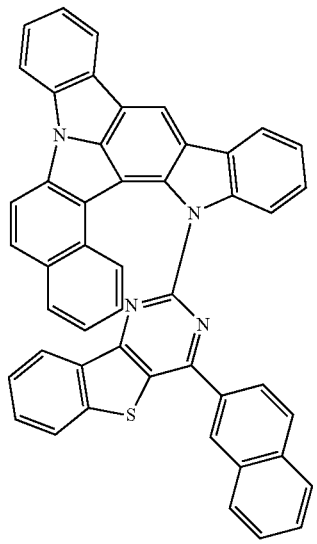 |
| 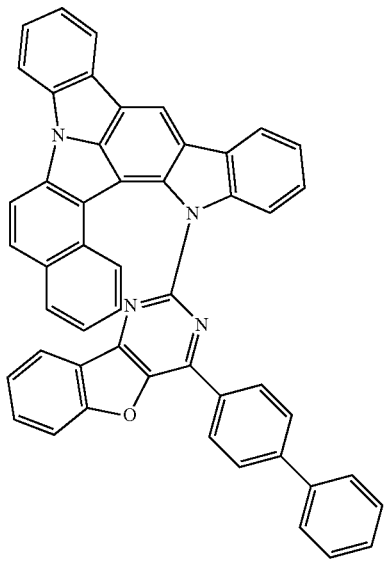 | 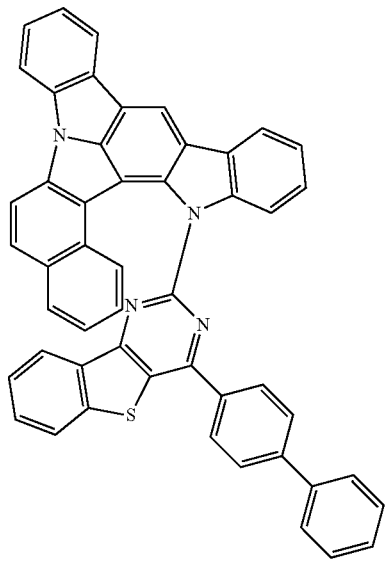 |
| 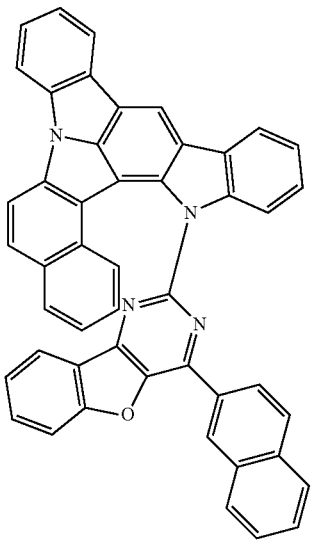 | 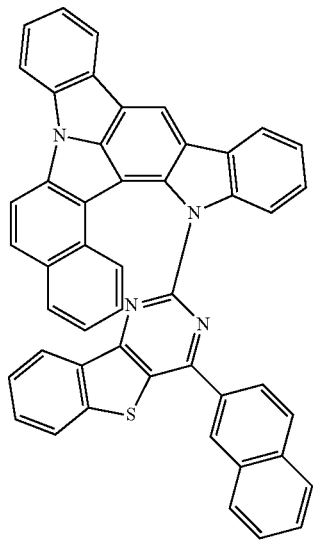 |

-continued
| 401 | 402 |
|---|---|
| 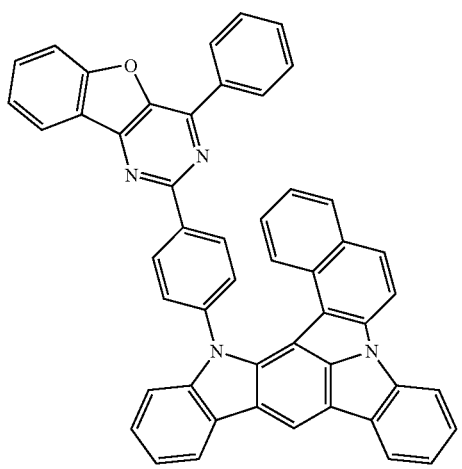 | 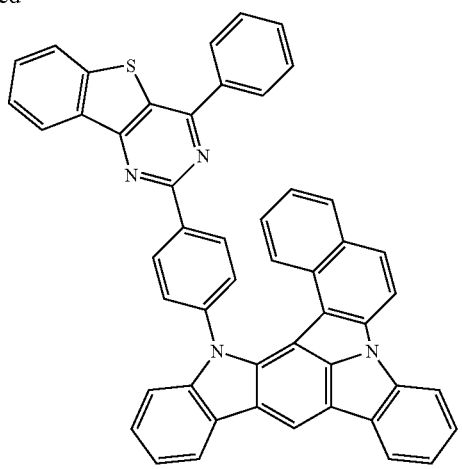 |
| 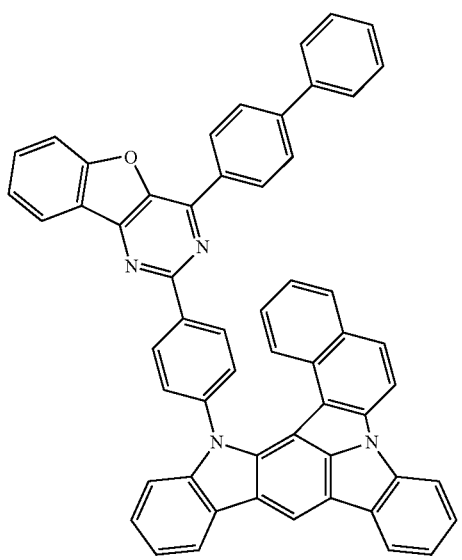 | 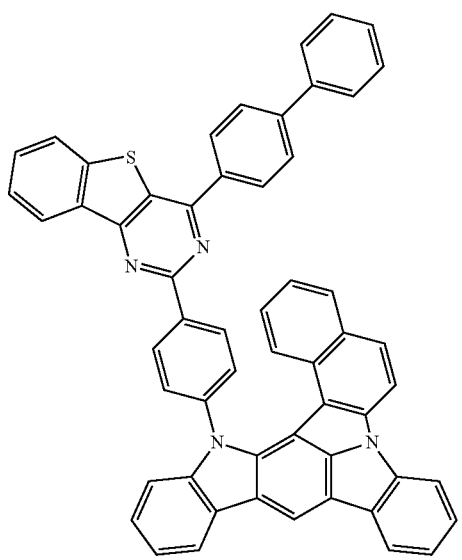 |
| 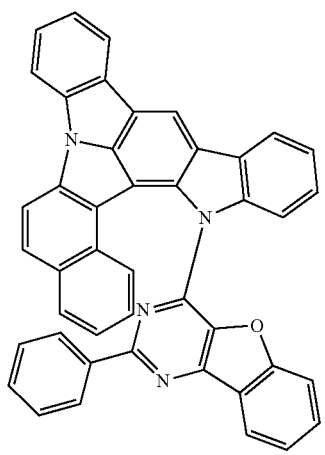 | 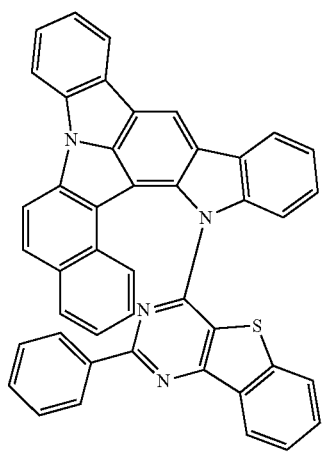 |

-continued
403
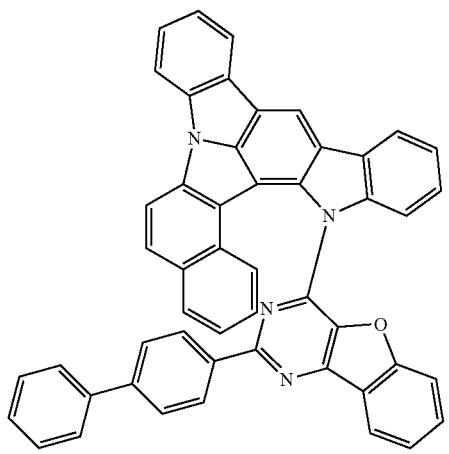
404
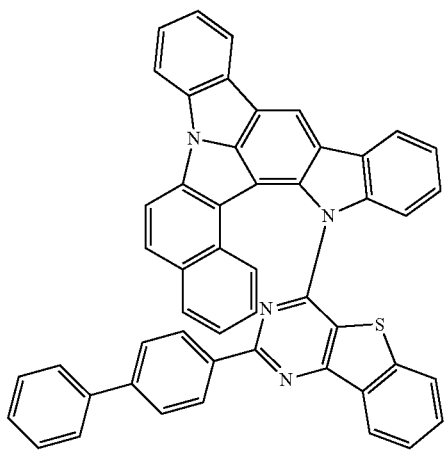
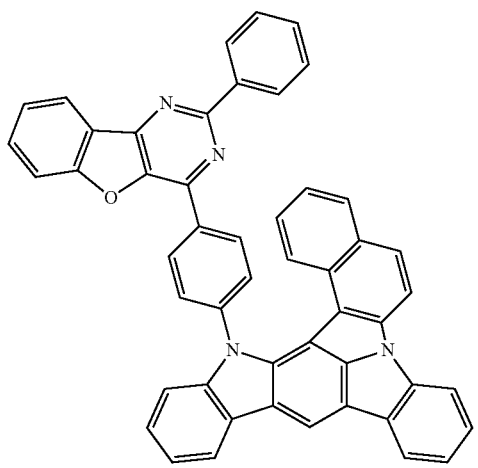
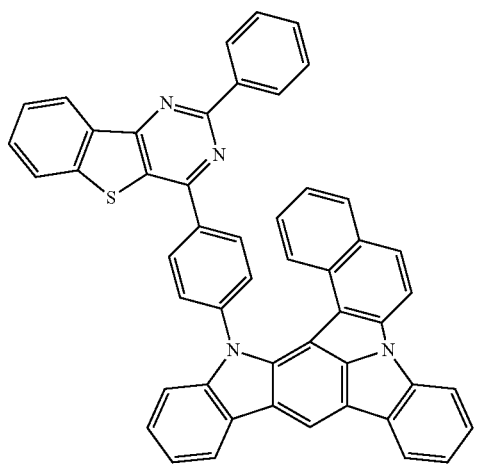
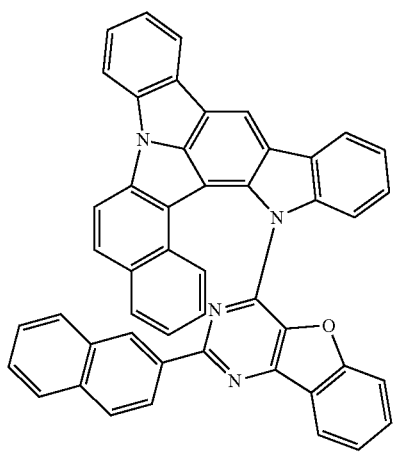
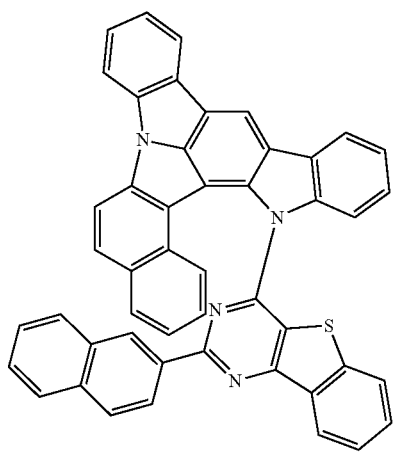

405
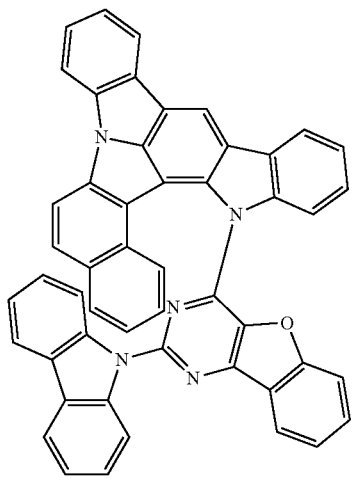
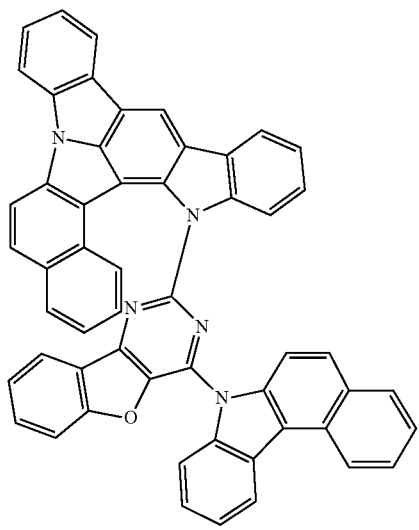
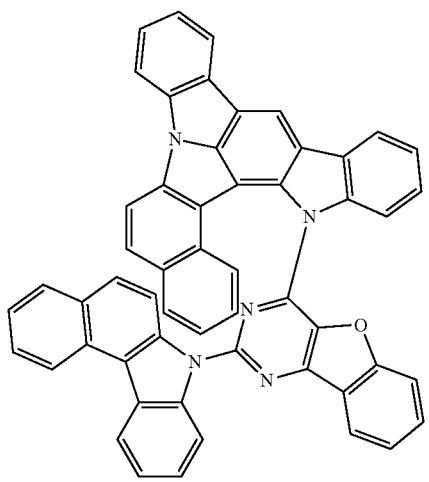
406
-continued
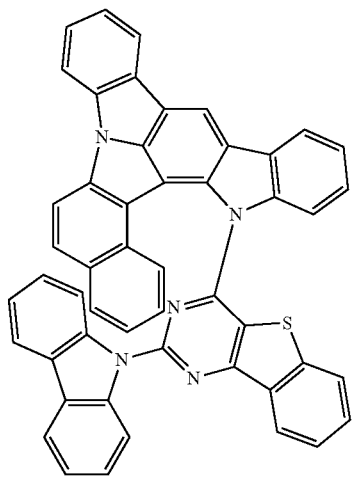
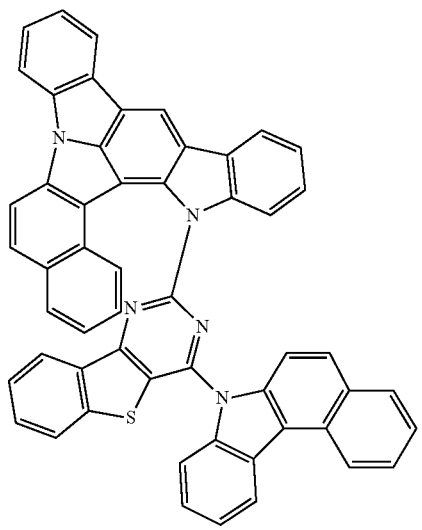
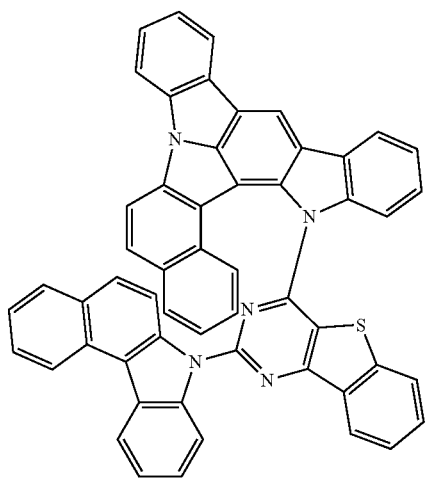

407
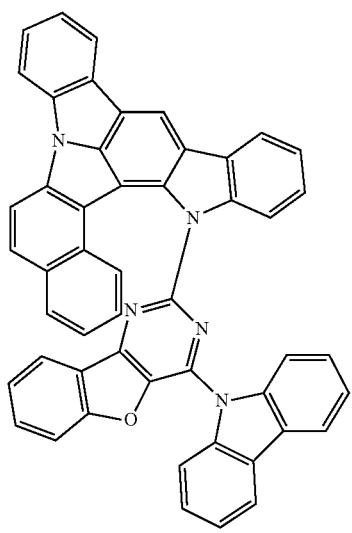
-continued
408
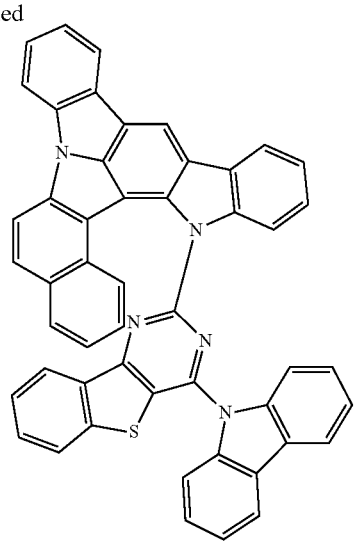
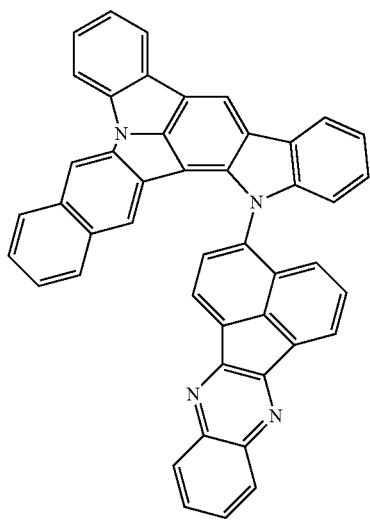
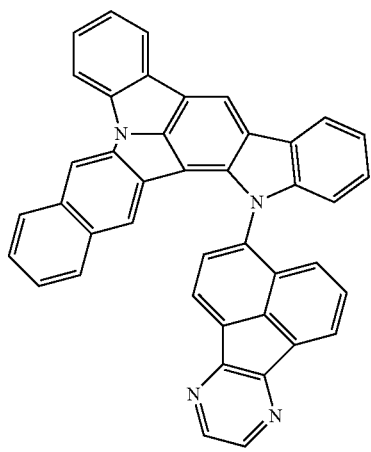
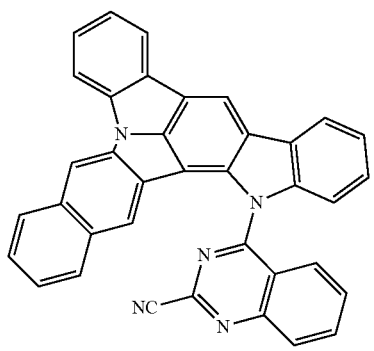
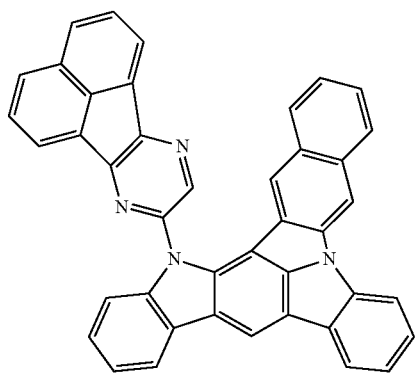

-continued
| 409 | 410 |
|---|---|
| 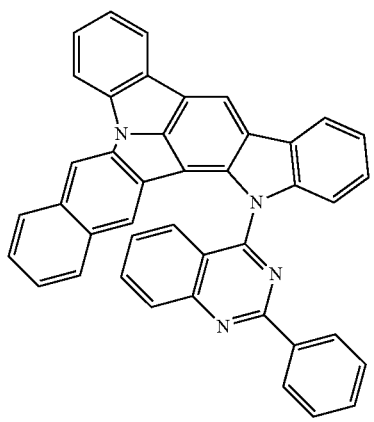 | 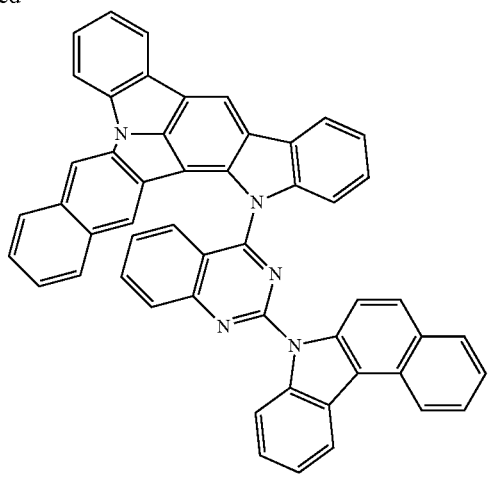 |
| 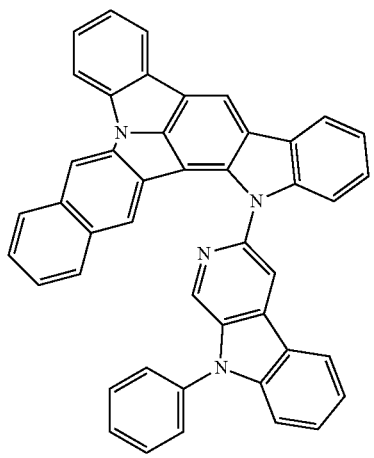 | 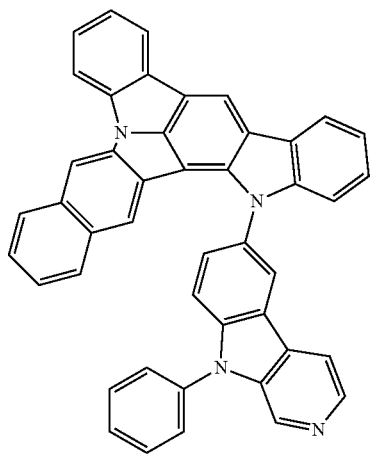 |
| 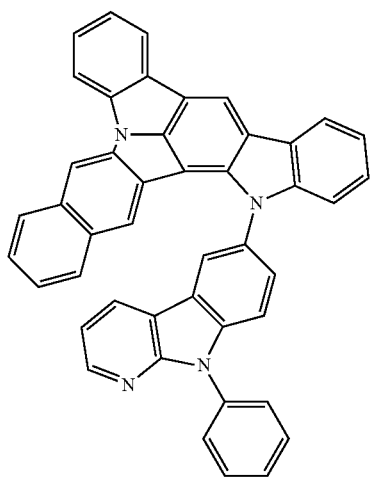 | 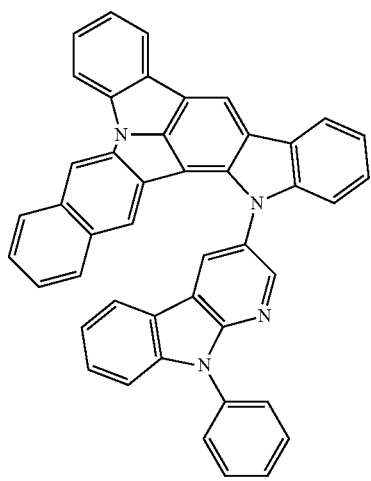 |

-continued
411
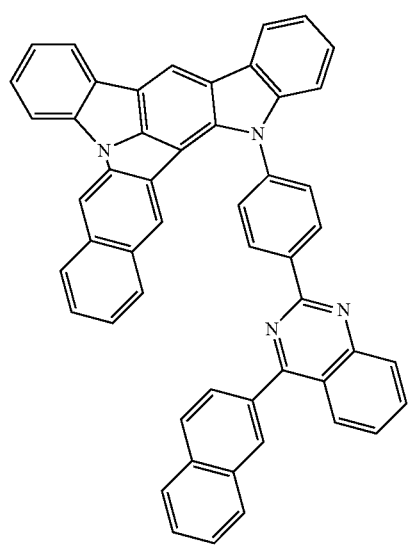
412
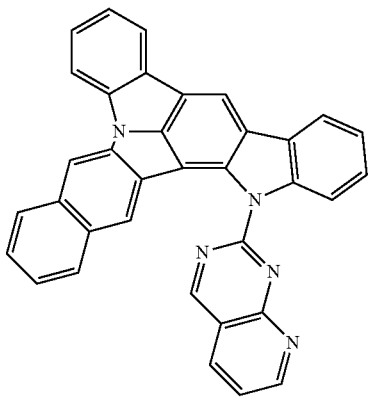
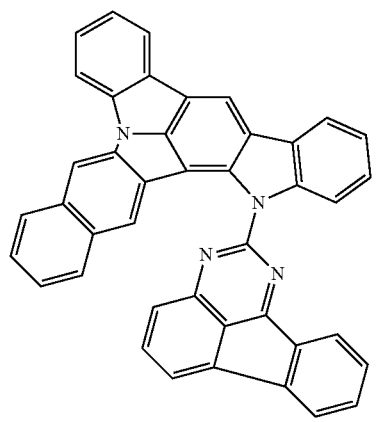
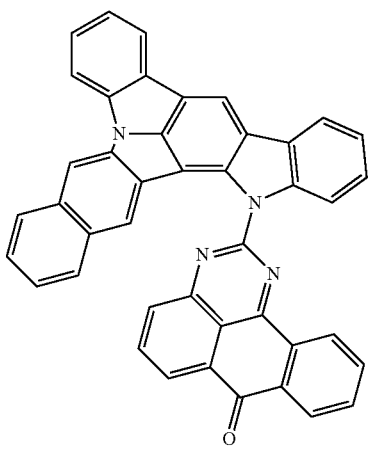
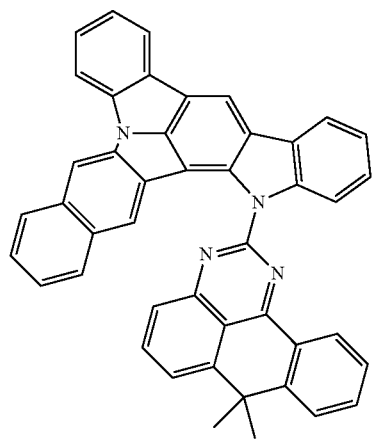
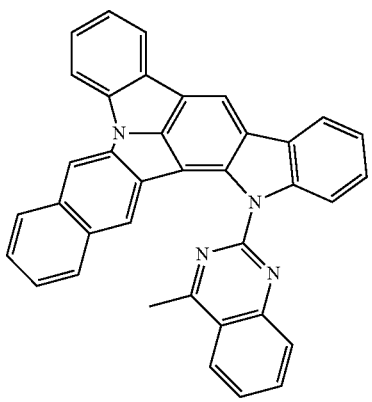

-continued
| 413 | 414 |
|---|---|
| 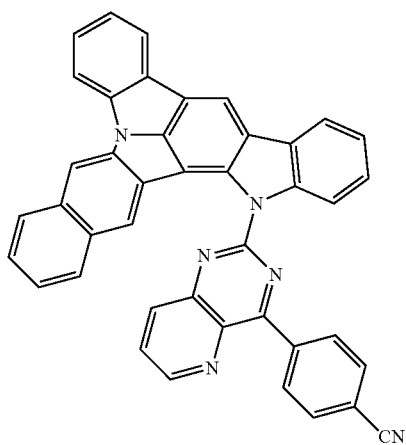 | 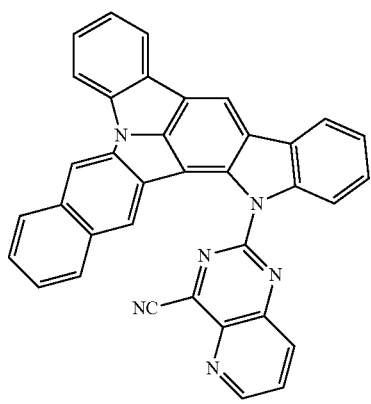 |
| 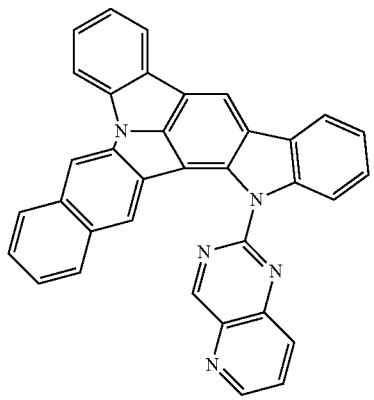 | 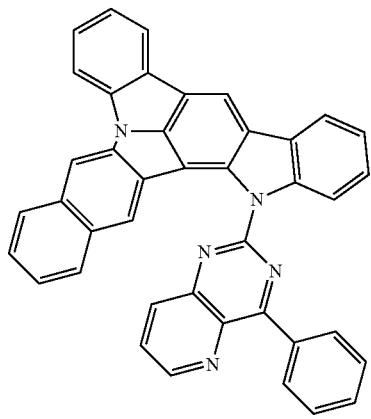 |
| 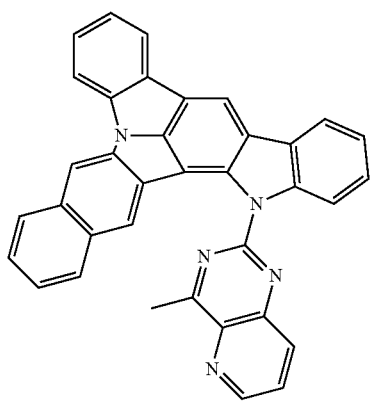 | 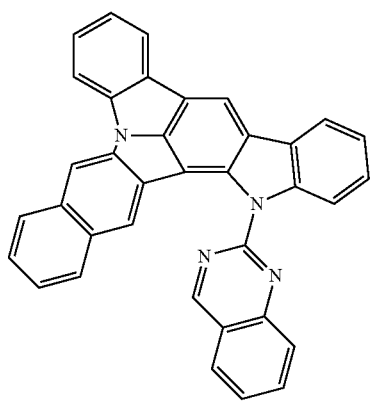 |

415 416
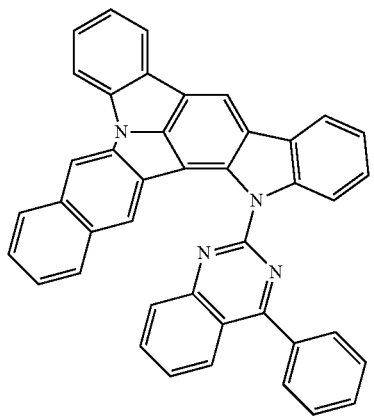
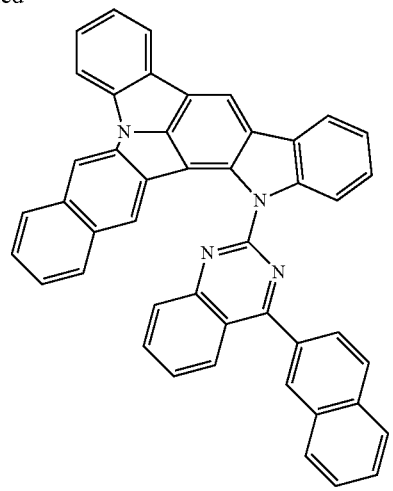
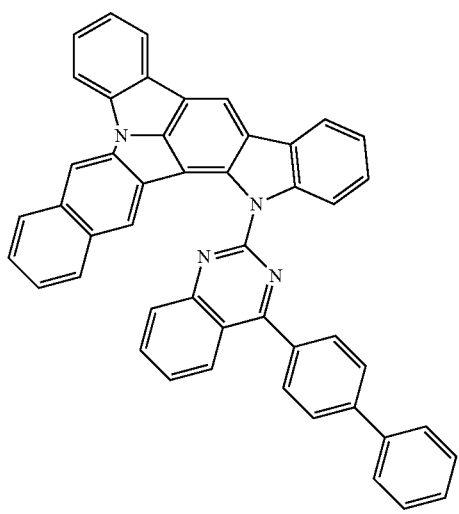
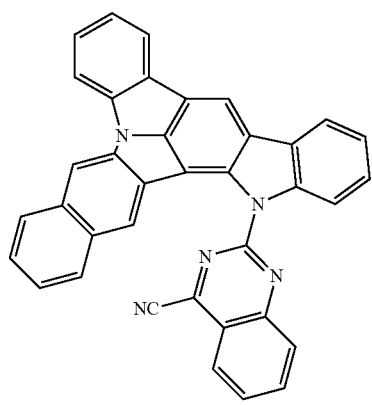
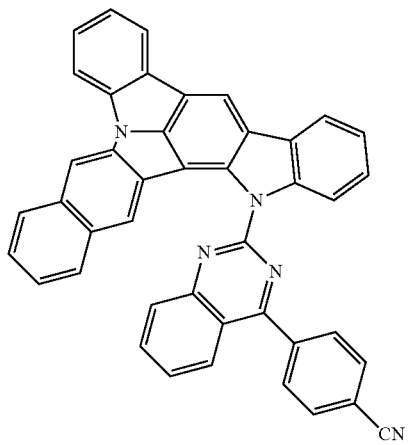
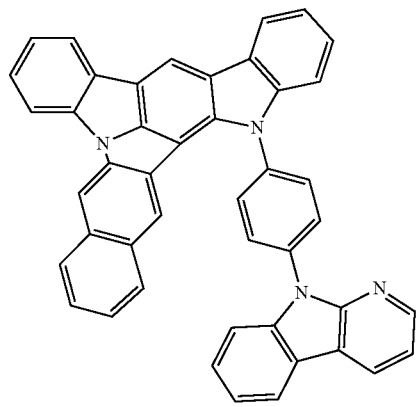

-continued
417
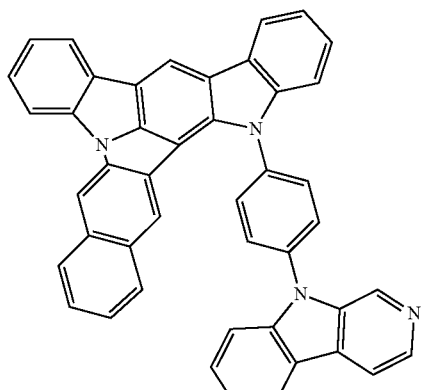
418
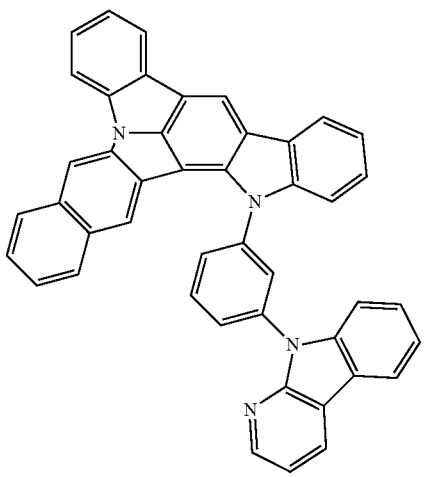
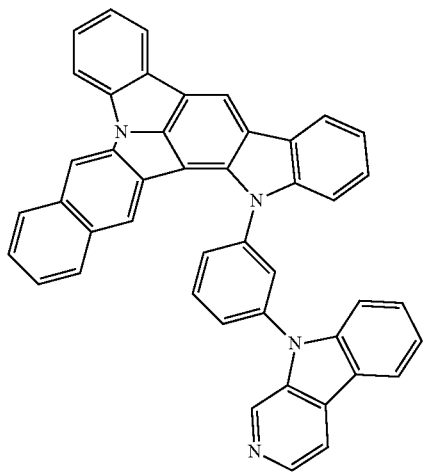
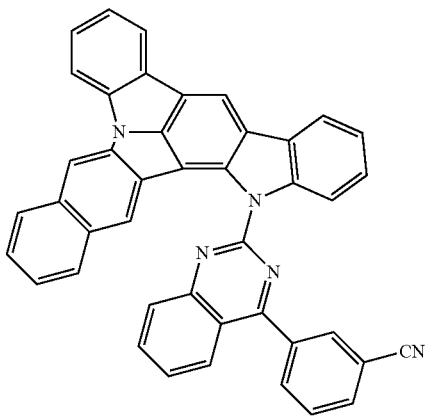
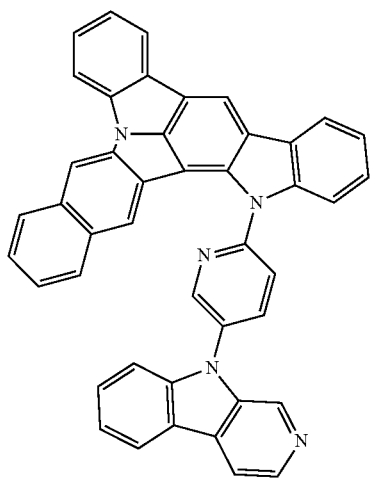
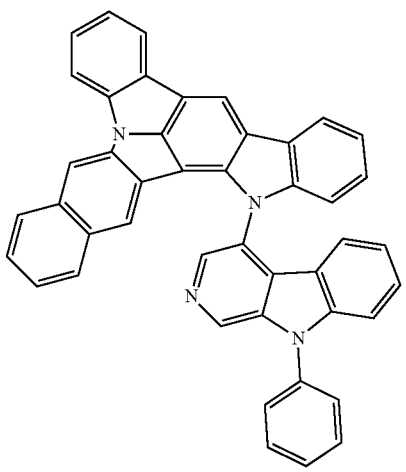

419
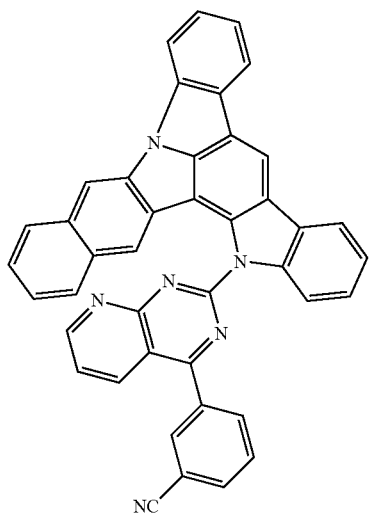
420
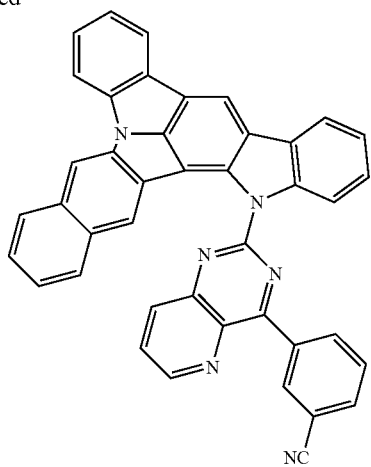
-continued
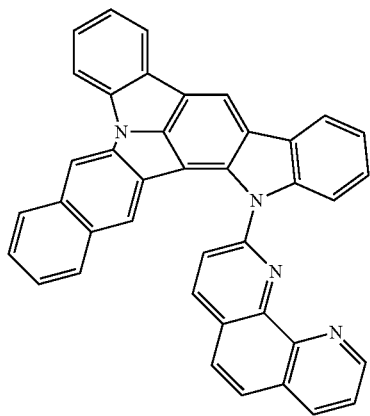
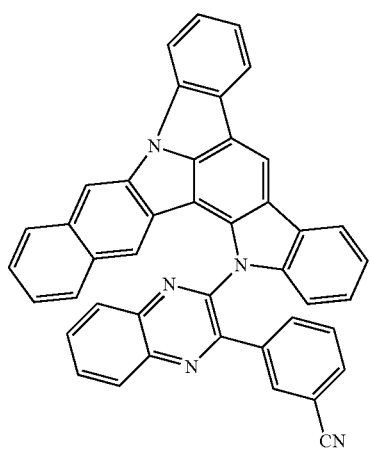
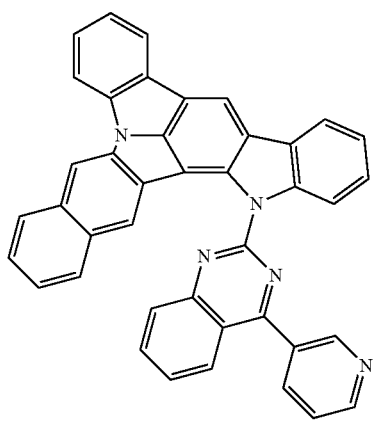
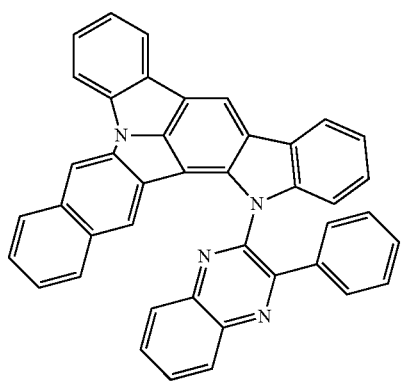

421
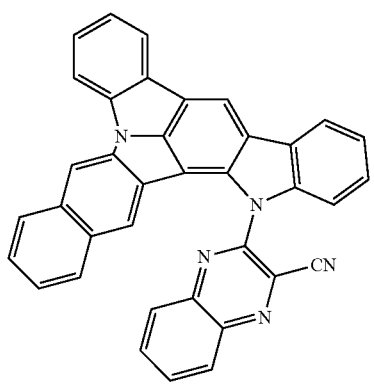
422
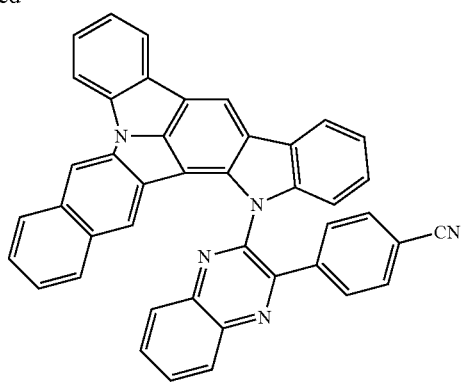
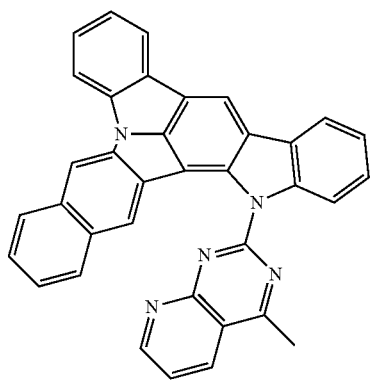
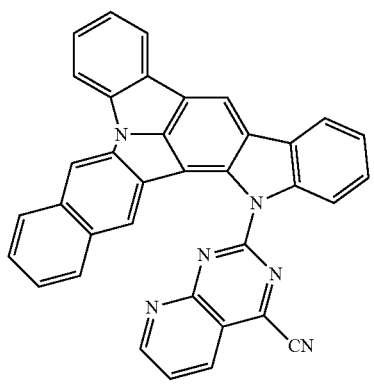
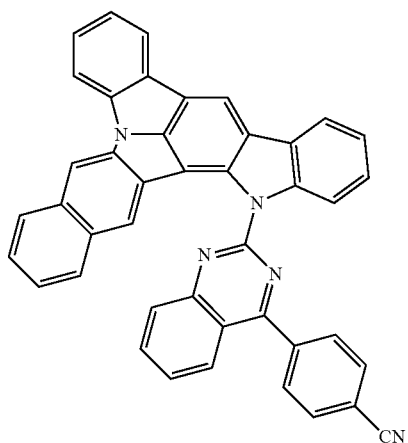

-continued
423
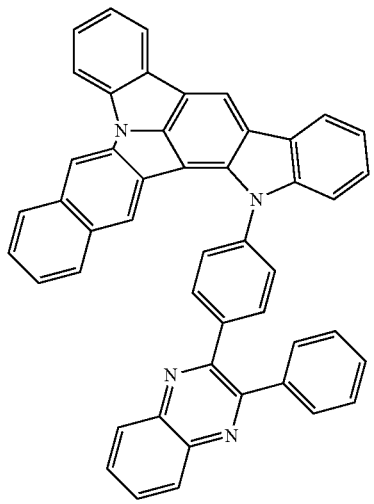
424
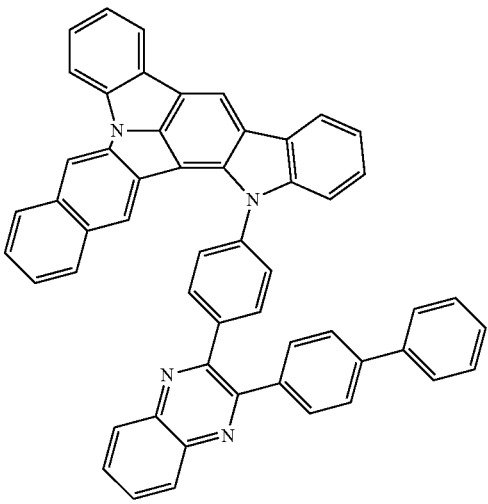
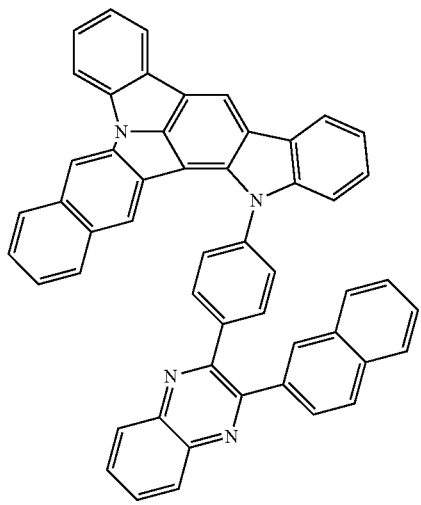
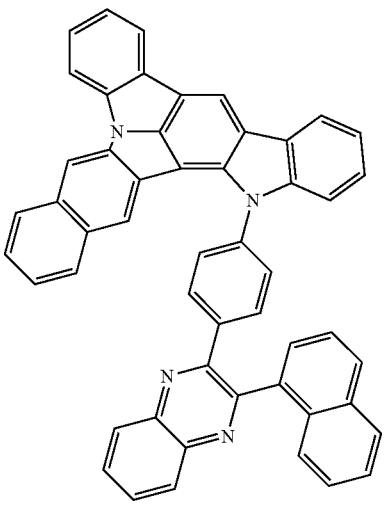
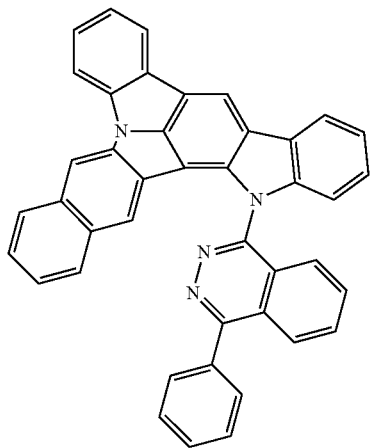
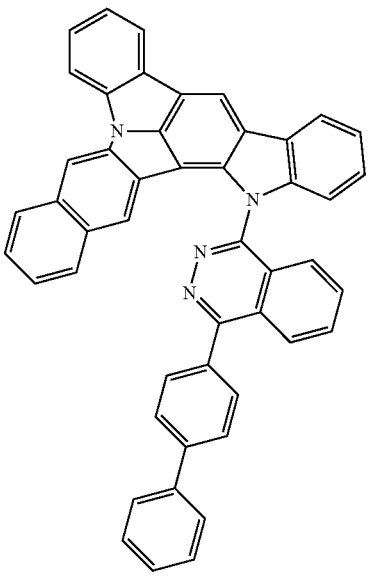

-continued
425
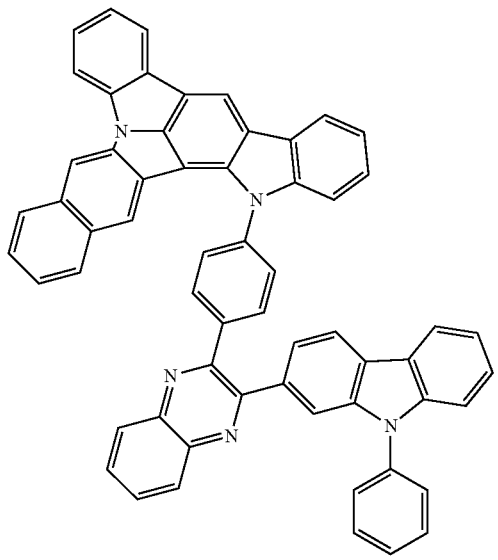
426
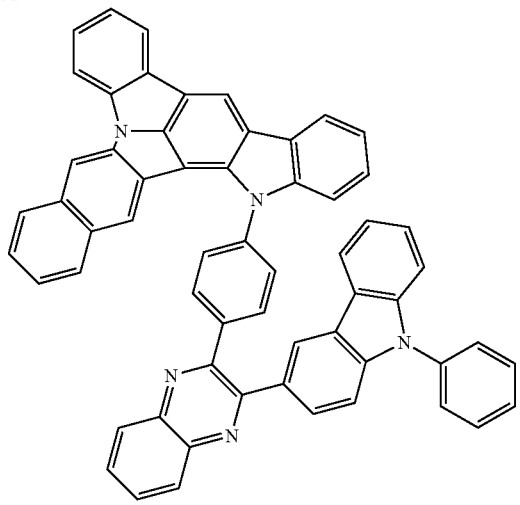
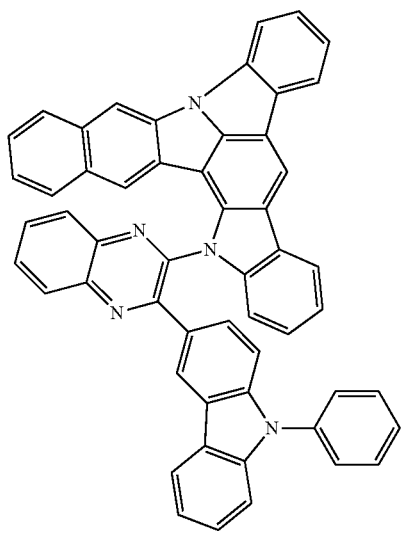
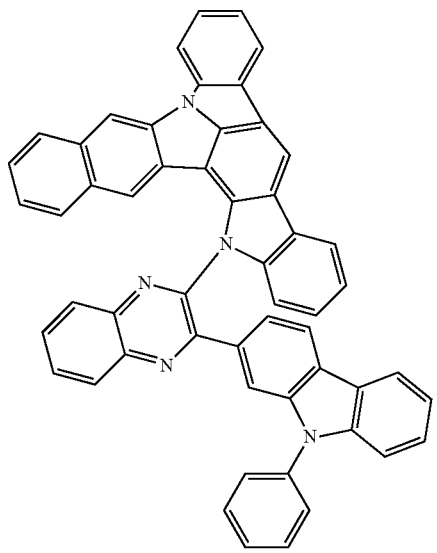
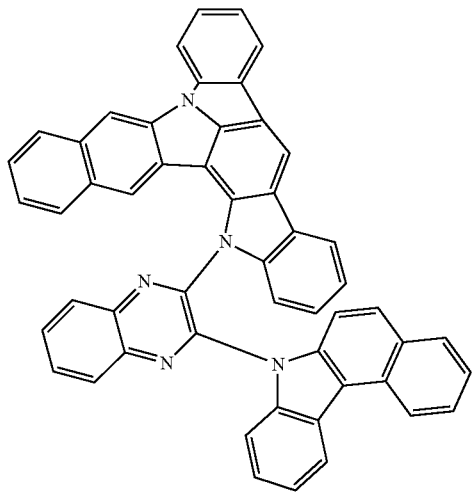
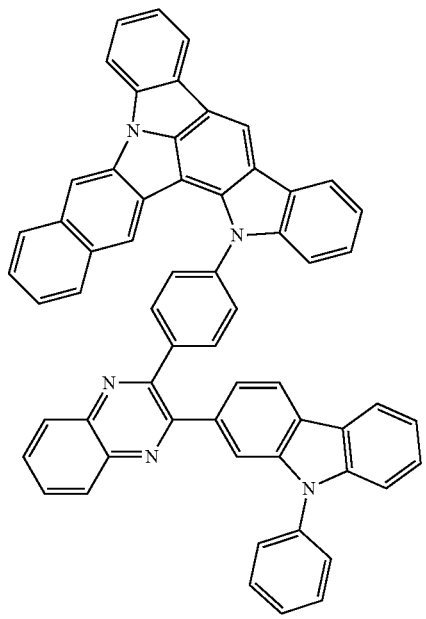

-continued
| 427 | 428 |
|---|---|
| 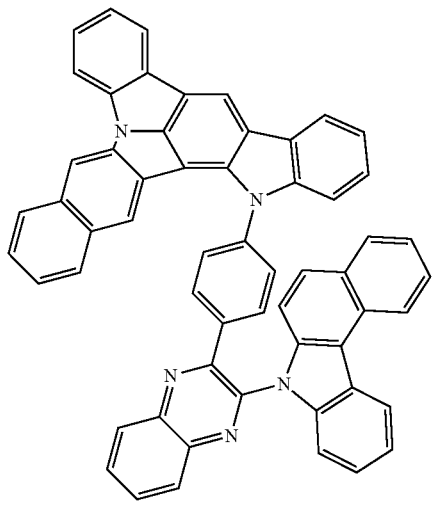 | 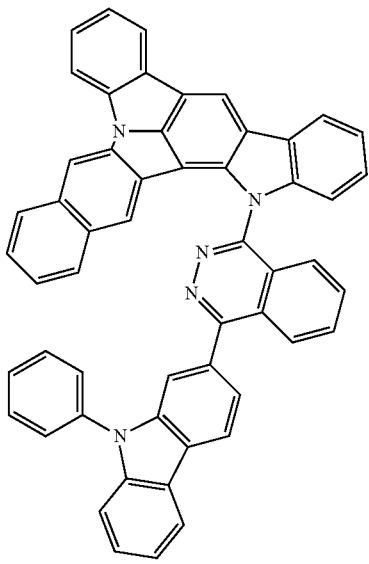 |
| 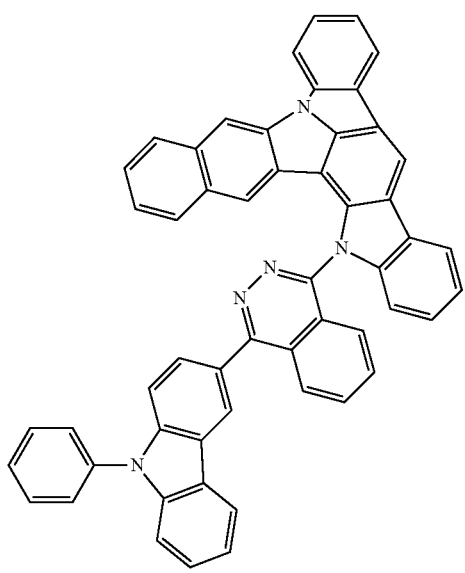 | 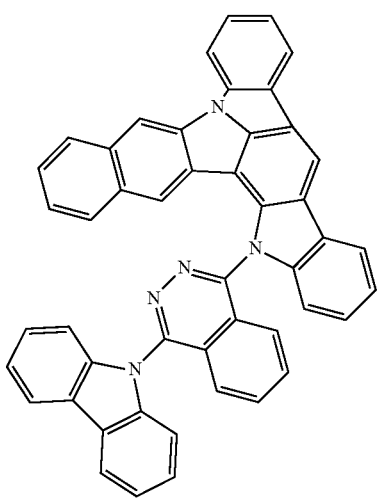 |
| 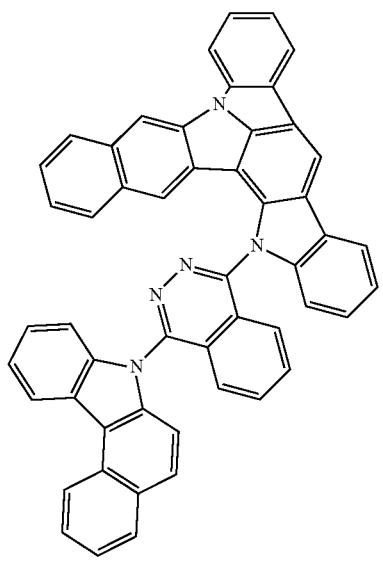 | 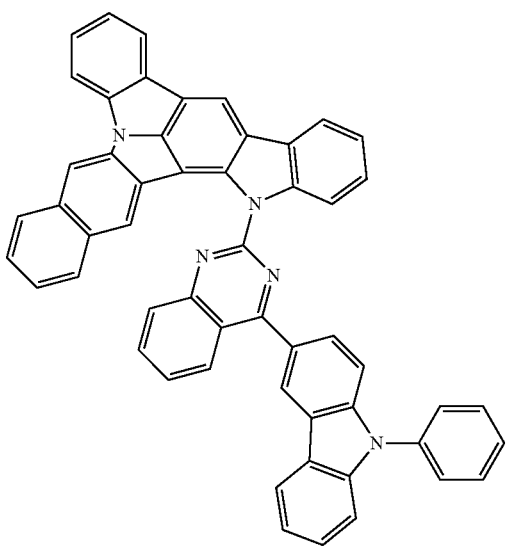 |

429
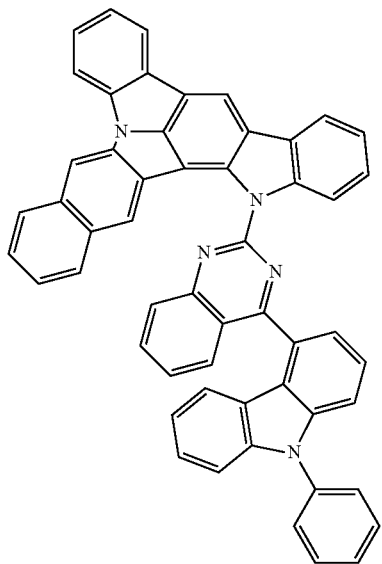
430
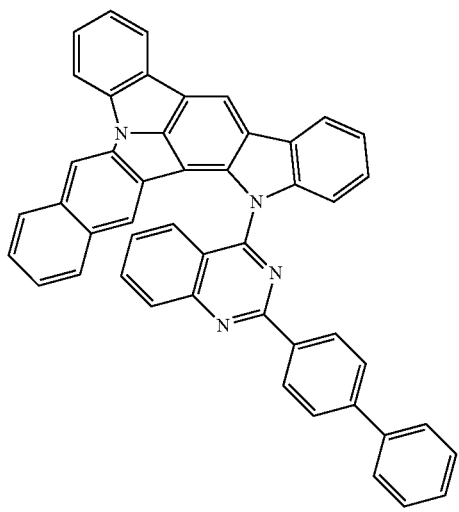
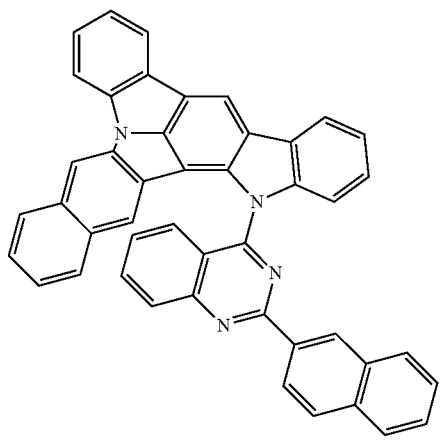
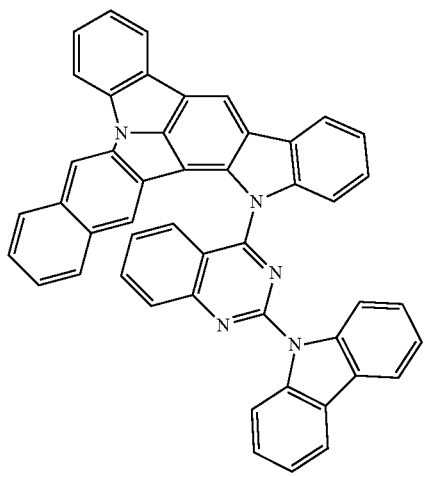
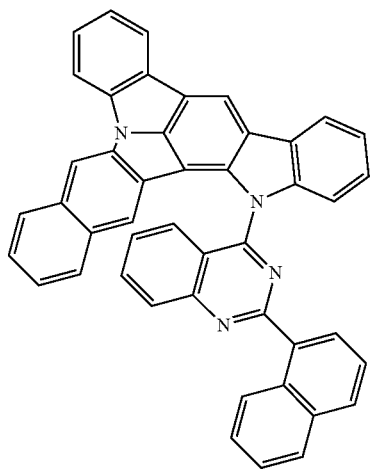

-continued
| 431 | 432 |
|---|---|
| 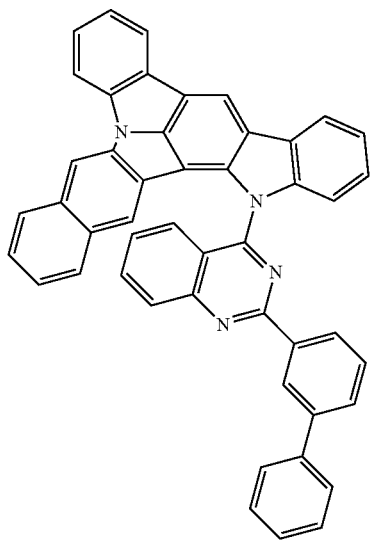 | 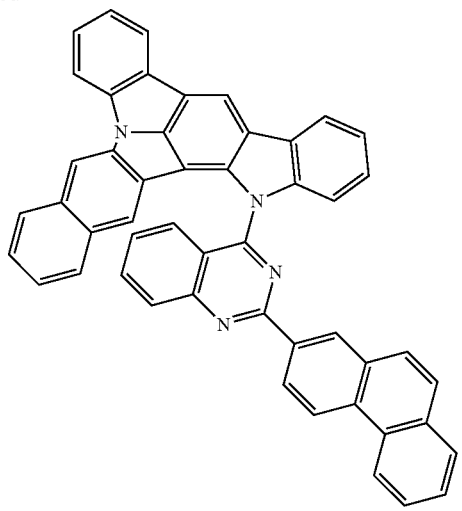 |
| 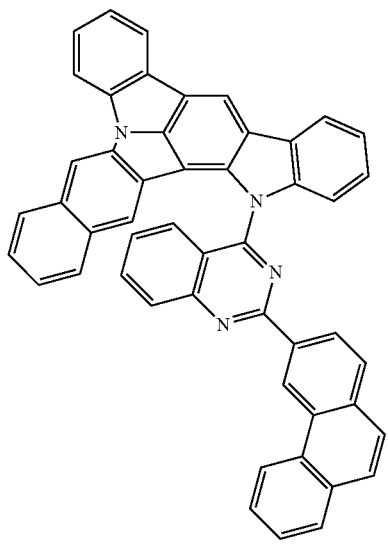 | 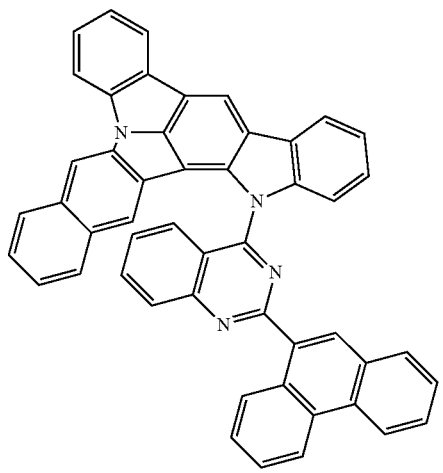 |
| 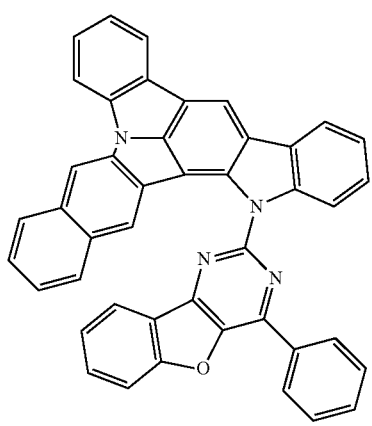 | 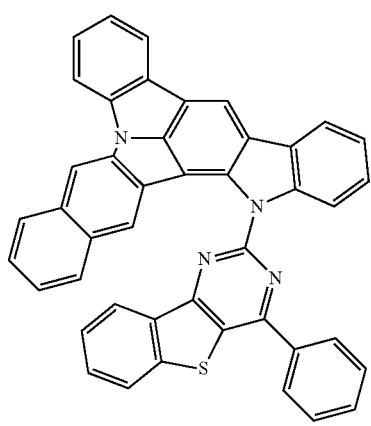 |

-continued
| 433 | 434 |
|---|---|
| 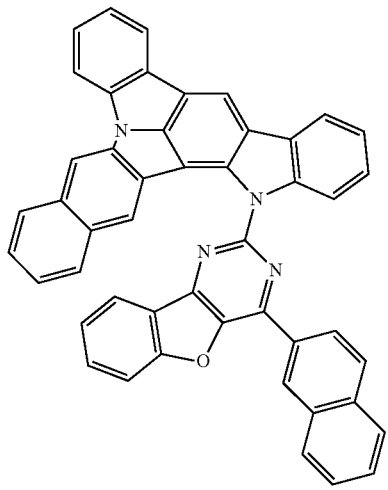 | 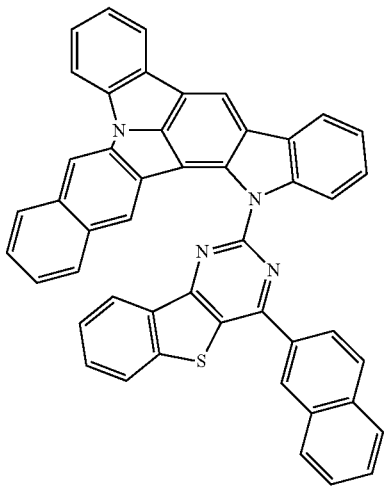 |
| 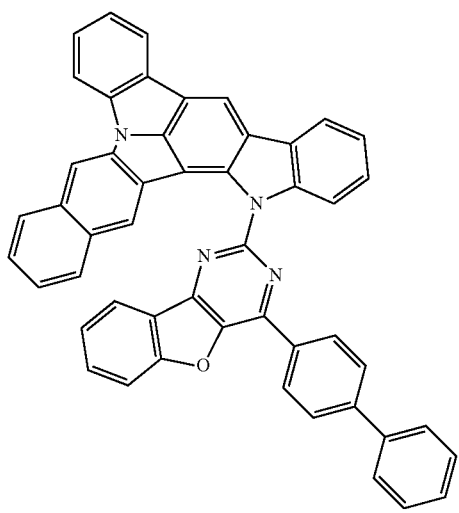 | 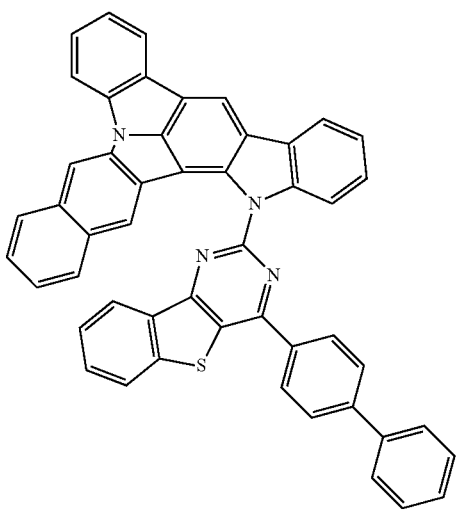 |
| 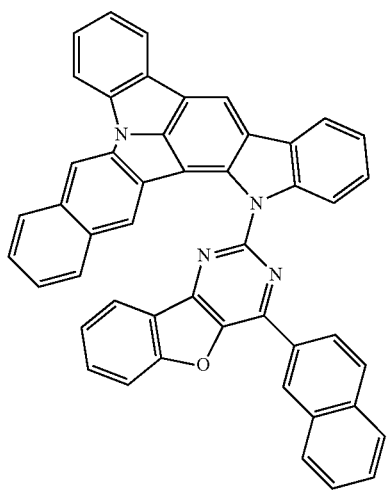 | 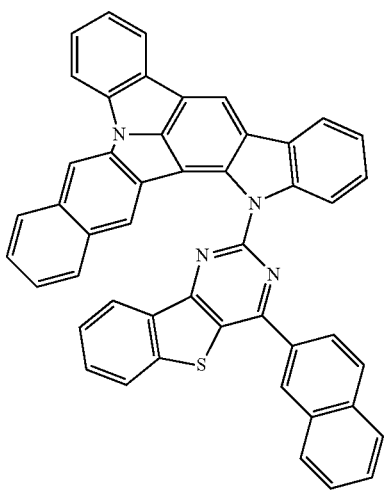 |

-continued
435
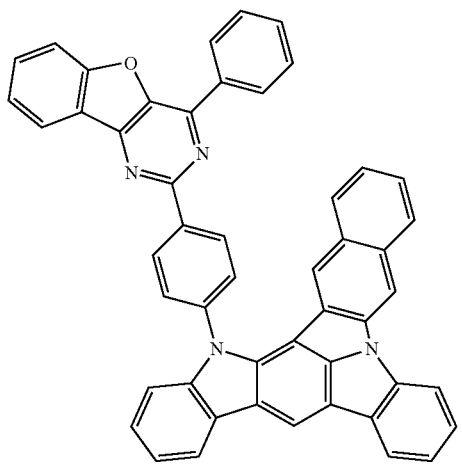
436
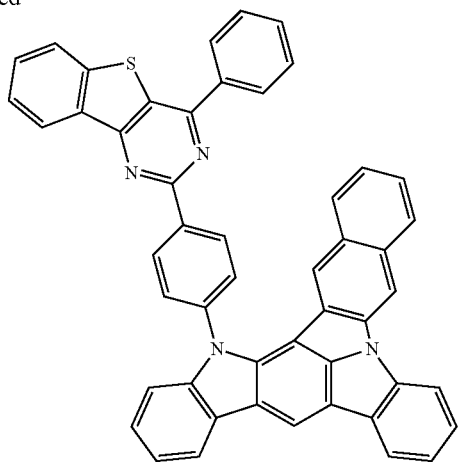
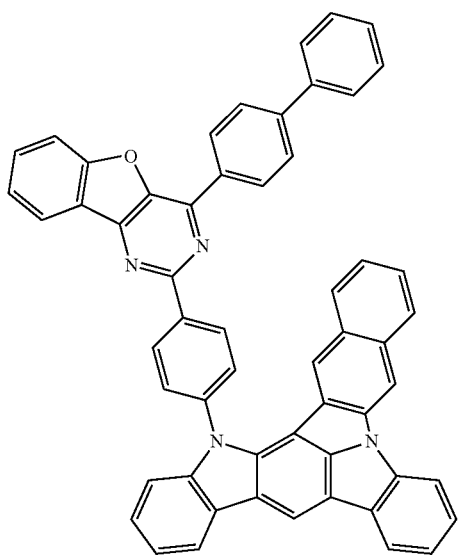
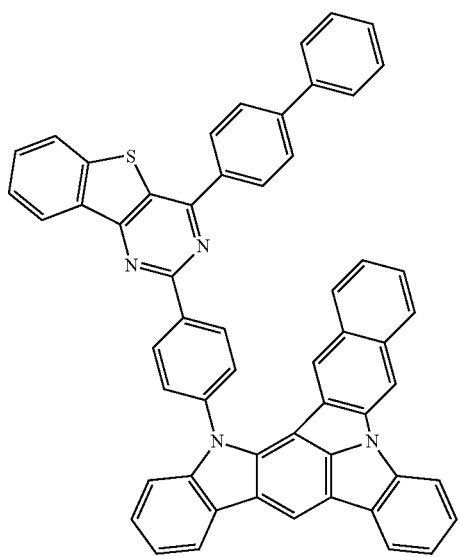
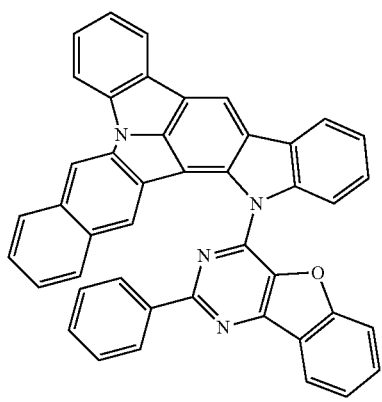
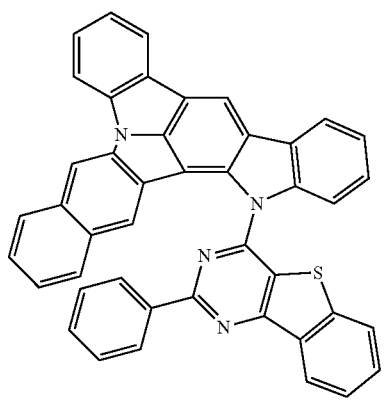

-continued
437 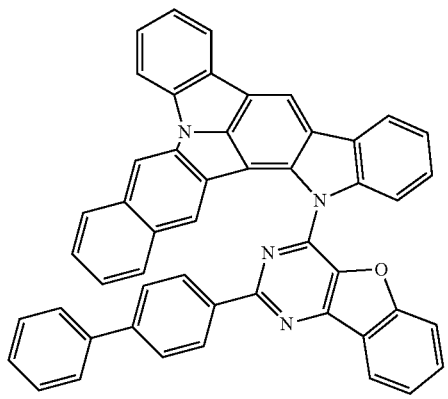 438 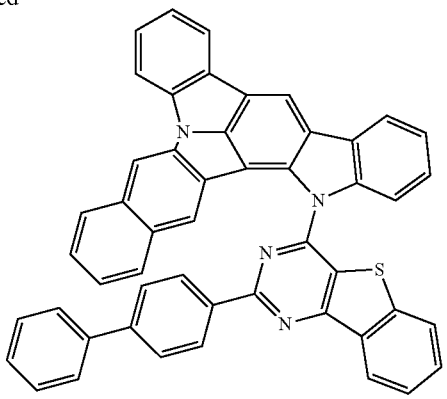
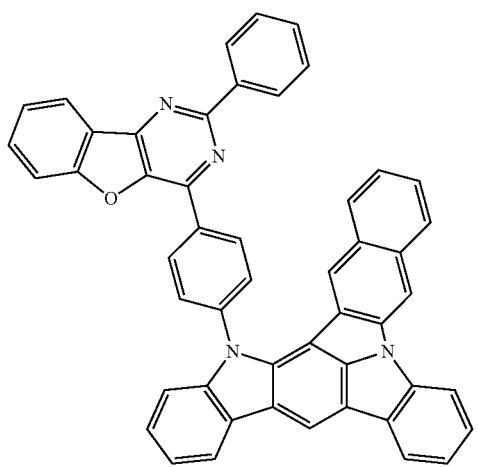 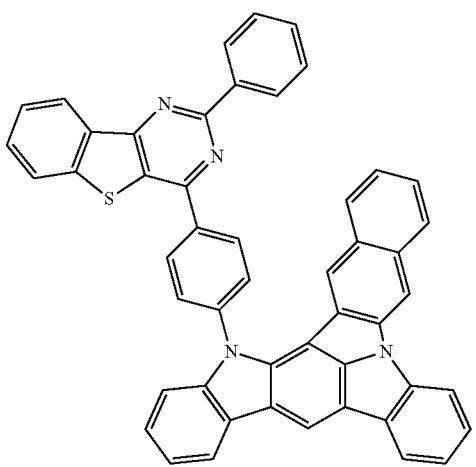
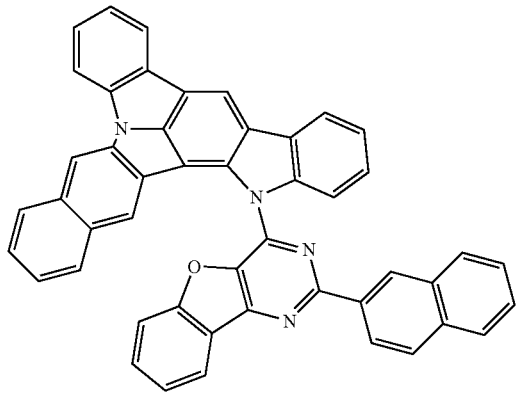 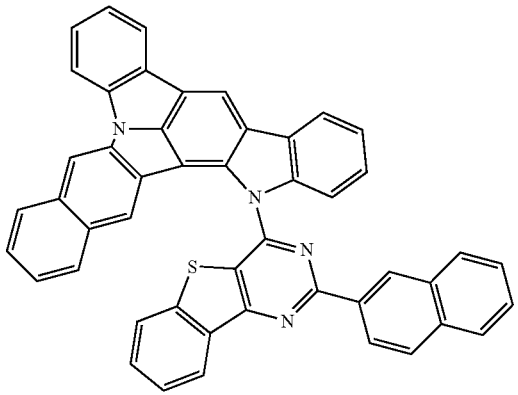
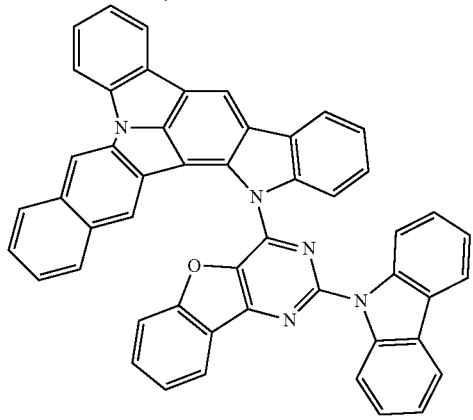 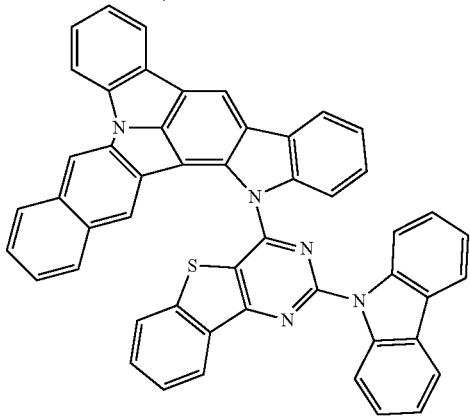

-continued
439 440
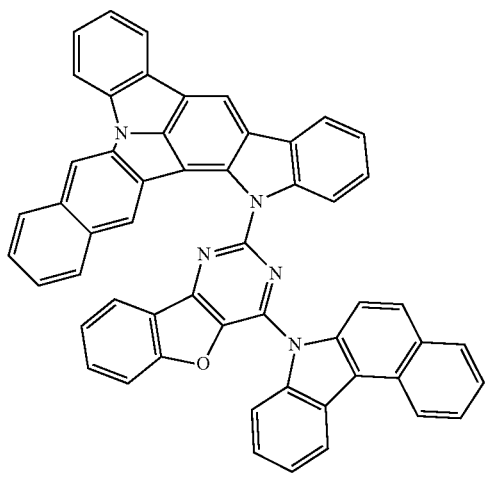 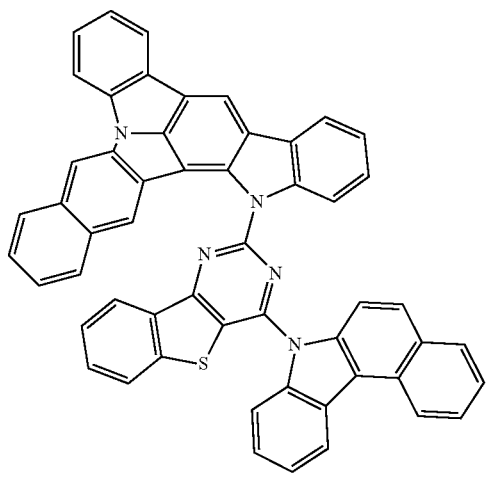
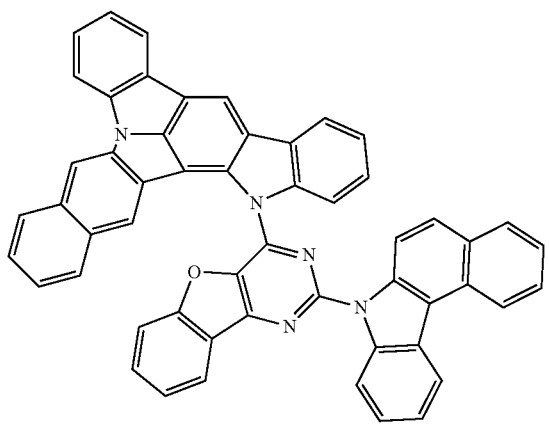 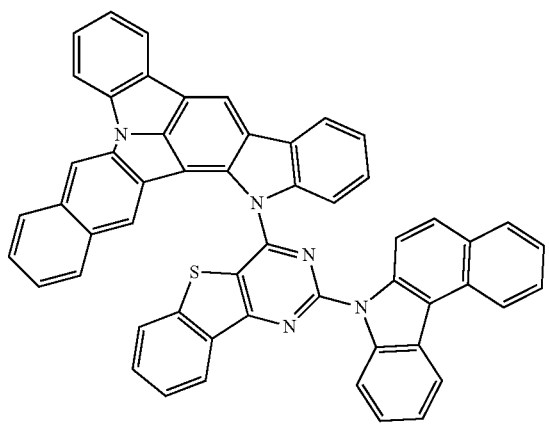
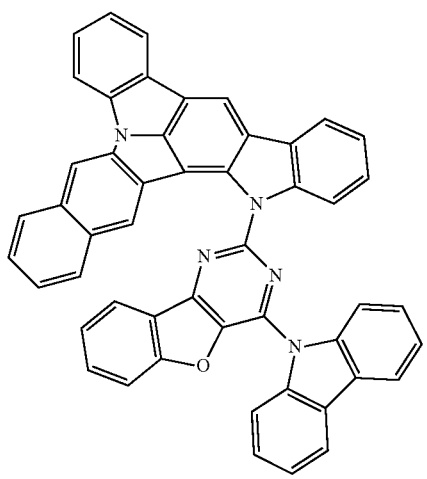 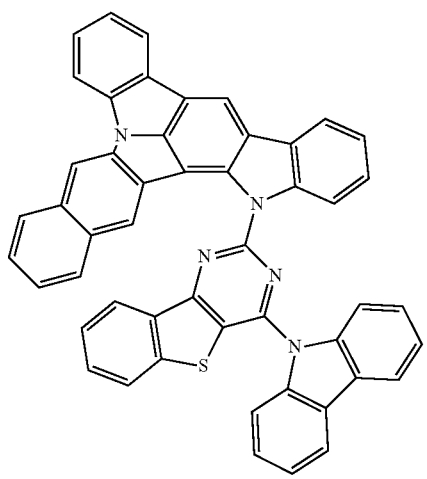

| 441 | 442 |
|---|---|
| 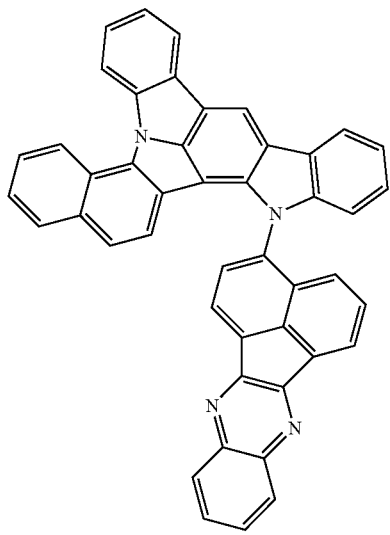 | 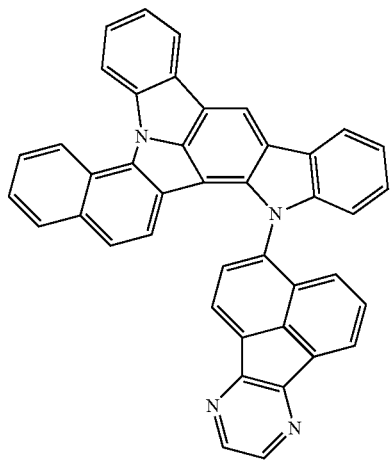 |
| 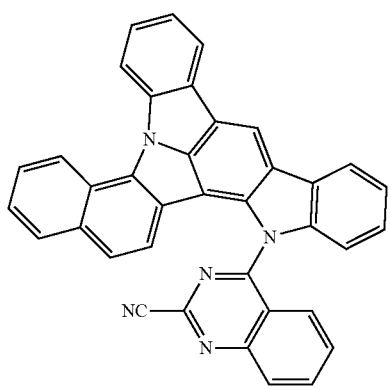 | 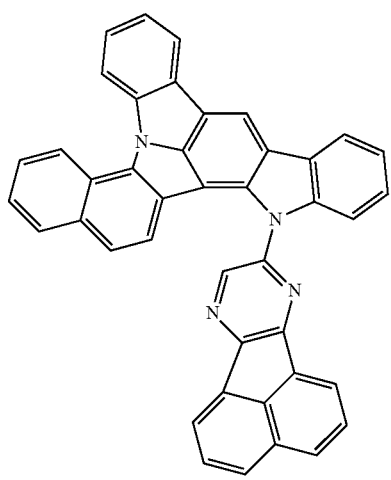 |
| 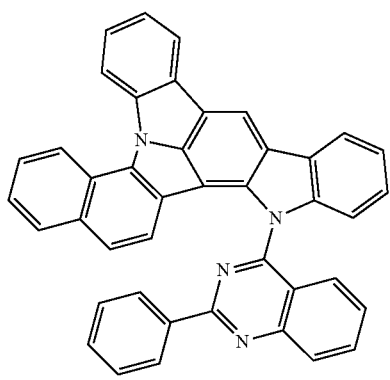 | 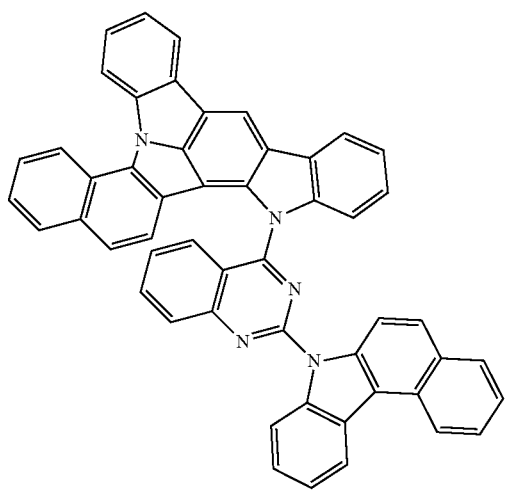 |

443 444
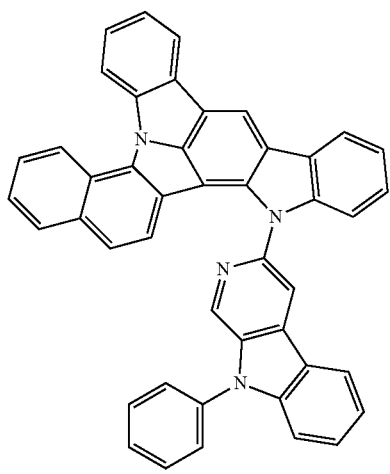 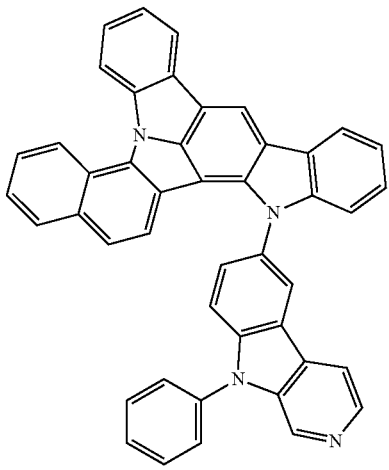
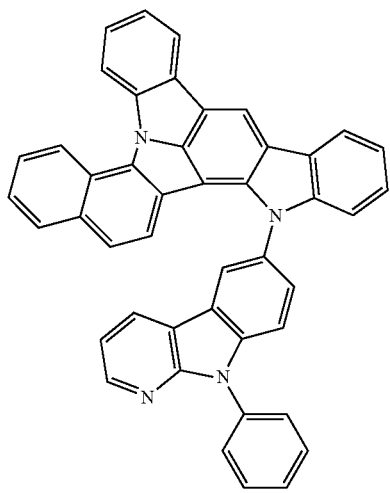 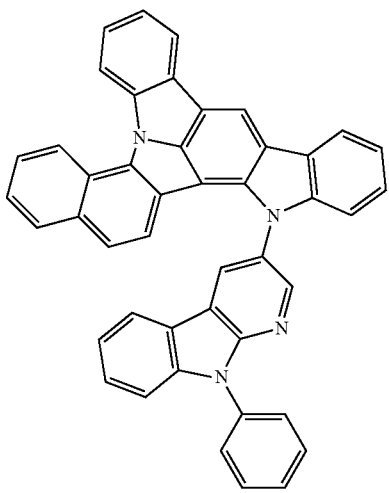
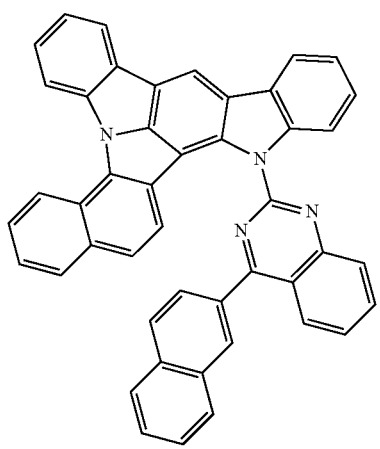 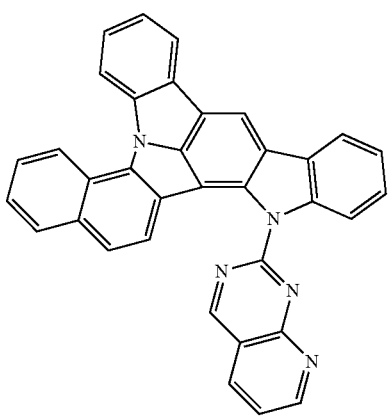

445 446
-continued
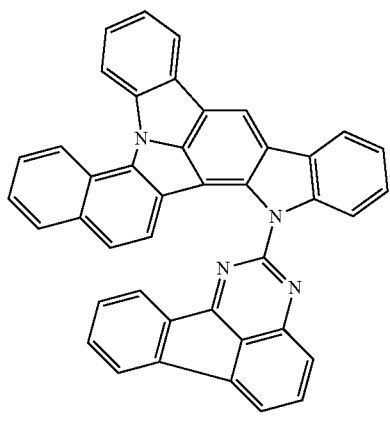 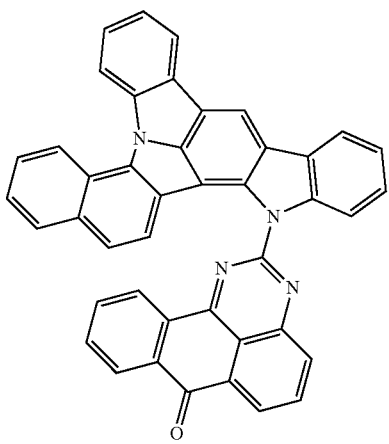
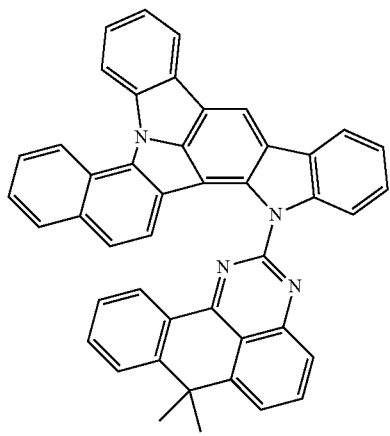 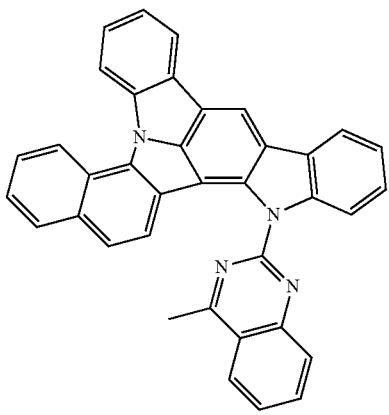
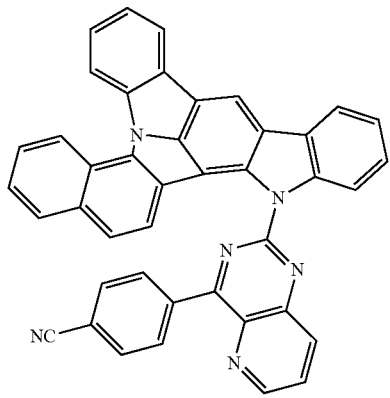 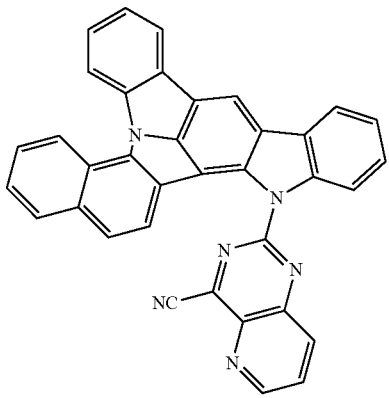
 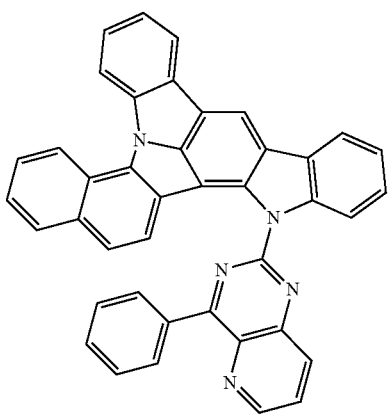

447 448
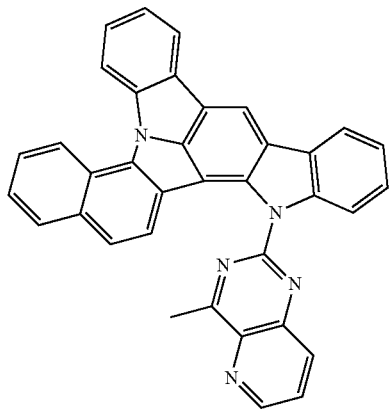 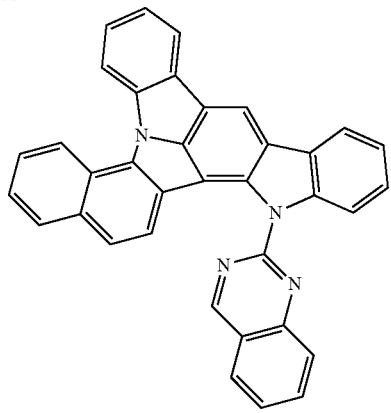
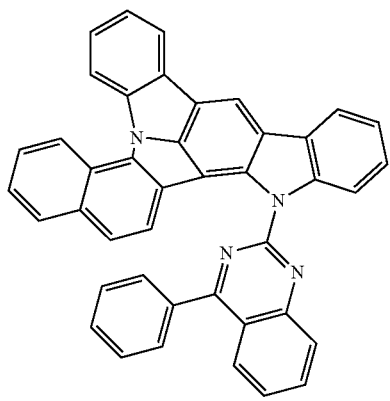 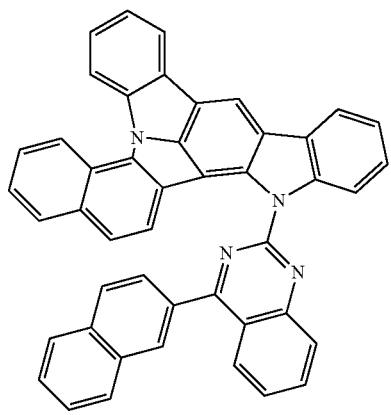
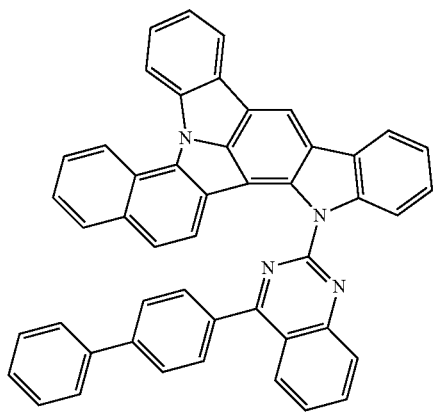 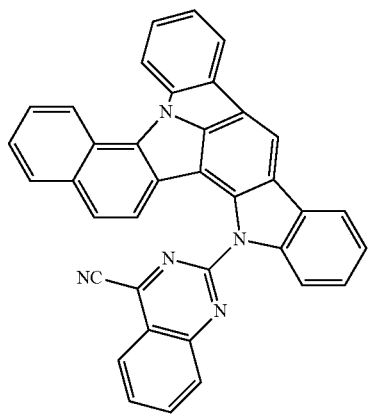
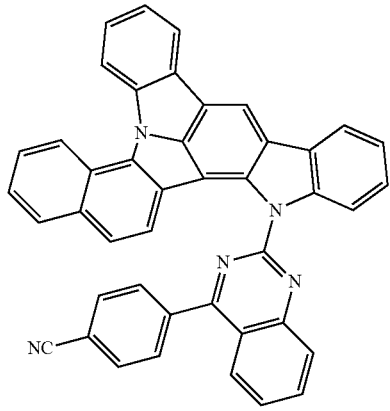 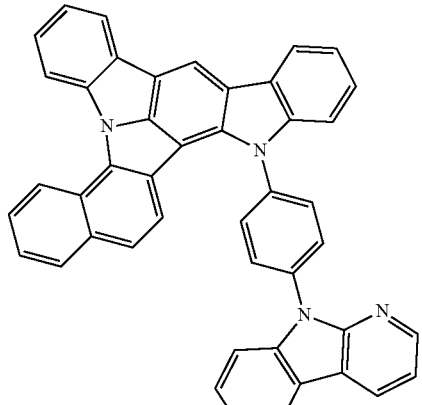

-continued
449
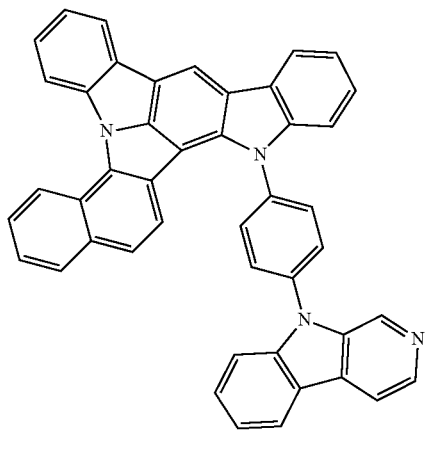
450
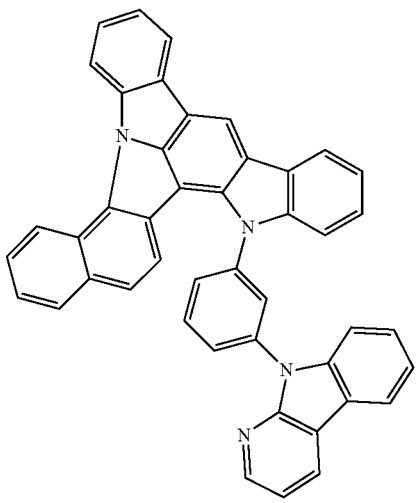
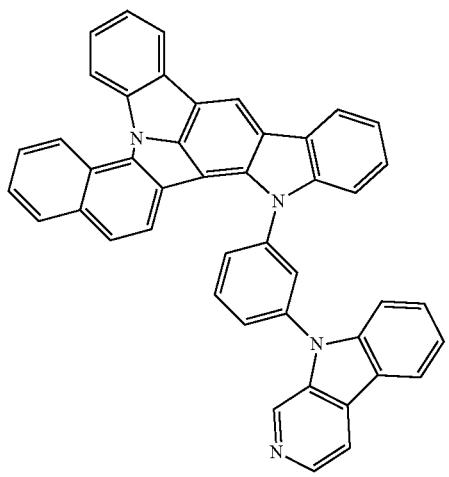
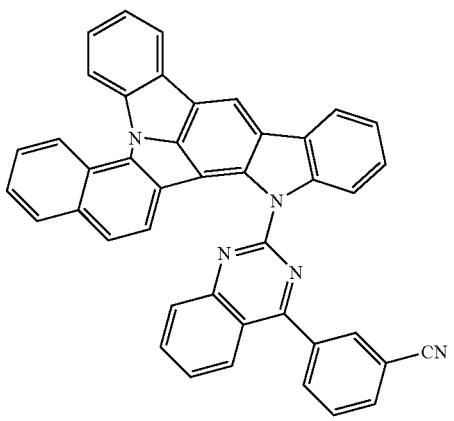
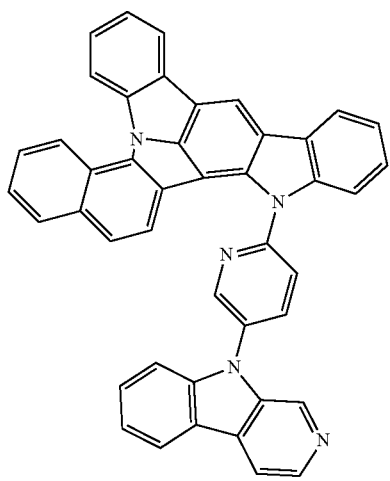
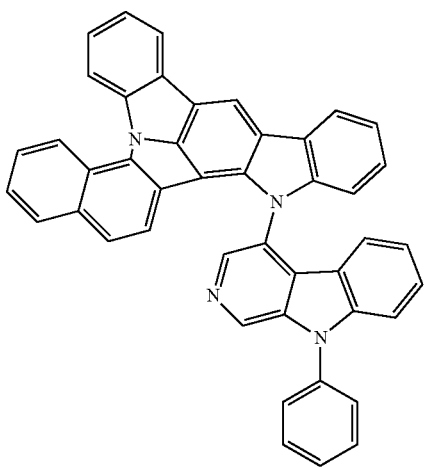

-continued
| 451 | 452 |
|---|---|
| 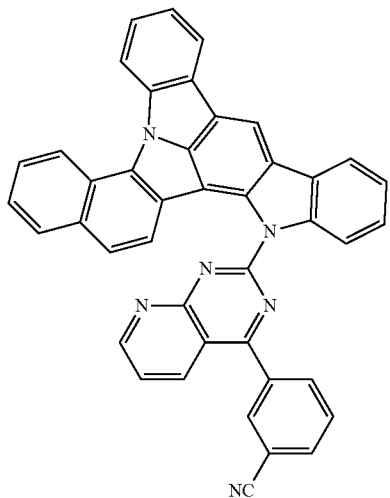 | 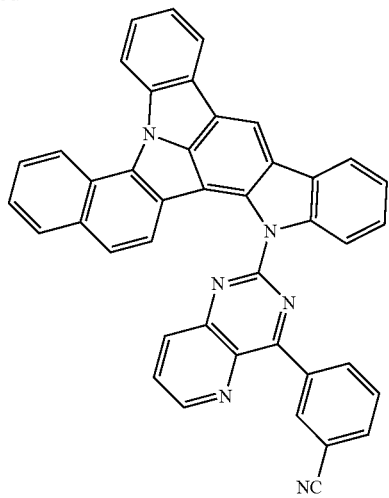 |
| 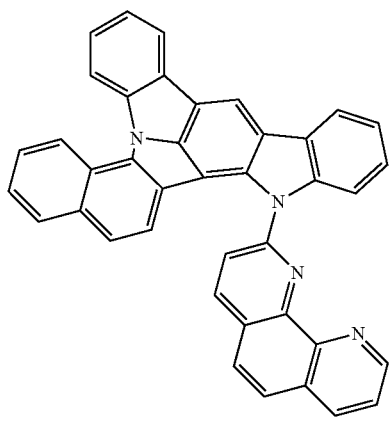 | 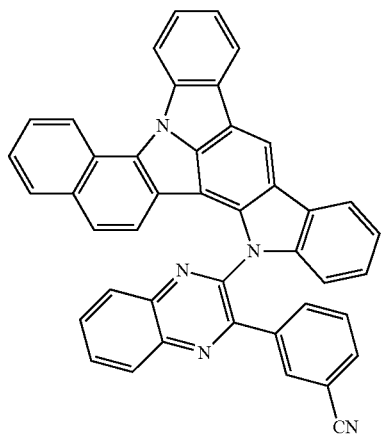 |
| 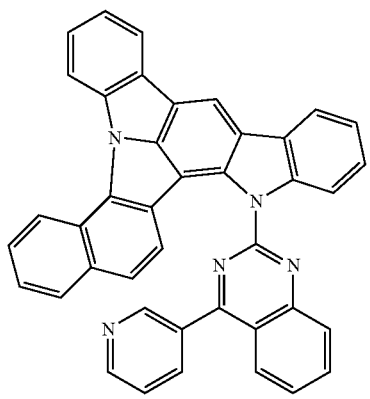 | 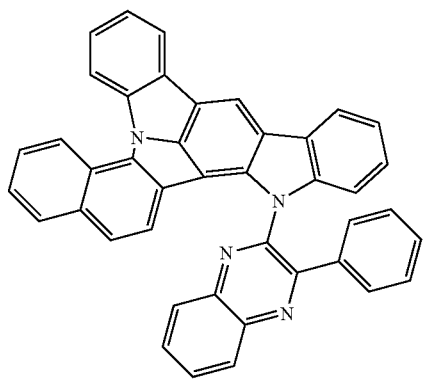 |
| 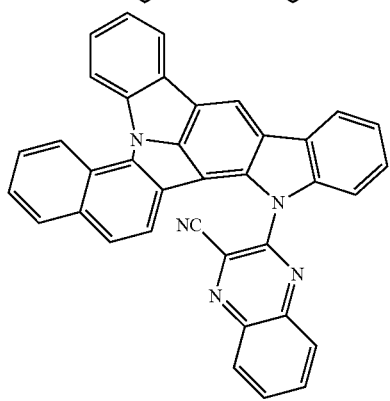 | 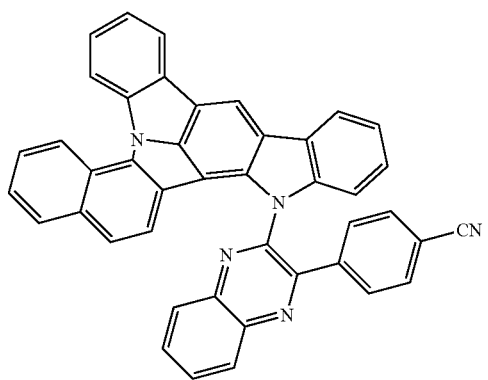 |

453 454
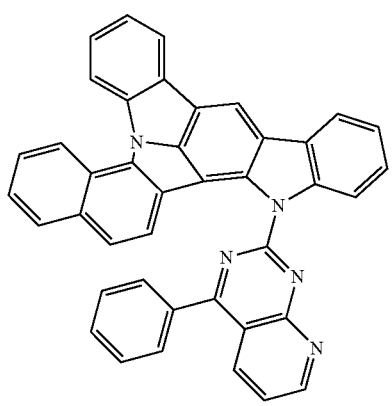
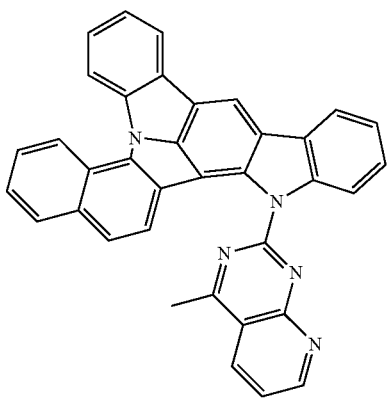
-continued
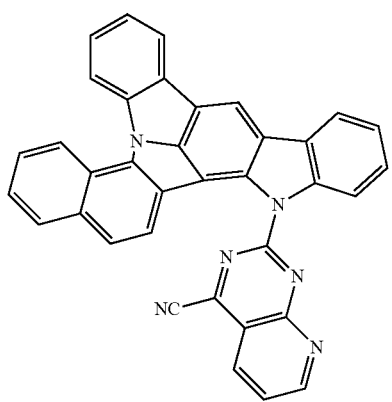
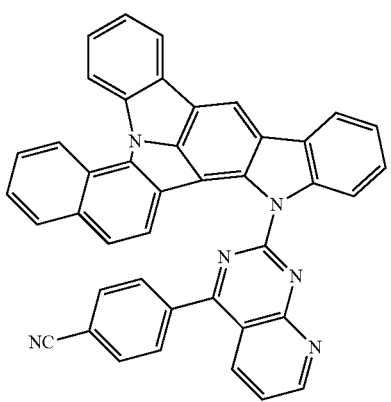
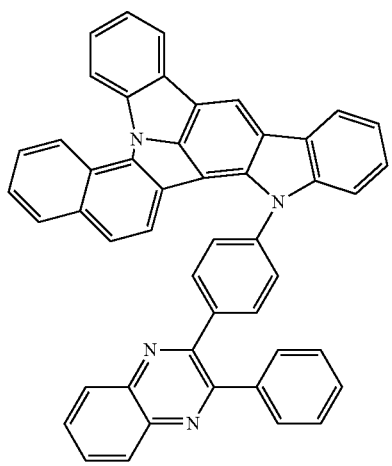
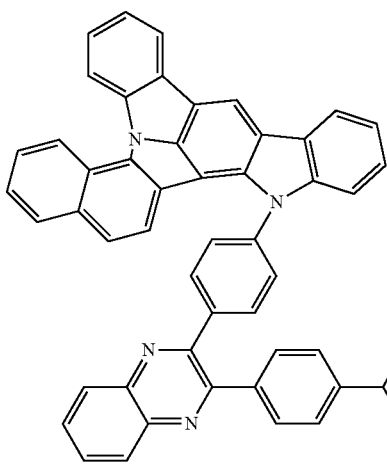

-continued
455
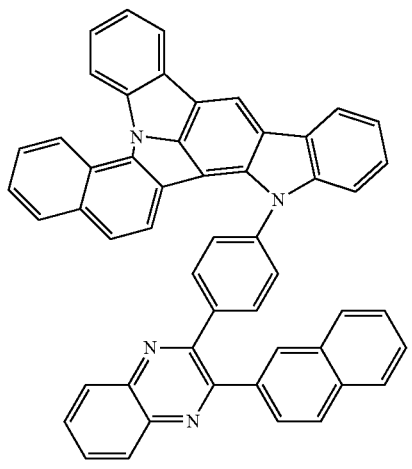
456
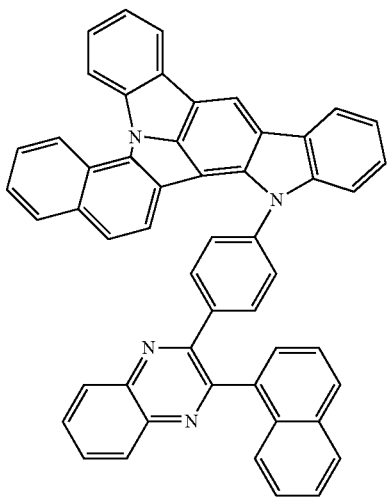
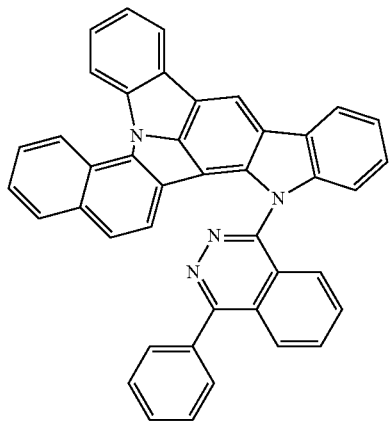
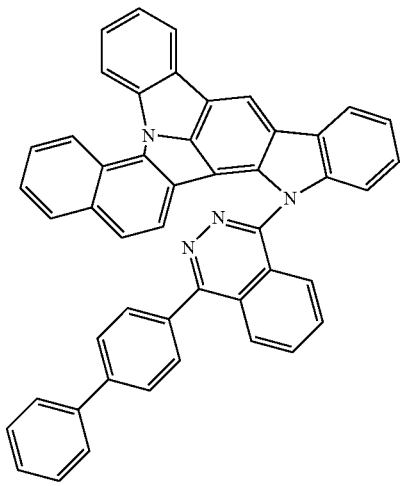
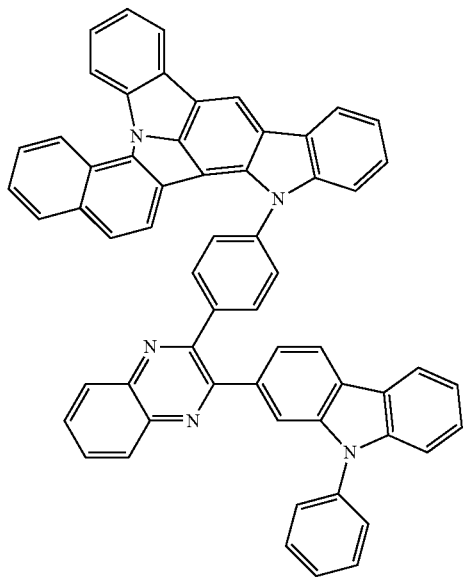
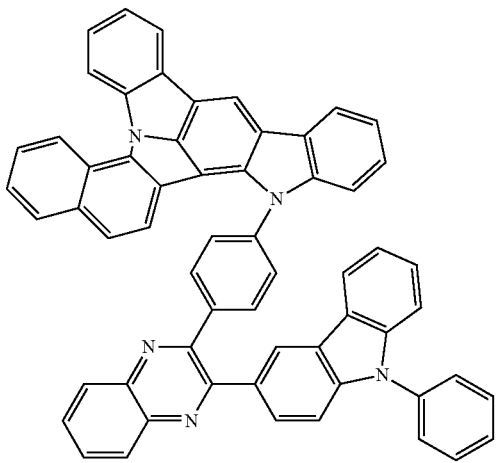

457
458
-continued
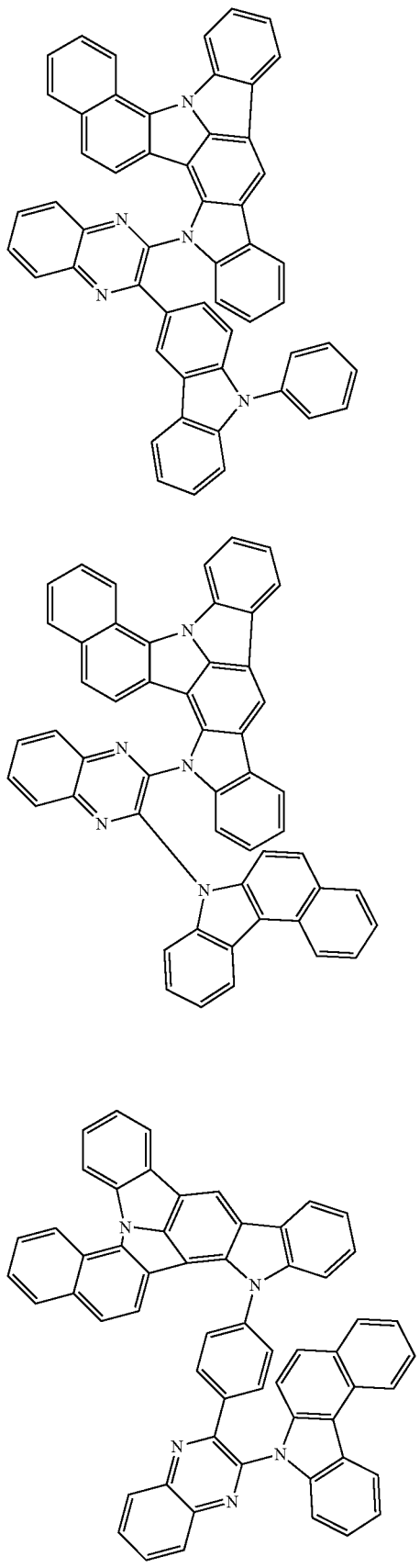
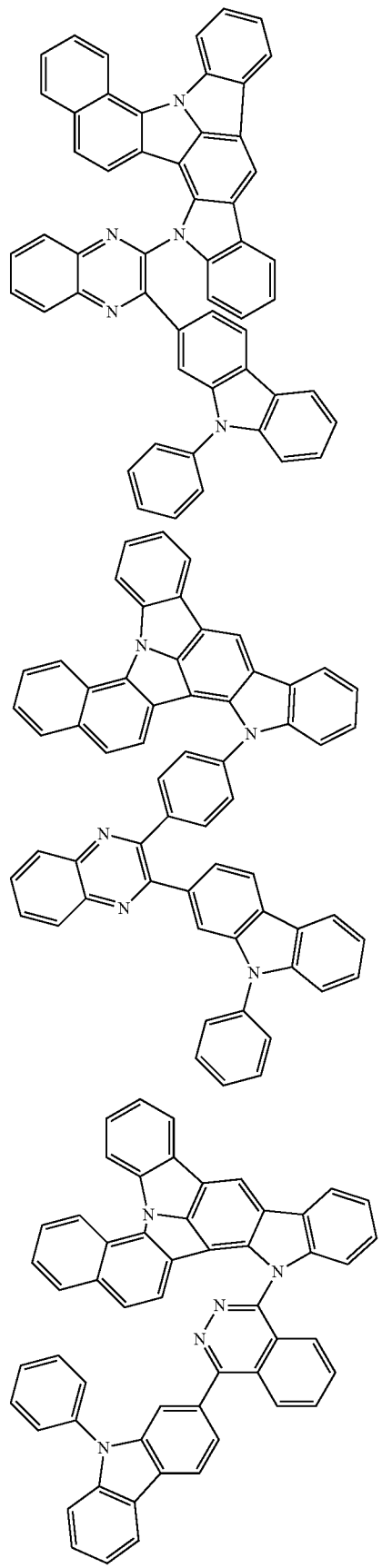

-continued
459
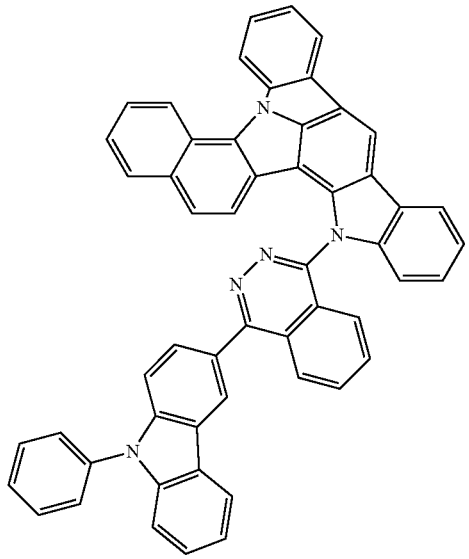
460
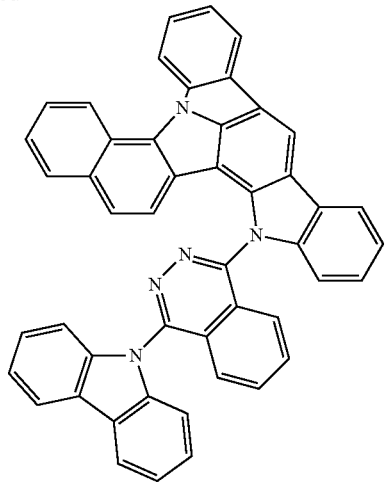
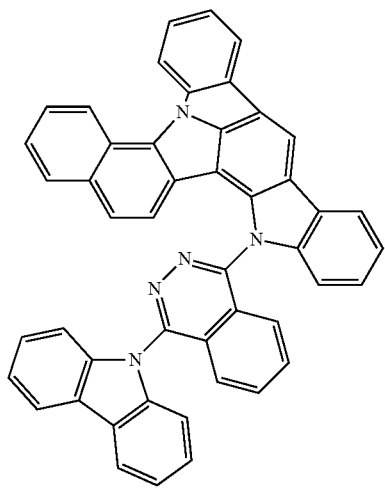
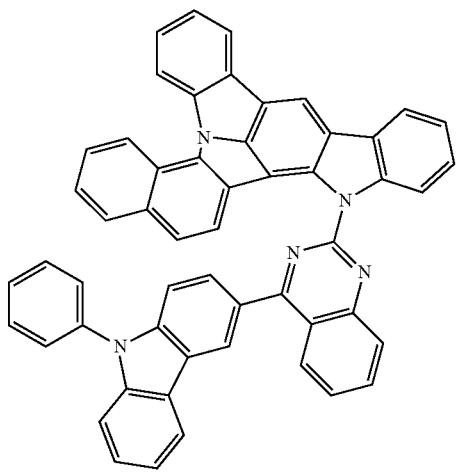
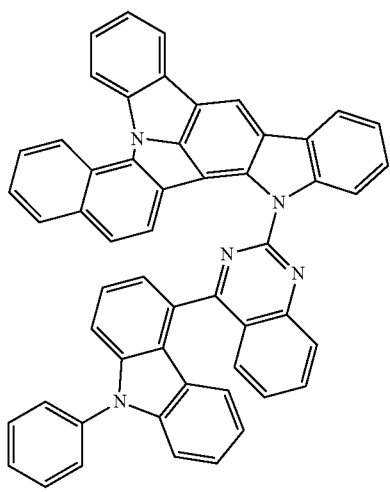
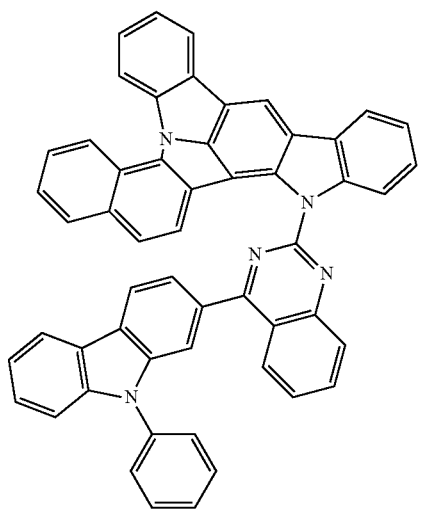

-continued
| 461 | 462 |
|---|---|
| 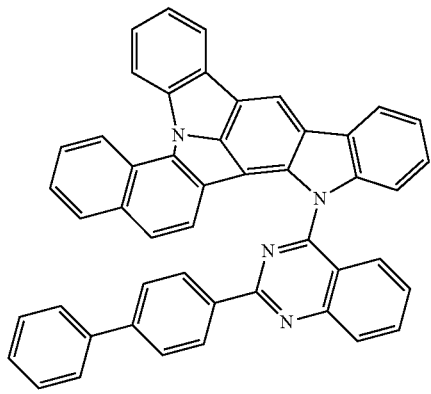 | 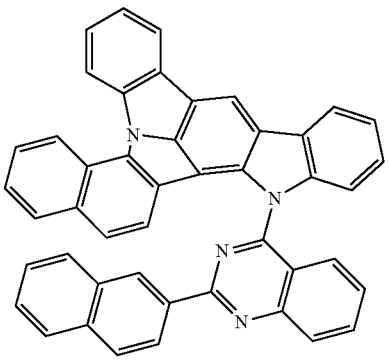 |
| 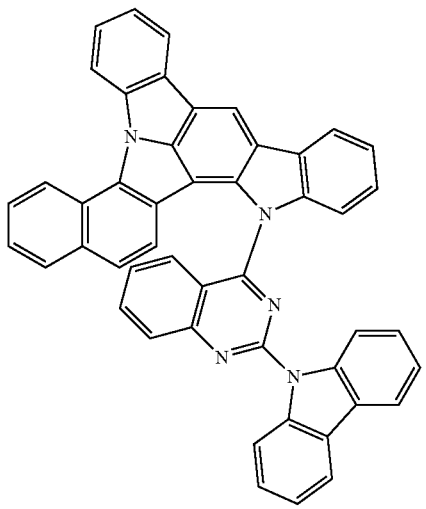 | 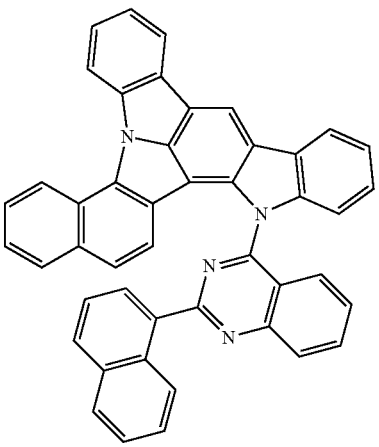 |
| 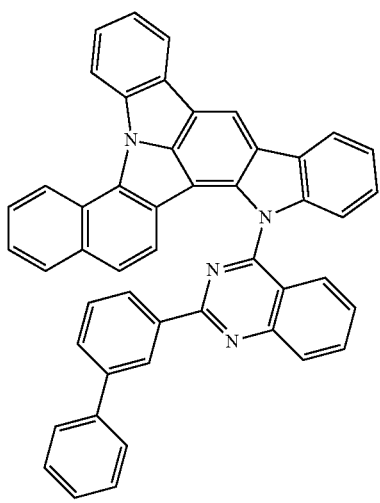 | 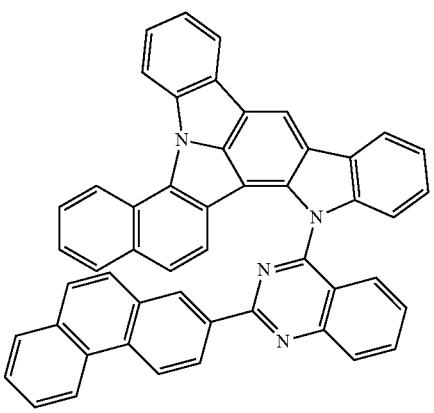 |

-continued
463
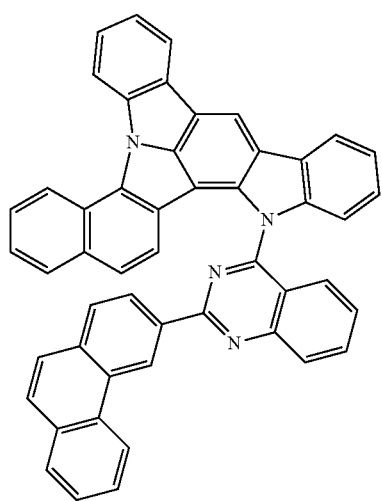
464
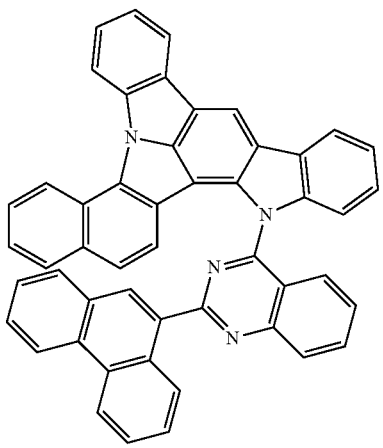
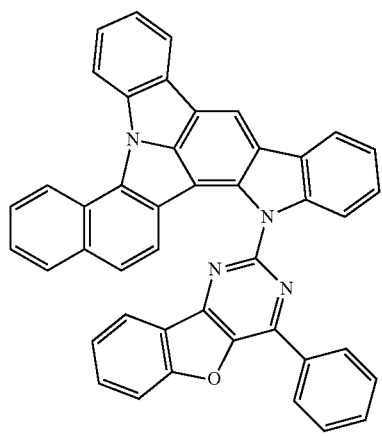
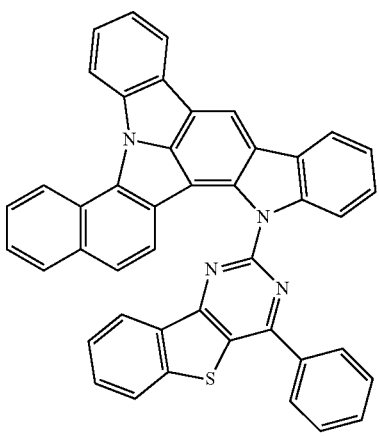
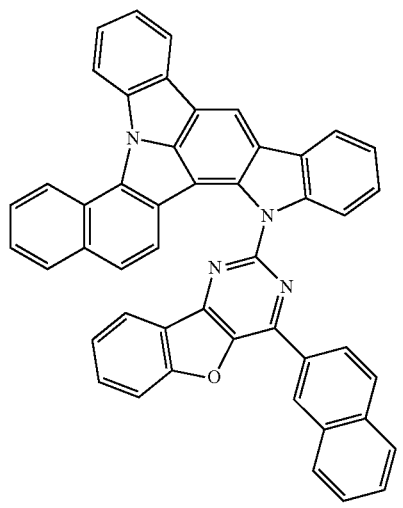
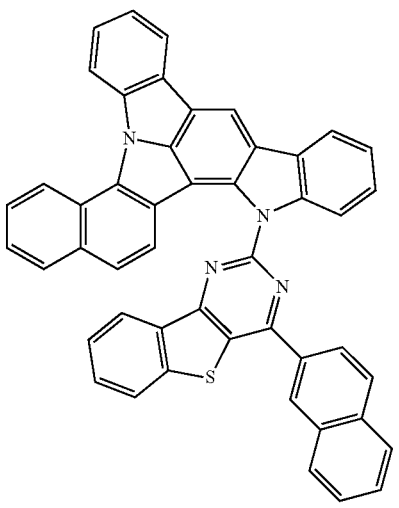

-continued
465
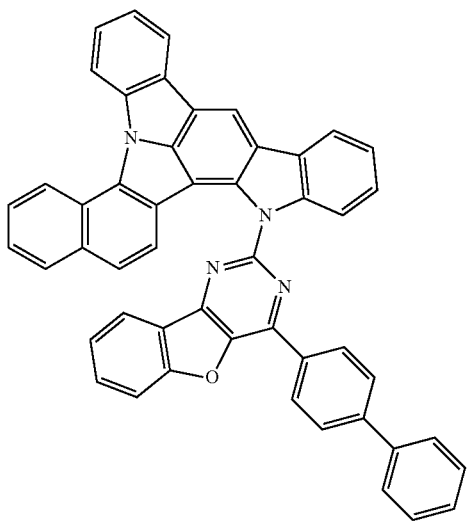
466
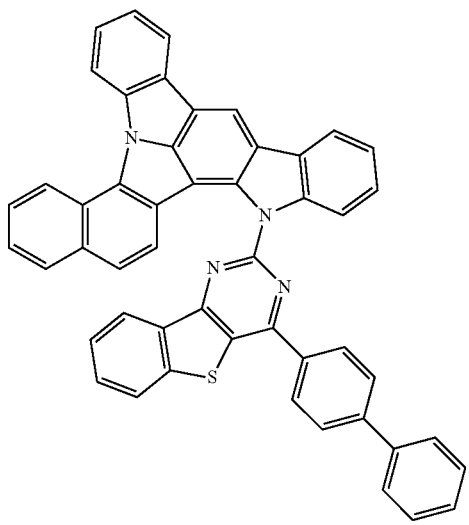
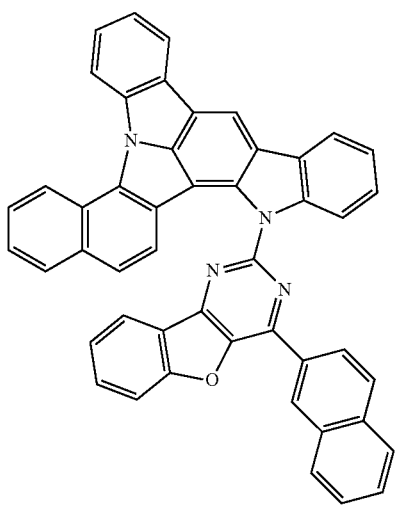
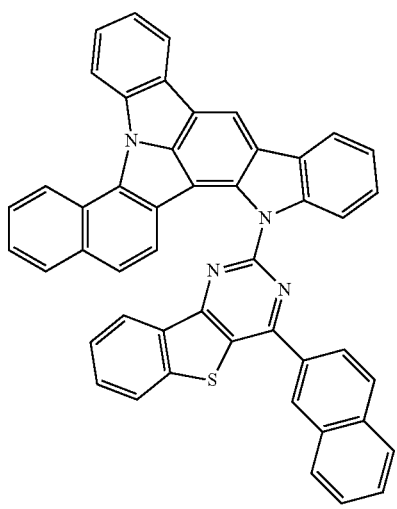
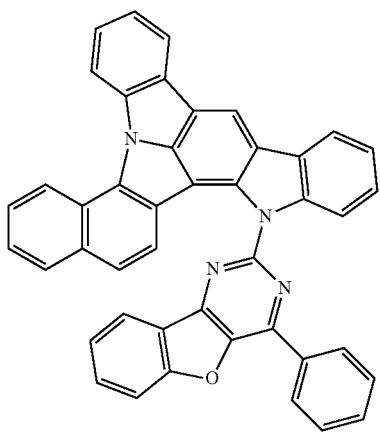
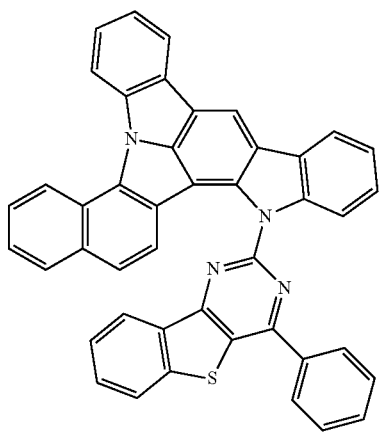

467
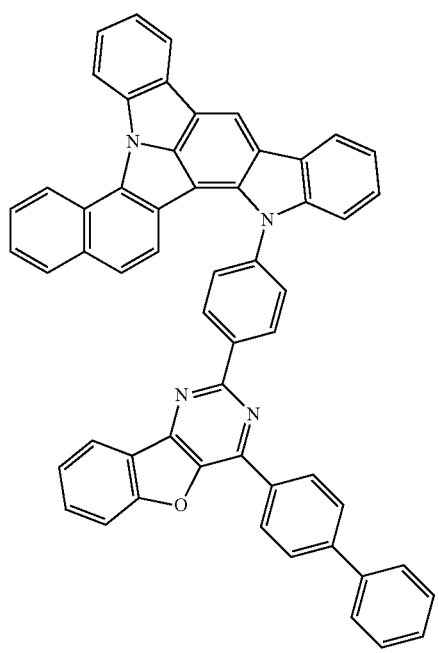
468
-continued
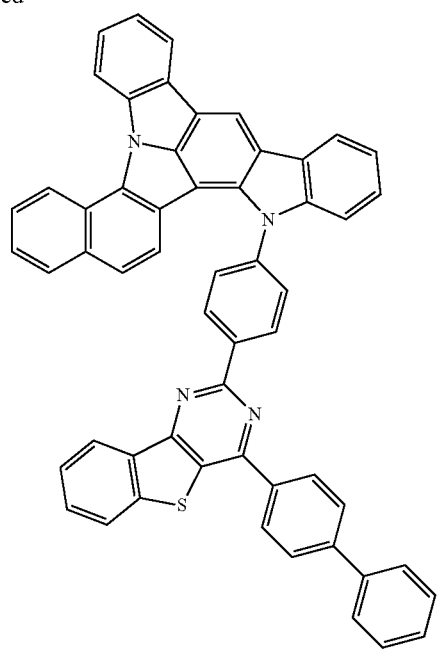
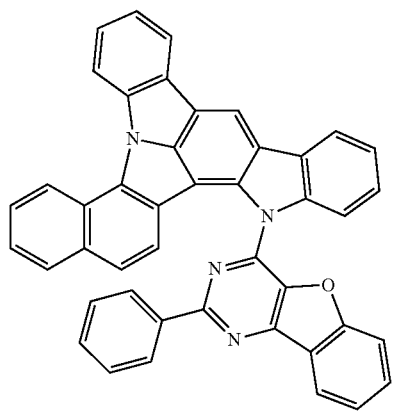
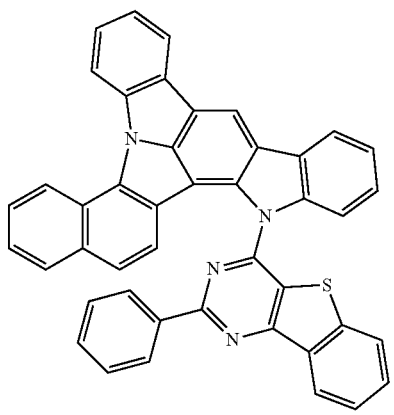
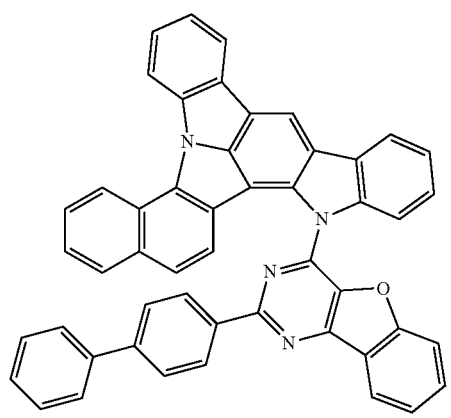
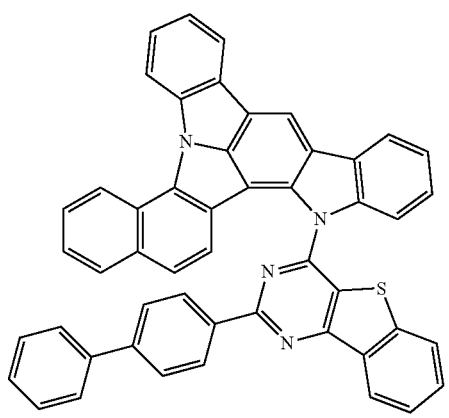

-continued
| 469 | 470 |
|---|---|
| 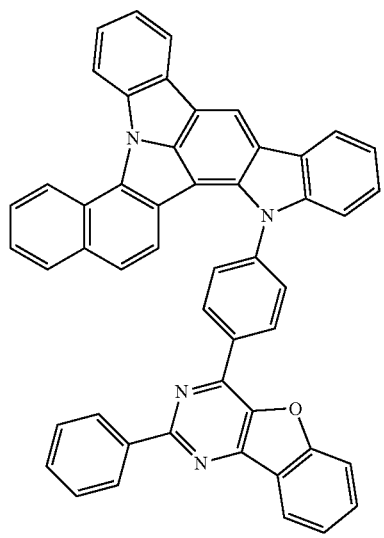 | 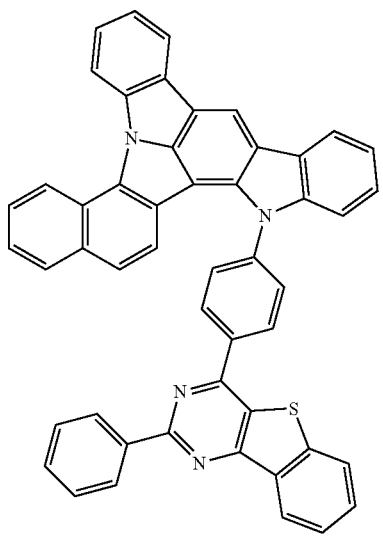 |
| 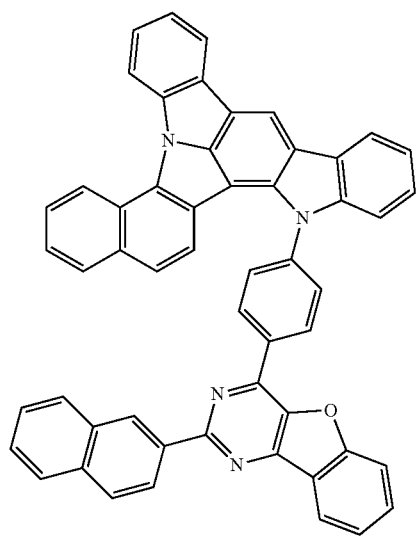 | 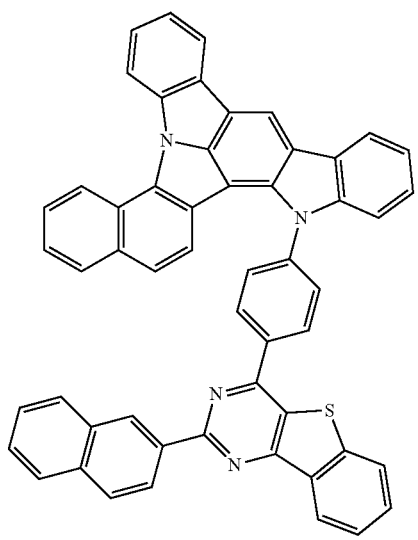 |
| 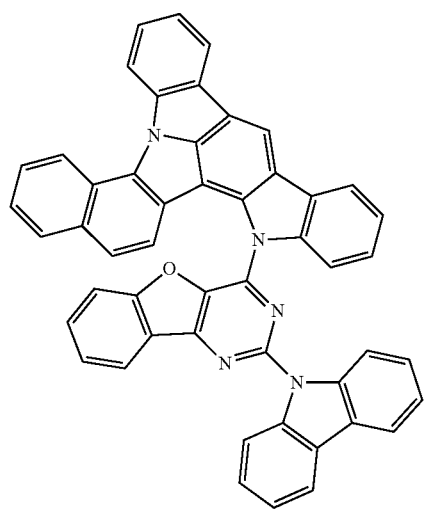 | 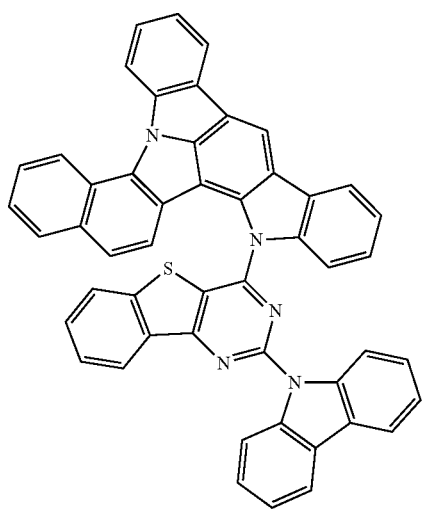 |

471
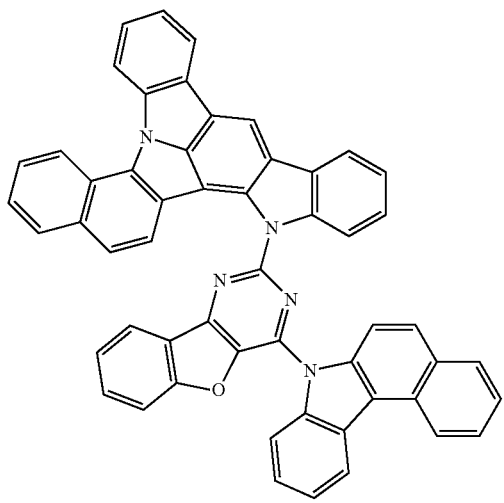
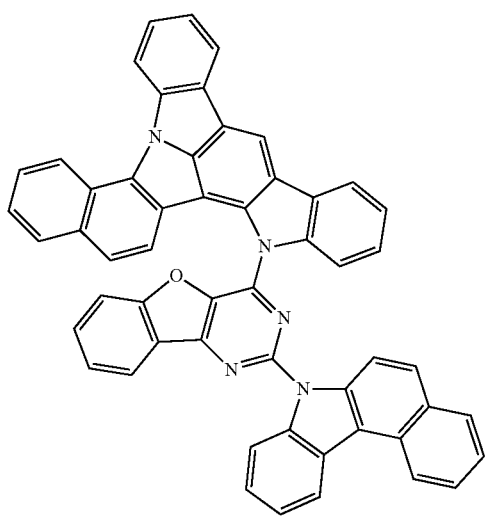
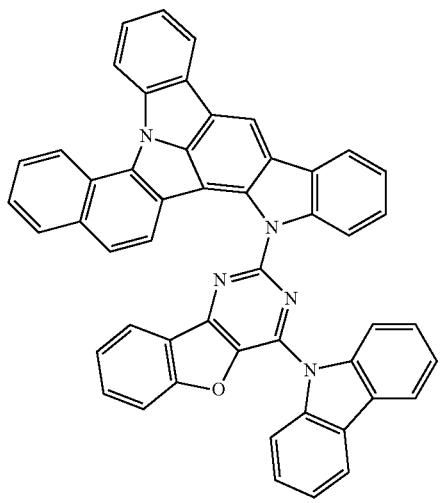
472
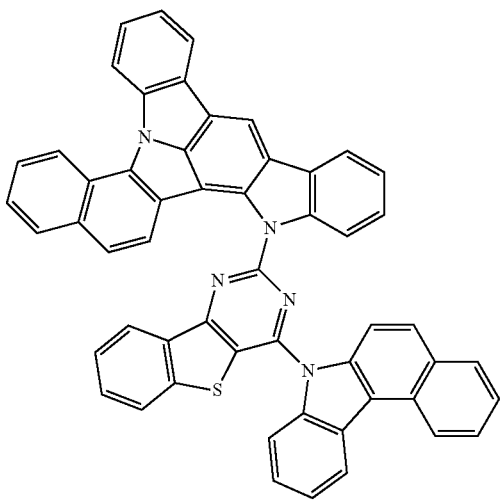
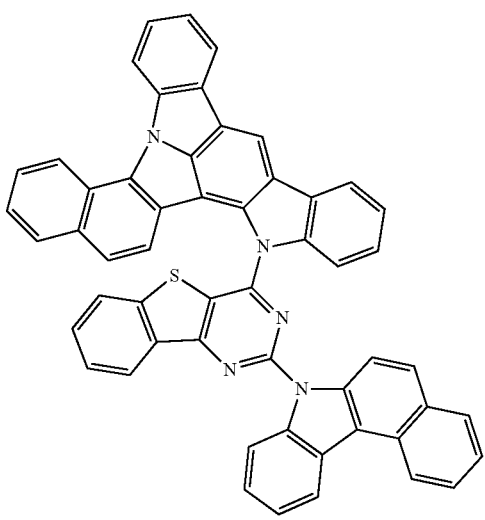
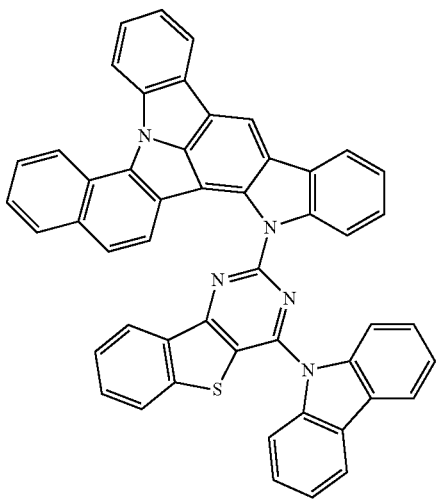

473
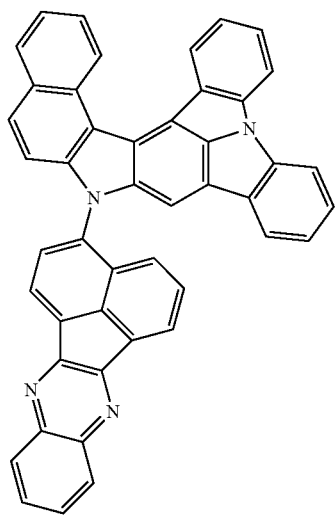
474
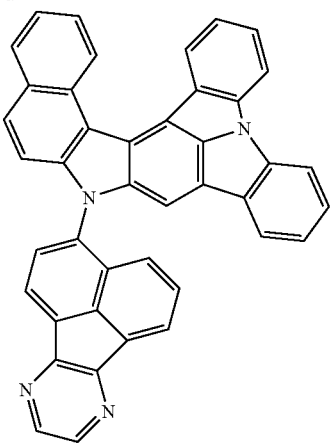
-continued
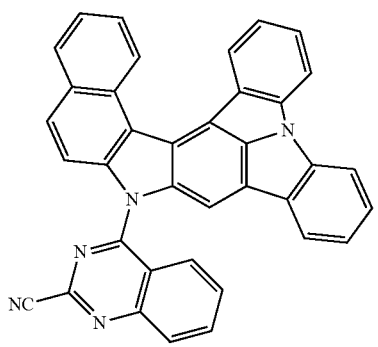
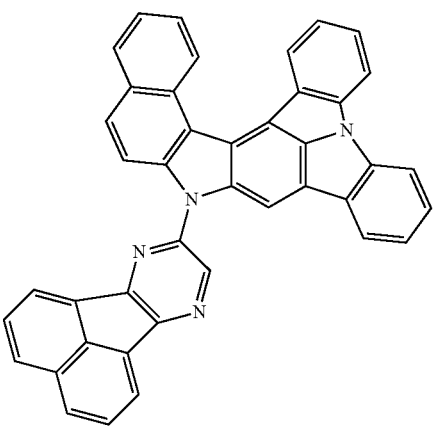
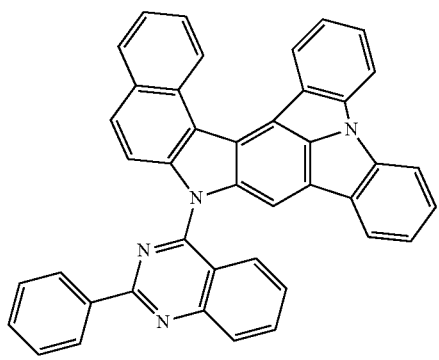
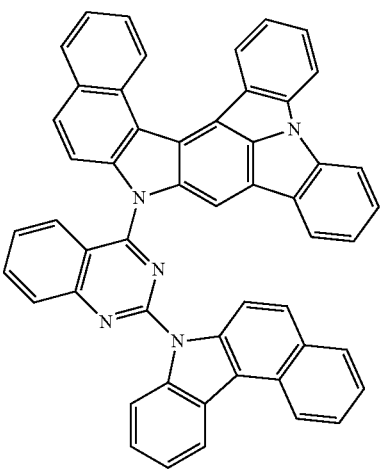

-continued
475
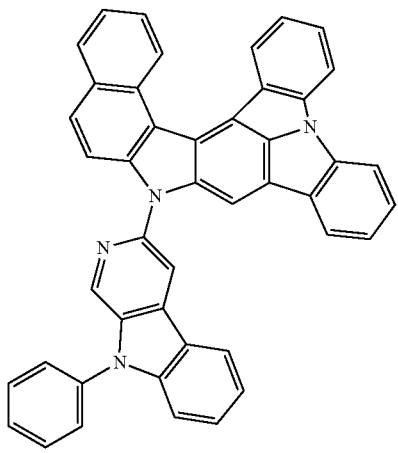
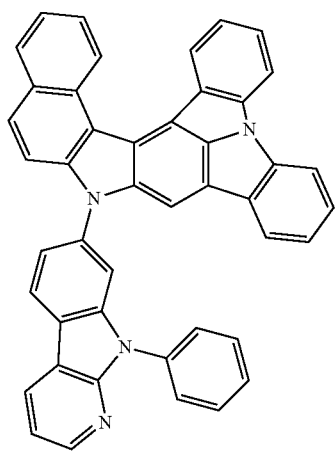
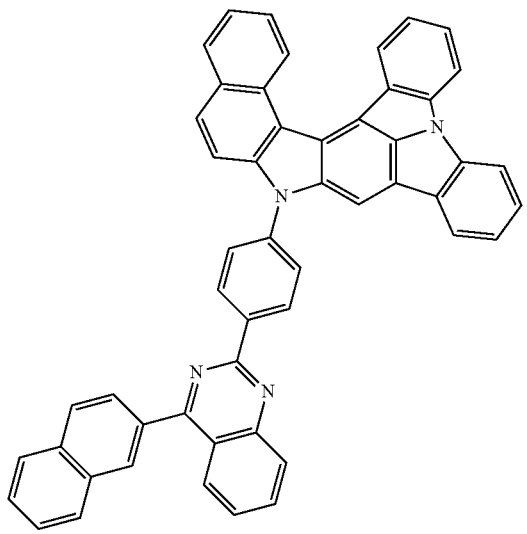
476
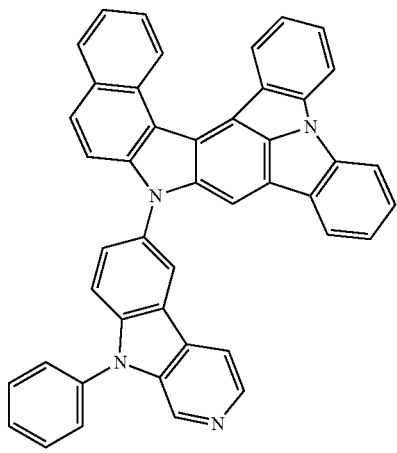
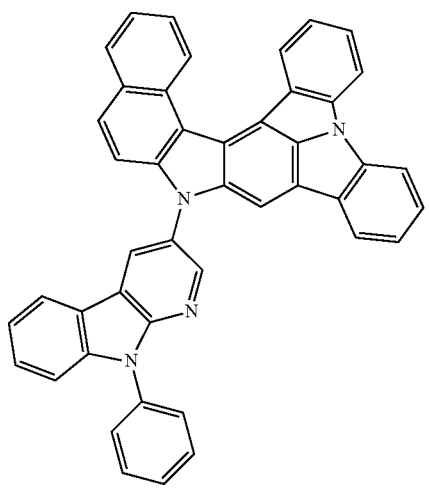
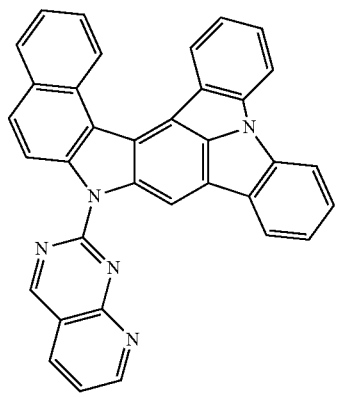

-continued
| 477 | 478 |
|---|---|
| 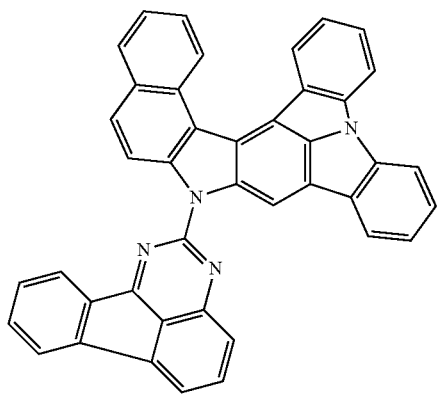 | 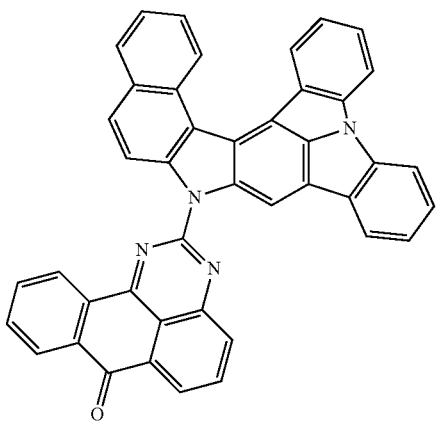 |
| 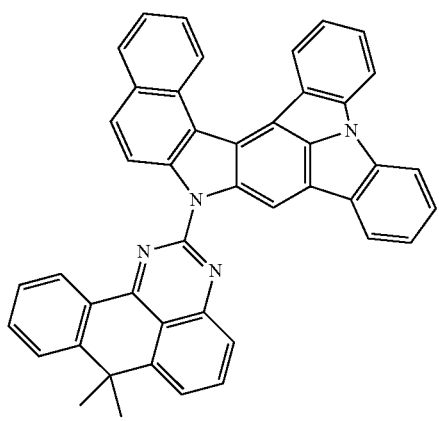 | 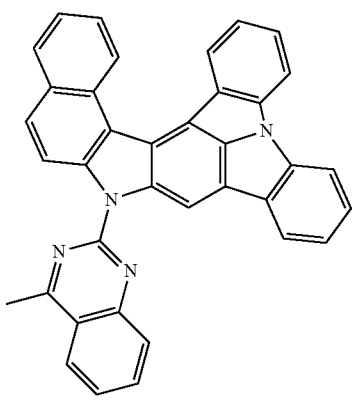 |
| 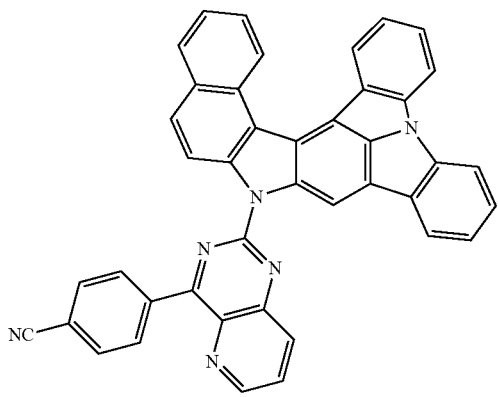 | 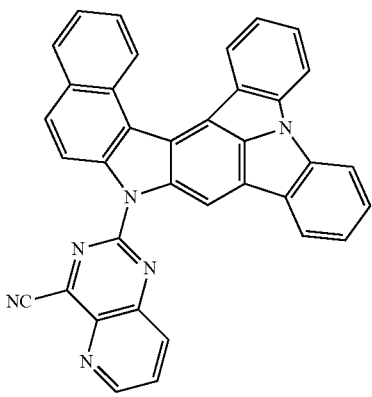 |
| 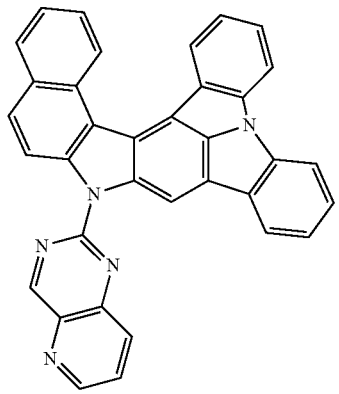 | 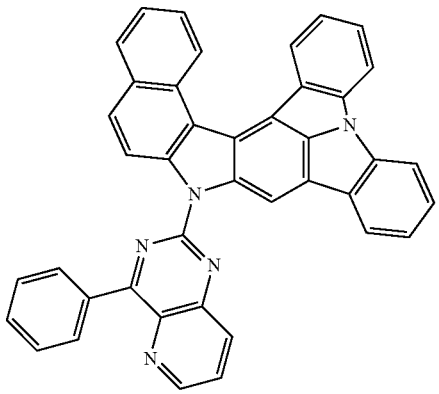 |

-continued
479
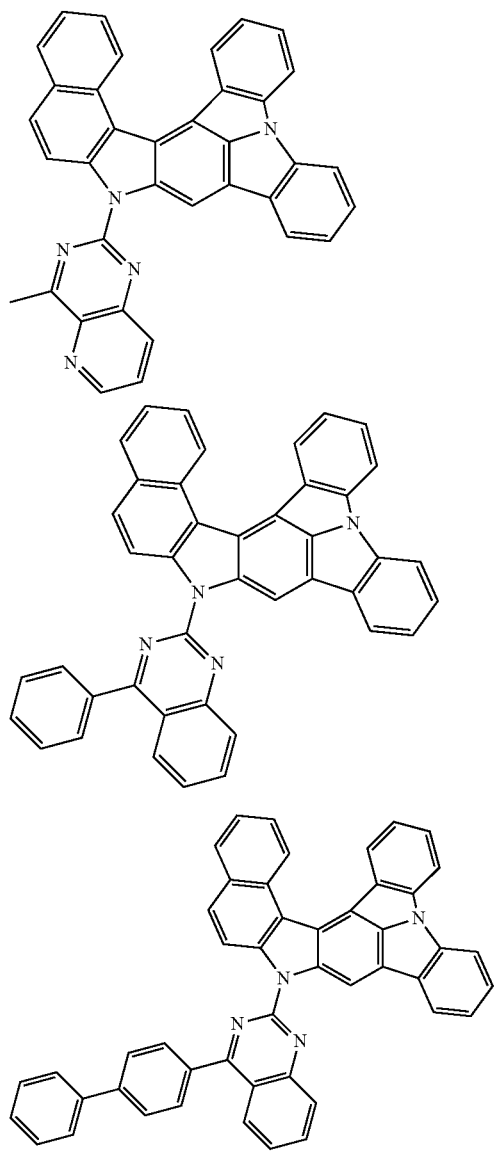
480
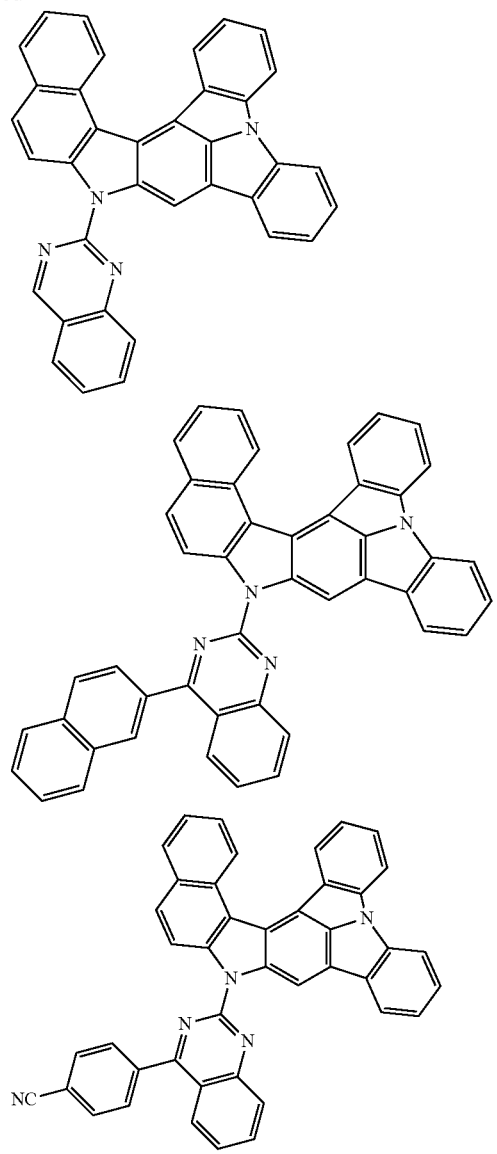
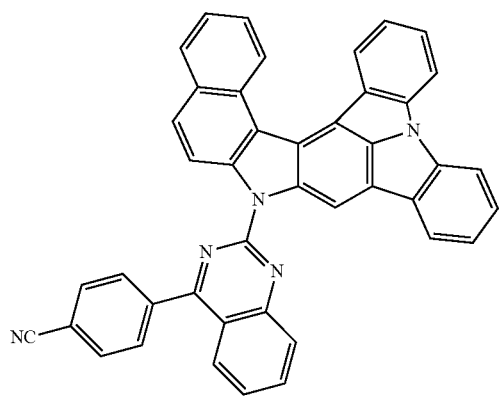
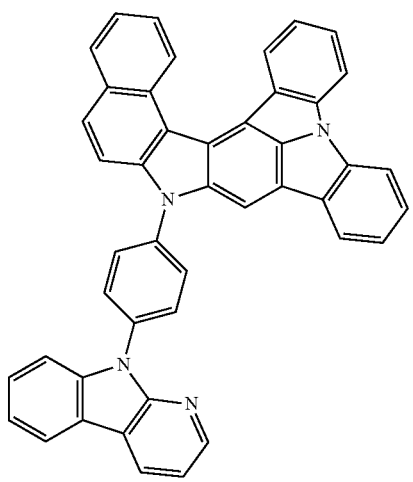

-continued
481
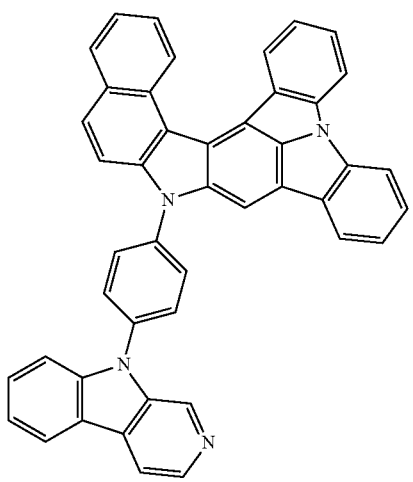
482
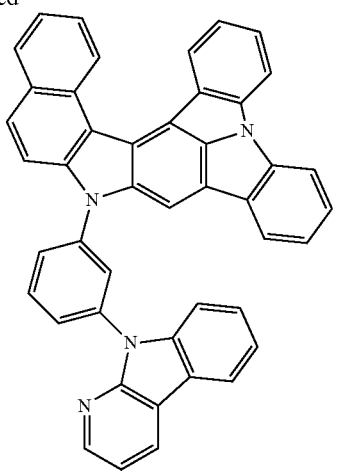
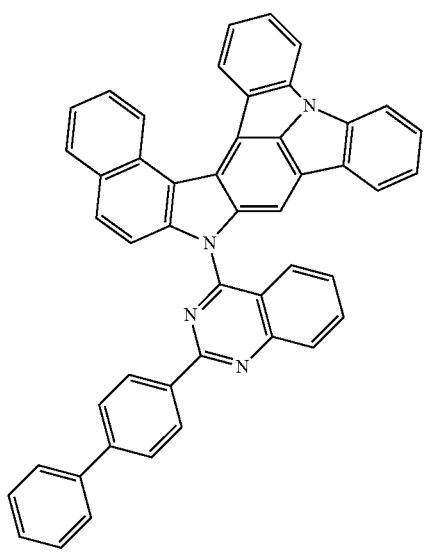
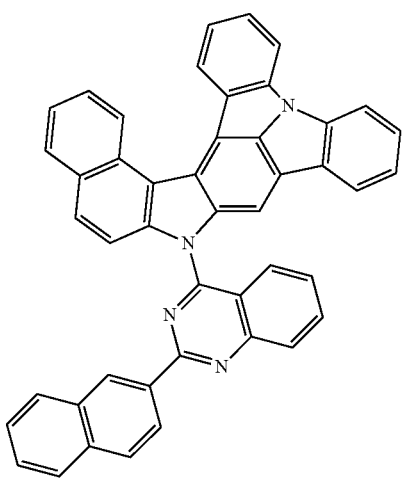
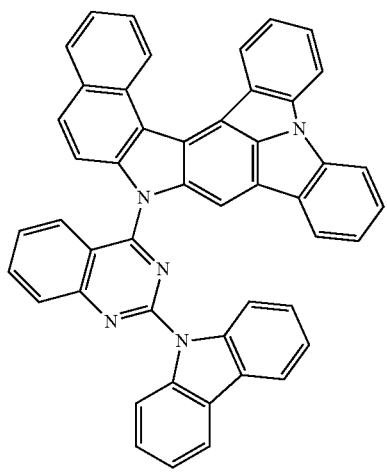
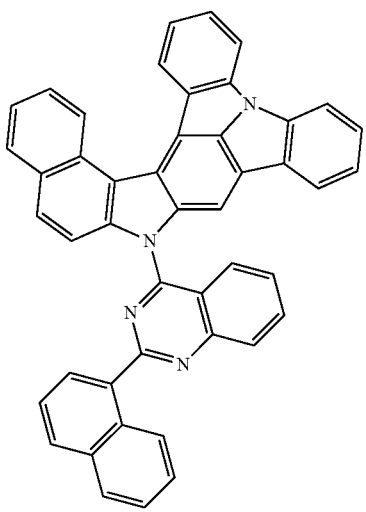

483 484
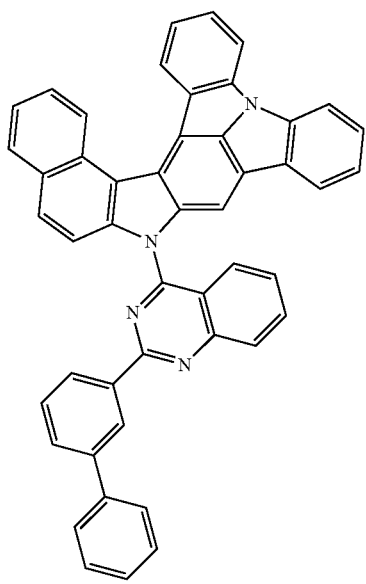 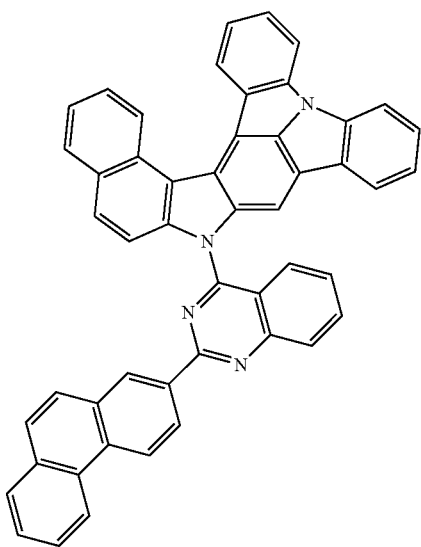
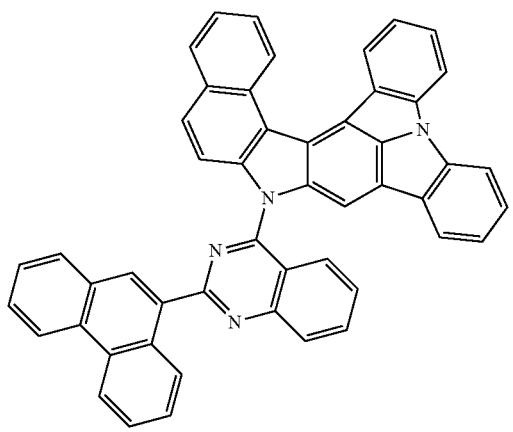
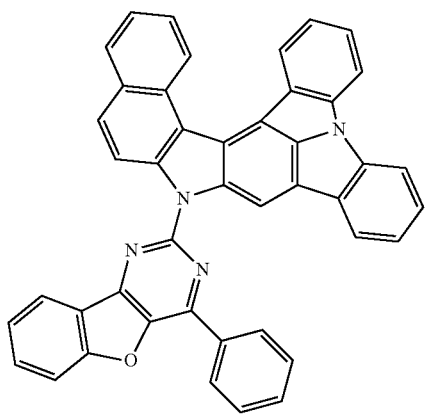 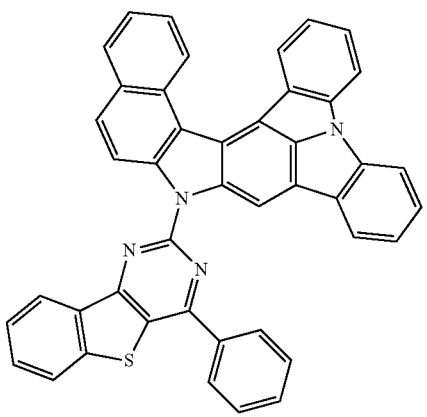

-continued
485
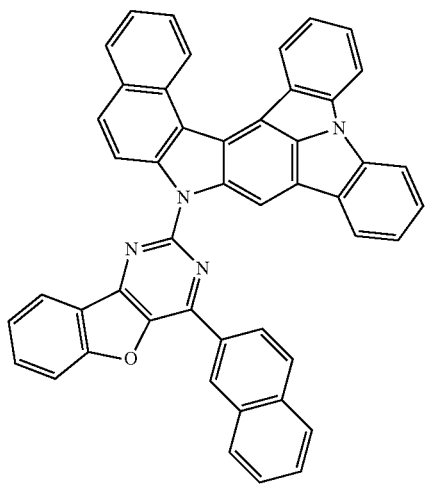
486
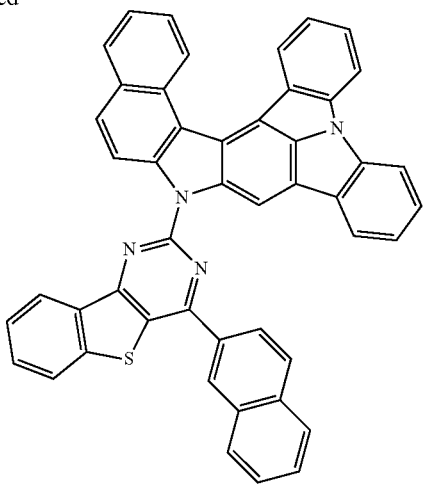
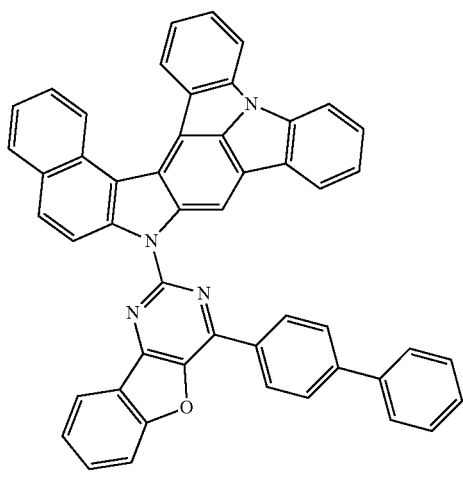
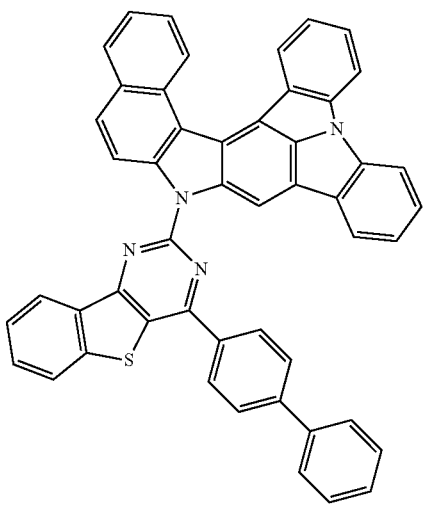
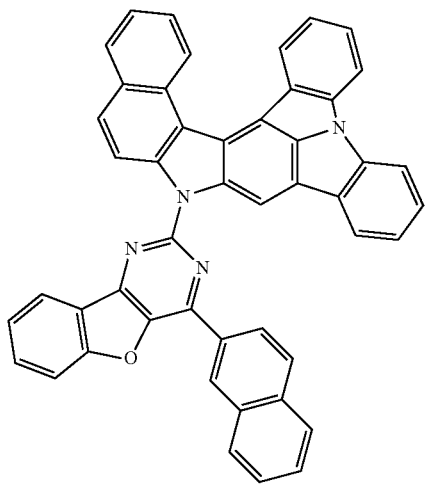
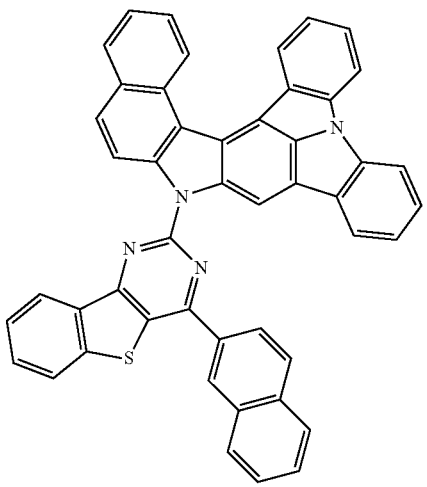

-continued
| 487 | 488 |
|---|---|
| 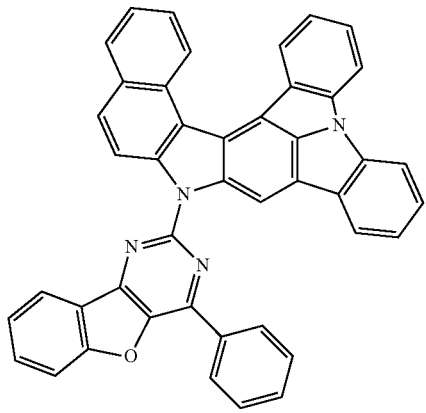 | 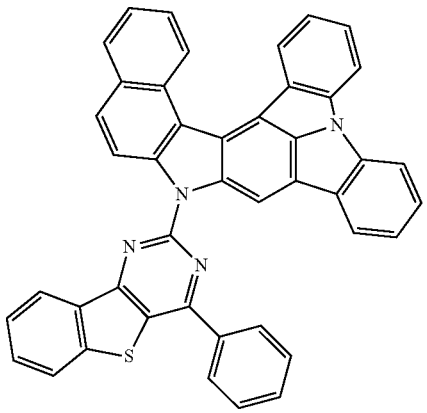 |
| 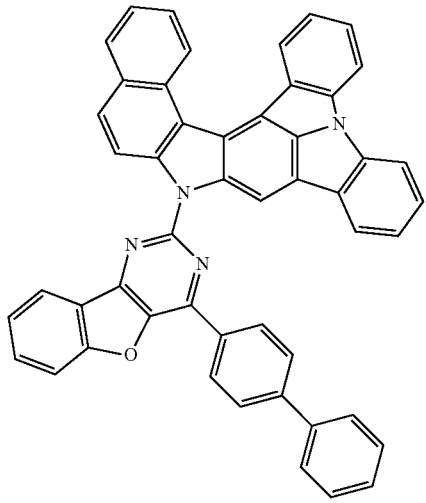 | 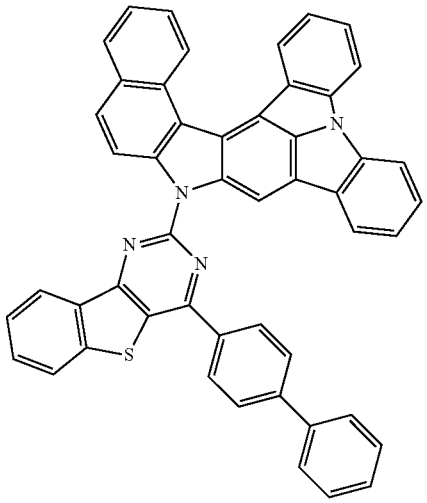 |
| 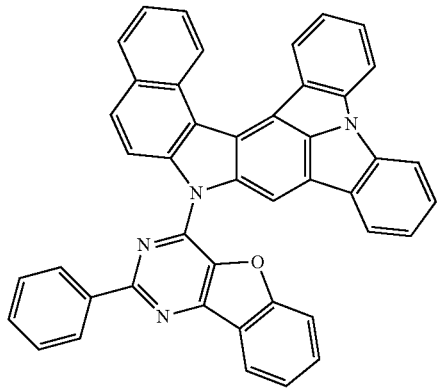 | 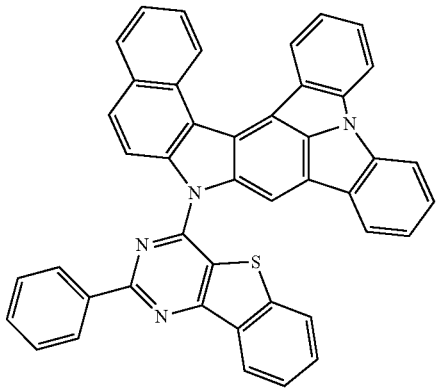 |
| 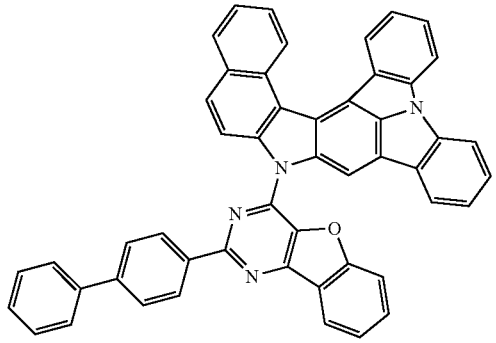 | 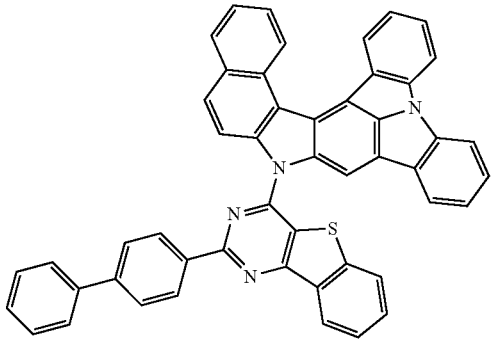 |

-continued
| 489 | 490 |
|---|---|
| 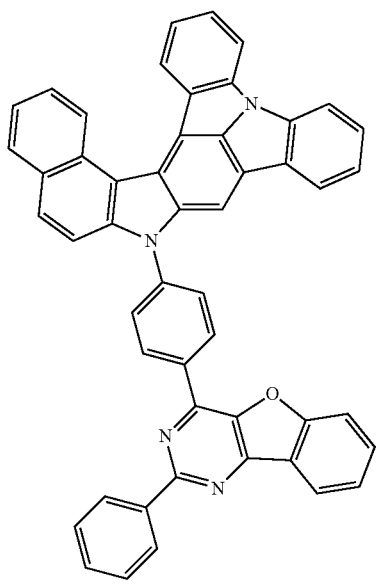 | 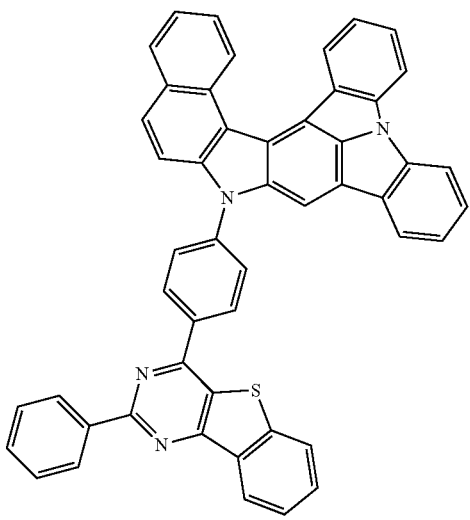 |
| 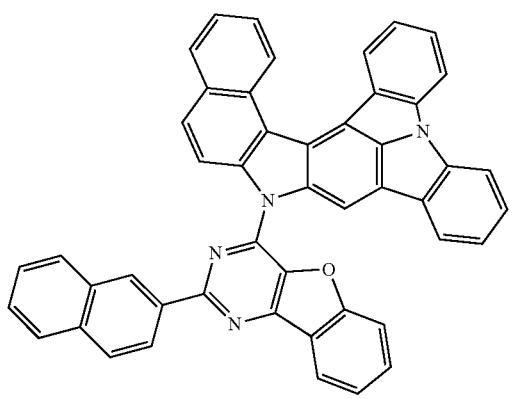 | 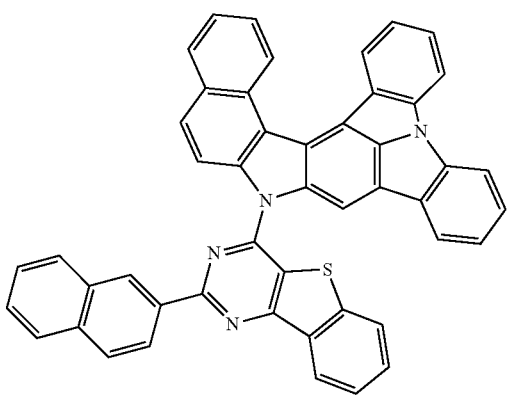 |
| 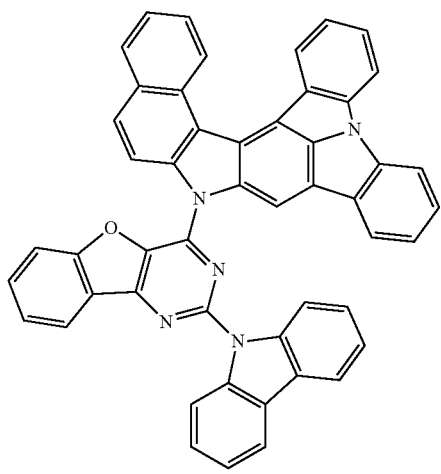 | 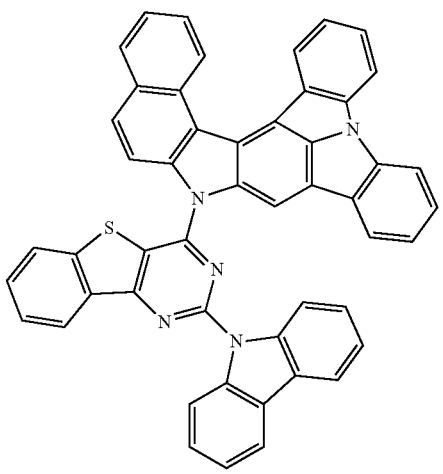 |

-continued
491
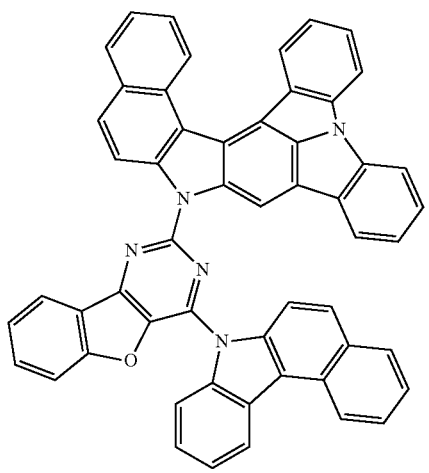
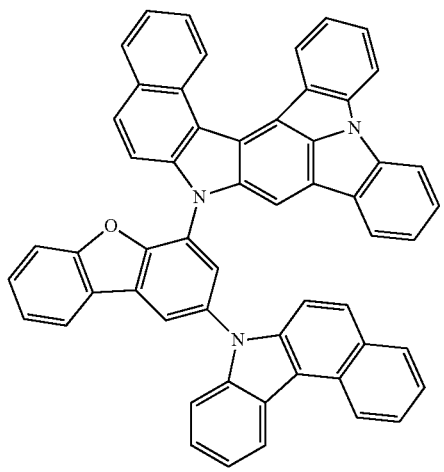
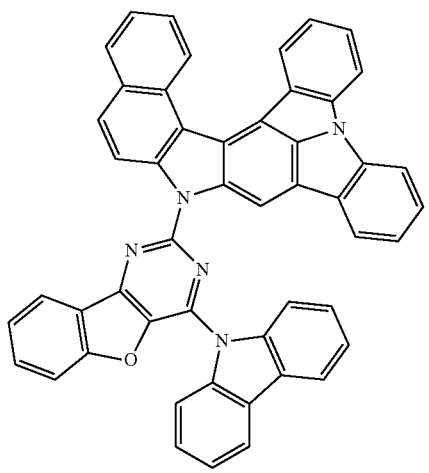
492
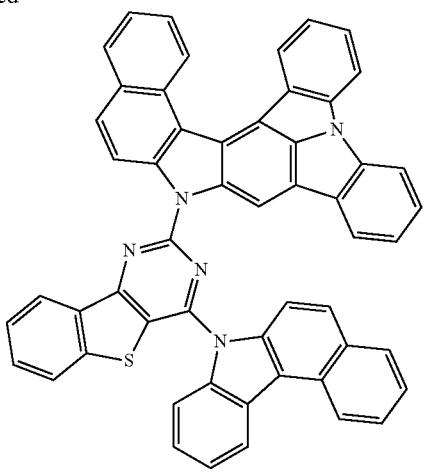
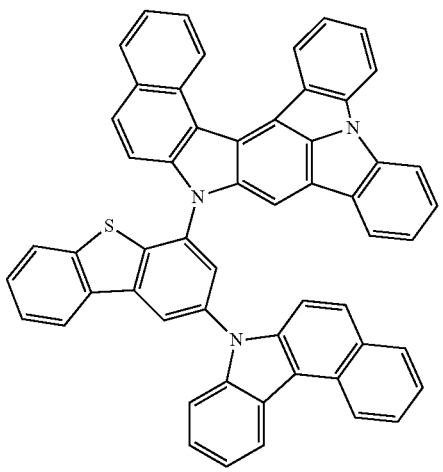
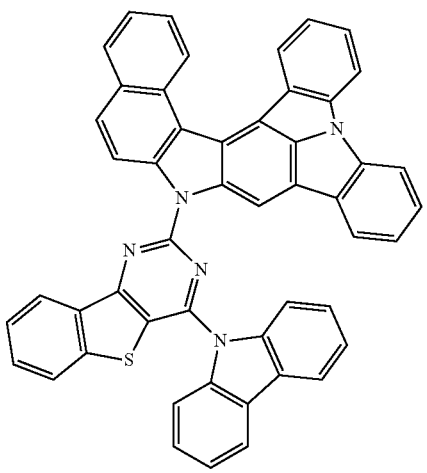

493
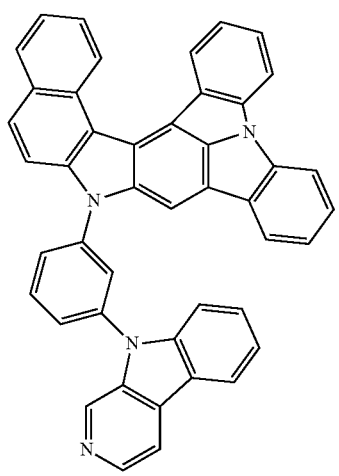
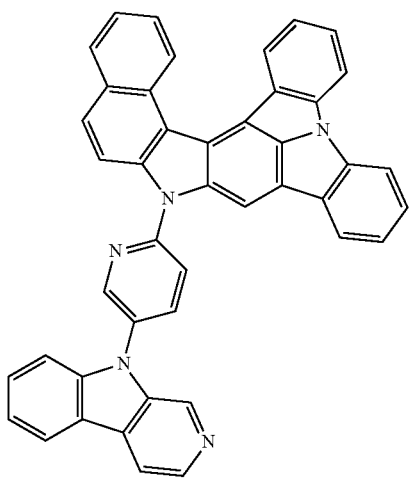
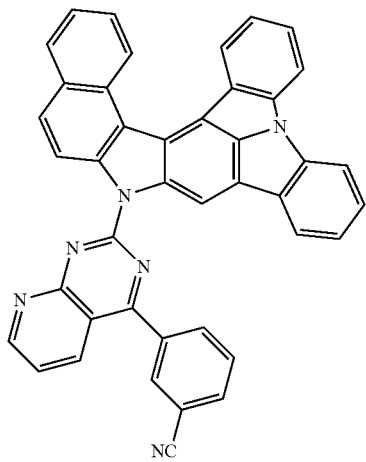
-continued
494
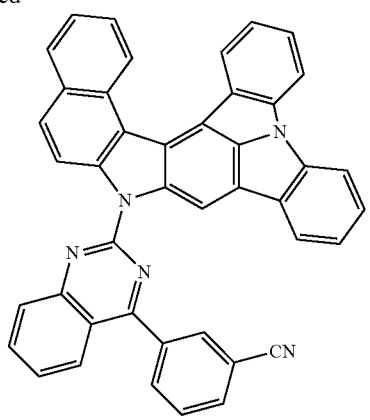
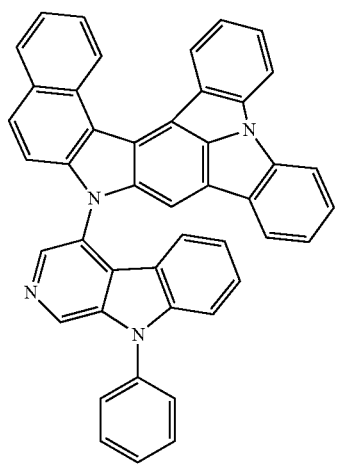
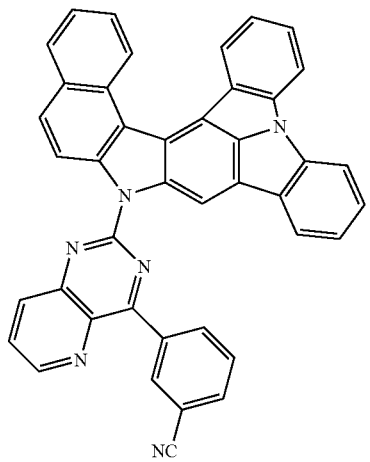

495 496
-continued
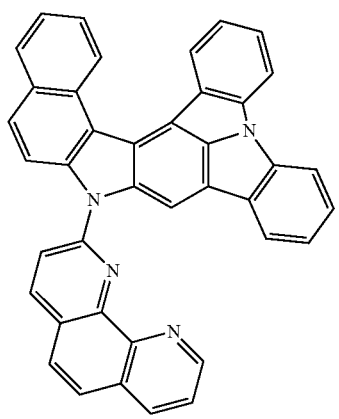
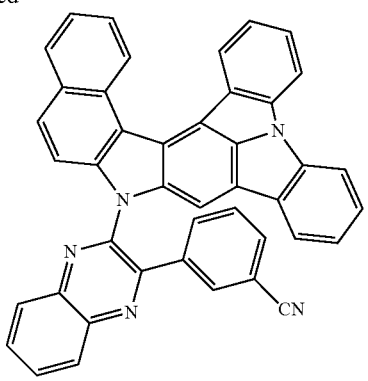
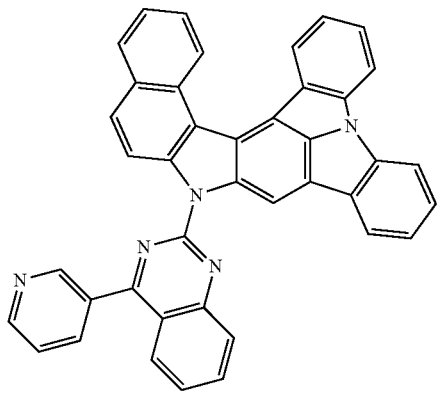
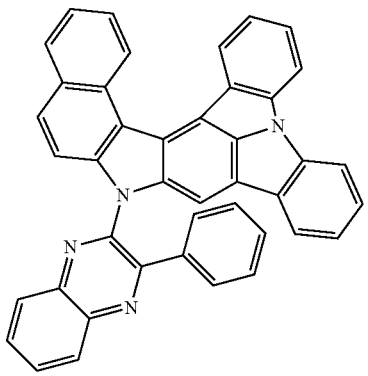
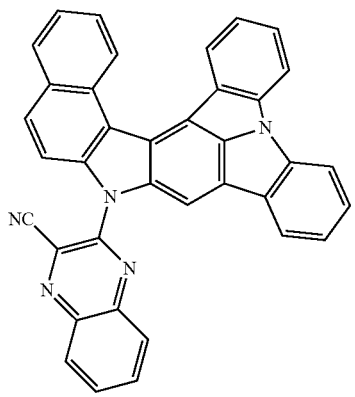
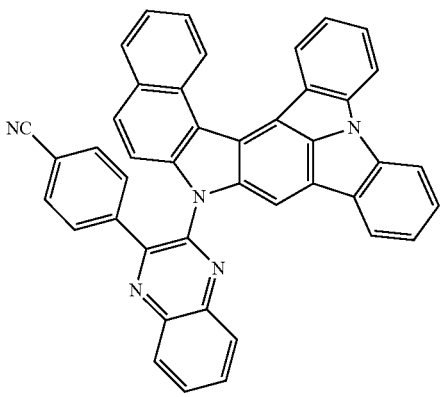
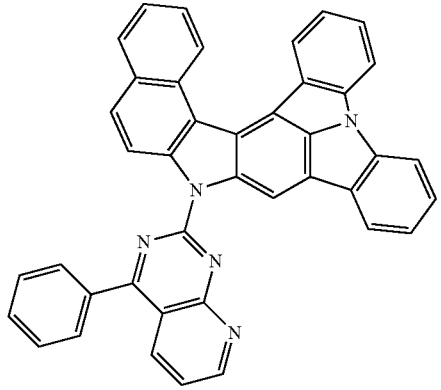
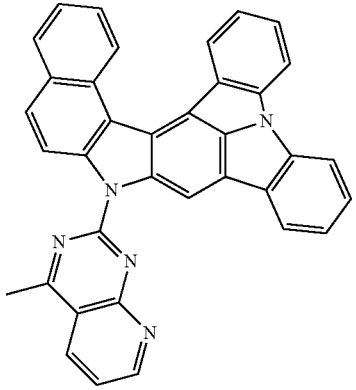

-continued
497
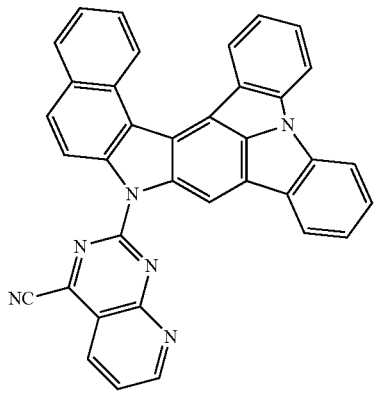
498
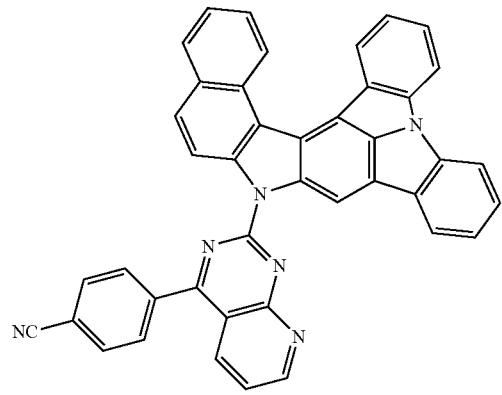
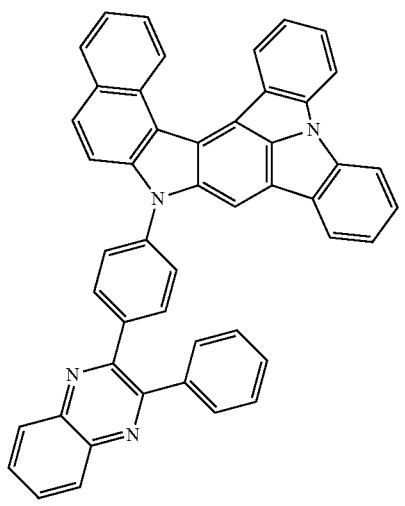
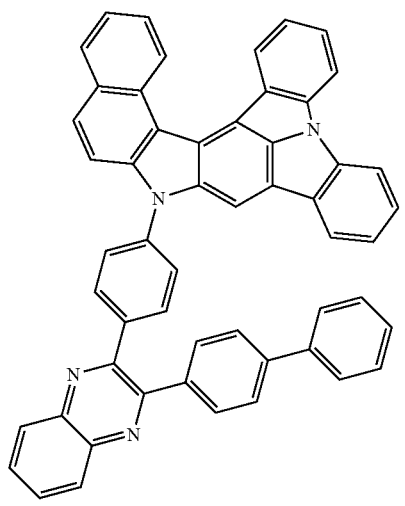
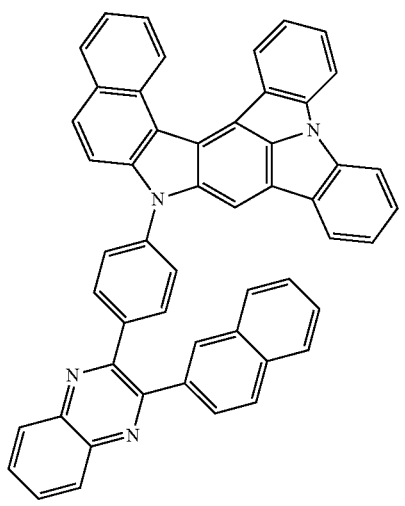
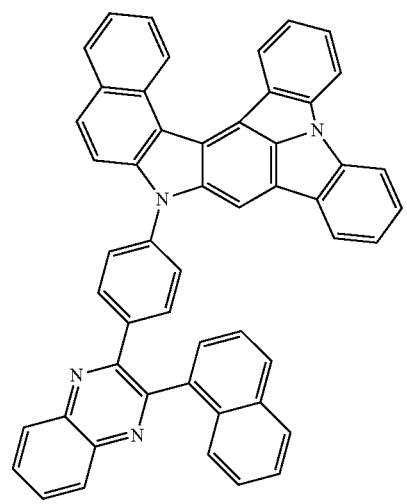

-continued
499
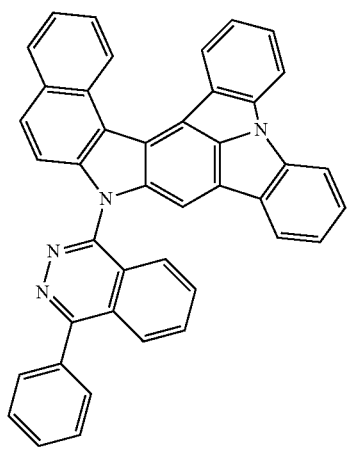
500
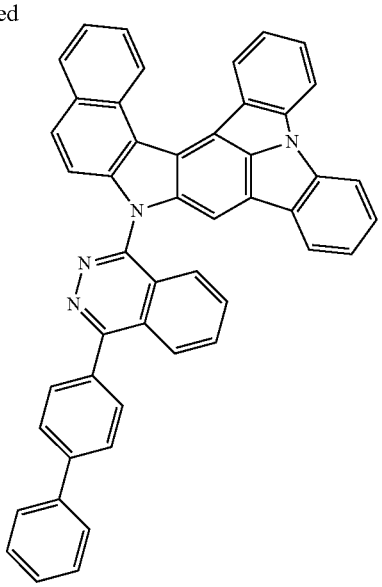
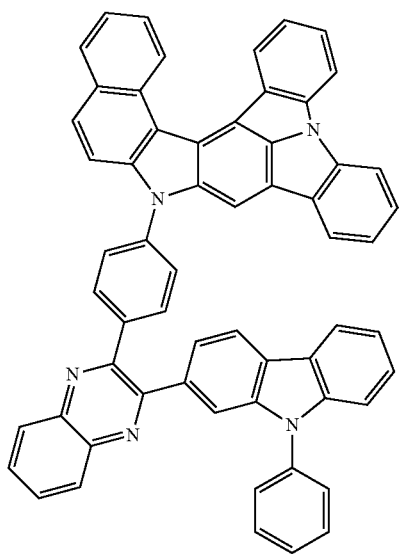
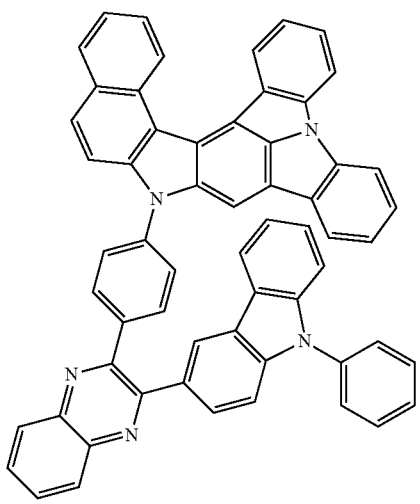
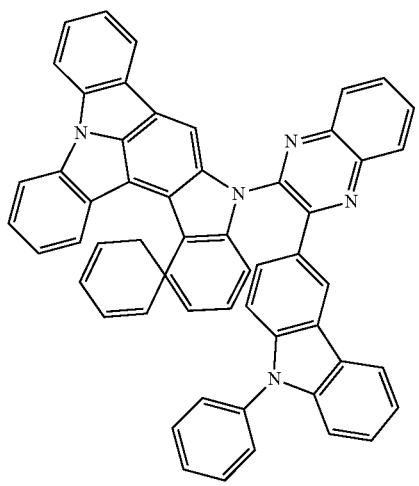
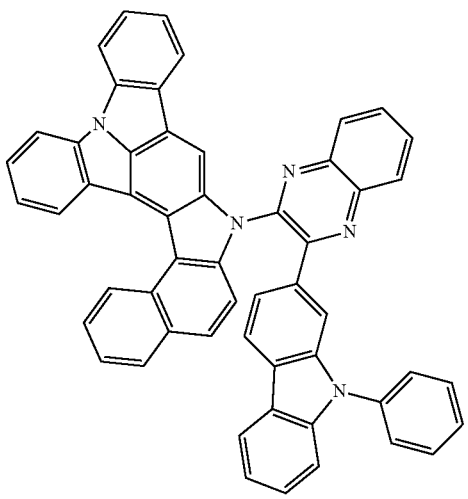

-continued
501
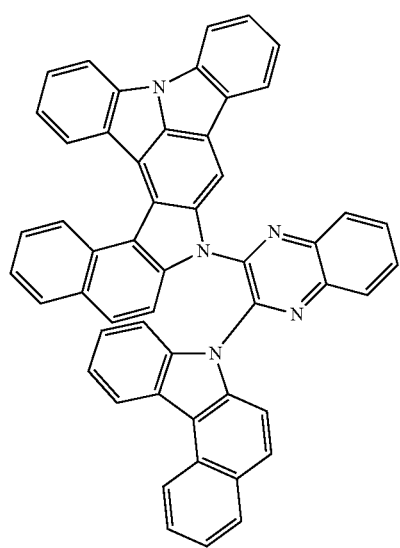
502
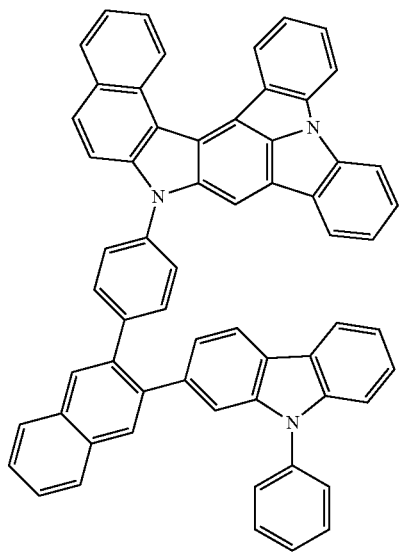
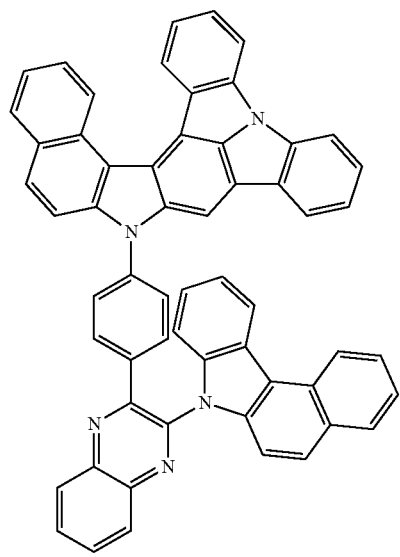
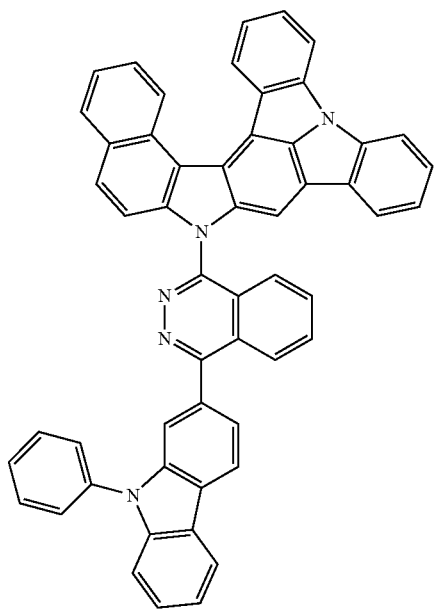

-continued
| 503 | 504 |
|---|---|
| 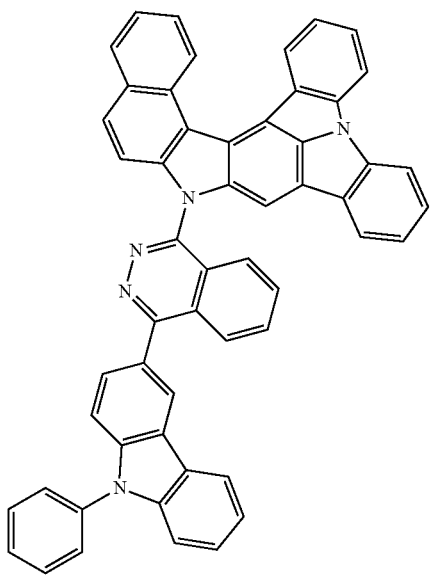 | 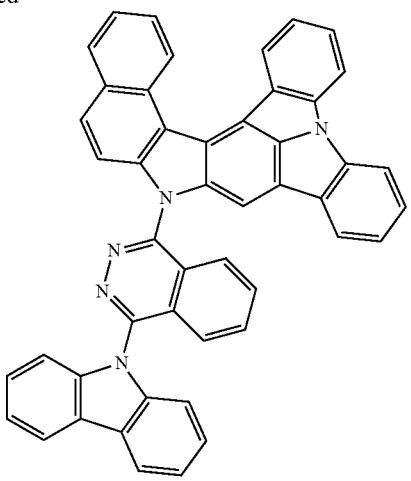 |
| 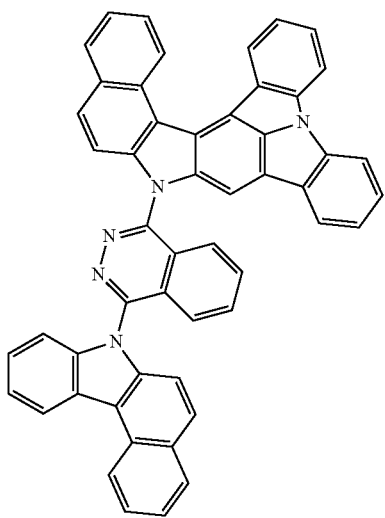 | 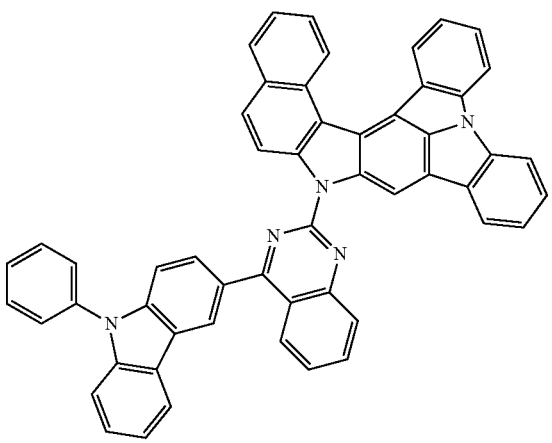 |
| 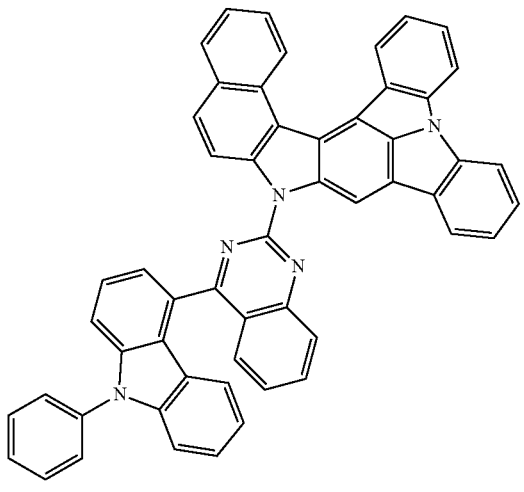 | 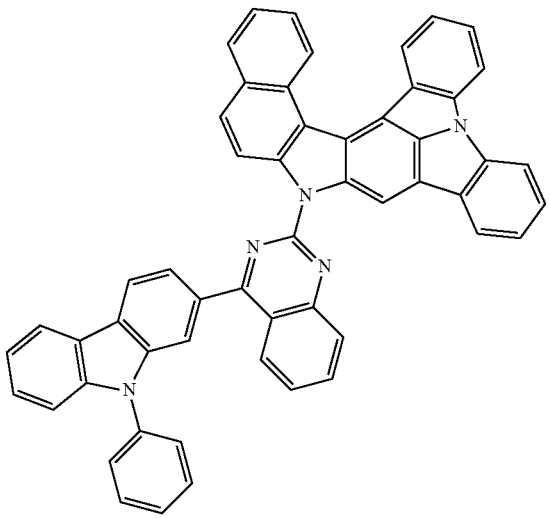 |

-continued
| 505 | 506 |
|---|---|
| 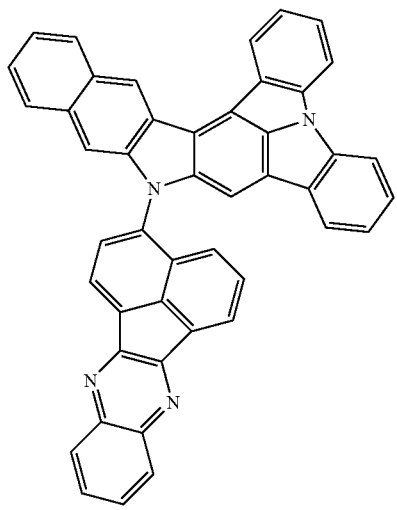 | 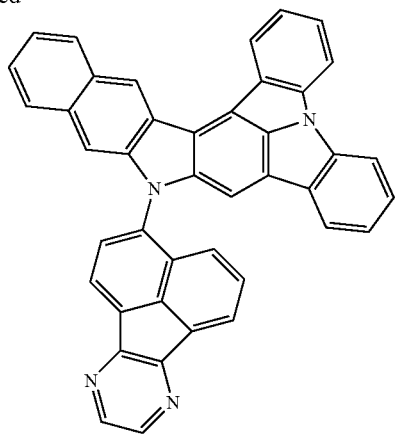 |
| 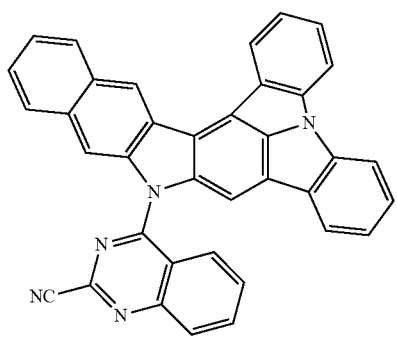 | 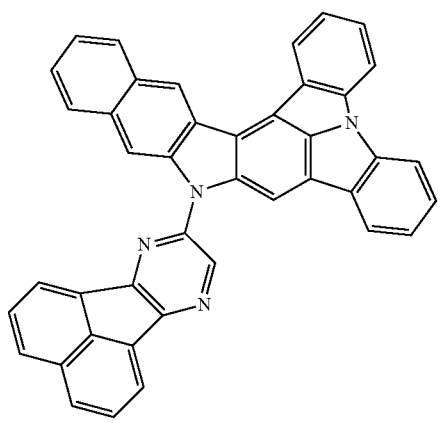 |
| 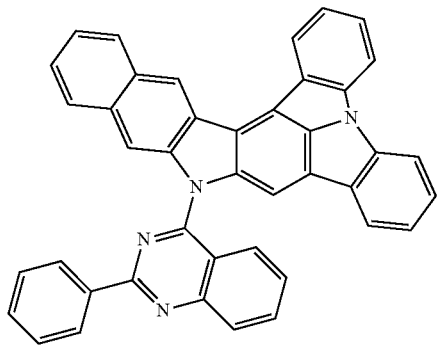 | 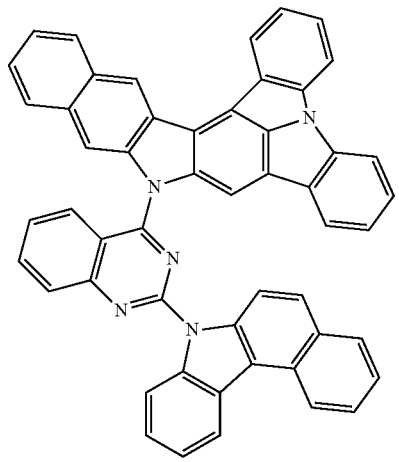 |

-continued
| 507 | 508 |
|---|---|
| 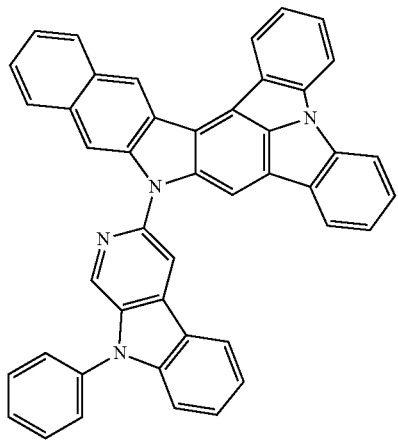 | 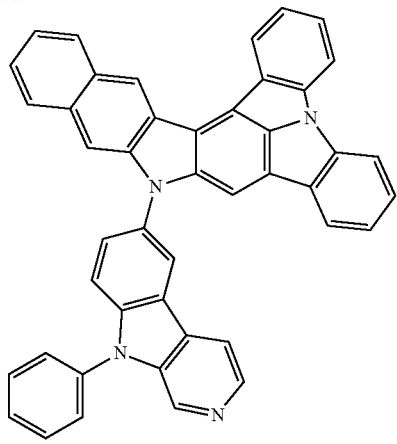 |
| 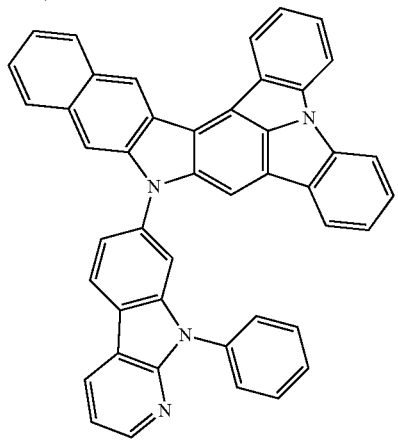 | 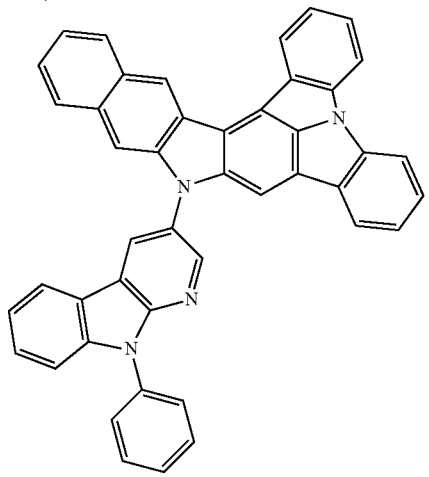 |
| 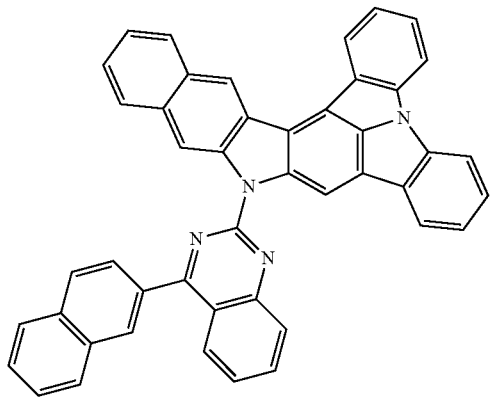 | 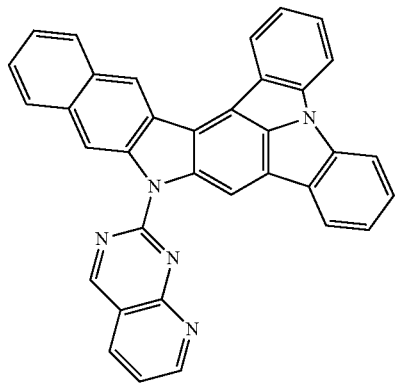 |
| 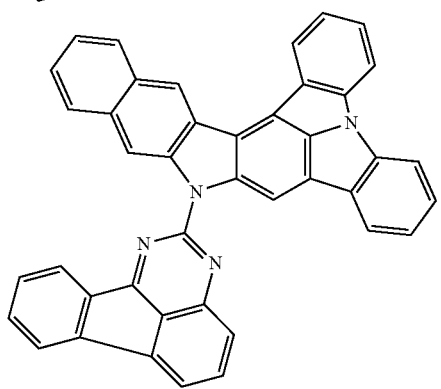 | 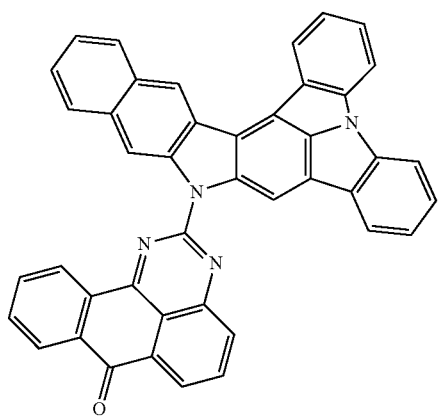 |

509 510
-continued
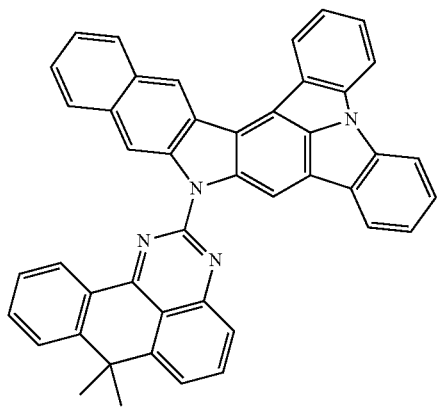 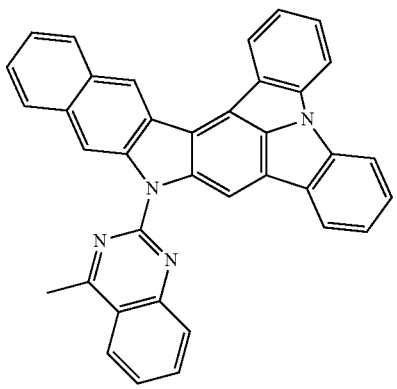
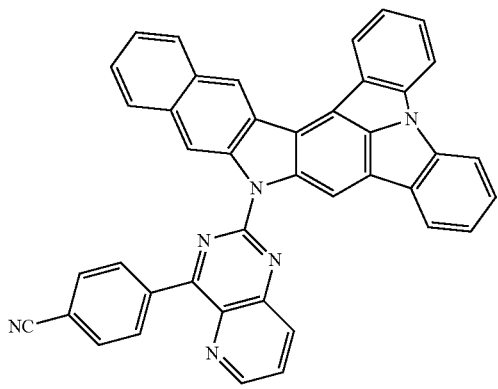 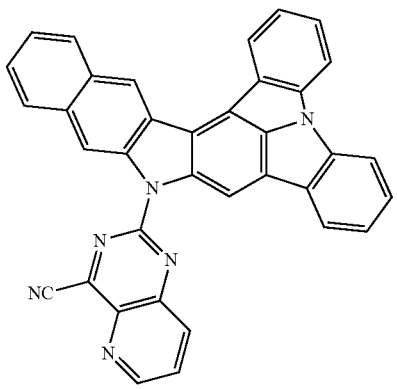
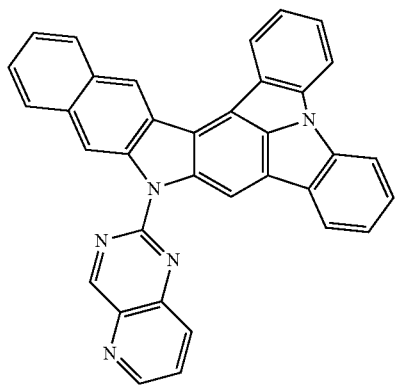 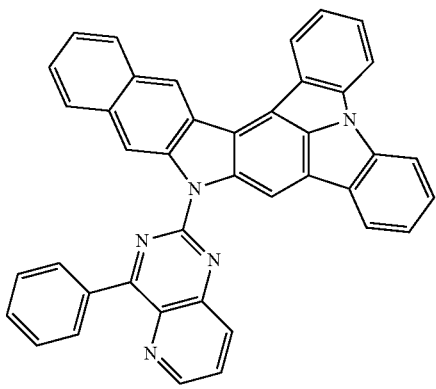
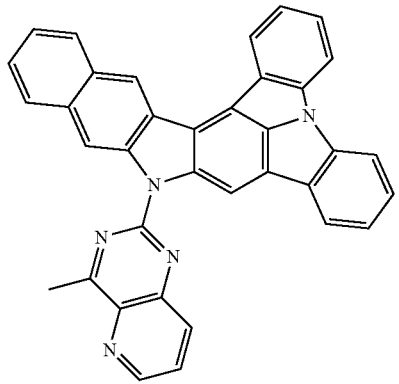 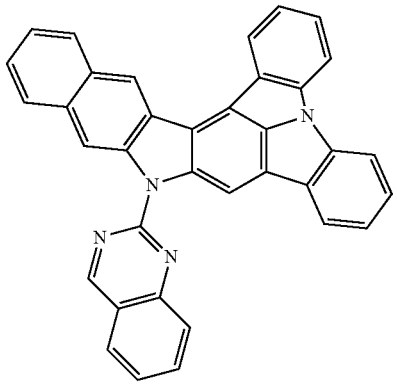

-continued
| 511 | 512 |
|---|---|
| 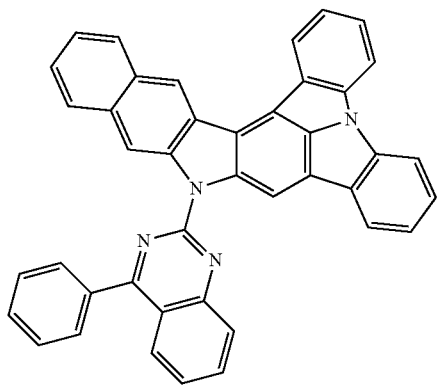 | 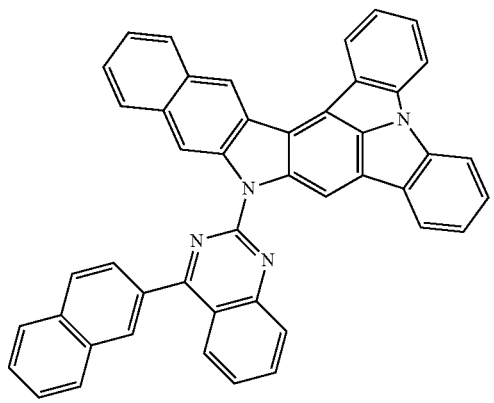 |
| 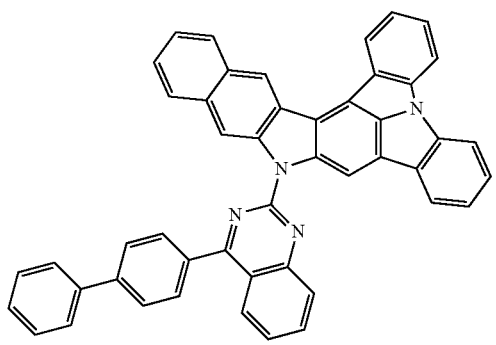 | 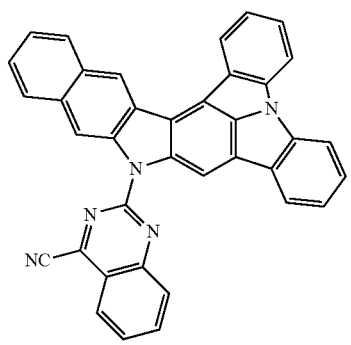 |
| 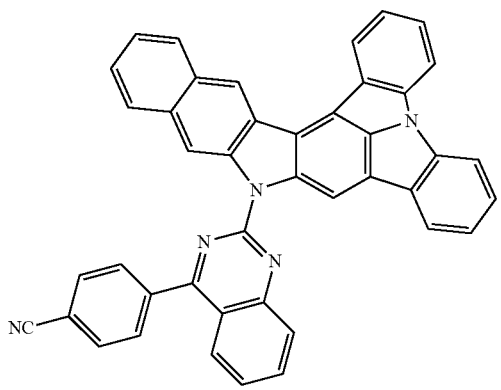 | 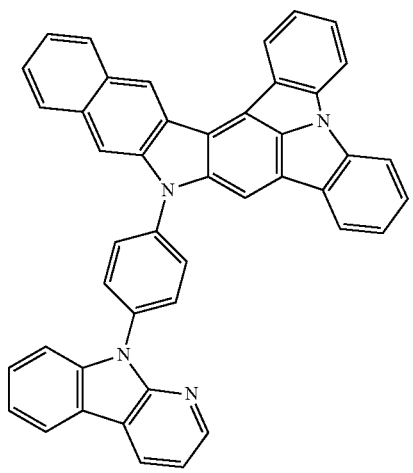 |
| 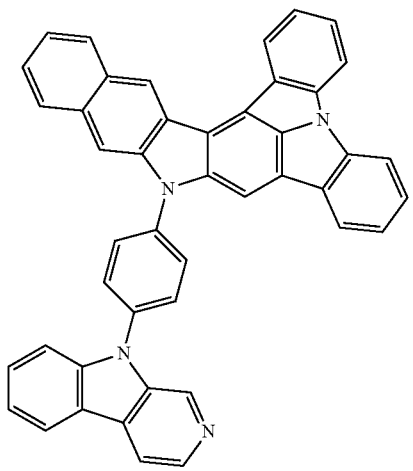 | 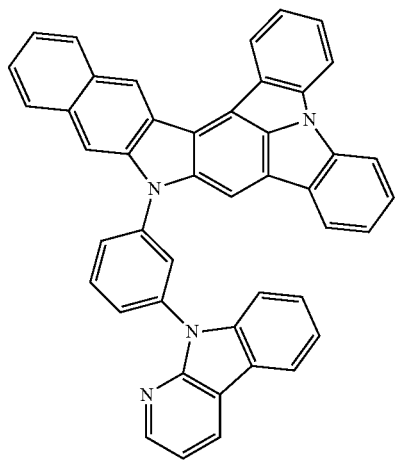 |

513
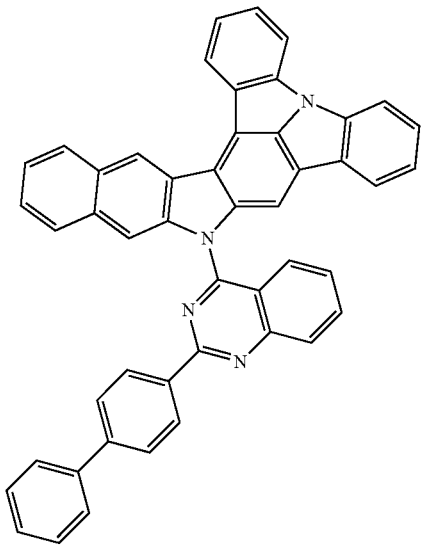
514
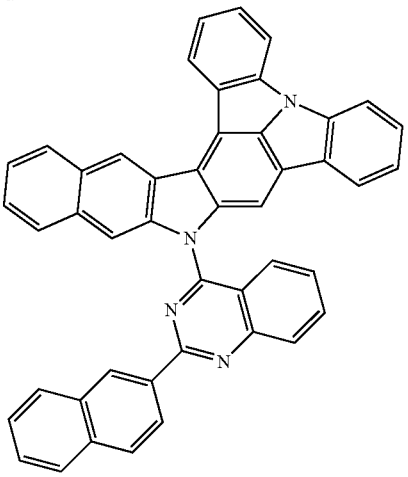
-continued
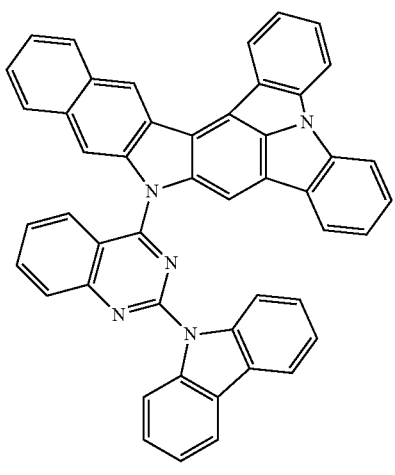
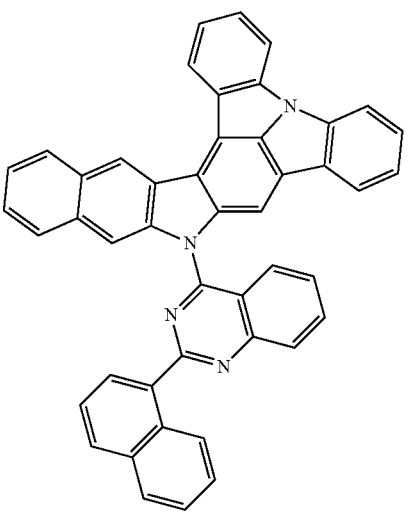
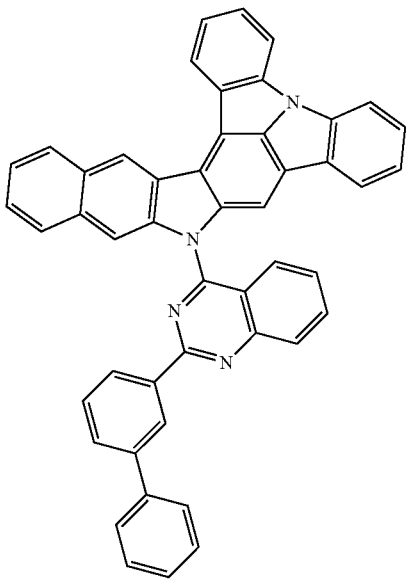
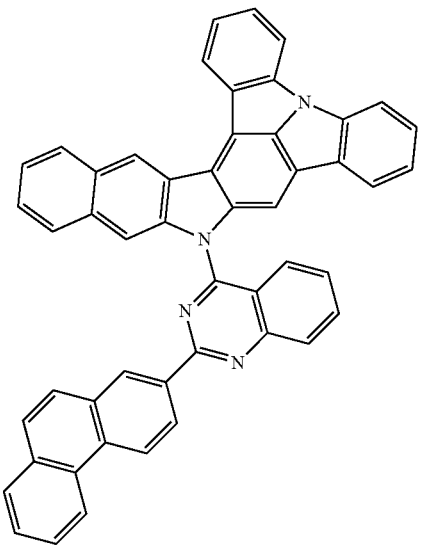

515
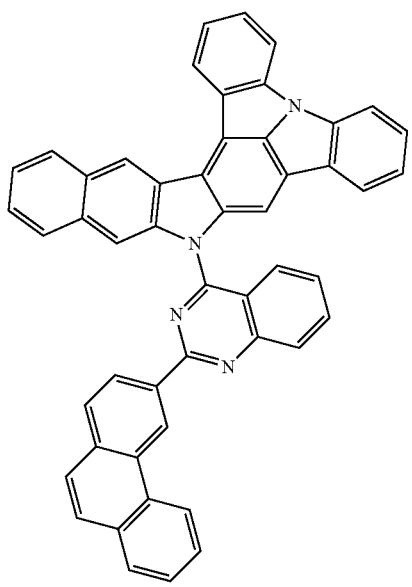
516
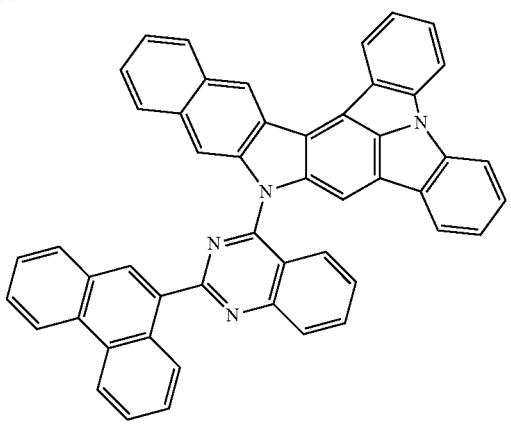
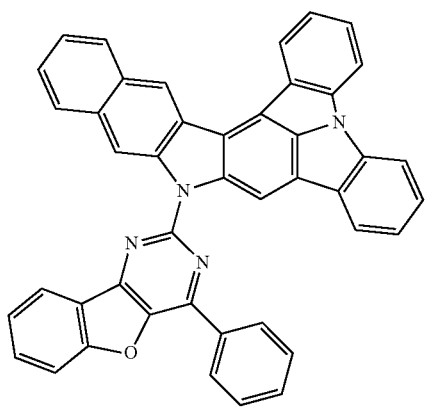
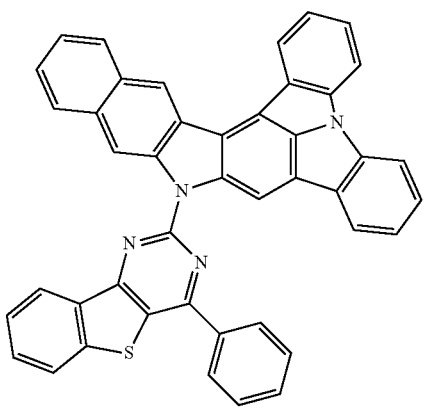
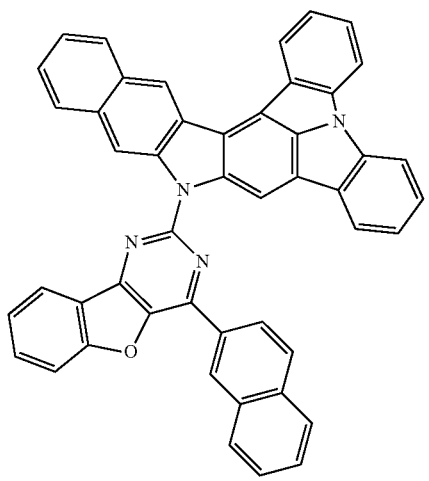
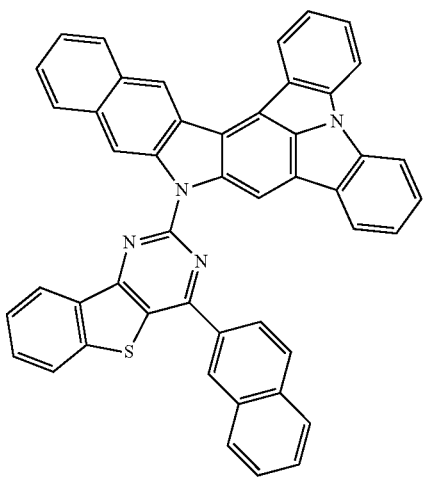

-continued
517
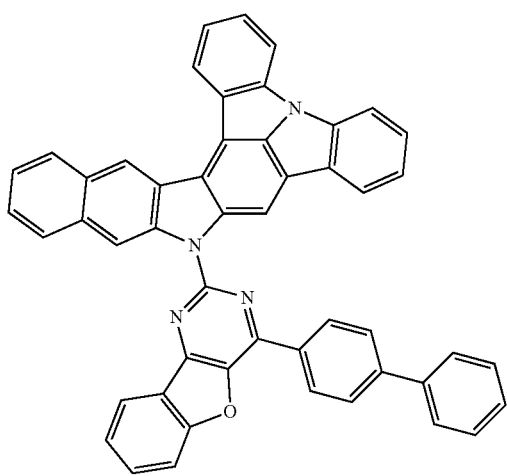
518
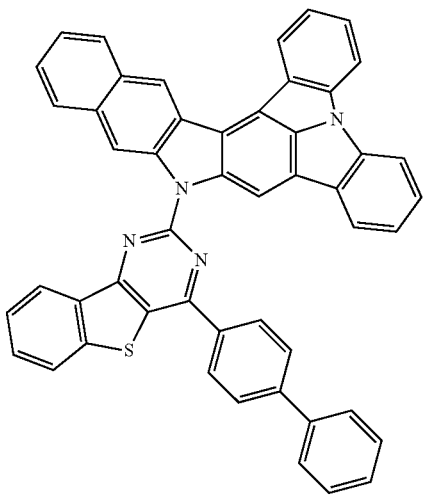
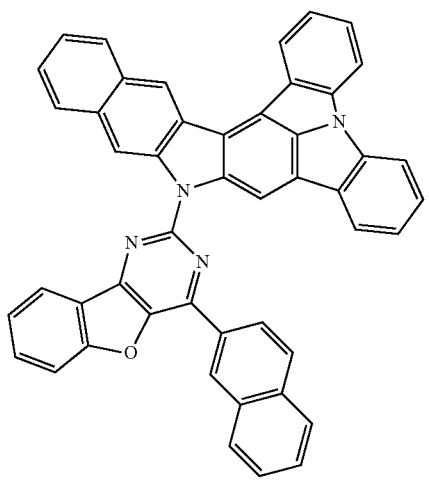
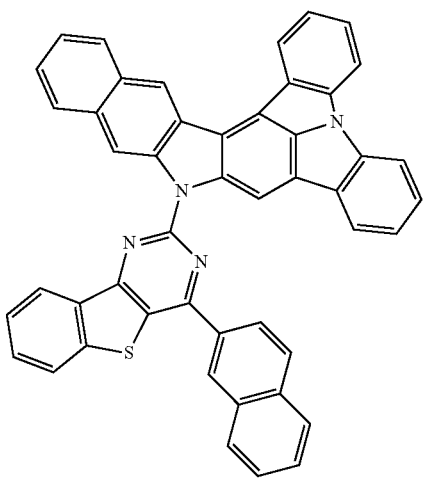
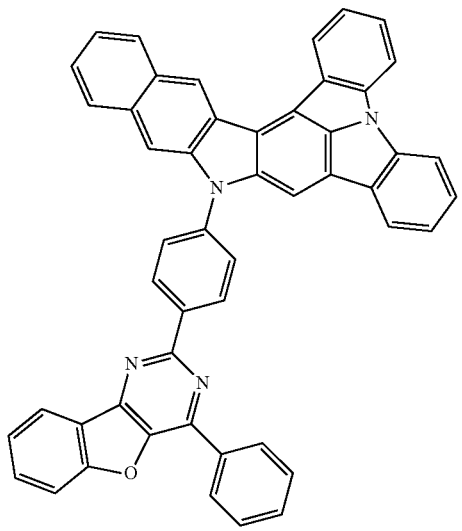
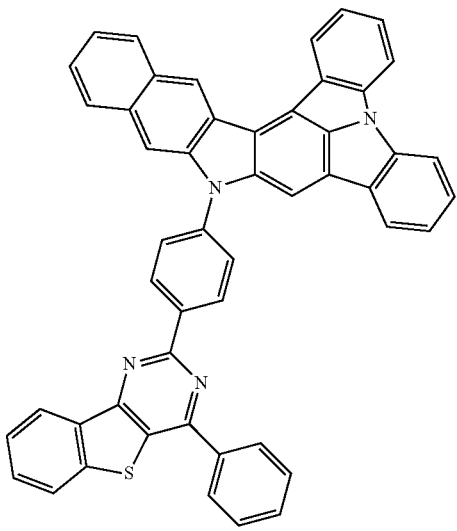

-continued
519
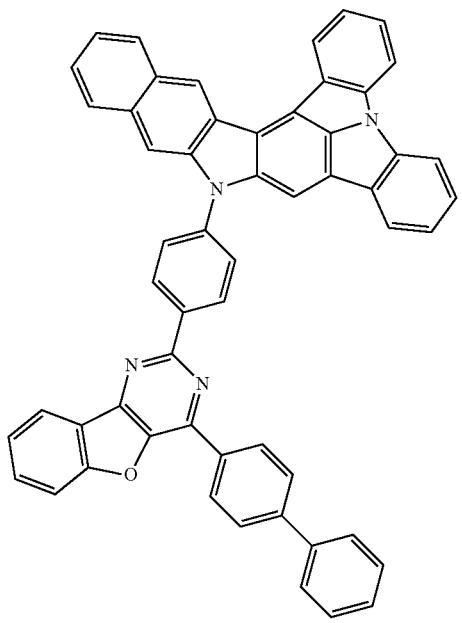
520
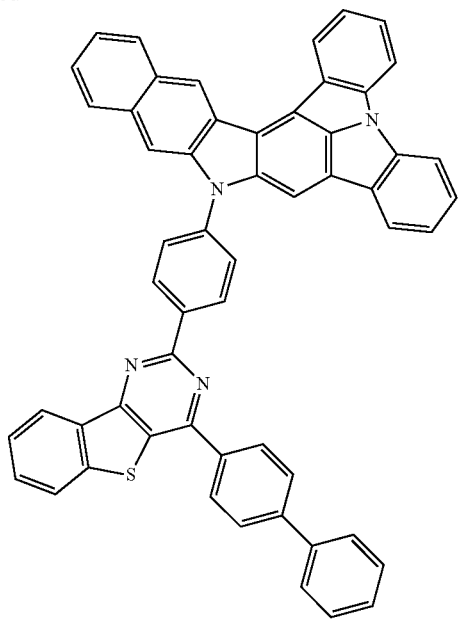
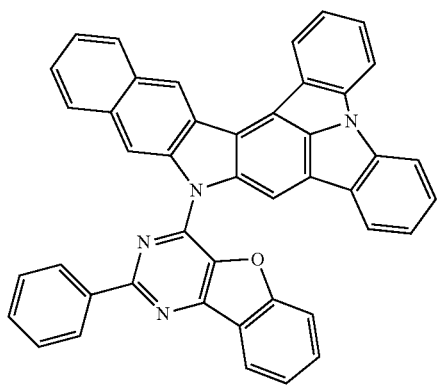
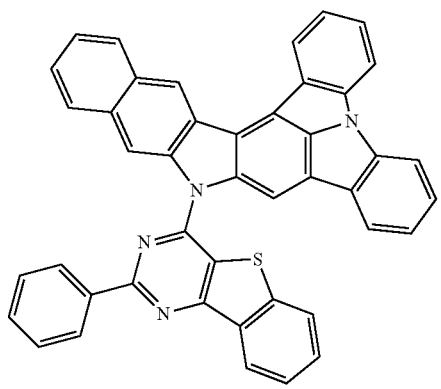
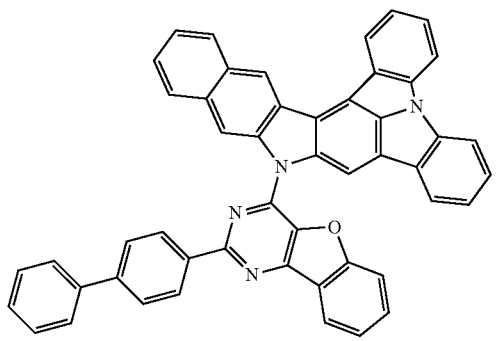
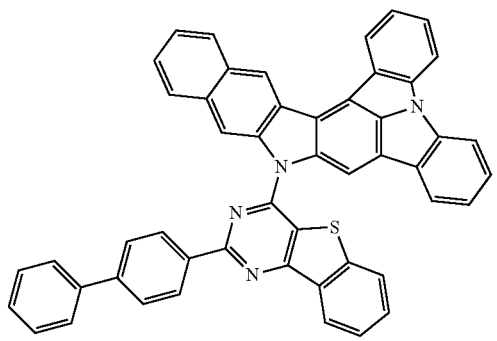

-continued
| 521 | 522 |
|---|---|
| 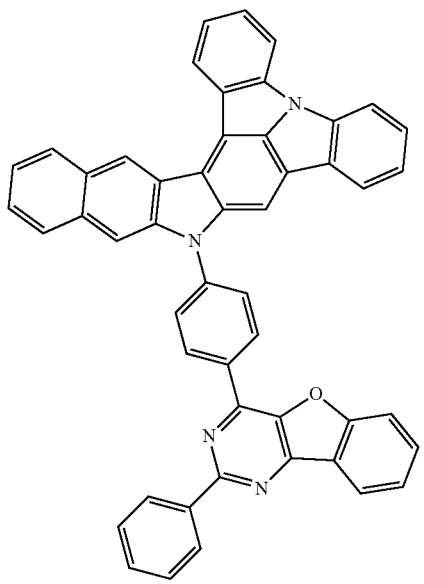 | 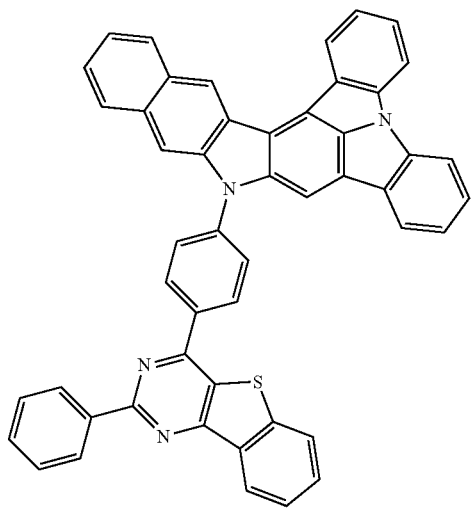 |
| 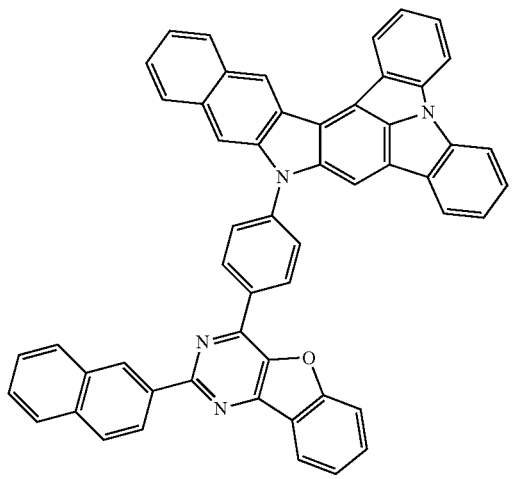 | 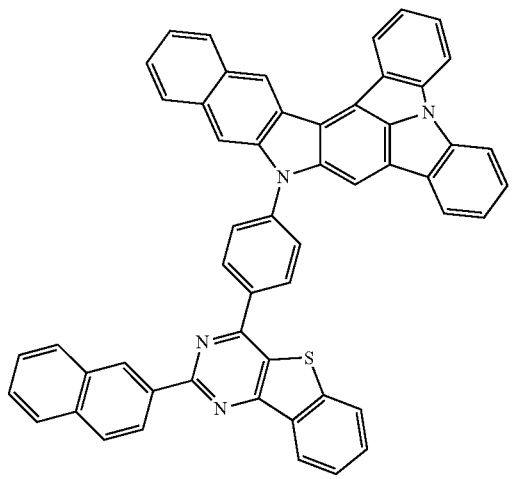 |
| 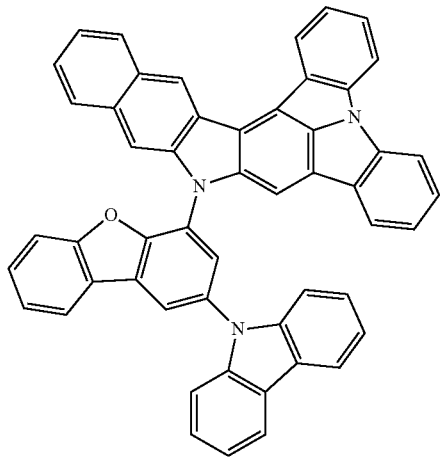 | 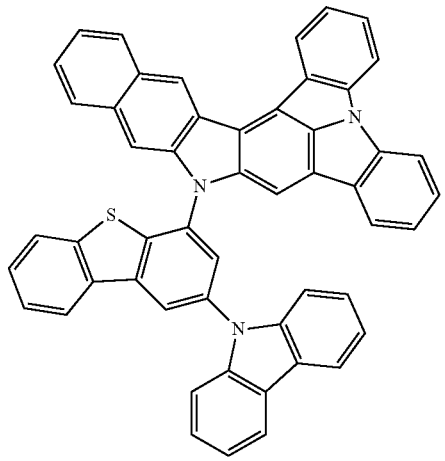 |

523
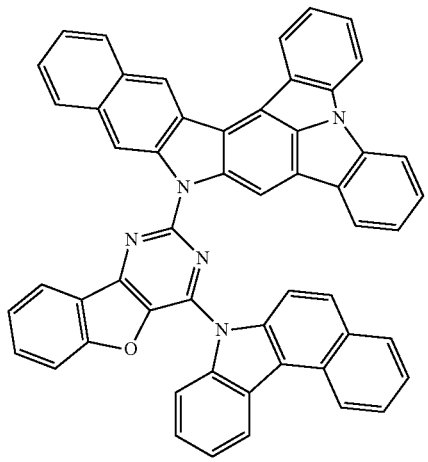
-continued
524
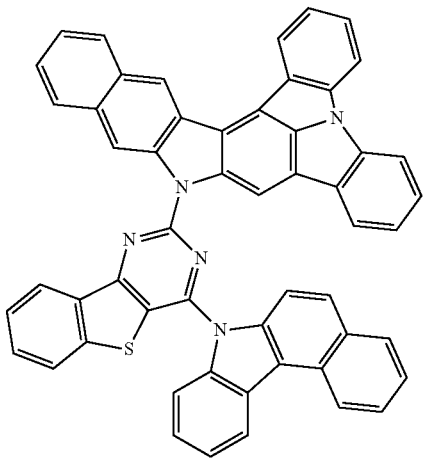
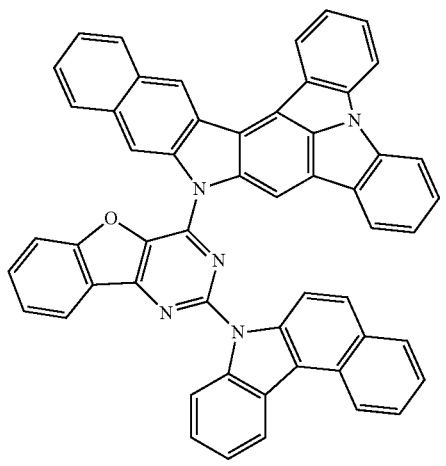
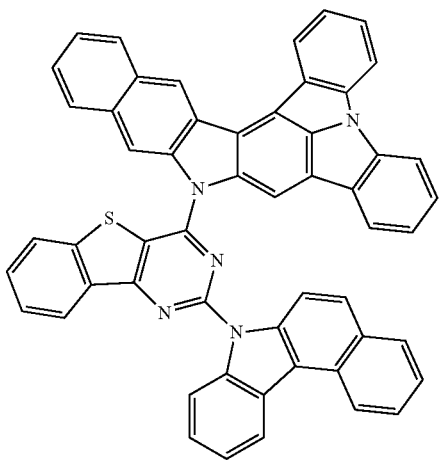
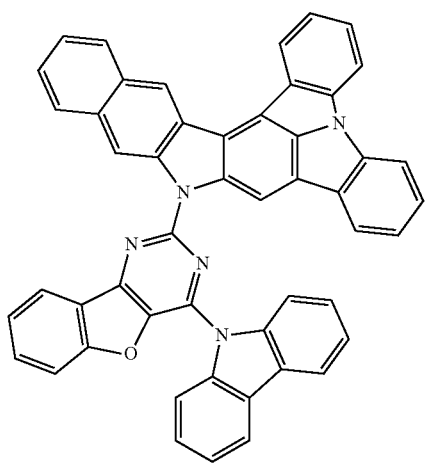
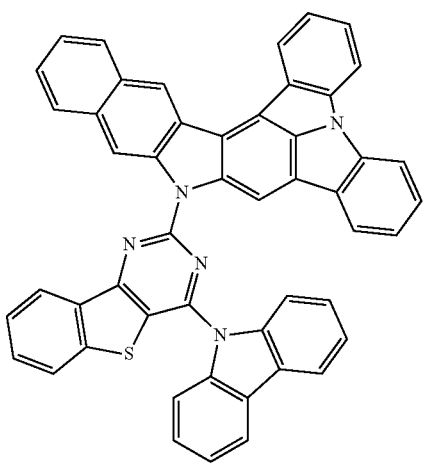

525 526
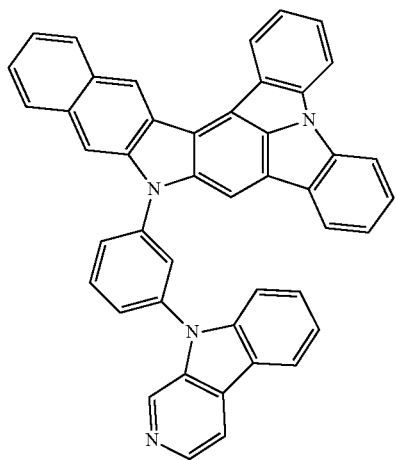
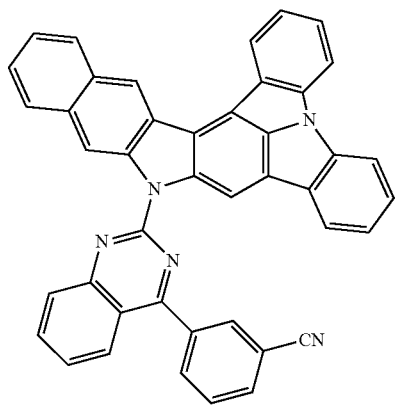
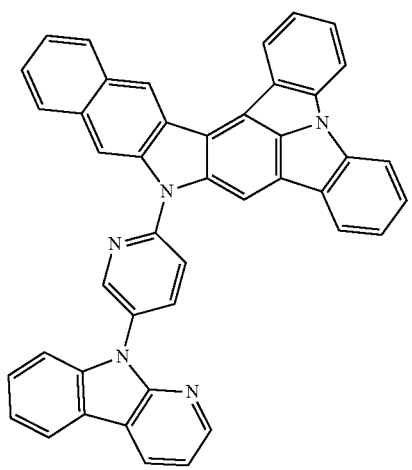
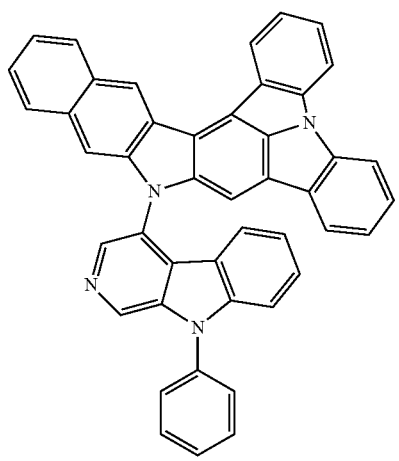
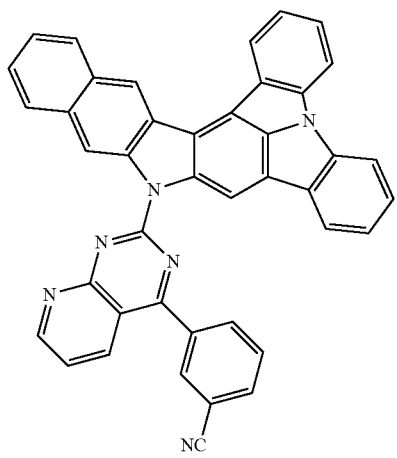
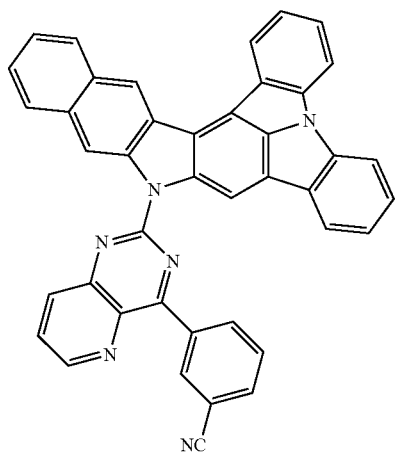

527
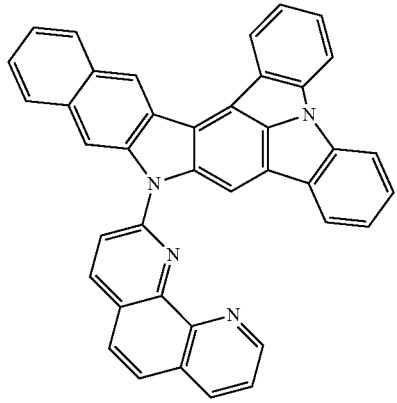
528
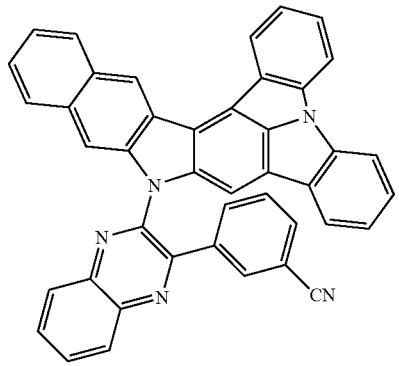
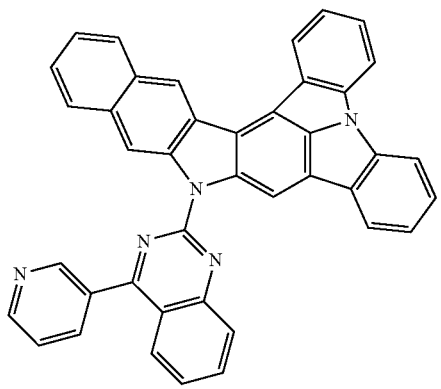
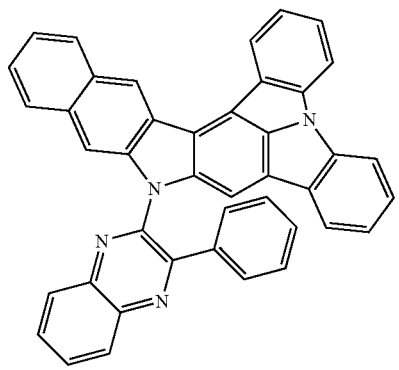
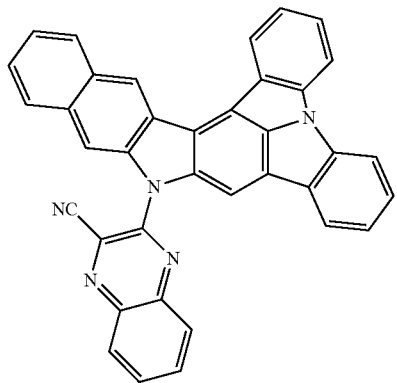
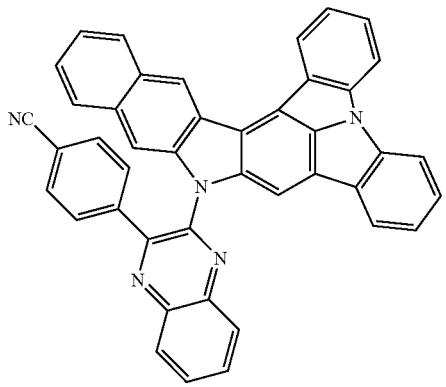
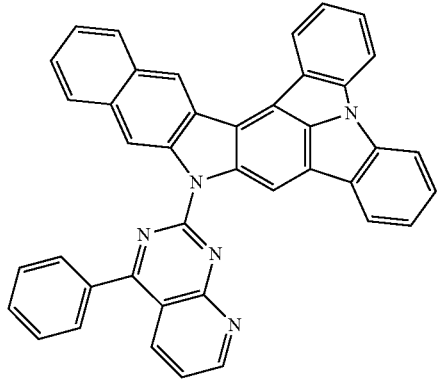
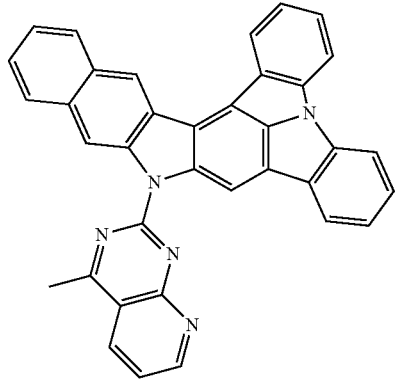

-continued
529
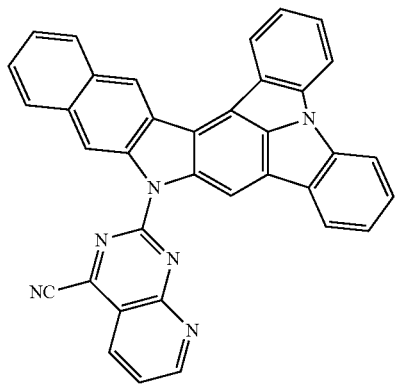
530
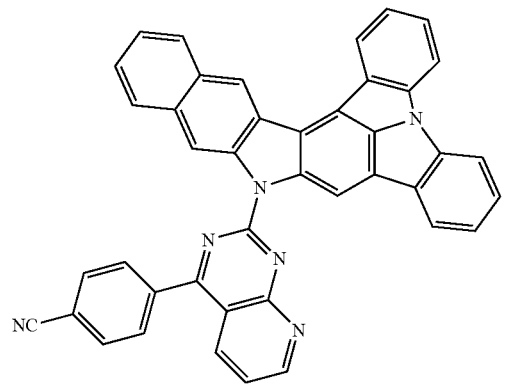
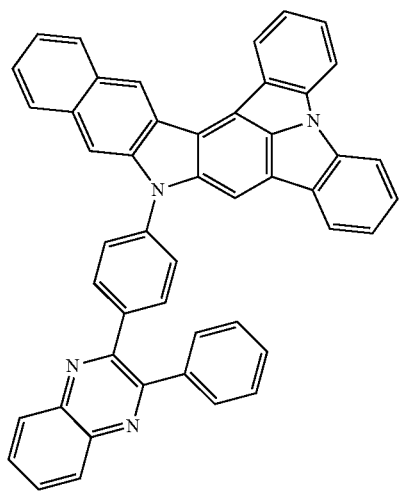
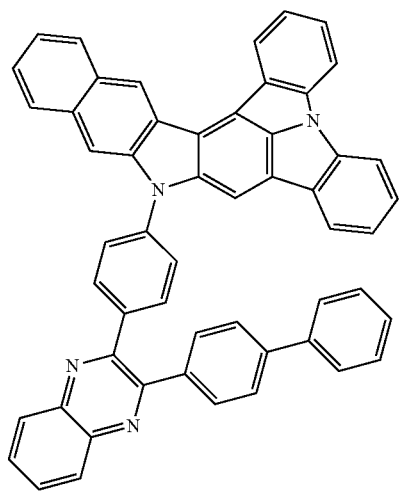
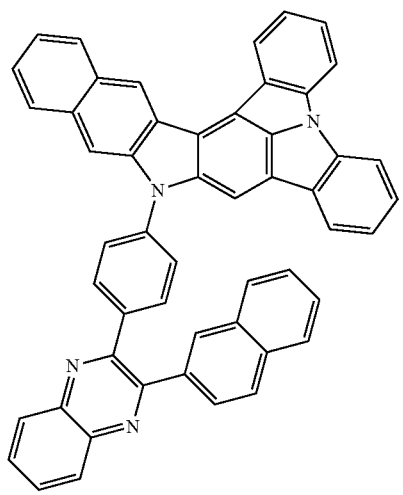
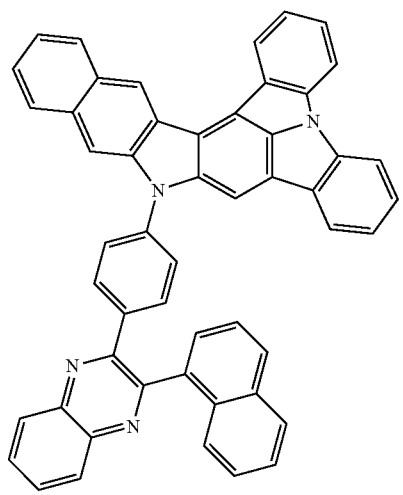

-continued
531
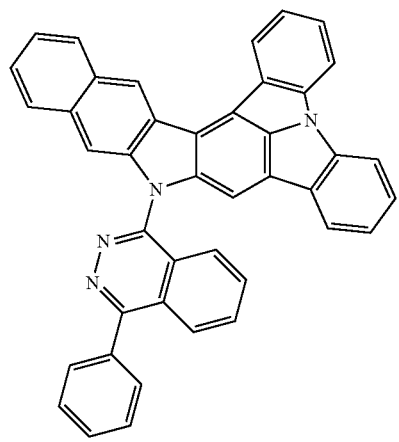
532
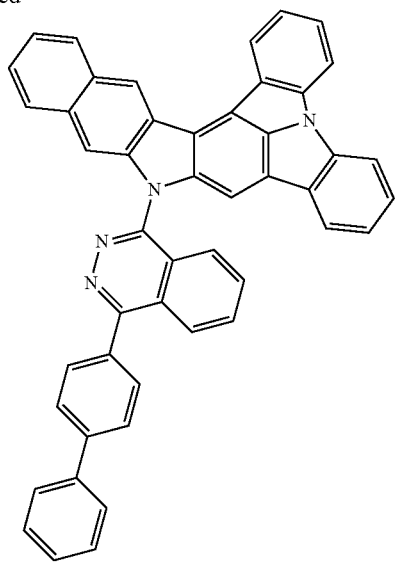
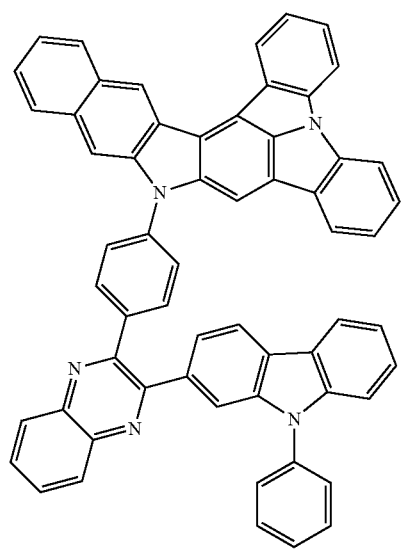
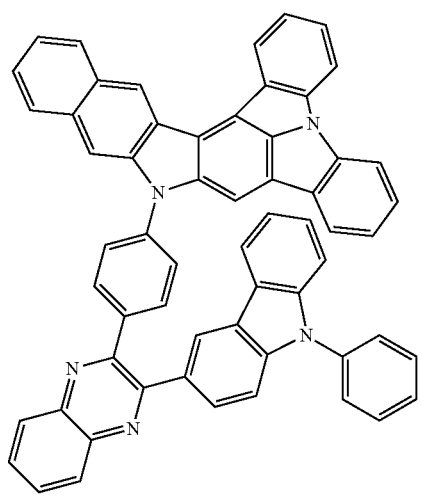
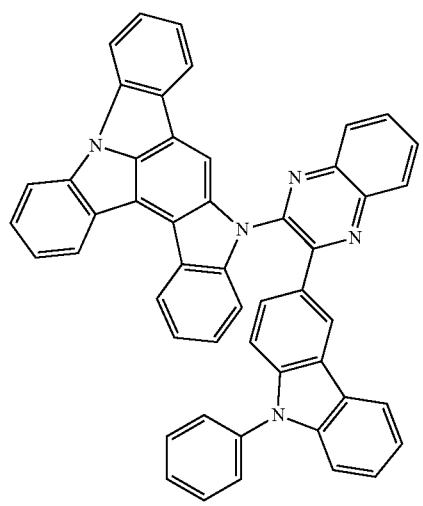
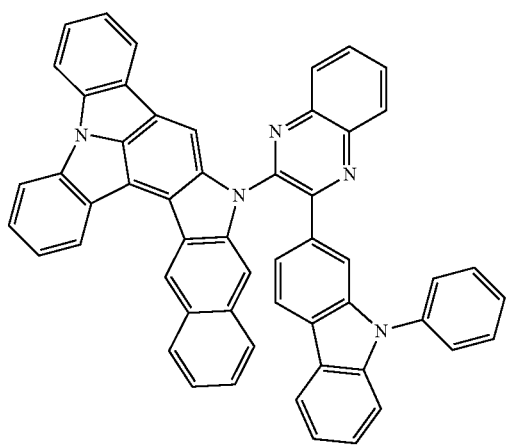

-continued
533
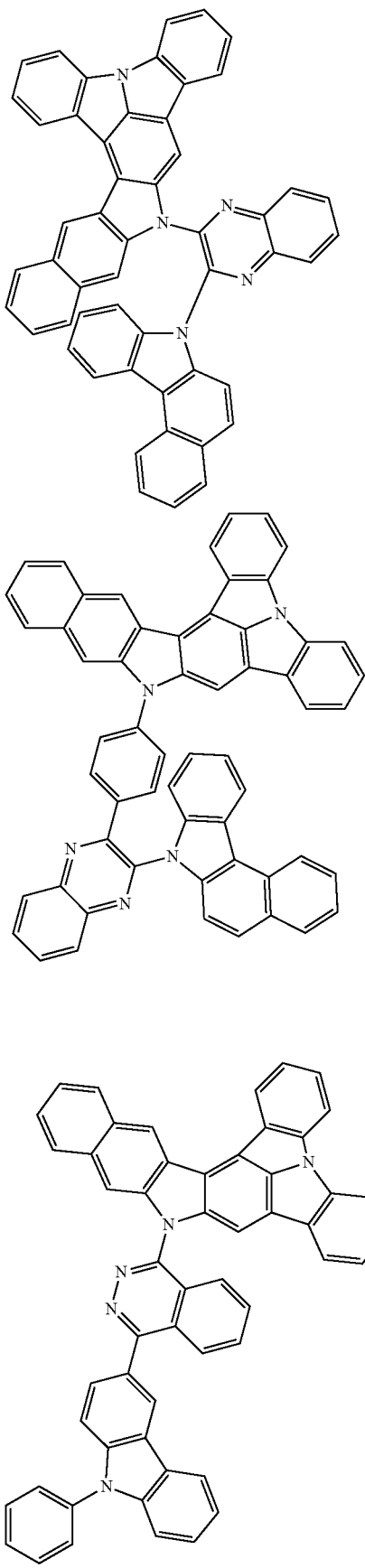
534
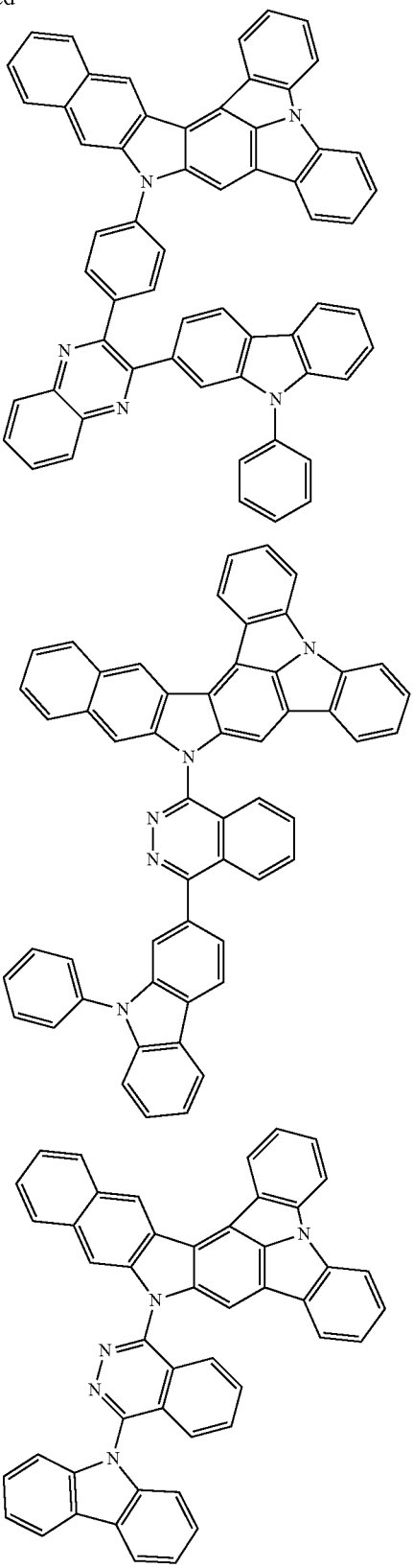

-continued
535
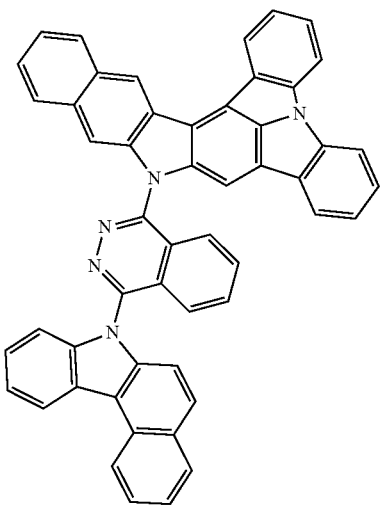
536
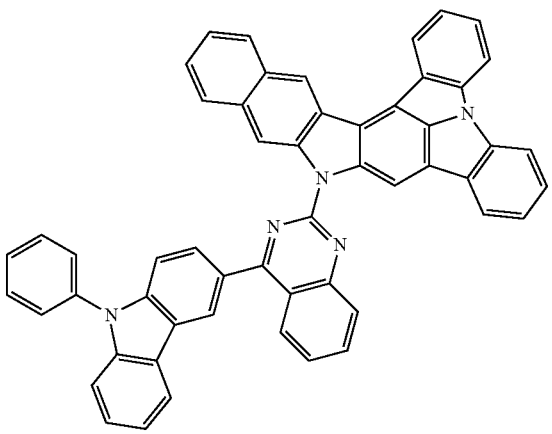
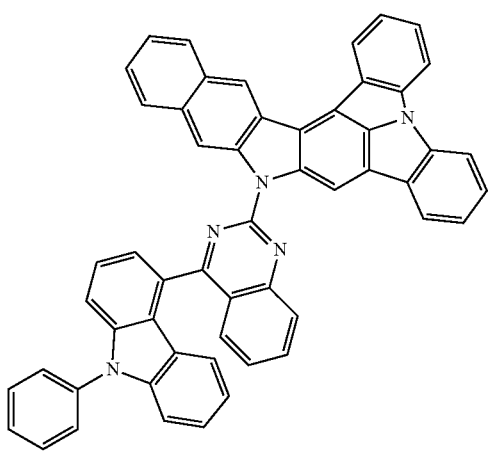
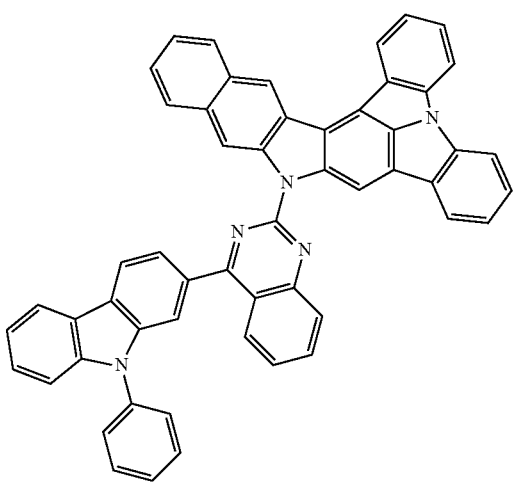
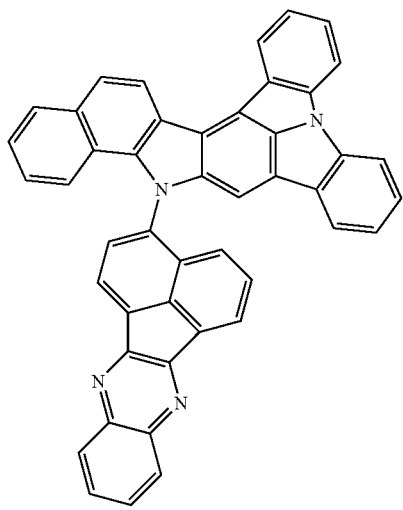
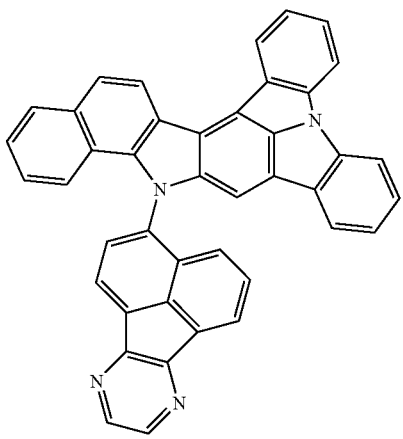

-continued
537
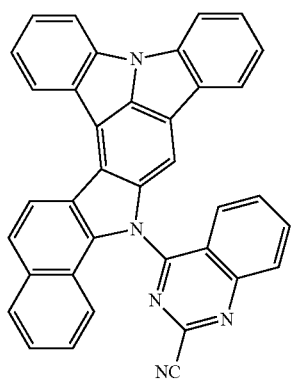
538
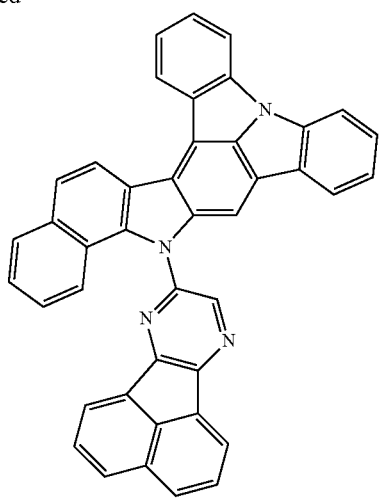
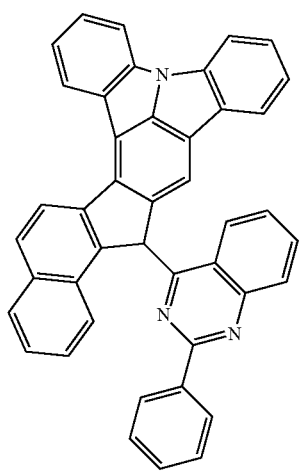
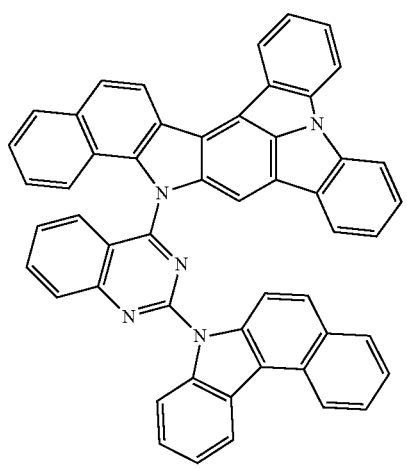
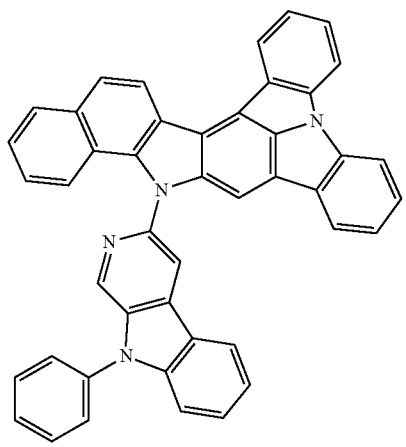
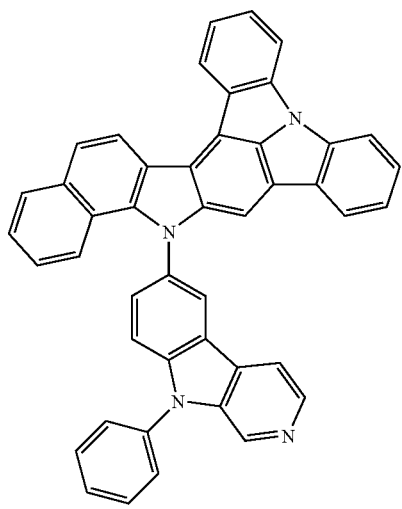

539
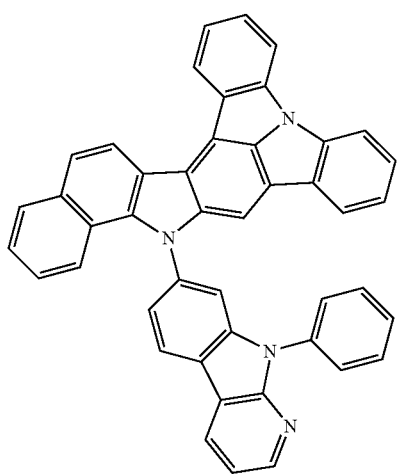
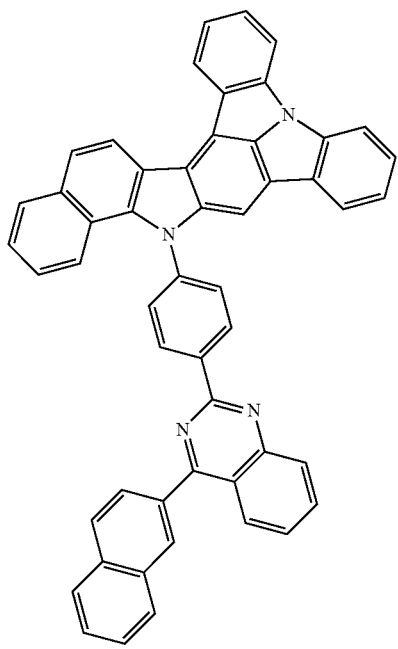
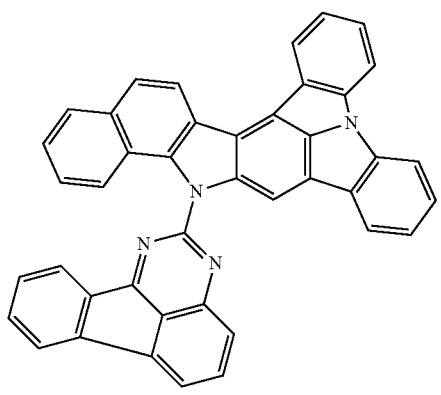
540
-continued
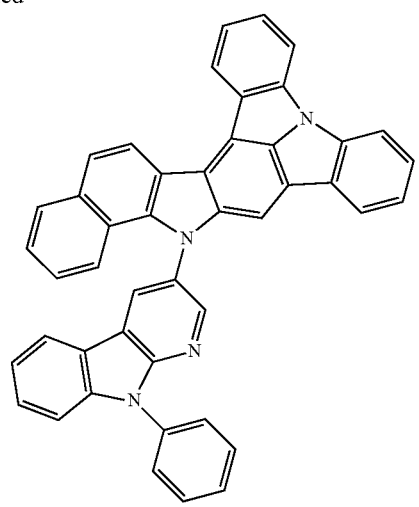
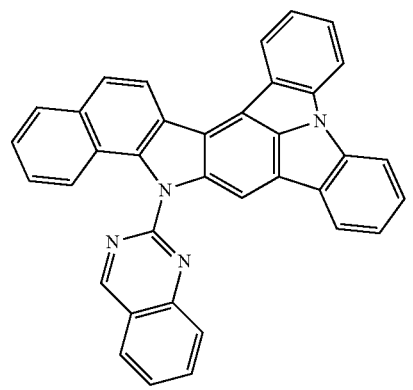
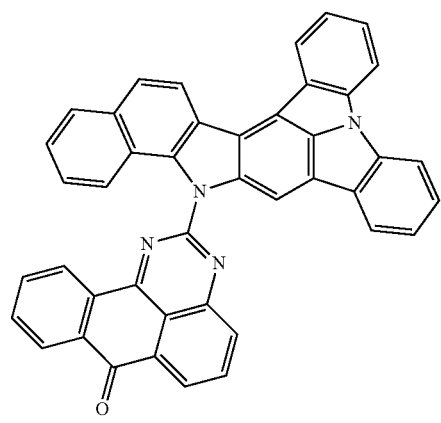

-continued
541
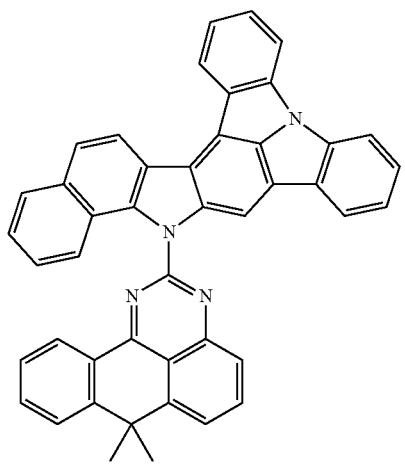
542
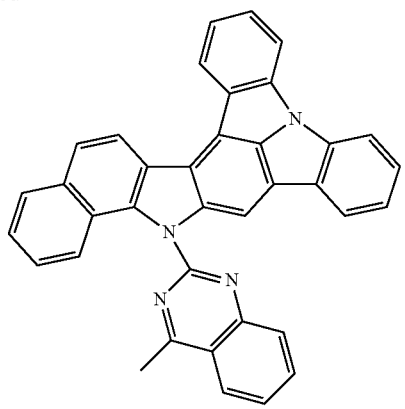
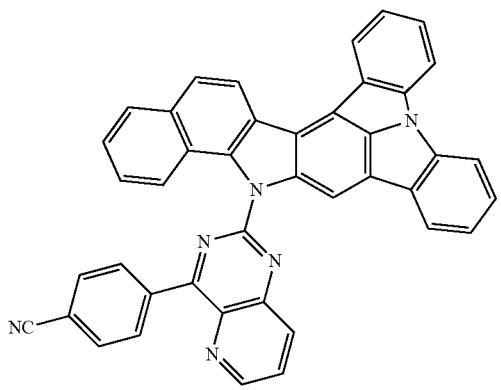
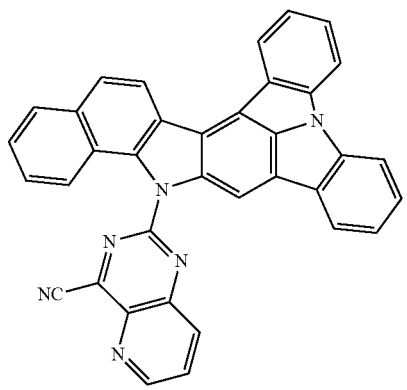
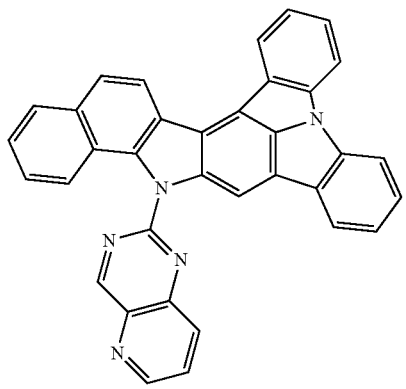
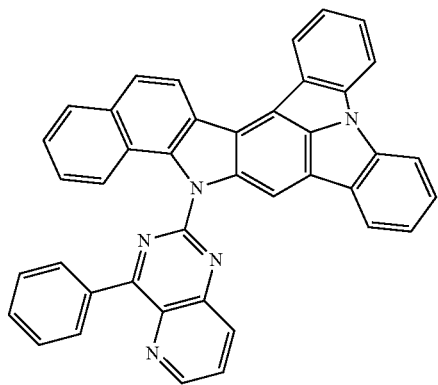
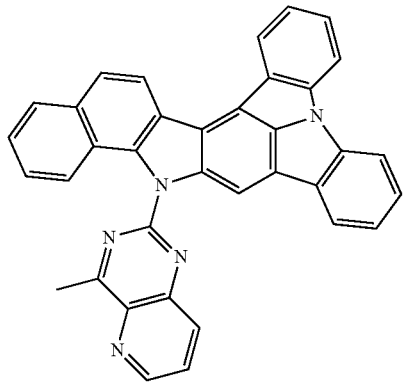
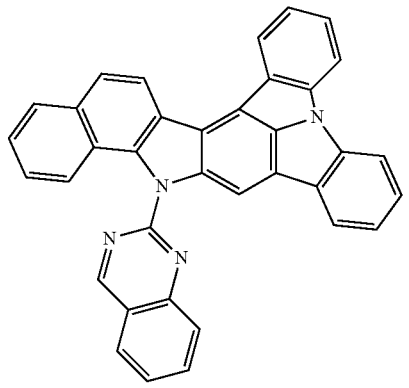

543 544
-continued
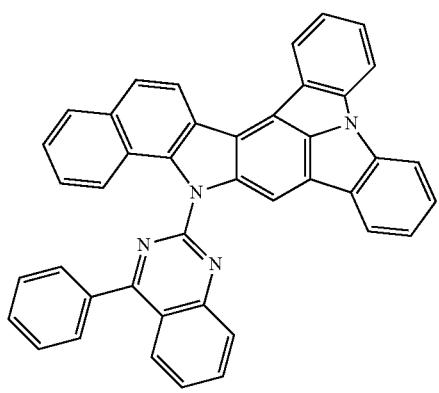
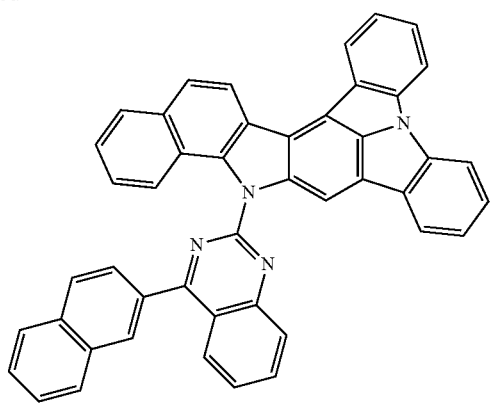
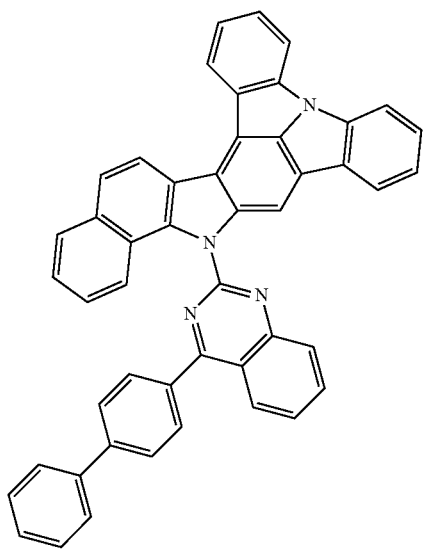
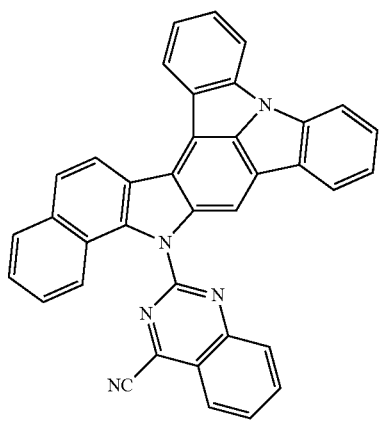
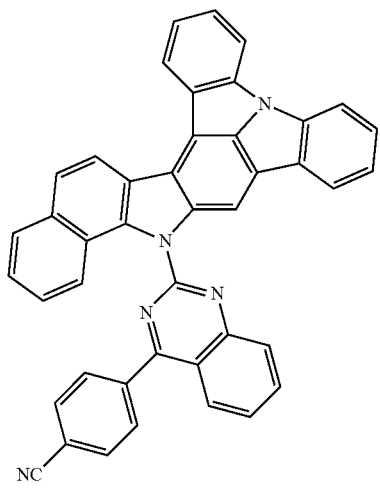
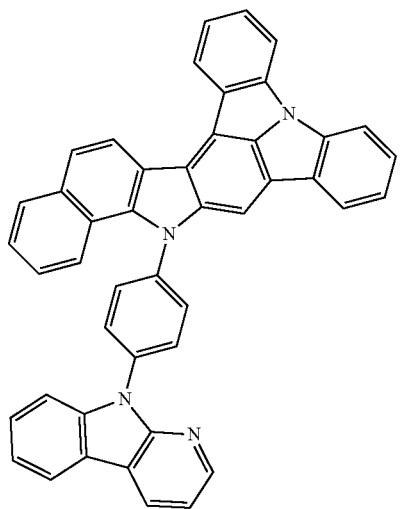

545
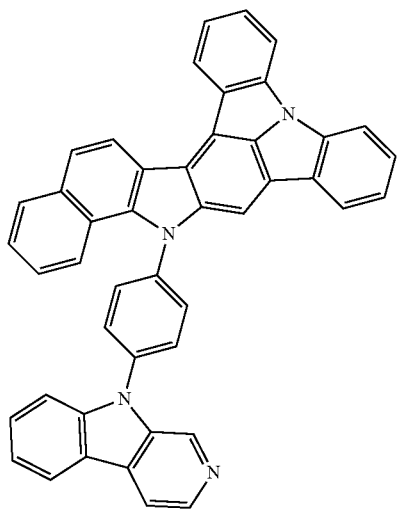
546
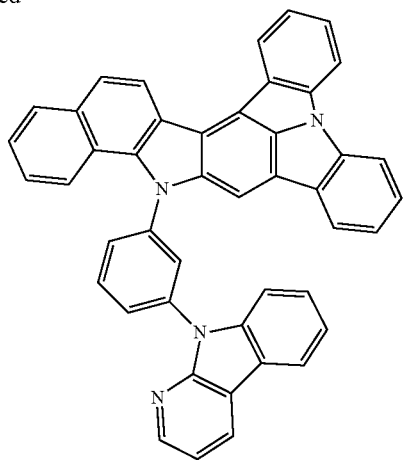
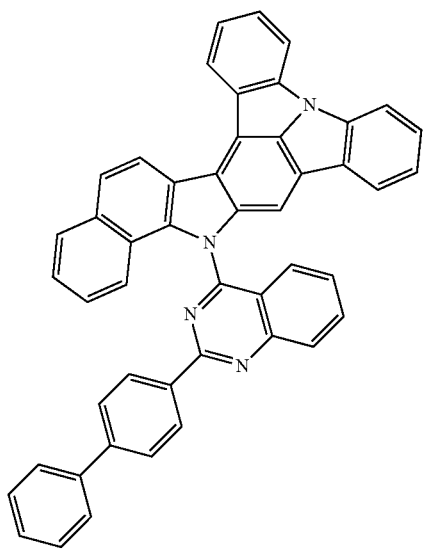
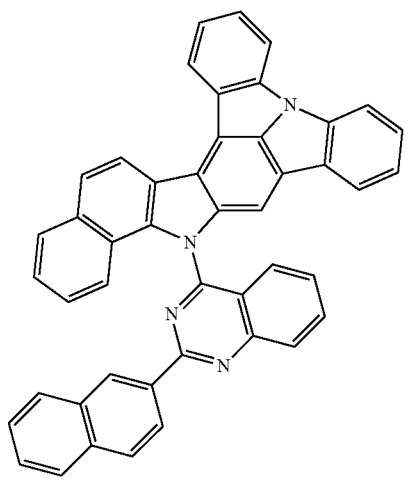
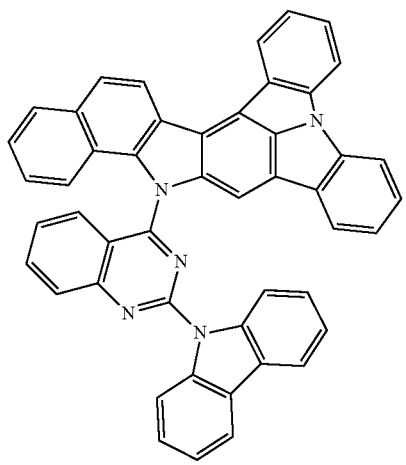
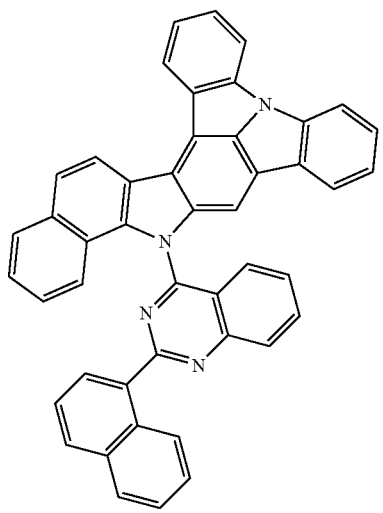

-continued
547
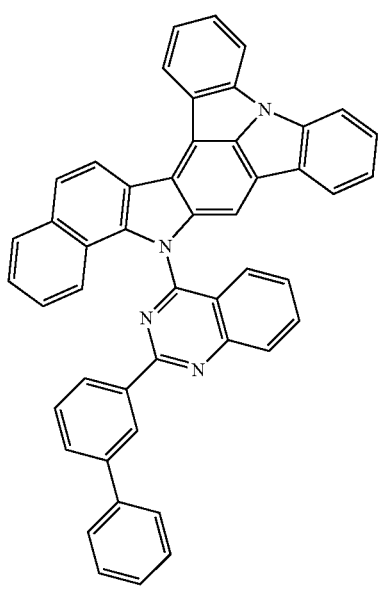
548
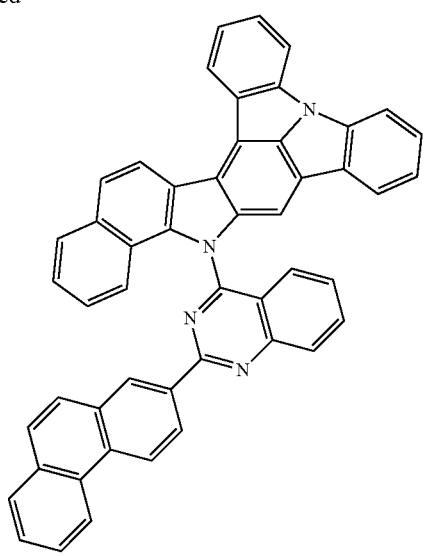
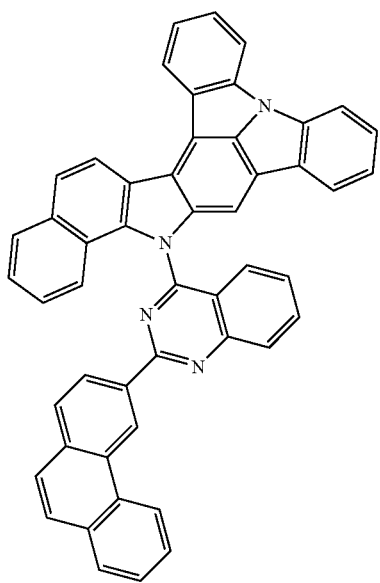
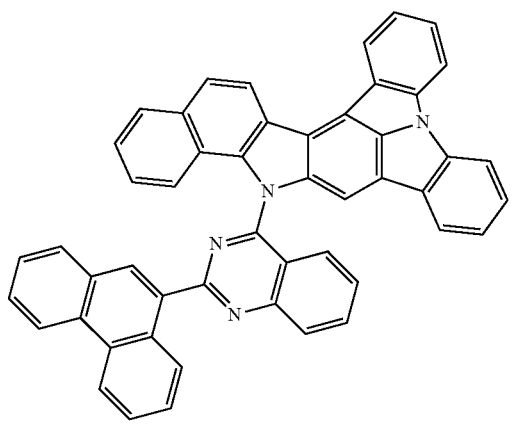
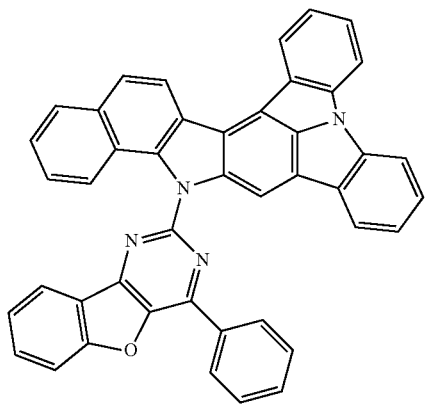
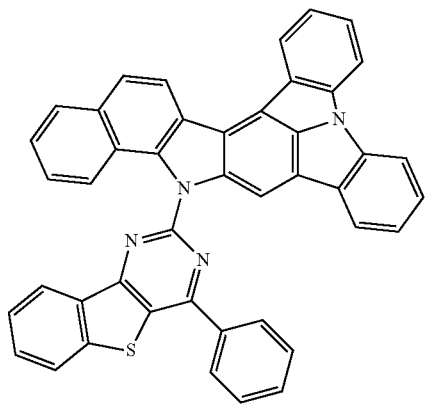

549
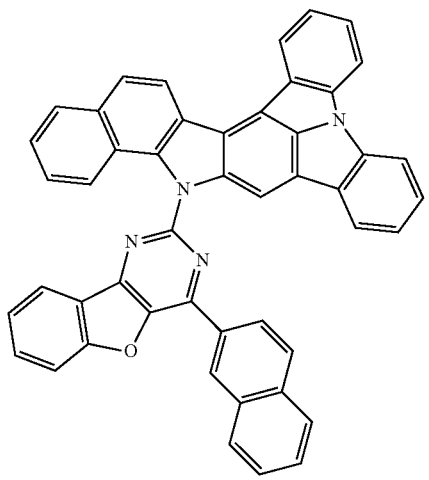
-continued
550
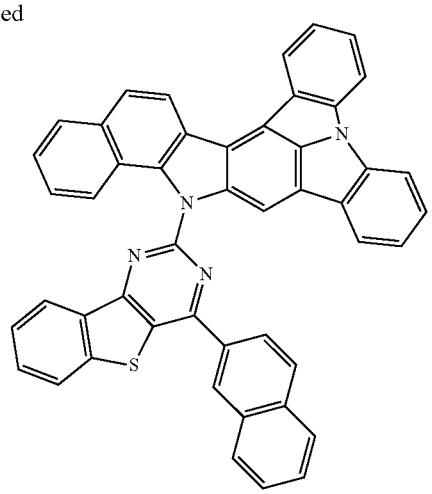
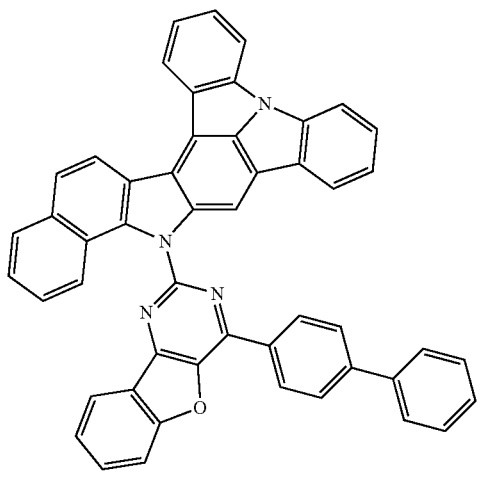
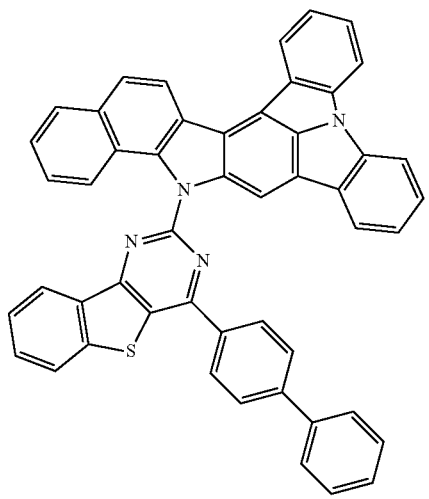
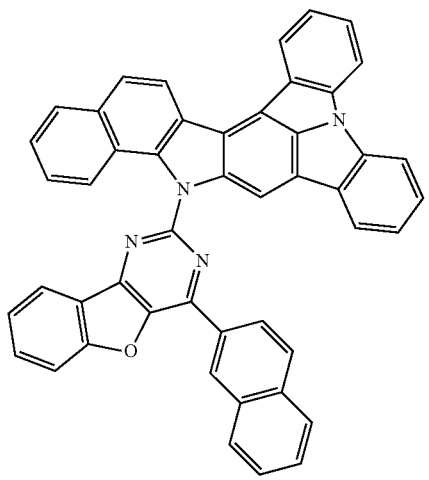
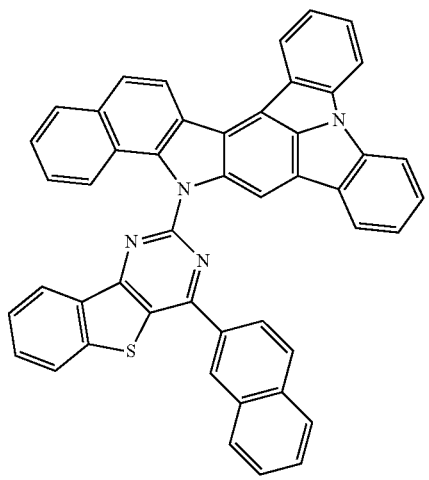

551 552
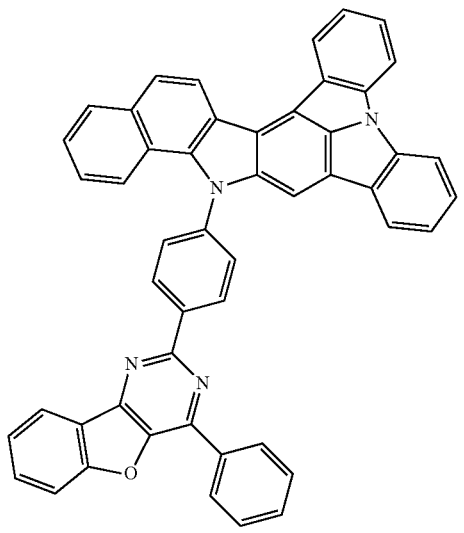 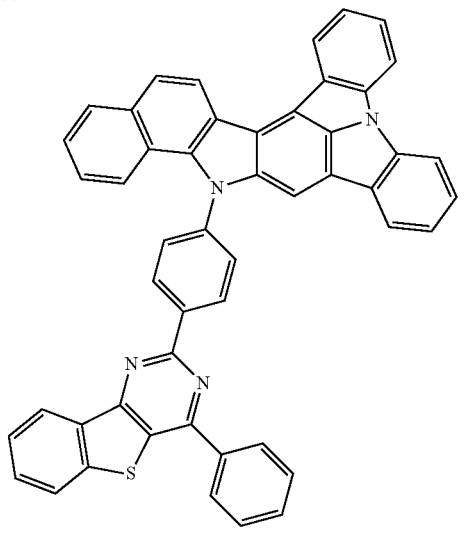
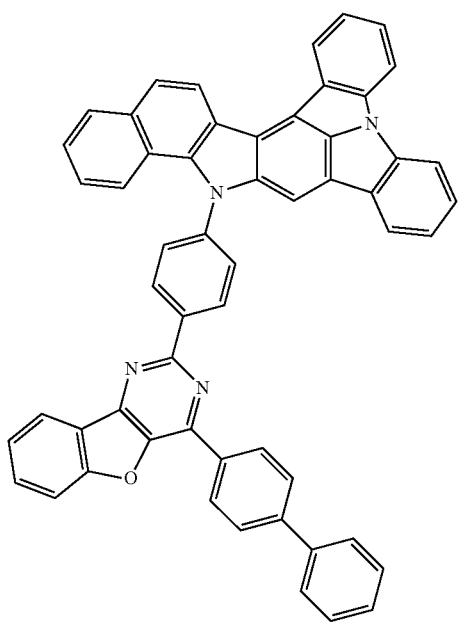 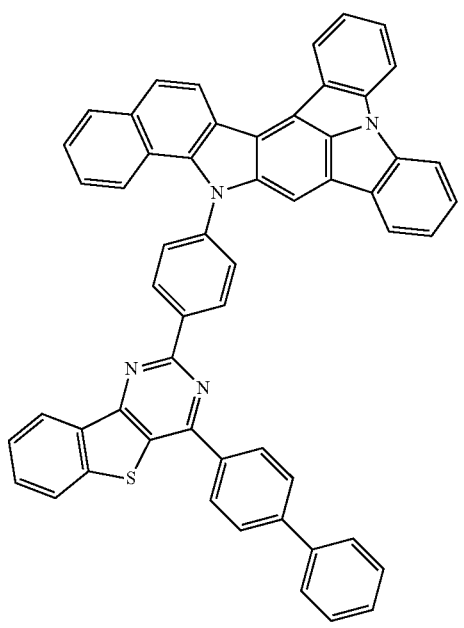
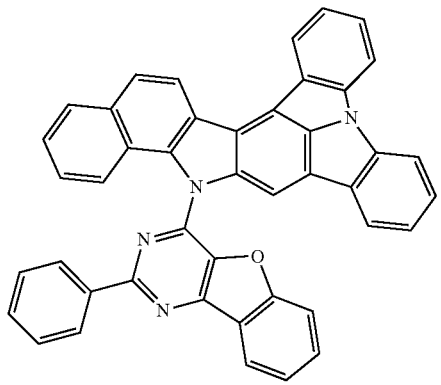 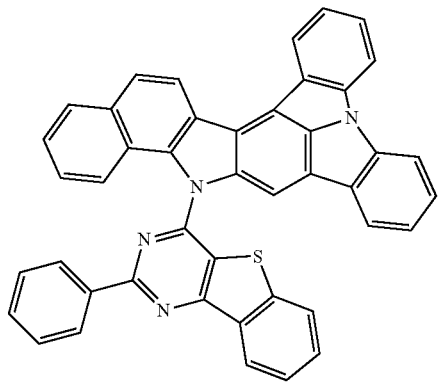

-continued
| 553 | 554 |
|---|---|
| 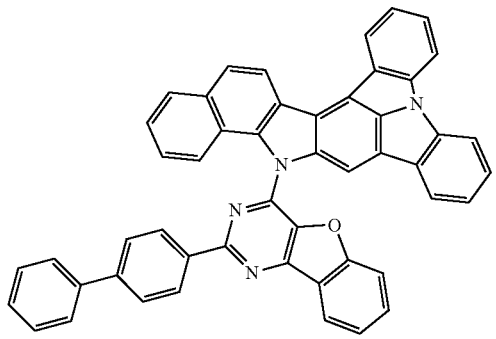 | 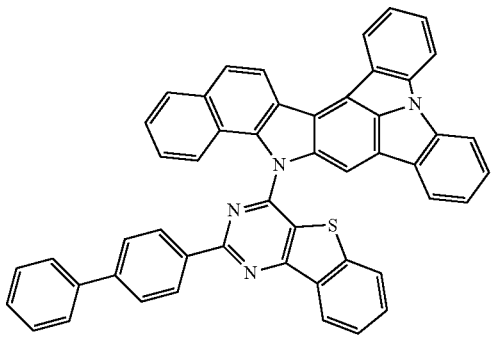 |
| 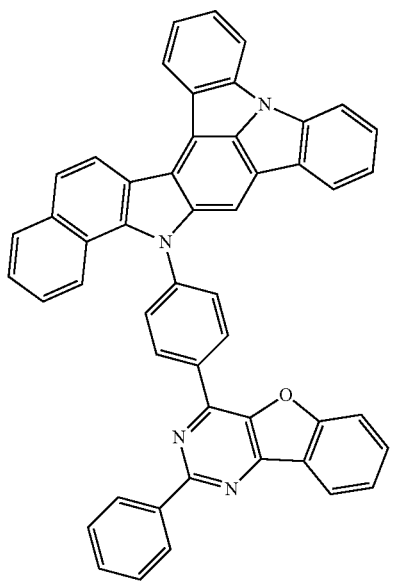 | 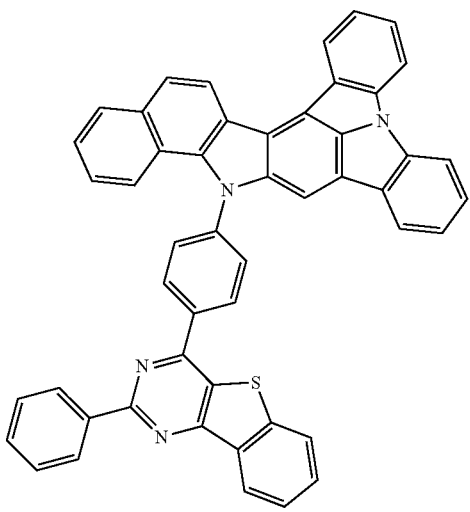 |
| 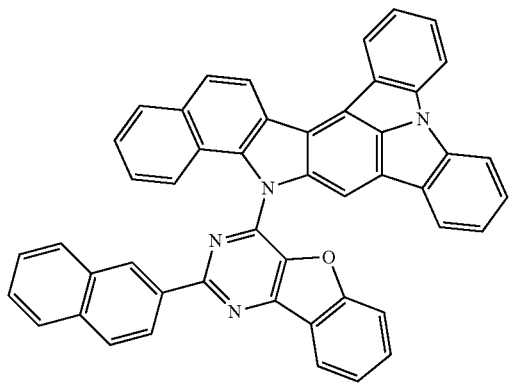 | 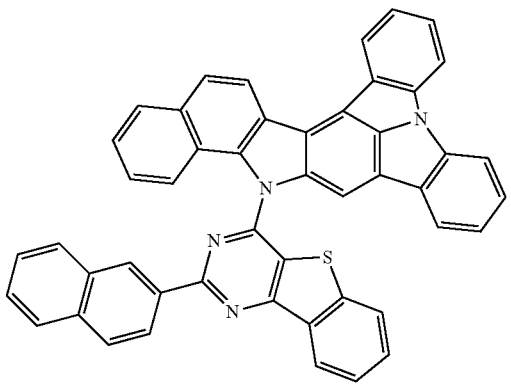 |

555
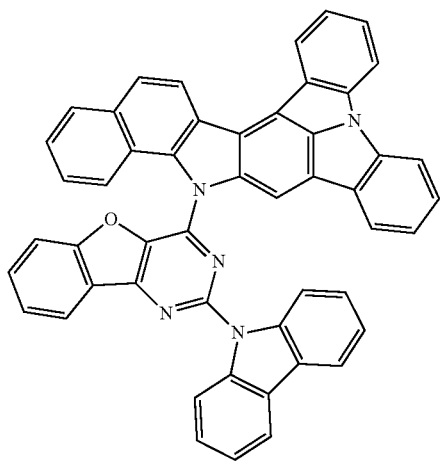
556
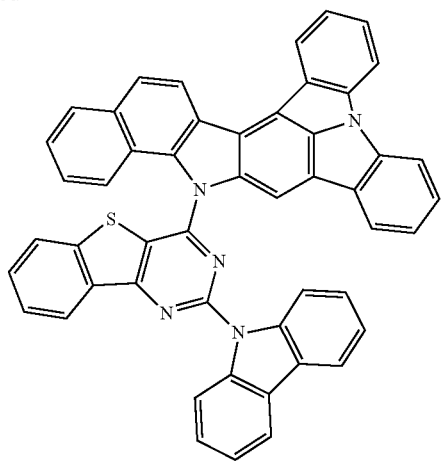
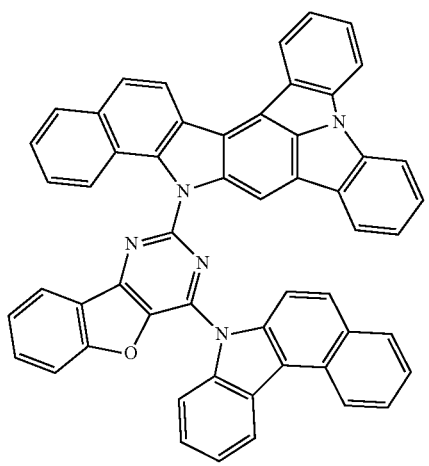
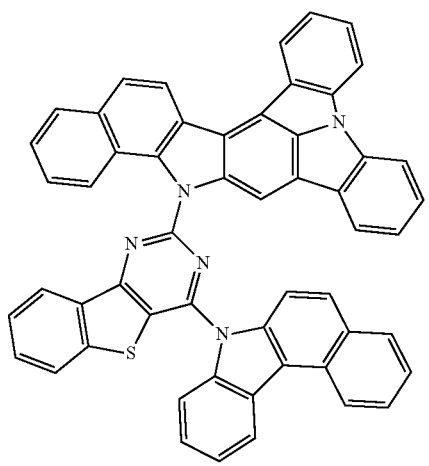
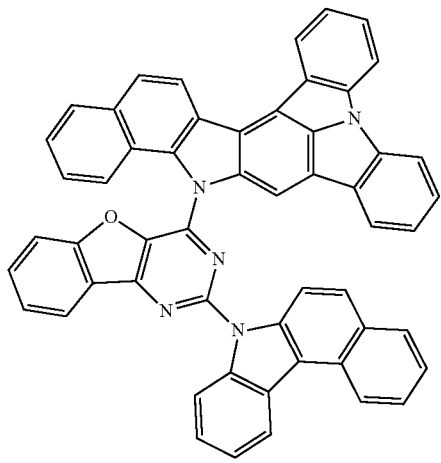
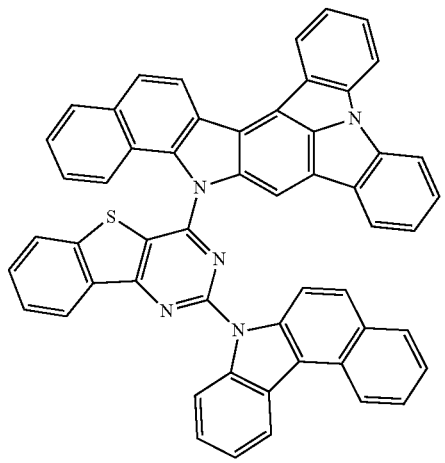

557
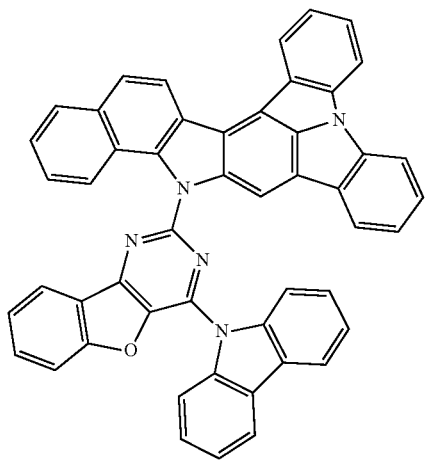
558
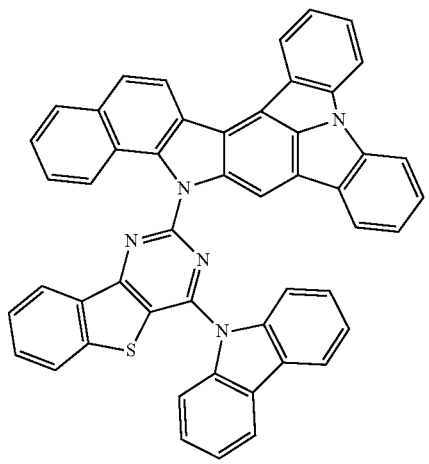
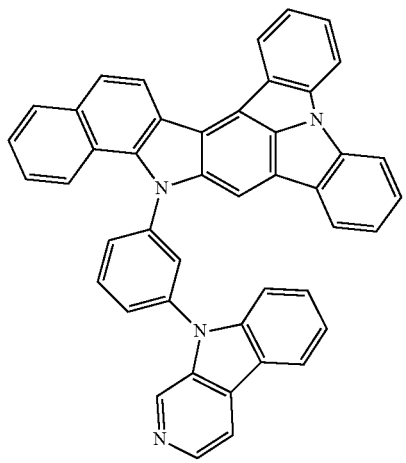
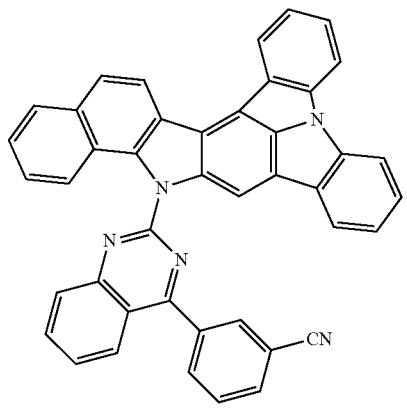
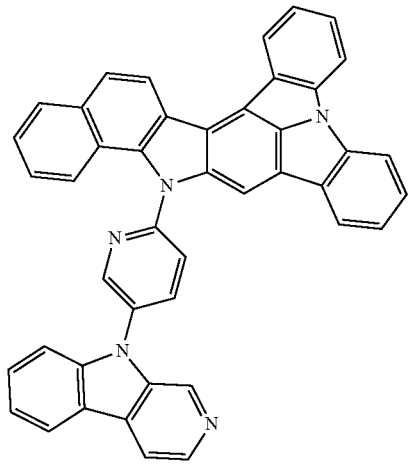
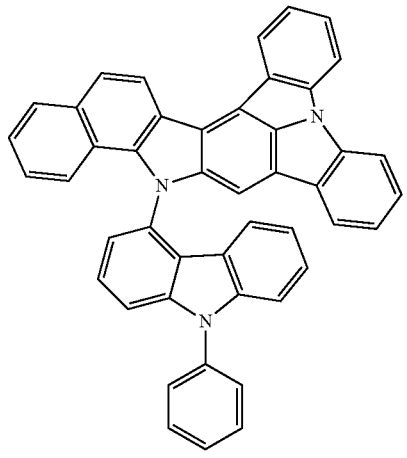

559 560
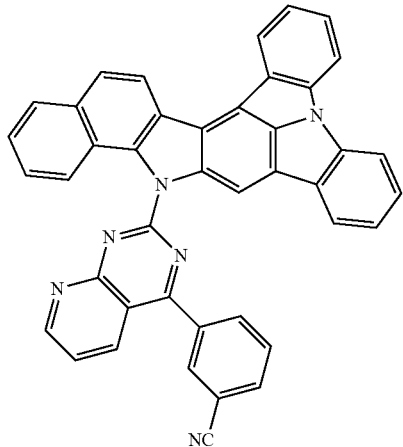 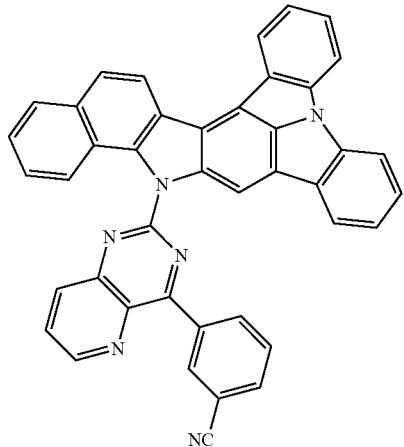
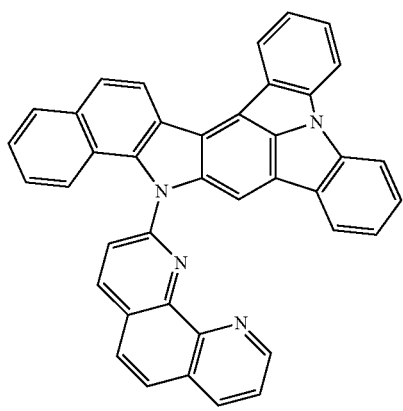 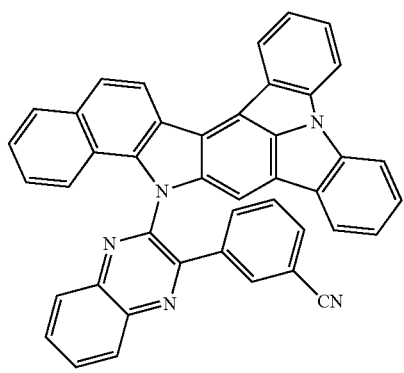
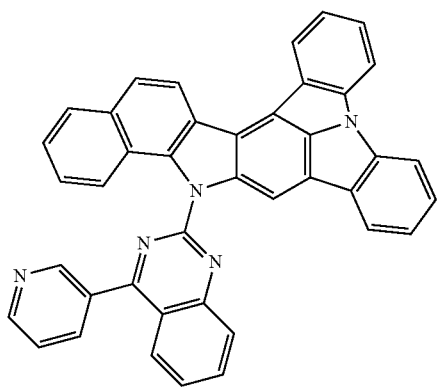 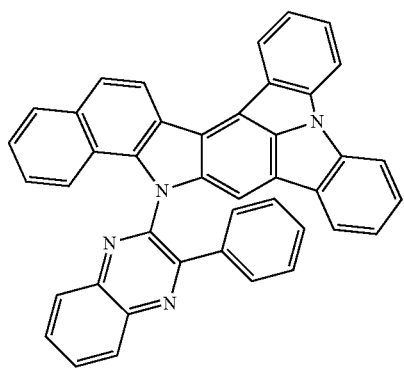
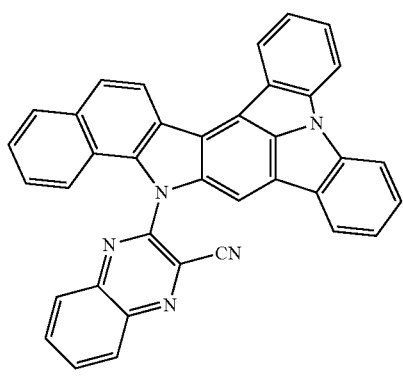 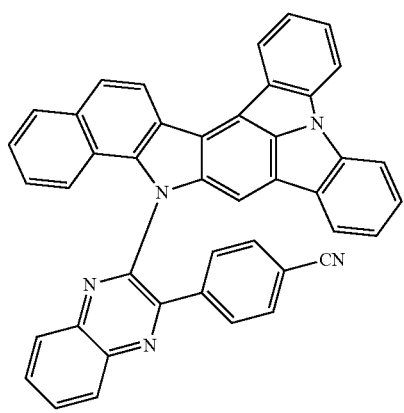

561
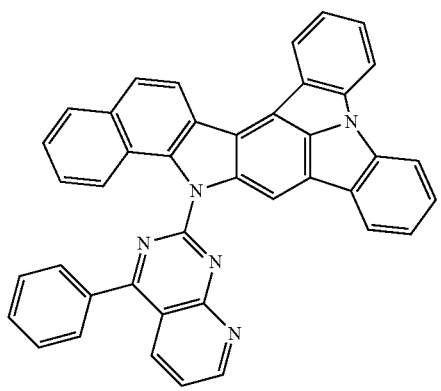
562
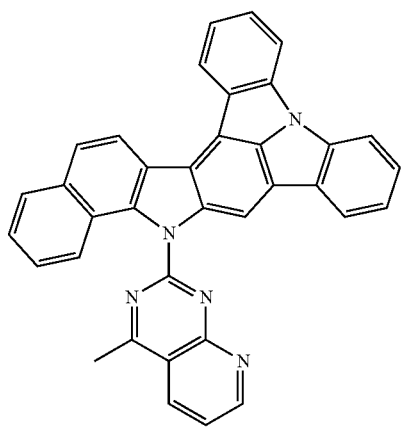
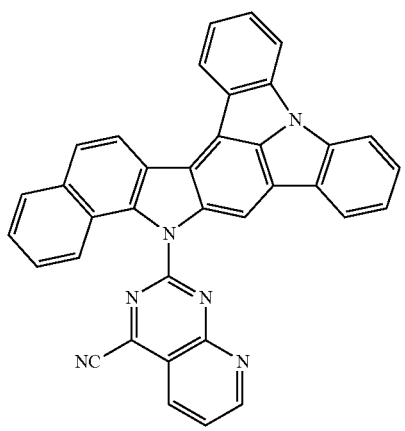
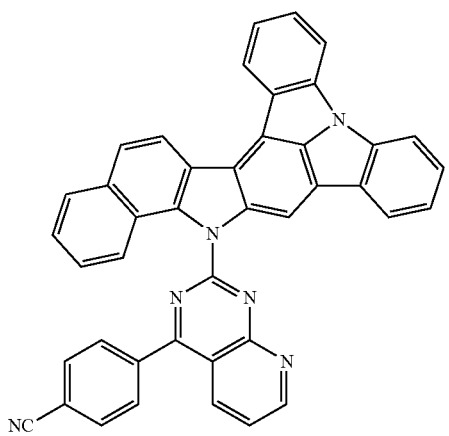
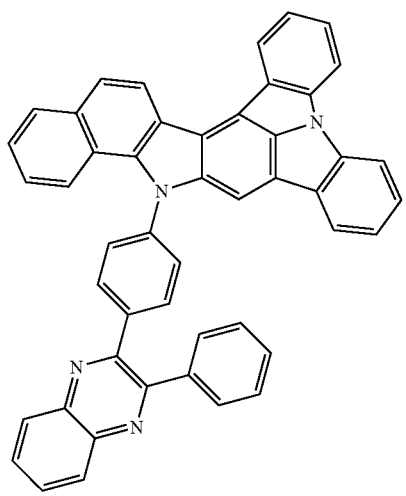
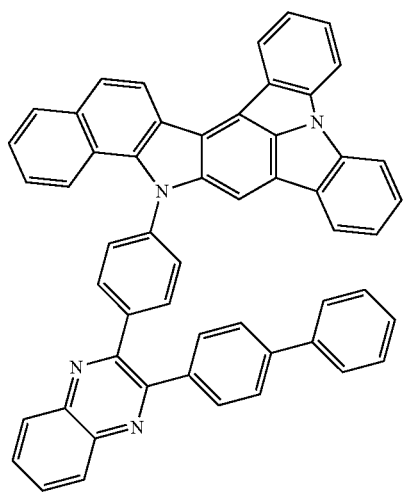

-continued
| 563 | 564 |
|---|---|
| 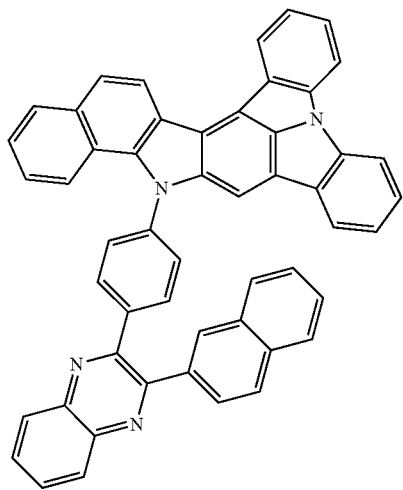 | 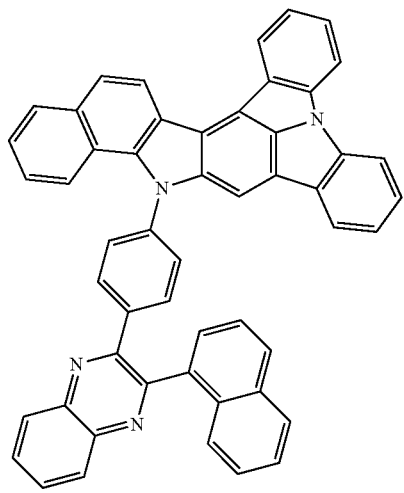 |
| 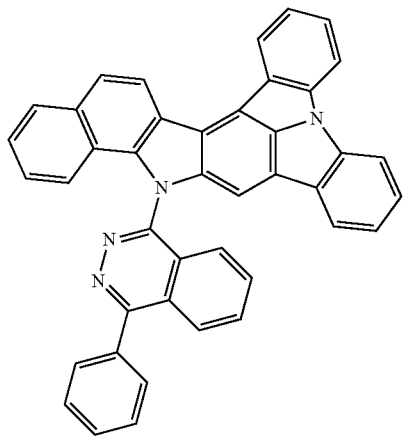 | 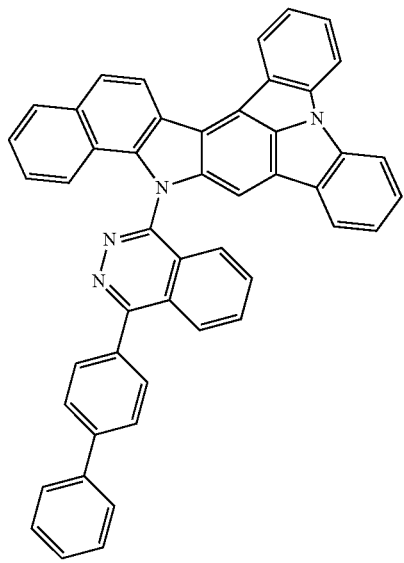 |
| 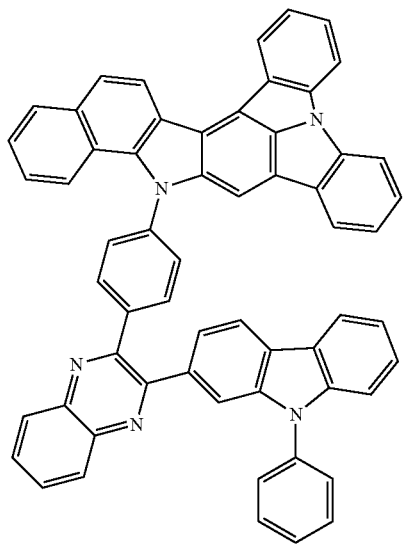 | 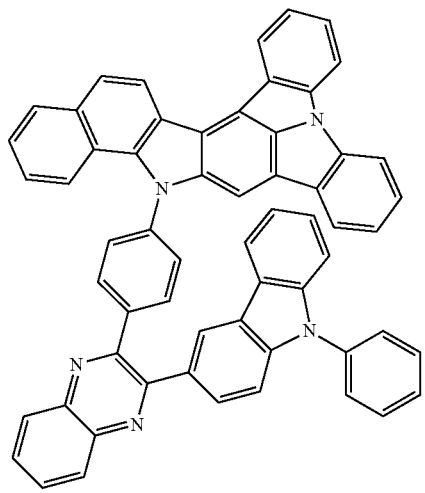 |

565
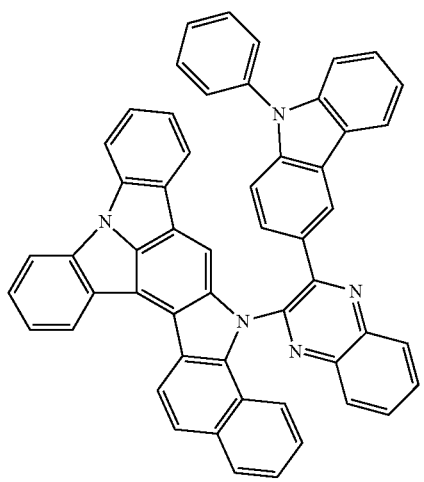
566
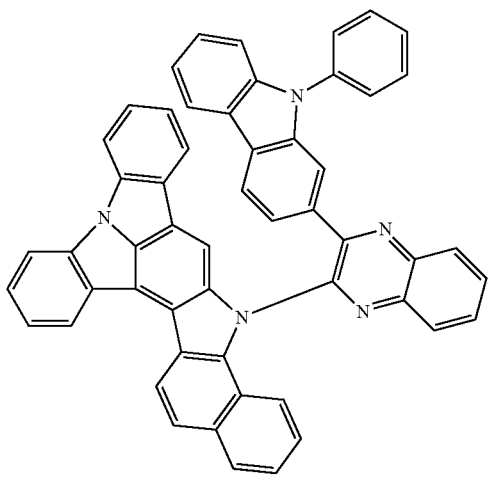
-continued
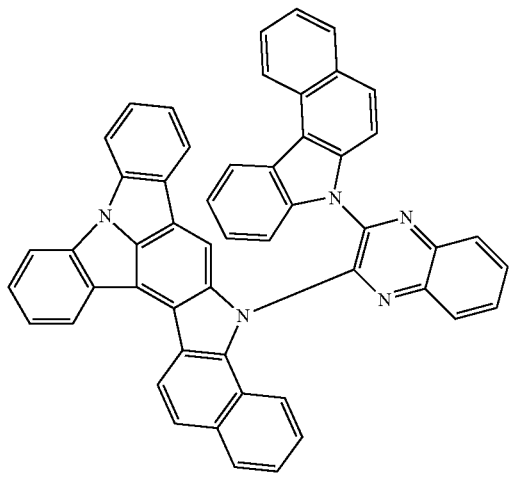
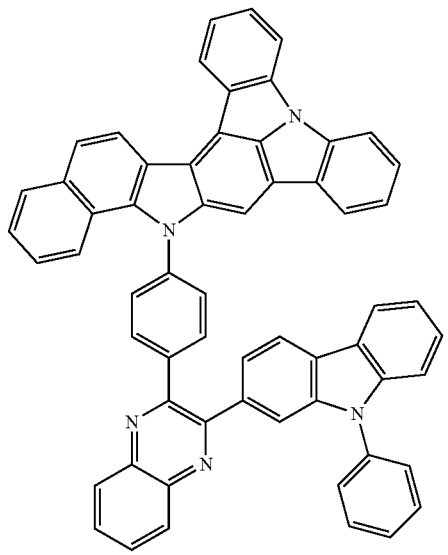
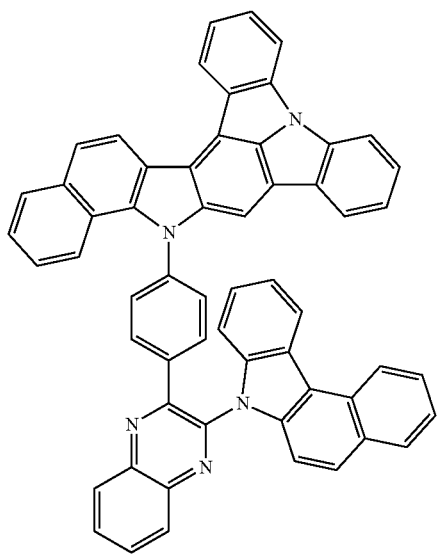
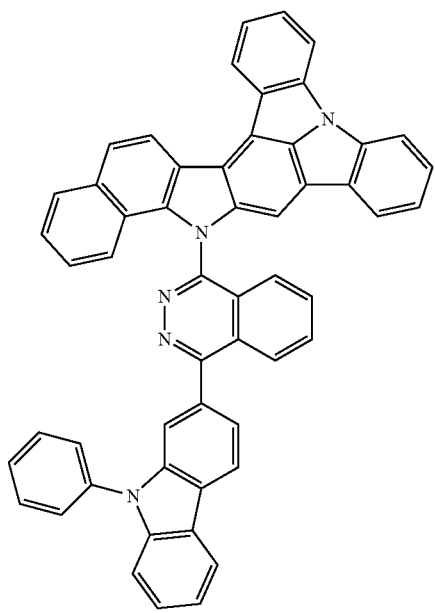

-continued
567
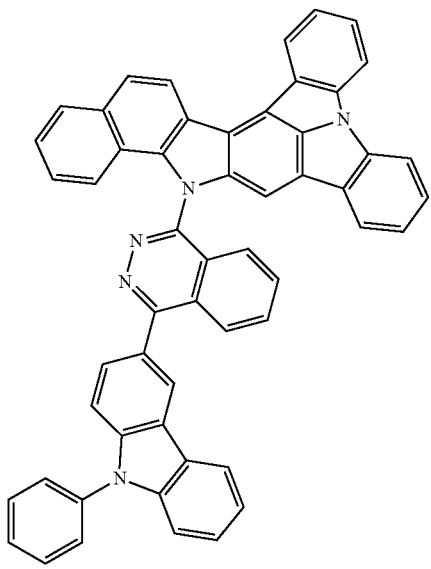
568
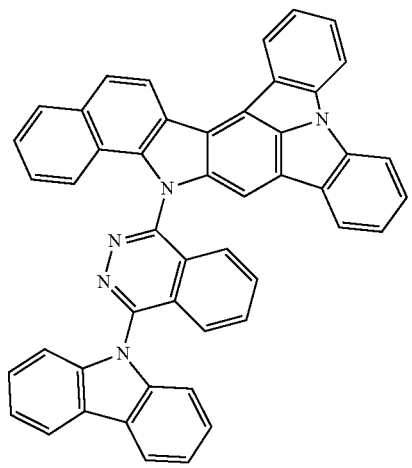
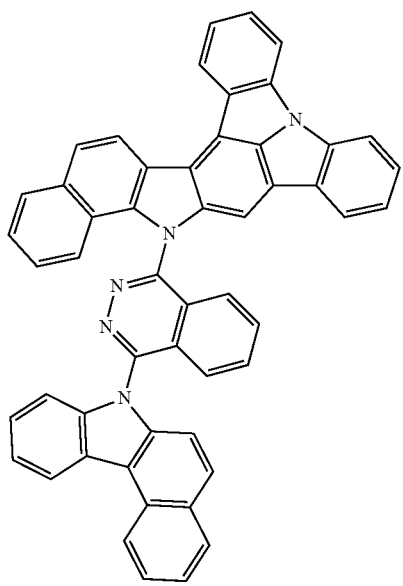
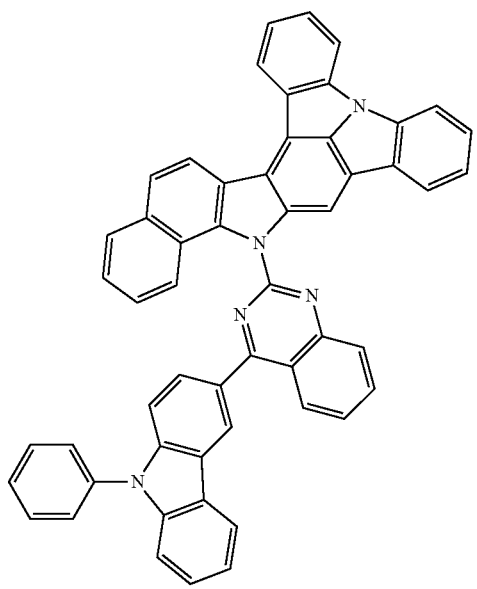
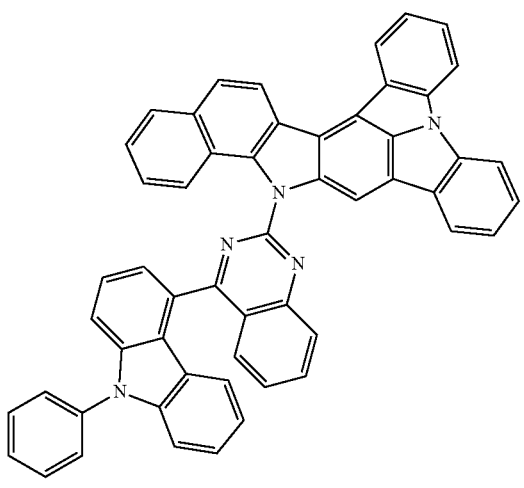
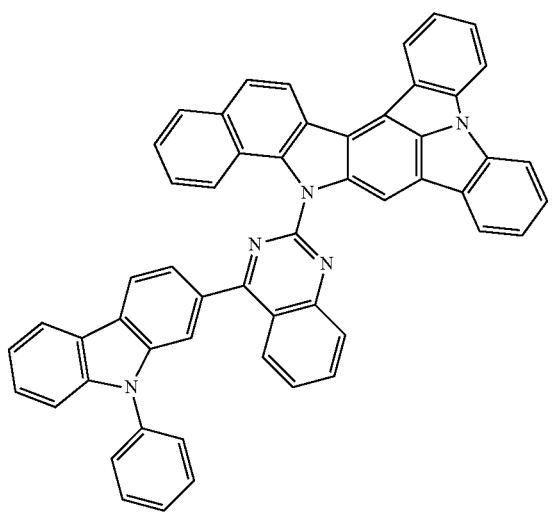

-continued
569
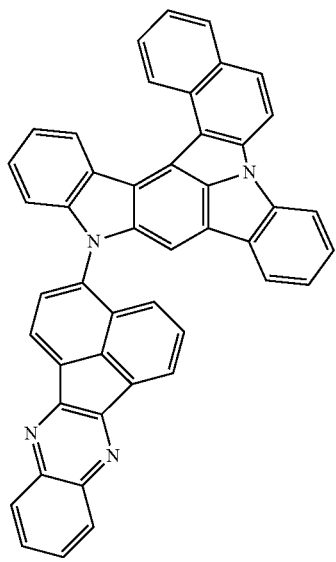
570
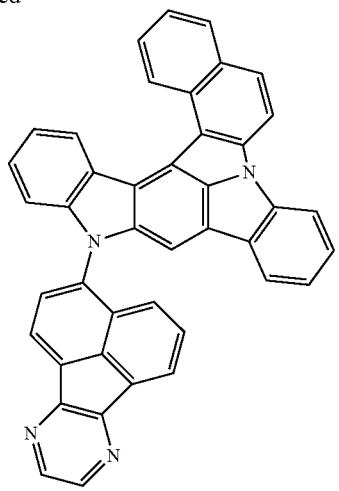
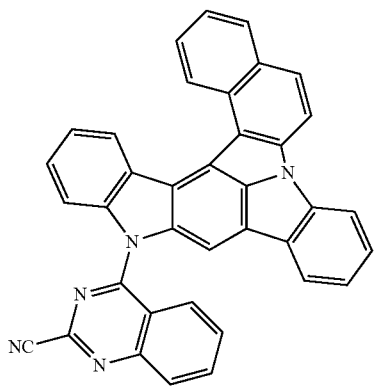
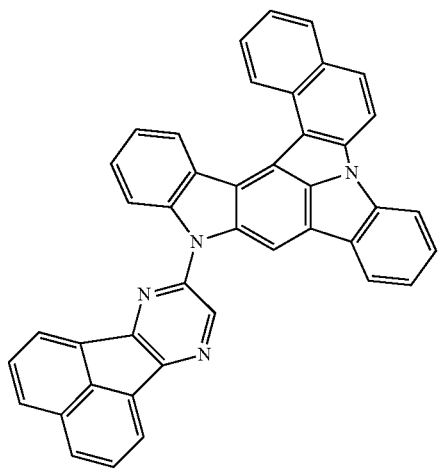
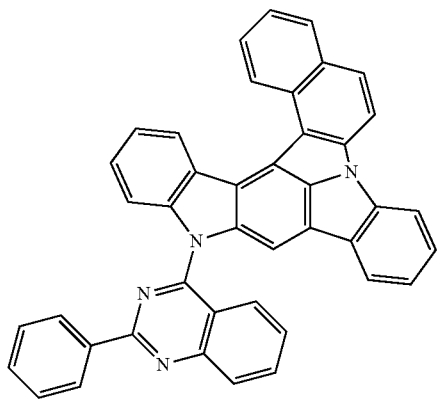
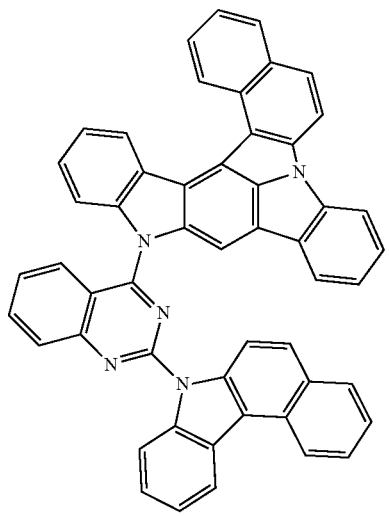

571
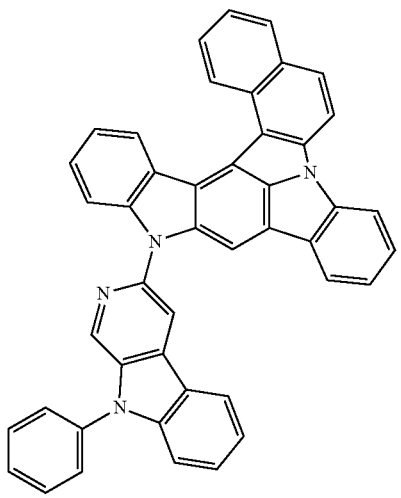
572
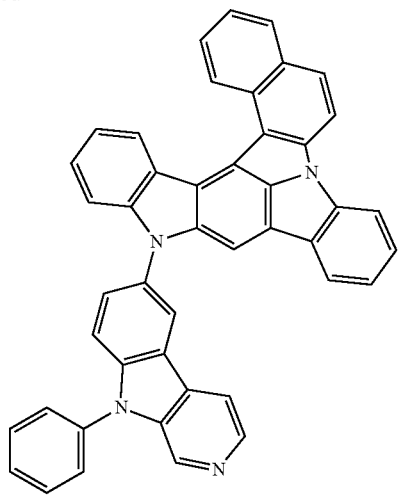
-continued
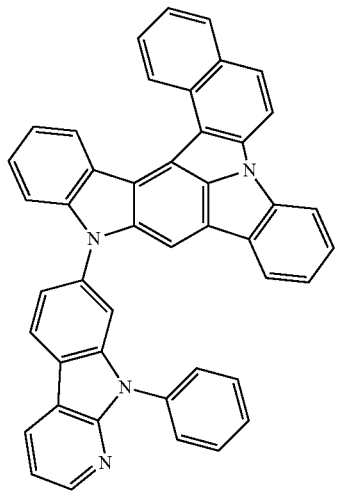
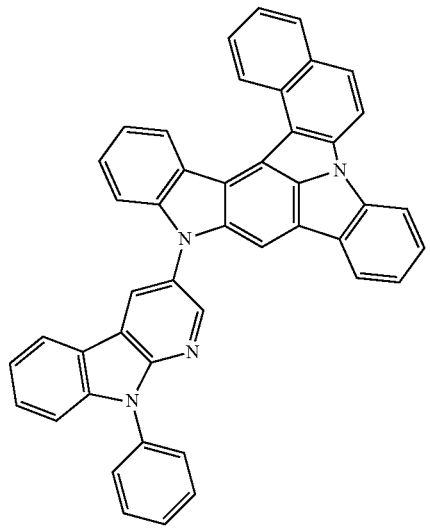
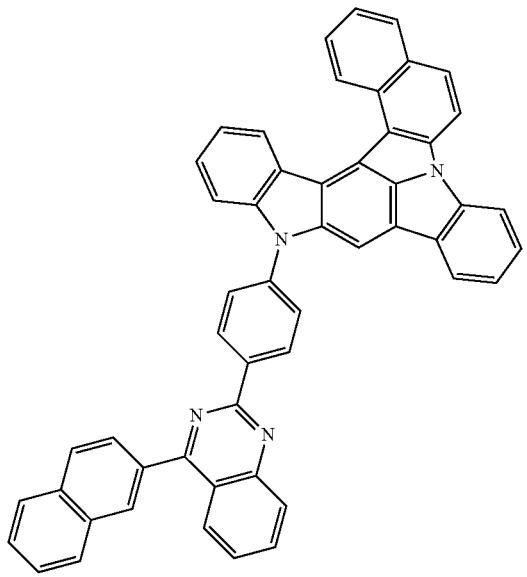
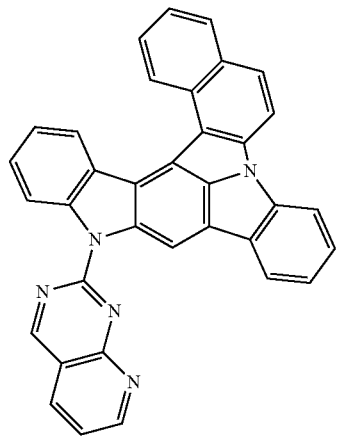

-continued
573
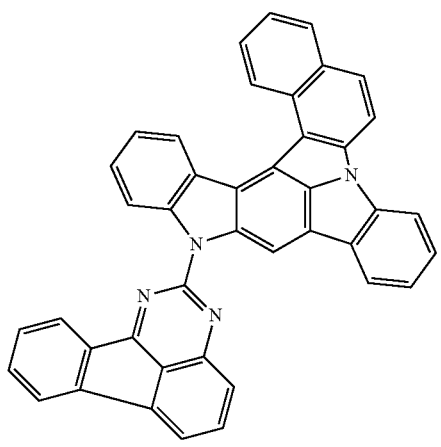
574
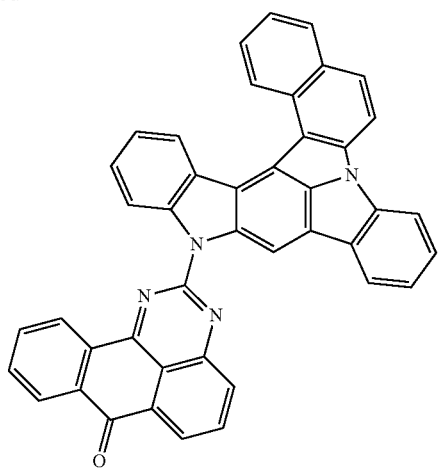
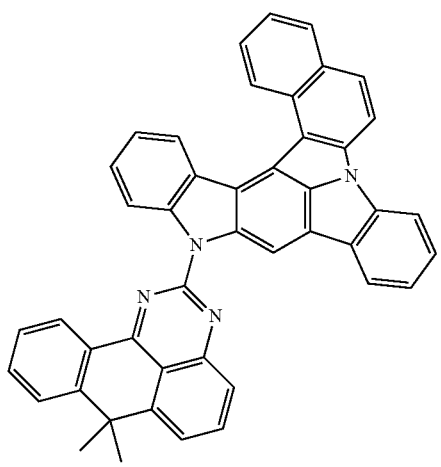
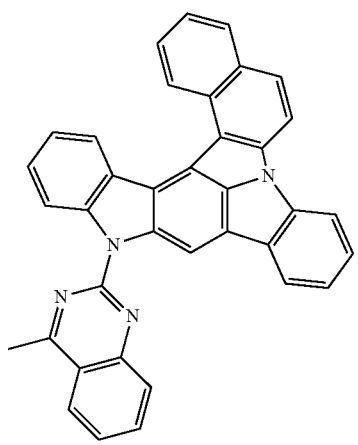
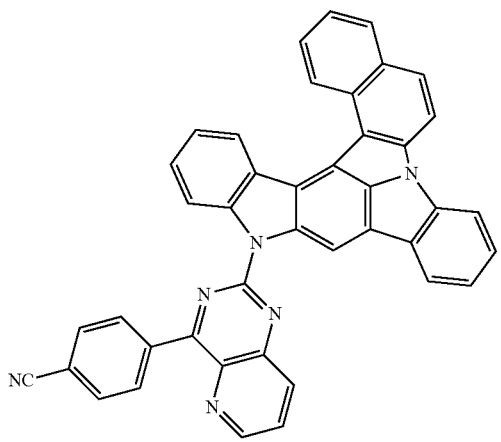
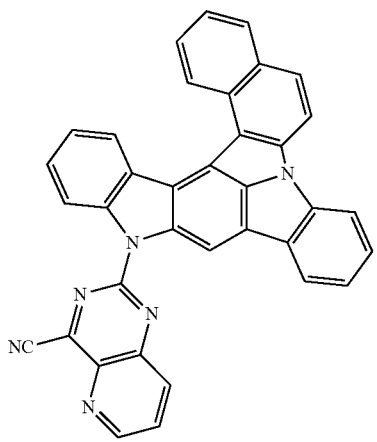

-continued
575
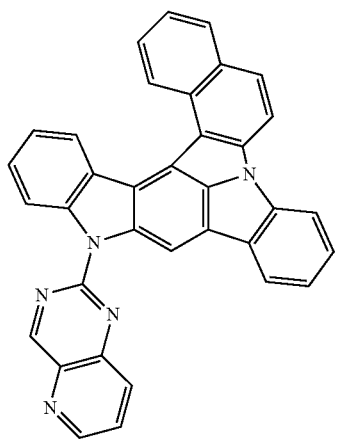
576
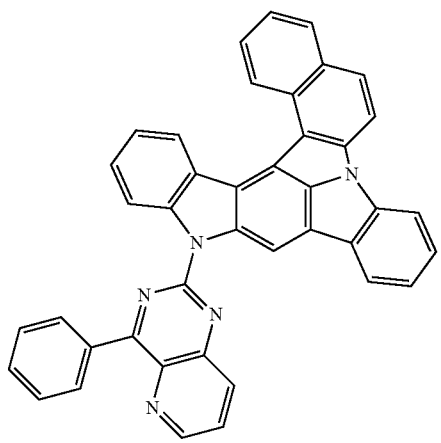
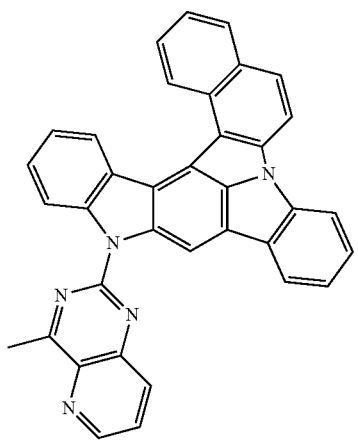
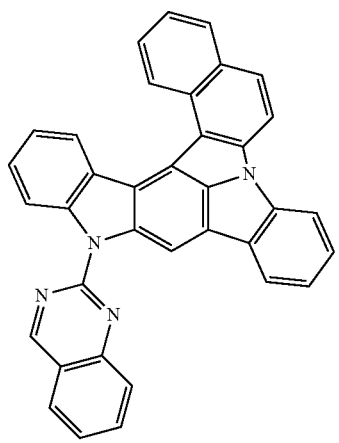
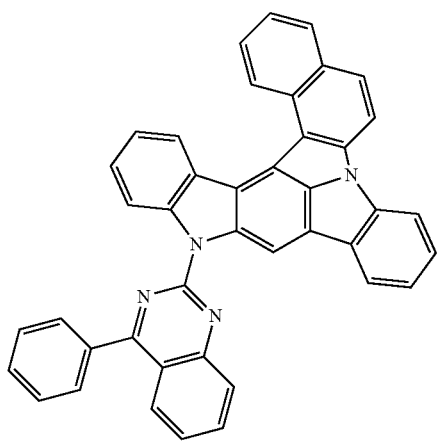
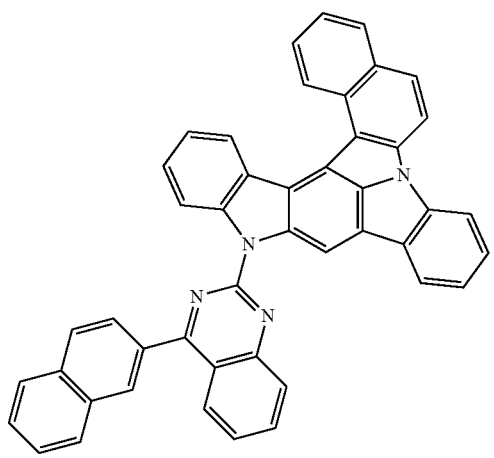

-continued
577 578
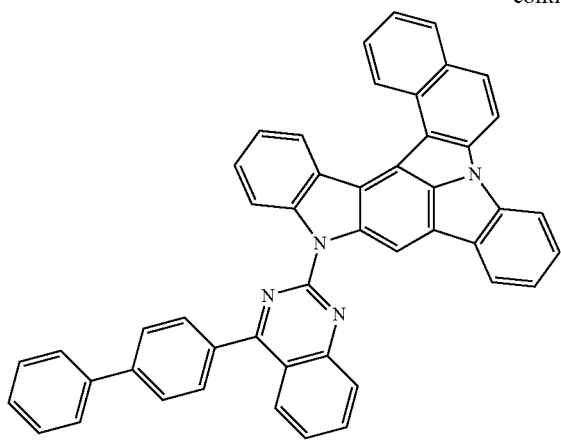 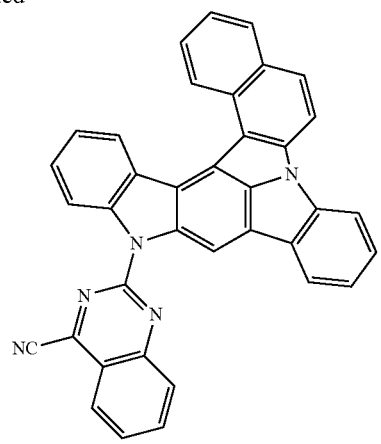
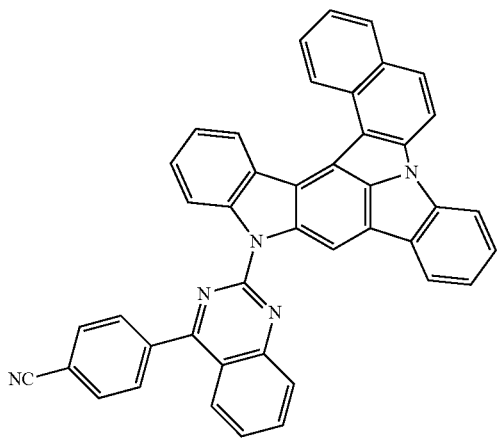 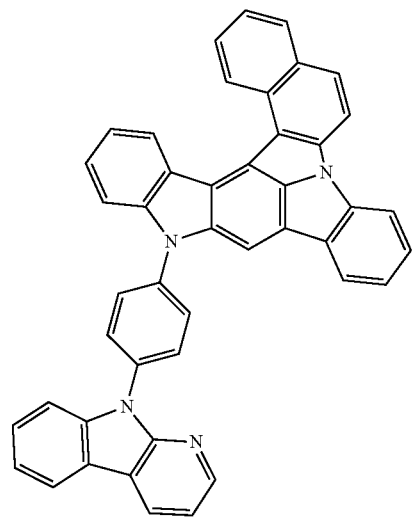
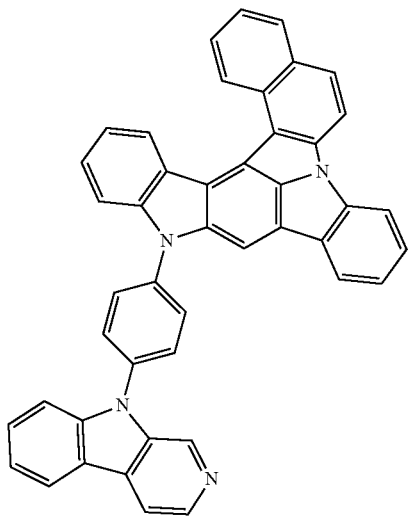 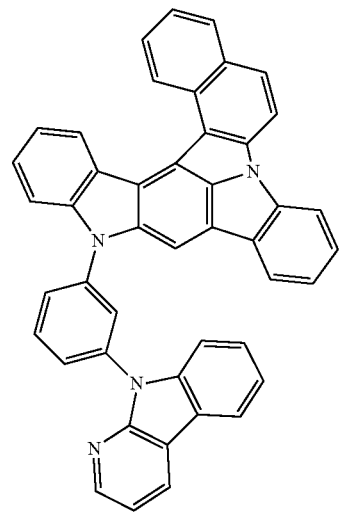

-continued
579
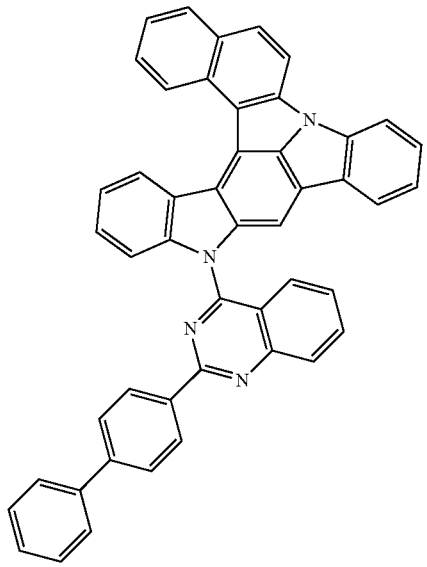
580
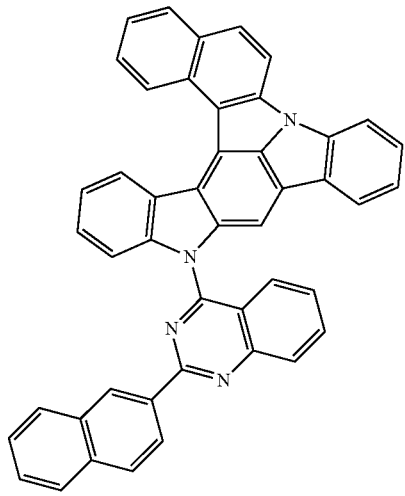
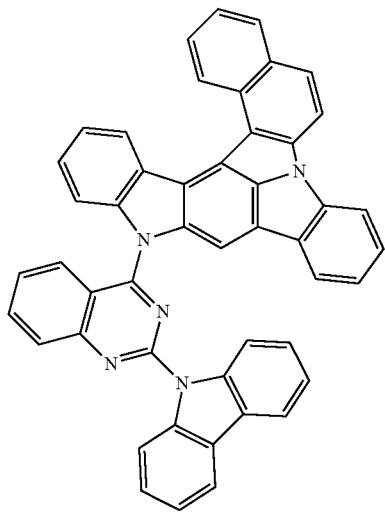
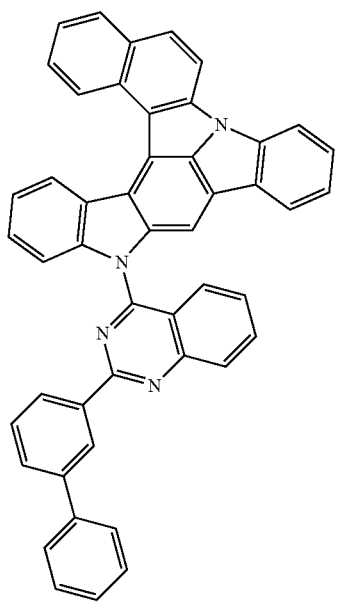
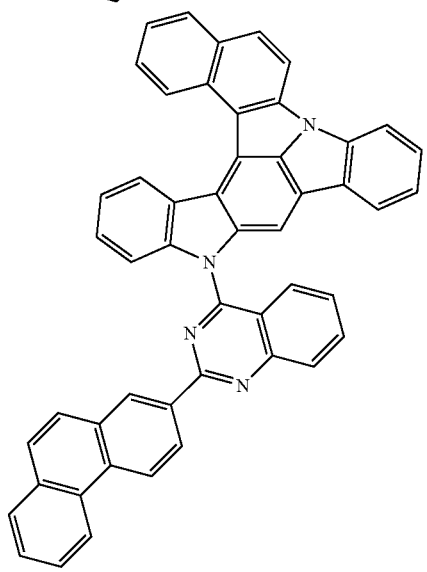

-continued
581 582
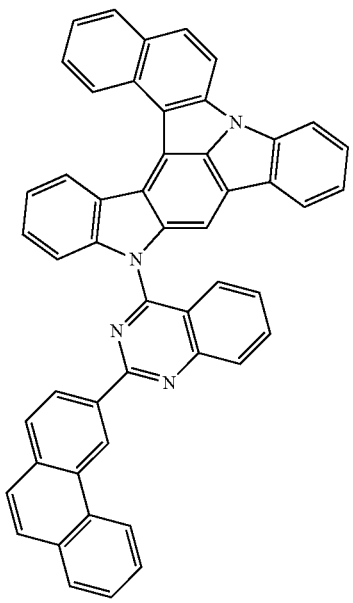
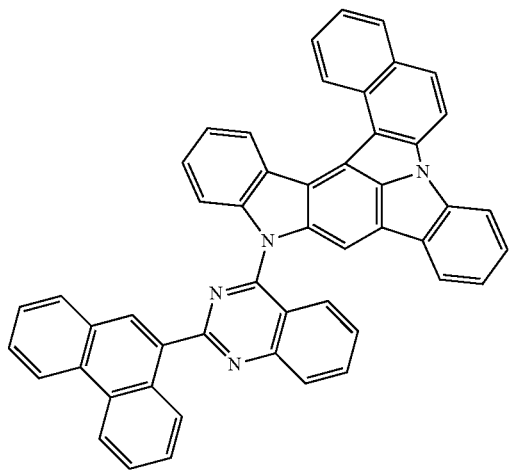
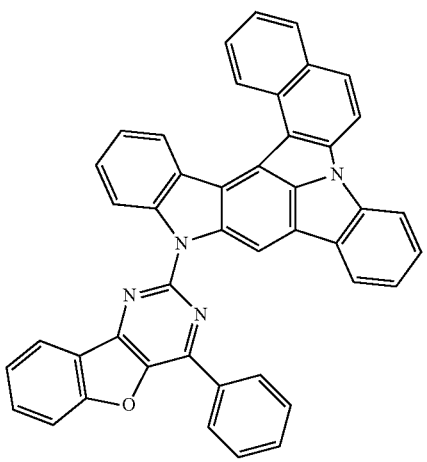
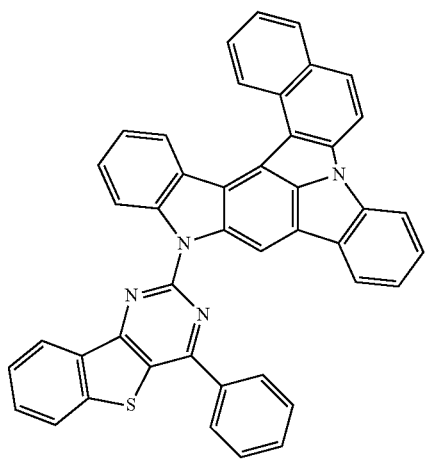
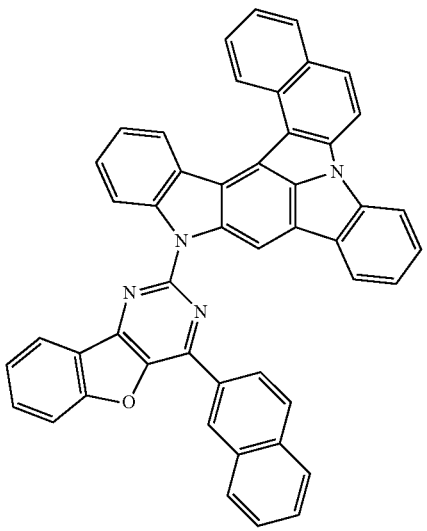
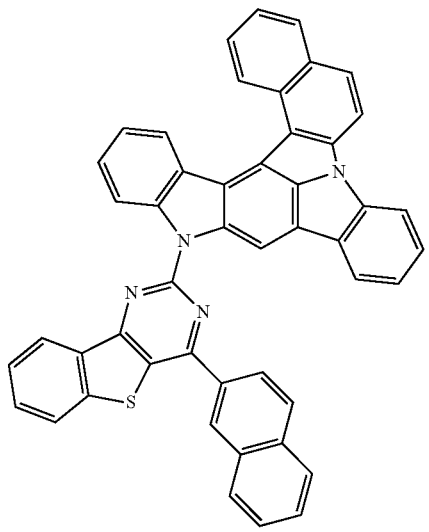

-continued
583
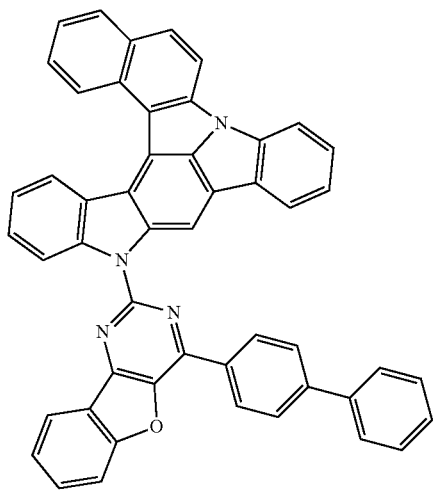
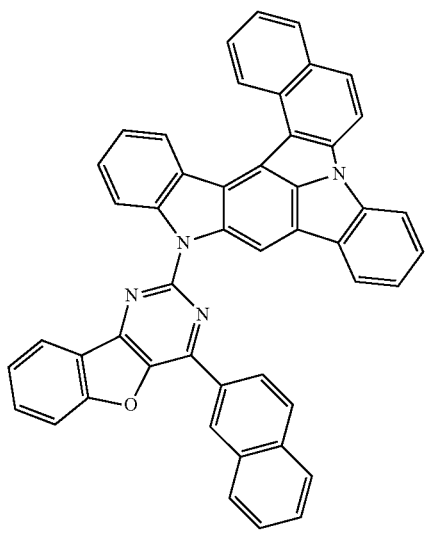
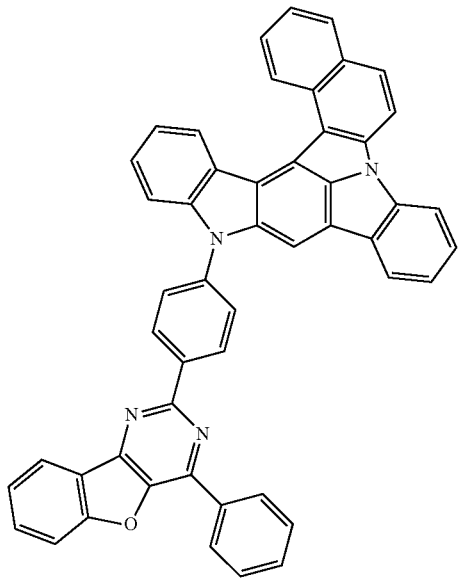
584
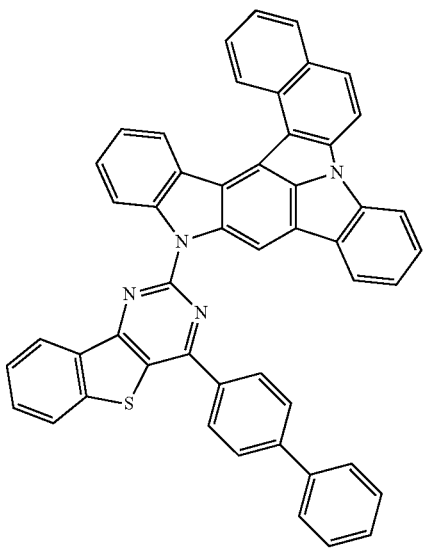
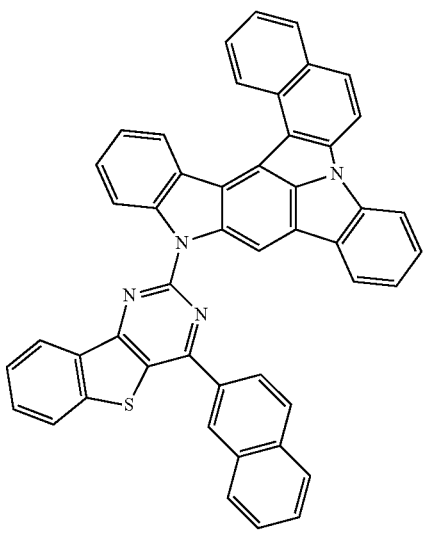
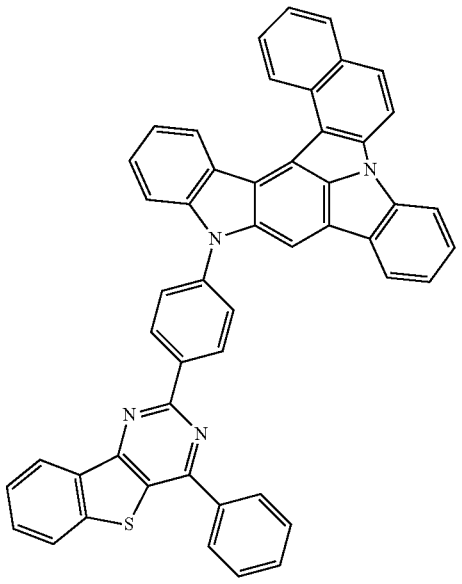

-continued
585
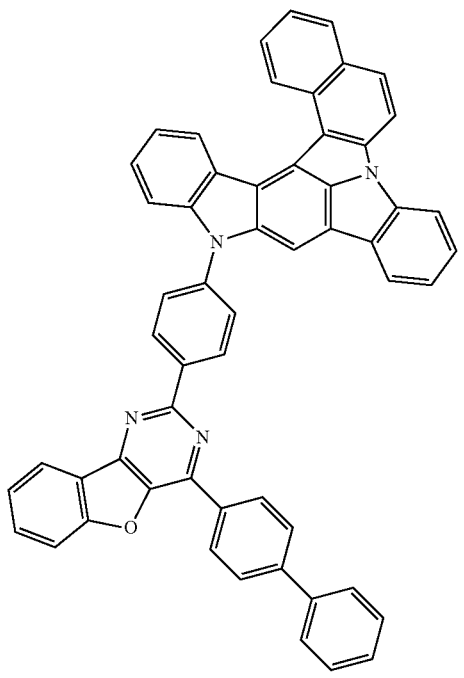
586
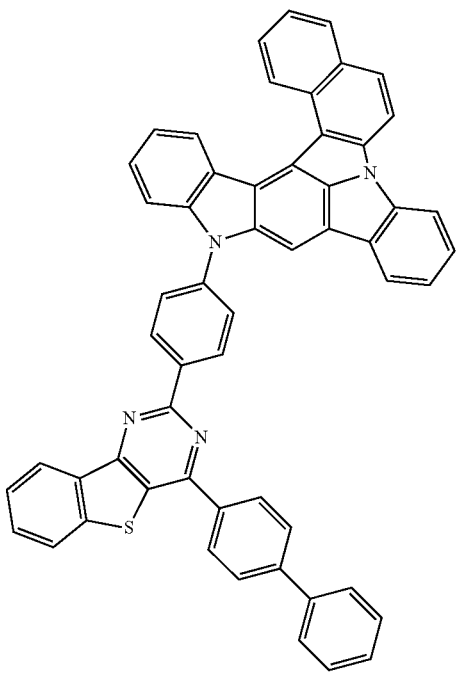
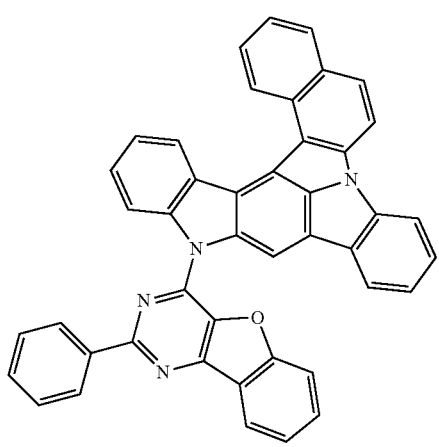
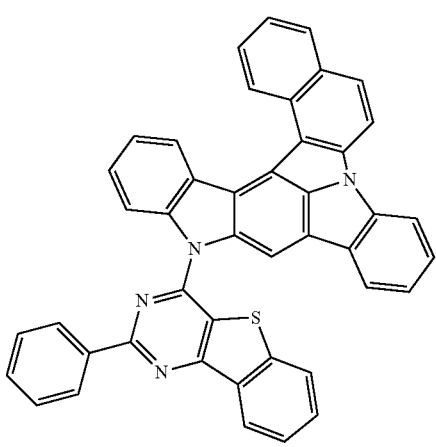
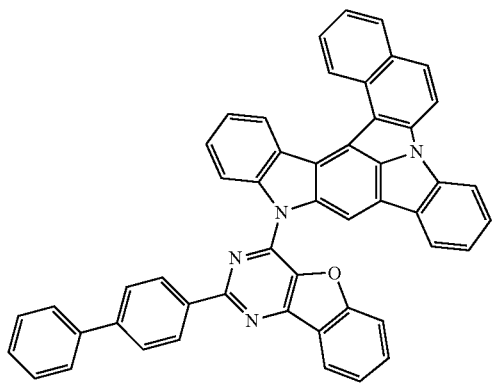
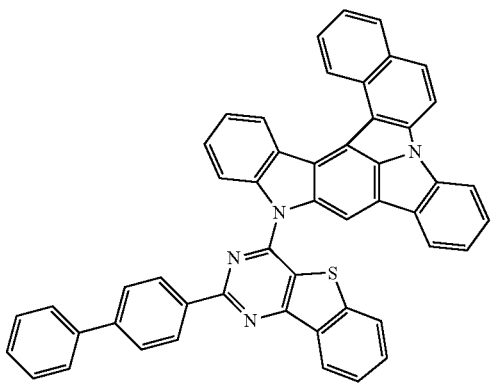

587 588
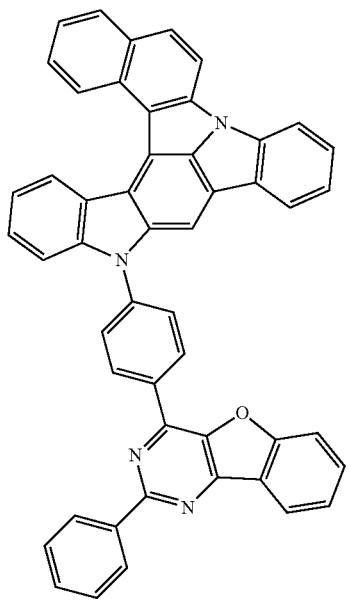
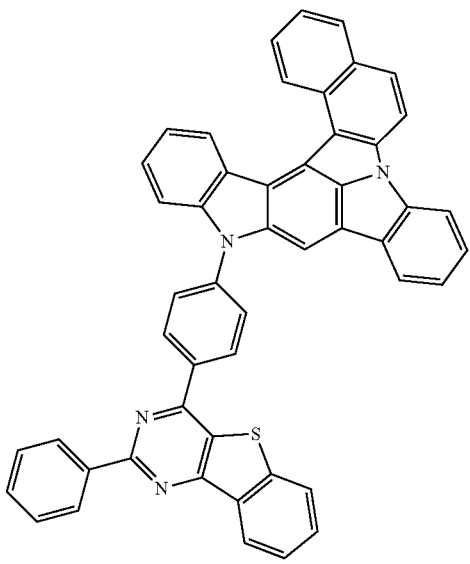
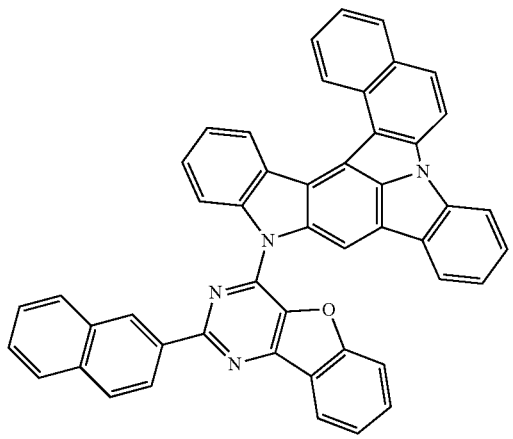
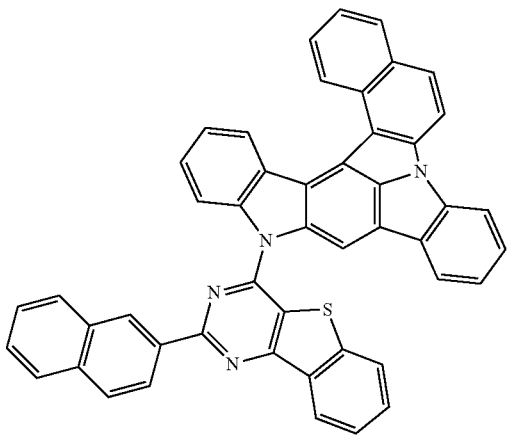
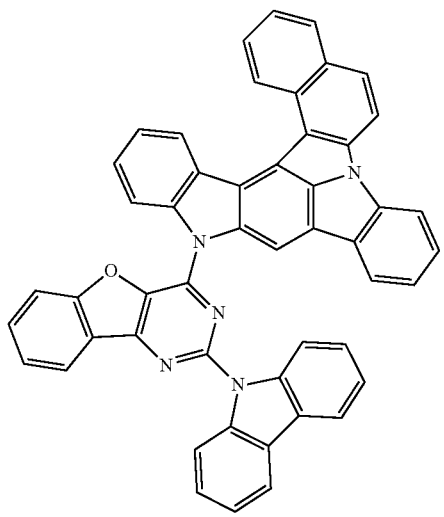
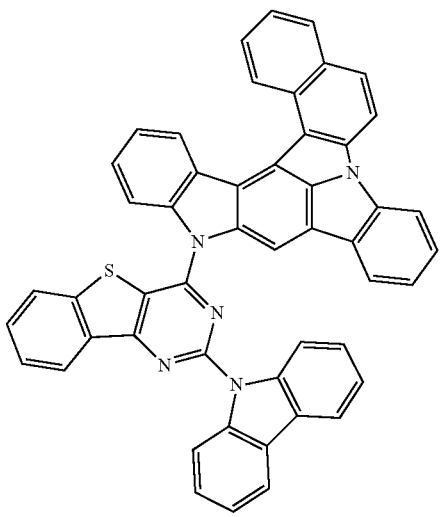

| 589 | 590 |
|---|---|
| 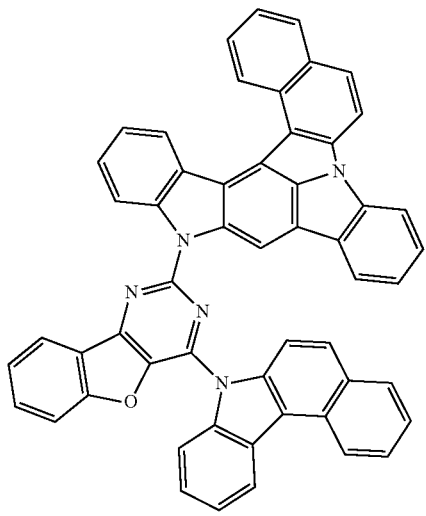 | 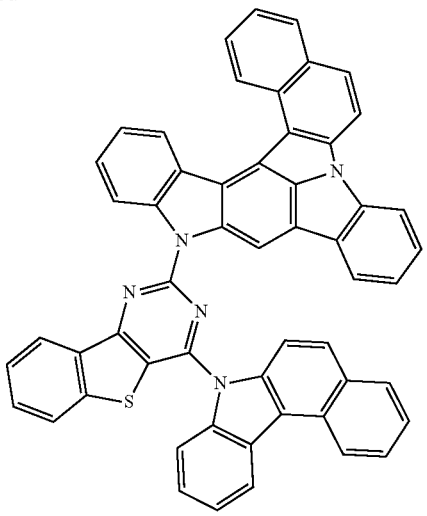 |
| 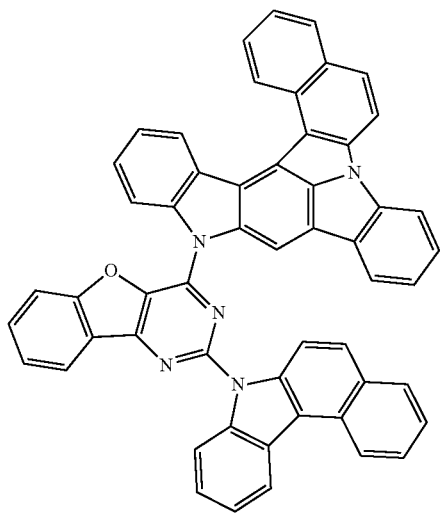 | 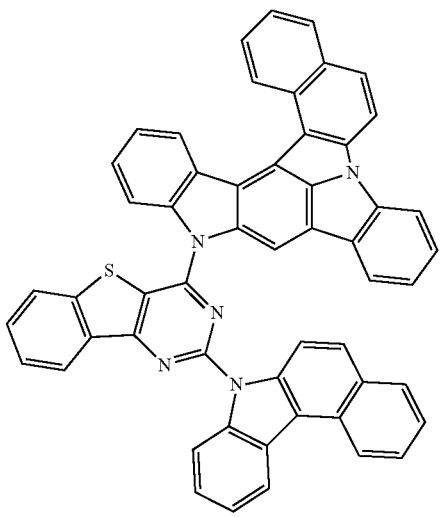 |
| 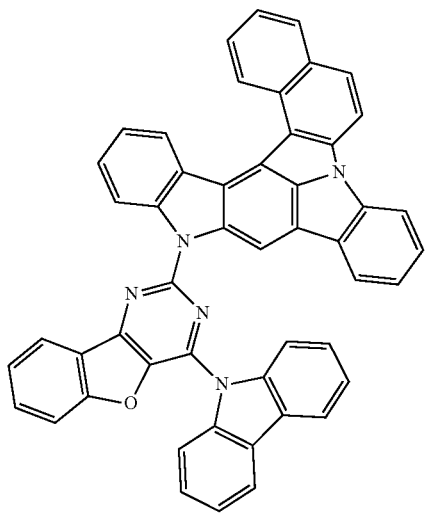 | 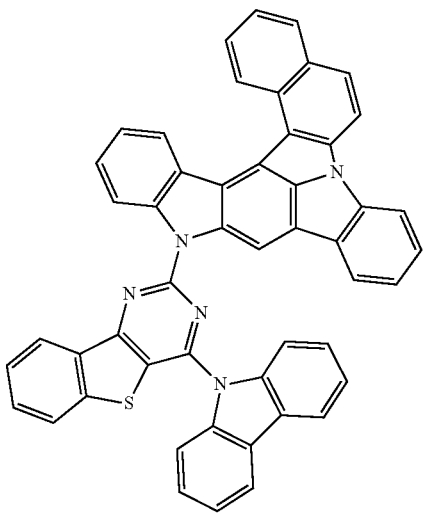 |

-continued
591
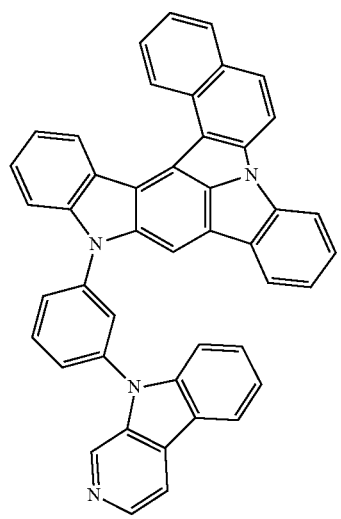
592
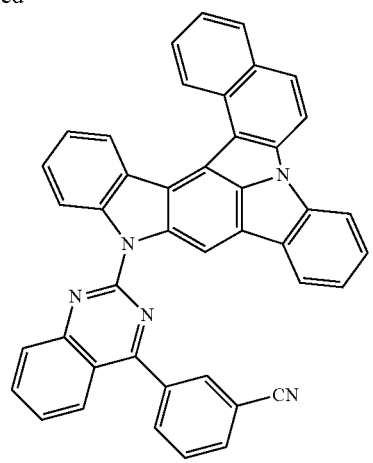
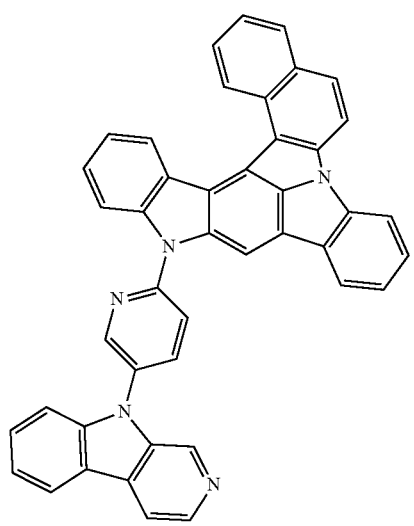
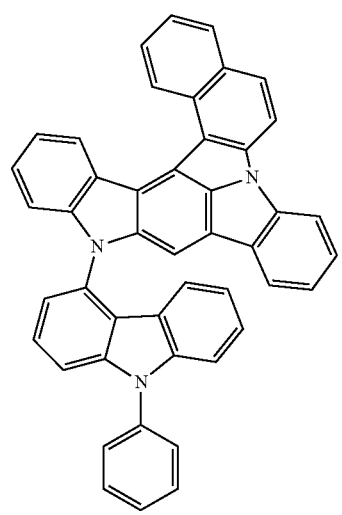
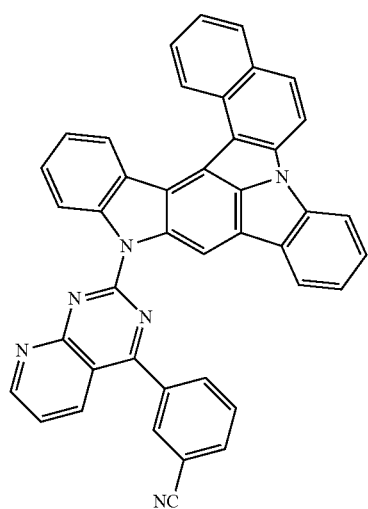
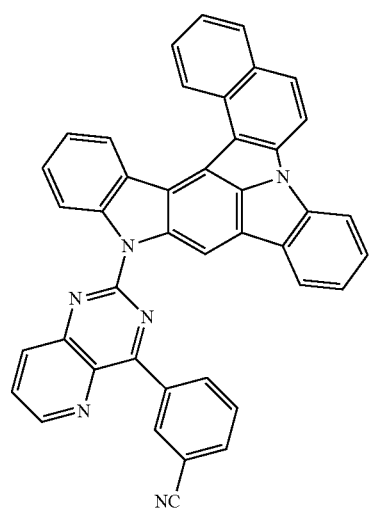

593
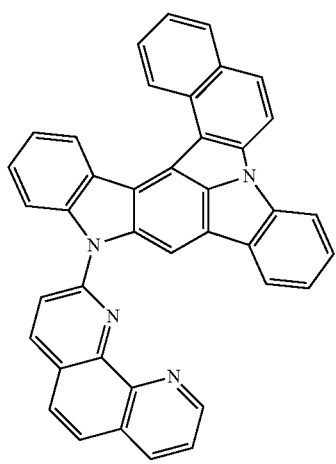
594
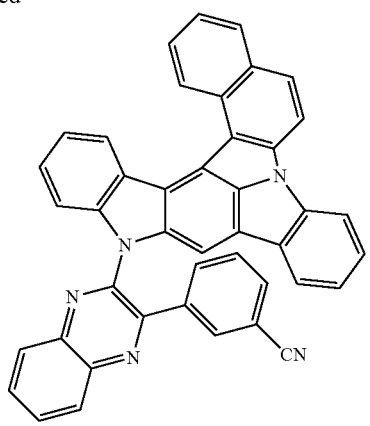
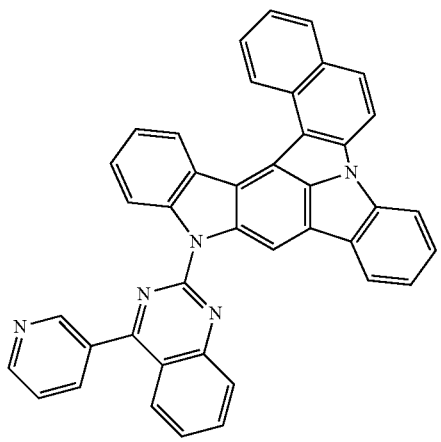
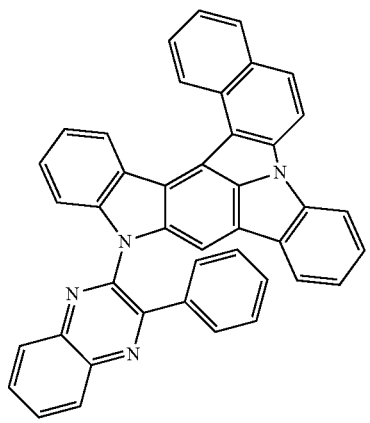
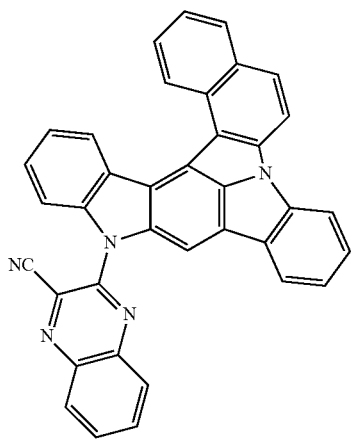
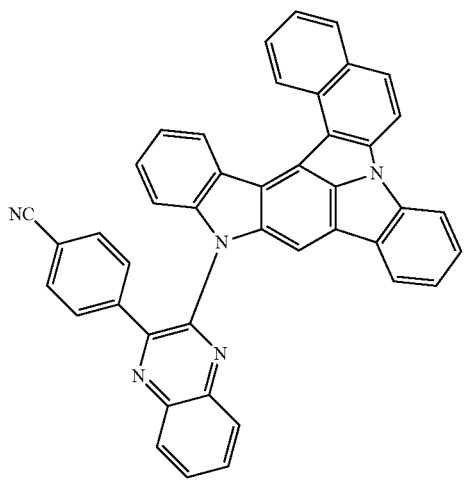

595 596
-continued
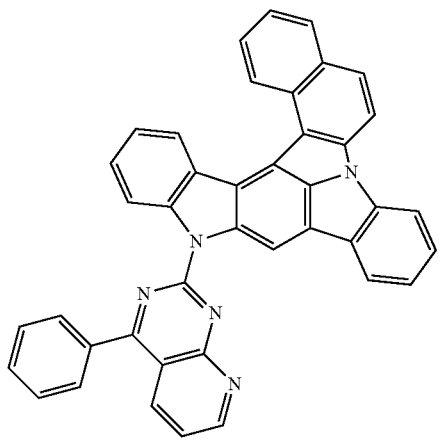
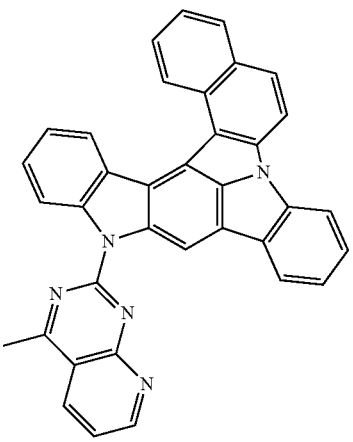
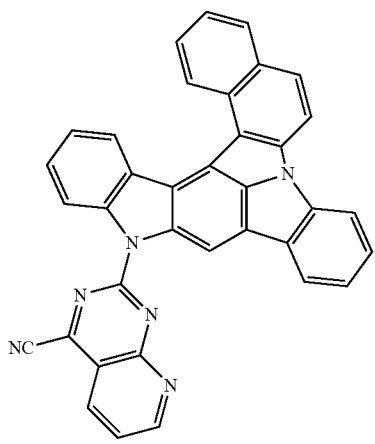
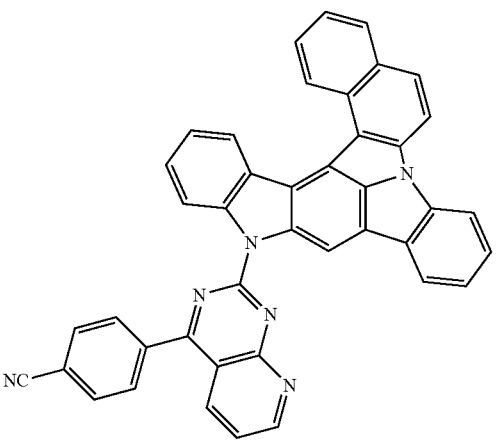
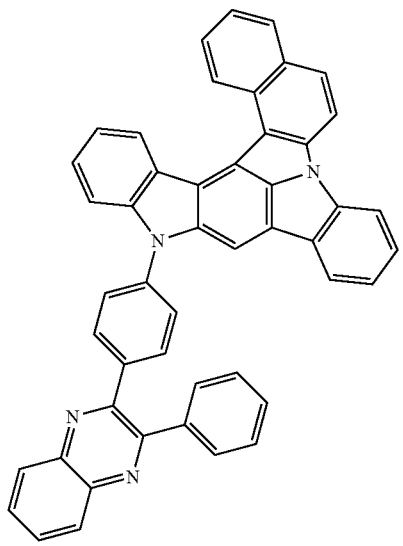
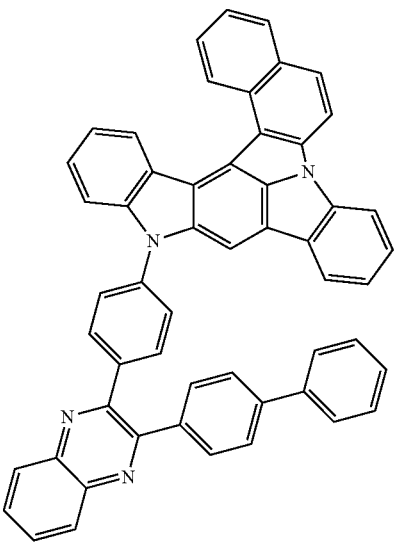

597
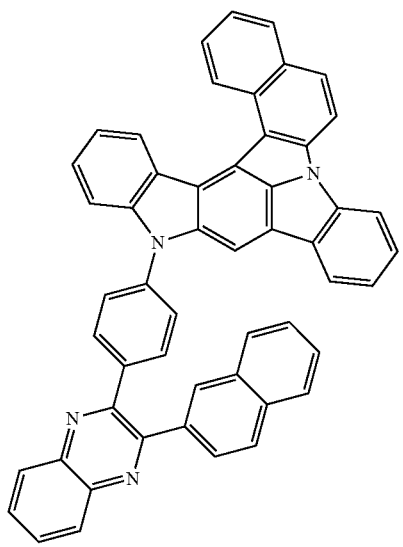
598
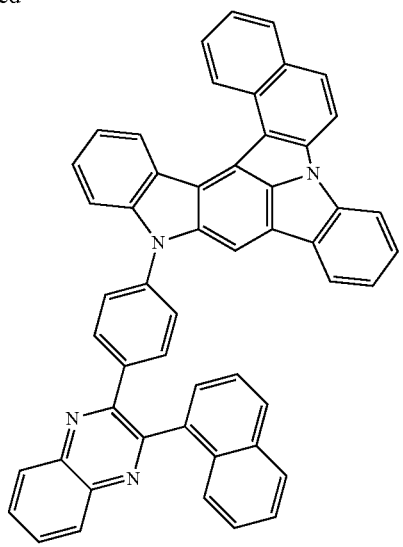
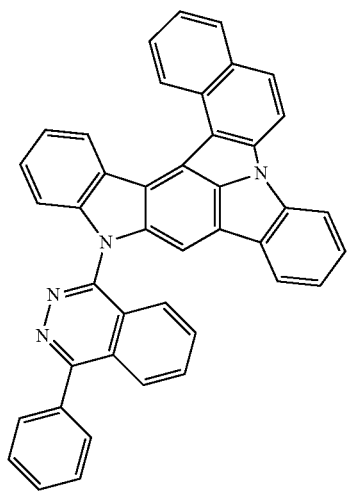
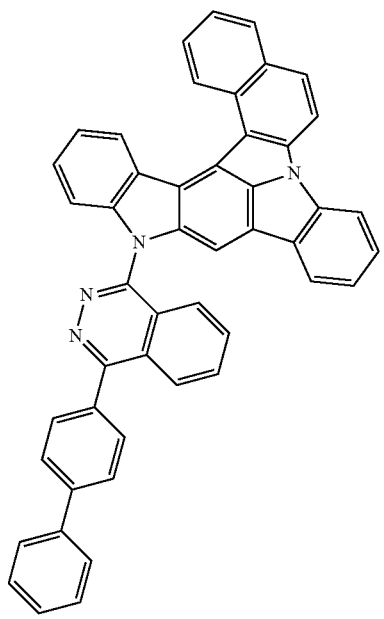

599
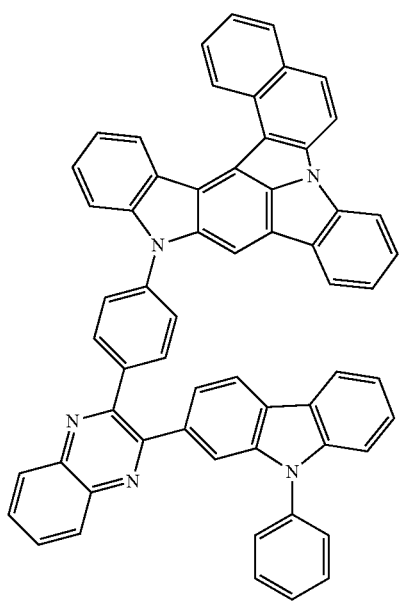
600
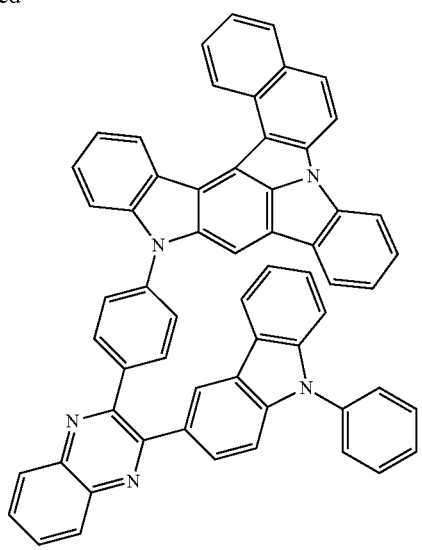
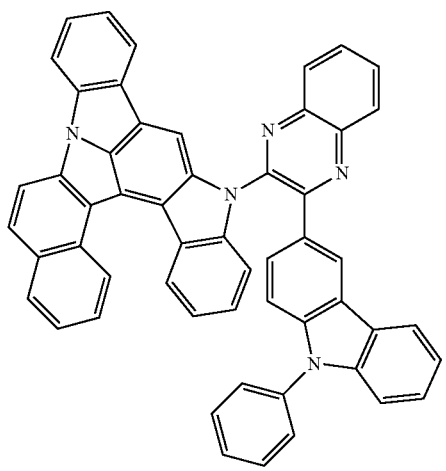
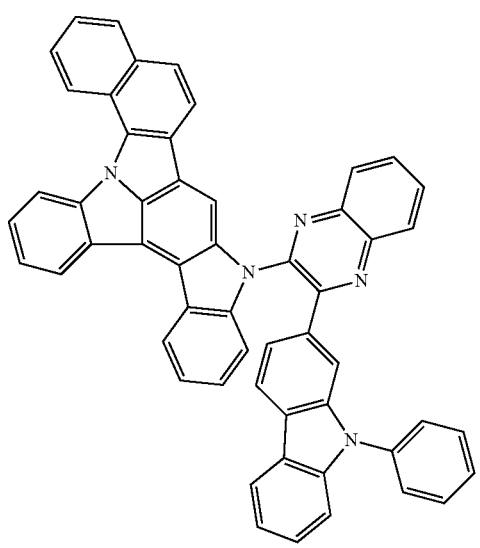

-continued
601
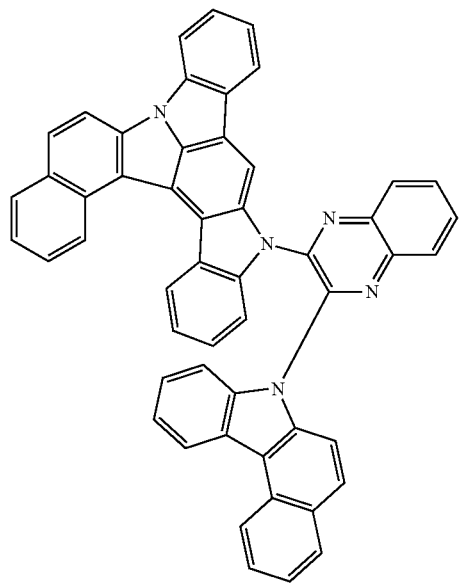
602
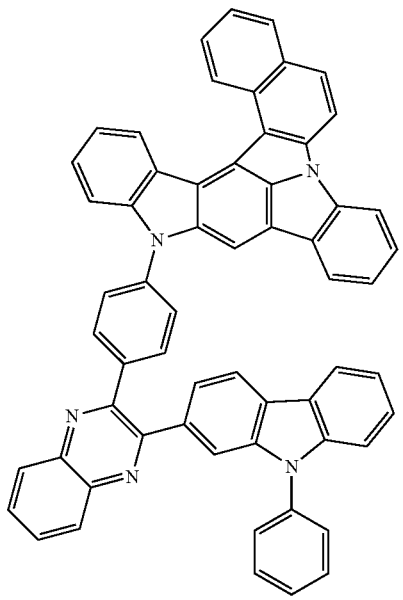
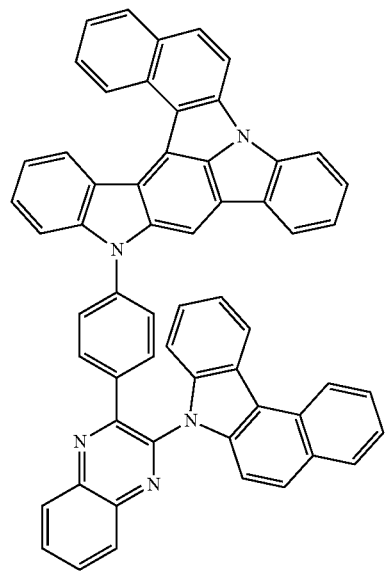
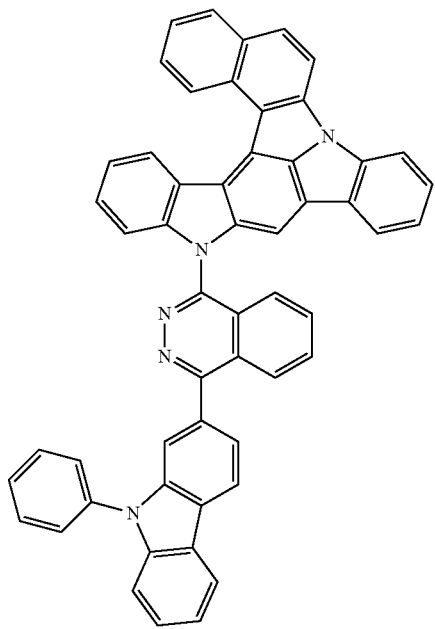

-continued
603
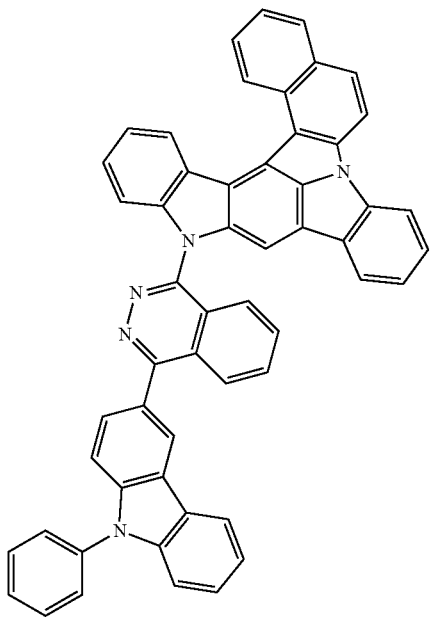
604
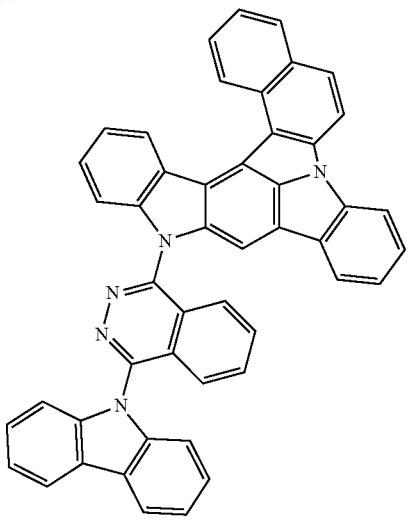
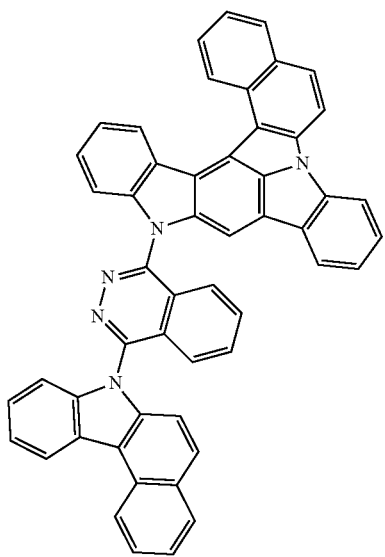
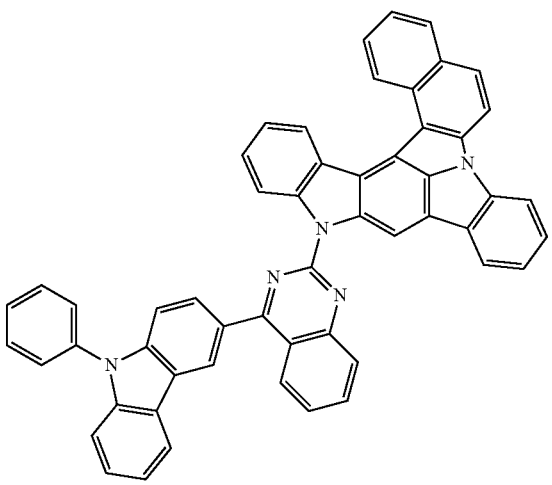
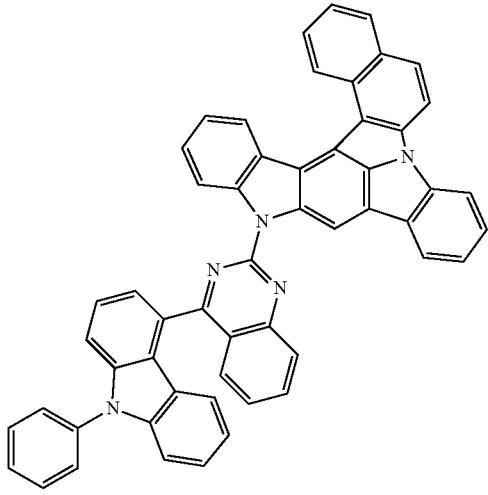
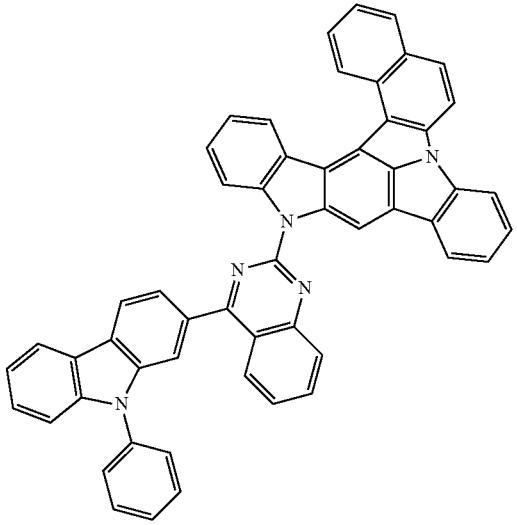

605
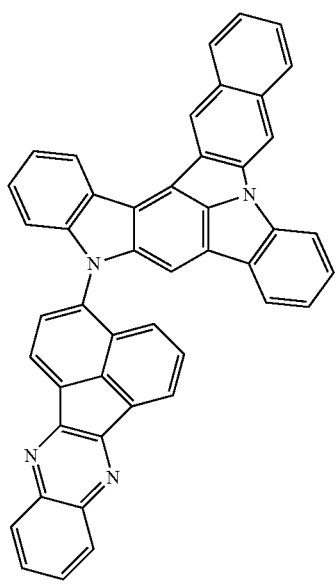
606
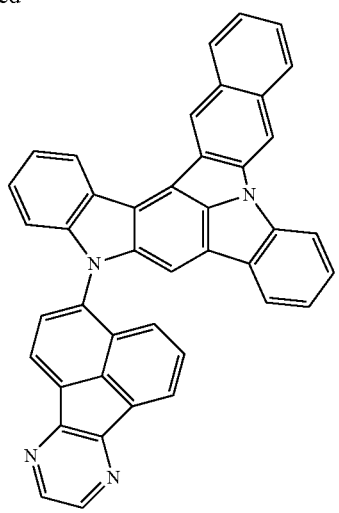
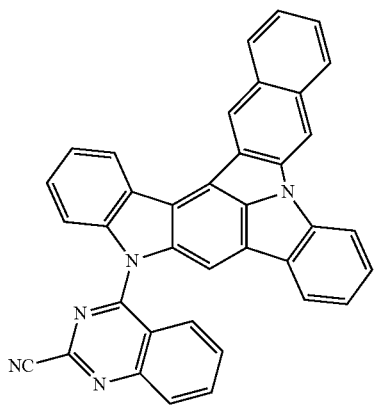
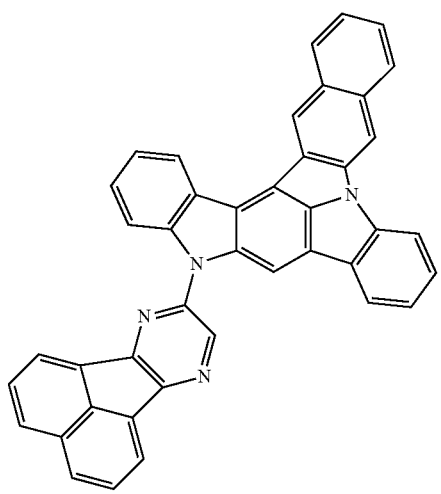
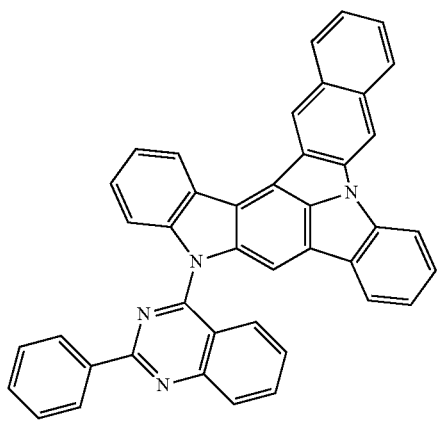
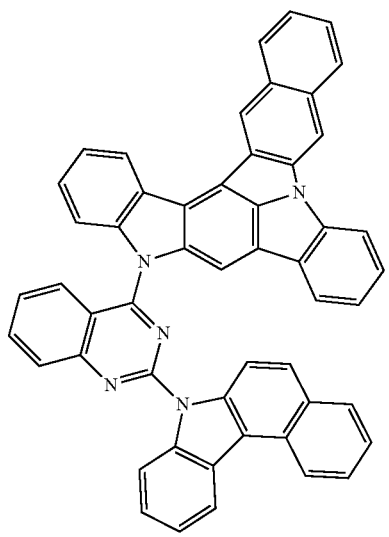

-continued
| 607 | 608 |
|---|---|
| 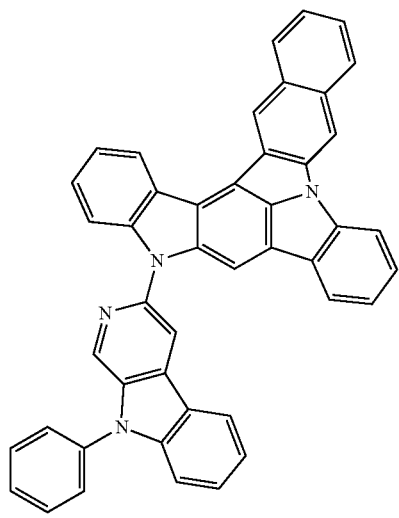 | 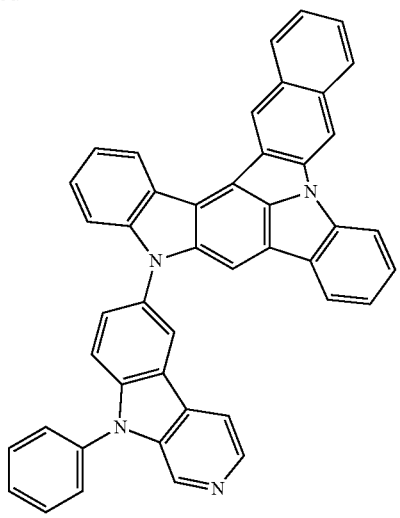 |
| 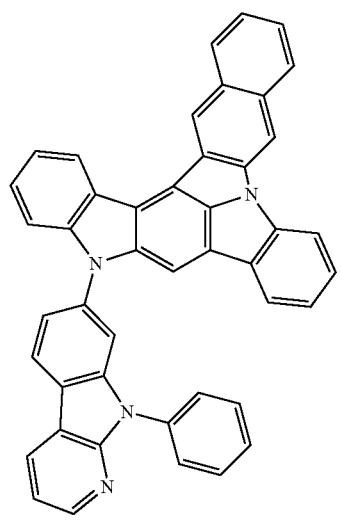 | 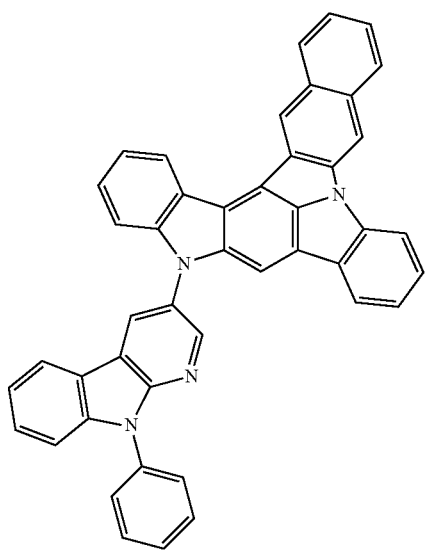 |
| 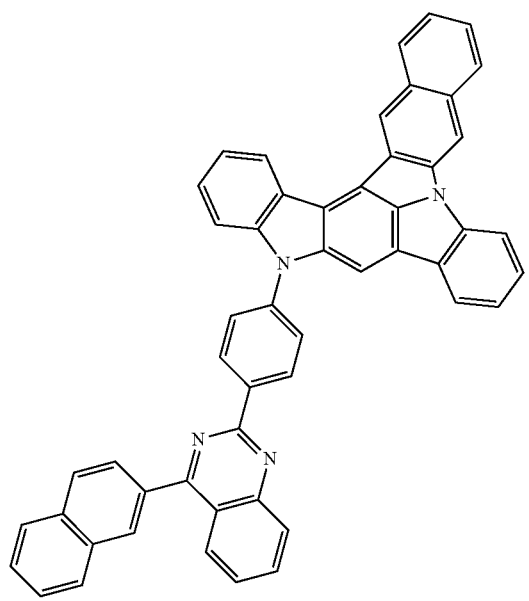 | 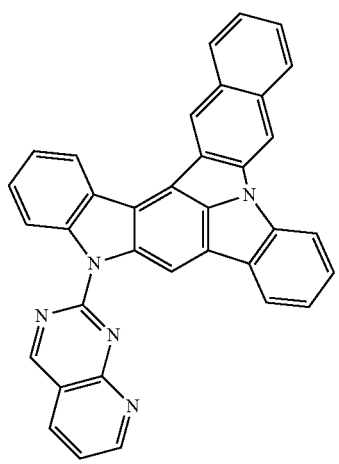 |

-continued
609 610
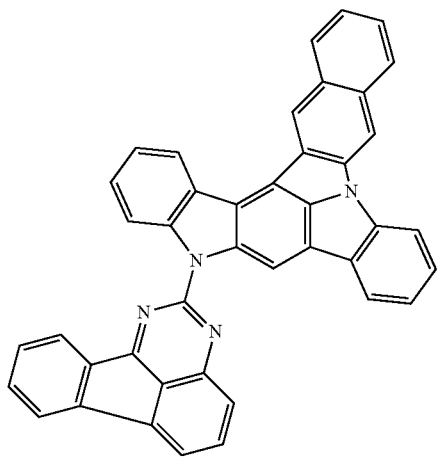 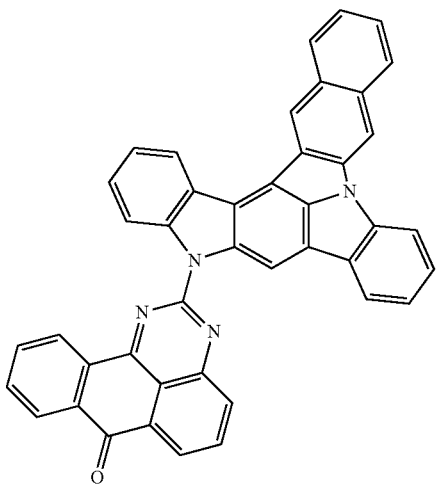
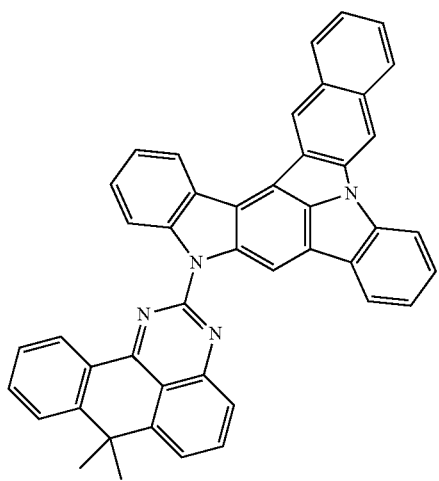 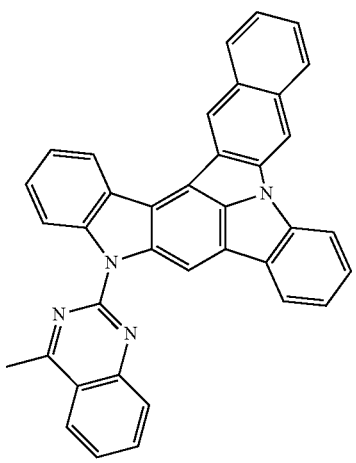
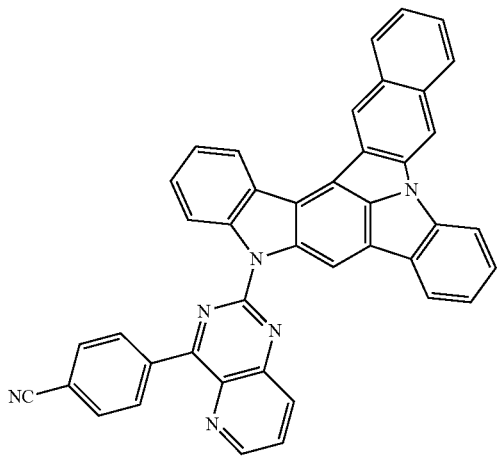 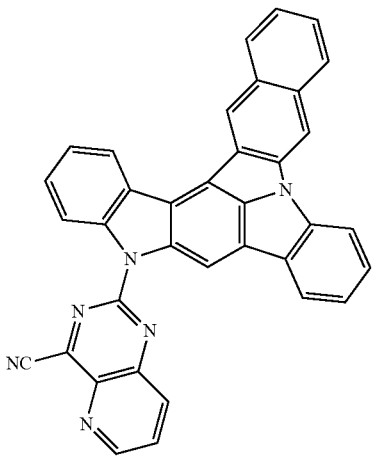

611
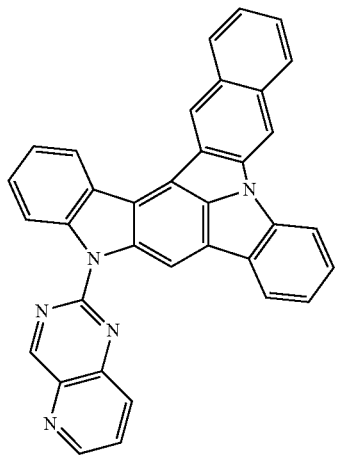
612
-continued
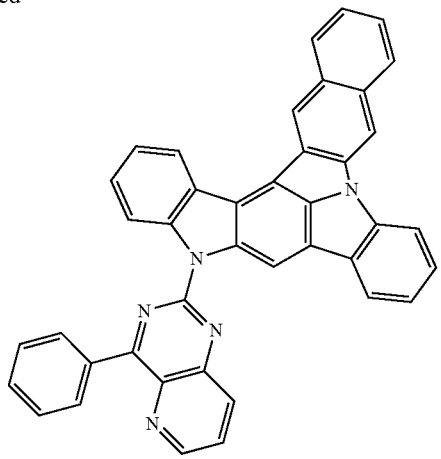
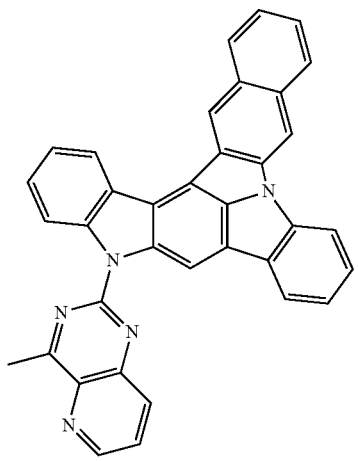
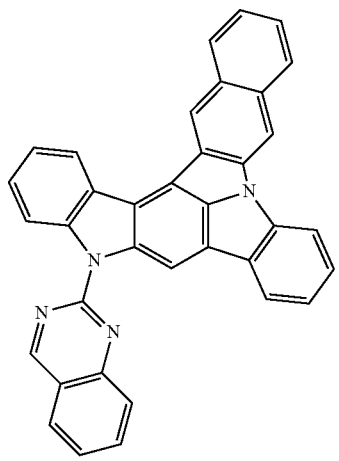
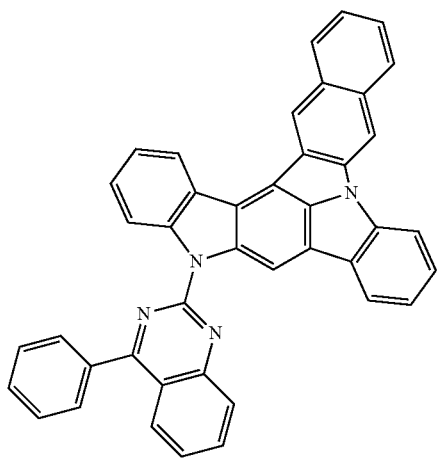
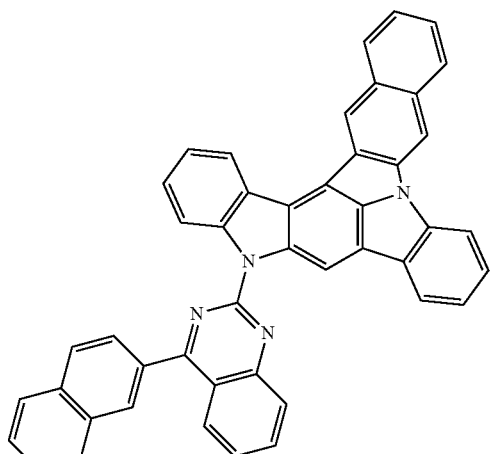

613
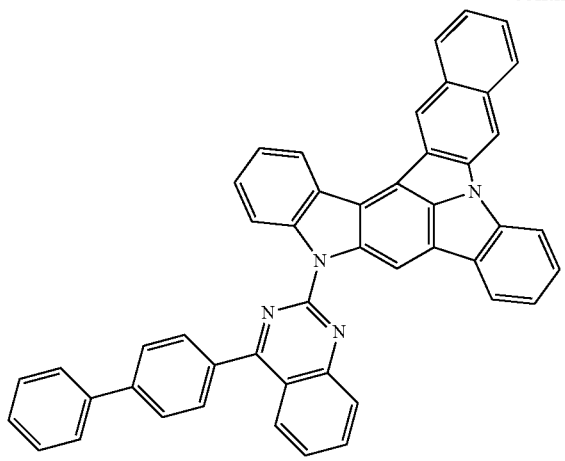
614
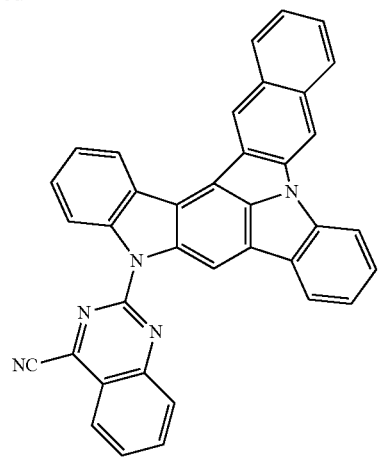
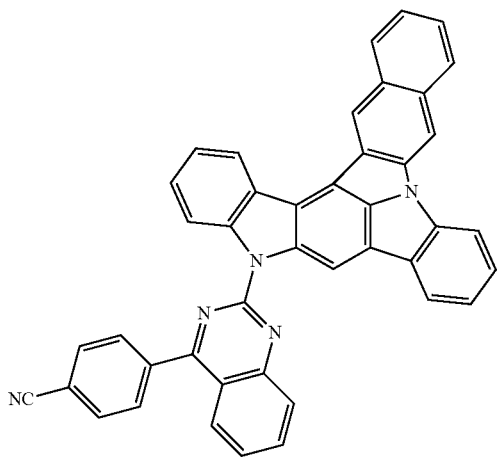
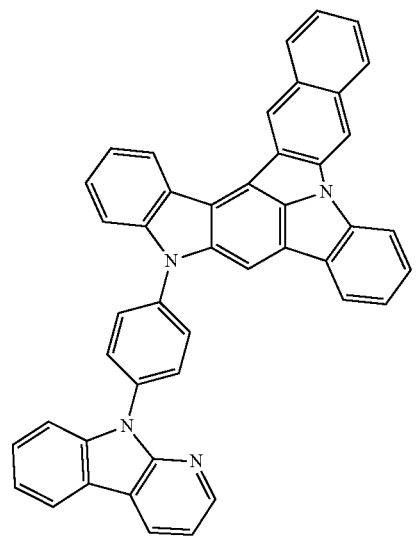
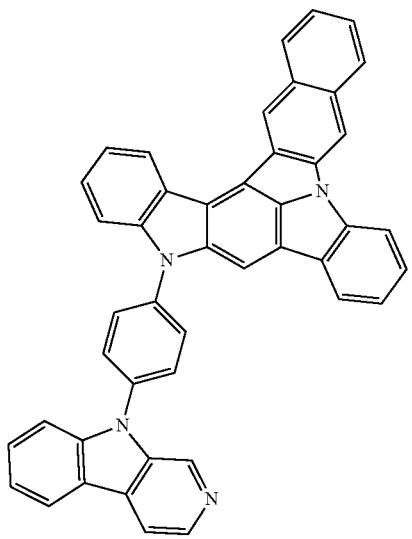
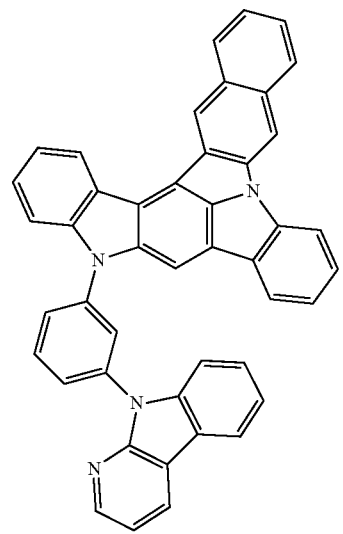

615
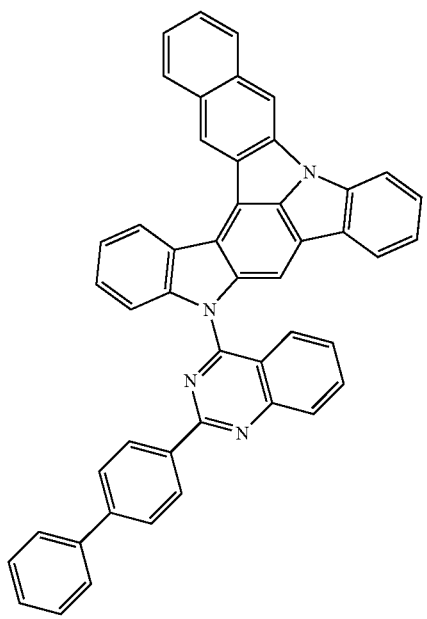
616
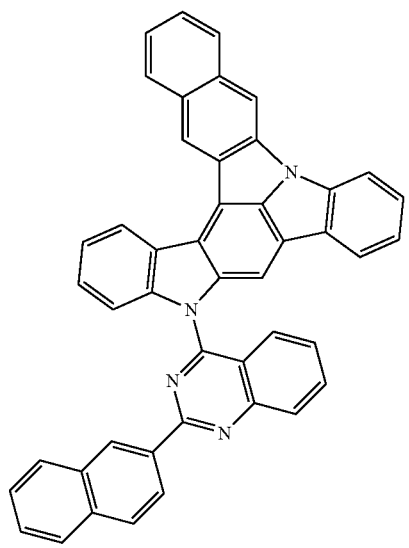
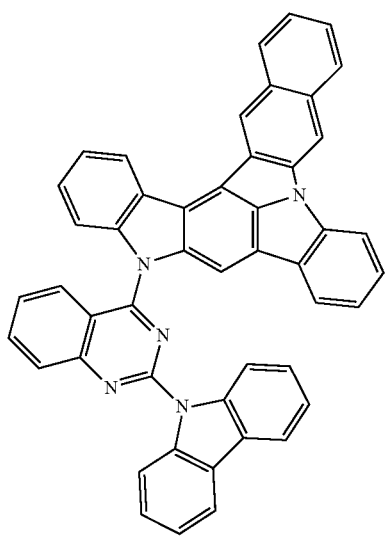
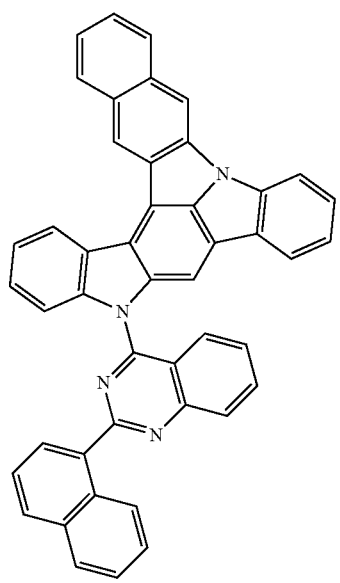

-continued
617
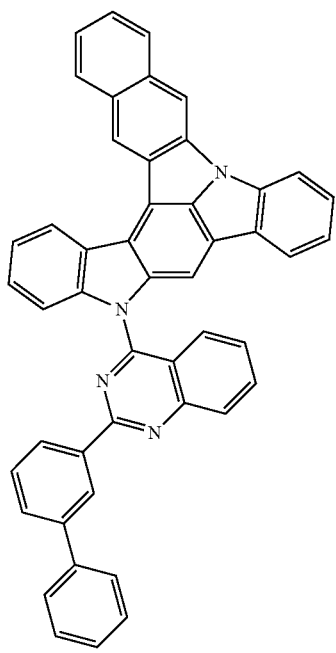
618
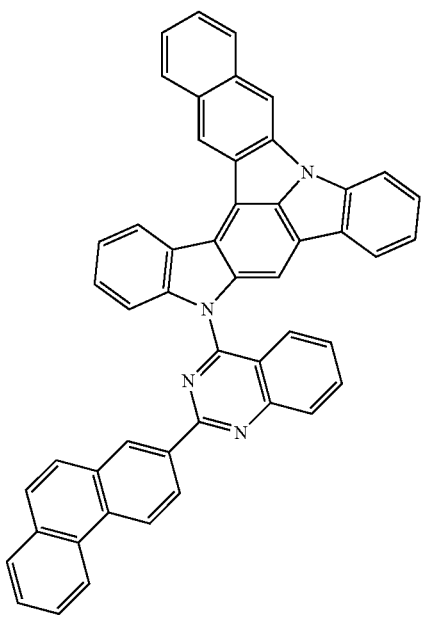
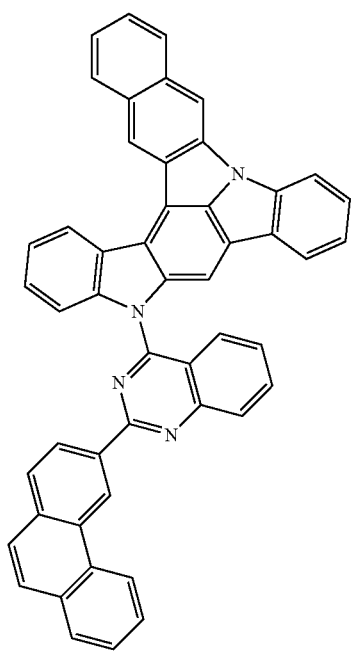
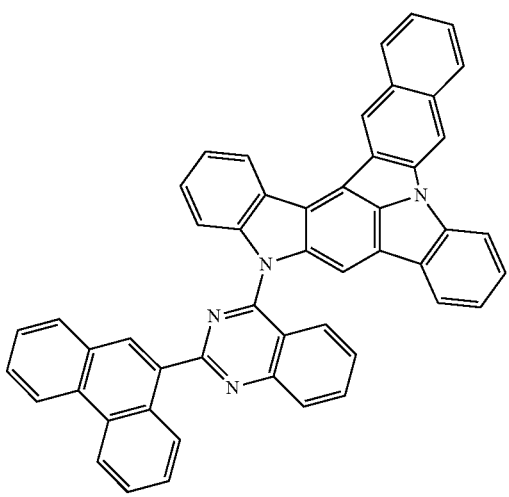

-continued
619
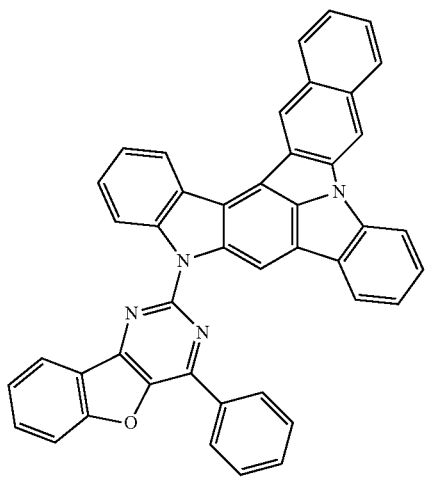
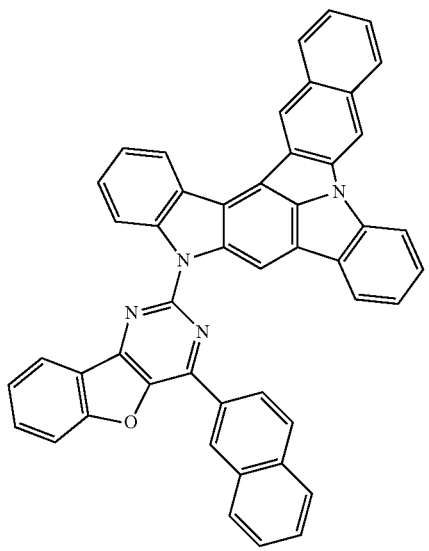
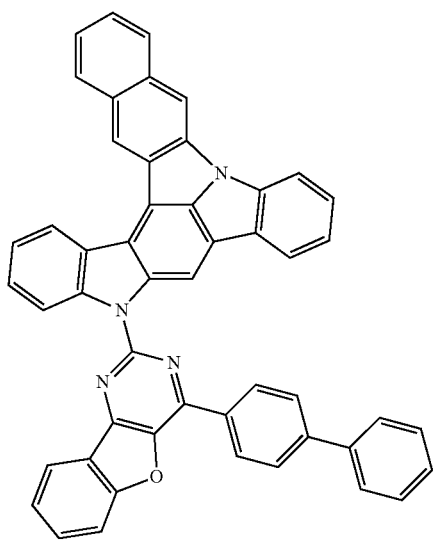
620
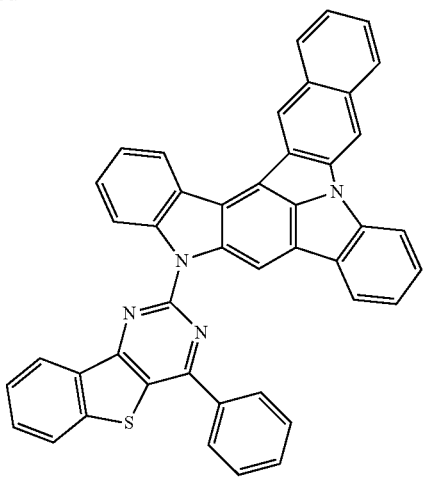
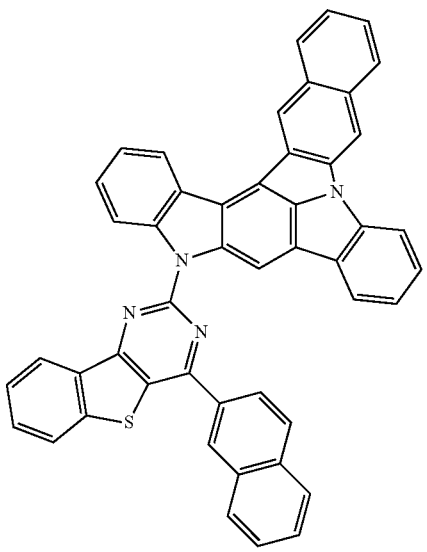
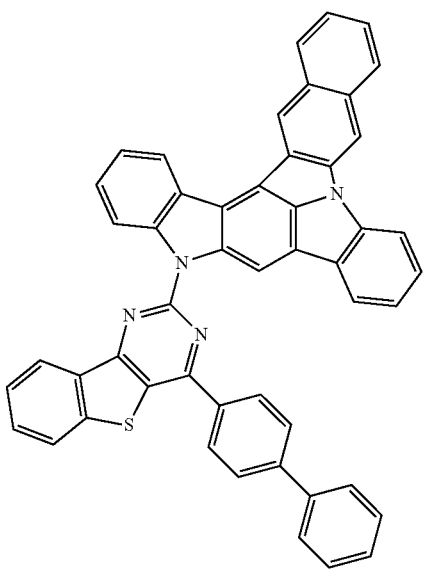

621 622
-continued
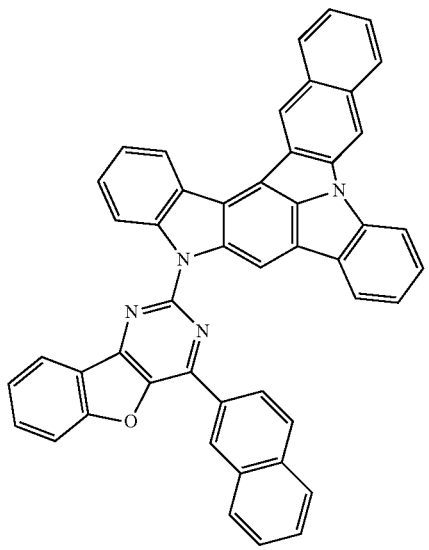
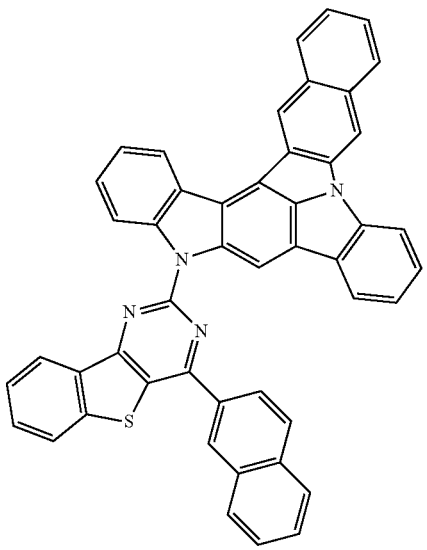
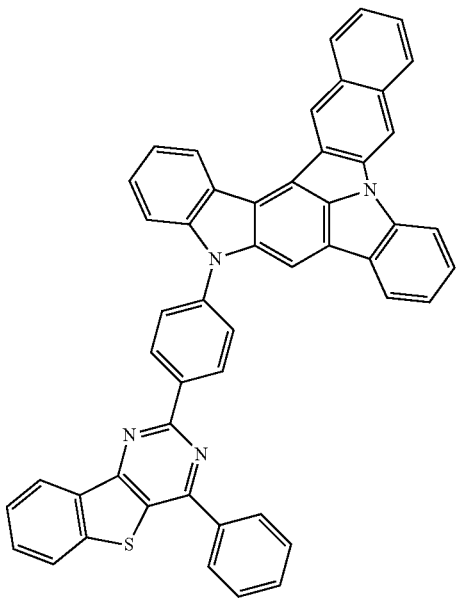

-continued
| 623 | 624 |
|---|---|
| 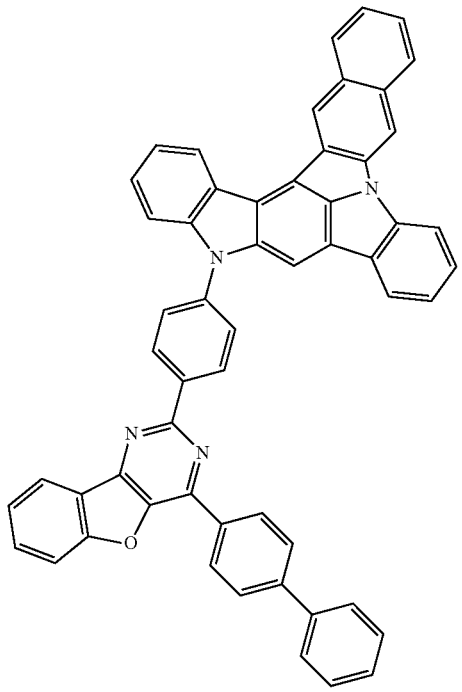 | 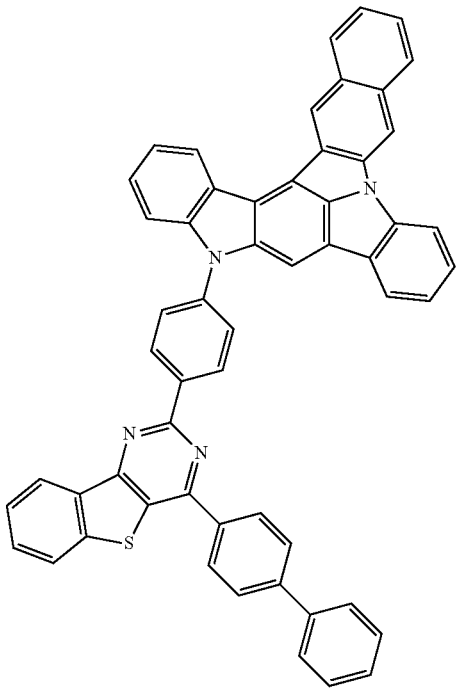 |
| 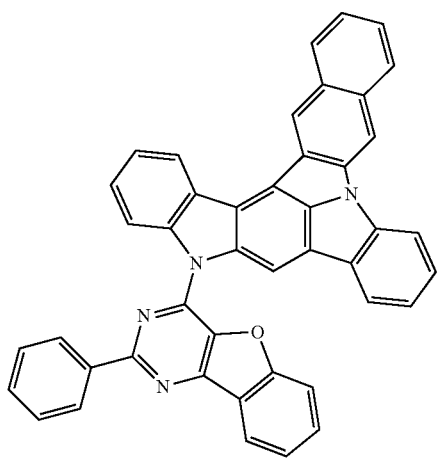 | 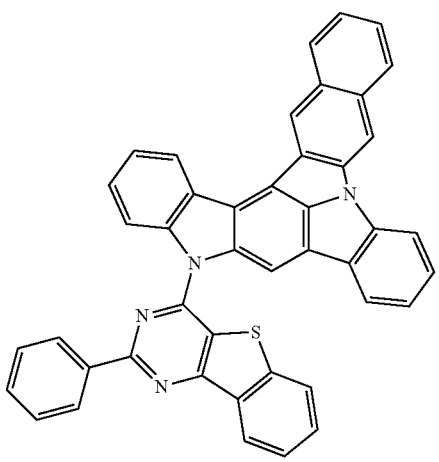 |
| 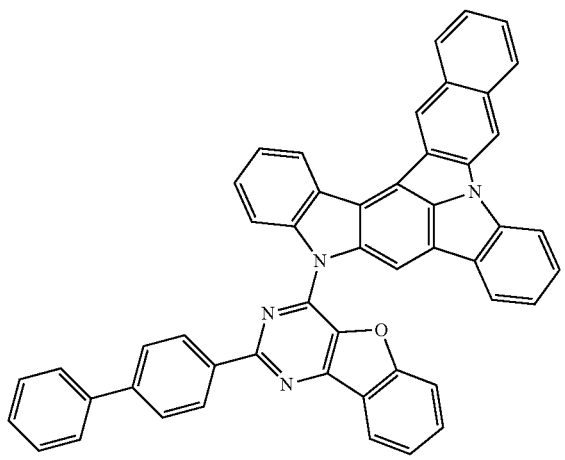 | 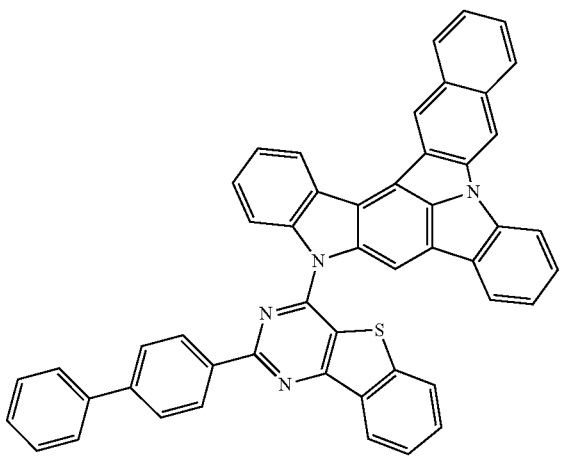 |

-continued
625
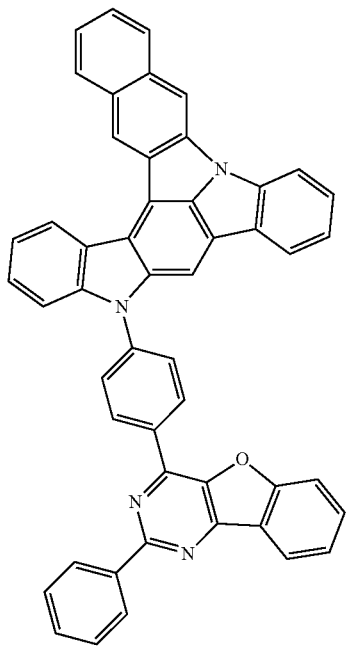
626
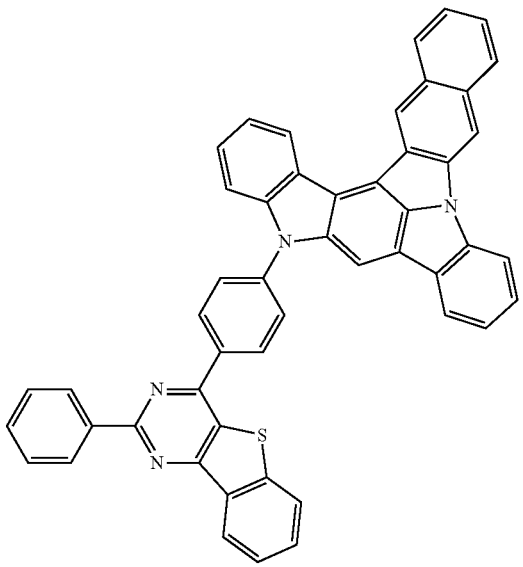
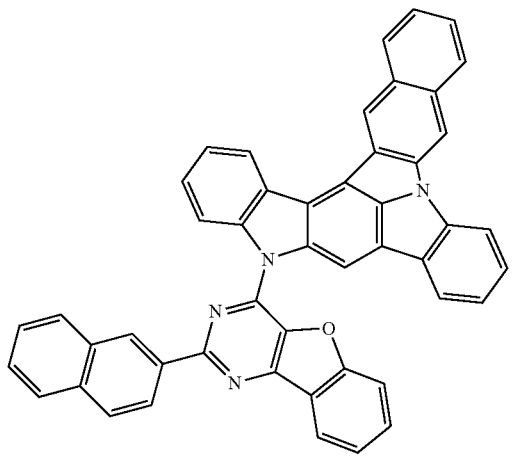
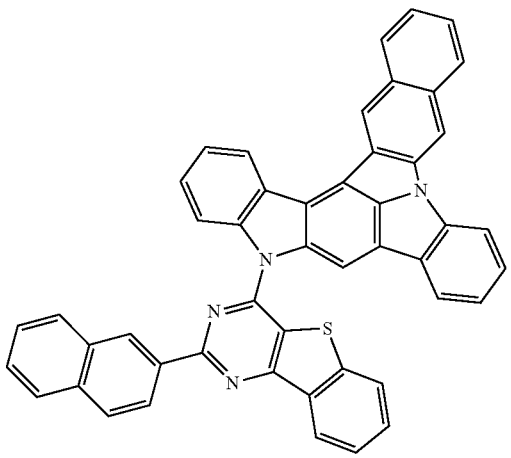
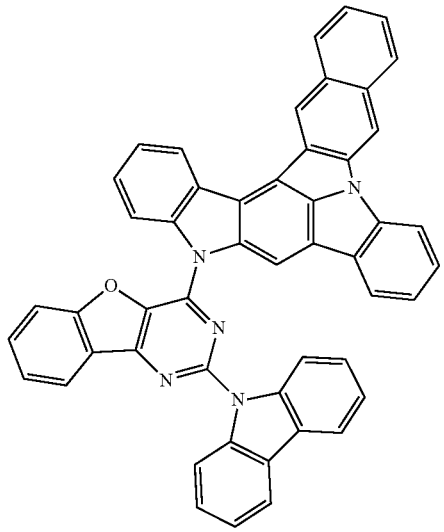
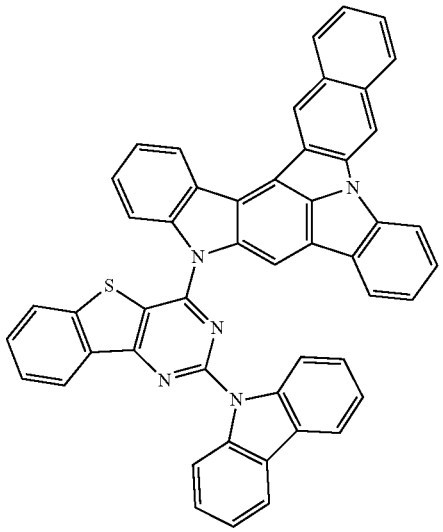

627 628
-continued
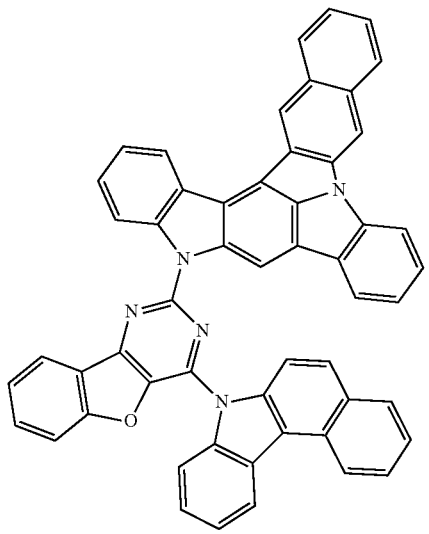 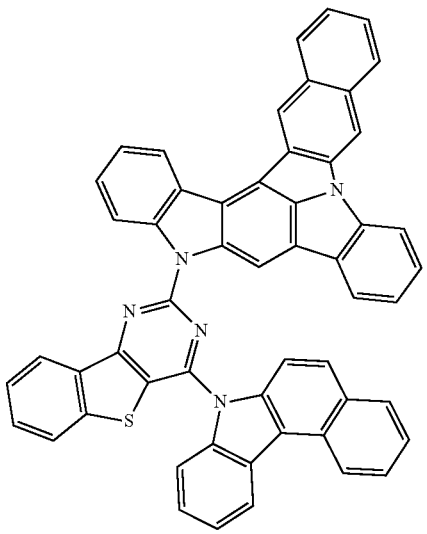
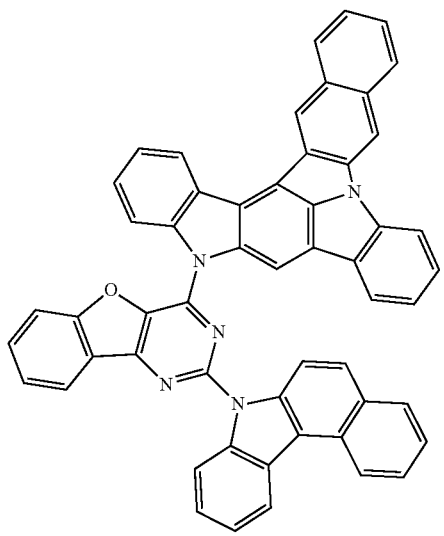 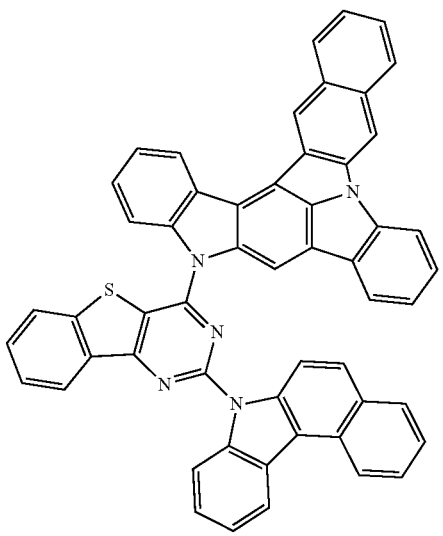
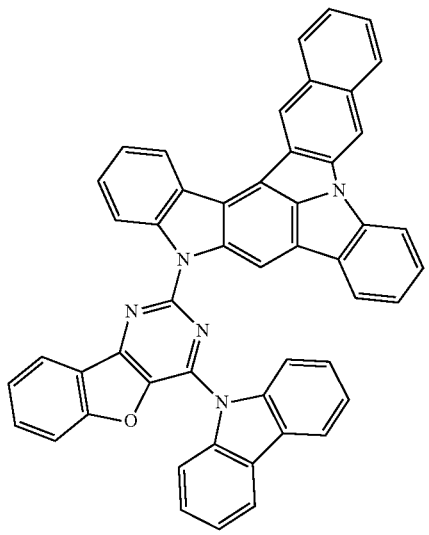 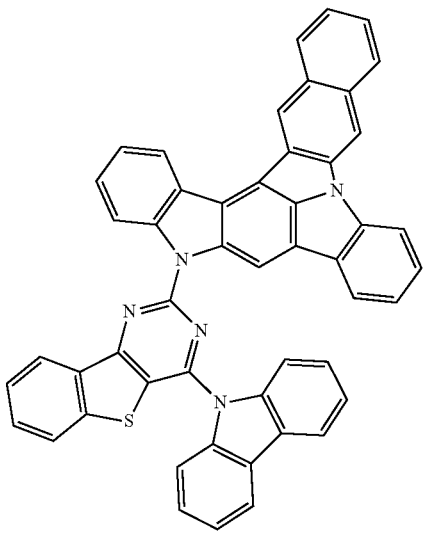

629
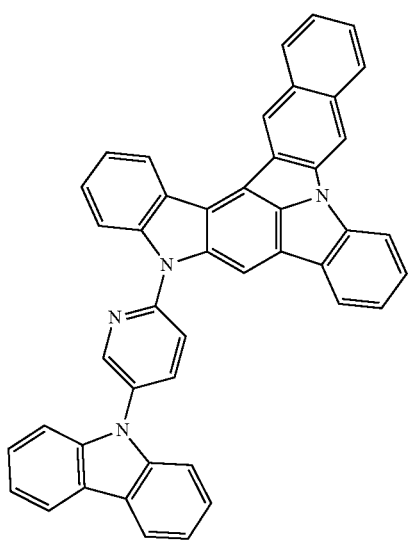
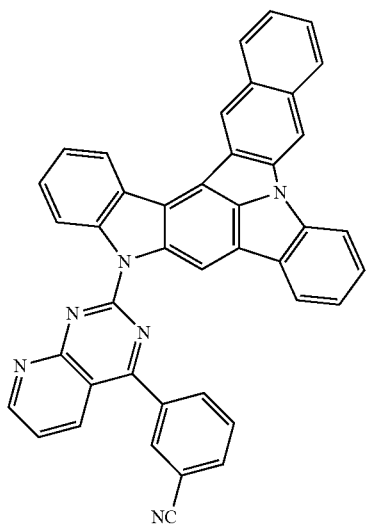
630
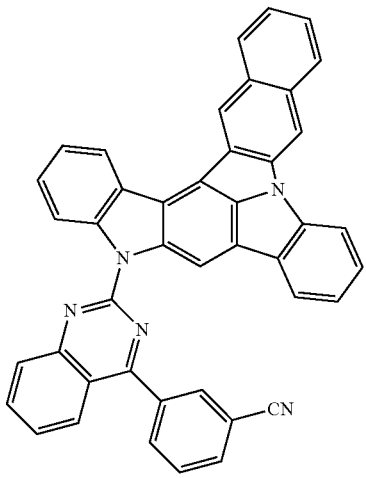
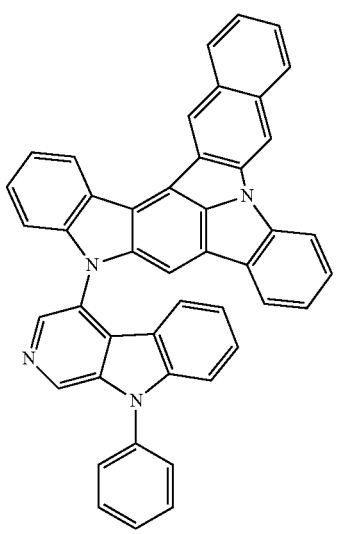
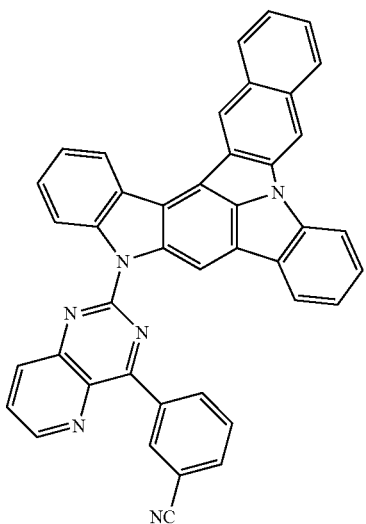

-continued
631
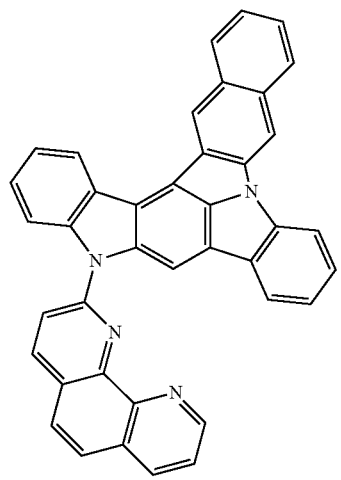
632
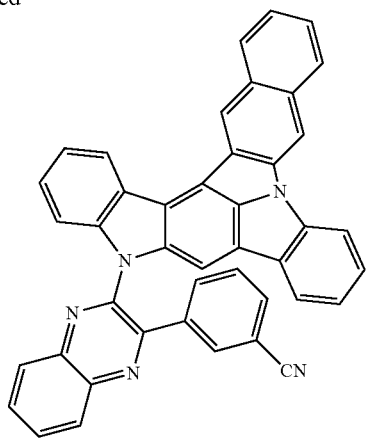
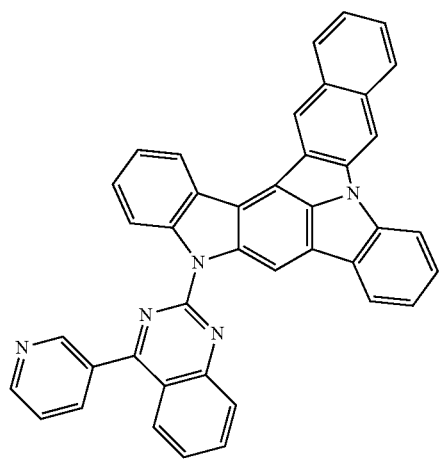
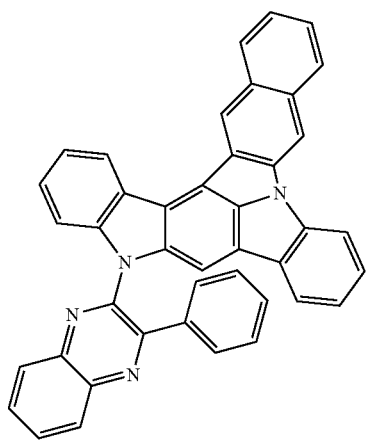
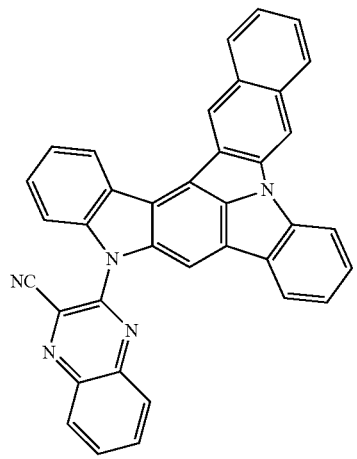
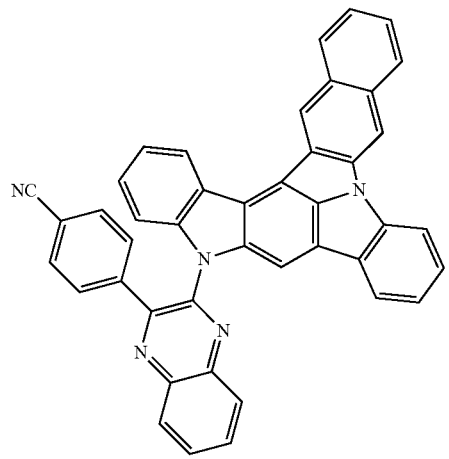

633
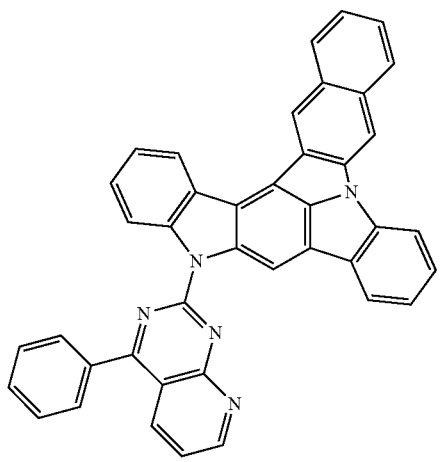
634
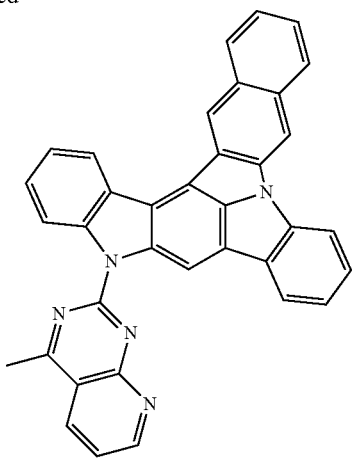
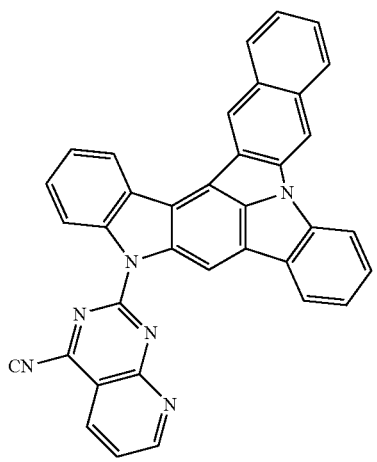
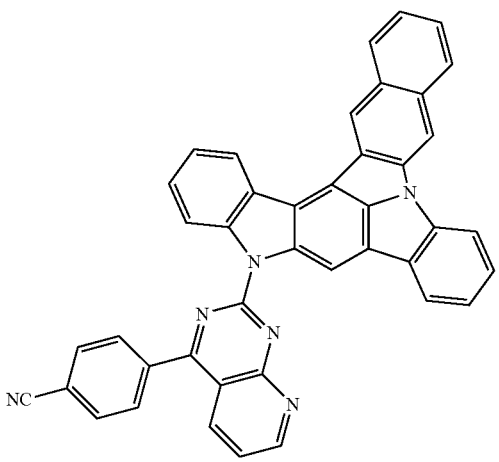
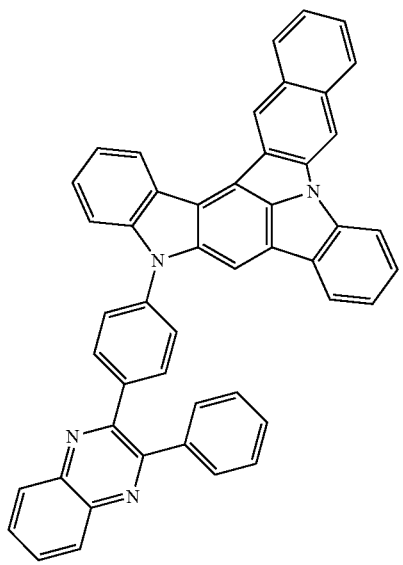
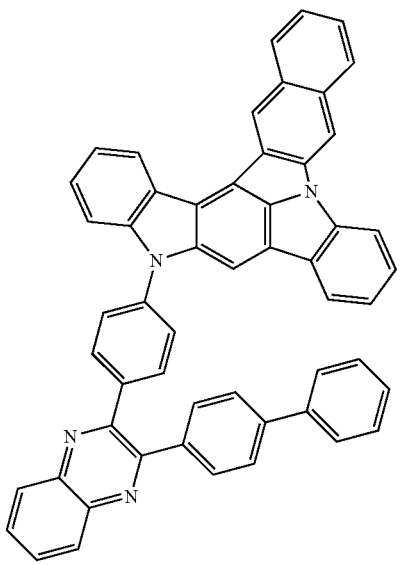

-continued
635
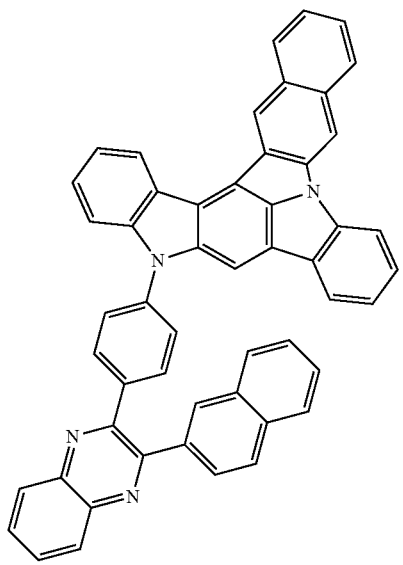
636
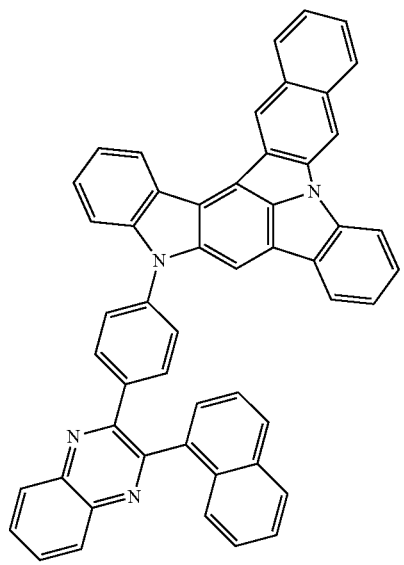
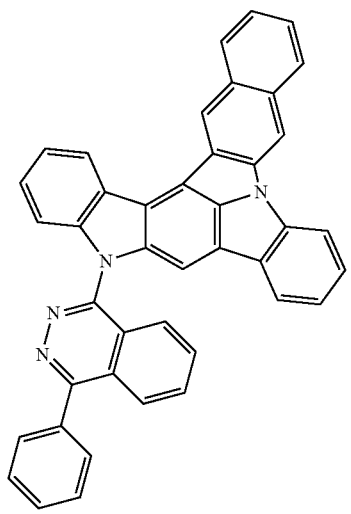
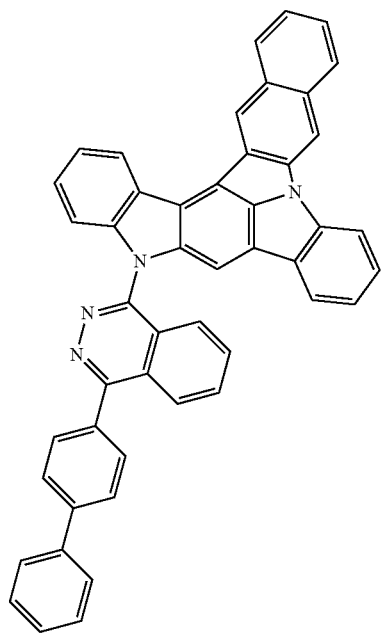

637 638
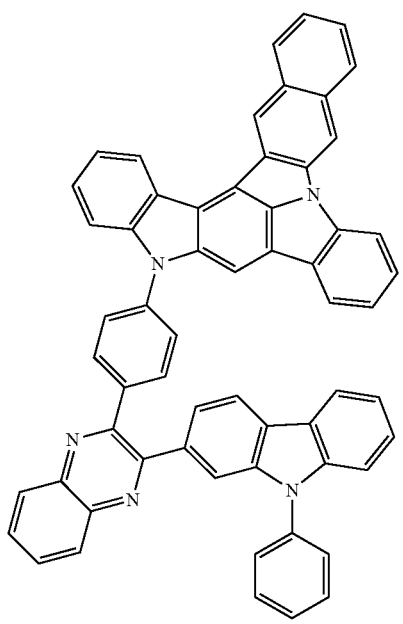 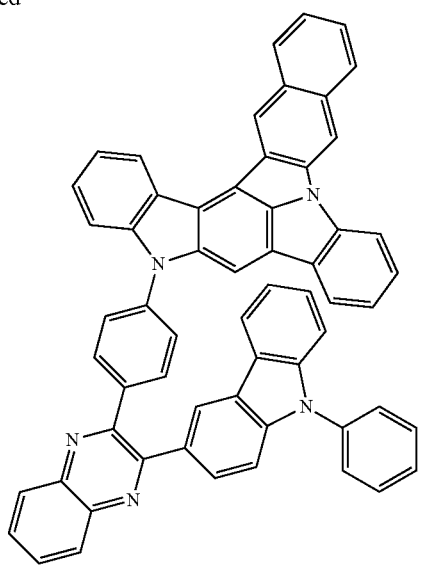
-continued
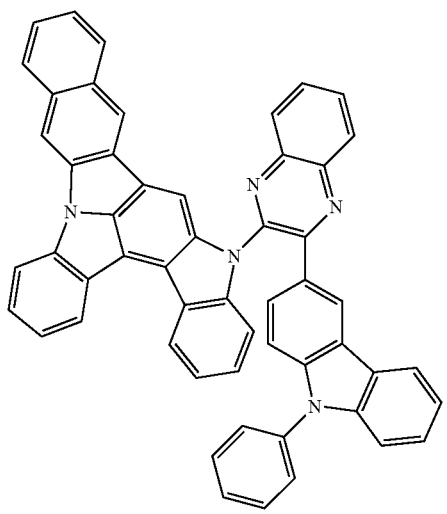 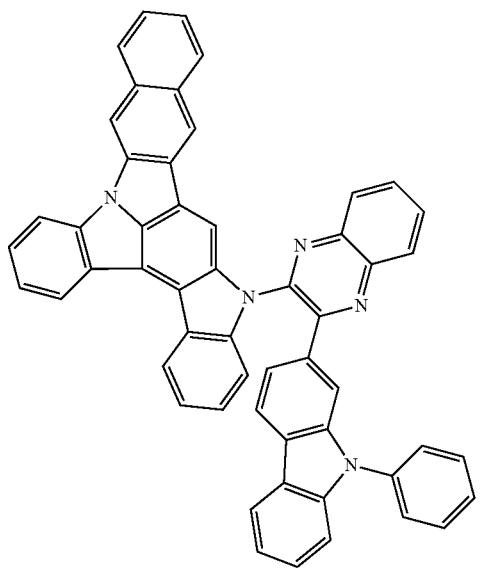

639
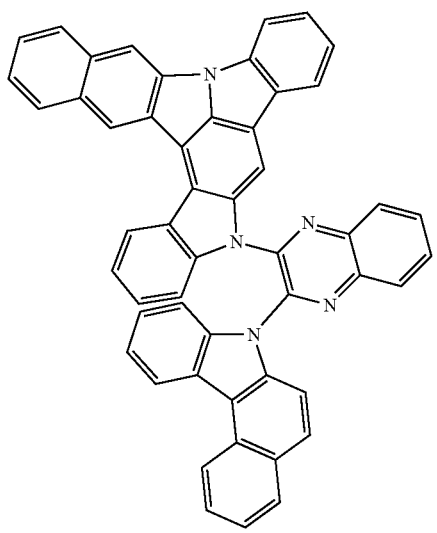
640
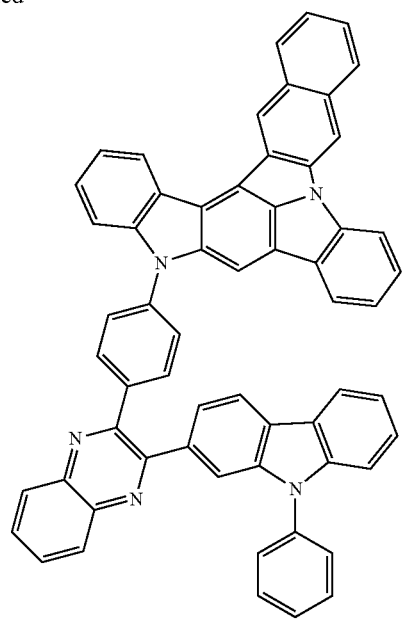
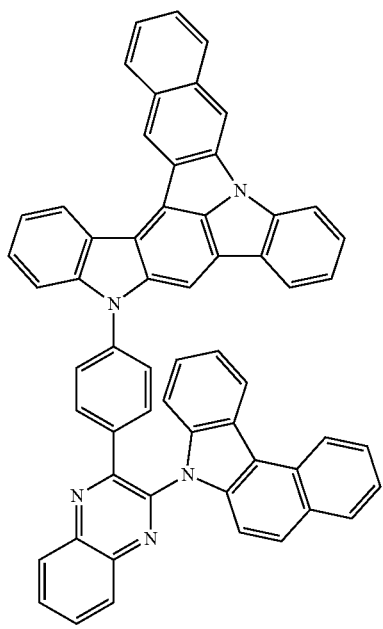
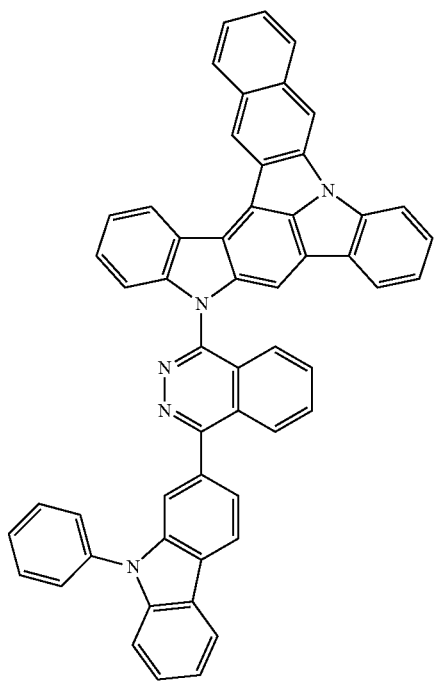

641
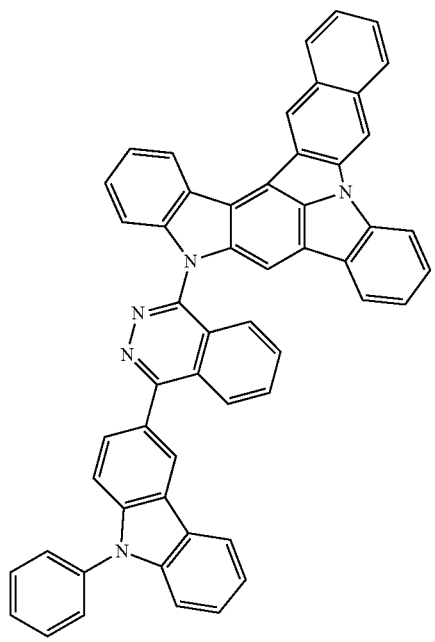
642
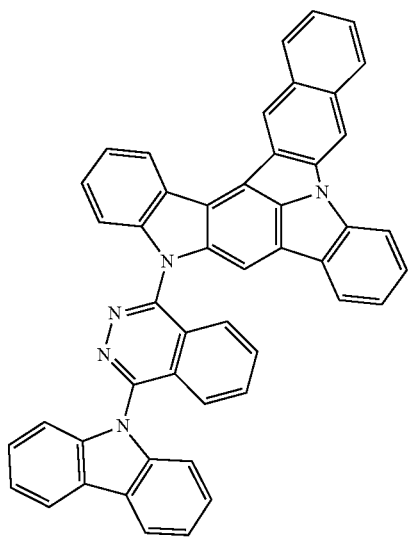
-continued
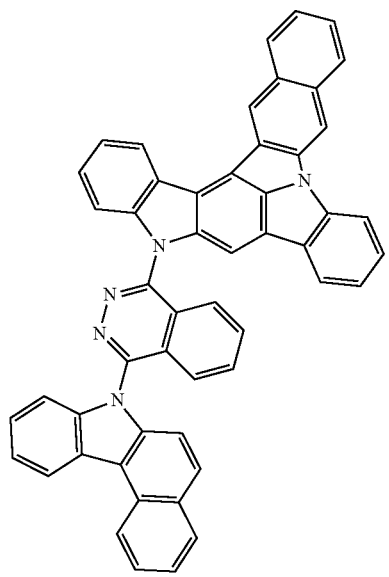
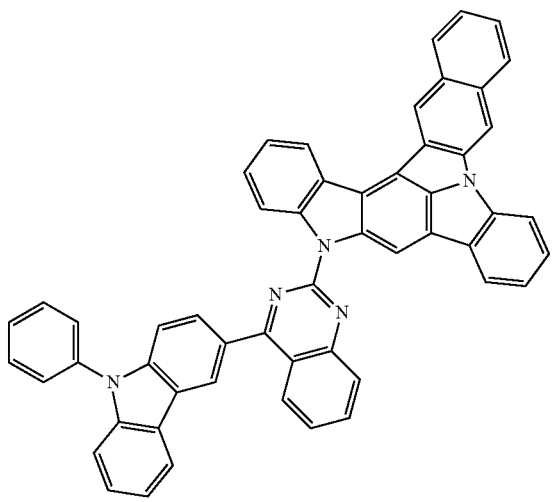

643 644
-continued
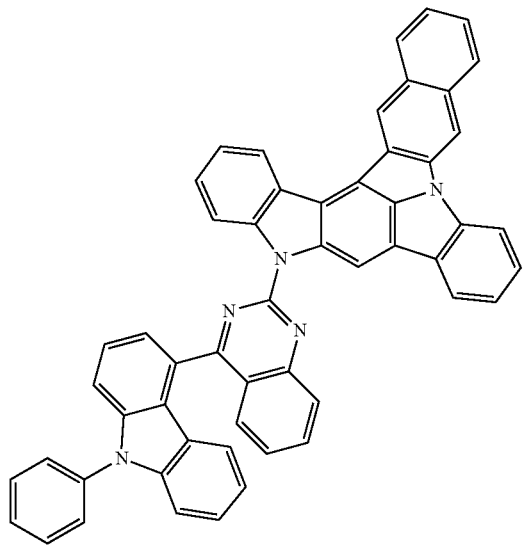
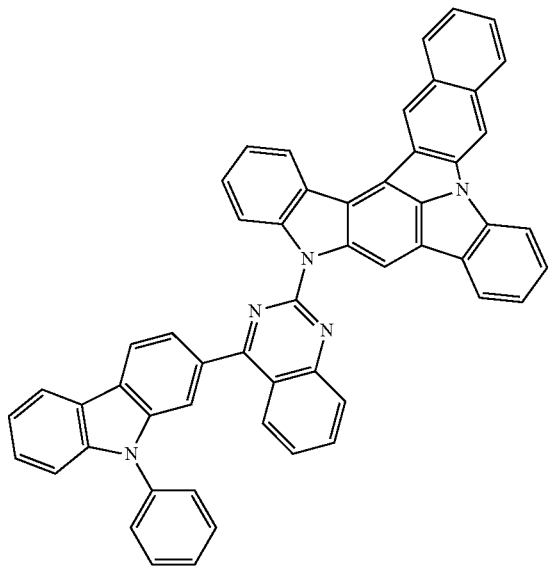
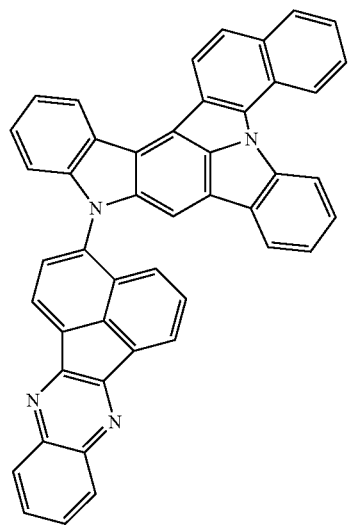
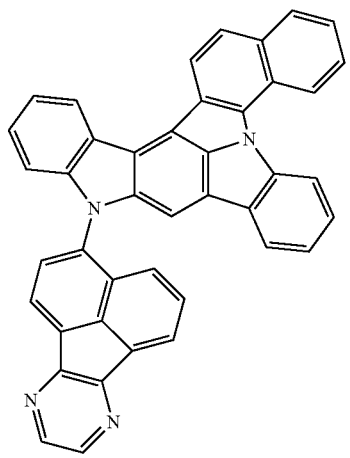
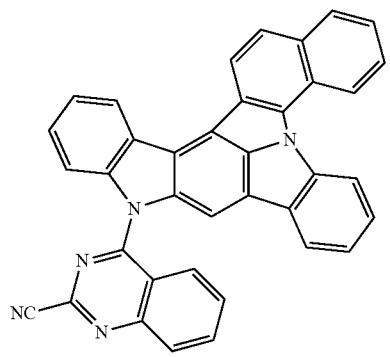
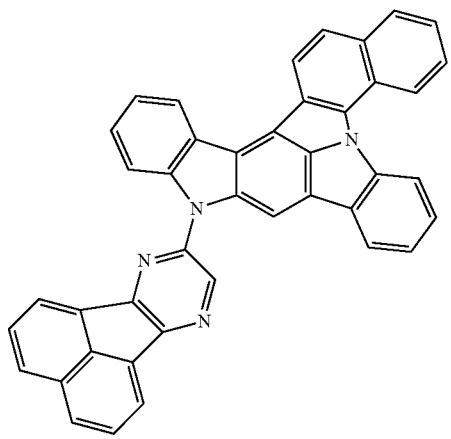

-continued
| 645 | 646 |
|---|---|
| 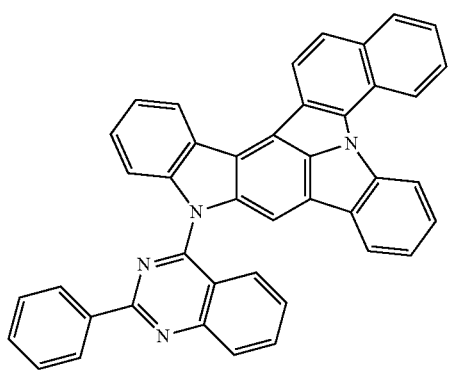 | 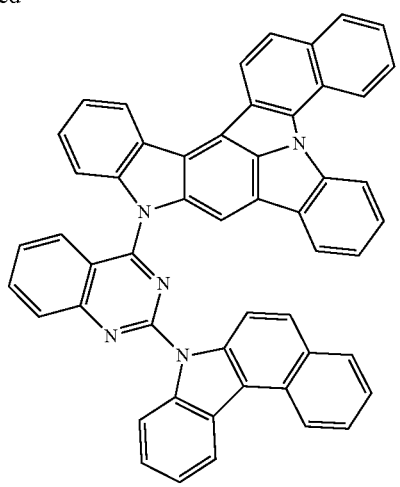 |
| 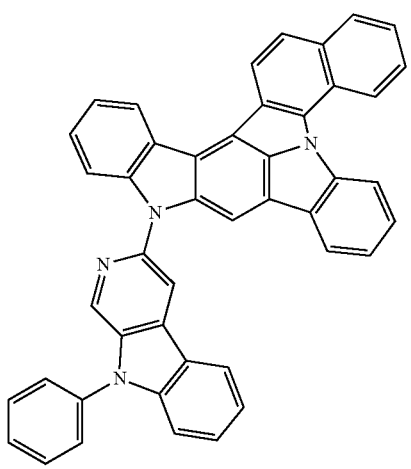 | 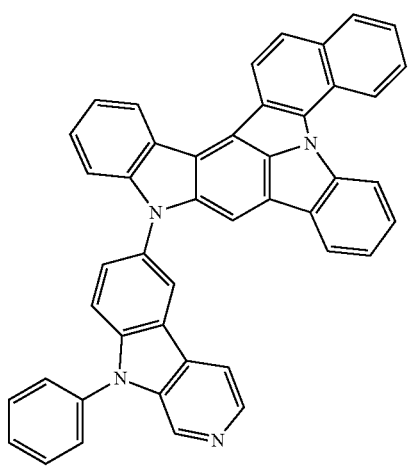 |
| 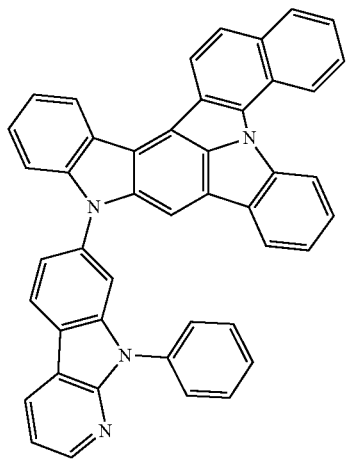 | 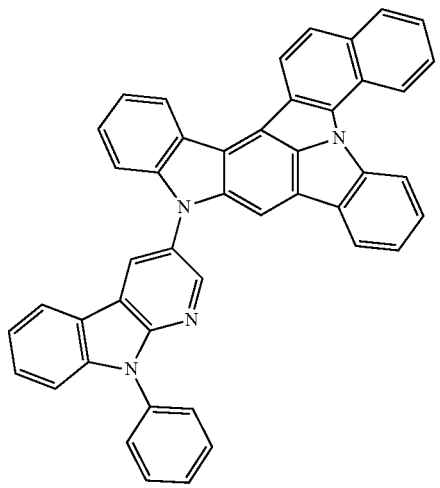 |

647
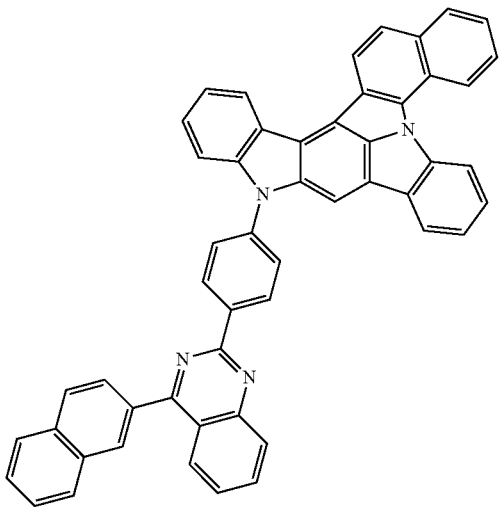
648
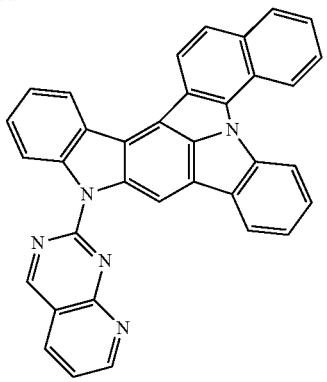
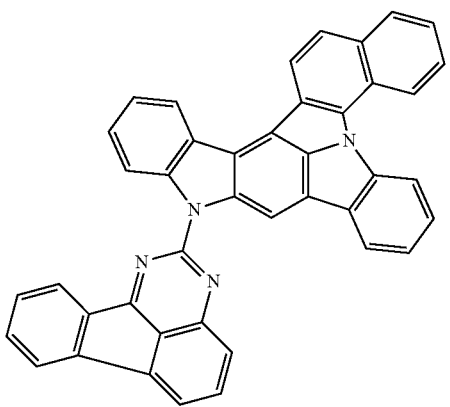
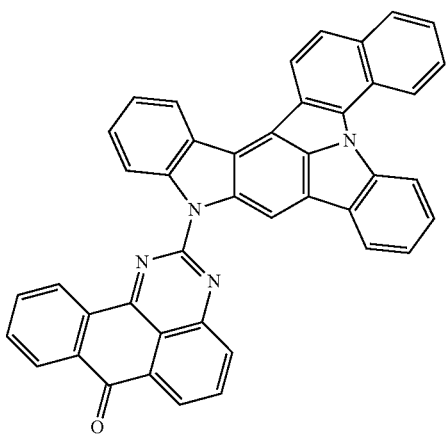
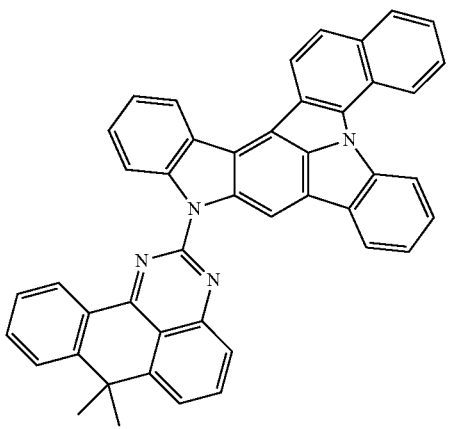
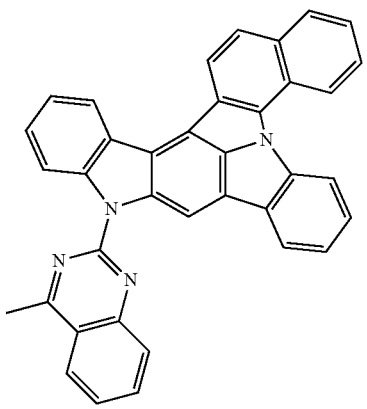

-continued
| 649 | 650 |
|---|---|
| 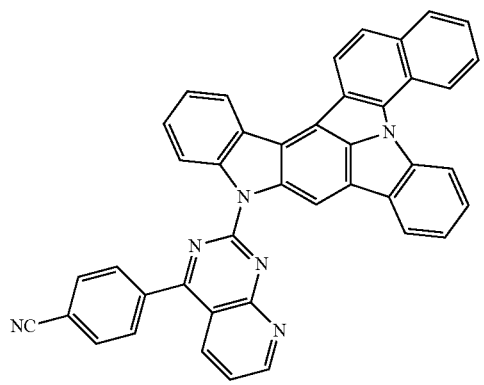 | 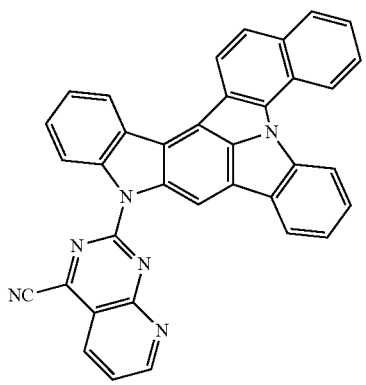 |
| 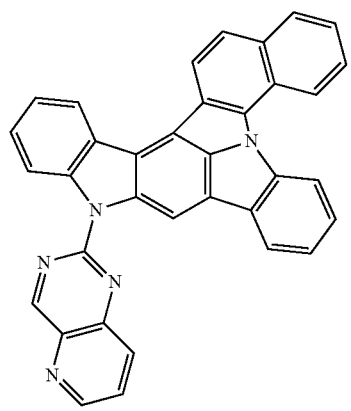 | 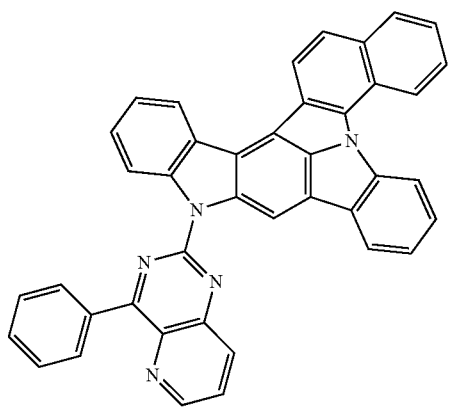 |
| 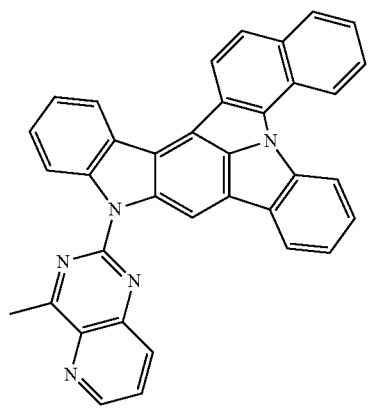 | 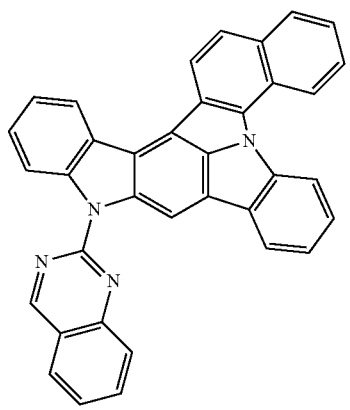 |
| 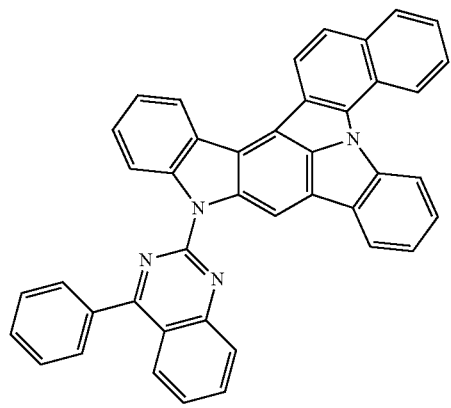 | 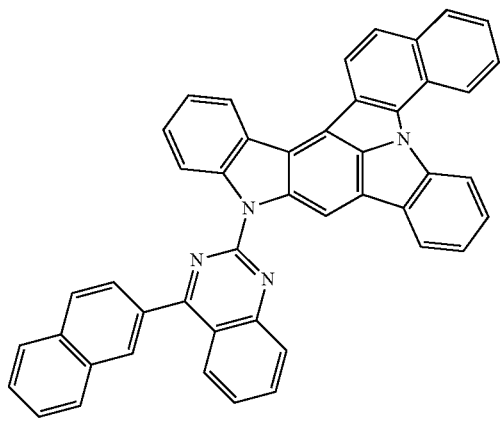 |

-continued
| 651 | 652 |
|---|---|
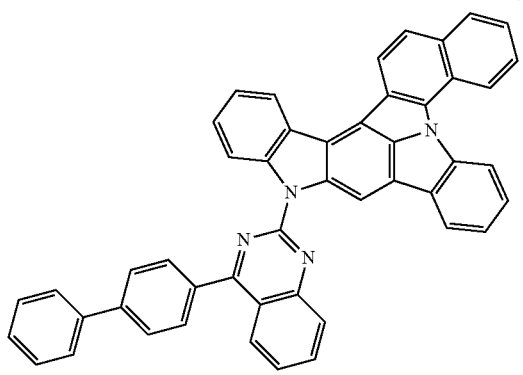 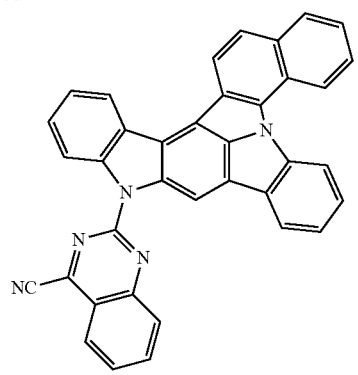
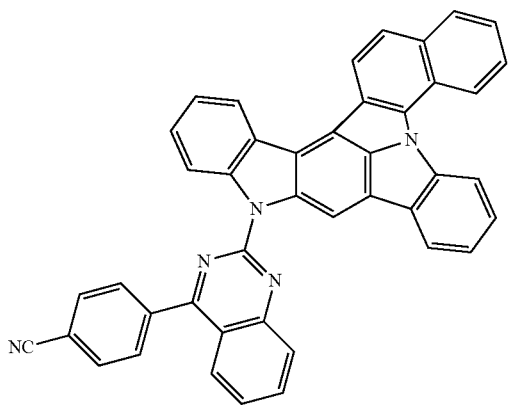 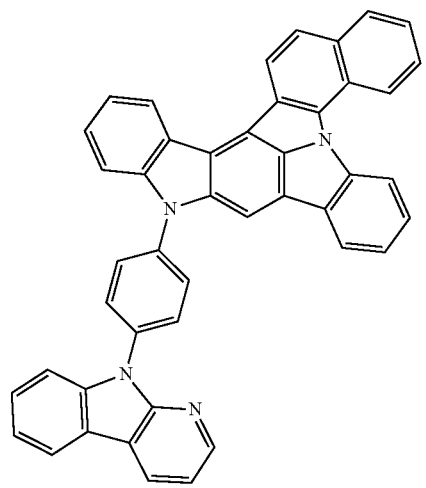
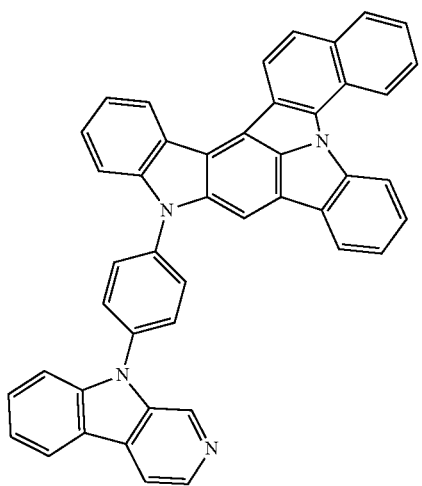 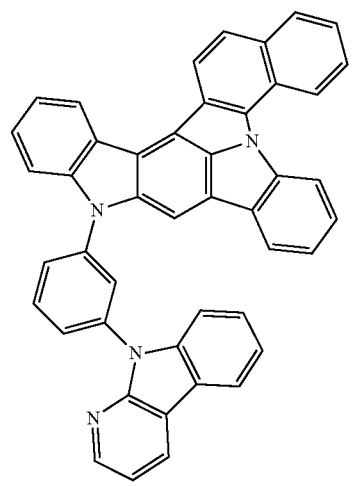

653     654
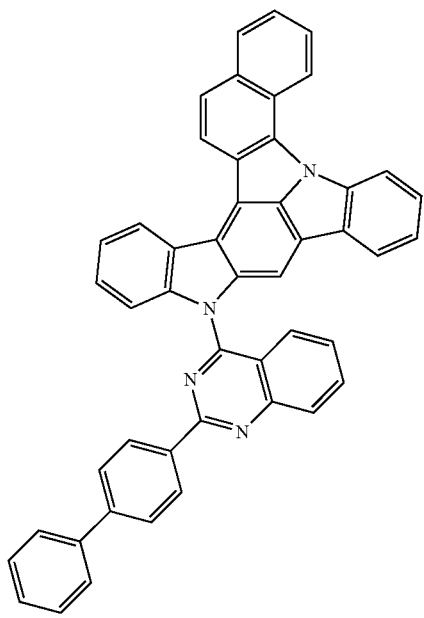 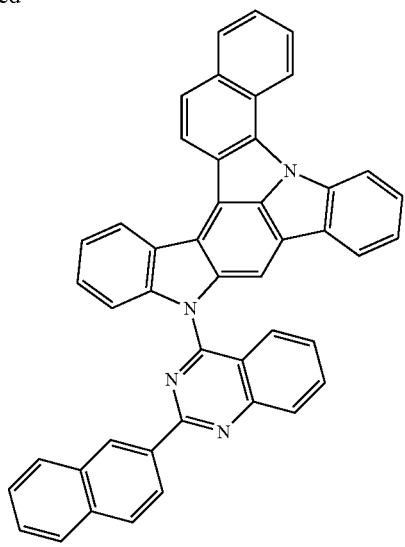
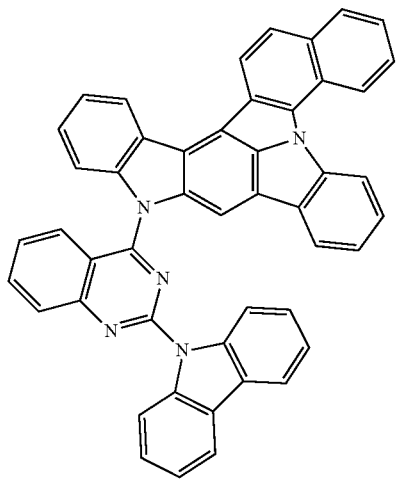 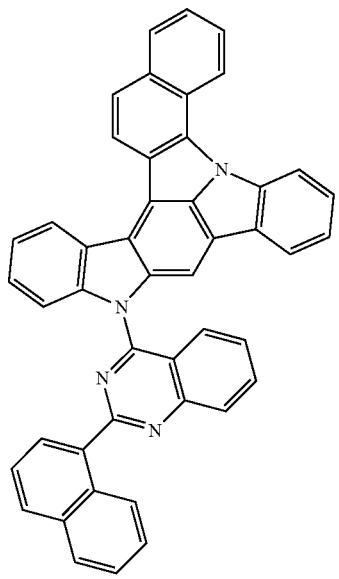

-continued
| 655 | 656 |
|---|---|
| 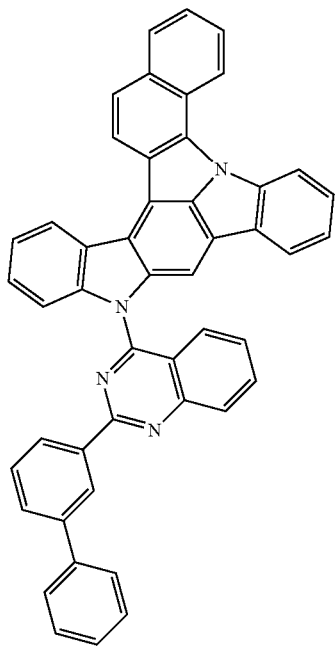 | 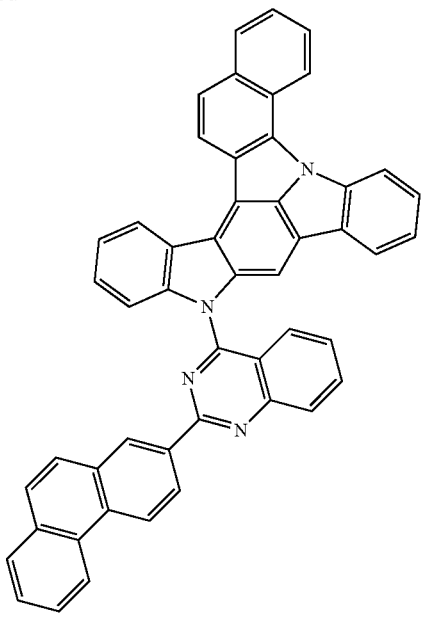 |
| 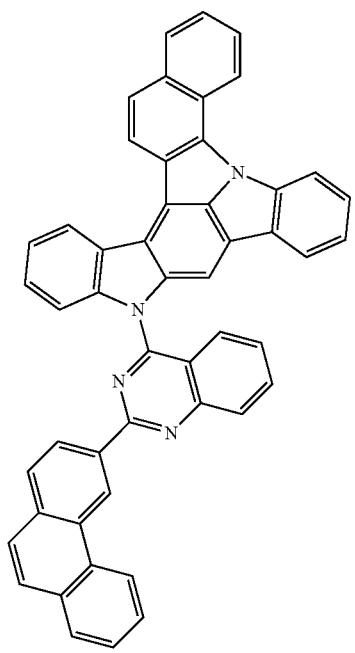 | 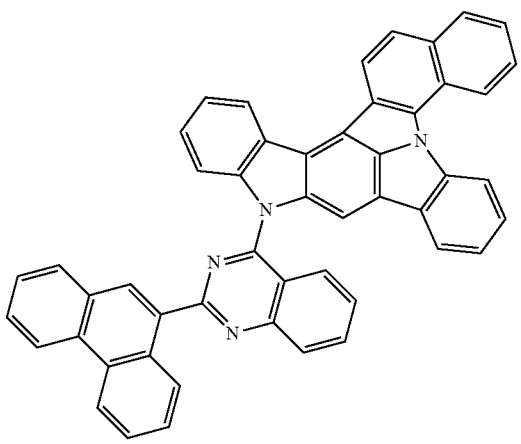 |
| 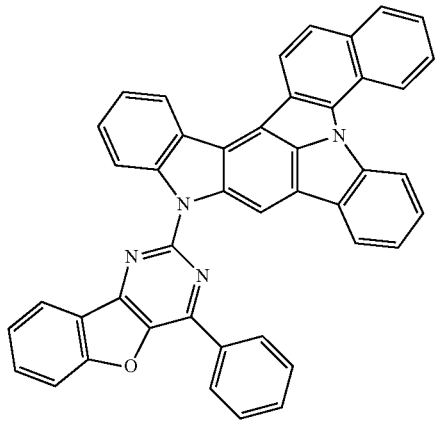 | 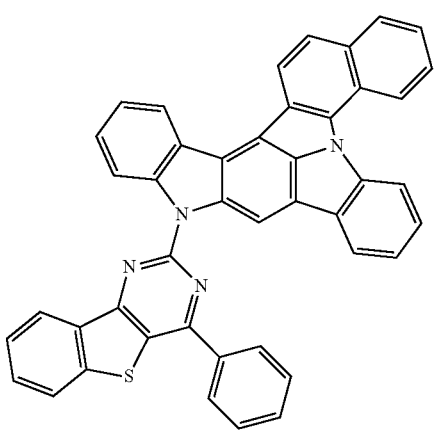 |

-continued
657
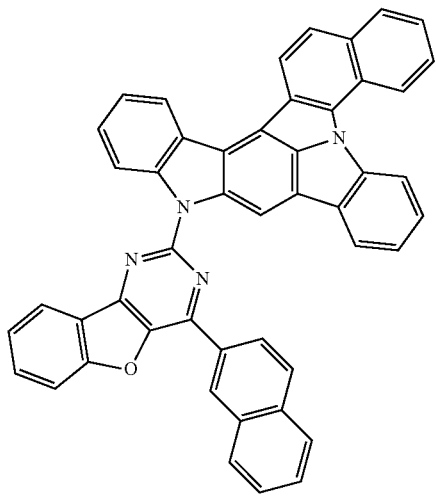
658
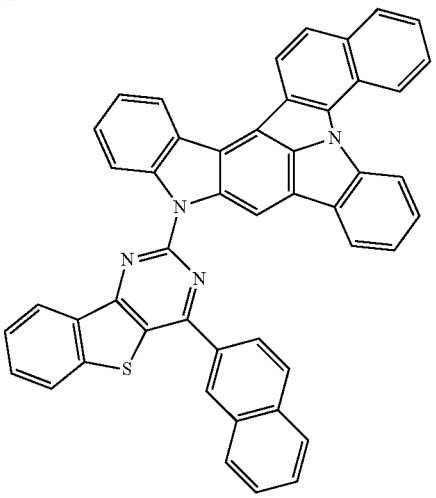
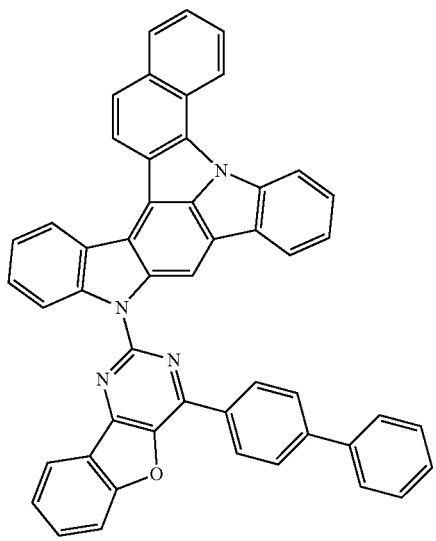
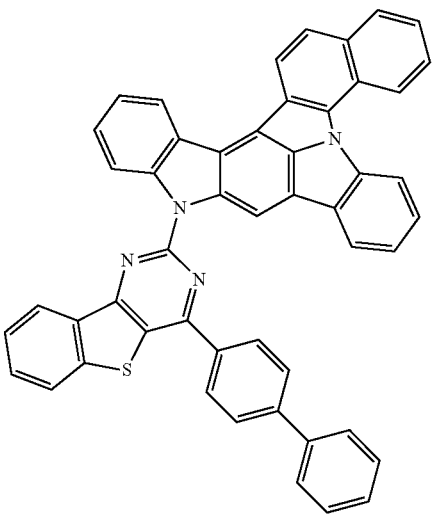
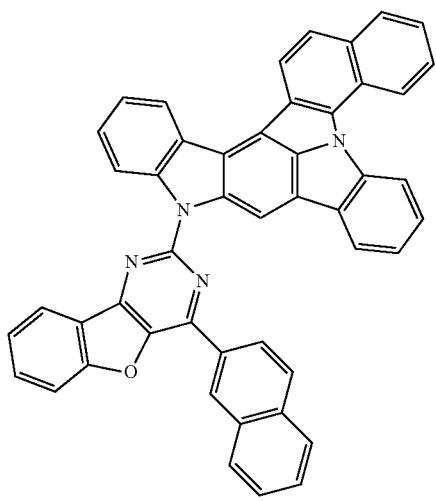
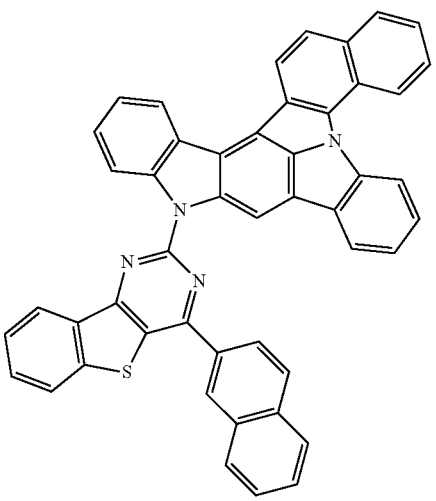

-continued
| 659 | 660 |
|---|---|
| 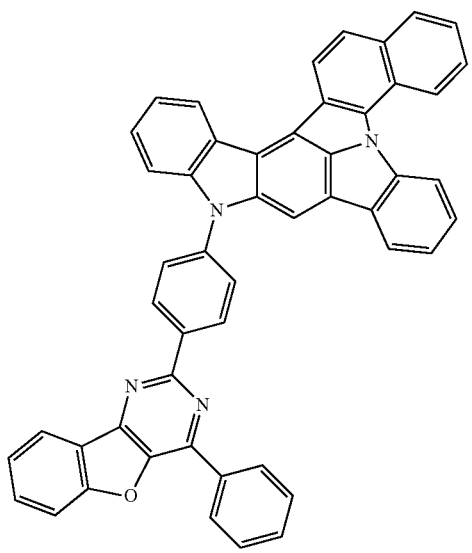 | 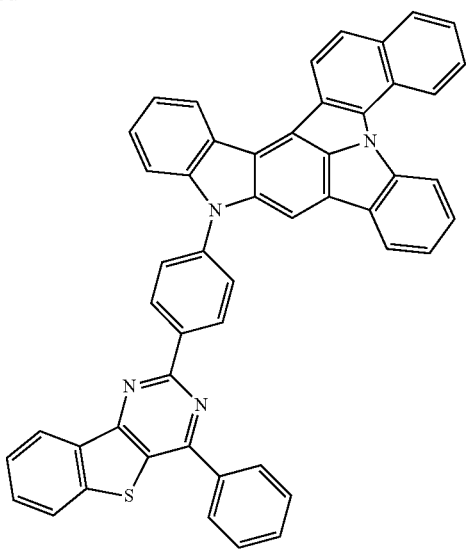 |
| 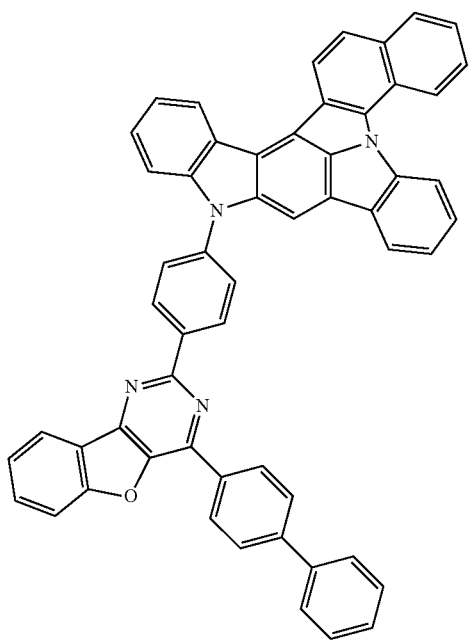 | 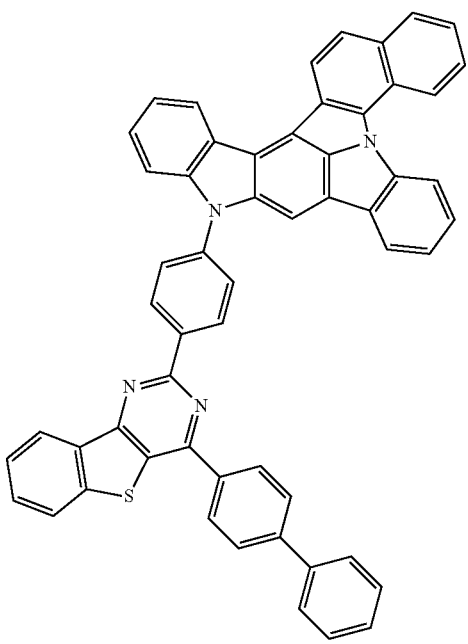 |
| 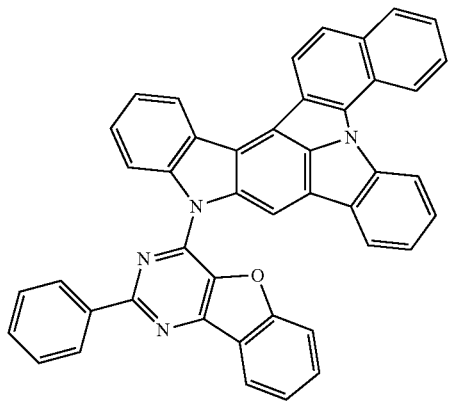 | 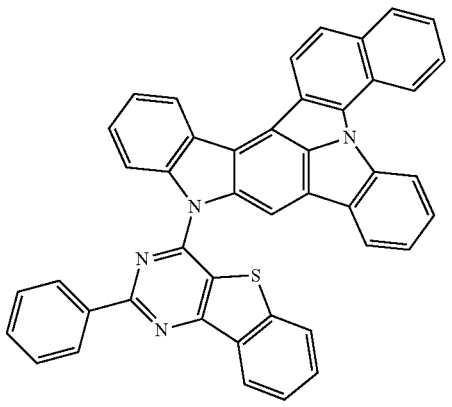 |

-continued
661 662
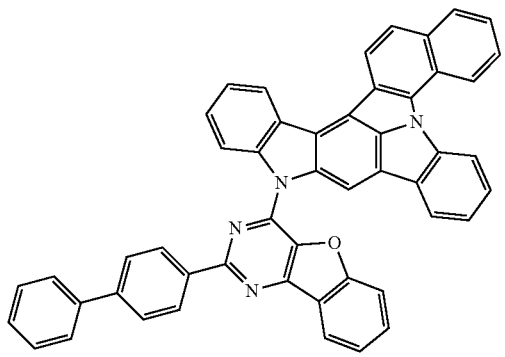
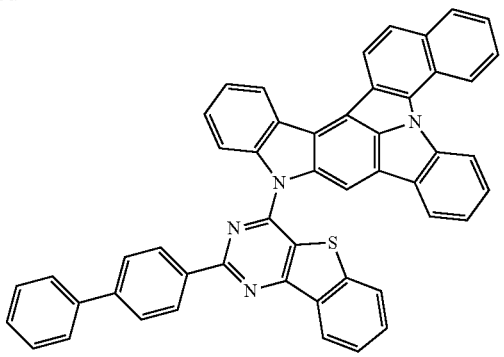
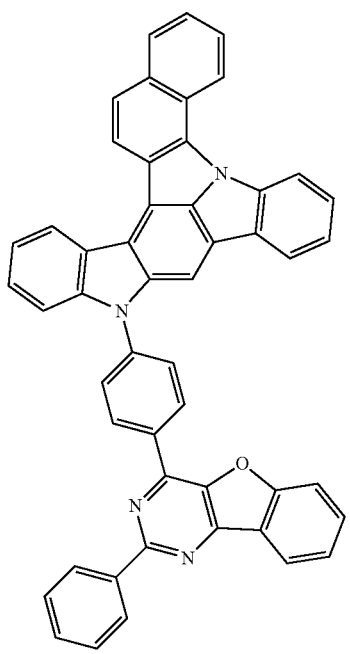
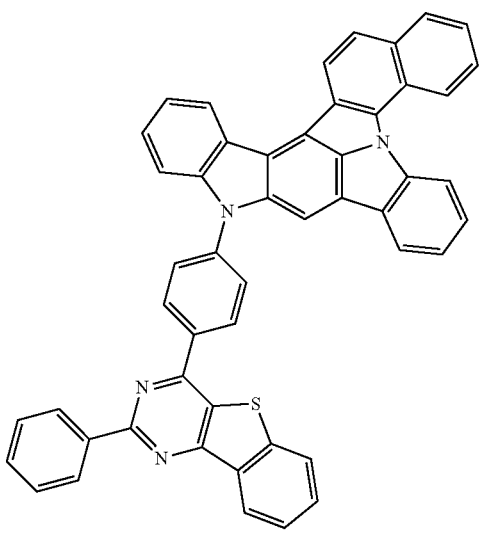
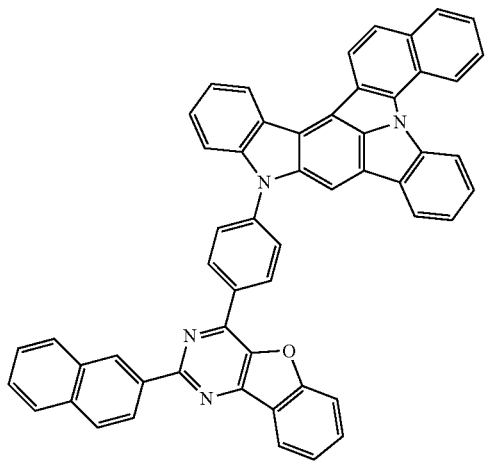
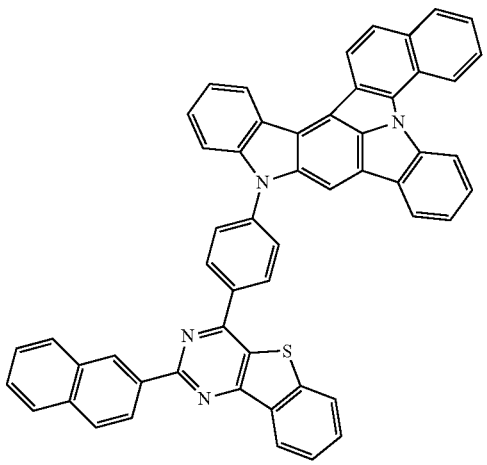

-continued
| 663 | 664 |
|---|---|
| 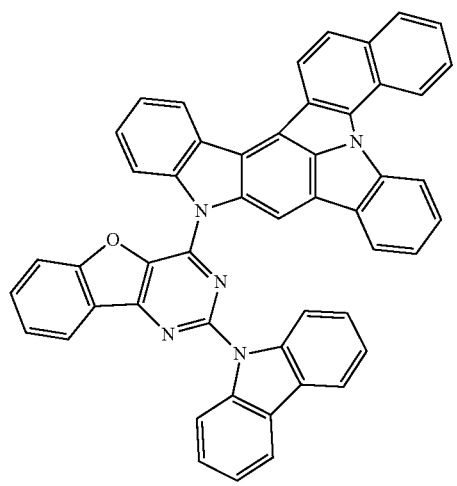 | 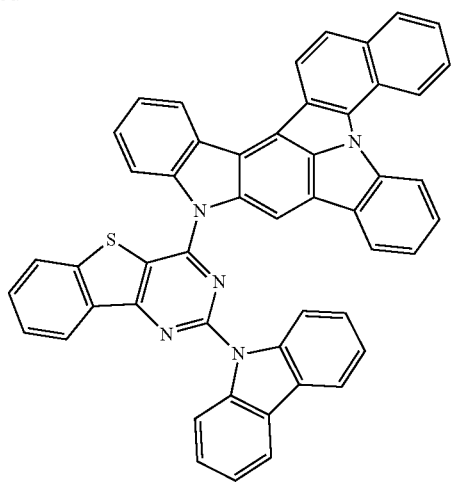 |
| 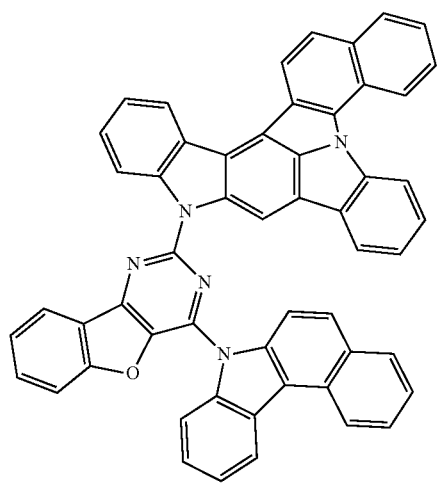 | 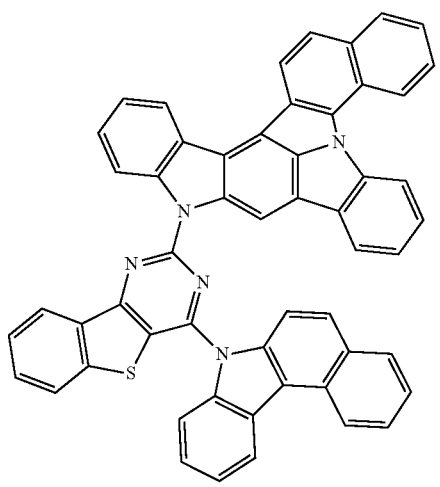 |
| 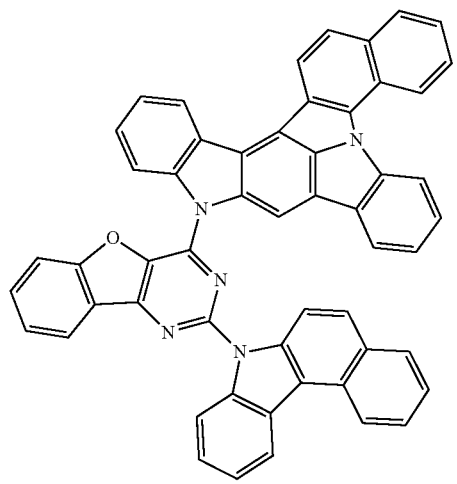 | 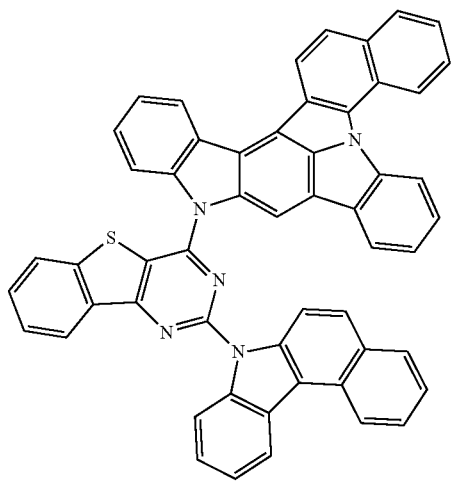 |

-continued
| 665 | 666 |
|---|---|
| 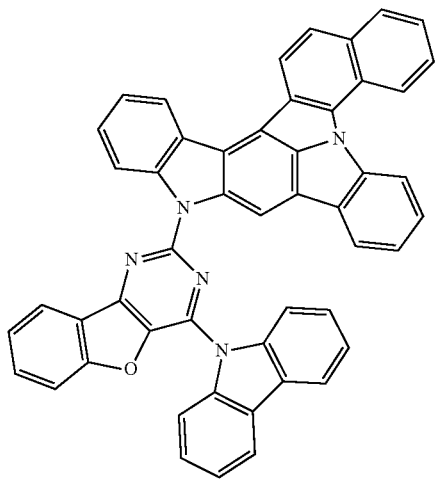 | 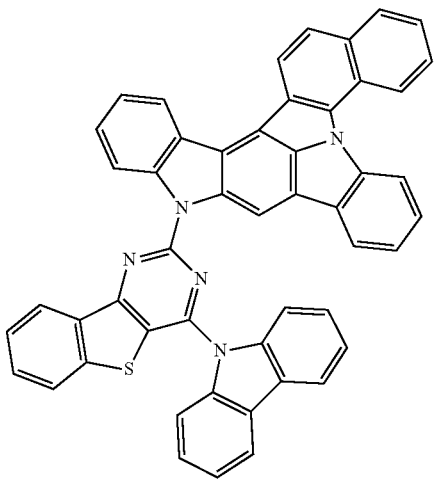 |
| 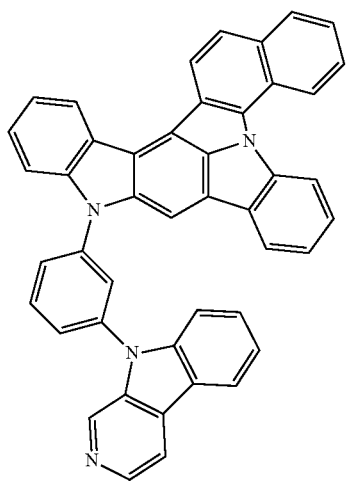 | 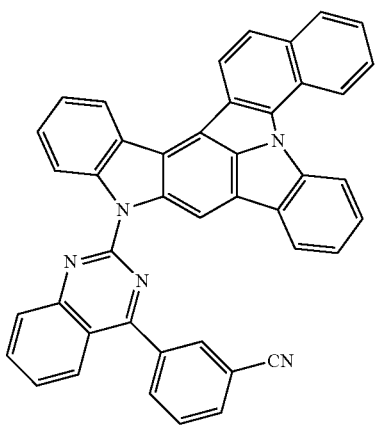 |
| 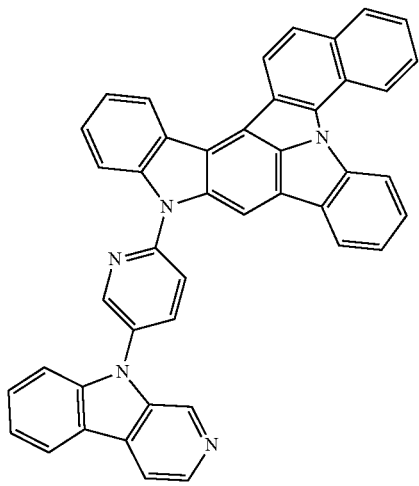 | 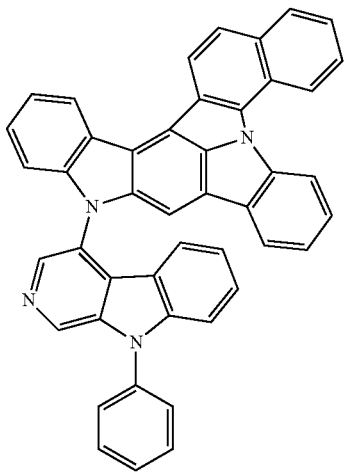 |

-continued
667 668
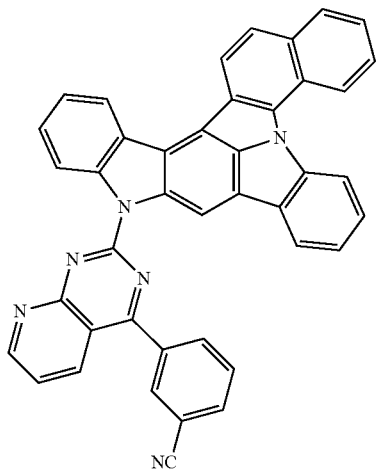 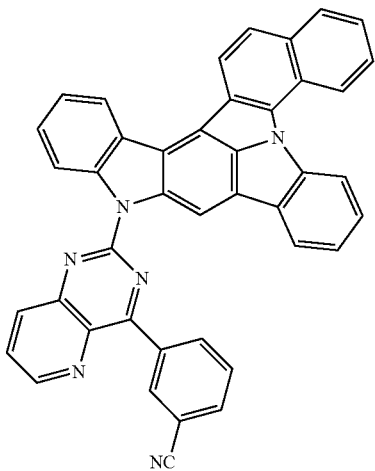
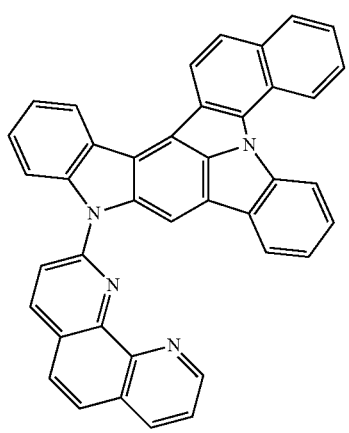 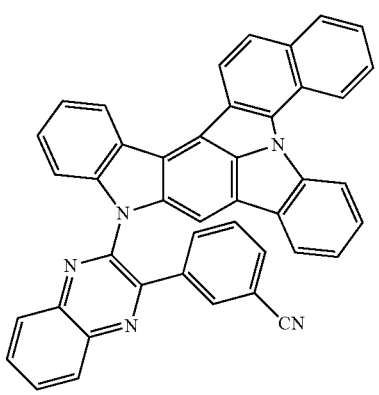
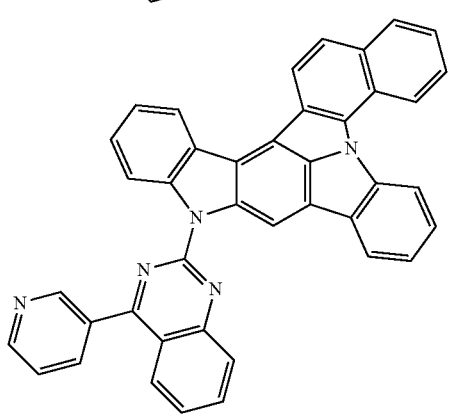 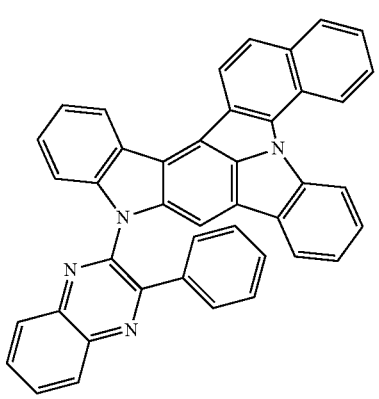
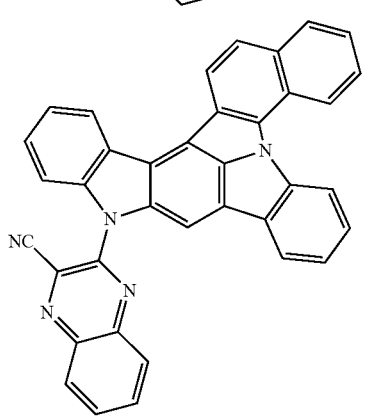 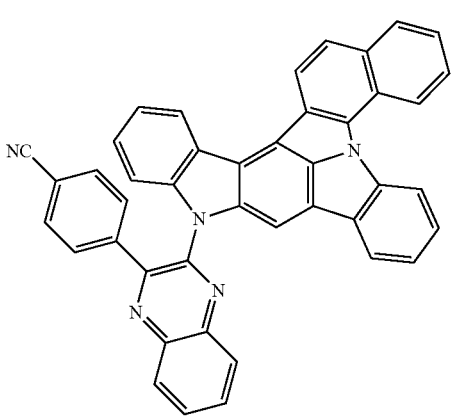

669 670
-continued
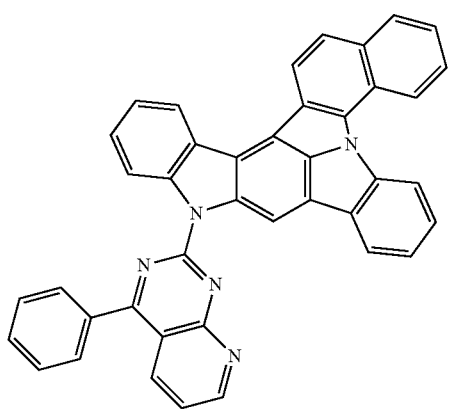
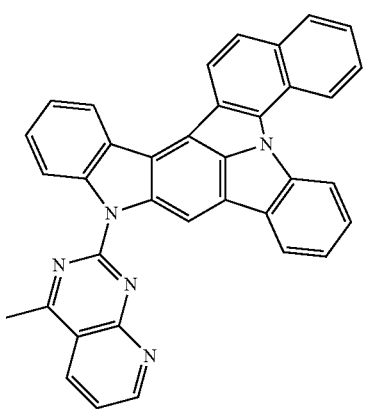
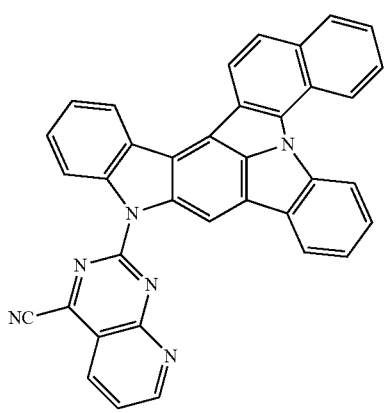
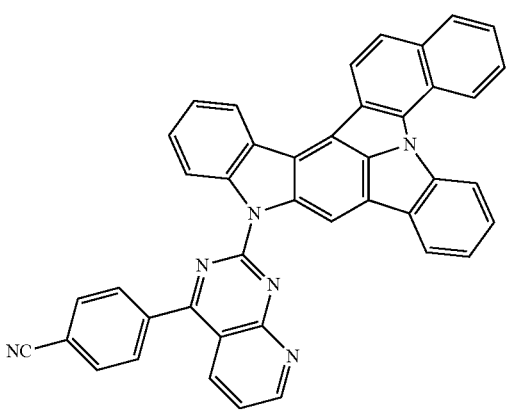
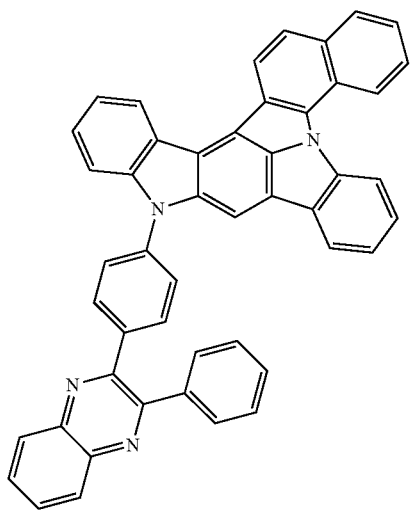
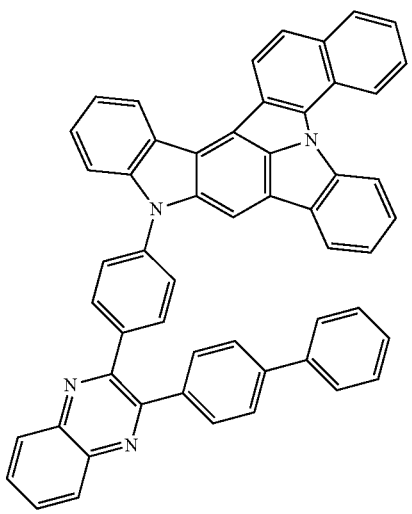

-continued
671
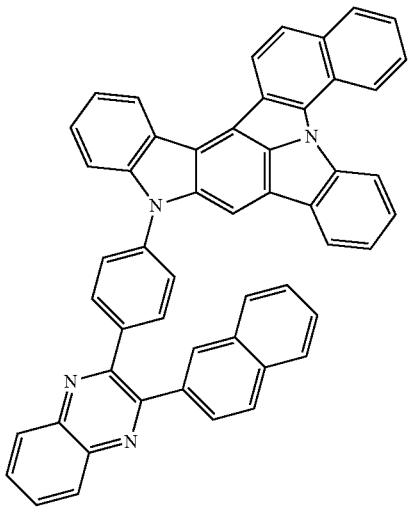
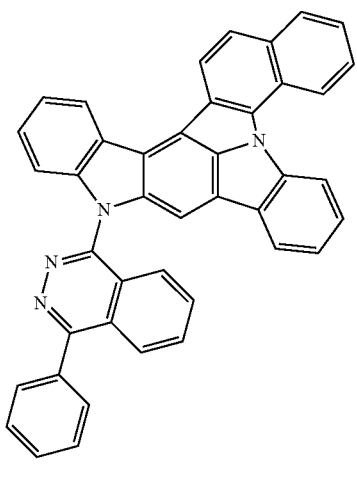
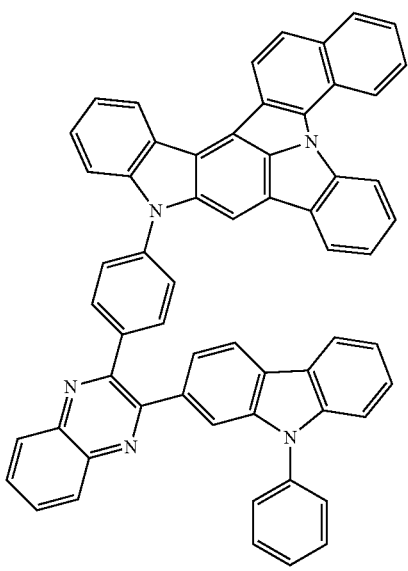
672
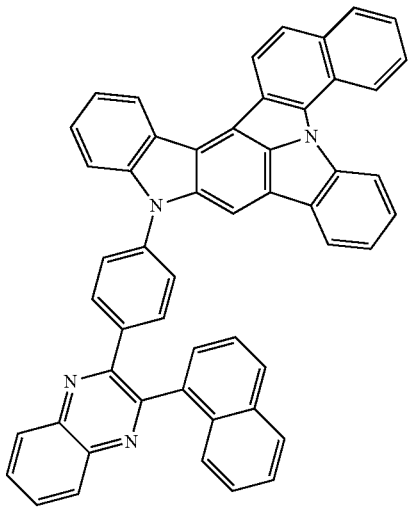
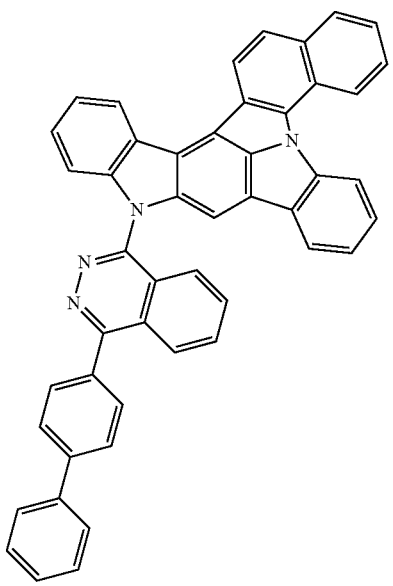
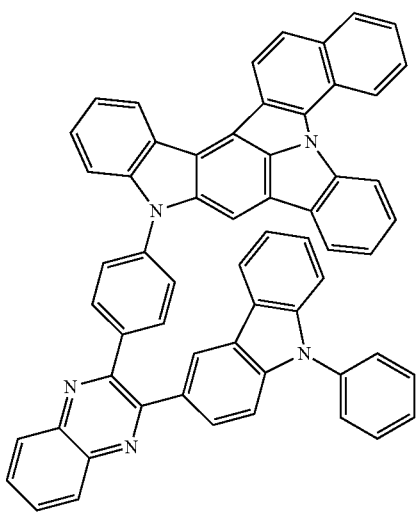

-continued
673
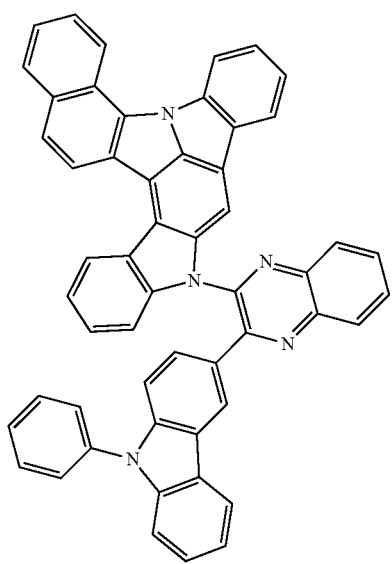
674
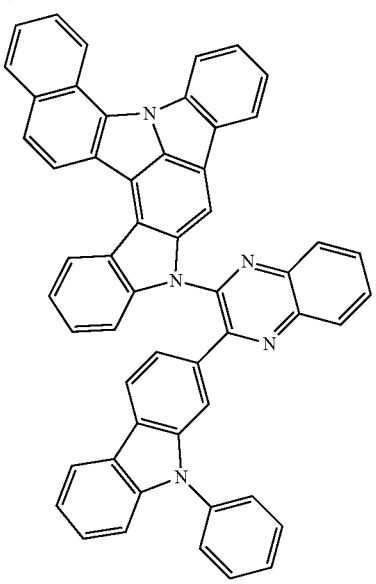
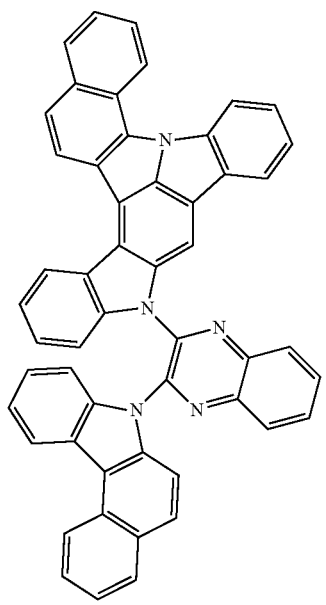
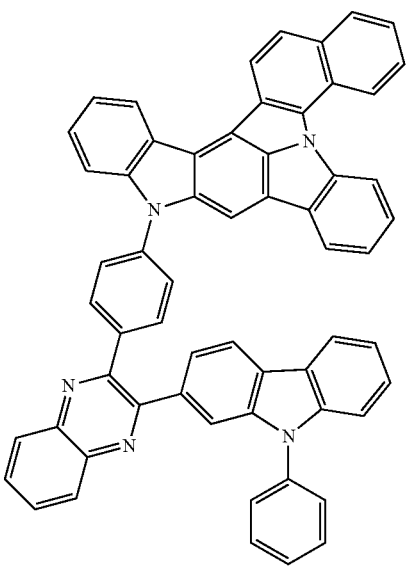

675 676
-continued
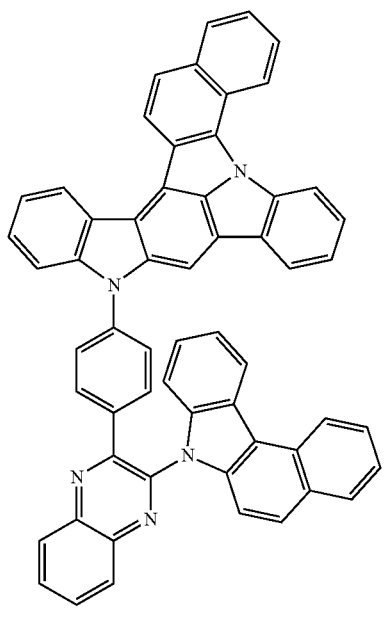 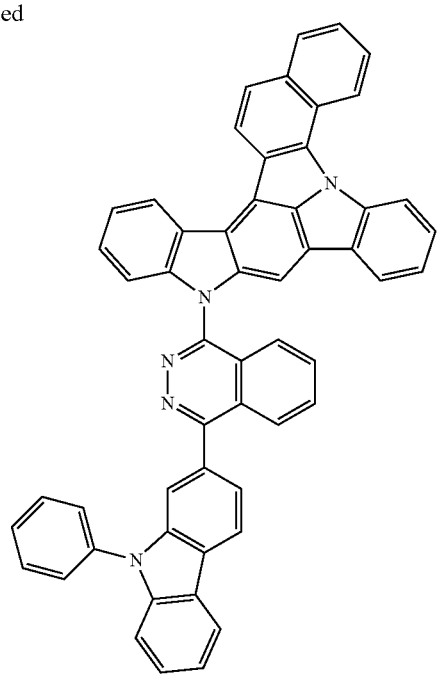
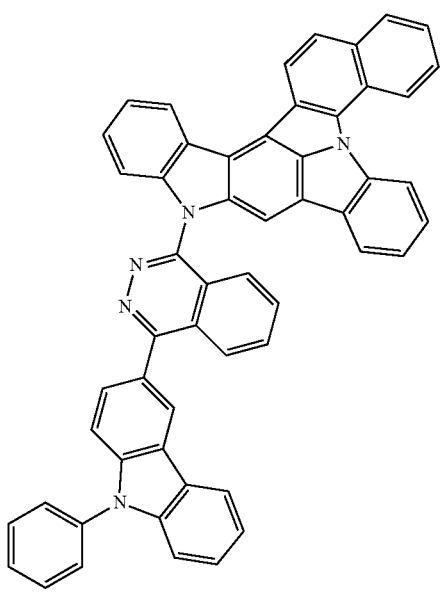 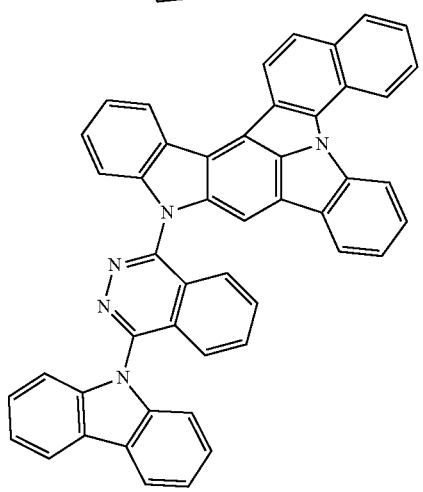
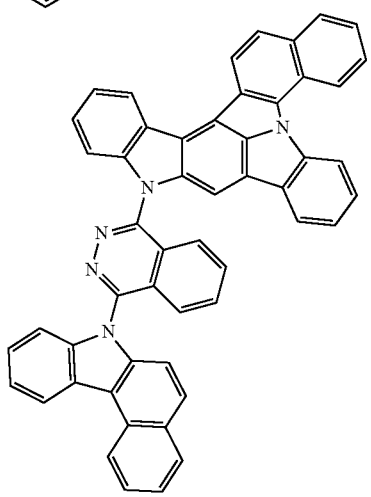 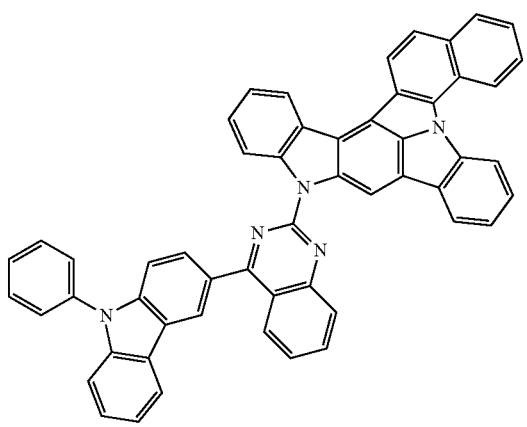

-continued
677
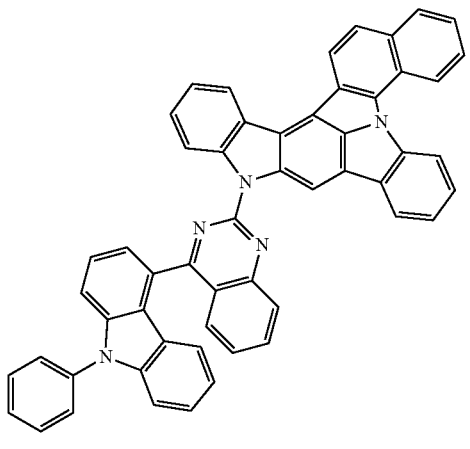
678
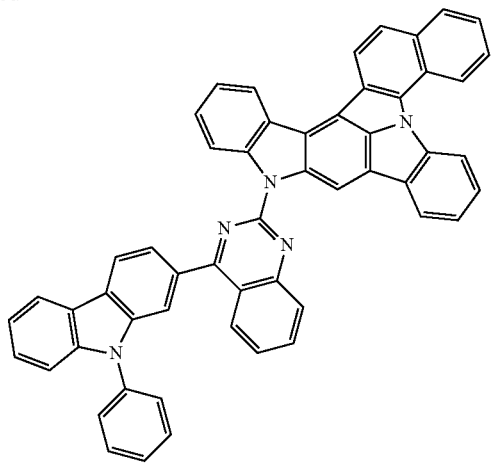
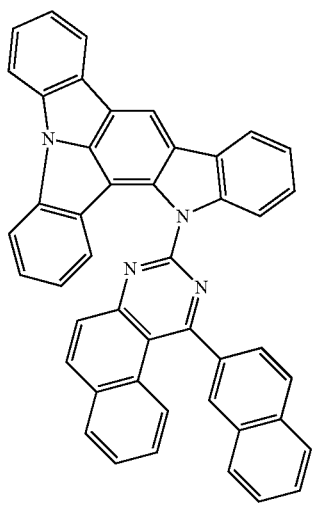
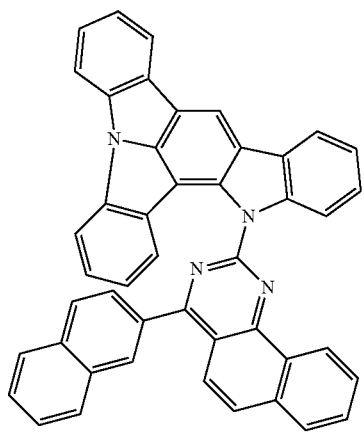
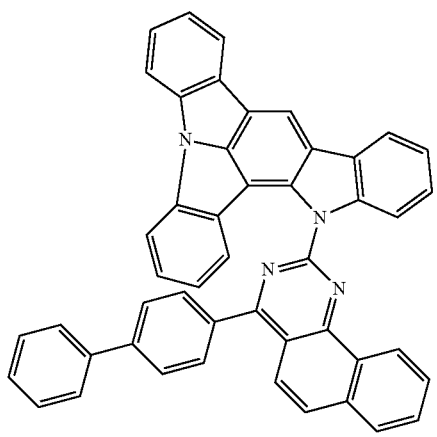
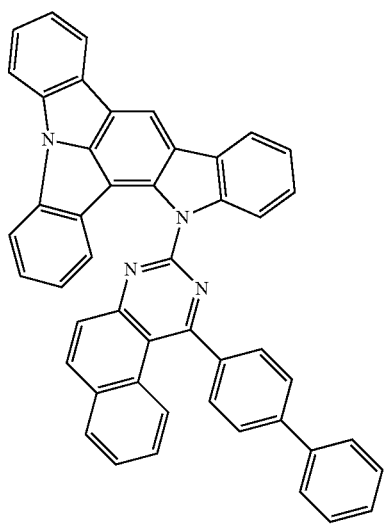

679
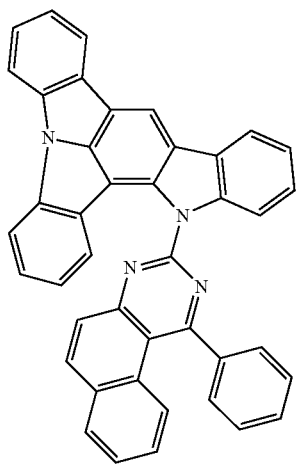
-continued
680
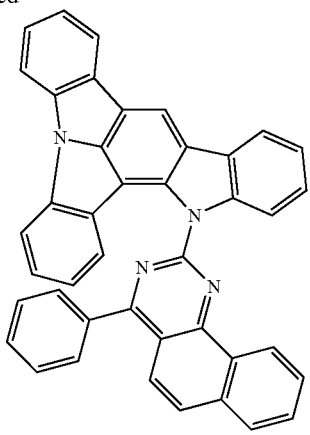
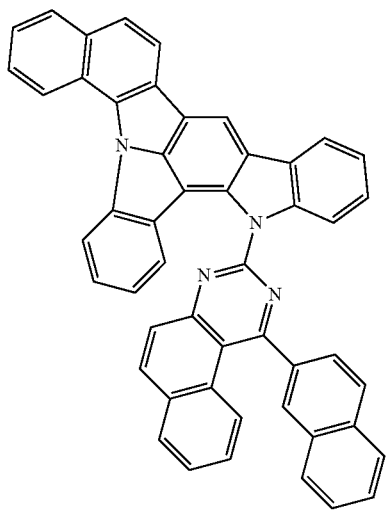
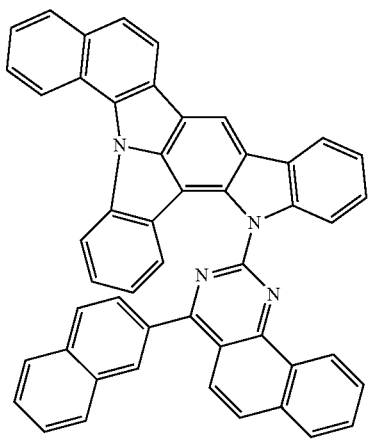
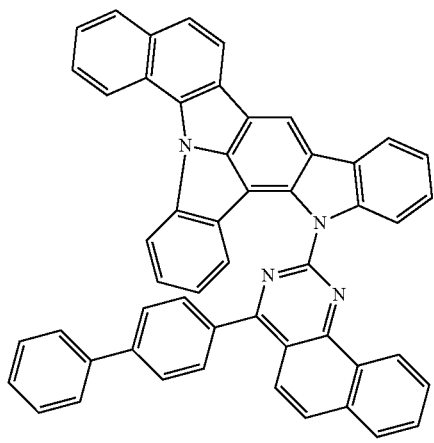
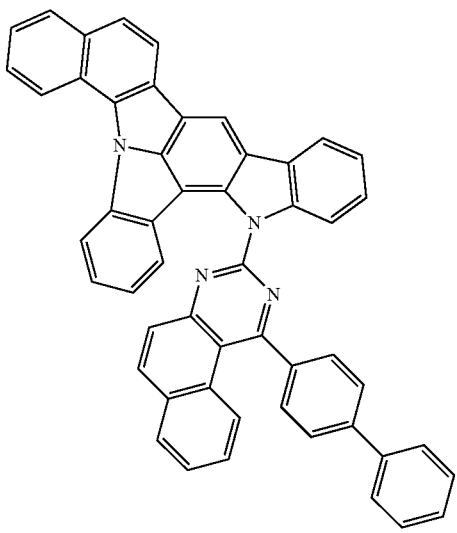

681
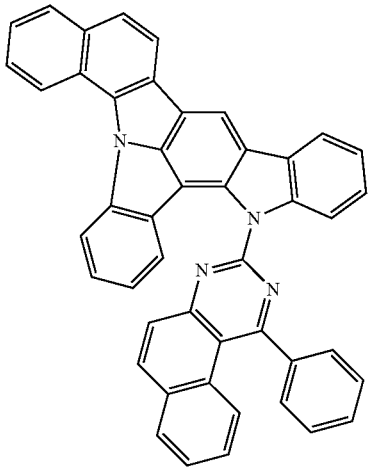
682
-continued
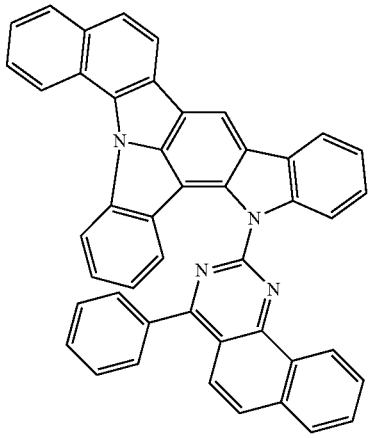
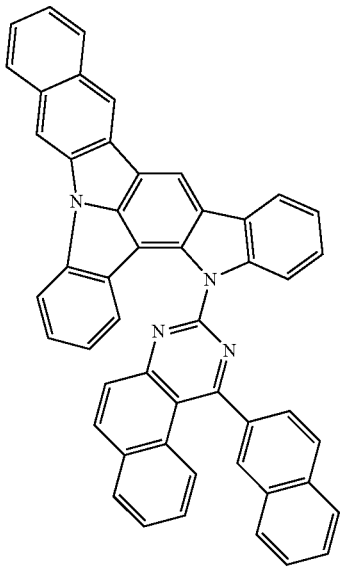
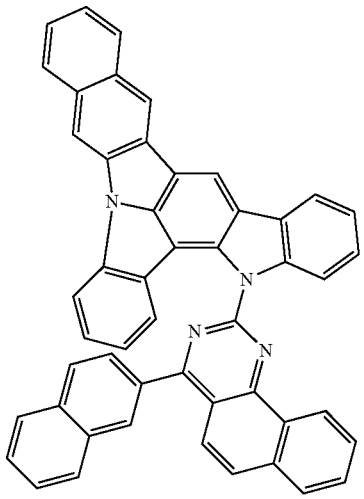
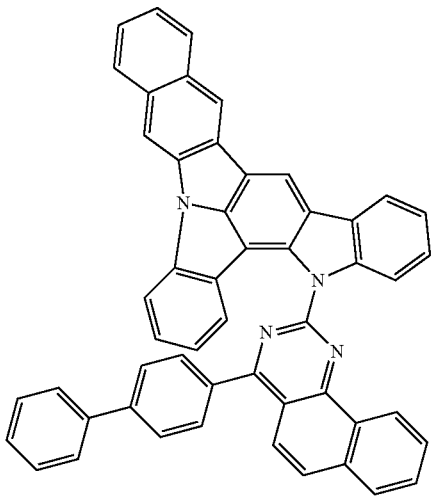
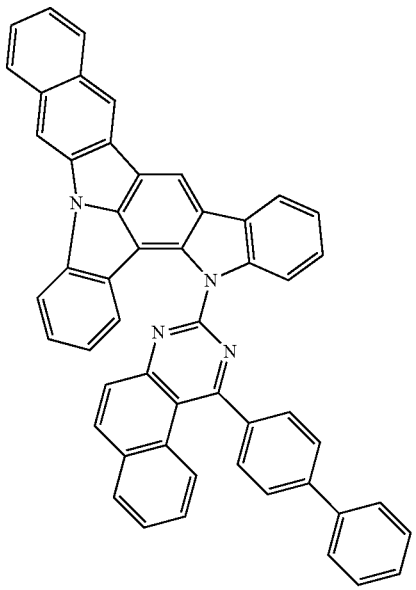

-continued
683
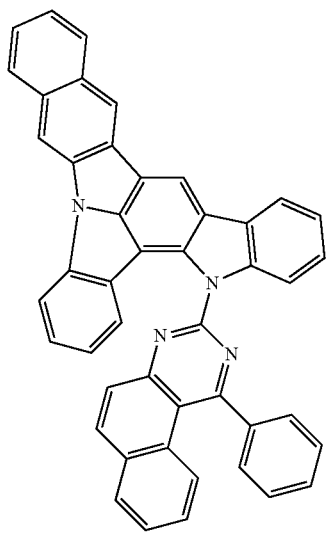
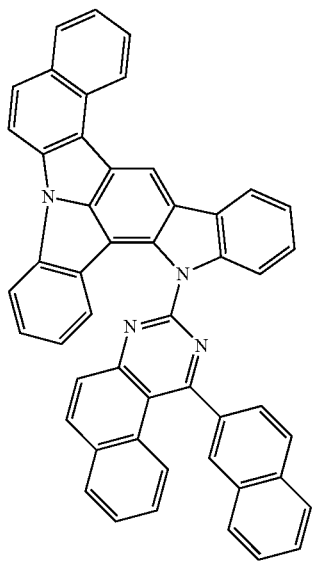
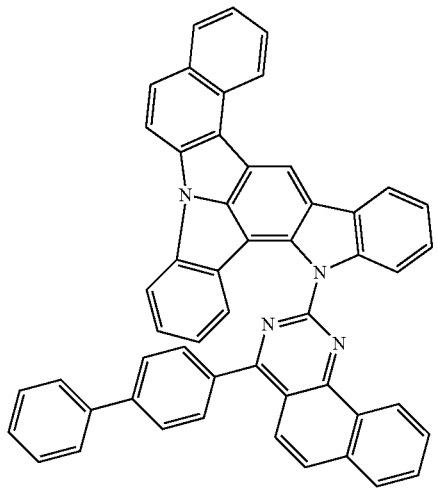
684
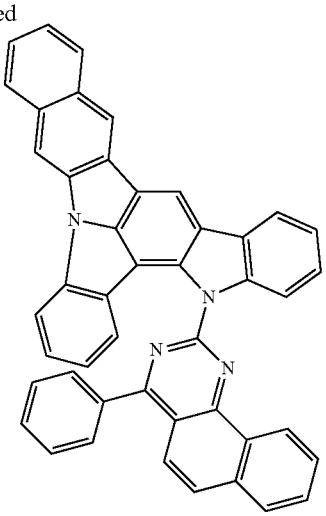
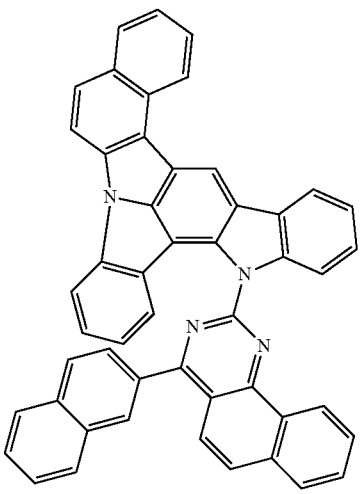
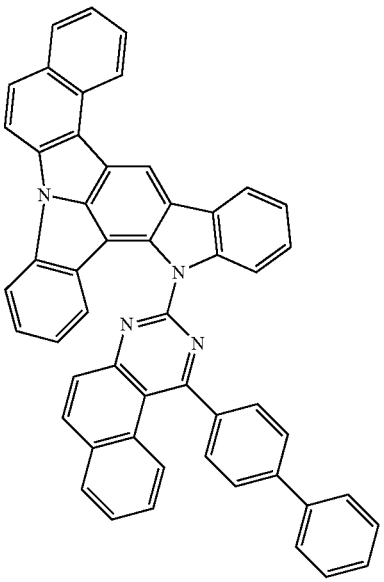

685
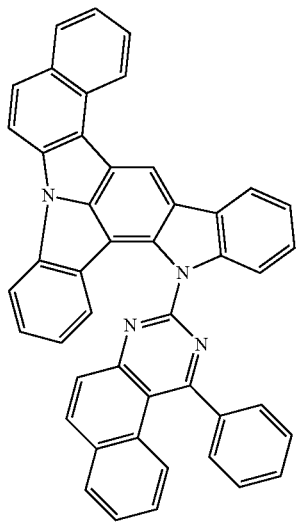
686
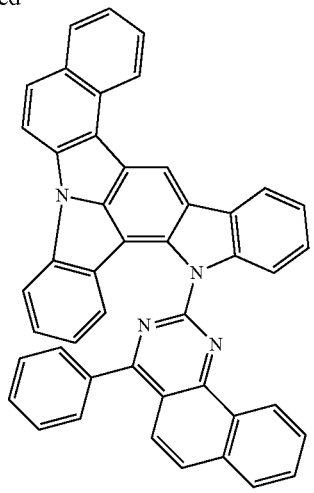
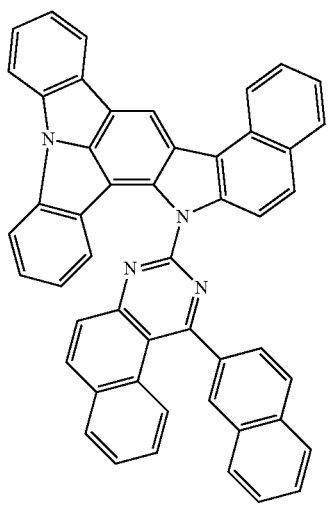
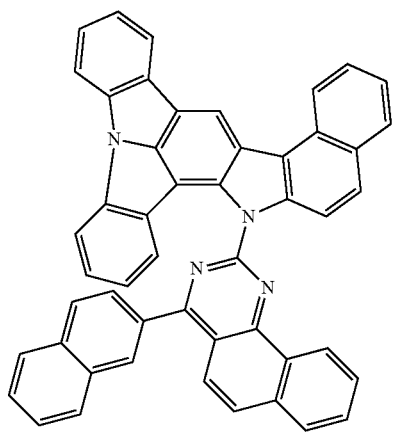
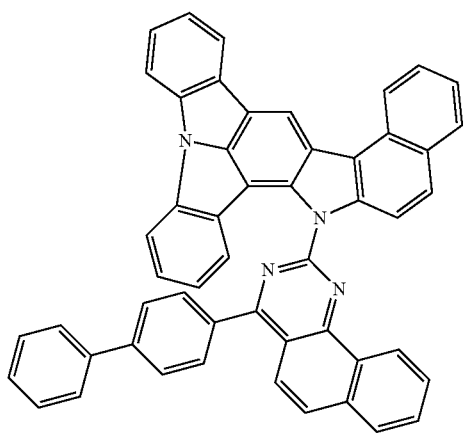
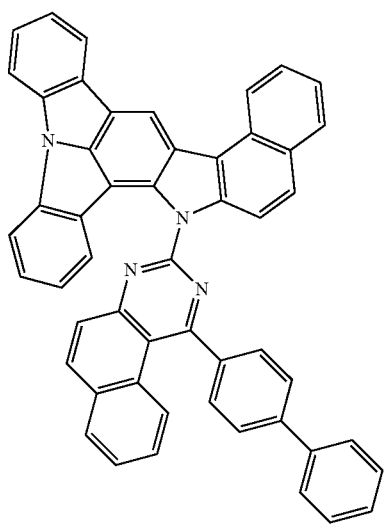

687
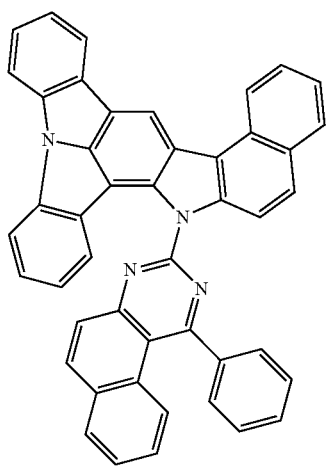
688
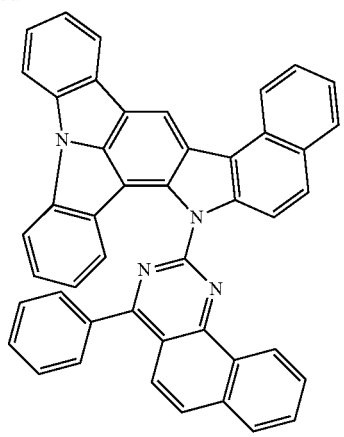
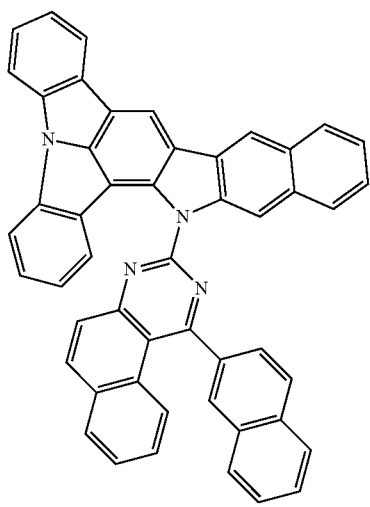
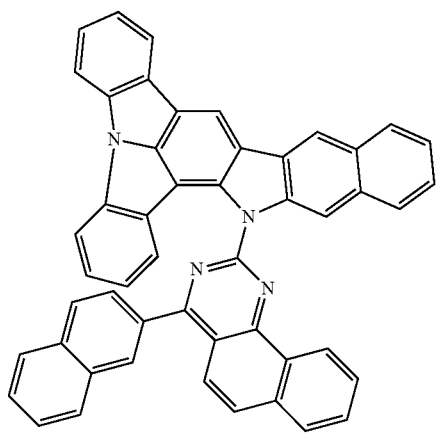
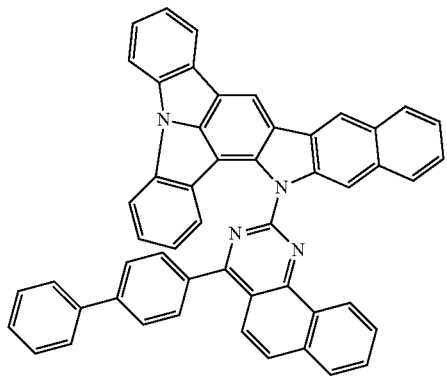
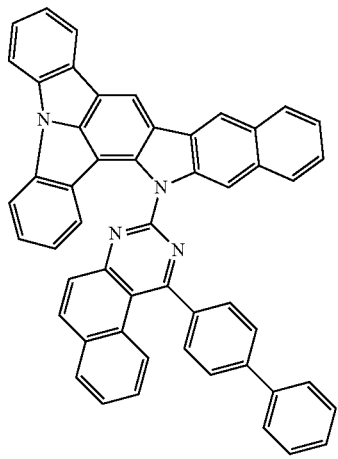

-continued
689
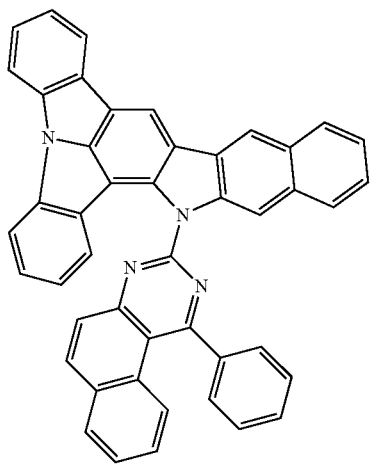
690
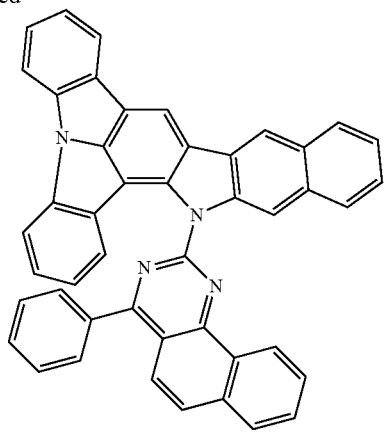
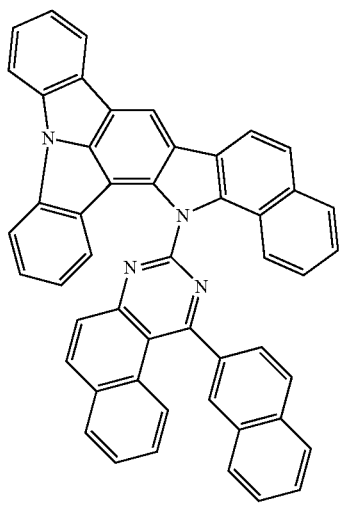
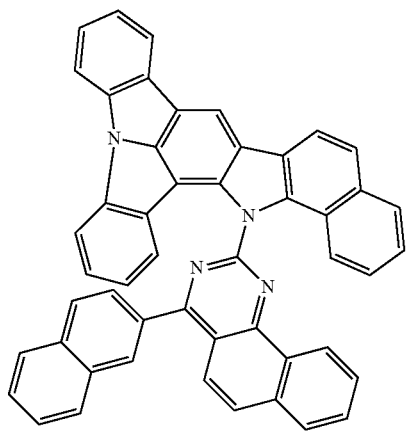
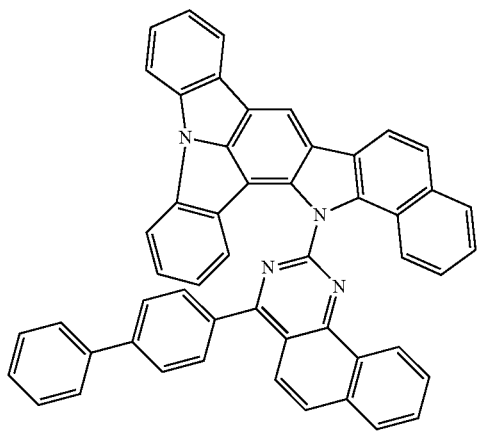
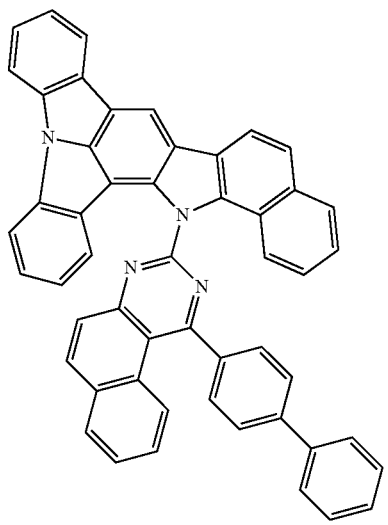

-continued
691
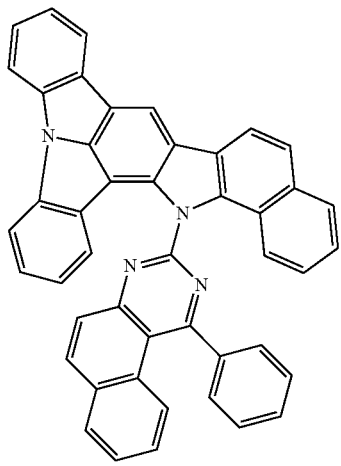
692
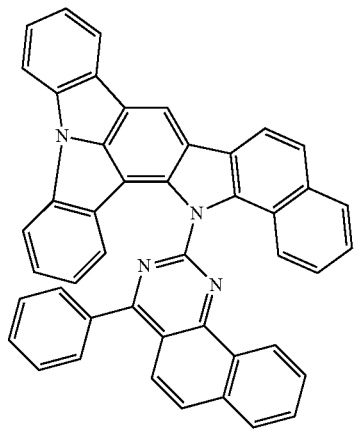
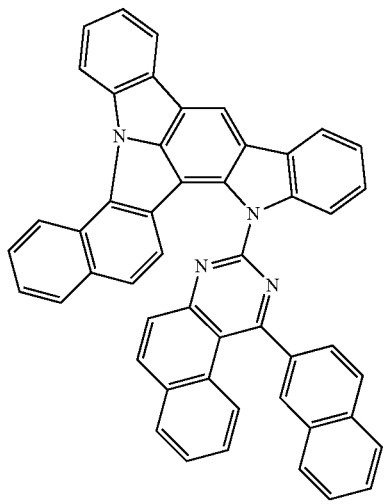
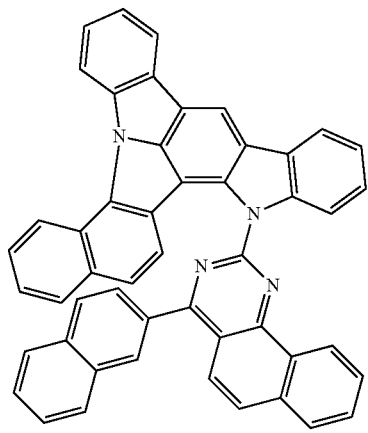
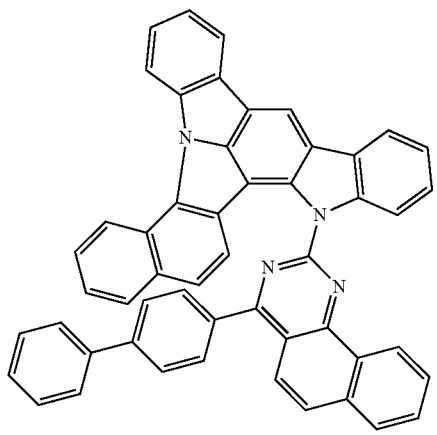
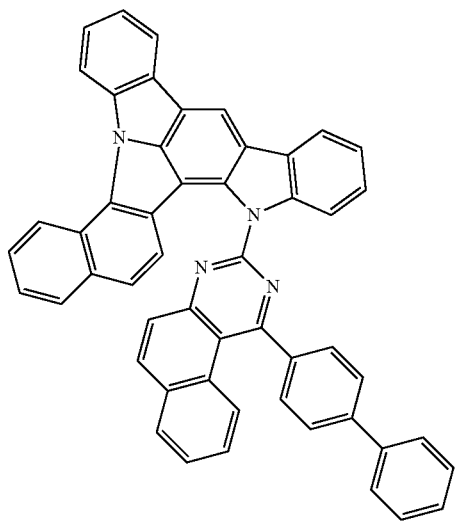

-continued
693 694
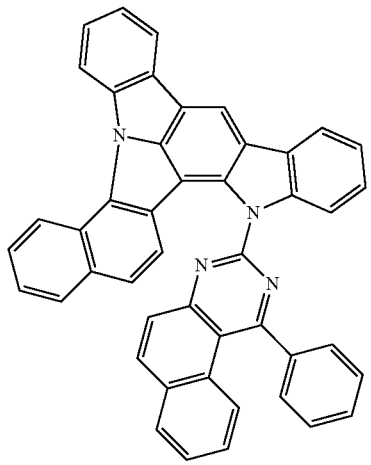 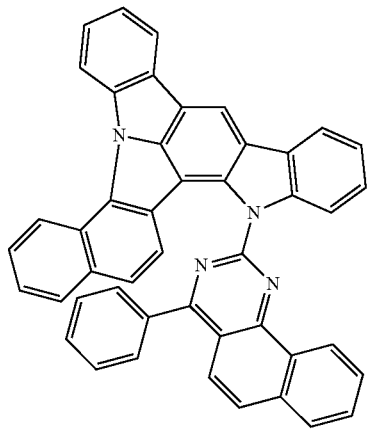
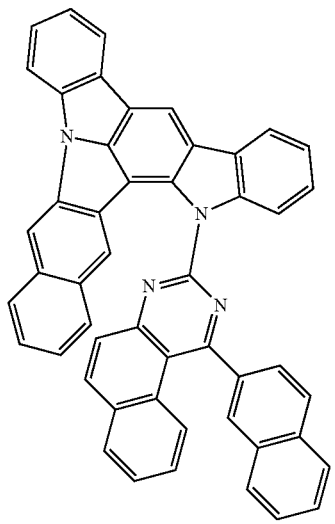 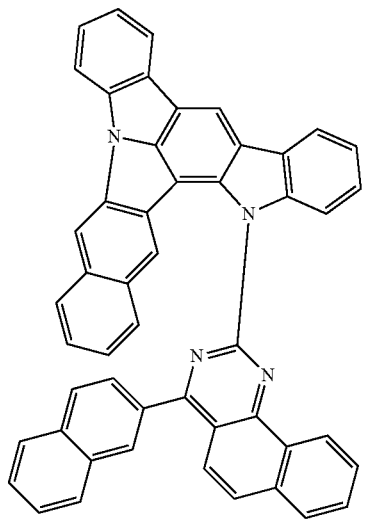
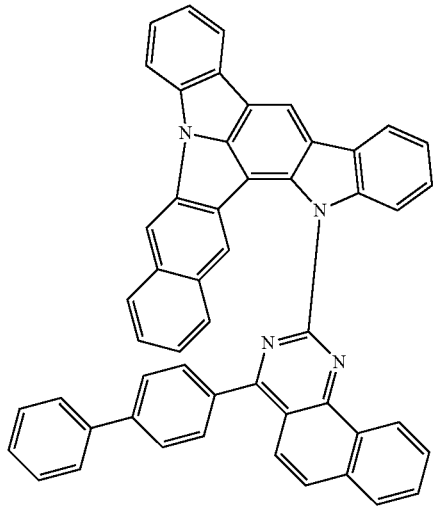 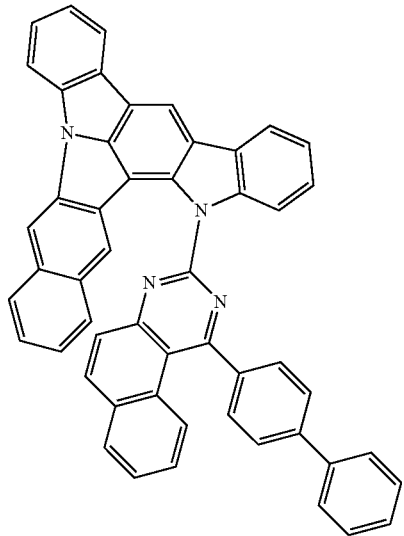

-continued
| 695 | 696 |
|---|---|
| 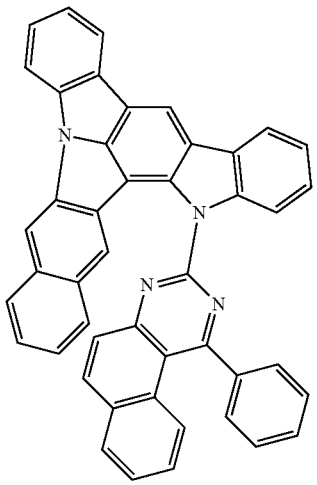 | 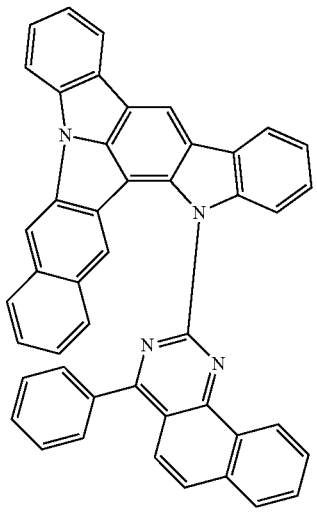 |
| 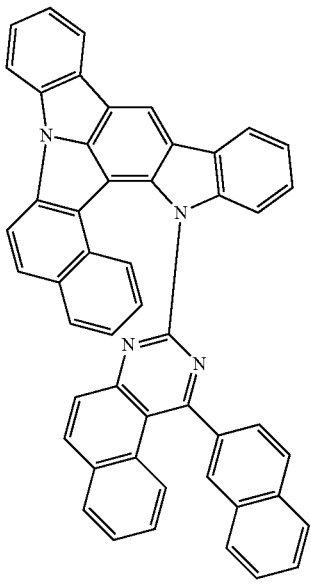 | 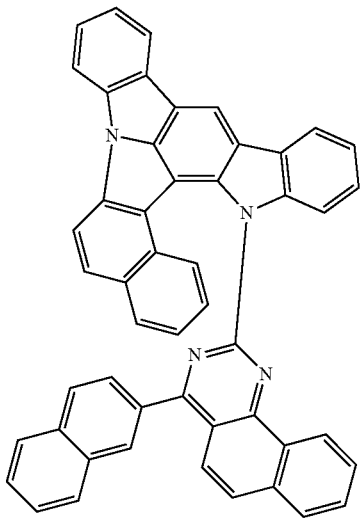 |
| 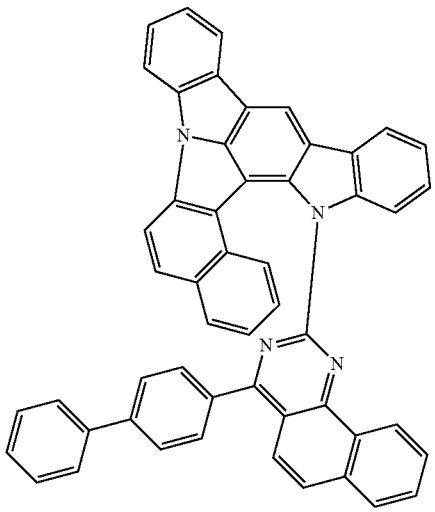 | 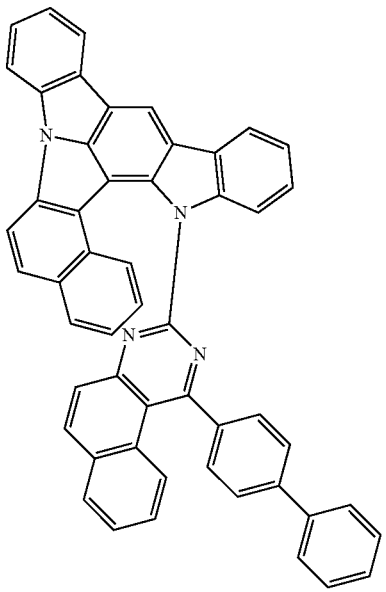 |

697 698
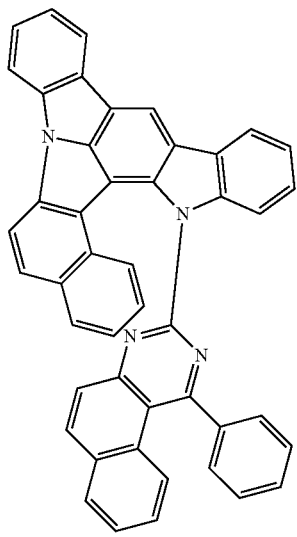 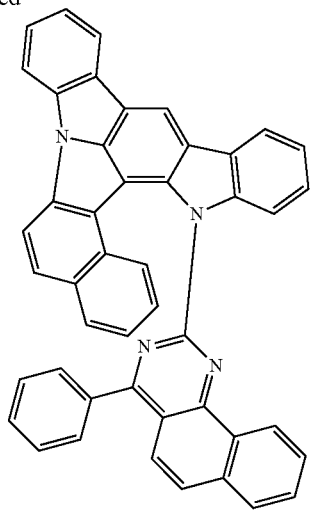
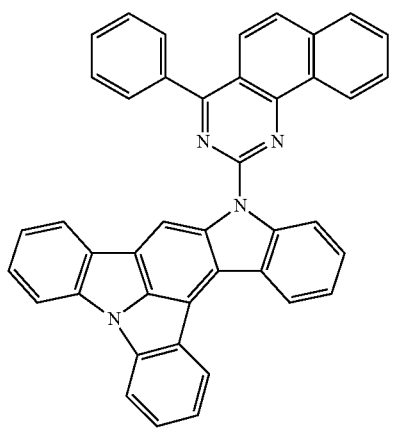 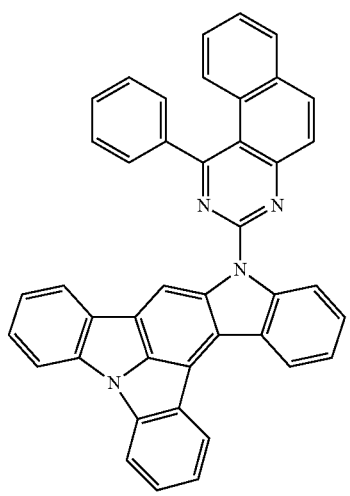
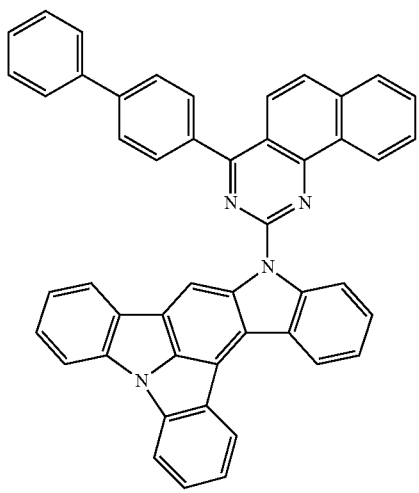 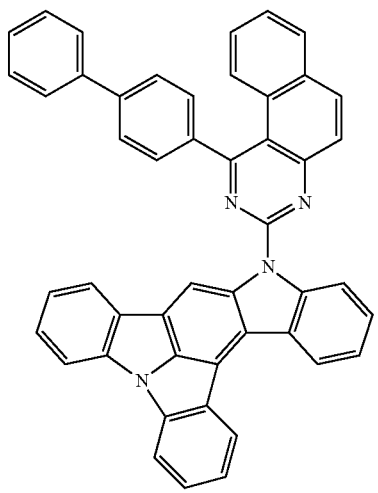

-continued
| 699 | 700 |
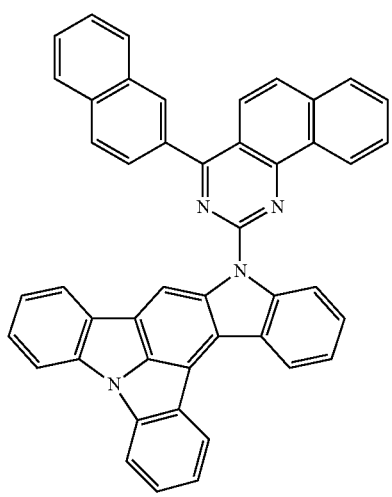
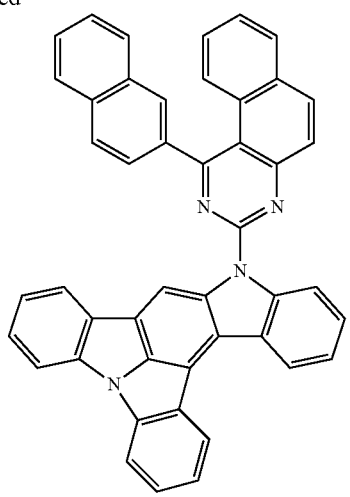
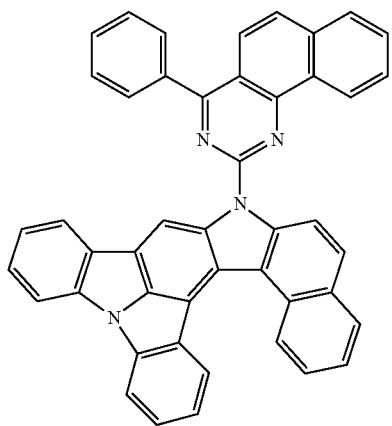
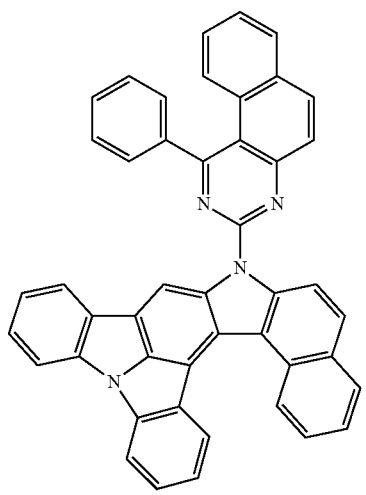
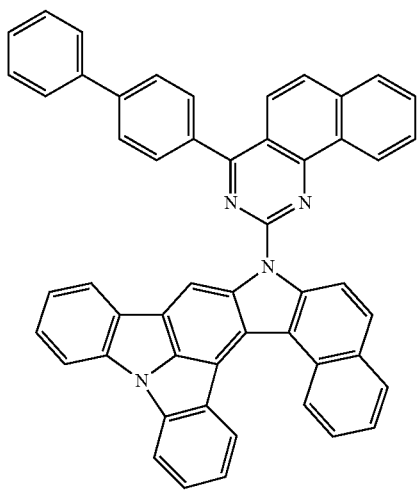
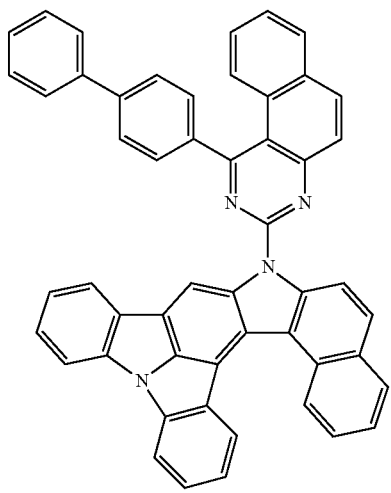

-continued
| 701 | 702 |
|---|---|
| 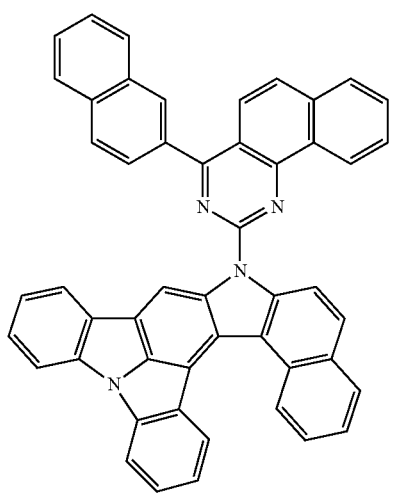 | 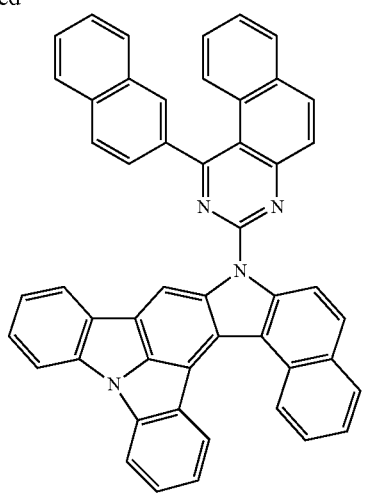 |
| 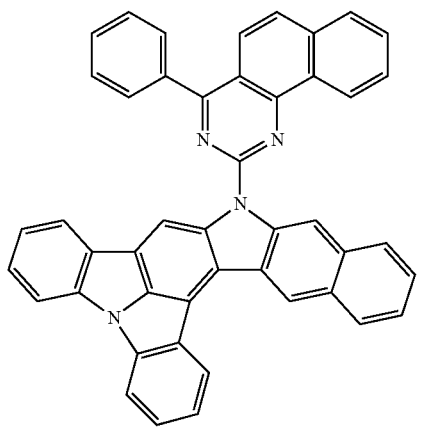 | 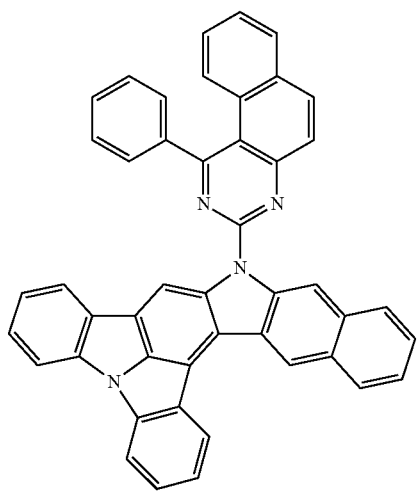 |
| 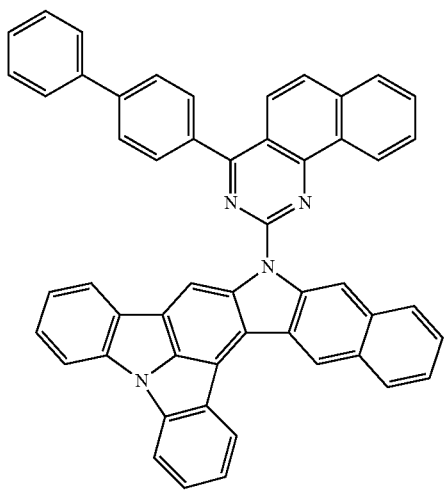 | 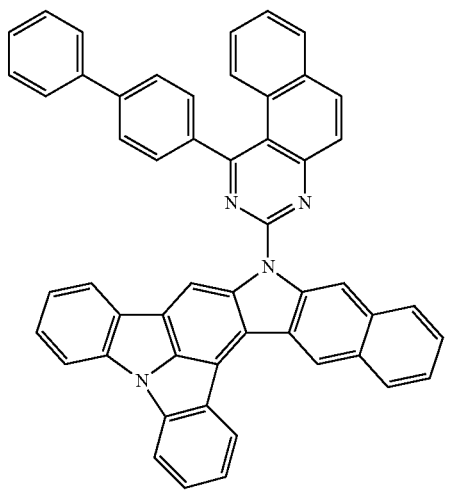 |

-continued
| 703 | 704 |
|---|---|
| 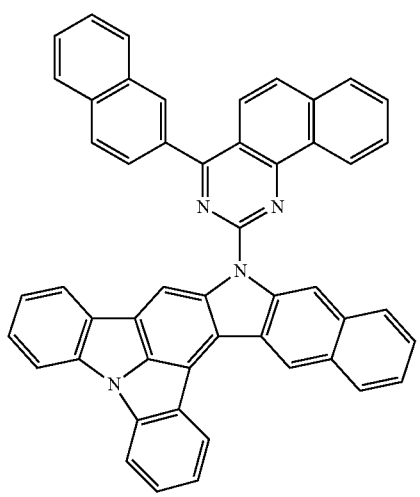 | 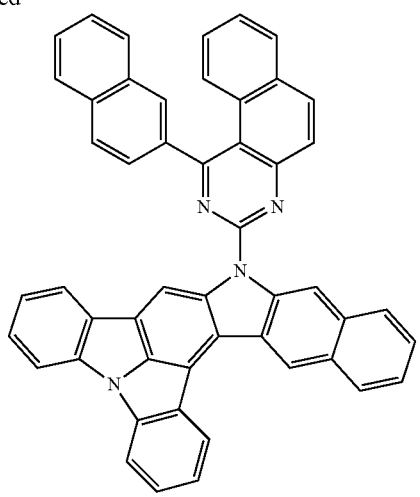 |
| 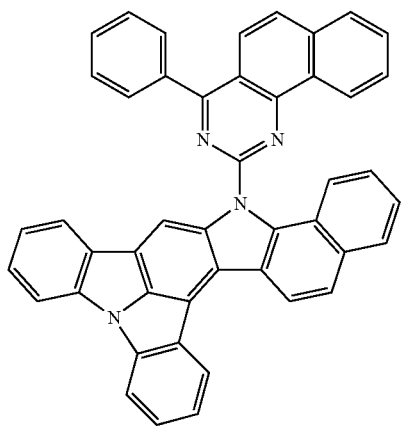 | 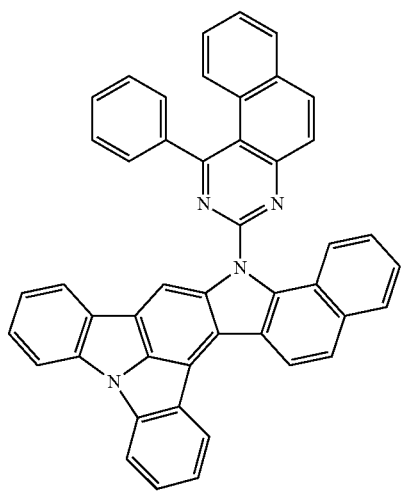 |
| 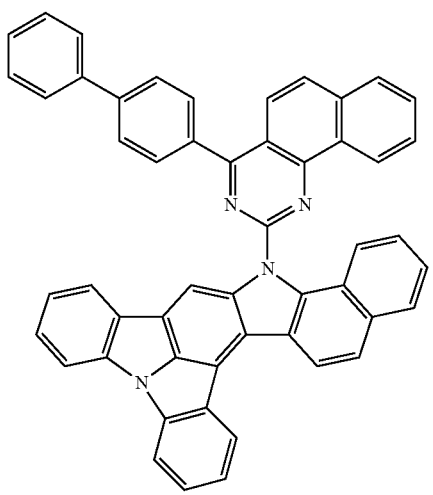 | 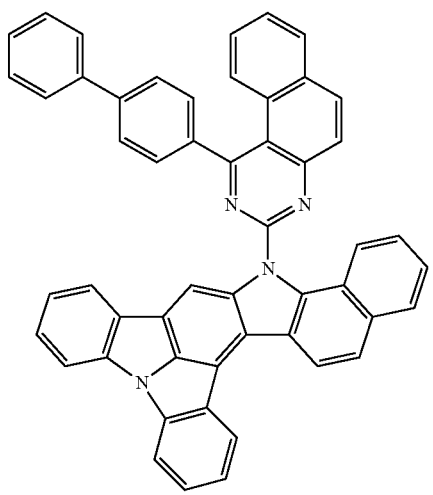 |

-continued
705
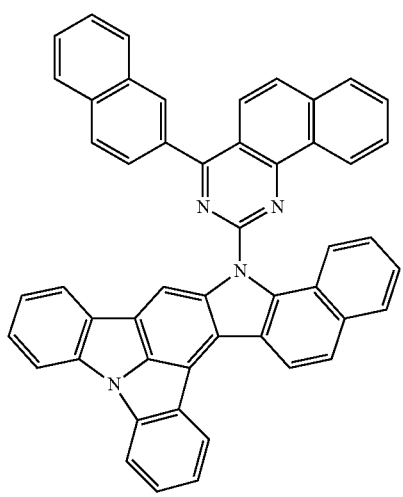
706
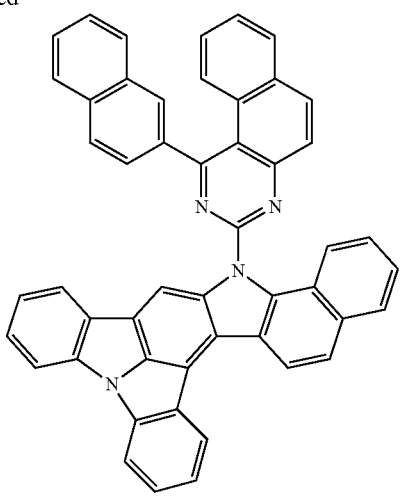
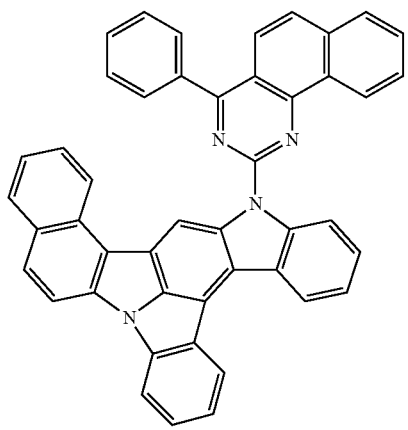
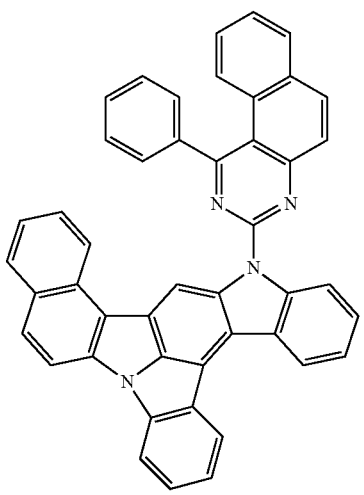
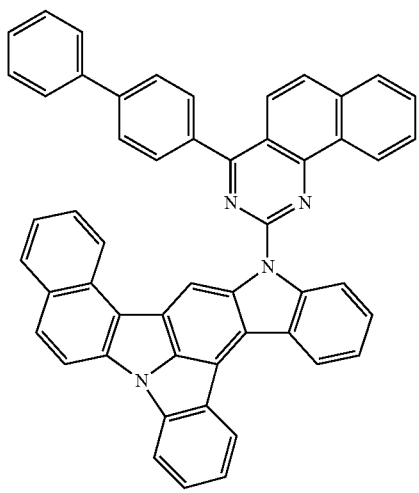
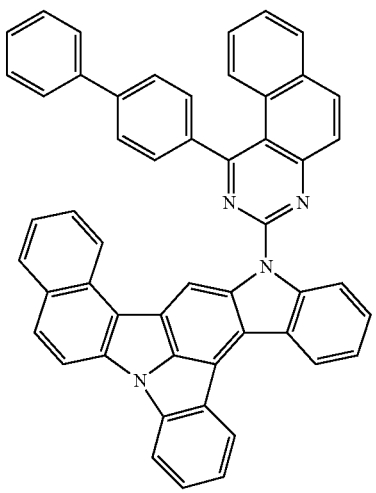

-continued
707
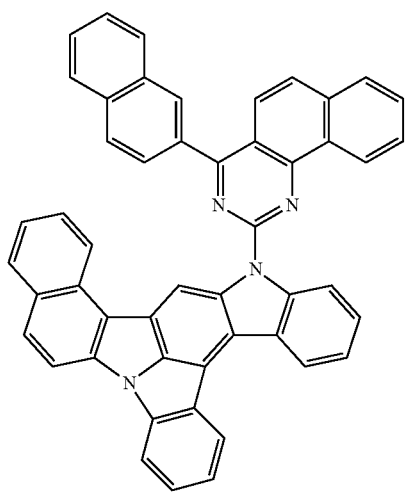
708
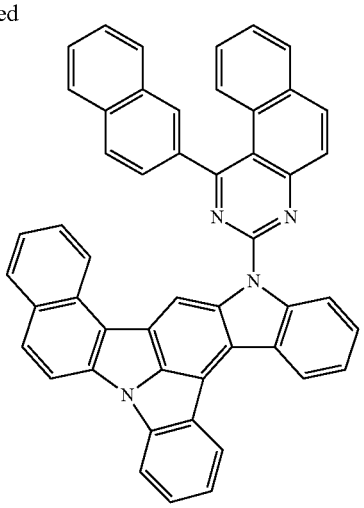
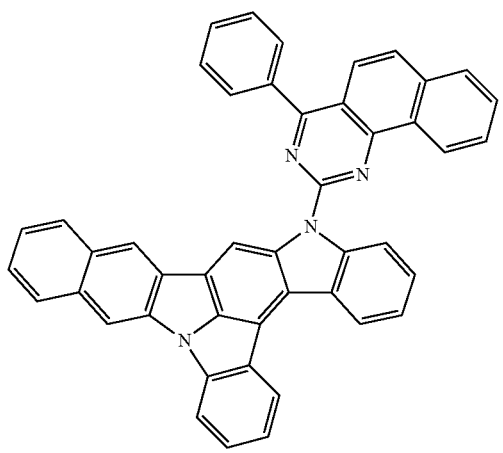
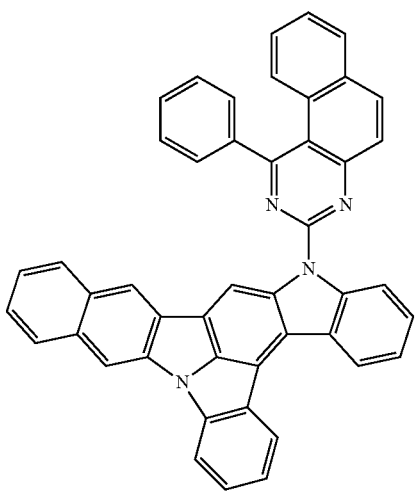
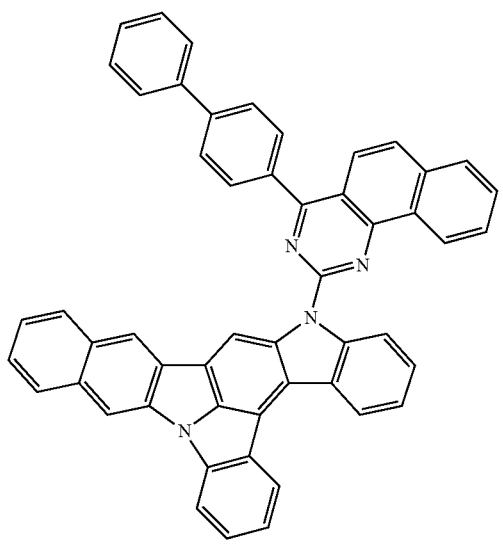
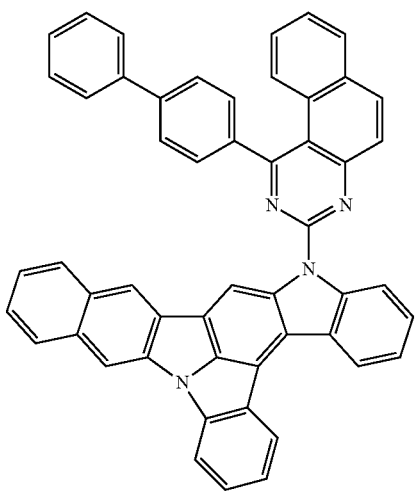

-continued
709
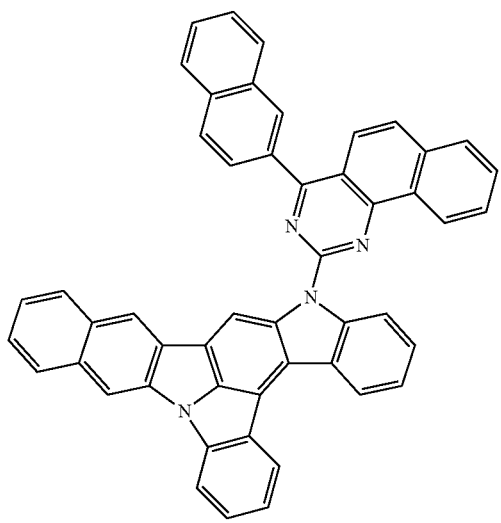
710
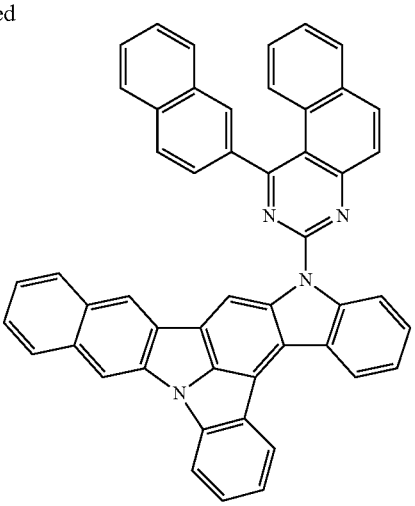
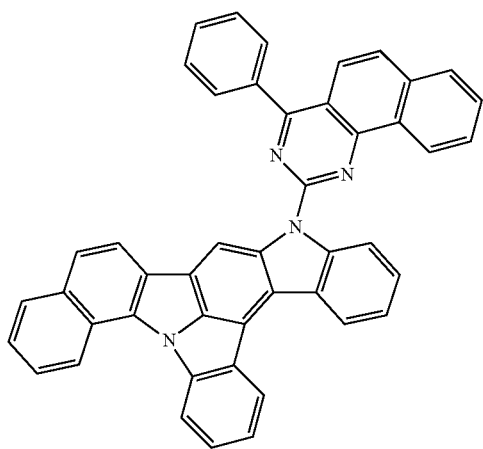
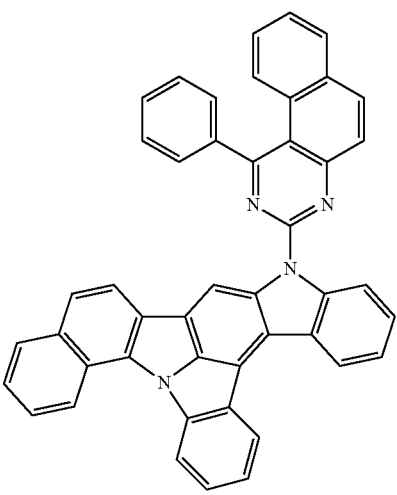
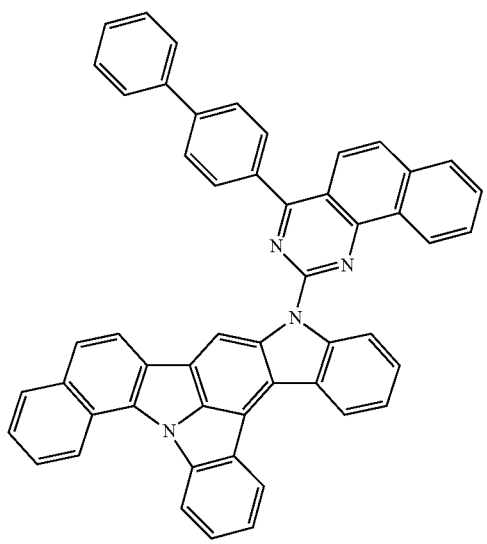
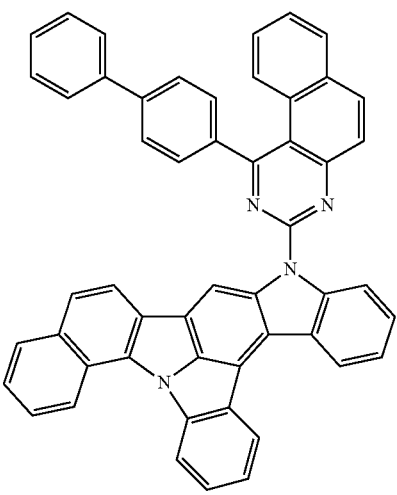

-continued
711
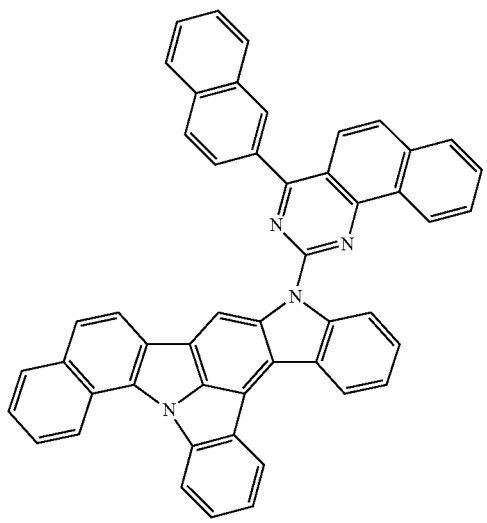
712
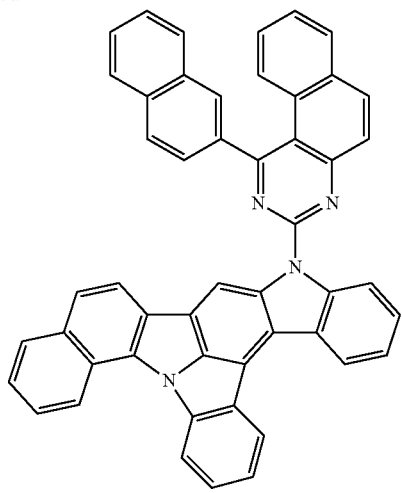
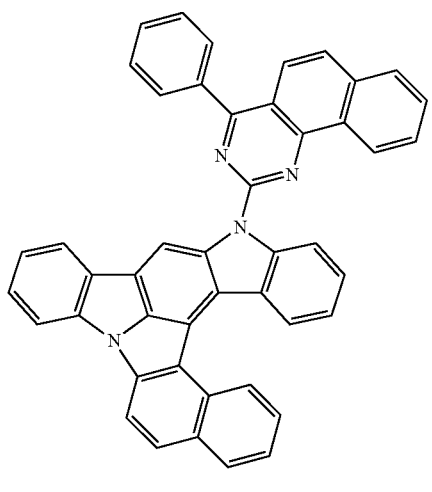
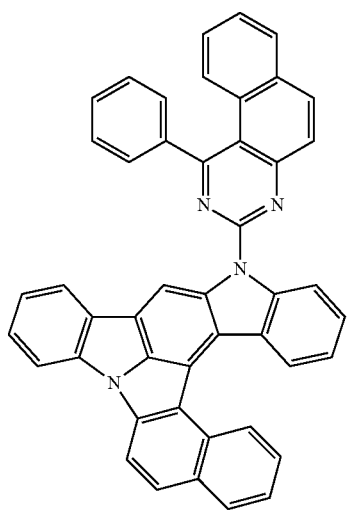
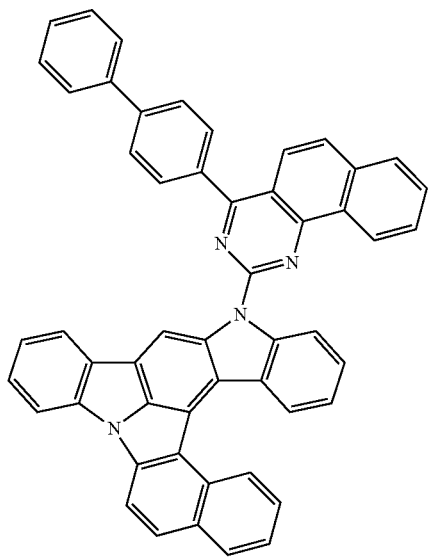
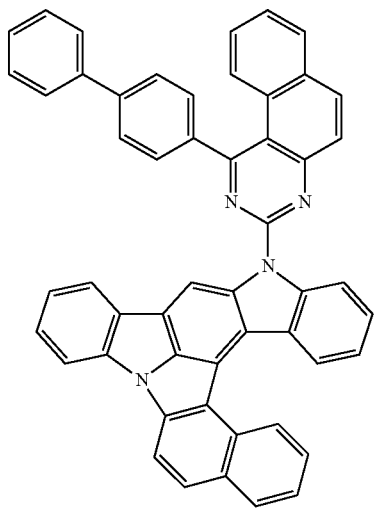

-continued
| 713 | 714 |
|---|---|
| 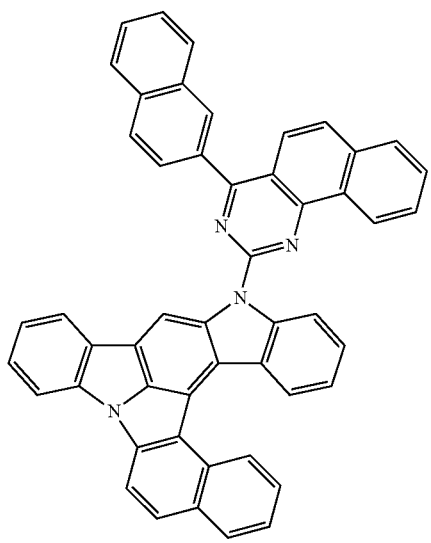 | 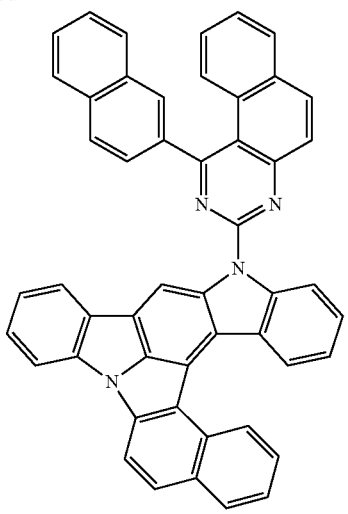 |
| 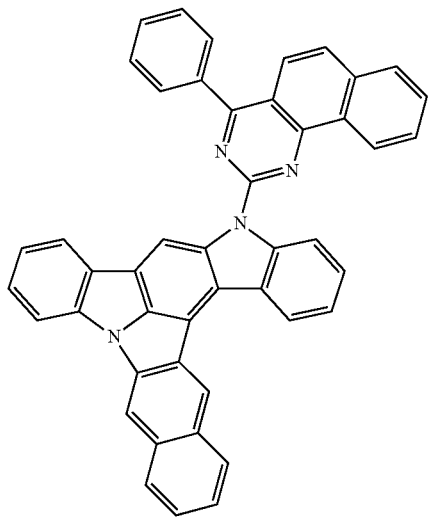 | 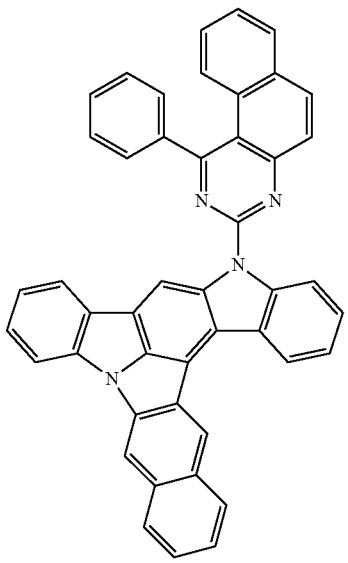 |
| 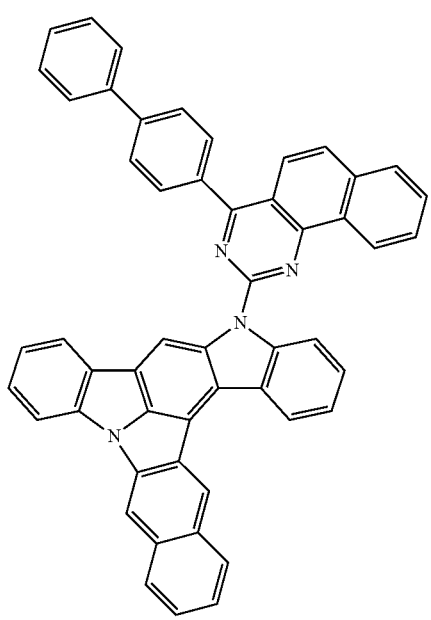 | 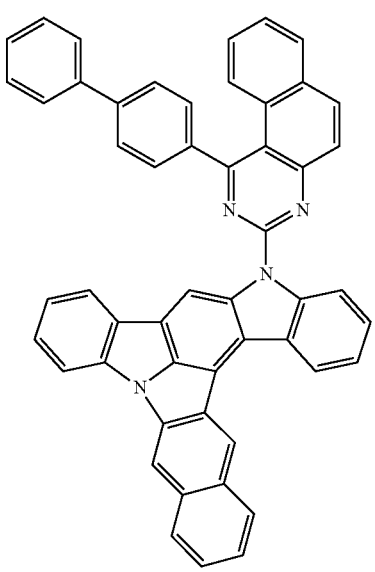 |

-continued
| 715 | 716 |
|---|---|
| 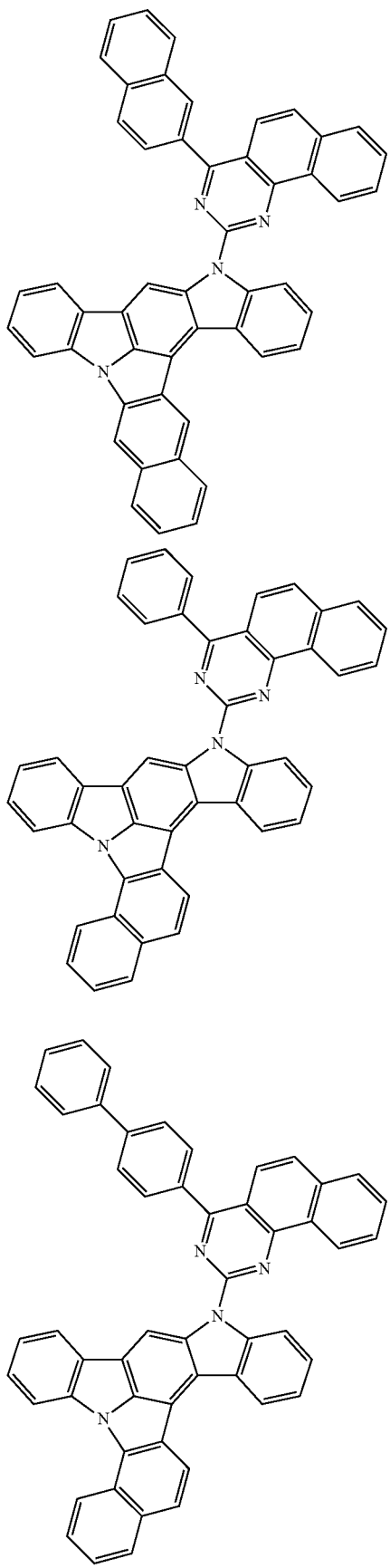 | 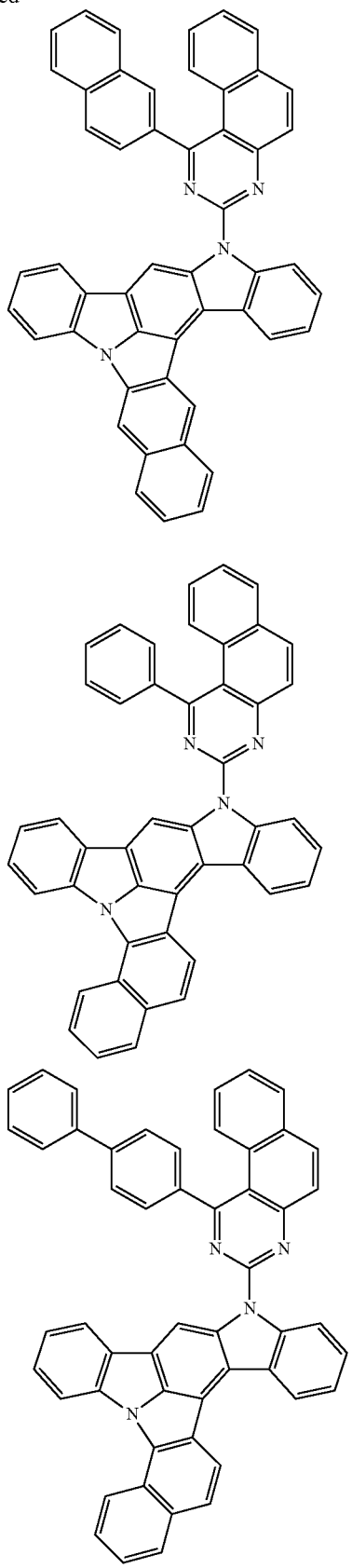 |

-continued
| 717 | 718 |
|---|---|
| 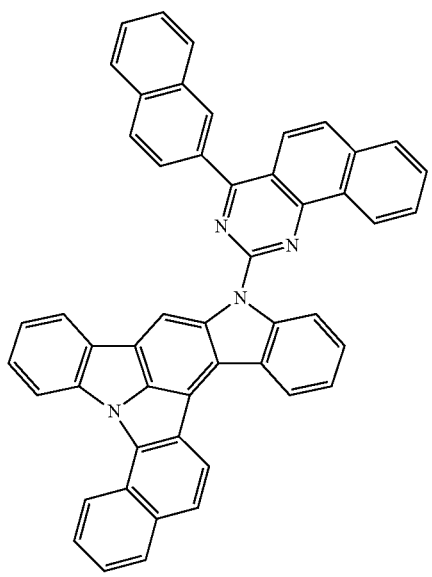 | 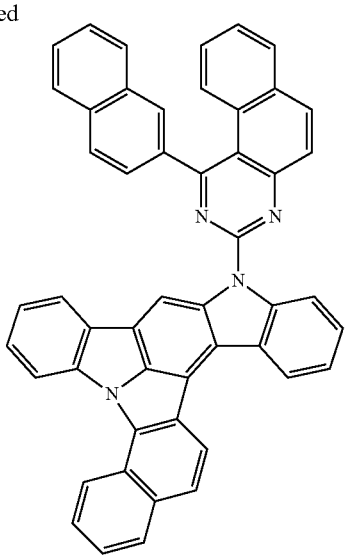 |
| 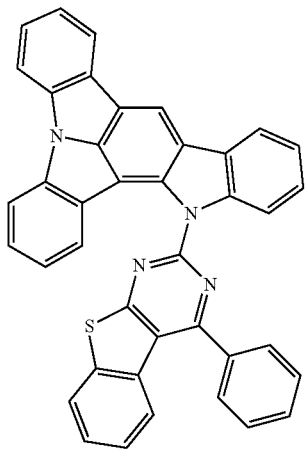 | 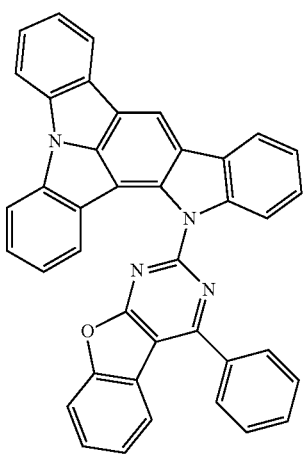 |
| 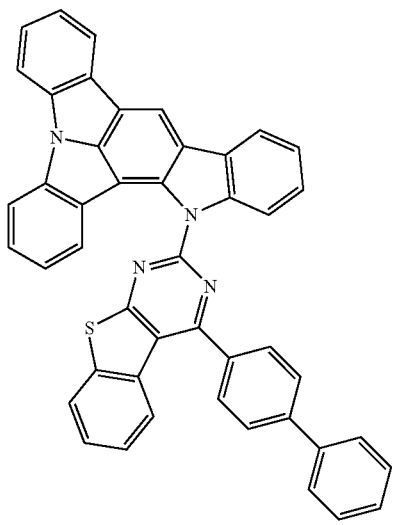 | 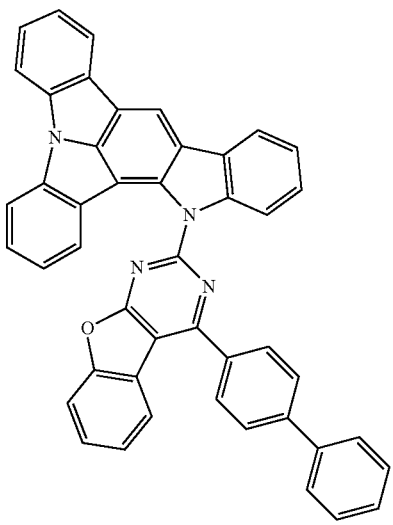 |

719
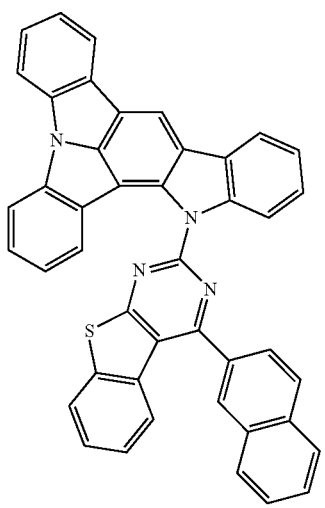
720
-continued
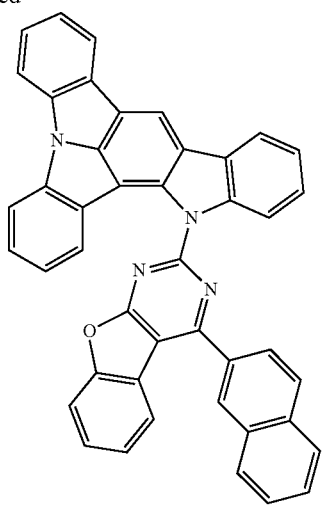
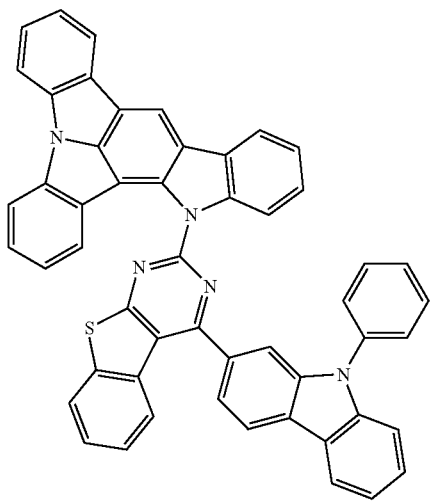
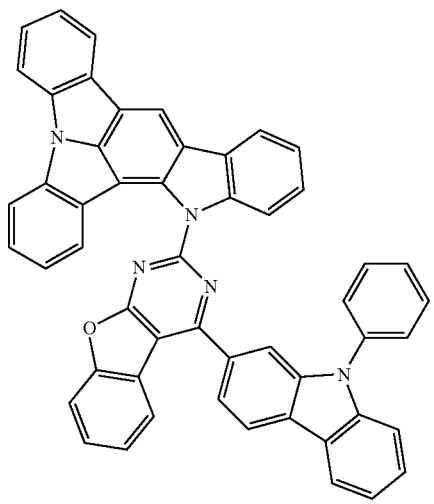
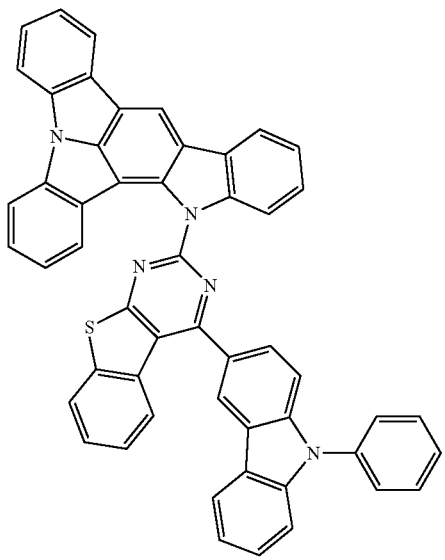
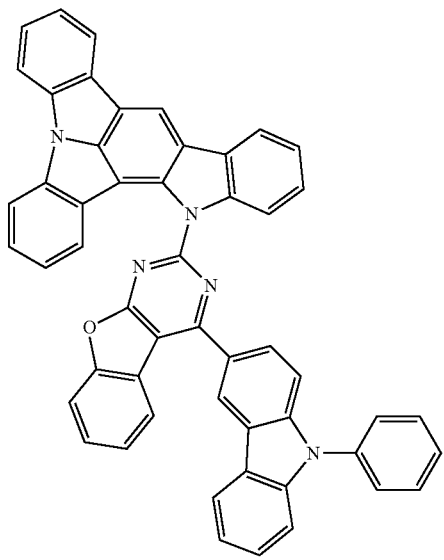

-continued
721
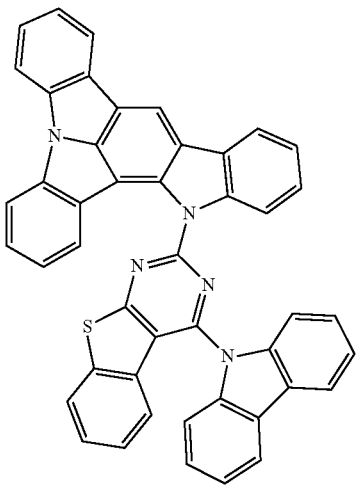
722
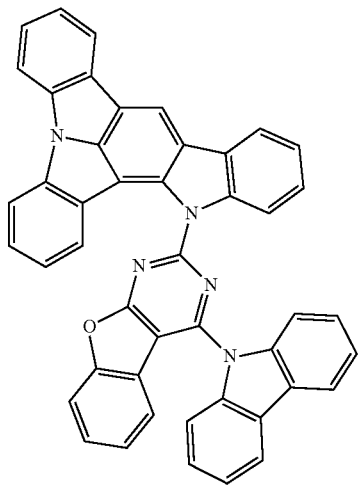
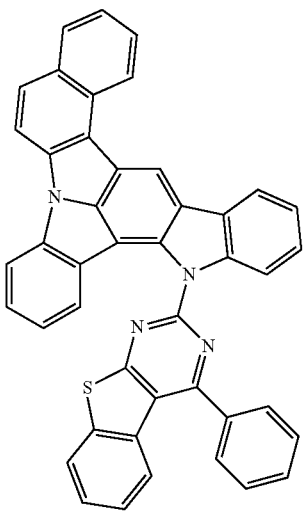
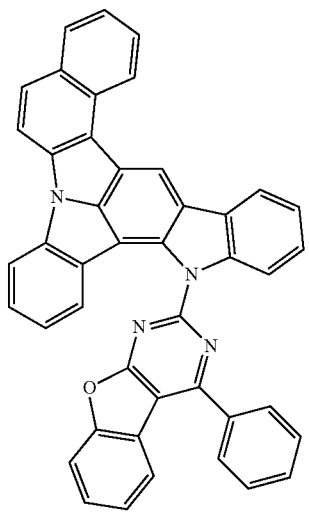
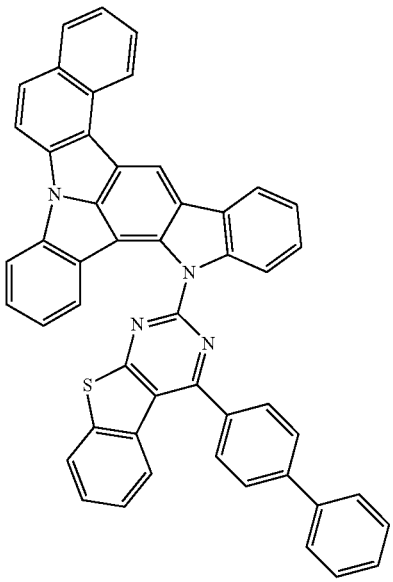
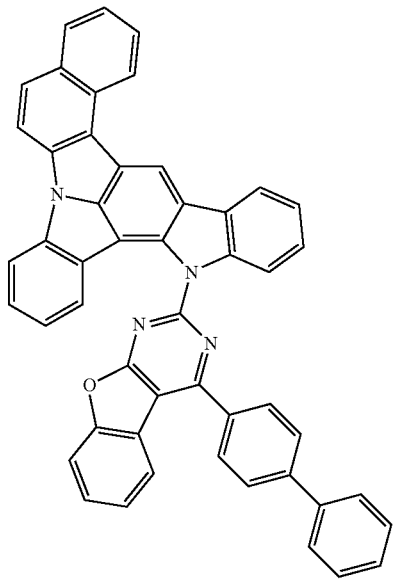

723
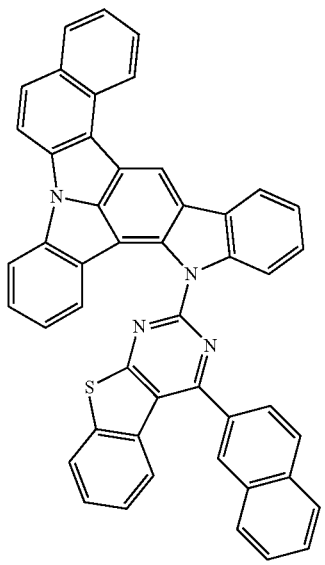
724
-continued
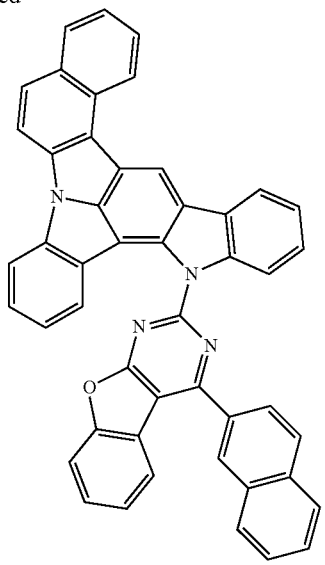
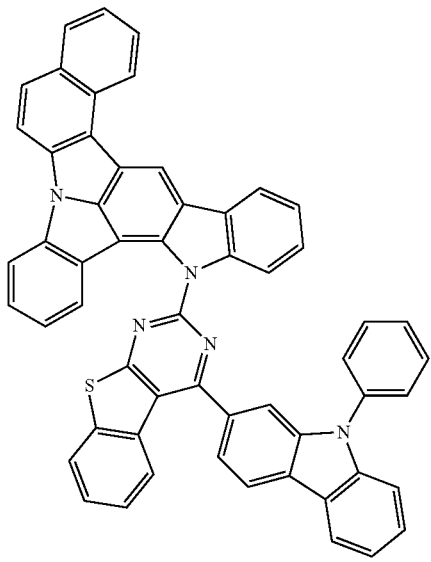
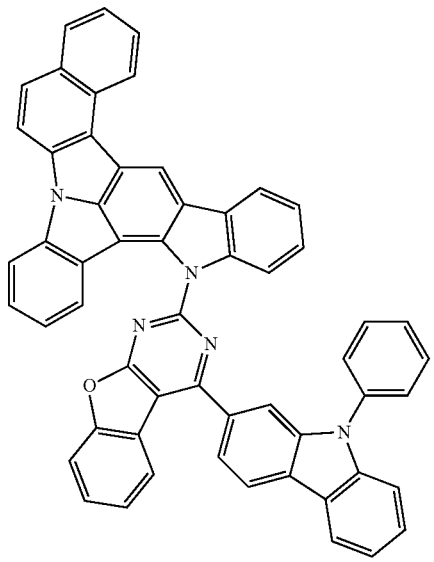

-continued
| 725 | 726 |
|---|---|
| 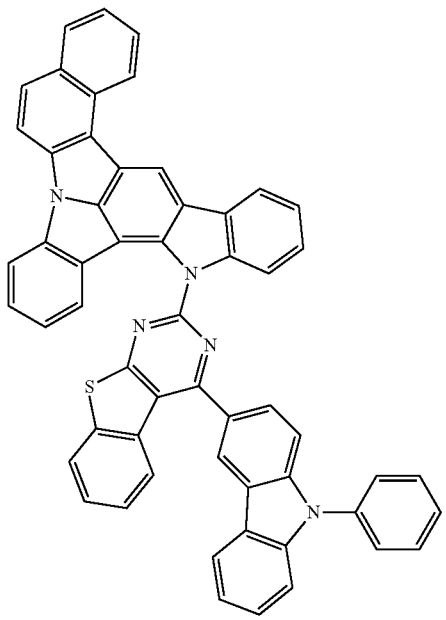 | 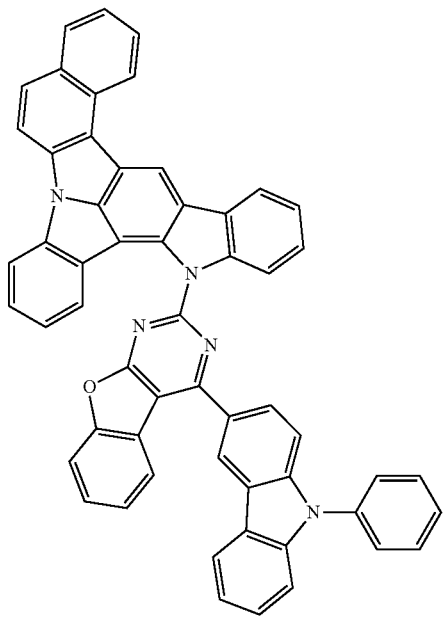 |
| 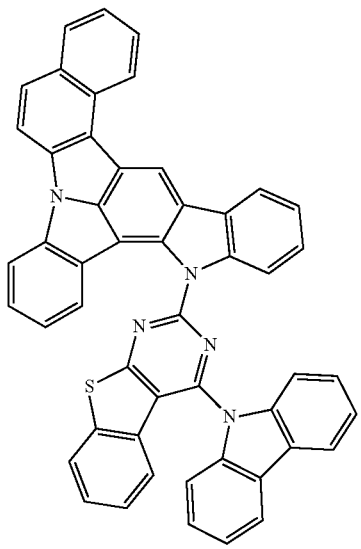 | 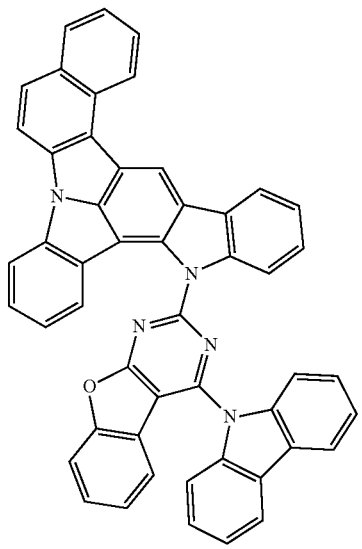 |
| 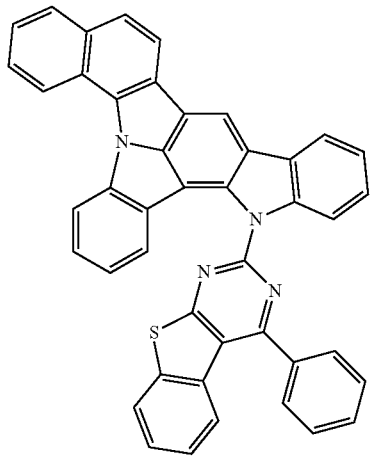 | 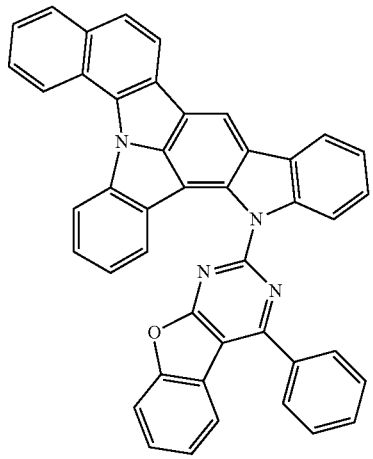 |

727    728
-continued
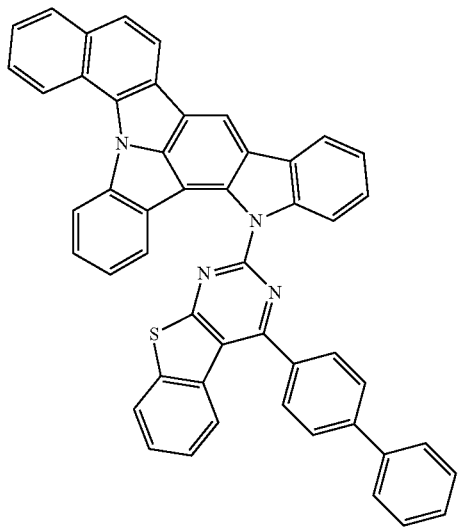 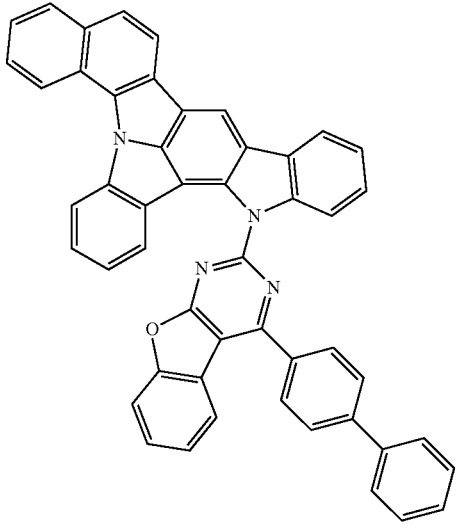
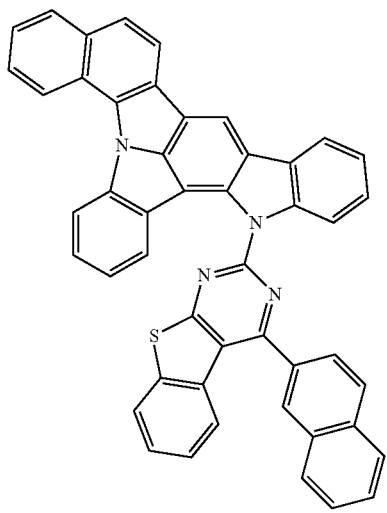 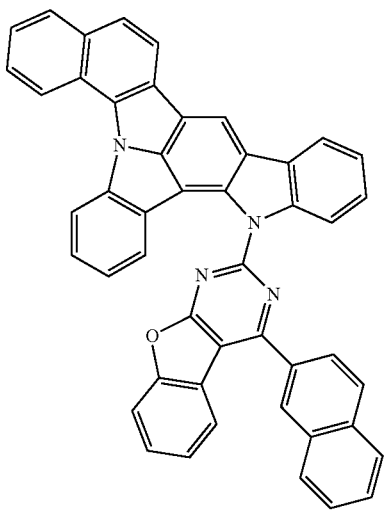
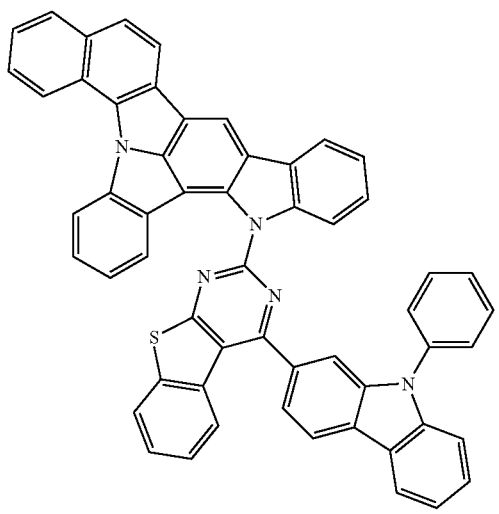 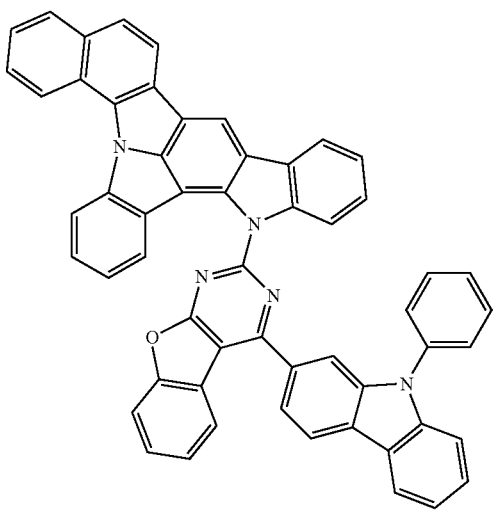

729
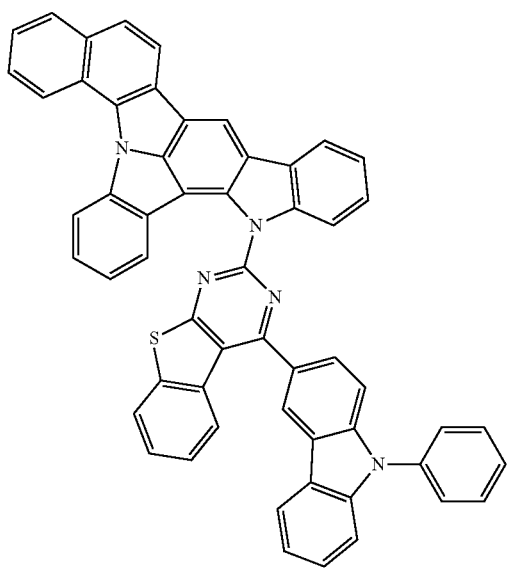
730
-continued
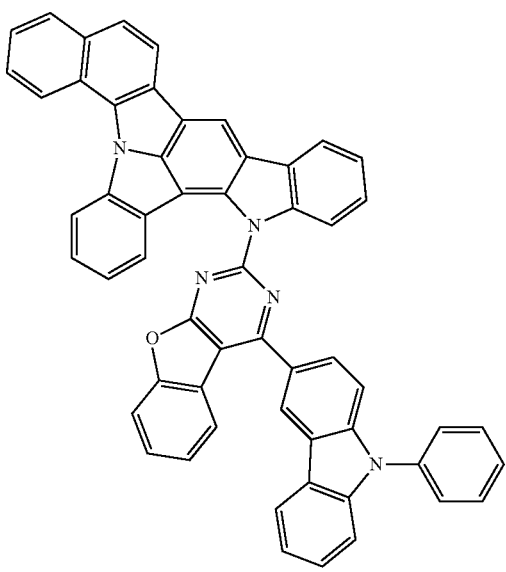
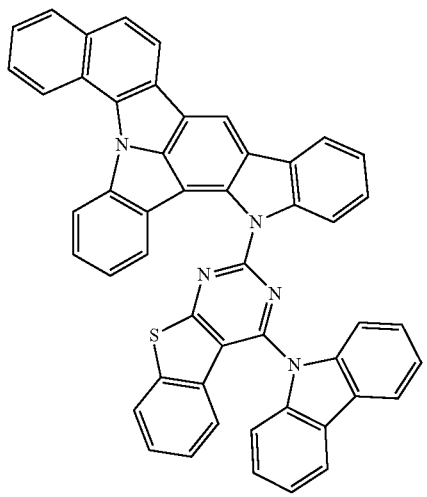
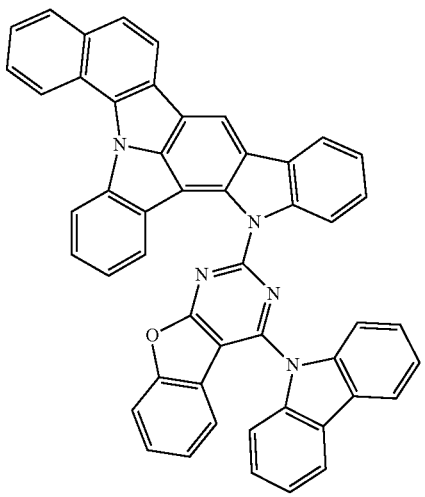
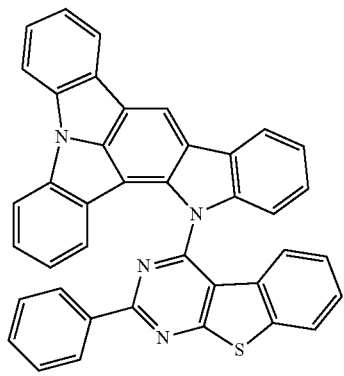
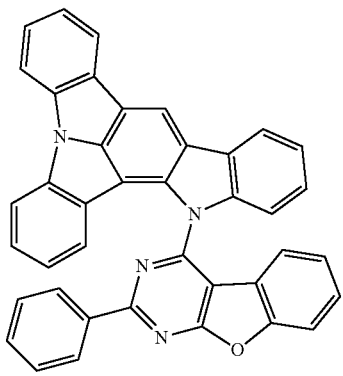

731 732
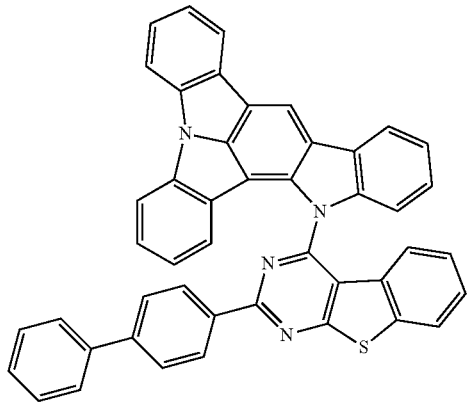 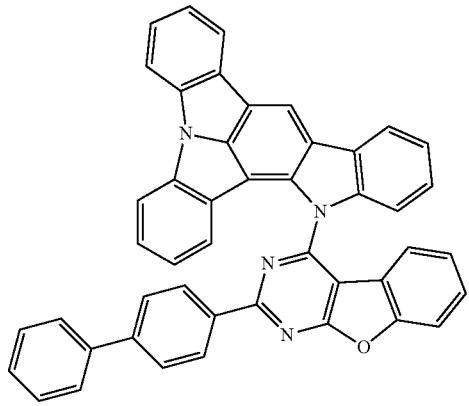
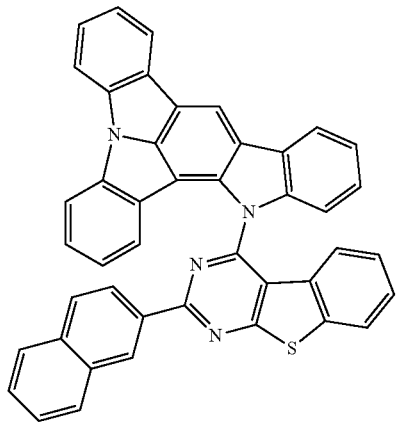 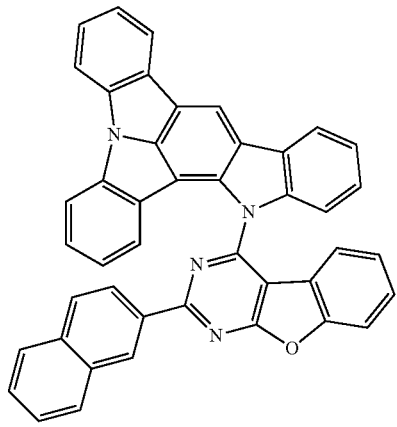
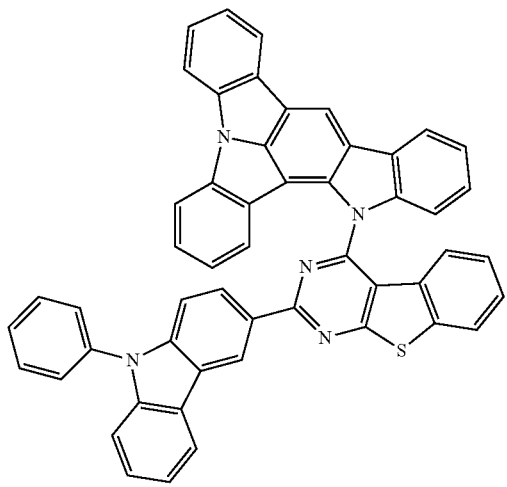 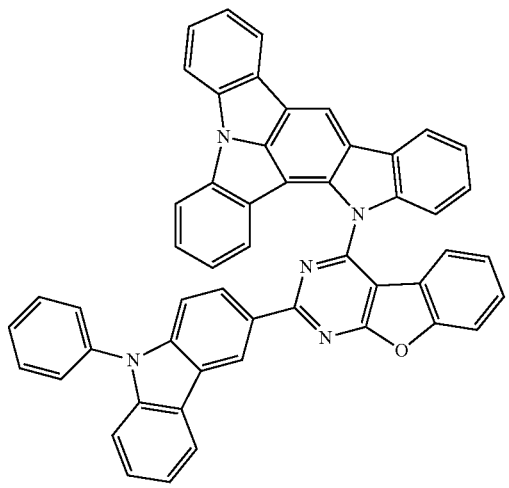

733
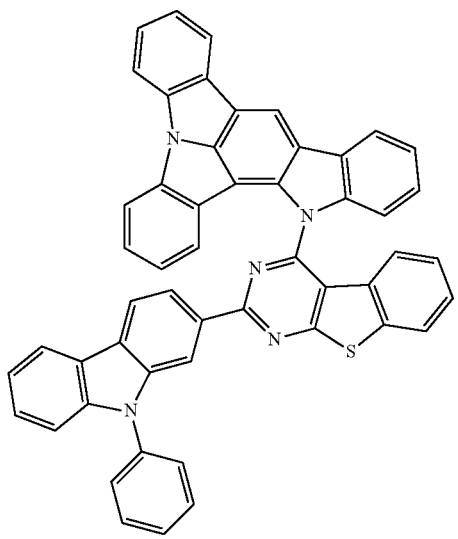
734
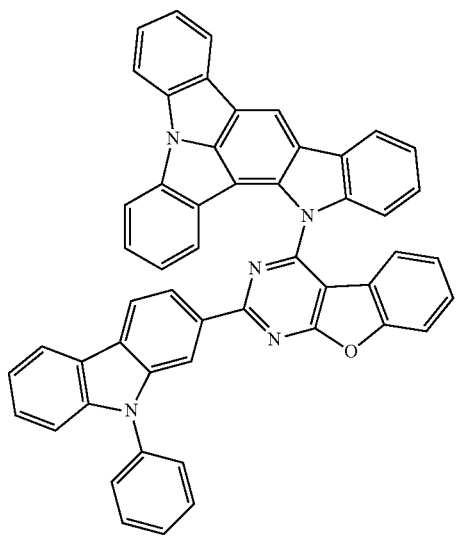
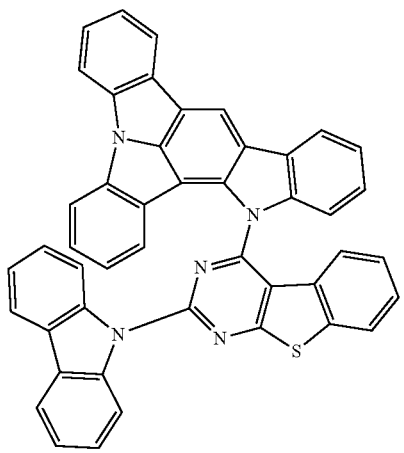
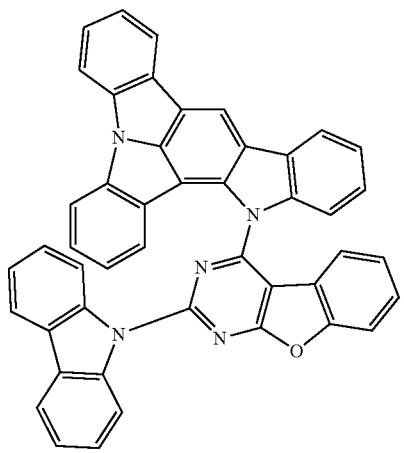
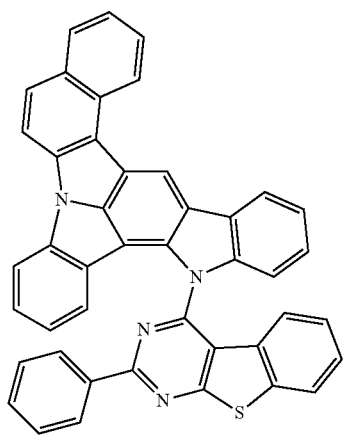
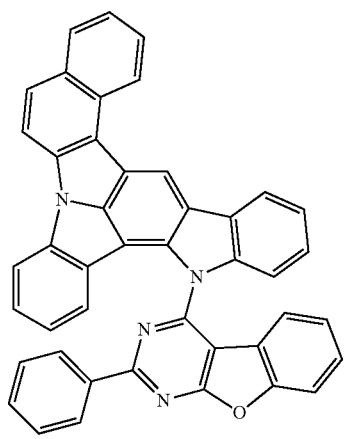

735
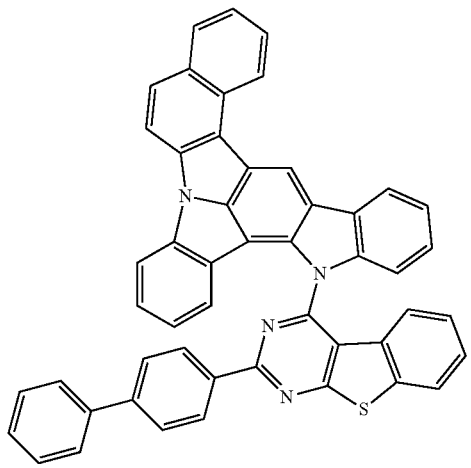
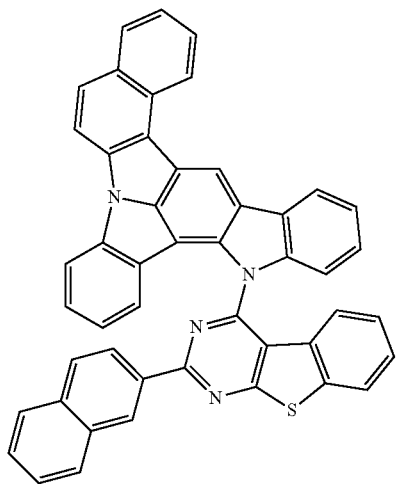
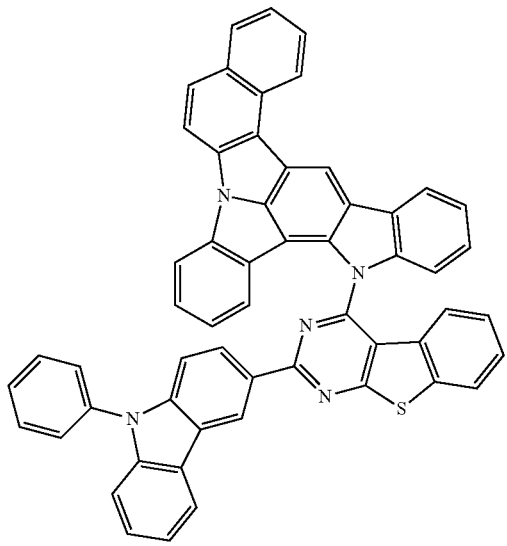
736
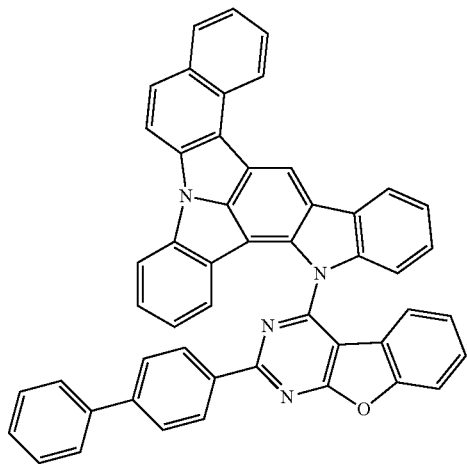
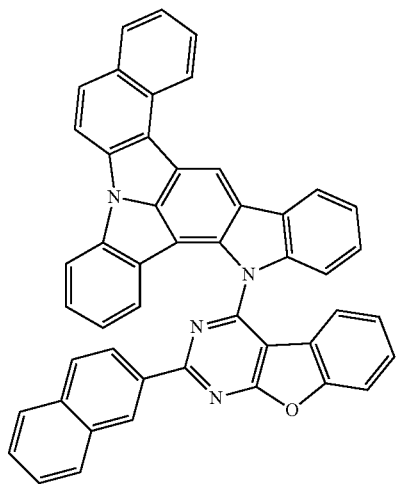
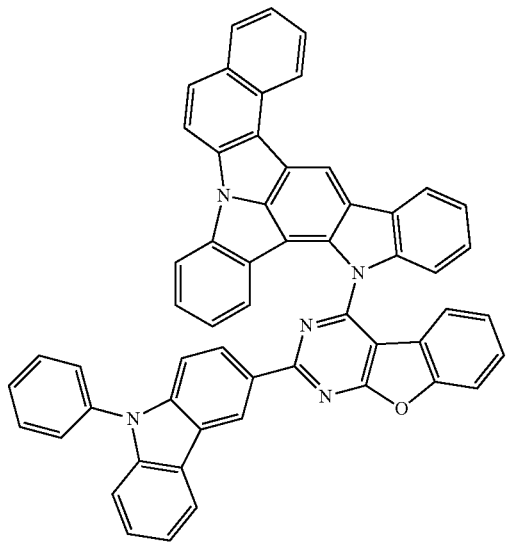

737 738
-continued
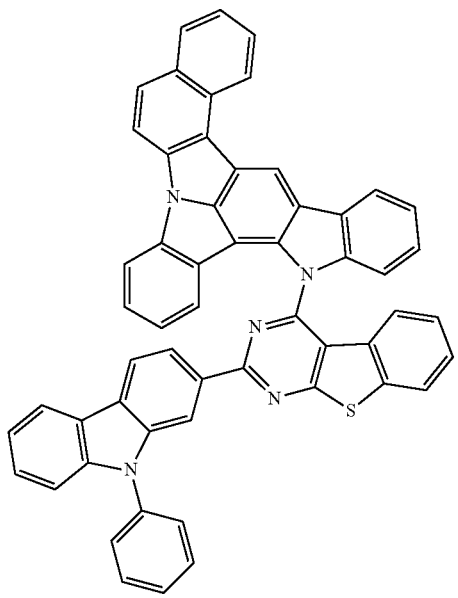
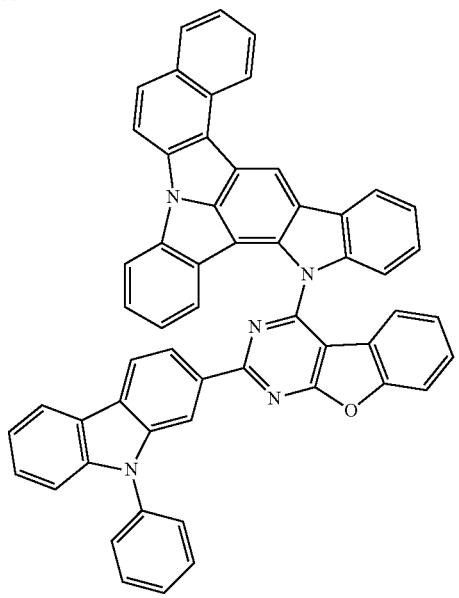
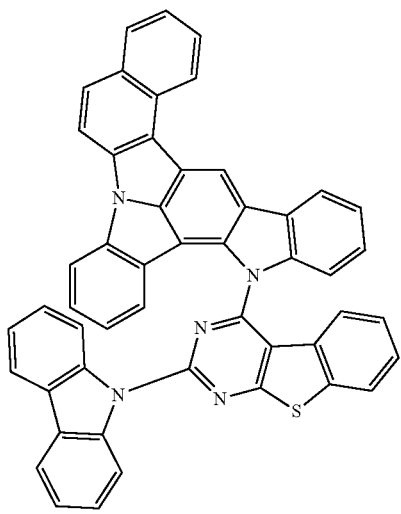
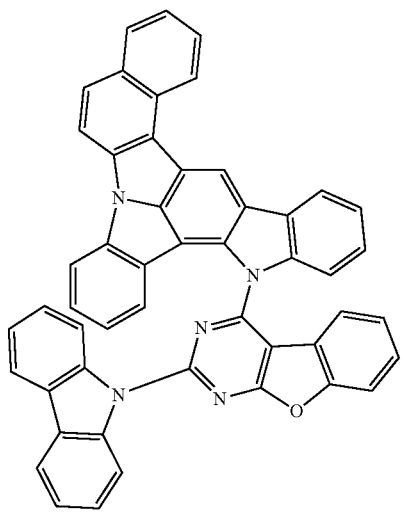
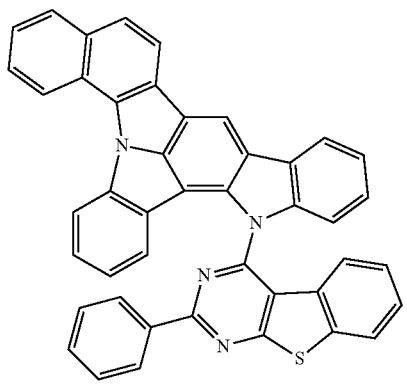
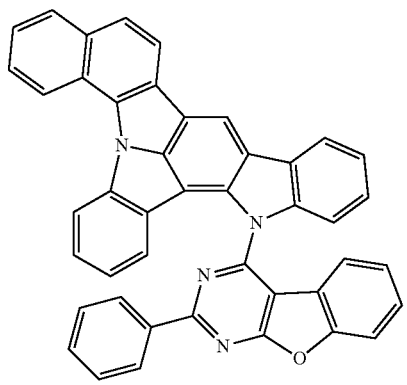

-continued
739 740
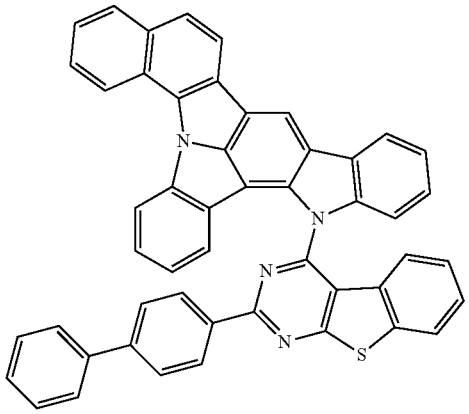
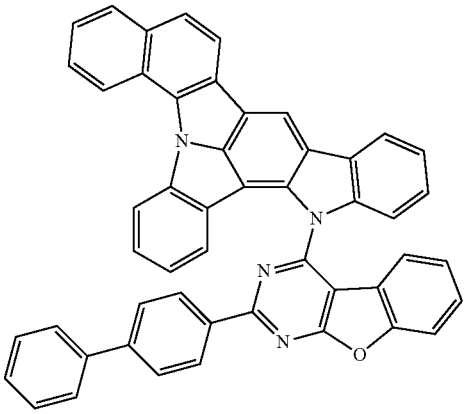
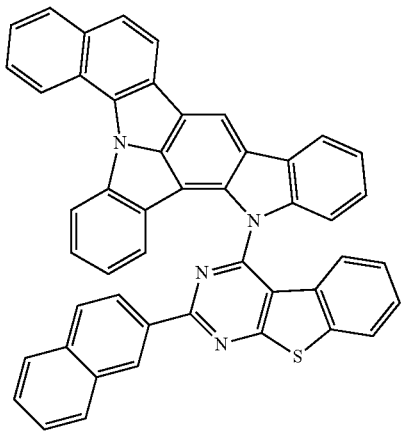
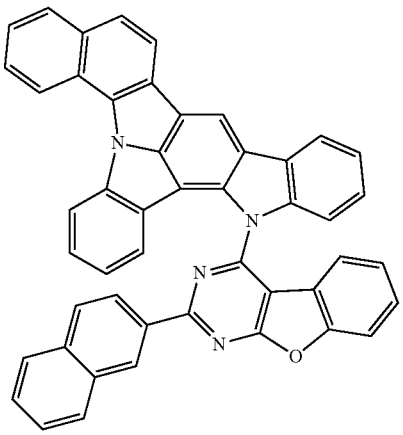
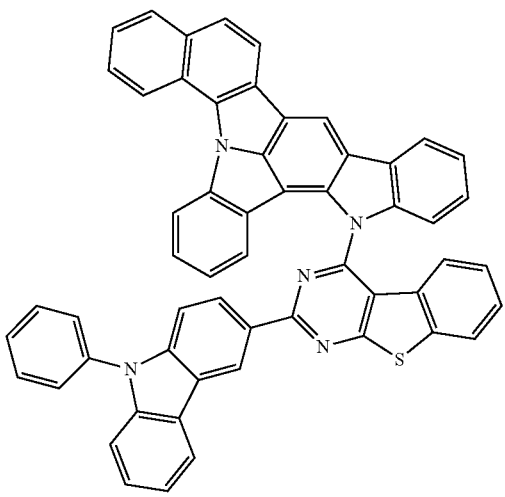
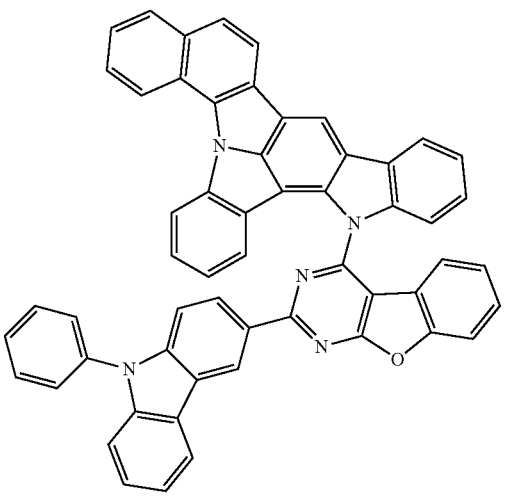

741            742
-continued
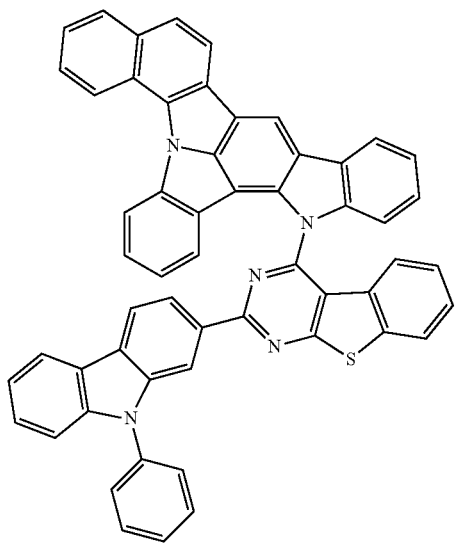
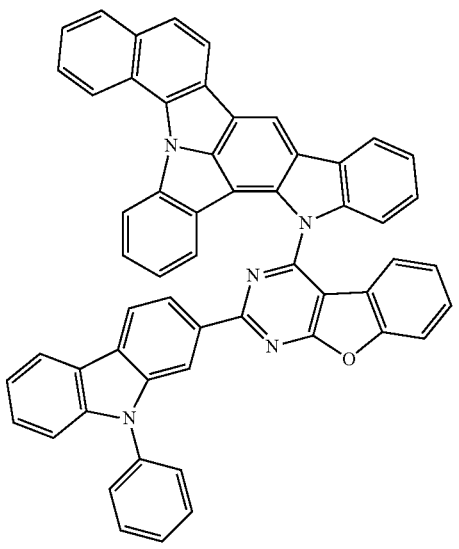
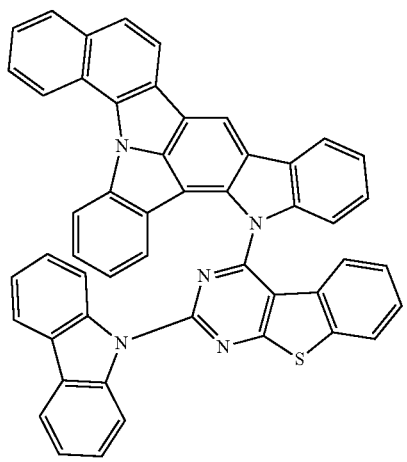
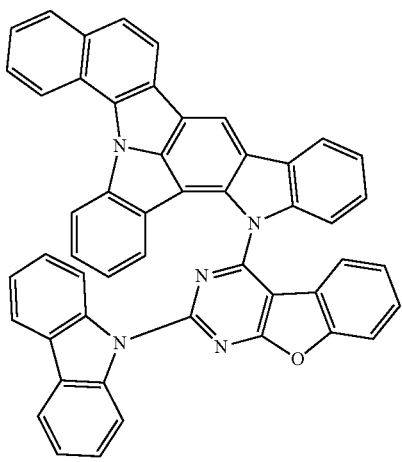
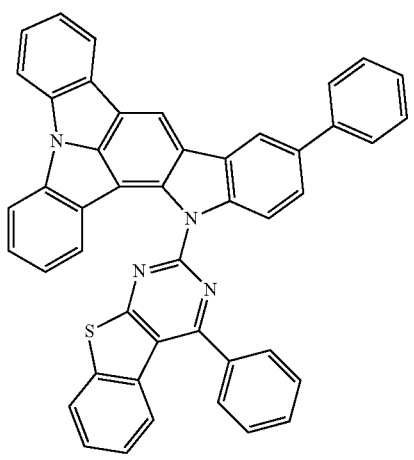
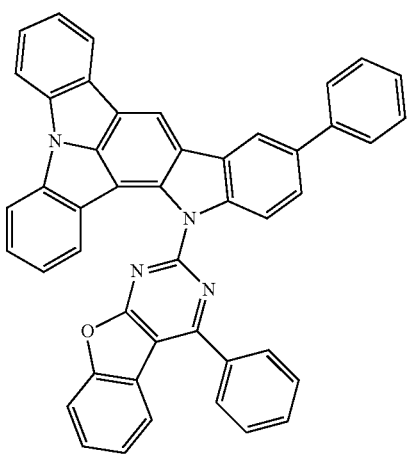

-continued
743 744
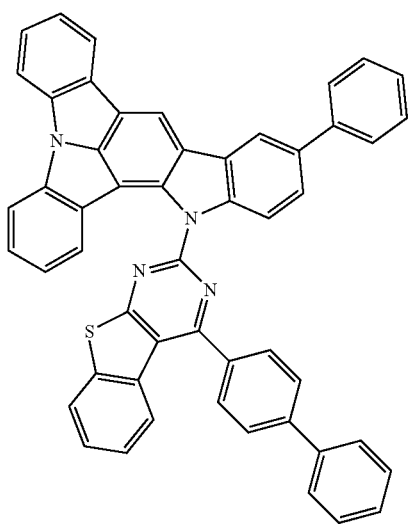
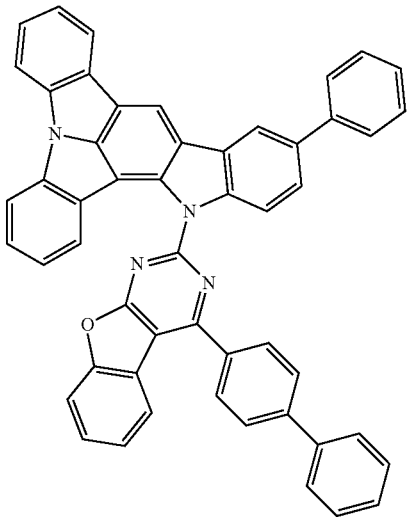
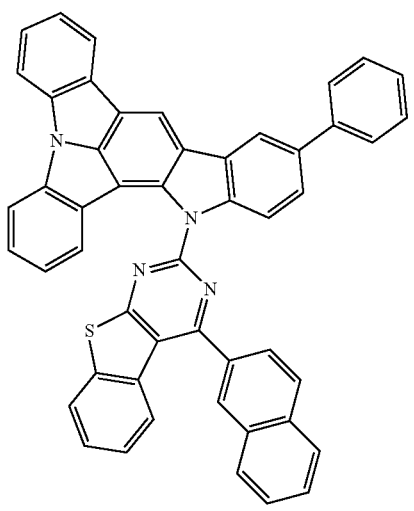
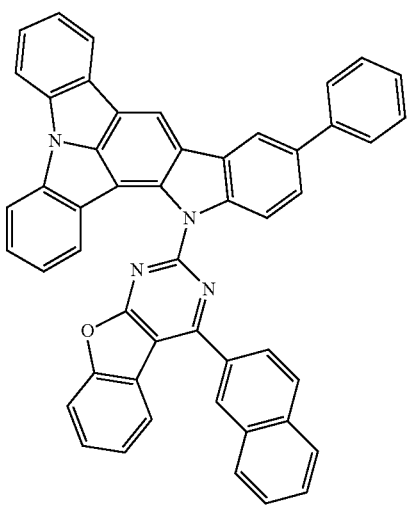
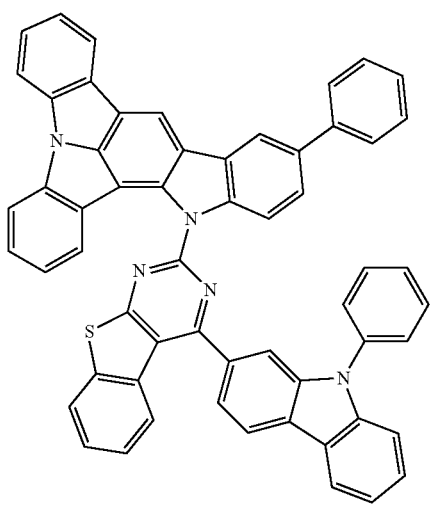
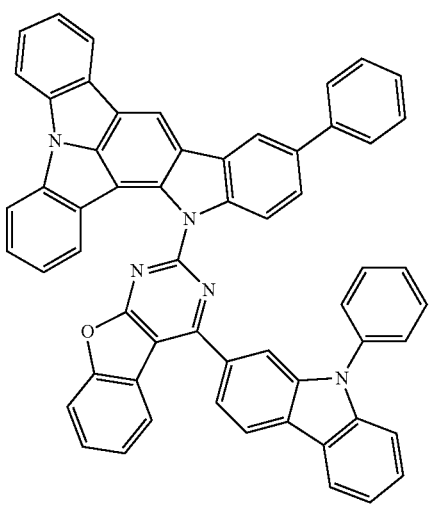

-continued
745
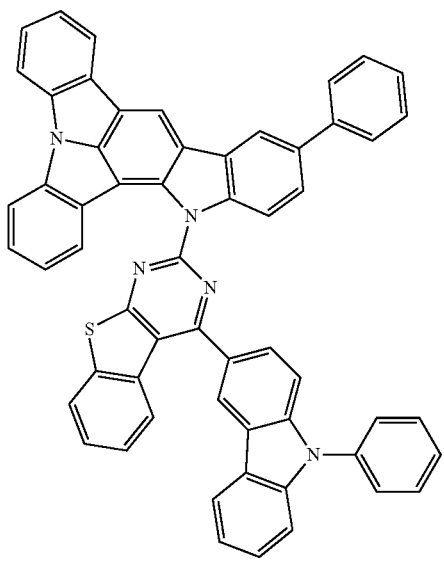
746
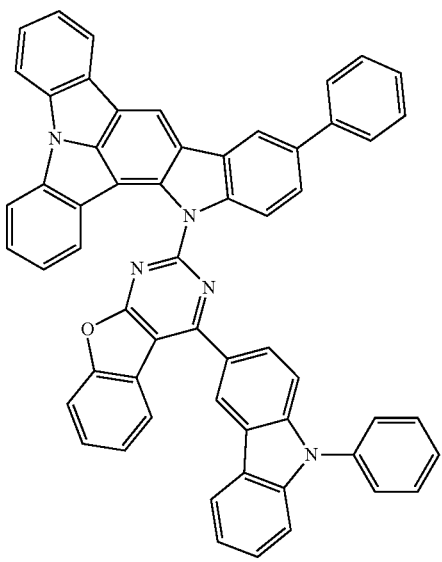
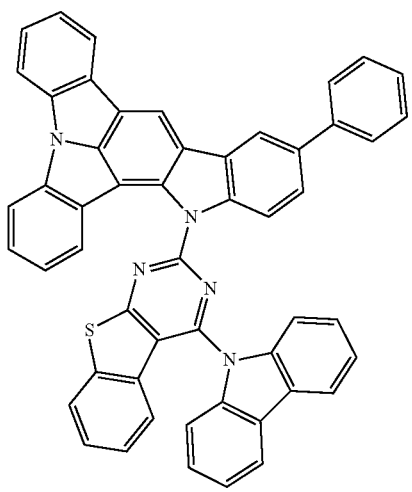
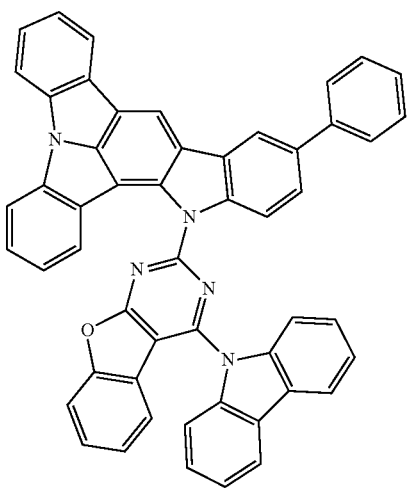
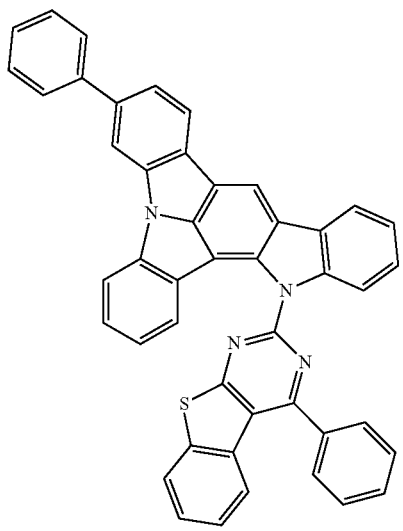
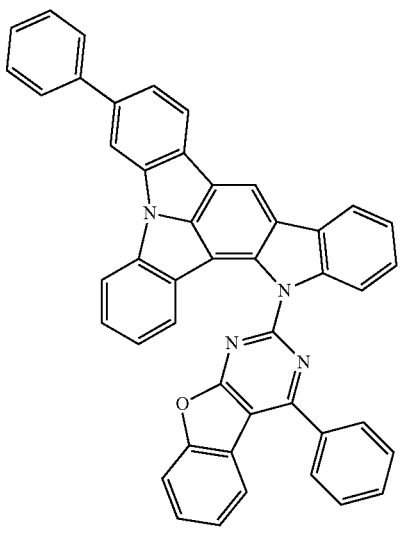

-continued
747
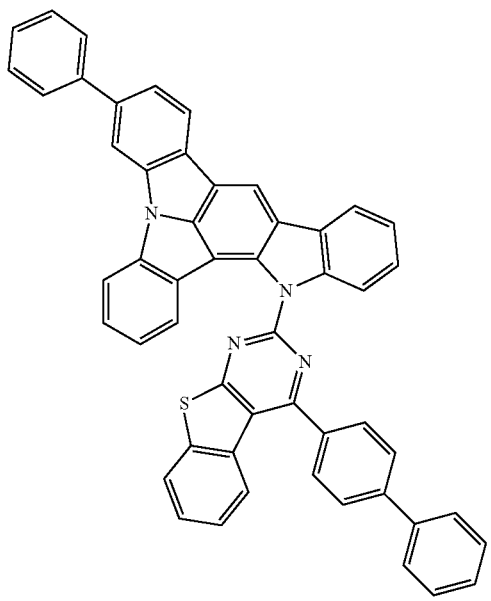
748
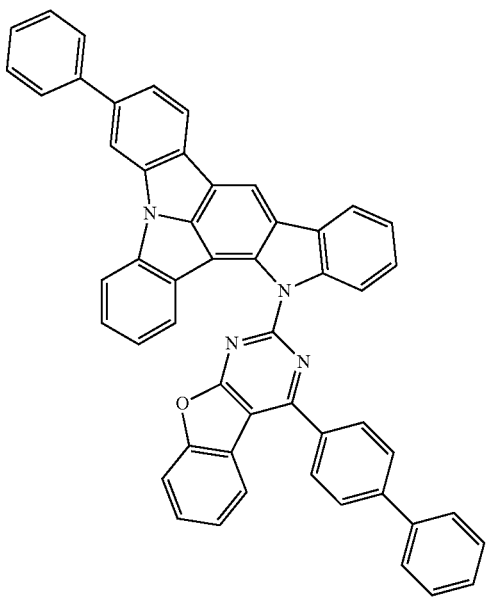
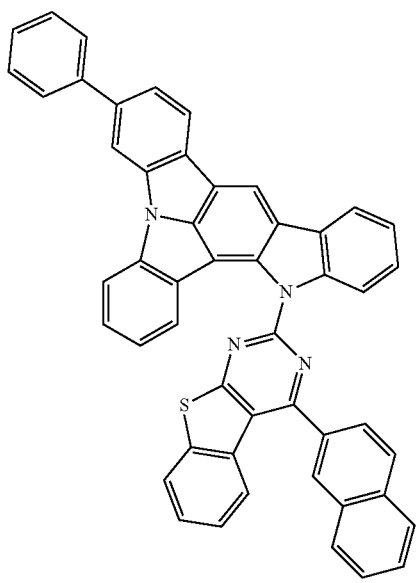
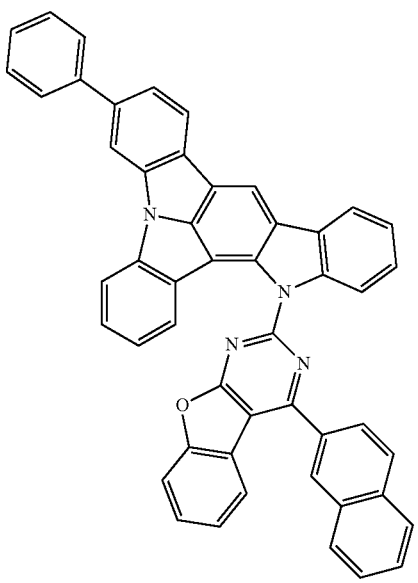

-continued
749
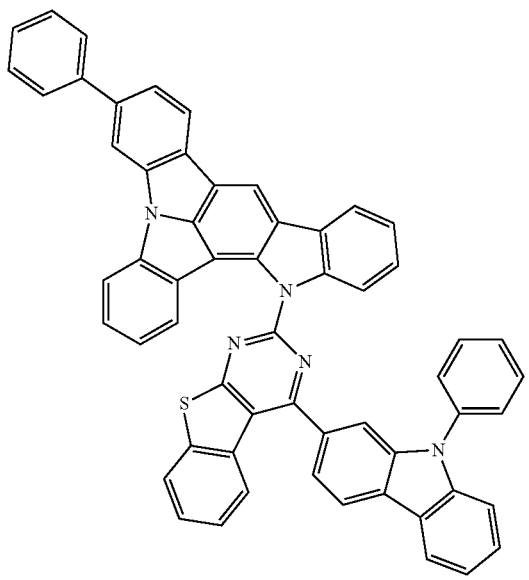
750
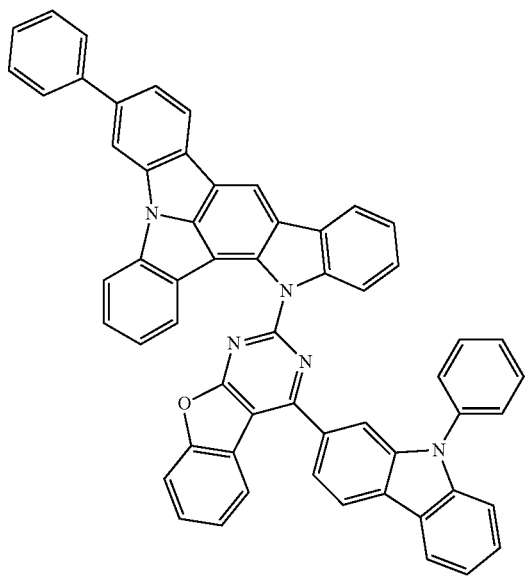
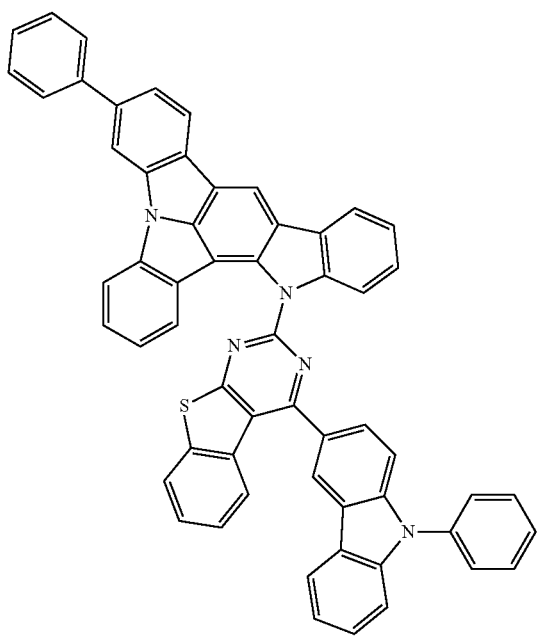
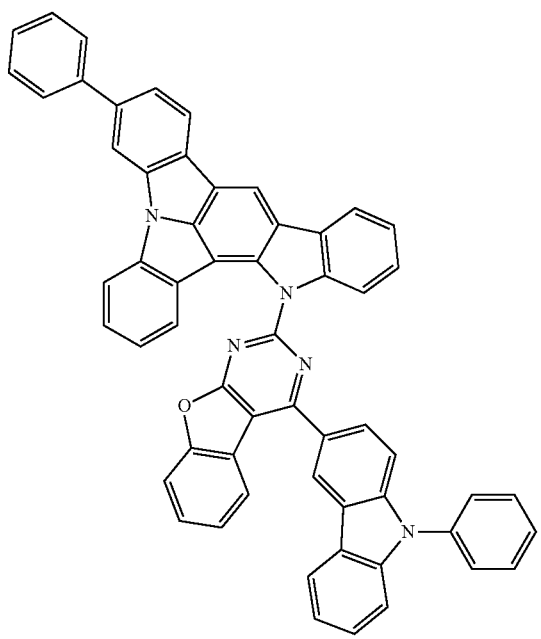

-continued
751
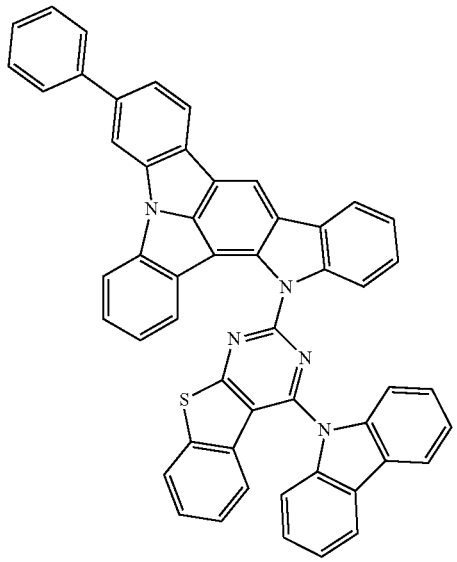
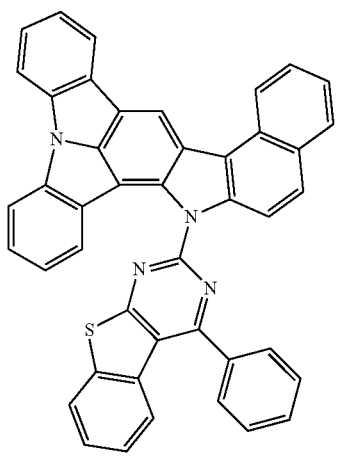
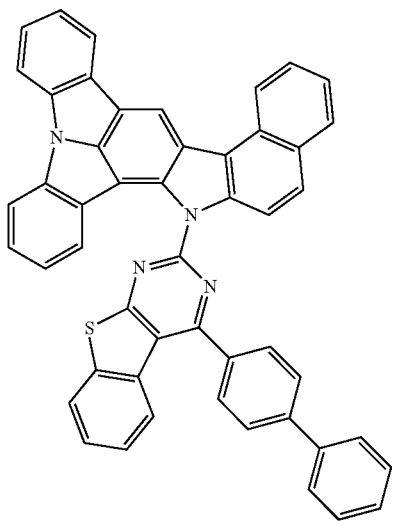
752
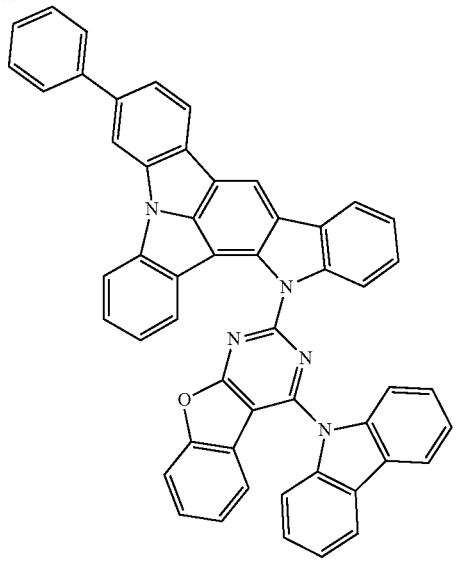
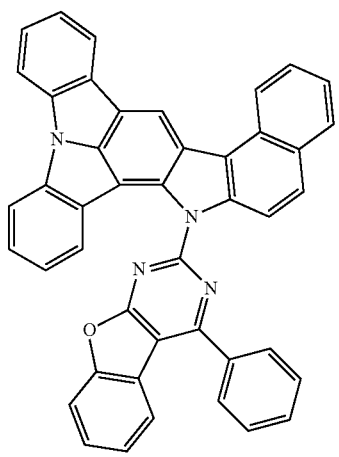
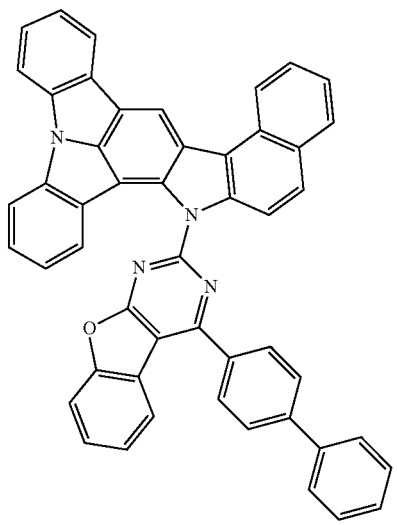

-continued
| 753 | 754 |
|---|---|
| 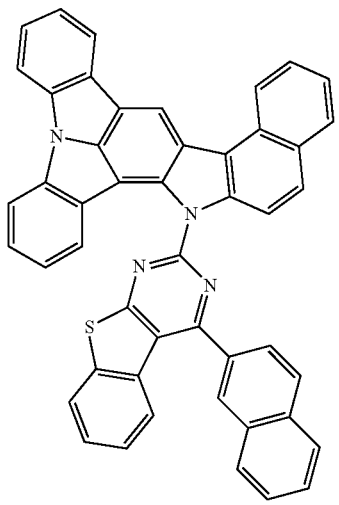 | 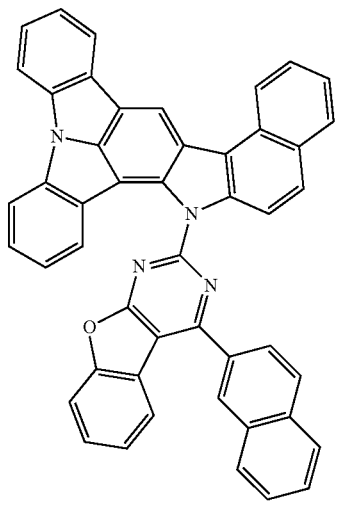 |
| 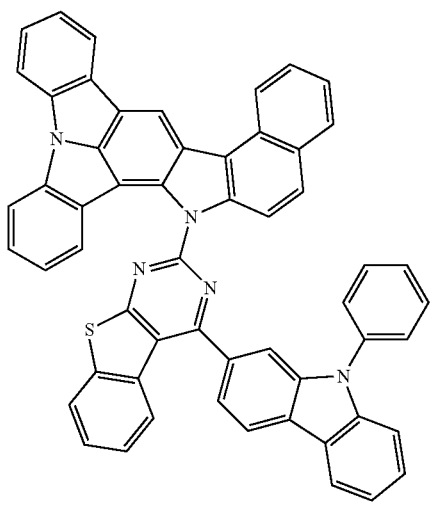 | 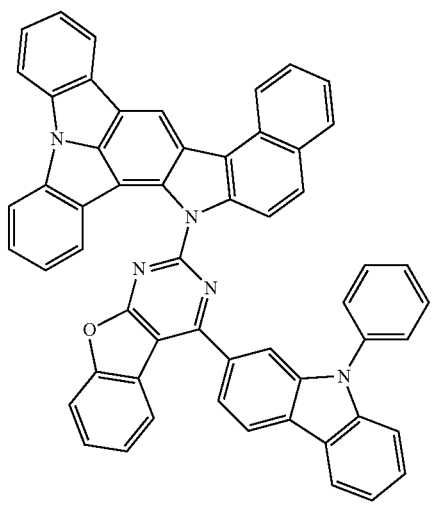 |
| 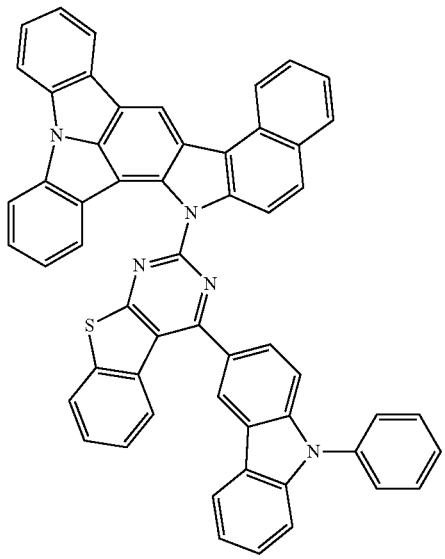 | 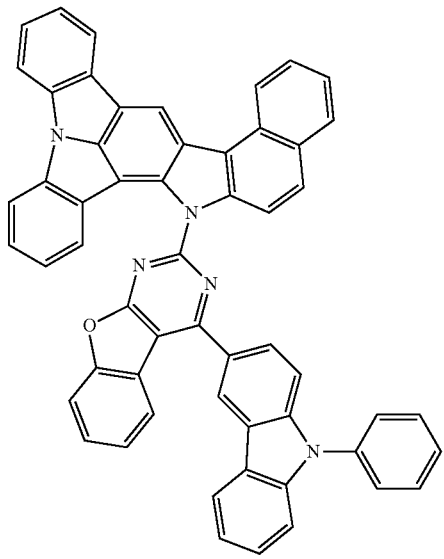 |

| 755 | 756 |
|---|---|
| 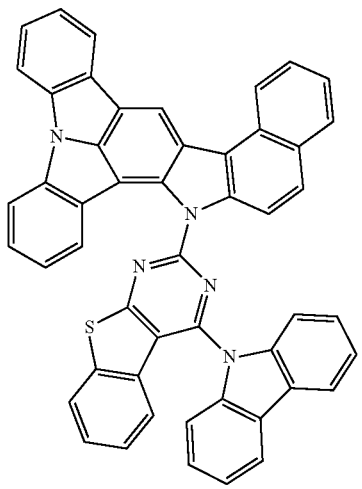 | 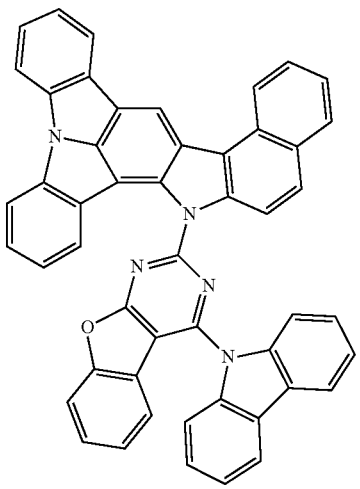 |
| 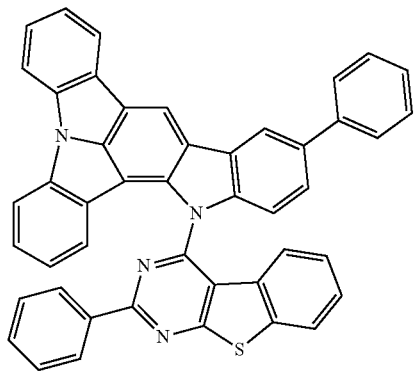 | 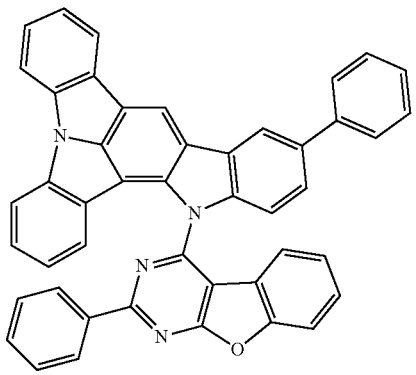 |
| 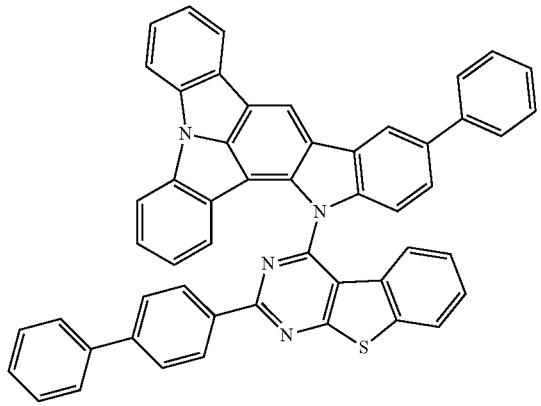 | 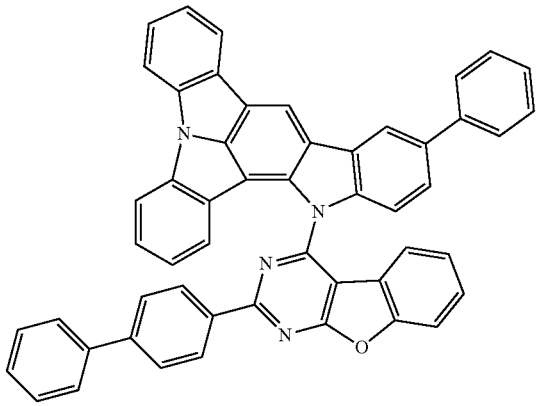 |
| 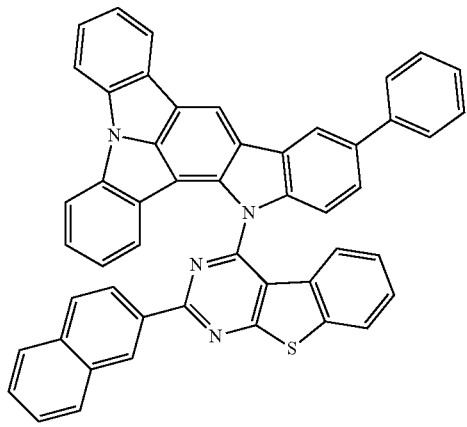 | 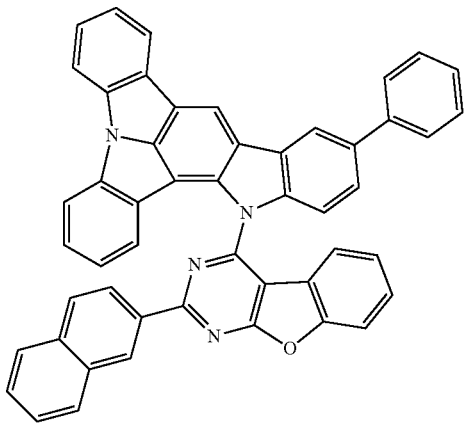 |
-continued 757
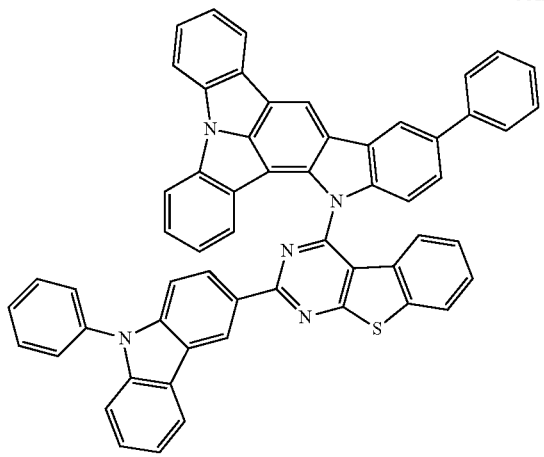
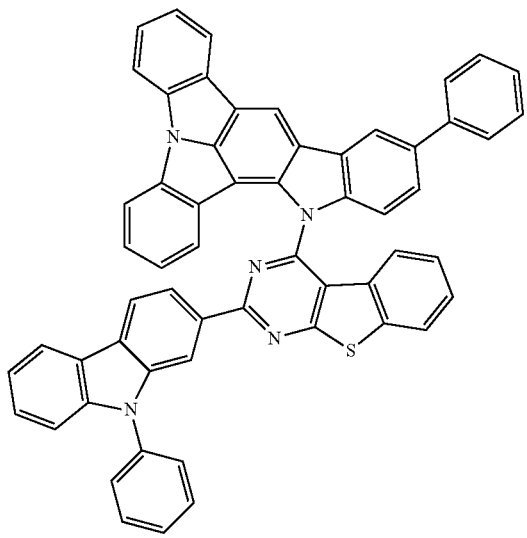
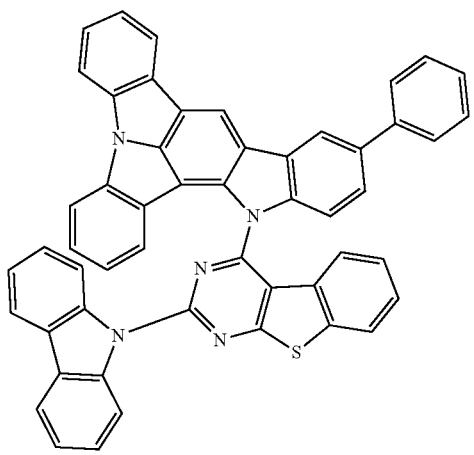
758
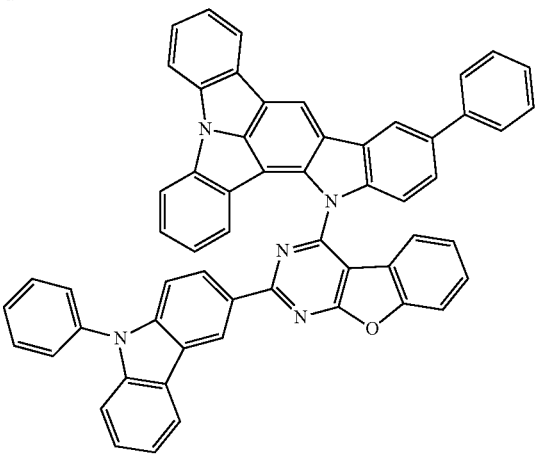
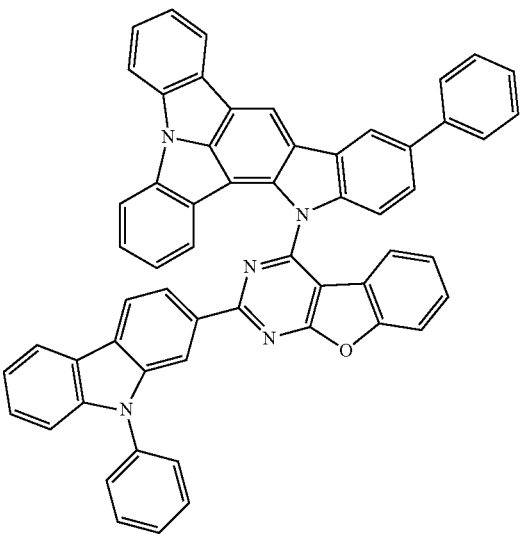
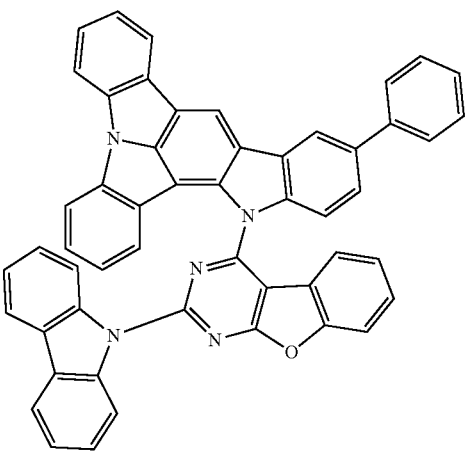

759
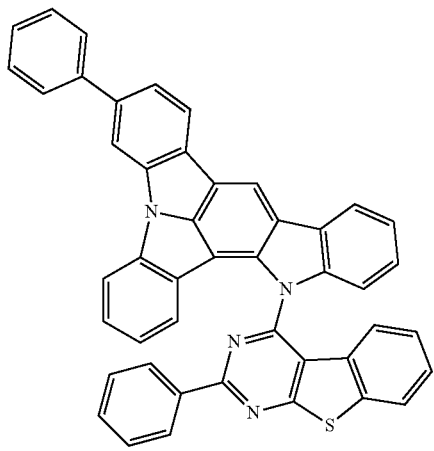
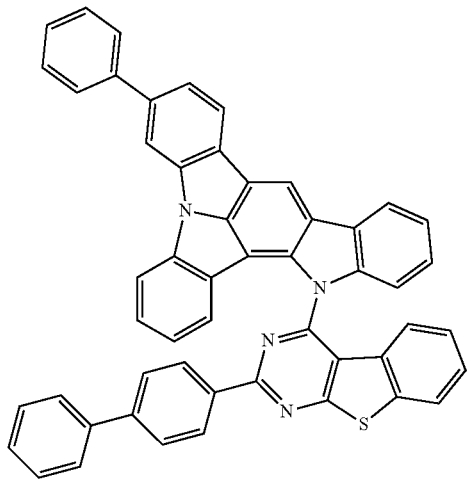
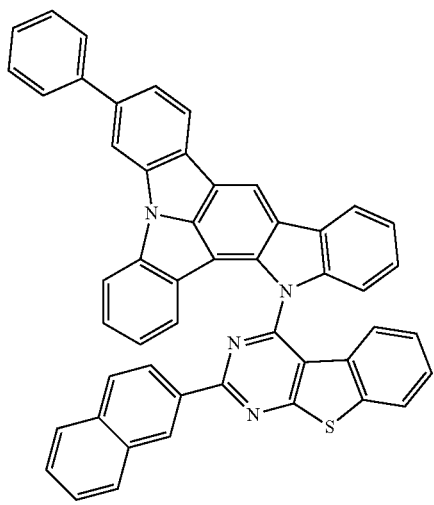
760
-continued
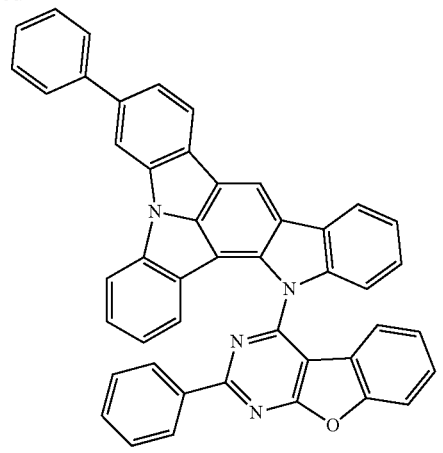
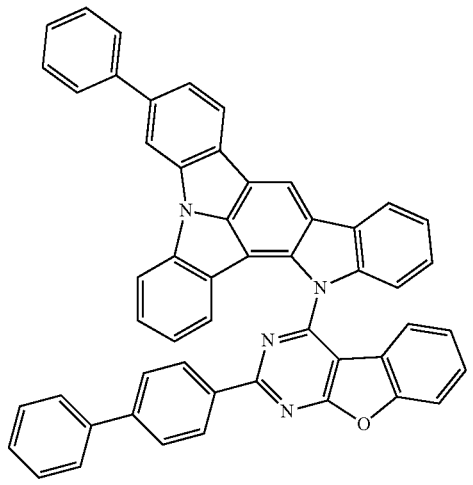
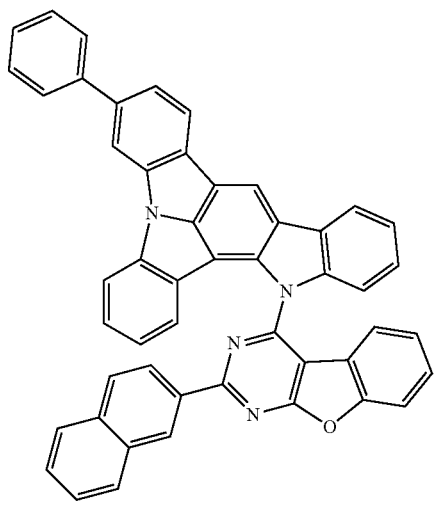

761
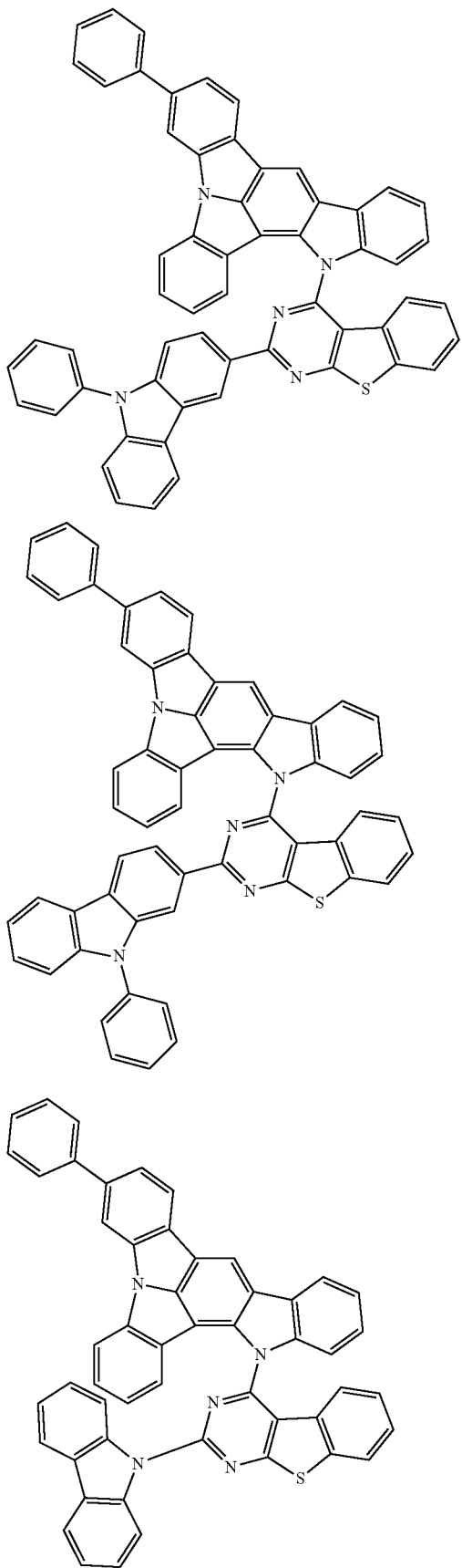
762
-continued
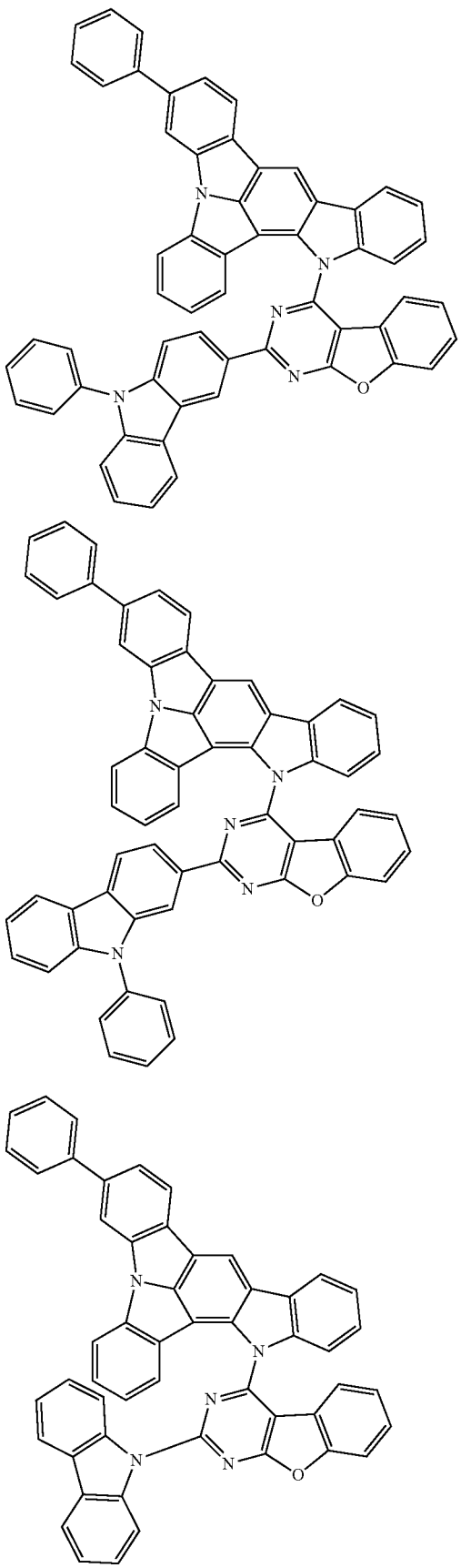

| 763 | 764 |
|---|---|
| 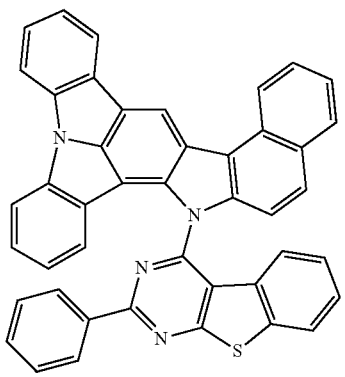 | 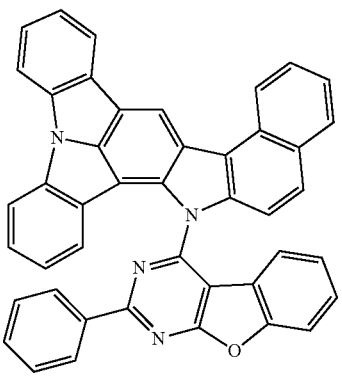 |
| 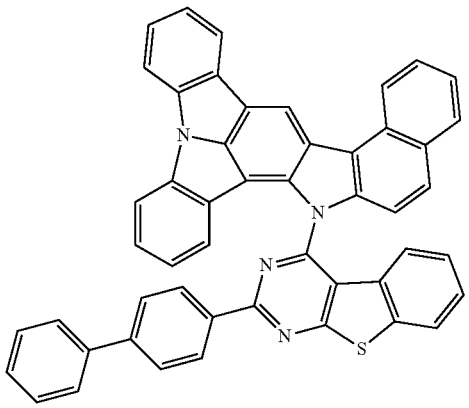 | 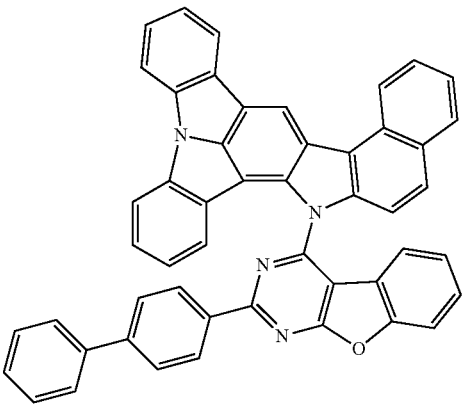 |
| 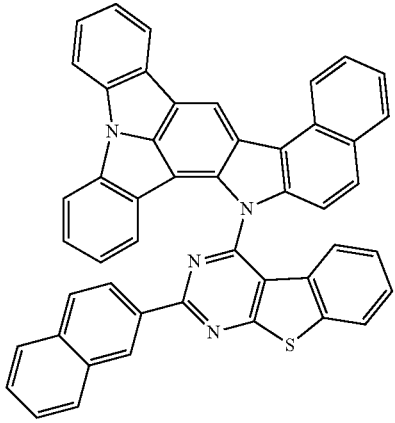 | 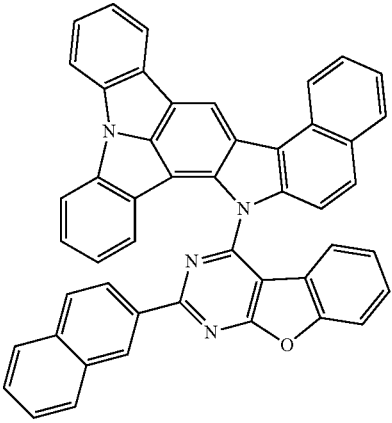 |
| 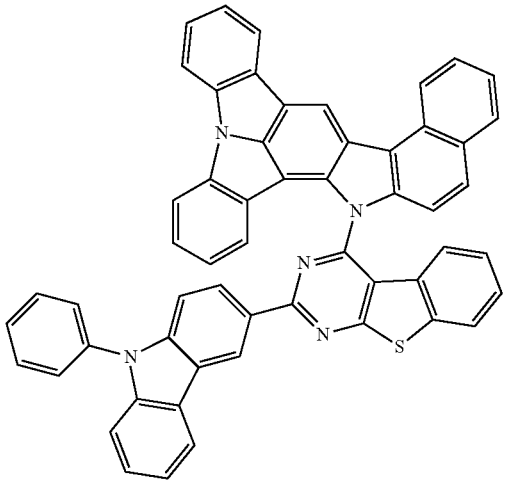 | |

-continued
765 766
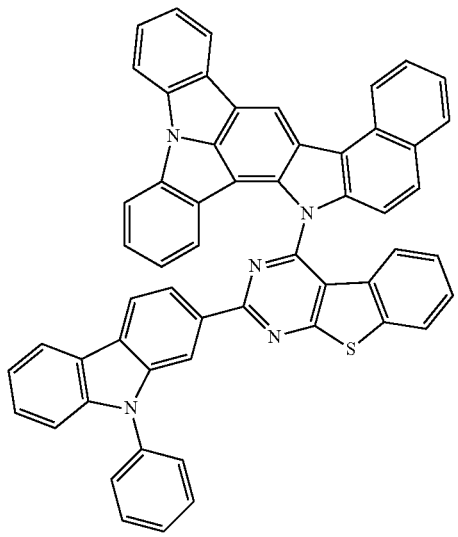
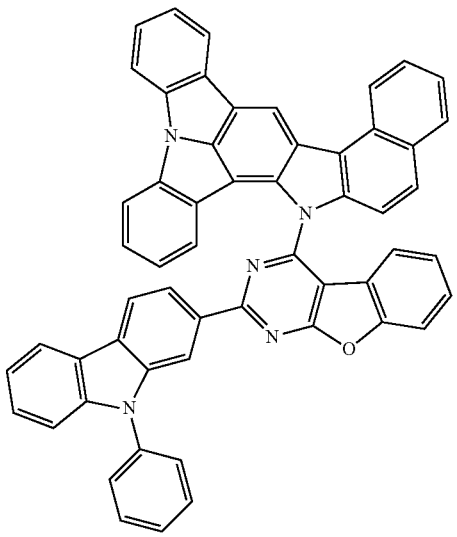
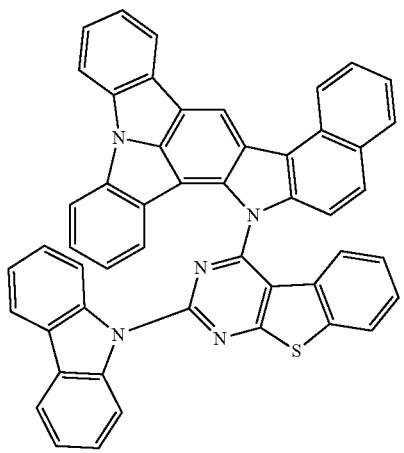
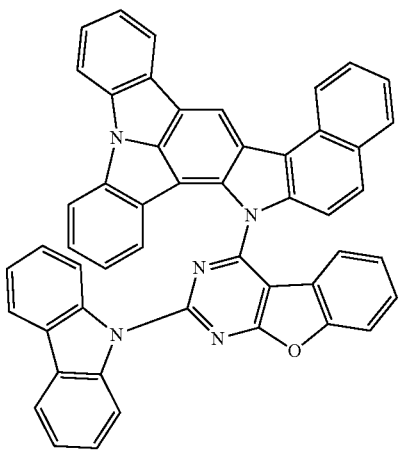
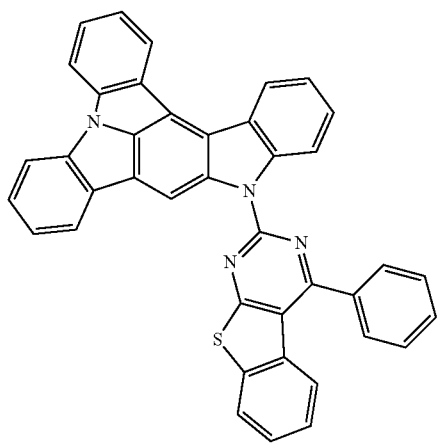
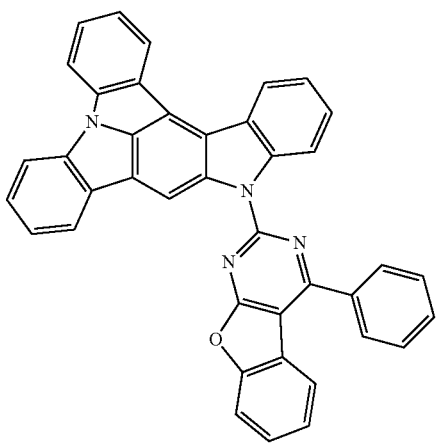

-continued
767
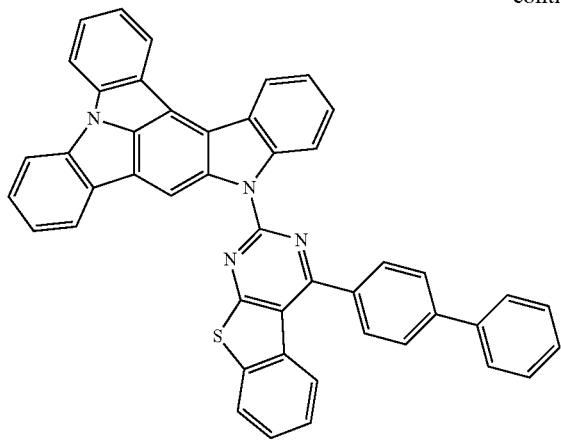
768
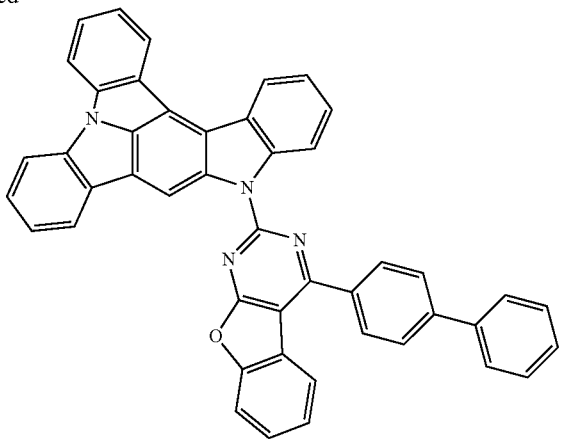
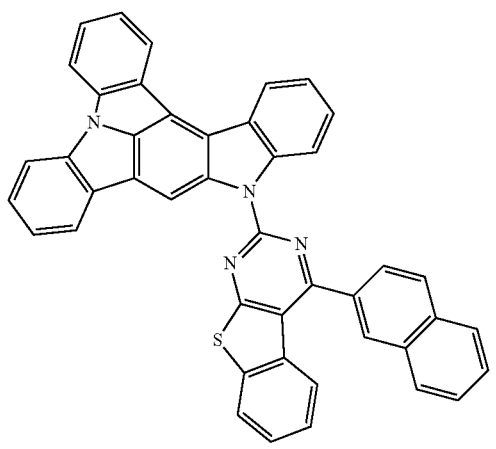
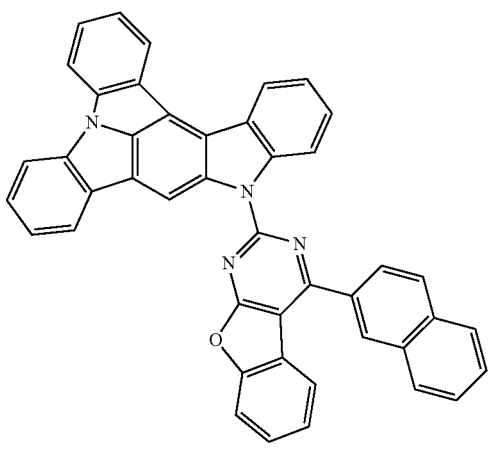
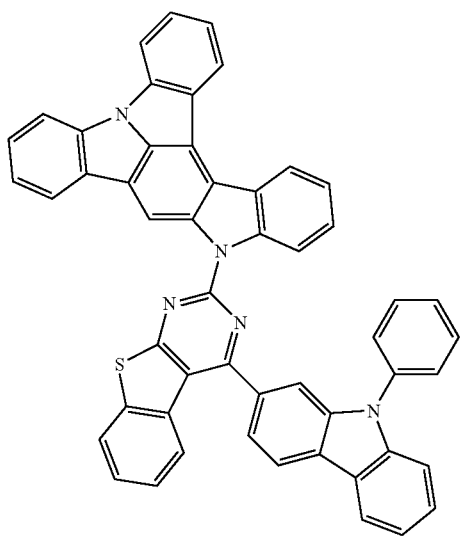
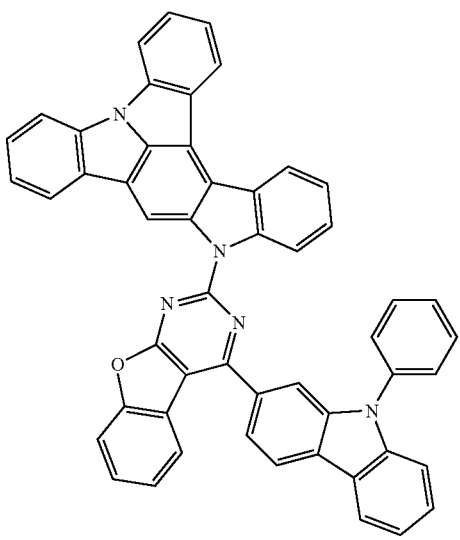

769 770
-continued
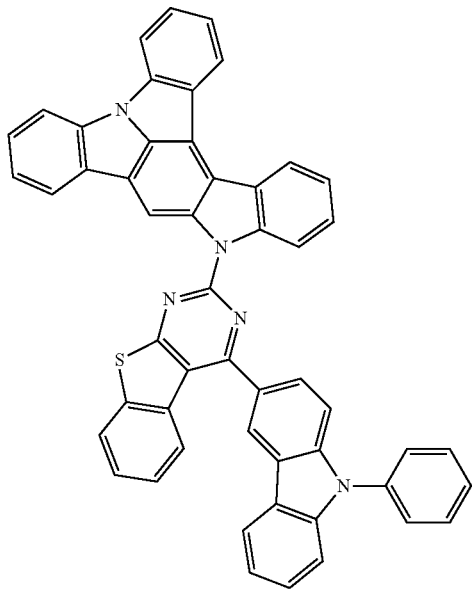
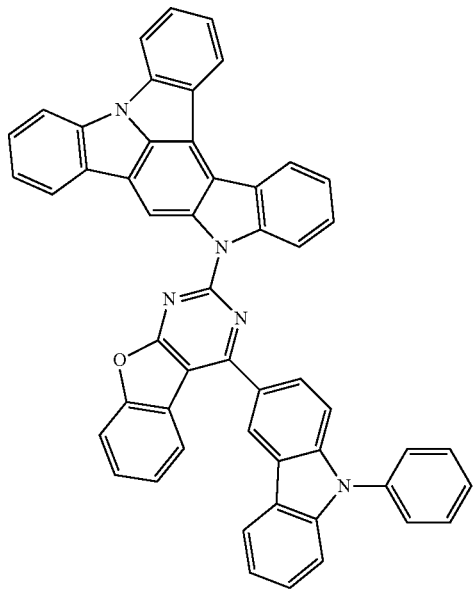
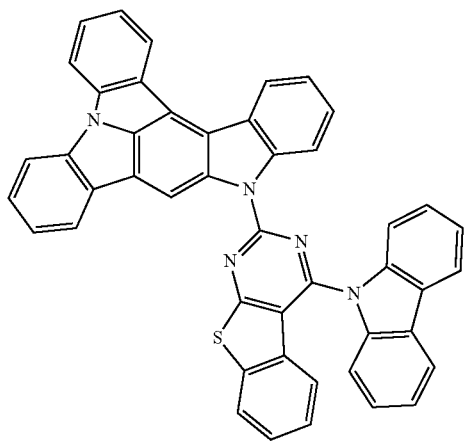
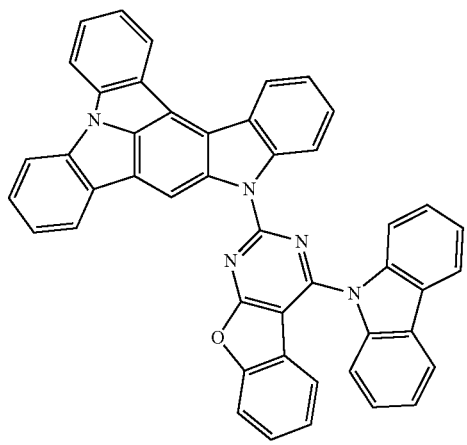
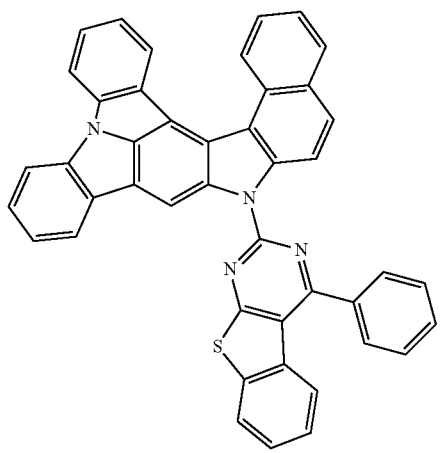
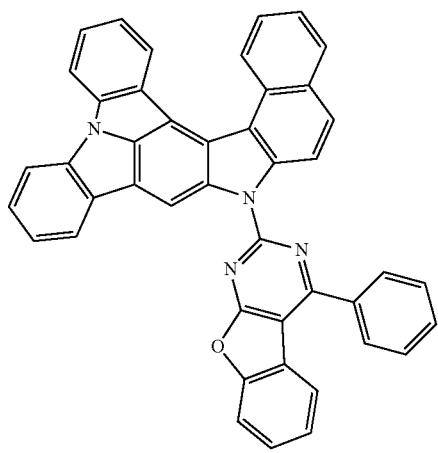

771
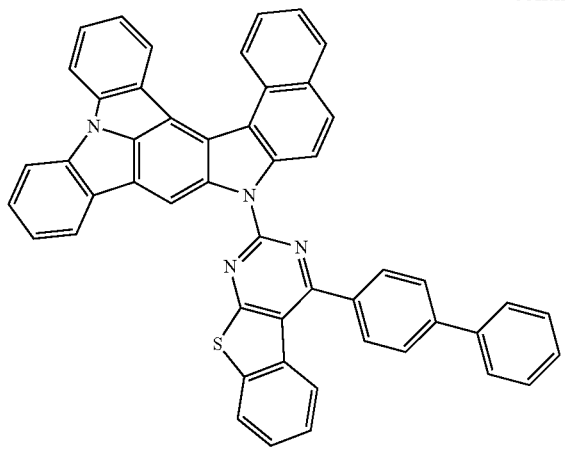
772
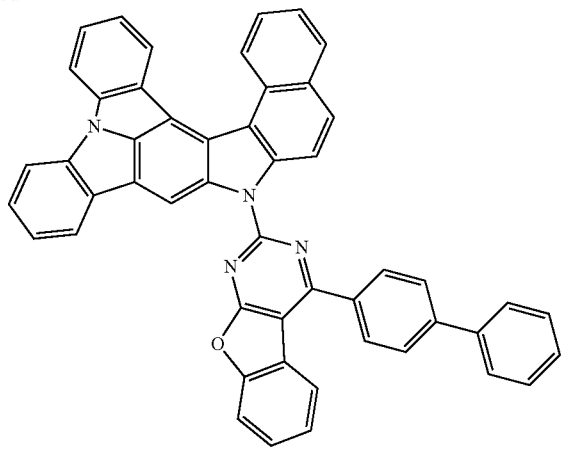
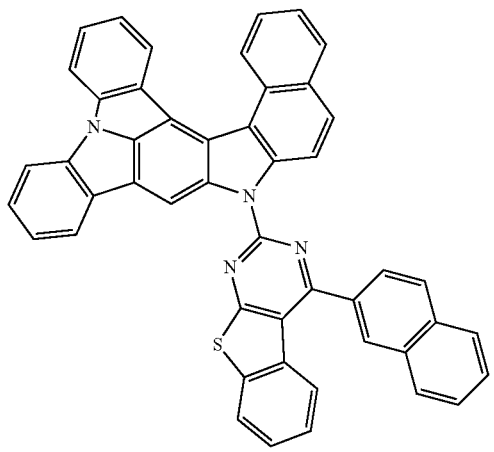
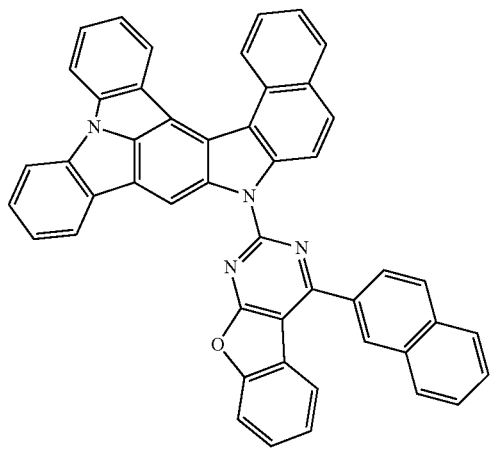
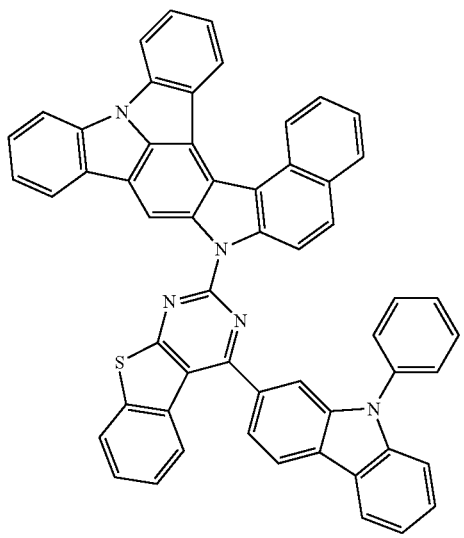
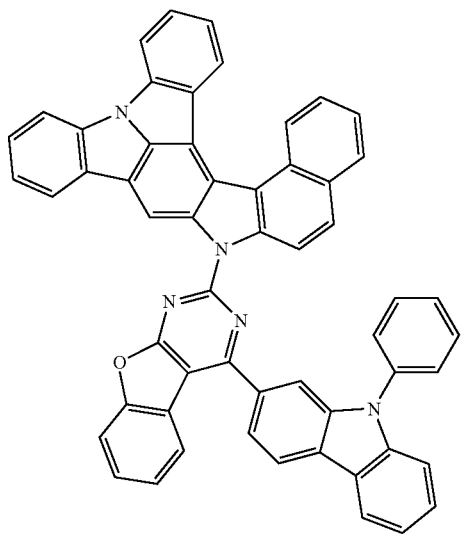

-continued
773
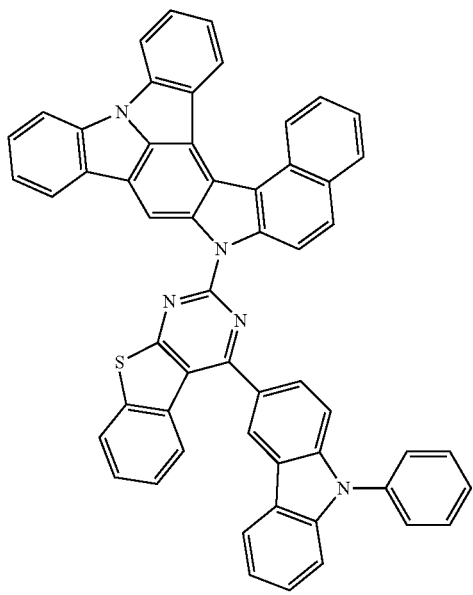
774
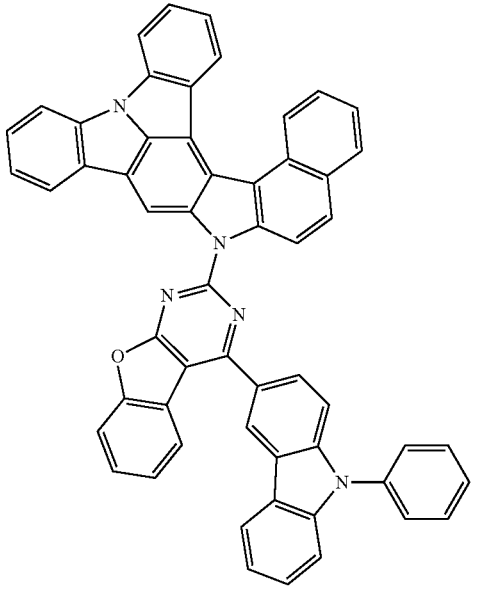
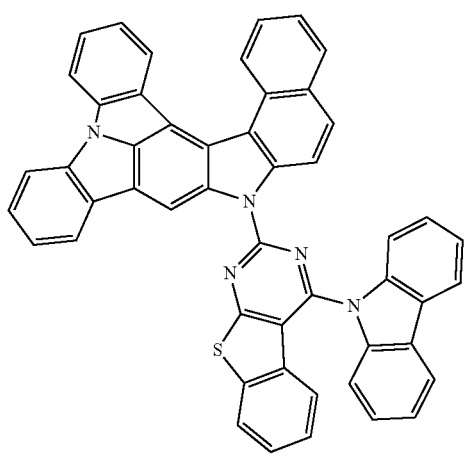
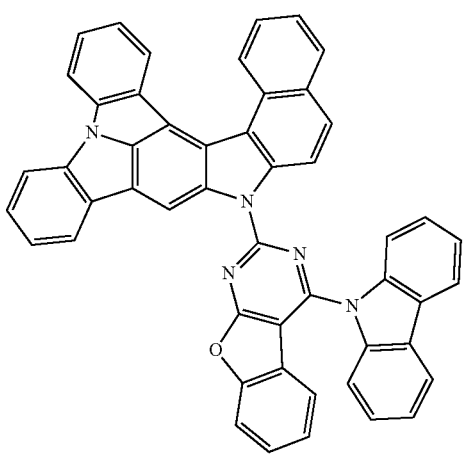
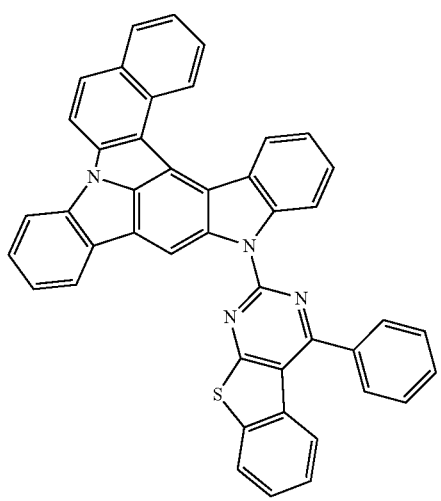
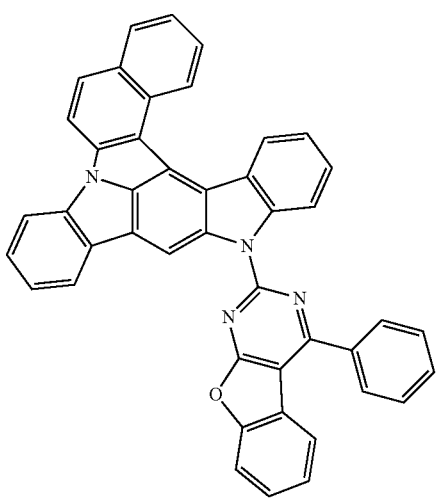

-continued
| 775 | 776 |
|---|---|
| 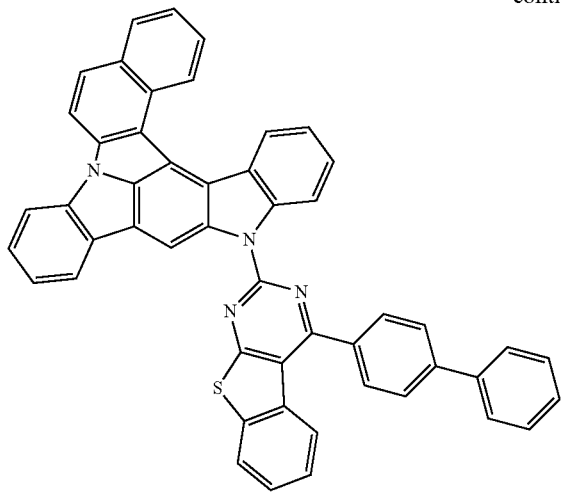 | 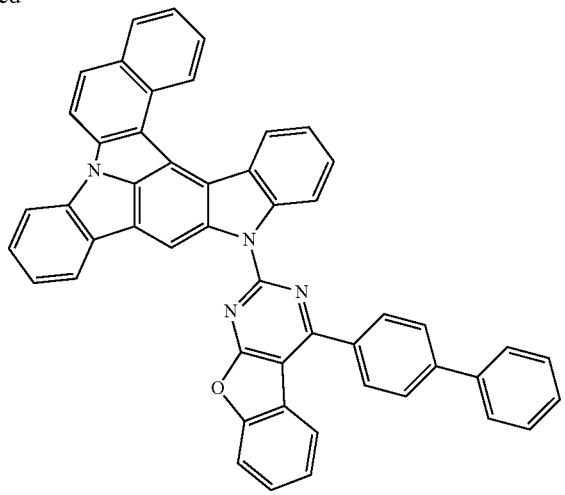 |
| 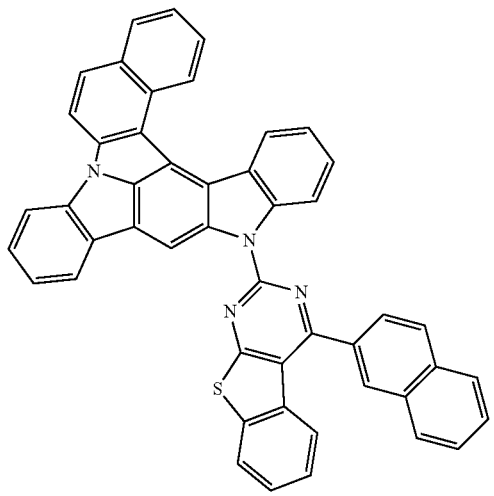 | 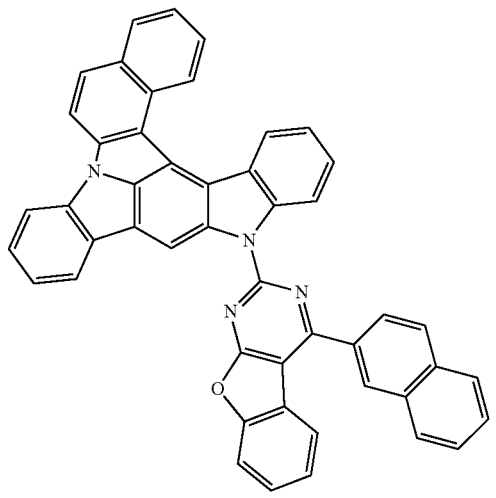 |
| 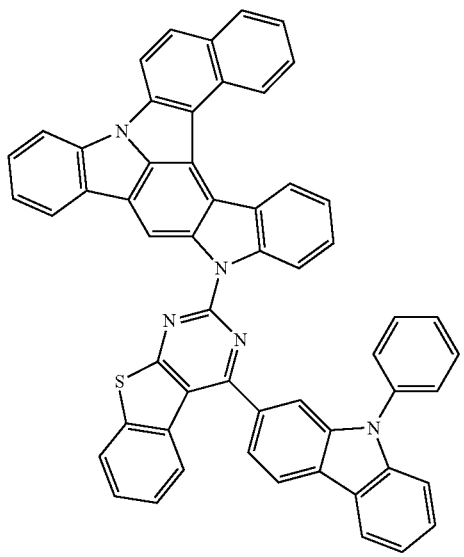 | 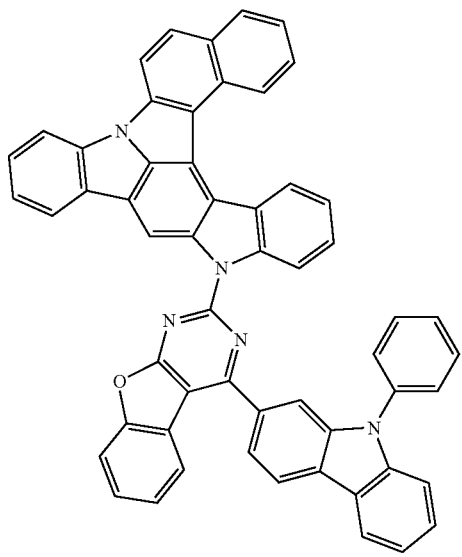 |

777
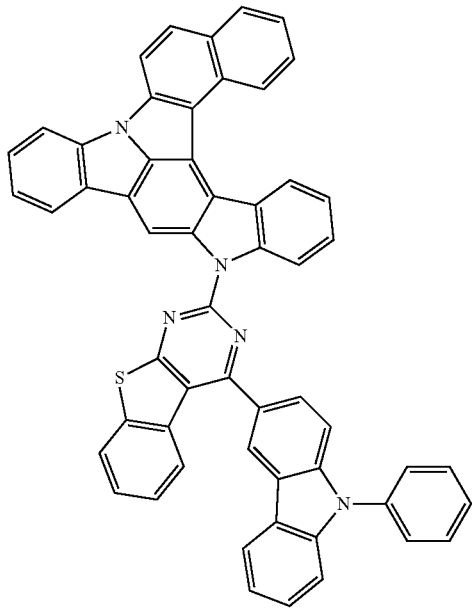
778
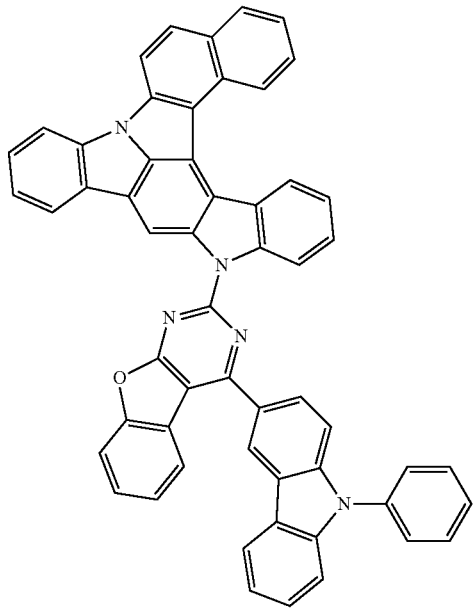
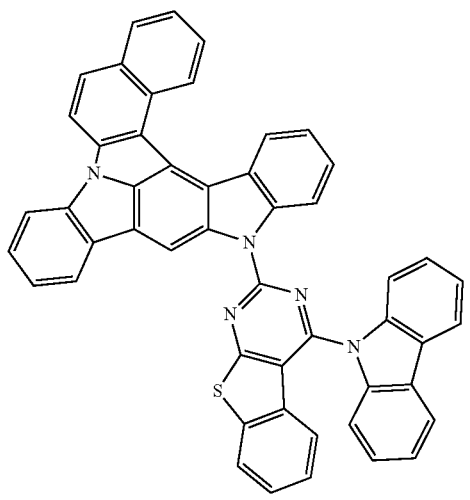
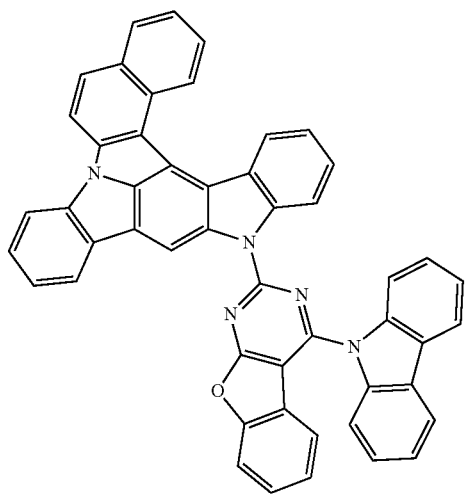
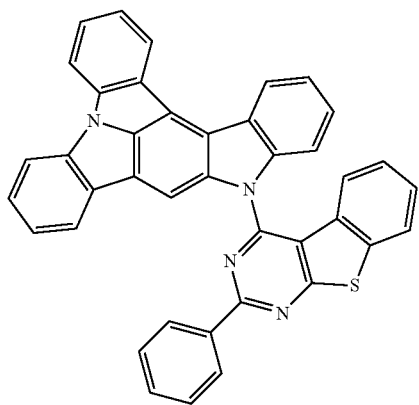
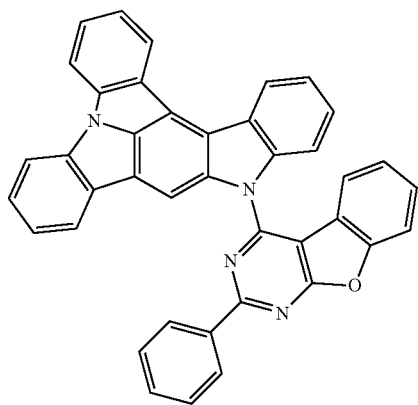

-continued
779
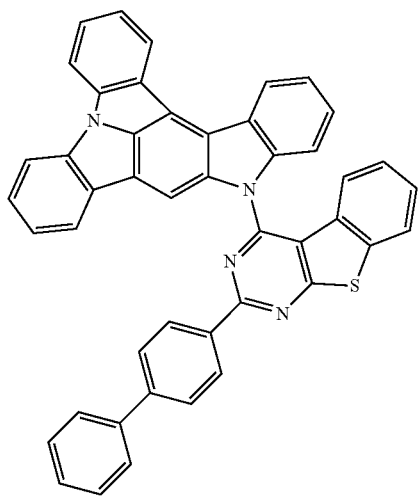
780
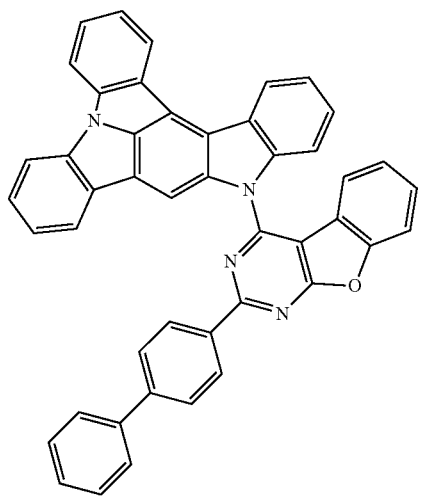
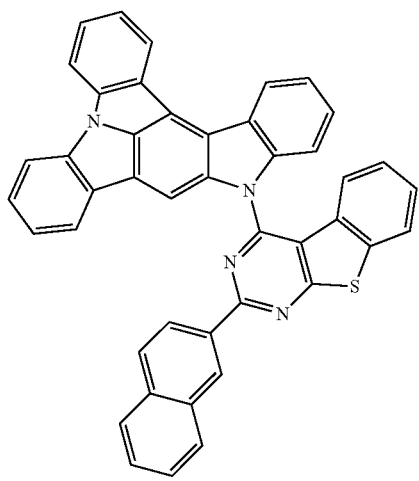
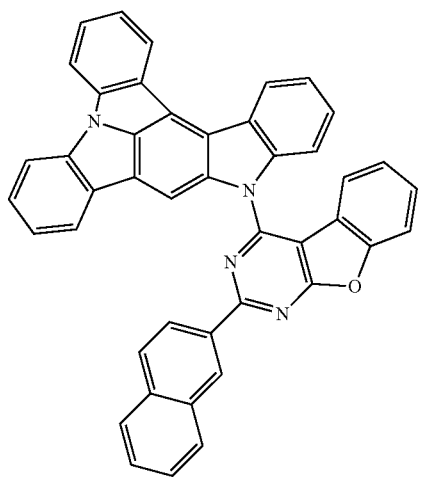
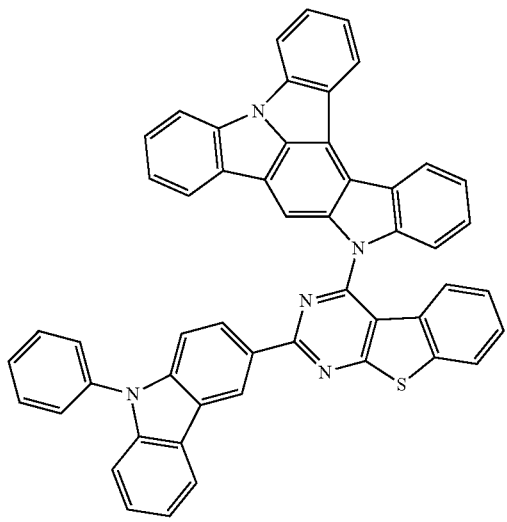
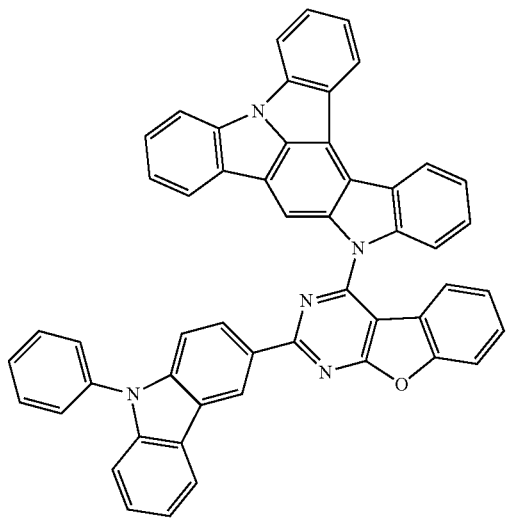

-continued
| 781 | 782 |
|---|---|
| 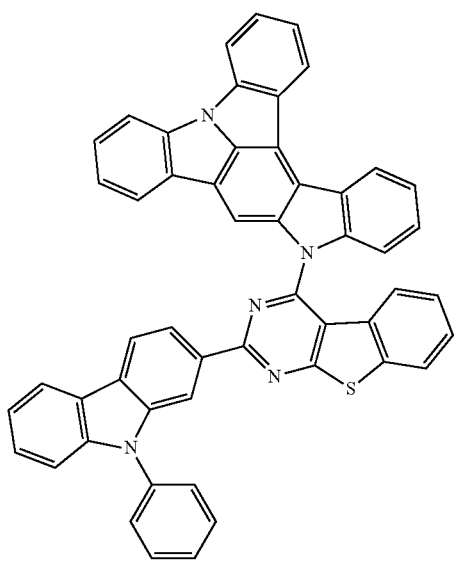 | 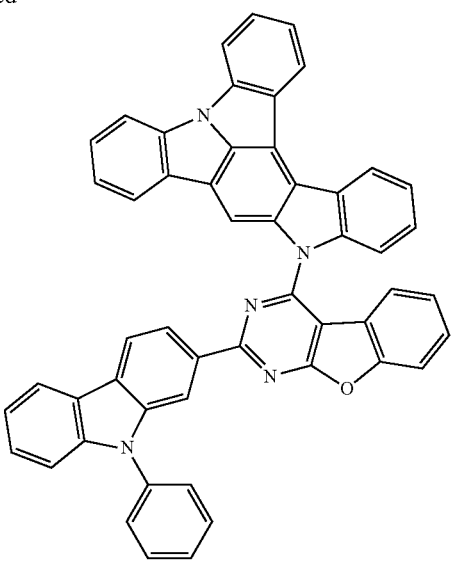 |
| 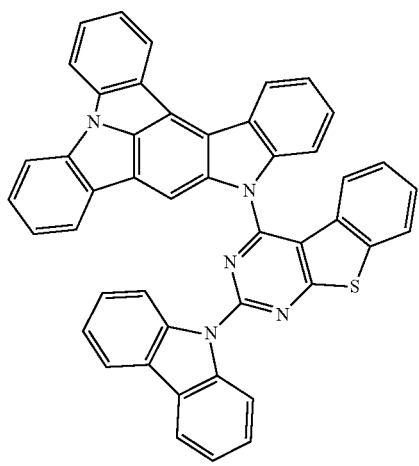 | 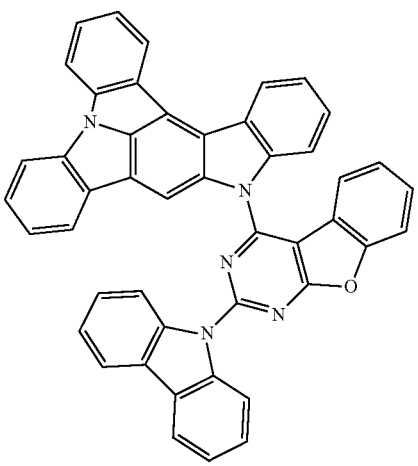 |
| 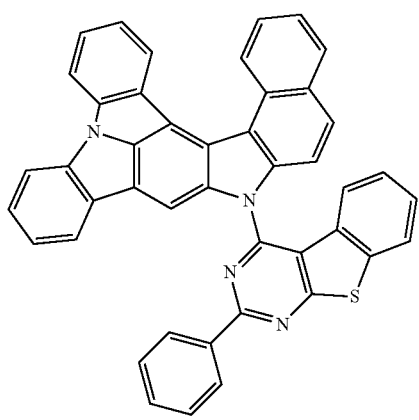 | 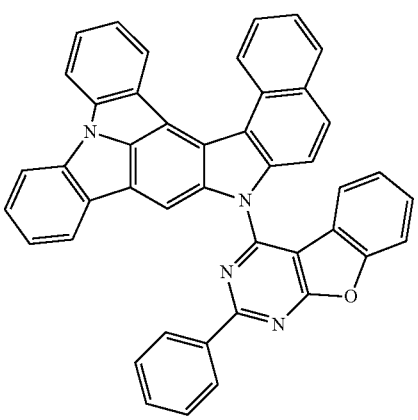 |

| 783 | 784 |
|---|---|
| 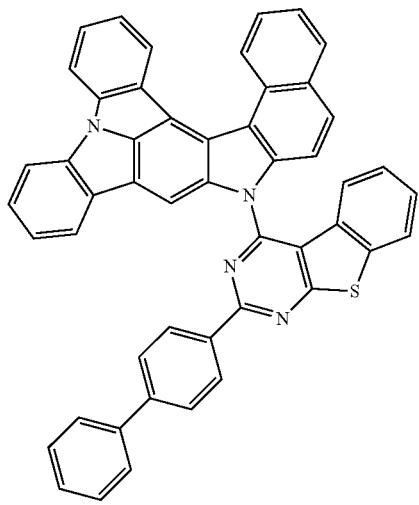 | 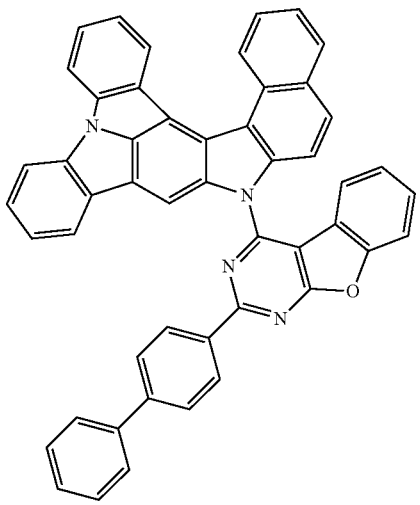 |
| 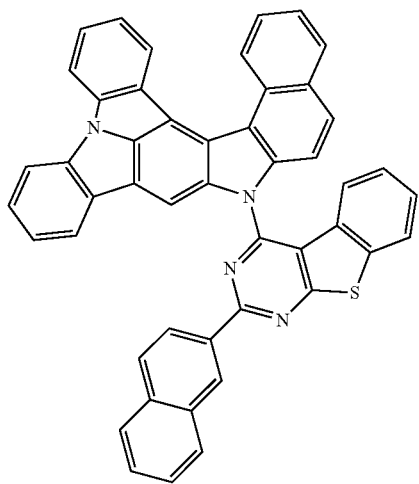 | 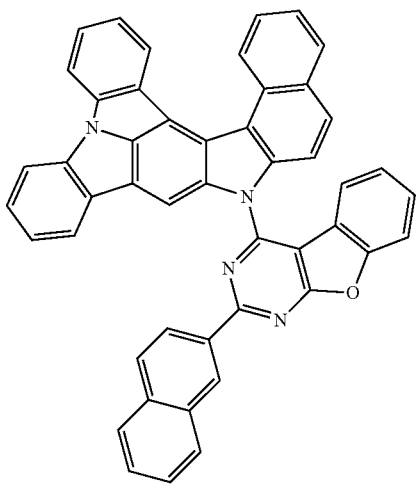 |
| 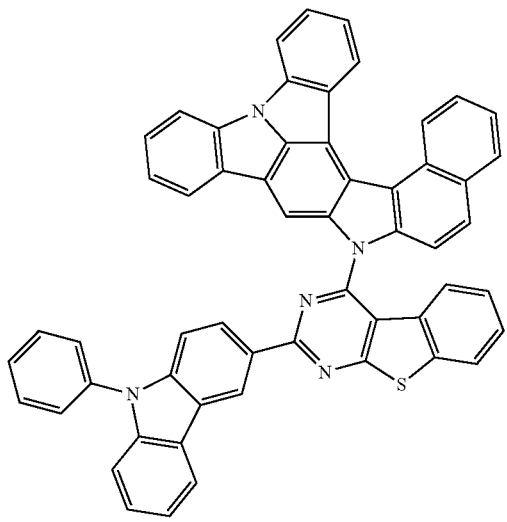 | 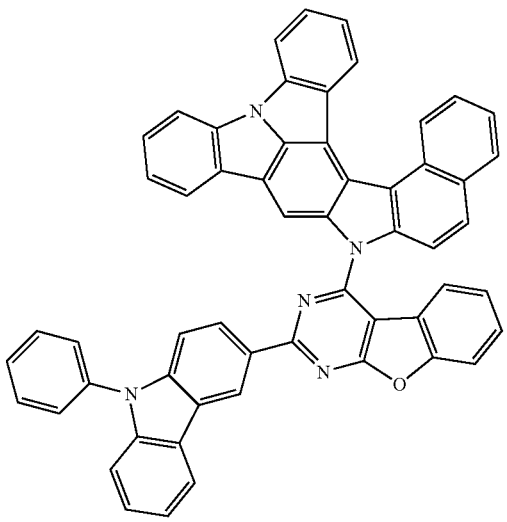 |

-continued
785
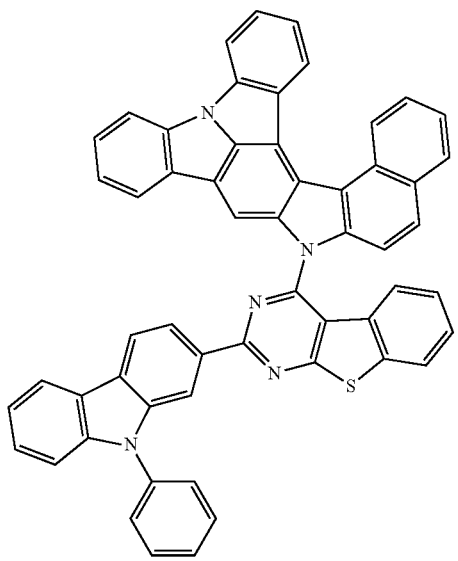
786
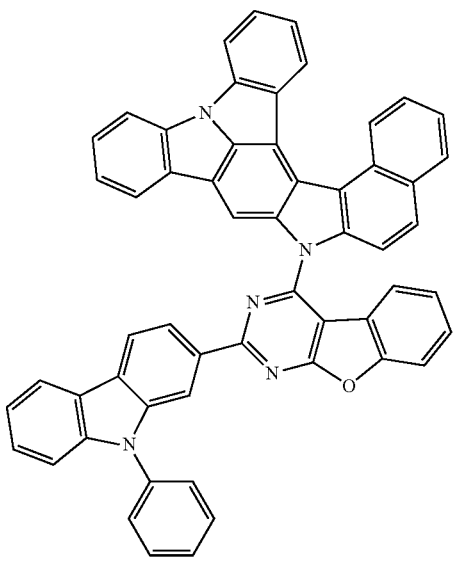
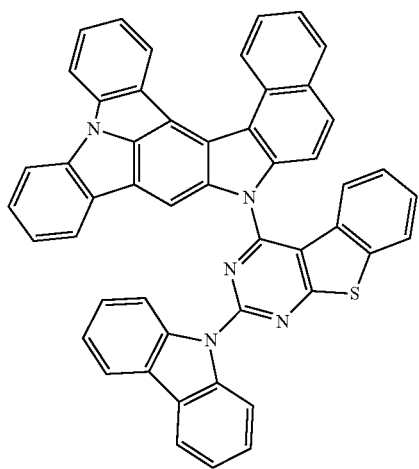
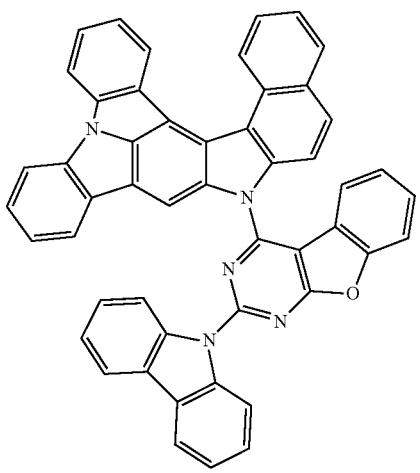
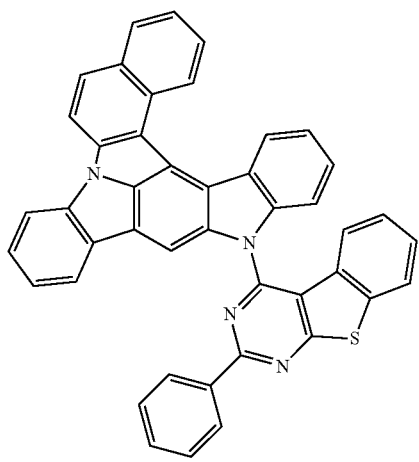
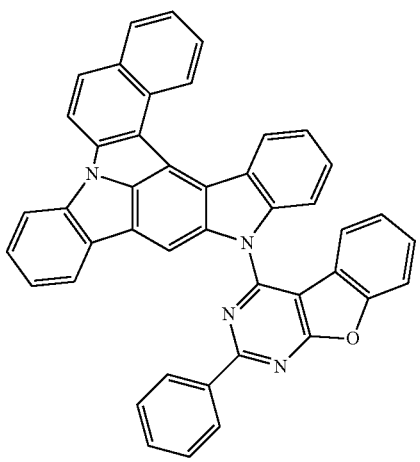

787
788
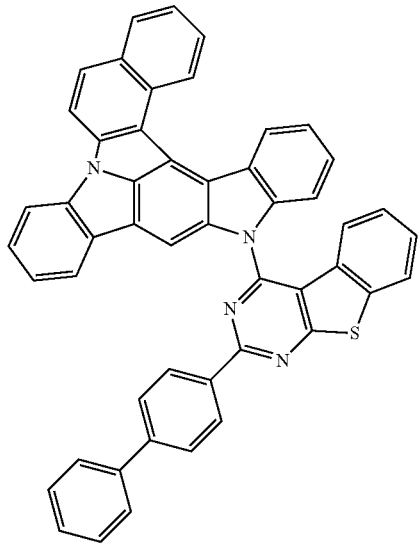
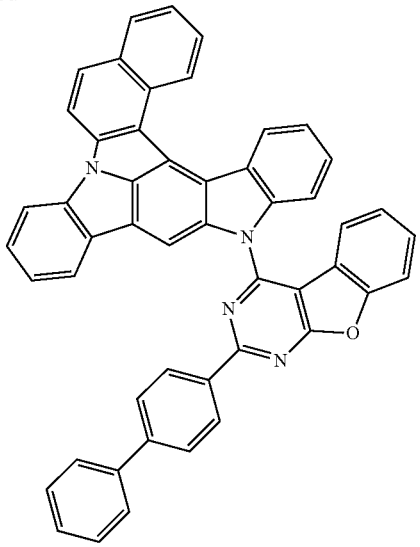
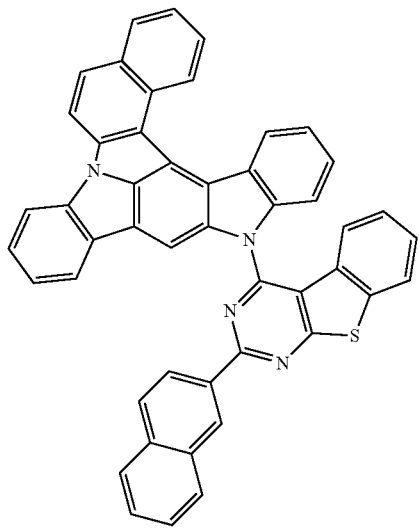
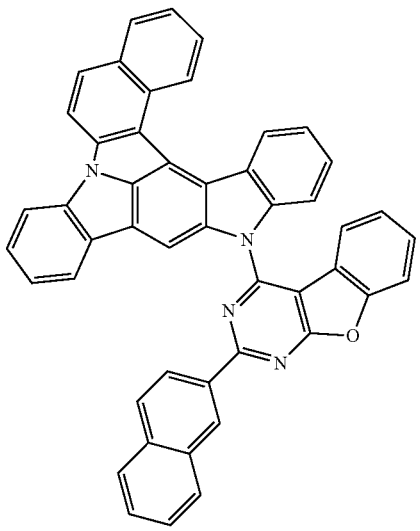
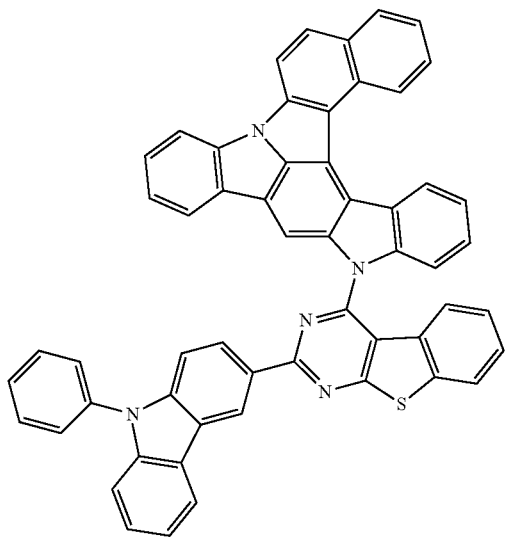
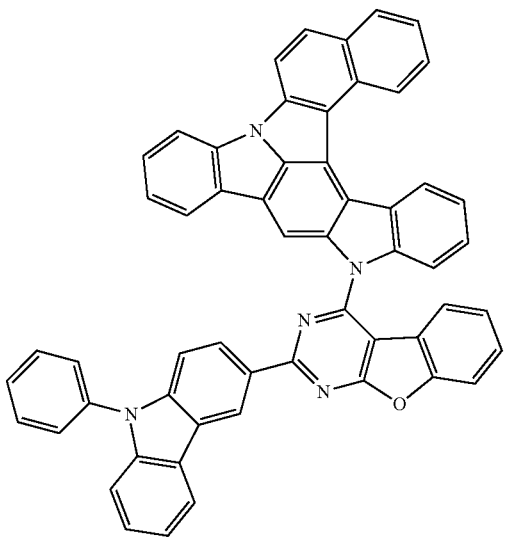

789
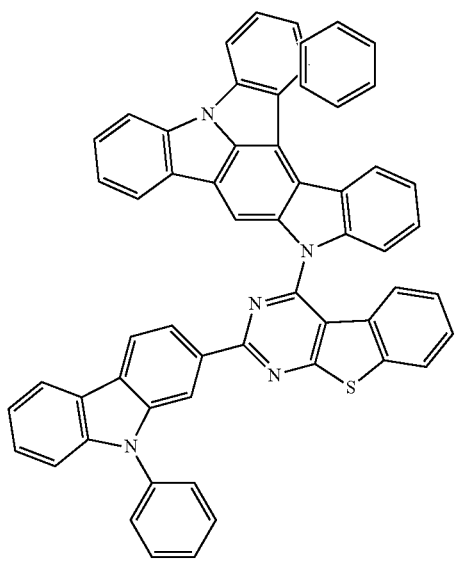
790
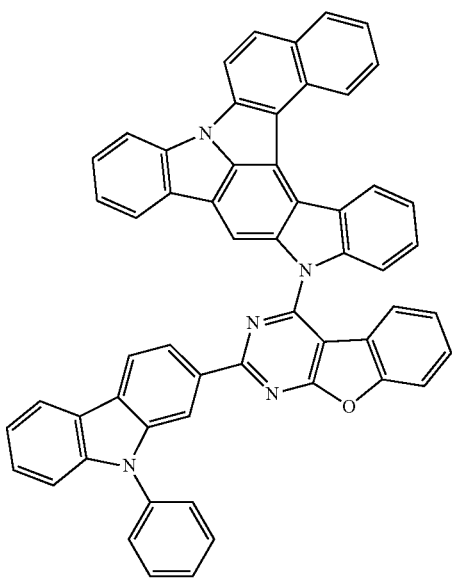
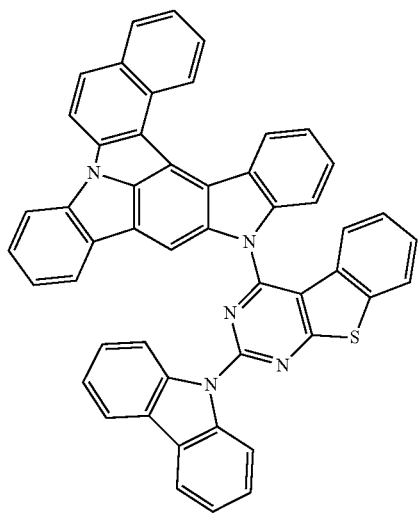
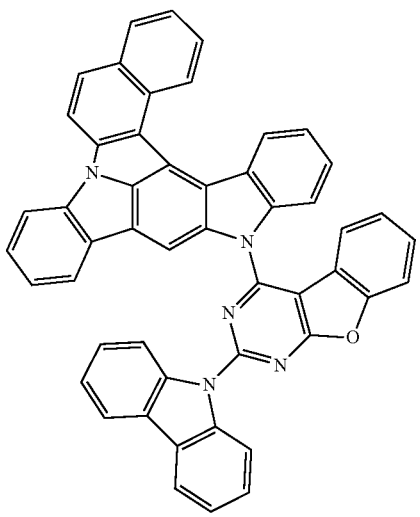
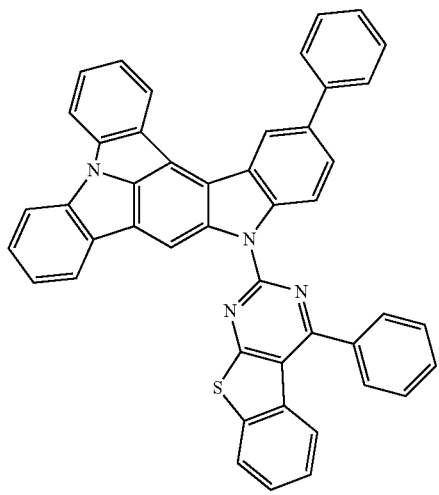
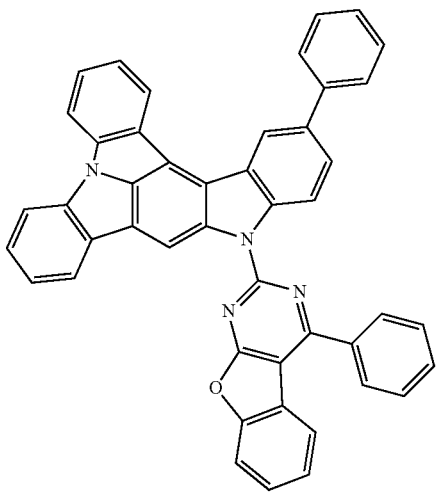

791
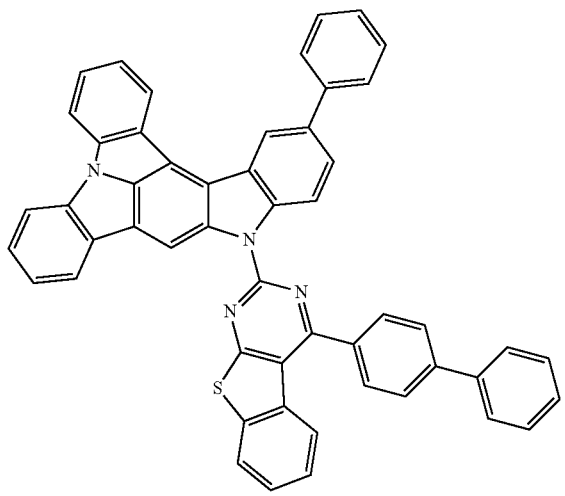
792
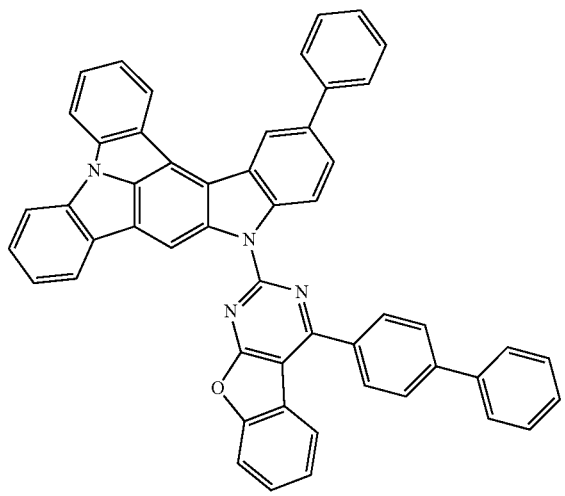
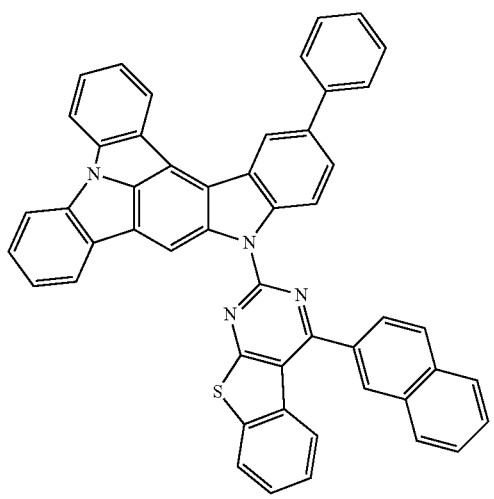
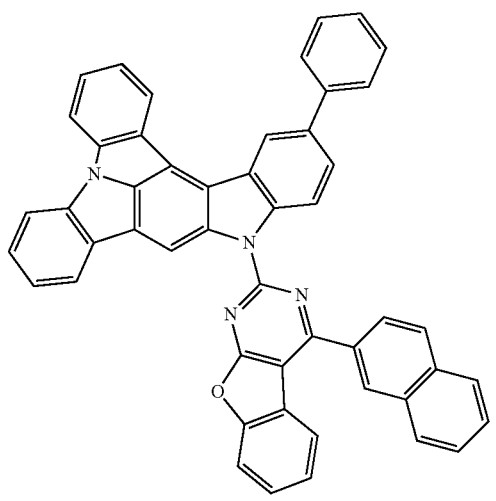
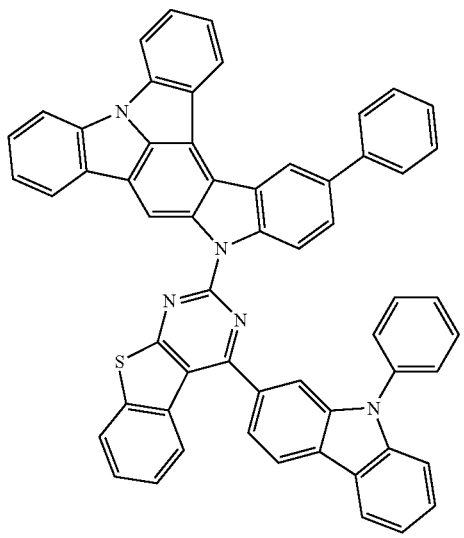
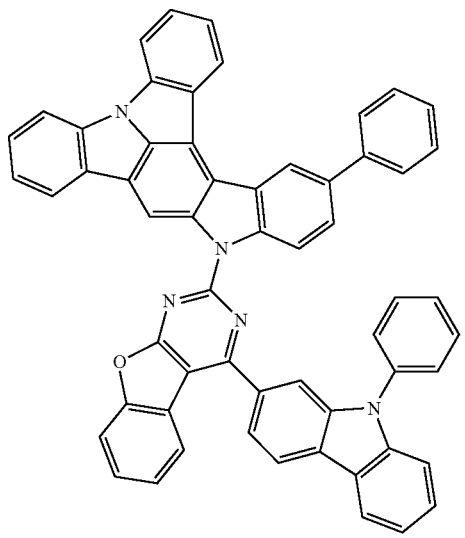

-continued
793
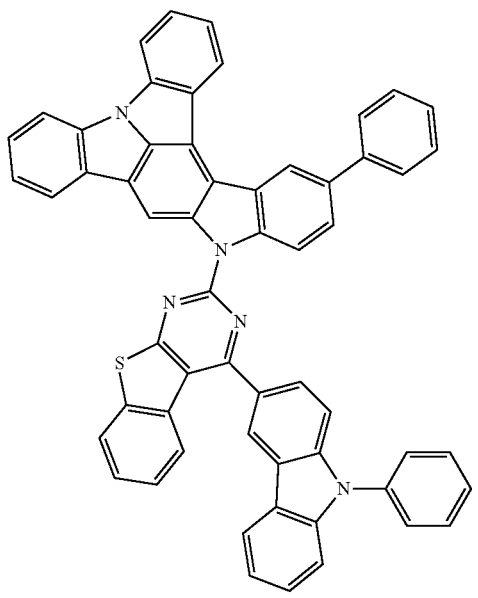
794
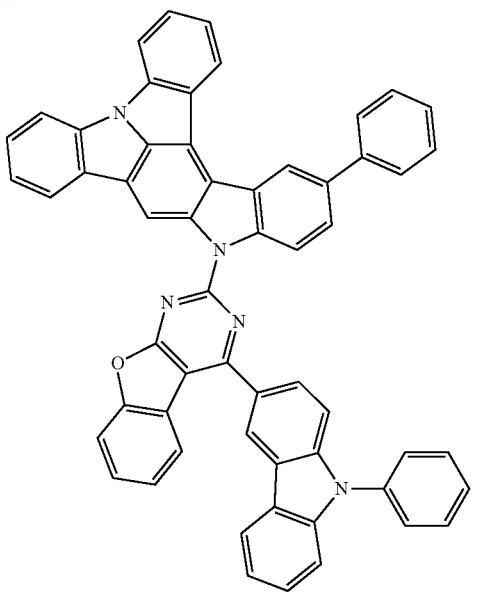
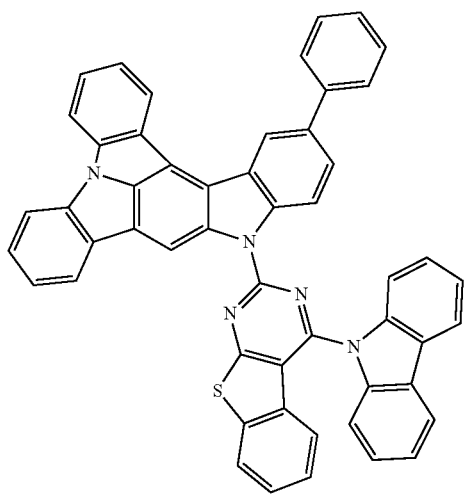
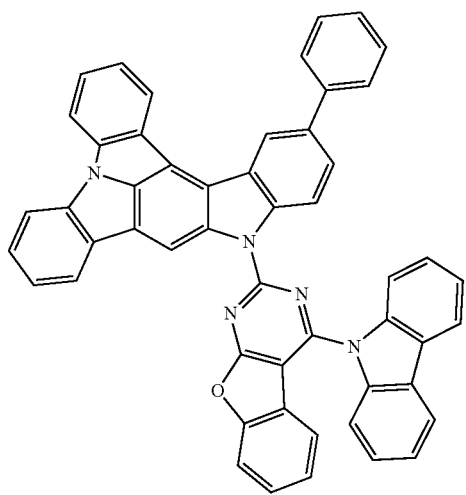
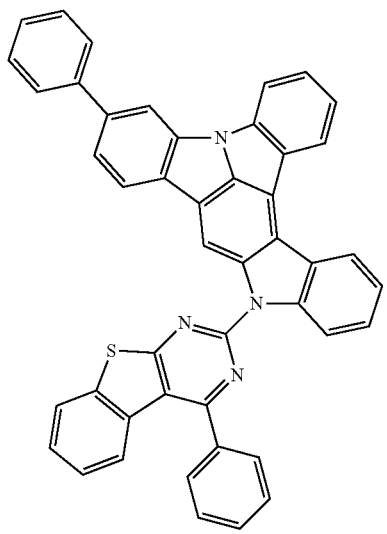
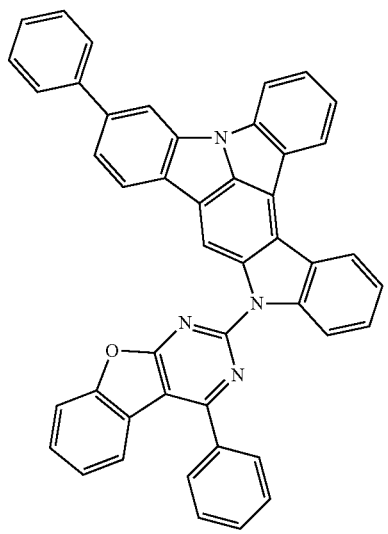

795
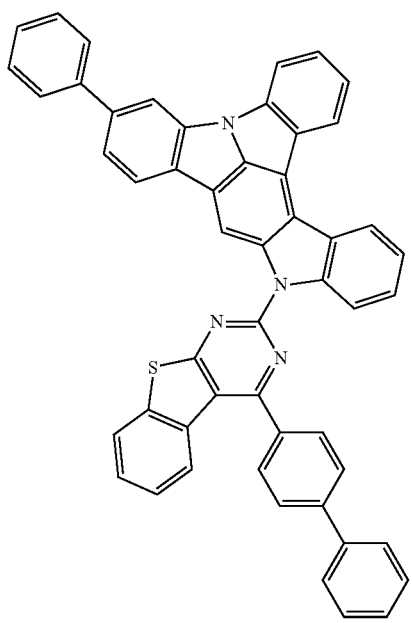
796
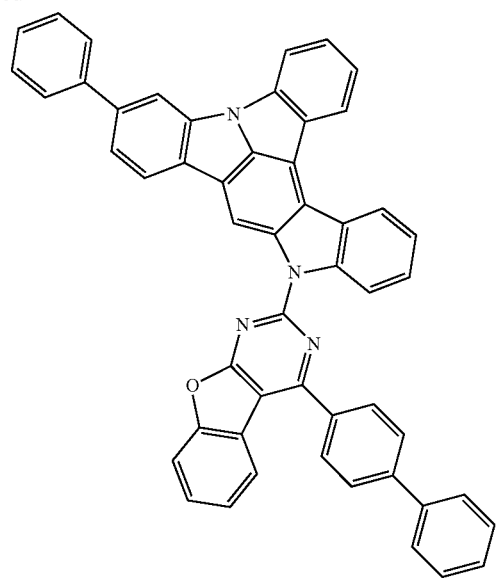
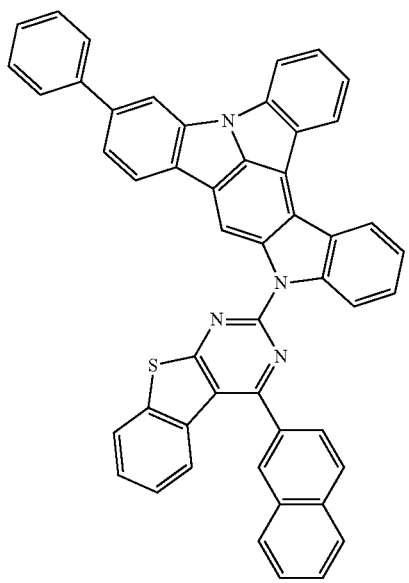
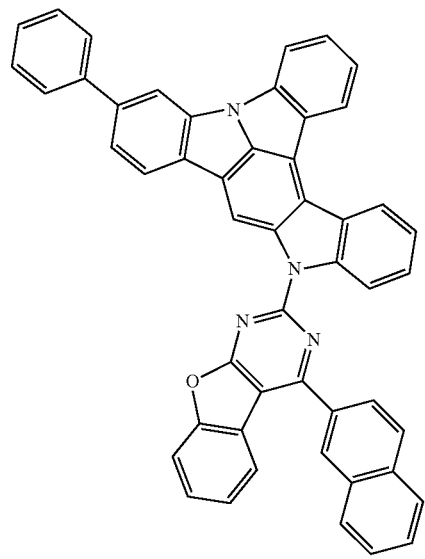

797
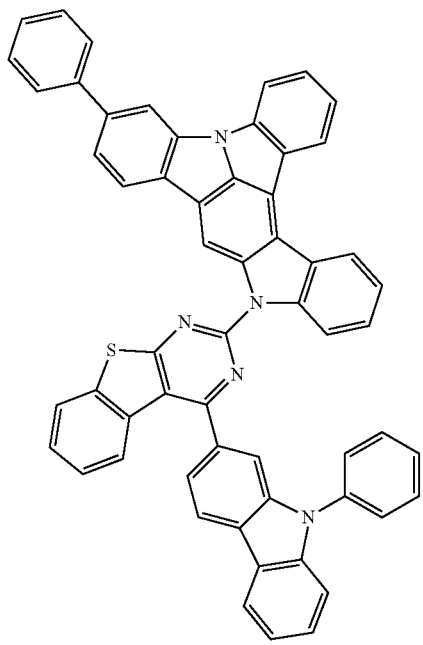
798
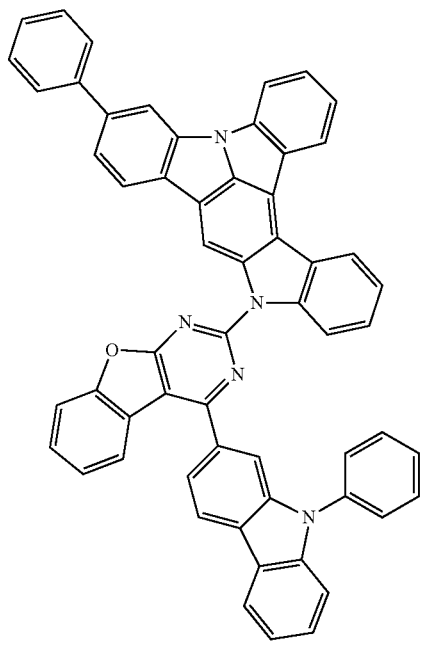
-continued
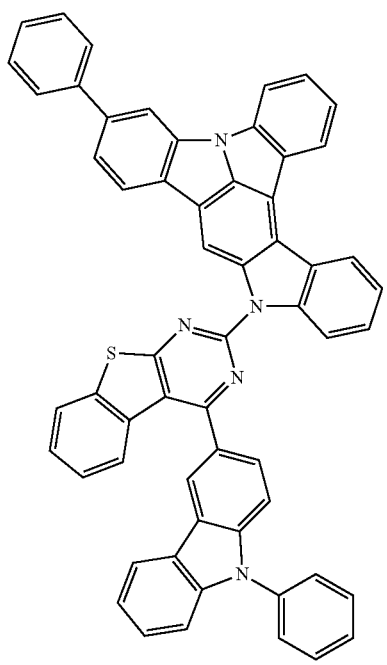
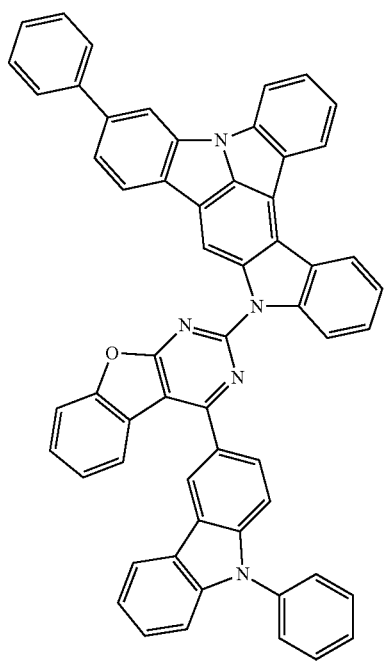

-continued
799
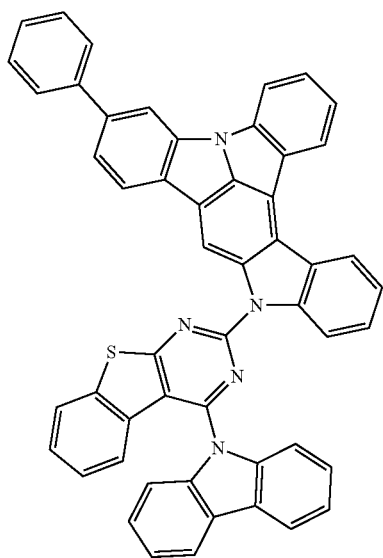
800
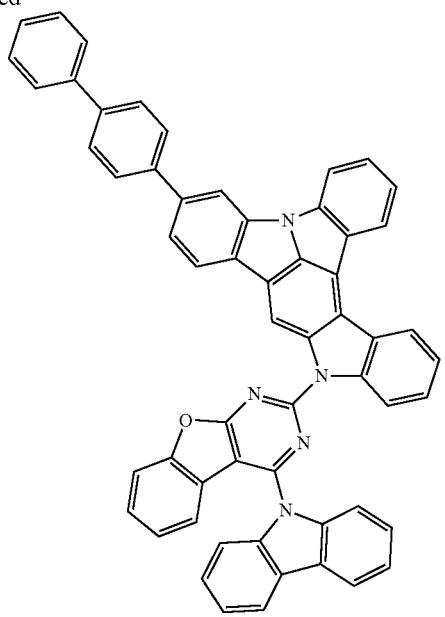
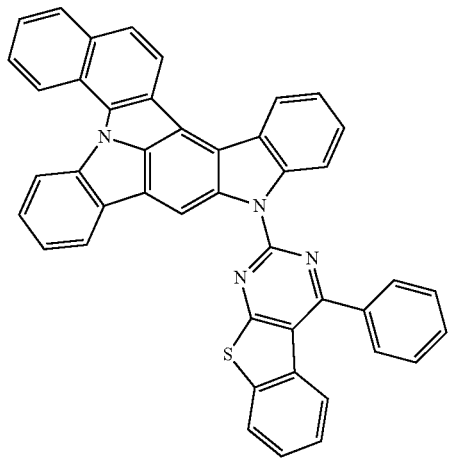
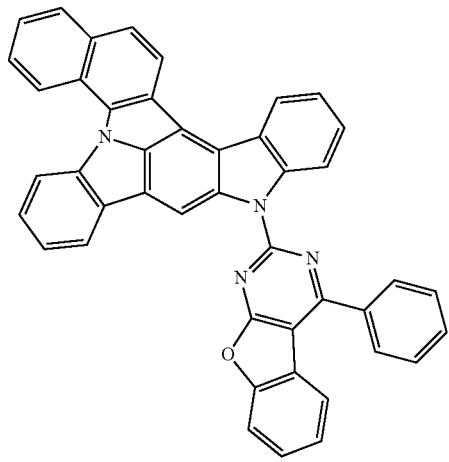
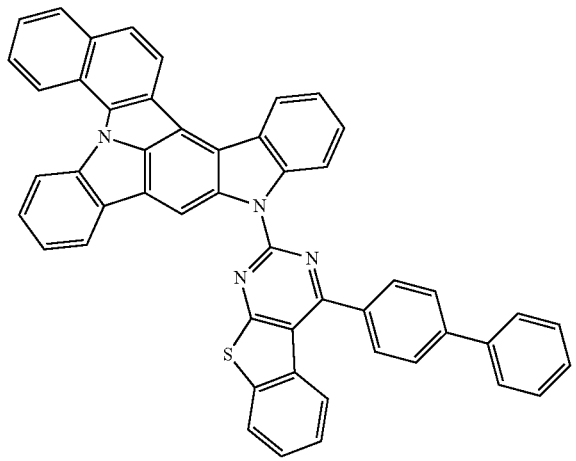
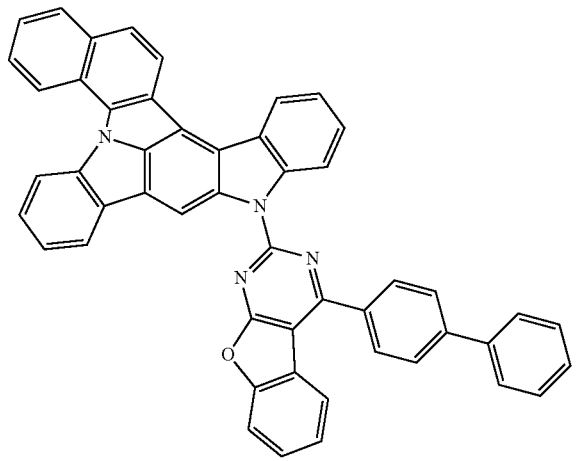

-continued
801
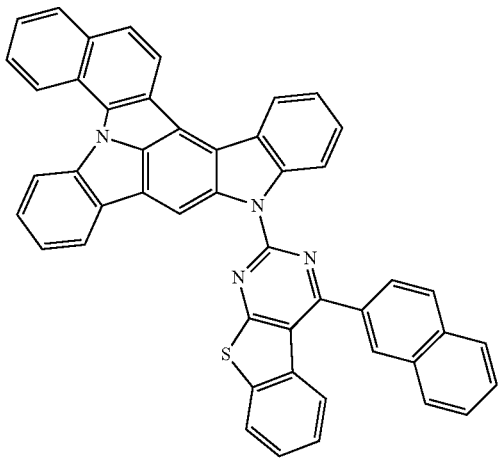
802
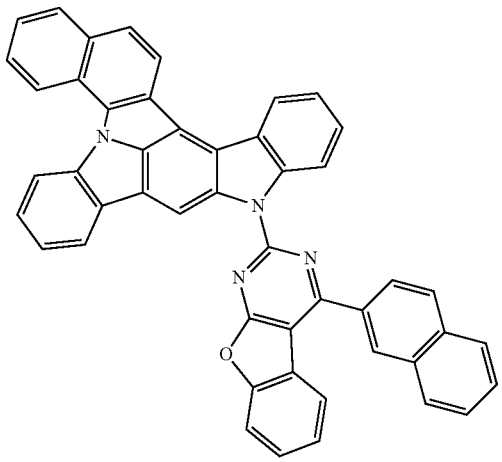
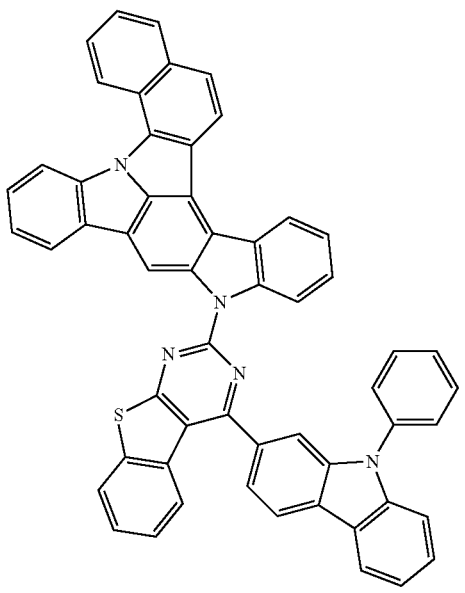
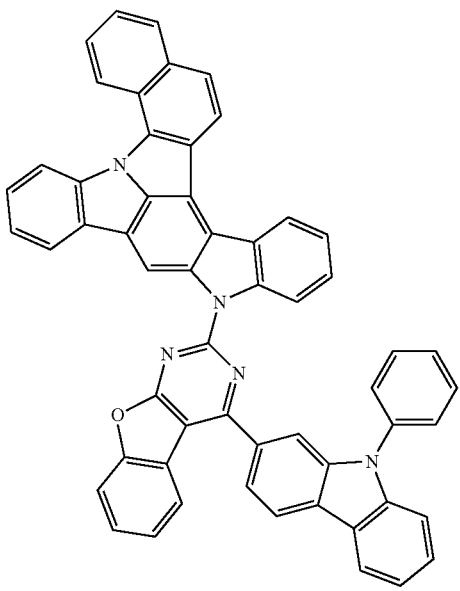
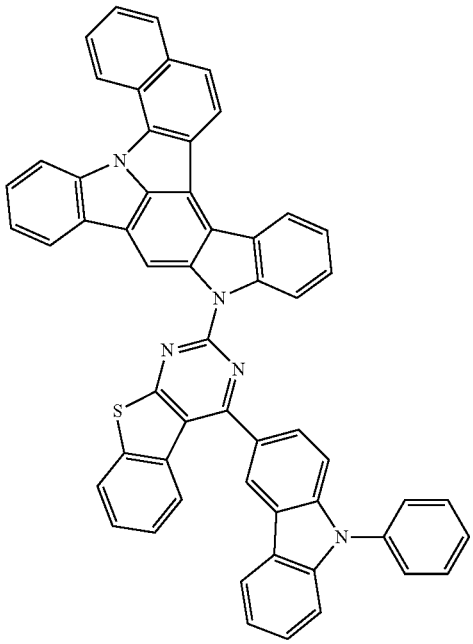
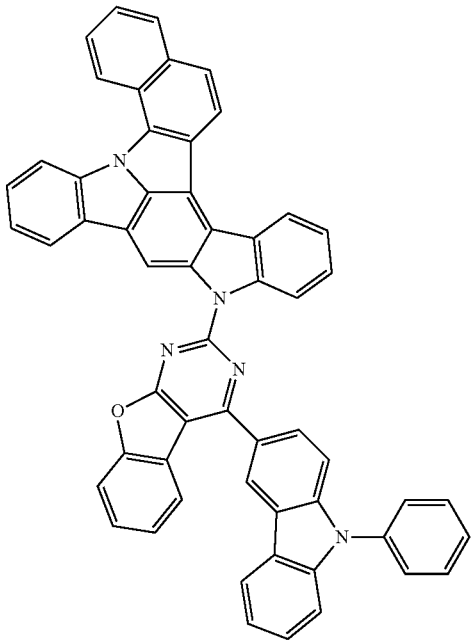

-continued
803
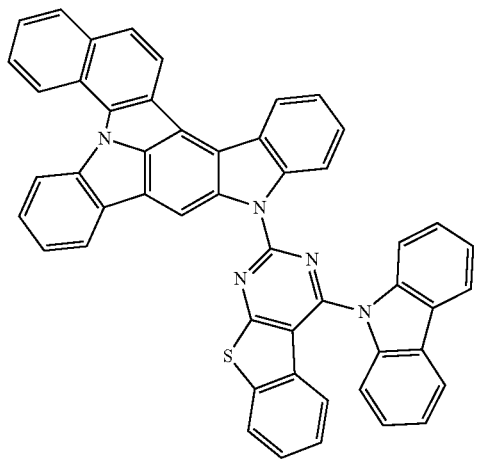
804
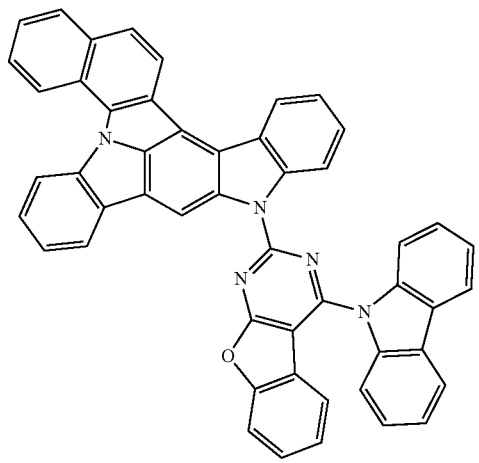
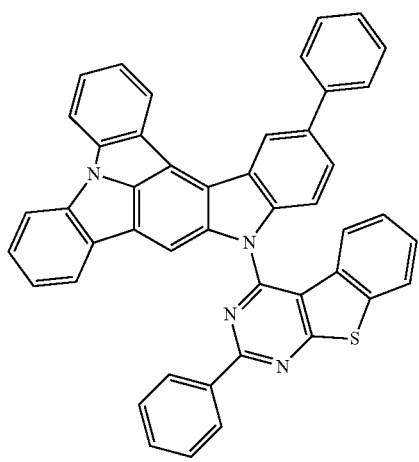
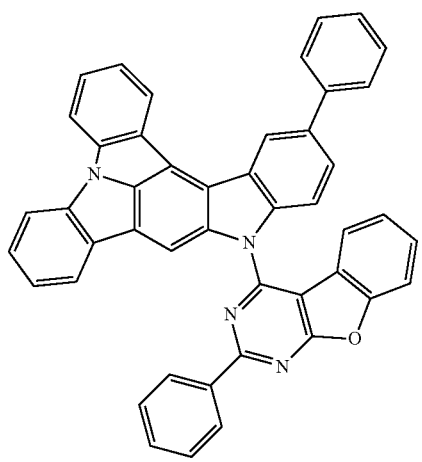
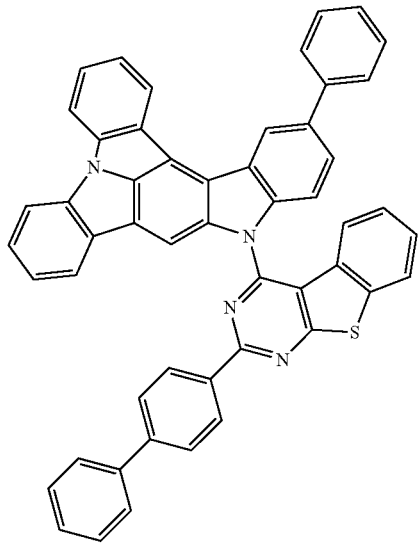
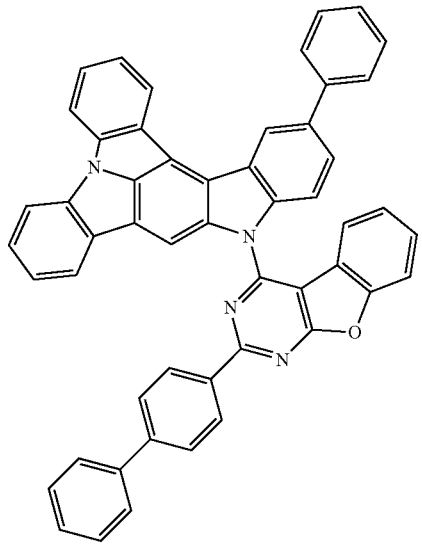

-continued
805
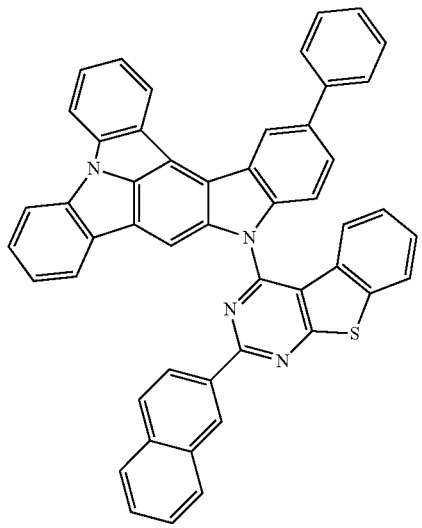
806
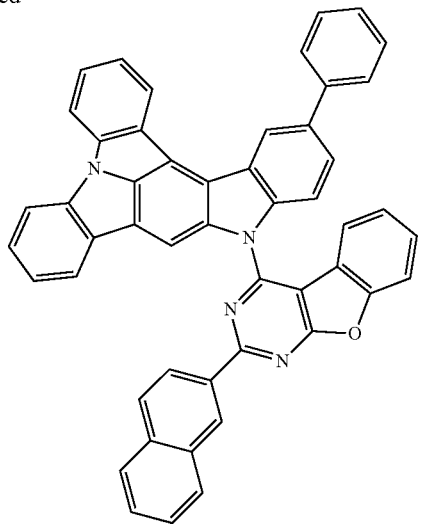
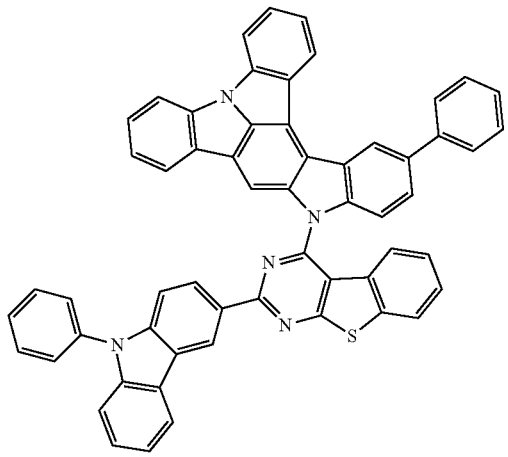
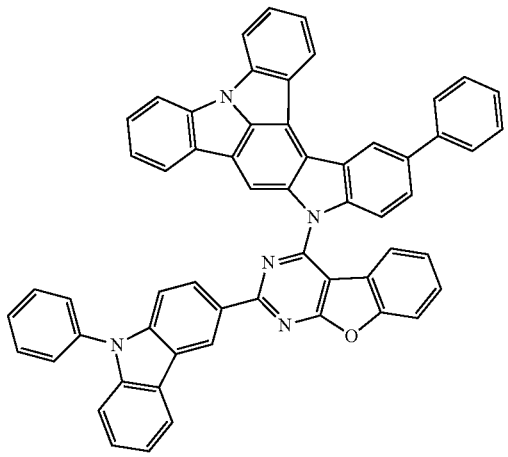
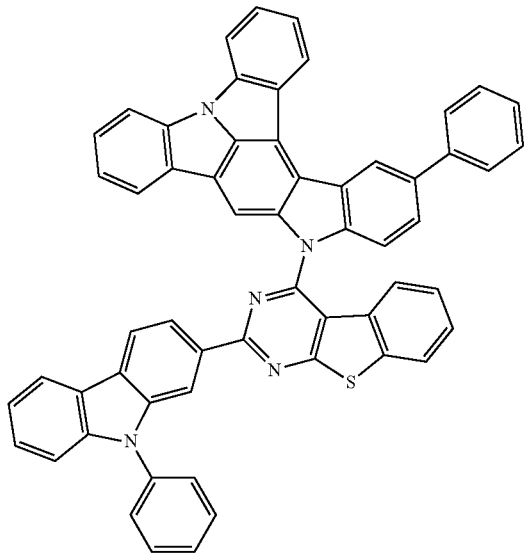
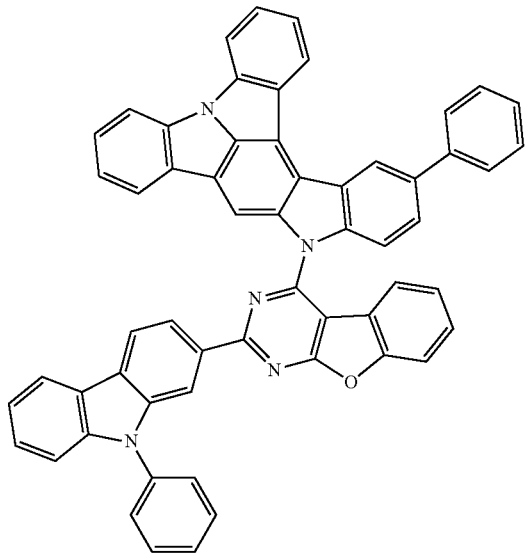

807 808
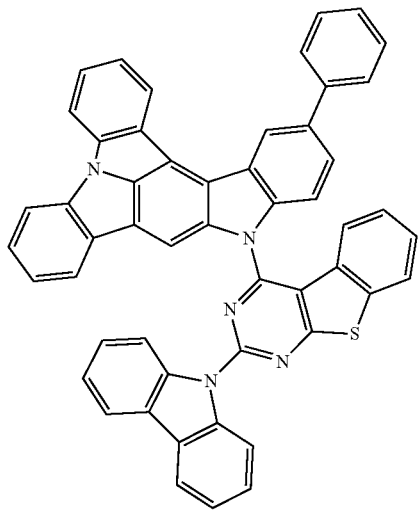
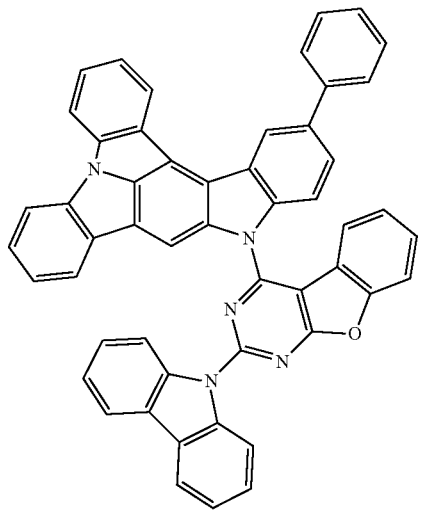
-continued
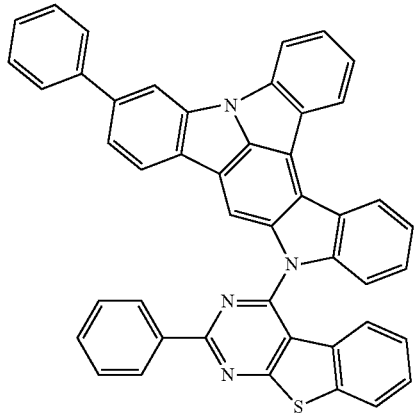
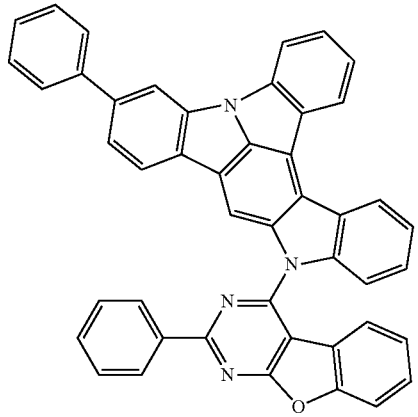
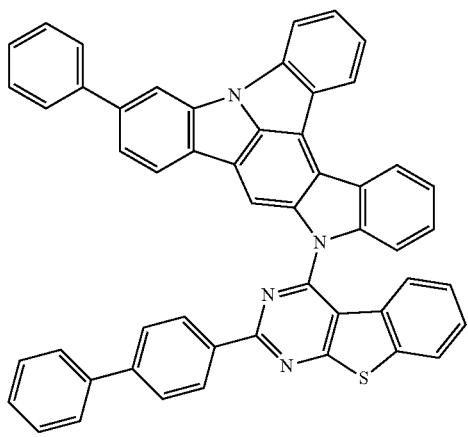
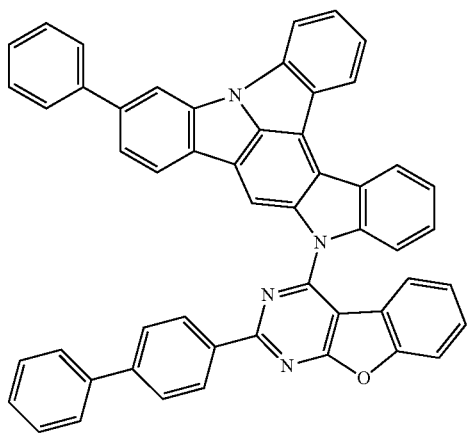

-continued
| 809 | 810 |
|---|---|
| 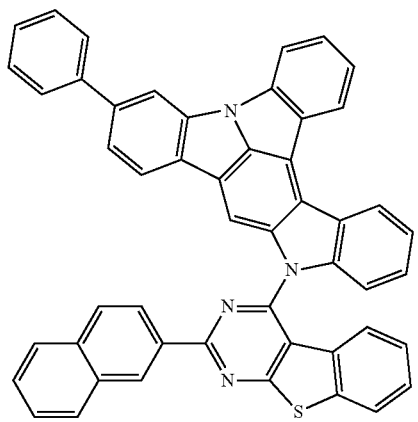 | 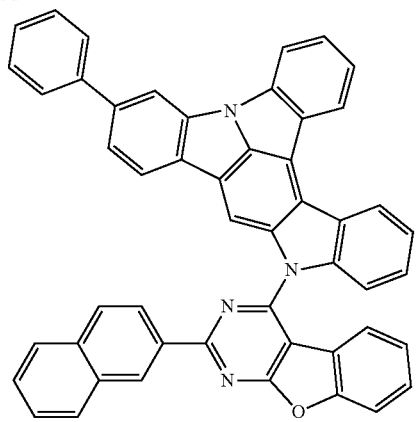 |
| 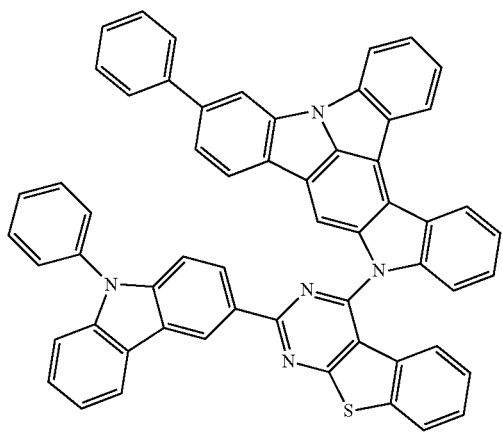 | 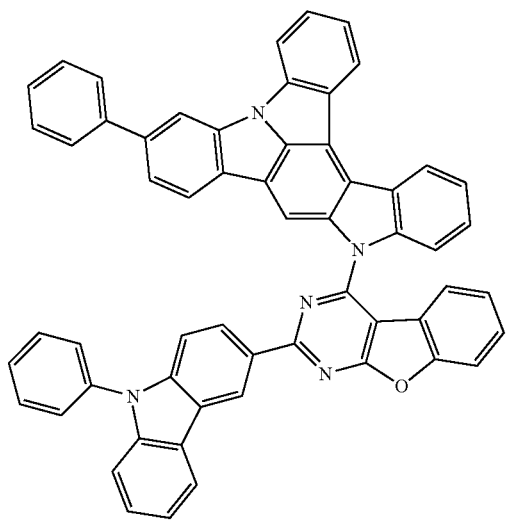 |
| 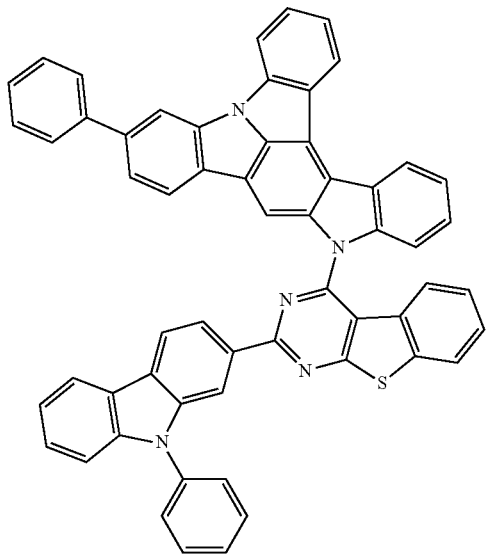 | 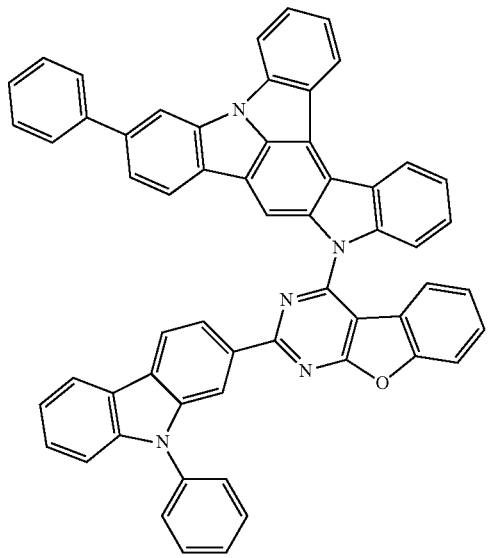 |

-continued
| 811 | 812 |
|---|---|
| 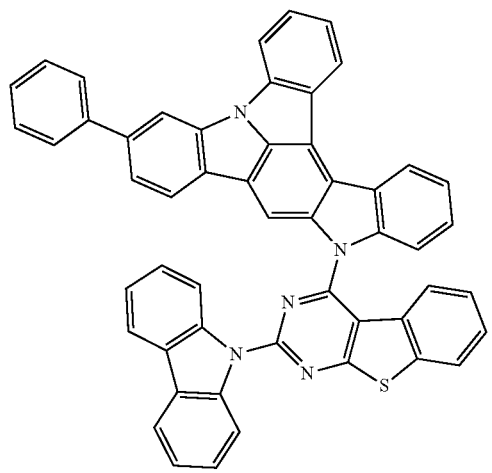 | 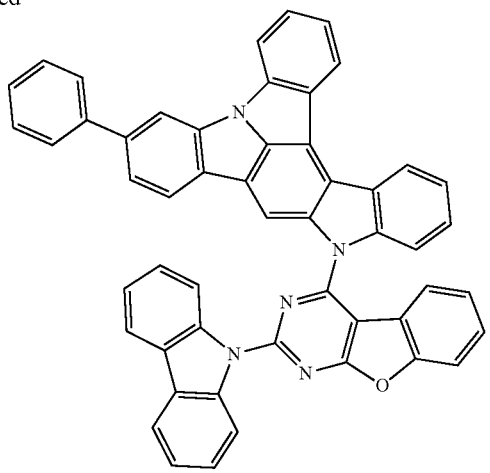 |
| 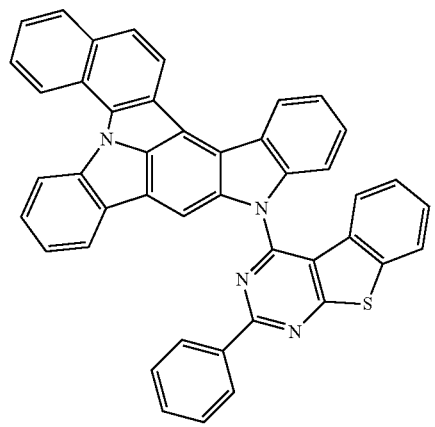 | 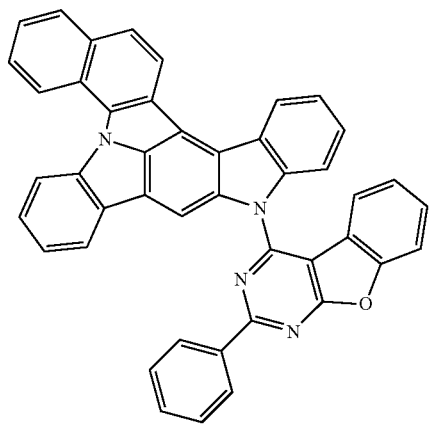 |
| 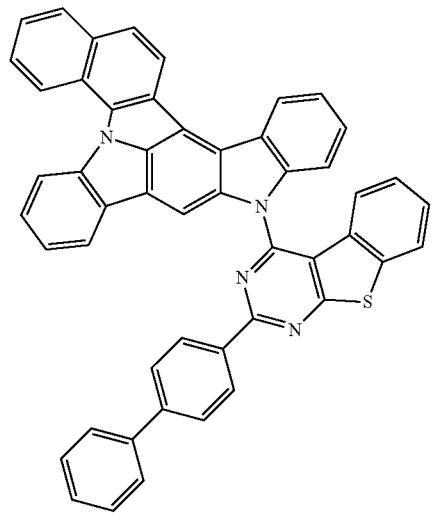 | 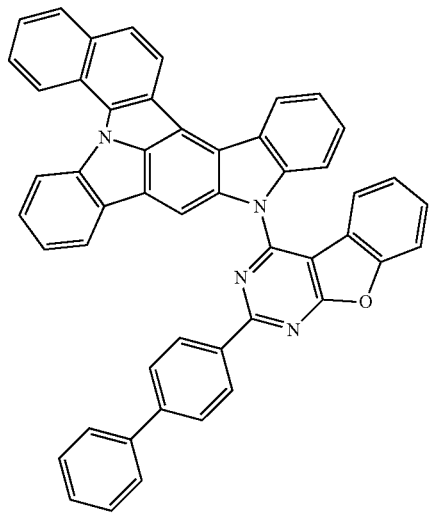 |

-continued
813
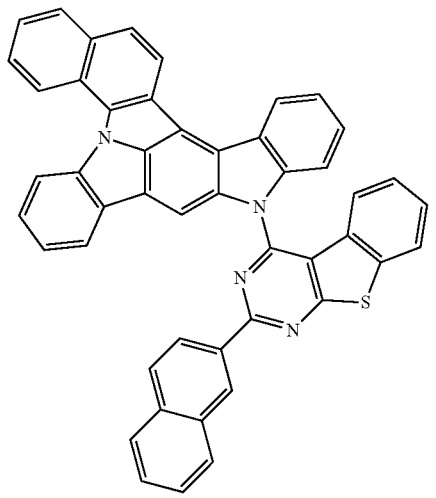
814
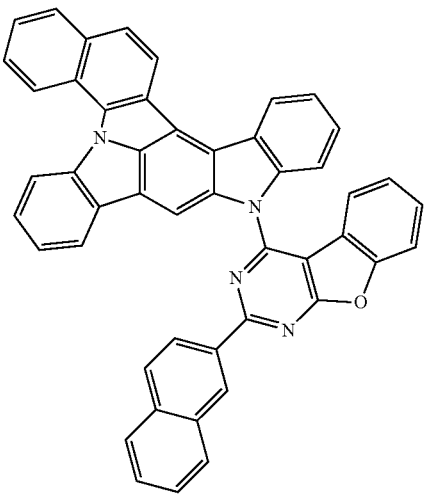
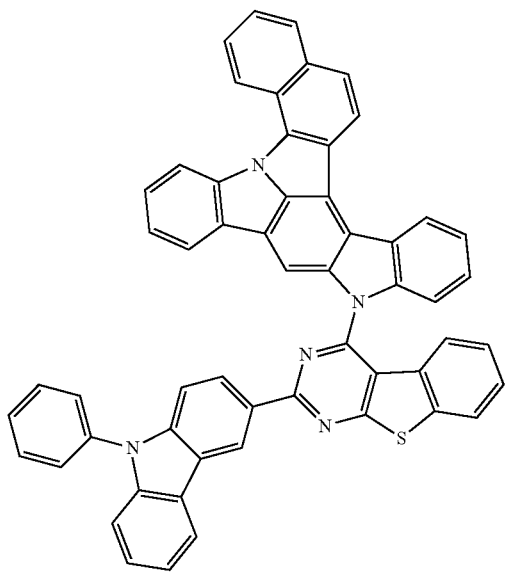
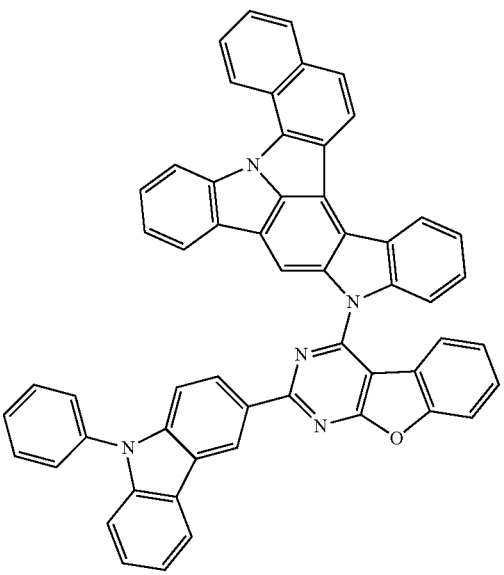
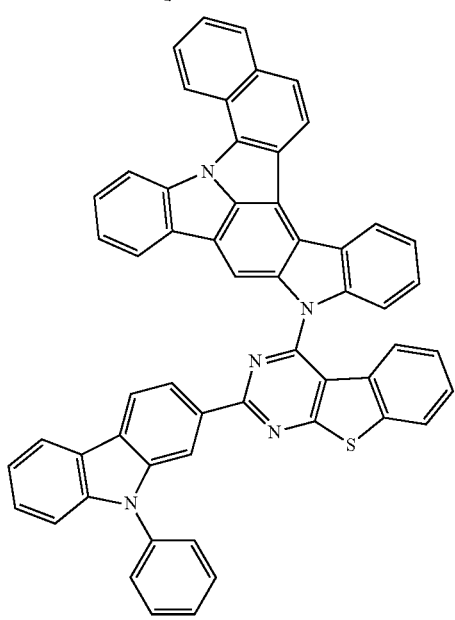
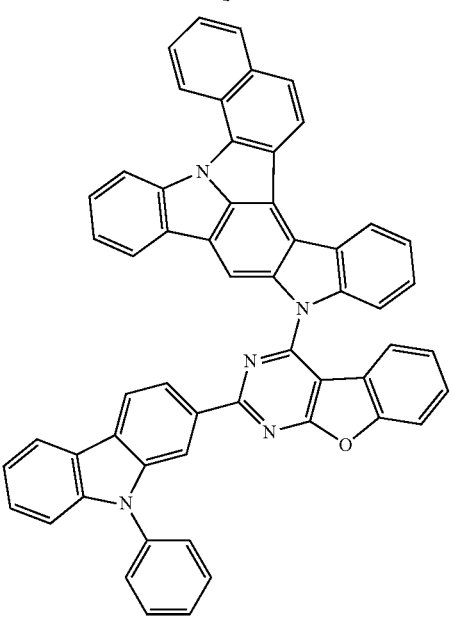

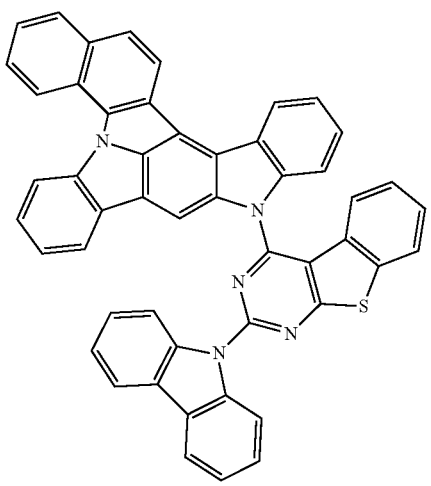
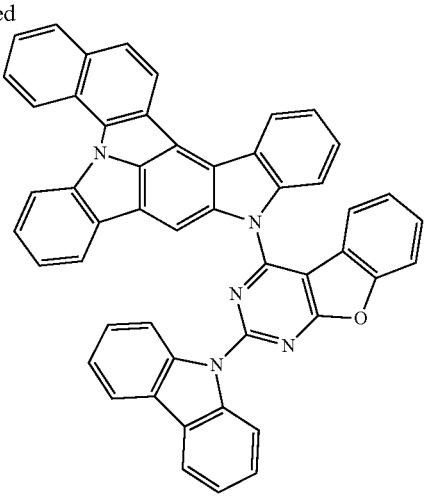

The compound represented by Chemical Formula 1 may undergo an amination reaction by an Ullmann or Buchwald-Hartwig coupling reaction, use a Suzuki or Heck coupling reaction, and use a Grignard reagent. In the other chemical formulae, synthesis may also be carried out by the same reactions.

For example, the core of Chemical Formula 2 and the core of Chemical Formula 3 may be prepared by the following Preparation Example 1 and the following Preparation Example 2, respectively, but the preparation method is not limited to the following Preparation Examples. The introduction of the additional substituent may be carried out by using materials and reaction conditions known in the art.

PREPARATION EXAMPLES

Preparation Example 1. Preparation of Core of Chemical Formula 2

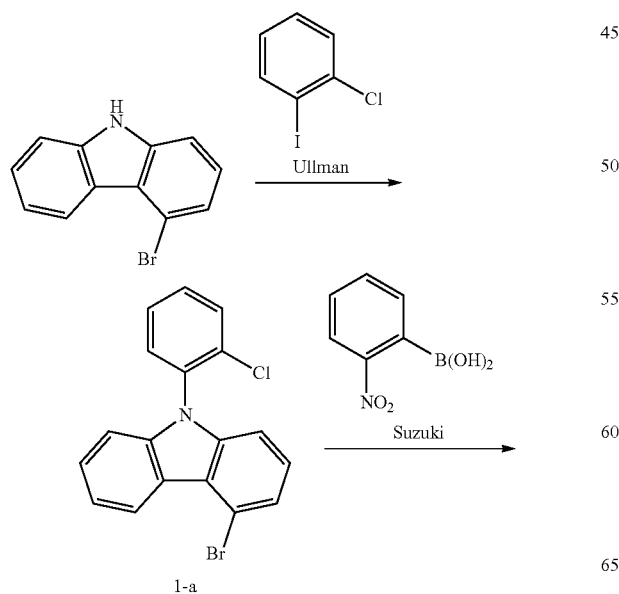

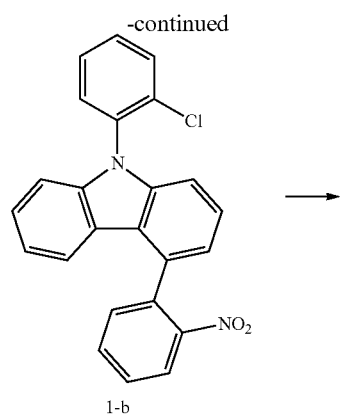

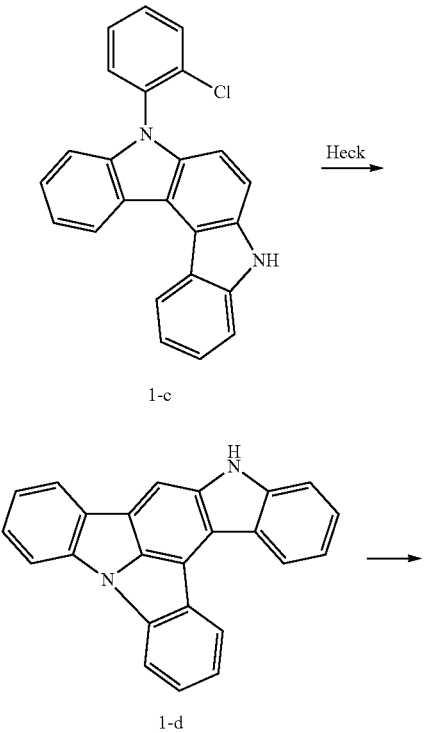

-continued

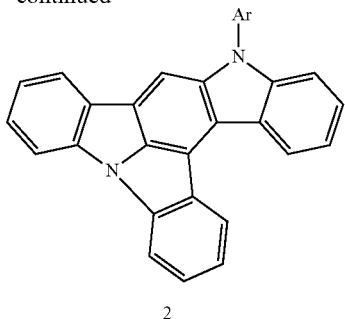

2

(1) Preparation of Chemical Formula 1-a 100 g (408.20 mmol, 1.0 eq) of 4-bromo-9H-carbazole, 116.53 g (489.83 mmol, 1.2 eq) of 1-chloro-2-iodobenzene, 51.88 g (816.39 mmol, 2.0 eq) of copper powder, and 259.94 g (1,224.59 mmol, 3.0 eq) of $K_3PO_4$ were put into 1,000 ml of xylene, and stirred under reflux. When the reaction was terminated, the resulting product was cooled to normal temperature, and then the copper powder was first filtered and removed. The solution in which the product was dissolved was placed under reduced pressure to remove all the solvent, and the product was completely dissolved in $CHCl_3$, washed with water, and again placed under reduced pressure to remove the solvent, and the resulting product was purified by using column chromatography. 131.86 g (371.46 mmol, yield 91%) of Chemical Formula 1-a was obtained.

(2) Preparation of Chemical Formula 1-b 131.86 g (371.46 mmol, 1.0 eq), of Chemical Formula 1-a, 74.46 g (445.75 mmol, 1.2 eq) of 2-(nitrophenyl) boronic acid, and 0.79 g (3.71 mmol, 0.01 eq) of $Pd(PPh_3)_4$ were dissolved in 900 ml of dioxane and stirred, and then 102.67 g (742.91 mmol, 2.0 eq) of $K_2CO_3$ was dissolved in 300 ml of water, the resulting solution was added thereto, and the resulting mixture was stirred under reflux. When the reaction was terminated, the organic layer was separated and then placed under reduced pressure to remove the solvent. The resulting product was subjected to column chromatography to obtain 121.25 g (304.59 mmol, yield 82%) of Chemical Formula 1-b.

(3) Preparation of Chemical Formula 1-c 121.25 g (304.59 mmol, 1.0 eq) of Chemical Formula 1-b and 151.83 g (913.76 mmol, 3.0 eq) of $P(OEt)_3$ were put, and stirred under reflux. When the reaction was terminated, a vacuum pump was used to maximally distill $P(OEt)_3$ and remove the $P(OEt)_3$. The resulting product was completely dissolved in EA and washed with water, and then the organic layer was separated and placed under reduced pressure to remove all the solvent. The resulting product was subjected to column chromatography to obtain 84.75 g (231.48 mmol, yield 76%) of Chemical Formula 1-c.

(4) Preparation of Chemical Formula 1-d 84.75 g (231.50 mmol, 1.0 eq) of Chemical Formula 1-c, 2.60 g (11.57 mmol, 0.05 eq) of $Pd(OAc)_2$, 6.07 g (23.15 mmol, 0.1 eq) of $PPh_3$, 63.98 g (463.00 mmol, 2.0 eq) of $K_2CO_3$, and 37.31 g (115.75 mmol, 0.5 eq) of tetra-n-butylammonium bromide were put into 550 mL of dimethylacetamide, and reaction was carried out. The reaction solution was stirred at 150° C. for 20 hours, and then the solvent was concentrated under reduced pressure. The concentrated solution was completely dissolved in $CHCl_3$ and then washed with water, and the solution in which the product was dissolved was concentrated under reduced pressure and purified by using column chromatography. 66.49 g (201.41 mmol, yield 87%) of Chemical Formula 1-d was obtained.

(5) Preparation of Core of Chemical Formula 2

A substituent Ar may be introduced into Chemical Formula 1-d to prepare the core of Chemical Formula 2. The definition of Ar is the same as that described in Chemical Formula 1. Here, L-Ar may be introduced thereinto instead of Ar.

Preparation Example 2. Preparation of Core of Chemical Formula 3

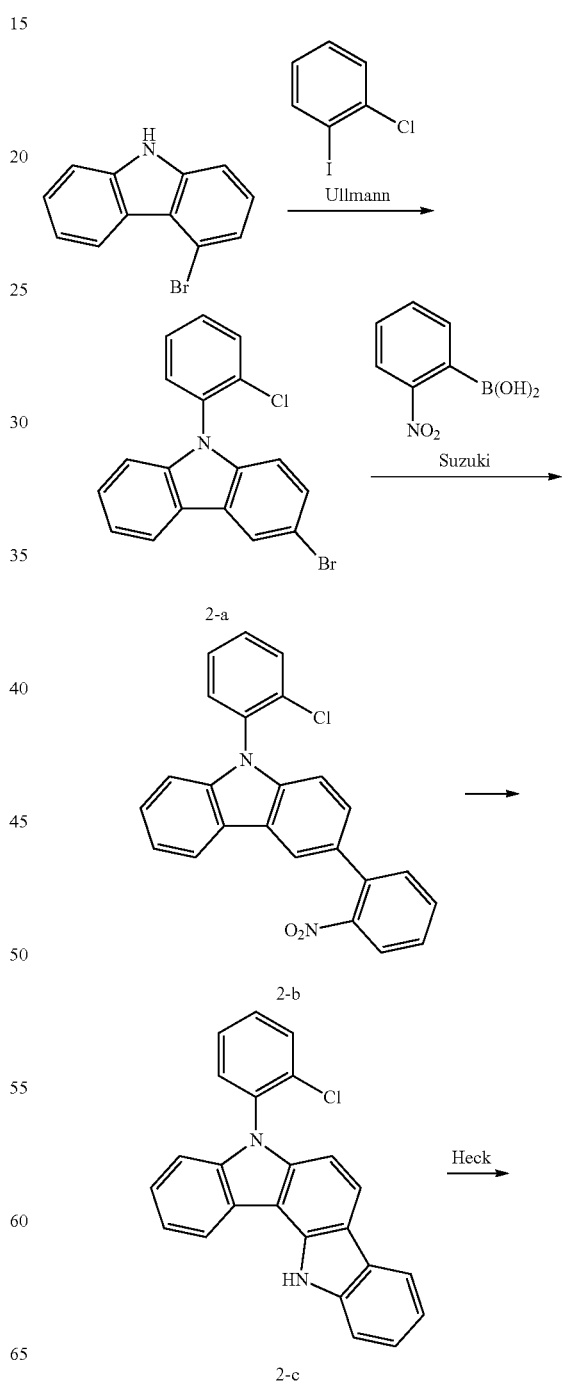

-continued

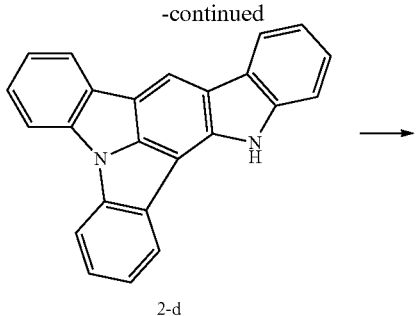

2-d

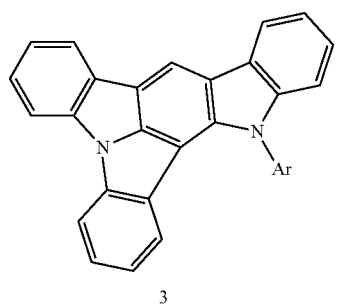

3

(1) Preparation of Chemical Formula 2-a 100 g (408.20 mmol, 1.0 eq) of 3-bromo-9H-carbazole, 116.53 g (489.84 mmol, 1.2 eq) of 1-chloro-2-iodobenzene, 51.88 g (816.39 mmol, 2.0 eq) of copper powder, and 259.94 g (1,224.59 mmol, 3.0 eq) of K₃PO₄ were put into 1,000 ml of xylene, and stirred under reflux. When the reaction was terminated, the resulting product was cooled to normal temperature, and then the copper powder was first filtered and removed. The solution in which the product was dissolved was placed under reduced pressure to remove all the solvent, and the product was completely dissolved in CHCl₃, washed with water, and again placed under reduced pressure to remove the solvent, and the resulting product was purified by using column chromatography. 130.41 g (367.38 mmol, yield 90%) of Chemical Formula 2-a was obtained.

(2) Preparation of Chemical Formula 2-b 130.41 g (367.38 mmol, 1.0 eq), of Chemical Formula 2-a, 73.64 g (440.85 mmol, 1.2 eq) of 2-(nitrophenyl) boronic acid, and 0.78 g (3.67 mmol, 0.01 eq) of Pd(PPh₃)₄ were dissolved in 900 ml of dioxane and stirred, and then 101.54 g (734.74 mmol, 2.0 eq) of K₂CO₃ was dissolved in 300 ml of water, the resulting solution was added thereto, and the resulting mixture was stirred under reflux. When the reaction was terminated, the organic layer was separated and then placed under reduced pressure to remove the solvent. The resulting product was subjected to column chromatography to obtain 121.38 g (304.91 mmol, yield 83%) of Chemical Formula 2-b.

(3) Preparation of Chemical Formula 2-c 121.38 g (304.91 mmol, 1.0 eq) of Chemical Formula 2-b and 151.99 g (914.74 mmol, 3.0 eq) of P(OEt)₃ were put, and stirred under reflux. When the reaction was terminated, a vacuum pump was used to maximally distill P(OEt)₃ and remove the P(OEt)₃. The resulting product was completely dissolved in EA and washed with water, and the organic layer was separated and placed under reduced pressure to remove all the solvent. The resulting product was subjected to column chromatography to obtain 81.49 g (222.58 mmol, yield 73%) of Chemical Formula 2-c.

(4) Preparation of Chemical Formula 2-d 81.49 g (222.58 mmol, 1.0 eq) of Chemical Formula 2-c, 2.50 g (11.13 mmol, 0.05 eq) of Pd(OAc)₂, 5.84 g (22.26 mmol, 0.1 eq) of PPh₃, 61.53 g (445.19 mmol, 2.0 eq) of K₂CO₃, and 35.87 g (111.30 mmol, 0.5 eq) of tetra-n-butylammonium bromide were put into 550 mL of dimethylacetamide, and reaction was carried out. The reaction solution was stirred at 150° C. for 20 hours, and then the solvent was concentrated under reduced pressure. The concentrated solution was completely dissolved in CHCl₃ and then washed with water, and the solution in which the product was dissolved was concentrated under reduced pressure and purified by using column chromatography. 65.40 g (198.11 mmol, yield 89%) of Chemical Formula 2-d was obtained.

(5) Preparation of Core of Chemical Formula 3

A substituent Ar may be introduced into Chemical Formula 2-d to prepare the core of Chemical Formula 3. The definition of Ar is the same as that described in Chemical Formula 1. Here, L-Ar may be introduced thereinto instead of Ar.

Preparation Example 3. Preparation of Core of Chemical Formula 26

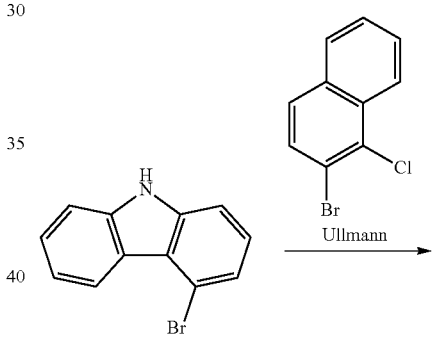

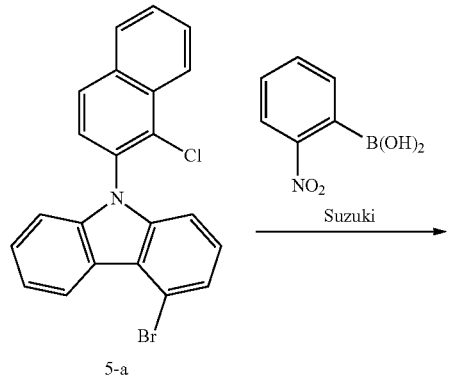

5-a

821
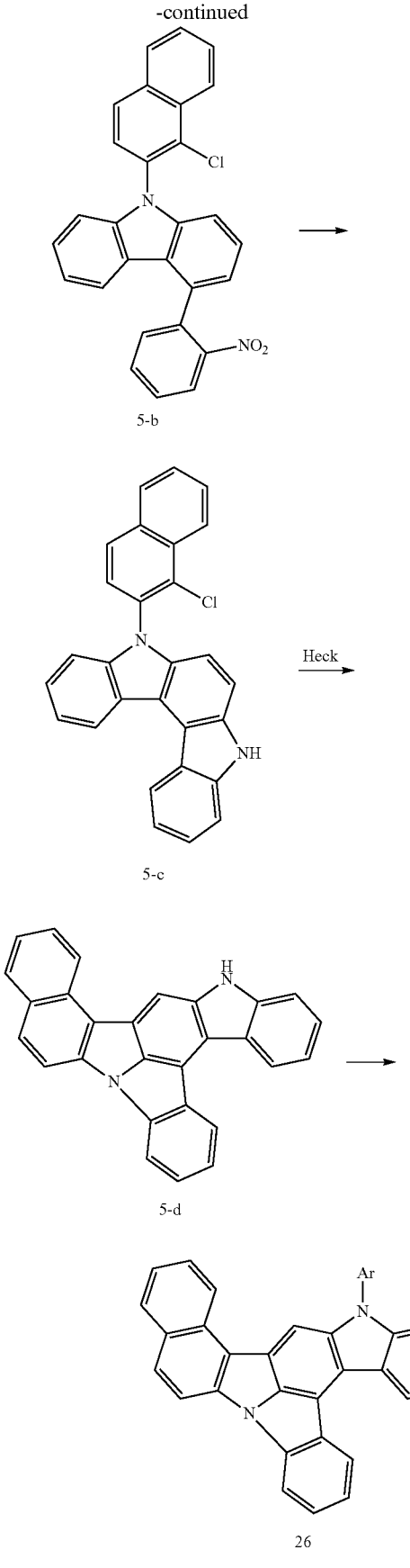
822
A core of Chemical Formula 26 was prepared by performing the preparation in the same manner as in Preparation Example 1, except that 2-bromo-1-chloronaphthalene was used instead of 1-chloro-2-iodobenzene in Preparation Example 1. Here, L-Ar may be introduced thereinto instead of Ar.
Preparation Example 4. Preparation of Core of Chemical Formula 27
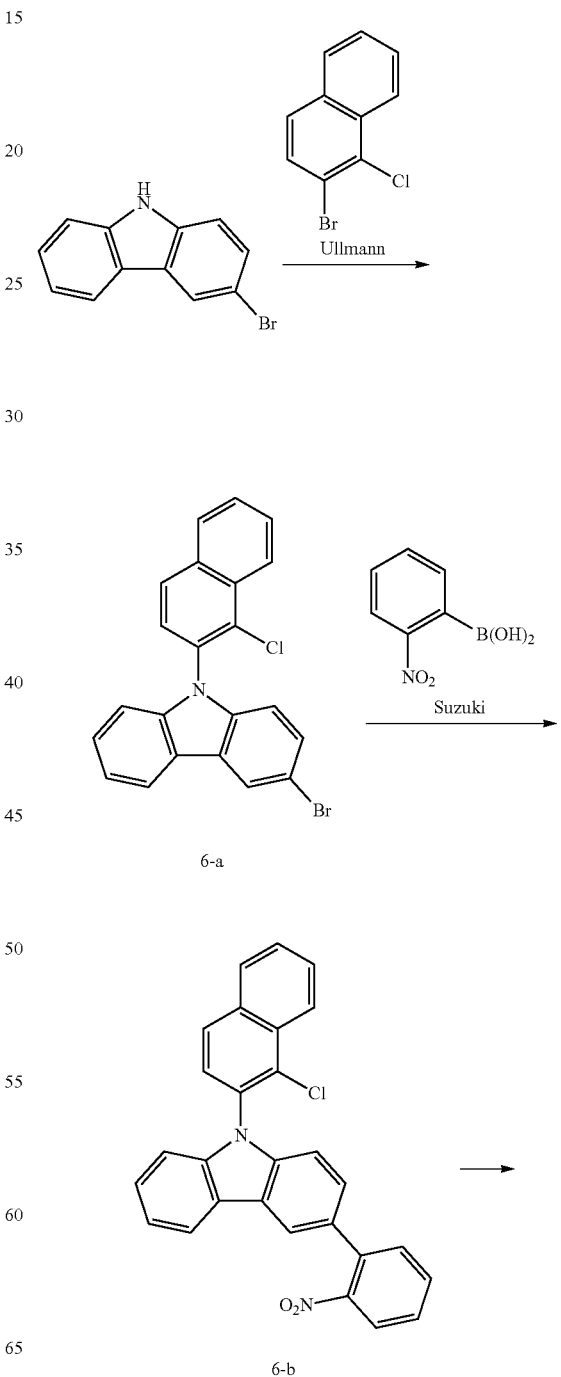

823
-continued

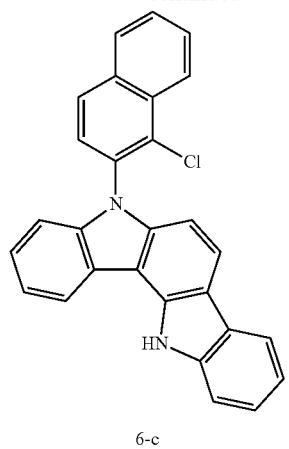

6-c

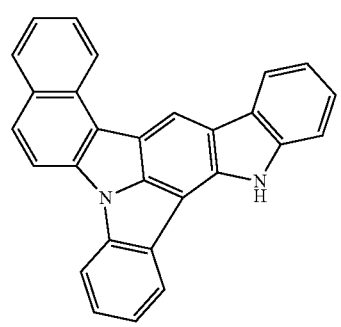

6-d

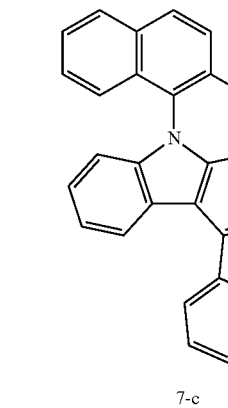

27

A core of Chemical Formula 27 was prepared by performing the preparation in the same manner as in Preparation Example 2, except that 2-bromo-1-chloronaphthalene was used instead of 1-chloro-2-iodobenzene in Preparation Example 2. Here, L-Ar may be introduced thereinto instead of Ar.

824

Preparation Example 5. Preparation of Core of Chemical Formula 34

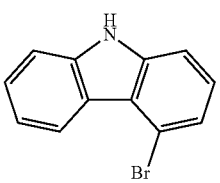 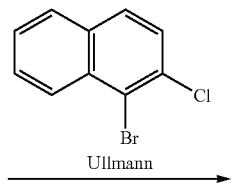
Ullmann →

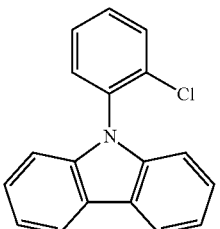 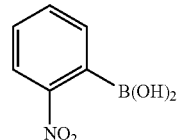
Suzuki →

7-a

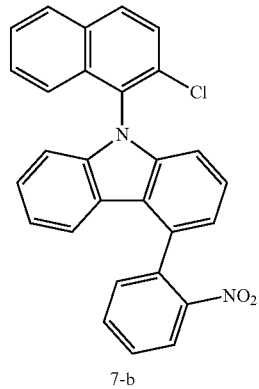

7-b

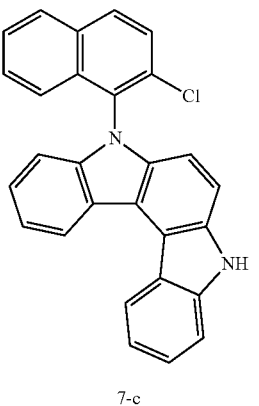
Heck →

7-c

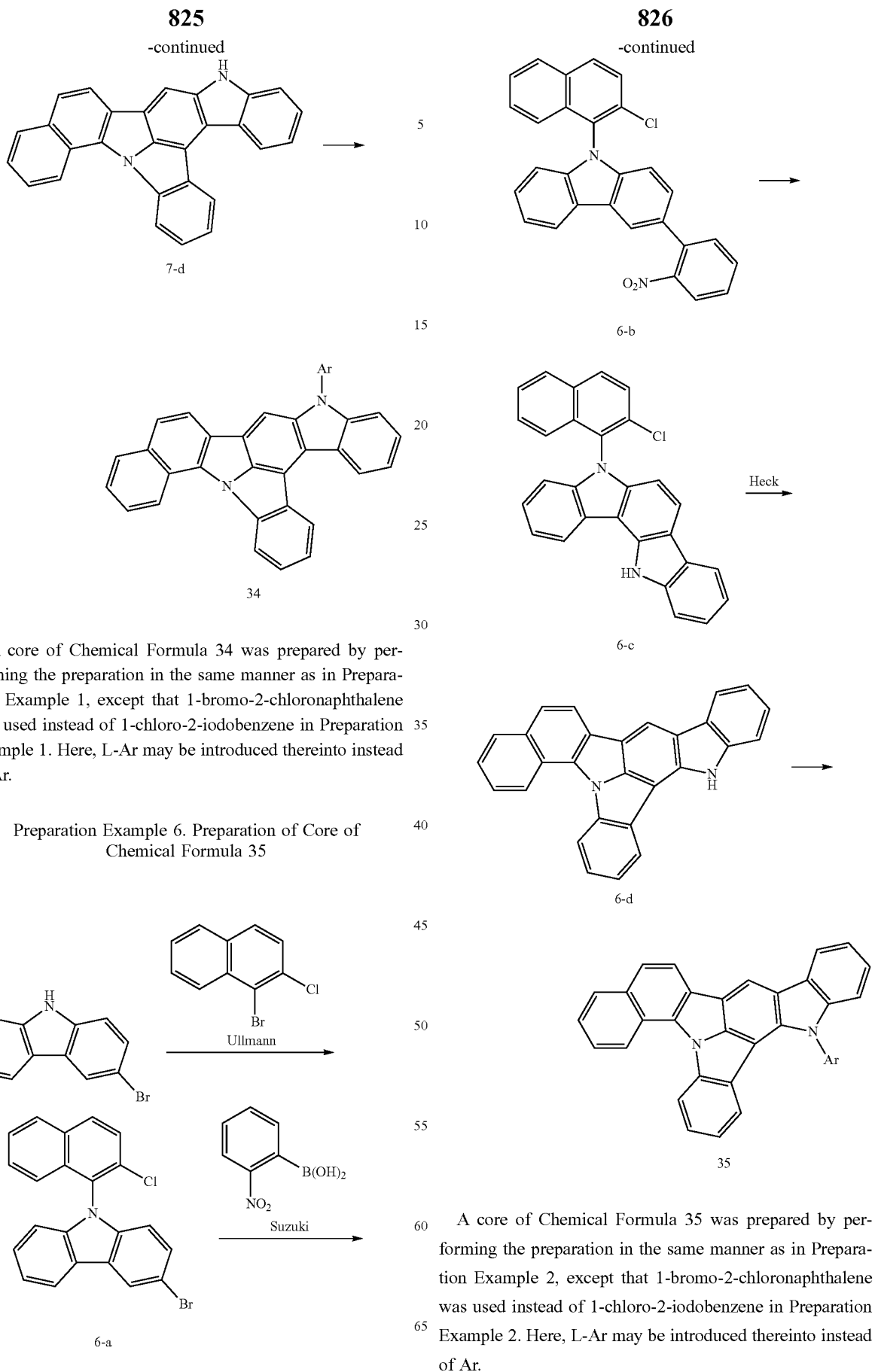

A core of Chemical Formula 34 was prepared by performing the preparation in the same manner as in Preparation Example 1, except that 1-bromo-2-chloronaphthalene was used instead of 1-chloro-2-iodobenzene in Preparation Example 1. Here, L-Ar may be introduced thereinto instead of Ar.

Preparation Example 6. Preparation of Core of Chemical Formula 35

A core of Chemical Formula 35 was prepared by performing the preparation in the same manner as in Preparation Example 2, except that 1-bromo-2-chloronaphthalene was used instead of 1-chloro-2-iodobenzene in Preparation Example 2. Here, L-Ar may be introduced thereinto instead of Ar.

Preparation Example 7. Preparation of Core of Chemical Formula 8

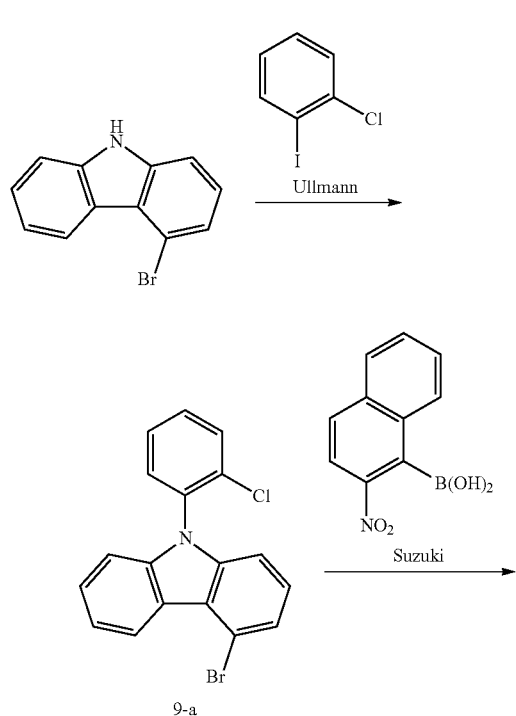

9-a 9-b 9-c

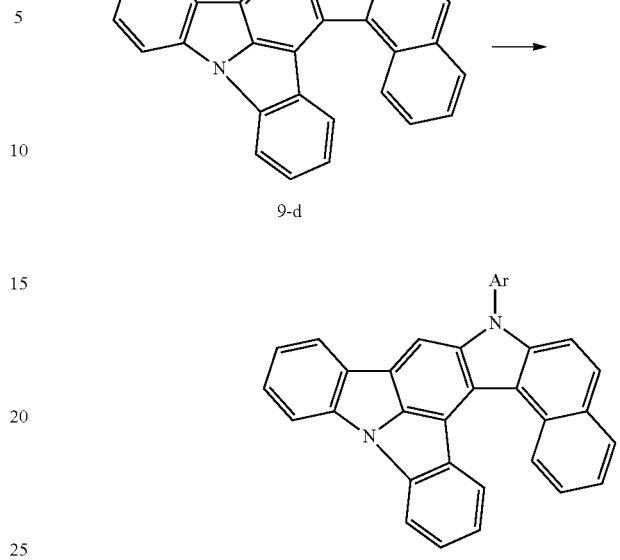

9-d

8

A core of Chemical Formula 8 was prepared by performing the preparation in the same manner as in Preparation Example 1, except that 2-(nitronaphthyl)boronic acid was used instead of 2-(nitrophenyl)boronic acid in Preparation Example 1. Here, L-Ar may be introduced thereinto instead of Ar.

Preparation Example 8. Preparation of Core of Chemical Formula 11

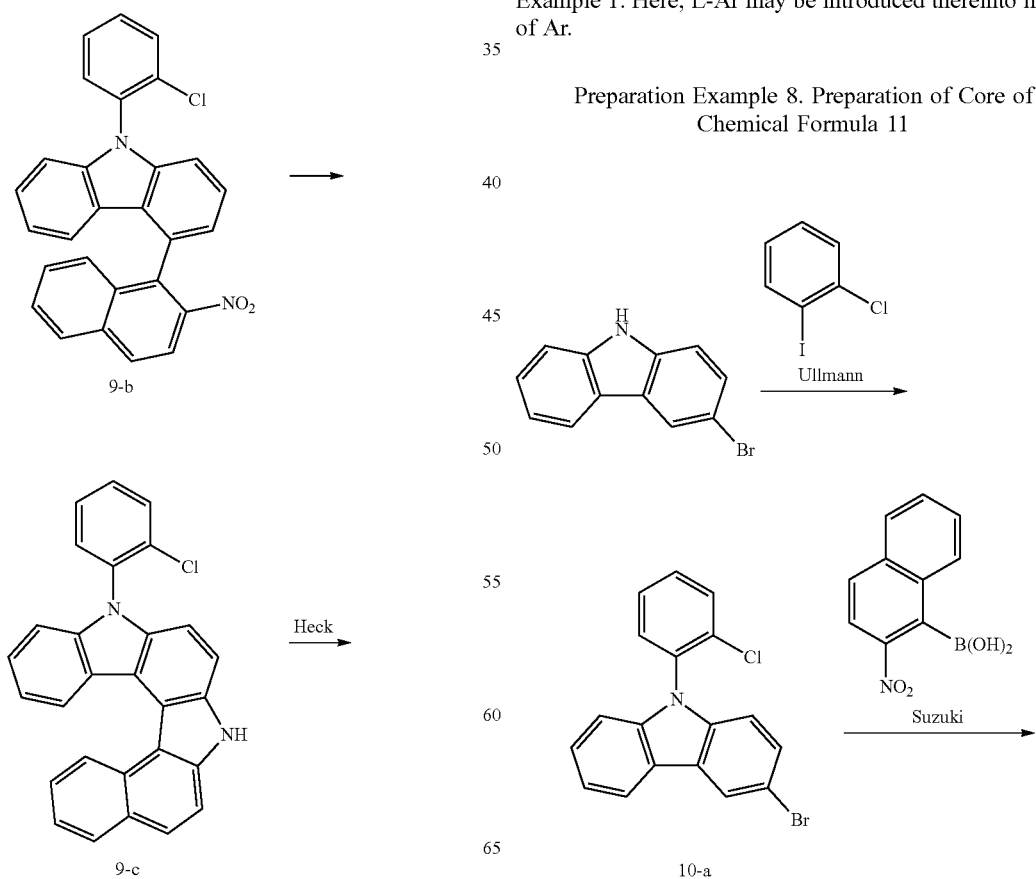

10-a

-continued

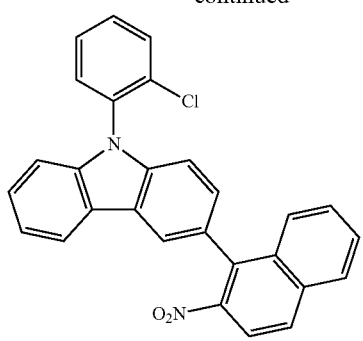

10-b

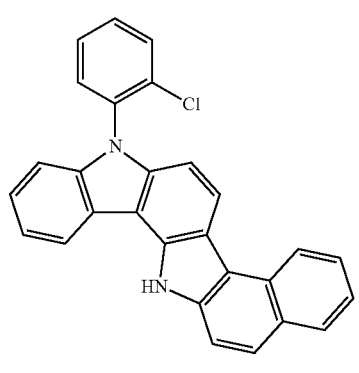

Heck 10-c

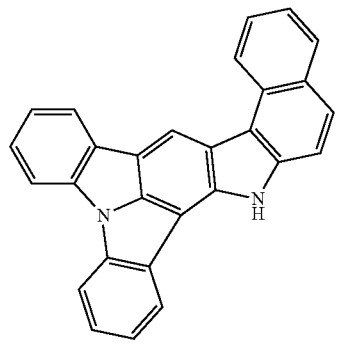

10-d

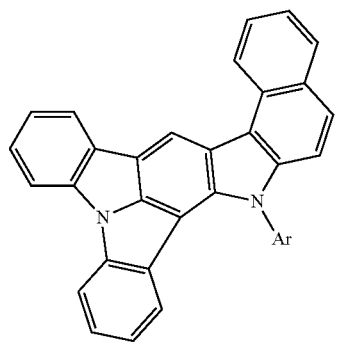

11

A core of Chemical Formula 11 was prepared by performing the preparation in the same manner as in Preparation Example 2, except that 2-(nitronaphthyl)boronic acid was used instead of 2-(nitrophenyl)boronic acid in Preparation Example 2. Here, L-Ar may be introduced thereinto instead of Ar.

Further, in Chemical Formula 1, the compound in the case where adjacent substituents in R1 to R13 combine with each other and are further fused may be prepared by the following General Preparation Examples 1 and 2, but the preparation method is not limited thereto.

In the following structure,

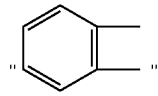

means that a phenyl group is further fused with Chemical Formula 2 or 3.

GENERAL PREPARATION EXAMPLES

General Preparation Example 1

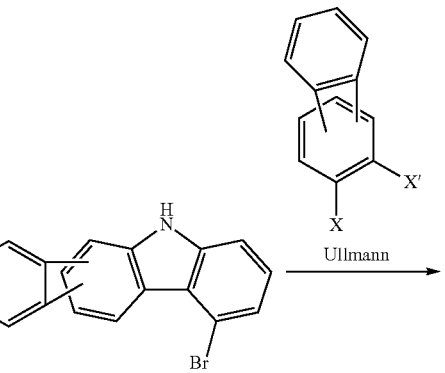

Ullmann

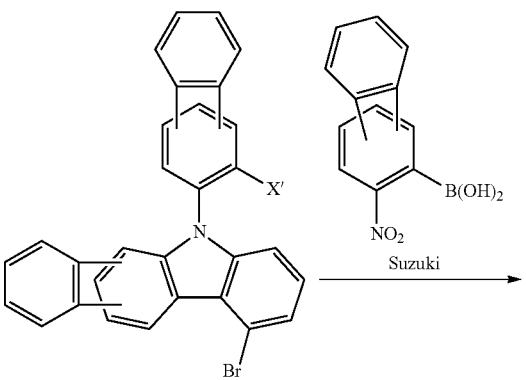

Suzuki

831
-continued
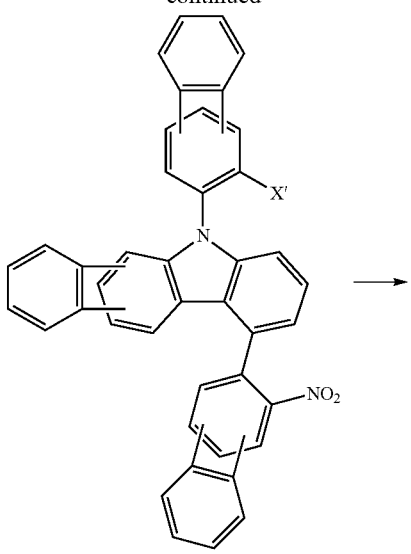
832
-continued
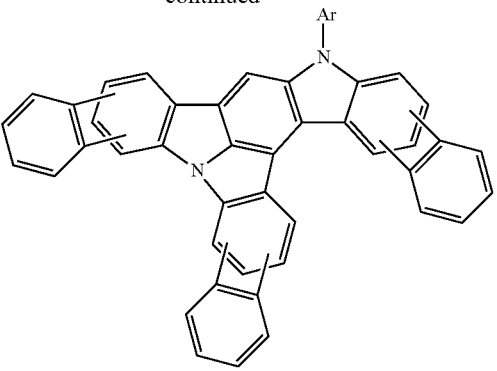
General Preparation Example 2
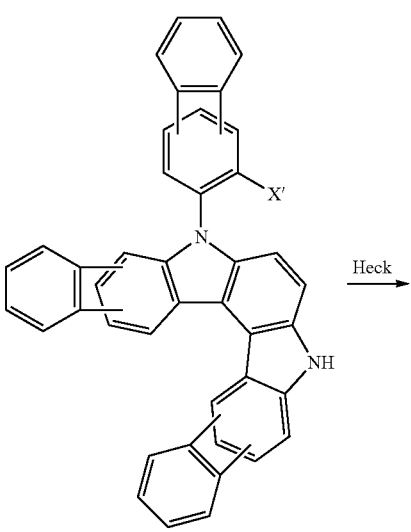
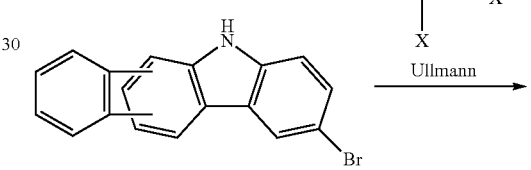
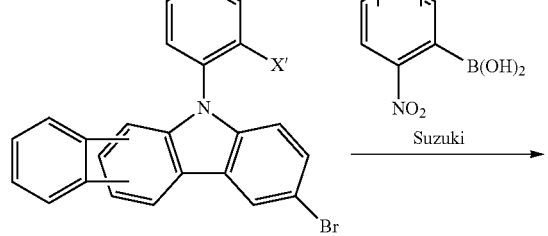
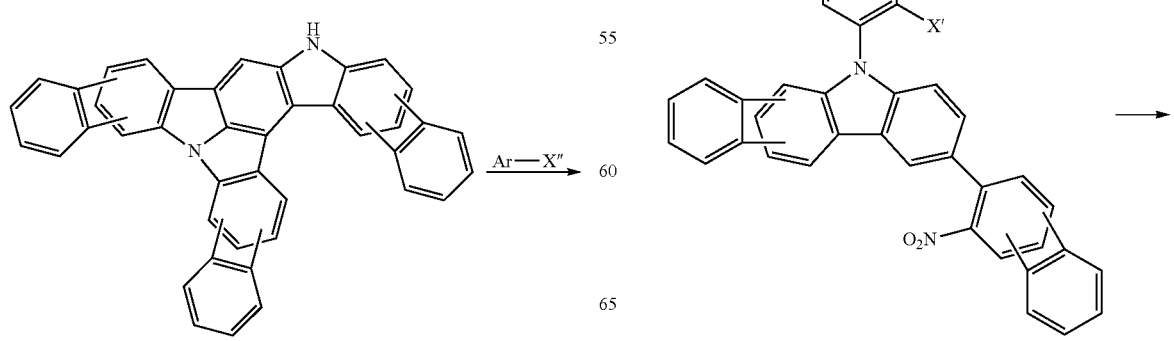

-continued

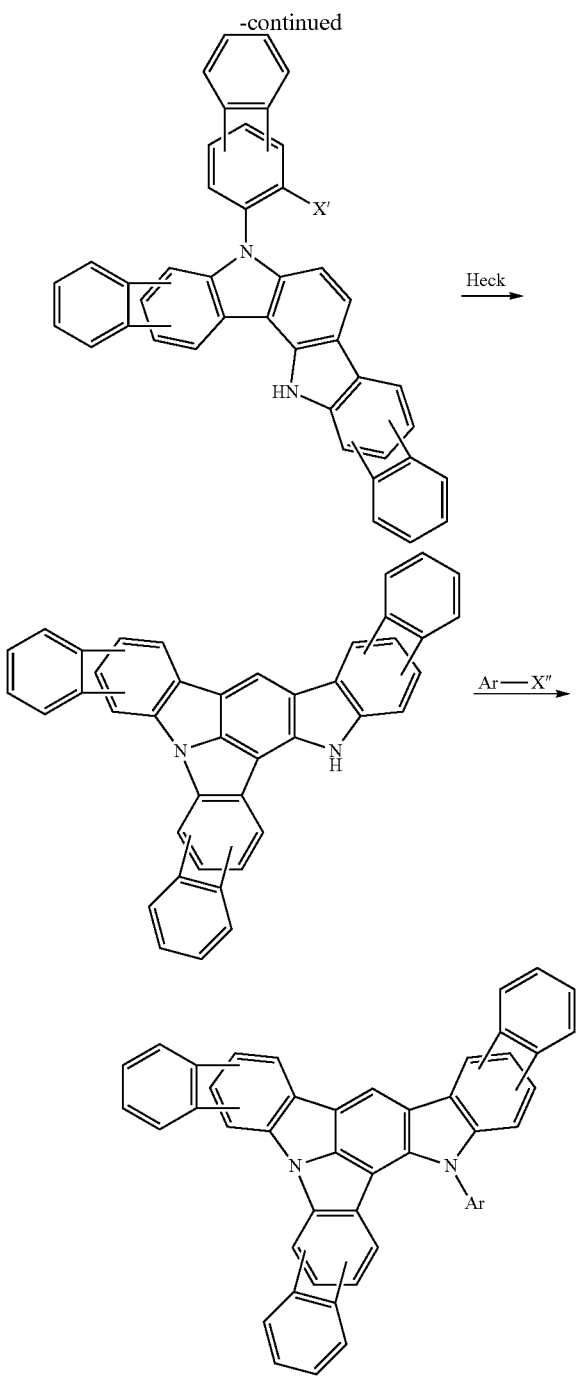

In General Preparation Examples 1 and 2,

X, X', and X" are the same as or different from each other, and each independently a halogen group, and the definition of Ar is the same as that in Chemical Formula 1. In General Preparation Examples, L-Ar may be introduced thereinto instead of Ar.

Further, another exemplary embodiment of the present specification provides an organic light emitting device including the compound represented by Chemical Formula 1.

The organic light emitting device according to an exemplary embodiment of the present specification includes: a first electrode; a second electrode provided to face the first electrode; and one or more organic material layers provided between the first electrode and the second electrode, in which one or more layers of the organic material layers include the compound of Chemical Formula 1.

The organic material layer of the organic light emitting device according to exemplary embodiments of the present specification may be composed of a single-layered structure, but may also be composed of a multi-layered structure in which two or more organic material layers are stacked. For example, the organic light emitting device according to exemplary embodiments of the present specification may have a structure including a hole injection layer, a hole transporting layer, a light emitting layer, an electron transporting layer, an electron injection layer, and the like as organic material layers. However, the structure of the organic light emitting device is not limited thereto, and may include a fewer number of organic layers.

In another exemplary embodiment, the organic material layer includes an electron transporting layer, an electron injection layer, a layer which simultaneously transports and injects electrons, a light emitting layer, a hole transporting layer, a hole injection layer, or a layer which simultaneously transports and injects holes, and the electron transporting layer, the electron injection layer, the layer which simultaneously transports and injects electrons, the light emitting layer, the hole transporting layer, the hole injection layer, or the layer which simultaneously transports and injects holes includes the compound of Chemical Formula 1.

According to an exemplary embodiment of the present specification, the organic material layer includes an electron transporting layer, an electron injection layer, or a layer which simultaneously transports and injects electrons, and the electron transporting layer, the electron injection layer, or the layer which simultaneously transports and injects electrons includes the compound of Chemical Formula 1.

In an exemplary embodiment of the present specification, the light emitting layer includes the compound of Chemical Formula 1.

In an exemplary embodiment of the present specification, the light emitting layer includes the compound of Chemical Formula 1 as a host.

In an exemplary embodiment of the present specification, the light emitting layer including the compound of Chemical Formula 1 may further include a dopant.

As the dopant, those known in the art may be used. For example, a phosphorescent dopant, specifically, an iridium-based complex may be used.

The dopant may be represented by the following compounds, but is not limited thereto.

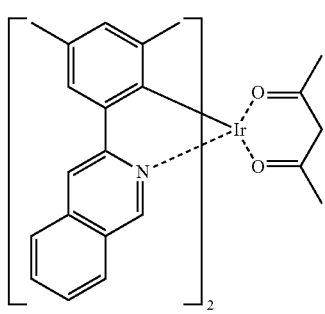

Dp-1

Dp-2
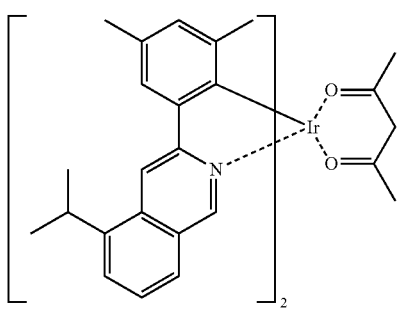
Dp-3
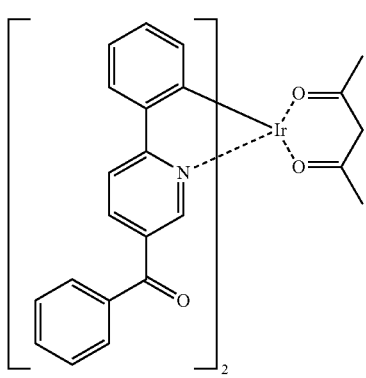
Dp-4
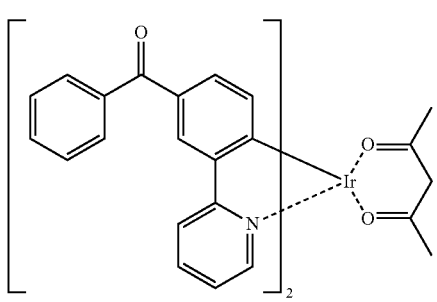
Dp-5
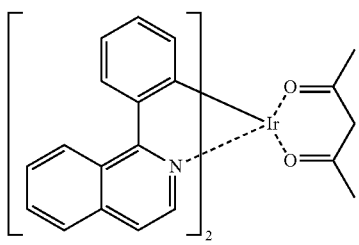
Dp-6
Dp-7
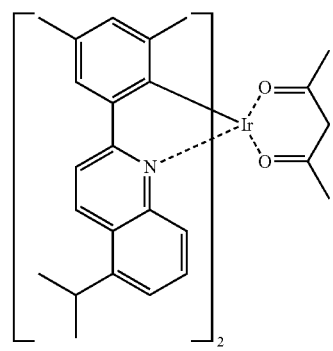
Dp-8
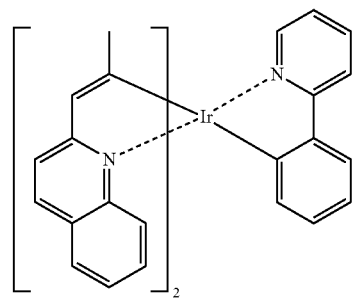
Dp-9
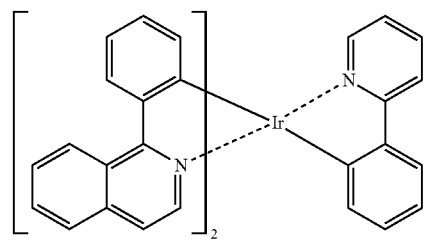
Dp-10
Dp-11
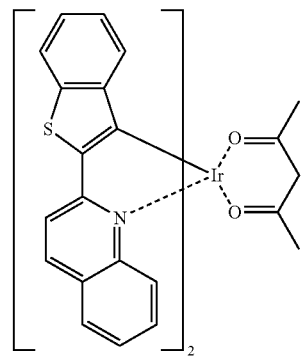

Dp-12 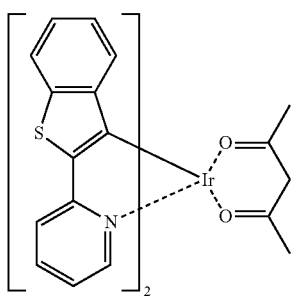
Dp-13 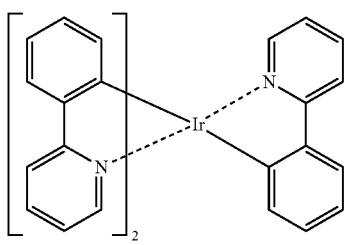
Dp-14 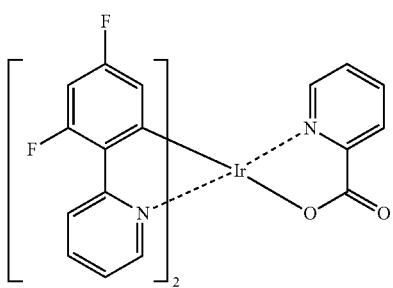
Dp-15 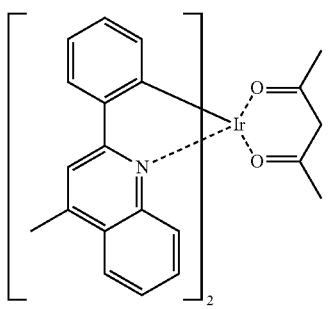
Dp-16 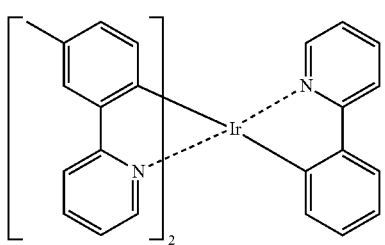
Dp-17 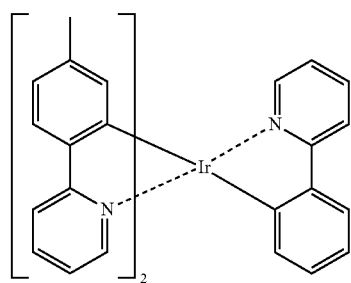
Dp-18 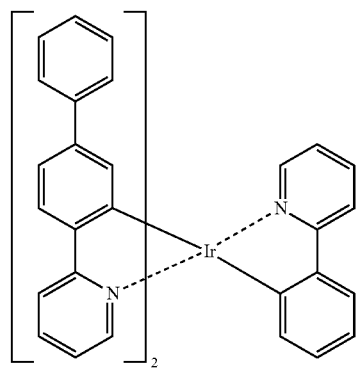
Dp-19 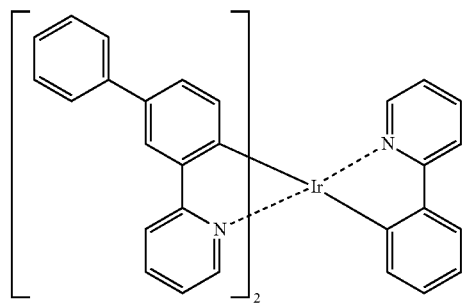
Dp-20 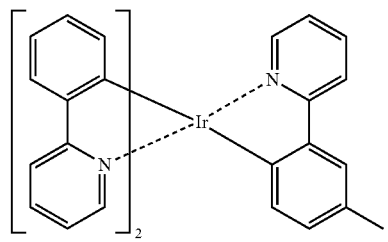
Dp-21 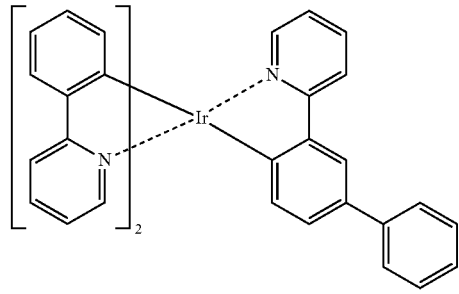

Dp-22 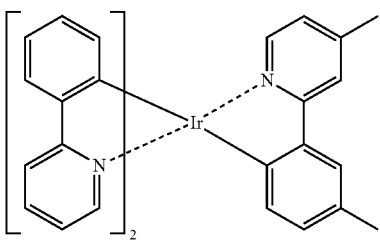

Dp-23 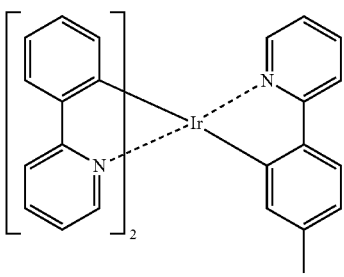

Dp-27 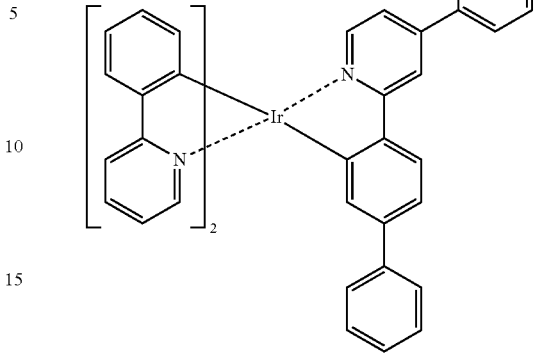

Dp-24 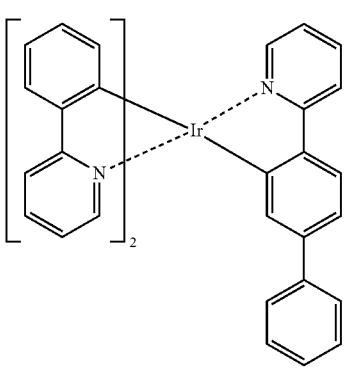

Dp-25 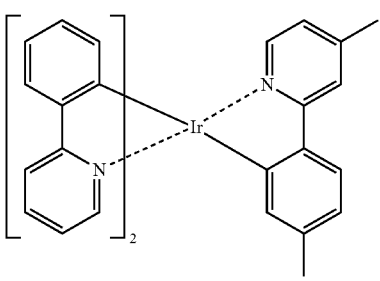

Dp-26 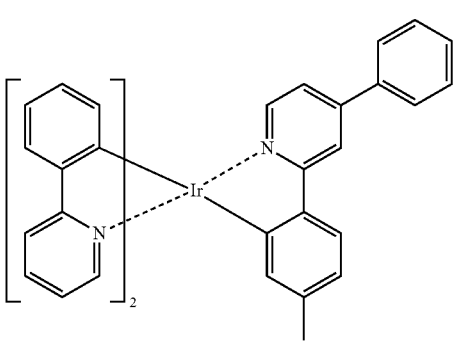

However, the dopant compound is not limited to the examples.

In an exemplary embodiment of the present specification, the organic material layer includes a hole injection layer, a hole transporting layer, or a layer which simultaneously transports and injects holes, and the hole injection layer, the hole transporting layer, or the layer which simultaneously transports and injects holes includes the compound of Chemical Formula 1.

In an exemplary embodiment of the present specification, the organic material layer may further include a hole injection layer or a hole transporting layer, which includes a compound including an arylamino group, a carbazole group, or a benzocarbazole group, in addition to the organic material layer including the compound of Chemical Formula 1.

In an exemplary embodiment of the present specification, the organic material layer including the compound of Chemical Formula 1 may include the compound of Chemical Formula 1 as a host, and may include another organic compound, metal or a metal compound as a dopant.

In another exemplary embodiment, the organic light emitting device may be an organic light emitting device having a structure (normal type) in which a positive electrode, one or more organic material layers, and a negative electrode are sequentially stacked on a substrate.

In still another exemplary embodiment, the organic light emitting device may be an organic light emitting device having a reverse-direction structure (inverted type) in which a negative electrode, one or more organic material layers, and a positive electrode are sequentially stacked on a substrate.

For example, the structure of the organic light emitting device according to the present invention is illustrated in FIGS. 1 to 5.

FIG. 1 illustrates the structure of an organic light emitting device in which a positive electrode 2, a hole injection layer 3, a hole transporting layer 4, a light emitting layer 5, an electron transporting layer 6, and a negative electrode 7 are sequentially stacked on a substrate 1. In the structure as described above, the compound represented by Chemical Formula 1 may be included in the hole injection layer 3, the hole transporting layer 4, the light emitting layer 5, or the electron transporting layer 6.

FIG. 2 illustrates the structure of an organic light emitting device in which a positive electrode 2, a hole injection layer 3, a hole transporting layer 4, a light emitting layer 5, and a negative electrode 7 are sequentially stacked on a substrate 1. In the structure as described above, the compound represented by Chemical Formula 1 may be included in the hole injection layer 3, the hole transporting layer 4, or the light emitting layer 5.

FIG. 3 illustrates the structure of an organic light emitting device in which a positive electrode 2, a hole transporting layer 4, a light emitting layer 5, an electron transporting layer 6, and a negative electrode 7 are sequentially stacked on a substrate 1. In the structure as described above, the compound represented by Chemical Formula 1 may be included in the hole transporting layer 4, the light emitting layer 5, or the electron transporting layer 6.

FIG. 4 illustrates the structure of an organic light emitting device in which a positive electrode 2, a light emitting layer 5, an electron transporting layer 6, and a negative electrode 7 are sequentially stacked on a substrate 1. In the structure as described above, the compound represented by Chemical Formula 1 may be included in the light emitting layer 5 or the electron transporting layer 6.

FIG. 5 illustrates the structure of an organic light emitting device in which a positive electrode 2, a light emitting layer 5, and a negative electrode 7 are sequentially stacked on a substrate 1. In the structure as described above, the compound represented by Chemical Formula 1 may be included in the light emitting layer 5.

When the organic light emitting device includes a plurality of organic material layers, the organic material layers may be formed of the same material or different materials.

The organic light emitting device of the present specification may be manufactured by the materials and methods known in the art, except that one or more layers of the organic material layers include the compound of the present specification, that is, the compound of Chemical Formula 1.

For example, the organic light emitting device of the present specification may be manufactured by sequentially stacking a first electrode, an organic material layer, and a second electrode on a substrate. In this case, the organic light emitting device may be manufactured by depositing a metal or a metal oxide having conductivity, or an alloy thereof on a substrate to form a positive electrode, forming an organic material layer including a hole injection layer, a hole transporting layer, a light emitting layer, and an electron transporting layer thereon, and then depositing a material, which may be used as a negative electrode, thereon, by using a physical vapor deposition (PVD) method such as sputtering or e-beam evaporation. In addition to the method as described above, an organic light emitting device may be made by sequentially depositing a negative electrode material, an organic material layer, and a positive electrode material on a substrate.

Further, the compound of Chemical Formula 1 may be formed as an organic material layer by not only a vacuum deposition method, but also a solution application method when an organic light emitting device is manufactured. Here, the solution application method means spin coating, dip coating, doctor blading, inkjet printing, screen printing, a spray method, roll coating, and the like, but is not limited thereto.

In addition to the method as described above, an organic light emitting device may also be made by sequentially depositing a negative electrode material, an organic material layer, and a positive electrode material on a substrate (International Publication No. 2003/012890). However, the manufacturing method is not limited thereto. In an exemplary embodiment of the present specification, the first electrode is a positive electrode, and the second electrode is a negative electrode.

In another exemplary embodiment, the first electrode is a negative electrode, and the second electrode is a positive electrode.

As the positive electrode material, a material having a large work function is usually preferred so as to smoothly inject holes into an organic material layer. Specific examples of the positive electrode material which may be used in the present invention include: a metal, such as vanadium, chromium, copper, zinc, and gold, or alloys thereof; a metal oxide, such as zinc oxide, indium oxide, indium tin oxide (ITO), and indium zinc oxide (IZO); a combination of metal and oxide, such as ZnO:Al or $SnO_2$:Sb; an electrically conductive polymer, such as poly(3-methylthiophene), poly [3,4-(ethylene-1,2-dioxy)thiophene] (PEDOT), polypyrrole, and polyaniline, and the like, but are not limited thereto.

As the negative electrode material, a material having a small work function is usually preferred so as to smoothly inject electrons into an organic material layer. Specific examples of the negative electrode material include: a metal, such as magnesium, calcium, sodium, potassium, titanium, indium, yttrium, lithium, gadolinium, aluminum, silver, tin, and lead, or alloys thereof; a multi-layered structural material, such as LiF/Al or $LiO_2$/Al, and the like, but are not limited thereto.

The hole injection material is a layer which injects holes from an electrode, and is preferably a compound which has a capability of transporting holes and thus has an effect of injecting holes at a positive electrode and an excellent effect of injecting holes for a light emitting layer or a light emitting material, prevents excitons produced from the light emitting layer from moving to an electron injection layer or an electron injection material, and is also excellent in the ability to form a thin film. It is preferred that the highest occupied molecular orbital (HOMO) of the hole injection material is between the work function of the positive electrode material and the HOMO of a peripheral organic material layer. Specific examples of the hole injection material include metal porphyrin, oligothiophene, an arylamine-based organic material, a hexanitrile hexaazatriphenylene-based organic material, a quinacridone-based organic material, a perylene-based organic material, anthraquinone, a polyaniline and polythiophene-based electrically conductive polymer, and the like, but are not limited thereto.

The hole transporting layer is a layer which receives holes from a hole injection layer and transports holes to a light emitting layer, and a hole transporting material is suitably a material which may receive holes from a positive electrode or a hole injection layer to transfer holes to a light emitting layer, and has a large mobility for the holes. Specific examples thereof include an arylamine-based organic material, an electrically conductive polymer, a block copolymer in which a conjugate portion and a non-conjugate portion are present together, and the like, but are not limited thereto.

The light emitting material is a material which may receive holes and electrons from a hole transporting layer and an electron transporting layer, respectively, and combine the holes and the electrons to emit light in a visible ray region, and is preferably a material having good quantum efficiency to fluorescence or phosphorescence. Specific examples thereof include: a 8-hydroxy-quinoline aluminum complex ($Alq_3$); a carbazole-based compound; a dimerized styryl compound; BAlq; a 10-hydroxybenzoquinoline-metal compound; a benzoxazole, benzthiazole and benzimidazole-based compound; a poly(p-phenylenevinylene) (PPV)-based polymer; a Spiro compound; polyfluorene, lubrene, and the like, but are not limited thereto.

The light emitting layer may include a host material and a dopant material. Examples of the host material include a fused aromatic ring derivative, or a hetero ring-containing compound, and the like. Specific examples of the fused aromatic ring derivative include an anthracene derivative, a pyrene derivative, a naphthalene derivative, a pentacene derivative, a phenanthrene compound, a fluoranthene compound, and the like, and specific examples of the hetero ring-containing compound include a carbazole derivative, a dibenzofuran derivative, a ladder-type furan compound, a pyrimidine derivative, and the like, but the examples thereof are not limited thereto.

Examples of the dopant material include an aromatic amine derivative, a styrylamine compound, a boron complex, a fluoranthene compound, a metal complex, and the like. Specifically, the aromatic amine derivative is a fused aromatic ring derivative having a substituted or unsubstituted arylamino group, and examples thereof include a pyrene, an anthracene, a chrysene, a periflanthene, and the like, which have an arylamino group, and the styrylamine compound is a compound in which a substituted or unsubstituted arylamine is substituted with at least one arylvinyl group, and one or two or more substituents selected from the group consisting of an aryl group, a silyl group, an alkyl group, a cycloalkyl group, and an arylamino group are substituted or unsubstituted. Specific examples thereof include styrylamine, styryldiamine, styryltriamine, styryltetramine, and the like, but are not limited thereto. Further, examples of the metal complex include an iridium complex, a platinum complex, and the like, but are not limited thereto.

The electron transporting material is a material which receives electrons from an electron injection layer and transports the electrons to a light emitting layer, and an electron transporting material is a material which may inject electrons well from a negative electrode and may transfer the electrons to a light emitting layer, and is suitably a material which has large mobility for the electrons. Specific examples thereof include: an Al complex of 8-hydroxyquinoline; a complex including Alq$_3$; an organic radical compound; a hydroxyflavone-metal complex, and the like, but are not limited thereto. The electron transporting layer may be used with any desired cathode material, as used according to the related art. In particular, appropriate examples of the cathode material are a typical material which has a low work function, followed by an aluminum layer or a silver layer. Specific examples thereof include cesium, barium, calcium, ytterbium, and samarium, in each case followed by an aluminum layer or a silver layer.

The electron injection layer is a layer which injects electrons from an electrode, and is preferably a compound which has a capability of transporting electrons, has an effect of injecting electrons from a negative electrode and an excellent effect of injecting electrons into a light emitting layer or a light emitting material, prevents excitons produced from the light emitting layer from moving to a hole injection layer, and is also excellent in the ability to form a thin film. Specific examples thereof include fluorenone, anthraquinodimethane, diphenoquinone, thiopyran dioxide, oxazole, oxadiazole, triazole, imidazole, perylenetetracarboxylic acid, fluorenylidene methane, anthrone, and the like, and derivatives thereof, a metal complex compound, a nitrogen-containing 5-membered ring derivative, and the like, but are not limited thereto.

Examples of the metal complex compound include 8-hydroxyquinolinato lithium, bis(8-hydroxyquinolinato) zinc, bis(8-hydroxyquinolinato) copper, bis(8-hydroxyquinolinato) manganese, tris(8-hydroxyquinolinato) aluminum, tris (2-methyl-8-hydroxyquinolinato) aluminum, tris(8-hydroxyquinolinato) gallium, bis(10-hydroxybenzo[h]quinolinato) beryllium, bis(10-hydroxybenzo[h]quinolinato) zinc, bis(2-methyl-8-quinolinato) chlorogallium, bis(2-methyl-8-quinolinato) (o-cresolato) gallium, bis(2-methyl-8-quinolinato) (1-naphtholato) aluminum, bis(2-methyl-8-quinolinato) (2-naphtholato) gallium, and the like, but are not limited thereto.

The organic light emitting device according to the present specification may be a top emission type, a bottom emission type, or a dual emission type according to the material to be used.

Hereinafter, the present invention will be described in more detail through the Examples. However, the following Examples are only to exemplify the present invention, but do not intend to limit the scope of the present invention.

SYNTHESIS EXAMPLES

Synthesis Example 1. Synthesis of Chemical Formula 1-d-1

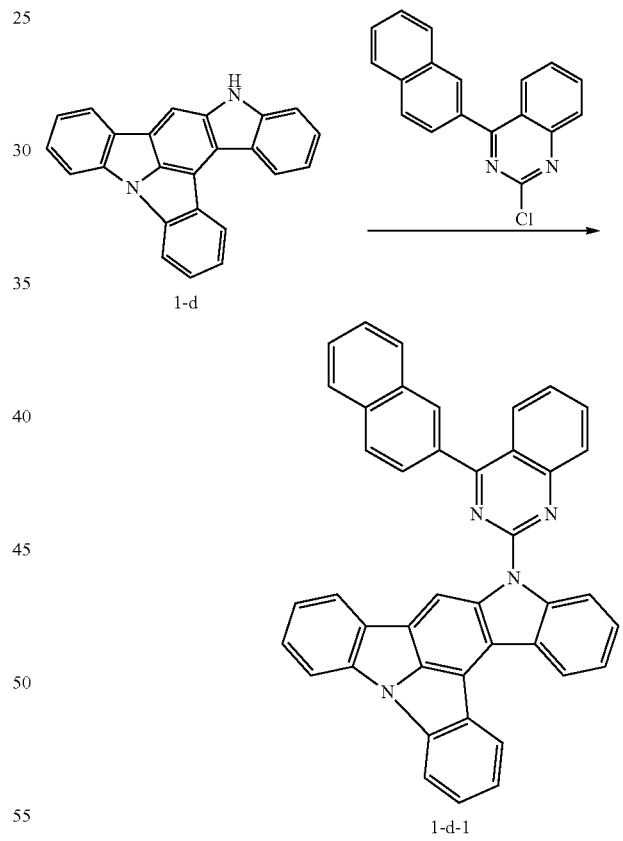

10.00 g (30.29 mmol, 1.0 eq) of Chemical Formula 1-d, 9.66 g (33.32 mmol, 1.1 eq) of 2-chloro-4-(naphthalen-2-yl)quinazoline, 19.29 g (90.88 mmol, 3 eq) of K$_3$PO$_4$, and 0.08 g (0.15 mmol, 0.005 eq) of Pd(t-Bu$_3$P)$_2$ were dissolved in 80 ml of xylene, and stirred under reflux. When the reaction was terminated, the resulting product was placed under reduced pressure to remove the solvent. Thereafter, the product was completely dissolved in CHCl$_3$, washed with water, and again placed under reduced pressure to remove the solvent, and the resulting product was subjected to column chromatography to obtain 14.09 g (26.66 mmol, yield 82%) of Chemical Formula 1-d-1.

LC/MS: m/z=584 [(M+1)$^+$]

The 2-chloro-4-(naphthalen-2-yl)quinazoline was synthesized through a Suzuki coupling reaction with naphthalene-2-ylboronic acid by using 2,4-dichloroquinazoline as a starting material.

Synthesis Example 2. Synthesis of Chemical Formula 1-d-2

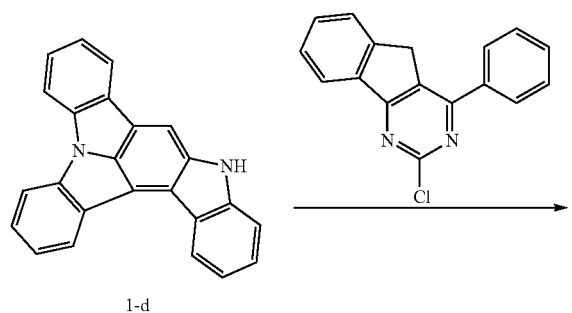

1-d

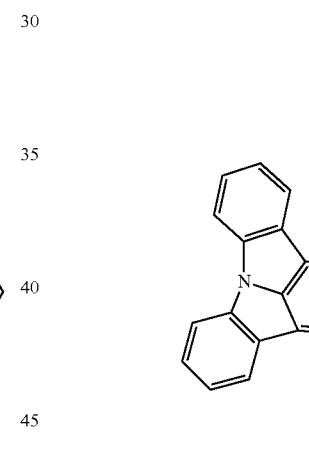

1-d-2

Synthesis Example 3. Synthesis of Chemical Formula 1-d-3

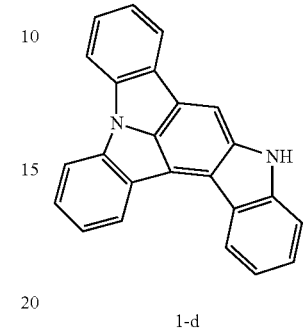

1-d

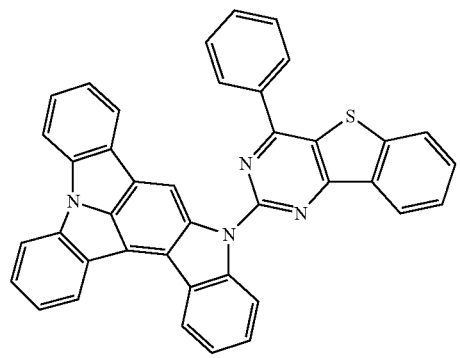

1-d-3

10.00 g (30.29 mmol, 1.0 eq) of Chemical Formula 1-d, 9.35 g (33.32 mmol, 1.1 eq) of 2-chloro-4-phenylbenzofuro[3,2-d]pyrimidine, 19.29 g (90.88 mmol, 3 eq) of K$_3$PO$_4$, and 0.07 g (0.15 mmol, 0.005 eq) of Pd(t-Bu$_3$P)$_2$ were dissolved in 80 ml of xylene, and stirred under reflux. When the reaction was terminated, the resulting product was placed under reduced pressure to remove the solvent. Thereafter, the product was completely dissolved in CHCl$_3$, washed with water, and again placed under reduced pressure to remove the solvent, and the resulting product was subjected to column chromatography to obtain 13.05 g (22.71 mmol, yield 75%) of Chemical Formula 1-d-2.

LC/MS: m/z=574 [(M+1)$^+$]

The 2-chloro-4-phenylbenzofuro[3,2-d]pyrimidine was synthesized through a Suzuki coupling reaction with phenyl boronic acid by using 2,4-dichlorobenzofuro[3,2-d]pyrimidine as a starting material.

10.00 g (30.29 mmol, 1.0 eq) of Chemical Formula 1-d, 9.88 g (33.32 mmol, 1.1 eq) of 2-chloro-4-phenylbenzo[4,5]thieno[3,2-d]pyrimidine, 19.29 g (90.88 mmol, 3 eq) of K$_3$PO$_4$, and 0.07 g (0.15 mmol, 0.005 eq) of Pd(t-Bu$_3$P)$_2$ were dissolved in 80 ml of xylene, and stirred under reflux. When the reaction was terminated, the resulting product was placed under reduced pressure to remove the solvent. Thereafter, the product was completely dissolved in CHCl$_3$, washed with water, and again placed under reduced pressure to remove the solvent, and the resulting product was subjected to column chromatography to obtain 13.77 g (23.32 mmol, yield 77%) of Chemical Formula 1-d-3.

LC/MS: m/z=590 [(M+1)$^+$]

The 2-chloro-4-phenylbenzo[4,5]thieno[3,2-d]pyrimidine was synthesized through a Suzuki coupling reaction with phenyl boronic acid by using 2,4-dichlorobenzothieno[3,2-d]pyrimidine as a starting material.

Synthesis Example 4. Synthesis of Chemical Formula 1-d-4

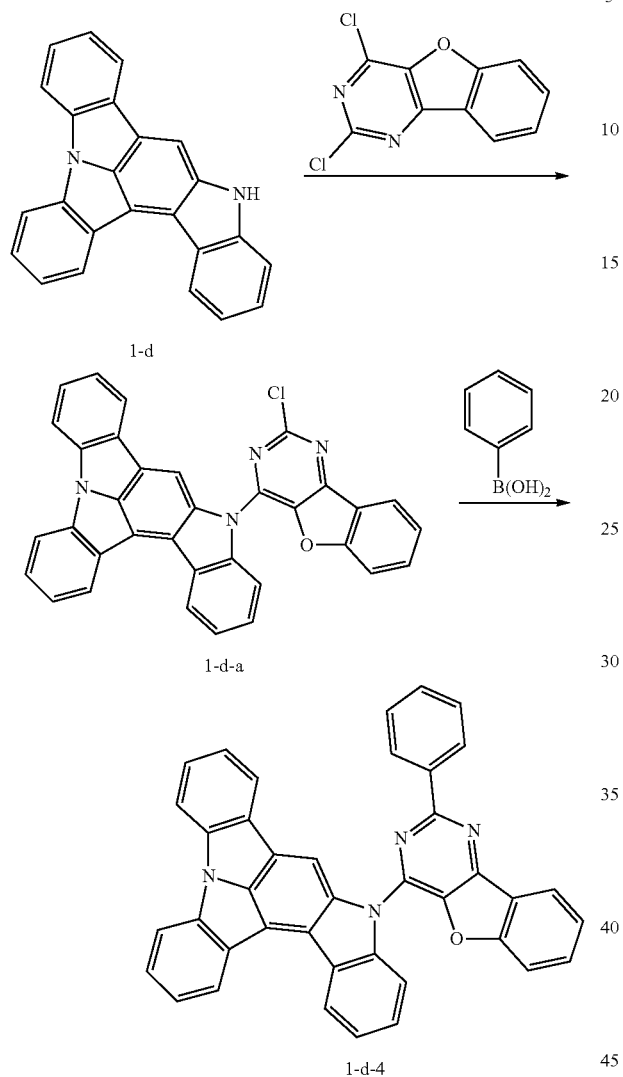

10.00 g (30.29 mmol, 1.0 eq) of Chemical Formula 1-d, 7.24 g (30.29 mmol, 1.0 eq) of 2,4-dichlorobenzofuro[3,2-d]pyrimidine, and 6.43 g (30.29 mmol, 1.0 eq) of $K_3PO_4$ were dissolved in 80 ml of THF, and stirred under reflux. When the reaction was terminated, the resulting product was placed under reduced pressure to remove the solvent. Thereafter, the product was completely dissolved in $CHCl_3$, washed with water, and again placed under reduced pressure to remove the solvent, and the resulting product was subjected to column chromatography to obtain 13.72 g (25.75 mmol, yield 85%) of Chemical Formula 1-d-a.

LC/MS: m/z=532 [(M+1)$^+$]

13.72 g (25.75 mmol, 1.0 eq) of Chemical Formula 1-d-a, 3.76 g (30.88 mmol, 1.2 eq) of phenyl boronic acid, 0.05 g (0.25 mmol, 0.01 eq) of Pd(PPh$_3$)$_4$, and 7.11 g (51.48 mmol, 2.0 eq) of $K_2CO_3$ were dissolved in 30 ml of water, the resulting solution was added thereto, and the resulting mixture was dissolved in 70 ml of dioxane and stirred under reflux. When the reaction was terminated, the organic layer was separated and then placed under reduced pressure to remove the solvent. Thereafter, the product was completely dissolved in $CHCl_3$, washed with water, and again placed under reduced pressure to remove the solvent, and the resulting product was subjected to column chromatography to obtain 13.46 g (23.42 mmol, yield 91%) of Chemical Formula 1-d-4.]

LC/MS: m/z=574 [(M+1)$^+$]

Synthesis Example 5. Synthesis of Chemical Formula 1-d-5

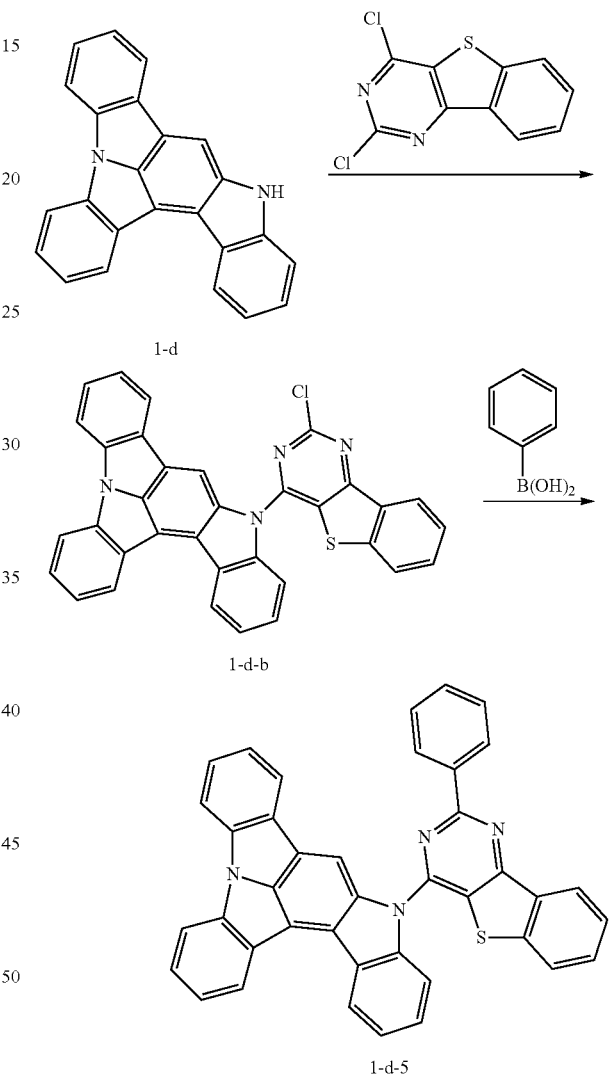

10.00 g (30.29 mmol, 1.0 eq) of Chemical Formula 1-d, 7.72 g (30.29 mmol, 1.0 eq) of dichlorobenzo[4,5]thieno[3,2-d]pyrimidine, and 6.43 g (30.29 mmol, 1.0 eq) of $K_3PO_4$ were dissolved in 80 ml of THF, and stirred under reflux. When the reaction was terminated, the resulting product was placed under reduced pressure to remove the solvent. Thereafter, the product was completely dissolved in $CHCl_3$, washed with water, and again placed under reduced pressure to remove the solvent, and the resulting product was subjected to column chromatography to obtain 13.80 g (25.14 mmol, yield 83%) of Chemical Formula 1-d-b.

LC/MS: m/z=548 [(M+1)$^+$]

13.80 g (25.14 mmol, 1.0 eq) of Chemical Formula 1-d-b, 3.67 g (30.16 mmol, 1.2 eq) of phenyl boronic acid, 0.05 g (0.25 mmol, 0.01 eq) of Pd(PPh$_3$)$_4$, and 6.94 g (50.26 mmol, 2.0 eq) of K$_2$CO$_3$ were dissolved in 30 ml of water, the resulting solution was added thereto, and the resulting mixture was dissolved in 70 ml of dioxane and stirred under reflux. When the reaction was terminated, the organic layer was separated and then placed under reduced pressure to remove the solvent. Thereafter, the product was completely dissolved in CHCl$_3$, washed with water, and again placed under reduced pressure to remove the solvent, and the resulting product was subjected to column chromatography to obtain 13.51 g (22.87 mmol, yield 88%) of Chemical Formula 1-d-5.

LC/MS: m/z=590 [(M+1)$^+$]

Synthesis Example 6. Synthesis of Chemical Formula 1-d-6

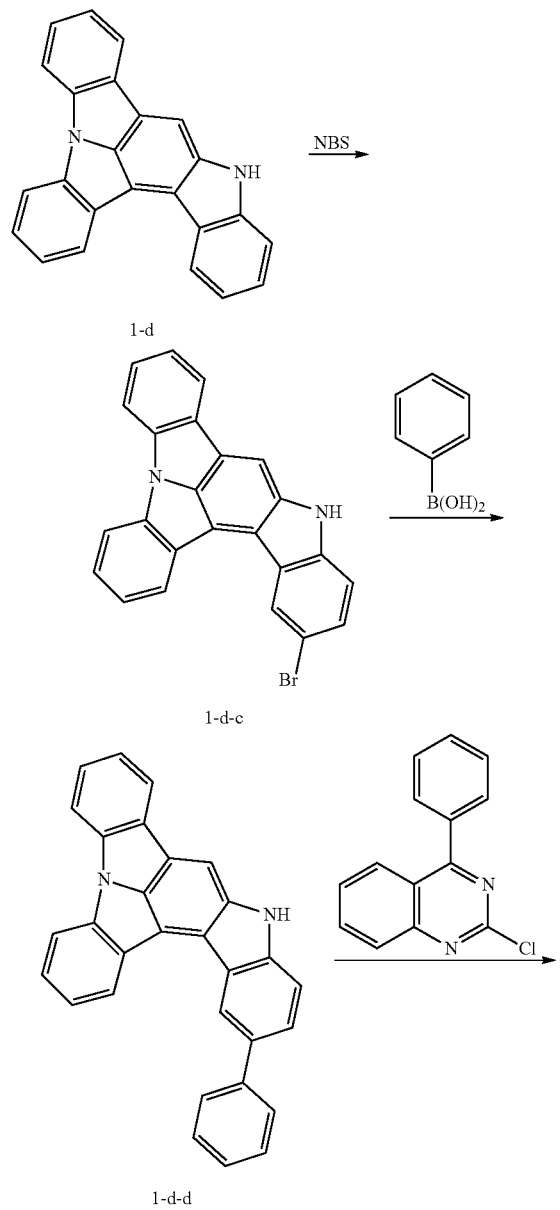

-continued

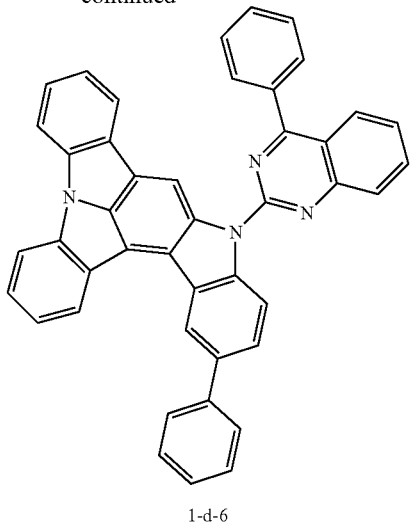

1-d-6

While 50.00 g (151.34 mmol, 1.0 eq) of Chemical Formula 1-d was dissolved in 700 ml of DMF, 26.93 g (151.34 mmol, 1.0 eq) of NBS was slowly added dropwise thereto. After the reaction was terminated, the reaction product was poured into 3 L of water and crystals were dropped thereto to filter the resulting product. The filtered product was completely dissolved in ethyl acetate, washed with water, and again placed under reduced pressure to remove about half of the amount of the solvent, and recrystallization was performed while adding ethanol thereto to obtain 52.64 g (128.64 mmol, yield 85%) of Chemical Formula 1-d-c.

LC/MS: m/z=408 [(M+1)$^+$]

52.64 g (128.64 mmol, 1.0 eq) of Chemical Formula 1-d-c, 18.82 g (154.33 mmol, 1.2 eq) of phenyl boronic acid, 0.27 g (1.28 mmol, 0.01 eq) of Pd(PPh$_3$)$_4$, and 35.54 g (257.22 mmol, 2.0 eq) of K$_2$CO$_3$ were dissolved in 150 ml of water and the resulting solution was added thereto, and the resulting mixture was dissolved in 300 ml of dioxane and stirred under reflux. When the reaction was terminated, the organic layer was separated and then placed under reduced pressure to remove the solvent. Thereafter, the product was completely dissolved in CHCl$_3$, washed with water, and again placed under reduced pressure to remove the solvent, and the resulting product was subjected to column chromatography to obtain 47.57 g (117.03 mmol, yield 91%) of Chemical Formula 1-d-d.

LC/MS: m/z=406 [(M+1)$^+$]

10.00 g (24.60 mmol, 1.0 eq) of Chemical Formula 1-d-d, 7.59 g (27.06 mmol, 1.1 eq) of 2-chloro-4-quinazoline, 17.64 g (17.64 mmol, 3 eq) of K$_3$PO$_4$, and 0.06 g (0.12 mmol, 0.005 eq) of Pd(t-Bu$_3$P)$_2$ were dissolved in 80 ml of xylene, and stirred under reflux. When the reaction was terminated, the resulting product was placed under reduced pressure to remove the solvent. Thereafter, the product was completely dissolved in CHCl$_3$, washed with water, and again placed under reduced pressure to remove the solvent, and the resulting product was subjected to column chromatography to obtain 11.26 g (18.45 mmol, yield 75%) of Chemical Formula 1-d-6.

LC/MS: m/z=610 [(M+1)$^+$]

Synthesis Example 7. Synthesis of Chemical Formula 1-d-7

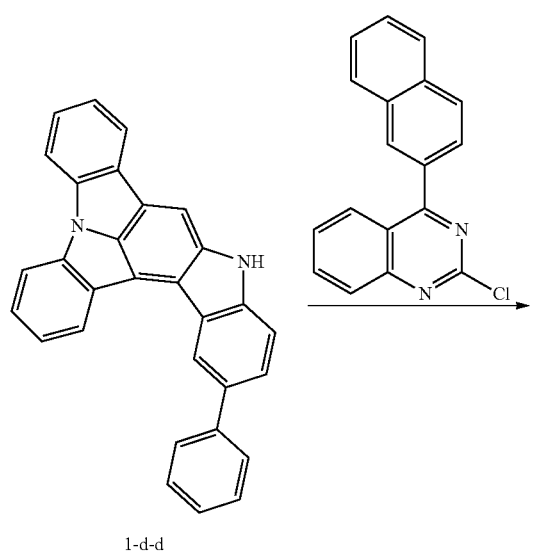

1-d-d 1-d-7

10.00 g (24.60 mmol, 1.0 eq) of Chemical Formula 1-d-d, 7.86 g (27.06 mmol, 1.1 eq) of 2-chloro-4-(naphthalen-2-yl)quinazoline, 17.64 g (17.64 mmol, 3 eq) of $K_3PO_4$, and 0.06 g (0.12 mmol, 0.005 eq) of $Pd(t-Bu_3P)_2$ were dissolved in 80 ml of xylene, and stirred under reflux. When the reaction was terminated, the resulting product was placed under reduced pressure to remove the solvent. Thereafter, the product was completely dissolved in $CHCl_3$, washed with water, and again placed under reduced pressure to remove the solvent, and the resulting product was subjected to column chromatography to obtain 12.51 g (18.94 mmol, yield 77%) of Chemical Formula 1-d-10.

LC/MS: m/z=660 [(M+1)$^+$]

Synthesis Example 8. Synthesis of Chemical Formula 1-d-8

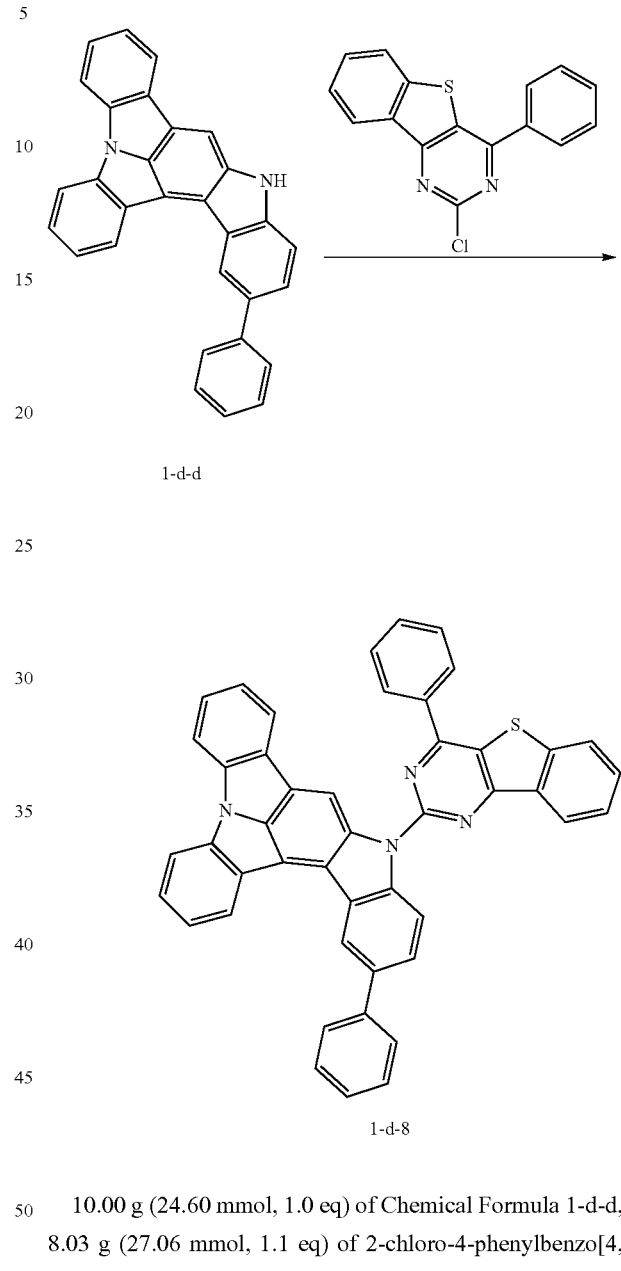

1-d-d 1-d-8

10.00 g (24.60 mmol, 1.0 eq) of Chemical Formula 1-d-d, 8.03 g (27.06 mmol, 1.1 eq) of 2-chloro-4-phenylbenzo[4,5]thieno[3,2-d]pyrimidine, 17.64 g (73.80 mmol, 3 eq) of $K_3PO_4$, and 0.06 g (0.12 mmol, 0.005 eq) of $Pd(t-Bu_3P)_2$ were dissolved in 80 ml of xylene, and stirred under reflux. When the reaction was terminated, the resulting product was placed under reduced pressure to remove the solvent. Thereafter, the product was completely dissolved in $CHCl_3$, washed with water, and again placed under reduced pressure to remove the solvent, and the resulting product was subjected to column chromatography to obtain 11.81 g (17.71 mmol, yield 72%) of Chemical Formula 1-d-8.

LC/MS: m/z=666 [(M+1)$^+$]

Synthesis Example 9. Synthesis of Chemical Formula 1-d-9

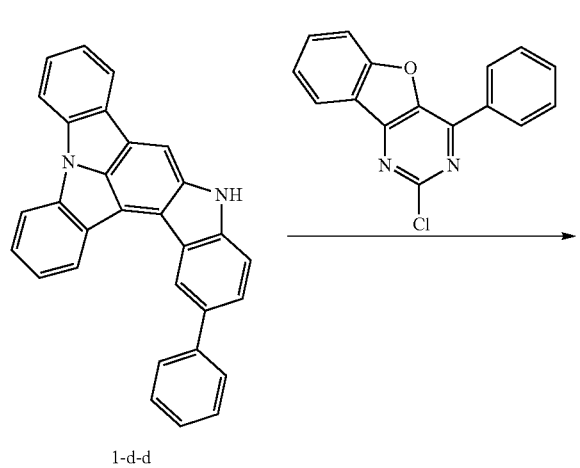

1-d-d

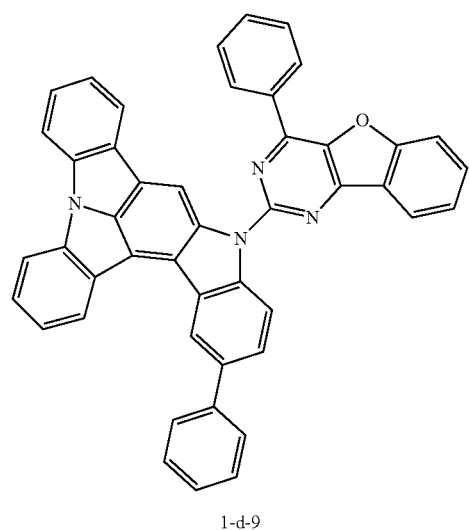

1-d-9

10.00 g (24.60 mmol, 1.0 eq) of Chemical Formula 1-d-d, 7.59 g (27.06 mmol, 1.1 eq) of 2-chloro-4-phenylbenzofuro[3,2-d]pyrimidine, 17.64 g (73.80 mmol, 3 eq) of $K_3PO_4$, and 0.06 g (0.12 mmol, 0.005 eq) of $Pd(t-Bu_3P)_2$ were dissolved in 80 ml of xylene, and stirred under reflux. When the reaction was terminated, the resulting product was placed under reduced pressure to remove the solvent. Thereafter, the product was completely dissolved in $CHCl_3$, washed with water, and again placed under reduced pressure to remove the solvent, and the resulting product was subjected to column chromatography to obtain 12.01 g (18.45 mmol, yield 75%) of Chemical Formula 1-d-9.

LC/MS: m/z=650 [(M+1)$^+$]

Synthesis Example 10. Synthesis of Chemical Formula 2-d-1

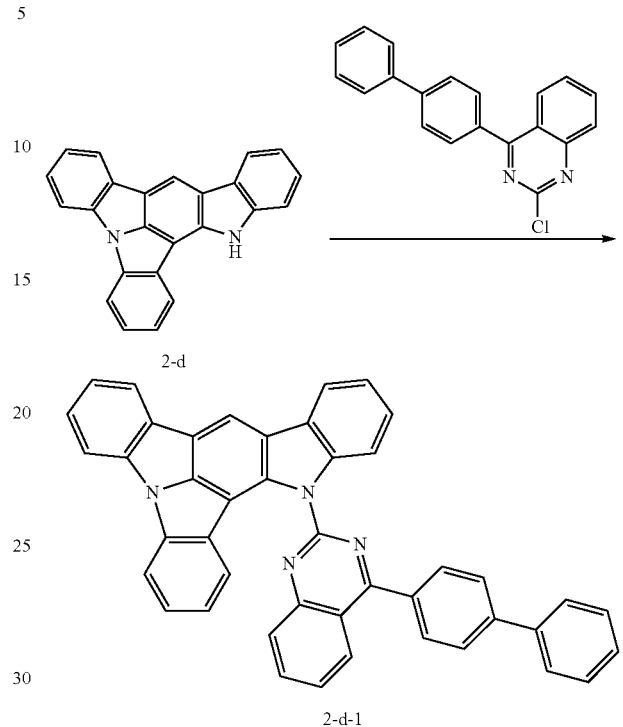

2-d-1

10.00 g (30.29 mmol, 1.0 eq) of Chemical Formula 2-d, 10.53 g (33.32 mmol, 1.1 eq) of 4-([1,1'-biphenyl]-4-yl)-2-chloroquinazoline, 19.29 g (90.88 mmol, 3 eq) of $K_3PO_4$, and 0.08 g (0.15 mmol, 0.005 eq) of $Pd(t-Bu_3P)_2$ were dissolved in 80 ml of xylene, and stirred under reflux. When the reaction was terminated, the resulting product was placed under reduced pressure to remove the solvent. Thereafter, the product was completely dissolved in $CHCl_3$, washed with water, and again placed under reduced pressure to remove the solvent, and the resulting product was subjected to column chromatography to obtain 14.88 g (24.23 mmol, yield 80%) of Chemical Formula 2-d-1. 1H NMR spectrum of the compound of Chemical Formula 2-d-1 is illustrated in FIG. 7.

LC/MS: m/z=610 [(M+1)$^+$]

Synthesis Example 11. Synthesis of Chemical Formula 2-d-2

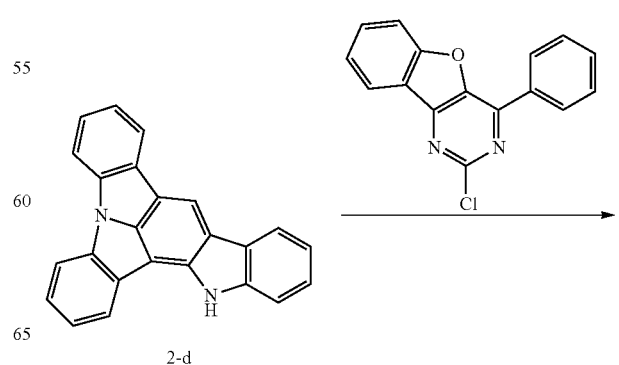

2-d

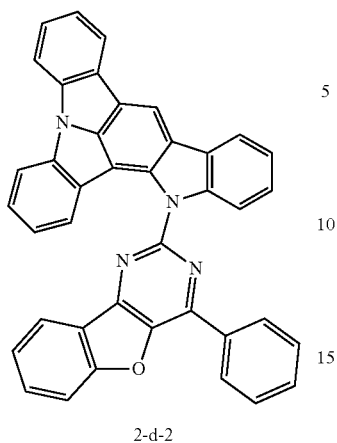

2-d-2

10.00 g (30.29 mmol, 1.0 eq) of Chemical Formula 2-d, 9.35 g (33.32 mmol, 1.1 eq) of 2-chloro-4-phenylbenzofuro[3,2-d]pyrimidine, 19.29 g (90.88 mmol, 3 eq) of $K_3PO_4$, and 0.08 g (0.15 mmol, 0.005 eq) of $Pd(t-Bu_3P)_2$ were dissolved in 80 ml of xylene, and stirred under reflux. When the reaction was terminated, the resulting product was placed under reduced pressure to remove the solvent. Thereafter, the product was completely dissolved in $CHCl_3$, washed with water, and again placed under reduced pressure to remove the solvent, and the resulting product was subjected to column chromatography to obtain 13.92 g (24.23 mmol, yield 80%) of Chemical Formula 2-d-2.

LC/MS: m/z=574 [(M+1)$^+$]

Synthesis Example 12. Synthesis of Chemical Formula 2-d-3

2-d-3

10.00 g (30.29 mmol, 1.0 eq) of Chemical Formula 2-d, 11.88 g (33.32 mmol, 1.1 eq) of 2-(4-chlorophenyl)-4-phenylbenzofuro[3,2-d]pyrimidine, 8.73 g (90.87 mmol, 3 eq) of sodium tert-butoxide, and 0.08 g (0.15 mmol, 0.005 eq) of $Pd(t-Bu_3P)_2$ were dissolved in 80 ml of xylene, and stirred under reflux. When the reaction was terminated, the resulting product was placed under reduced pressure to remove the solvent. Thereafter, the product was completely dissolved in $CHCl_3$, washed with water, and again placed under reduced pressure to remove the solvent, and the resulting product was subjected to column chromatography to obtain 15.17 g (23.32 mmol, yield 77%) of Chemical Formula 2-d-3.

LC/MS: m/z=650 [(M+1)$^+$]

Synthesis Example 13. Synthesis of Chemical Formula 2-d-4

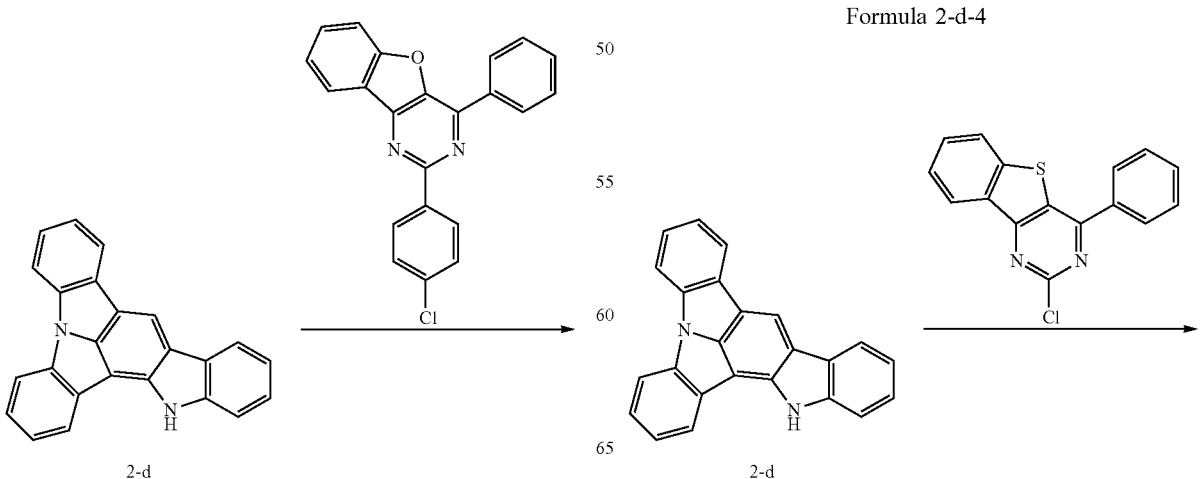

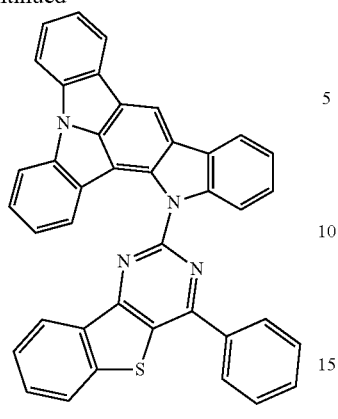

2-d-4

10.00 g (30.29 mmol, 1.0 eq) of Chemical Formula 2-d, 9.89 g (33.32 mmol, 1.1 eq) of 2-chloro-4-phenylbenzo[4,5]thieno[3,2-d]pyrimidine, 19.29 g (90.88 mmol, 3 eq) of $K_3PO_4$, and 0.08 g (0.15 mmol, 0.005 eq) of $Pd(t-Bu_3P)_2$ were dissolved in 80 ml of xylene, and stirred under reflux. When the reaction was terminated, the resulting product was placed under reduced pressure to remove the solvent. Thereafter, the product was completely dissolved in $CHCl_3$, washed with water, and again placed under reduced pressure to remove the solvent, and the resulting product was subjected to column chromatography to obtain 14.31 g (24.23 mmol, yield 80%) of Chemical Formula 2-d-4.

LC/MS: m/z=590 [(M+1)⁺]

Synthesis Example 14. Synthesis of Chemical Formula 2-d-5

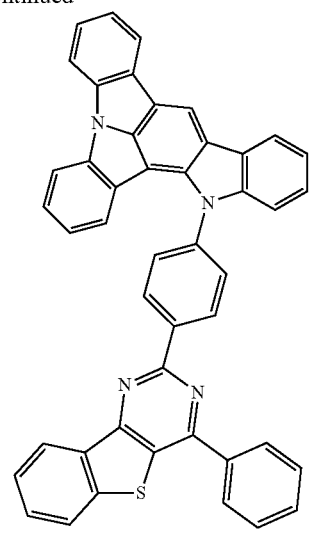

2-d-5

10.00 g (30.29 mmol, 1.0 eq) of Chemical Formula 2-d, 12.42 g (33.32 mmol, 1.1 eq) of 2-(4-chlorophenyl)-4-phenylbenzo[4,5]thieno[3,2-d]pyrimidine, 8.73 g (90.87 mmol, 3 eq) of sodium tert-butoxide, and 0.08 g (0.15 mmol, 0.005 eq) of $Pd(t-Bu_3P)_2$ were dissolved in 80 ml of xylene, and stirred under reflux. When the reaction was terminated, the resulting product was placed under reduced pressure to remove the solvent. Thereafter, the product was completely dissolved in $CHCl_3$, washed with water, and again placed under reduced pressure to remove the solvent, and the resulting product was subjected to column chromatography to obtain 14.95 g (22.41 mmol, yield 74%) of Chemical Formula 2-d-5.

LC/MS: m/z=666 [(M+1)⁺]

Synthesis Example 15. Synthesis of Chemical Formula 2-d-6

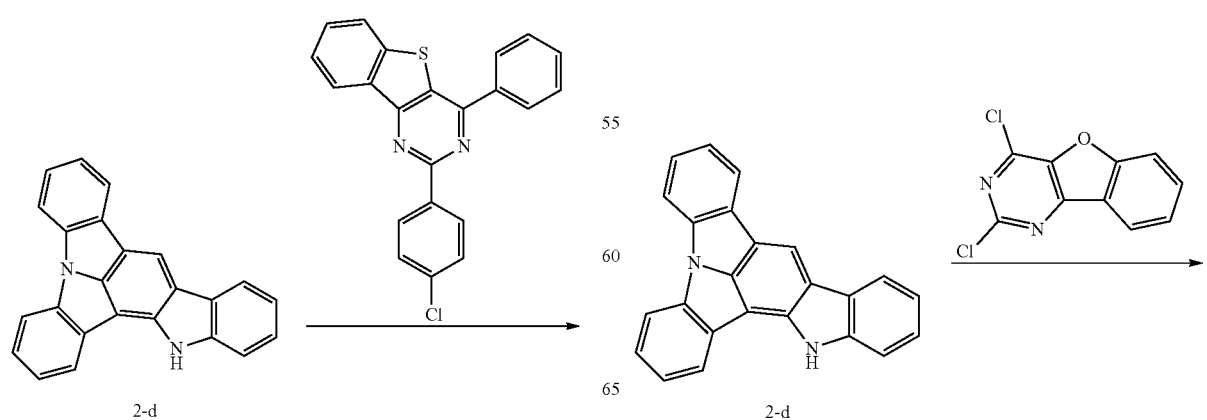

859
-continued

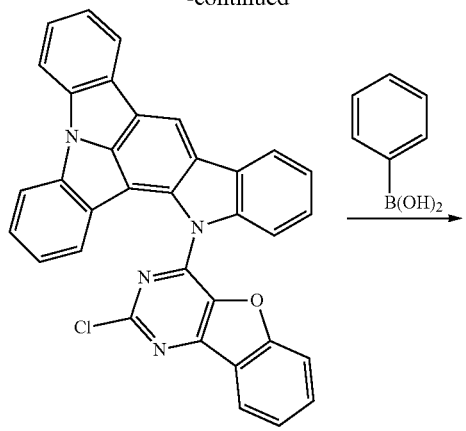

2-d-a

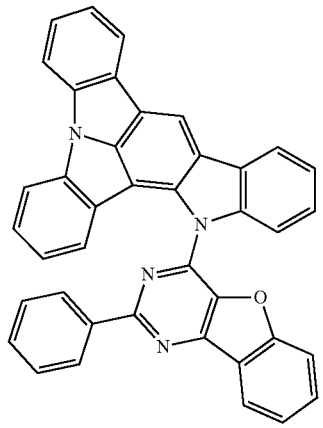

2-d-6

10.00 g (30.29 mmol, 1.0 eq) of Chemical Formula 2-d, 7.24 g (30.29 mmol, 1.0 eq) of 2,4-dichlorobenzofuro[3,2-d]pyrimidine, and 6.43 g (30.29 mmol, 1.0 eq) of $K_3PO_4$ were dissolved in 80 ml of THF, and stirred under reflux. When the reaction was terminated, the resulting product was placed under reduced pressure to remove the solvent. Thereafter, the product was completely dissolved in $CHCl_3$, washed with water, and again placed under reduced pressure to remove the solvent, and the resulting product was subjected to column chromatography to obtain 14.31 g (26.84 mmol, yield 80%) of Chemical Formula 2-d-a.

LC/MS: m/z=532 [(M+1)$^+$]

14.31 g (26.84 mmol, 1.0 eq) of Chemical Formula 2-d-a, 3.92 g (32.21 mmol, 1.2 eq) of phenyl boronic acid, 0.05 g (0.25 mmol, 0.01 eq) of Pd(PPh$_3$)$_4$, and 7.42 g (51.48 mmol, 2.0 eq) of $K_2CO_3$ were dissolved in 30 ml of water and the resulting solution was added thereto, and the resulting mixture was dissolved in 70 ml of dioxane and stirred under reflux. When the reaction was terminated, the organic layer was separated and then placed under reduced pressure to remove the solvent. Thereafter, the product was completely dissolved in $CHCl_3$, washed with water, and again placed under reduced pressure to remove the solvent, and the resulting product was subjected to column chromatography to obtain 12.80 g (22.28 mmol, yield 83%) of Chemical Formula 2-d-6.

LC/MS: m/z=574 [(M+1)$^+$]

860

Synthesis Example 16. Synthesis of Chemical Formula 2-d-7

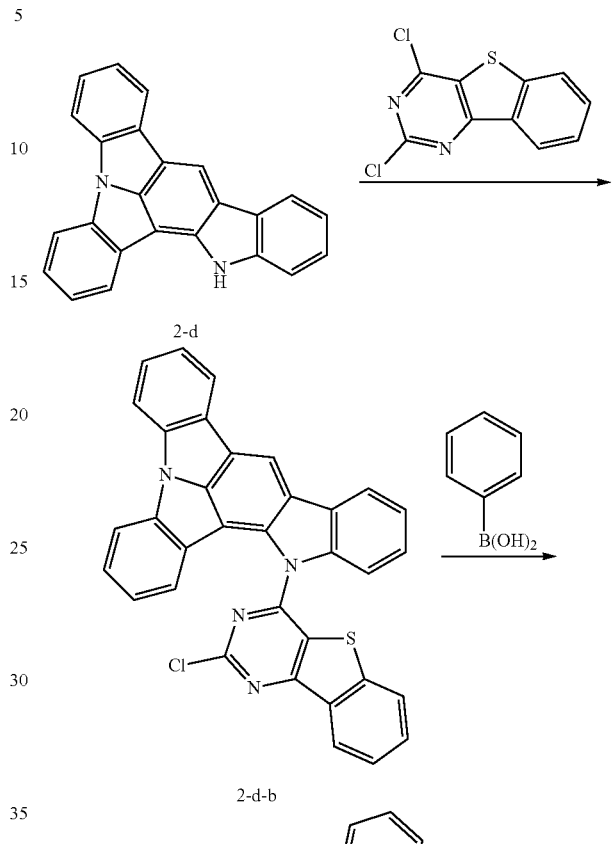

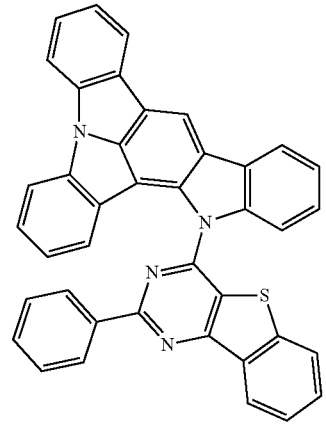

2-d-7

10.00 g (30.29 mmol, 1.0 eq) of Chemical Formula 2-d, 7.73 g (30.29 mmol, 1.0 eq) of 2,4-dichlorobenzo[4,5]thieno[3,2-d]pyrimidine, and 6.43 g (30.29 mmol, 1.0 eq) of $K_3PO_4$ were dissolved in 80 ml of THF, and stirred under reflux. When the reaction was terminated, the resulting product was placed under reduced pressure to remove the solvent. Thereafter, the product was completely dissolved in $CHCl_3$, washed with water, and again placed under reduced pressure to remove the solvent, and the resulting product was subjected to column chromatography to obtain 13.63 g (24.83 mmol, yield 82%) of Chemical Formula 2-d-b.

LC/MS: m/z=578 [(M+1)$^+$]

13.63 g (24.83 mmol, 1.0 eq) of Chemical Formula 2-d-b, 3.81 g (31.27 mmol, 1.2 eq) of phenyl boronic acid, 0.05 g (0.25 mmol, 0.01 eq) of Pd(PPh$_3$)$_4$, and 7.20 g (52.12 mmol, 2.0 eq) of K$_2$CO$_3$ were dissolved in 30 ml of water, the resulting solution was added thereto, and the resulting mixture was dissolved in 70 ml of dioxane and stirred under reflux. When the reaction was terminated, the organic layer was separated and then placed under reduced pressure to remove the solvent. Thereafter, the product was completely dissolved in CHCl$_3$, washed with water, and again placed under reduced pressure to remove the solvent, and the resulting product was subjected to column chromatography to obtain 12.47 g (21.11 mmol, yield 81%) of Chemical Formula 2-d-7.

LC/MS: m/z=590 [(M+1)$^+$]

Synthesis Example 17. Synthesis of Chemical Formula 2-d-8

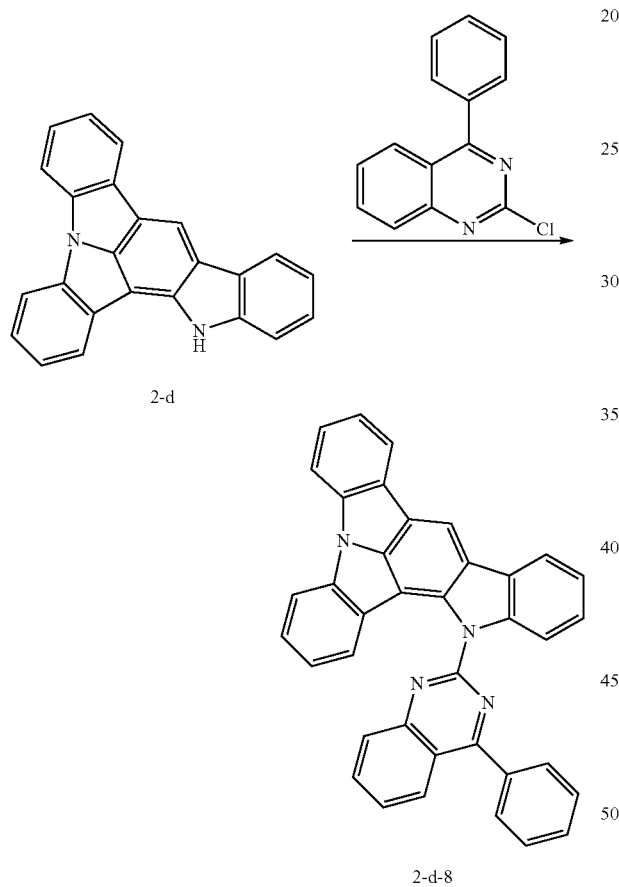

10.00 g (30.29 mmol, 1.0 eq) of Chemical Formula 2-d, 8.02 g (33.32 mmol, 1.1 eq) of 2-chloro-4-phenylquinazoline, 19.29 g (90.88 mmol, 3 eq) of K$_3$PO$_4$, and 0.08 g (0.15 mmol, 0.005 eq) of Pd(t-Bu$_3$P)$_2$ were dissolved in 80 ml of xylene, and stirred under reflux. When the reaction was terminated, the resulting product was placed under reduced pressure to remove the solvent. Thereafter, the product was completely dissolved in CHCl$_3$, washed with water, and again placed under reduced pressure to remove the solvent, and the resulting product was subjected to column chromatography to obtain 12.46 g (23.32 mmol, yield 77%) of Chemical Formula 2-d-8.

LC/MS: m/z=534 [(M+1)$^+$]

Synthesis Example 18. Synthesis of Chemical Formula 2-d-9

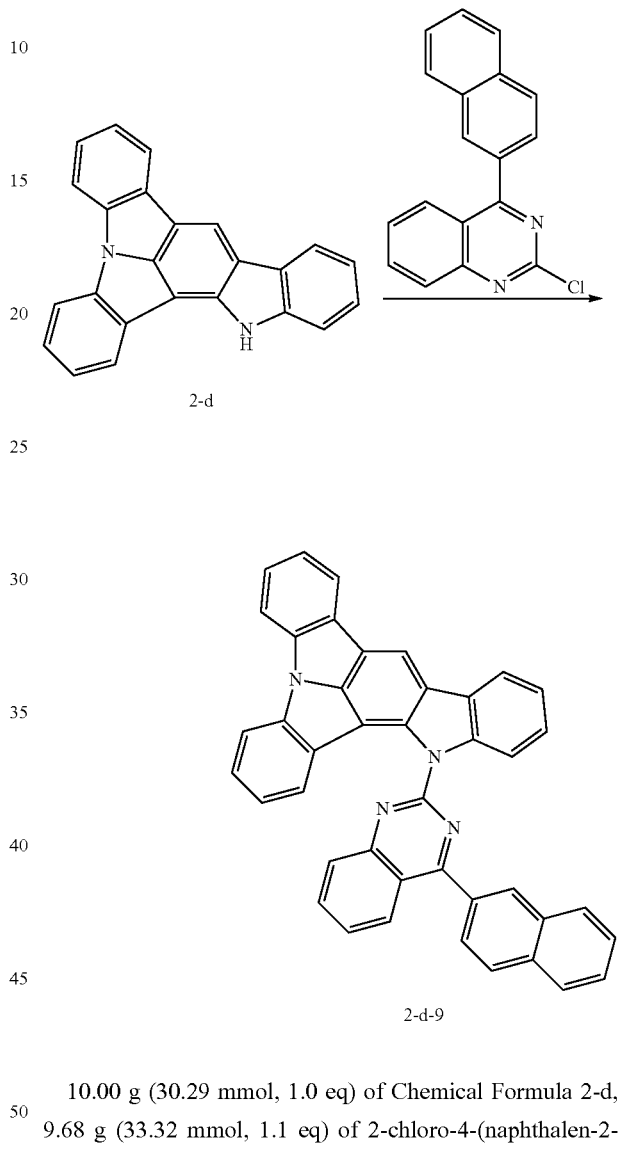

10.00 g (30.29 mmol, 1.0 eq) of Chemical Formula 2-d, 9.68 g (33.32 mmol, 1.1 eq) of 2-chloro-4-(naphthalen-2-yl)quinazoline, 19.29 g (90.88 mmol, 3 eq) of K$_3$PO$_4$, and 0.08 g (0.15 mmol, 0.005 eq) of Pd(t-Bu$_3$P)$_2$ were dissolved in 80 ml of xylene, and stirred under reflux. When the reaction was terminated, the resulting product was placed under reduced pressure to remove the solvent. Thereafter, the product was completely dissolved in CHCl$_3$, washed with water, and again placed under reduced pressure to remove the solvent, and the resulting product was subjected to column chromatography to obtain 13.28 g (22.71 mmol, yield 75%) of Chemical Formula 2-d-9.

LC/MS: m/z=584 [(M+1)$^+$]

Synthesis Example 19. Synthesis of Chemical Formula 2-d-10

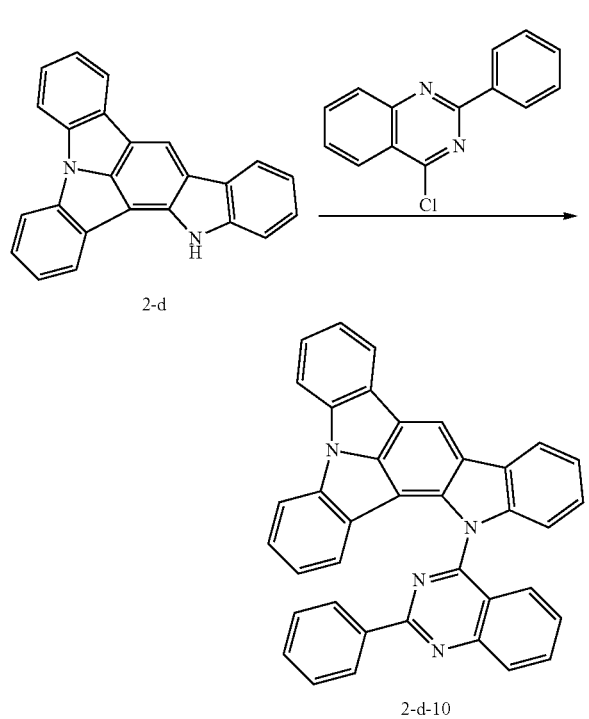

10.00 g (30.29 mmol, 1.0 eq) of Chemical Formula 2-d, 8.02 g (33.32 mmol, 1.1 eq) of 4-chloro-2-phenylquinazoline, 19.29 g (90.88 mmol, 3 eq) of $K_3PO_4$, and 0.08 g (0.15 mmol, 0.005 eq) of $Pd(t-Bu_3P)_2$ were dissolved in 80 ml of xylene, and stirred under reflux. When the reaction was terminated, the resulting product was placed under reduced pressure to remove the solvent. Thereafter, the product was completely dissolved in $CHCl_3$, washed with water, and again placed under reduced pressure to remove the solvent, and the resulting product was subjected to column chromatography to obtain 11.66 g (21.81 mmol, yield 72%) of Chemical Formula 2-d-13.

LC/MS: m/z=534 [(M+1)$^+$]

Synthesis Example 20. Synthesis of Chemical Formula 2-d-11

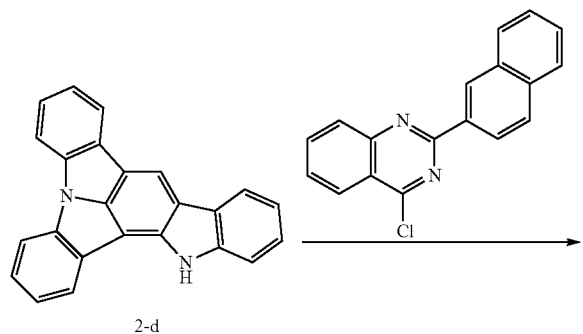

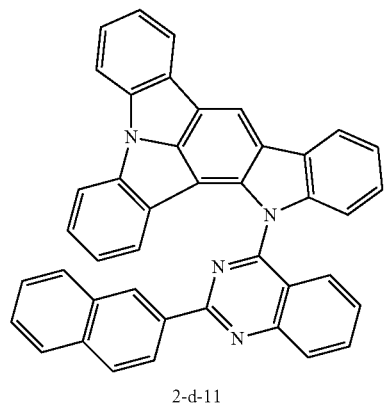

10.00 g (30.29 mmol, 1.0 eq) of Chemical Formula 2-d, 9.68 g (33.32 mmol, 1.1 eq) of 4-chloro-2-(naphthalen-2-yl)quinazoline, 19.29 g (90.88 mmol, 3 eq) of $K_3PO_4$, and 0.08 g (0.15 mmol, 0.005 eq) of $Pd(t-Bu_3P)_4$ were dissolved in 80 ml of xylene, and stirred under reflux. When the reaction was terminated, the resulting product was placed under reduced pressure to remove the solvent. Thereafter, the product was completely dissolved in $CHCl_3$, washed with water, and again placed under reduced pressure to remove the solvent, and the resulting product was subjected to column chromatography to obtain 12.57 g (21.50 mmol, yield 71%) of Chemical Formula 2-d-11.

LC/MS: m/z=584 [(M+1)$^+$]

Synthesis Example 21. Synthesis of Chemical Formula 2-d-12

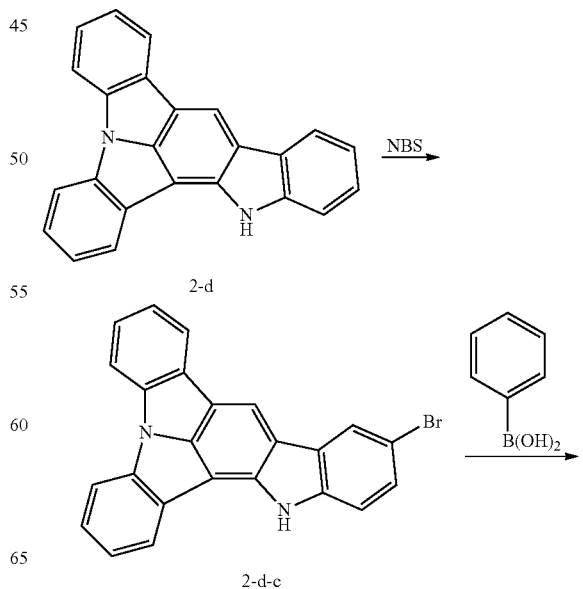

-continued

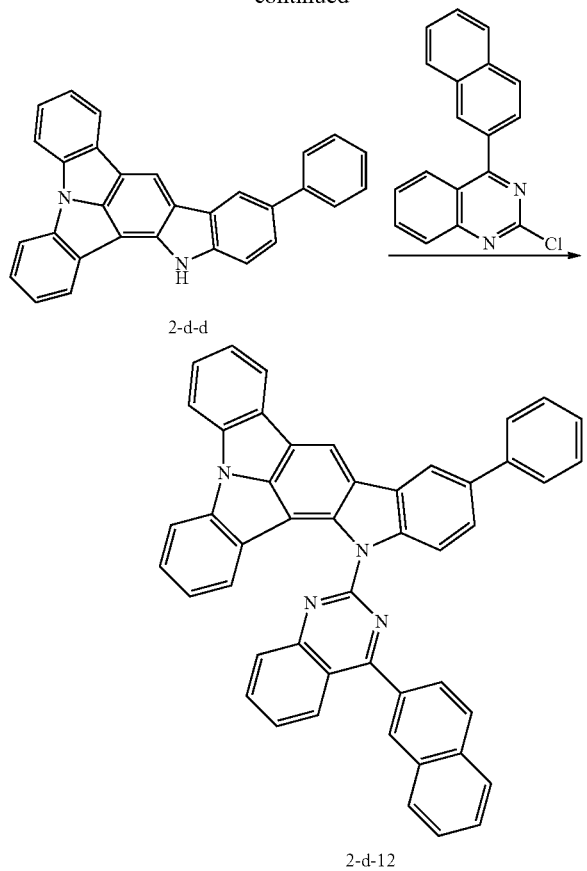

2-d-d 2-d-12

While 50.00 g (151.34 mmol, 1.0 eq) of Chemical Formula 2-d was dissolved in 700 ml of DMF, 26.93 g (151.34 mmol, 1.0 eq) of NBS was slowly added dropwise thereto. After the reaction, the reaction product was poured into 3 L of water and crystals were dropped thereto to filter the resulting product. The filtered product was completely dissolved in ethyl acetate, washed with water, and again placed under reduced pressure to remove about half of the amount of the solvent, and recrystallization was performed while adding ethanol thereto to obtain 53.88 g (131.66 mmol, yield 87%) of Chemical Formula 2-d-c. 1H NMR spectrum of the compound of Chemical Formula 2-d-c is illustrated in FIG. 6.

LC/MS: m/z=408 [(M+1)$^+$]

53.88 g (131.66 mmol, 1.0 eq) of Chemical Formula 2-d-c, 19.26 g (154.33 mmol, 1.2 eq) of phenyl boronic acid, 0.28 g (1.28 mmol, 0.01 eq) of Pd(PPh$_3$)$_4$, and 36.38 g (263.29 mmol, 2.0 eq) of K$_2$CO$_3$ were dissolved in 150 ml of water and the resulting solution was added thereto, and the resulting mixture was dissolved in 300 ml of dioxane and stirred under reflux. When the reaction was terminated, the organic layer was separated and then placed under reduced pressure to remove the solvent. Thereafter, the product was completely dissolved in CHCl$_3$, washed with water, and again placed under reduced pressure to remove the solvent, and the resulting product was subjected to column chromatography to obtain 48.69 g (119.79 mmol, yield 90%) of Chemical Formula 2-d.

LC/MS: m/z=406 [(M+1)$^+$]

10.00 g (24.60 mmol, 1.0 eq) of Chemical Formula 2-d-d, 7.86 g (27.06 mmol, 1.1 eq) of 2-chloro-4-(naphthalen-2-yl)quinazoline, 17.64 g (17.64 mmol, 3 eq) of K$_3$PO$_4$, and 0.06 g (0.12 mmol, 0.005 eq) of Pd(t-Bu$_3$P)$_2$ were dissolved in 80 ml of xylene, and stirred under reflux. When the reaction was terminated, the resulting product was placed under reduced pressure to remove the solvent. Thereafter, the product was completely dissolved in CHCl$_3$, washed with water, and again placed under reduced pressure to remove the solvent, and the resulting product was subjected to column chromatography to obtain 10.81 g (17.71 mmol, yield 72%) of Chemical Formula 2-d-12.

LC/MS: m/z=660 [(M+1)$^+$]

Synthesis Example 22. Synthesis of Chemical Formula 2-d-13

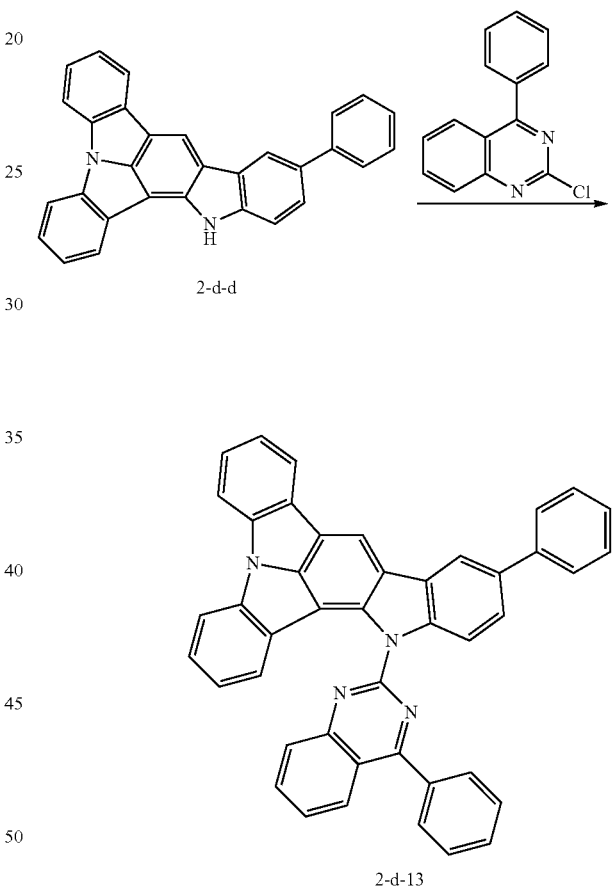

2-d-d 2-d-13

10.00 g (24.60 mmol, 1.0 eq) of Chemical Formula 2-d-d, 6.51 g (27.06 mmol, 1.1 eq) of 2-chloro-4-phenylquinazoline, 15.66 g (73.80 mmol, 3 eq) of K$_3$PO$_4$, and 0.08 g (0.15 mmol, 0.005 eq) of Pd(t-Bu$_3$P)$_2$ were dissolved in 80 ml of xylene, and stirred under reflux. When the reaction was terminated, the resulting product was placed under reduced pressure to remove the solvent. Thereafter, the product was completely dissolved in CHCl$_3$, washed with water, and again placed under reduced pressure to remove the solvent, and the resulting product was subjected to column chromatography to obtain 10.66 g (17.46 mmol, yield 71%) of Chemical Formula 2-d-13.

LC/MS: m/z=610 [(M+1)$^+$]

Synthesis Example 23. Synthesis of Chemical Formula 2-d-14

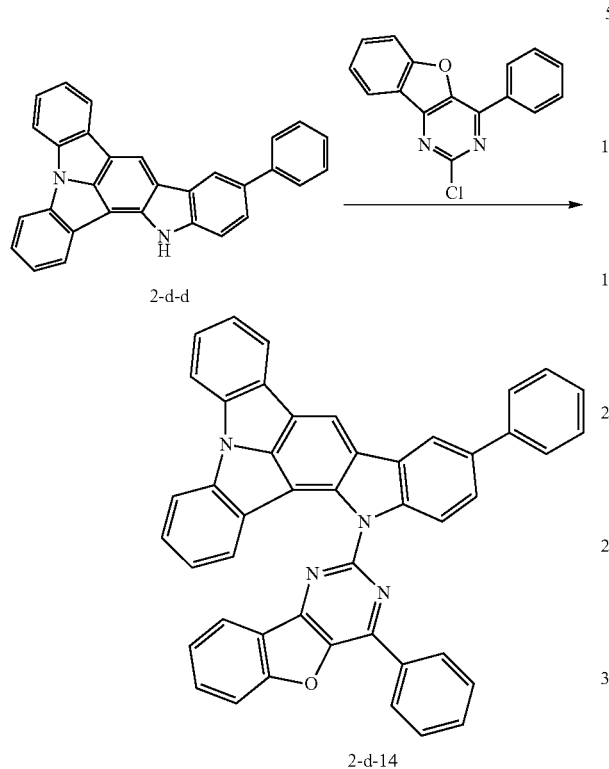

2-d-14

10.00 g (24.60 mmol, 1.0 eq) of Chemical Formula 2-d-d, 7.59 g (27.06 mmol, 1.1 eq) of 2-chloro-4-phenylbenzofuro[3,2-d]pyrimidine, 15.66 g (73.80 mmol, 3 eq) of $K_3PO_4$, and 0.08 g (0.15 mmol, 0.005 eq) of $Pd(t-Bu_3P)_2$ were dissolved in 80 ml of xylene, and stirred under reflux. When the reaction was terminated, the resulting product was placed under reduced pressure to remove the solvent. Thereafter, the product was completely dissolved in $CHCl_3$, washed with water, and again placed under reduced pressure to remove the solvent, and the resulting product was subjected to column chromatography to obtain 12.00 g (18.45 mmol, yield 75%) of Chemical Formula 2-d-14.

LC/MS: m/z=650 [(M+1)⁺]

Synthesis Example 24. Synthesis of Chemical Formula 2-d-15

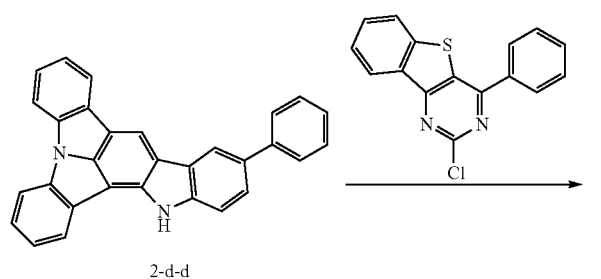

2-d-d

-continued

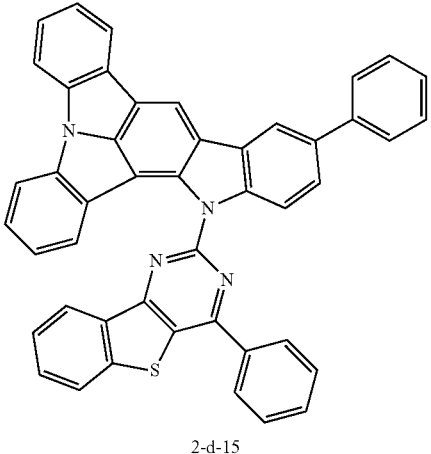

2-d-15

10.00 g (24.60 mmol, 1.0 eq) of Chemical Formula 2-d-d, 8.03 g (27.06 mmol, 1.1 eq) of 2-chloro-4-phenylbenzo[4,5]thieno[3,2-d]pyrimidine, 15.66 g (73.80 mmol, 3 eq) of $K_3PO_4$, and 0.08 g (0.15 mmol, 0.005 eq) of $Pd(t-Bu_3P)_2$ were dissolved in 80 ml of xylene, and stirred under reflux. When the reaction was terminated, the resulting product was placed under reduced pressure to remove the solvent. Thereafter, the product was completely dissolved in $CHCl_3$, washed with water, and again placed under reduced pressure to remove the solvent, and the resulting product was subjected to column chromatography to obtain 12.63 g (18.94 mmol, yield 77%) of Chemical Formula 2-d-15.

LC/MS: m/z=666 [(M+1)⁺]

Synthesis Example 25. Synthesis of Chemical Formula 2-d-16

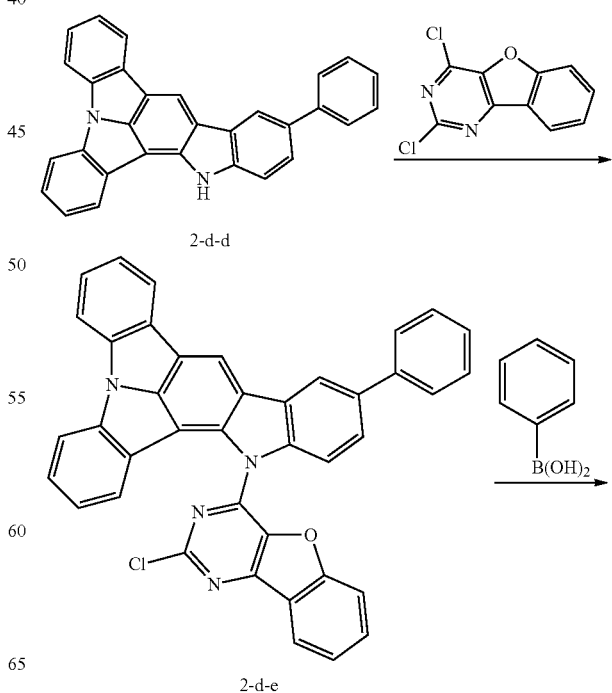

2-d-d 2-d-e

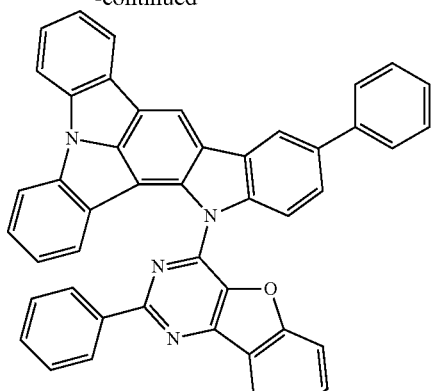

2-d-16

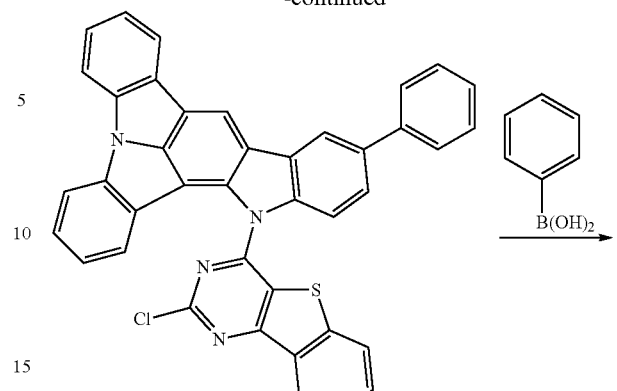

2-d-f 10.00 g (24.60 mmol, 1.0 eq) of Chemical Formula 2-d-d, 5.88 g (24.60 mmol, 1.0 eq) of 2,4-dichlorobenzofuro[3,2-d]pyrimidine, and 5.22 g (24.60 mmol, 1.0 eq) of $K_3PO_4$ were dissolved in 80 ml of THF, and stirred under reflux. When the reaction was terminated, the resulting product was placed under reduced pressure to remove the solvent. Thereafter, the product was completely dissolved in $CHCl_3$, washed with water, and again placed under reduced pressure to remove the solvent, and the resulting product was subjected to column chromatography to obtain 12.28 g (20.17 mmol, yield 82%) of Chemical Formula 2-d-e.

LC/MS: m/z=608 [(M+1)$^+$]

12.28 g (20.17 mmol, 1.0 eq) of Chemical Formula 2-d-e, 3.43 g (28.19 mmol, 1.2 eq) of phenyl boronic acid, 0.05 g (0.23 mmol, 0.01 eq) of Pd(PPh$_3$)$_4$, and 6.49 g (46.98 mmol, 2.0 eq) of $K_2CO_3$ were dissolved in 30 ml of water, the resulting solution was added thereto, and the resulting mixture was dissolved in 70 ml of dioxane and stirred under reflux. When the reaction was terminated, the organic layer was separated and then placed under reduced pressure to remove the solvent. Thereafter, the product was completely dissolved in $CHCl_3$, washed with water, and again placed under reduced pressure to remove the solvent, and the resulting product was subjected to column chromatography to obtain 12.38 g (19.03 mmol, yield 81%) of Chemical Formula 2-d-16.

LC/MS: m/z=650 [(M+1)$^+$]

Synthesis Example 26. Synthesis of Chemical Formula 2-d-17

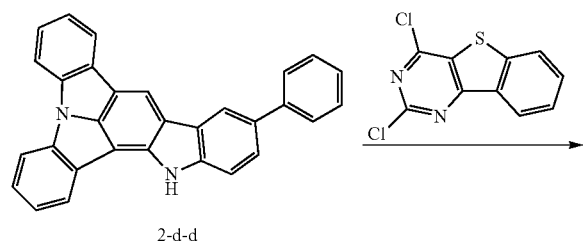

2-d-d

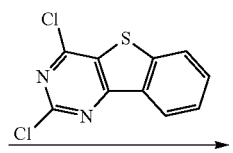

2-d-17

10.00 g (24.60 mmol, 1.0 eq) of Chemical Formula 2-d-d, 6.27 g (24.60 mmol, 1.0 eq) of 2,4-dichlorobenzofuro[3,2-d]pyrimidine, and 5.22 g (24.60 mmol, 1.0 eq) of $K_3PO_4$ were dissolved in 80 ml of THF, and stirred under reflux. When the reaction was terminated, the resulting product was placed under reduced pressure to remove the solvent. Thereafter, the product was completely dissolved in $CHCl_3$, washed with water, and again placed under reduced pressure to remove the solvent, and the resulting product was subjected to column chromatography to obtain 13.07 g (20.91 mmol, yield 85%) of Chemical Formula 2-d-f.

LC/MS: m/z=624 [(M+1)$^+$]

13.07 g (20.91 mmol, 1.0 eq) of Chemical Formula 2-d-f, 3.35 g (27.46 mmol, 1.2 eq) of phenyl boronic acid, 0.05 g (0.23 mmol, 0.01 eq) of Pd(PPh$_3$)$_4$, and 6.33 g (45.78 mmol, 2.0 eq) of $K_2CO_3$ were dissolved in 30 ml of water, the resulting solution was added thereto, and the resulting mixture was dissolved in 70 ml of dioxane and stirred under reflux. When the reaction was terminated, the organic layer was separated and then placed under reduced pressure to remove the solvent. Thereafter, the product was completely dissolved in $CHCl_3$, washed with water, and again placed under reduced pressure to remove the solvent, and the resulting product was subjected to column chromatography to obtain 12.36 g (18.54 mmol, yield 81%) of Chemical Formula 2-d-17.

LC/MS: m/z=650 [(M+1)$^+$]

Synthesis Example 27. Synthesis of Chemical Formula 2-d-18

Synthesis Example 28. Synthesis of Chemical Formula 2-d-19

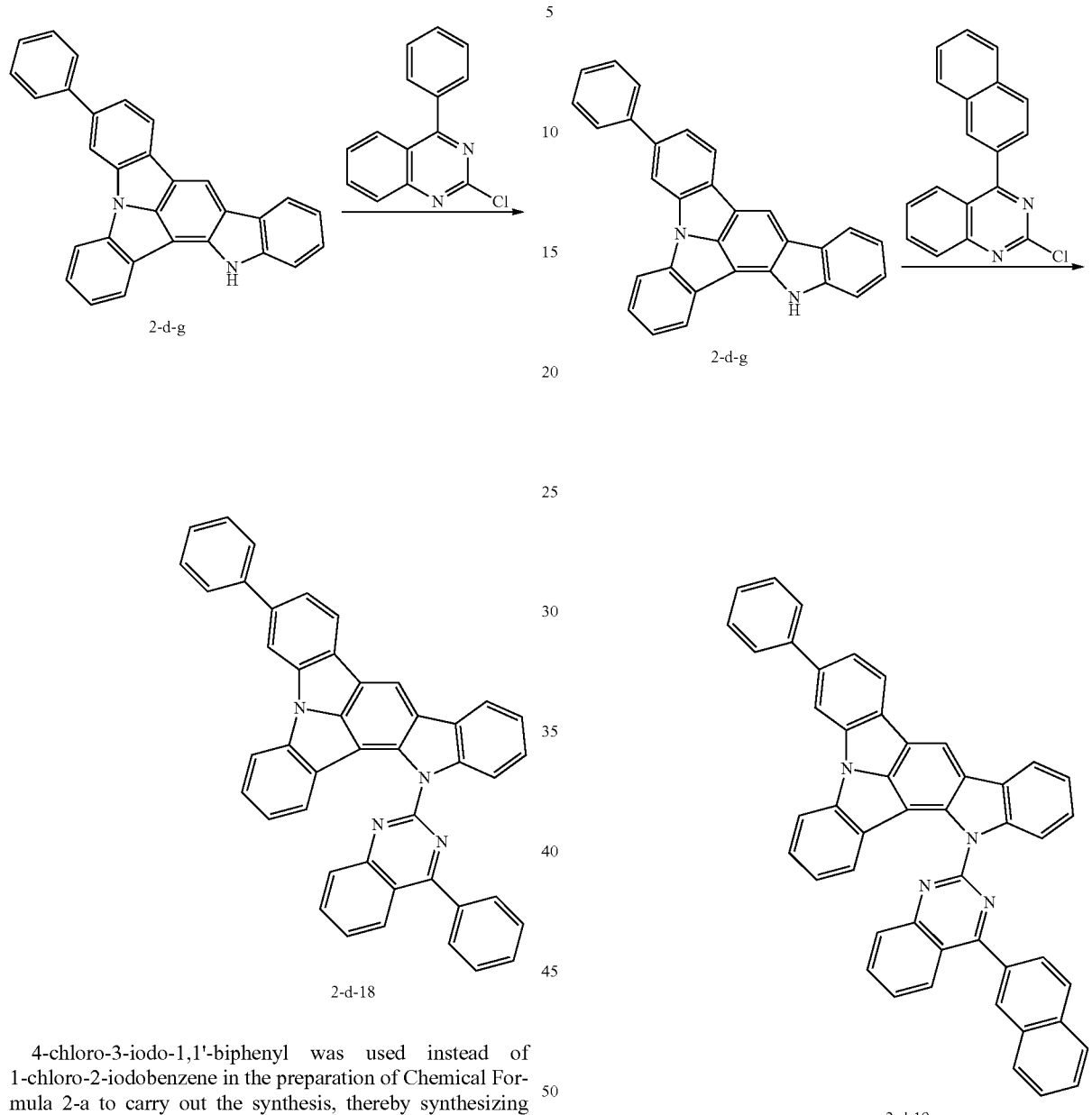

2-d-18

2-d-19

4-chloro-3-iodo-1,1'-biphenyl was used instead of 1-chloro-2-iodobenzene in the preparation of Chemical Formula 2-a to carry out the synthesis, thereby synthesizing Chemical Formula 2-d-g in the same manner as in the method of Chemical Formula 2-d.

LC/MS: m/z=406 [(M+1)$^+$]

10.00 g (24.60 mmol, 1.0 eq) of Chemical Formula 2-d-g, 6.51 g (27.06 mmol, 1.1 eq) of 2-chloro-4-phenylquinazoline, 15.66 g (73.80 mmol, 3 eq) of $K_3PO_4$, and 0.08 g (0.12 mmol, 0.005 eq) of Pd(t-Bu$_3$P)$_2$ were dissolved in 80 ml of xylene, and stirred under reflux. When the reaction was terminated, the resulting product was placed under reduced pressure to remove the solvent. Thereafter, the product was completely dissolved in CHCl$_3$, washed with water, and again placed under reduced pressure to remove the solvent, and the resulting product was subjected to column chromatography to obtain 12.77 g (20.91 mmol, yield 85%) of Chemical Formula 2-d-18.

LC/MS: m/z=610 [(M+1)$^+$]

10.00 g (24.60 mmol, 1.0 eq) of Chemical Formula 2-d-g, 7.86 g (27.06 mmol, 1.1 eq) of 2-chloro-4-(naphthalen-2-yl)quinazoline, 15.66 g (73.80 mmol, 3 eq) of $K_3PO_4$, and 0.08 g (0.12 mmol, 0.005 eq) of Pd(t-Bu$_3$P)$_2$ were dissolved in 80 ml of xylene, and stirred under reflux. When the reaction was terminated, the resulting product was placed under reduced pressure to remove the solvent. Thereafter, the product was completely dissolved in CHCl$_3$, washed with water, and again placed under reduced pressure to remove the solvent, and the resulting product was subjected to column chromatography to obtain 13.49 g (20.41 mmol, yield 83%) of Chemical Formula 2-d-22.

LC/MS: m/z=660 [(M+1)$^+$]

Synthesis Example 29. Synthesis of Chemical Formula 6-d-1

Synthesis Example 30. Synthesis of Chemical Formula 6-d-2

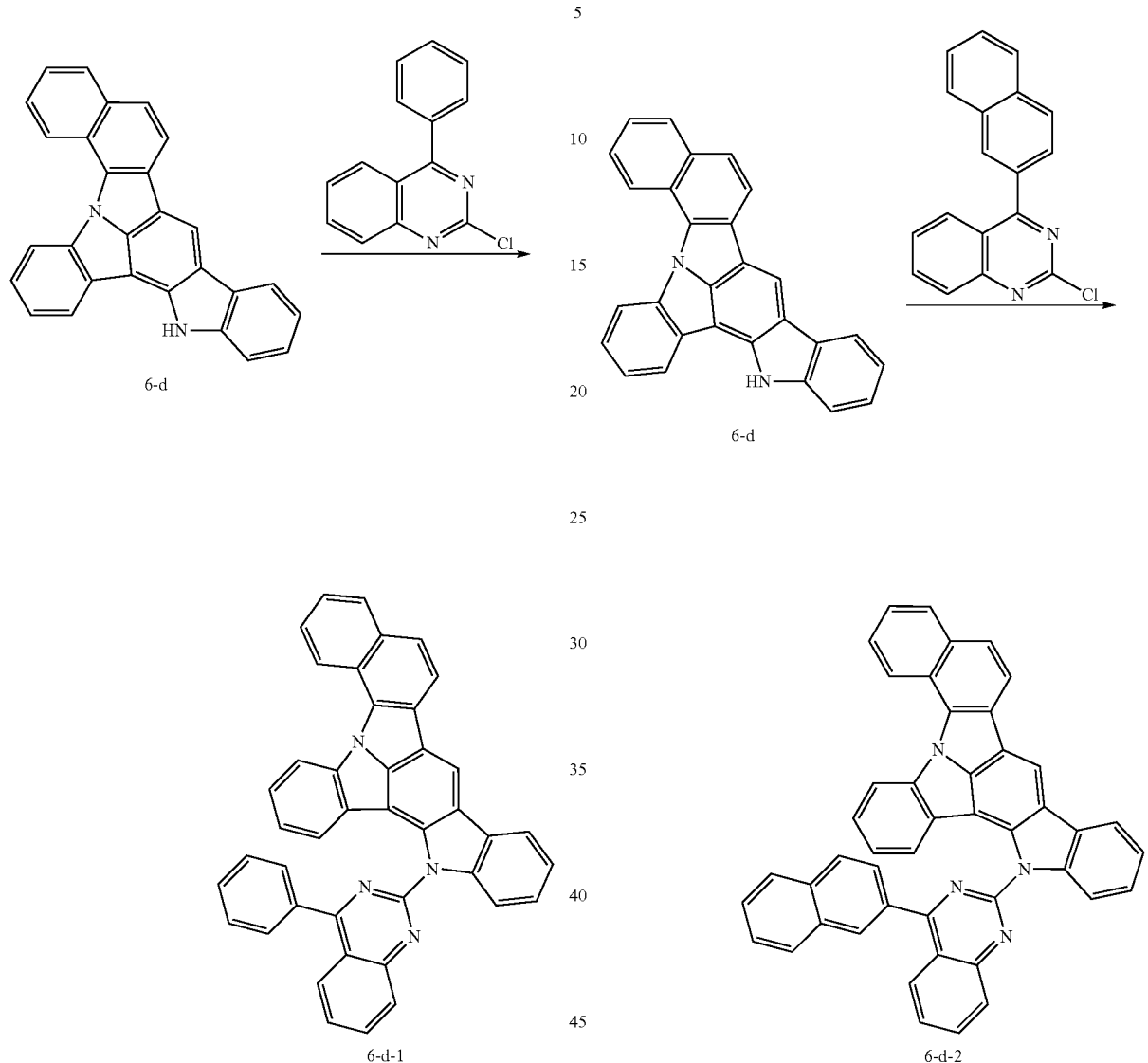

10.00 g (26.28 mmol, 1.0 eq) of Chemical Formula 6-d, 6.95 g (28.91 mmol, 1.1 eq) of 2-chloro-4-phenylquinazoline, 16.73 g (78.85 mmol, 3 eq) of $K_3PO_4$, and 0.07 g (0.13 mmol, 0.005 eq) of $Pd(t-Bu_3P)_2$ were dissolved in 80 ml of xylene, and stirred under reflux. When the reaction was terminated, the resulting product was placed under reduced pressure to remove the solvent. Thereafter, the product was completely dissolved in $CHCl_3$, washed with water, and again placed under reduced pressure to remove the solvent, and the resulting product was subjected to column chromatography to obtain 11.98 g (20.50 mmol, yield 78%) of Chemical Formula 6-d-1.

LC/MS: m/z=584 [(M+1)$^+$]

10.00 g (26.28 mmol, 1.0 eq) of Chemical Formula 6-d, 8.40 g (28.91 mmol, 1.1 eq) of 2-chloro-4-(naphthalen-2-yl)quinazoline, 16.73 g (78.85 mmol, 3 eq) of $K_3PO_4$, and 0.07 g (0.13 mmol, 0.005 eq) of $Pd(t-Bu_3P)_2$ were dissolved in 80 ml of xylene, and stirred under reflux. When the reaction was terminated, the resulting product was placed under reduced pressure to remove the solvent. Thereafter, the product was completely dissolved in $CHCl_3$, washed with water, and again placed under reduced pressure to remove the solvent, and the resulting product was subjected to column chromatography to obtain 13.18 g (20.76 mmol, yield 79%) of Chemical Formula 6-d-2.

LC/MS: m/z=634 [(M+1)$^+$]

Synthesis Example 31. Synthesis of Chemical Formula 6-d-3

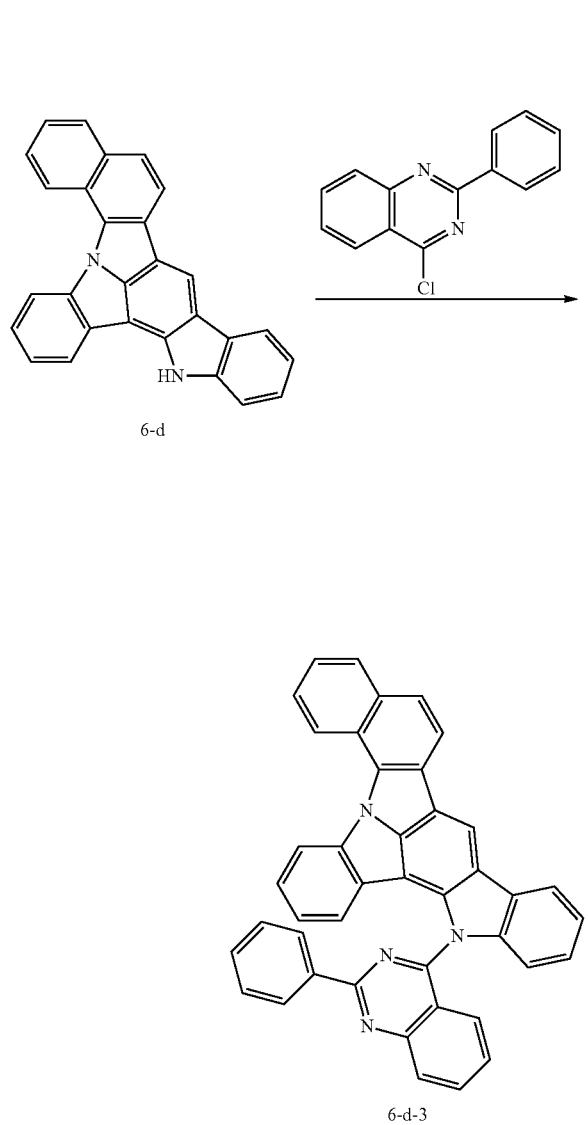

10.00 g (26.28 mmol, 1.0 eq) of Chemical Formula 6-d, 6.95 g (28.91 mmol, 1.1 eq) of 4-chloro-2-phenylquinazoline, 16.73 g (78.85 mmol, 3 eq) of $K_3PO_4$, and 0.07 g (0.13 mmol, 0.005 eq) of $Pd(t-Bu_3P)_2$ were dissolved in 80 ml of xylene, and stirred under reflux. When the reaction was terminated, the resulting product was placed under reduced pressure to remove the solvent. Thereafter, the product was completely dissolved in $CHCl_3$, washed with water, and again placed under reduced pressure to remove the solvent, and the resulting product was subjected to column chromatography to obtain 11.37 g (19.45 mmol, yield 74%) of Chemical Formula 6-d-3.

LC/MS: m/z=584 [(M+1)$^+$]

Synthesis Example 32. Synthesis of Chemical Formula 6-d-4

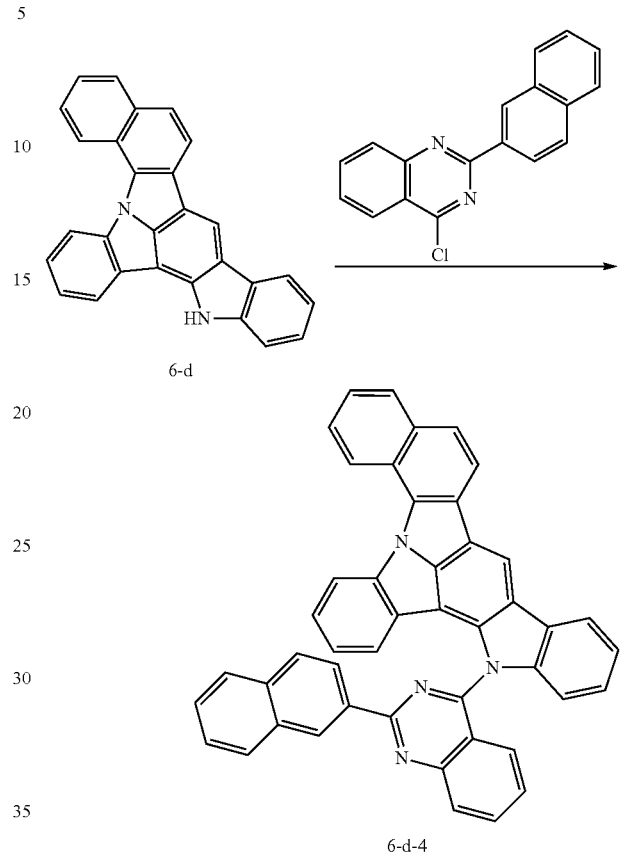

10.00 g (26.28 mmol, 1.0 eq) of Chemical Formula 6-d, 8.40 g (28.91 mmol, 1.1 eq) of 4-chloro-2-(naphthalen-2-yl)quinazoline, 16.73 g (78.85 mmol, 3 eq) of $K_3PO_4$, and 0.07 g (0.13 mmol, 0.005 eq) of $Pd(t-Bu_3P)_2$ were dissolved in 80 ml of xylene, and stirred under reflux. When the reaction was terminated, the resulting product was placed under reduced pressure to remove the solvent. Thereafter, the product was completely dissolved in $CHCl_3$, washed with water, and again placed under reduced pressure to remove the solvent, and the resulting product was subjected to column chromatography to obtain 11.84 g (18.66 mmol, yield 71%) of Chemical Formula 6-d-4.

LC/MS: m/z=634 [(M+1)$^+$]

<Experimental Example 1> to <Experimental Example 12>

The compounds prepared in the Synthesis Examples were subjected to high-purity sublimation purification by a typically known method, and then red organic light emitting devices were manufactured by the following method.

A glass substrate (Corning 7059 glass) thinly coated with indium tin oxide (ITO) to have a thickness of 1,000 Å was put into distilled water in which a dispersant was dissolved, and ultrasonically washed. A product manufactured by Fischer Co. was used as the detergent, and distilled water twice filtered using a filter manufactured by Millipore Co., was used as the distilled water. After the ITO was washed for 30 minutes, ultrasonic washing was conducted repeatedly twice using distilled water for 10 minutes. After the washing using distilled water was completed, ultrasonic washing was conducted using isopropyl alcohol, acetone, and methanol solvents in this order, and drying was then conducted.

The substrate was mounted in a vacuum chamber, then the base pressure was maintained at $1 \times 10^{-6}$ torr, and then as the organic material, DNTPD (700 Å) was deposited as a hole injection layer on the ITO. α-NPB (300 Å) was deposited as a hole transporting layer thereon, and the compounds in the following Table 1, which had been synthesized in the above-described Synthesis Examples, were subjected to sublimation purification, and then used as a host (95 wt %), and as the dopant, Dp-7 (5 wt %) was co-deposited (300 Å) to deposit a light emitting layer. As a hole blocking layer, BCP (50 Å) was deposited thereon, and ET-1 and ET-2 were evaporated at a rate of 2:1 to deposit an electron transfer layer having a thickness of 300 Å on the light emitting layer. ET-2 (5 Å) as the electron injection layer and an Al negative electrode (1,000 Å) were deposited in this order to manufacture an OLED device.

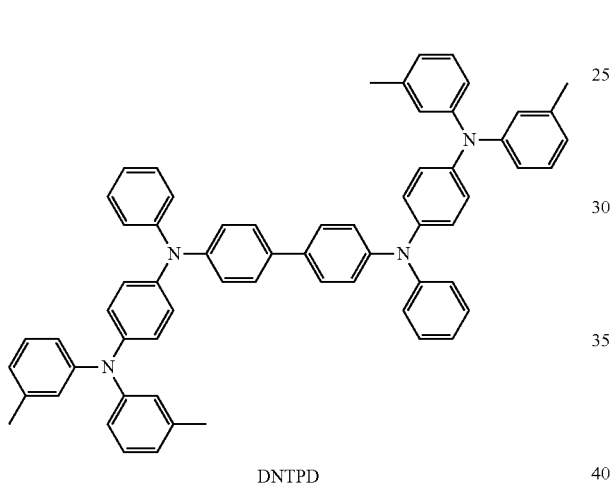

DNTPD

NPB

BCP

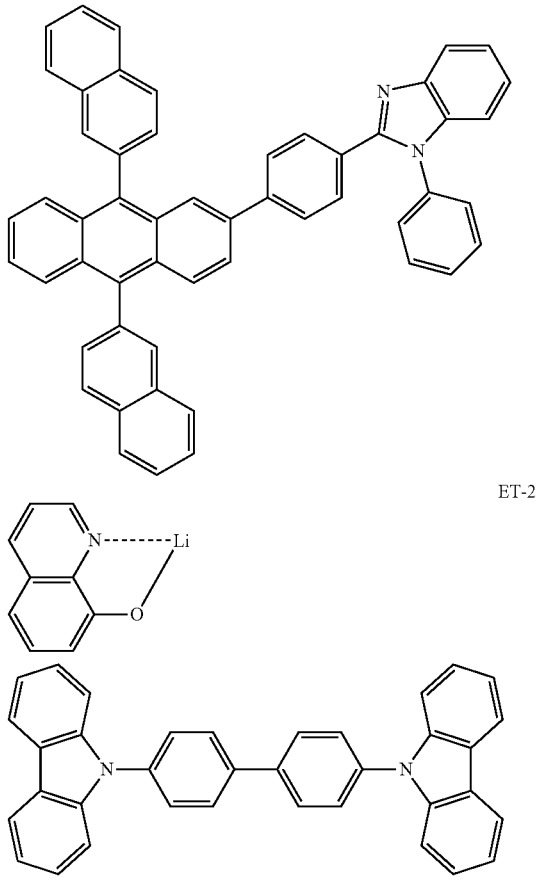

ET-1

ET-2

CBP

Comparative Example 1

The organic light emitting device in Comparative Example 1 was manufactured in the same manner as in Experimental Examples 1 to 12, except that CBP frequently used as a general phosphorescent host material was used instead of the compound of the present invention as the host of the light emitting layer in the structures of the organic light emitting devices in Experimental Examples 1 to 12.

The driving voltage, current efficiency, and service life of the organic light emitting devices manufactured according to the Experimental Examples 1 to 12 and Comparative Example 1 were measured, and the results are shown in the following Table 1.

TABLE 1

| | Compound | Driving voltage (V) | Current efficiency (cd/A) | Service life (T95) | CIE x | CIE y |
|---|---|---|---|---|---|---|
| Experimental Example 1 | 1-d-1 | 4.2 | 42.7 | 250 | 0.686 | 0.331 |
| Experimental Example 2 | 1-d-3 | 4.4 | 47.2 | 100 | 0.685 | 0.313 |
| Experimental Example 3 | 1-d-7 | 4.1 | 44.3 | 280 | 0.687 | 0.337 |
| Experimental Example 4 | 2-d-4 | 4.2 | 46.80 | 95 | 0.686 | 0.314 |

TABLE 1-continued

| Compound | Driving voltage (V) | Current efficiency (cd/A) | Service life (T95) | CIE x | CIE y |
|---|---|---|---|---|---|
| Experimental Example 5 | 2-d-8 | 3.8 | 50.8 | 390 | 0.688 | 0.313 |
| Experimental Example 6 | 2-d-9 | 3.9 | 52.3 | 390 | 0.678 | 0.322 |
| Experimental Example 7 | 2-d-11 | 3.7 | 47.0 | 110 | 0.686 | 0.314 |
| Experimental Example 8 | 2-d-12 | 4.0 | 57.5 | 410 | 0.688 | 0.312 |
| Experimental Example 9 | 2-d-13 | 4.1 | 52.2 | 405 | 0.684 | 0.346 |
| Experimental Example 10 | 2-d-15 | 4.3 | 51.6 | 105 | 0.682 | 0.318 |
| Experimental Example 11 | 6-d-1 | 3.5 | 42.0 | 320 | 0.686 | 0.312 |
| Experimental Example 12 | 6-d-4 | 3.6 | 46.6 | 120 | 0.688 | 0.312 |
| Comparative Example 1 | CBP | 6.1 | 20.7 | 57 | 0.675 | 0.330 |

As can be seen from the results in Table 1, it can be seen that the organic light emitting device using the compound of the present invention improves the light emitting efficiency while lowering the driving voltage, and contributes to an effect of increasing the service life. In general, a lower driving voltage and a higher efficiency than CBP used as a comparative host material were exhibited, and excellent results were exhibited even in terms of service life.

EXPLANATION OF REFERENCE NUMERALS AND SYMBOLS

1: Substrate
2: Positive electrode
3: Hole injection layer
4: Hole transporting layer
5: Light emitting layer
6: Electron transporting layer
7: Negative electrode

The invention claimed is:

1. A compound represented by one of the following Chemical Formulae 6 to 11:

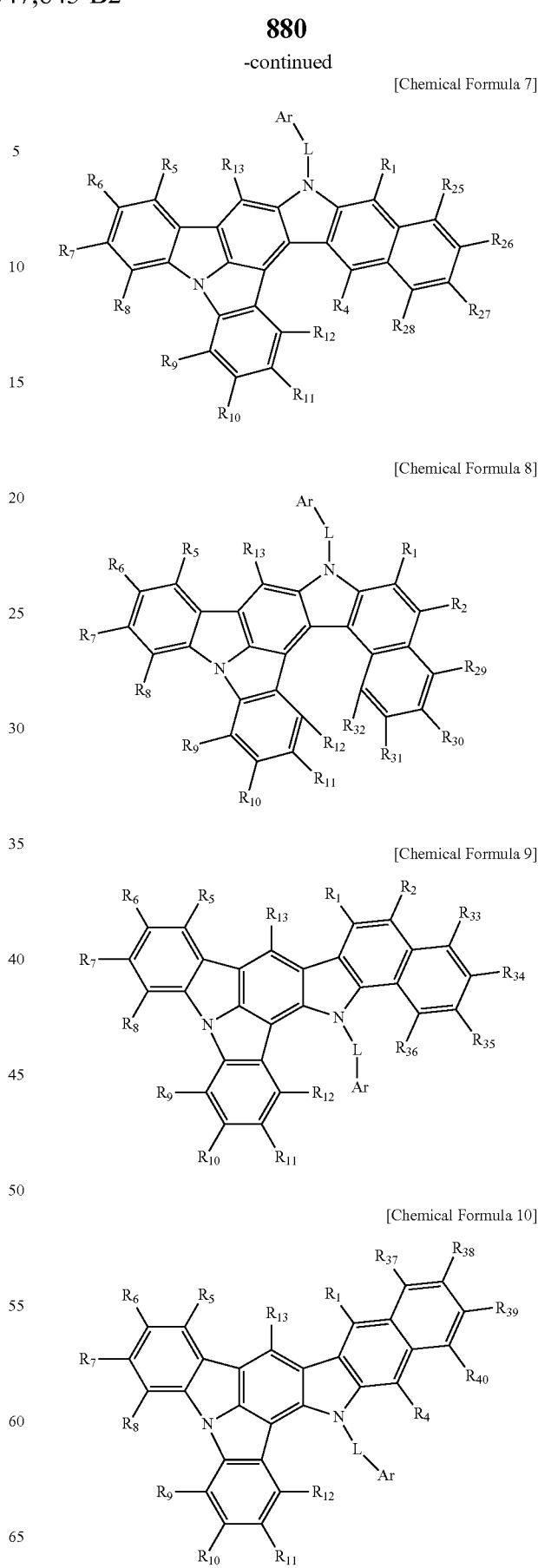

[Chemical Formula 6]

[Chemical Formula 7]

[Chemical Formula 8]

[Chemical Formula 9]

[Chemical Formula 10]

-continued

[Chemical Formula 11]

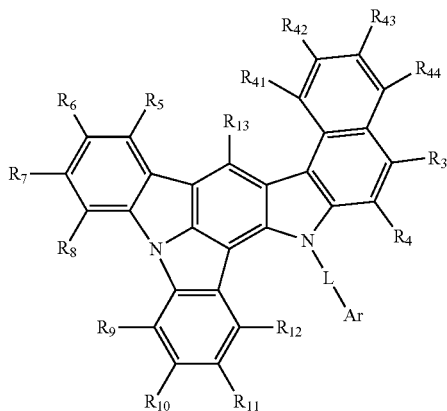

wherein in Chemical Formulae 6 to 11,
Ar is a substituted or unsubstituted bicyclic or heterocyclic group, with the proviso that the substituted or unsubstituted bicyclic or heterocyclic group does not include an oxygen atom as a heteroatom,
L is a direct bond; a substituted or unsubstituted arylene group; or a substituted or unsubstituted heteroarylene group,
$R_1$ to $R_{13}$ are the same as or different from each other, and each independently hydrogen; deuterium; a nitrile group; a substituted or unsubstituted alkyl group; a substituted or unsubstituted alkenyl group; a substituted or unsubstituted cycloalkyl group; a substituted or unsubstituted aryl group; a substituted or unsubstituted aromatic or aliphatic heterocyclic group; a substituted or unsubstituted alkoxy group; a substituted or unsubstituted aryloxy group; a substituted or unsubstituted alkylamine group; a substituted or unsubstituted arylamine group; a substituted or unsubstituted aralkylamine group; a substituted or unsubstituted alkylarylamine group; or a substituted or unsubstituted heteroarylamine group, or combine with an adjacent substituent to form a ring, and
$R_{21}$ to $R_{44}$ are the same as or different from each other, and each independently hydrogen; deuterium; a nitrile group; a substituted or unsubstituted alkyl group; a substituted or unsubstituted alkenyl group; a substituted or unsubstituted cycloalkyl group; a substituted or unsubstituted aryl group; a substituted or unsubstituted aromatic or aliphatic heterocyclic group; a substituted or unsubstituted alkoxy group; a substituted or unsubstituted aryloxy group; a substituted or unsubstituted alkylamine group; a substituted or unsubstituted arylamine group; a substituted or unsubstituted aralkylamine group; a substituted or unsubstituted alkylarylamine group; or a substituted or unsubstituted heteroarylamine group, or combine with an adjacent substituent to form a ring.

2. The compound of claim 1, wherein Ar is a substituted or unsubstituted bicyclic or heterocyclic group including N.

3. The compound of claim 1, wherein Ar is a substituted or unsubstituted bicyclic or heterocyclic group including two or more N's.

4. The compound of claim 1, wherein Ar is an unsubstituted bicyclic or heterocyclic group including two or more N's, which are unsubstituted or substituted with a nitrile group, an alkyl group, an aryl group, a heteroaryl group, an arylheteroaryl group, a heteroarylaryl group, and an aryl group which is substituted with a nitrile group.

5. The compound of claim 1, wherein Ar is represented by one of the following Chemical Formulae A to F:

[Chemical Formula A]

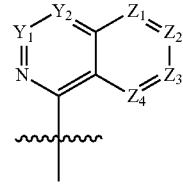

[Chemical Formula B]

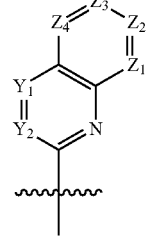

[Chemical Formula C]

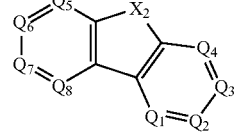

[Chemical Formula D]

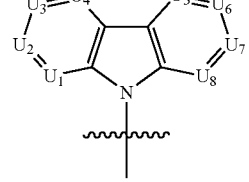

[Chemical Formula E]

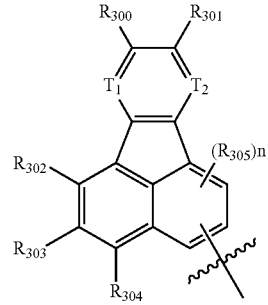

[Chemical Formula F]

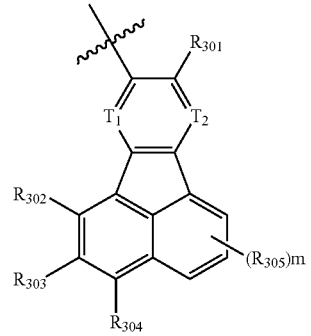

in Chemical Formulae A to F, $Y_1$, $Y_2$, $Z_1$ to $Z_4$, $Q_1$ to $Q_8$, $T_1$, $T_2$ and $U_1$ to $U_8$ are the same as or different from each other, and each independently N or CRd, provided that one of $Q_1$ to $Q_4$ is C linked to L, $X_2$ is $NAr_1$, or S, $Ar_1$, Rd, and $R_{300}$ to $R_{305}$ are the same as or different from each other, and each independently hydrogen; deuterium; a nitrile group; a substituted or unsubstituted alkyl group; a substituted or unsubstituted alkenyl group; a substituted or unsubstituted cycloalkyl group; a substituted or unsubstituted aryl group; a substituted or unsubstituted aromatic or aliphatic heterocyclic group; a substituted or unsubstituted alkoxy group; a substituted or unsubstituted aryloxy group; a substituted or unsubstituted alkylamine group; a substituted or unsubstituted arylamine group; a substituted or unsubstituted aralkylamine group; a substituted or unsubstituted alkylarylamine group; or a substituted or unsubstituted heteroarylamine group, or combine with an adjacent group to form a ring, and n is an integer of 0 to 2, m is an integer of 0 to 3, and when n or m is 2, $R_{305}$'s are the same as or different from each other.

6. A compound represented by one of the following Chemical Formulae 16 to 21:

[Chemical Formula 16]

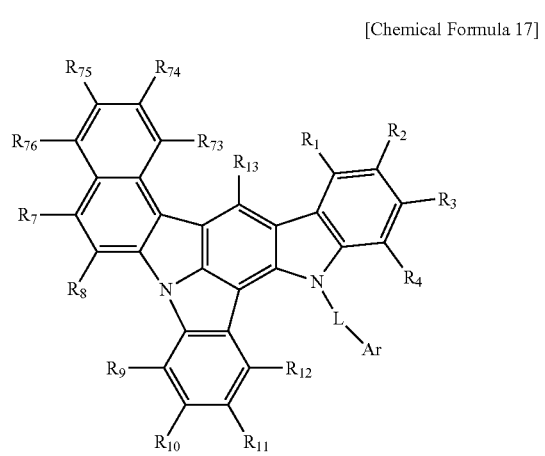

[Chemical Formula 17]

[Chemical Formula 18]

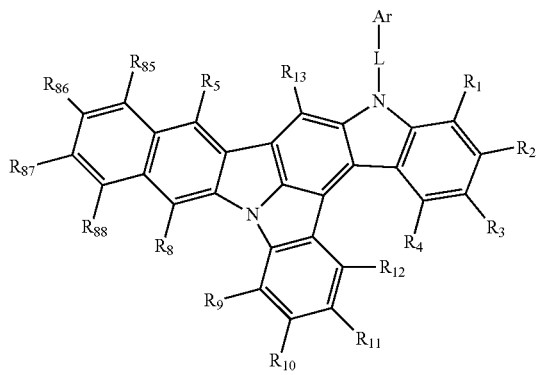

[Chemical Formula 19]

[Chemical Formula 20]

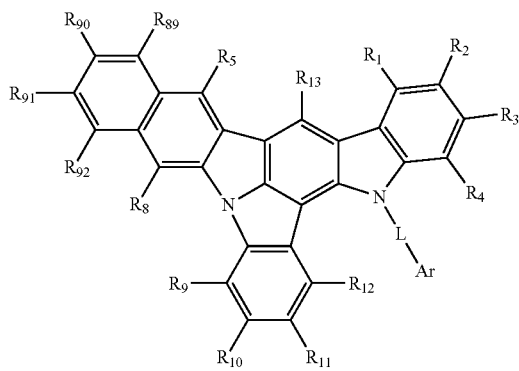

[Chemical Formula 21]

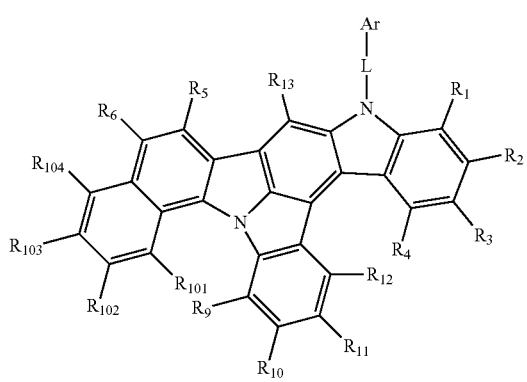

wherein in Chemical Formulae 16 to 21,

Ar is a substituted or unsubstituted bicyclic or heterocyclic group,

L is a direct bond; a substituted or unsubstituted arylene group; or a substituted or unsubstituted heteroarylene group, and $R_1$ to $R_{13}$ are the same as or different from each other, and each independently hydrogen; deuterium; a nitrile group; a substituted or unsubstituted alkyl group; a substituted or unsubstituted alkenyl group; a substituted or unsubstituted cycloalkyl group; a substituted or unsubstituted aryl group; a substituted or unsubstituted aromatic or aliphatic heterocyclic group; a substituted or unsubstituted alkoxy group; a substituted or unsubstituted aryloxy group; a substituted or unsubstituted alkylamine group; a substituted or unsubstituted arylamine group; a substituted or unsubstituted aralkylamine group; a substituted or unsubstituted alkylarylamine group; or a substituted or unsubstituted heteroarylamine group, or combine with an adjacent substituent to form a ring, and $R_{69}$ to $R_{108}$ are the same as or different from each other, and each independently hydrogen; deuterium; a nitrile group; a substituted or unsubstituted alkyl group; a substituted or unsubstituted alkenyl group; a substituted or unsubstituted cycloalkyl group; a substituted or unsubstituted aryl group; a substituted or unsubstituted aromatic or aliphatic heterocyclic group; a substituted or unsubstituted alkoxy group; a substituted or unsubstituted aryloxy group; a substituted or unsubstituted alkylamine group; a substituted or unsubstituted arylamine group; a substituted or unsubstituted aralkylamine group; a substituted or unsubstituted alkylarylamine group; or a substituted or unsubstituted heteroarylamine group, or combine with an adjacent substituent to form a ring.

7. A compound represented by one of the following Chemical Formulae 22 to 27:

[Chemical Formula 22]

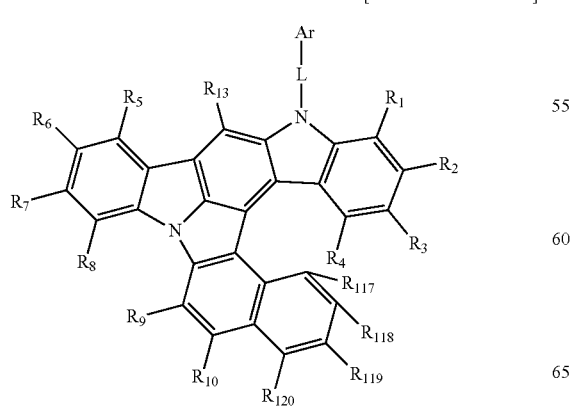

-continued

[Chemical Formula 23]

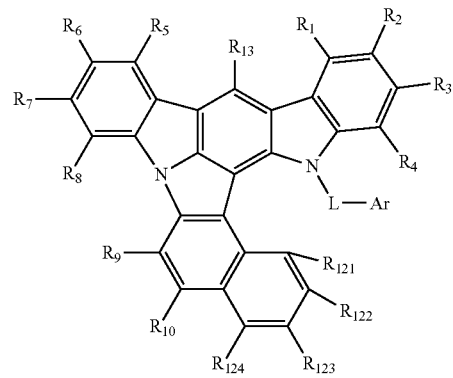

[Chemical Formula 24]

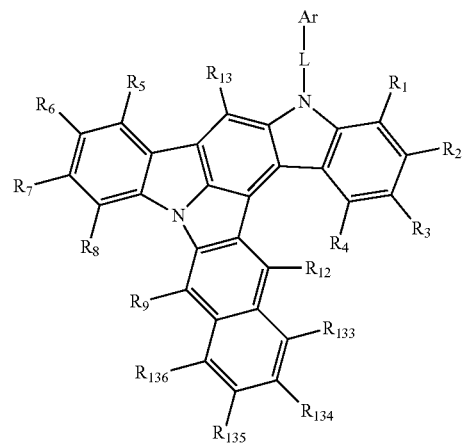

[Chemical Formula 25]

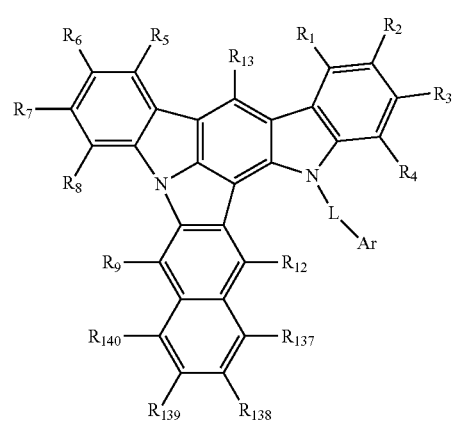

-continued

[Chemical Formula 26]

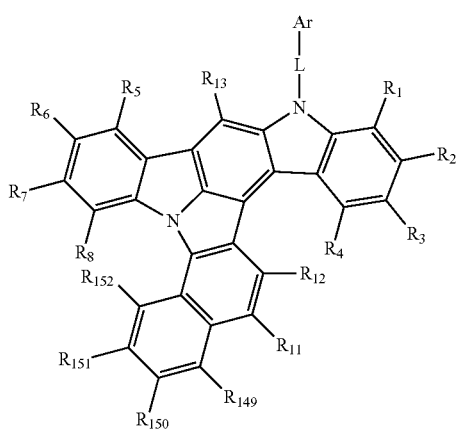

[Chemical Formula 27]

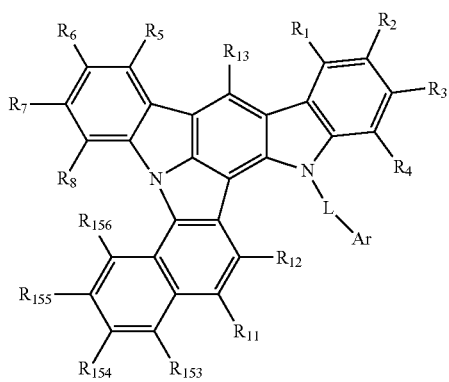

wherein in Chemical Formulae 22 to 27,

Ar is a substituted or unsubstituted bicyclic or heterocyclic group,

L is a direct bond; a substituted or unsubstituted arylene group; or a substituted or unsubstituted heteroarylene group, and $R_1$ to $R_{13}$ are the same as or different from each other, and each independently hydrogen; deuterium; a nitrile group; a substituted or unsubstituted alkyl group; a substituted or unsubstituted alkenyl group; a substituted or unsubstituted cycloalkyl group; a substituted or unsubstituted aryl group; a substituted or unsubstituted aromatic or aliphatic heterocyclic group; a substituted or unsubstituted alkoxy group; a substituted or unsubstituted aryloxy group; a substituted or unsubstituted alkylamine group; a substituted or unsubstituted arylamine group; a substituted or unsubstituted aralkylamine group; a substituted or unsubstituted alkylarylamine group; or a substituted or unsubstituted heteroarylamine group, or combine with an adjacent substituent to form a ring, and $R_{117}$ to $R_{156}$ are the same as or different from each other, and each independently hydrogen; deuterium; a nitrile group; a substituted or unsubstituted alkyl group; a substituted or unsubstituted alkenyl group; a substituted or unsubstituted cycloalkyl group; a substituted or unsubstituted aryl group; a substituted or unsubstituted aromatic or aliphatic heterocyclic group; a substituted or unsubstituted alkoxy group; a substituted or unsubstituted aryloxy group; a substituted or unsubstituted alkylamine group; a substituted or unsubstituted arylamine group; a substituted or unsubstituted aralkylamine group; a substituted or unsubstituted alkylarylamine group; or a substituted or unsubstituted heteroarylamine group, or combine with an adjacent substituent to form a ring.

8. A compound represented by any one of the following compounds:

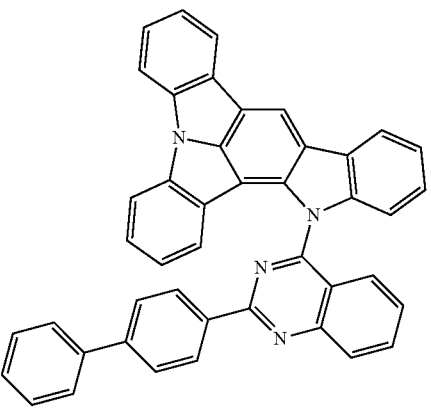

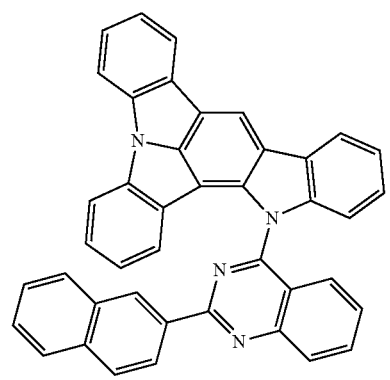

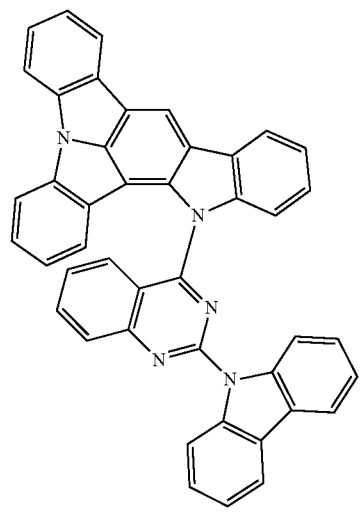

889
-continued
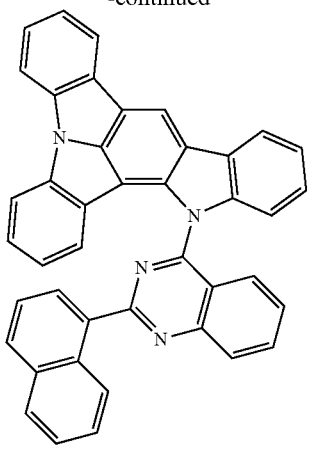
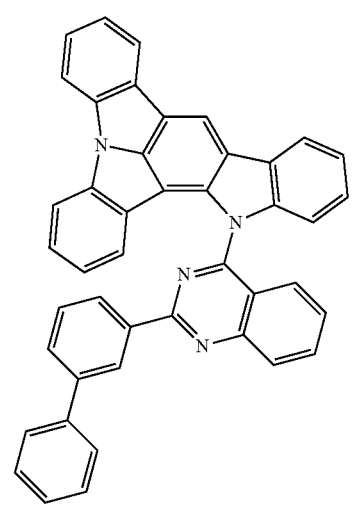
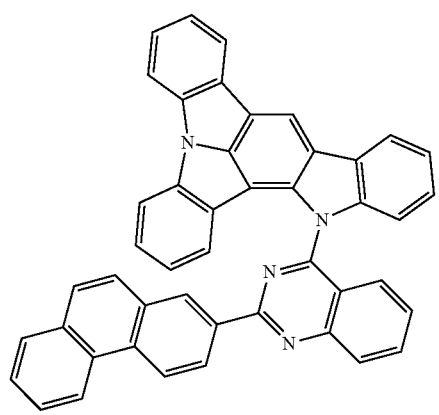
890
-continued
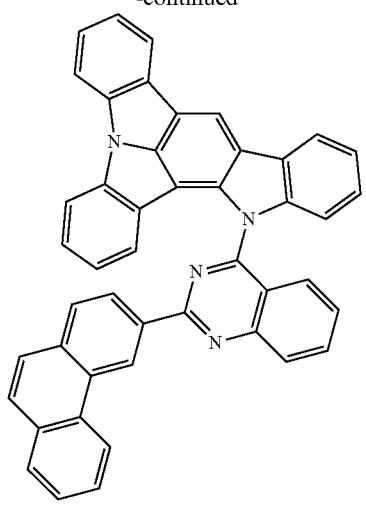
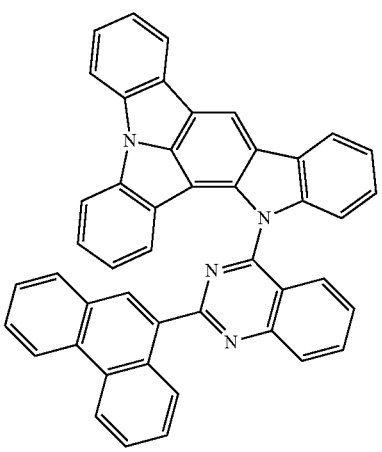
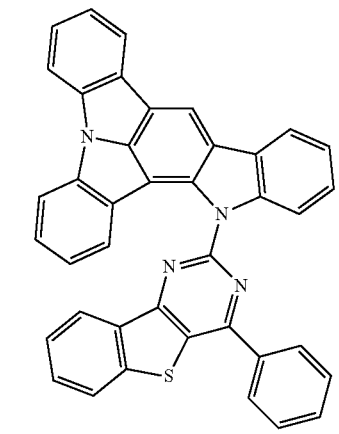

891
-continued
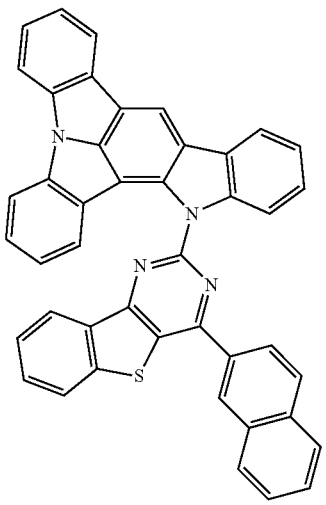
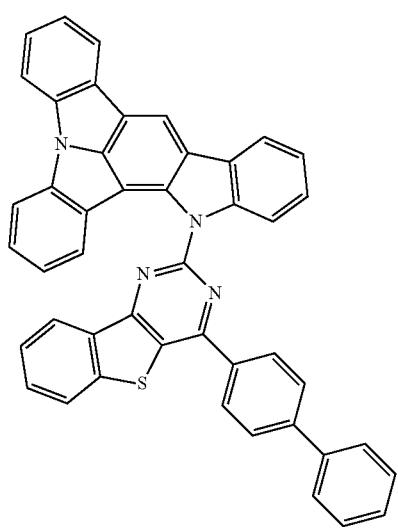
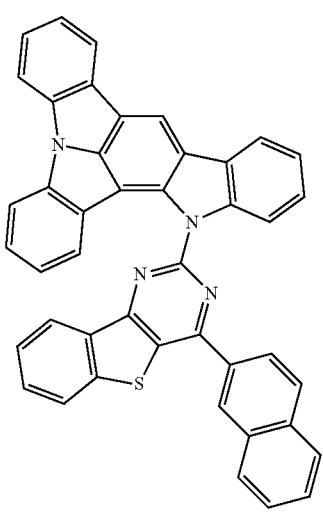
892
-continued
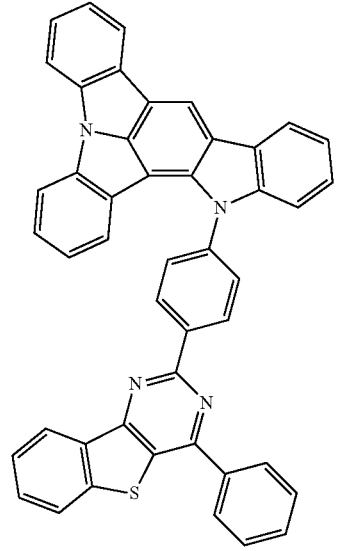
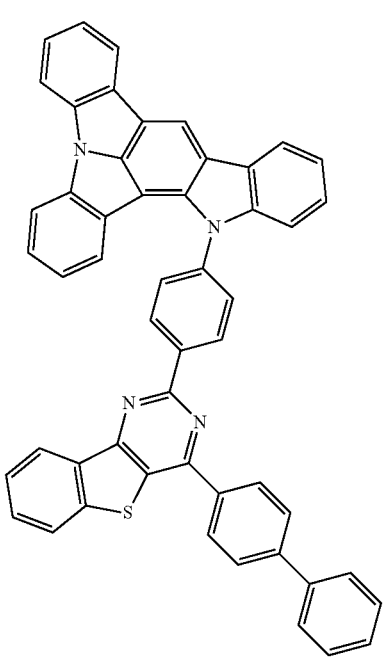
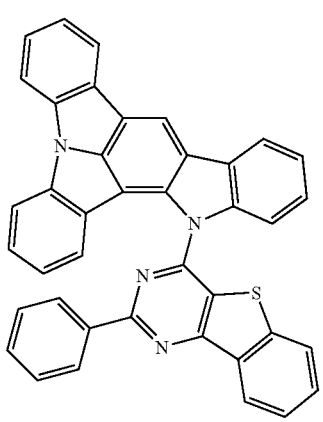

893
-continued
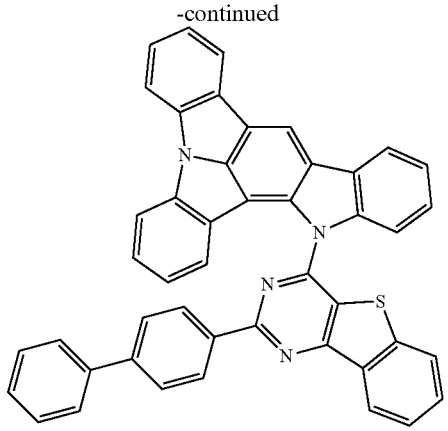
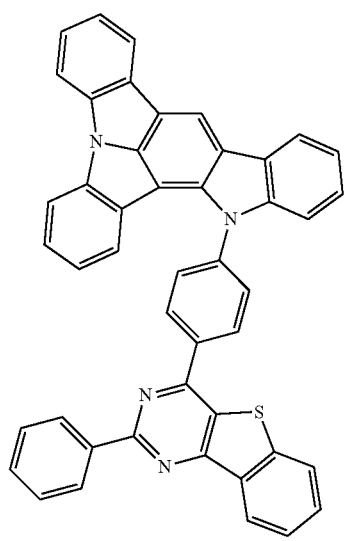
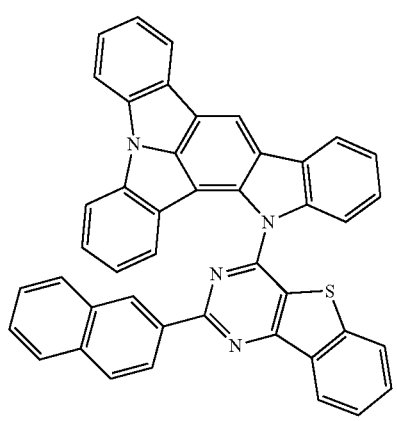
894
-continued
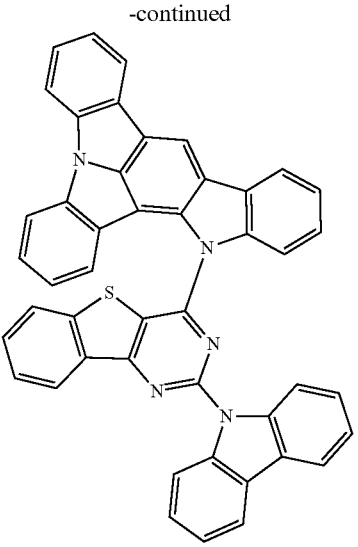
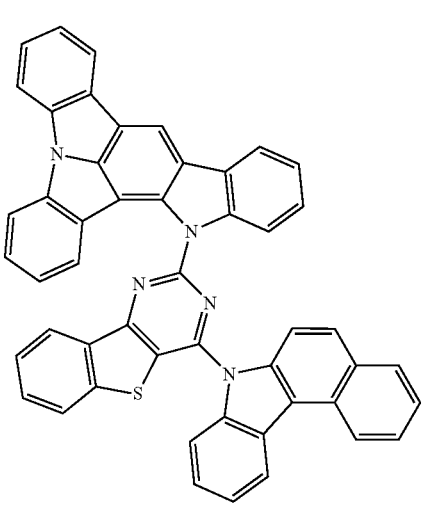
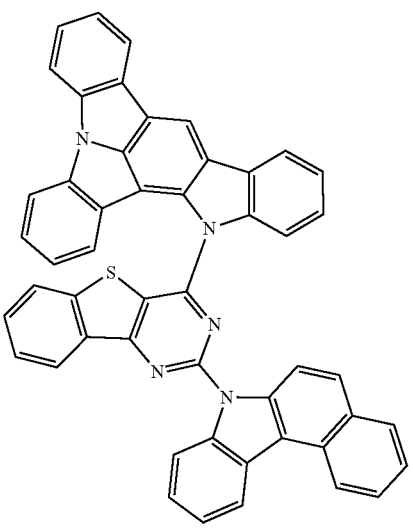

895
-continued
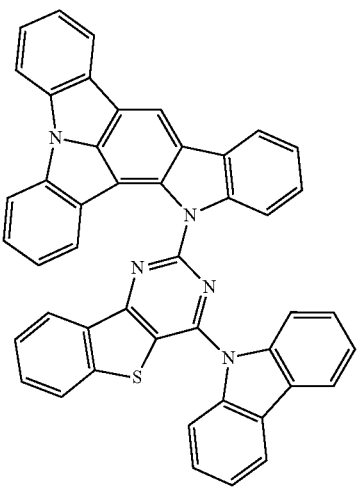
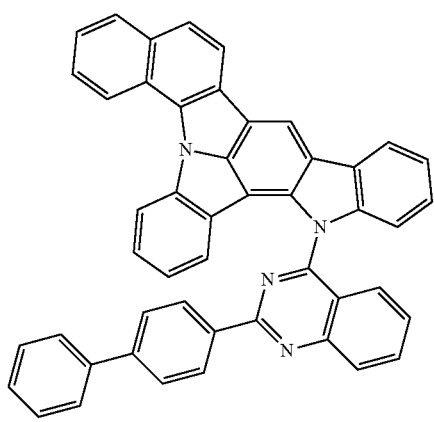
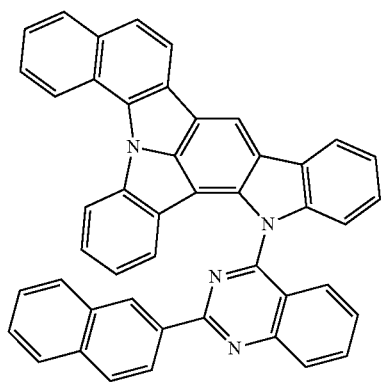
896
-continued
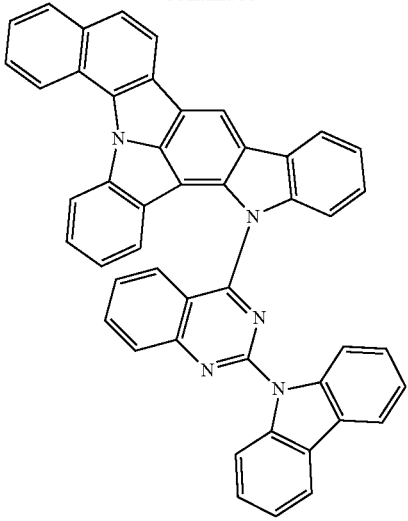
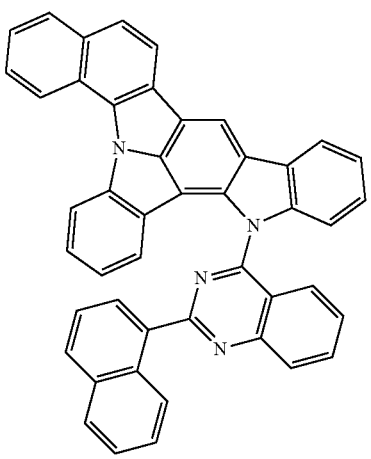
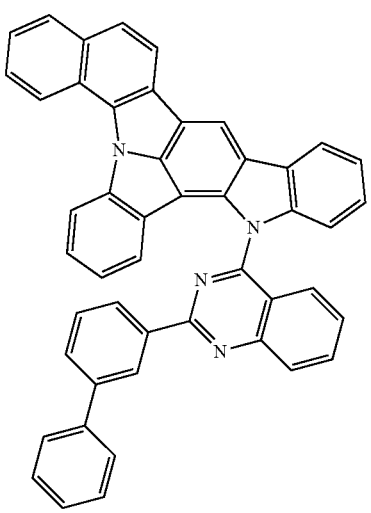

897
-continued
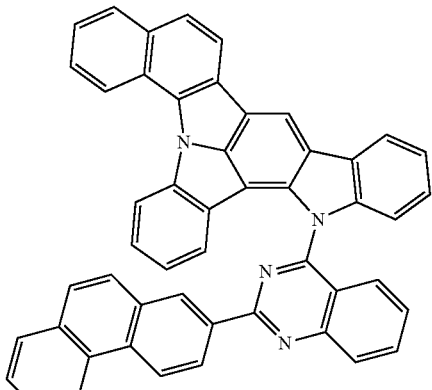
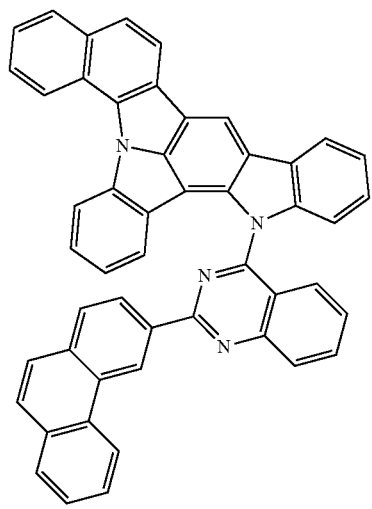
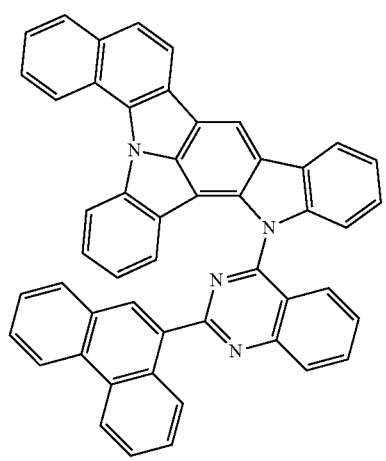
898
-continued
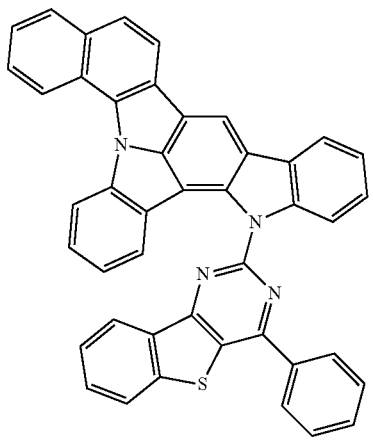
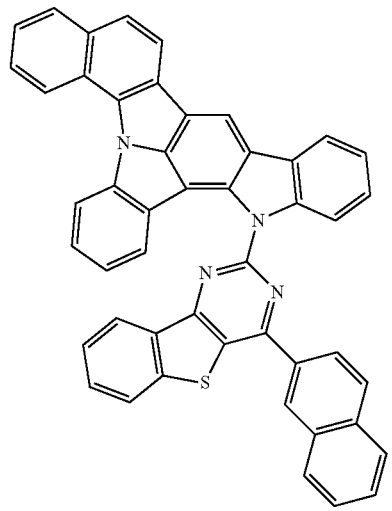
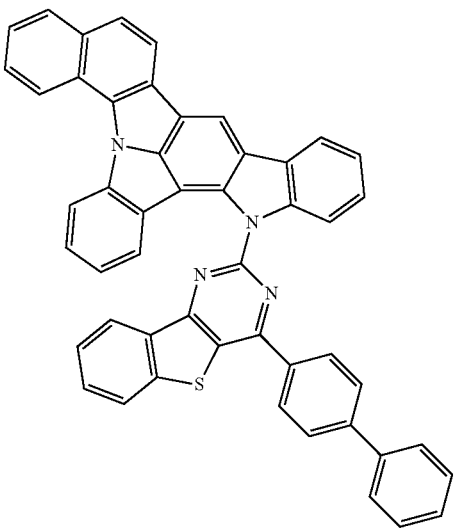

899
-continued
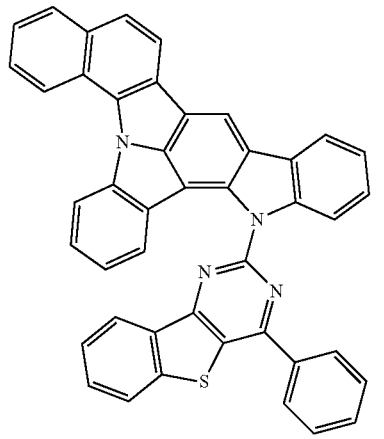
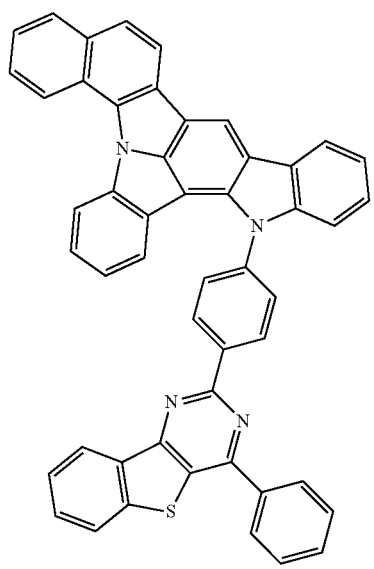
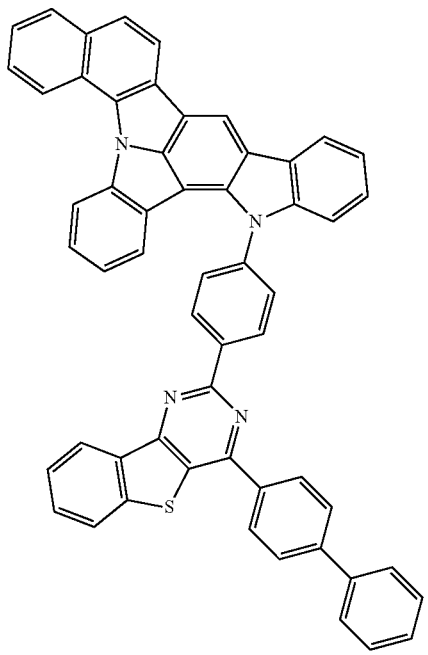
900
-continued
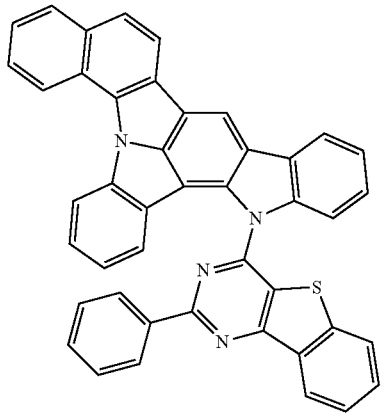
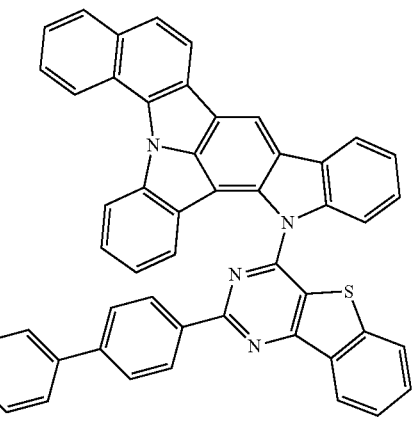
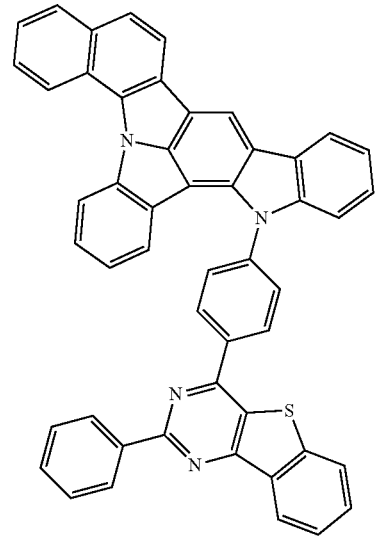

901
-continued
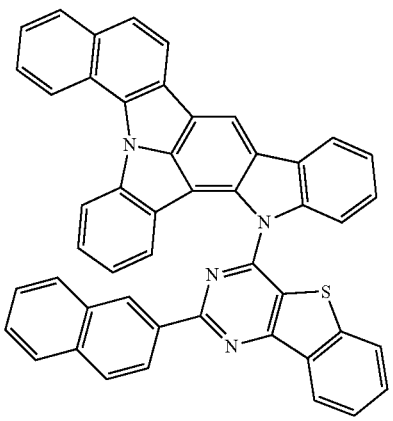
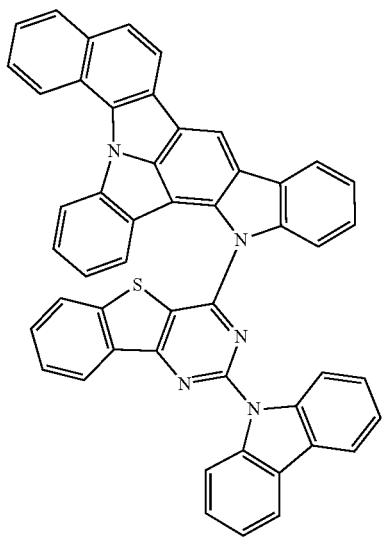
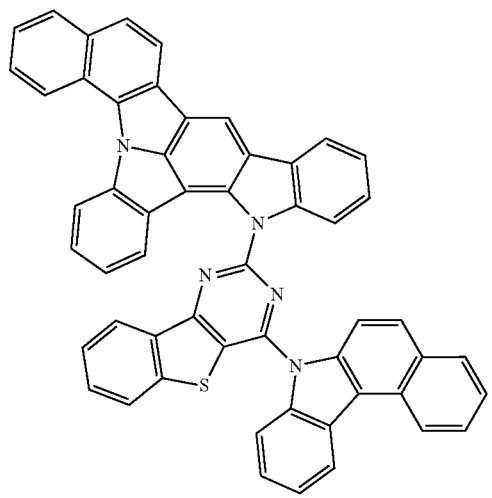
902
-continued
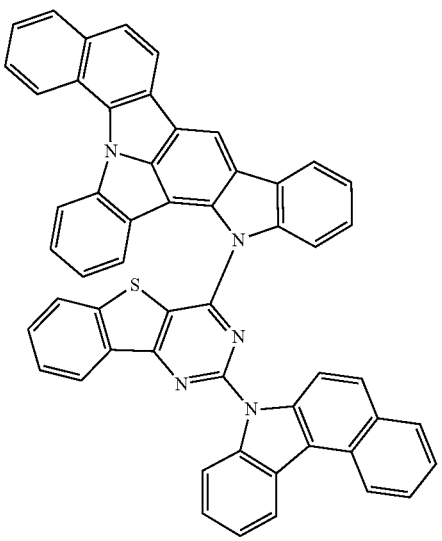
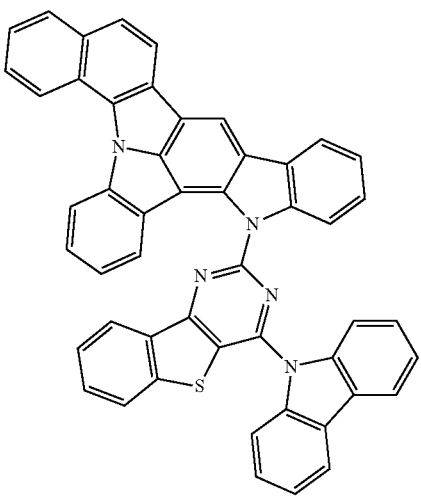
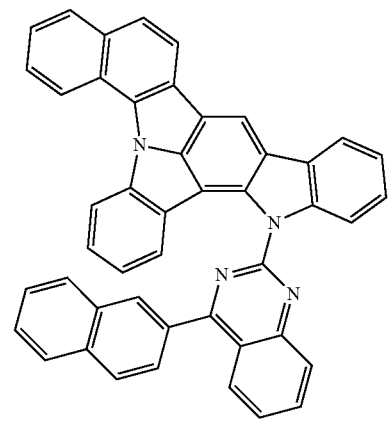

903
-continued
904
-continued
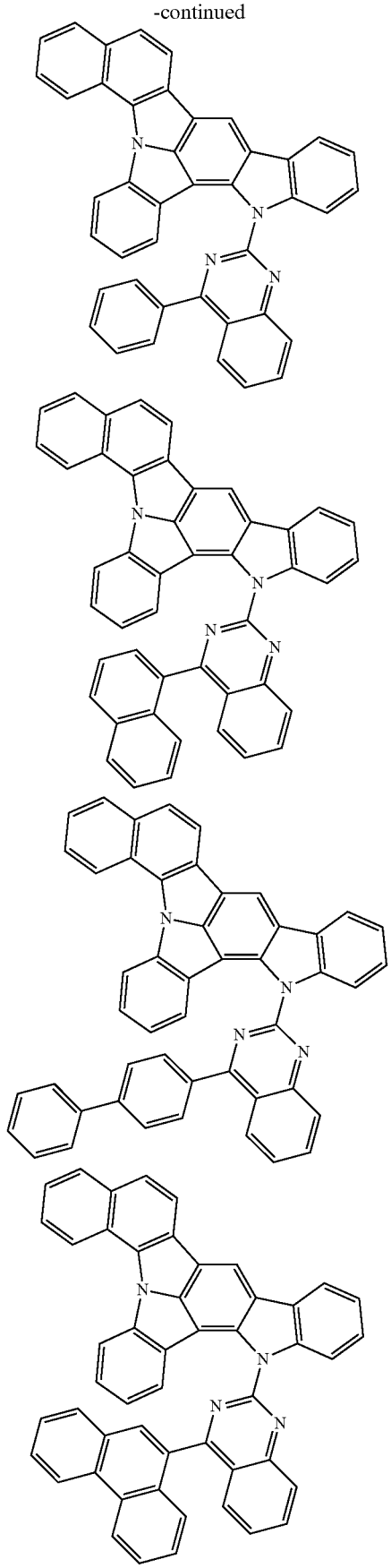
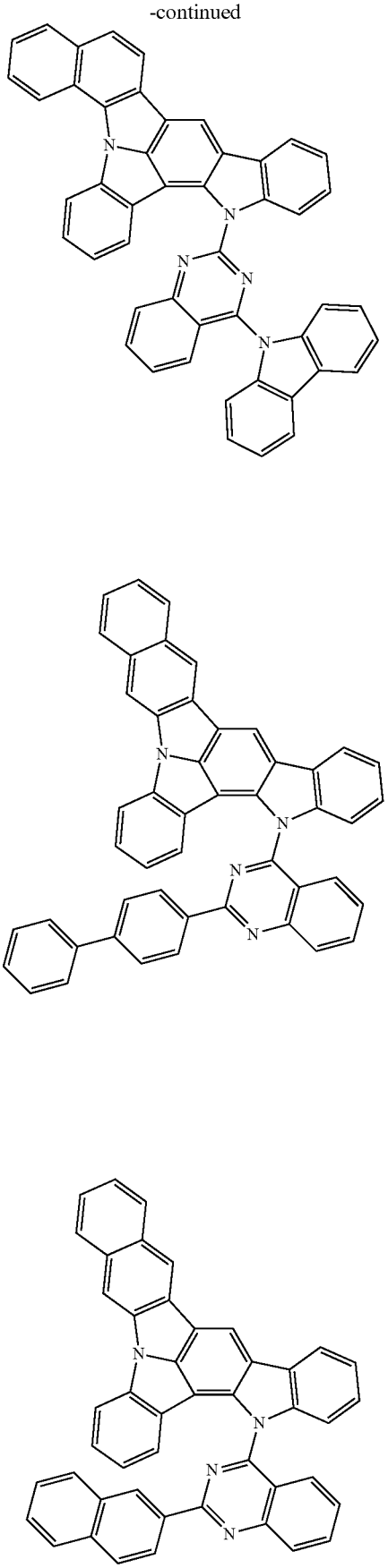

905
-continued
906
-continued
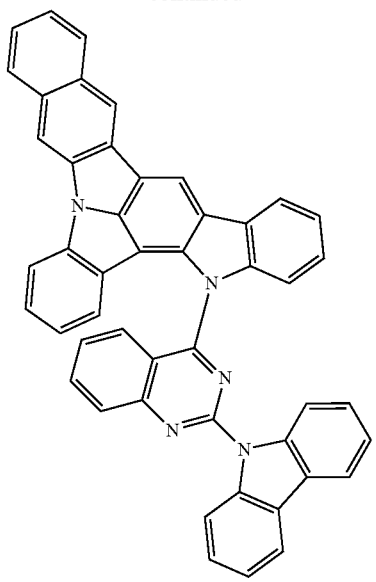
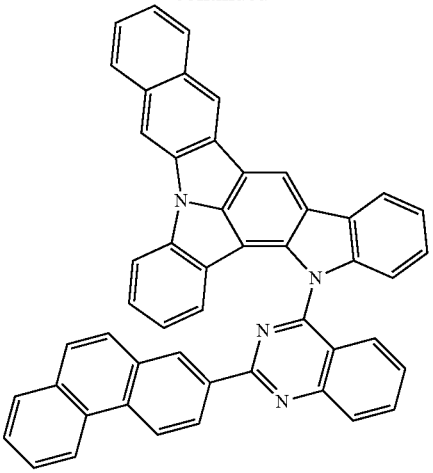
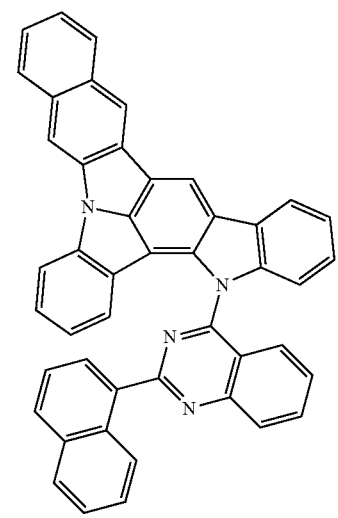
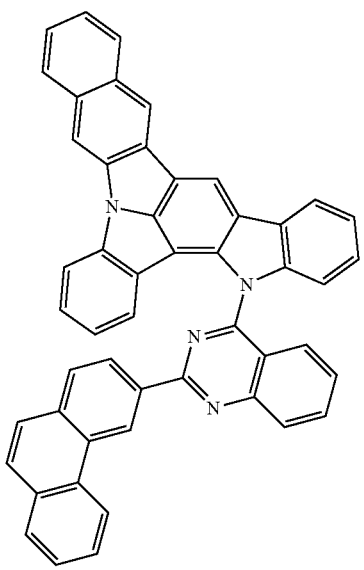
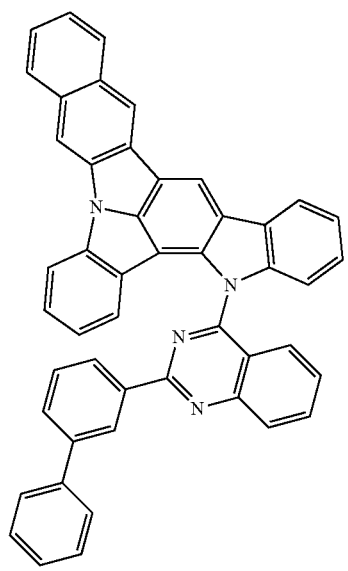

907
-continued
908
-continued
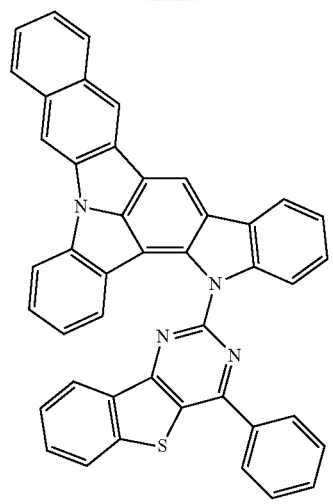
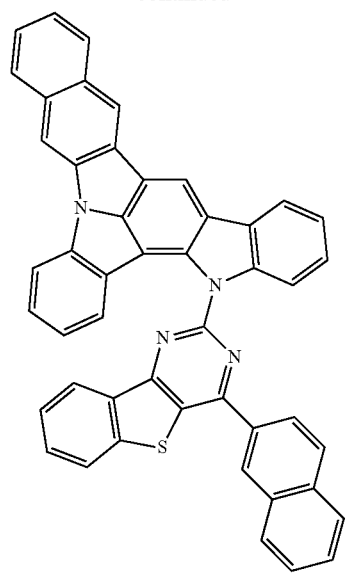

909
-continued
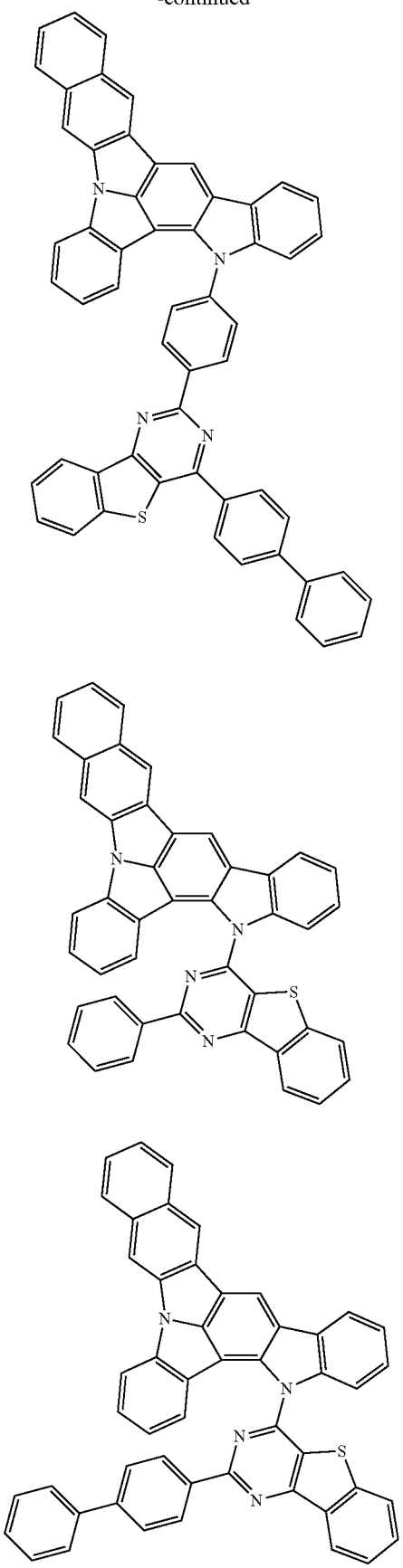 [SMILES: c1ccc(-c2ccc(-c3nc(-c4ccc(-n5c6ccccc6c6cc7c8cc9ccccc9cc8n8c9ccccc9c(c65)c78)cc4)nc4c3sc3ccccc34)cc2)cc1 ; c1ccc(-c2nc(-n3c4ccccc4c4cc5c6cc7ccccc7cc6n6c7ccccc7c(c43)c56)c3sc4ccccc4c3n2)cc1 ; c1ccc(-c2ccc(-c3nc(-n4c5ccccc5c5cc6c7cc8ccccc8cc7n7c8ccccc8c(c54)c67)c4sc5ccccc5c4n3)cc2)cc1]
910
-continued
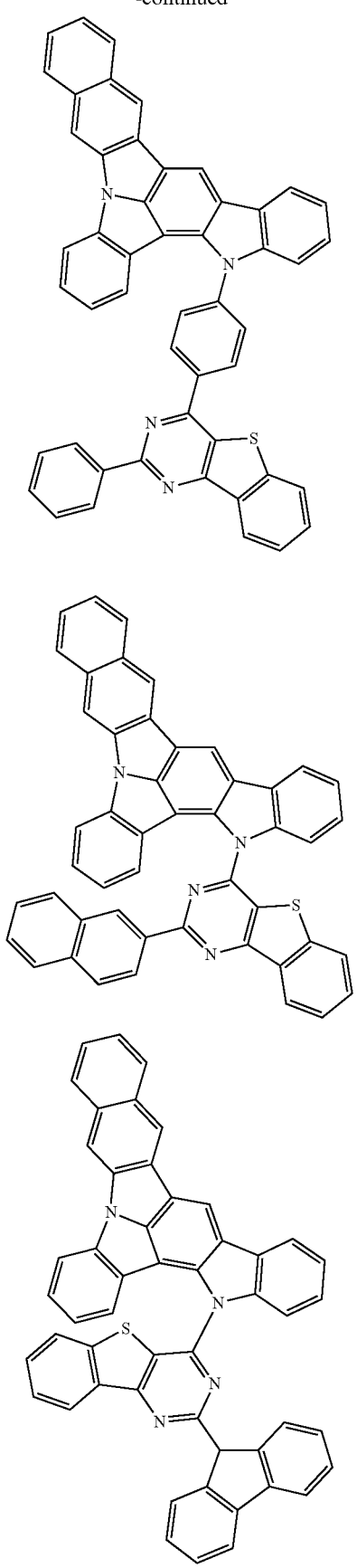

911
-continued
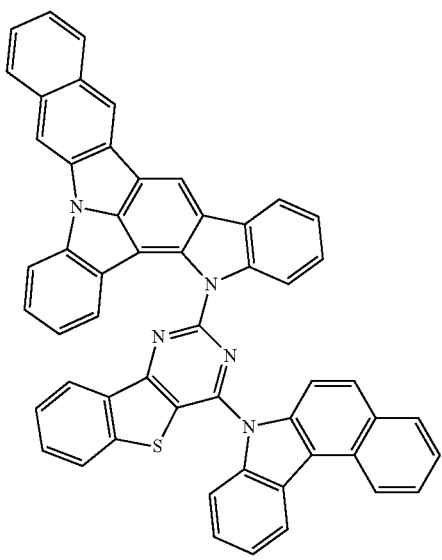
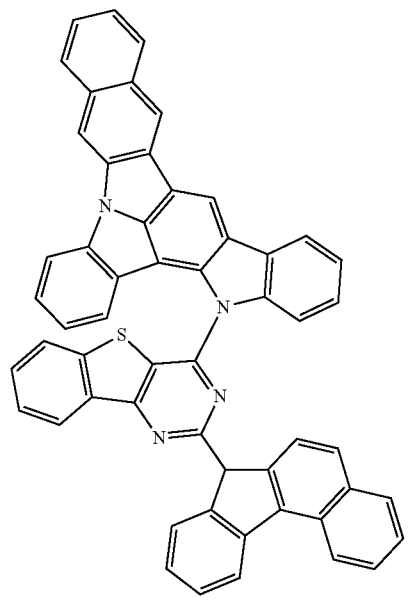
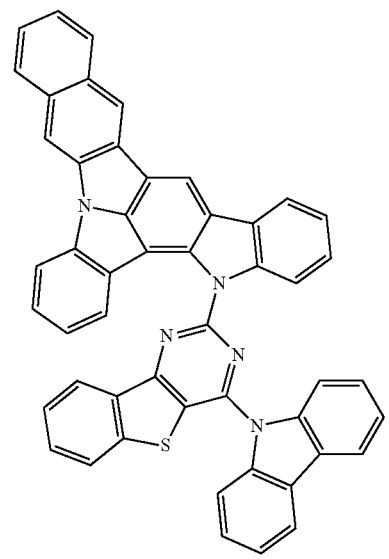
912
-continued
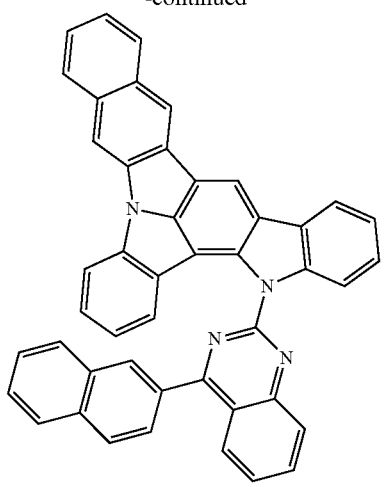
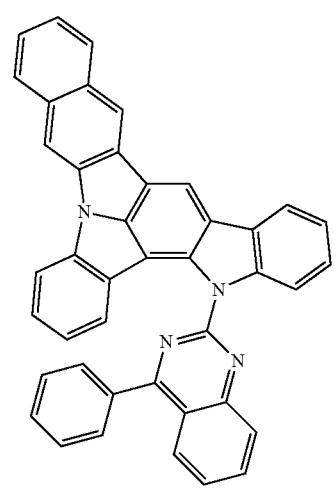
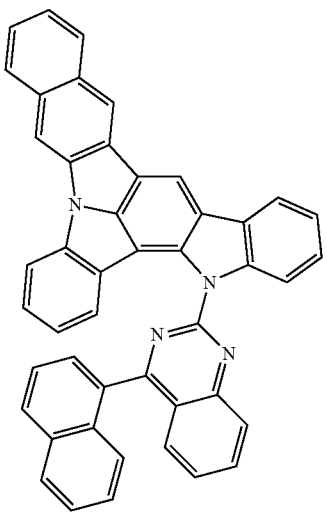

913
-continued
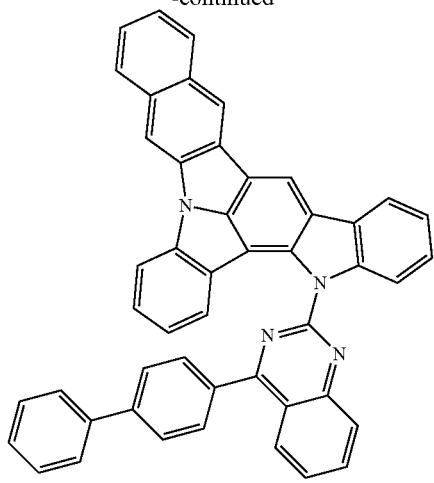
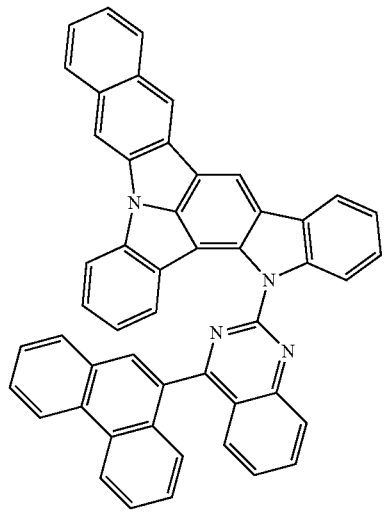
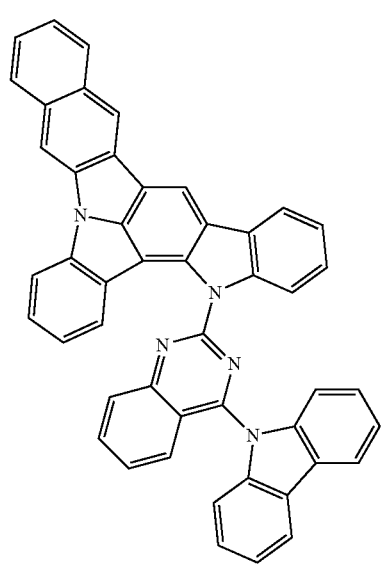
914
-continued
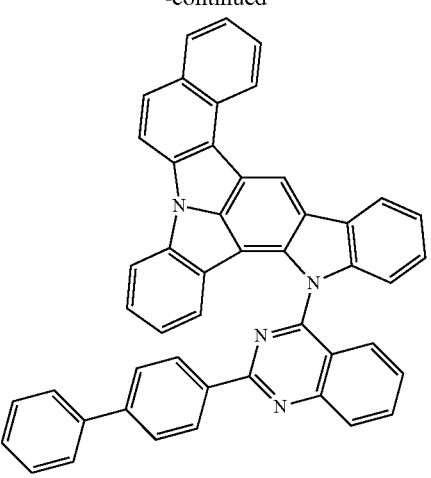
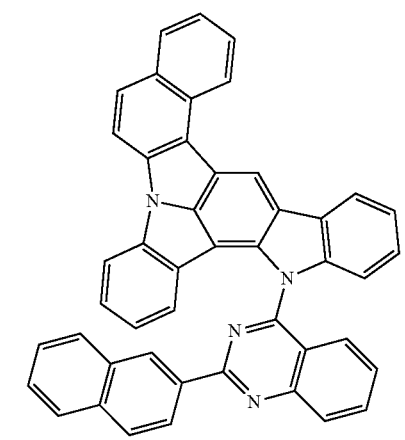
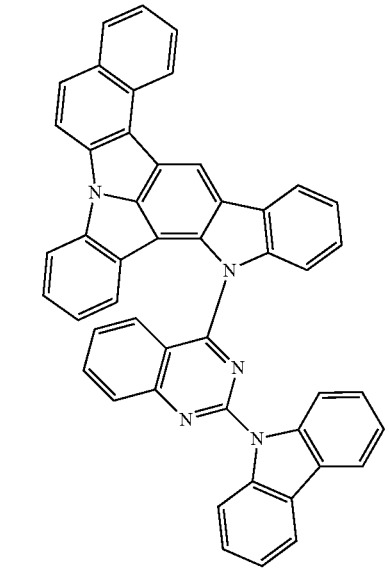

915
-continued
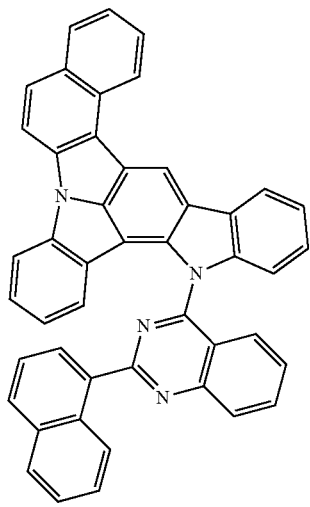
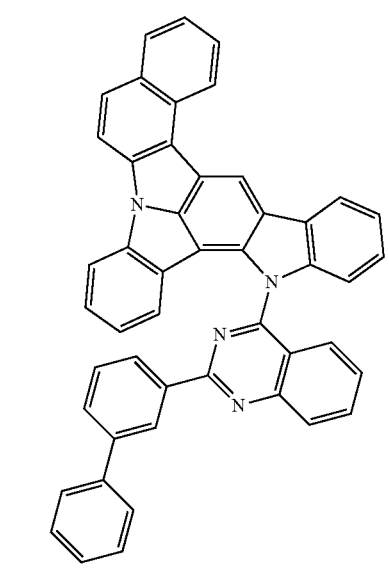
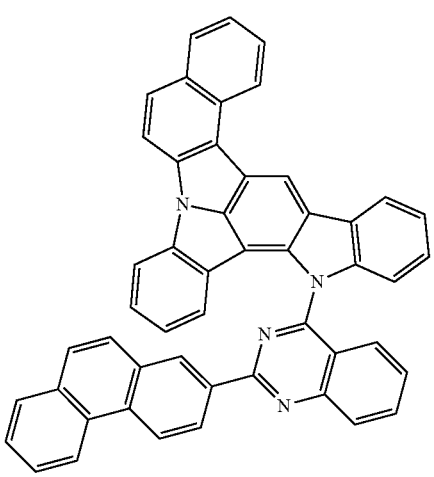
916
-continued
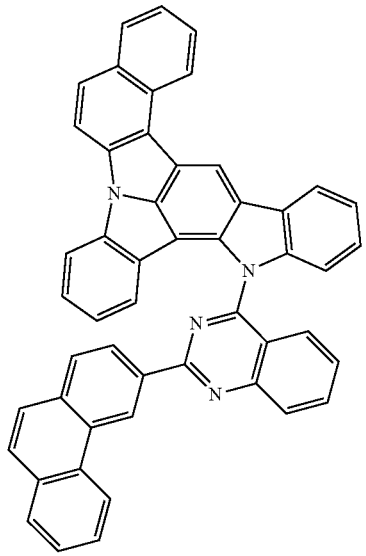
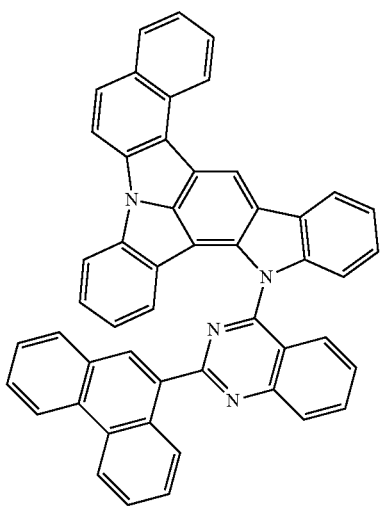
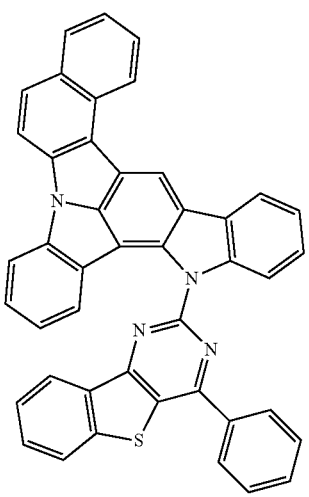

917
-continued
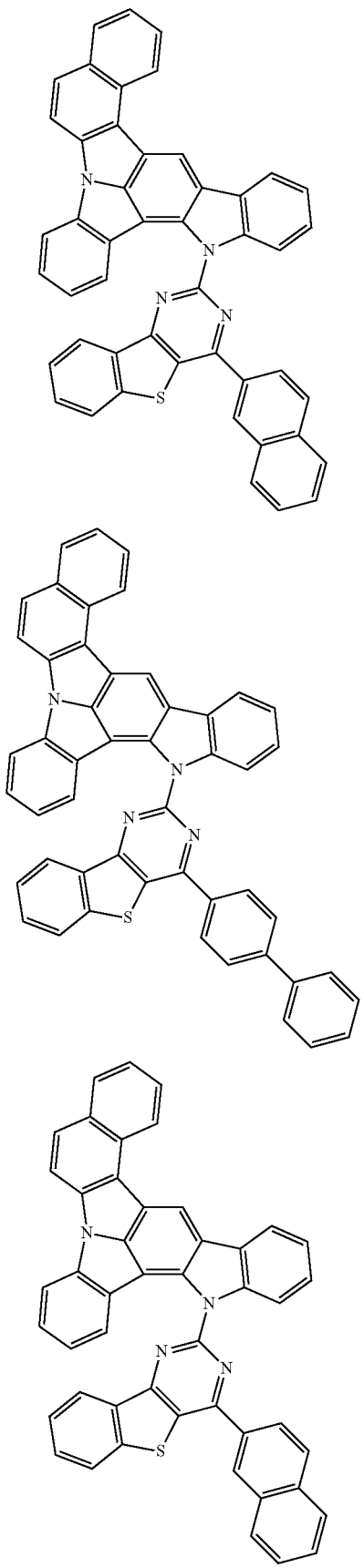 [SMILES: c1ccc2cc(-c3nc(-n4c5ccccc5c5cc6c7c8ccccc8ccc7n7c8ccccc8c(c54)c67)nc4c3sc3ccccc34)ccc2c1 ; c1ccc(-c2ccc(-c3nc(-n4c5ccccc5c5cc6c7c8ccccc8ccc7n7c8ccccc8c(c54)c67)nc4c3sc3ccccc34)cc2)cc1 ; c1ccc2cc(-c3nc(-n4c5ccccc5c5cc6c7c8ccccc8ccc7n7c8ccccc8c(c54)c67)nc4c3sc3ccccc34)ccc2c1]
918
-continued
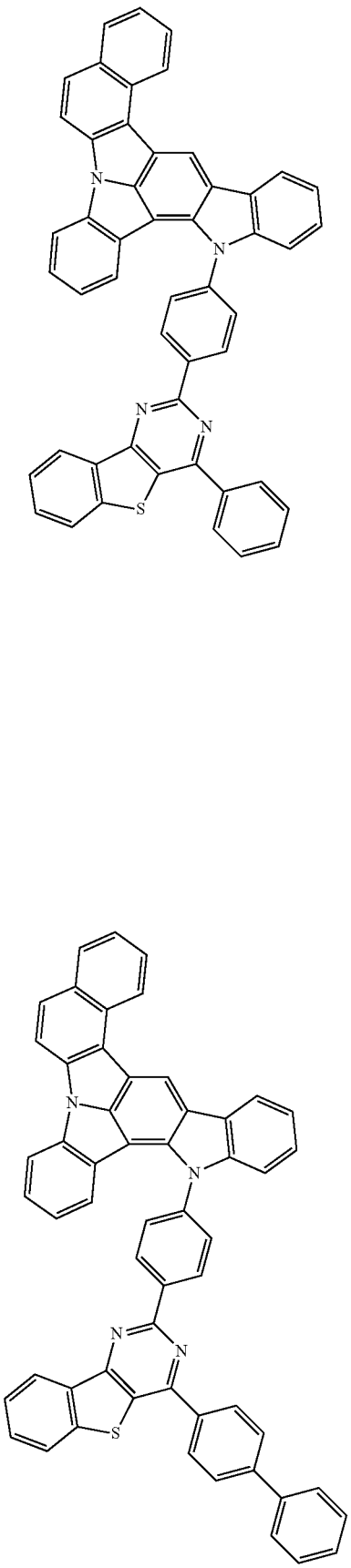

919
-continued
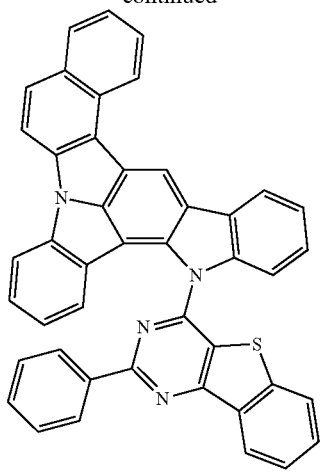
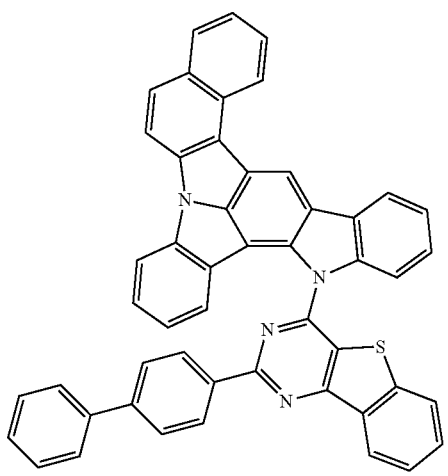
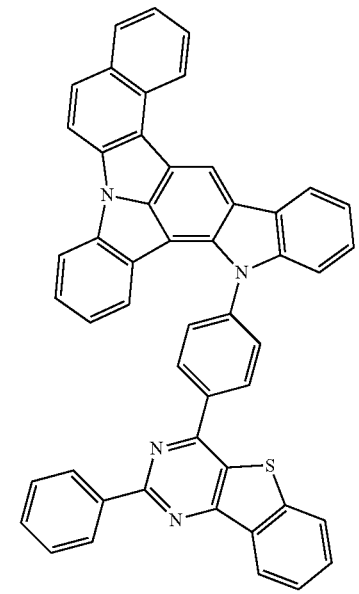
920
-continued
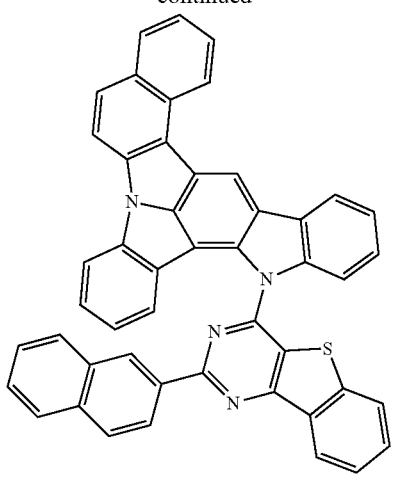
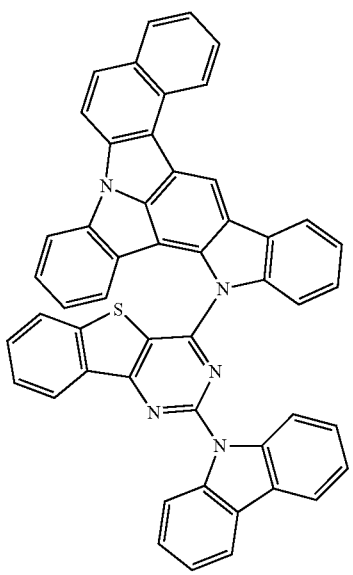
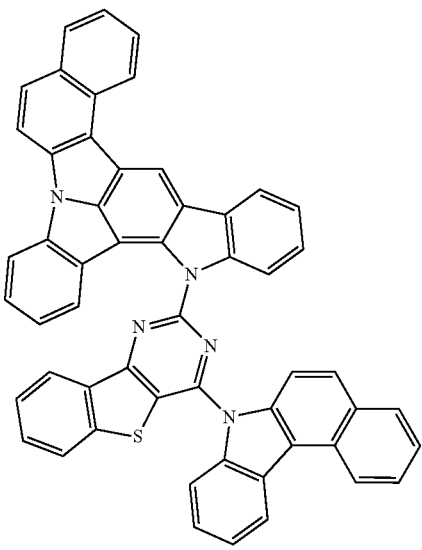

921
-continued
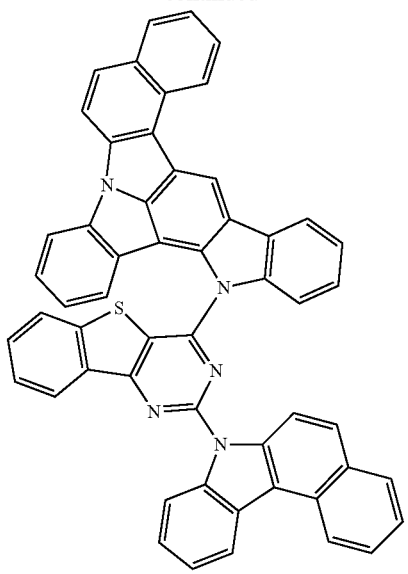
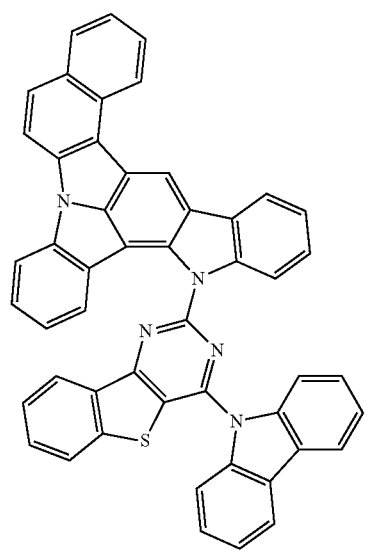
922
-continued
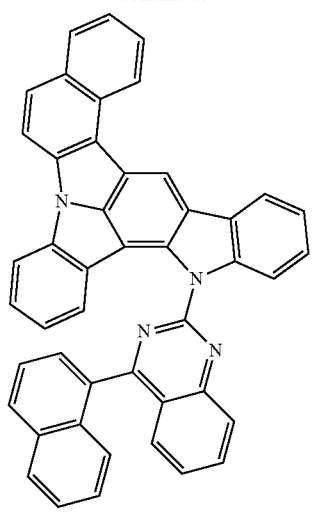
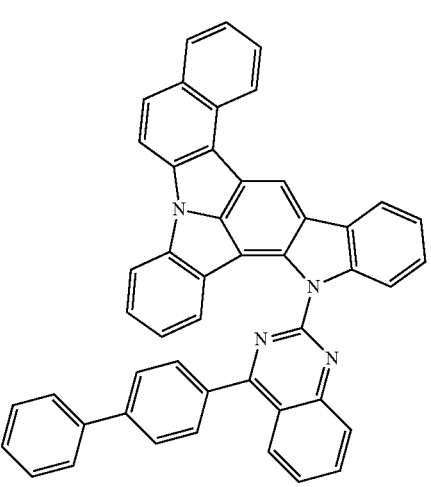
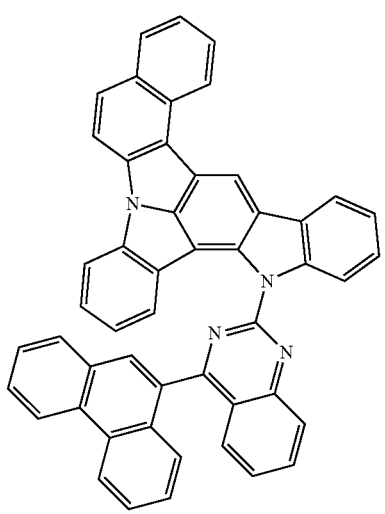

923 -continued
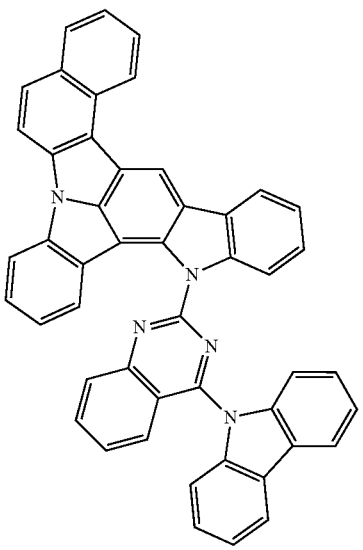
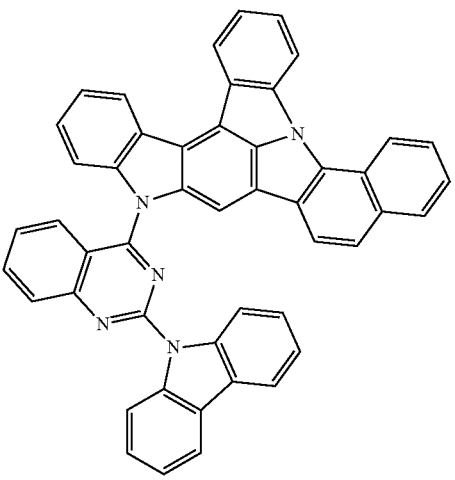
924 -continued
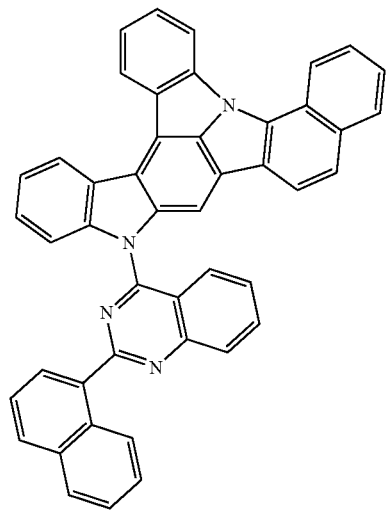
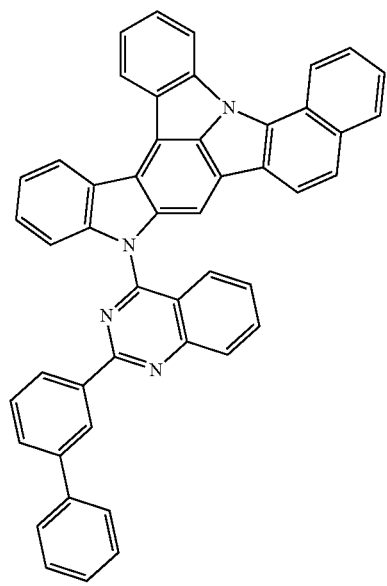

925
-continued
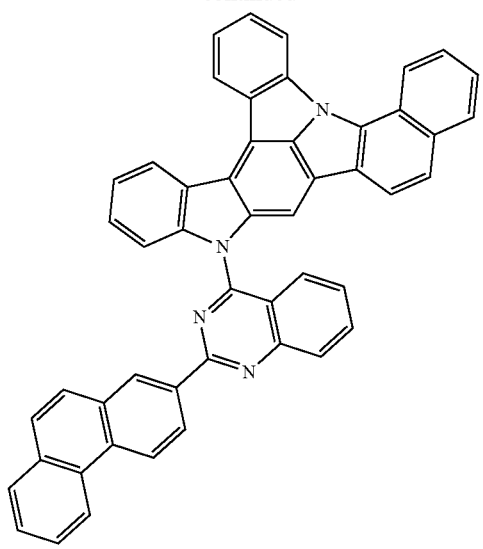
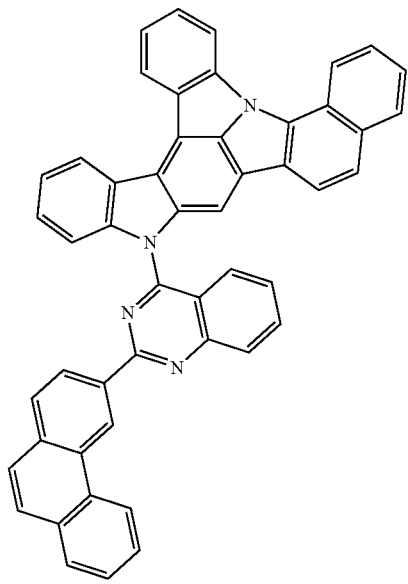
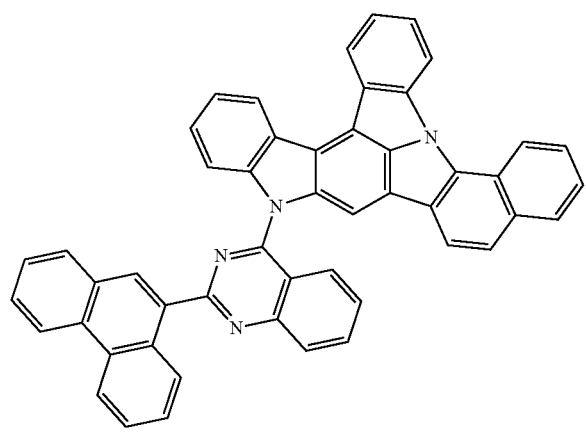
926
-continued
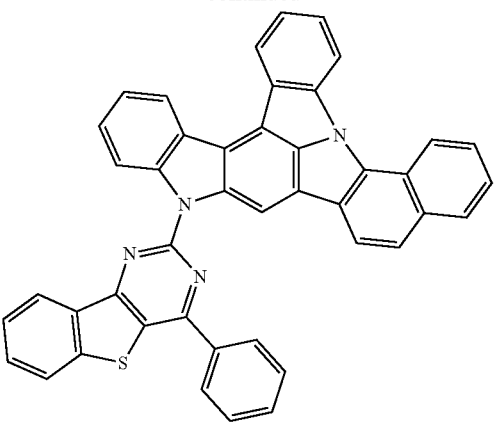
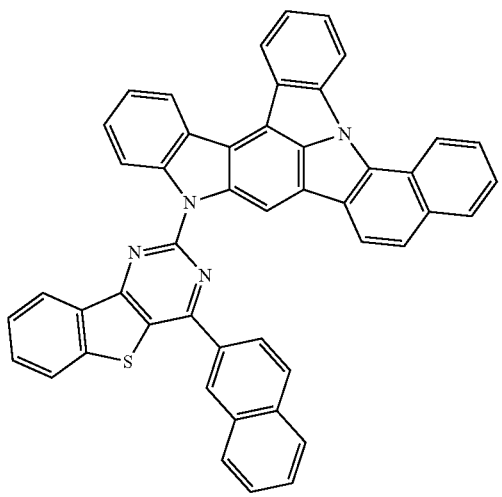
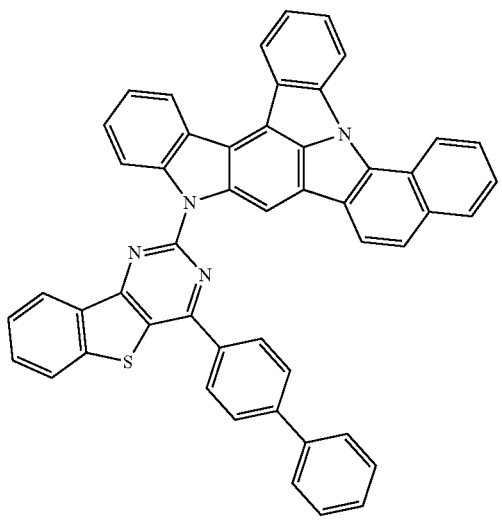

927
-continued
928
-continued
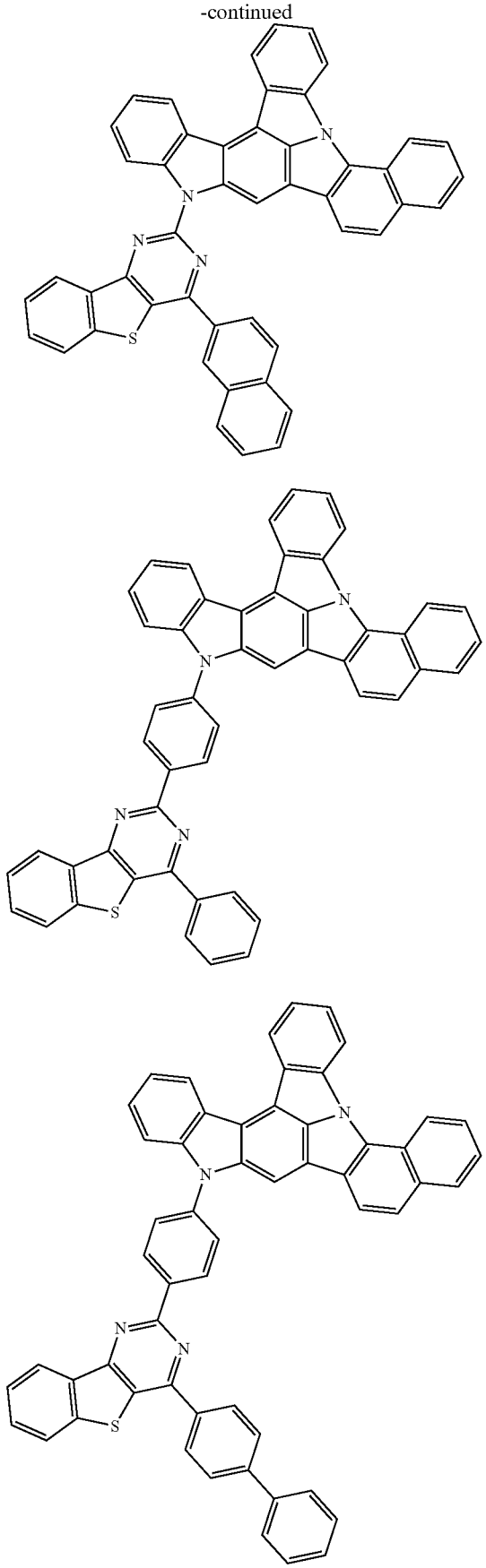
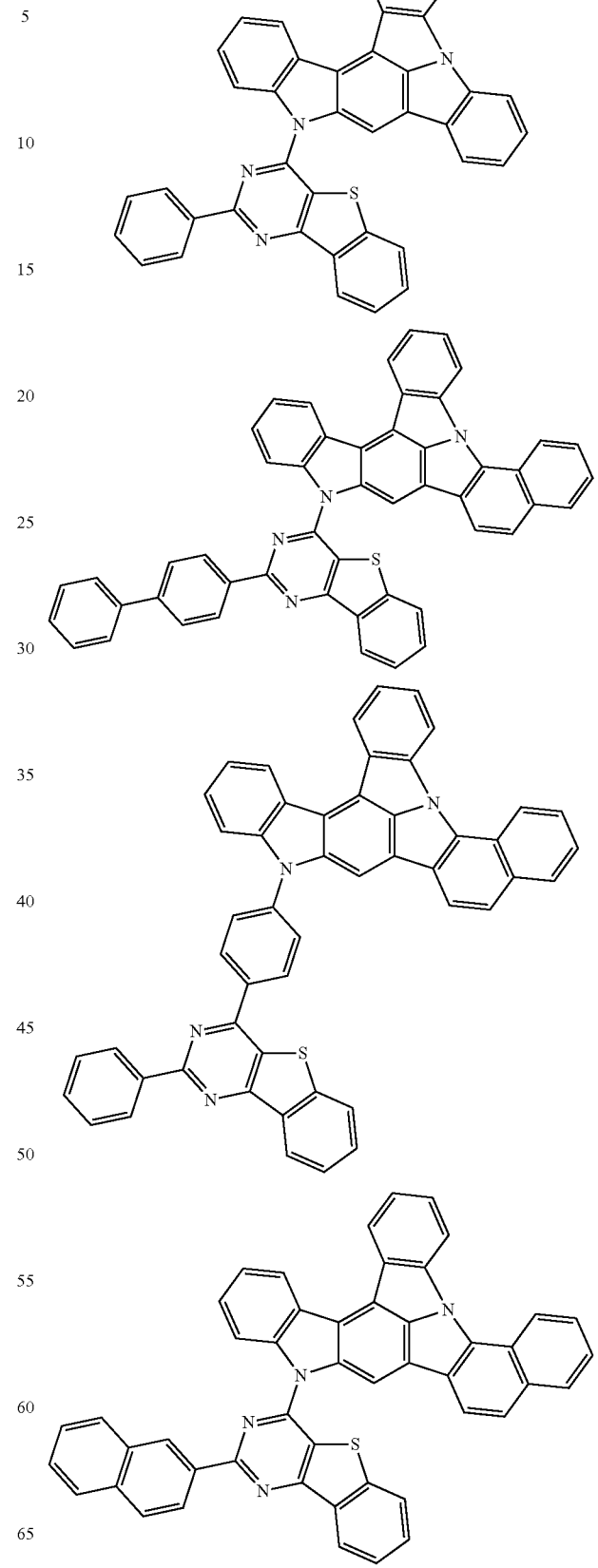

929
-continued
930
-continued
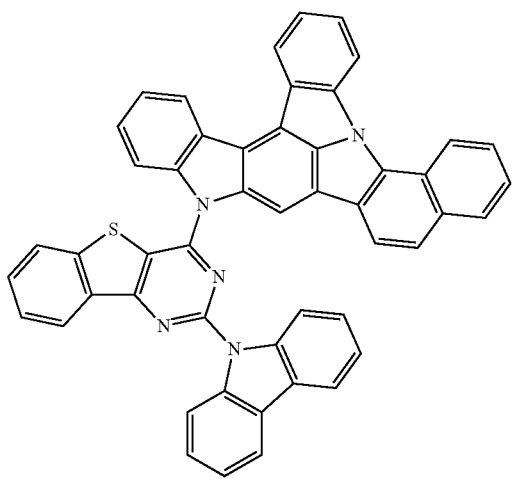
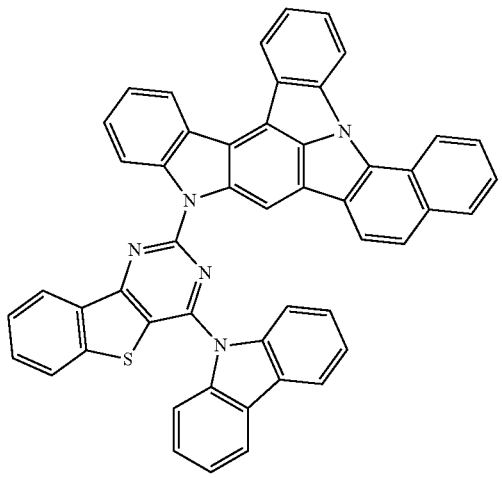
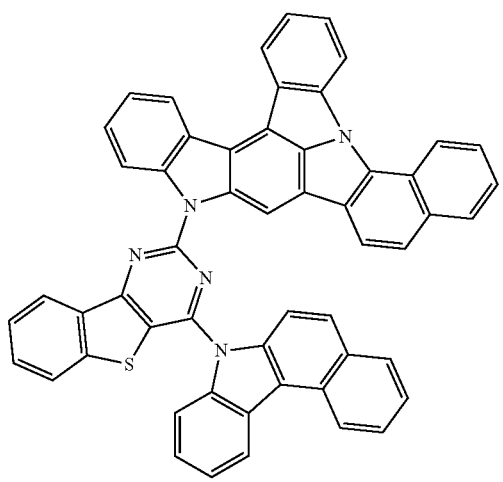
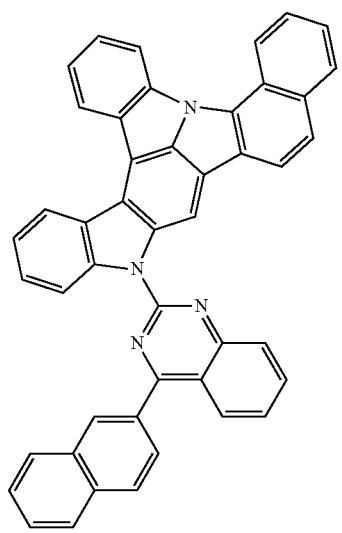
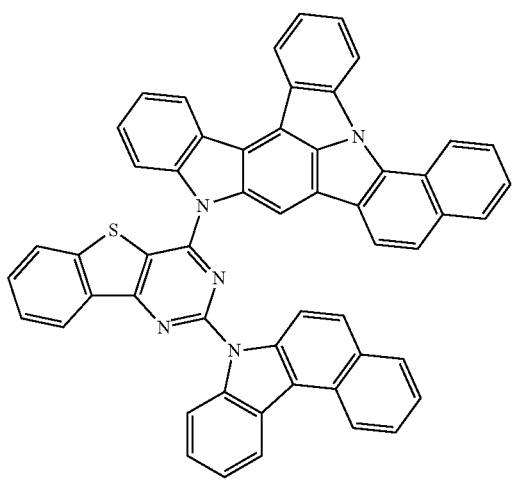
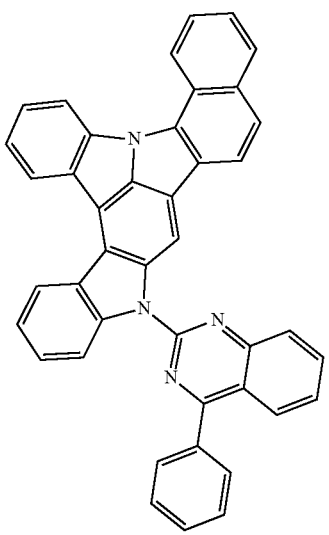

931
-continued
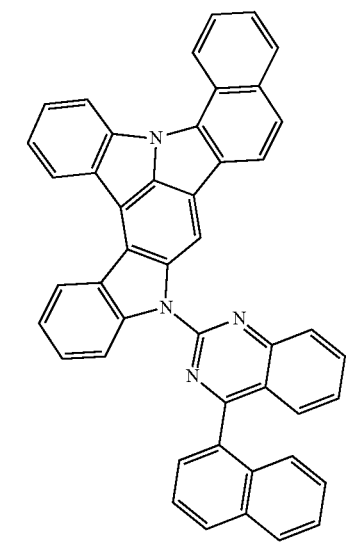
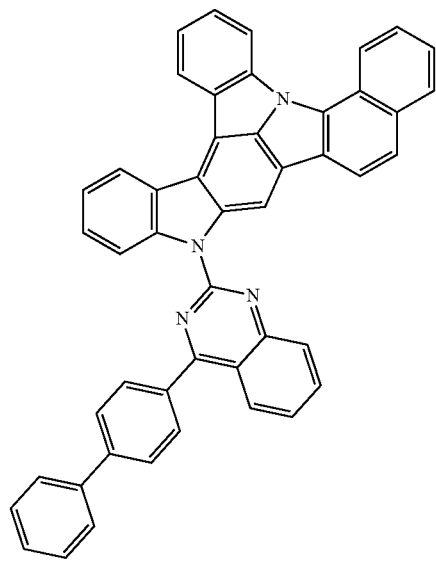
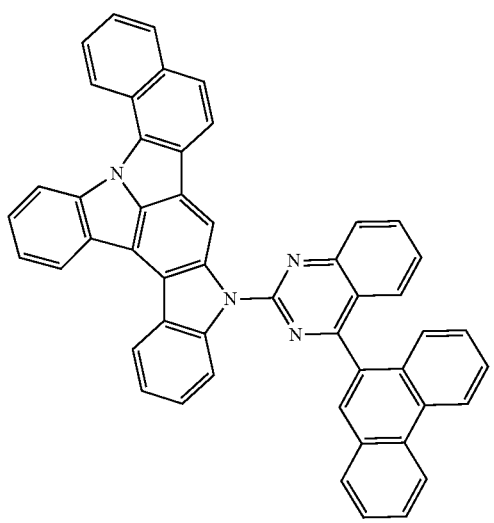
932
-continued
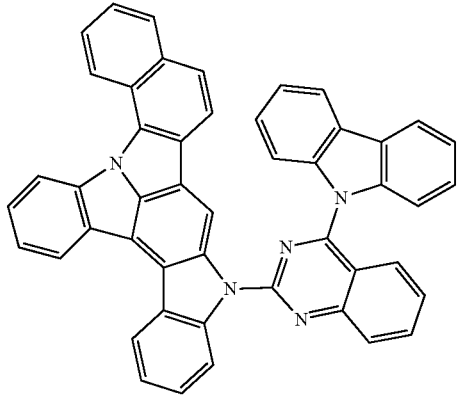
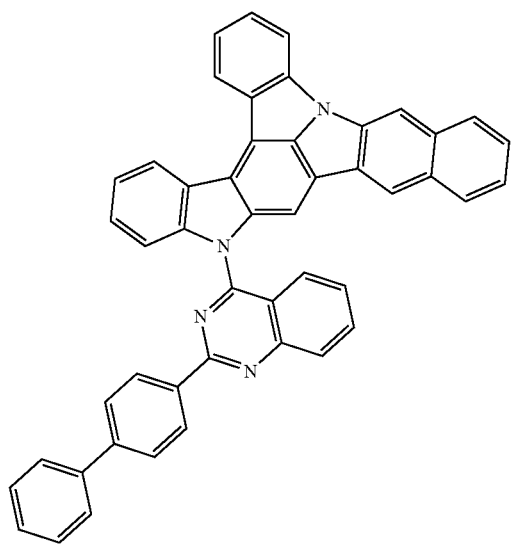
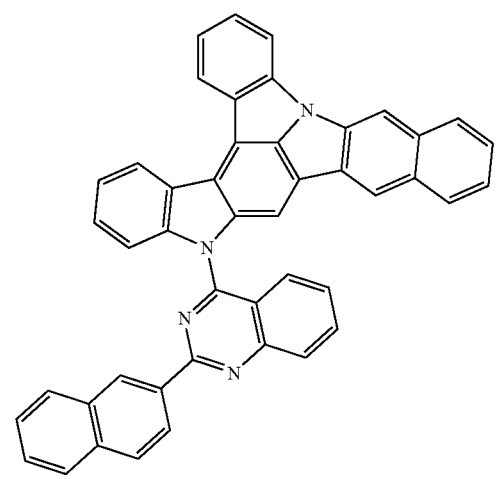

933
-continued
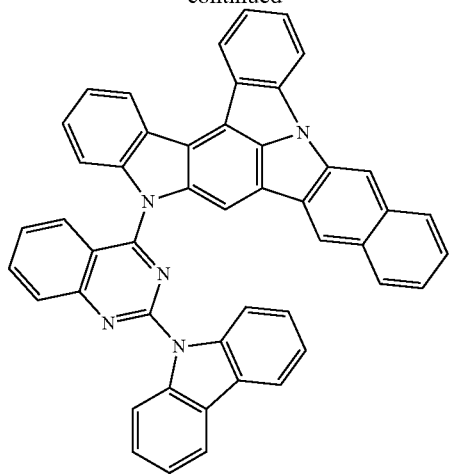
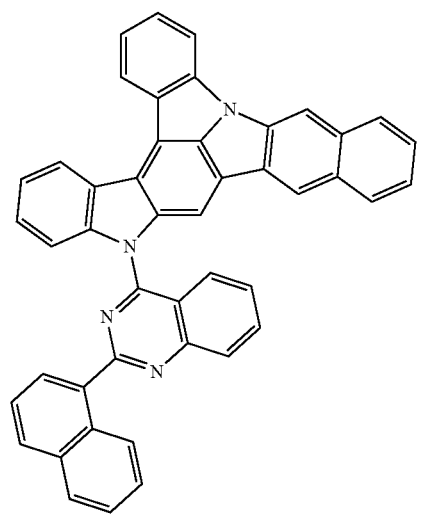
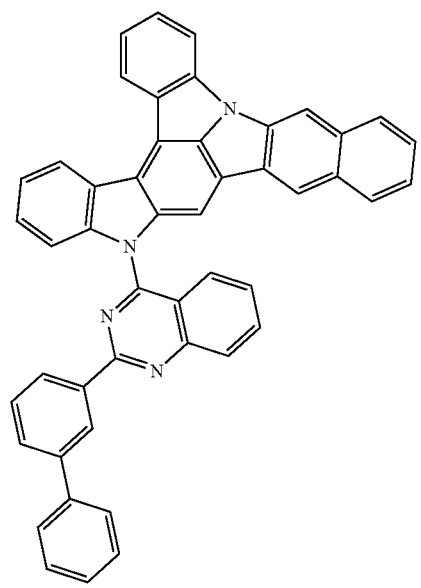
934
-continued
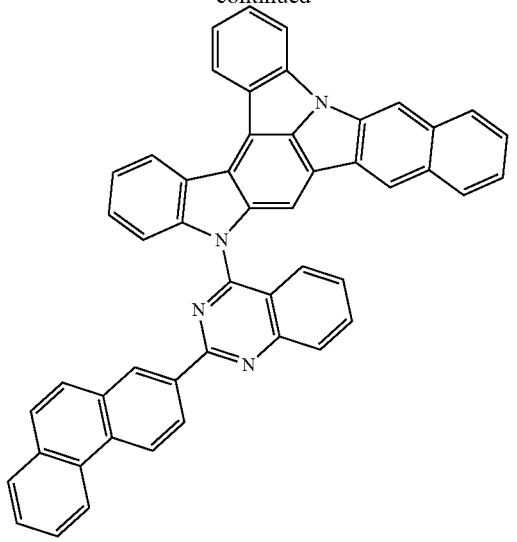
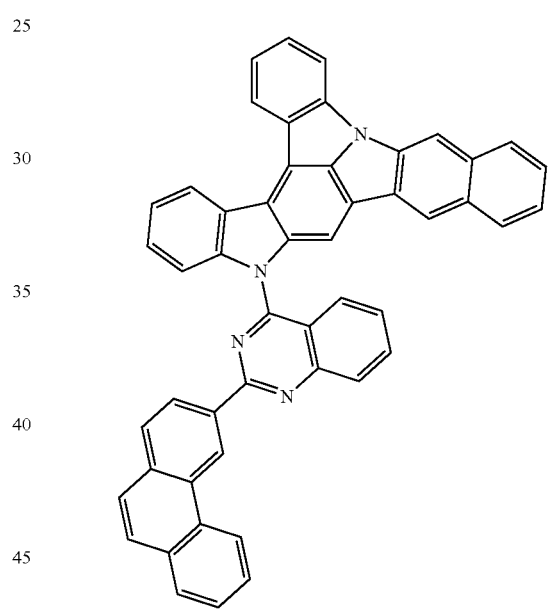
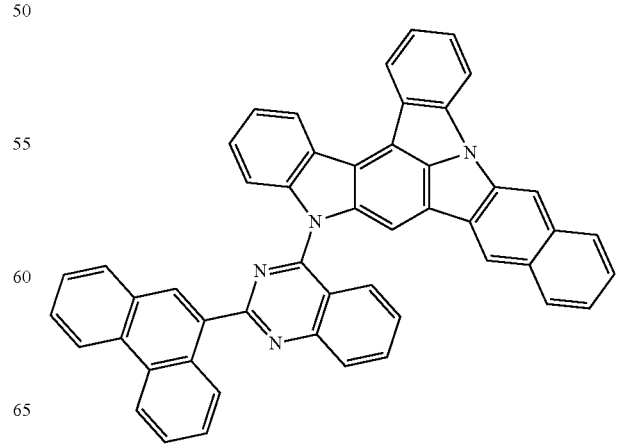

935
-continued
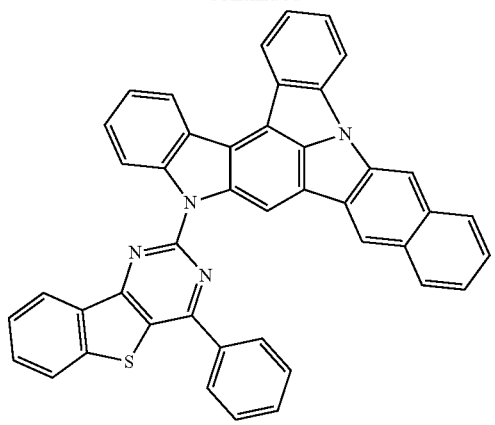
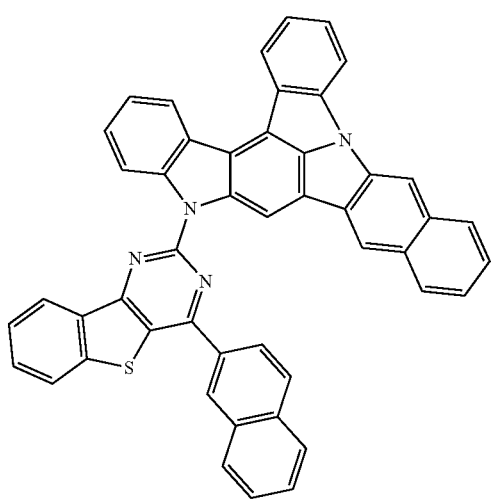
936
-continued
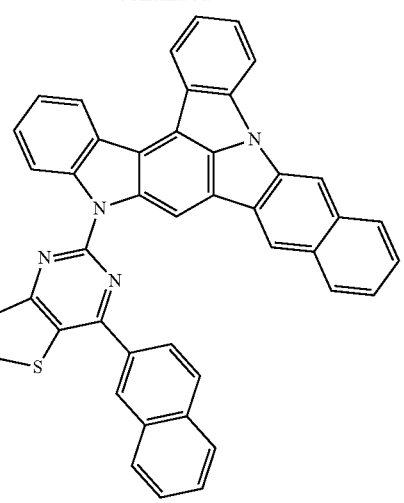
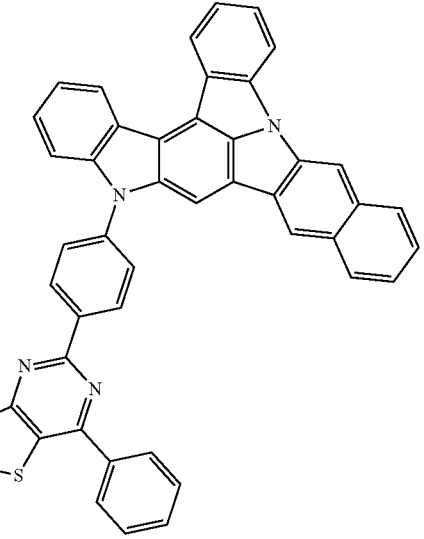
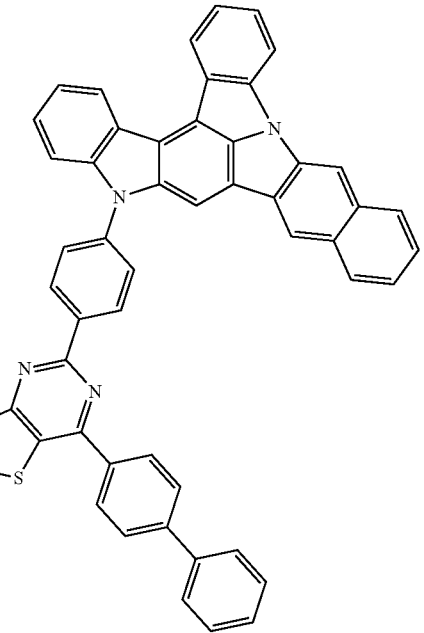

937
-continued
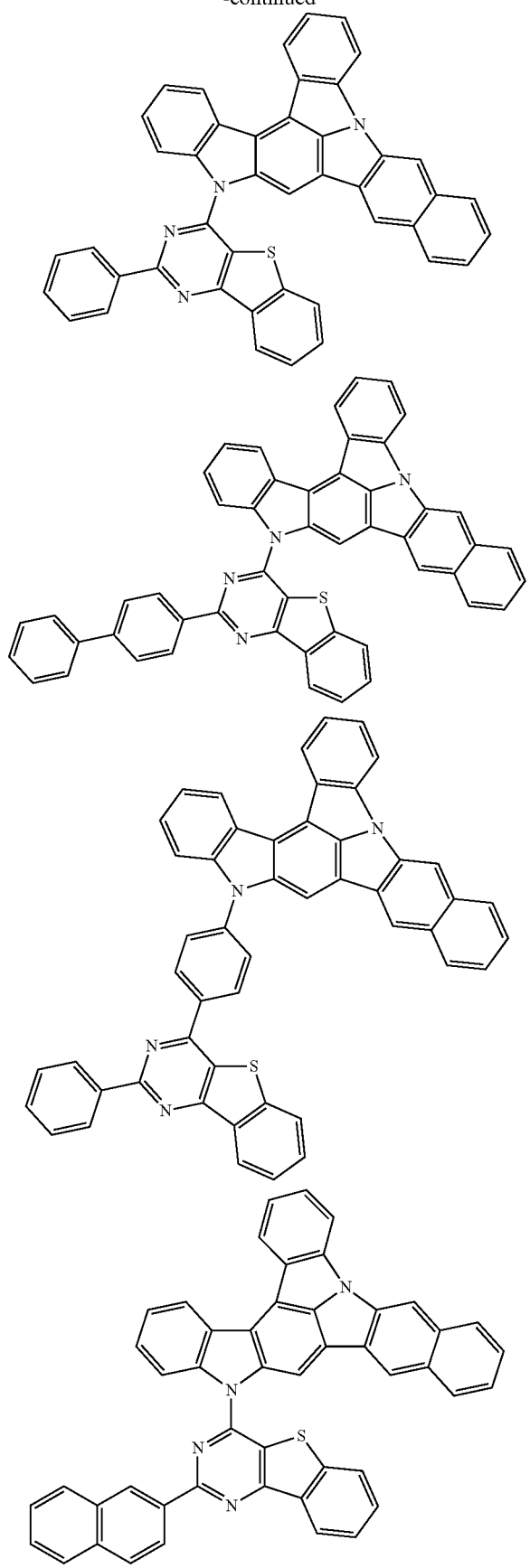
938
-continued
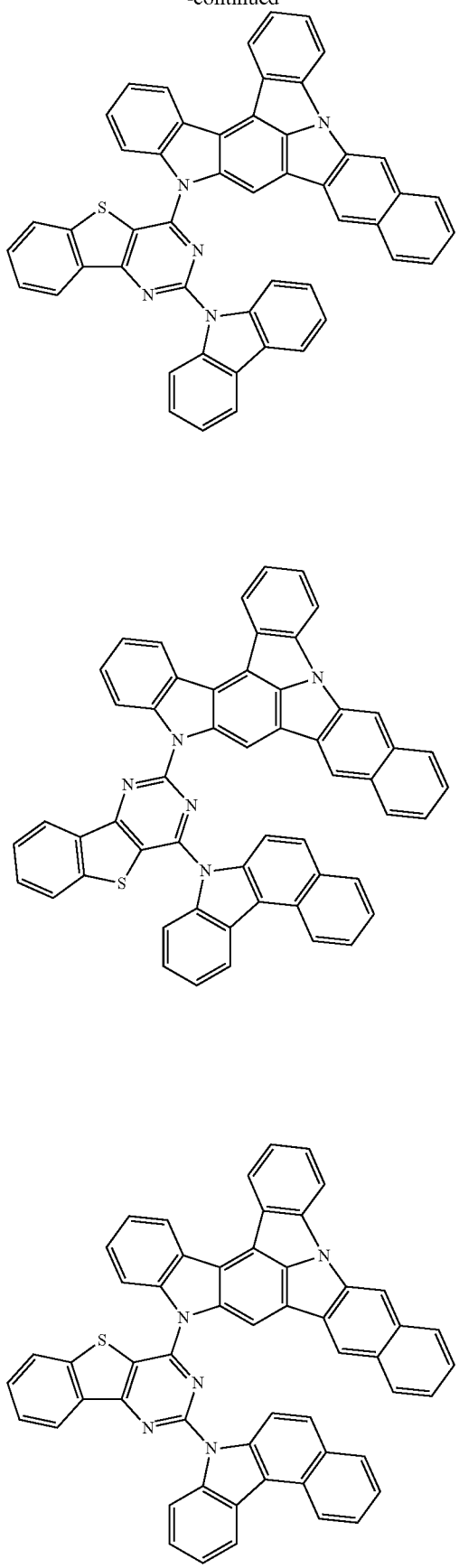

939
-continued
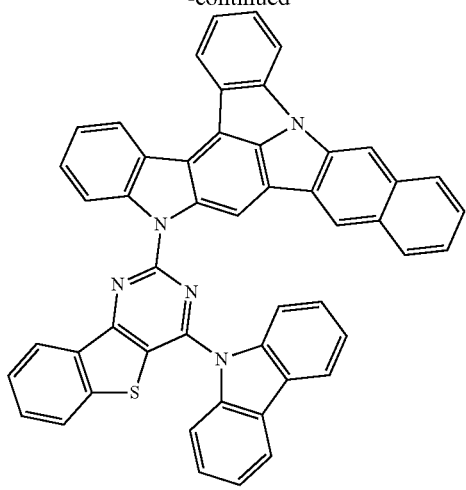
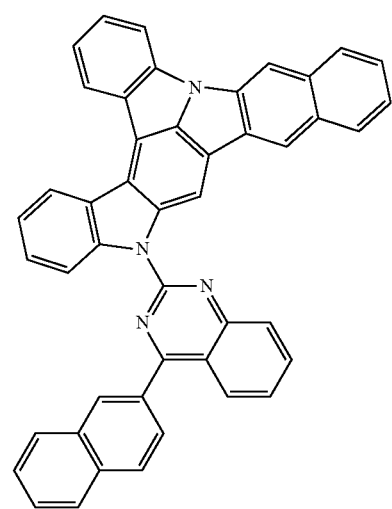
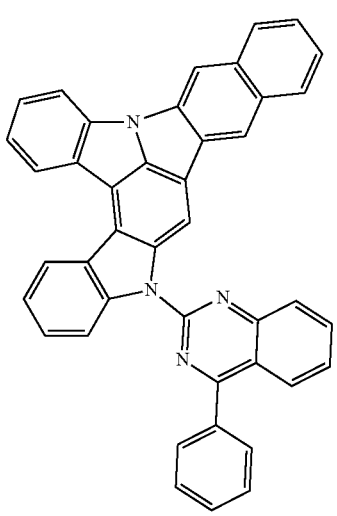
940
-continued
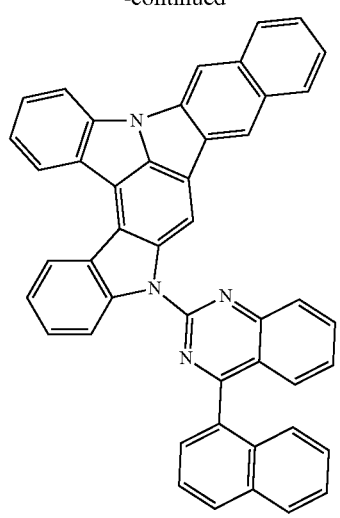
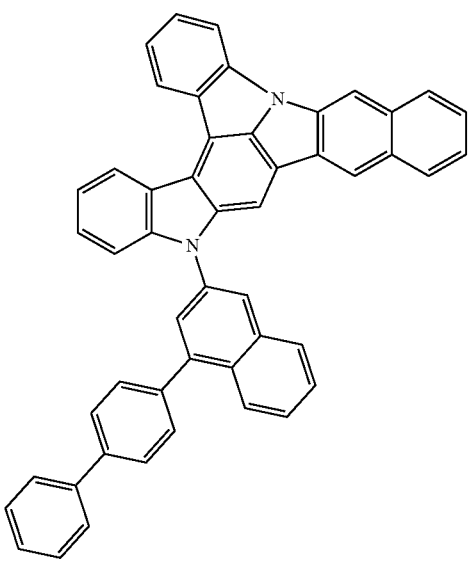
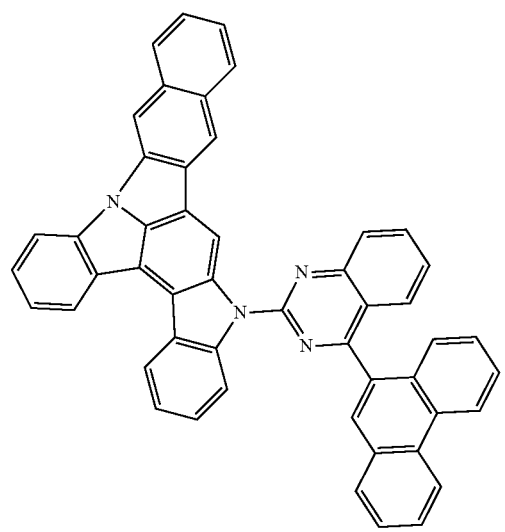

941
-continued
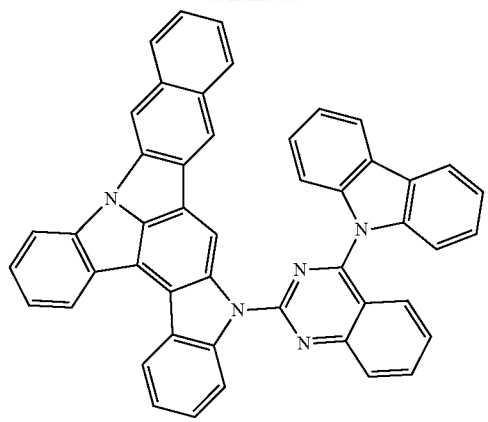
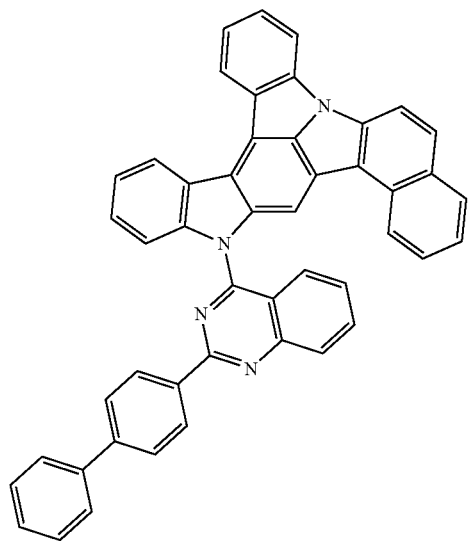
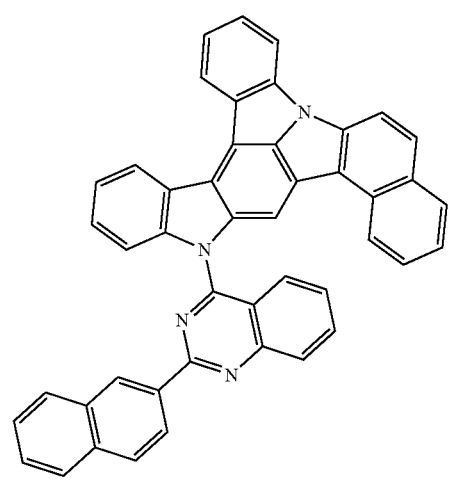
942
-continued
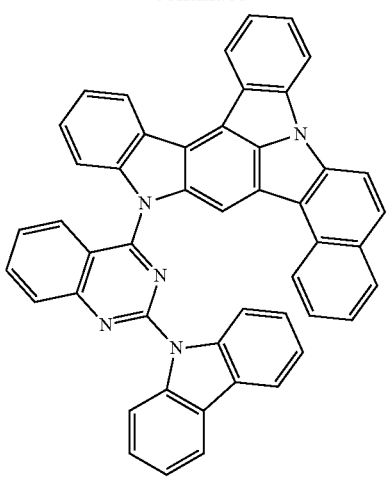
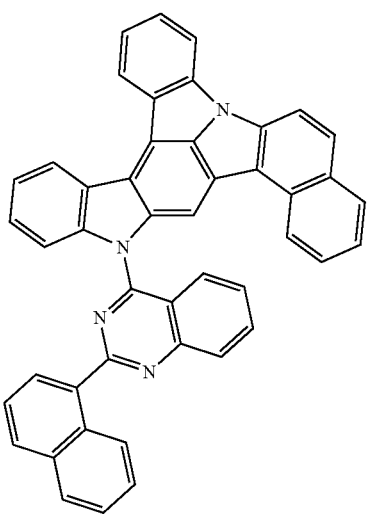
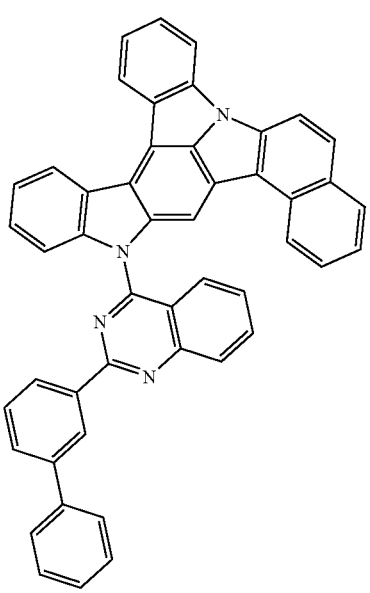

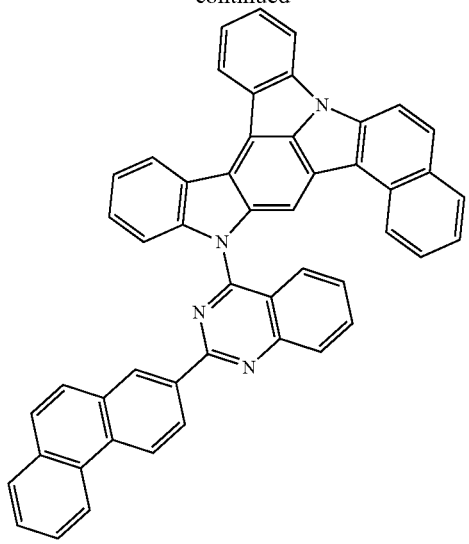
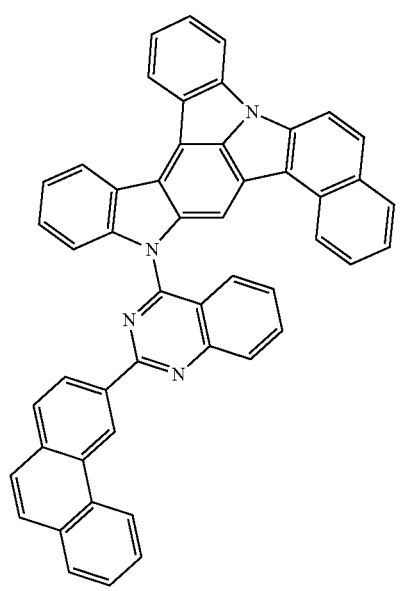
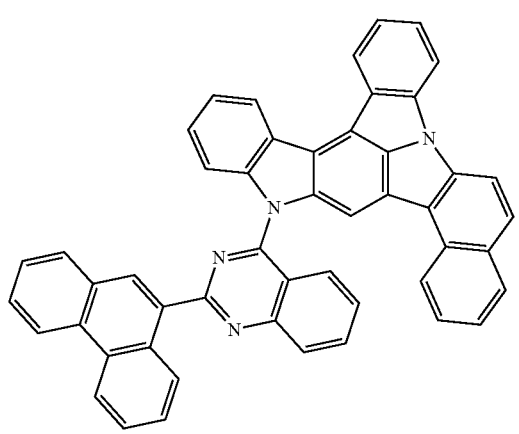
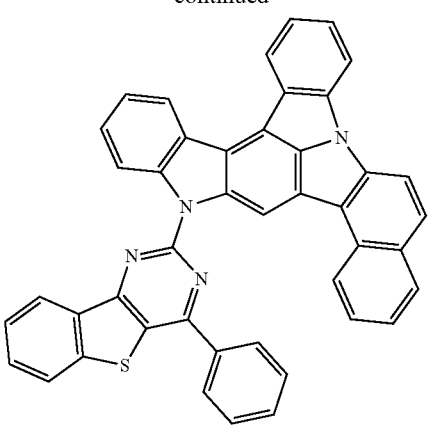
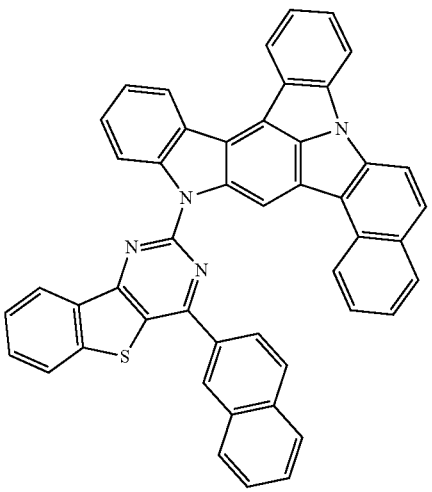
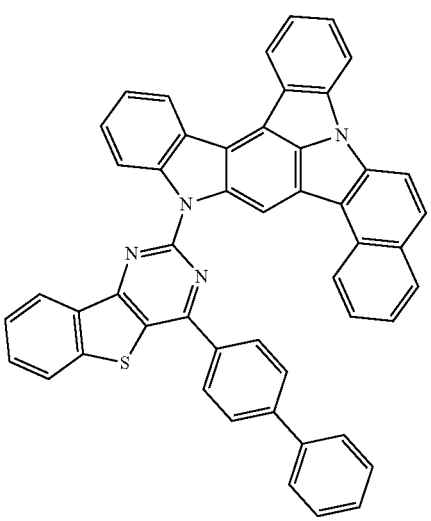

945
-continued
946
-continued
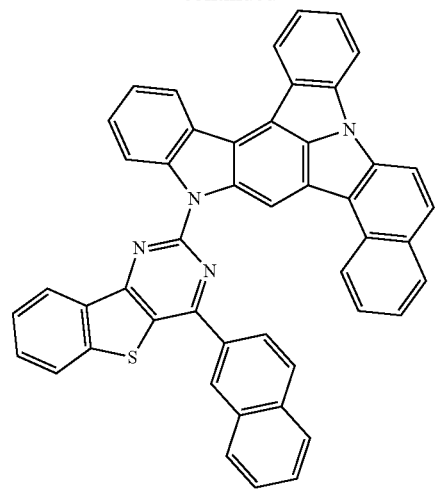
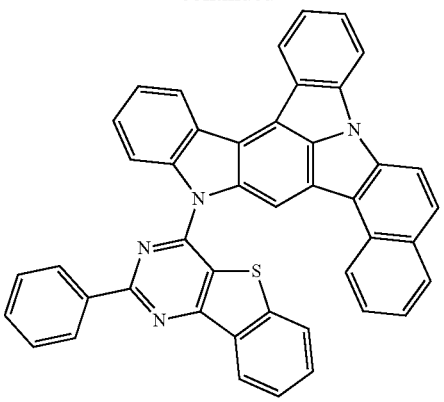
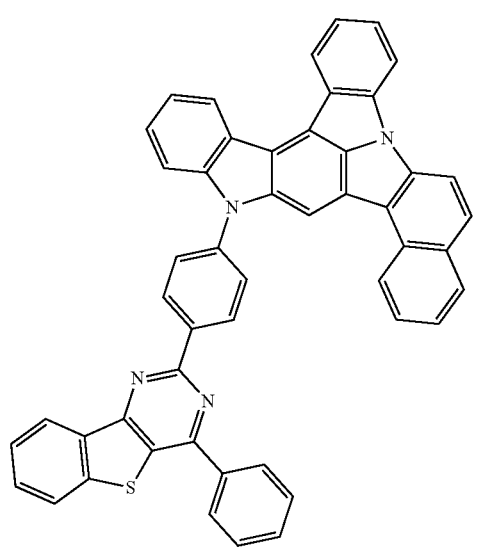
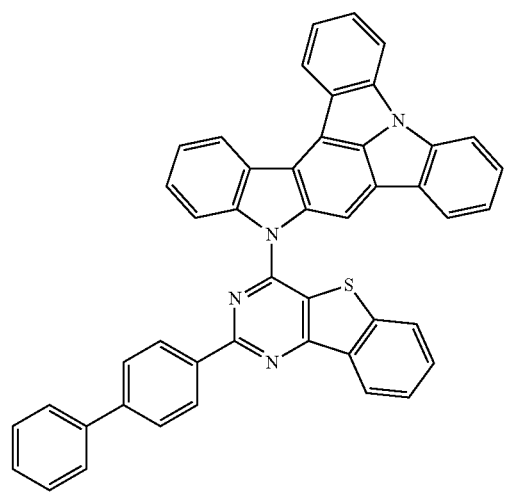
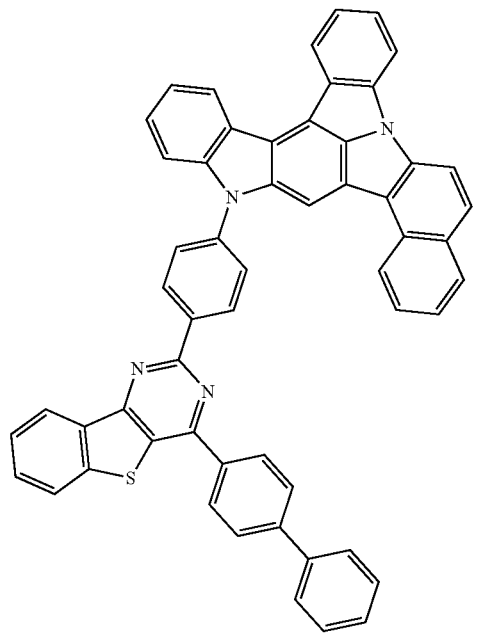
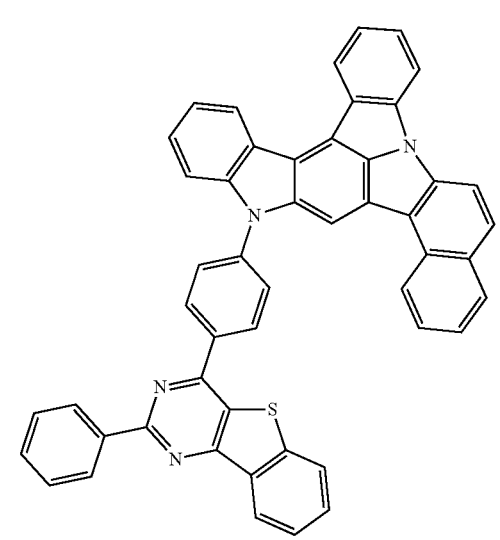

947
-continued
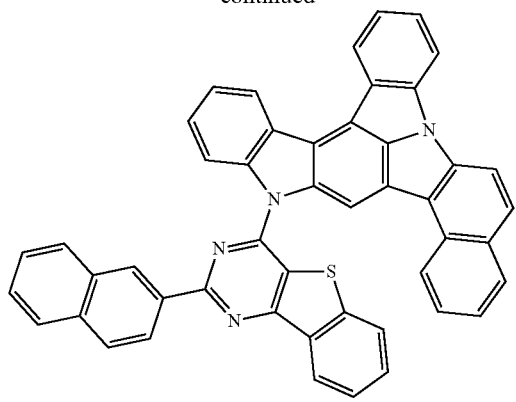
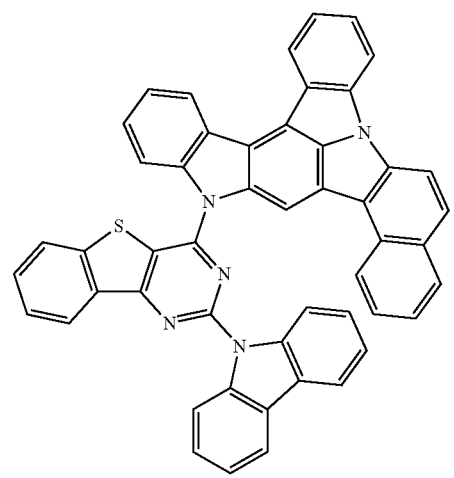
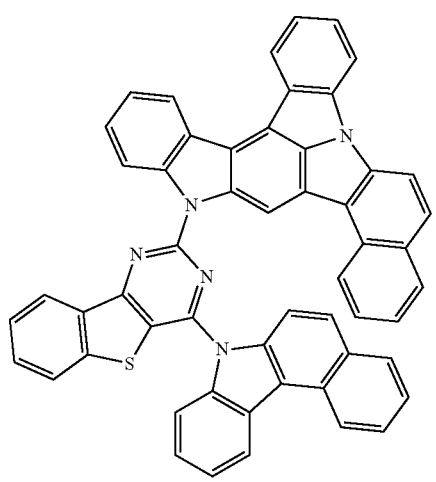
948
-continued
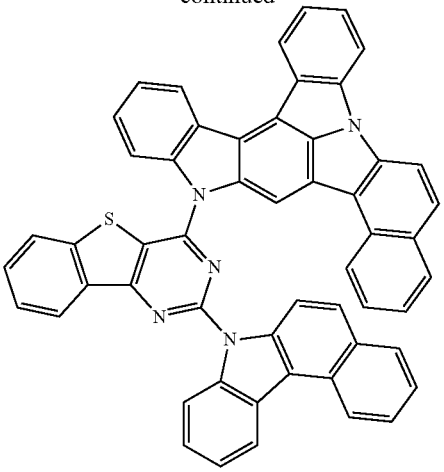
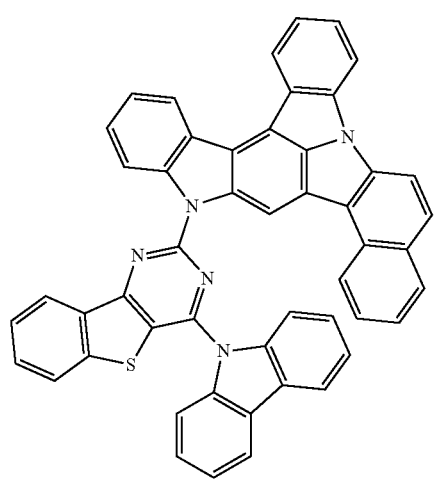
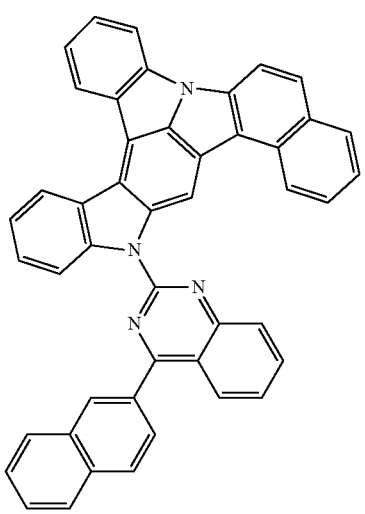

949
-continued
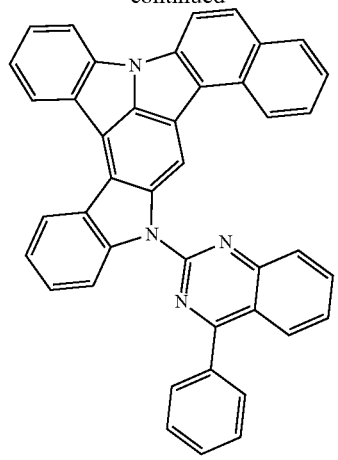
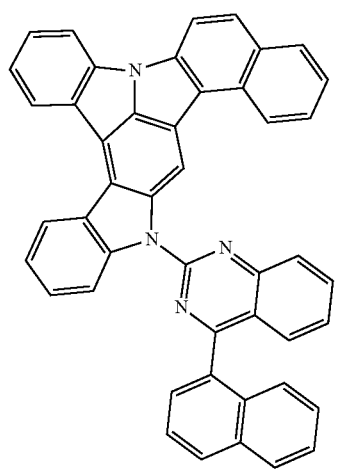
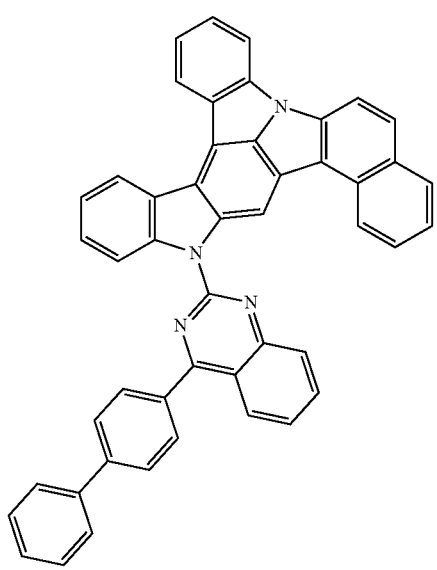
950
-continued
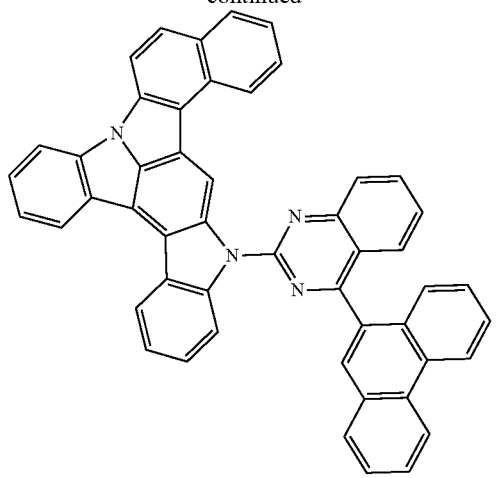
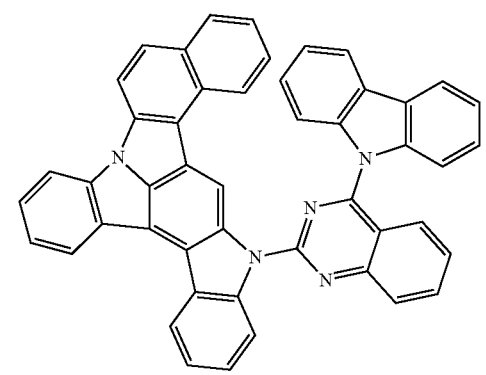
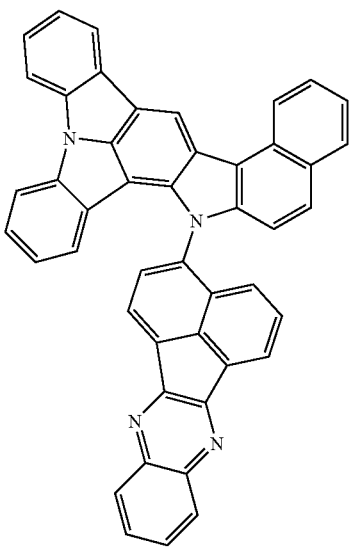

| 951 -continued | 952 -continued |
|---|---|
| 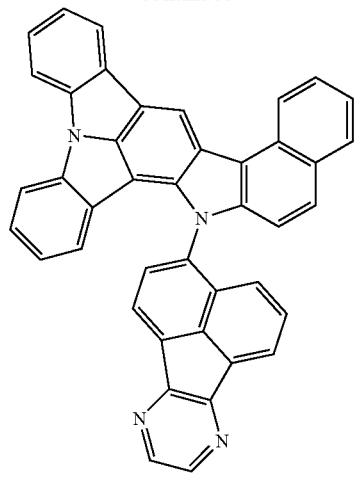 | 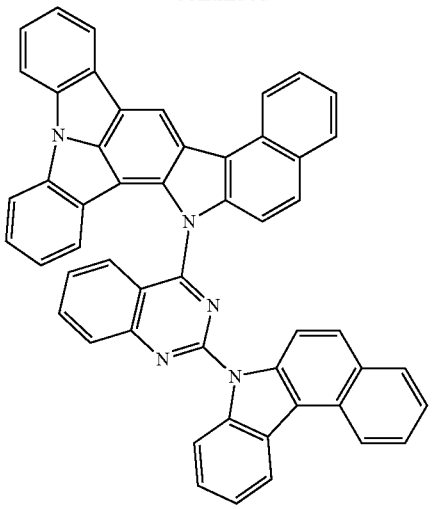 |
| 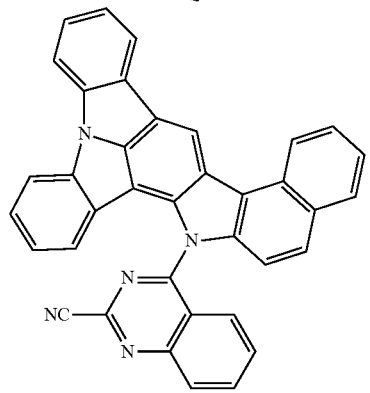 | 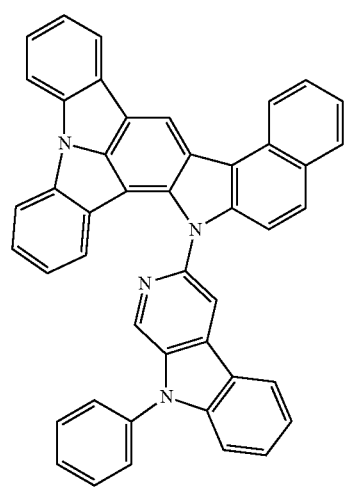 |
| 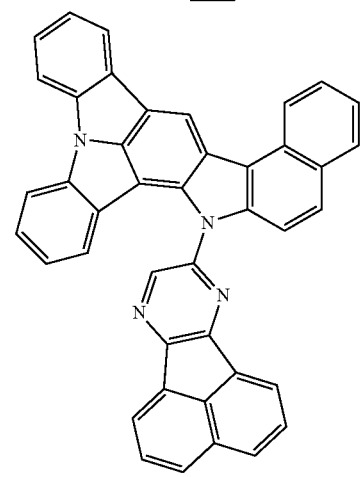 | |
| 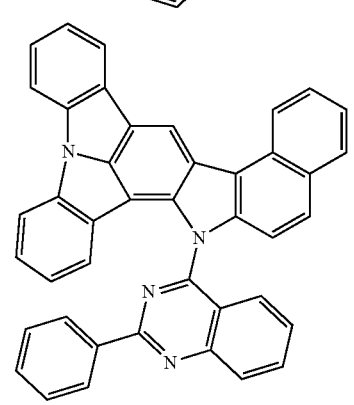 | 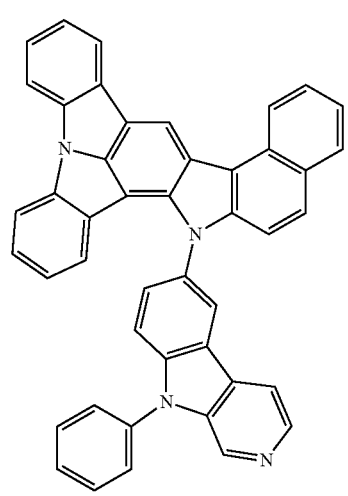 |

953
-continued
954
-continued
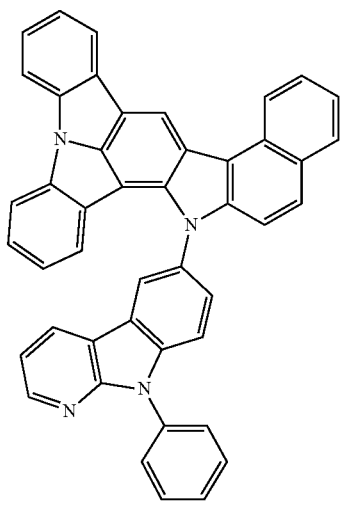
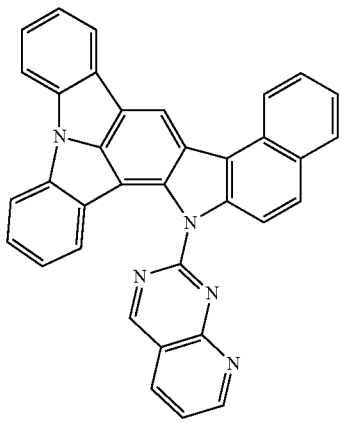
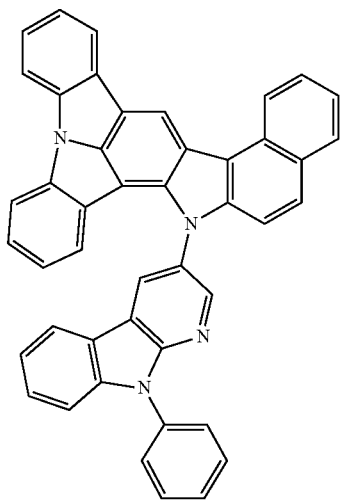
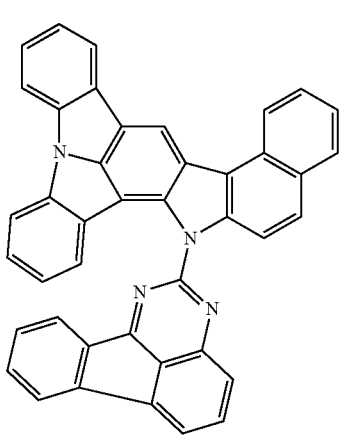
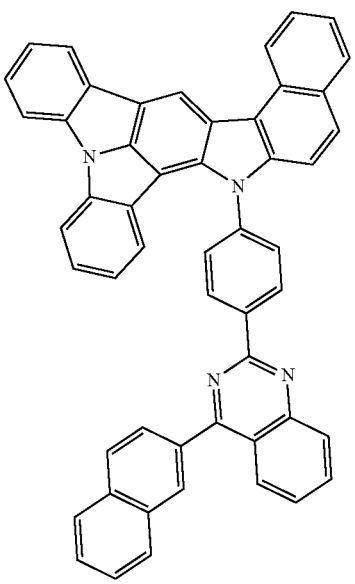
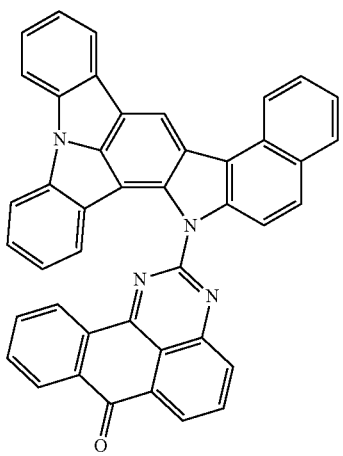

955
-continued
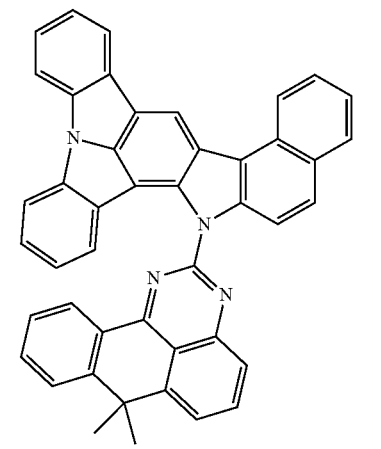
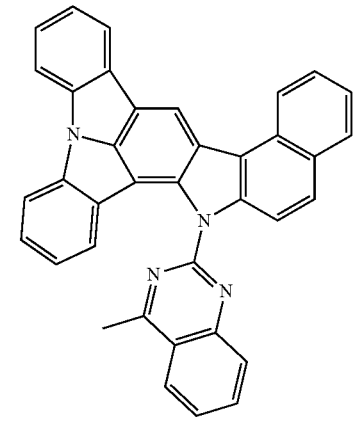
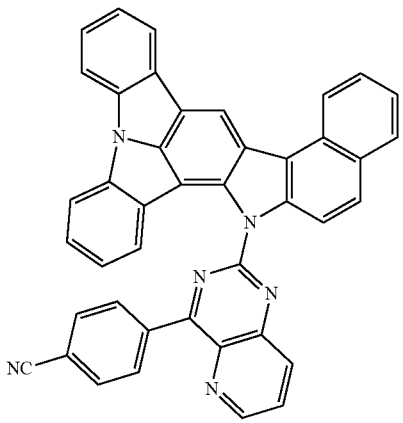
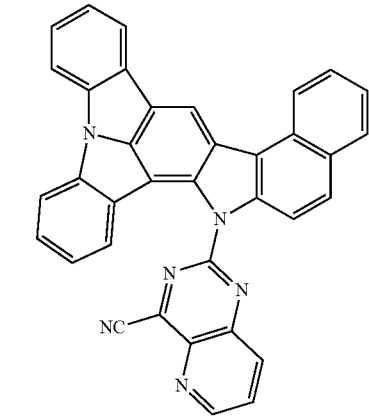
956
-continued
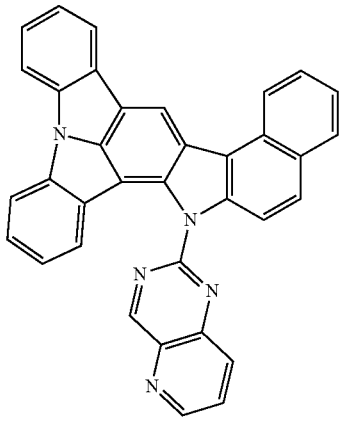
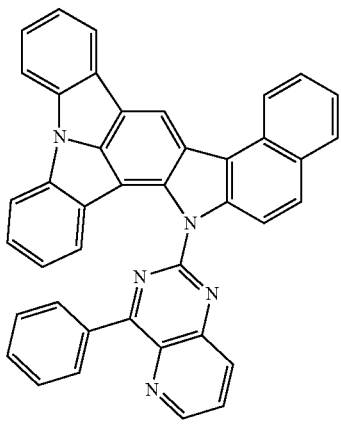
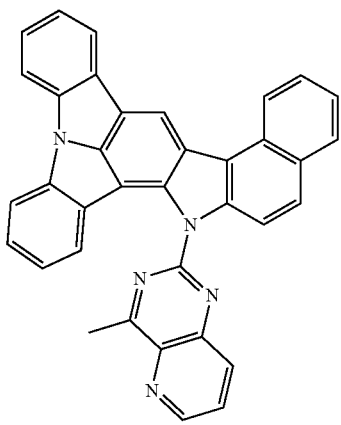
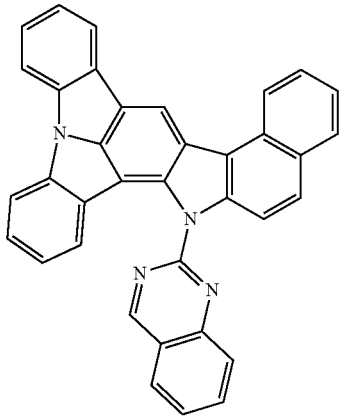

957
-continued
958
-continued
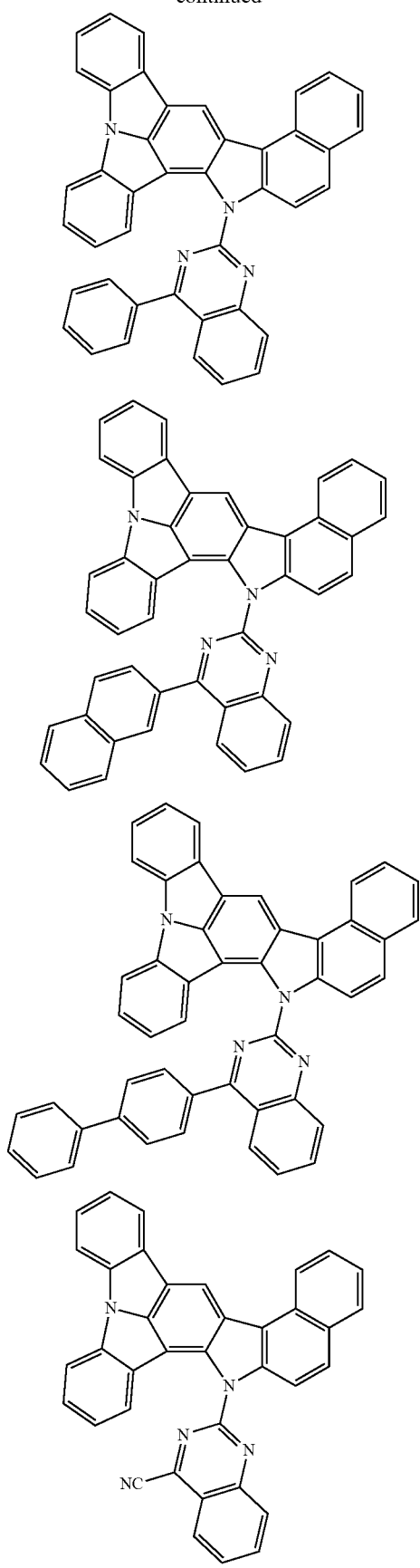
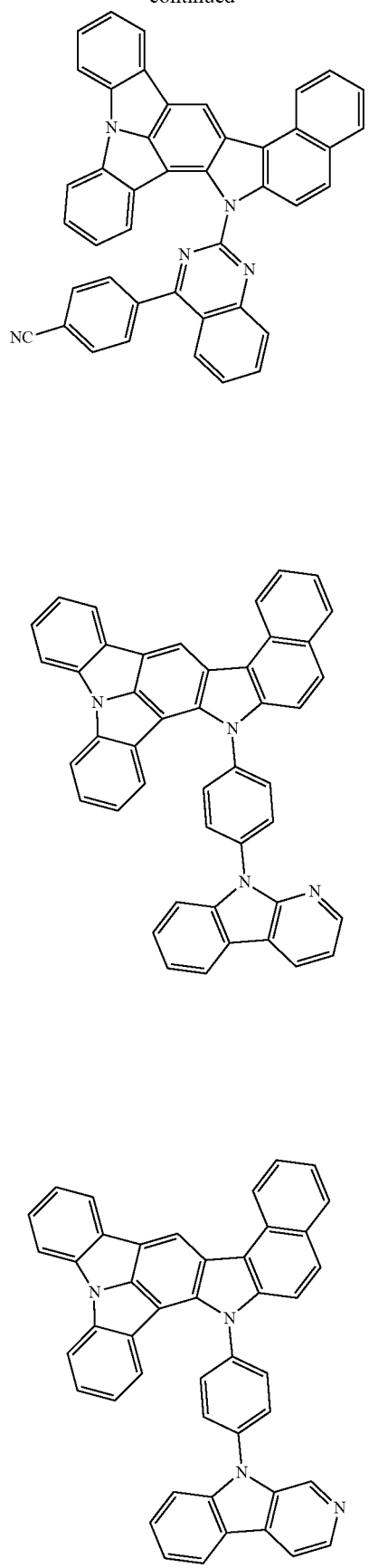

959
-continued
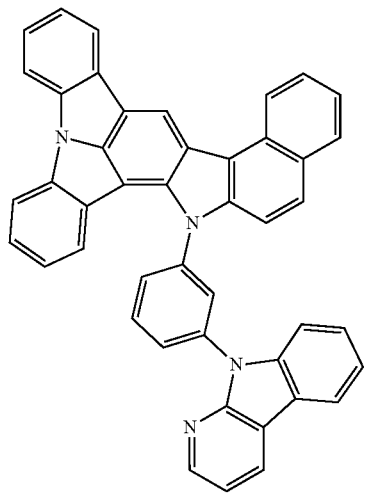
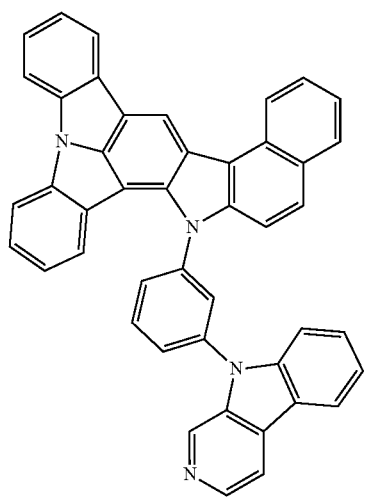
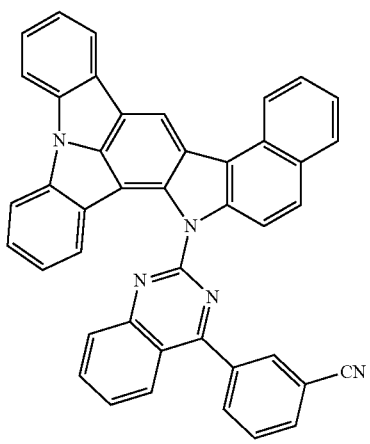
960
-continued
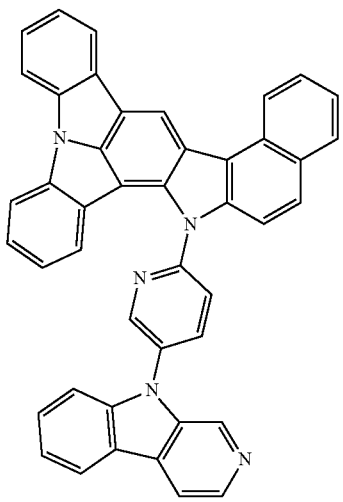
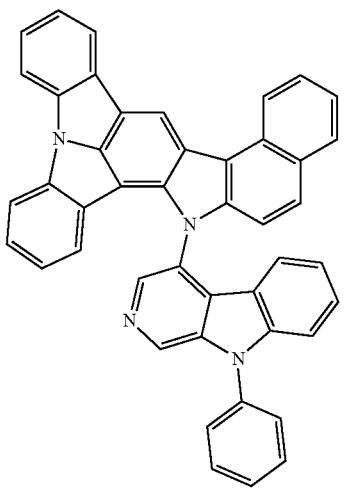
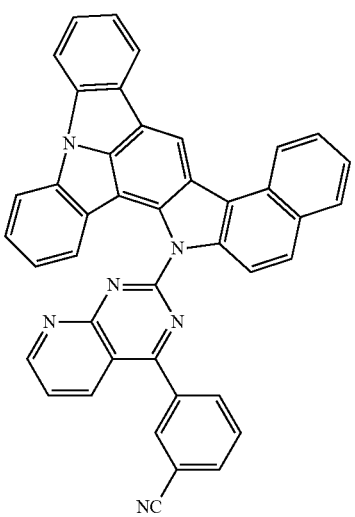

961
-continued
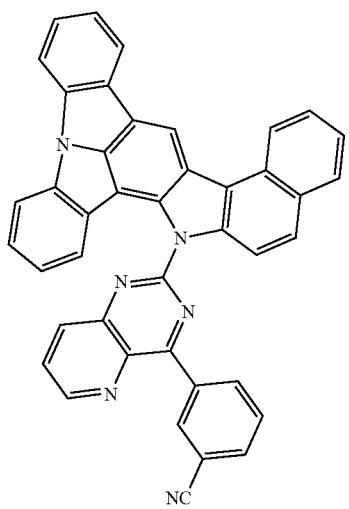
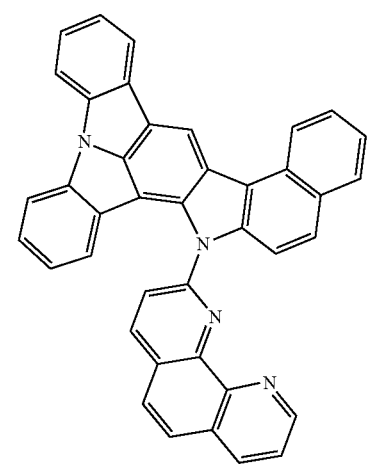
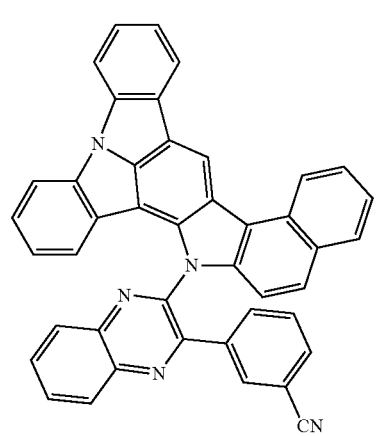
962
-continued
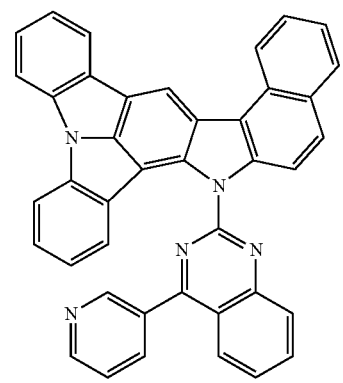
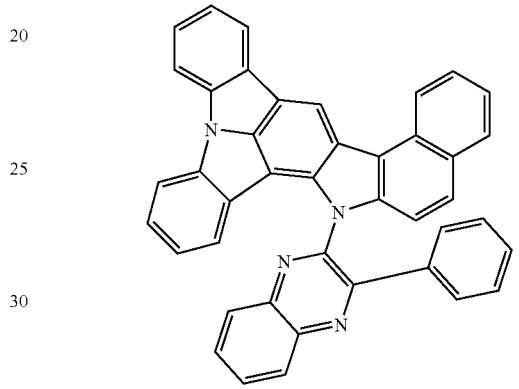
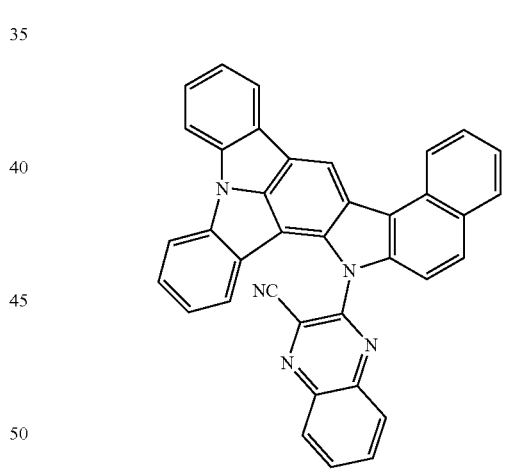
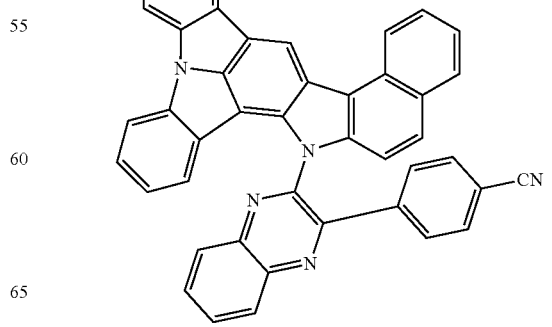

963
-continued
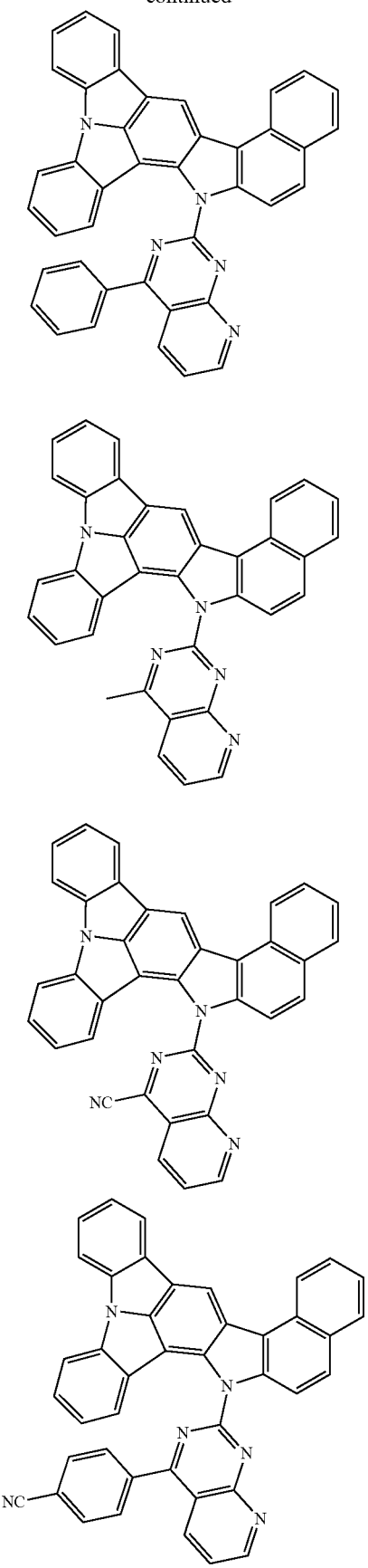
964
-continued
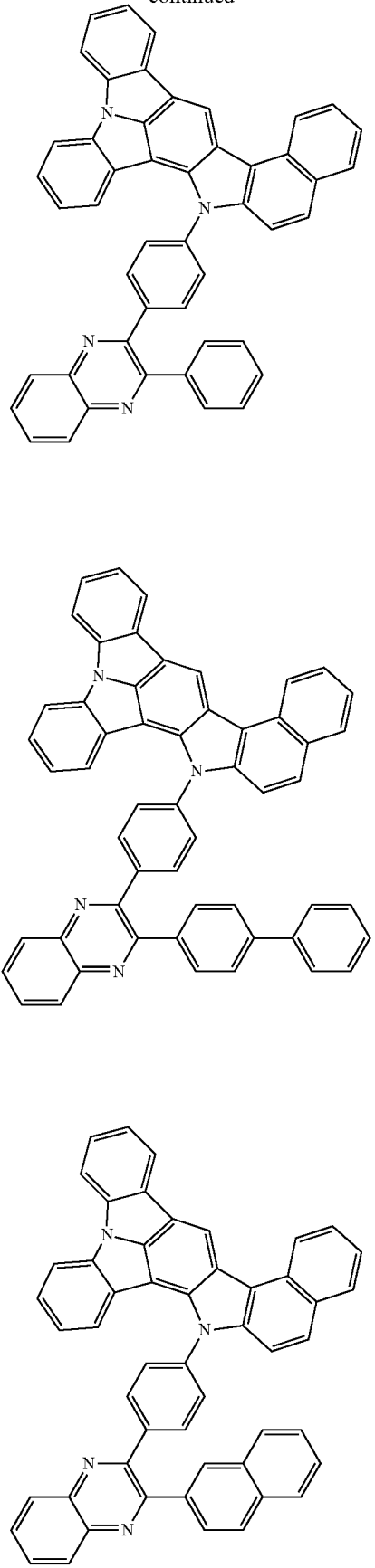

965
-continued
966
-continued
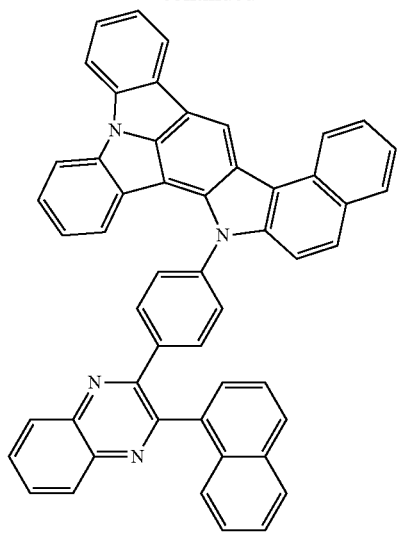
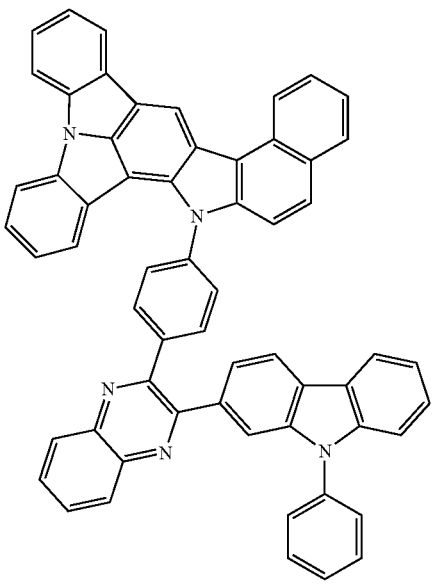
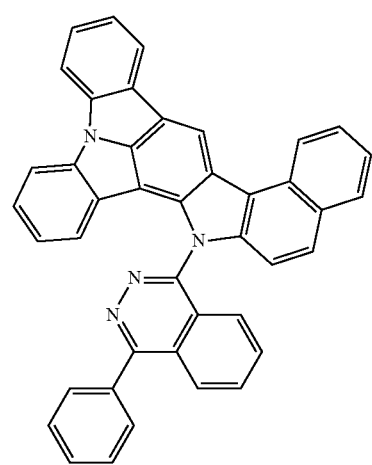
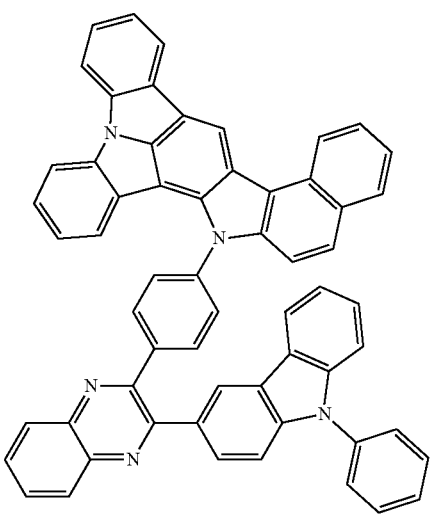
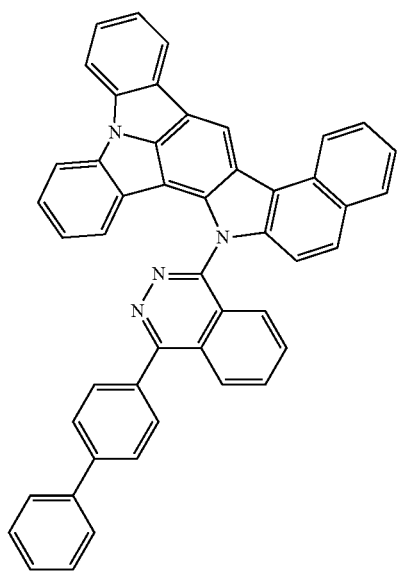
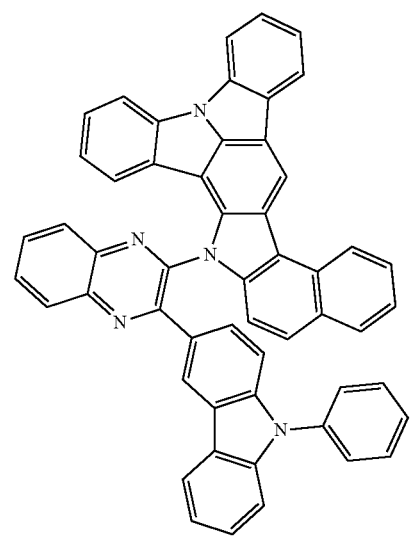

967
-continued
968
-continued
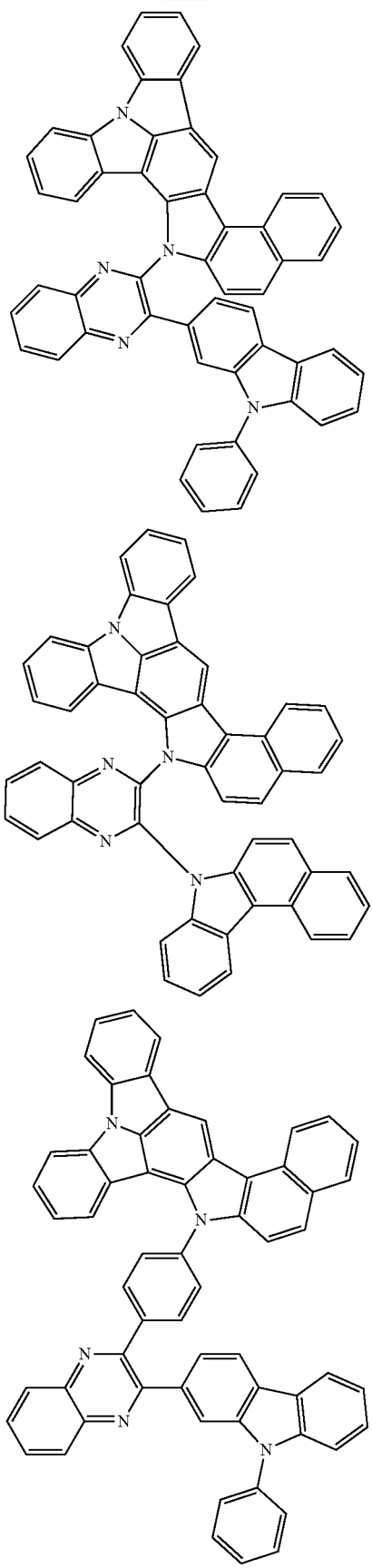
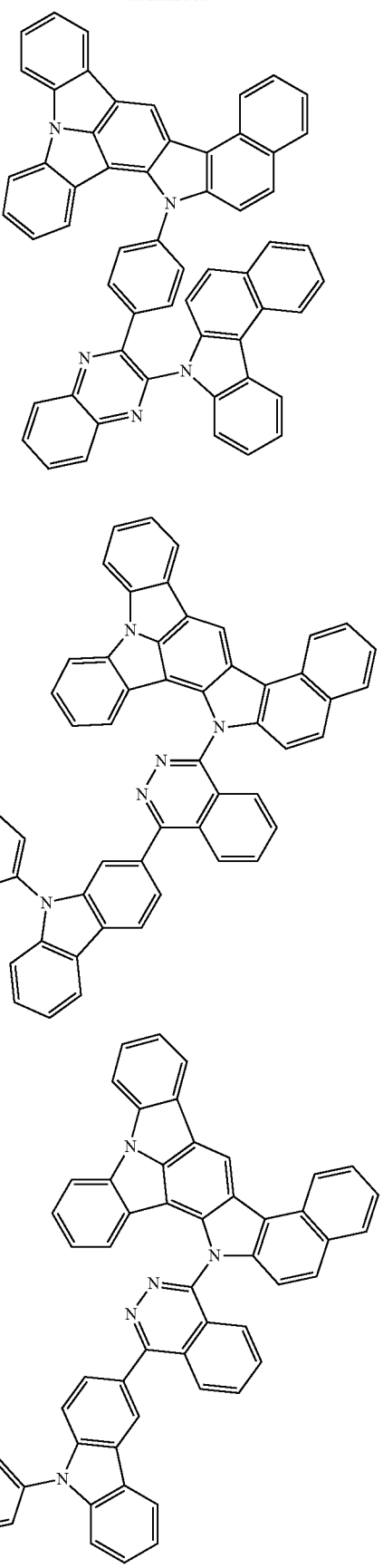

| 969 -continued | 970 -continued |
|---|---|
| 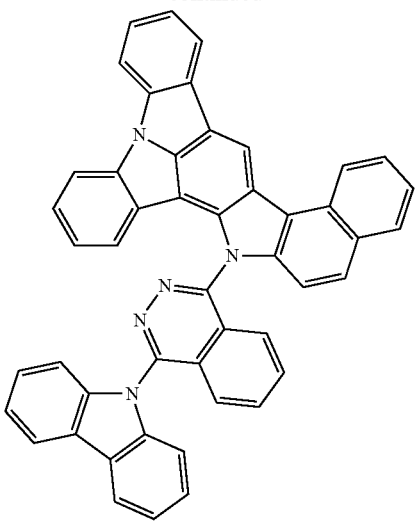 | 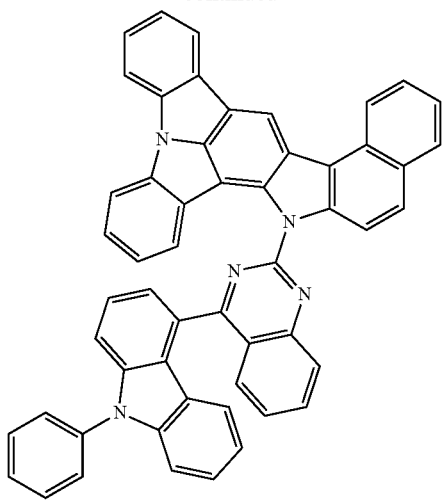 |
| 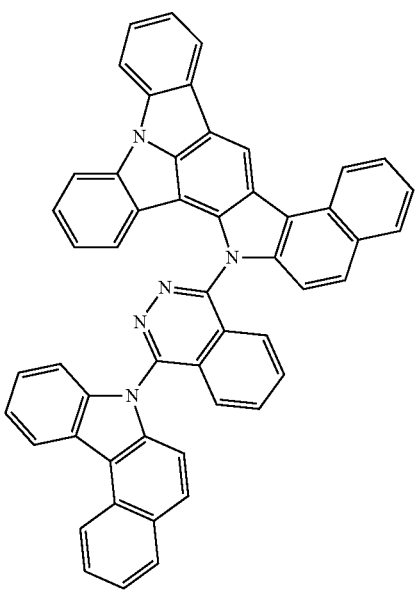 | 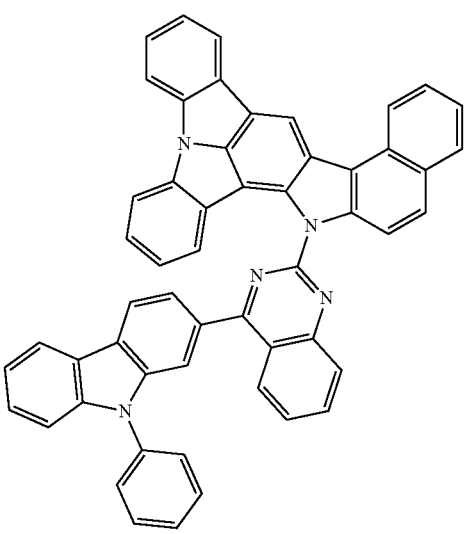 |
| 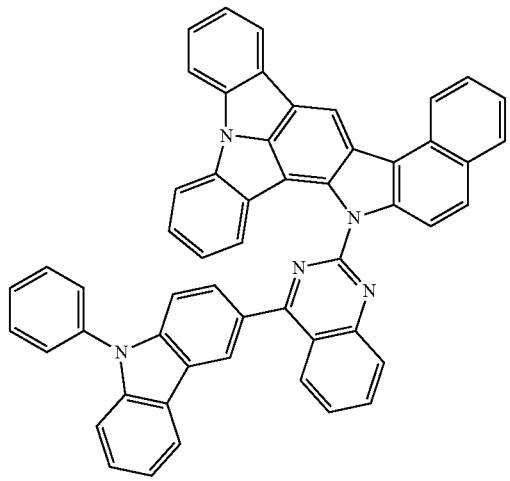 | 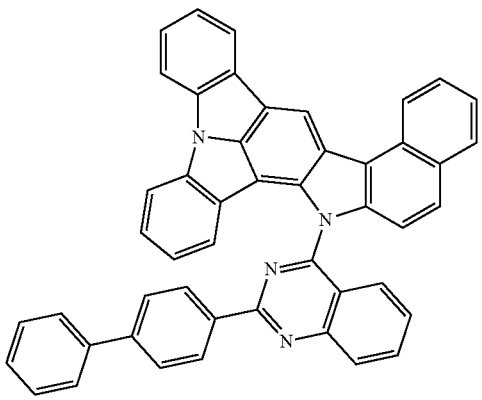 |

| 971 | 972 |
|---|---|
| -continued | -continued |
| 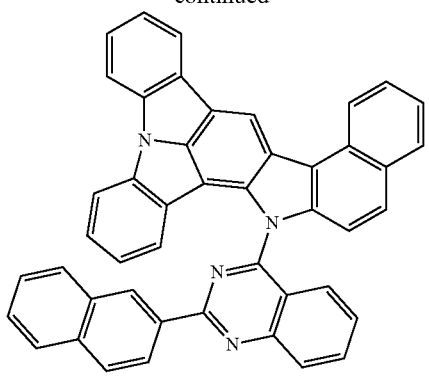 | 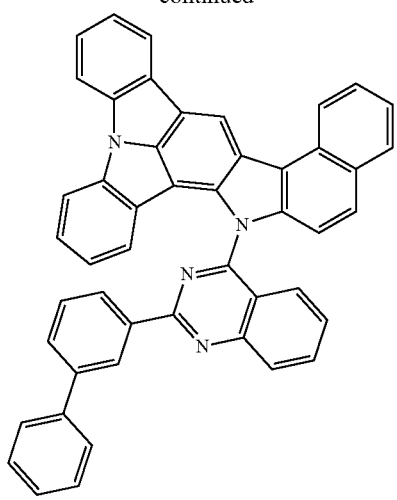 |
| 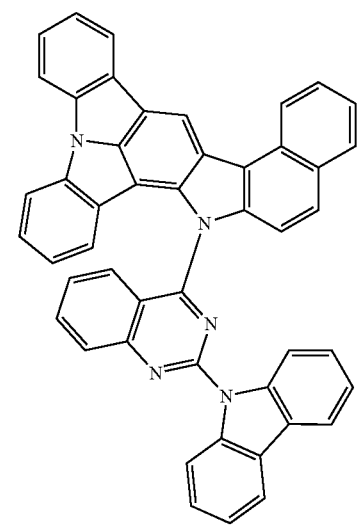 | 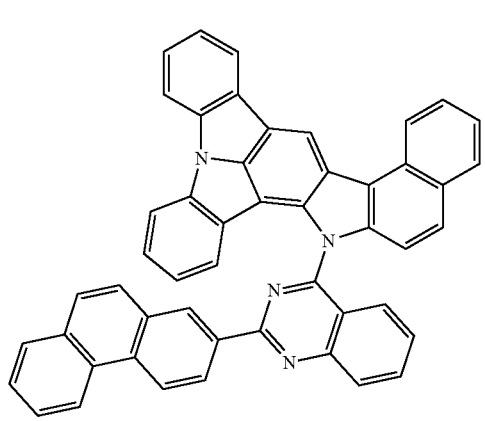 |
| 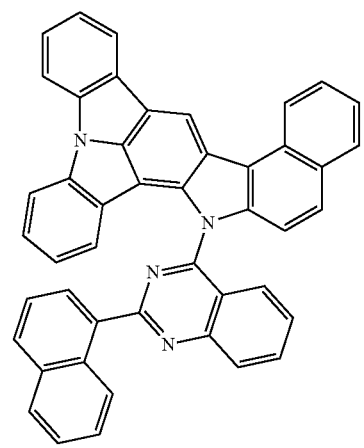 | 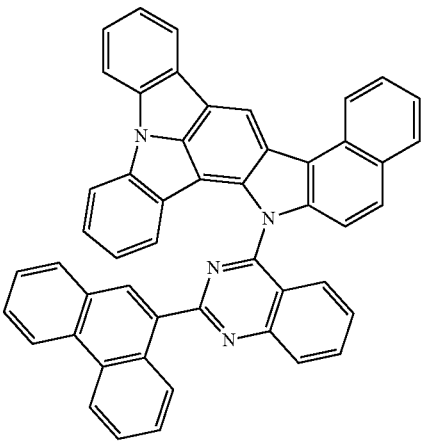 |

973
-continued
974
-continued
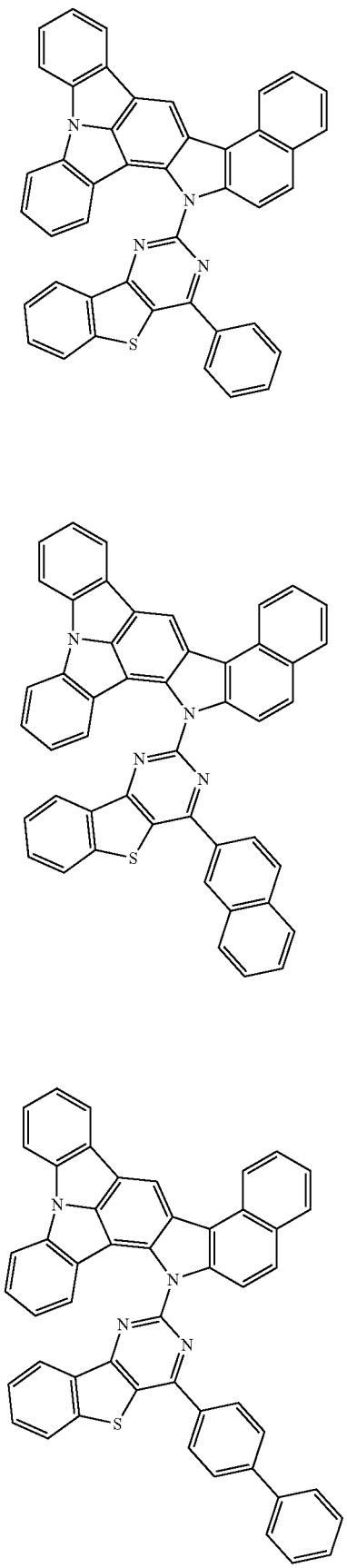
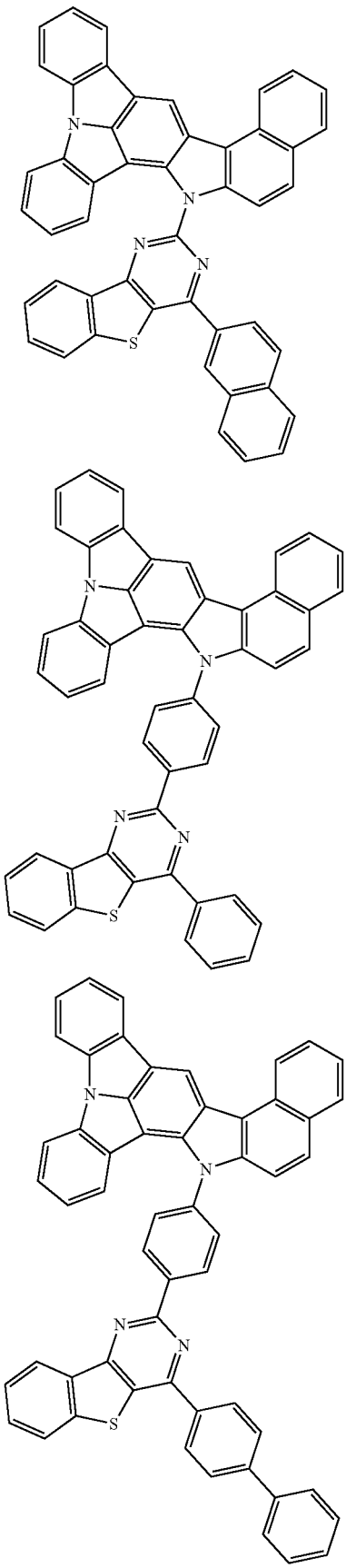 [SMILES: c1ccc2cc(-c3nc(-n4c5ccc6ccccc6c5c5cc6c7ccccc7n7c8ccccc8c(c54)c67)nc4c3sc3ccccc34)ccc2c1 ; c1ccc(-c2nc(-c3ccc(-n4c5ccc6ccccc6c5c5cc6c7ccccc7n7c8ccccc8c(c54)c67)cc3)nc3c2sc2ccccc23)cc1 ; c1ccc(-c2ccc(-c3nc(-c4ccc(-n5c6ccc7ccccc7c6c6cc7c8ccccc8n8c9ccccc9c(c65)c78)cc4)nc4c3sc3ccccc34)cc2)cc1]

975
-continued
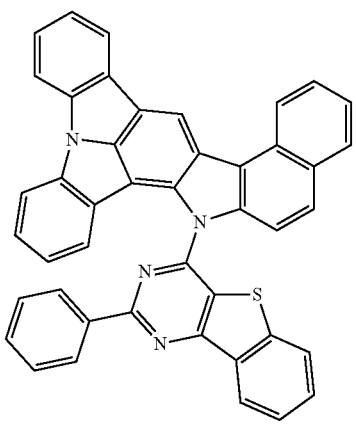
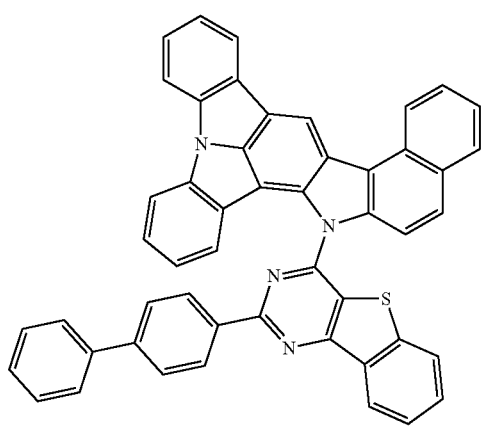
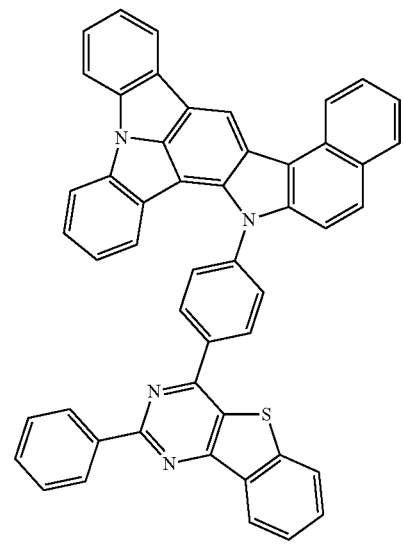
976
-continued
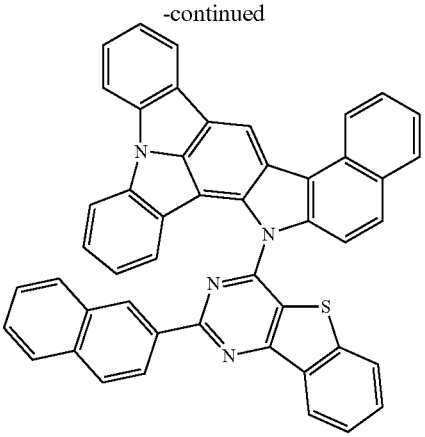
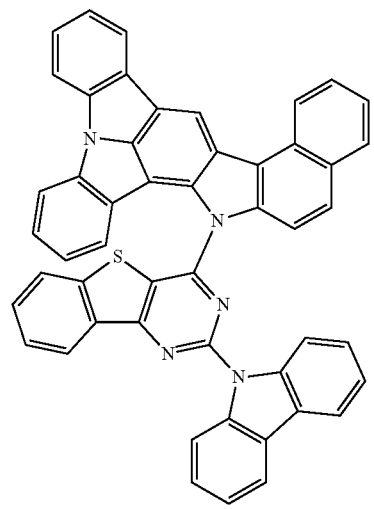
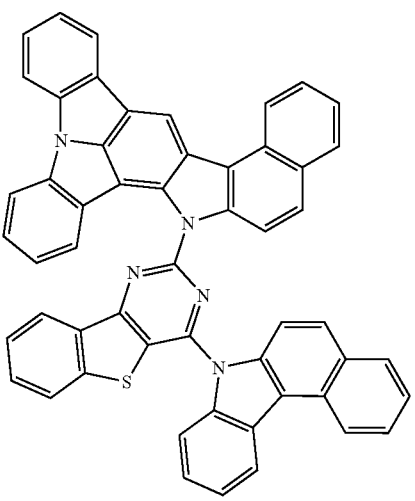

977
-continued
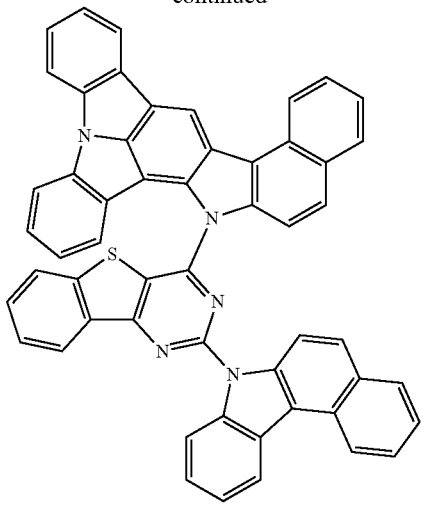
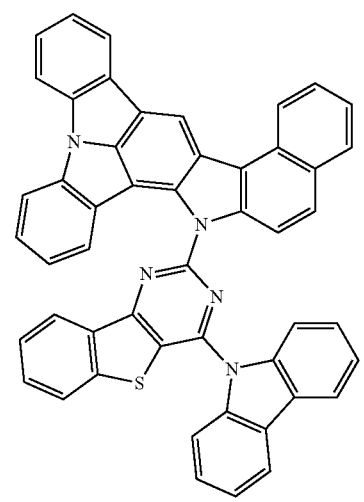
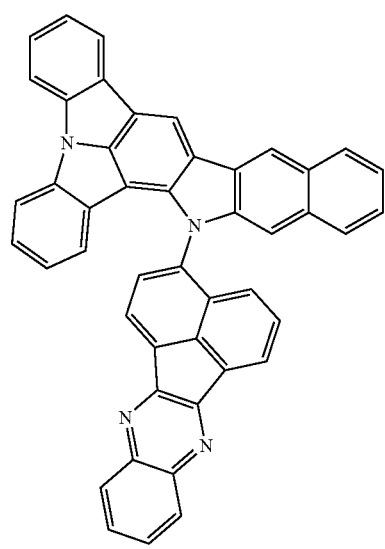
978
-continued
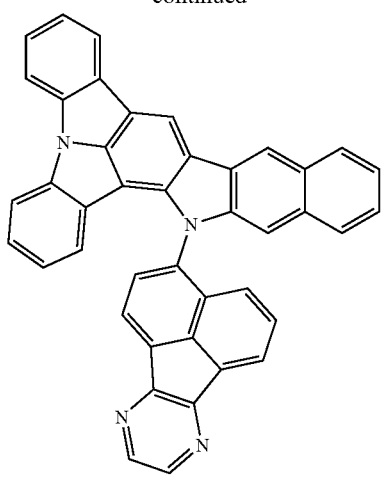
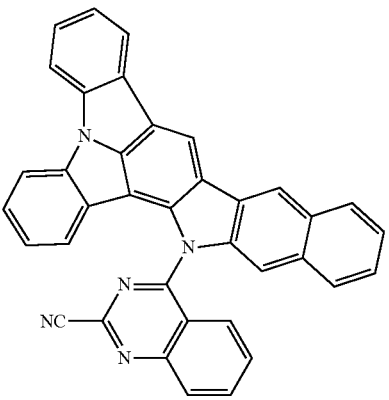
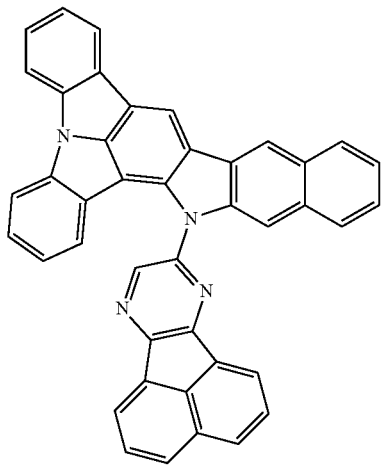
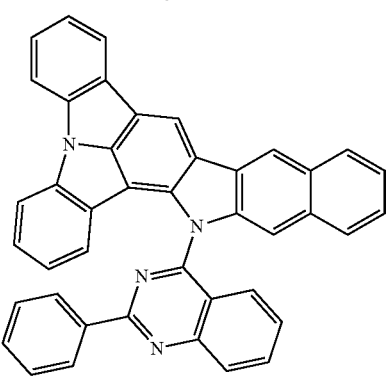

979
-continued
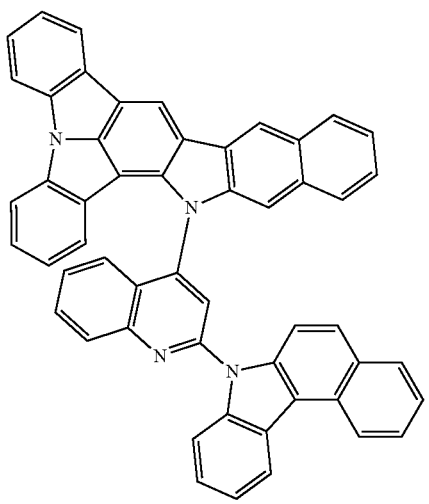
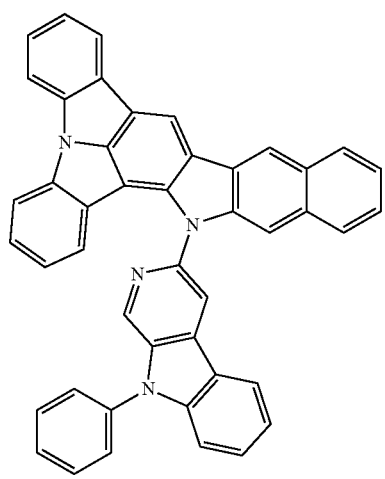
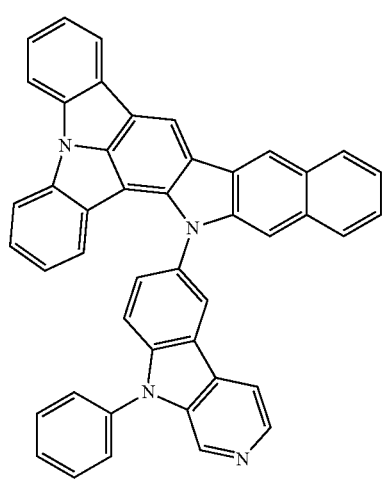
980
-continued
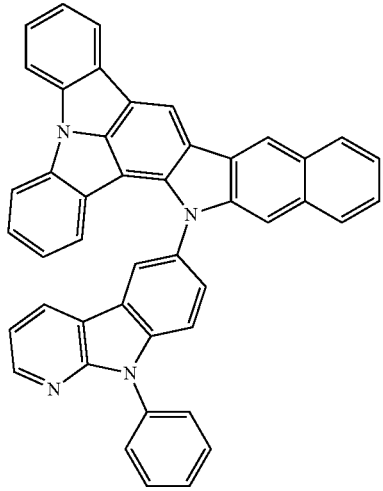
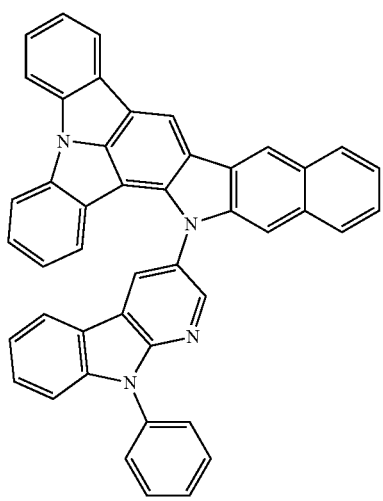
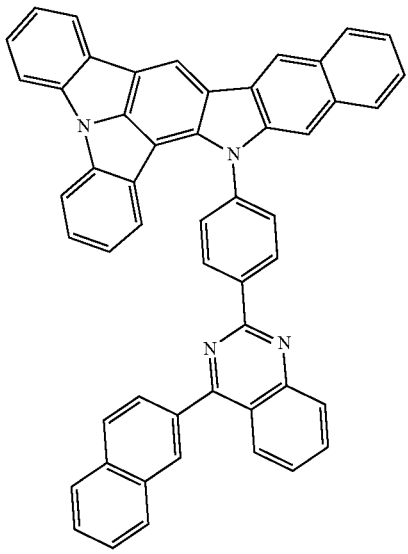

981
-continued
982
-continued
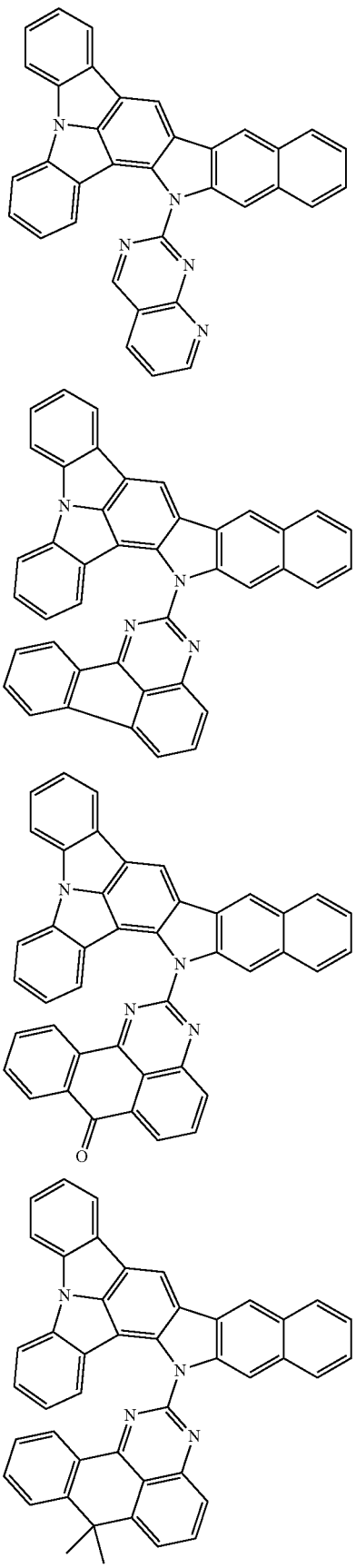
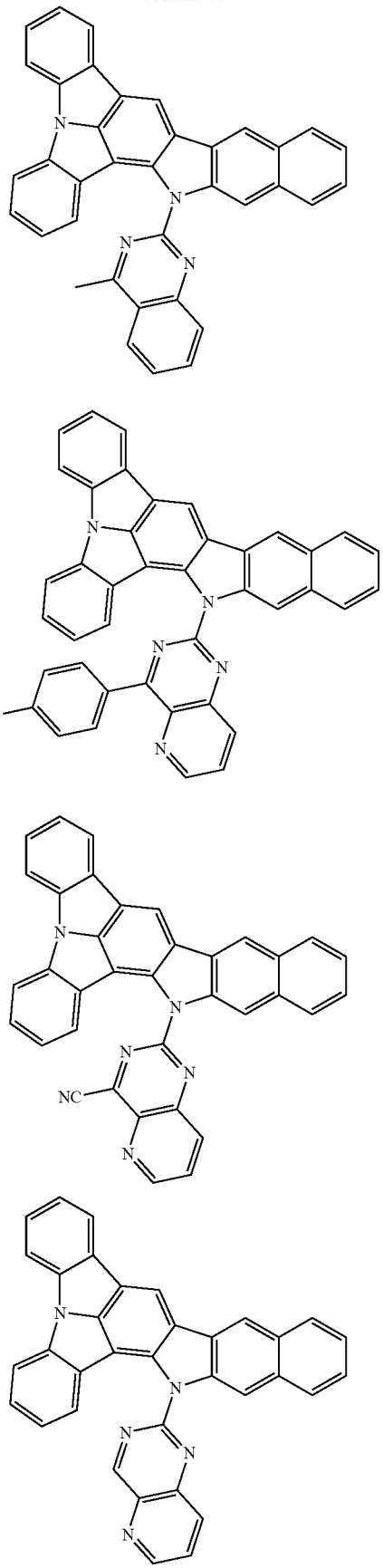

983
-continued
984
-continued
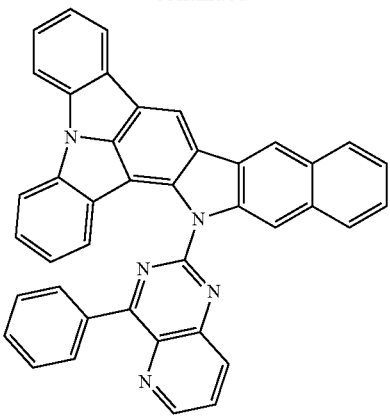
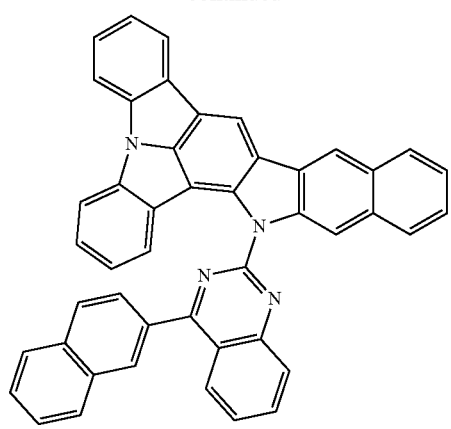
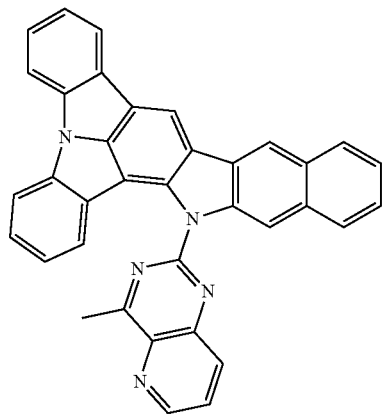
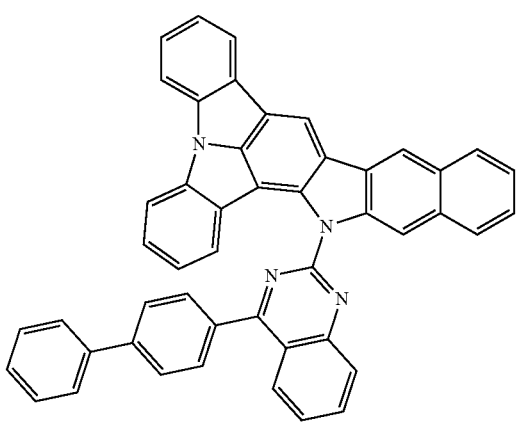
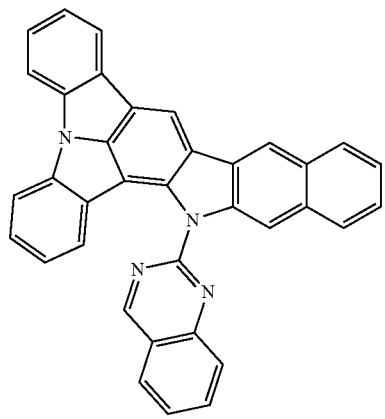
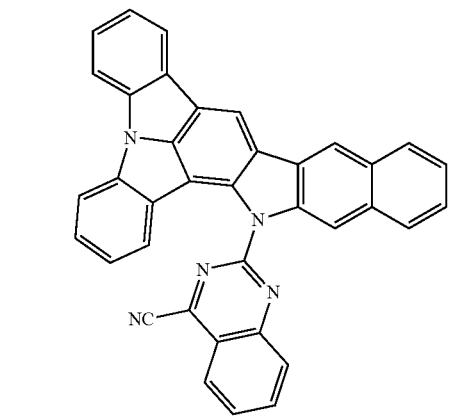
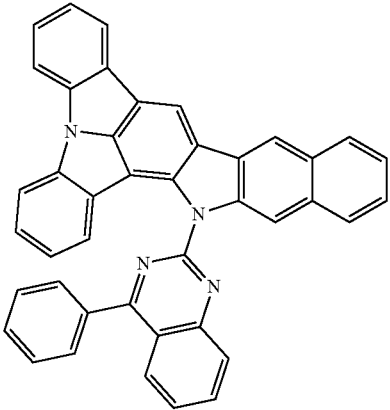
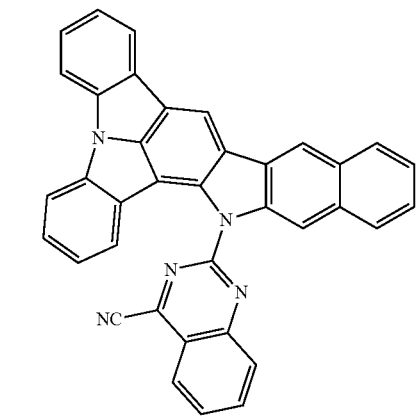

985
-continued
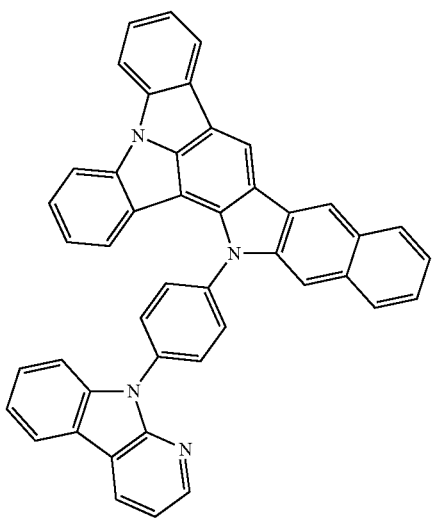
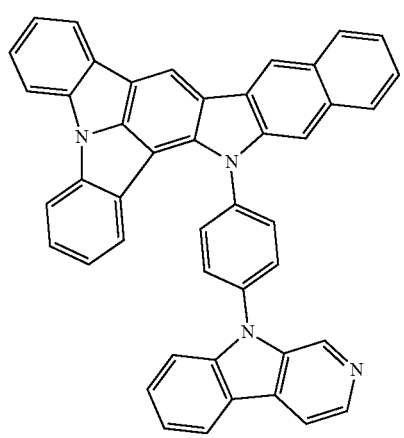
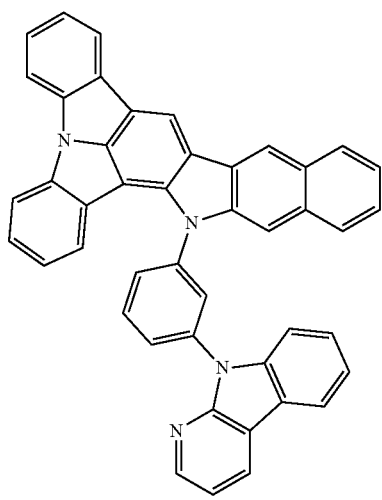
986
-continued
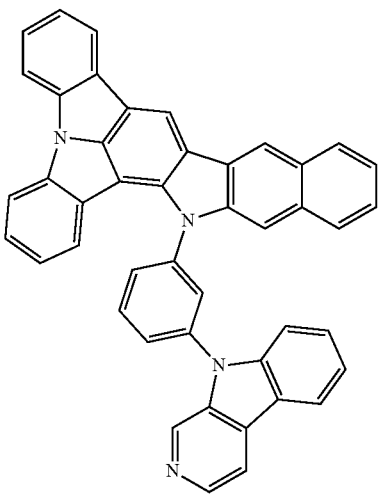
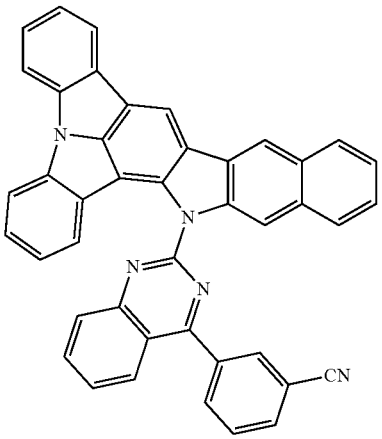
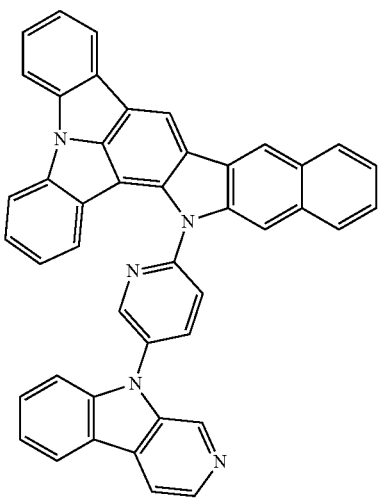

987
-continued
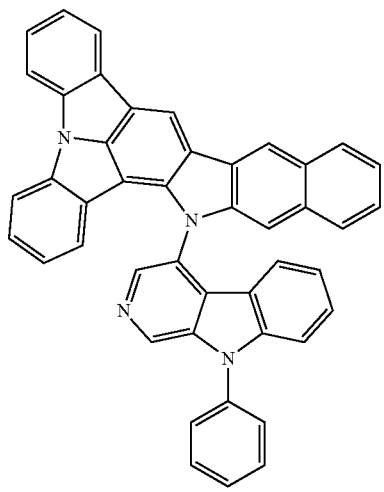
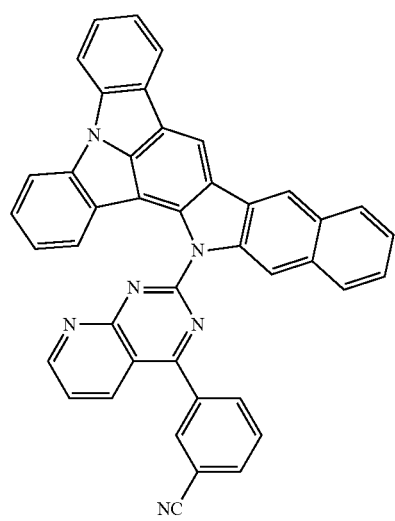
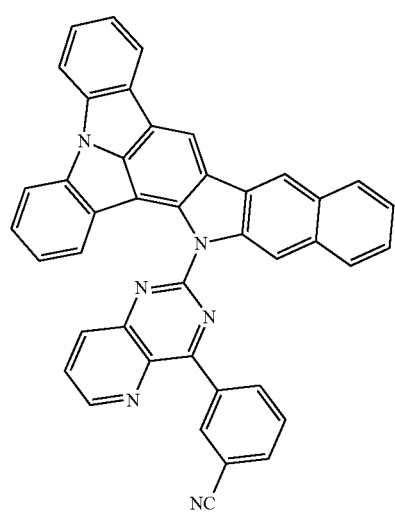
988
-continued
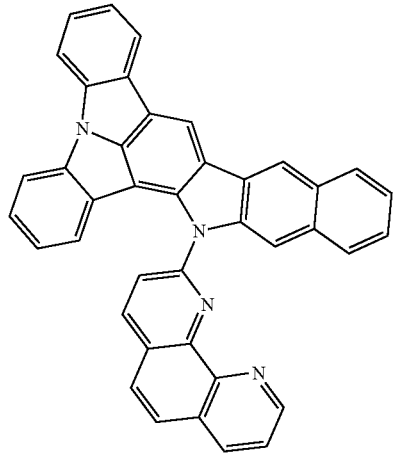
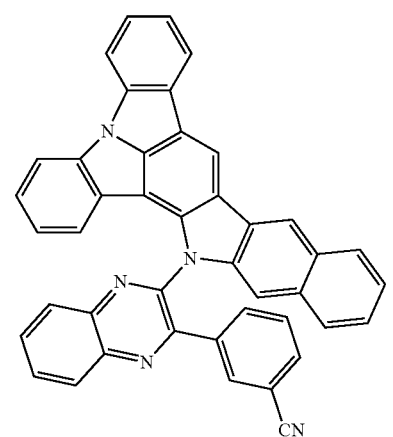
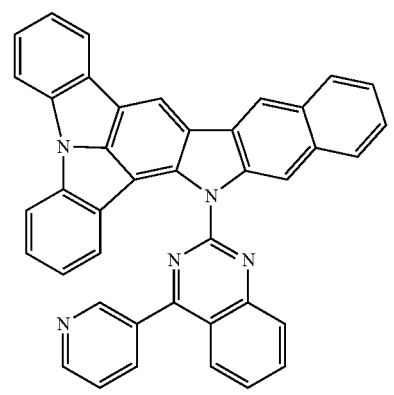
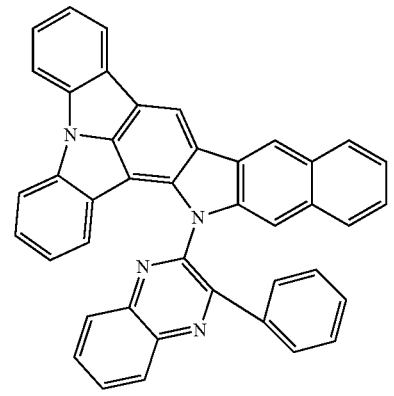

989
-continued
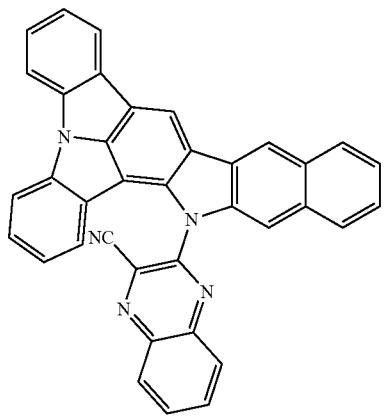
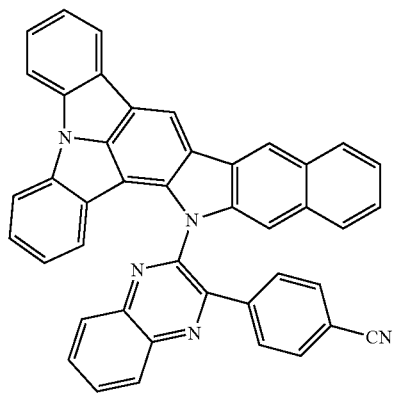
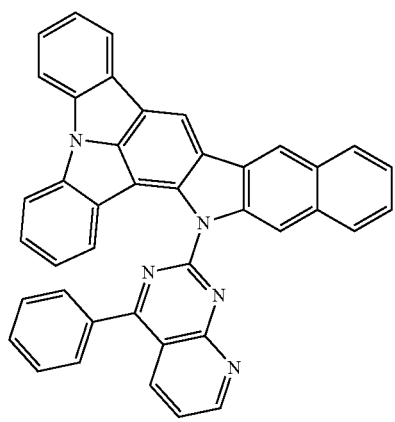
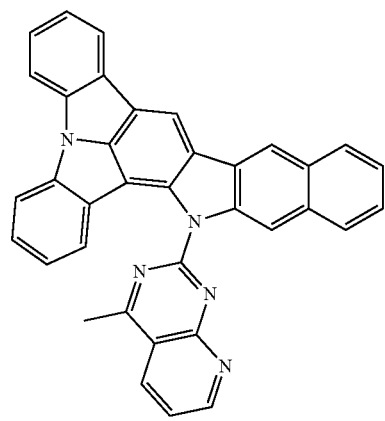
990
-continued
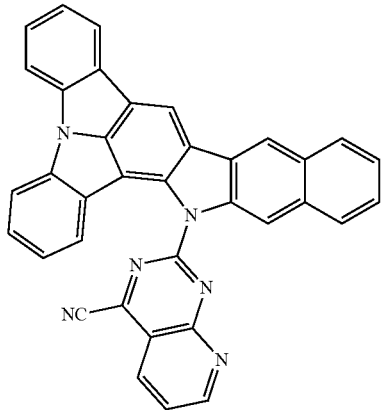
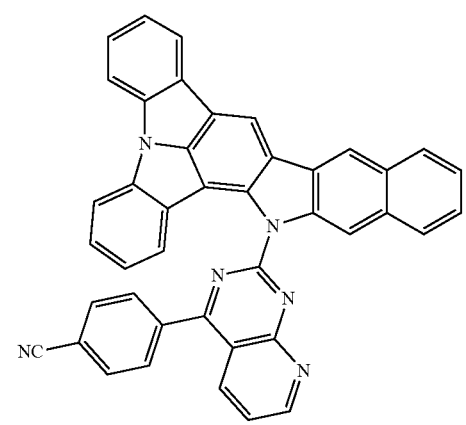
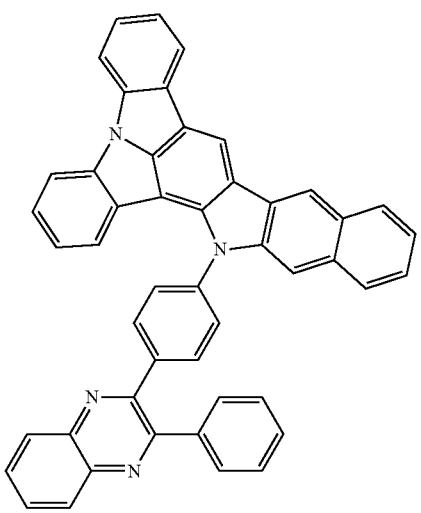

991
-continued
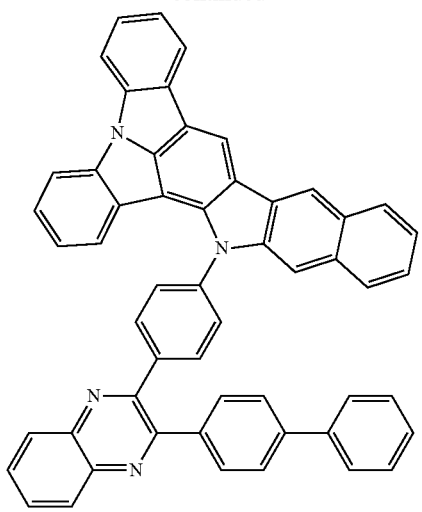
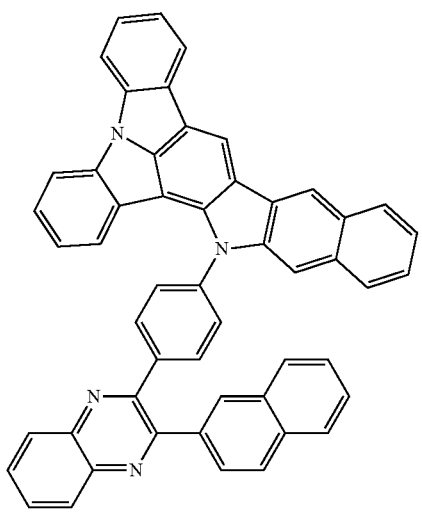
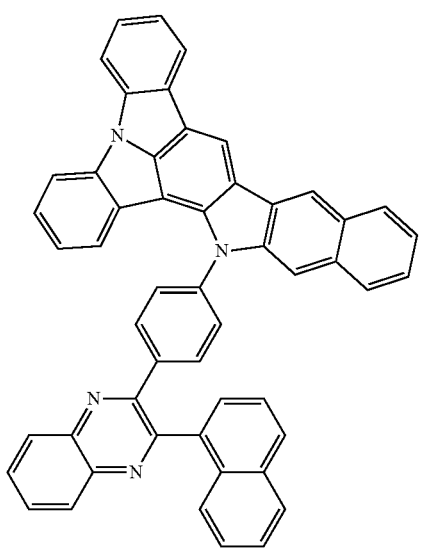
992
-continued
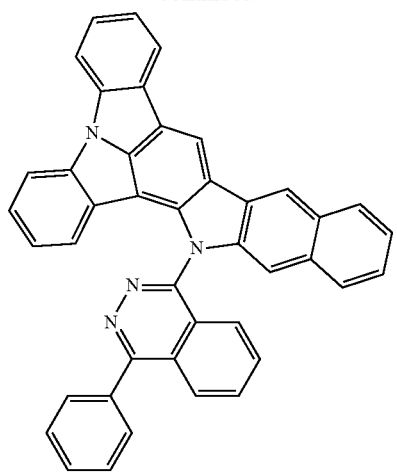
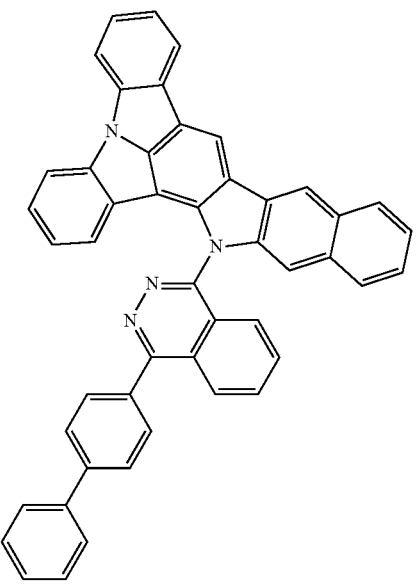
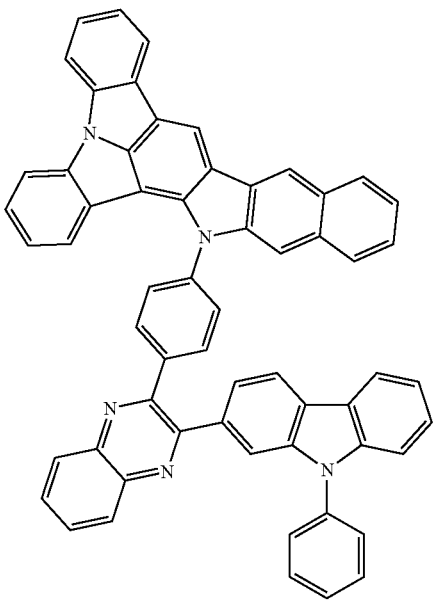

993
-continued
994
-continued
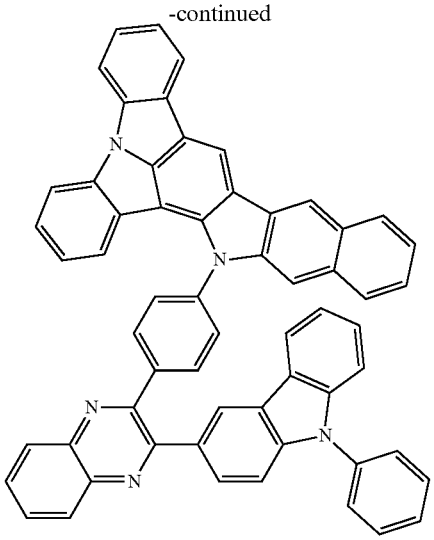
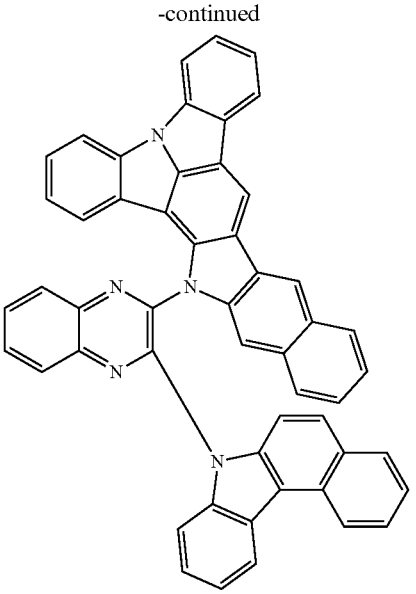

995
-continued
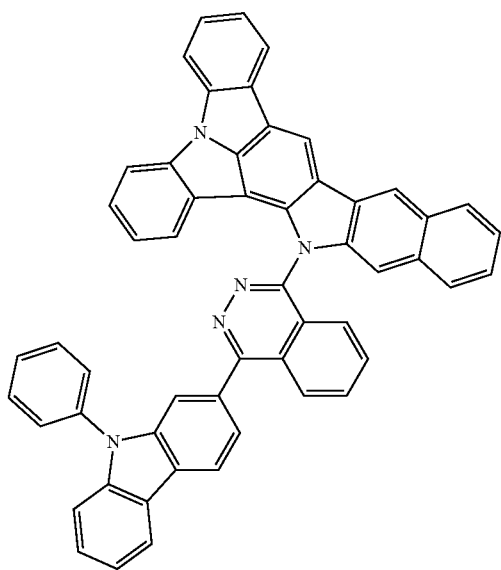
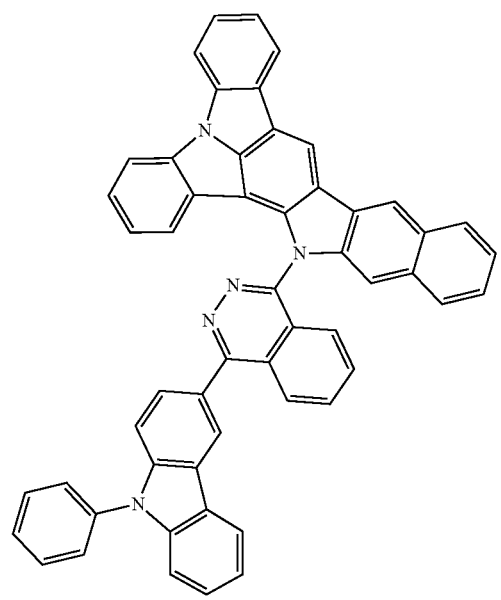
996
-continued
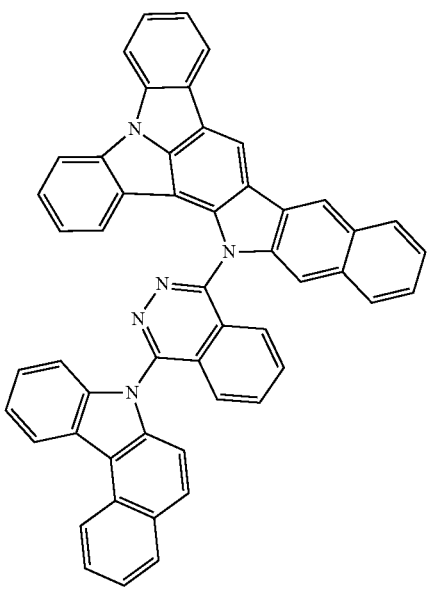
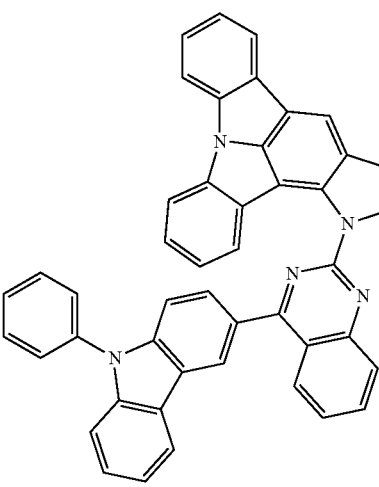
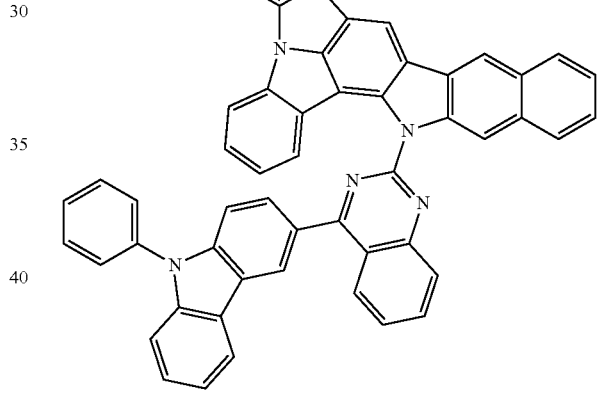
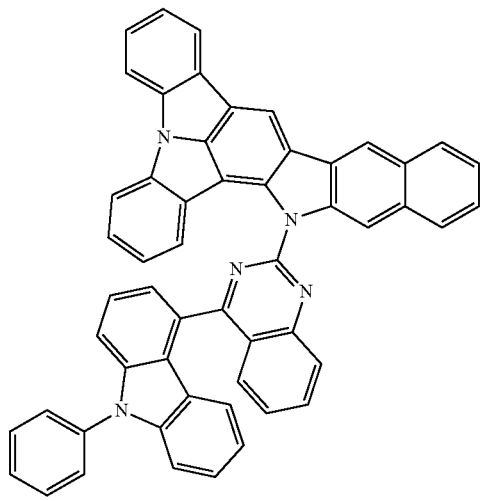

997
-continued
998
-continued
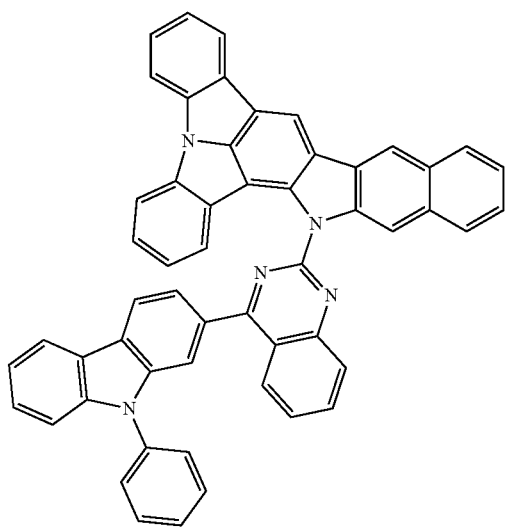
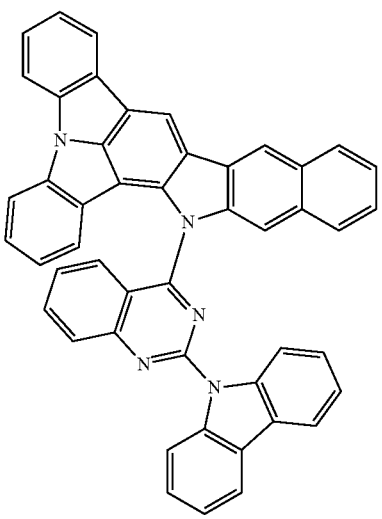
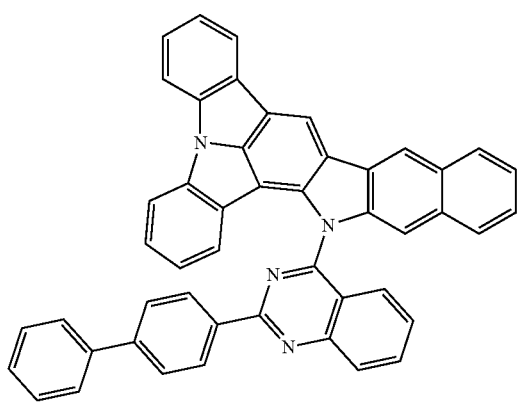
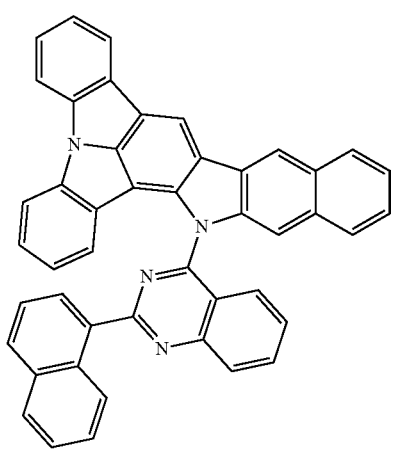
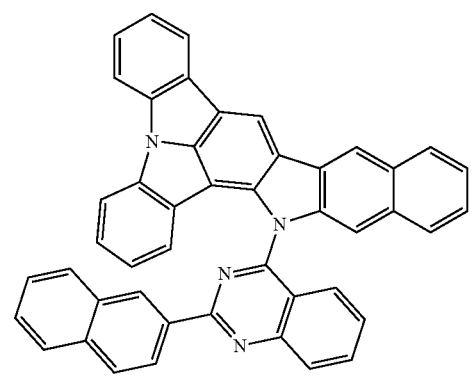
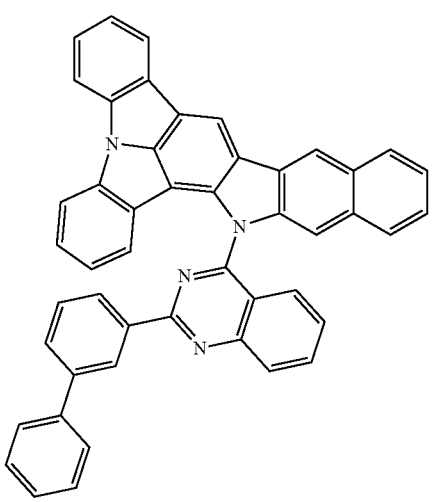

999
-continued
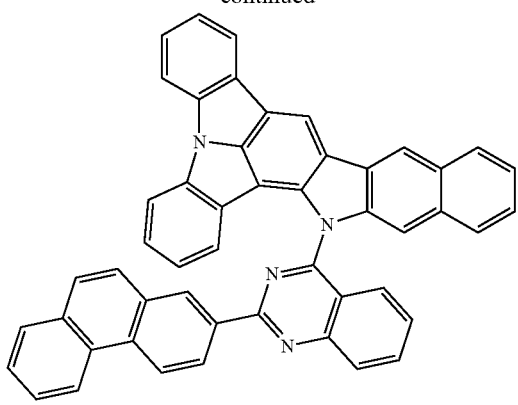
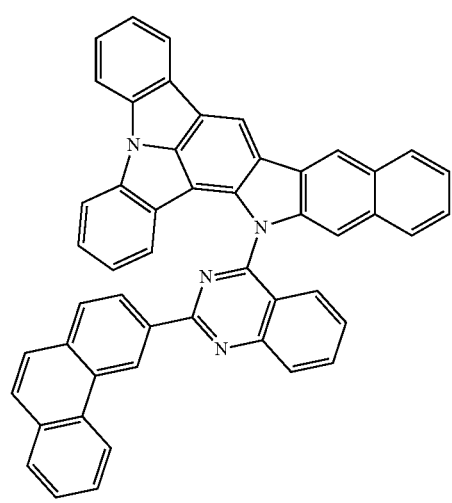
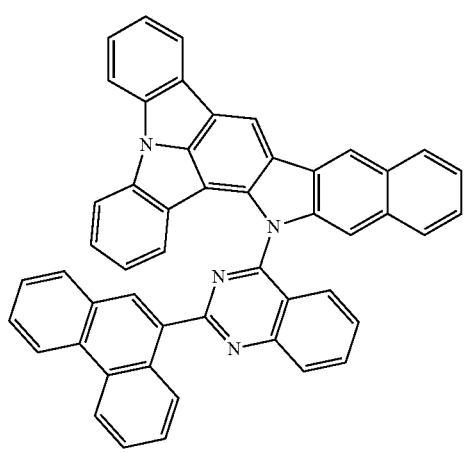
1000
-continued
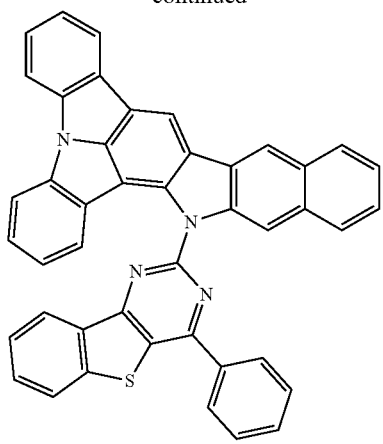
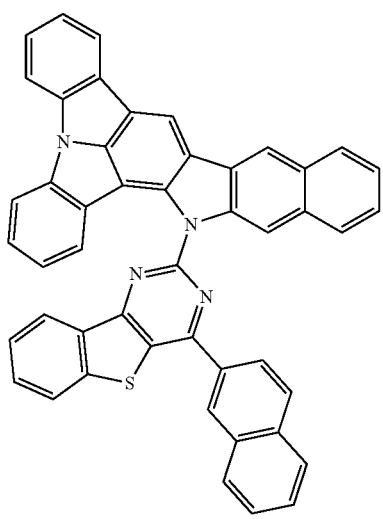
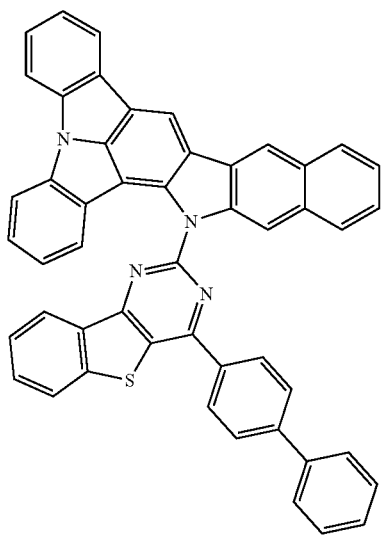

1001
-continued
1002
-continued
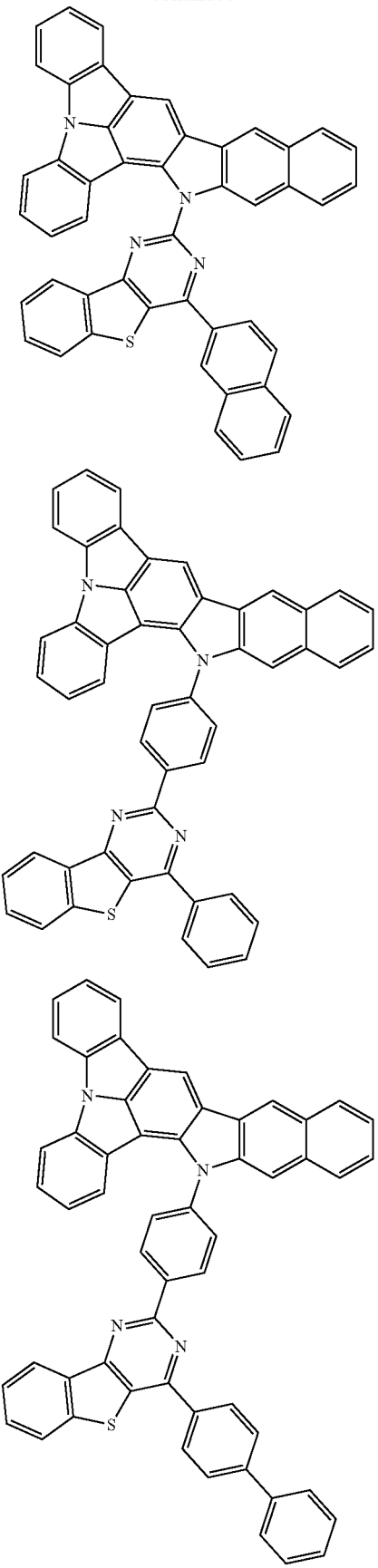
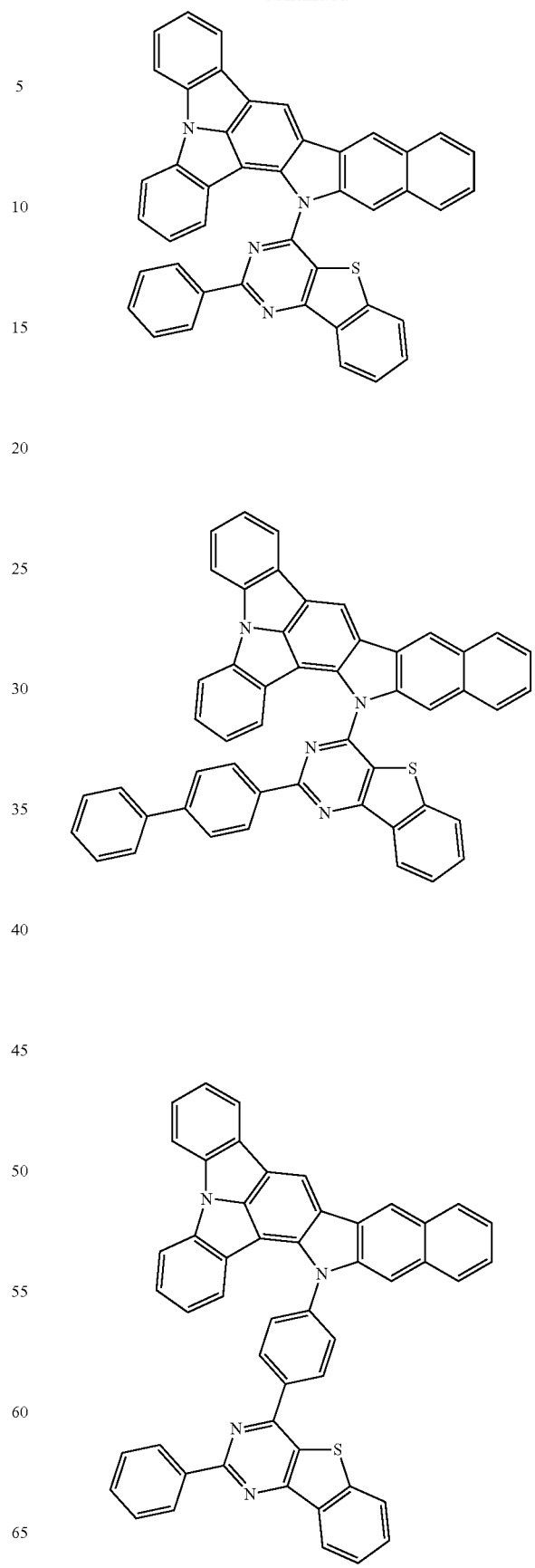

1003
-continued
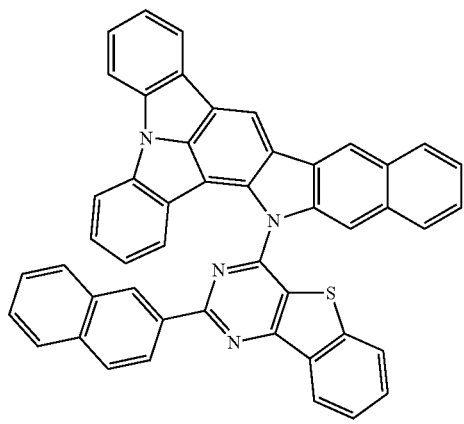
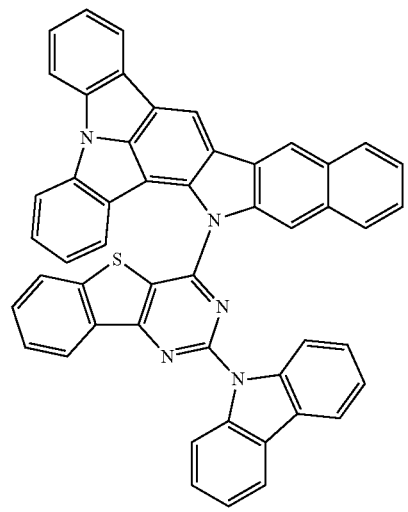
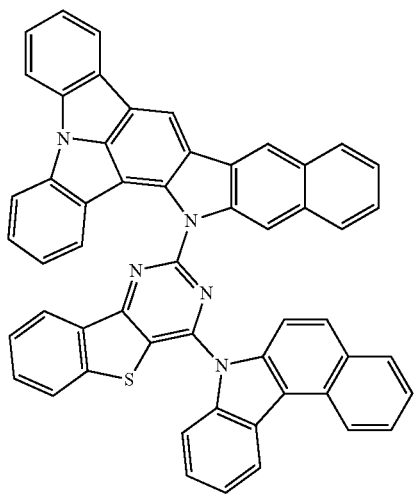
1004
-continued
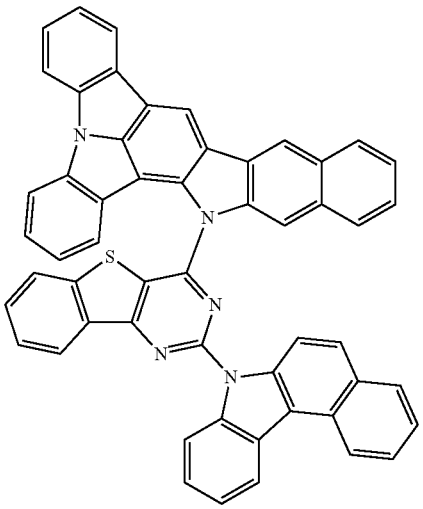
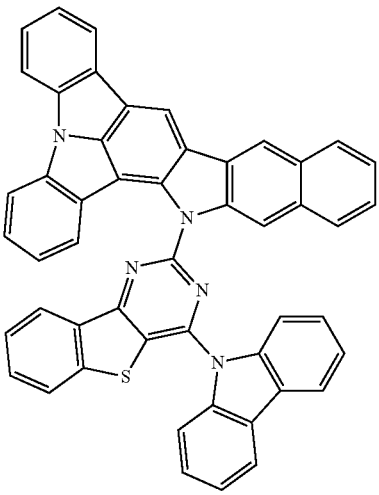
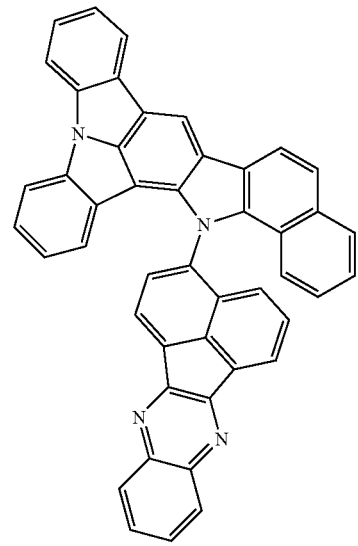

1005
-continued
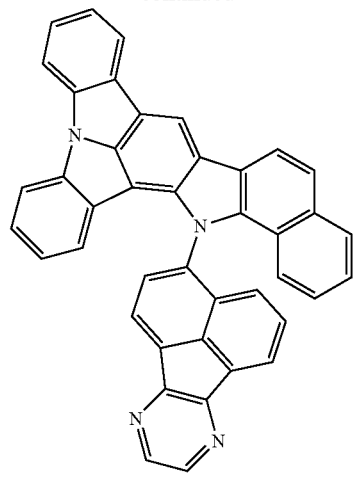
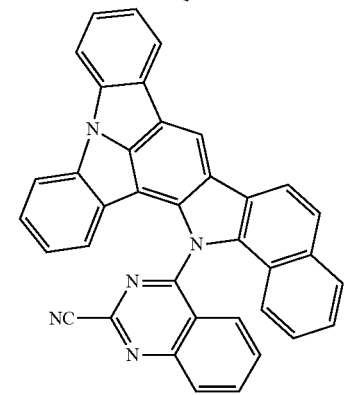
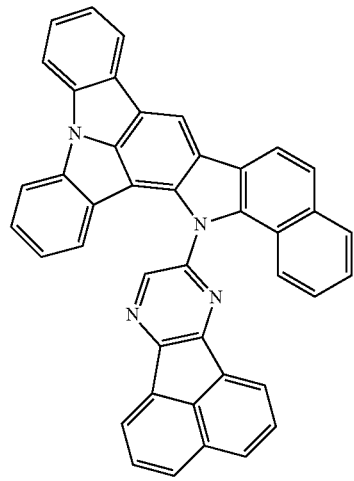
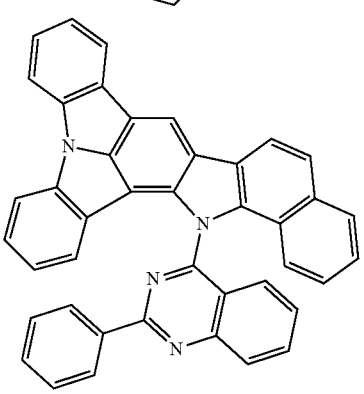
1006
-continued
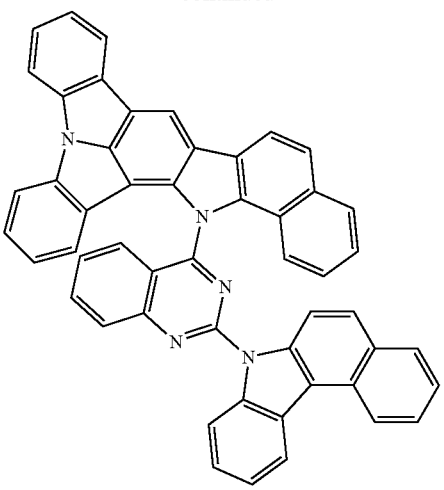
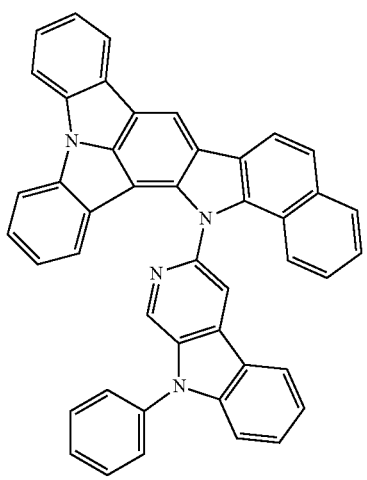
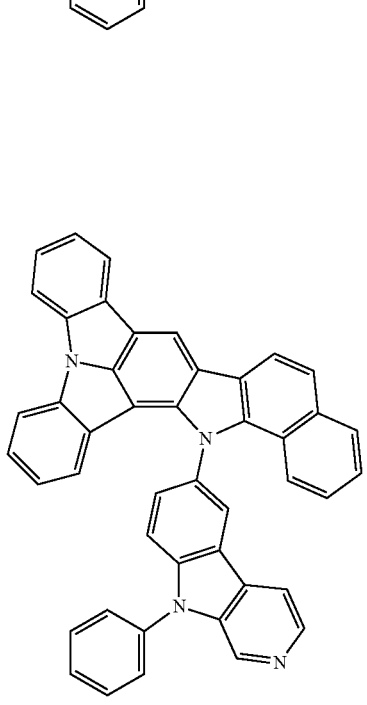

1007
-continued
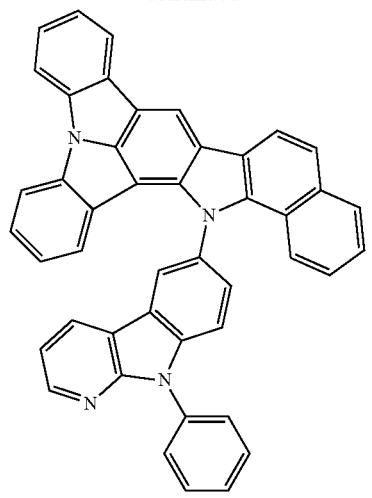
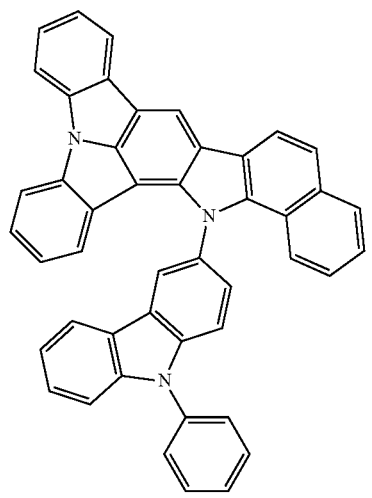
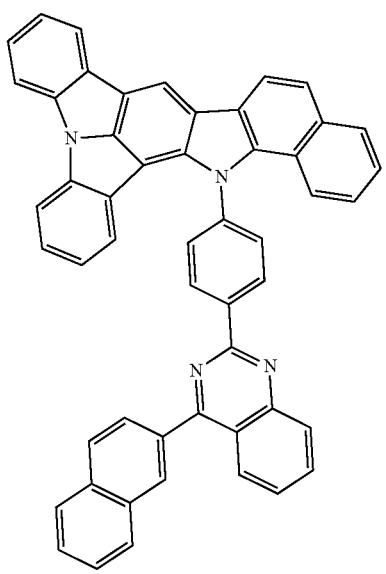
1008
-continued
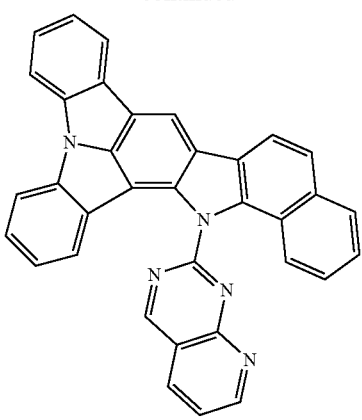
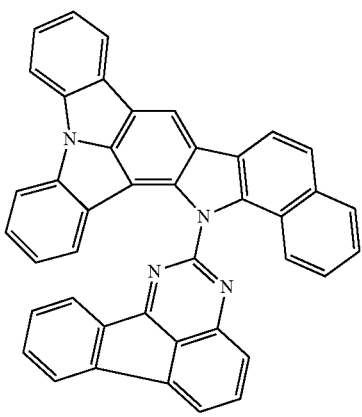
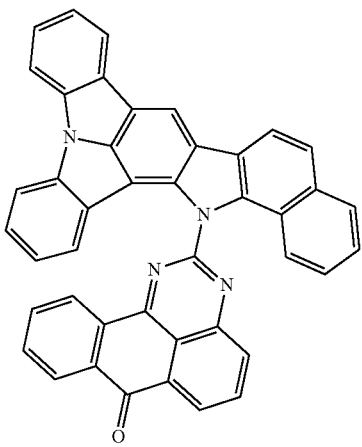
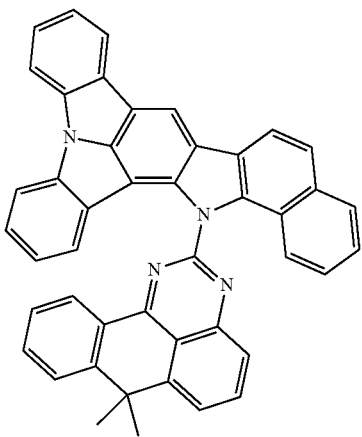

1009
-continued
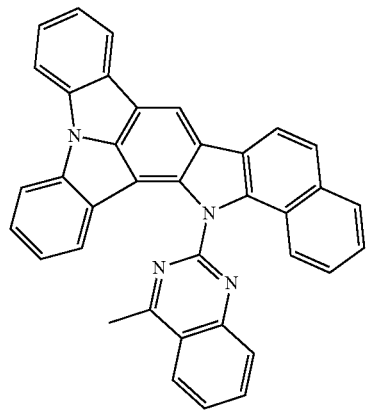
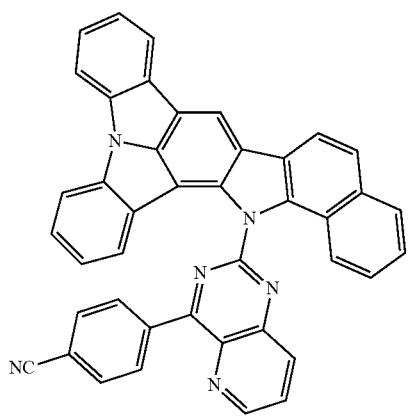
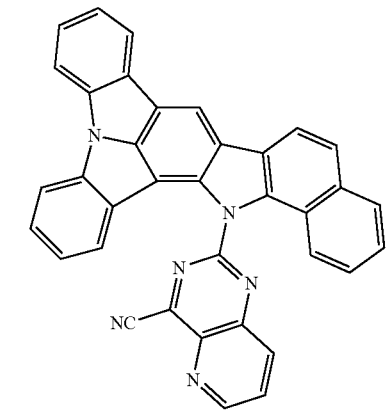
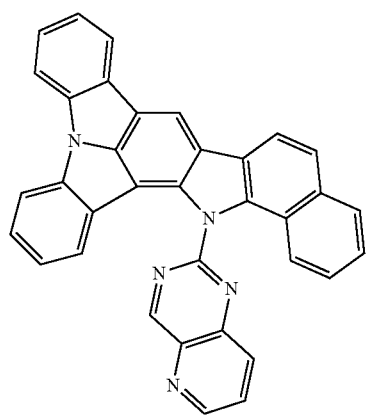
1010
-continued
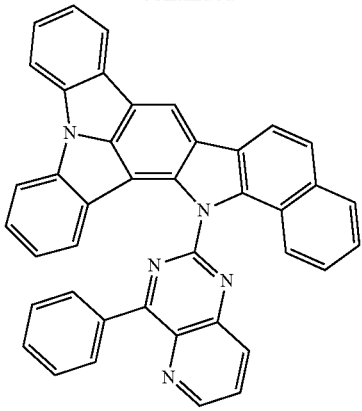
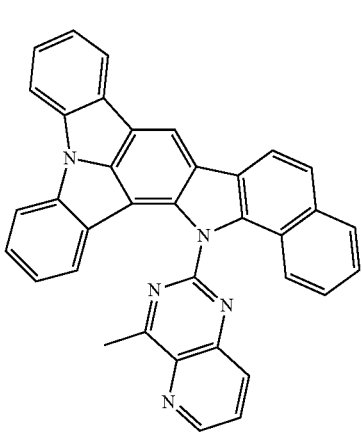
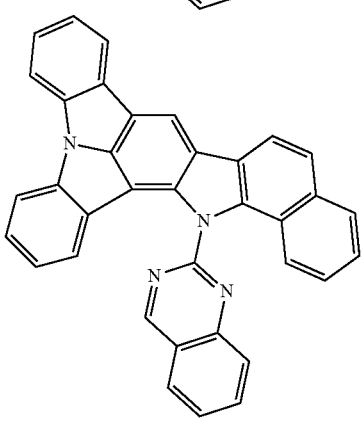
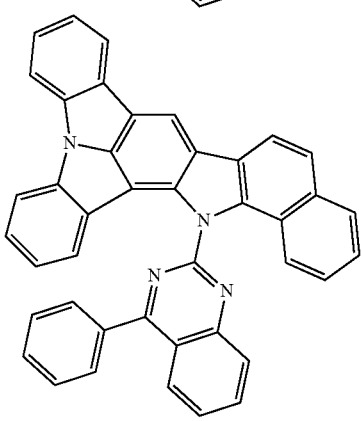

| 1011 -continued | 1012 -continued |
|---|---|
| 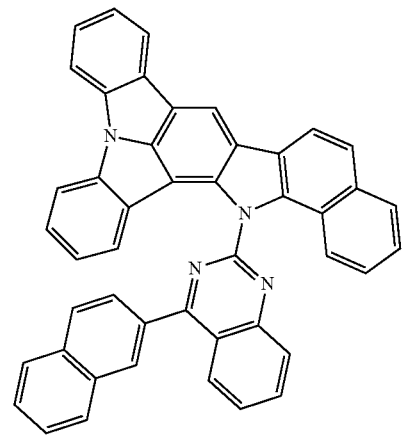 | 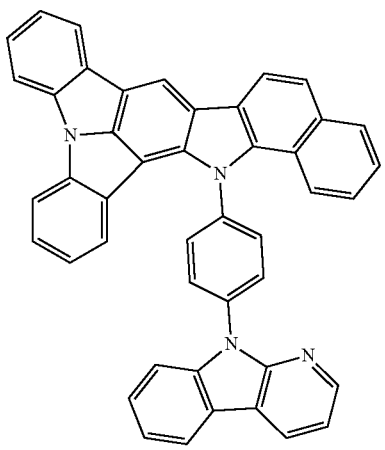 |
| 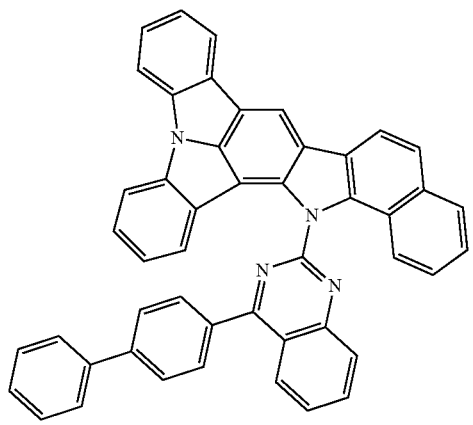 | 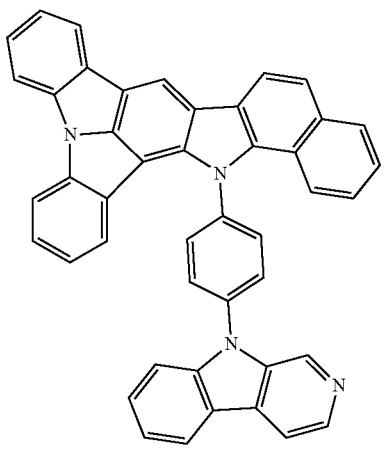 |
| 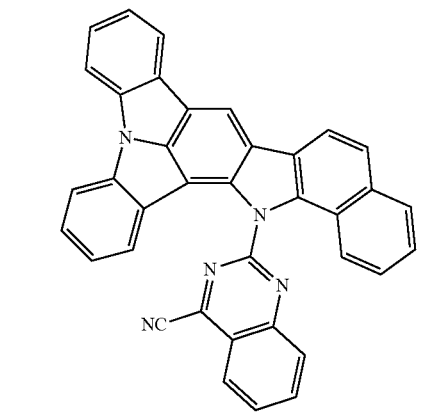 | |
| 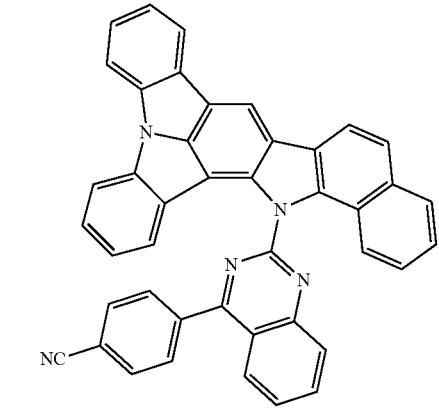 | 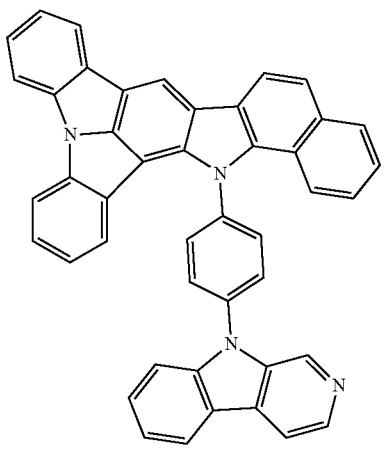 |

1013
-continued
1014
-continued
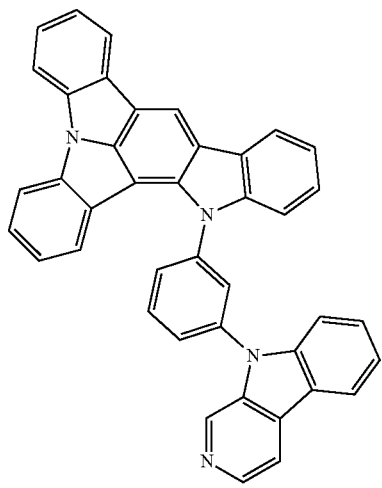
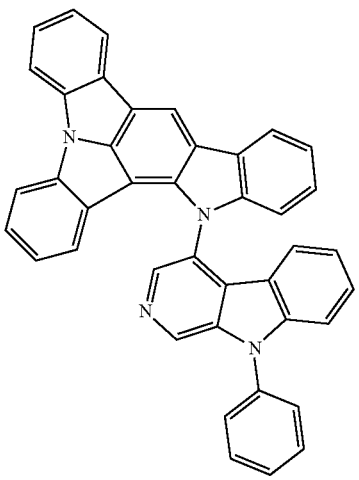
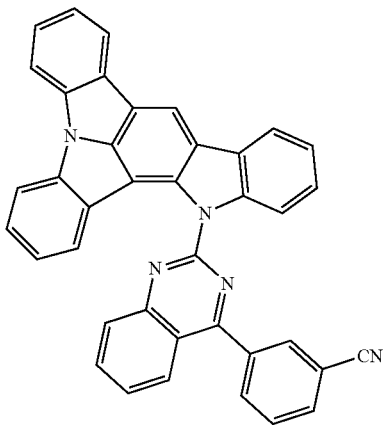
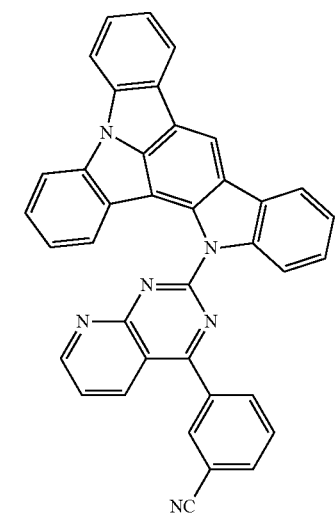
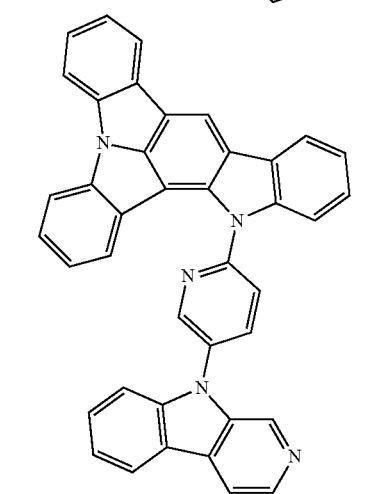
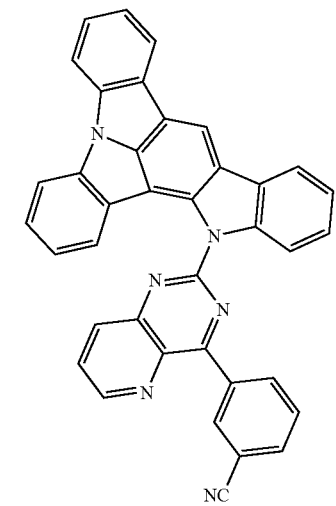 [SMILES: N#Cc1cccc(-c2nc(-n3c4ccccc4c4cc5c6ccccc6n6c7ccccc7c(c43)c56)nc3cccnc23)c1]

1015
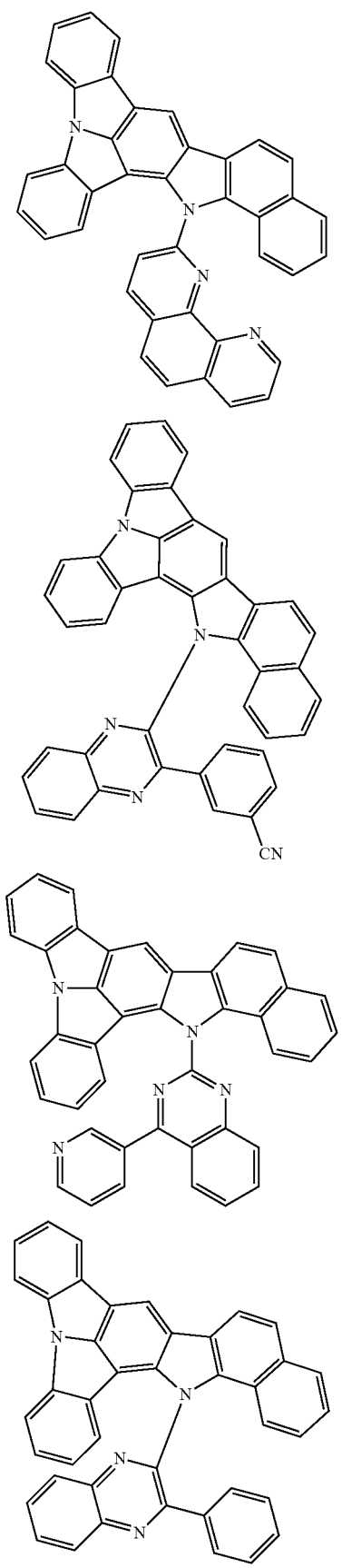
1016
-continued
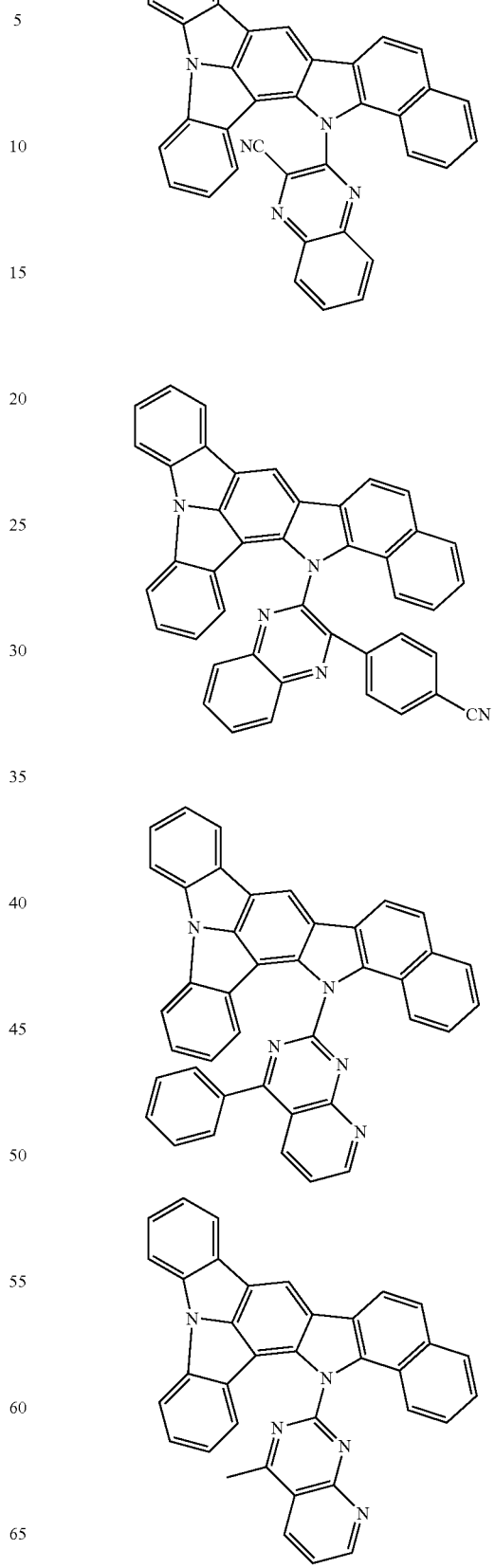

1017
-continued
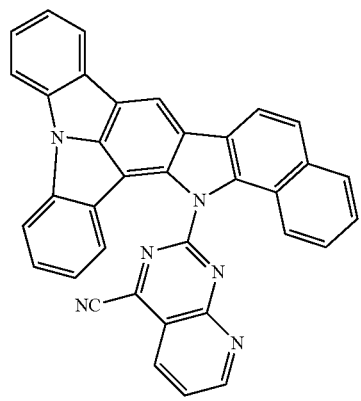
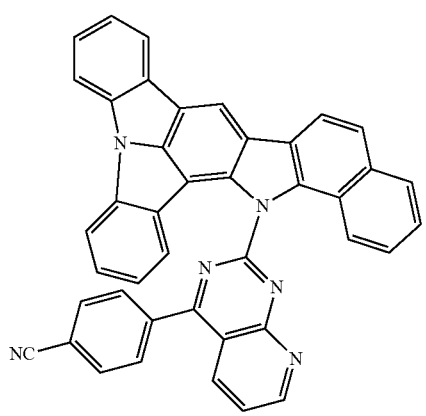
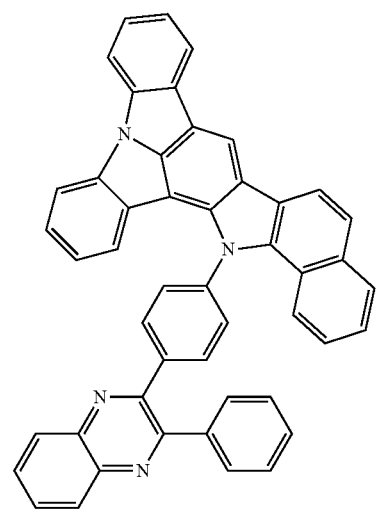
1018
-continued
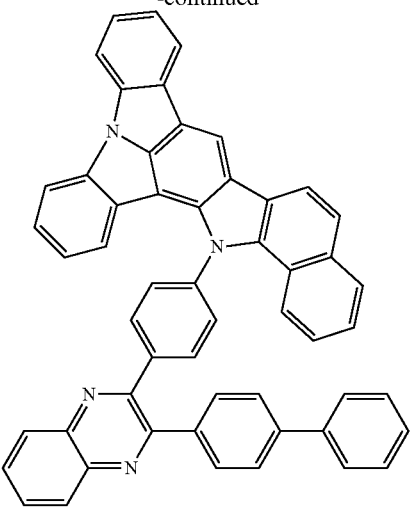
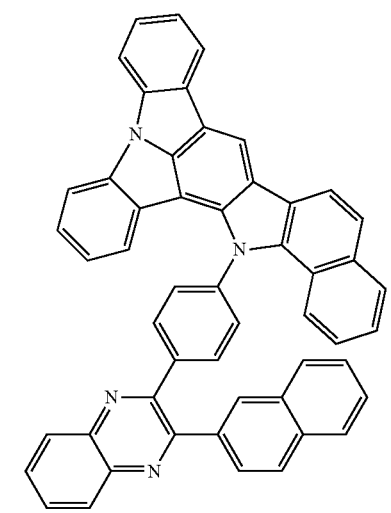
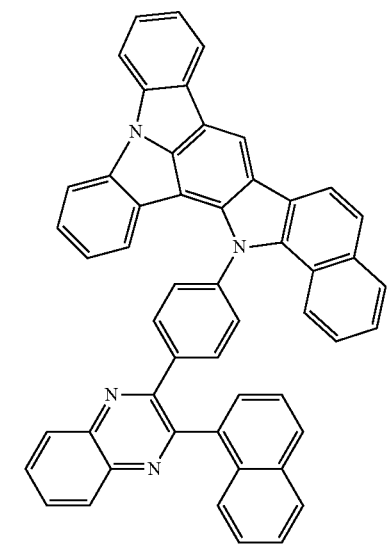

1019
-continued
1020
-continued
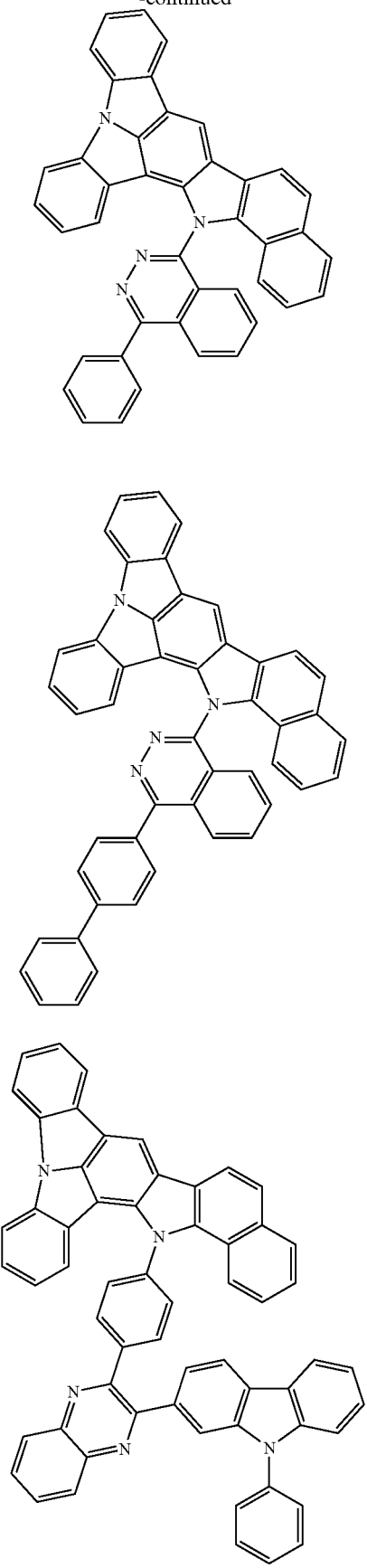
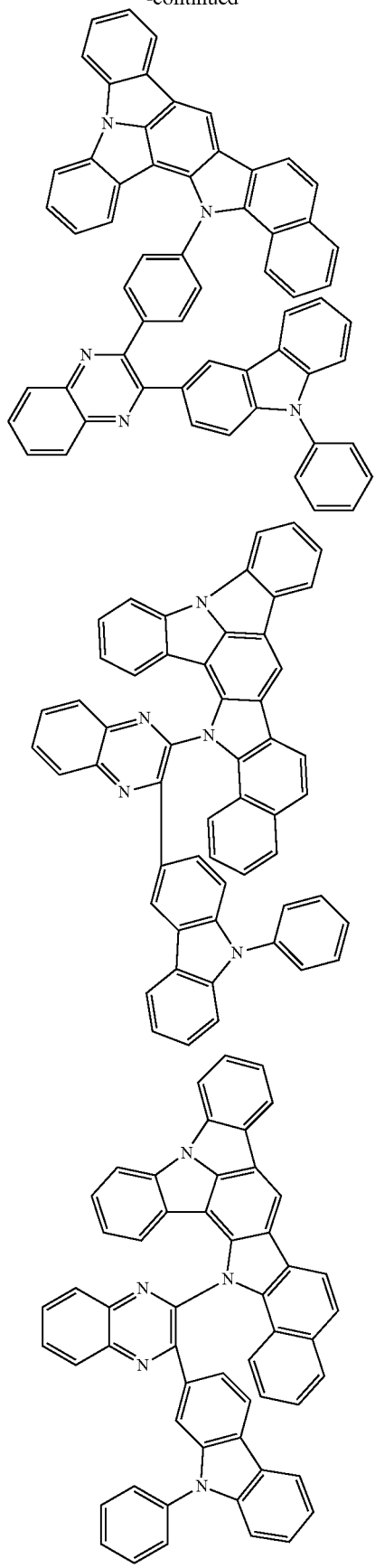

1021
-continued
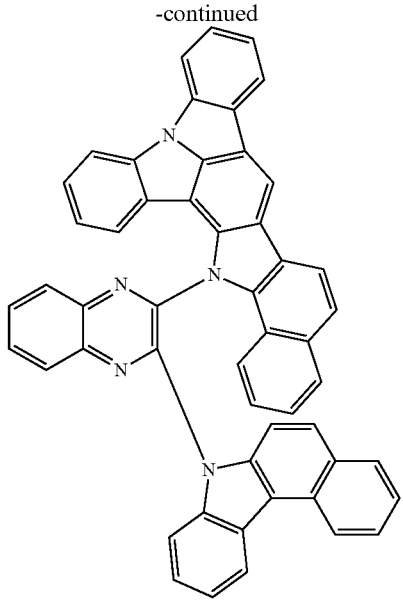
1022
-continued
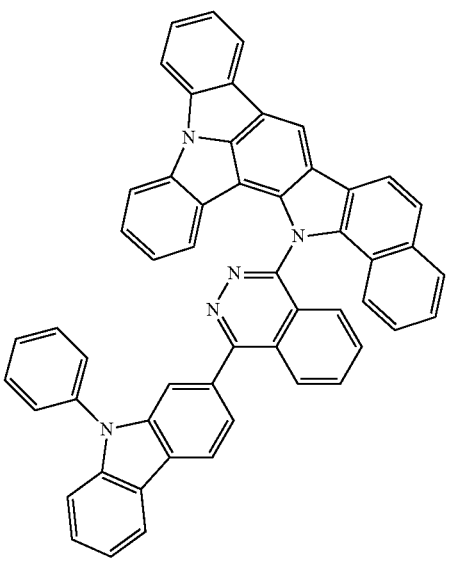
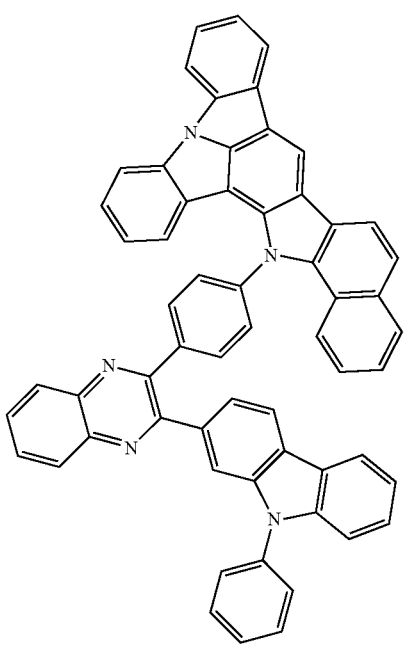
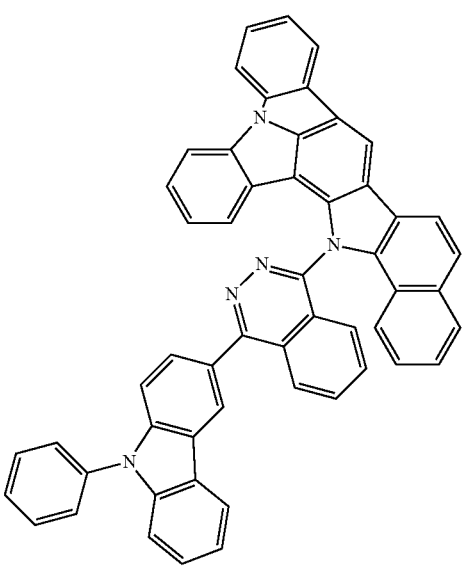

1023
-continued
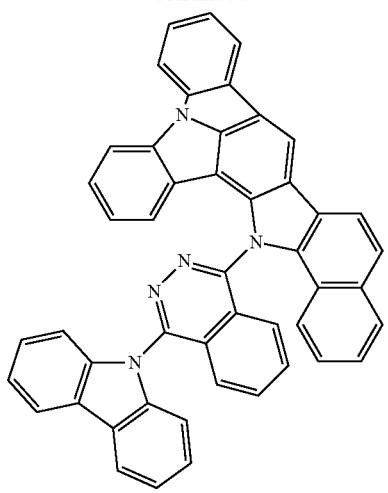
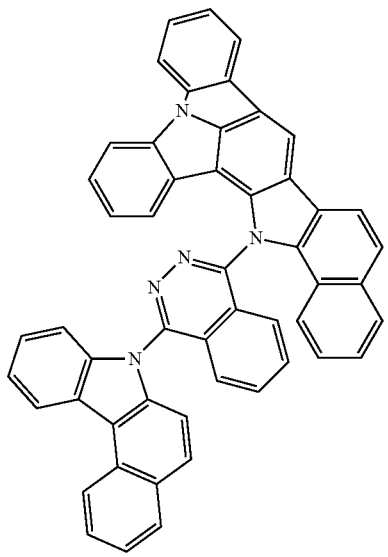
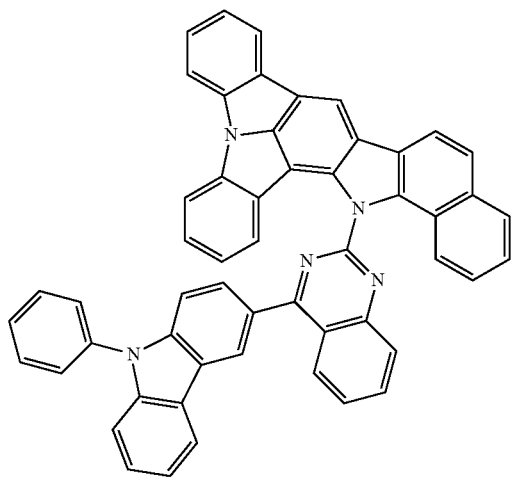
1024
-continued
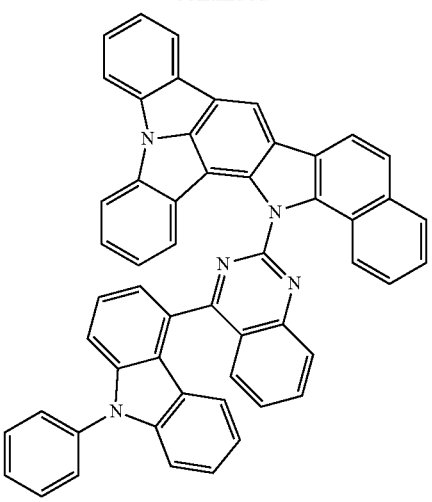
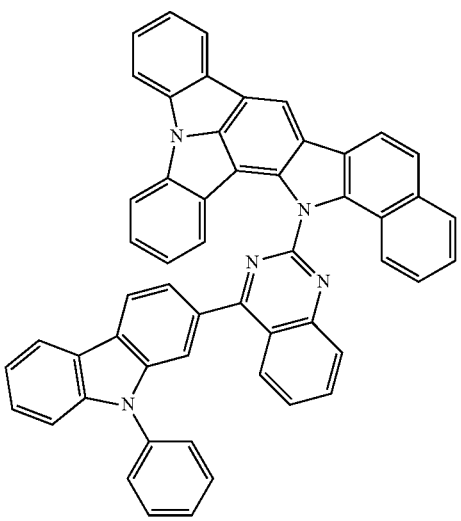
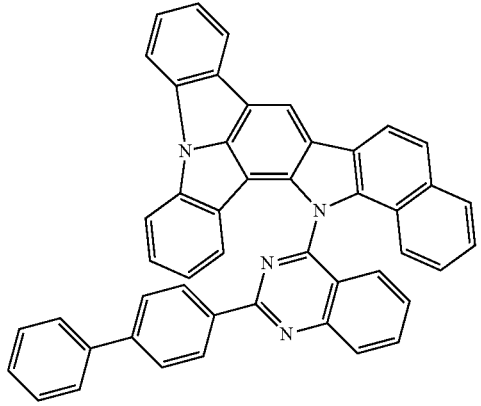

1025
-continued
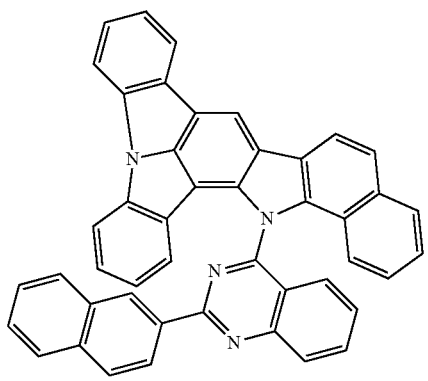
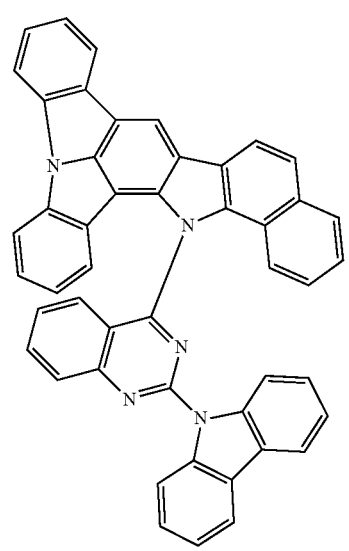
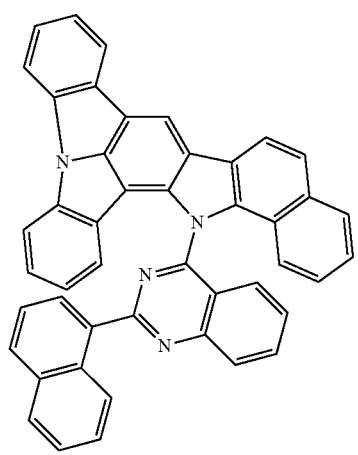
1026
-continued
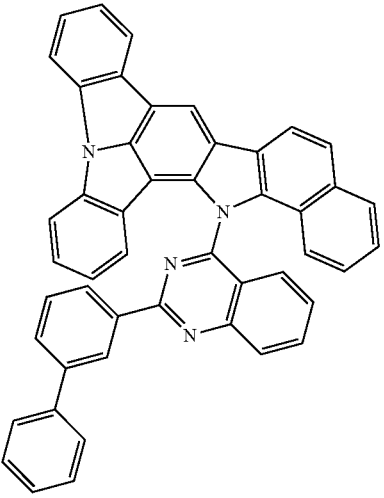
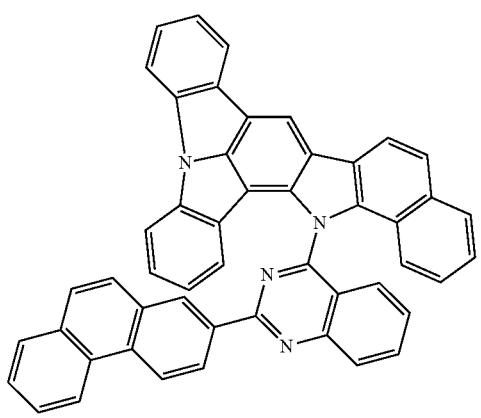
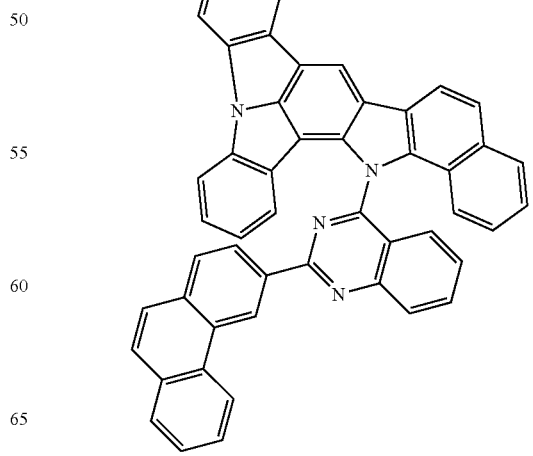

1027
-continued
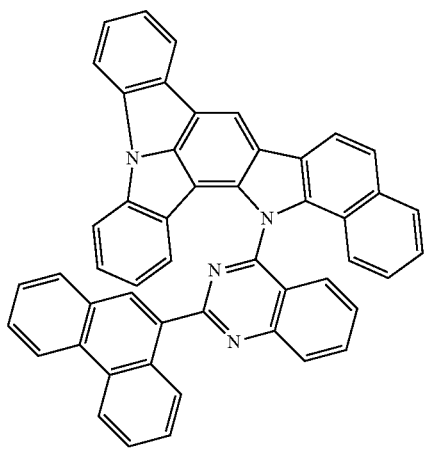
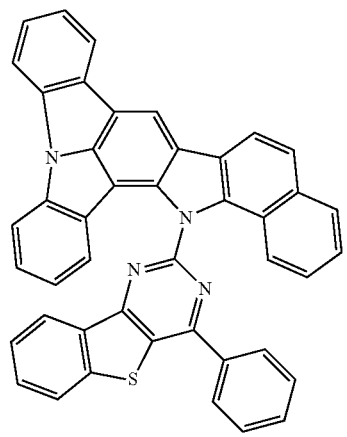
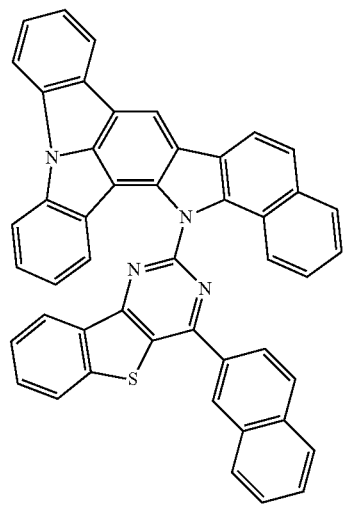
1028
-continued
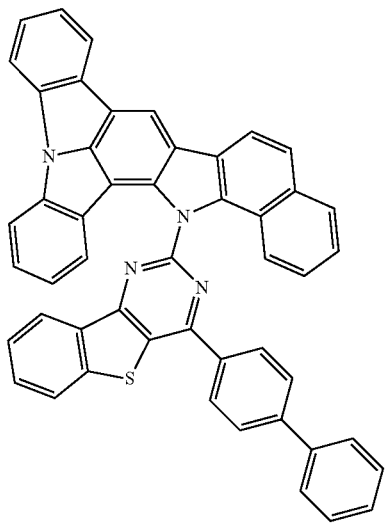
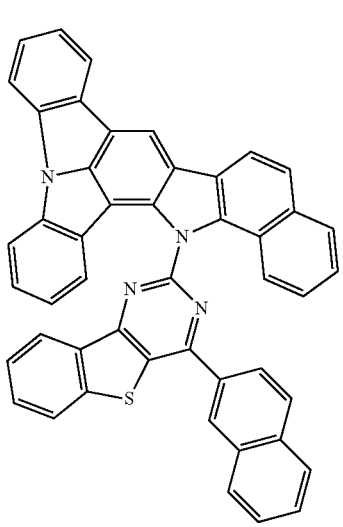
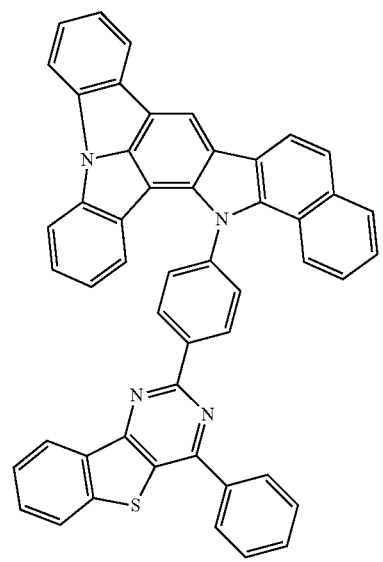

1029
-continued
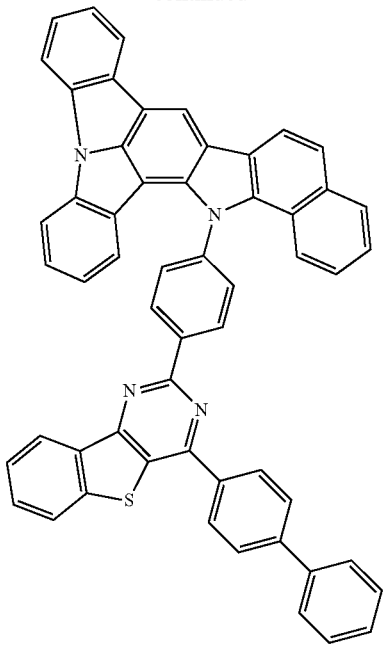
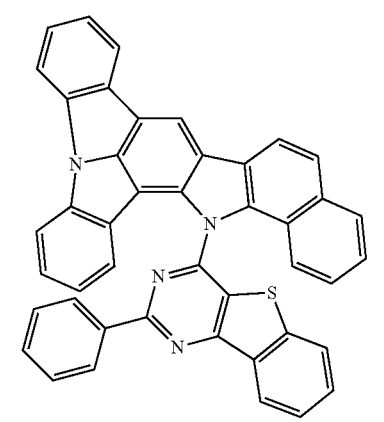
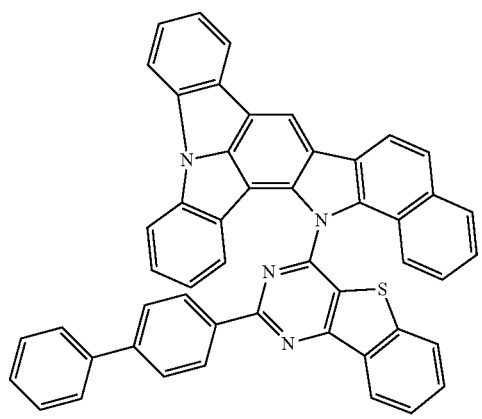
1030
-continued
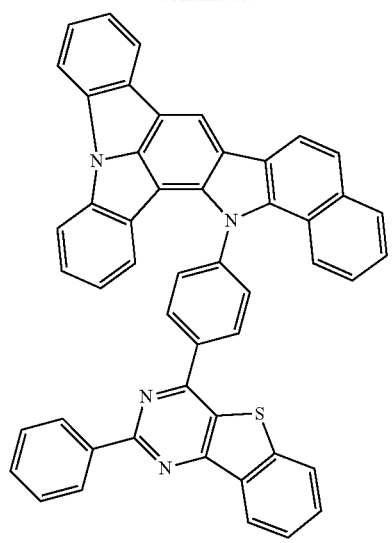
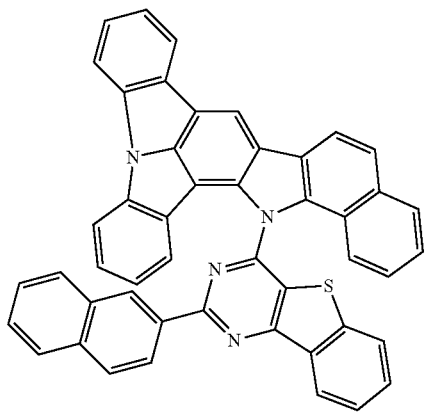
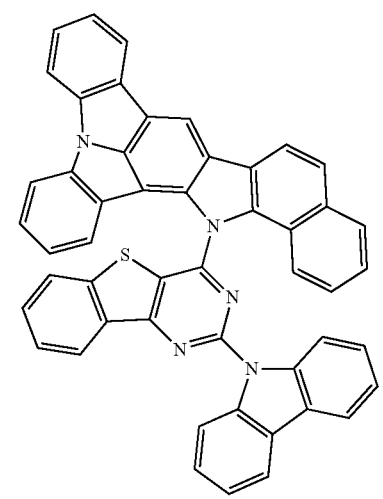

1031
-continued
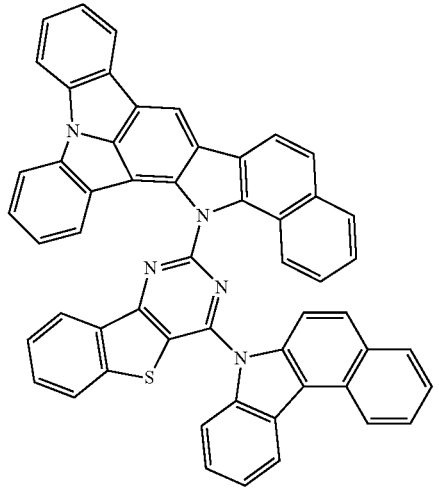
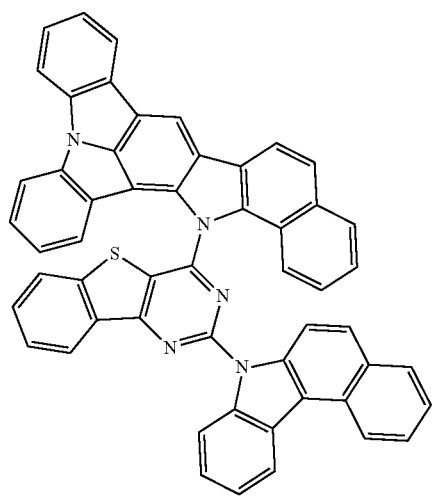
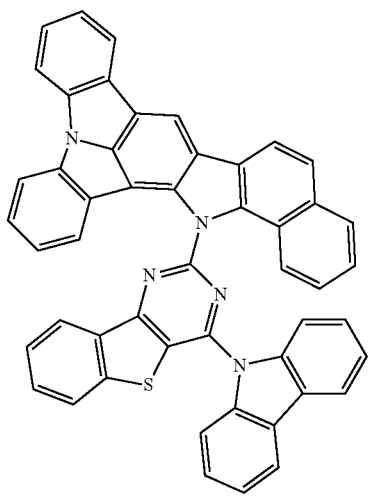
1032
-continued
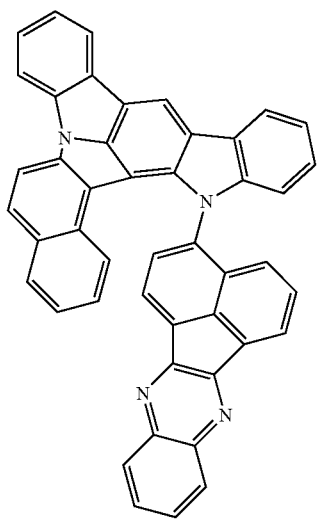
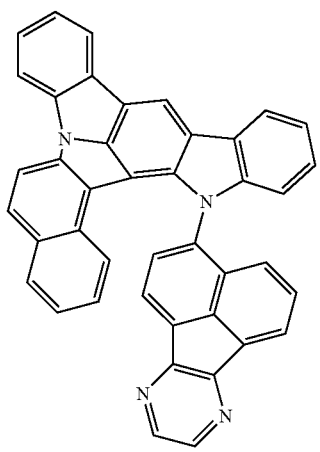
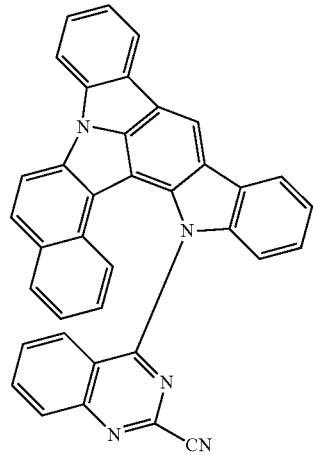

1033
-continued
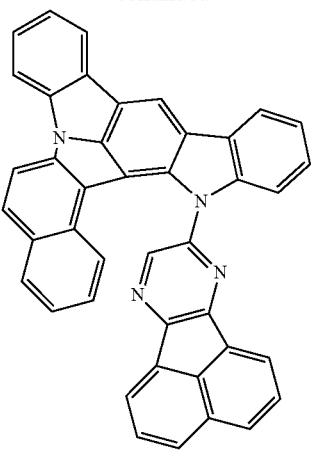
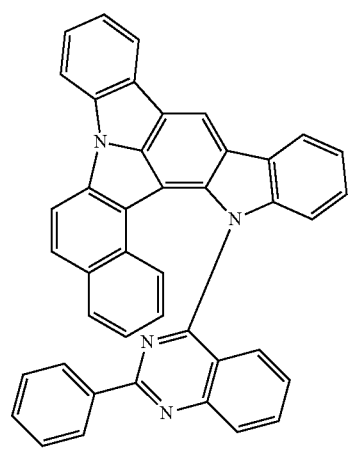
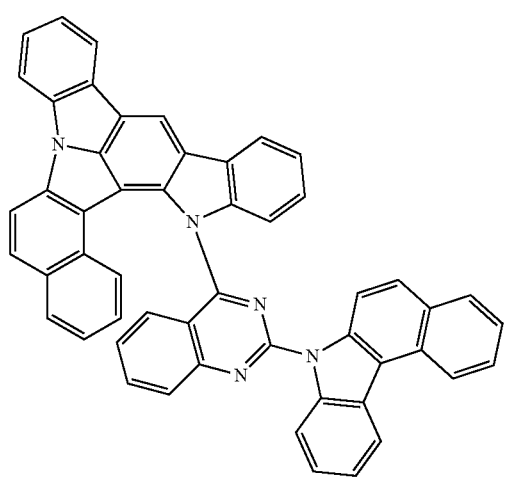
1034
-continued
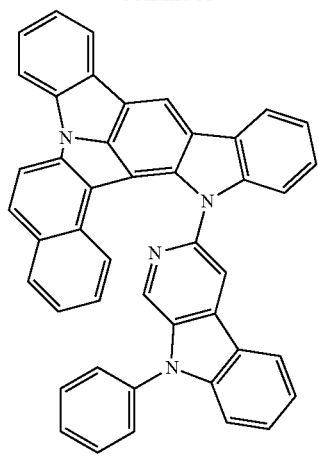
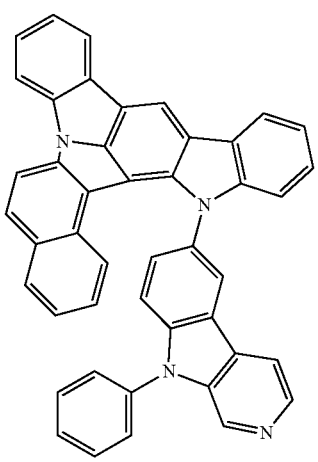
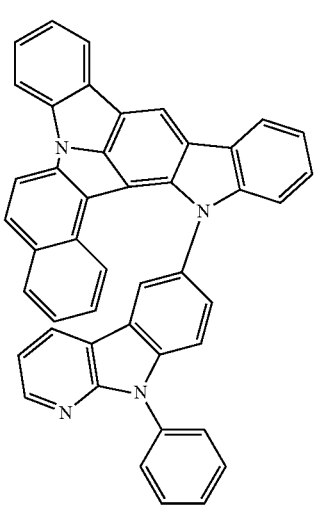

1035
-continued
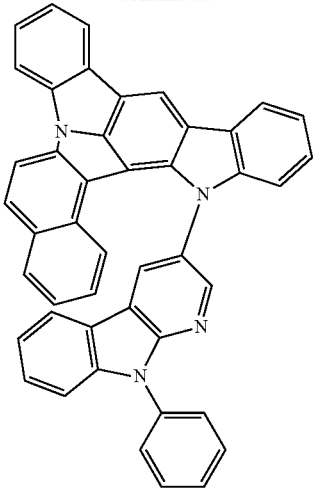
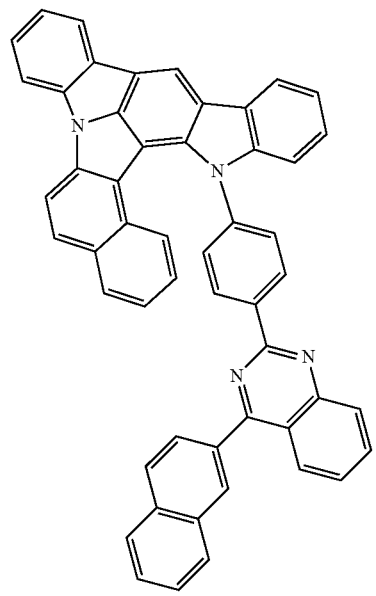
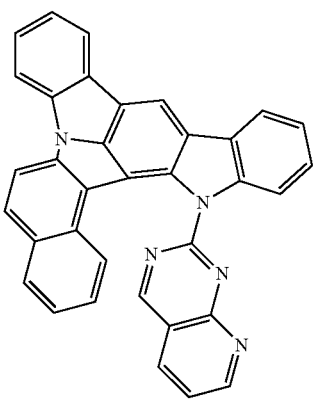
1036
-continued
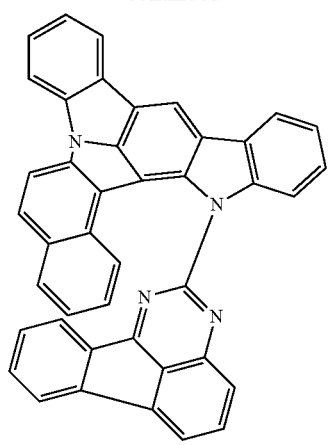
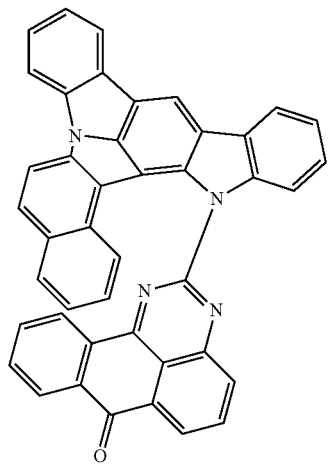
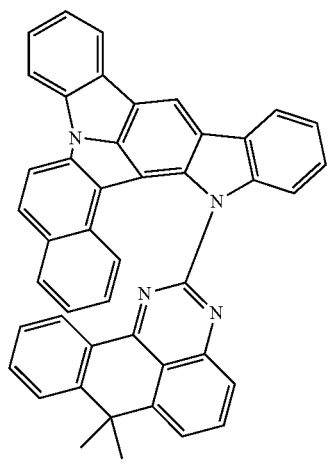

1037
-continued

1038
-continued

1039
-continued
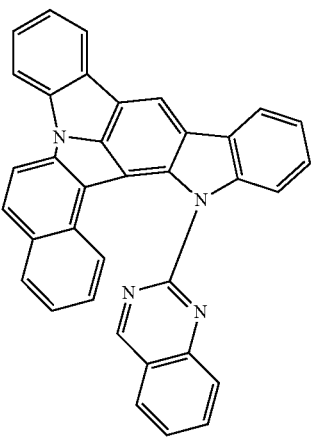
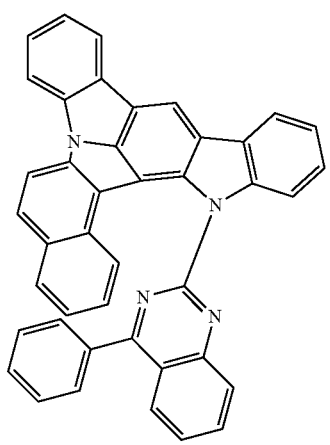
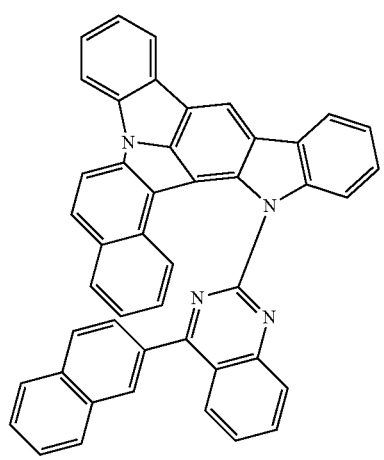
1040
-continued
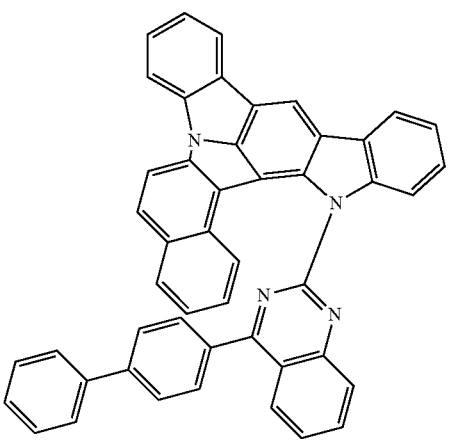
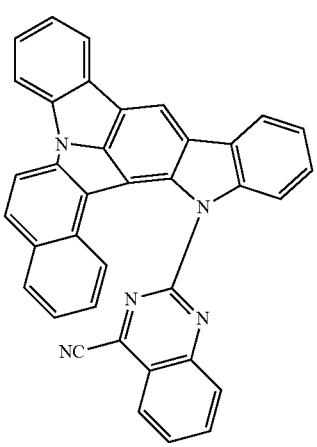
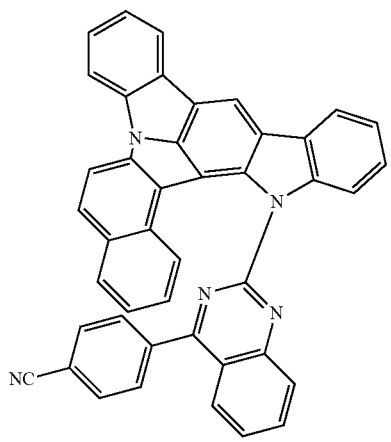

1041
-continued
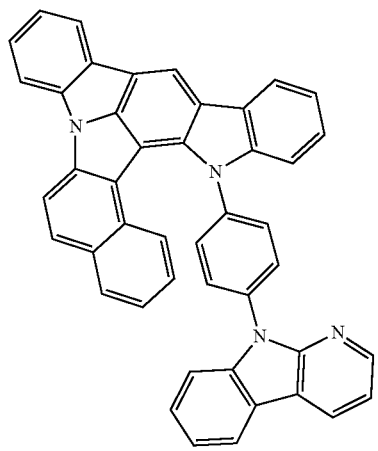
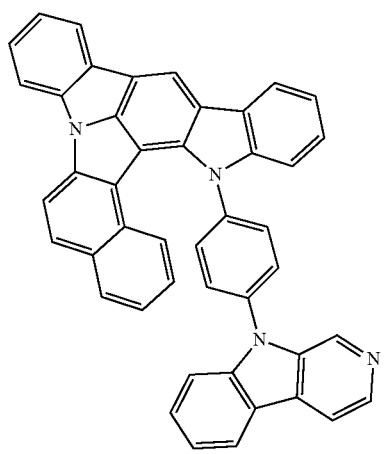
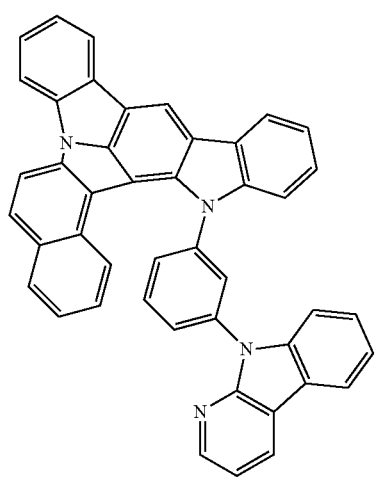
1042
-continued
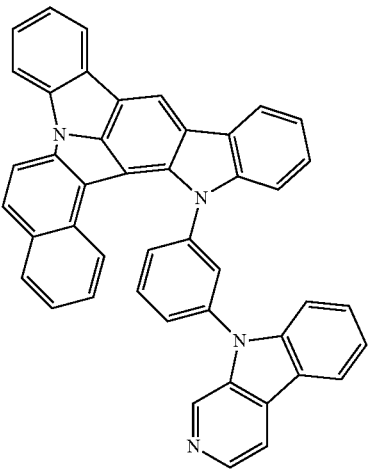
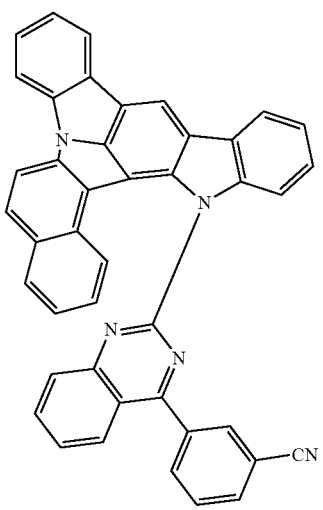
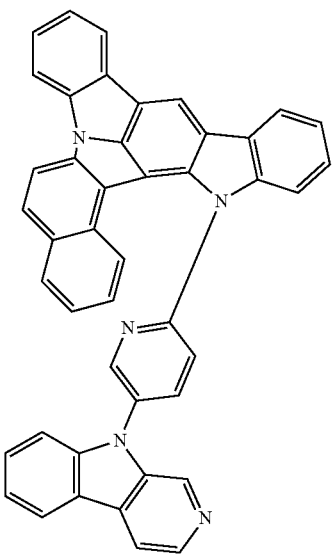

1043
-continued
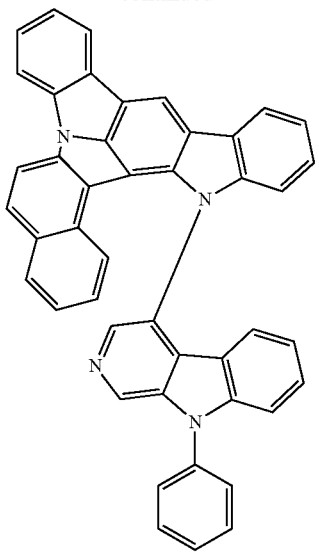
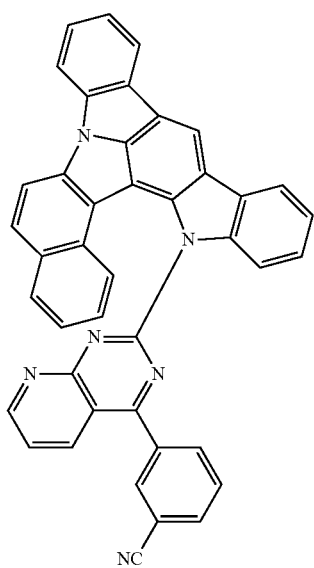
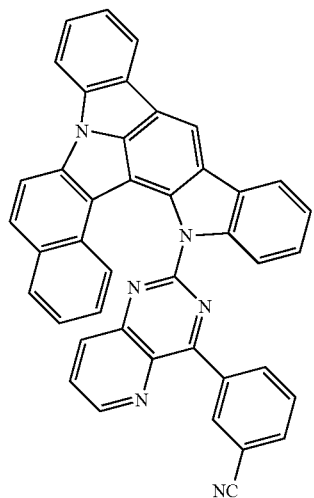
1044
-continued
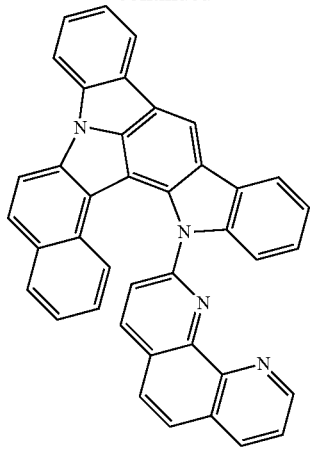
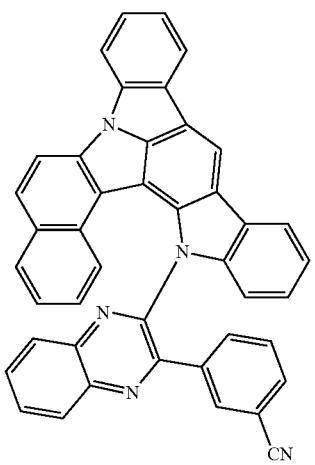
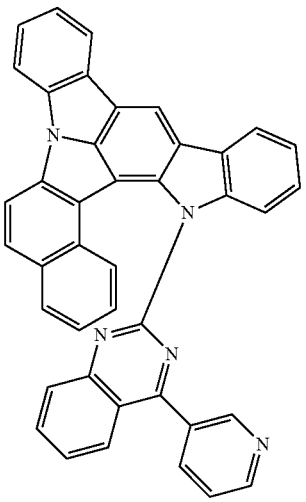

1045
-continued
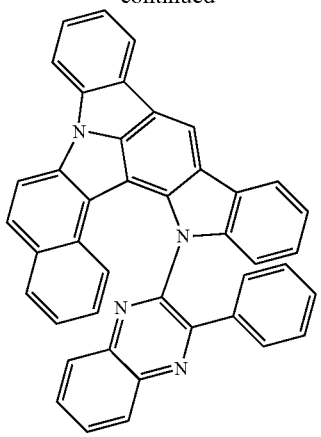
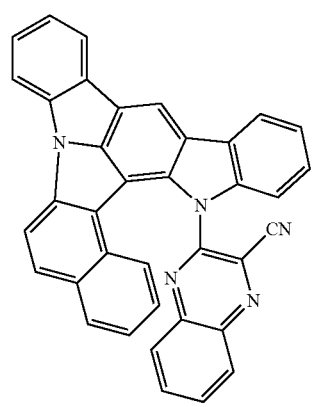
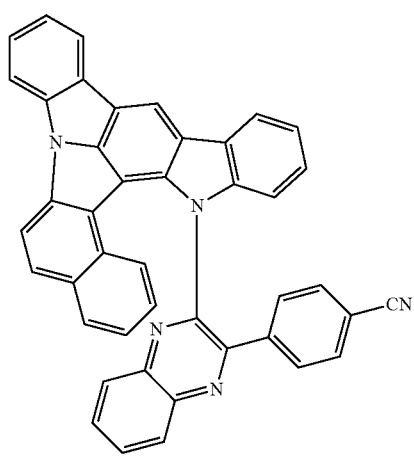
1046
-continued
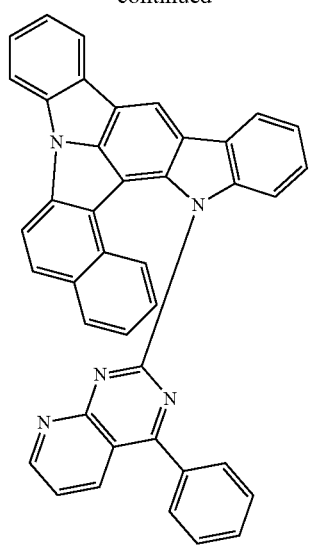
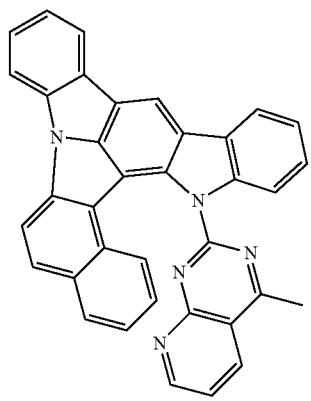
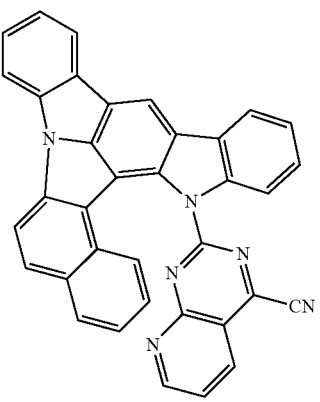

1047
-continued
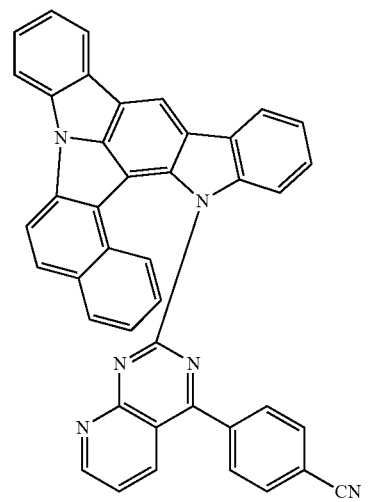
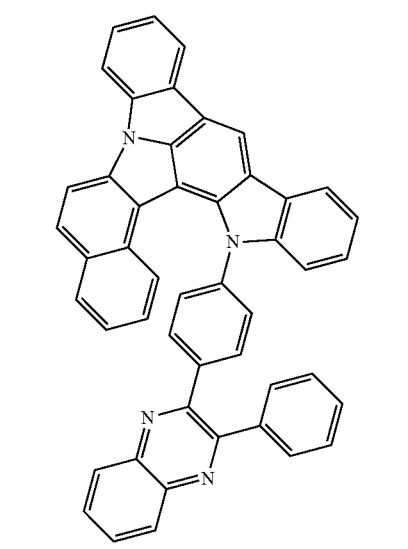
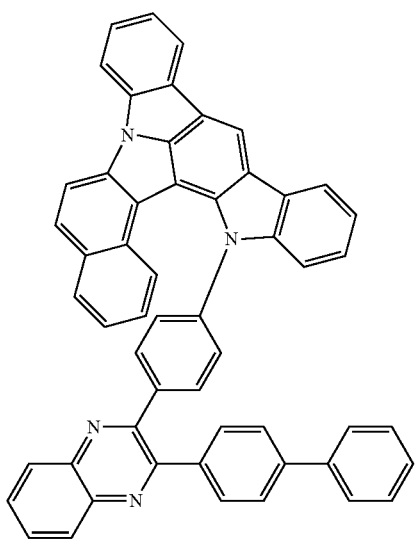
1048
-continued
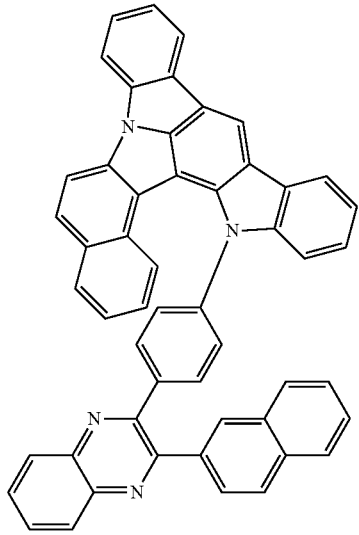
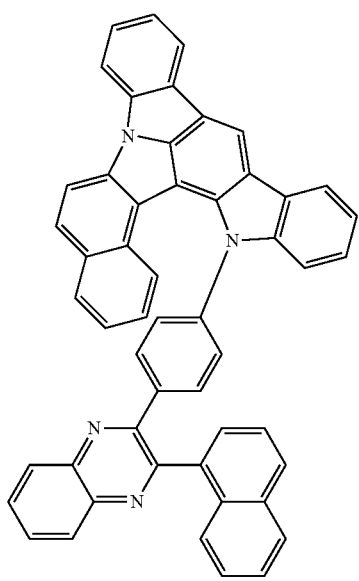
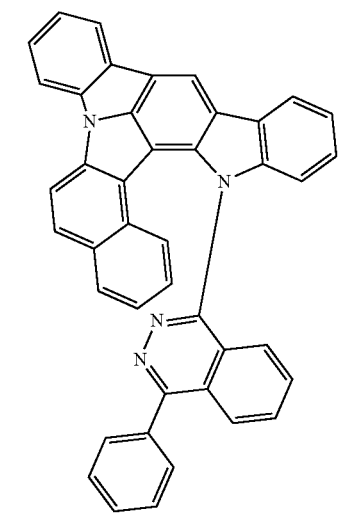

1049
-continued
1050
-continued
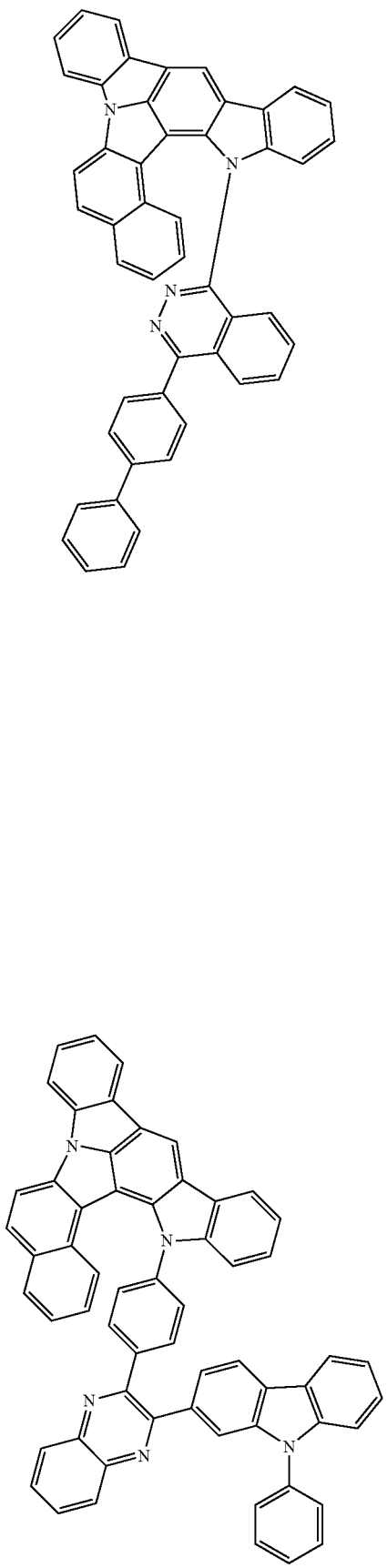
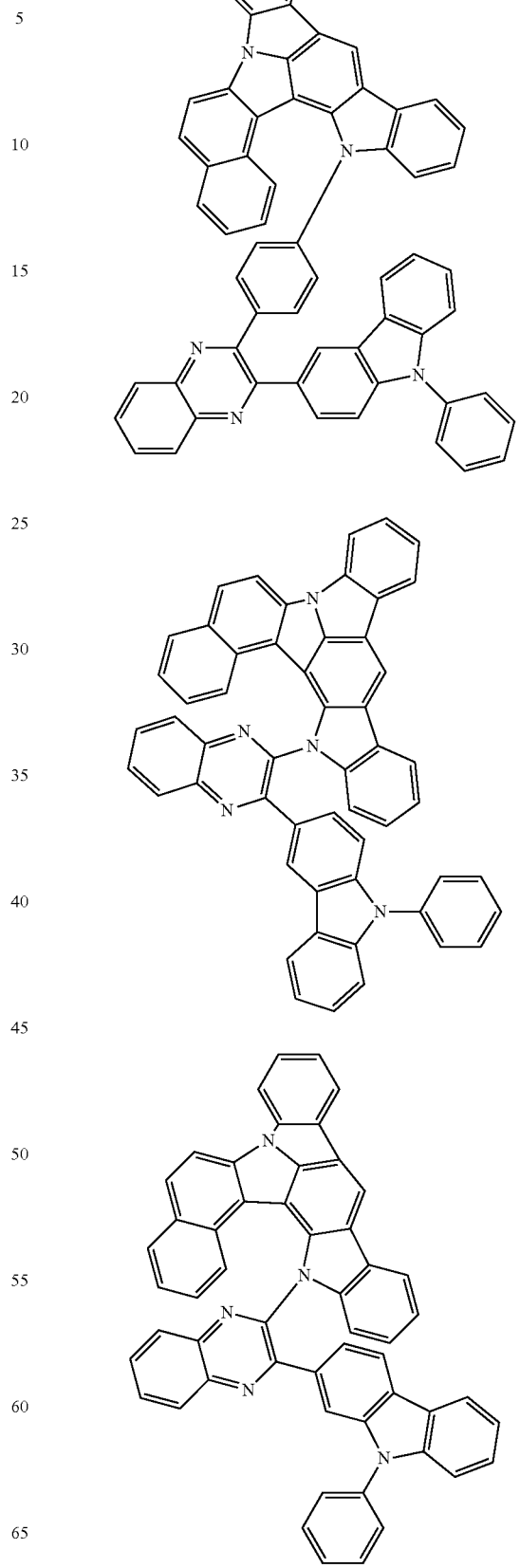

1051
-continued
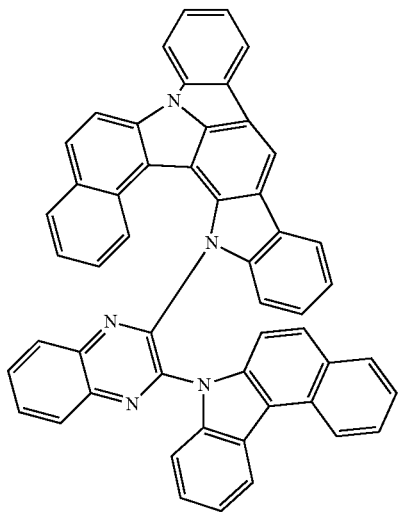
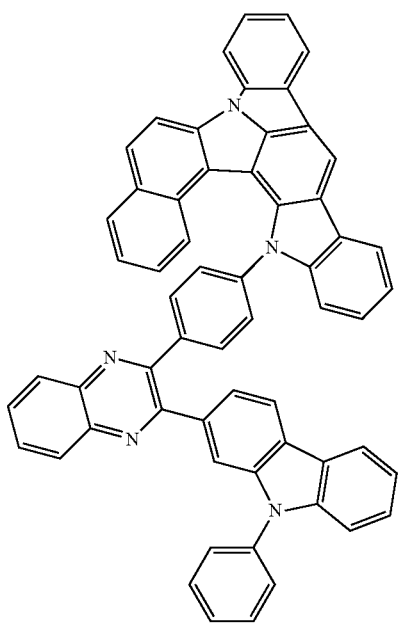
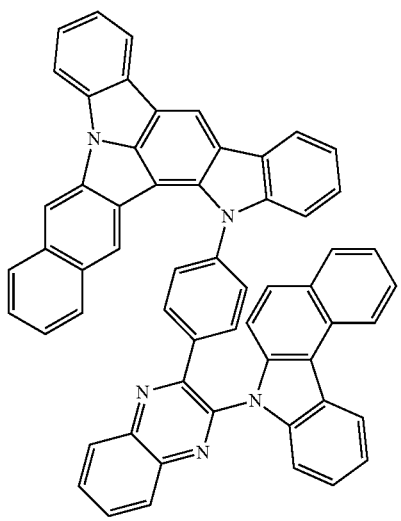
1052
-continued
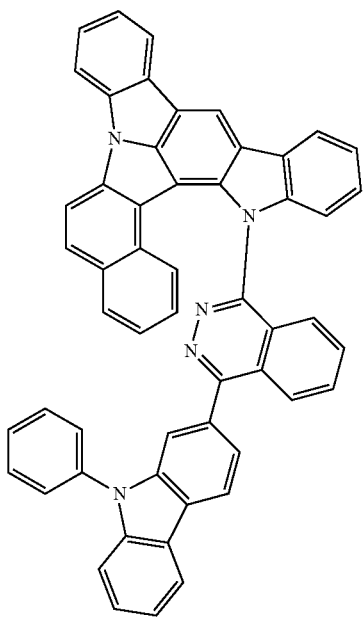
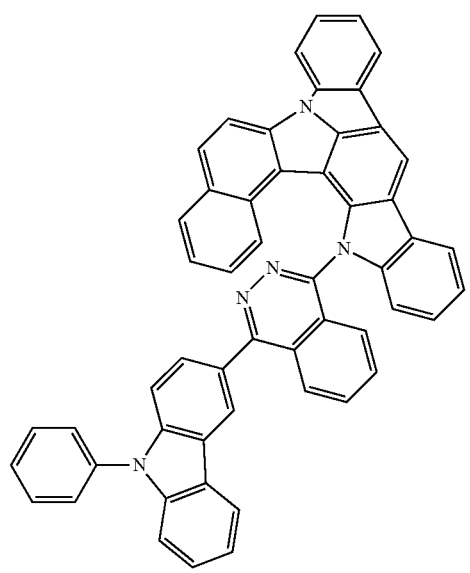
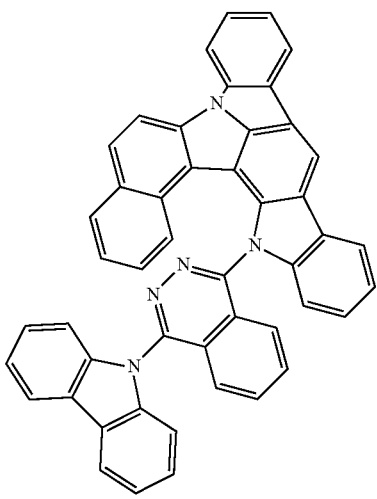

1053
-continued
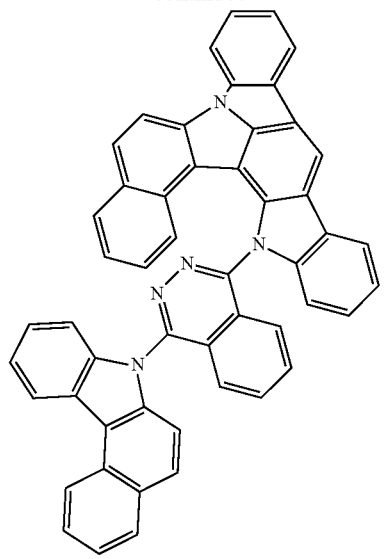
1054
-continued
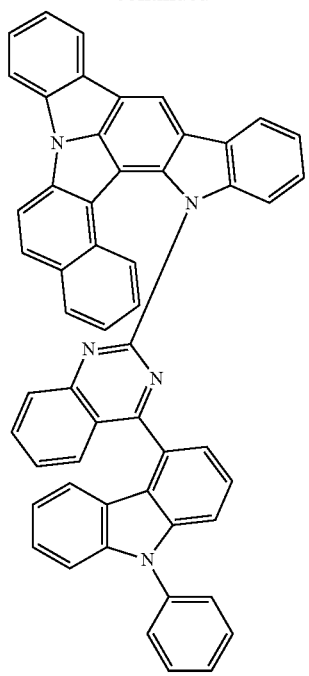
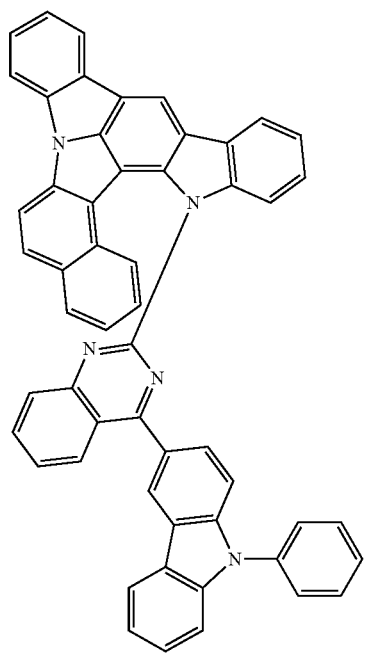
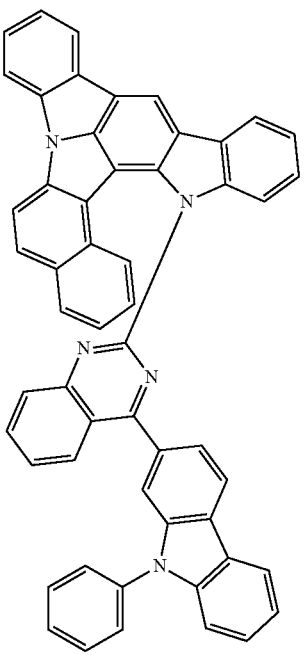

1055
-continued
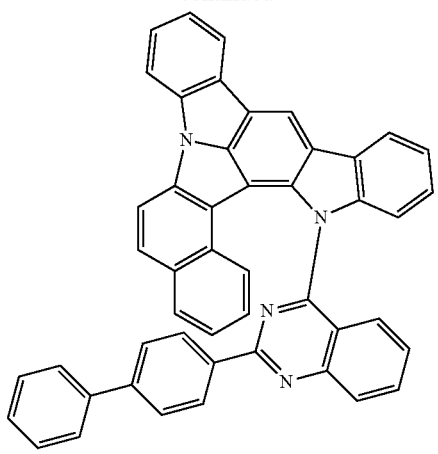
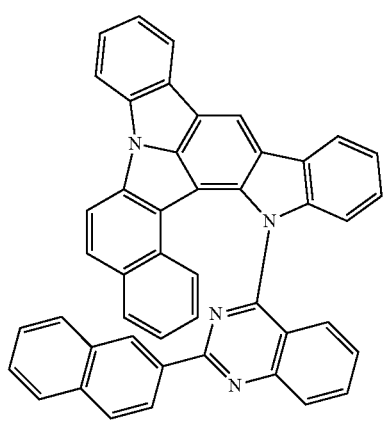
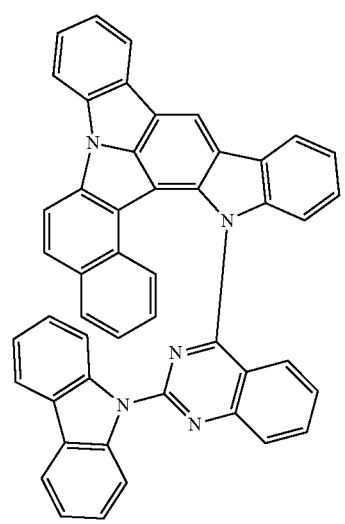
1056
-continued
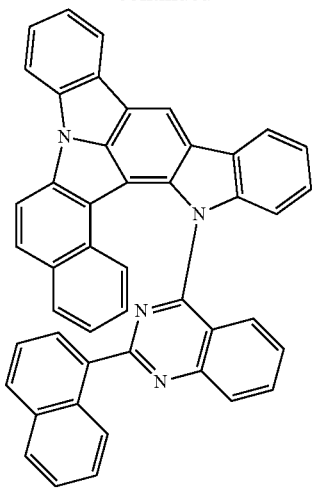
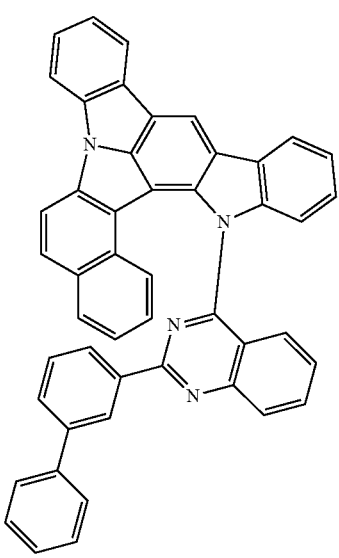
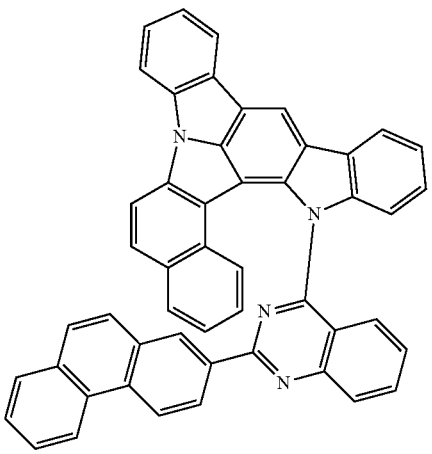

1057
-continued
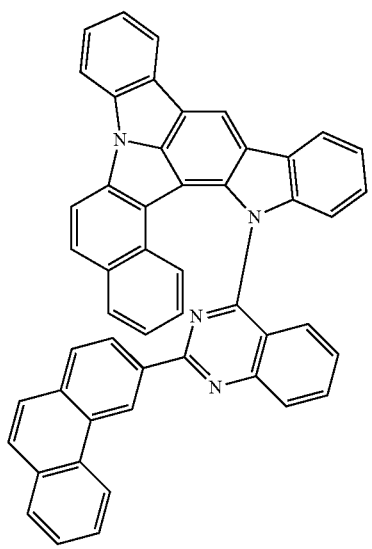
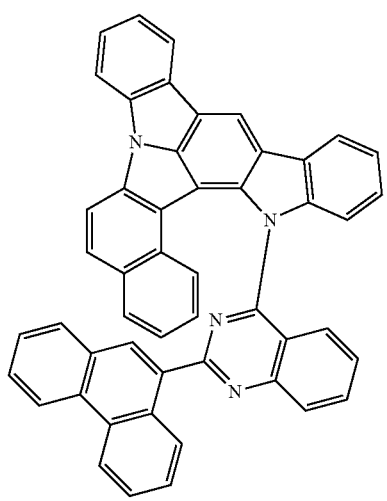
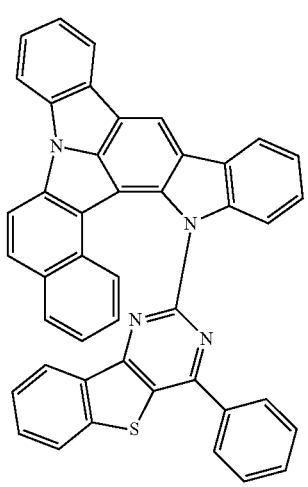
1058
-continued
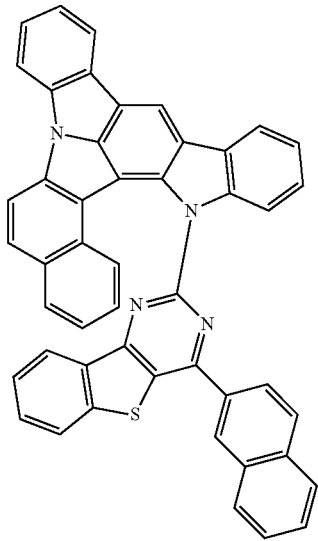
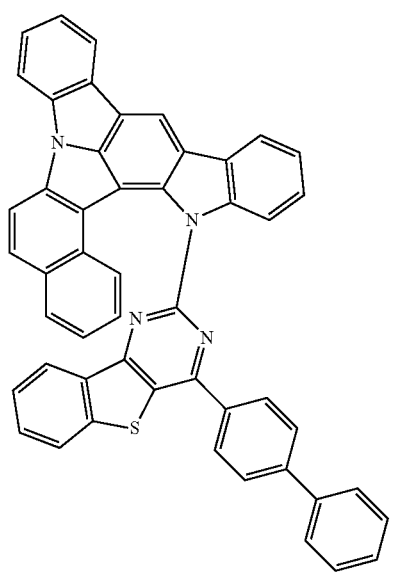
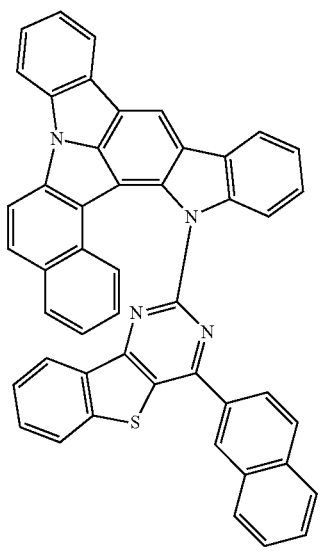

1059
-continued
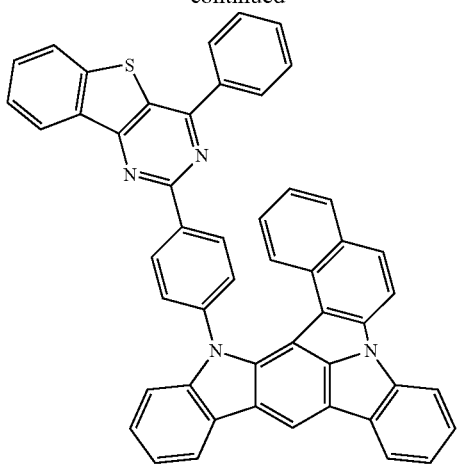
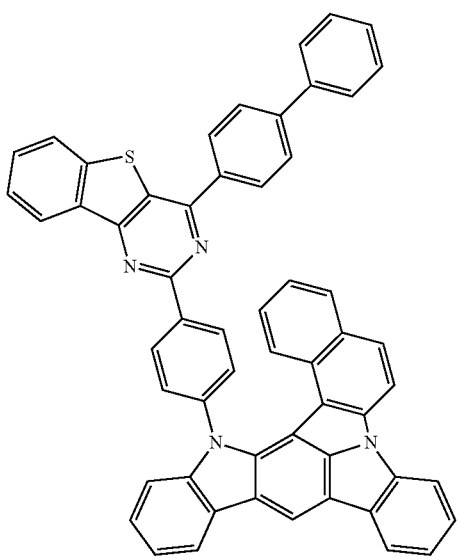
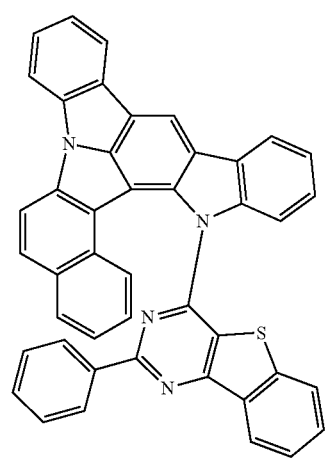
1060
-continued
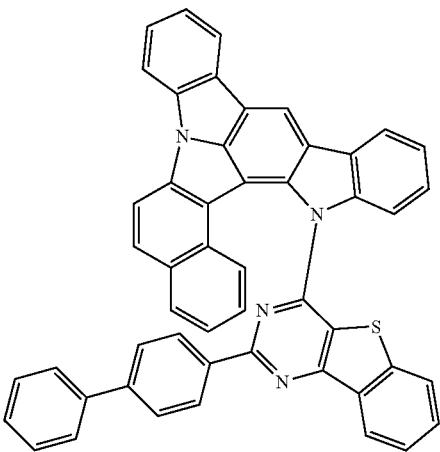
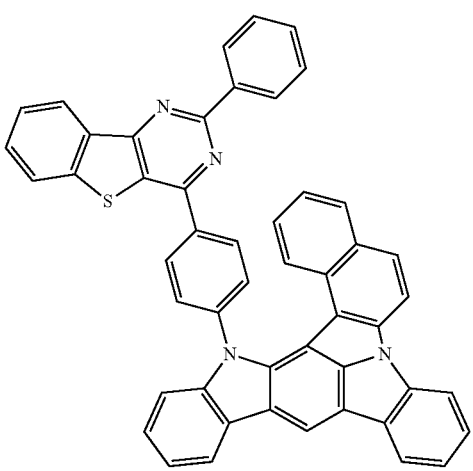
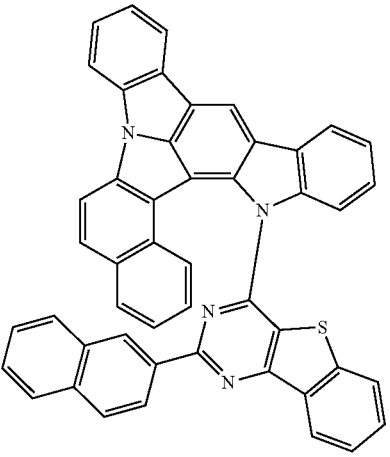

1061
-continued
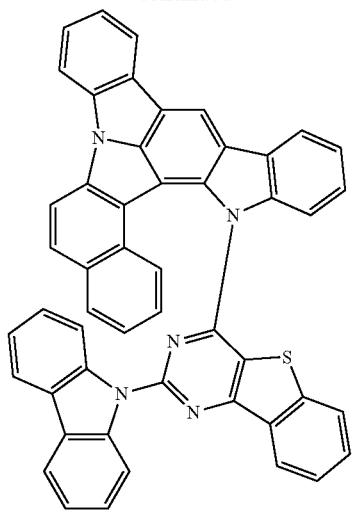
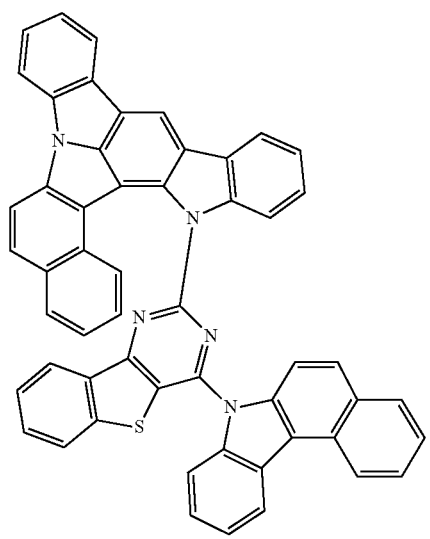
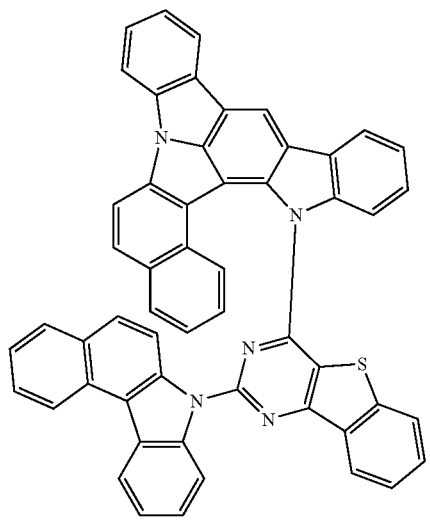
1062
-continued
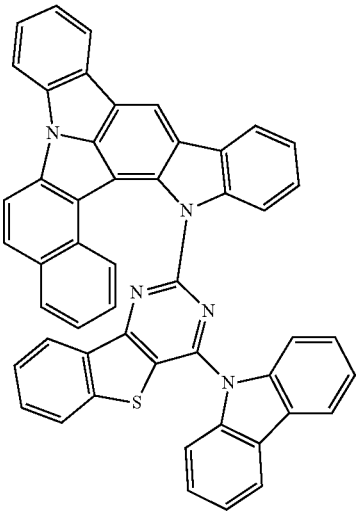
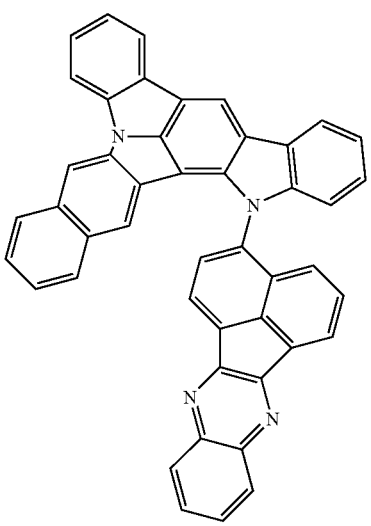
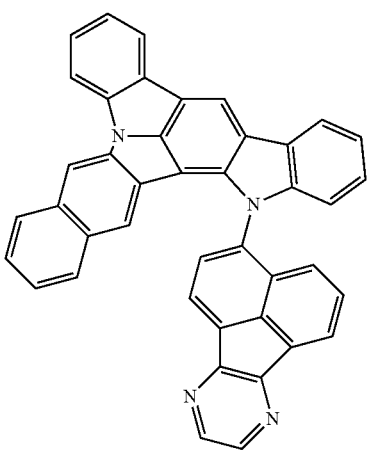

1063
-continued
1064
-continued
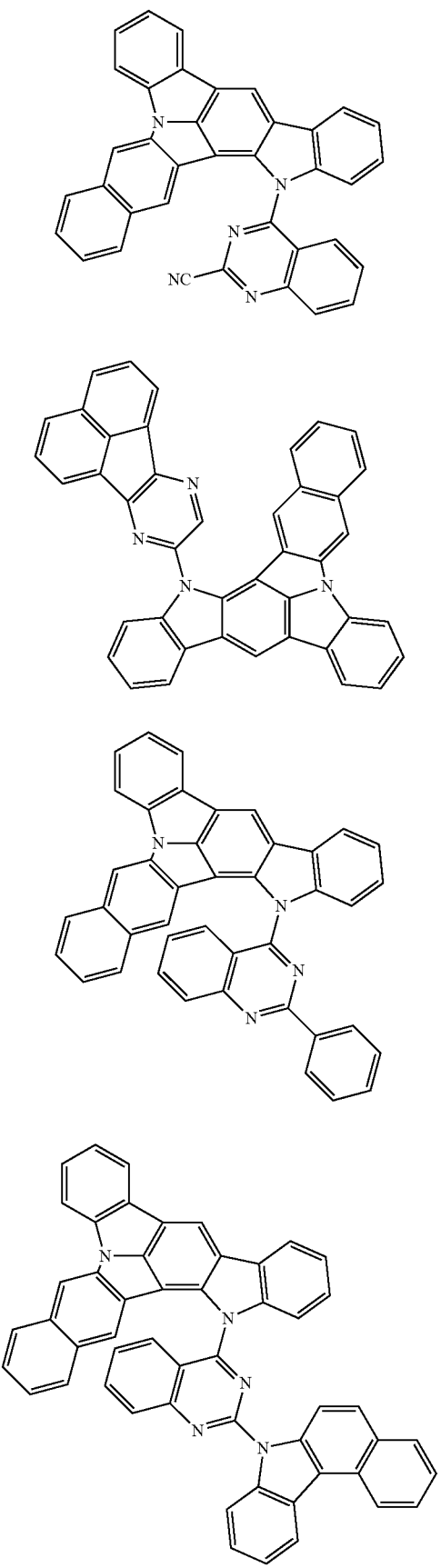
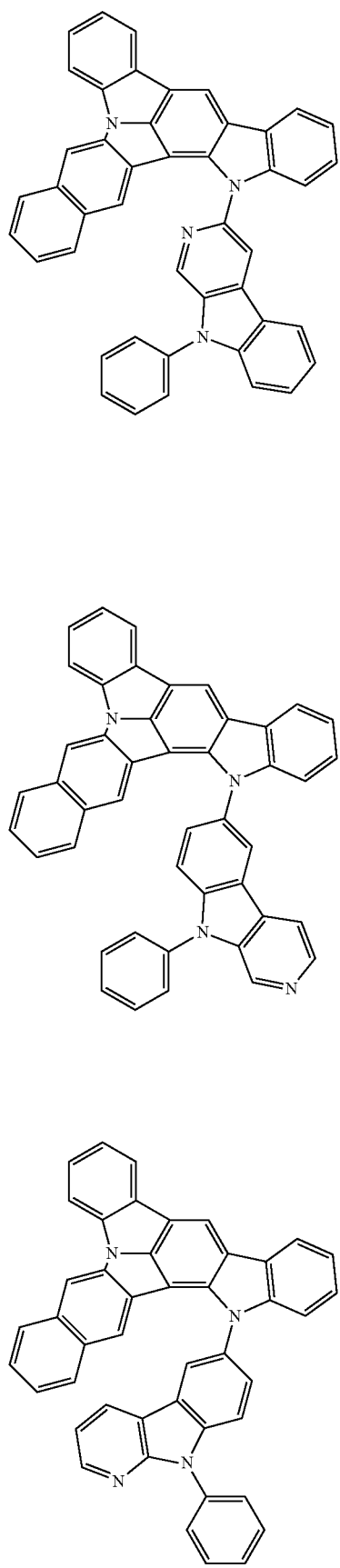

1065
-continued
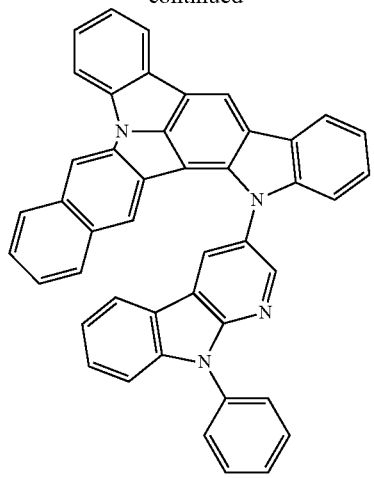
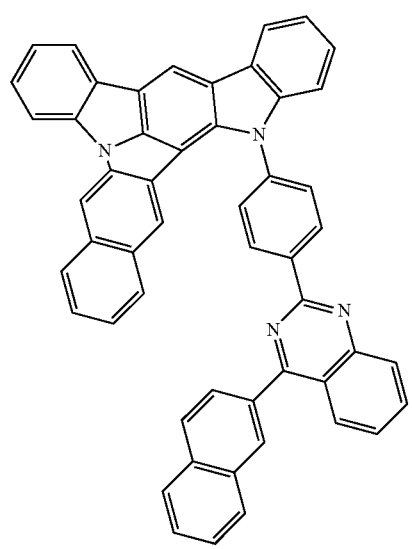
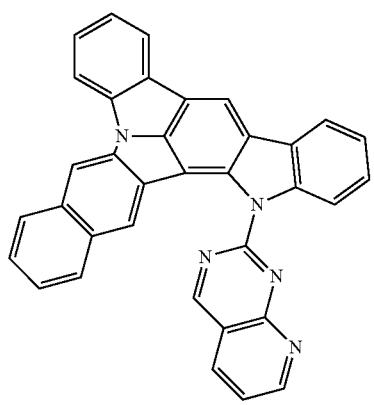
1066
-continued
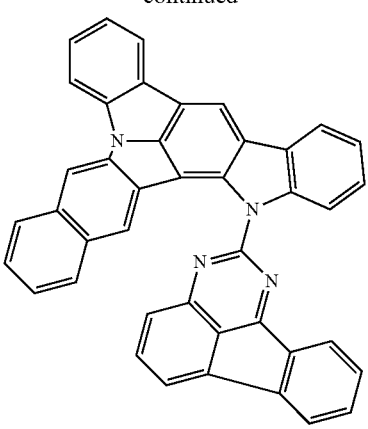
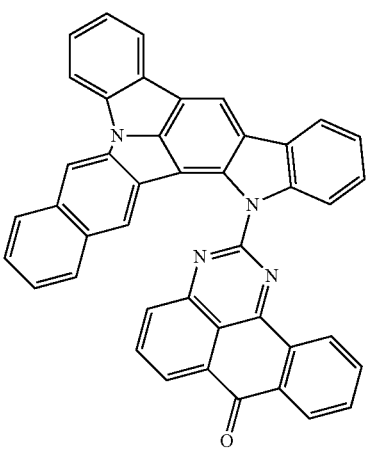
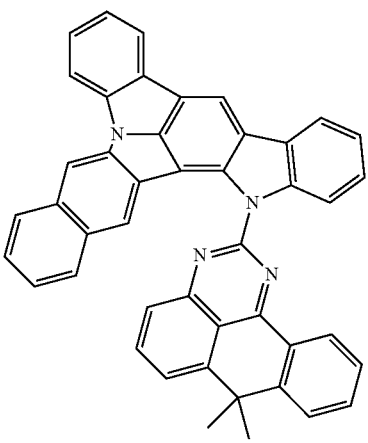
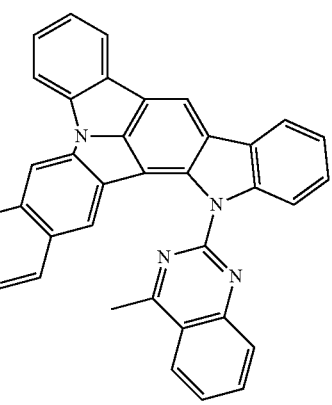

1067
-continued
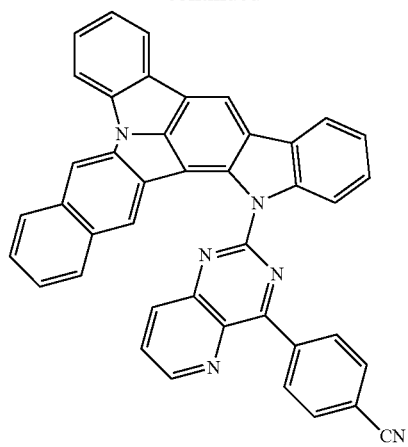
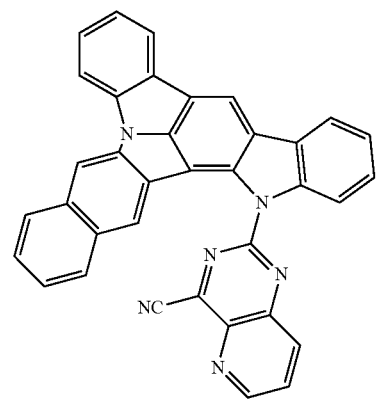
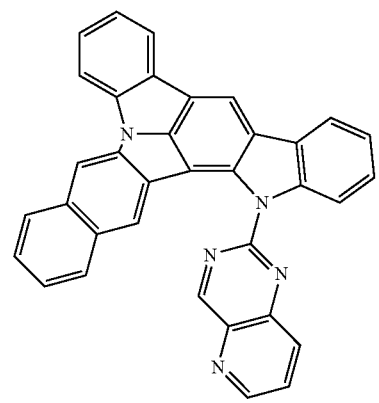
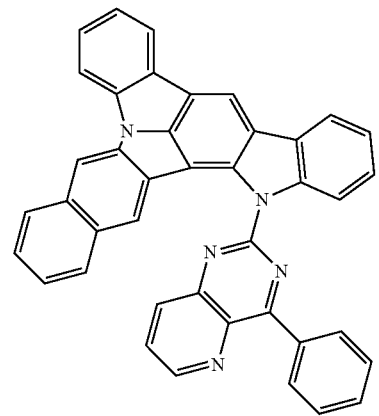
1068
-continued
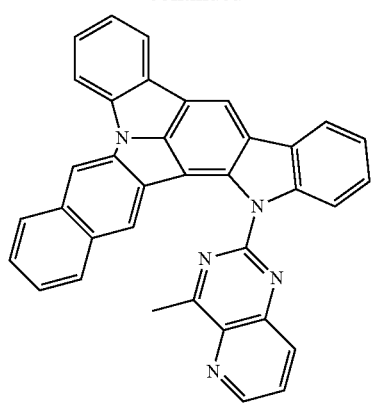
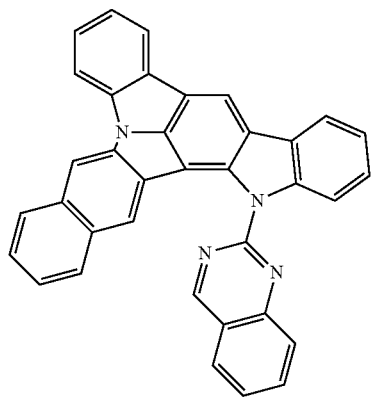
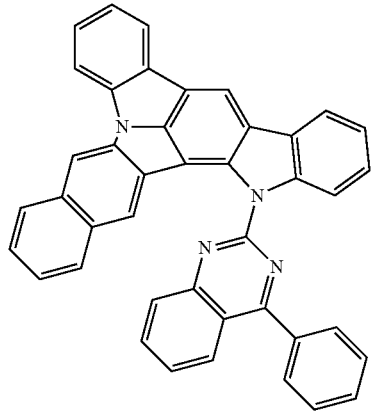
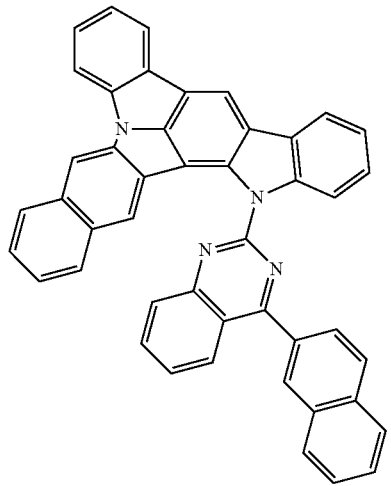

1069
-continued
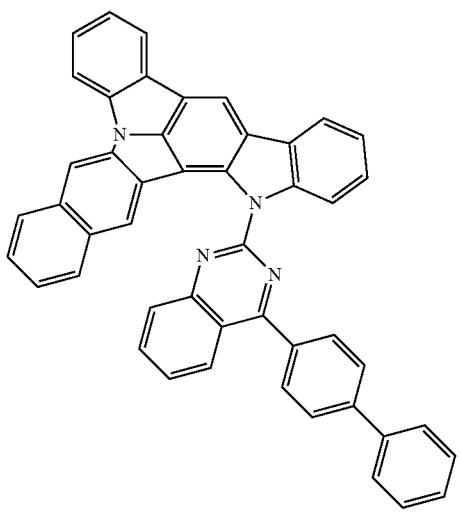
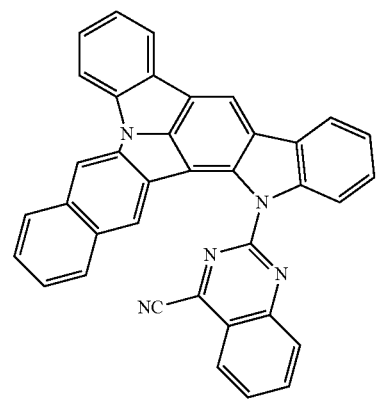
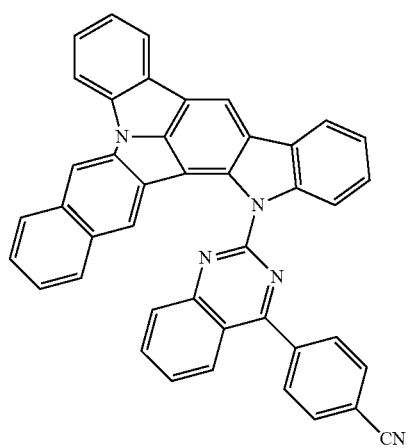
1070
-continued
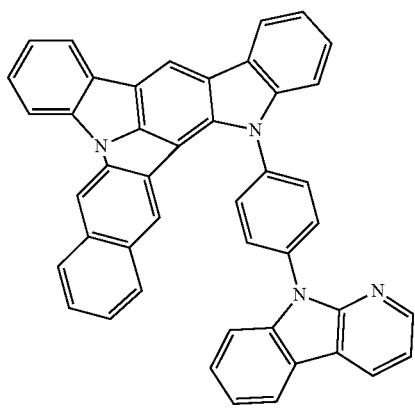
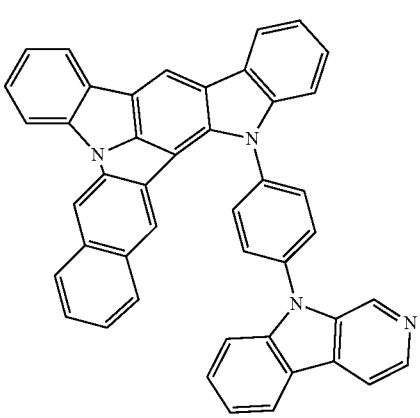
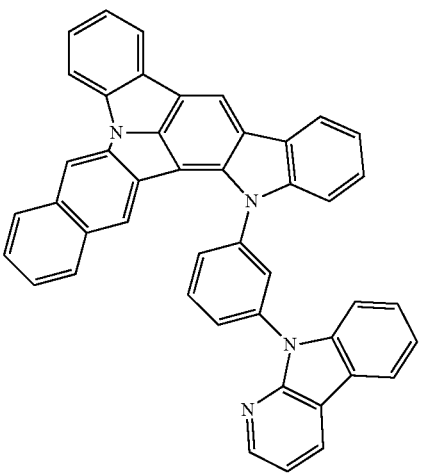

1071
-continued
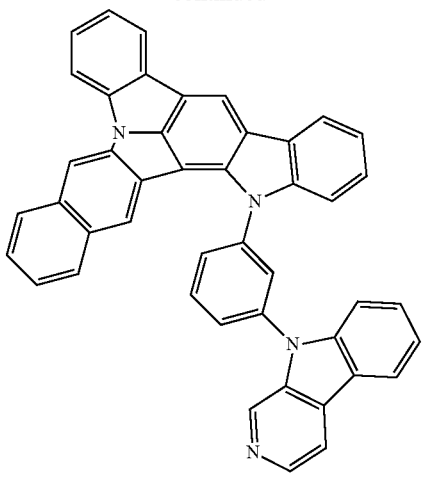
1072
-continued
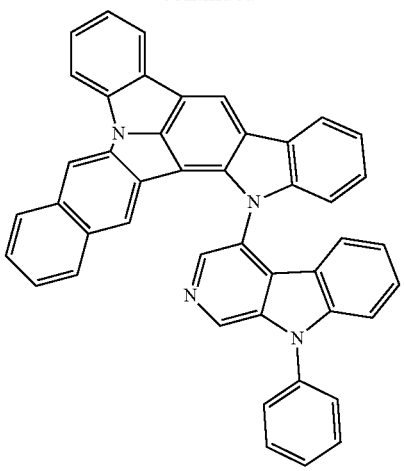
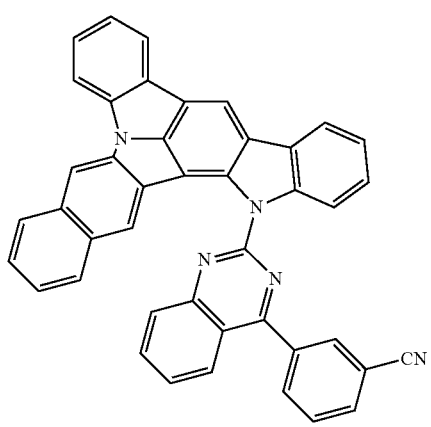
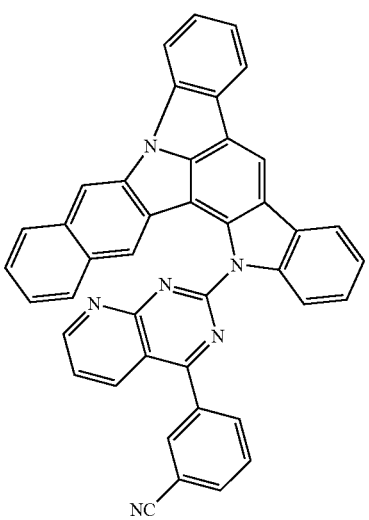
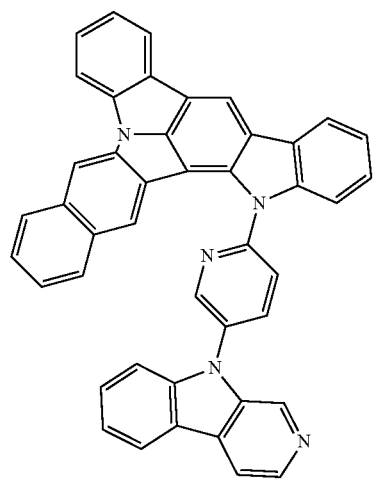
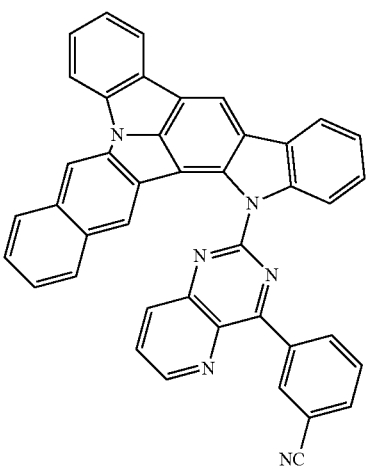

1073
-continued
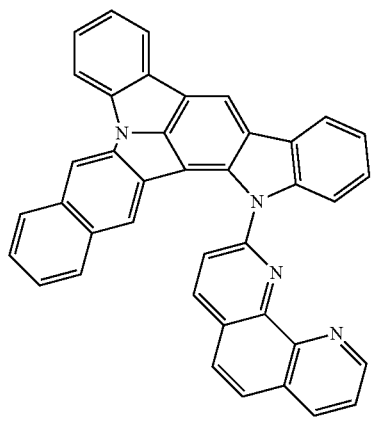
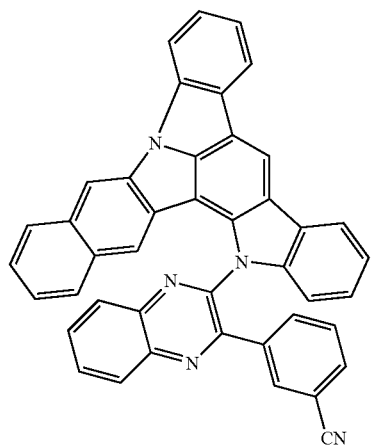
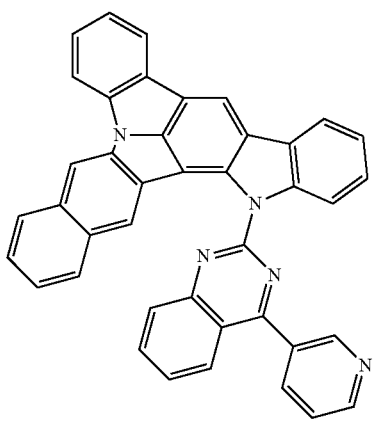
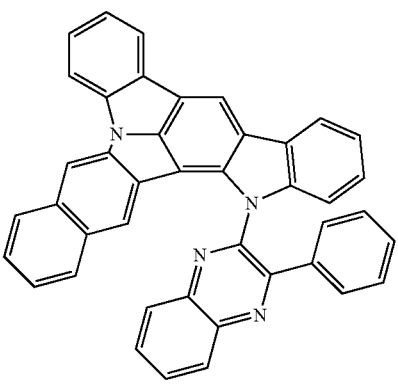
1074
-continued
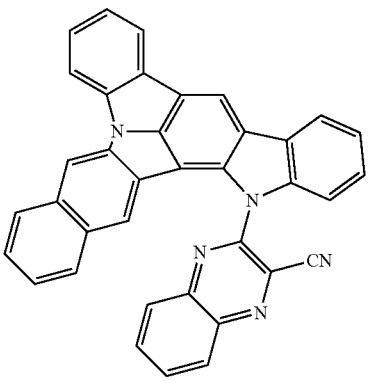
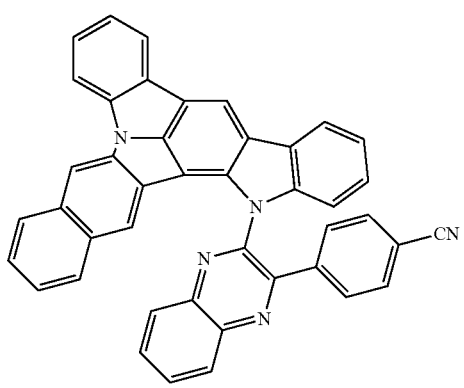
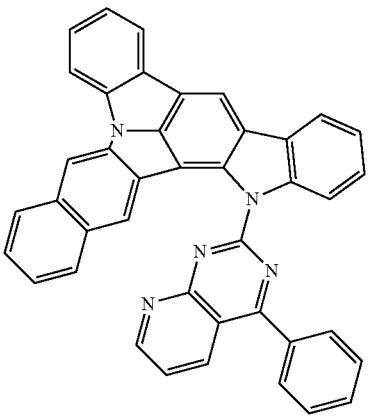
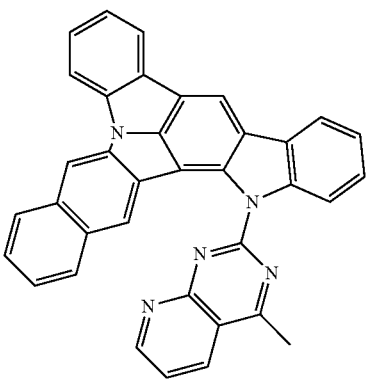

1075
-continued
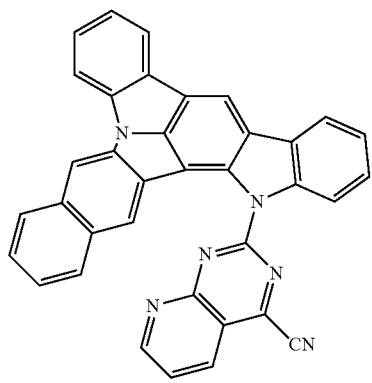
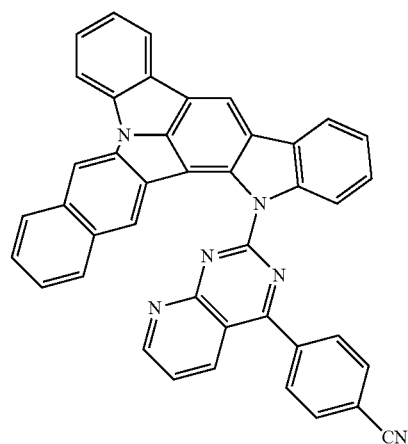
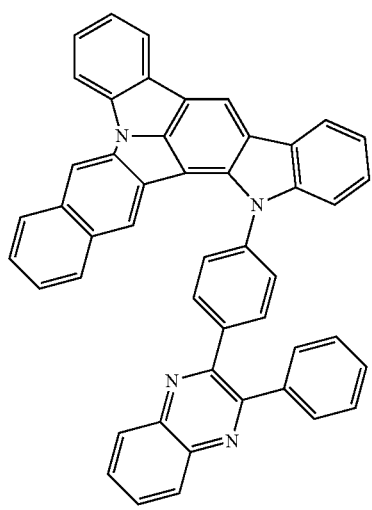
1076
-continued
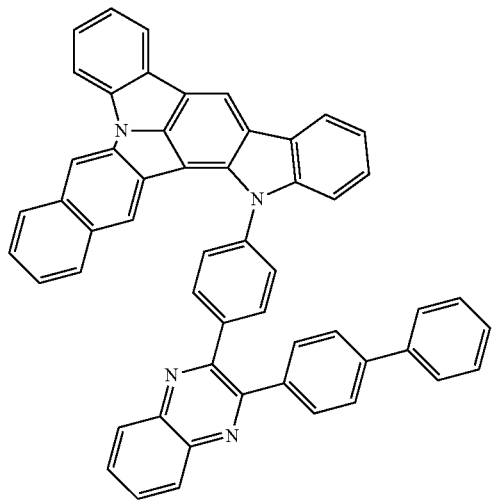
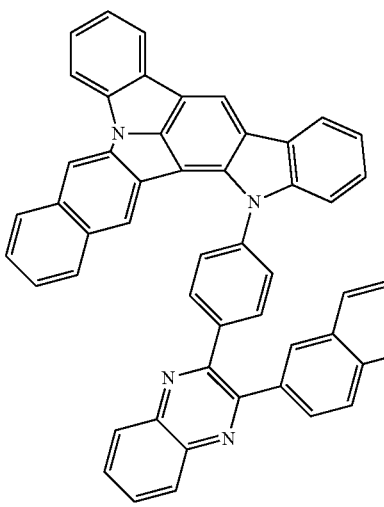

1077
-continued
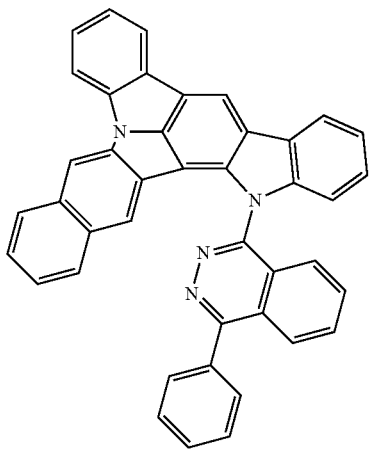
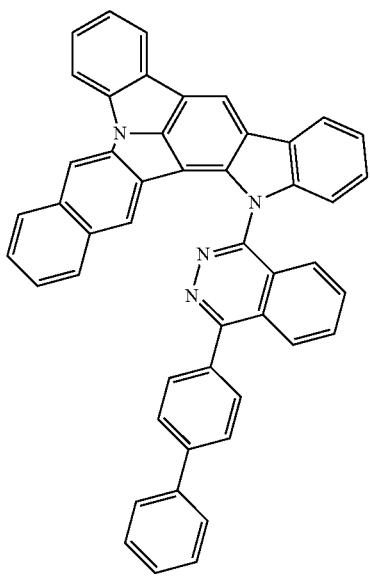
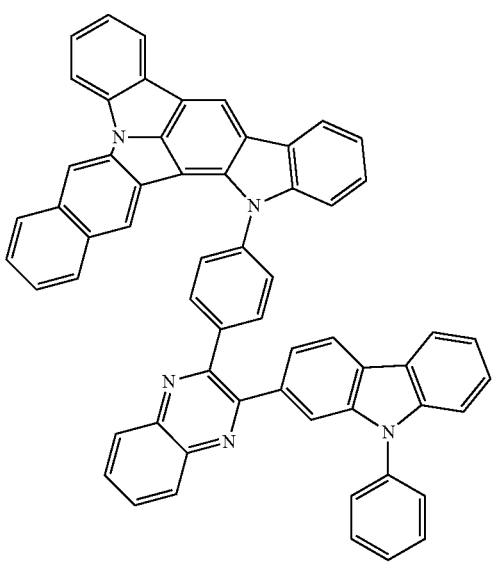
1078
-continued
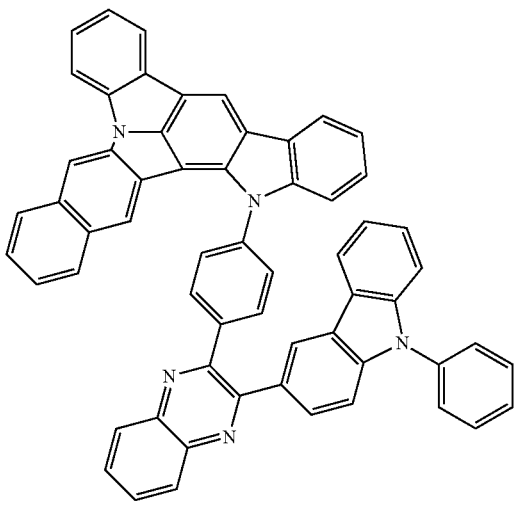
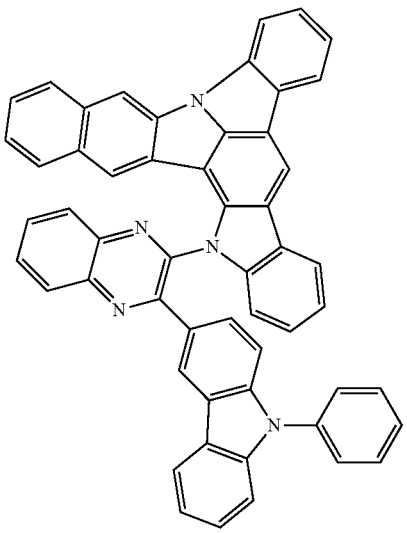
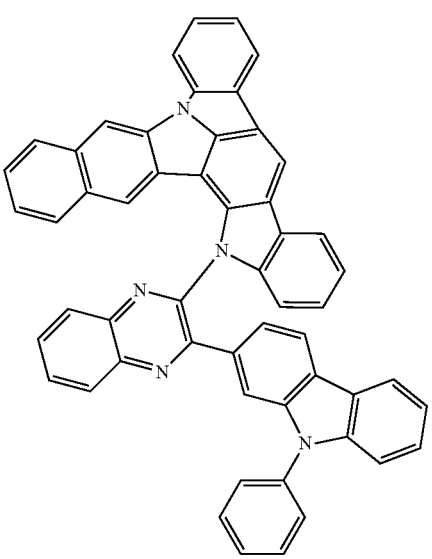

1079
-continued
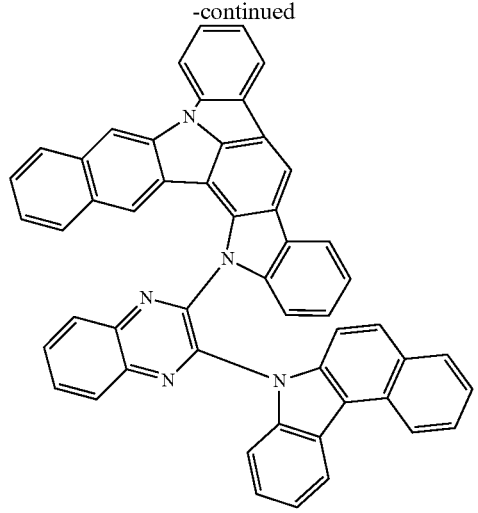
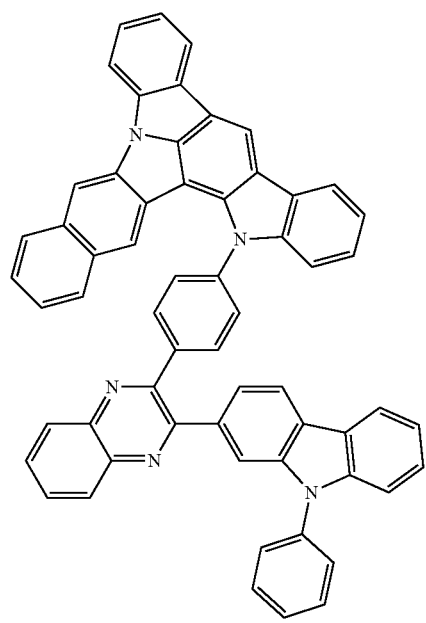
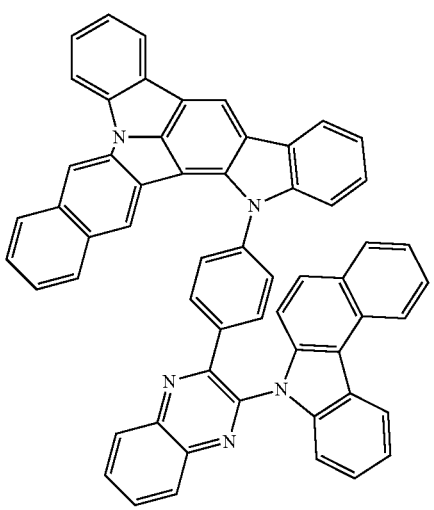
1080
-continued
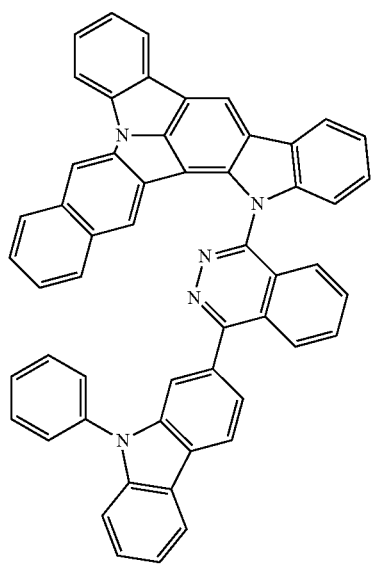
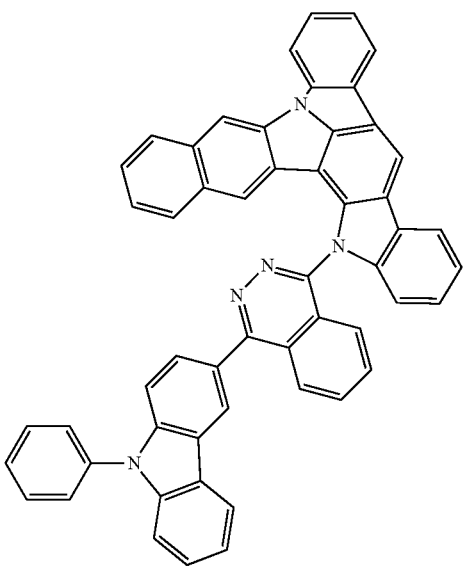
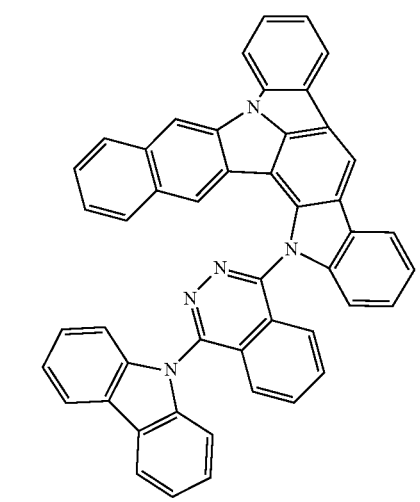

| 1081 | 1082 |
|---|---|
| 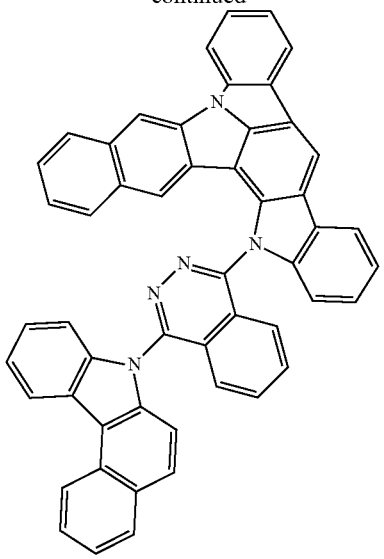 | 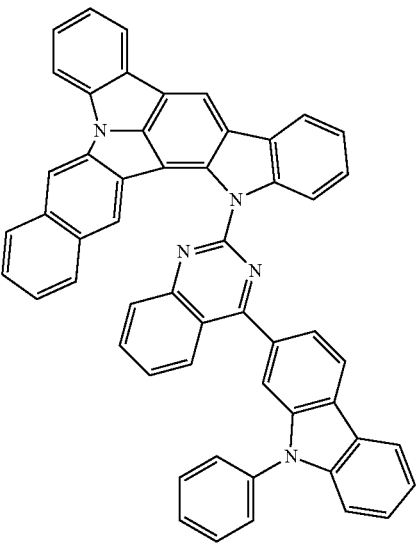 |
| 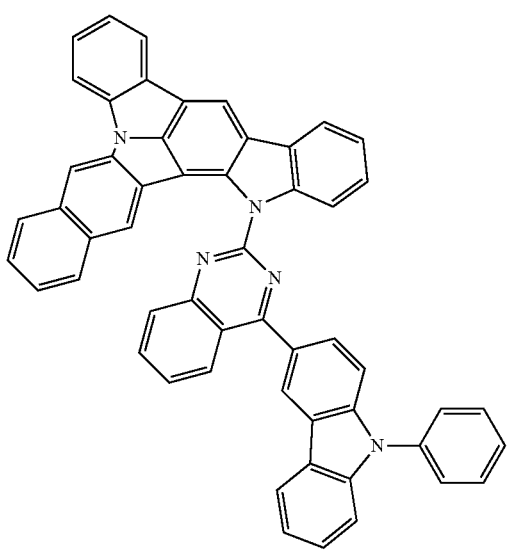 | 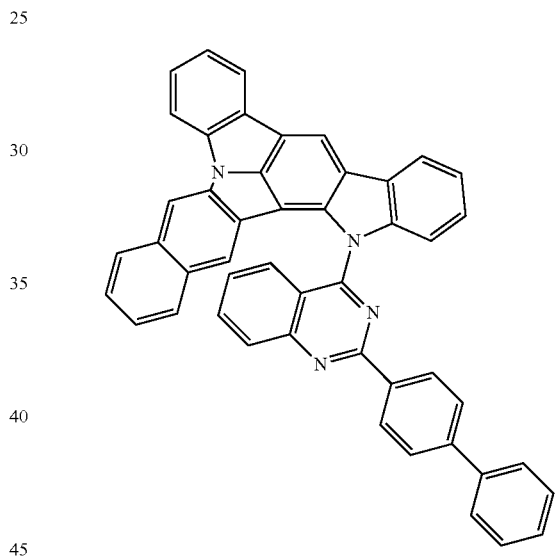 |
| 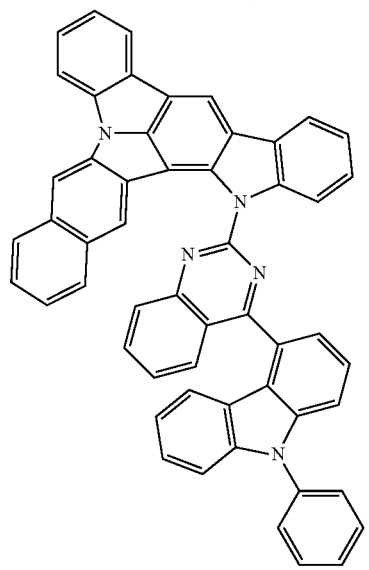 | 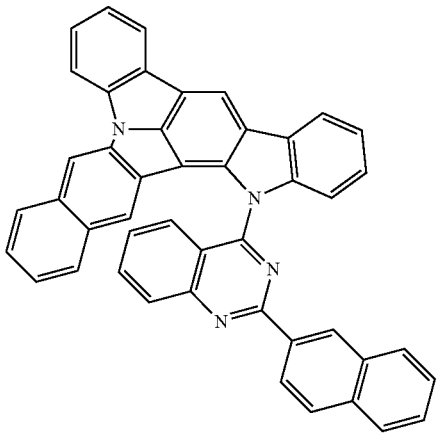 |

1083
-continued
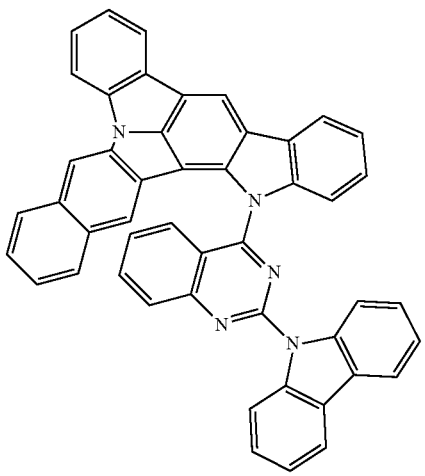
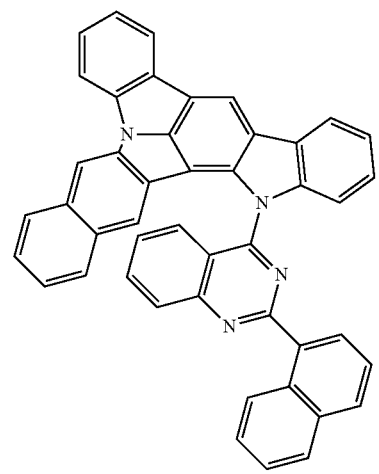
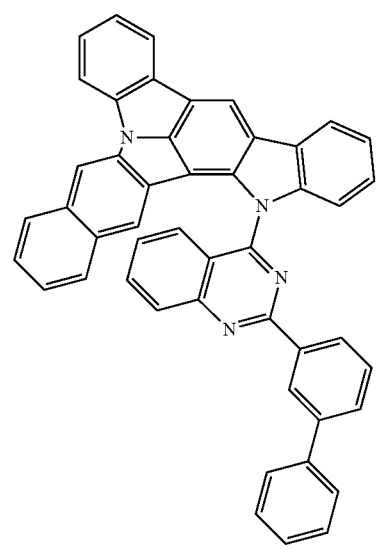
1084
-continued
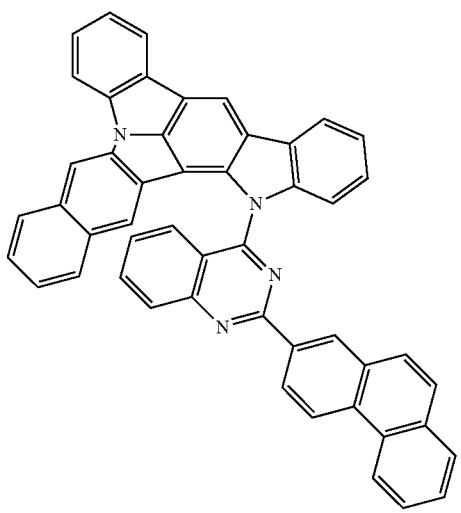
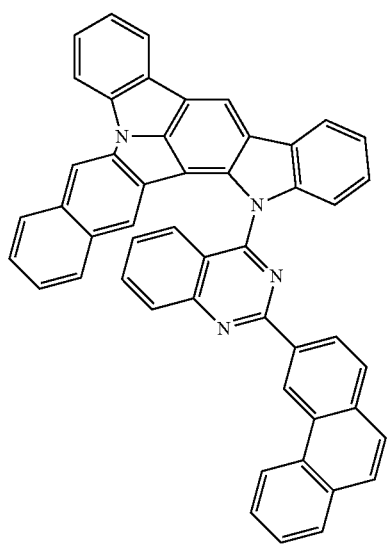
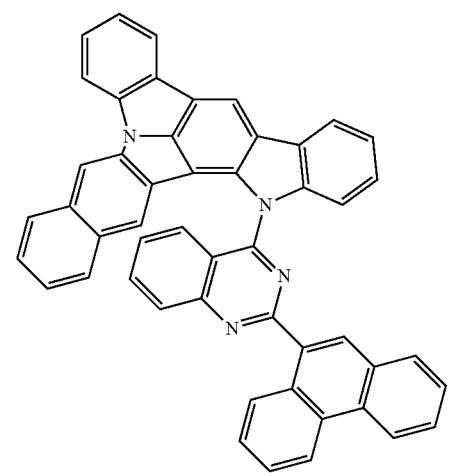

1085
-continued
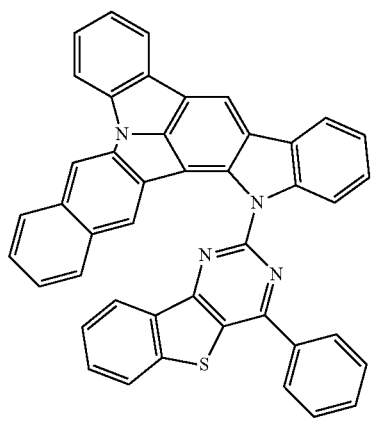
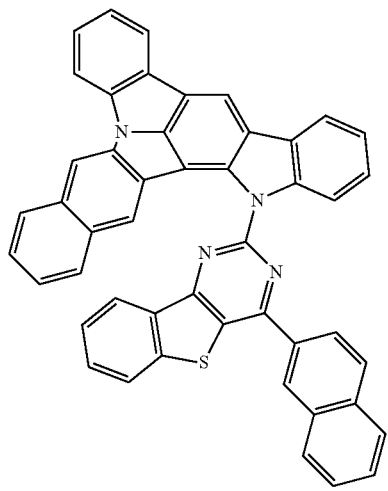
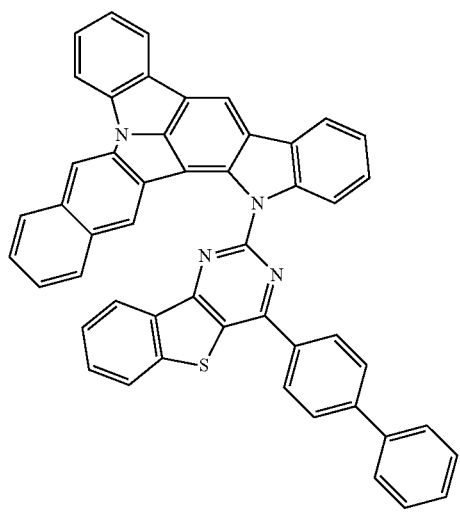
1086
-continued
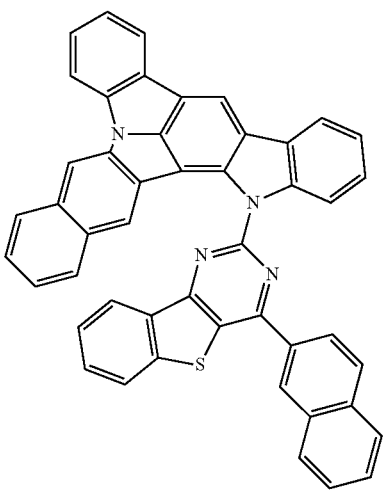
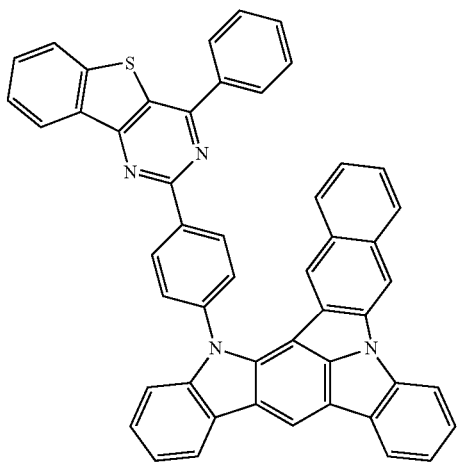
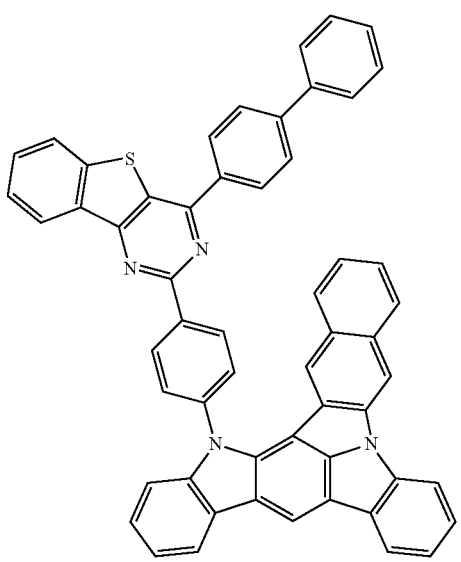

1087
-continued
1088
-continued
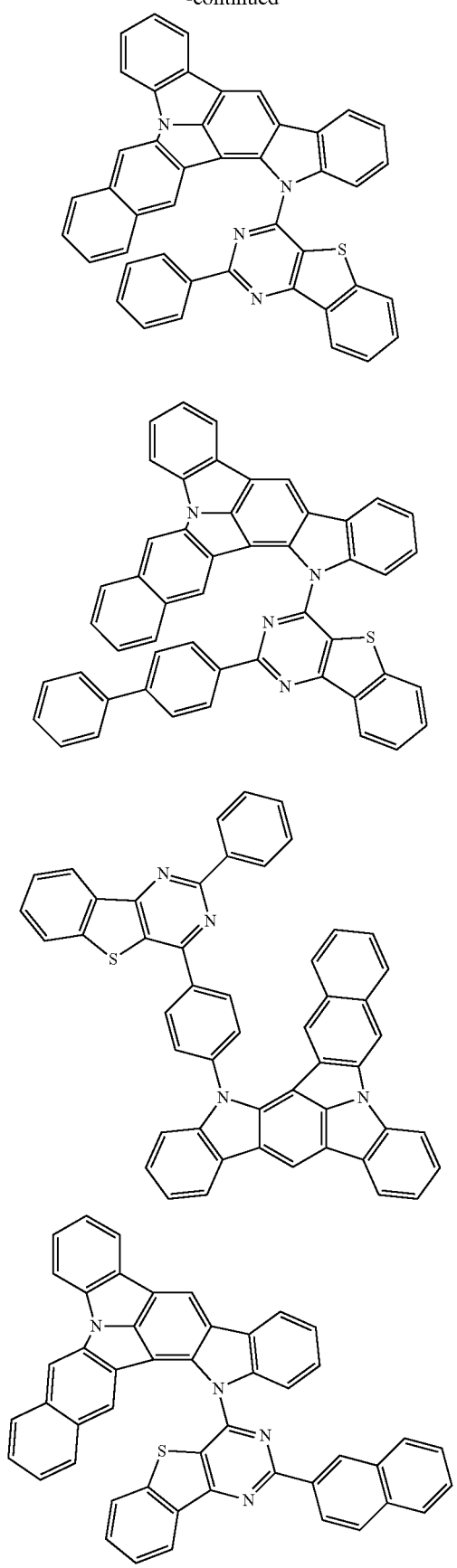
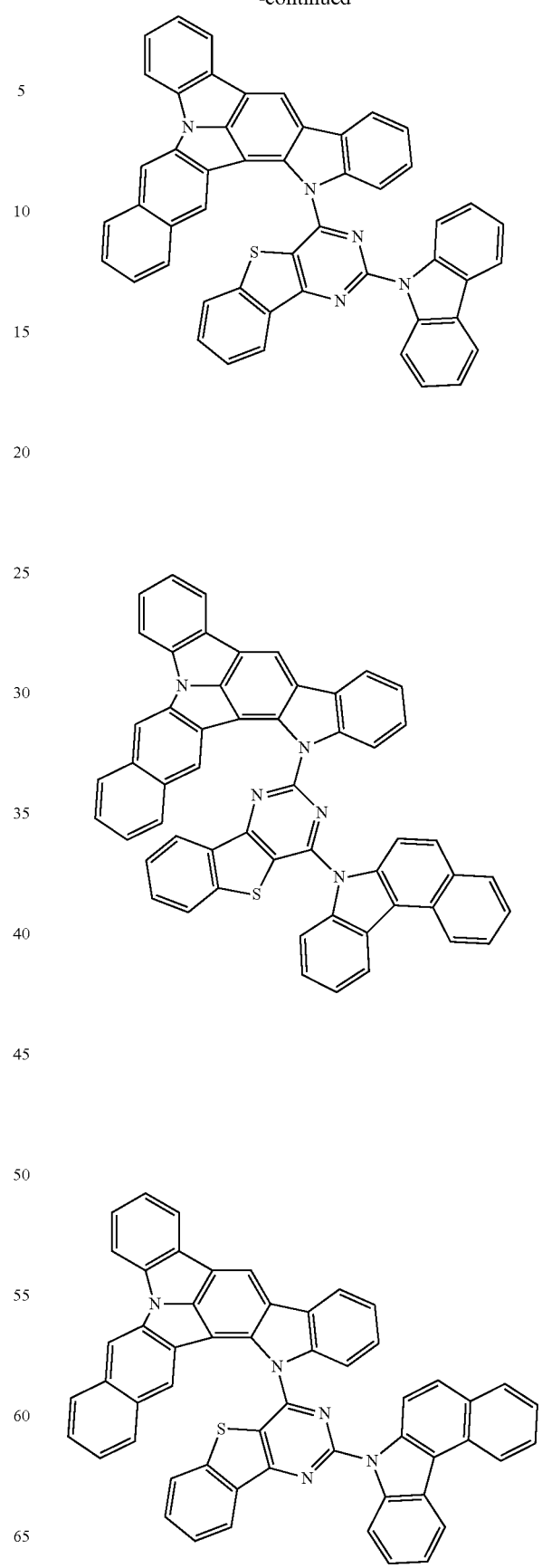

1089
-continued
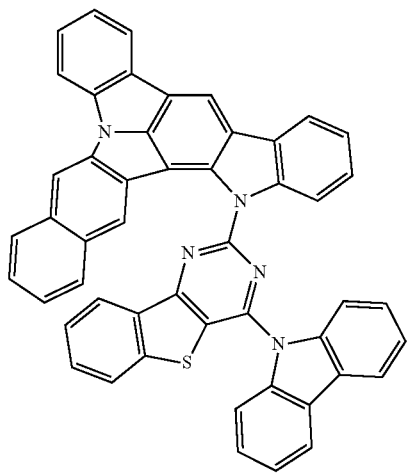 [SMILES: c1ccc2cc3c(cc2c1)c1c2c(cc4c5ccccc5n3c41)c1ccccc1n2-c1nc(-n2c3ccccc3c3ccccc32)c2sc3ccccc3c2n1]
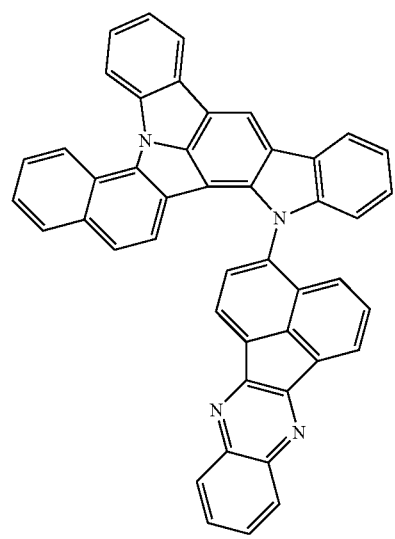
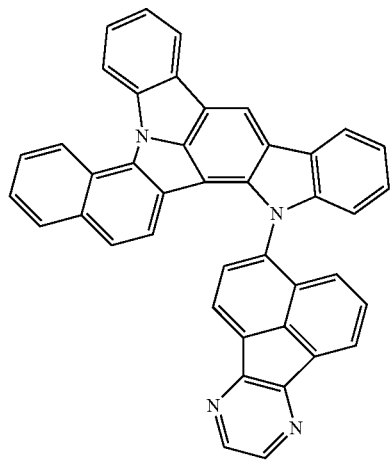
1090
-continued
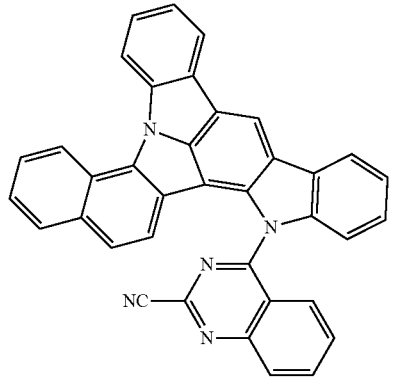
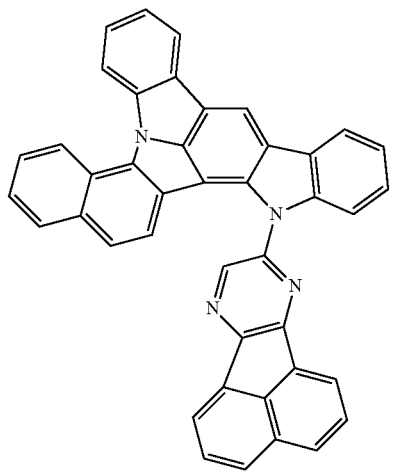
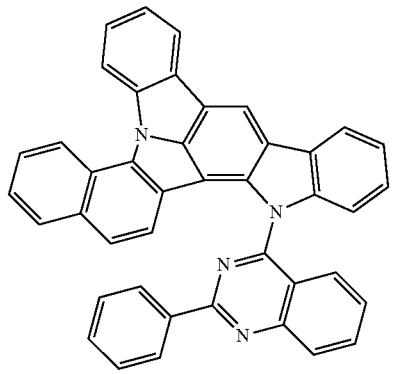
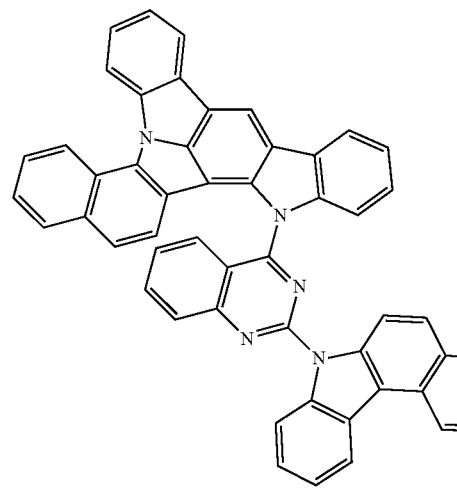

1091
-continued
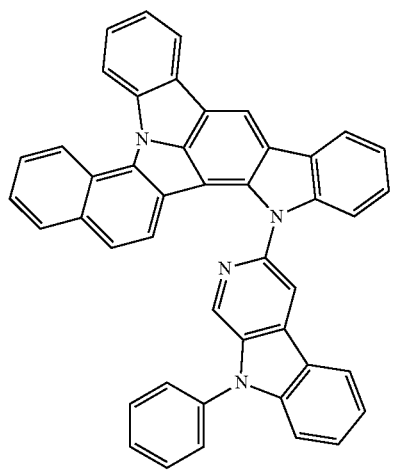
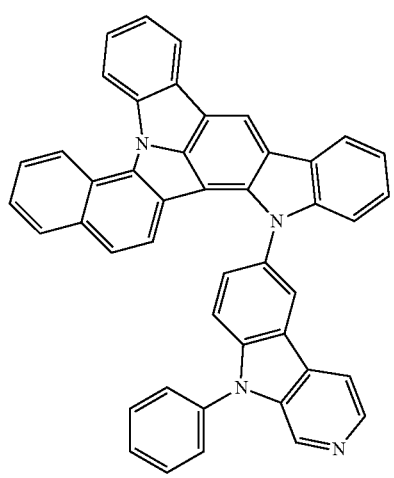
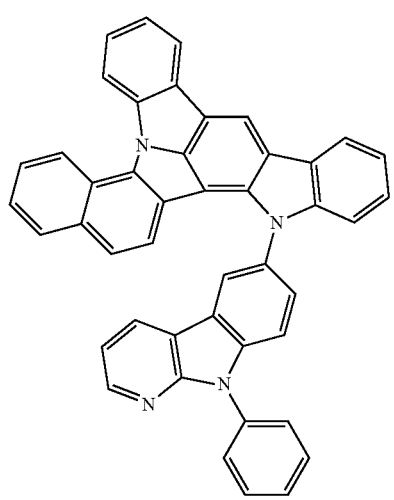
1092
-continued
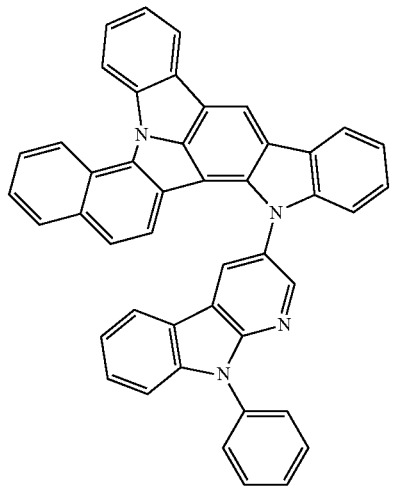
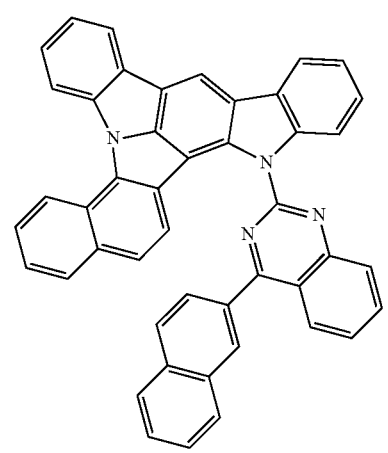
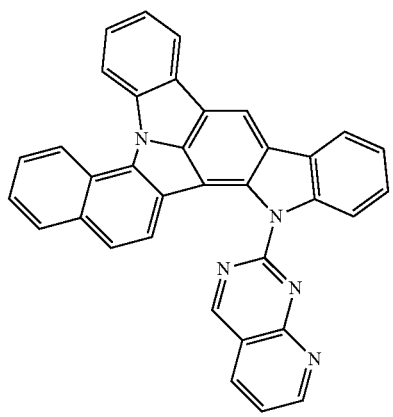

US 10,347,845 B2
1093
-continued
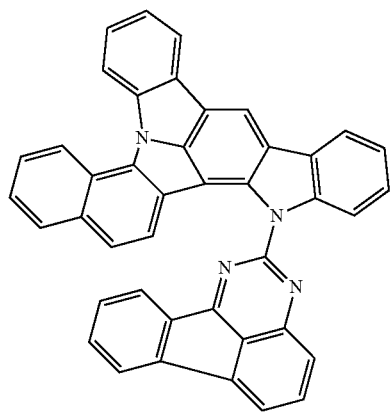
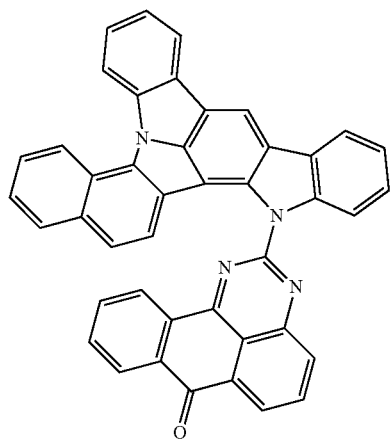
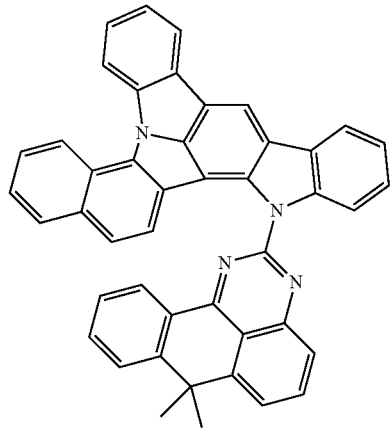
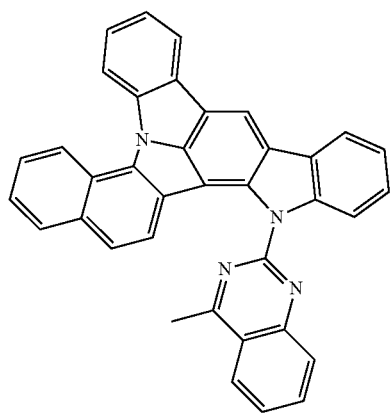
1094
-continued
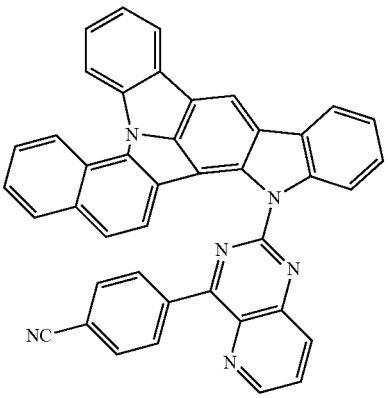
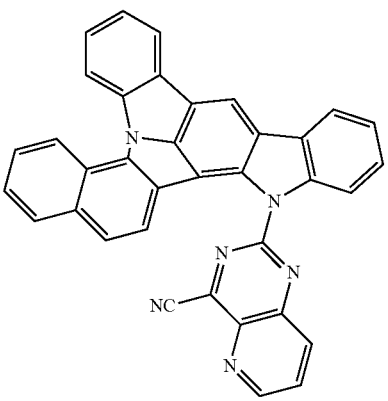
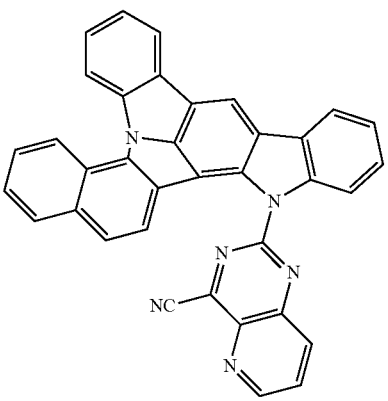
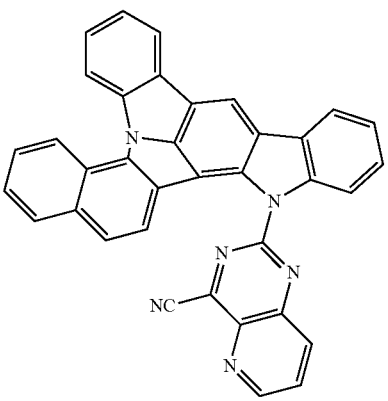

US 10,347,845 B2
1095
-continued
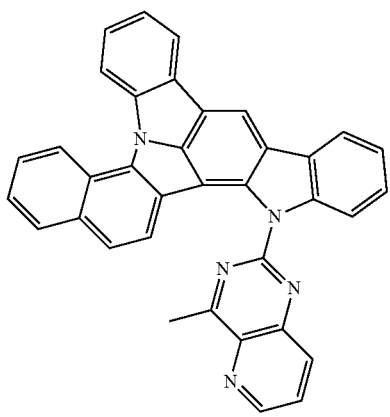
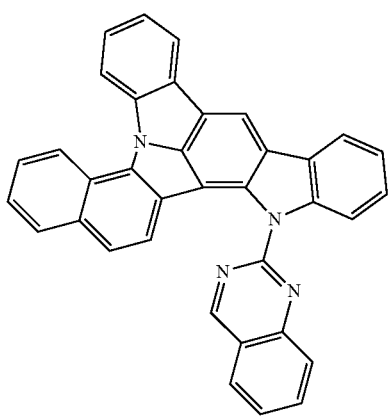
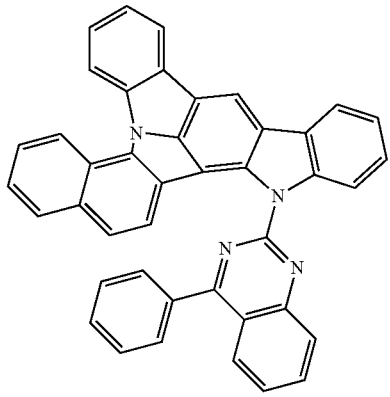
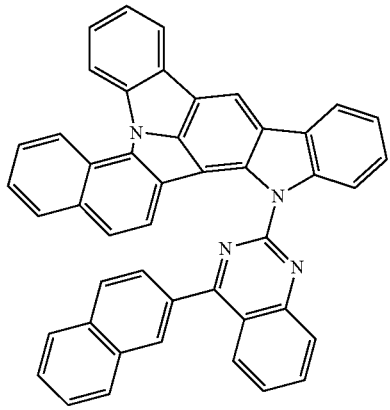
1096
-continued
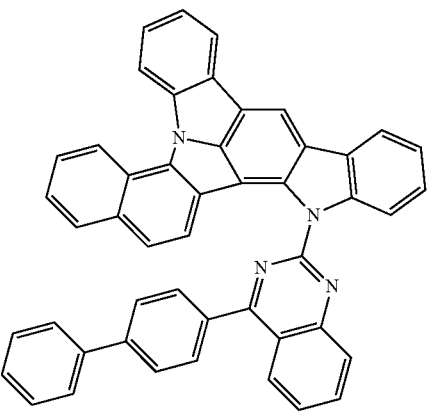
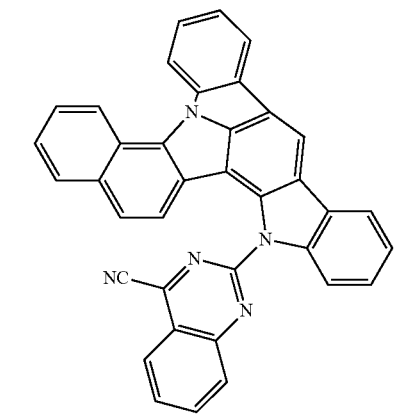
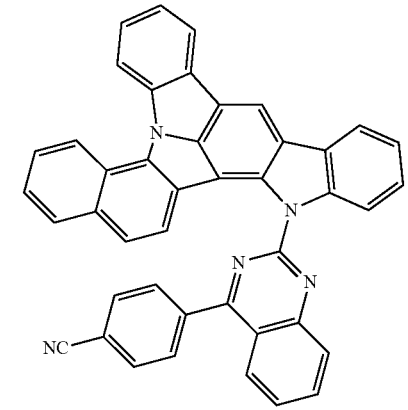
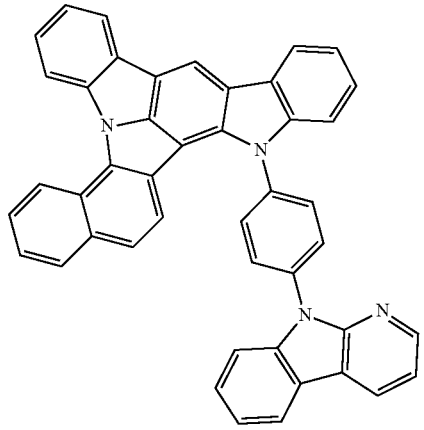

1097
-continued
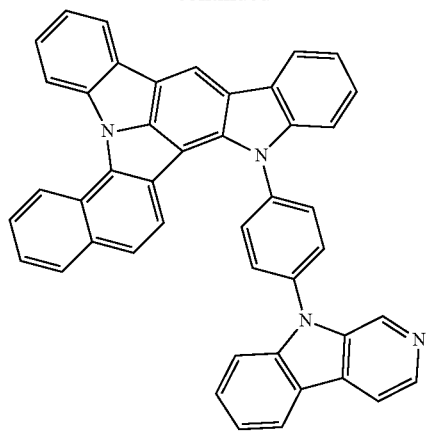
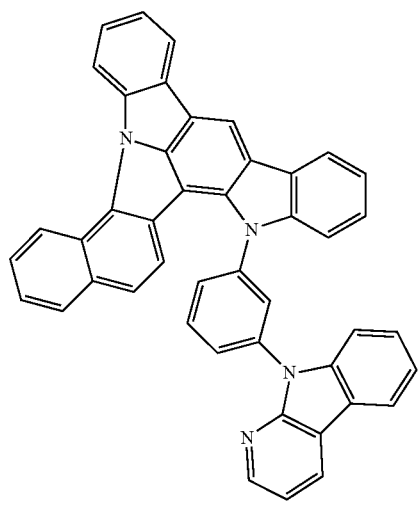
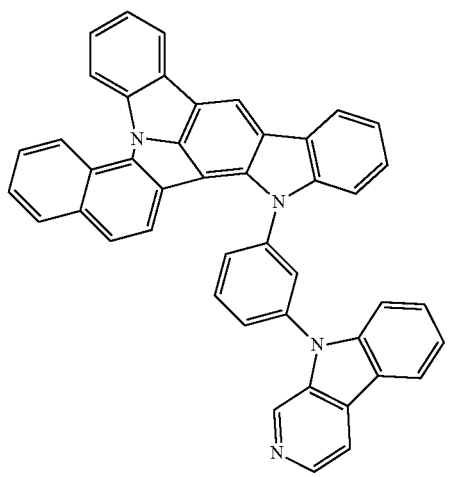
1098
-continued
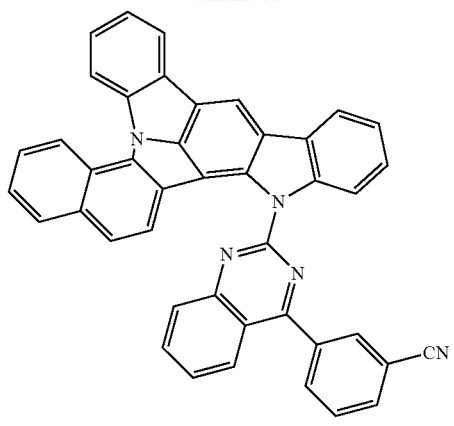
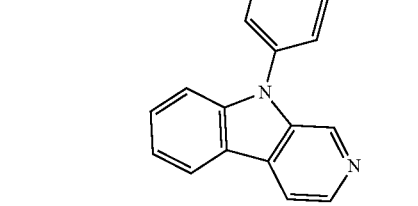
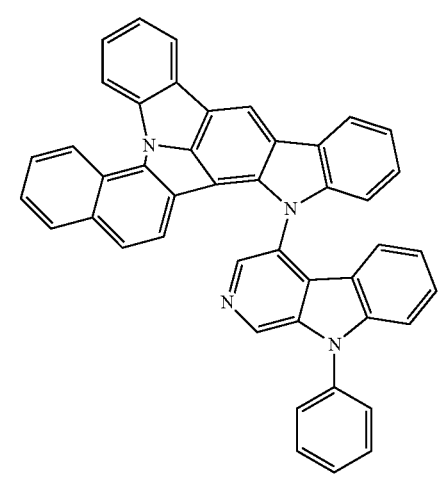

1099
-continued
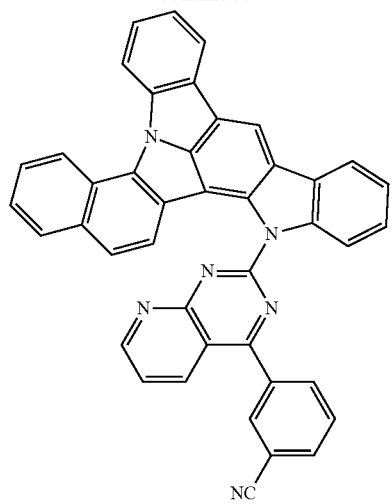
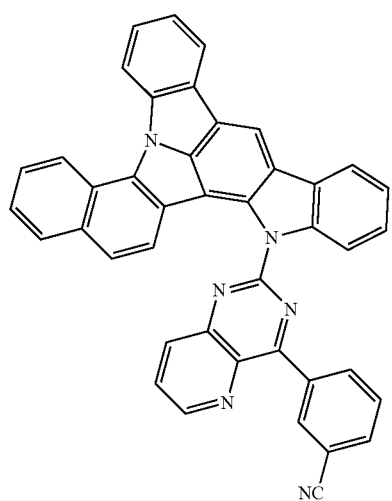
1100
-continued
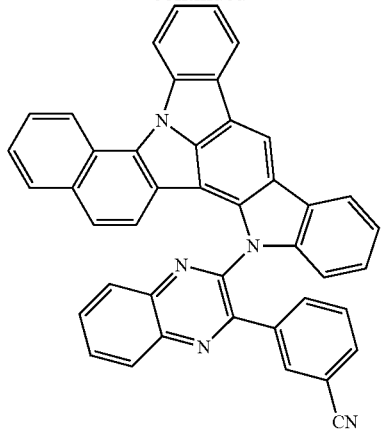
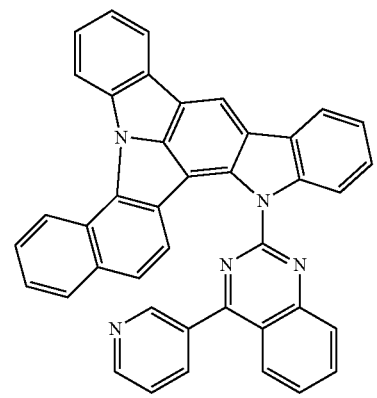
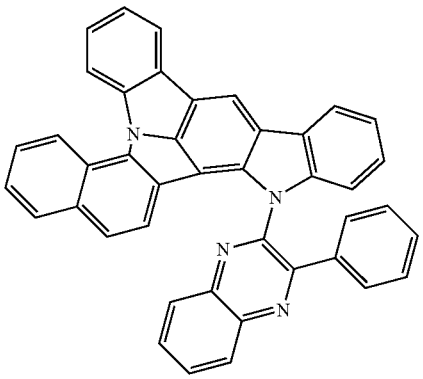
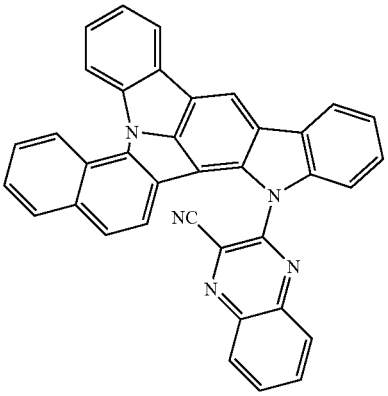

1101
-continued
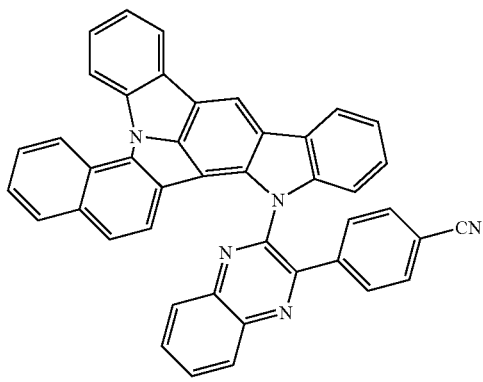
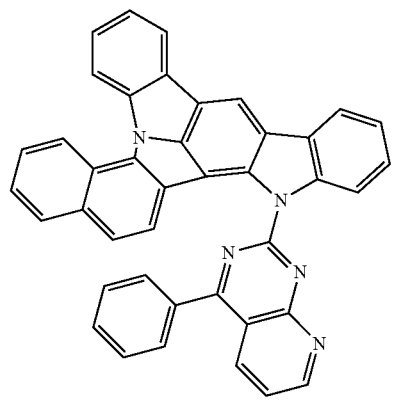
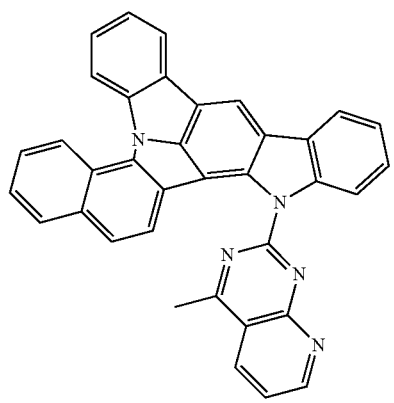
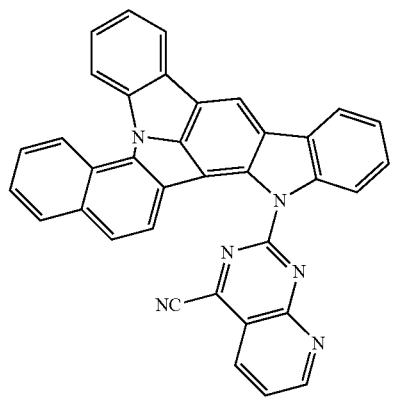
1102
-continued
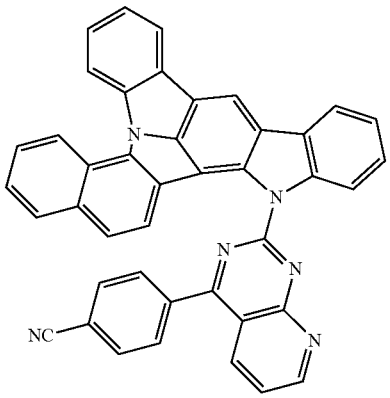
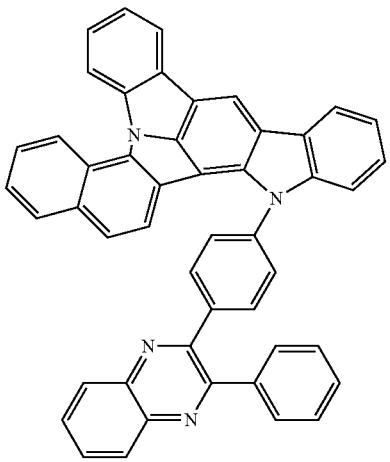
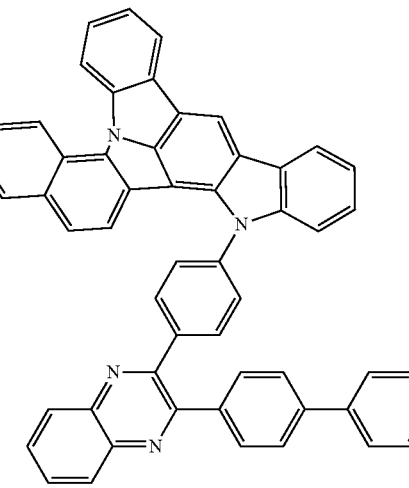

1103
-continued
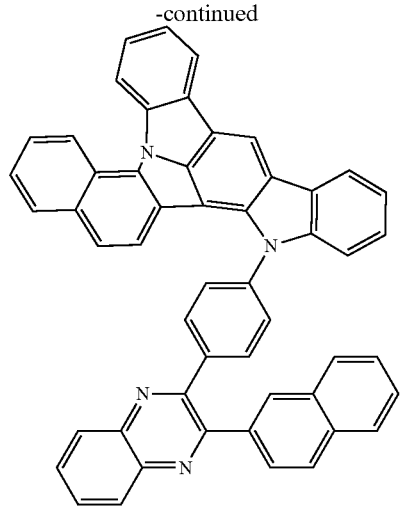
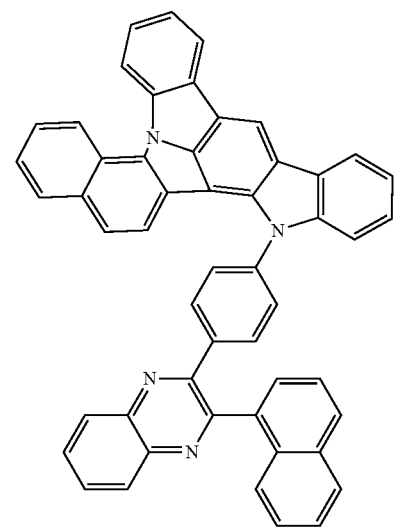
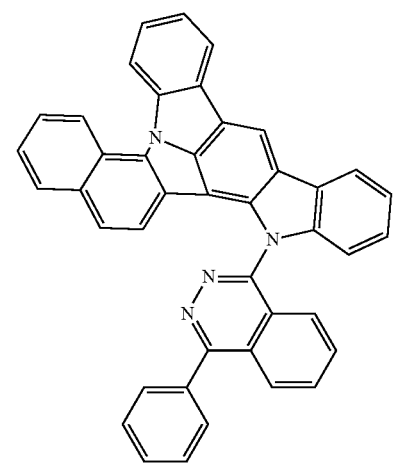
1104
-continued
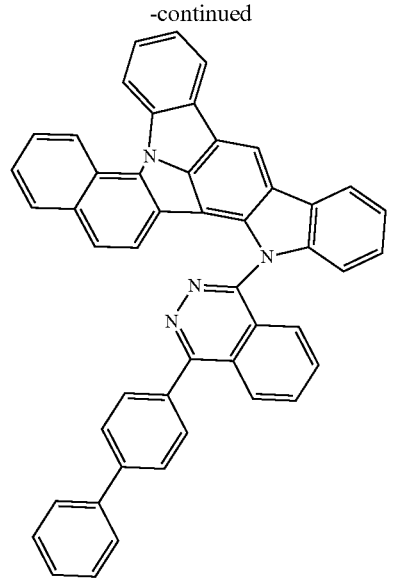
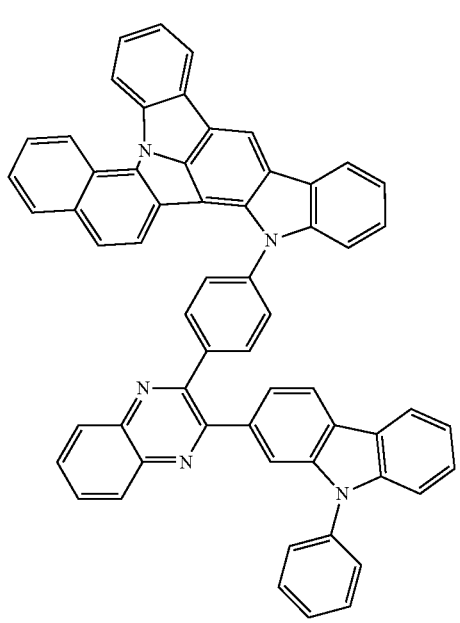
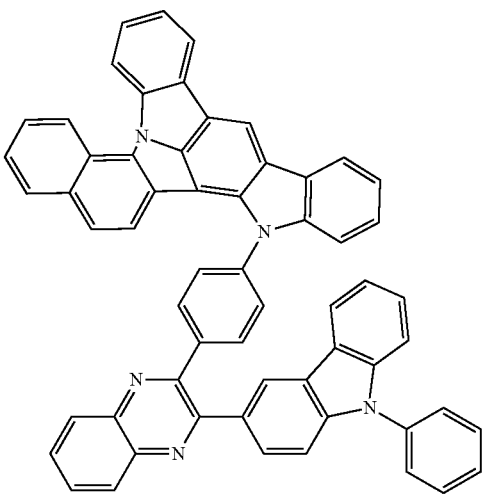

1105
-continued
1106
-continued
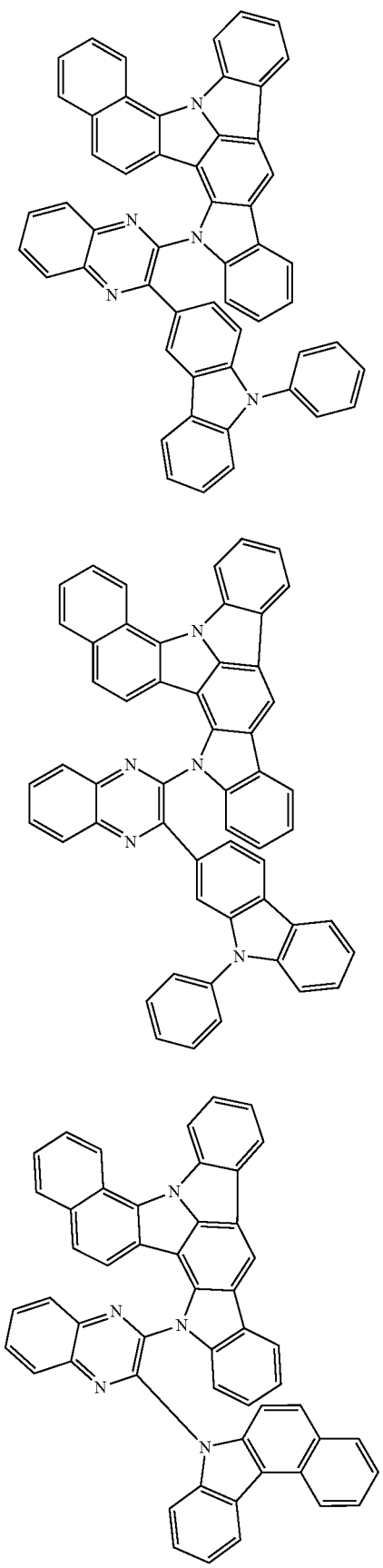
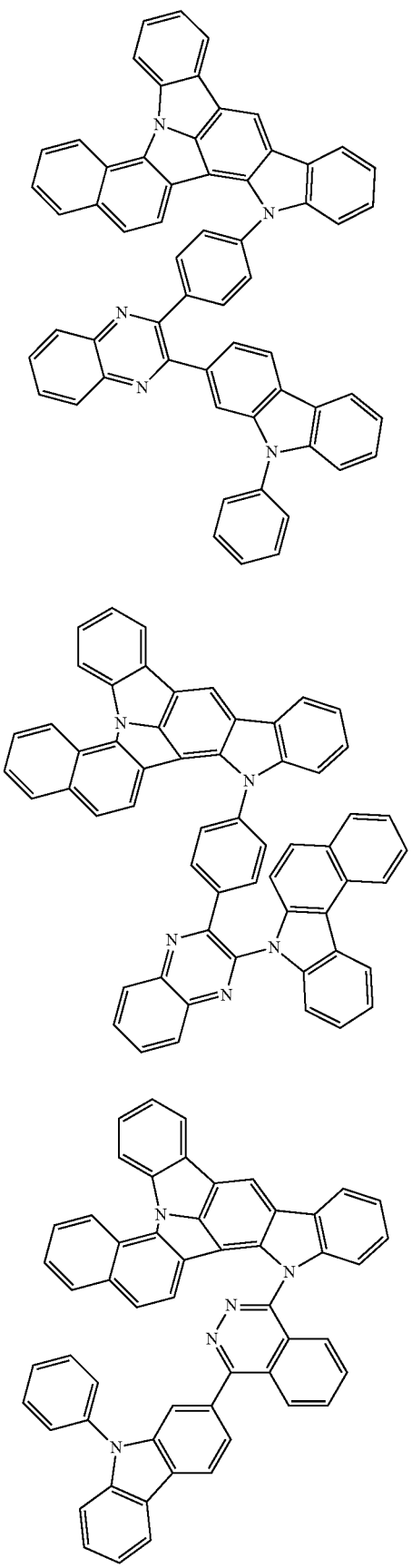

1107
-continued
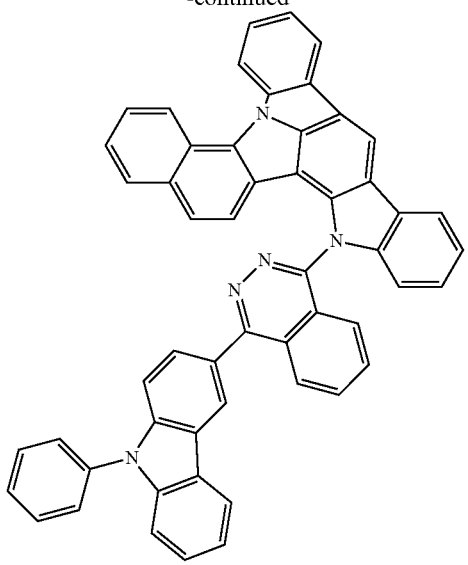
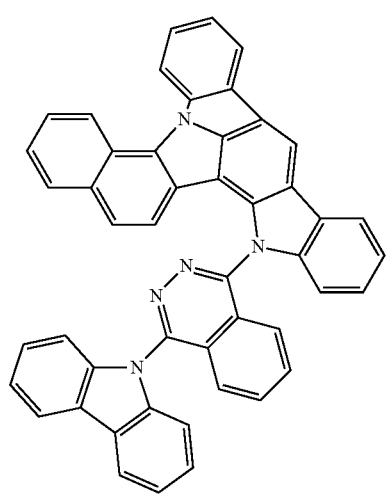
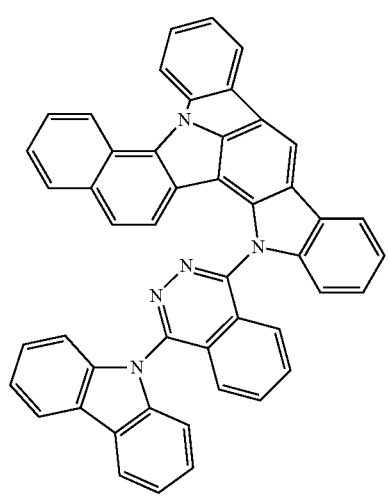
1108
-continued
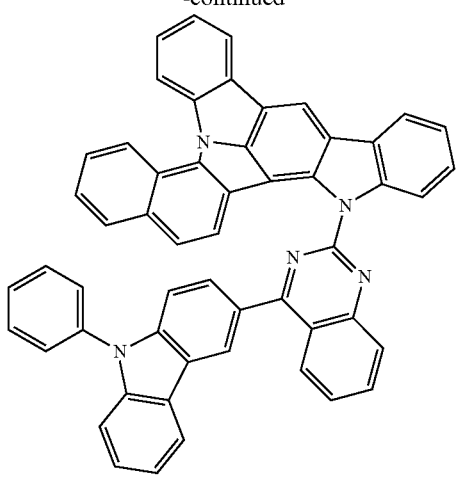
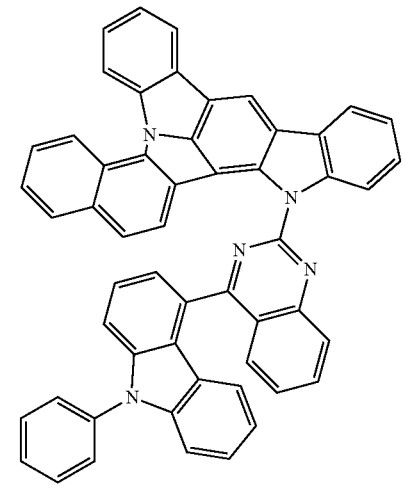
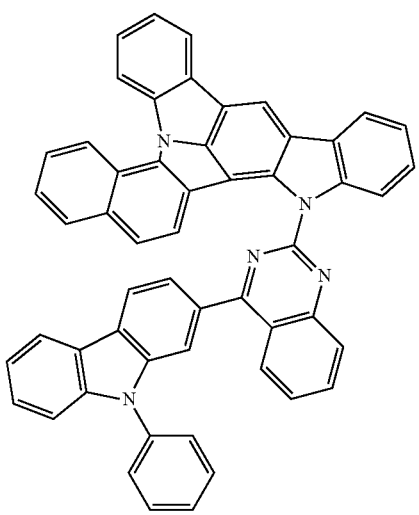

1109
-continued
1110
-continued
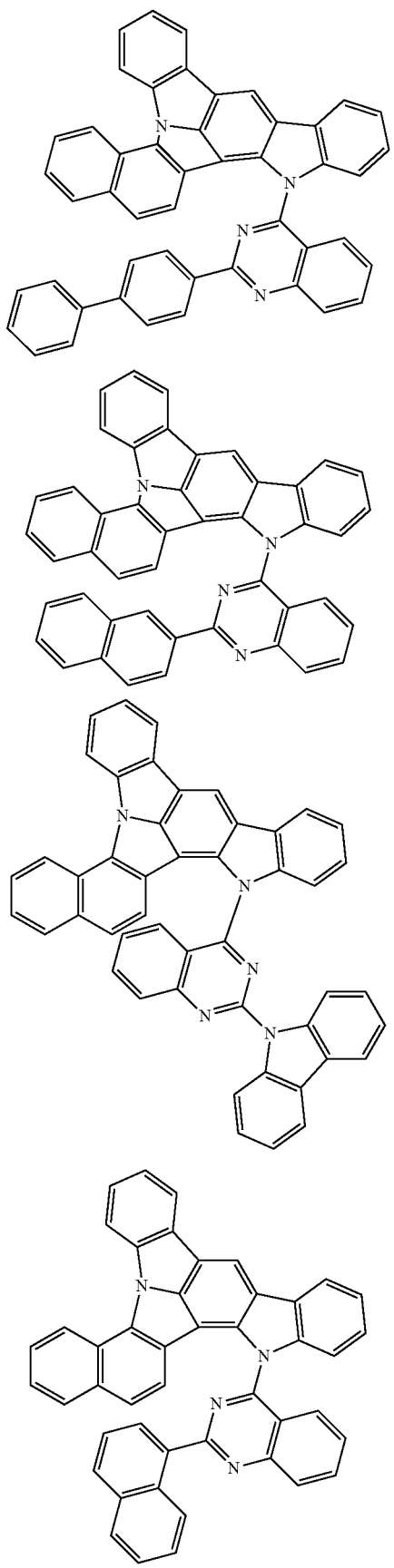
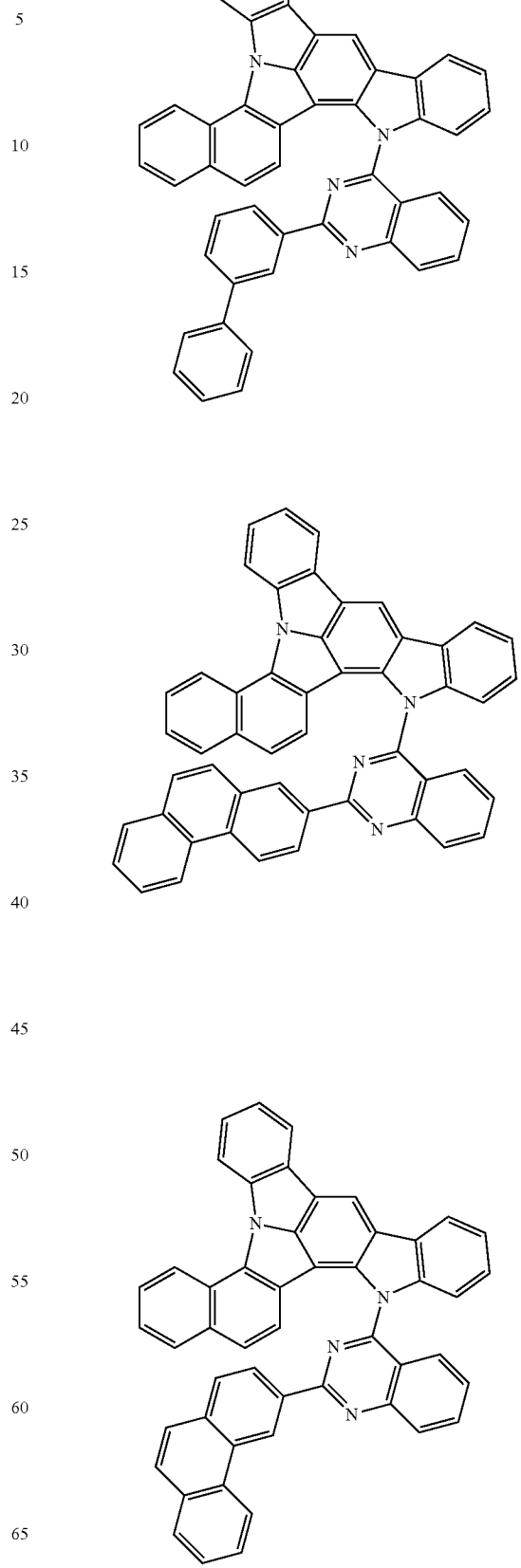

1111
-continued
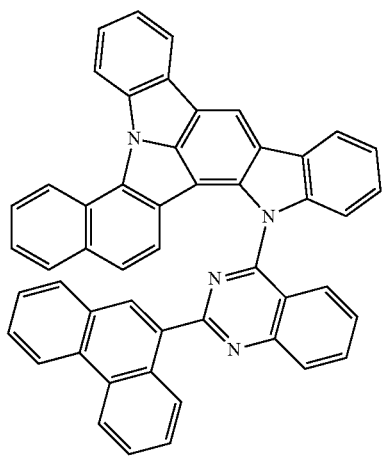
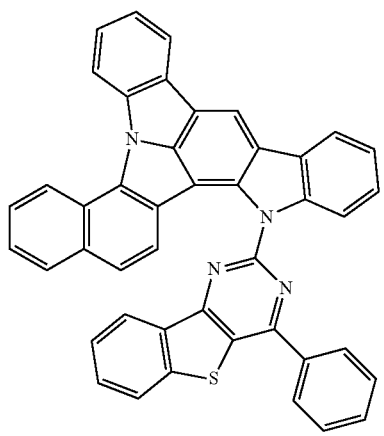
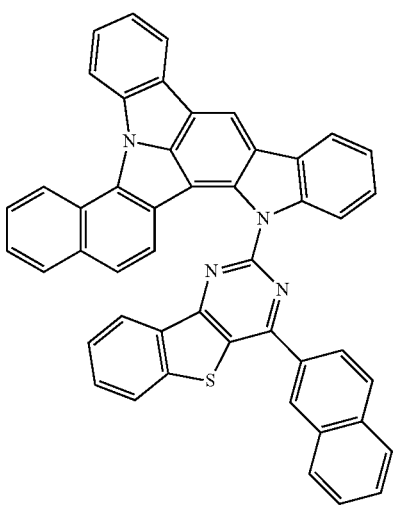
1112
-continued
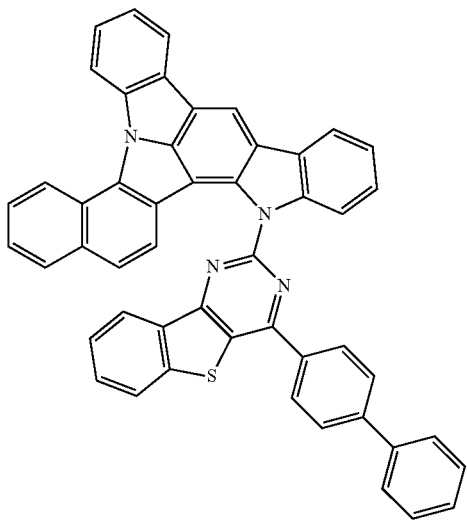
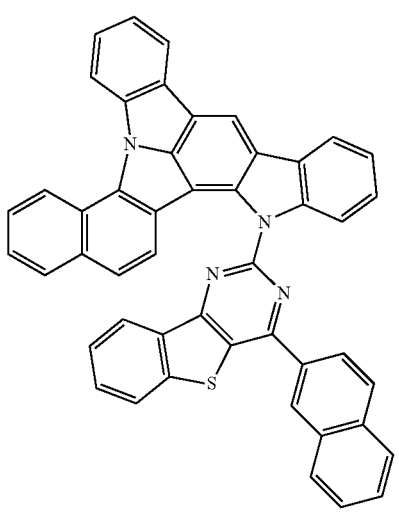
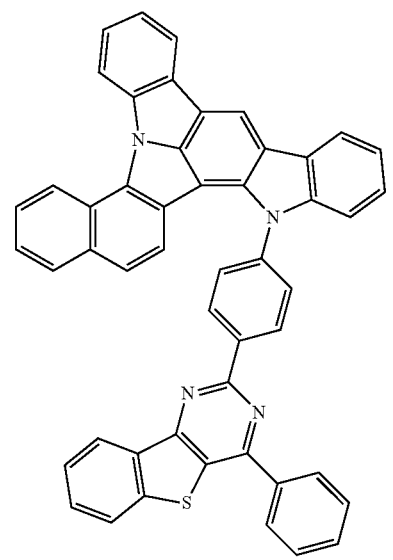

1113
-continued
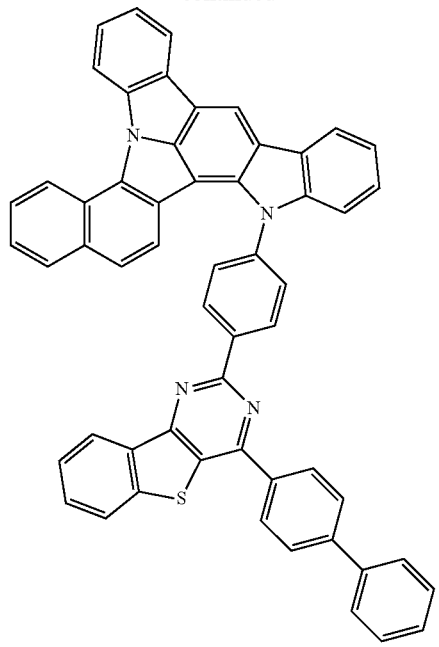
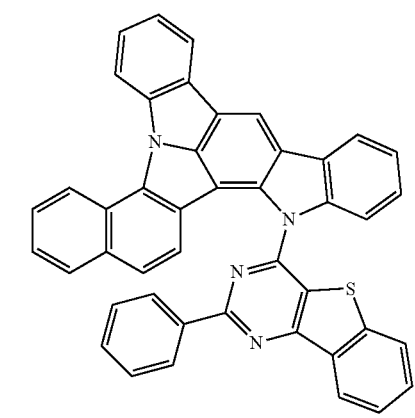
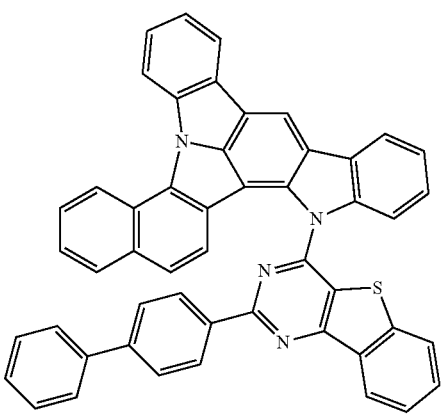
1114
-continued
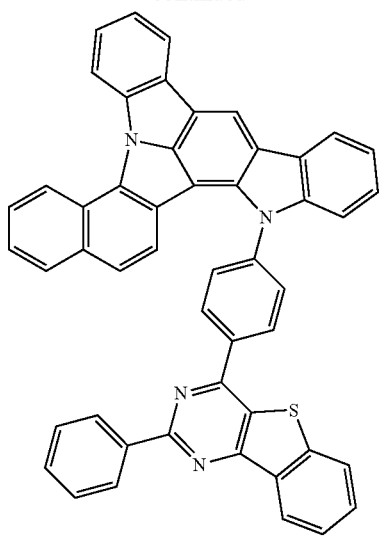
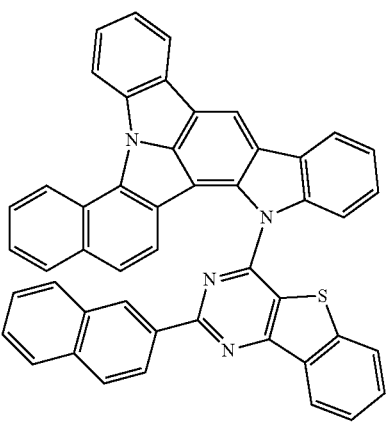
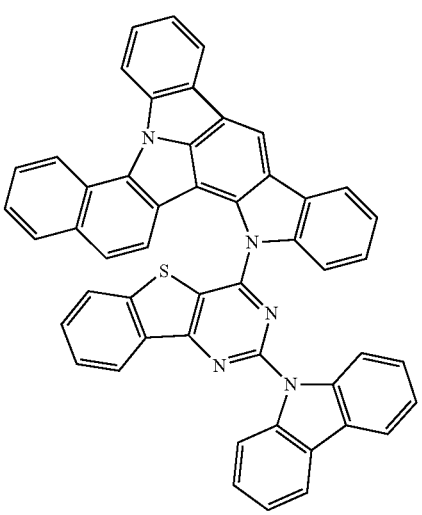

1115
-continued
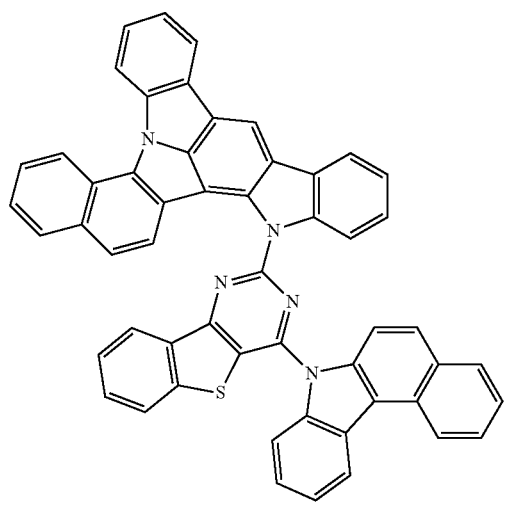
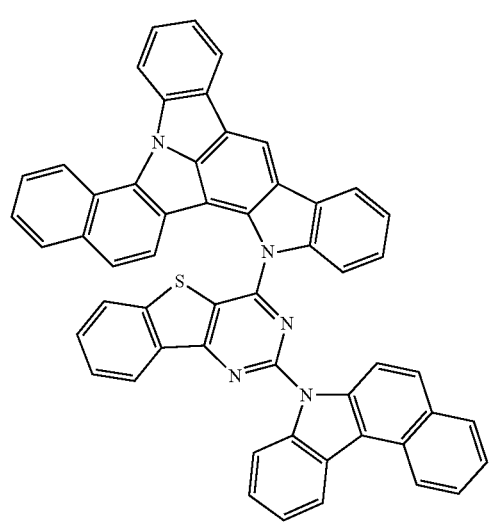
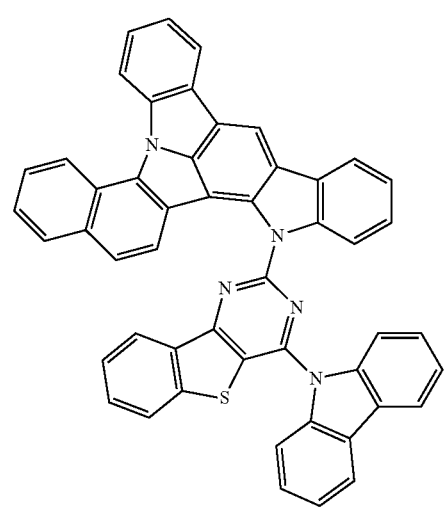
1116
-continued
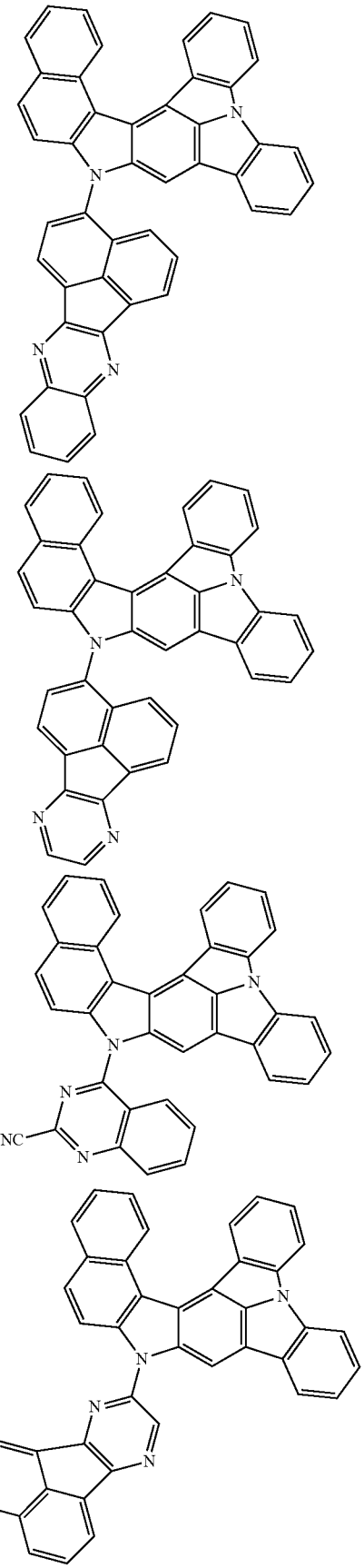

1117
-continued
1118
-continued
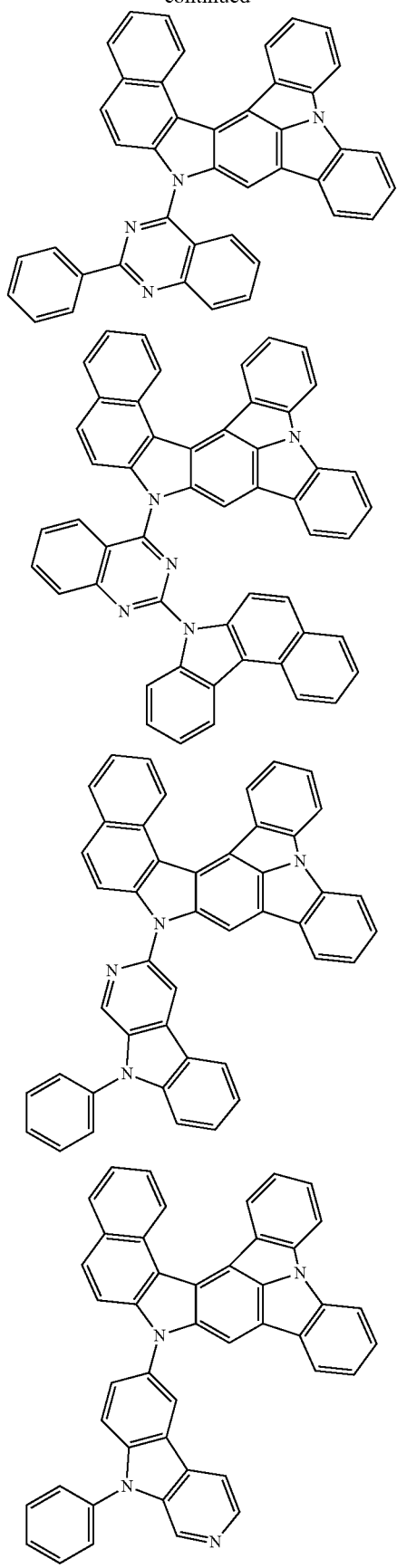
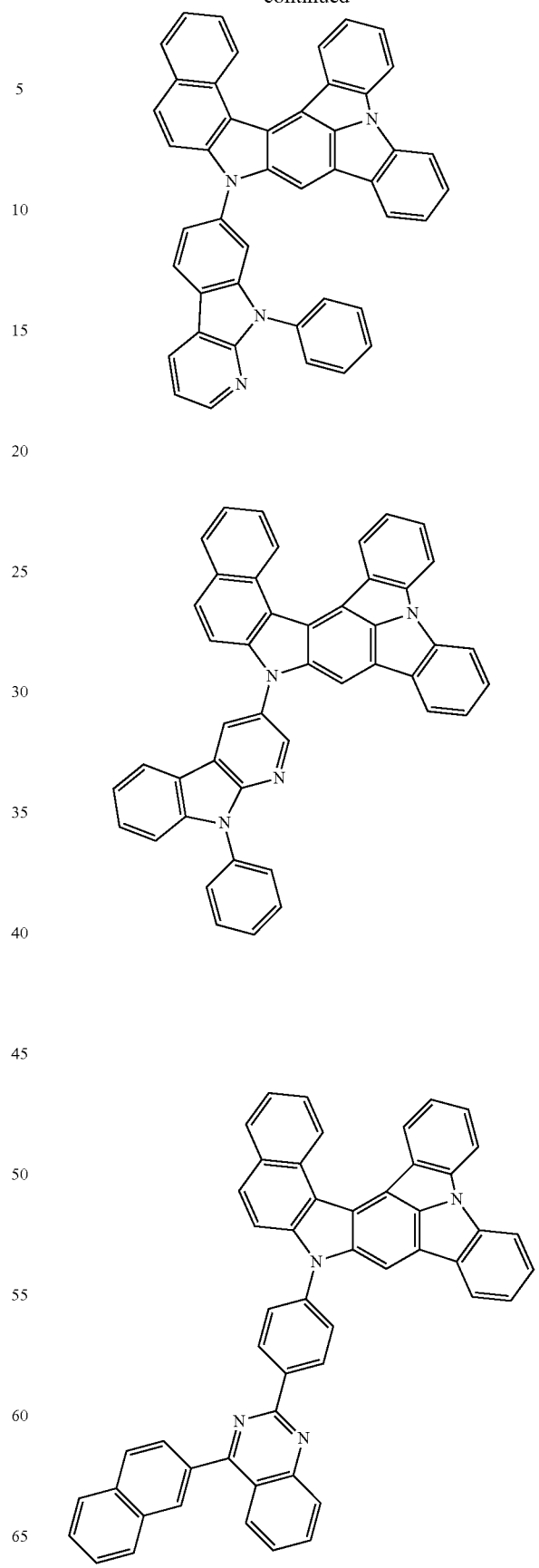

1119
-continued
1120
-continued
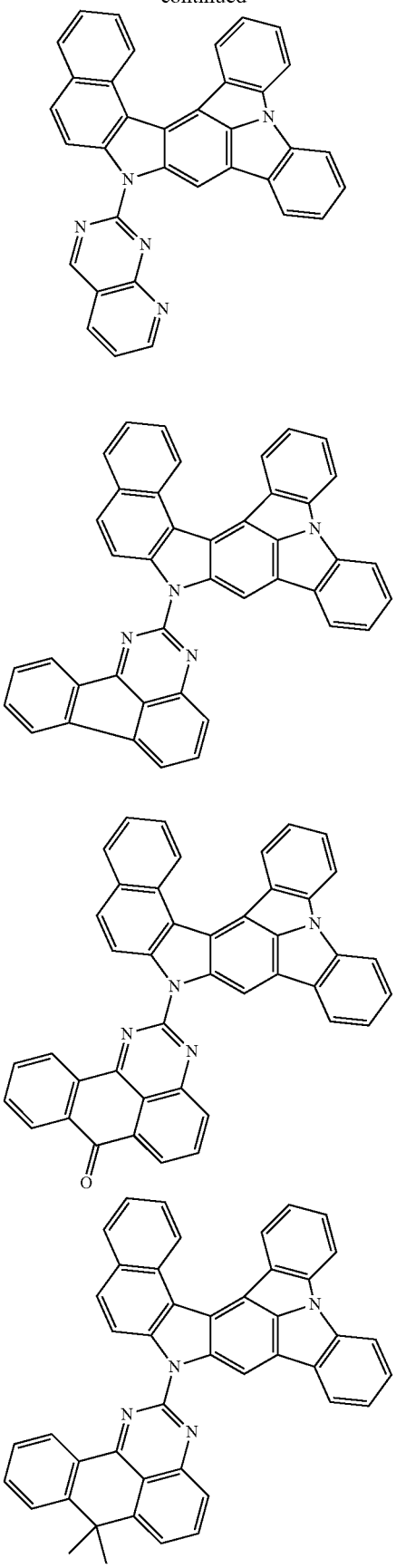
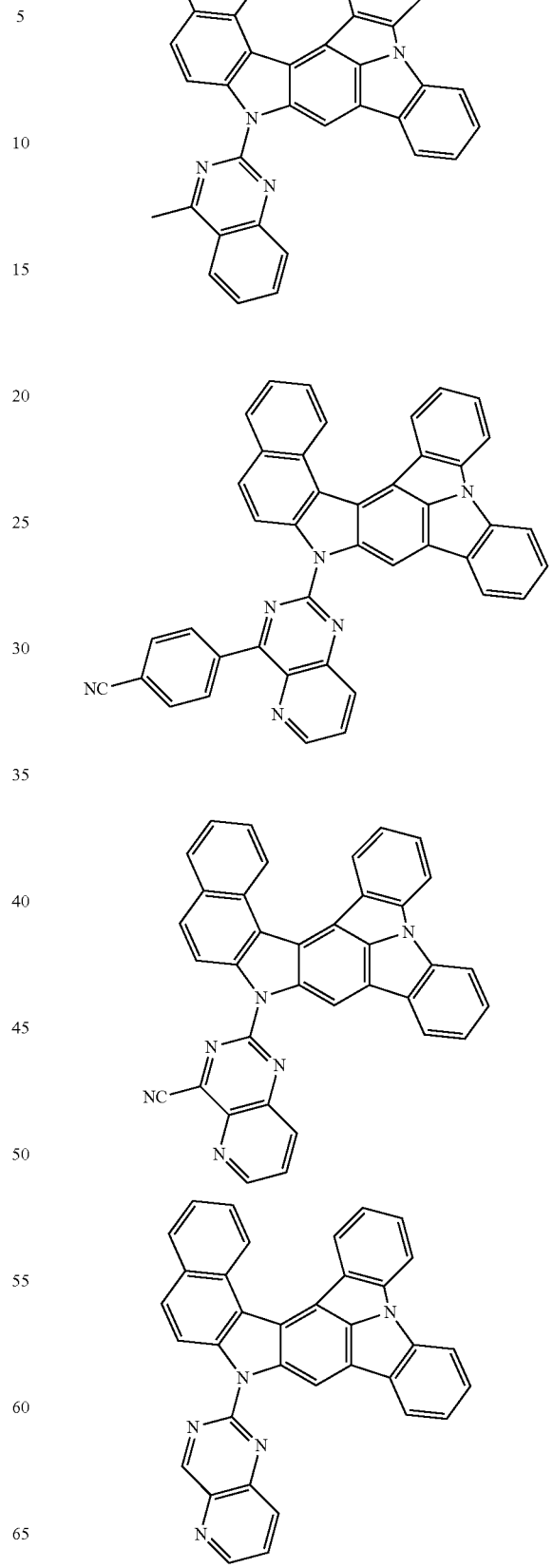

1121
-continued
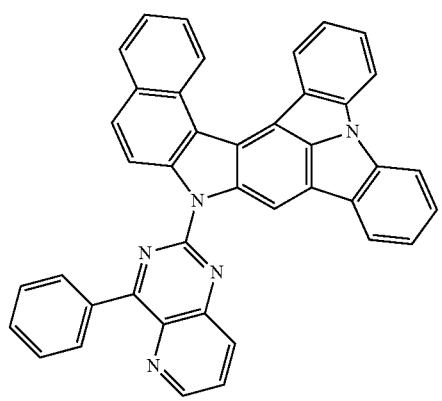
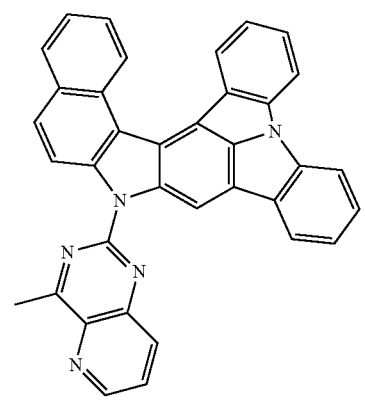
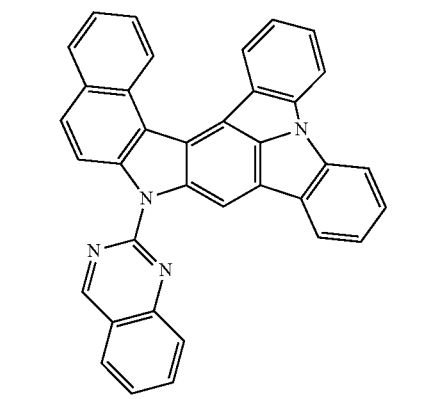
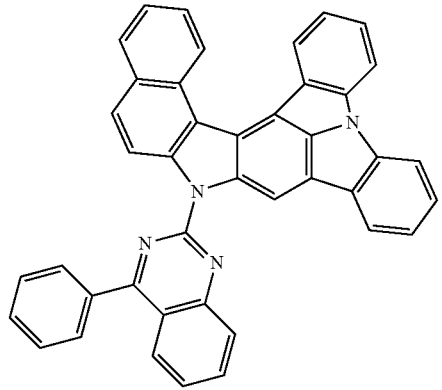
1122
-continued
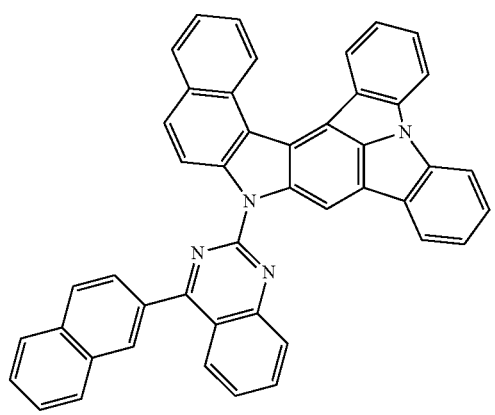
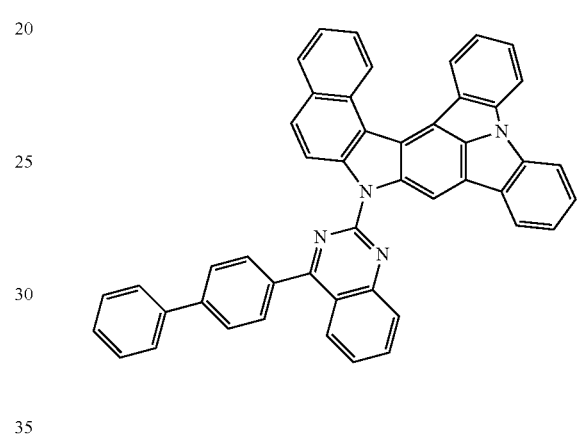
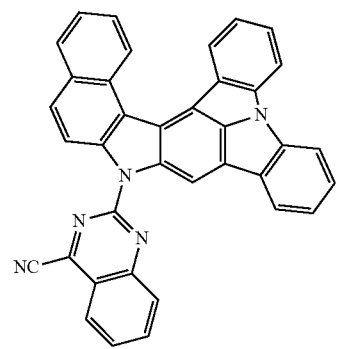
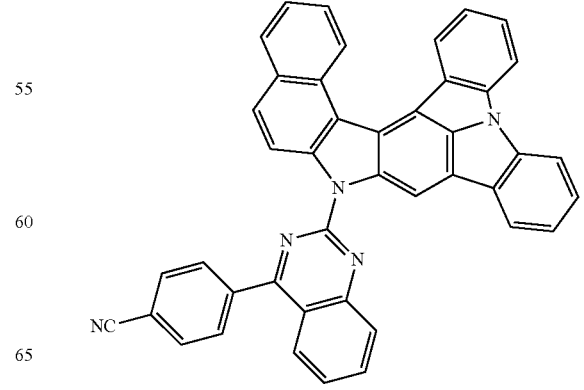

1123
-continued
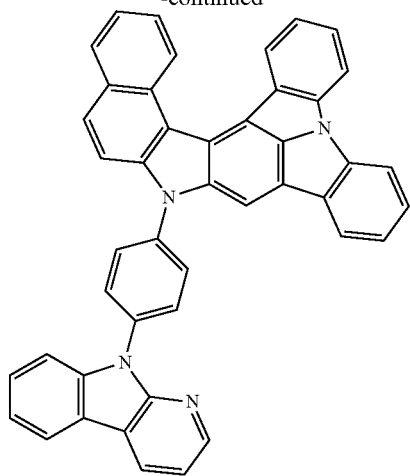
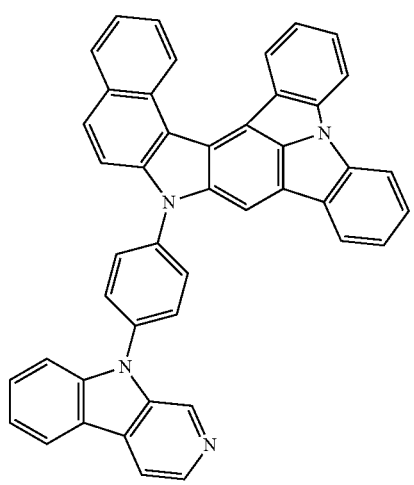
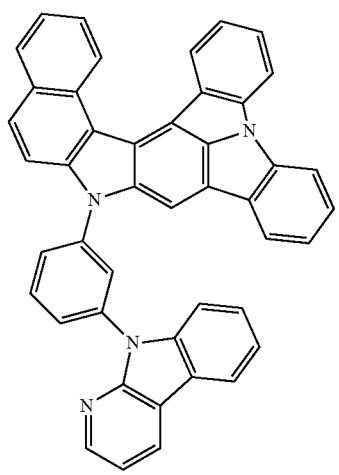
1124
-continued
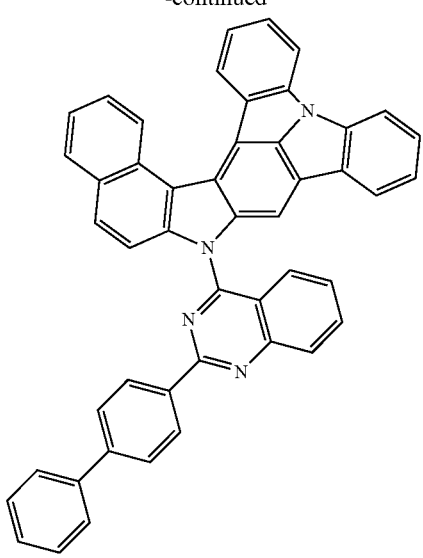
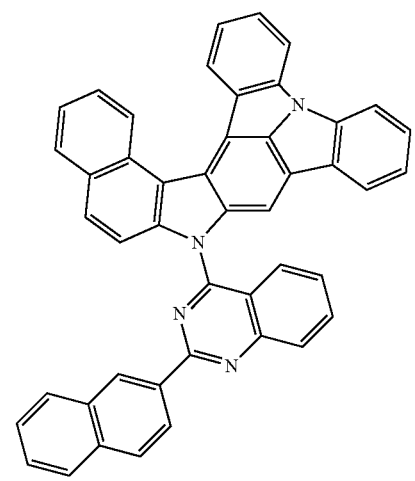
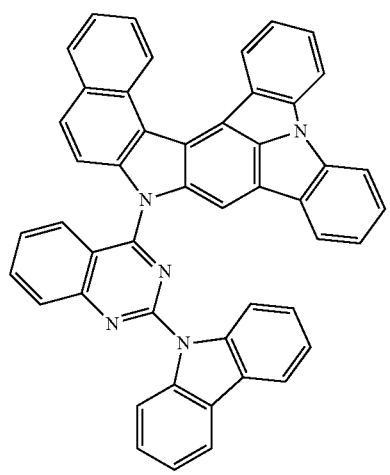

1125
-continued
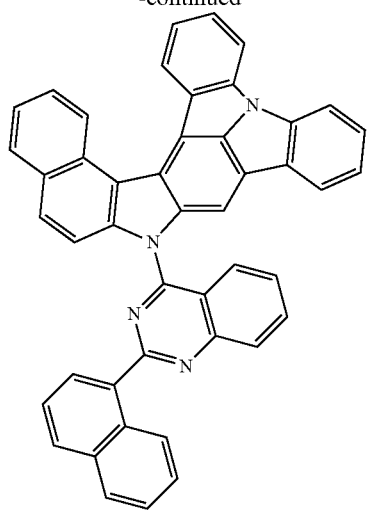
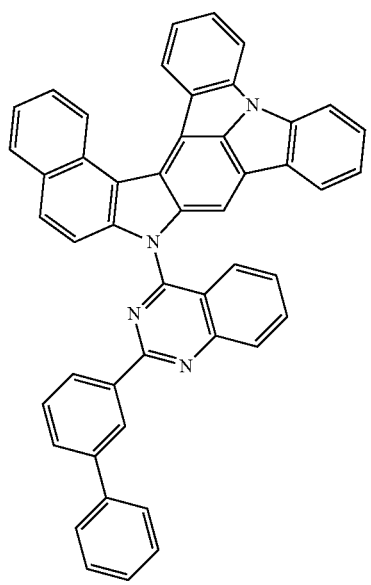
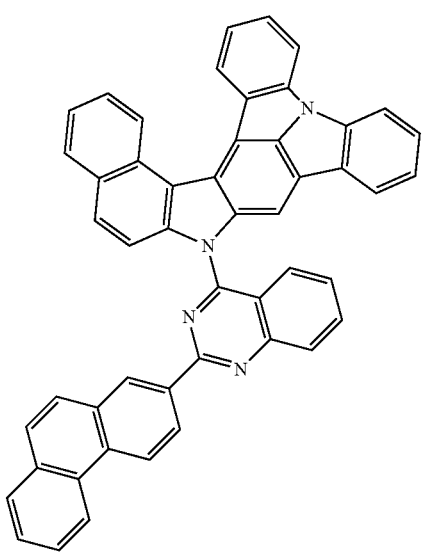
1126
-continued
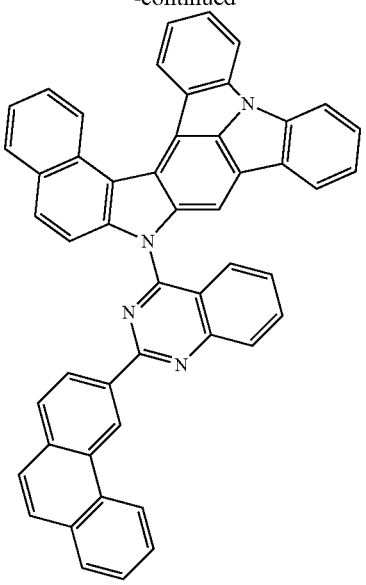
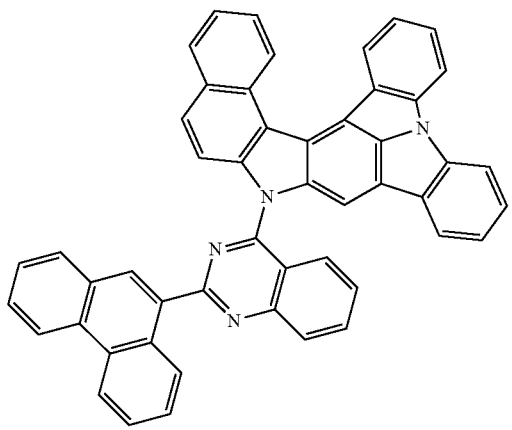
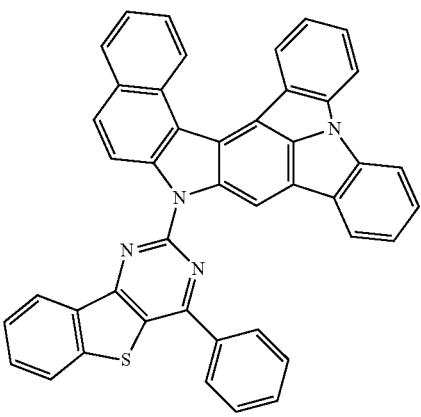

1127
-continued
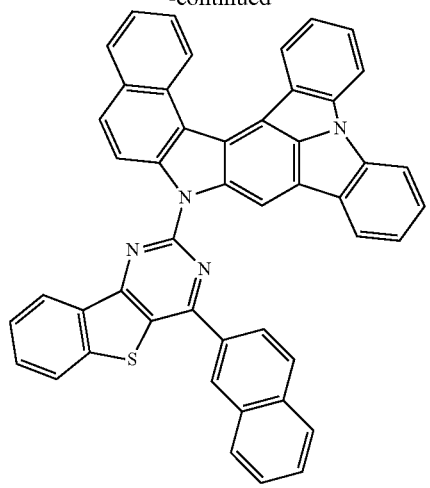
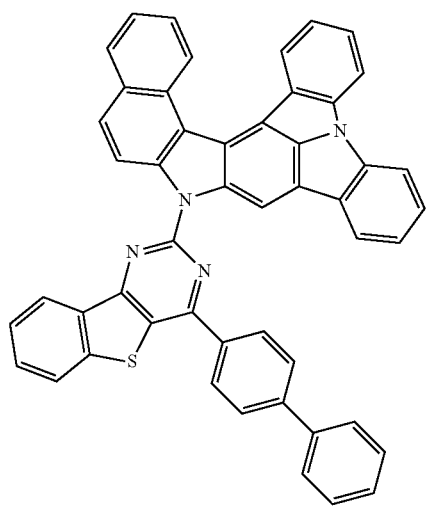
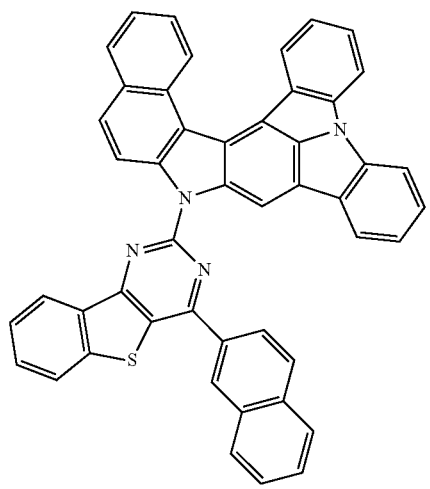
1128
-continued
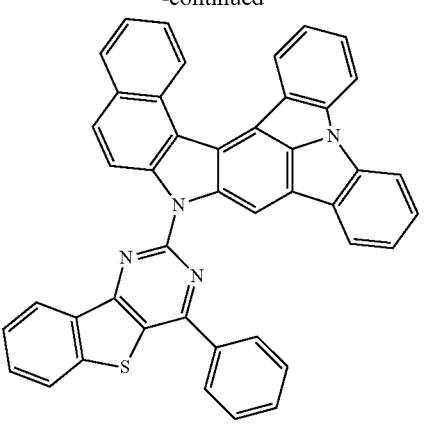
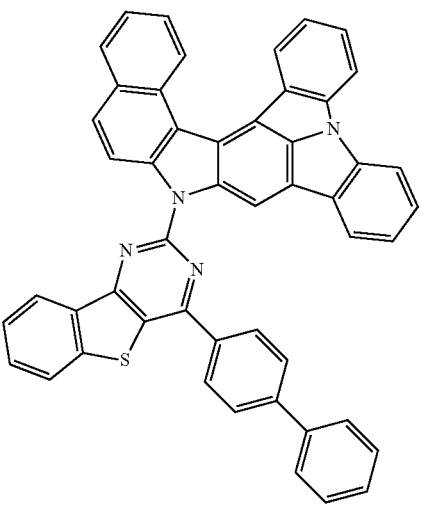
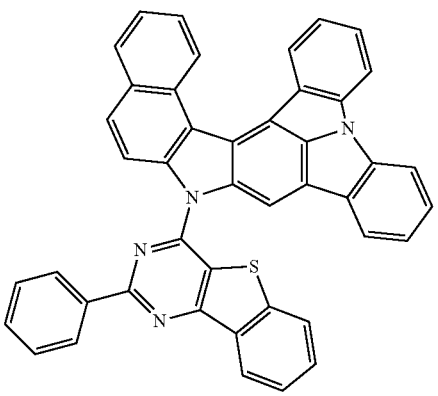
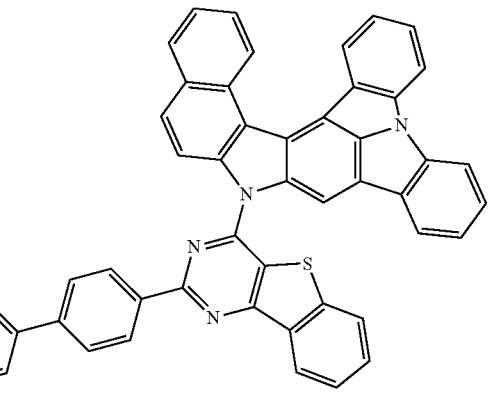

1129
-continued
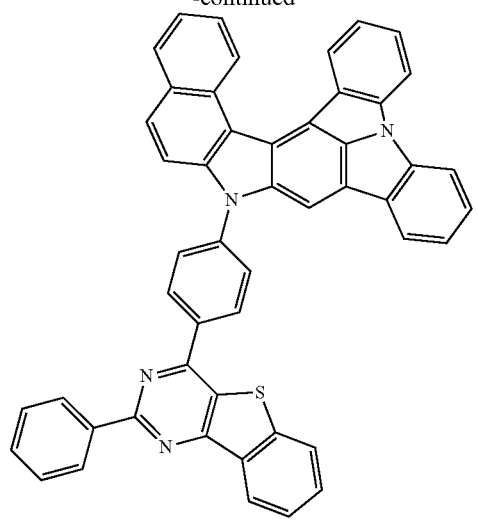
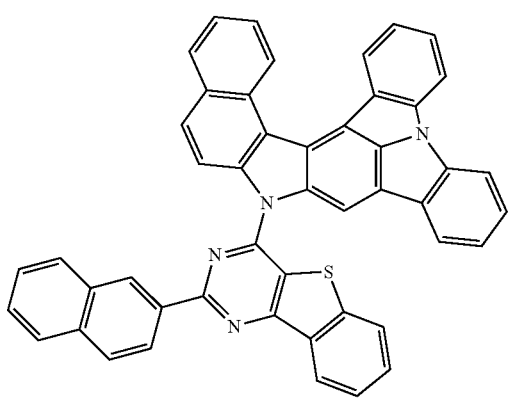
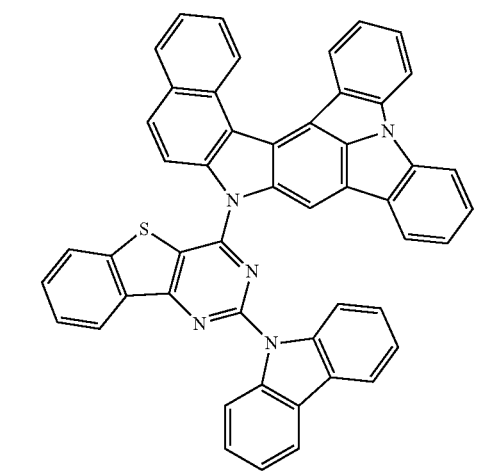
1130
-continued
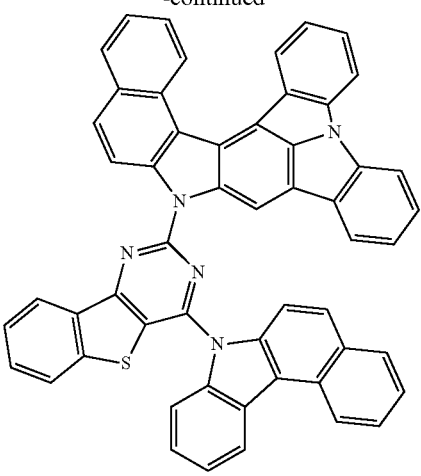
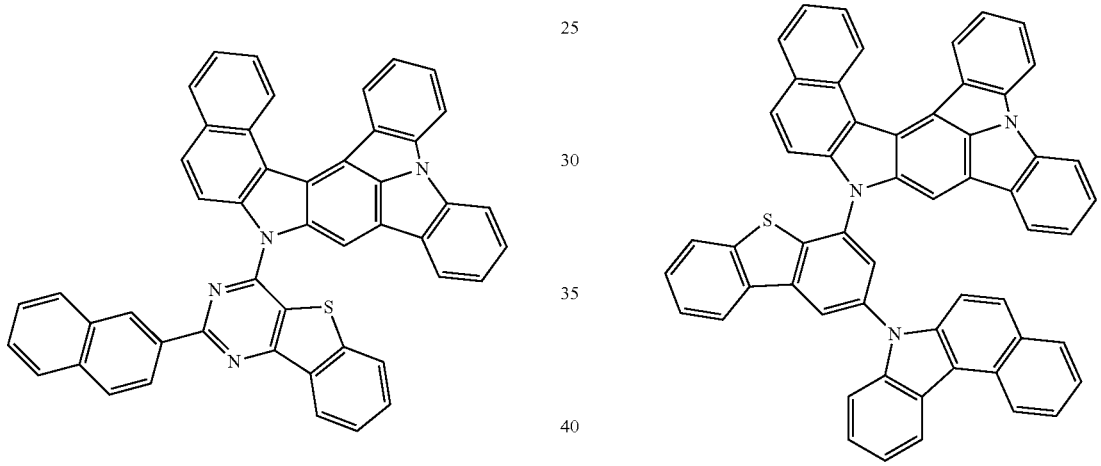
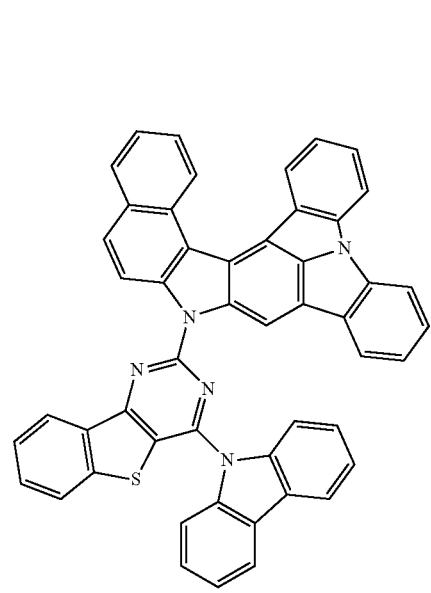

| 1131 | 1132 |
|---|---|
| -continued | -continued |
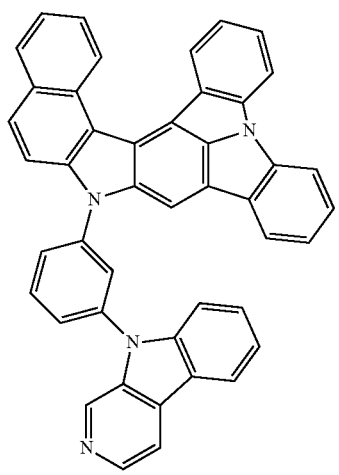
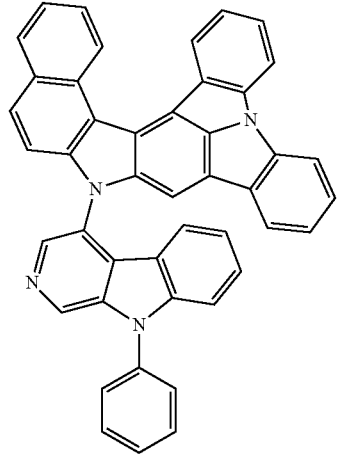
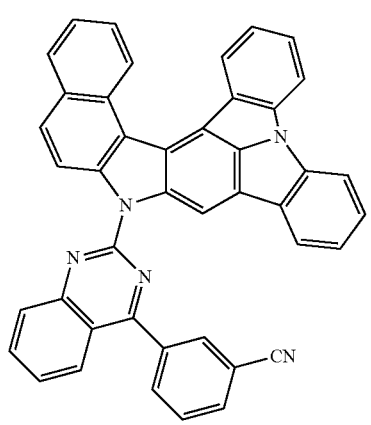
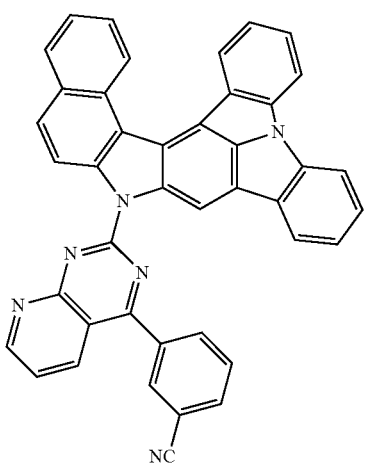
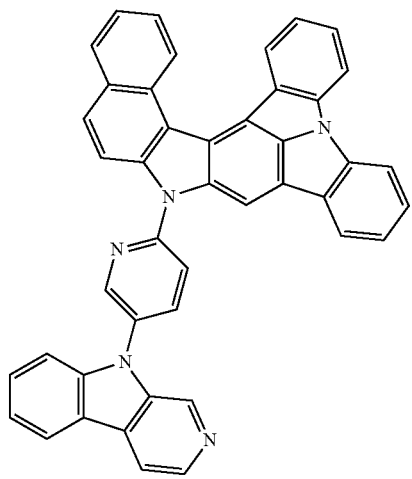
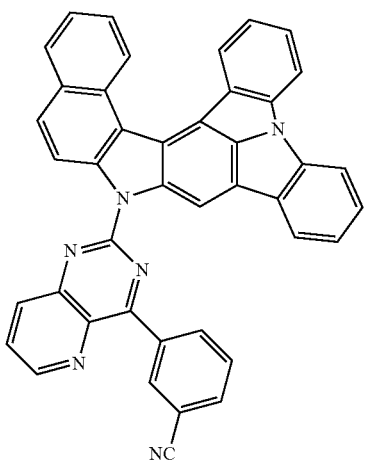

1133
-continued
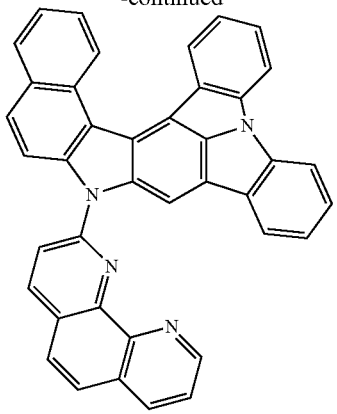
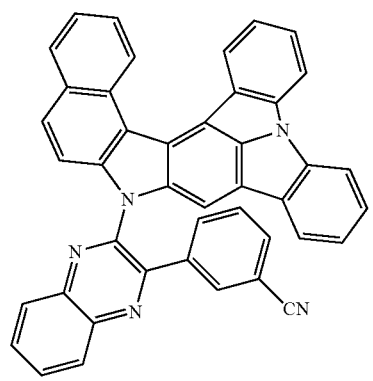
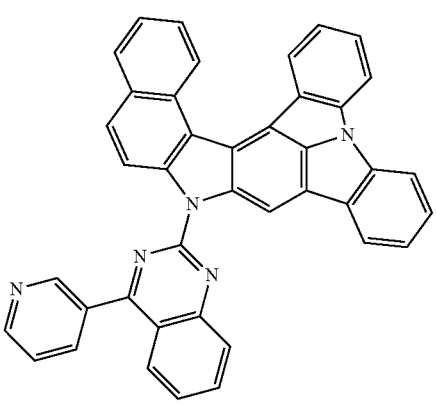
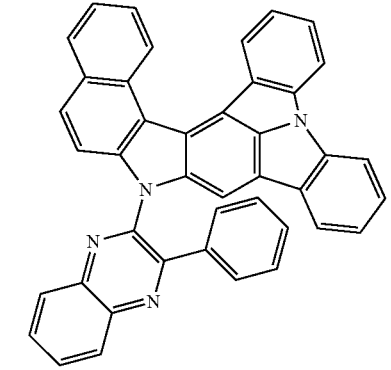
1134
-continued
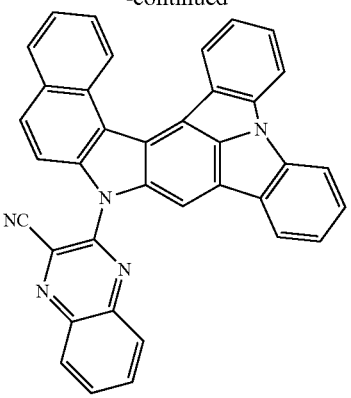
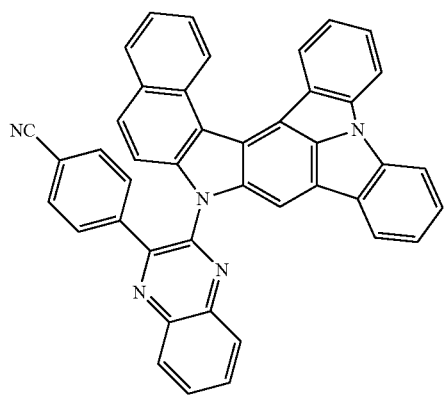
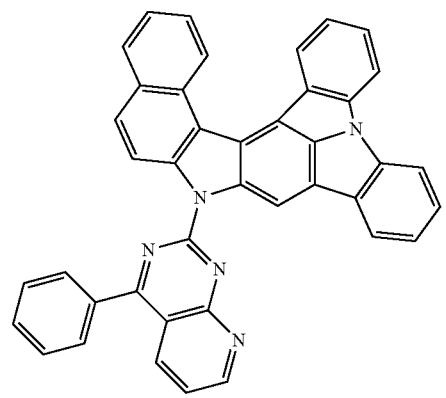
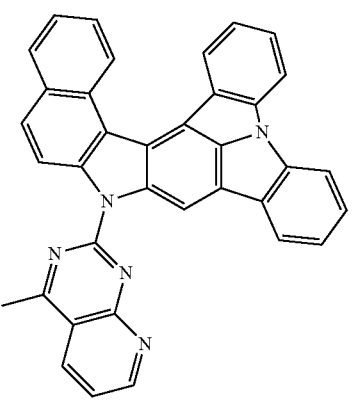

1135
-continued
1136
-continued
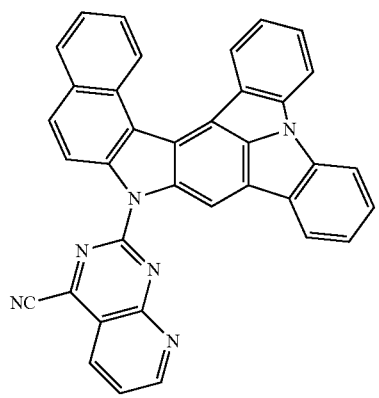
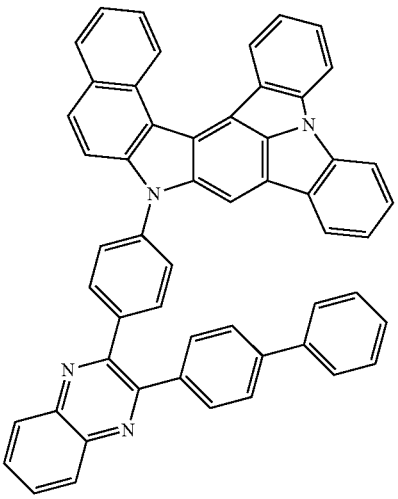
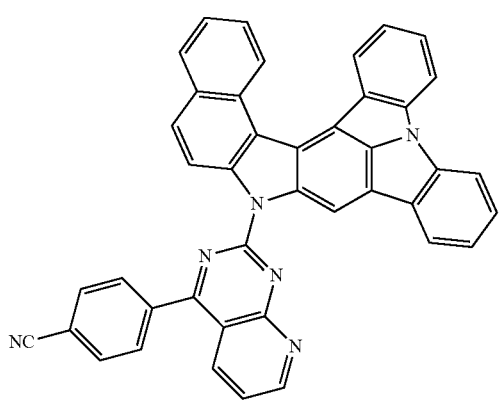
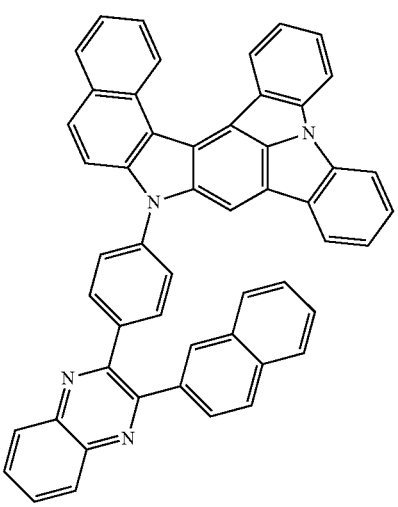
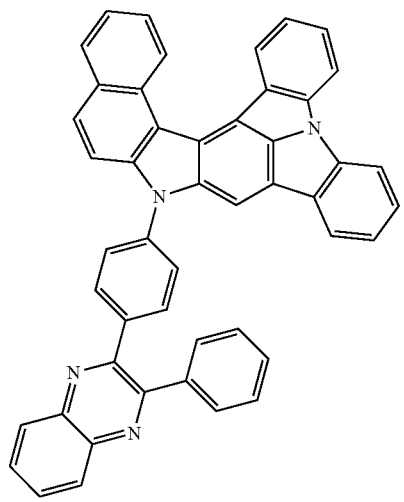
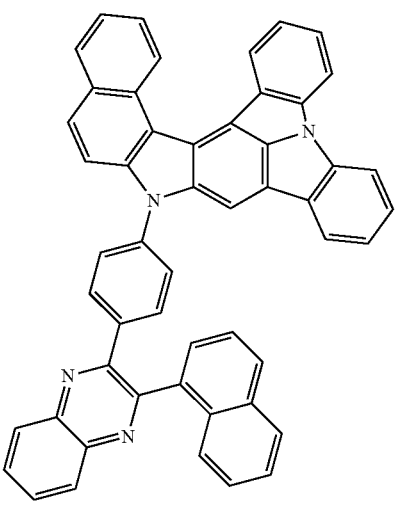

1137
-continued
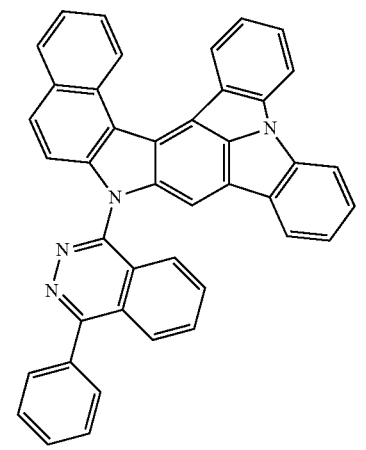
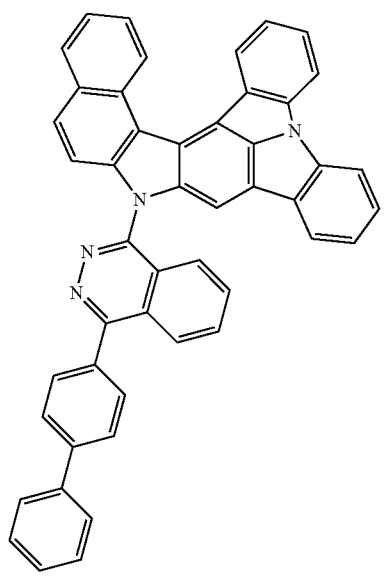
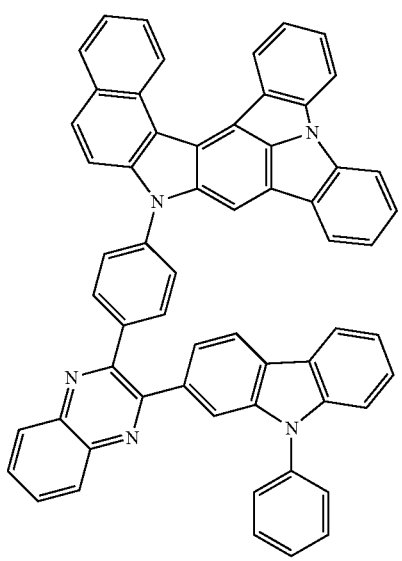
1138
-continued
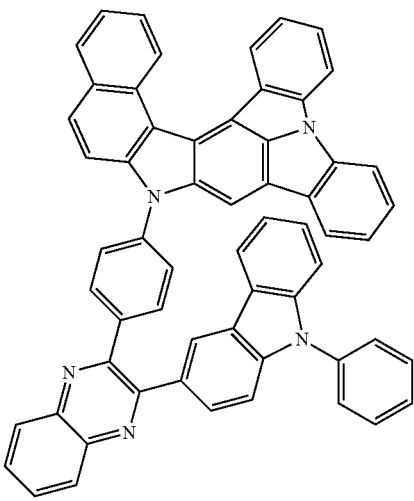
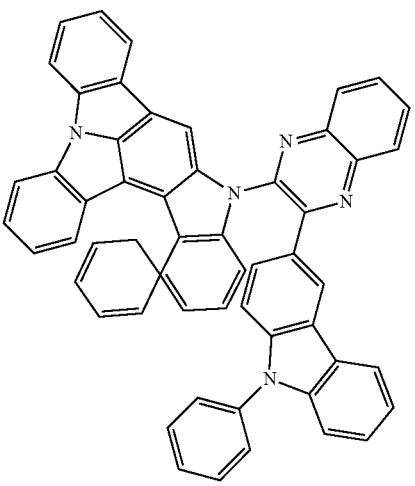
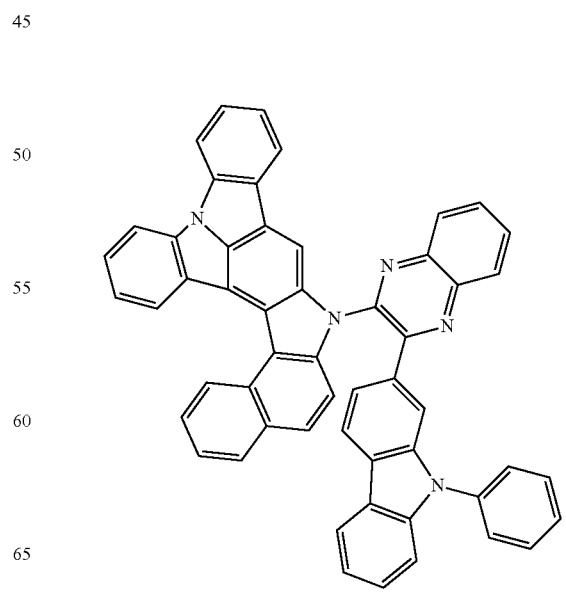

1139
-continued
1140
-continued
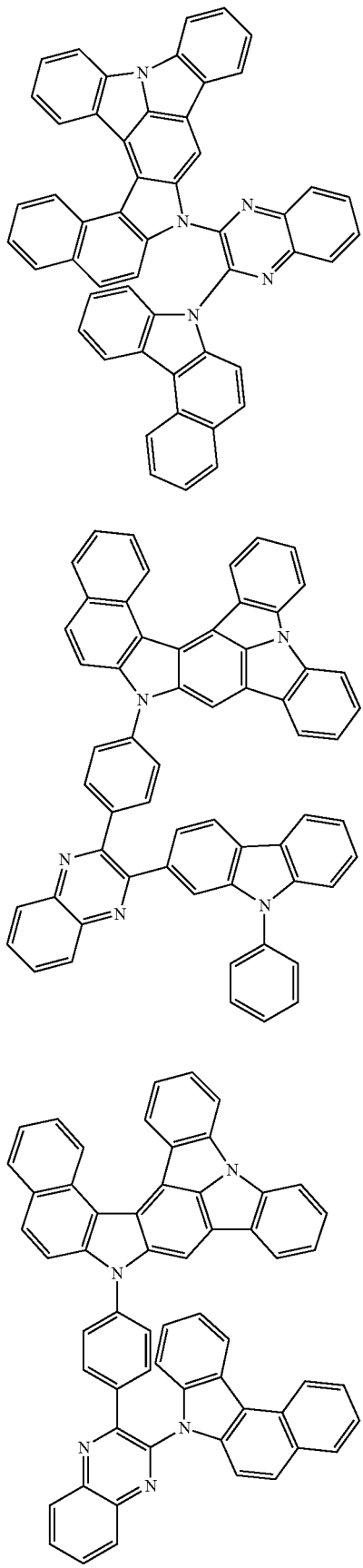
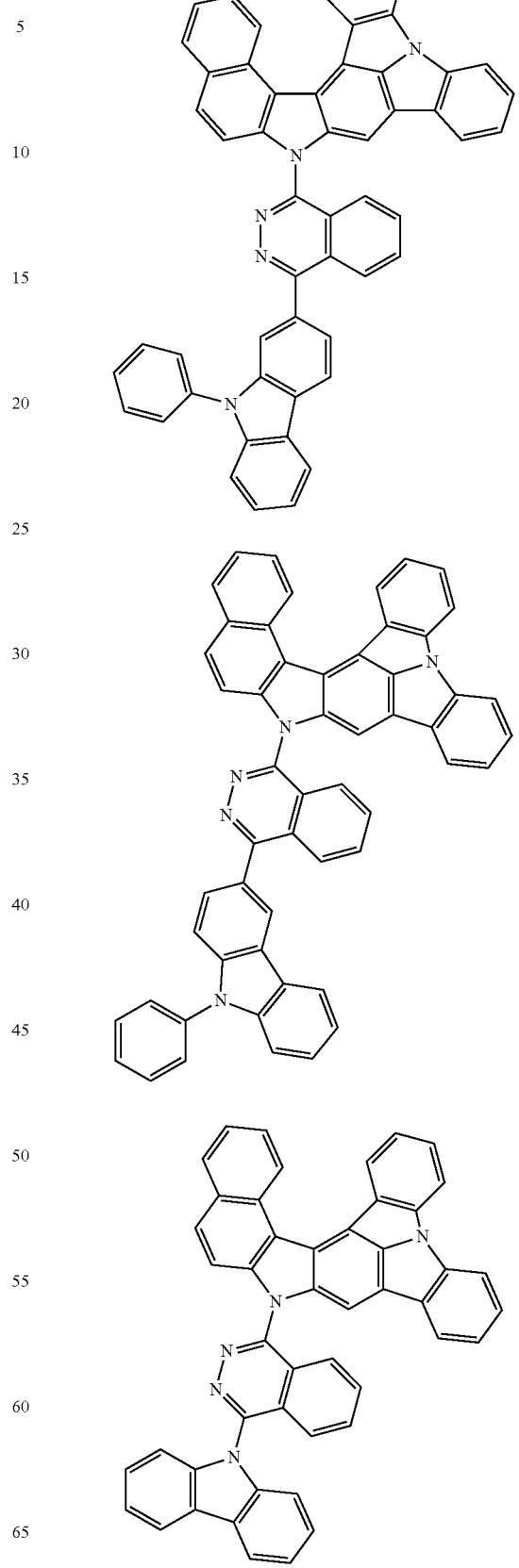

1141
-continued
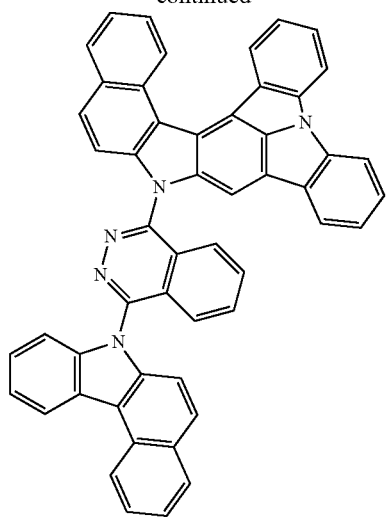
1142
-continued
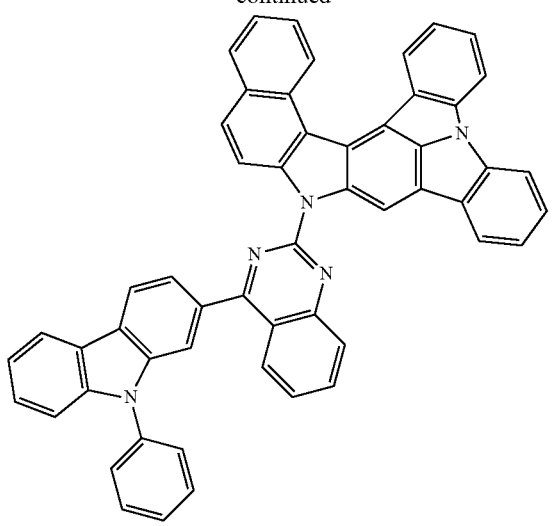
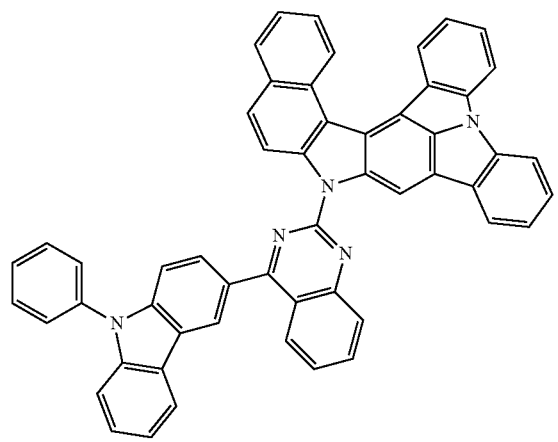
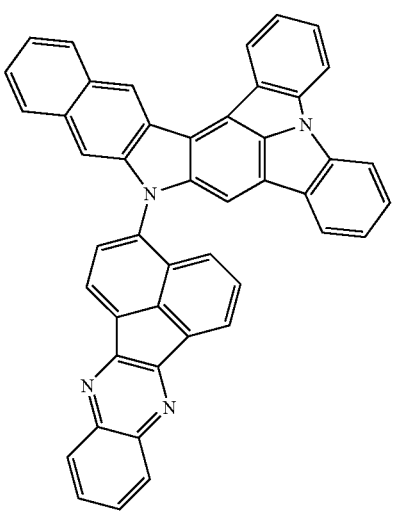
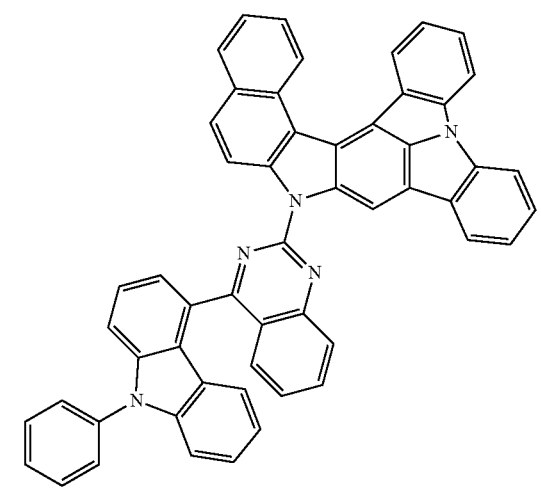
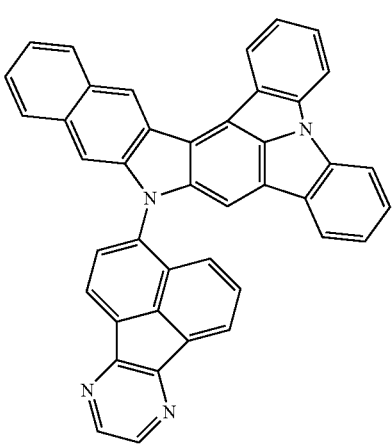

1143
-continued
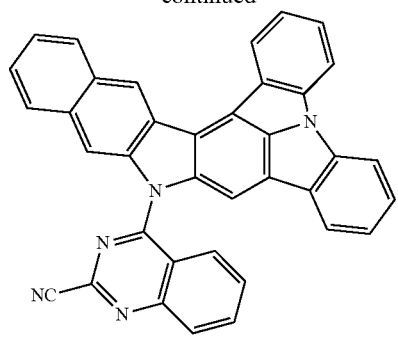
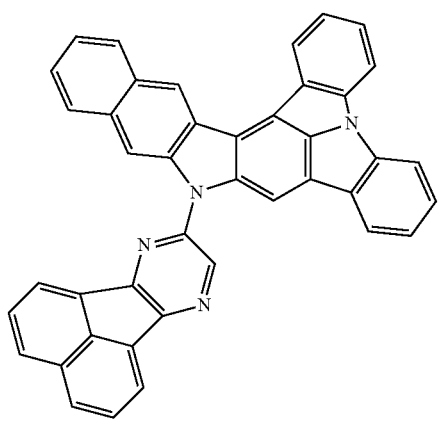
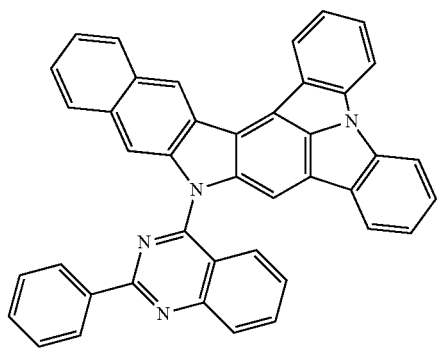
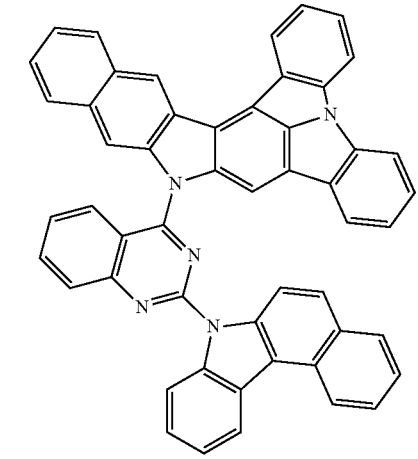
1144
-continued
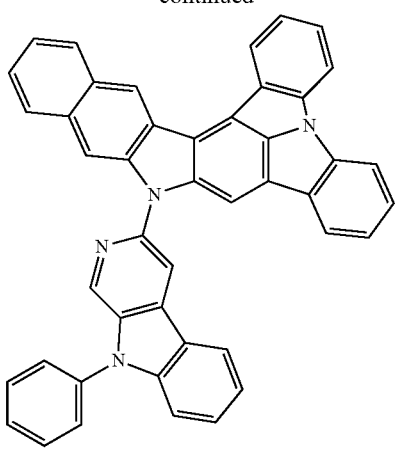
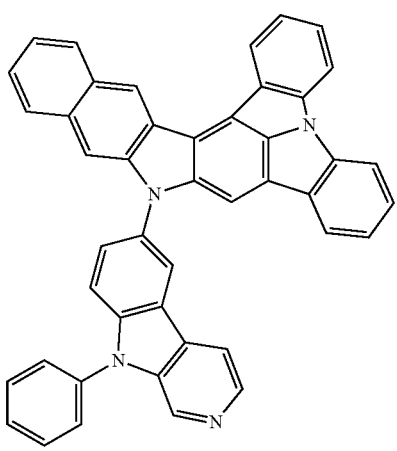
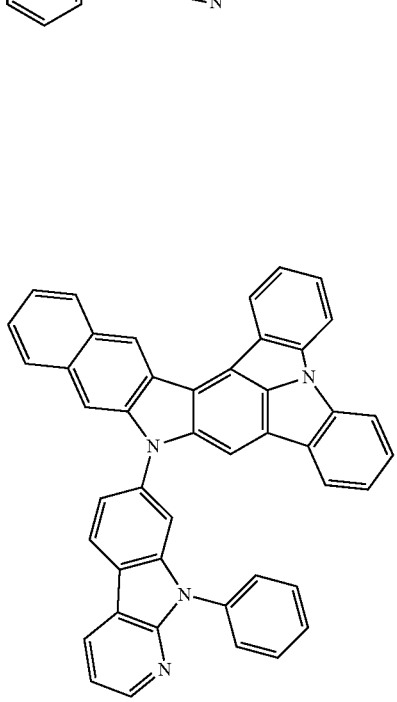

1145
-continued
1146
-continued
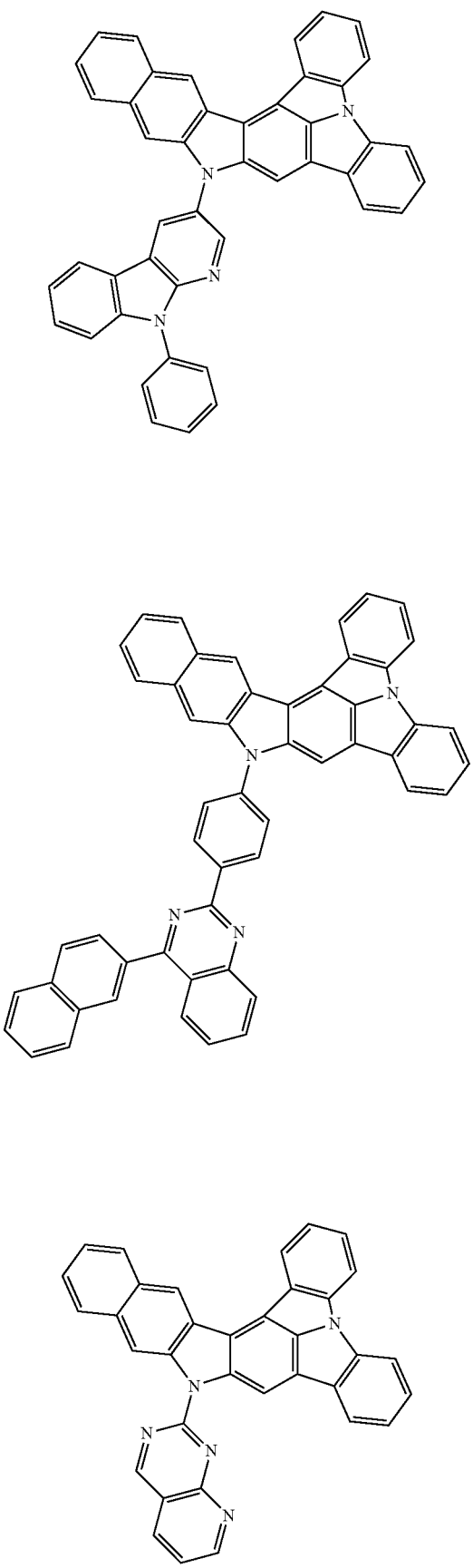
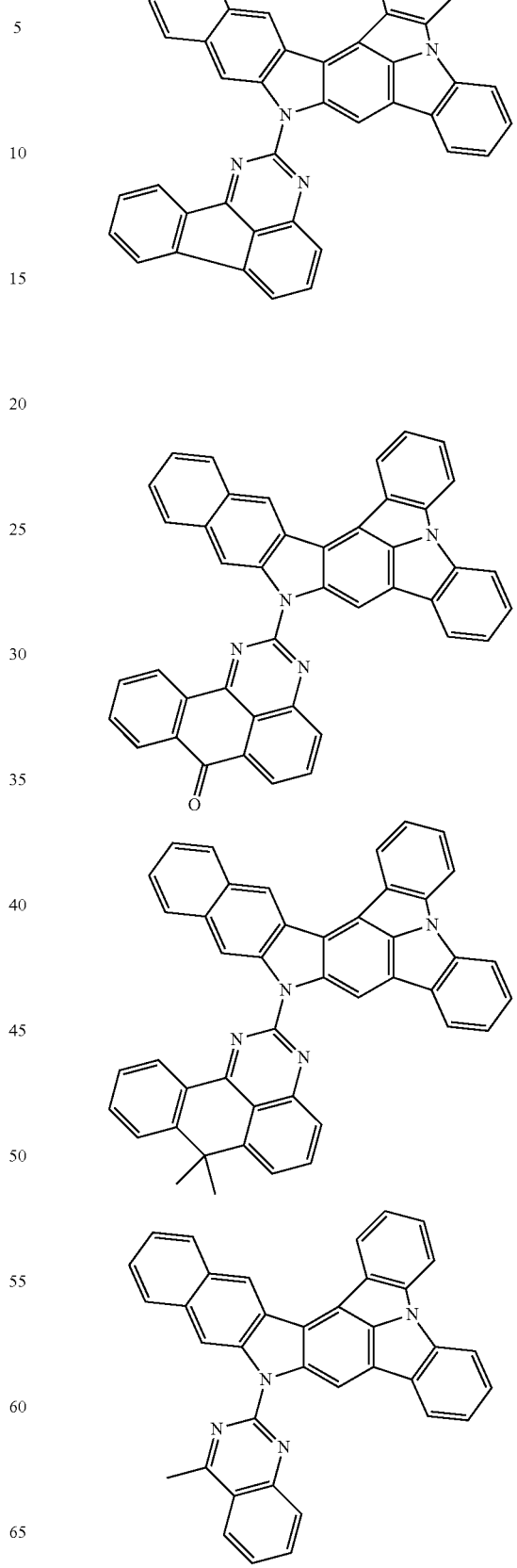

1147
-continued
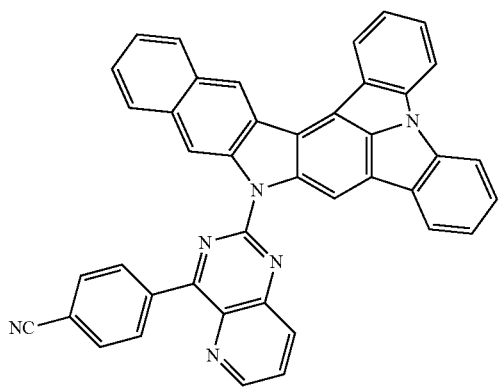
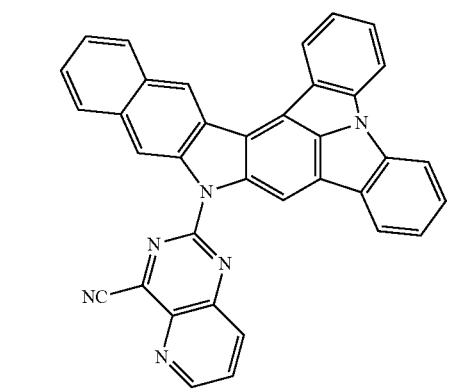
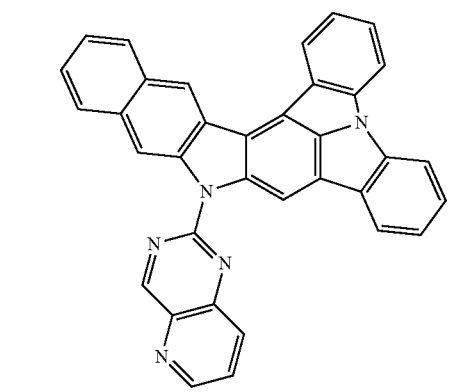
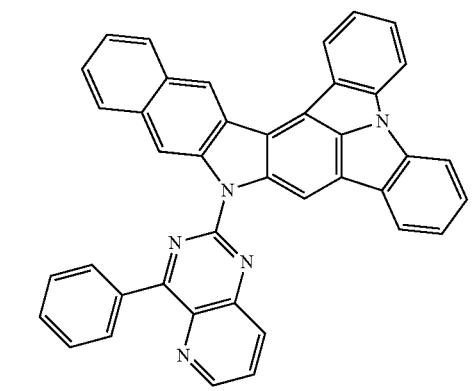
1148
-continued
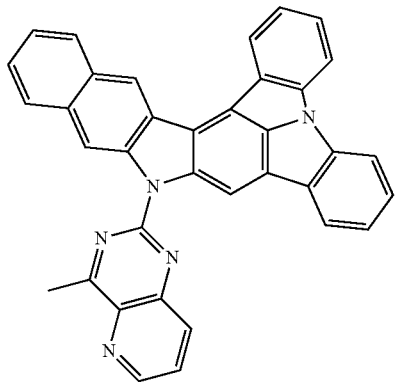
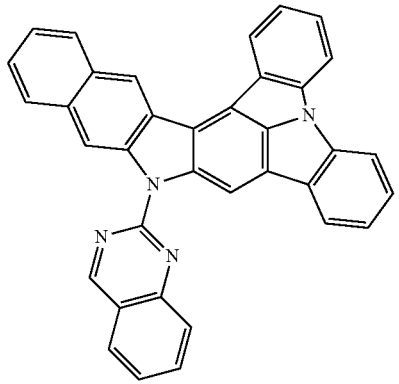
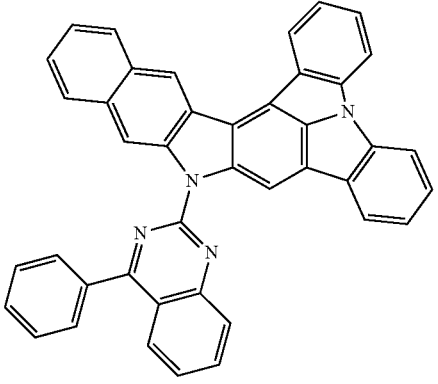
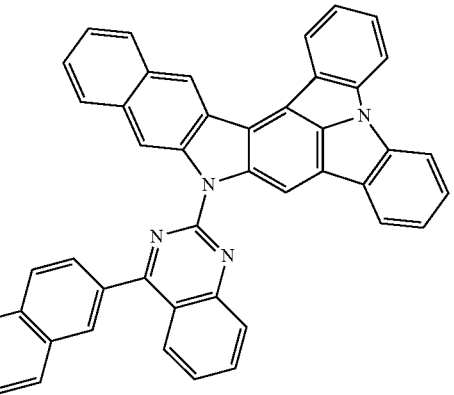

1149
-continued
1150
-continued
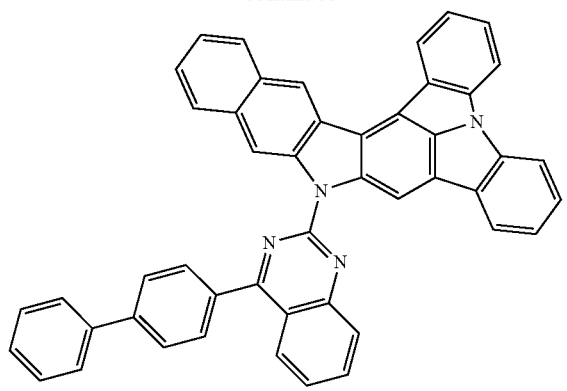
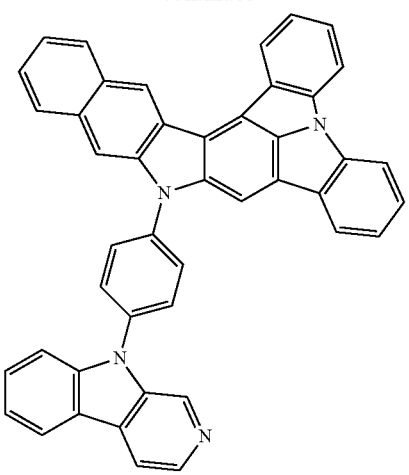
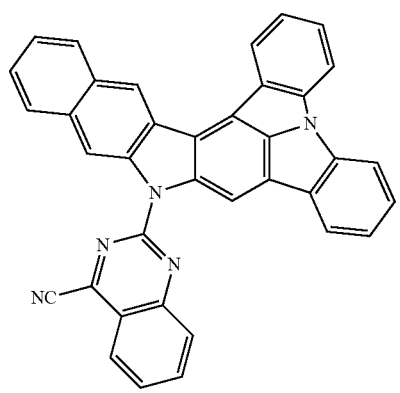
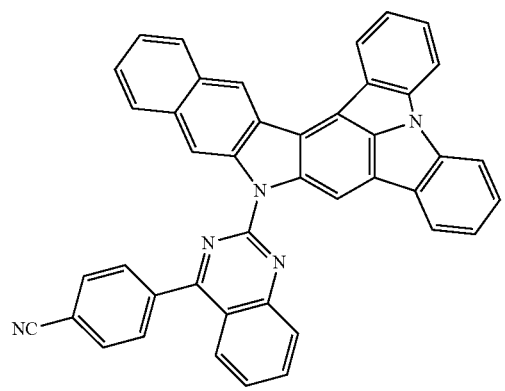
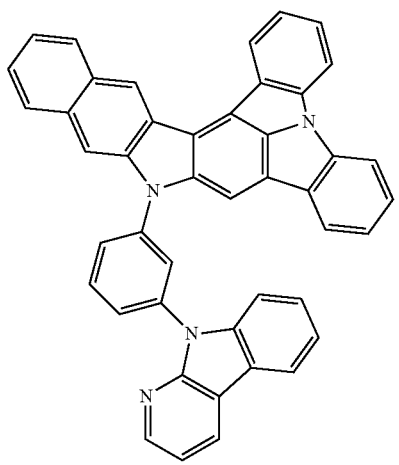 [SMILES: c1cc(-n2c3cc4ccccc4cc3c3c4c5ccccc5n5c6ccccc6c(cc32)c45)cc(-n2c3ccccc3c3cccnc32)c1]
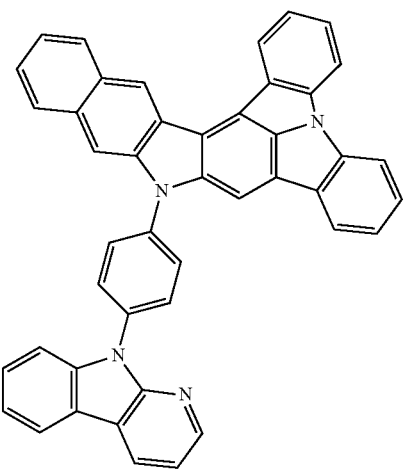
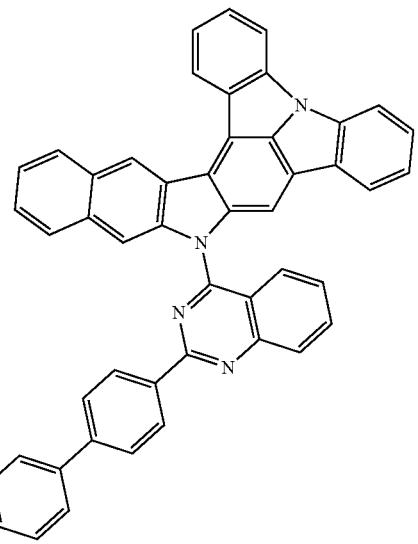

1151
-continued
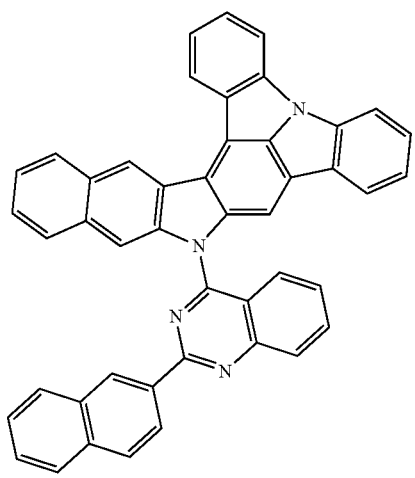
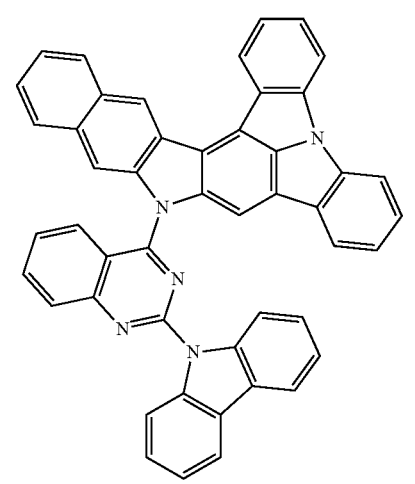
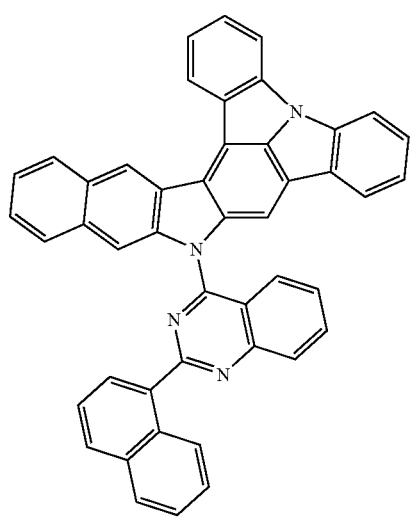
1152
-continued
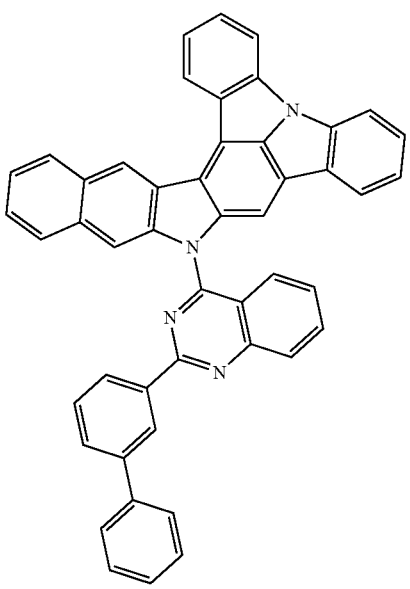
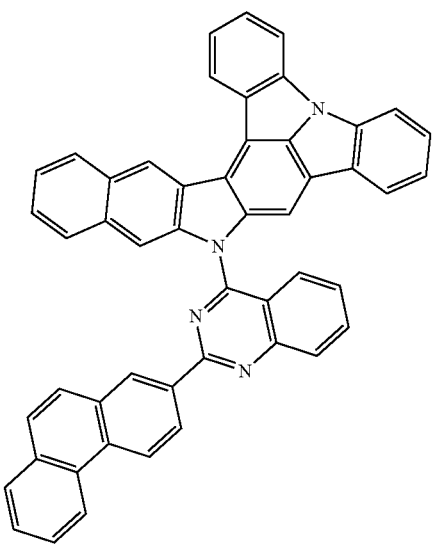
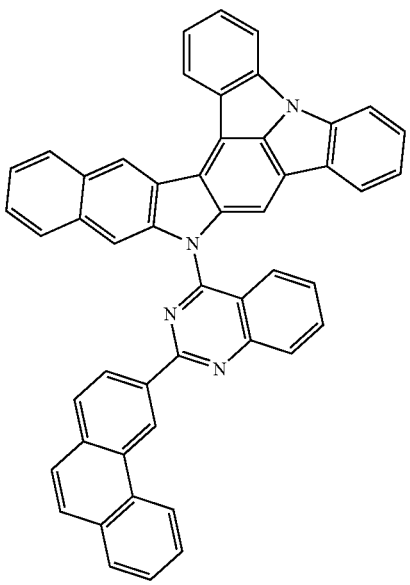

1153
-continued
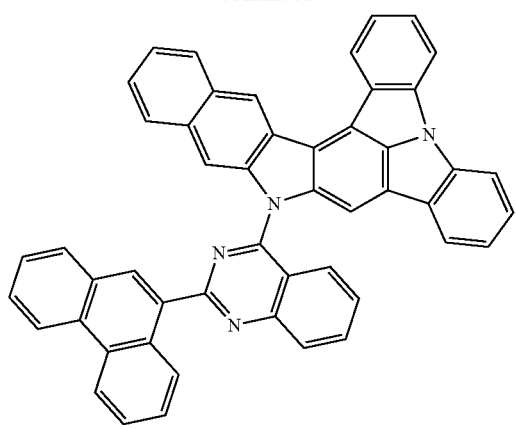
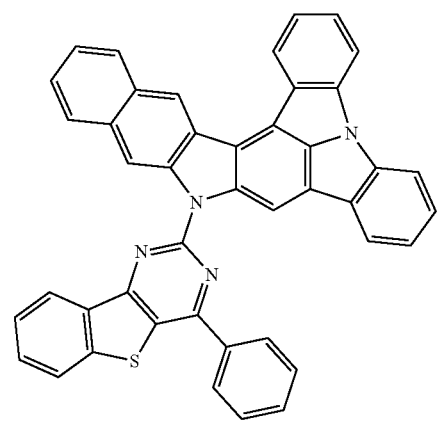
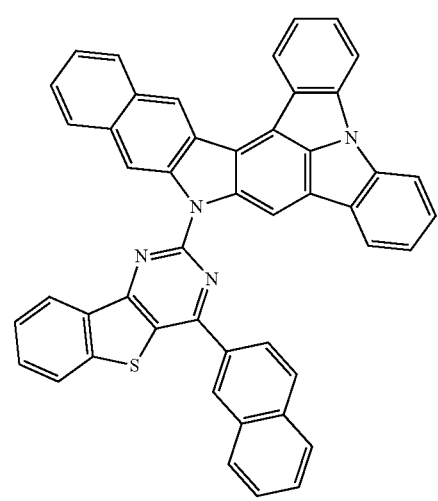
1154
-continued
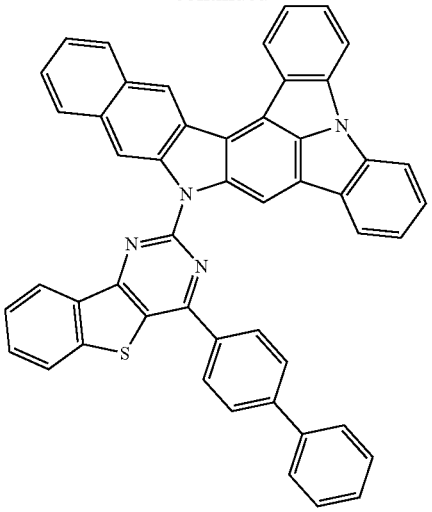
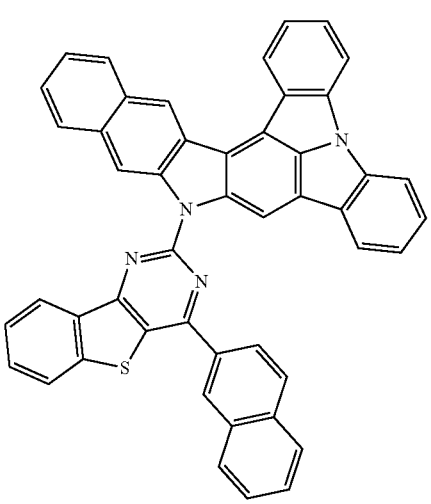 [SMILES: c1ccc2cc(-c3nc(-n4c5cc6ccccc6cc5c5c6c7ccccc7n7c8ccccc8c(cc54)c67)nc4c3sc3ccccc34)ccc2c1]
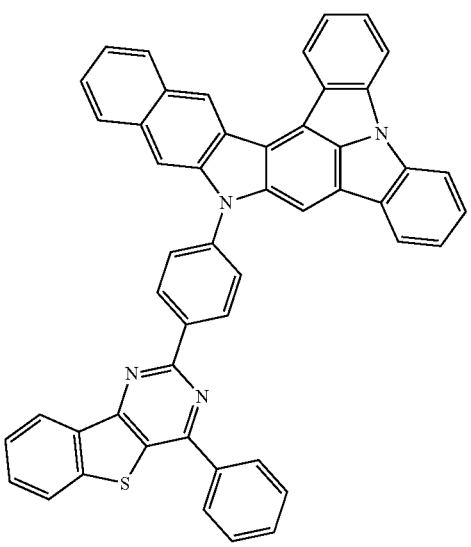

1155
-continued
1156
-continued
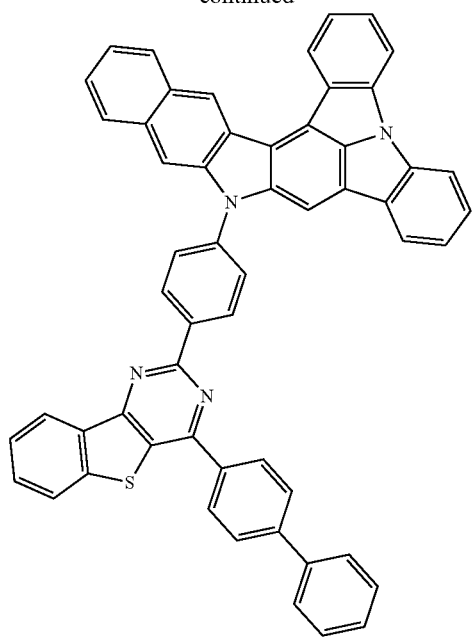
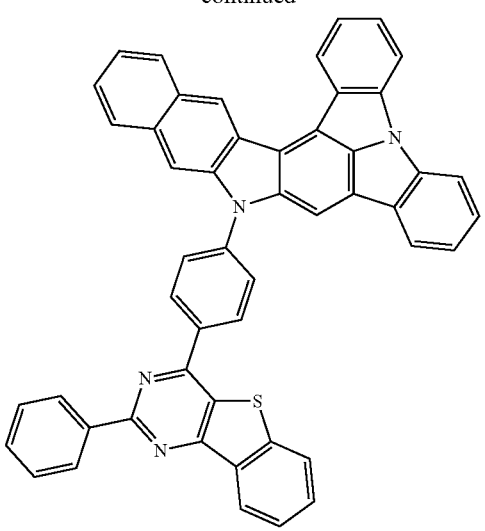
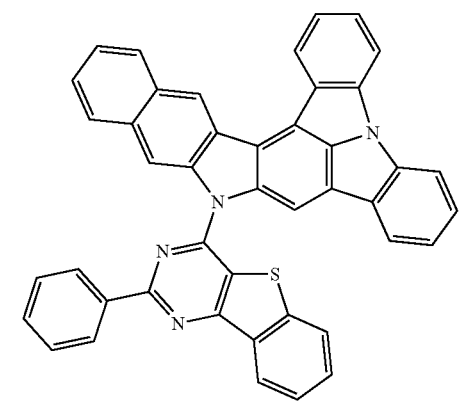
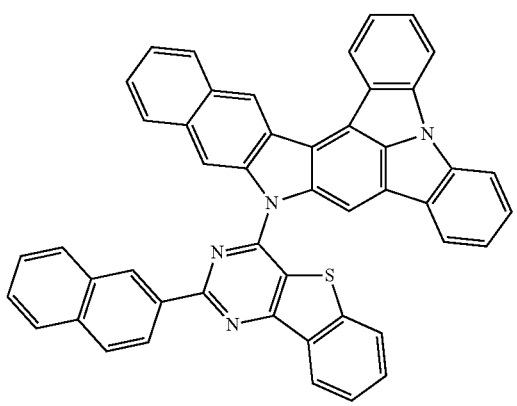
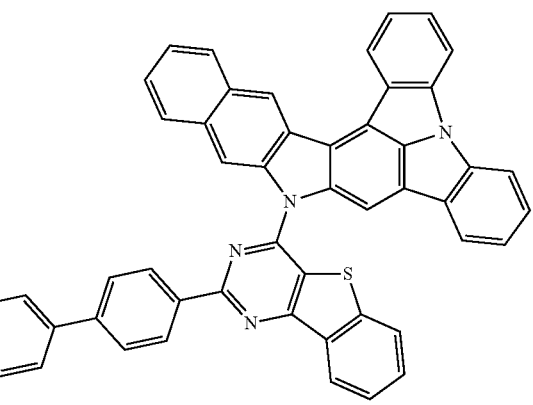
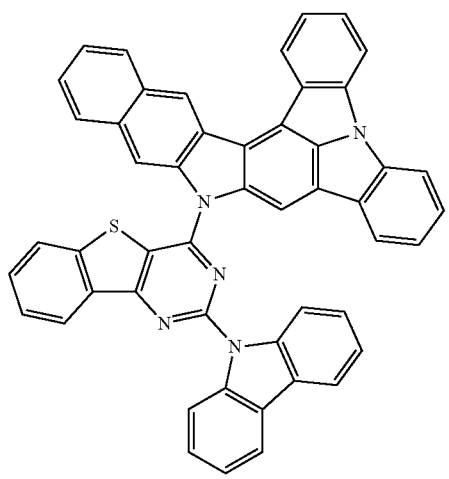

1157
-continued
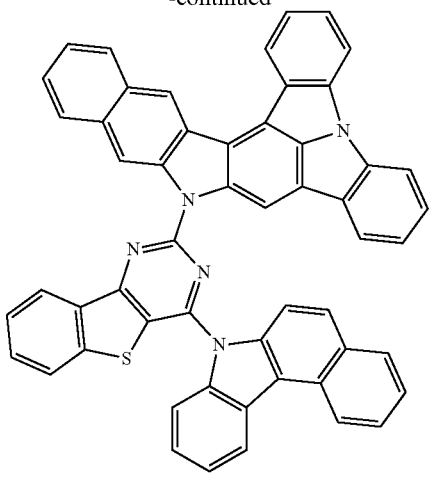
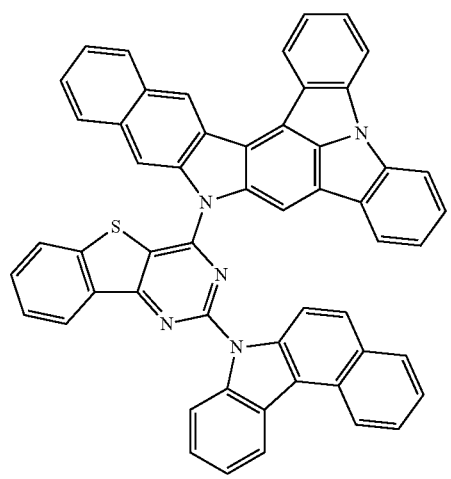
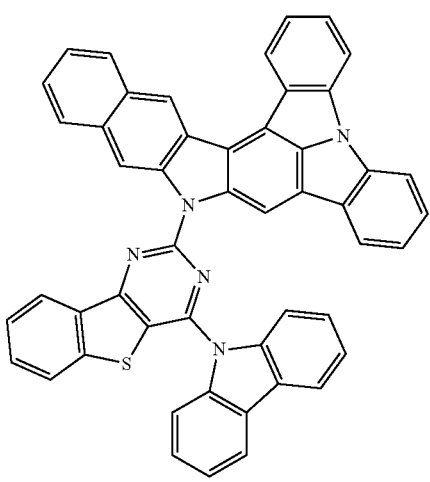
1158
-continued
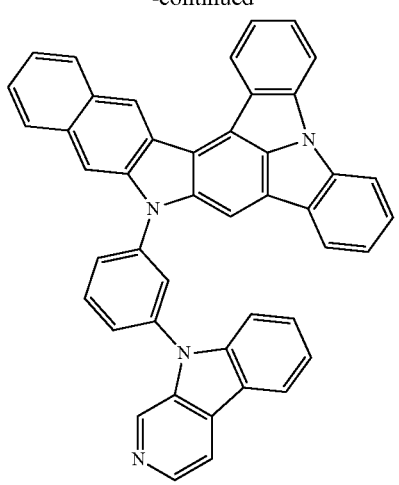
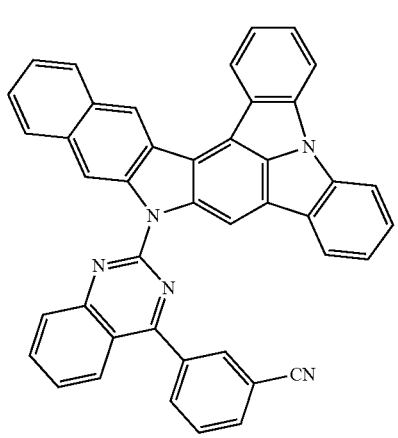
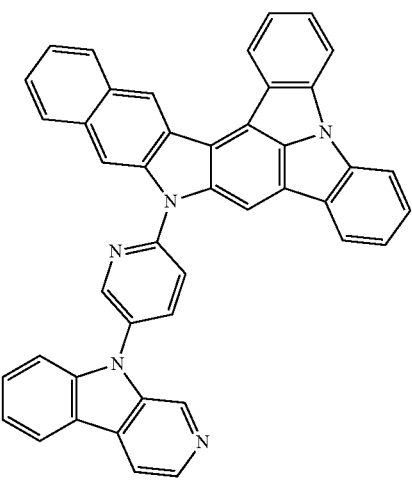

1159
-continued
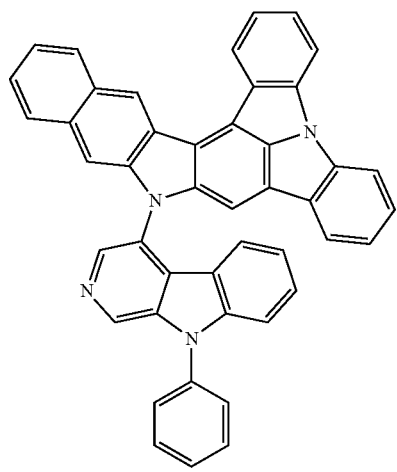
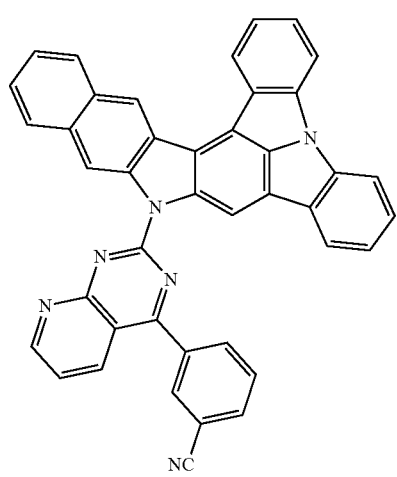
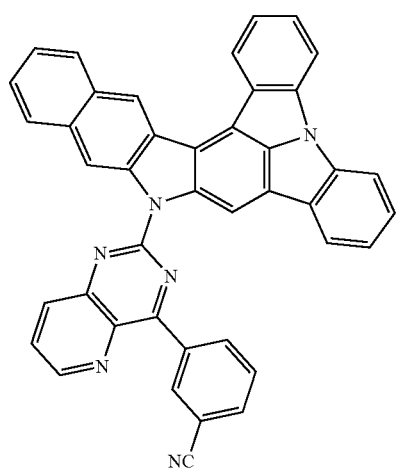
1160
-continued
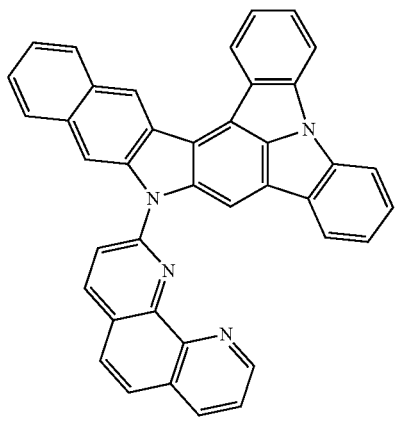
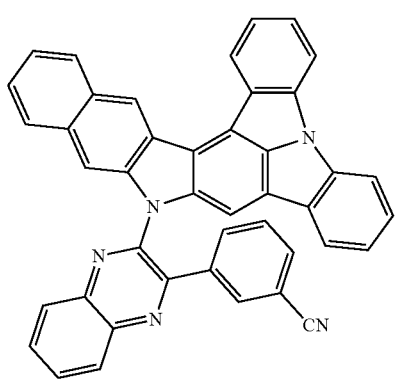
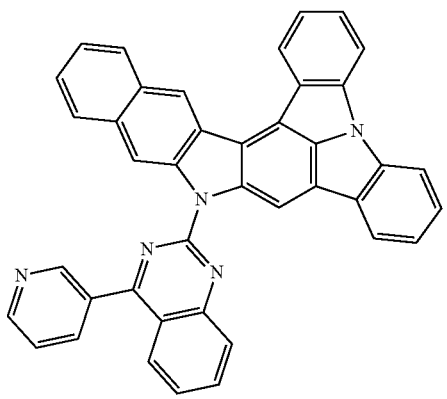
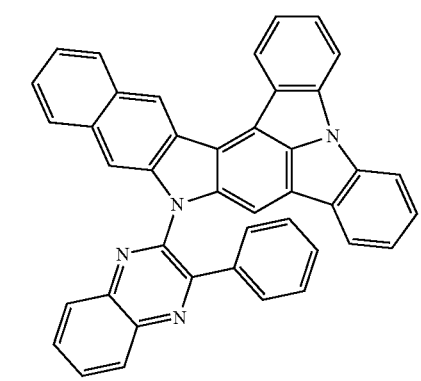

1161
-continued
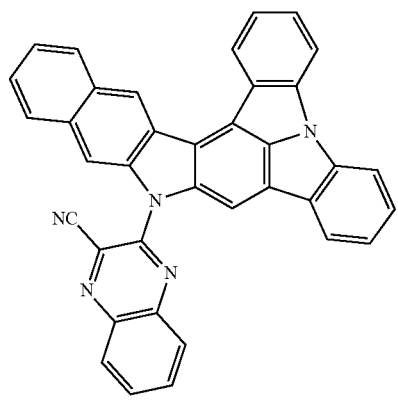
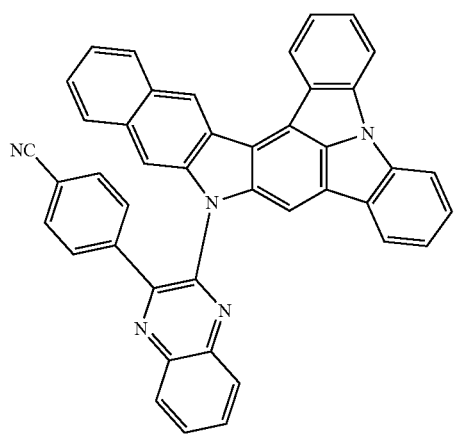
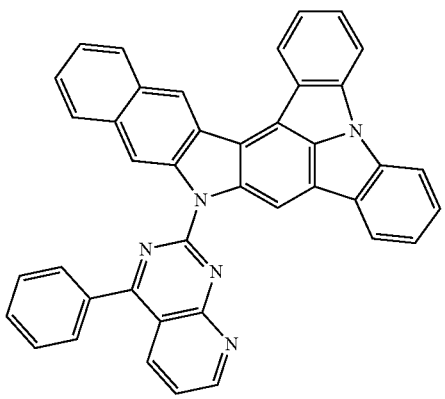
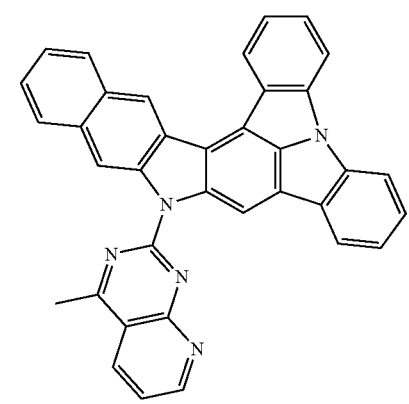
1162
-continued
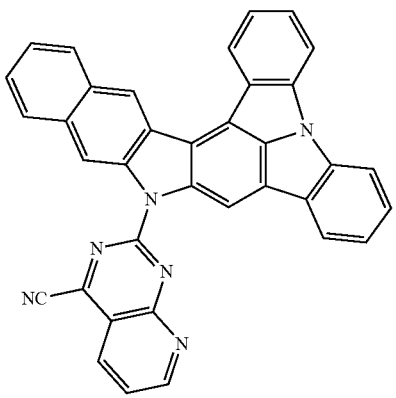
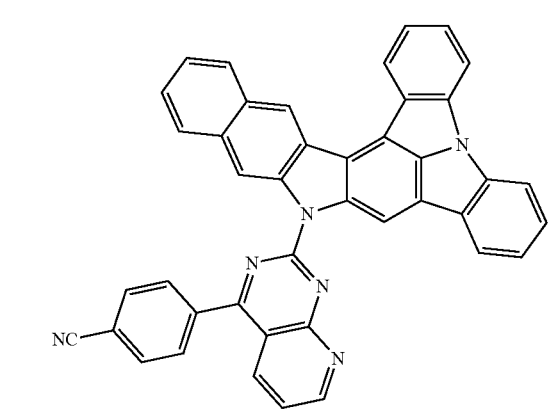
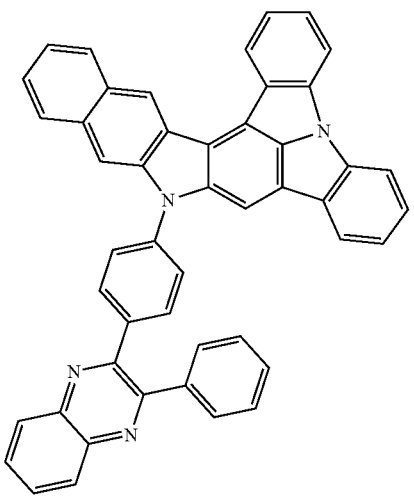

1163
-continued
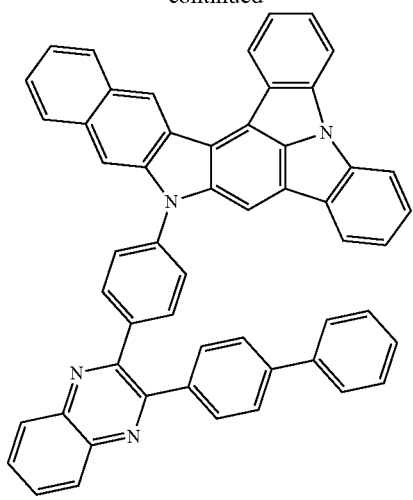
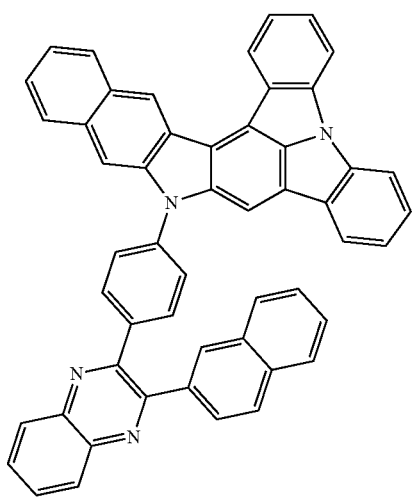
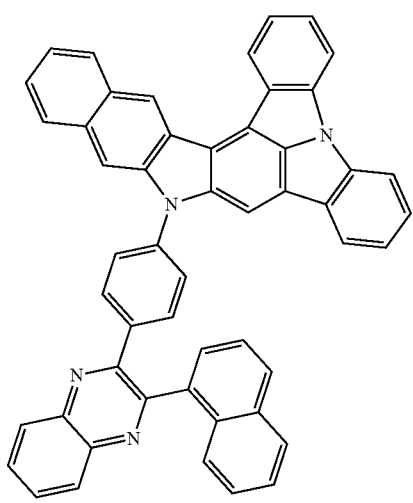
1164
-continued
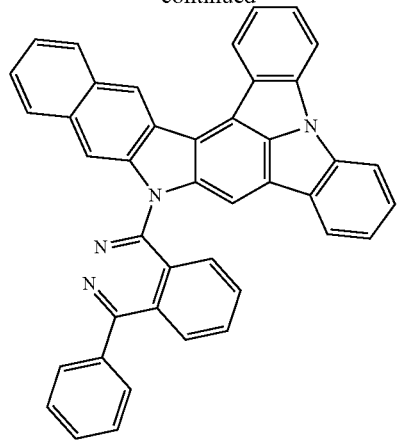
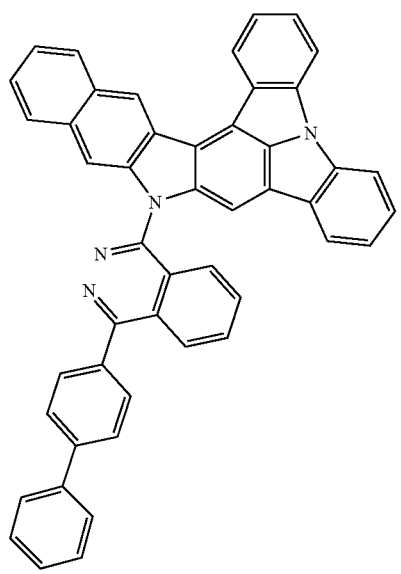
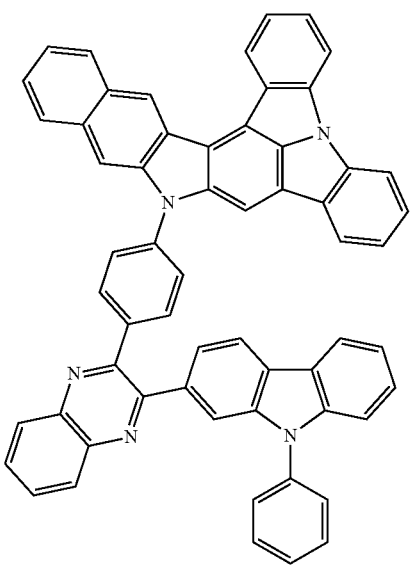

1165
-continued
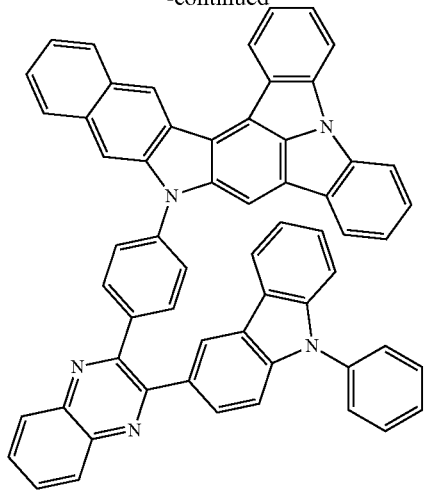
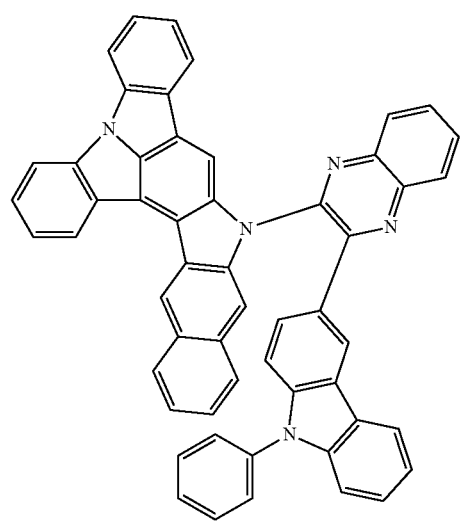
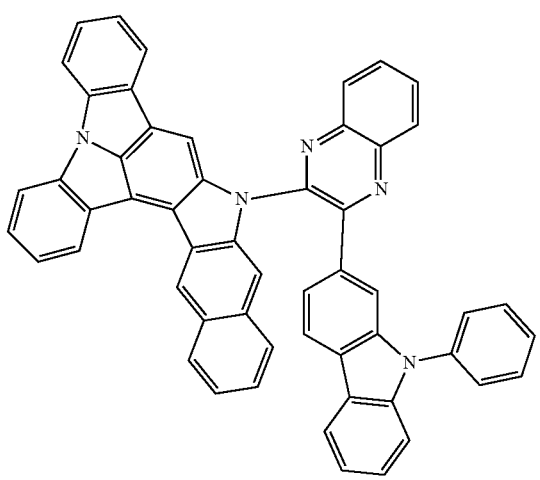
1166
-continued
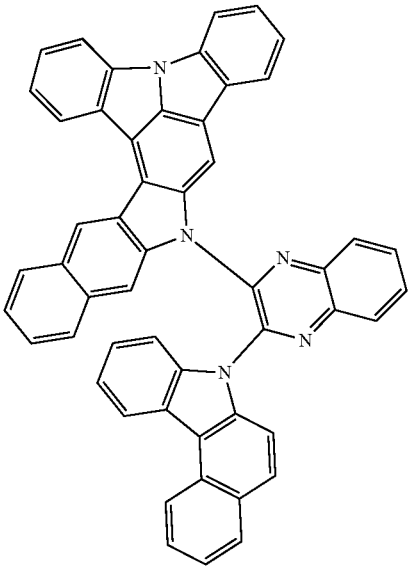
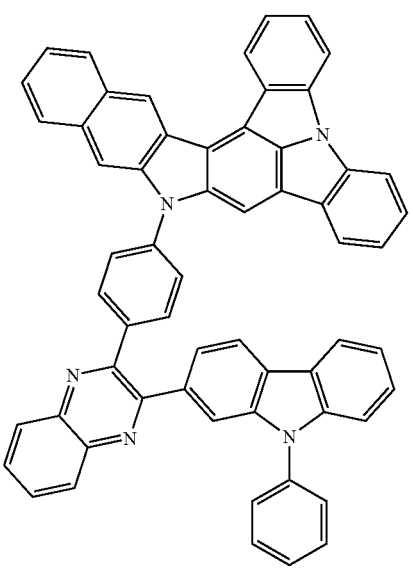
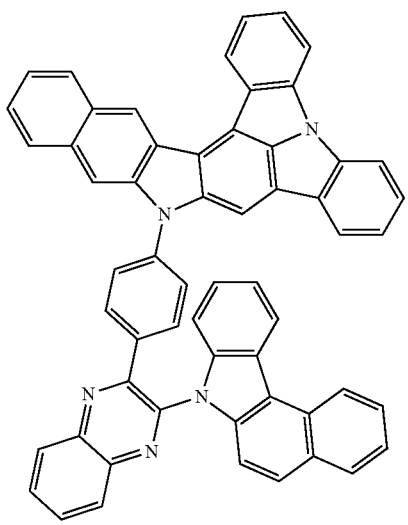

1167
-continued
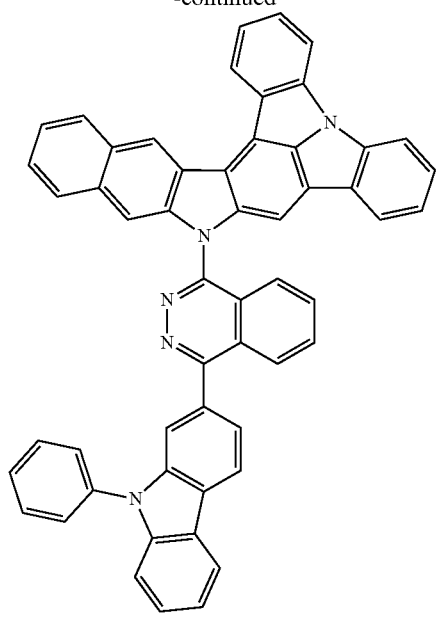
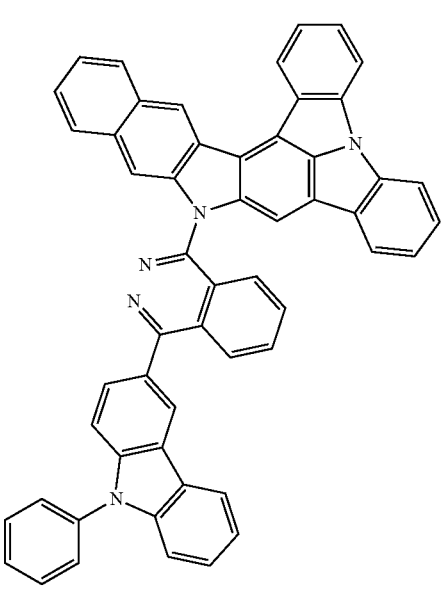
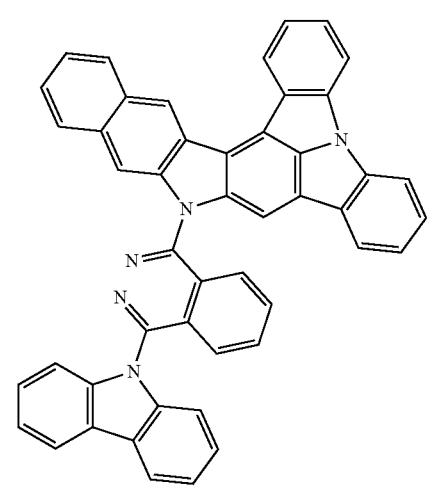
1168
-continued
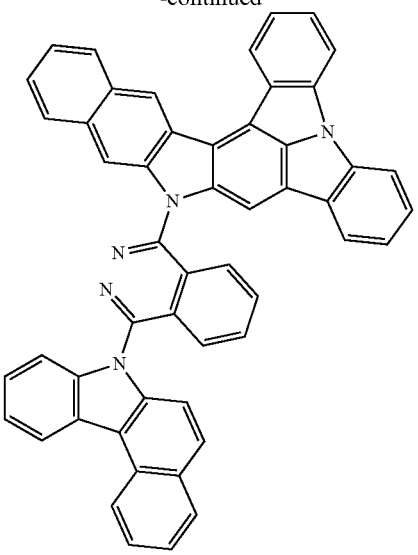
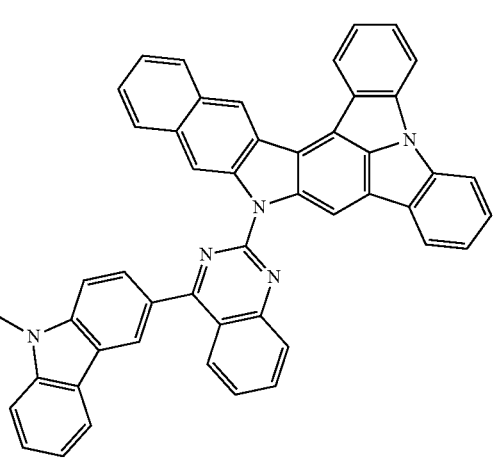
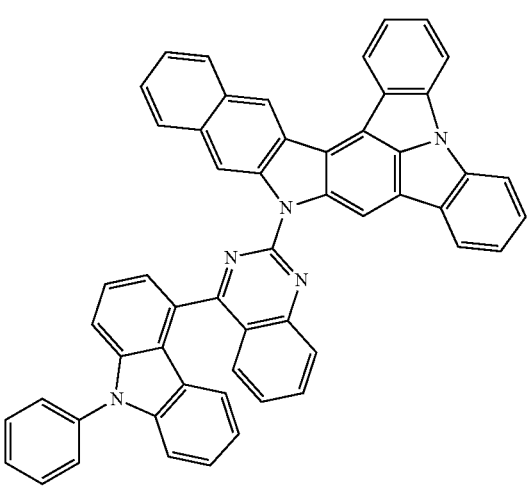

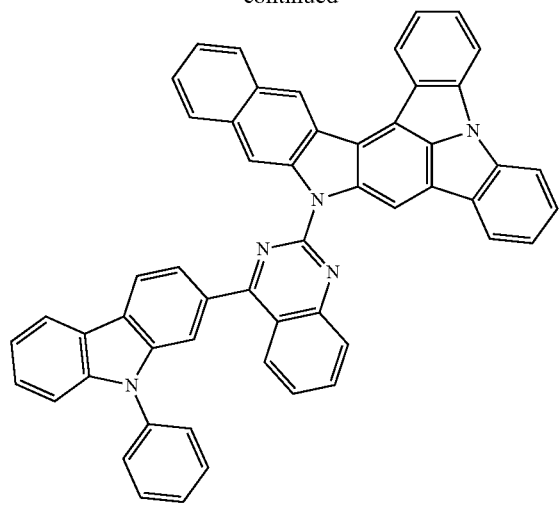
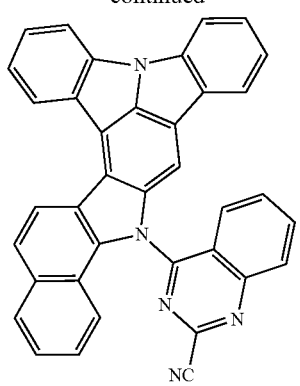
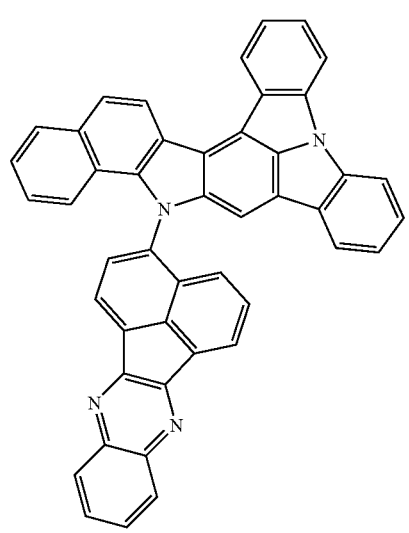
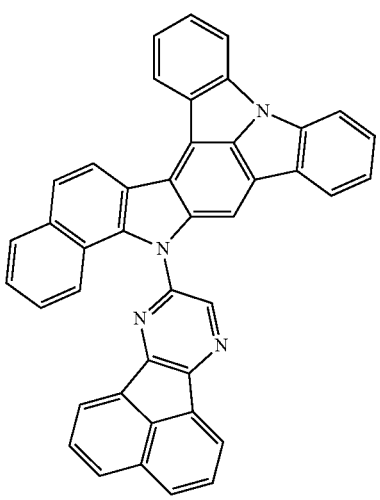
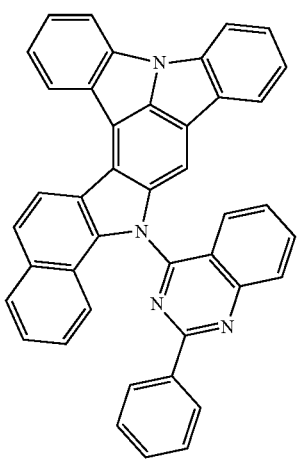

1171
-continued
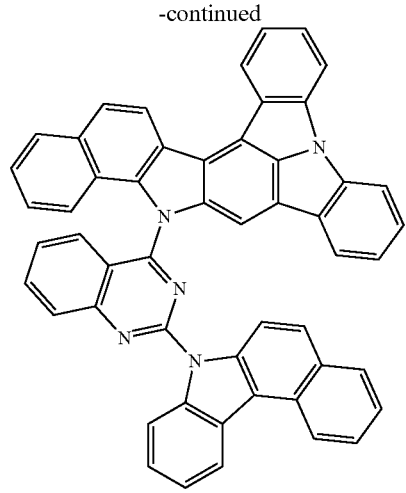
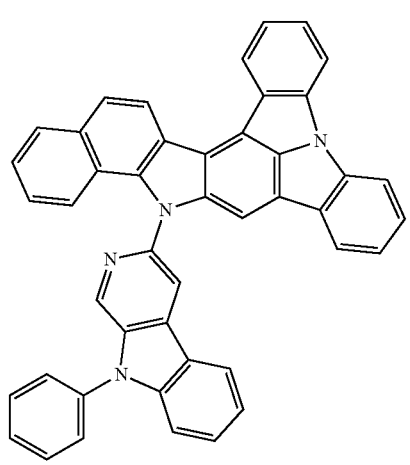
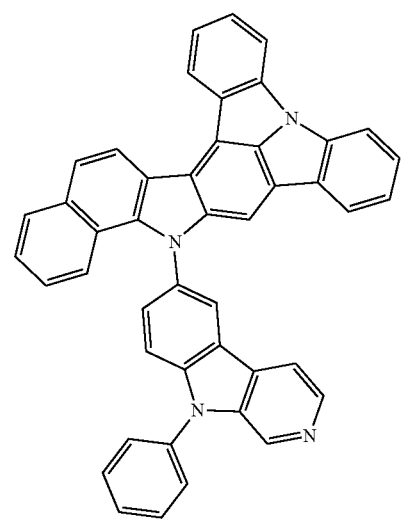
1172
-continued
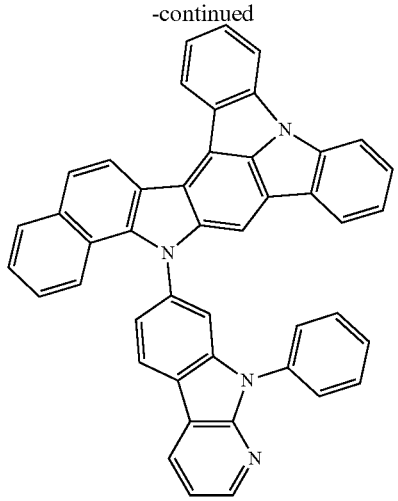
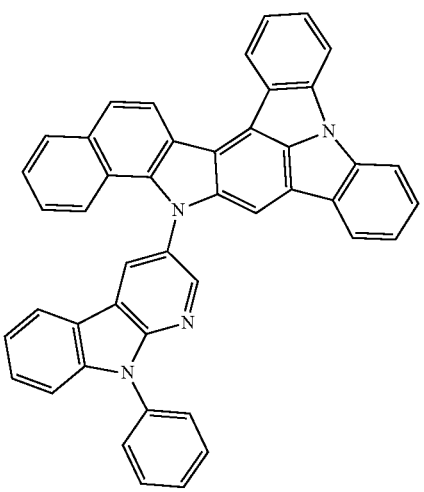
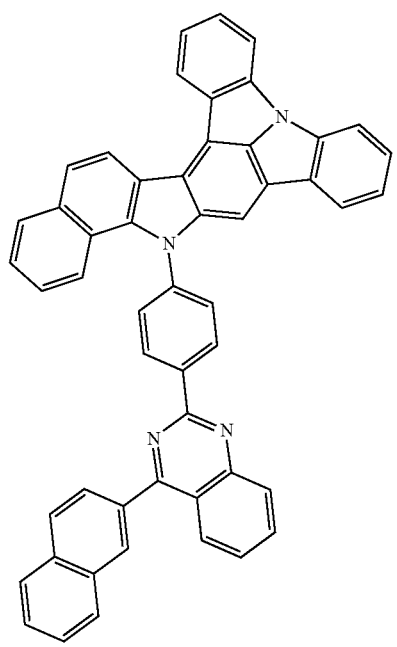

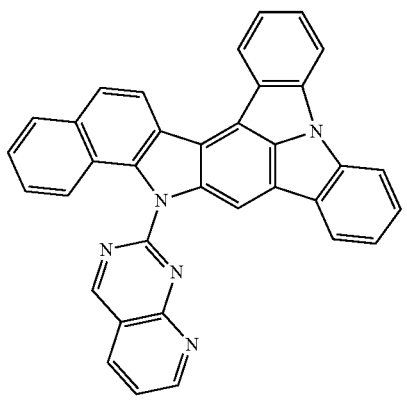
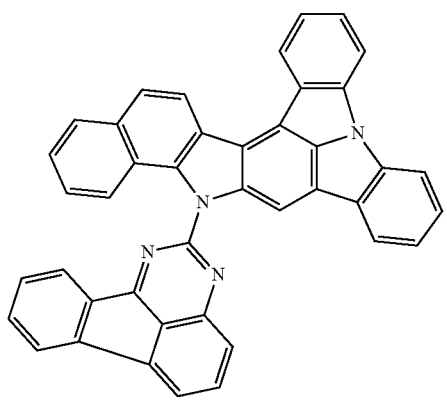
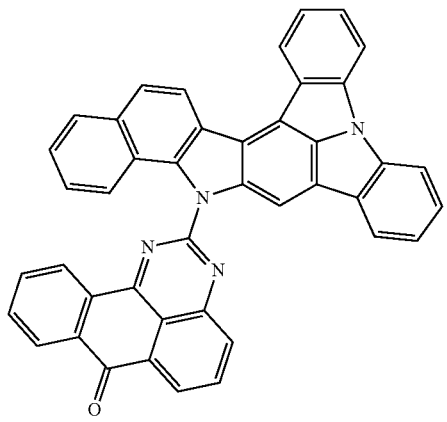
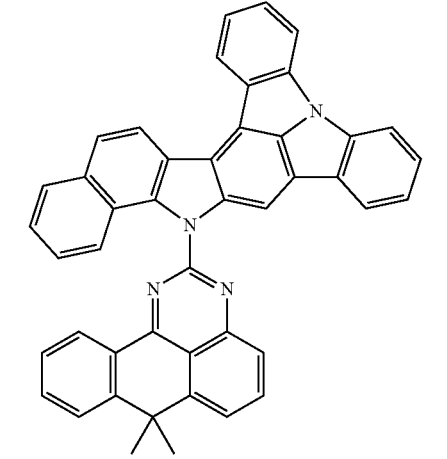
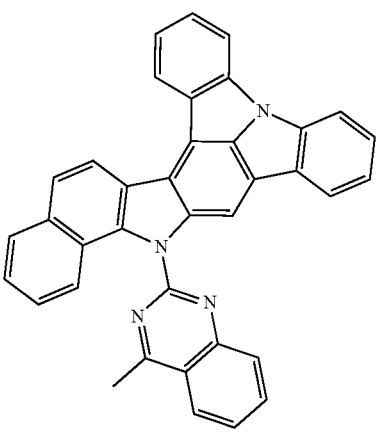
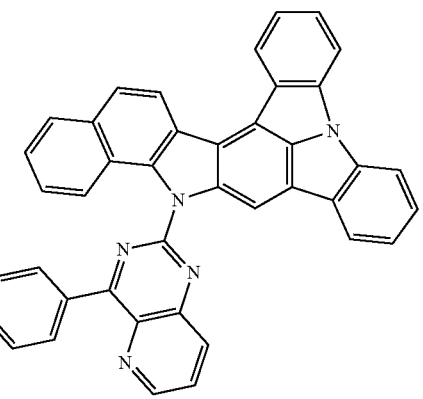
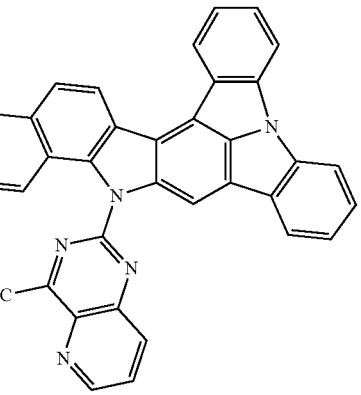
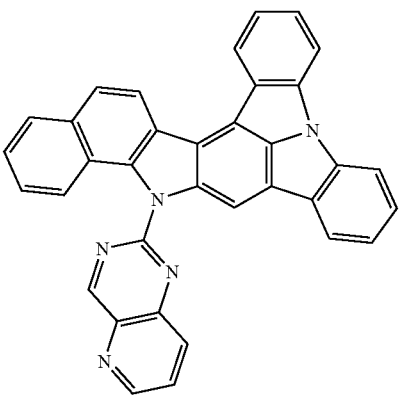

1175
-continued
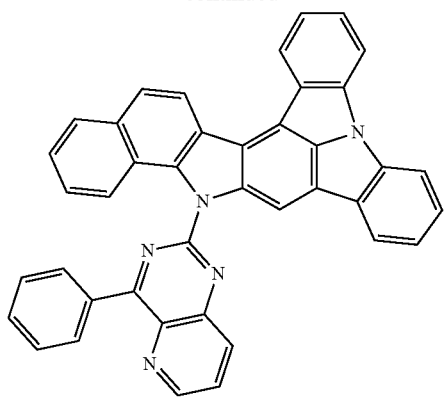
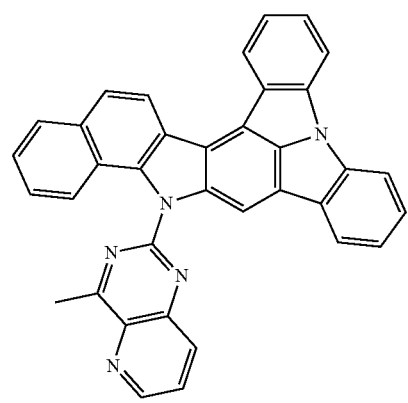
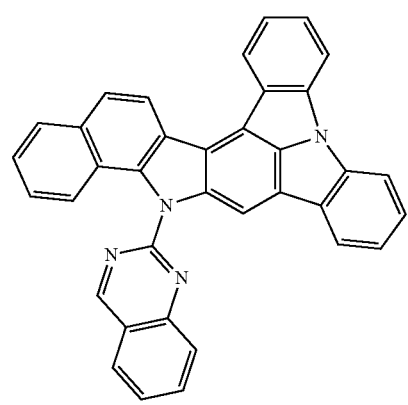
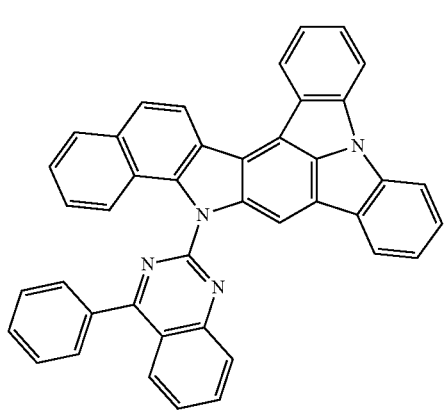
1176
-continued
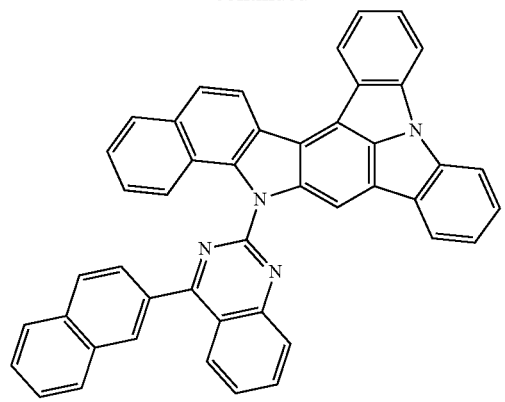
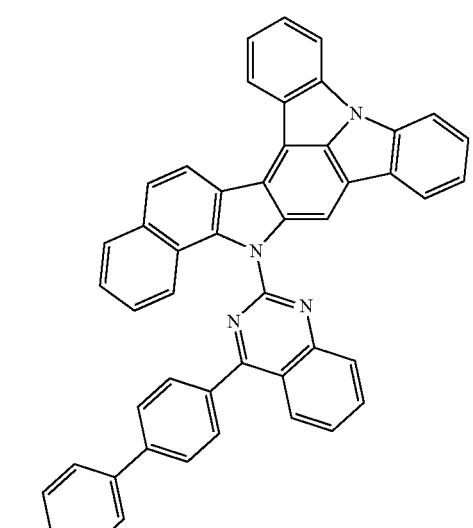
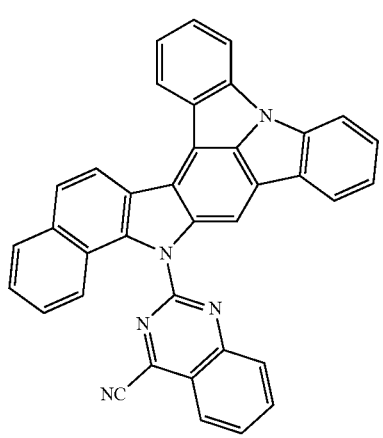

1177
-continued
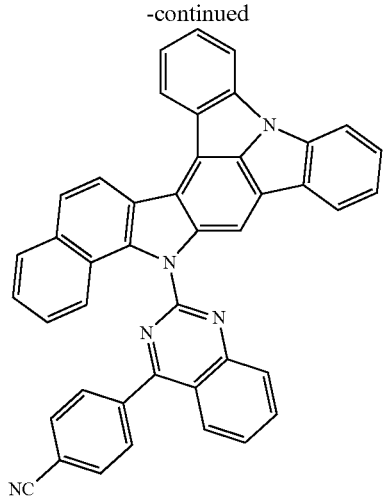
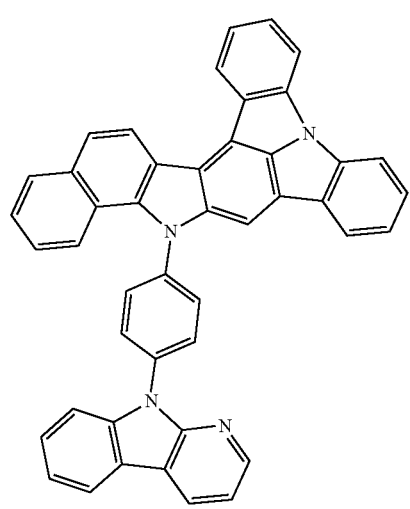
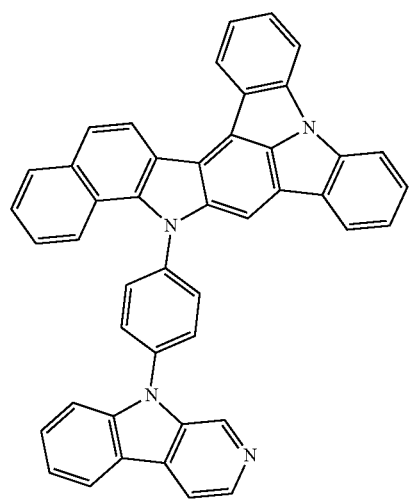
1178
-continued
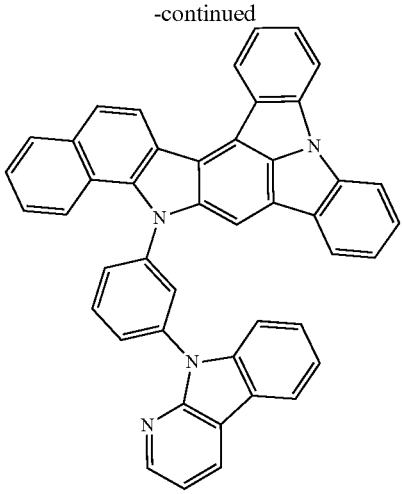
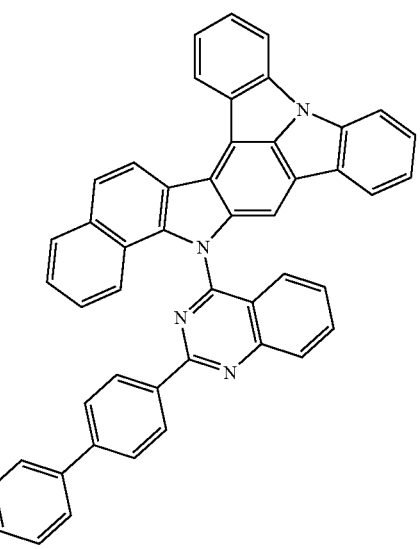
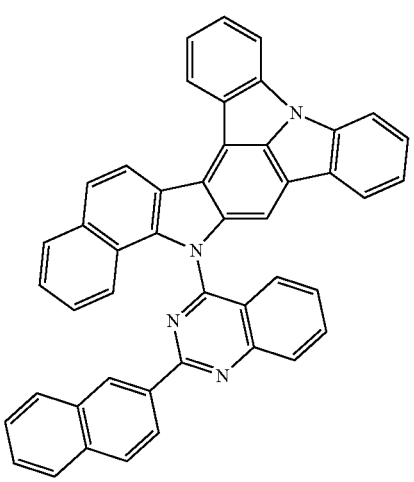

1179
-continued
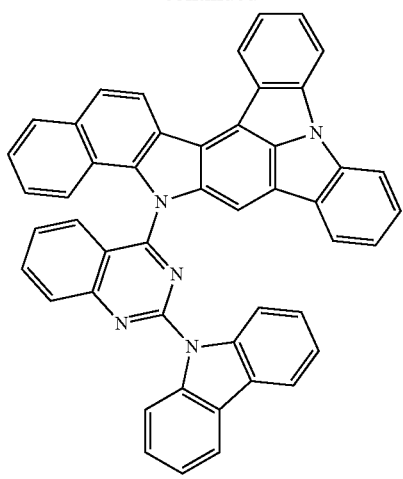
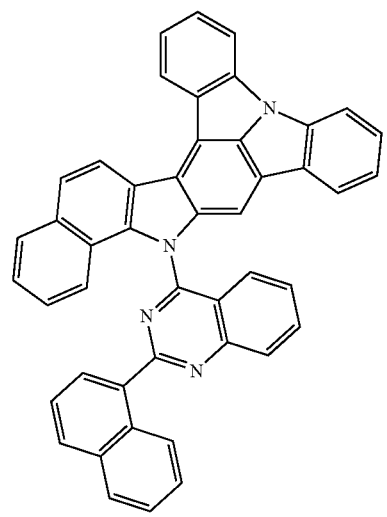
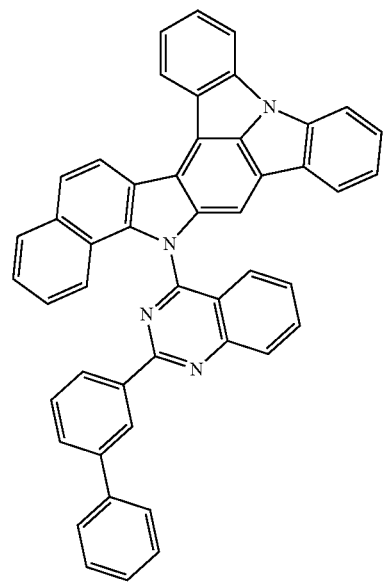
1180
-continued
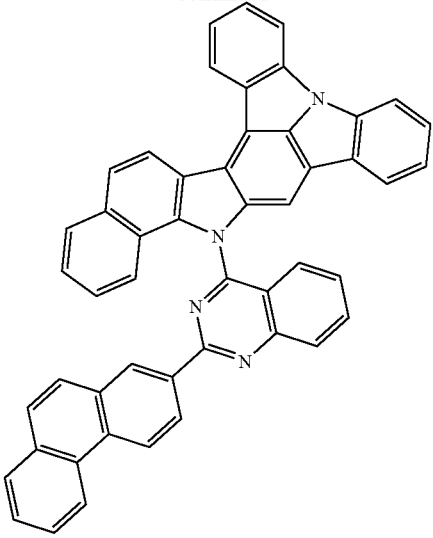
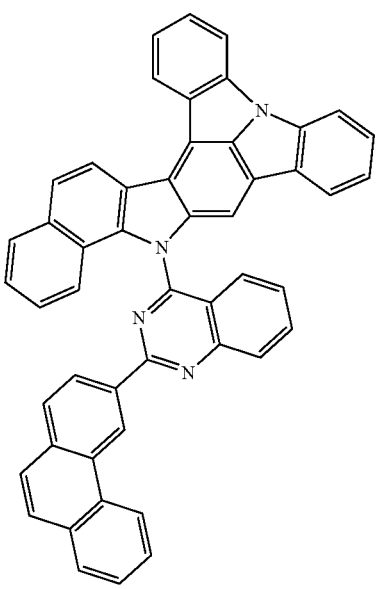
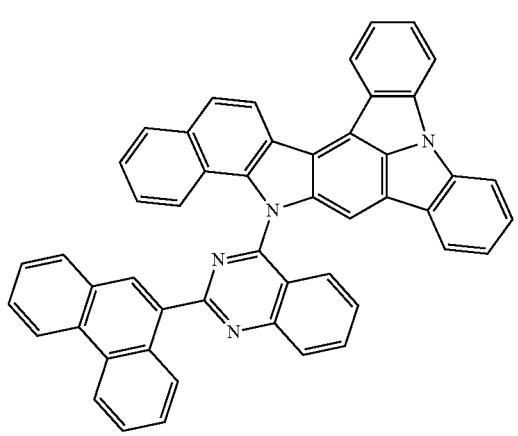

1181
-continued
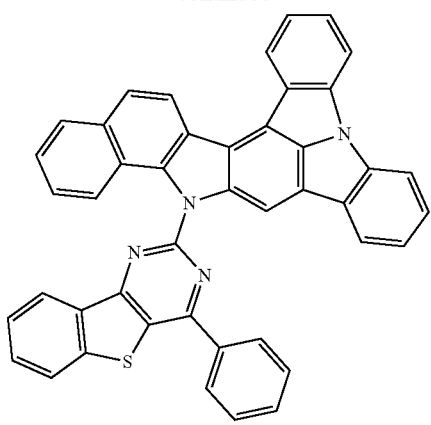
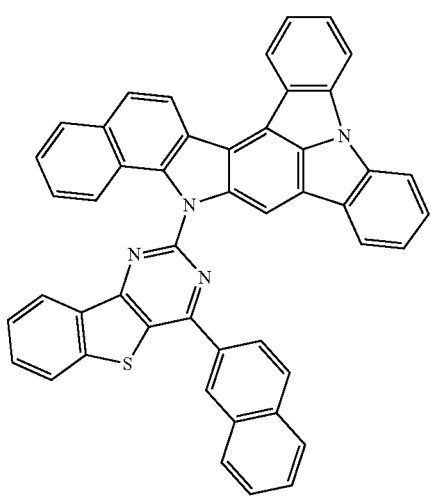
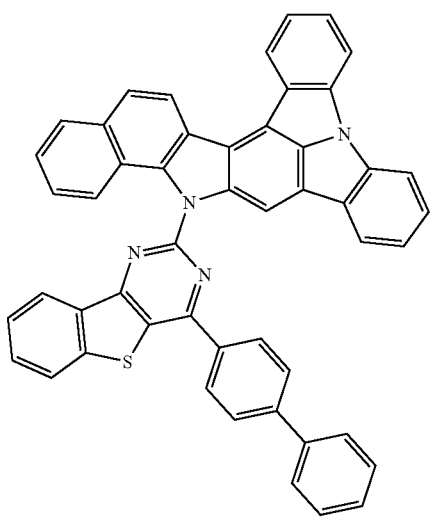
1182
-continued
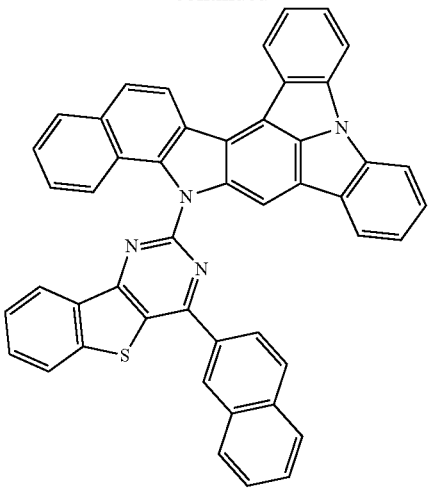
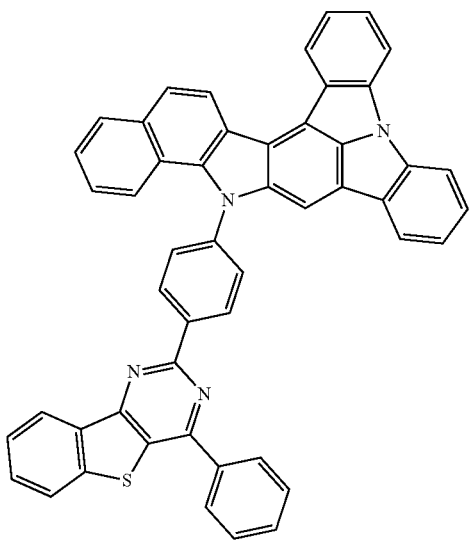
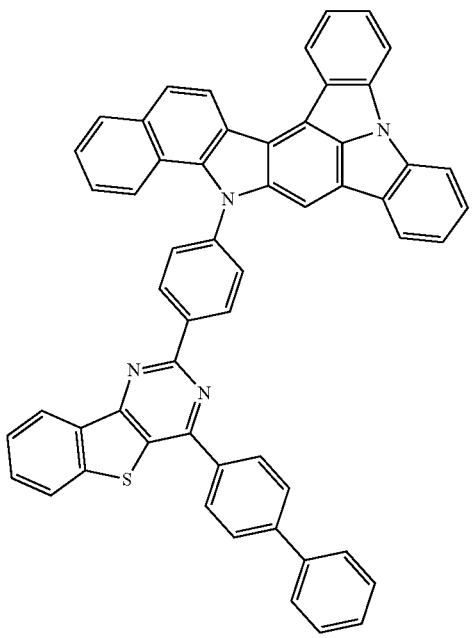

1183
-continued
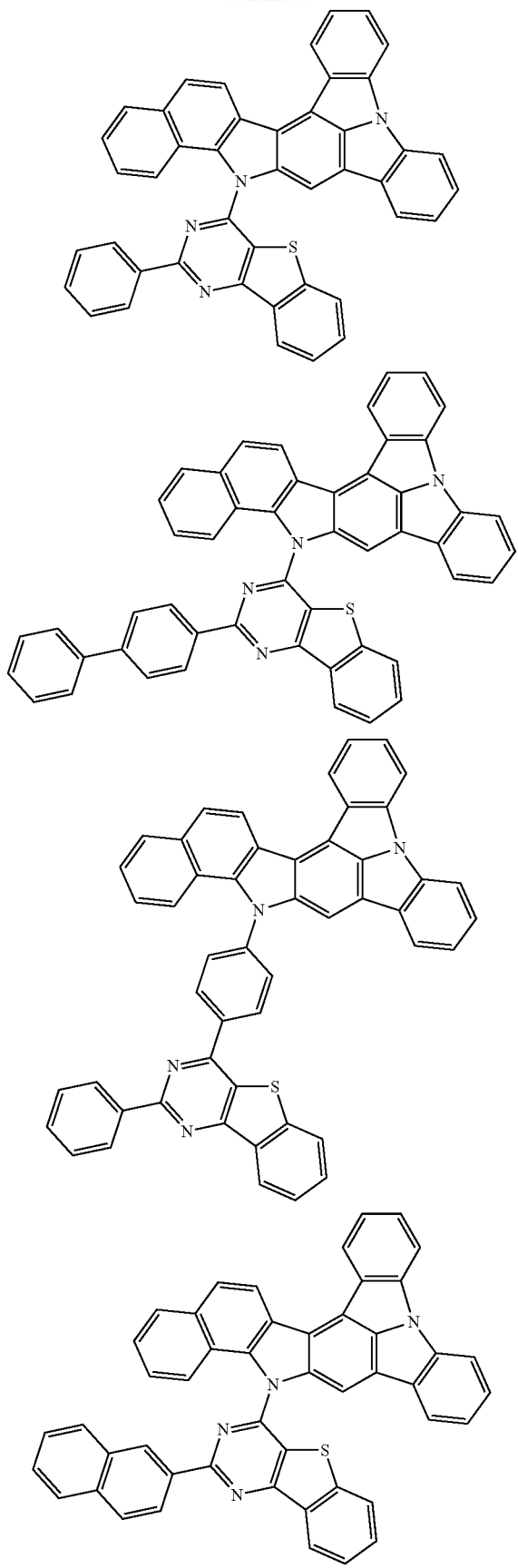
1184
-continued
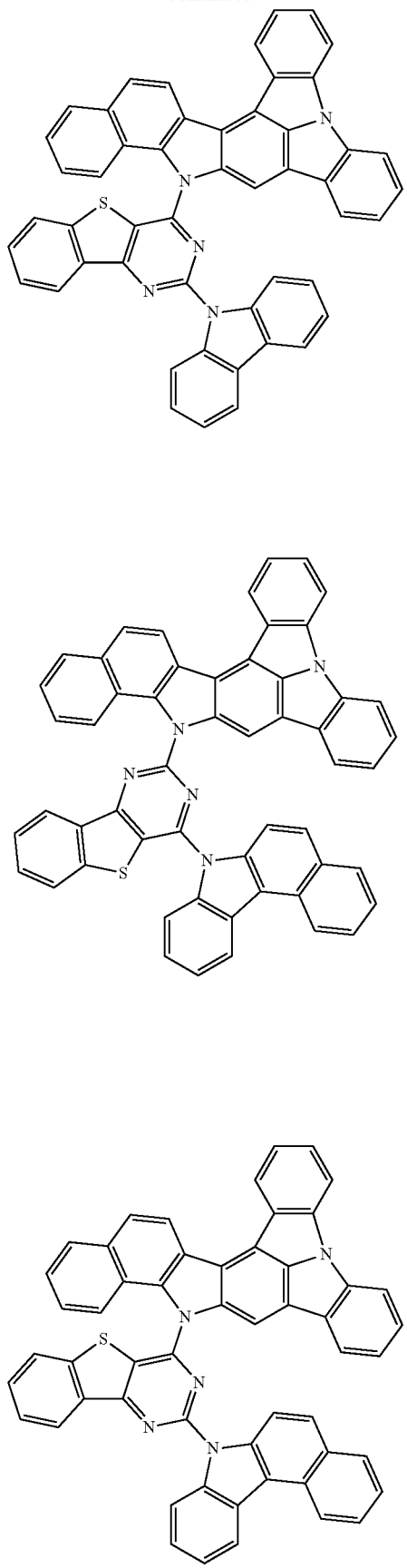

1185
-continued
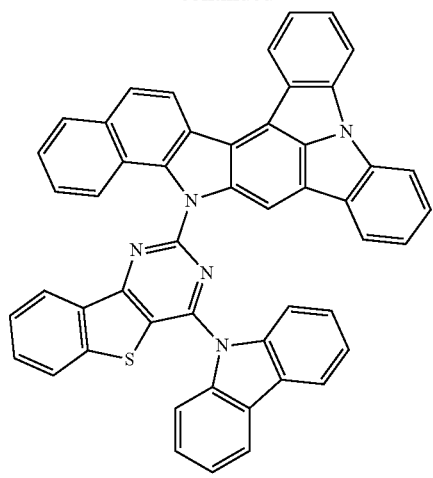
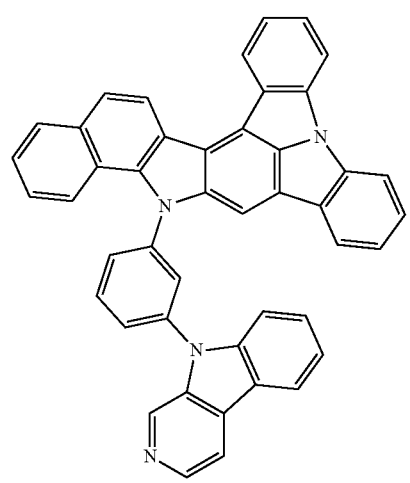
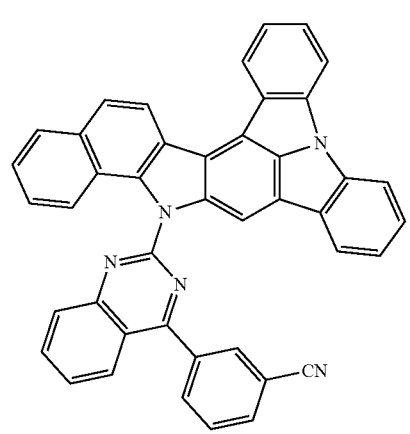
1186
-continued
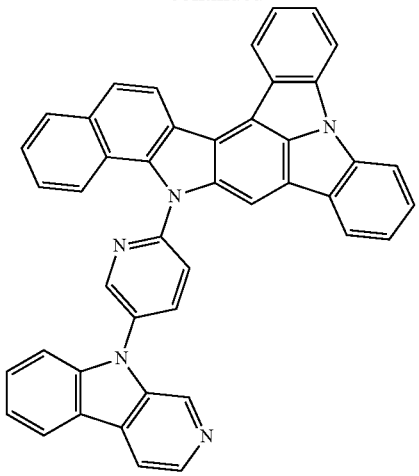
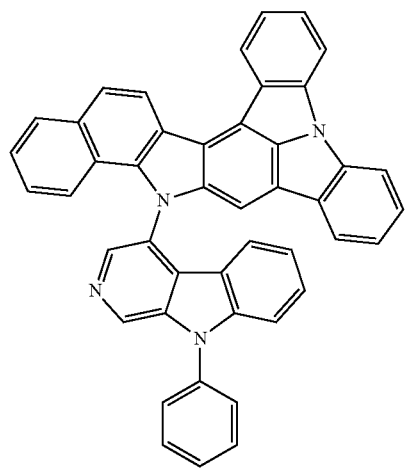
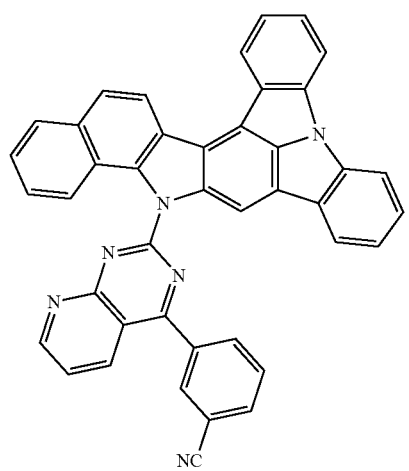

1187
-continued
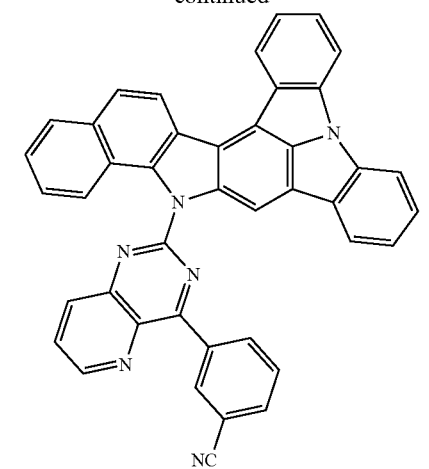
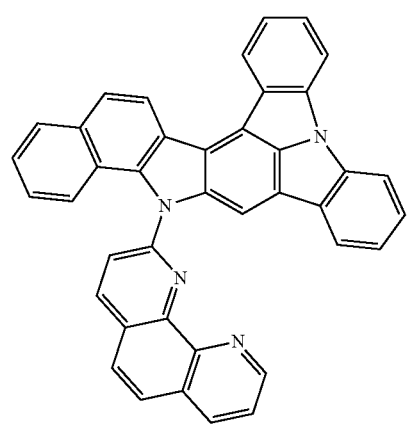
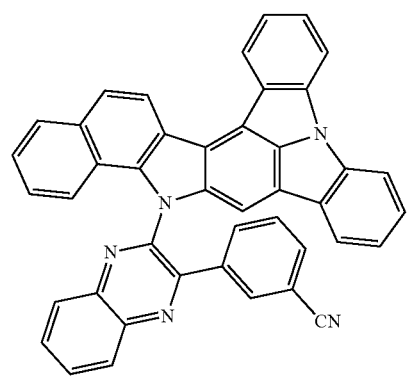
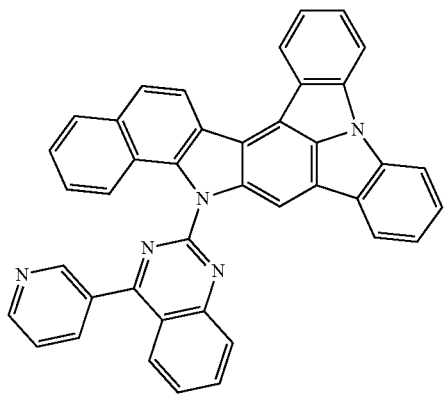
1188
-continued
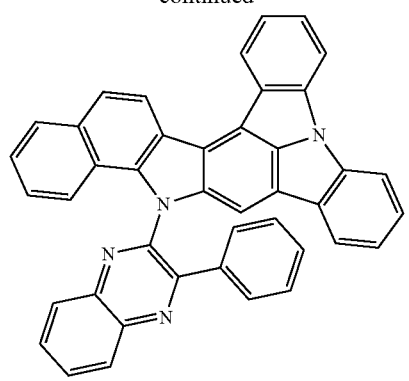
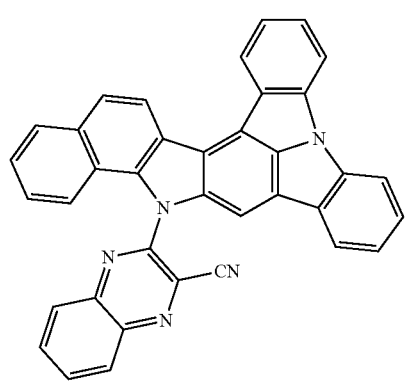
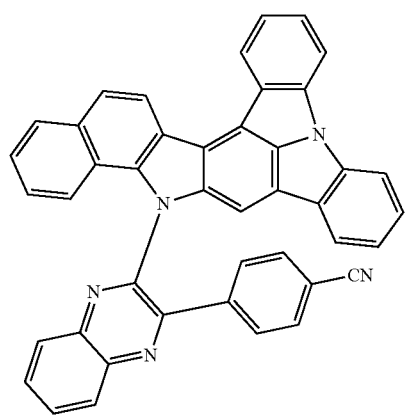
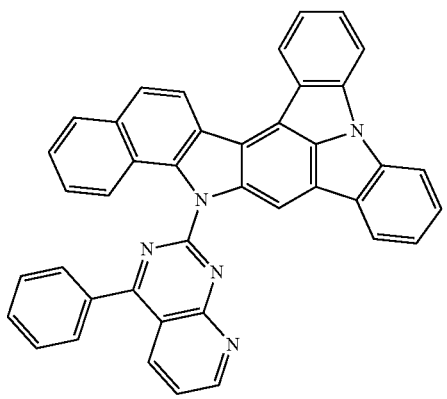

1189
-continued
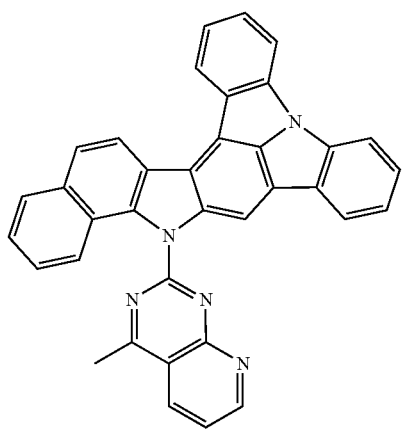
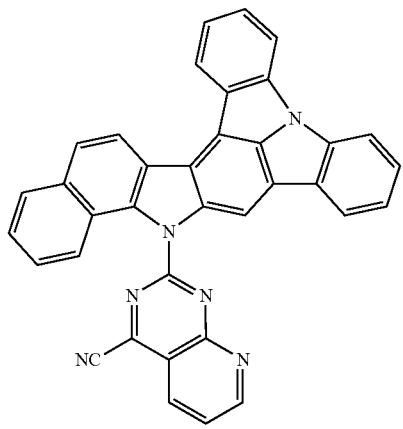
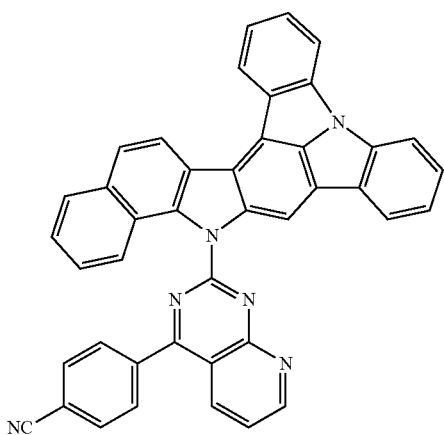
1190
-continued
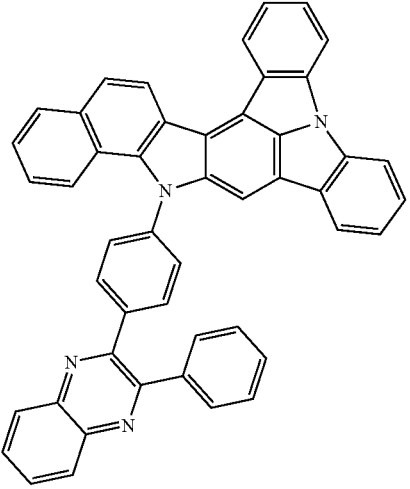
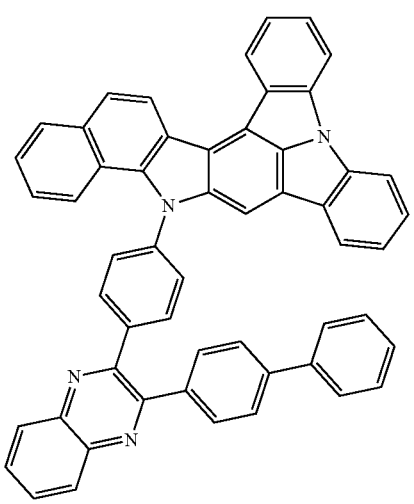
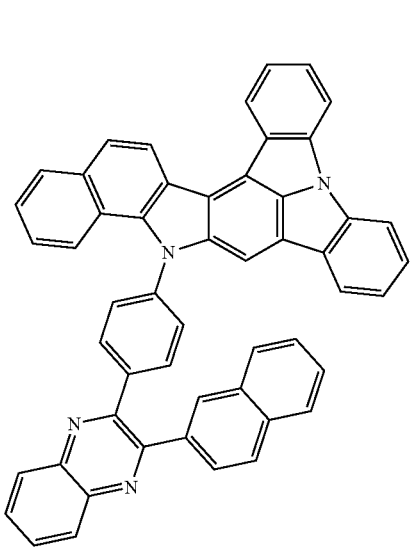

1191
-continued
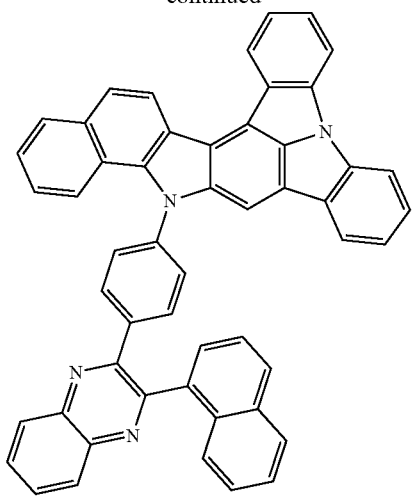
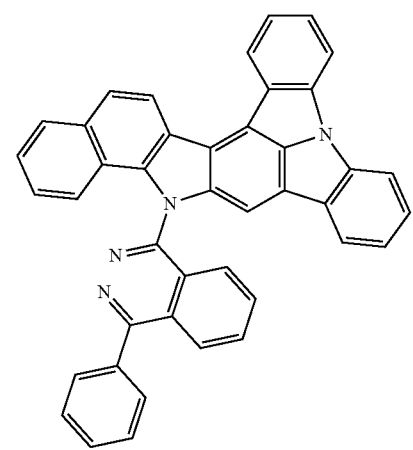
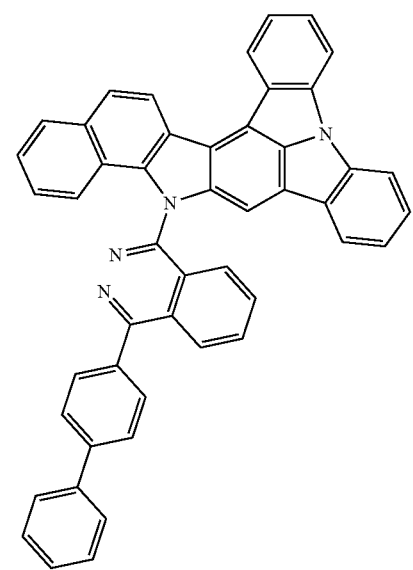
1192
-continued
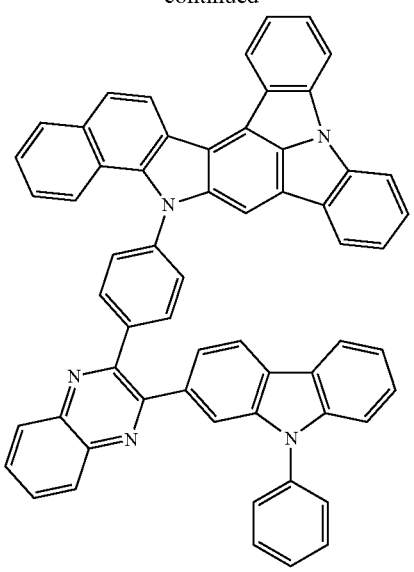
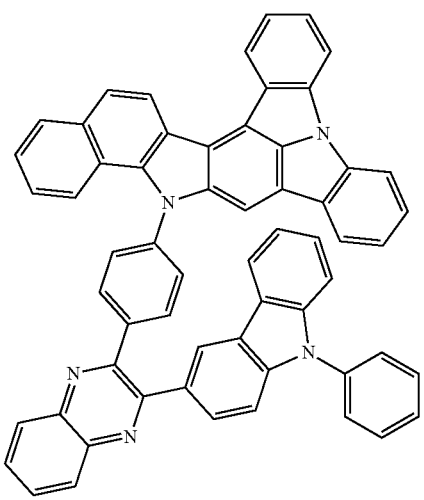
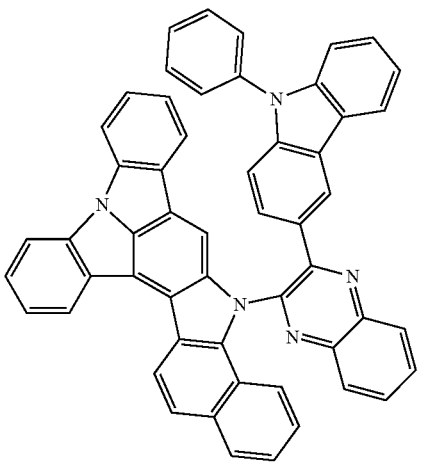

1193
-continued
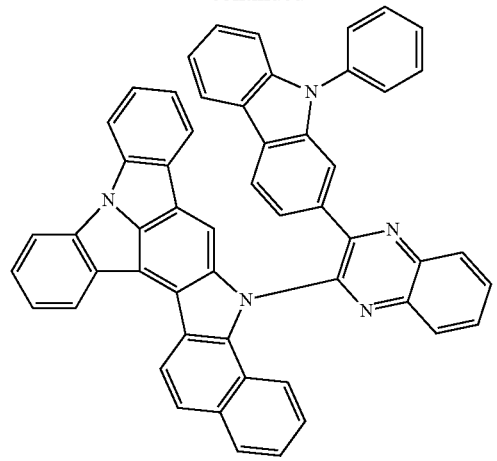
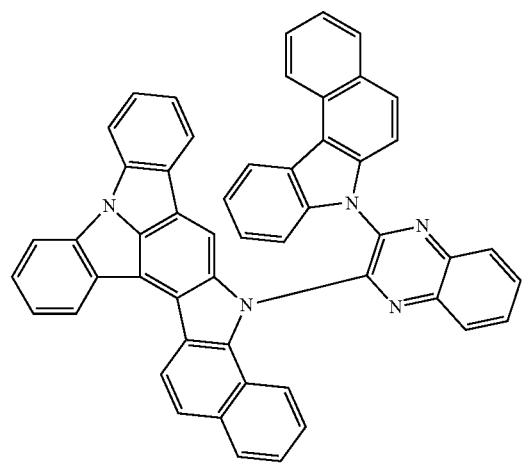
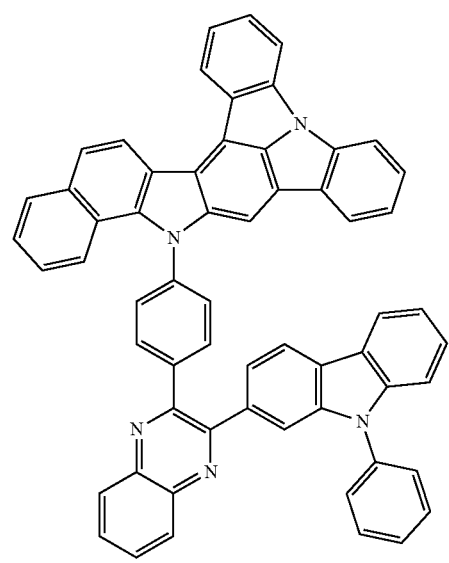
1194
-continued
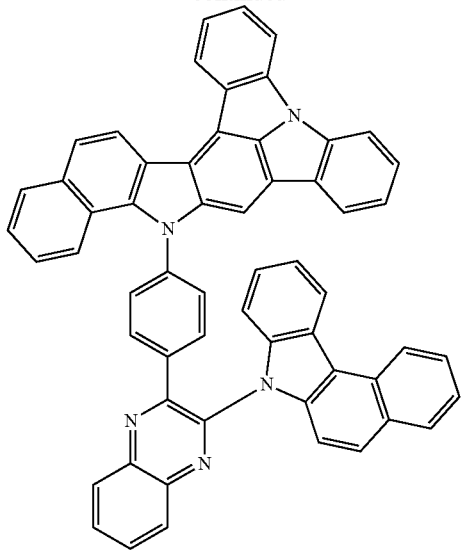
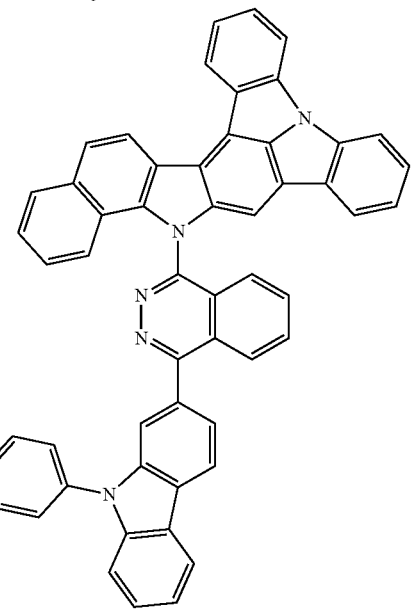
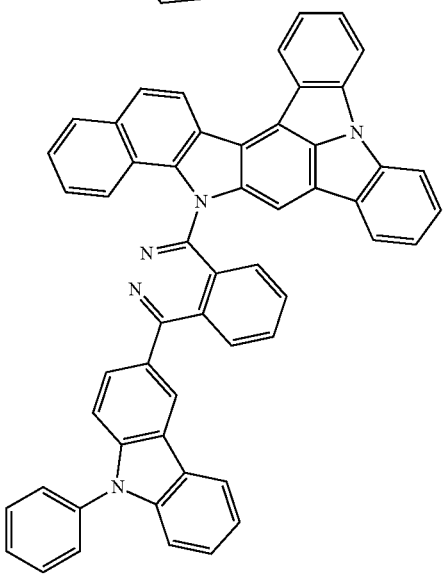

1195
-continued
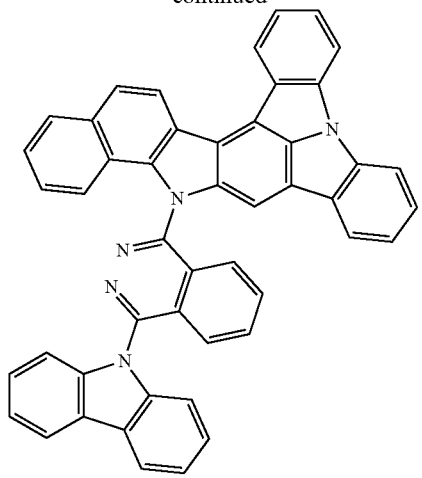
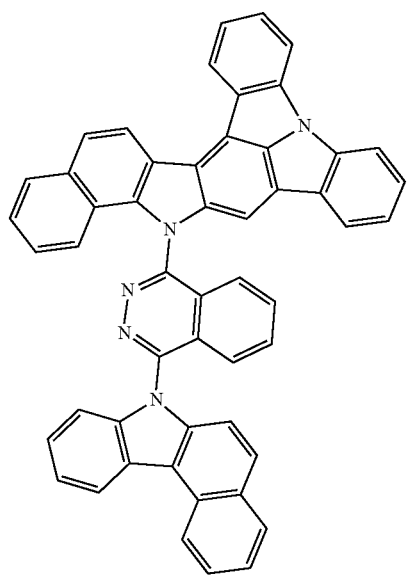
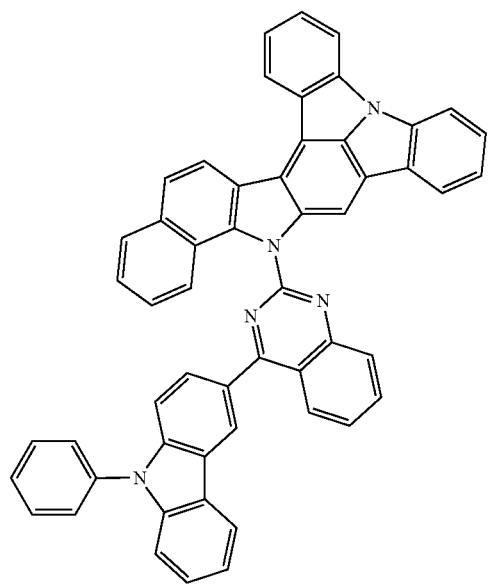
1196
-continued
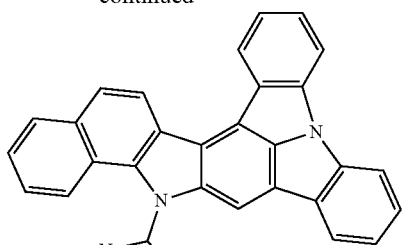
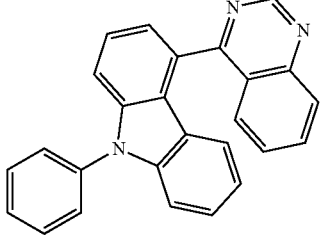
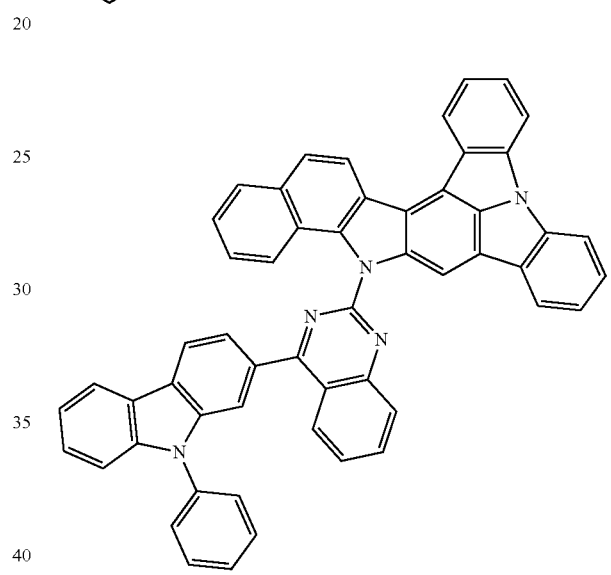
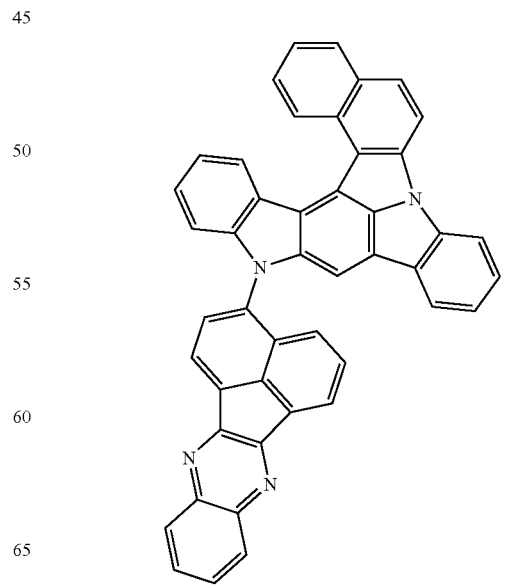

1197
-continued
1198
-continued
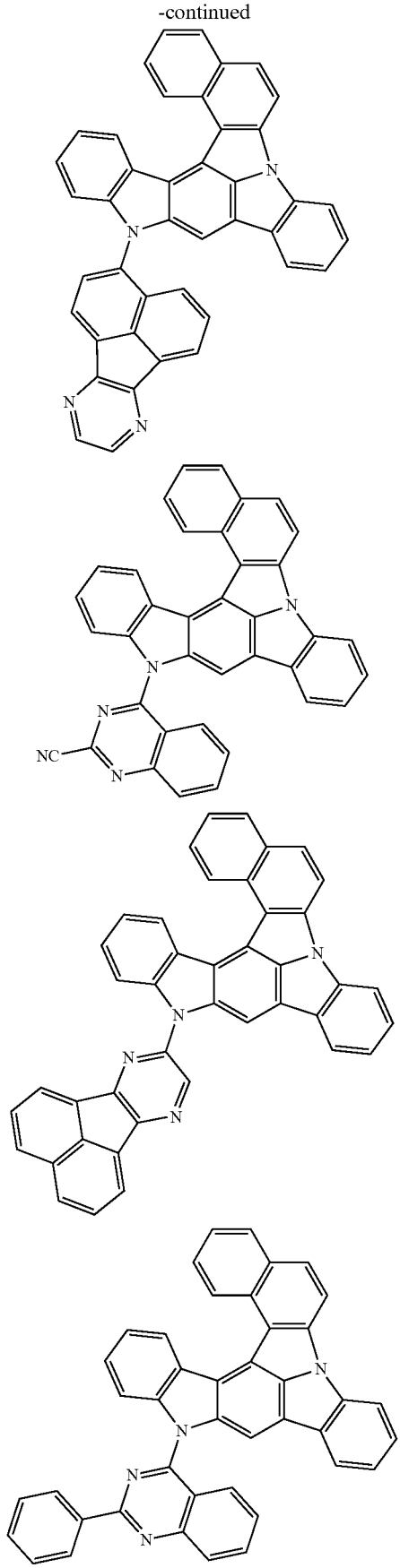
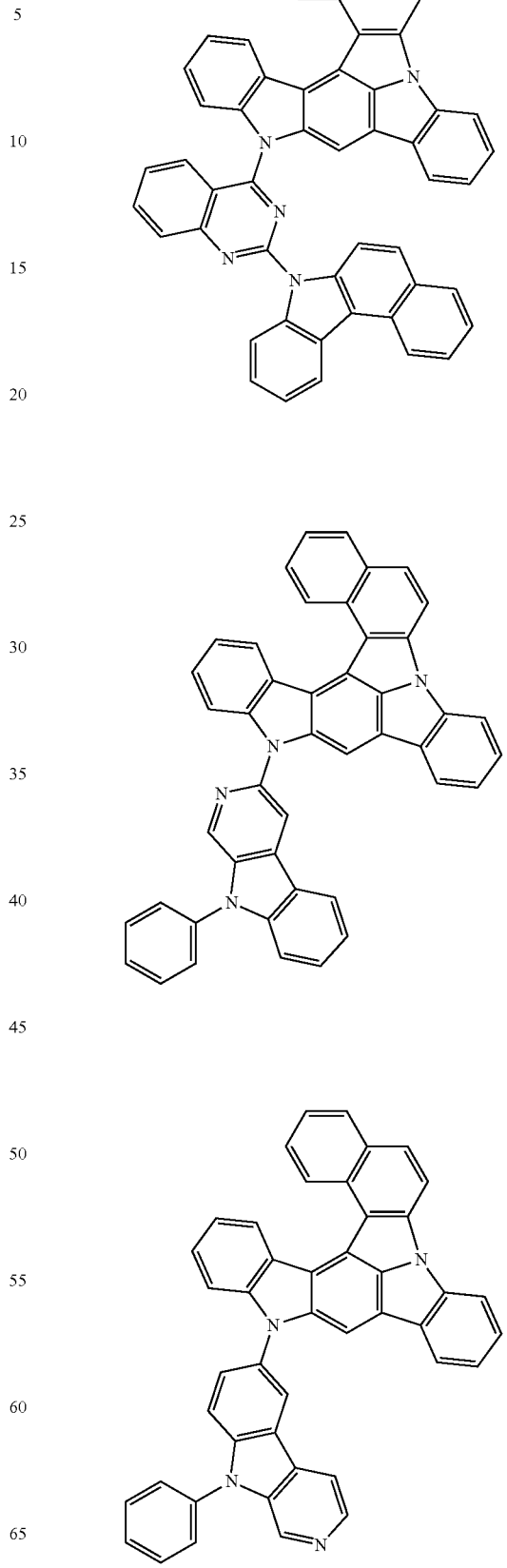

| 1199 | 1200 |
|---|---|
| -continued | -continued |
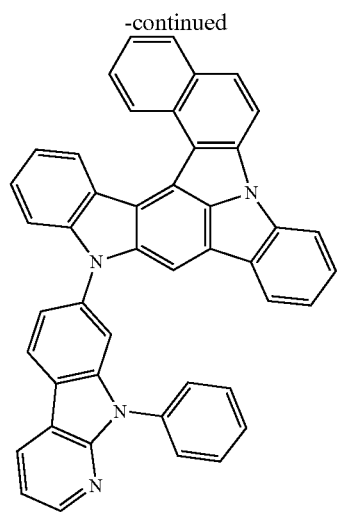
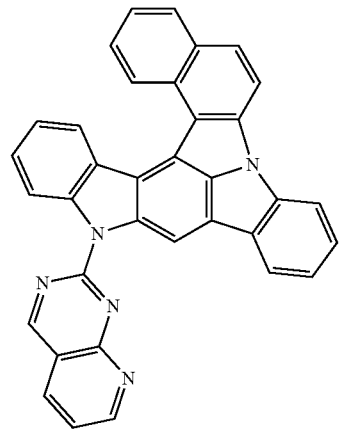
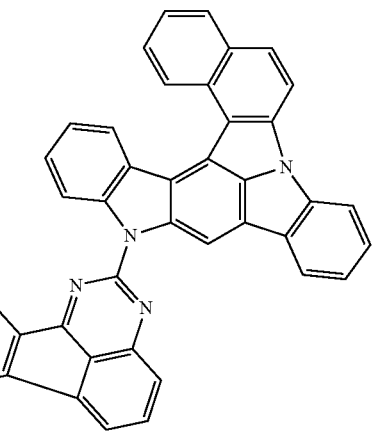
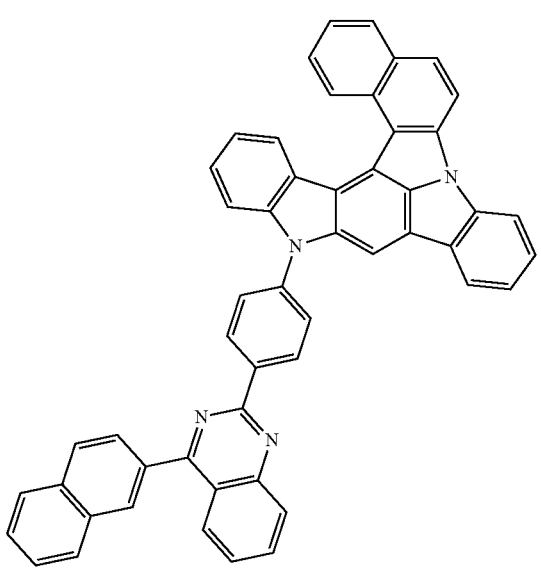
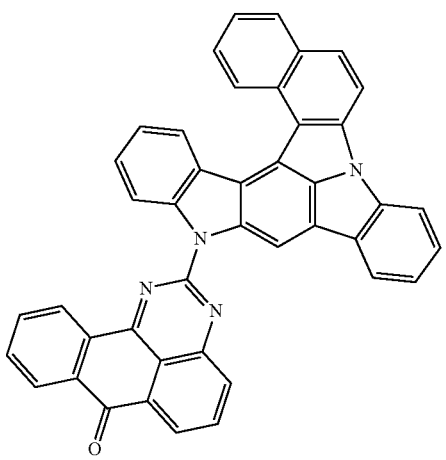

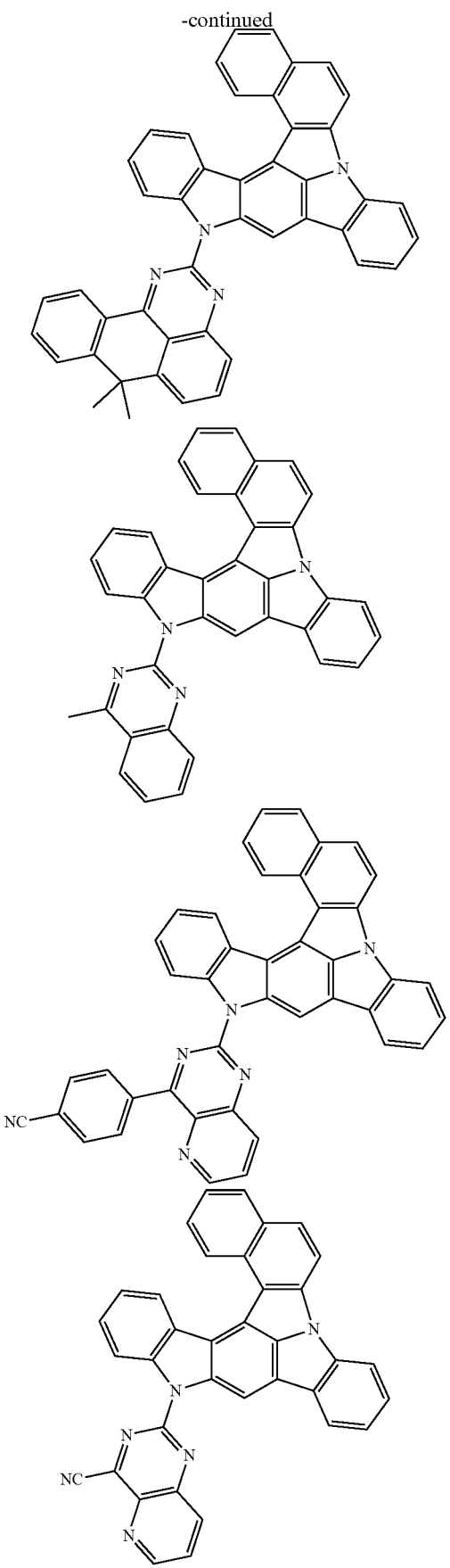

1203
-continued
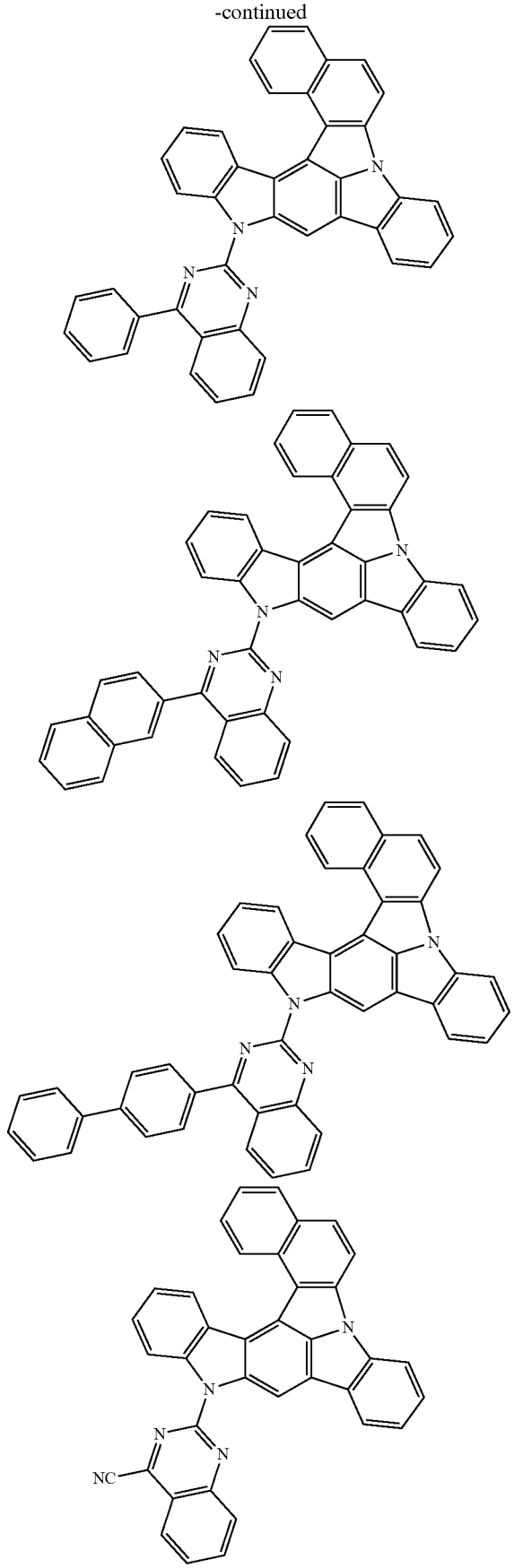
1204
-continued
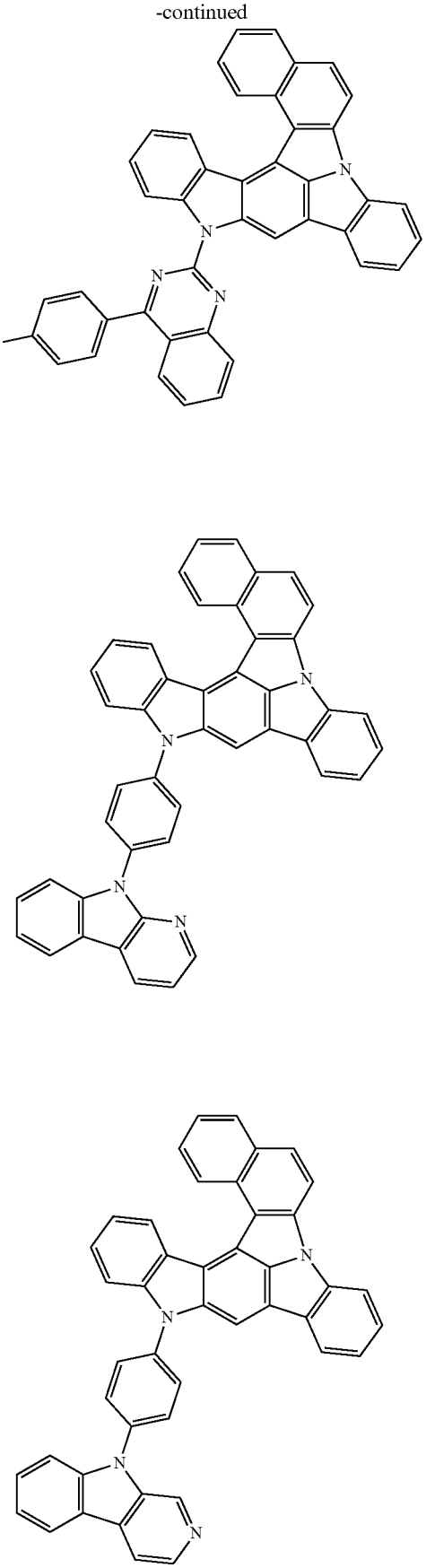

1205
-continued
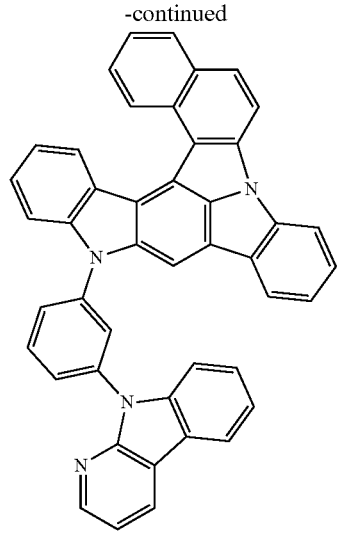
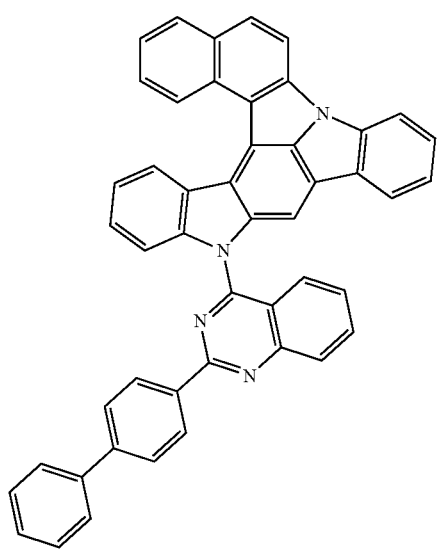
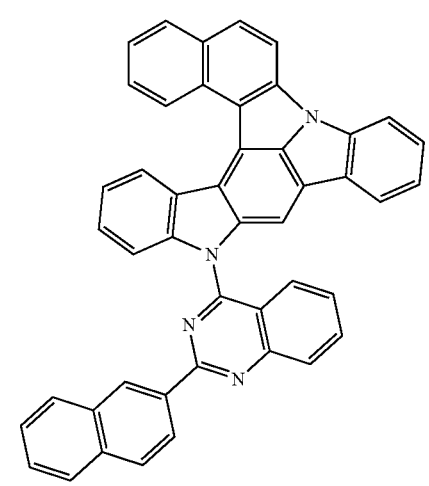
1206
-continued
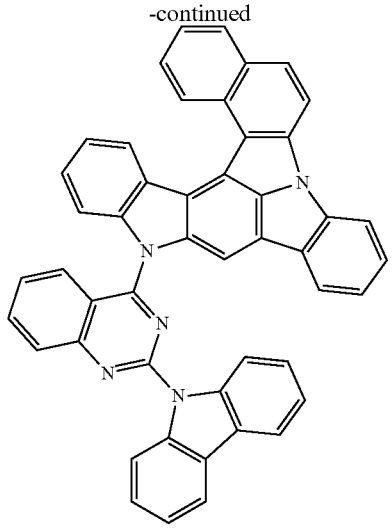
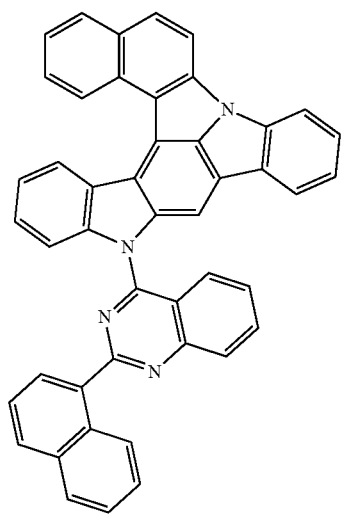
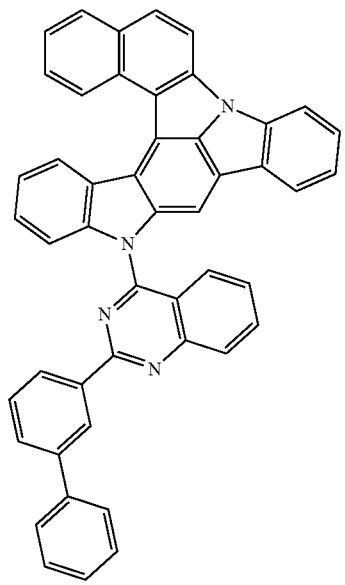

1207
-continued
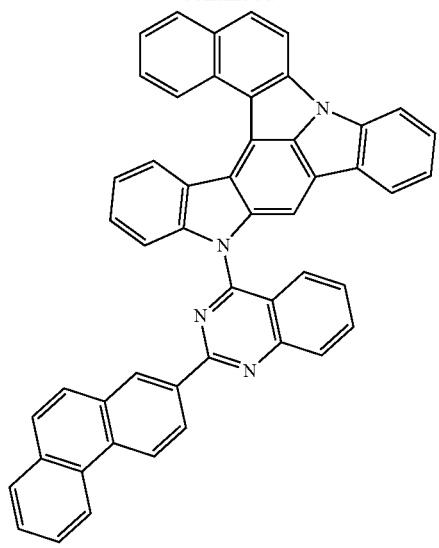
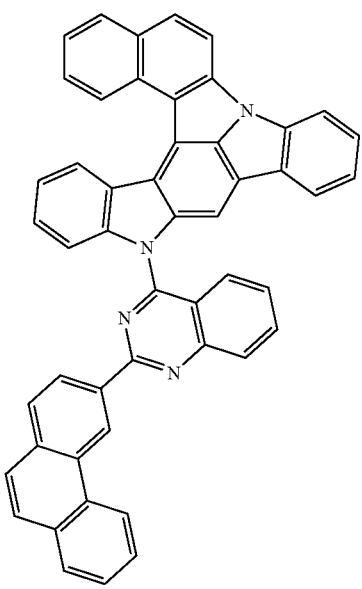
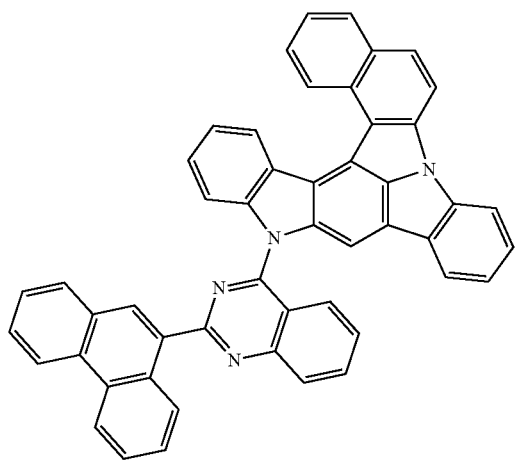
1208
-continued
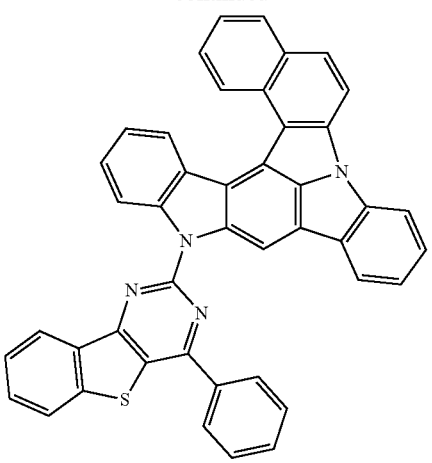
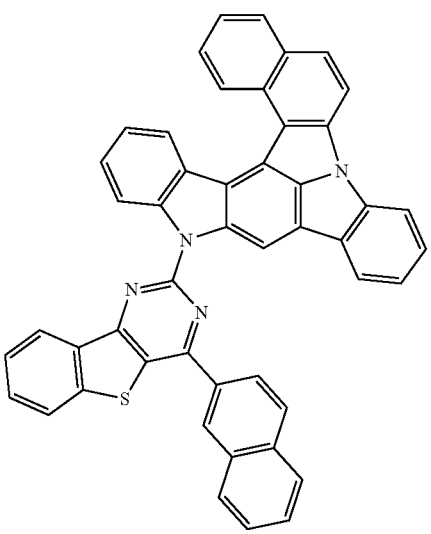 [SMILES: c1ccc2cc(-c3nc(-n4c5ccccc5c5c6c7c8ccccc8ccc7n7c8ccccc8c(cc54)c67)nc4c3sc3ccccc34)ccc2c1]
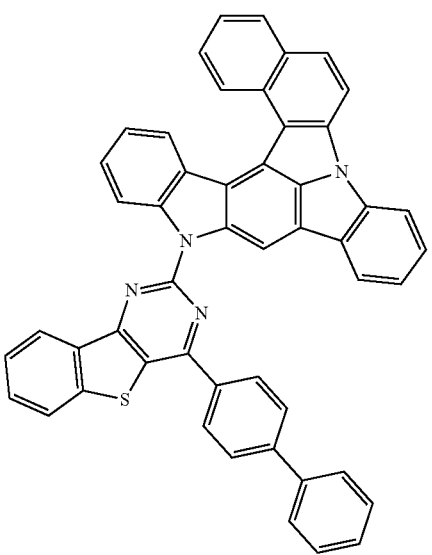

1209
-continued
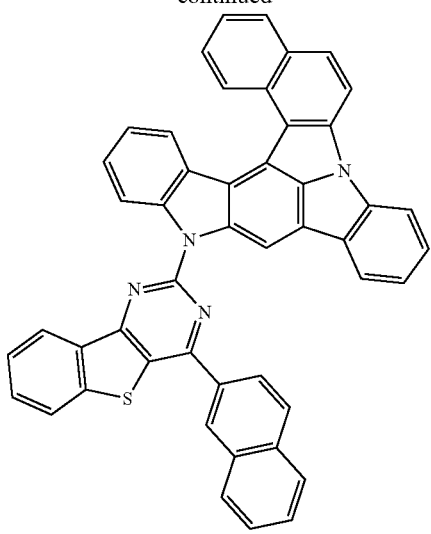
1210
-continued
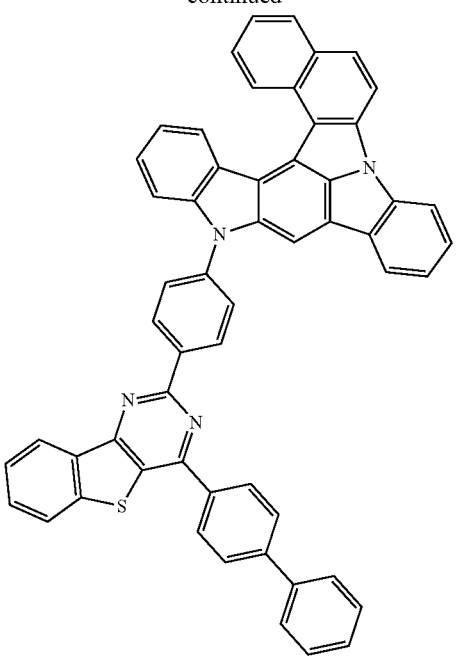
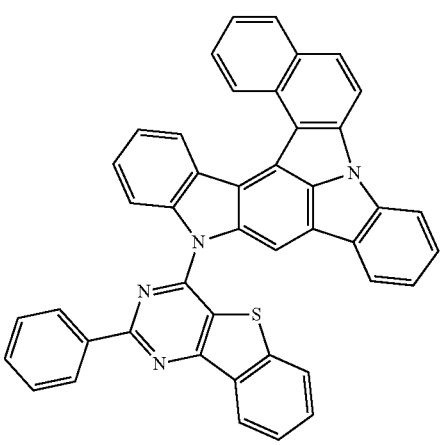
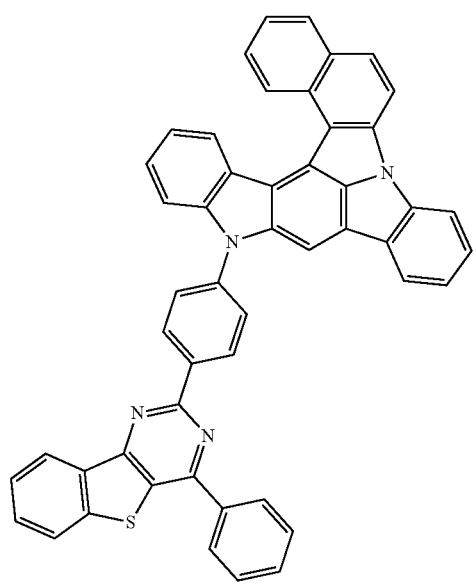
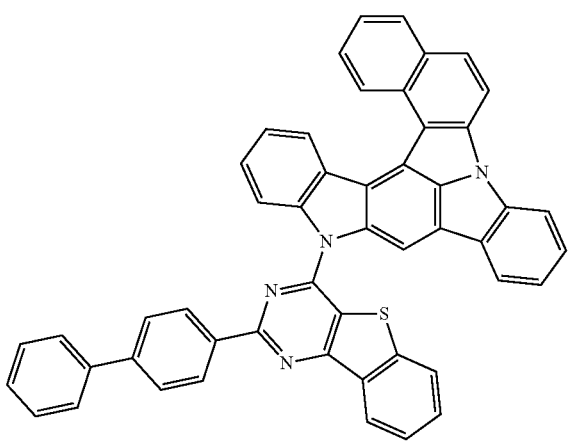

1211
-continued
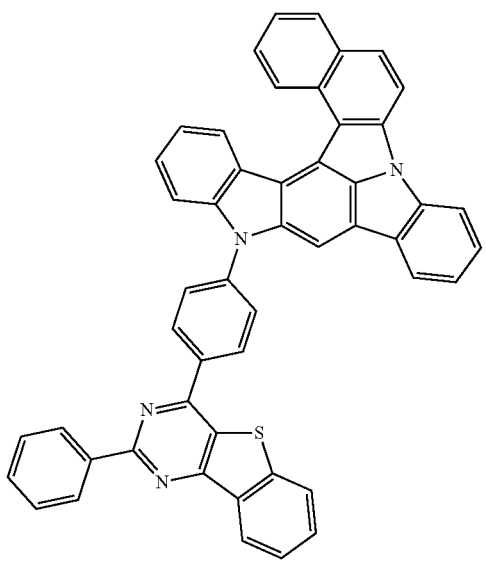
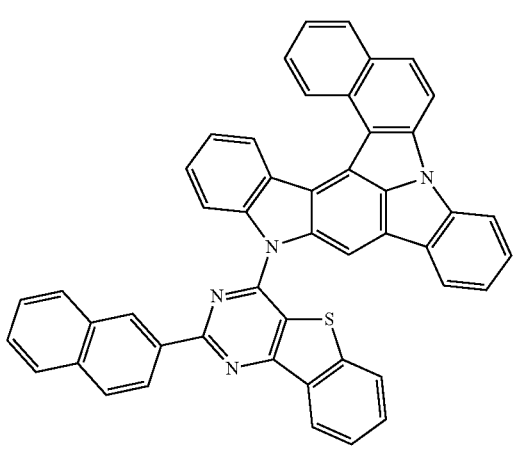
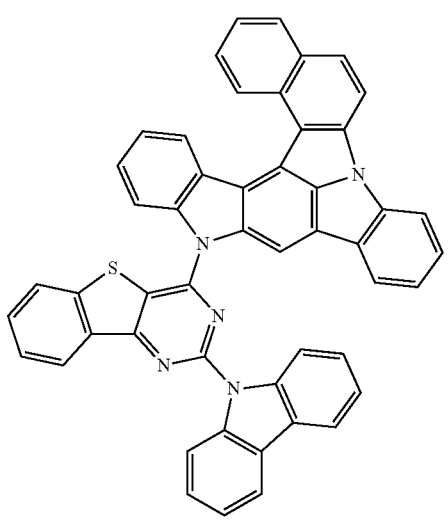
1212
-continued
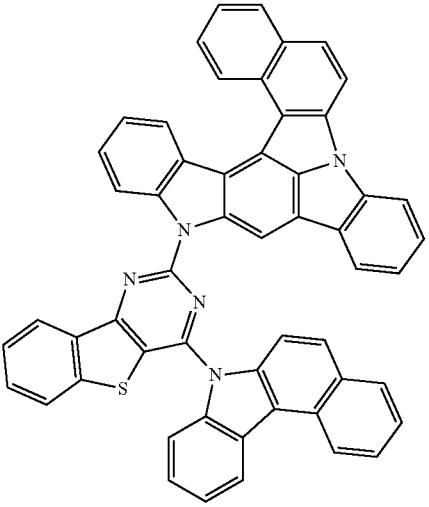
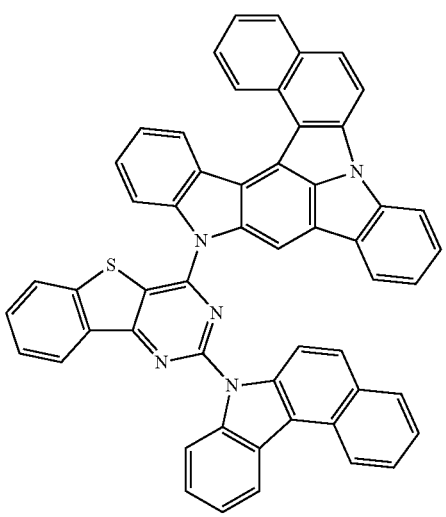
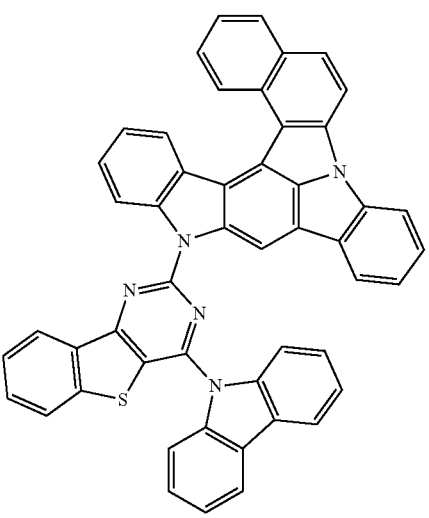

1213
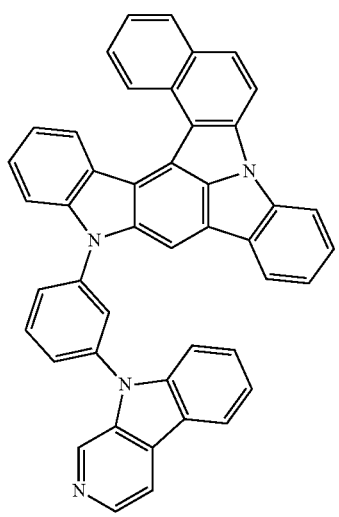
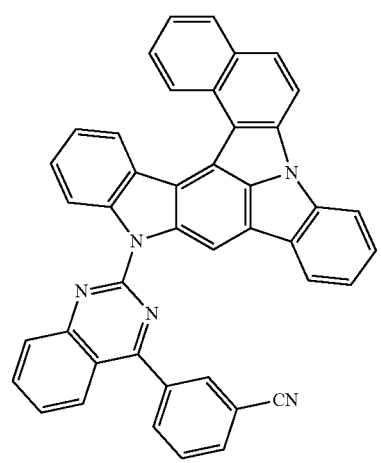
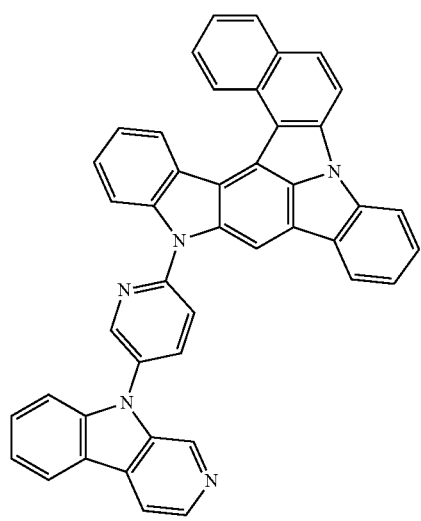
1214
-continued
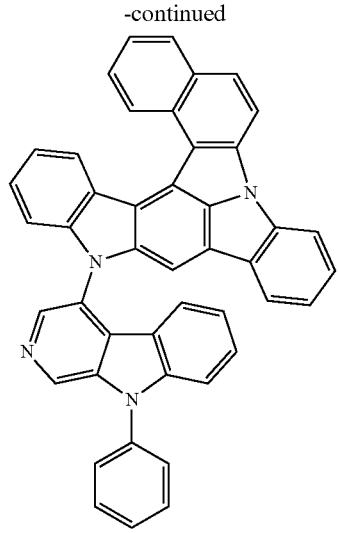
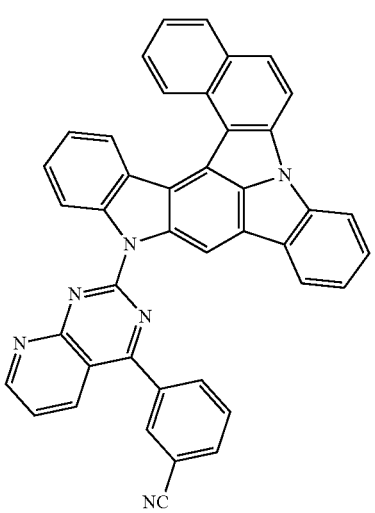
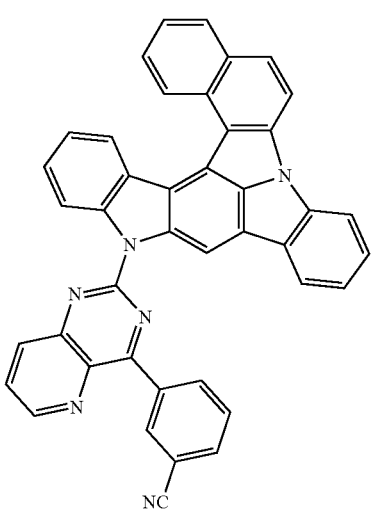

1215
-continued
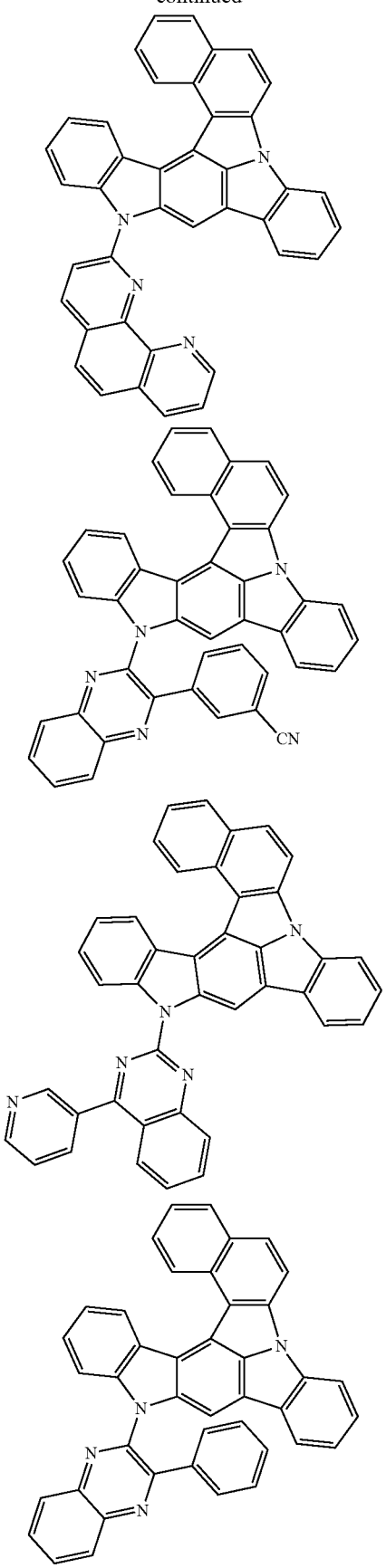
1216
-continued
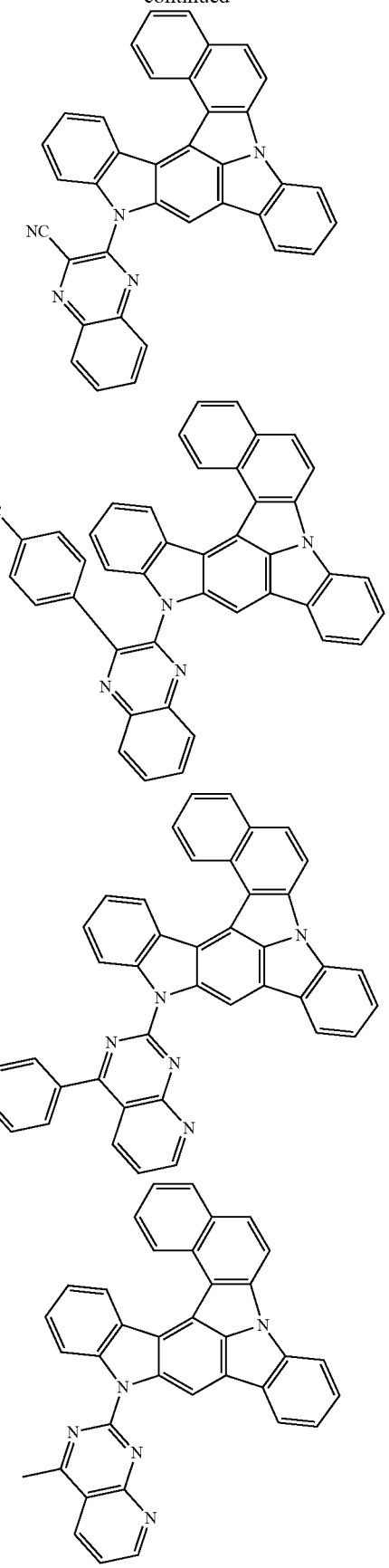

1217
-continued
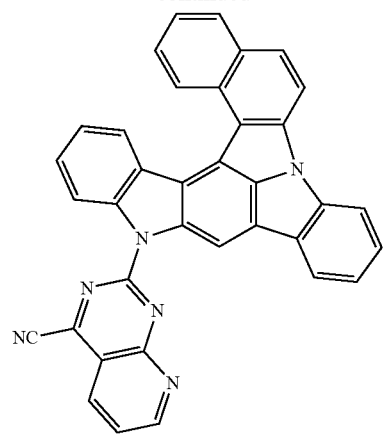
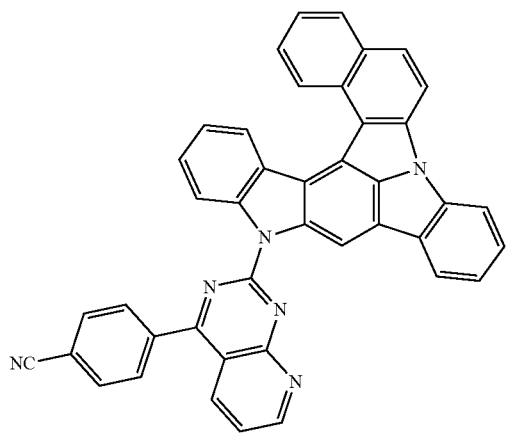
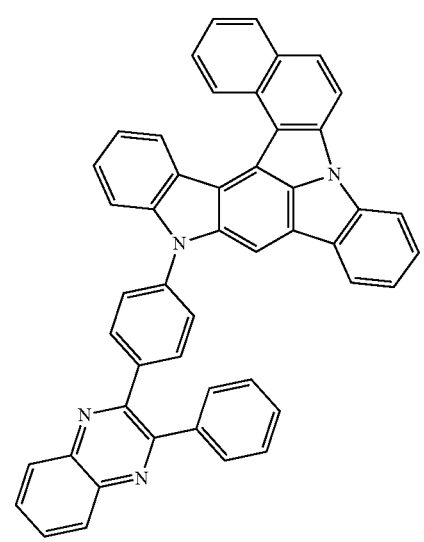
1218
-continued
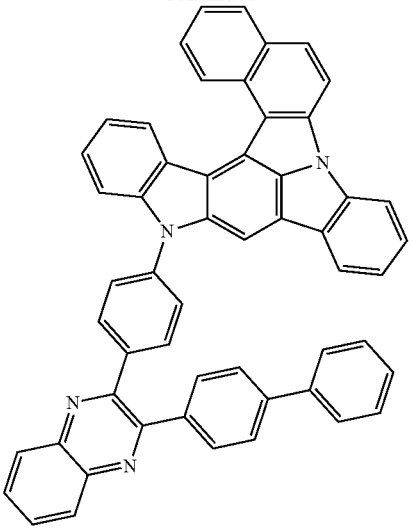
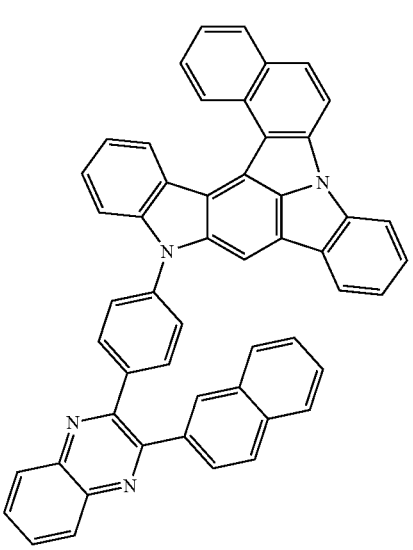
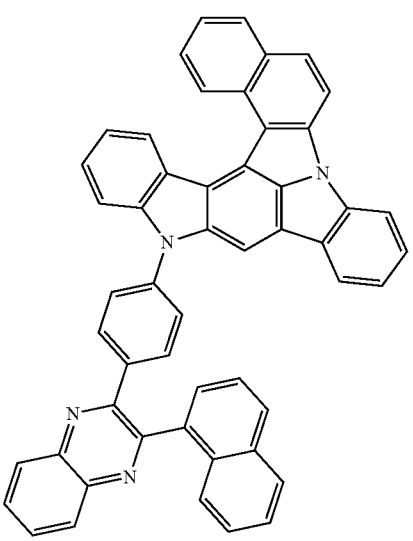

1219
-continued
1220
-continued
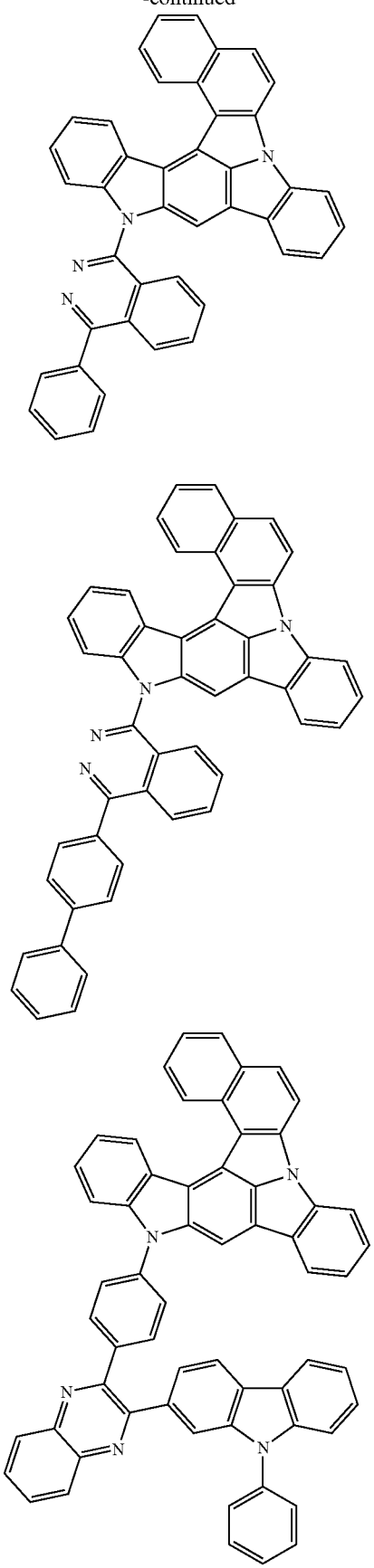
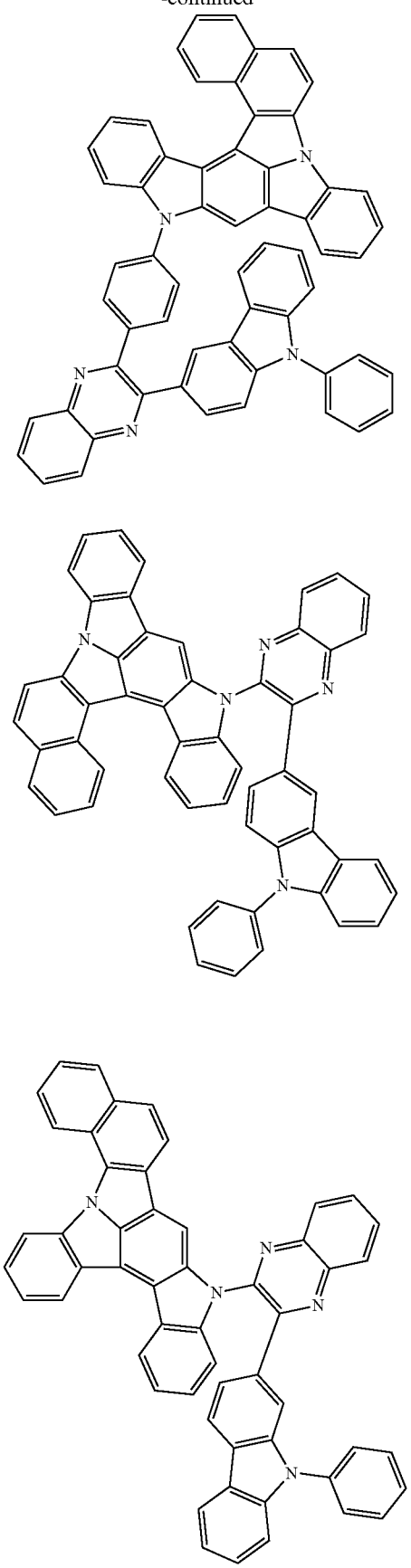

1221
-continued
1222
-continued
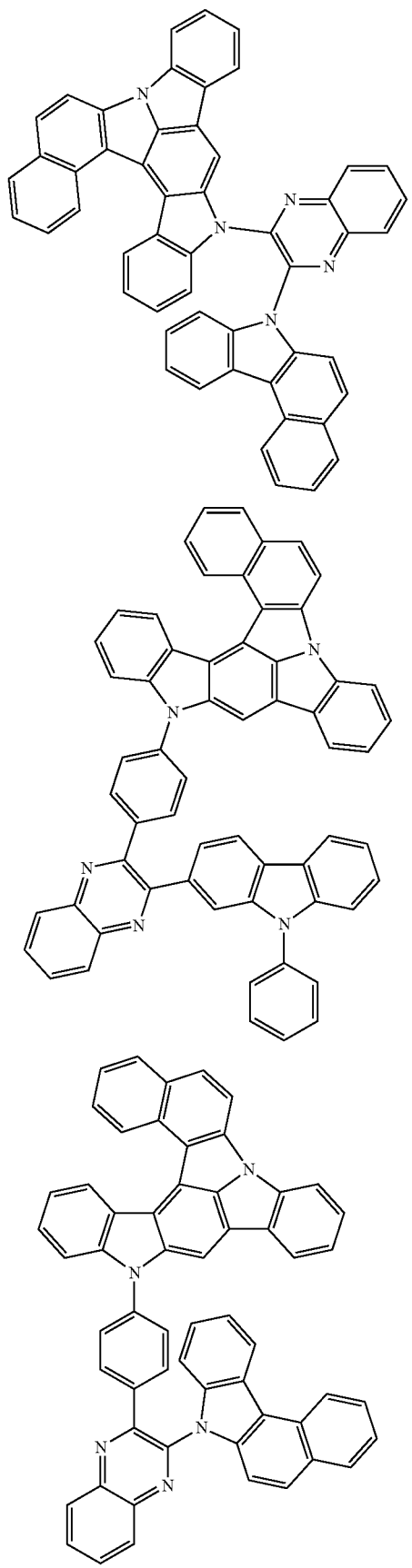

1223
-continued
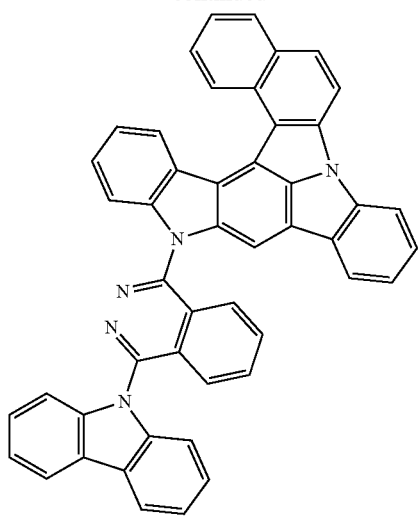
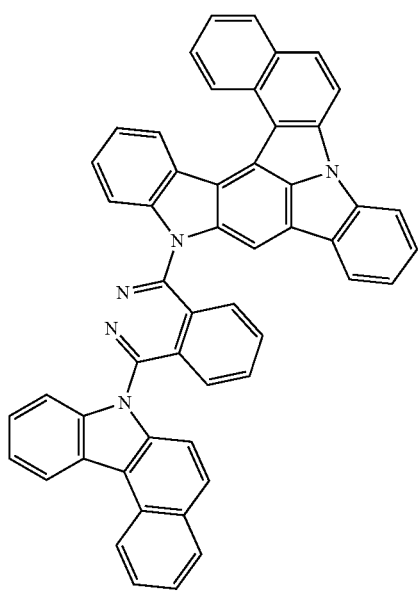
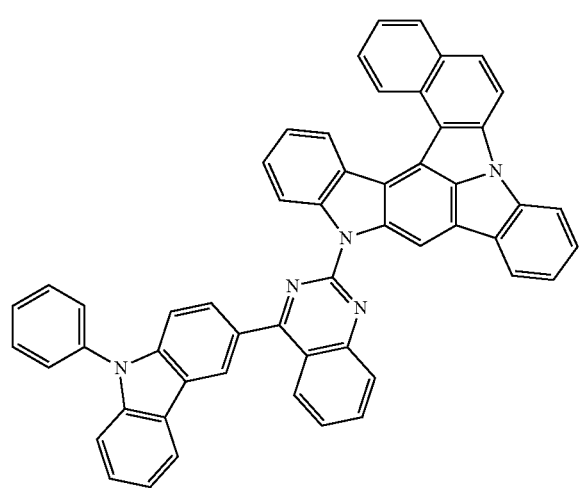
1224
-continued
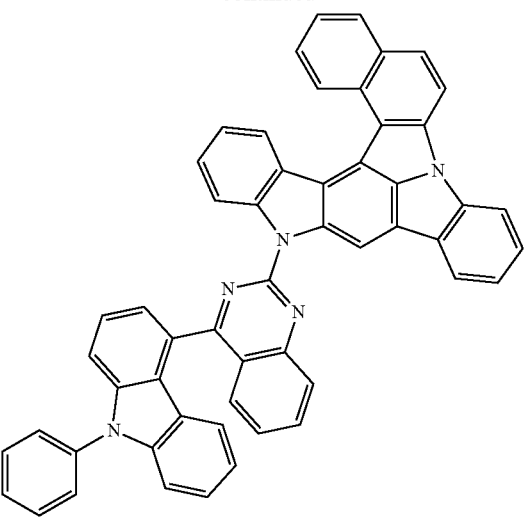
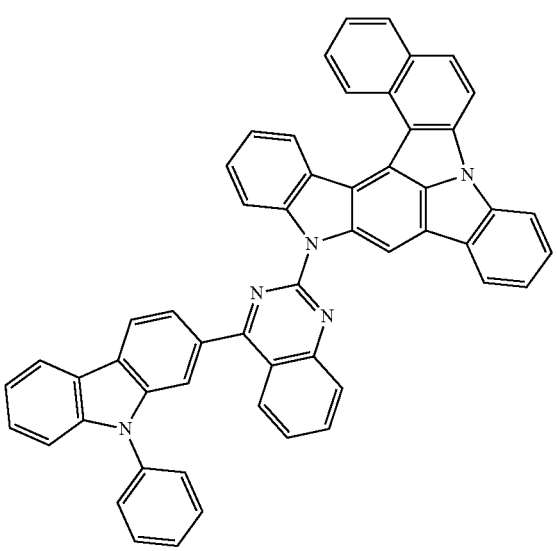
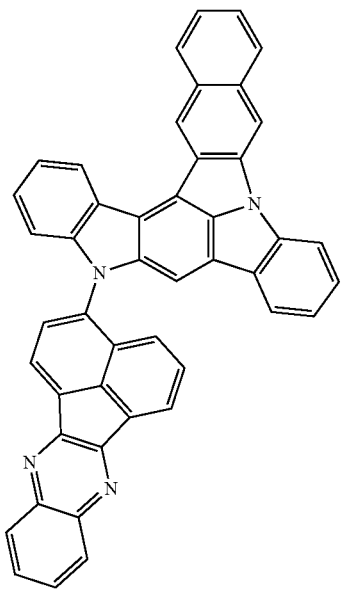

1225
-continued
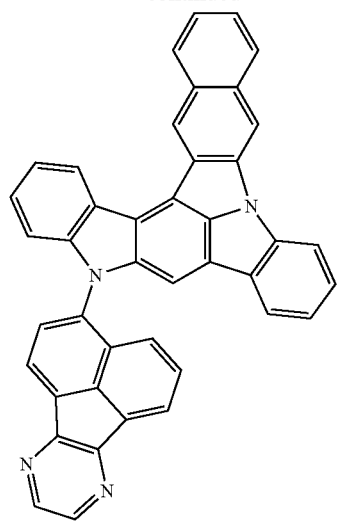
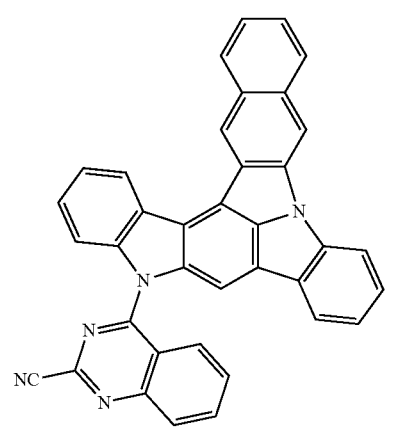
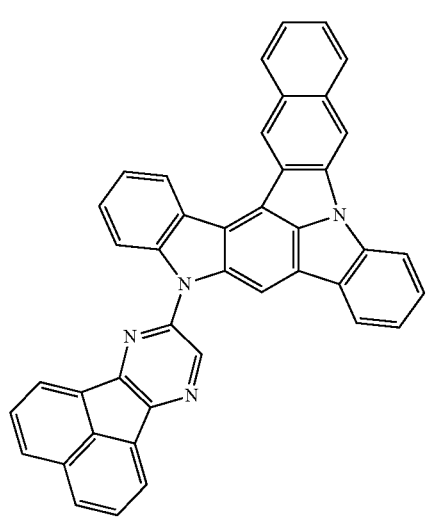
1226
-continued
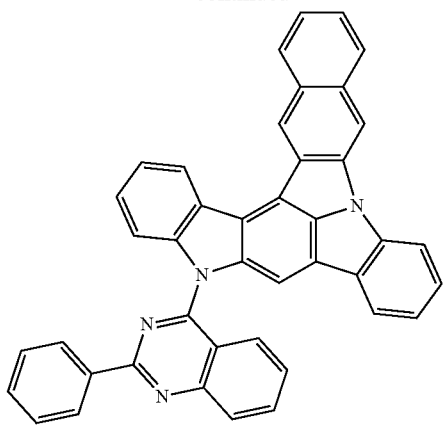
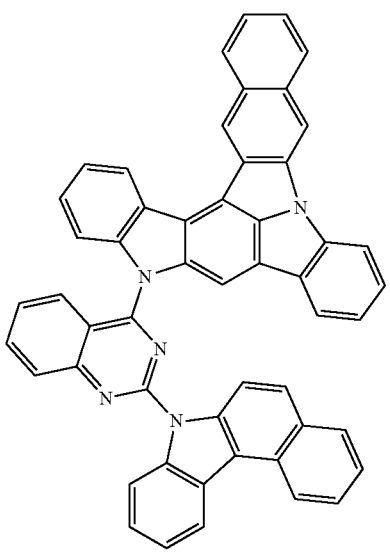
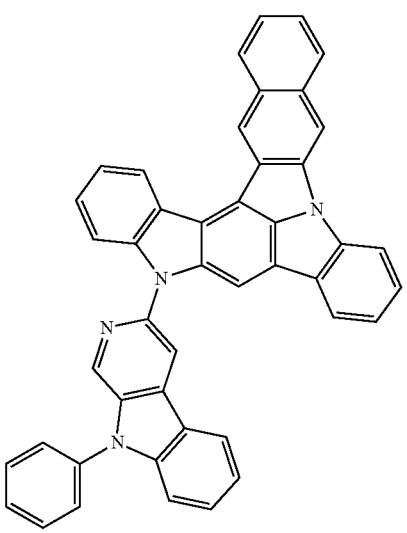

1227
-continued
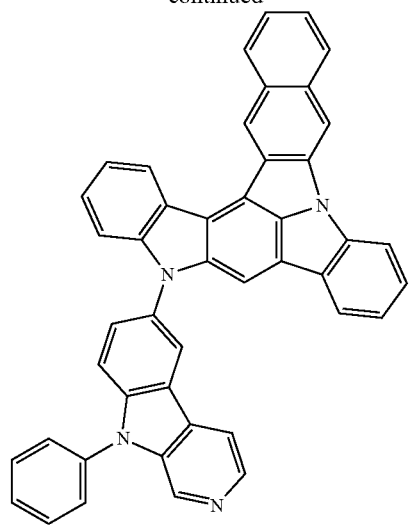
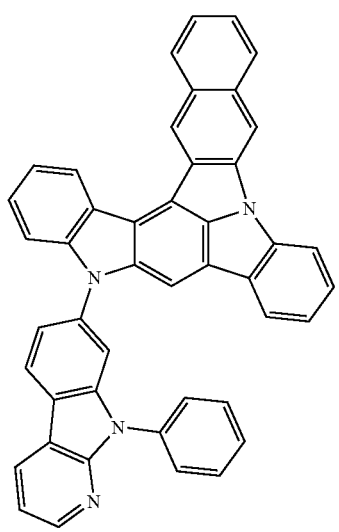
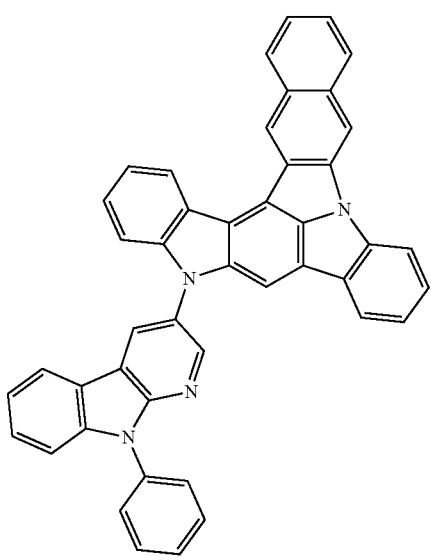
1228
-continued
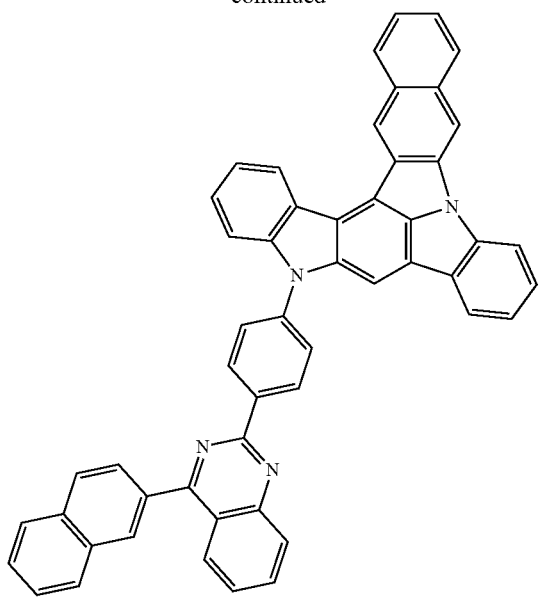
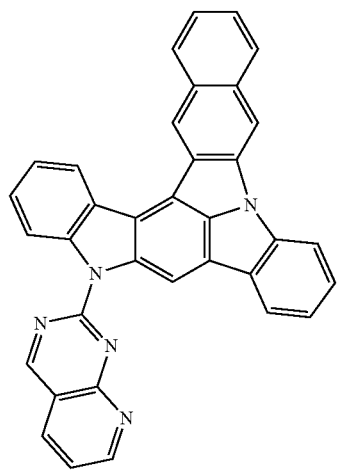
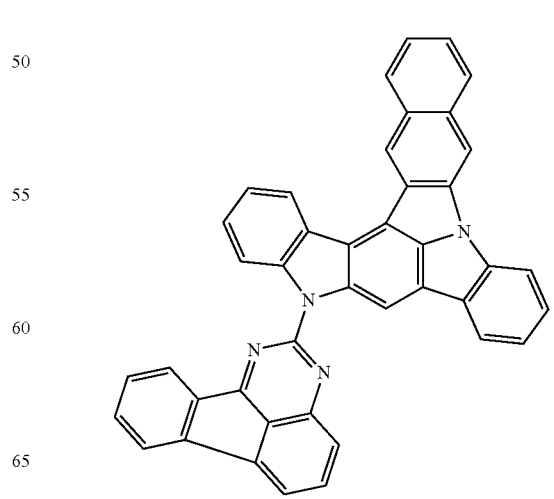

1229
-continued
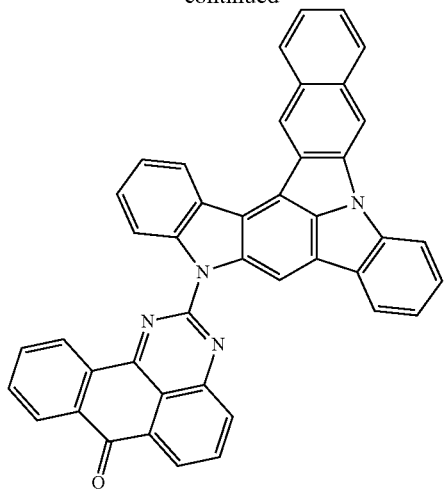
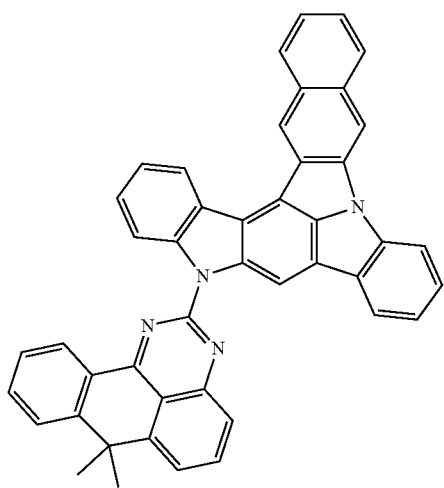
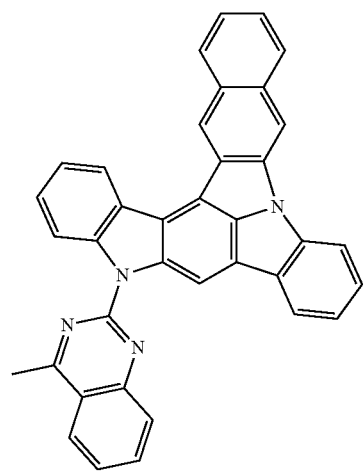
1230
-continued
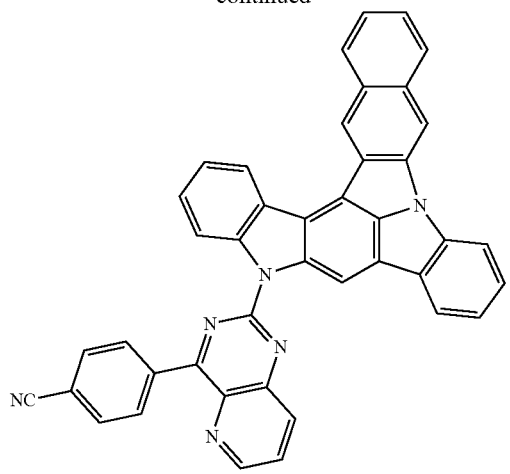
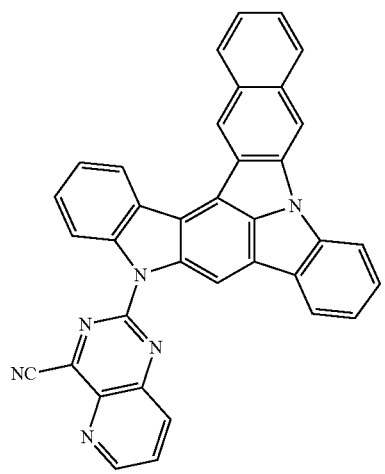
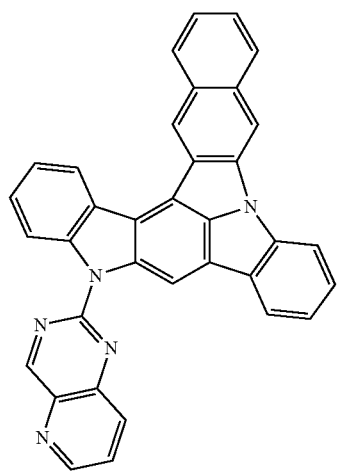

1231
-continued
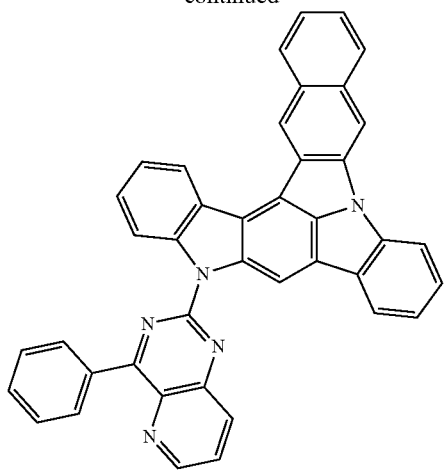
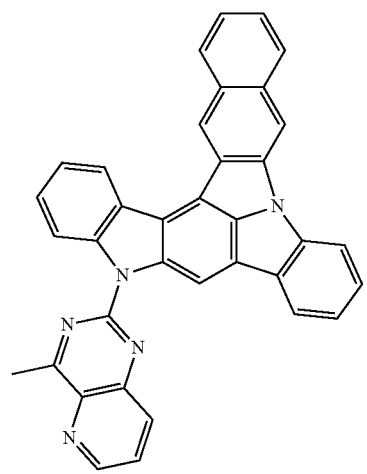
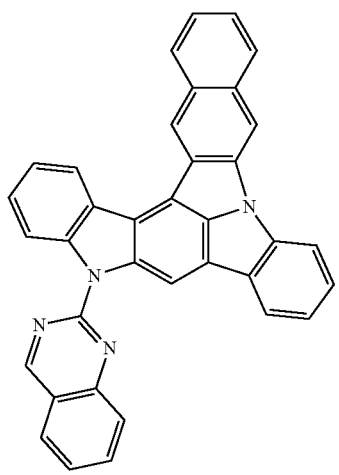
1232
-continued
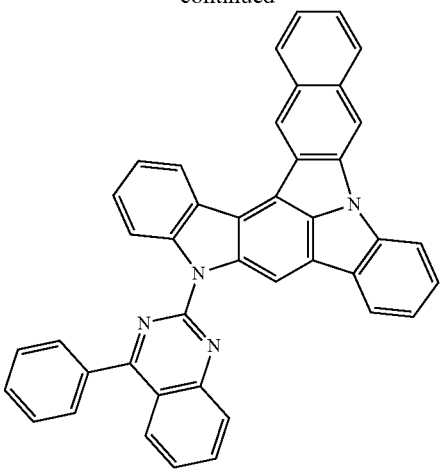
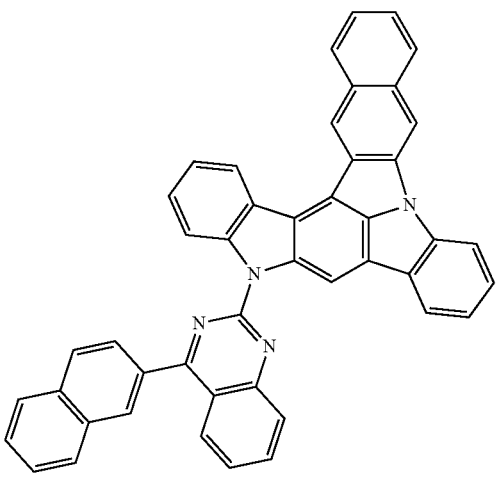
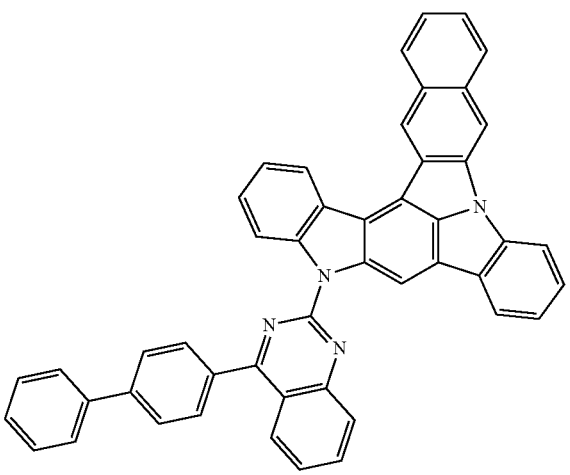

1233
-continued
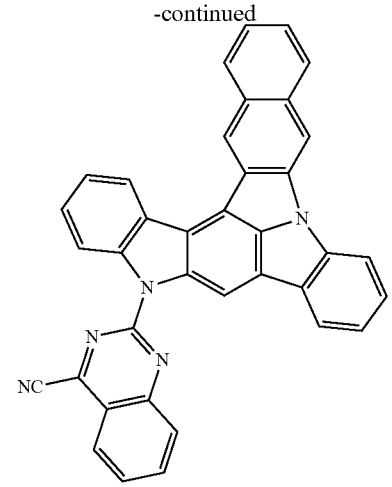
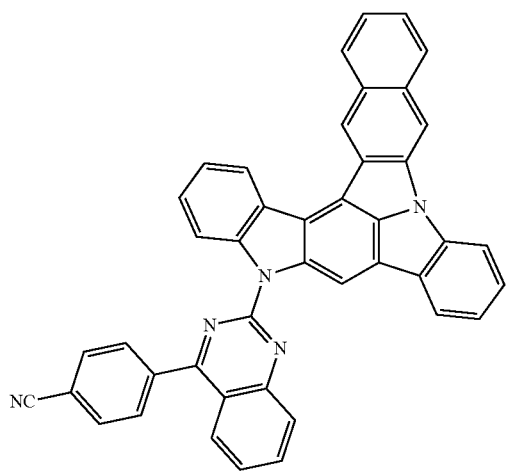
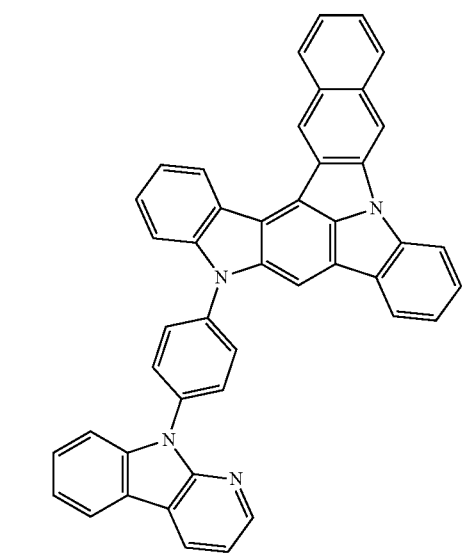
1234
-continued
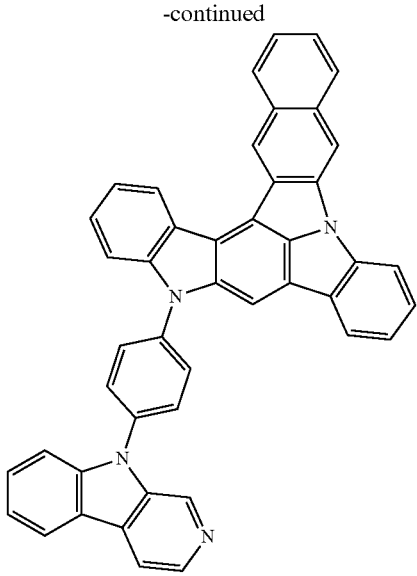
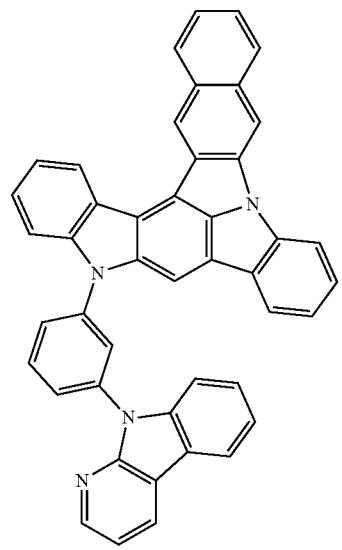
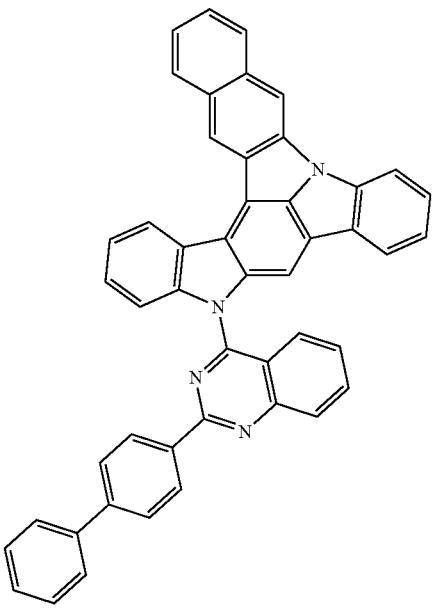

1235
-continued
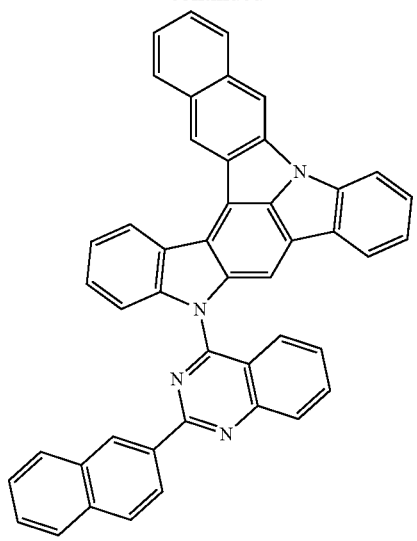
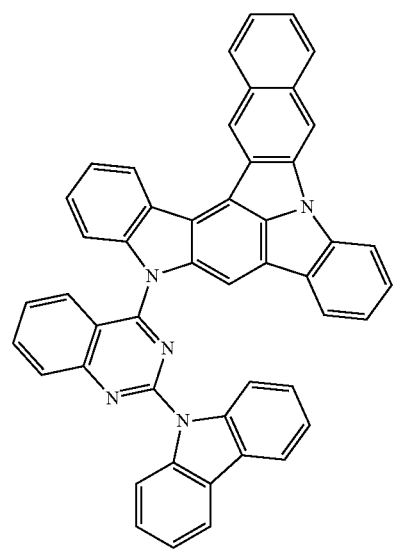
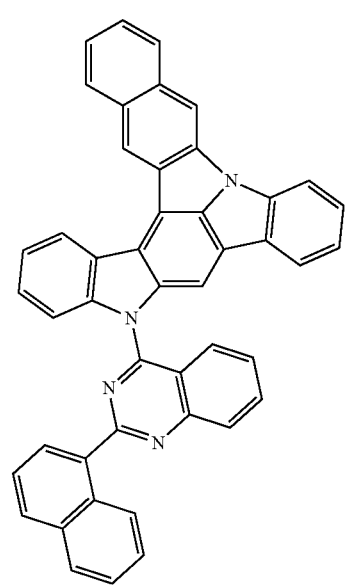
1236
-continued
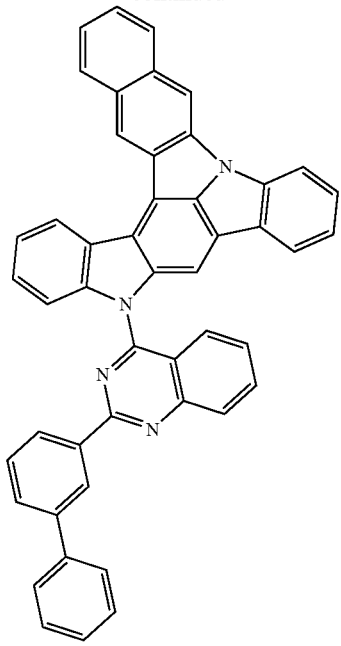
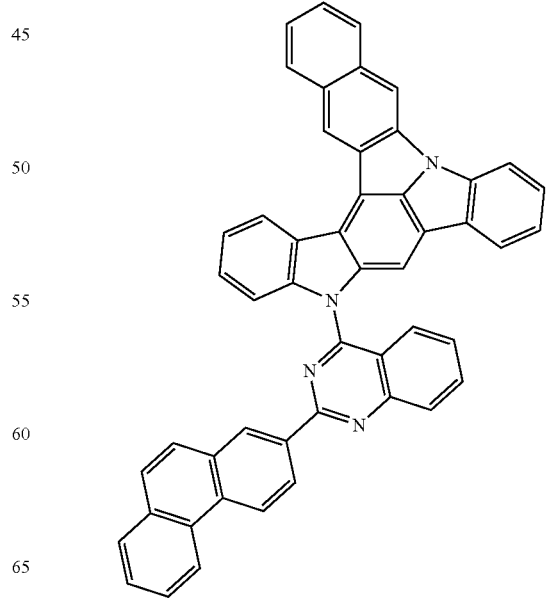

1237
-continued
1238
-continued
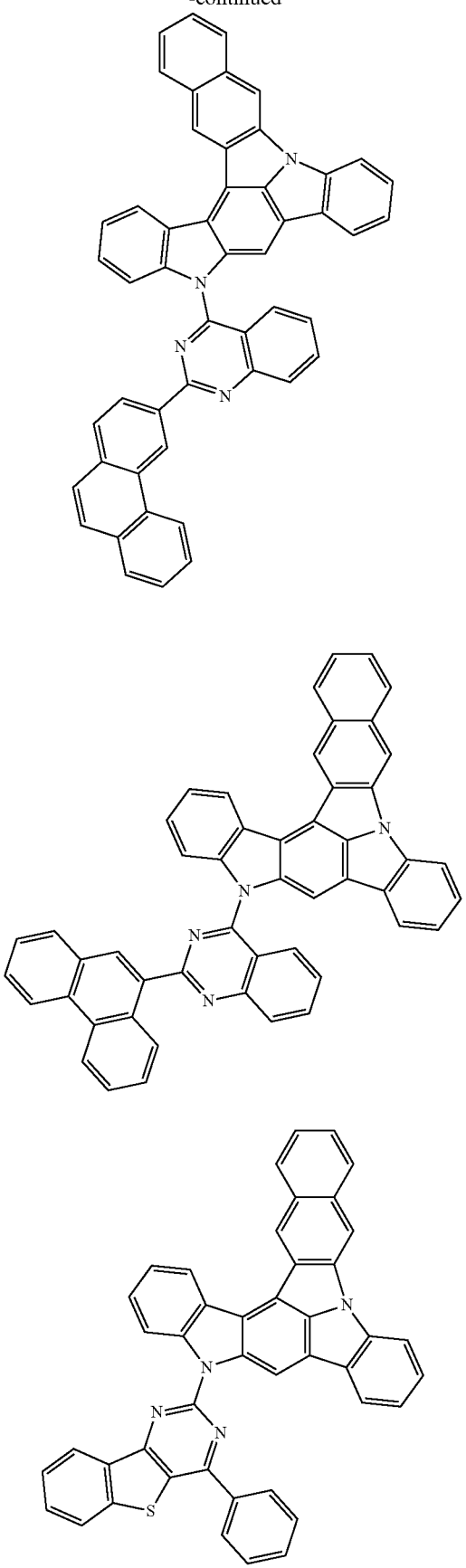
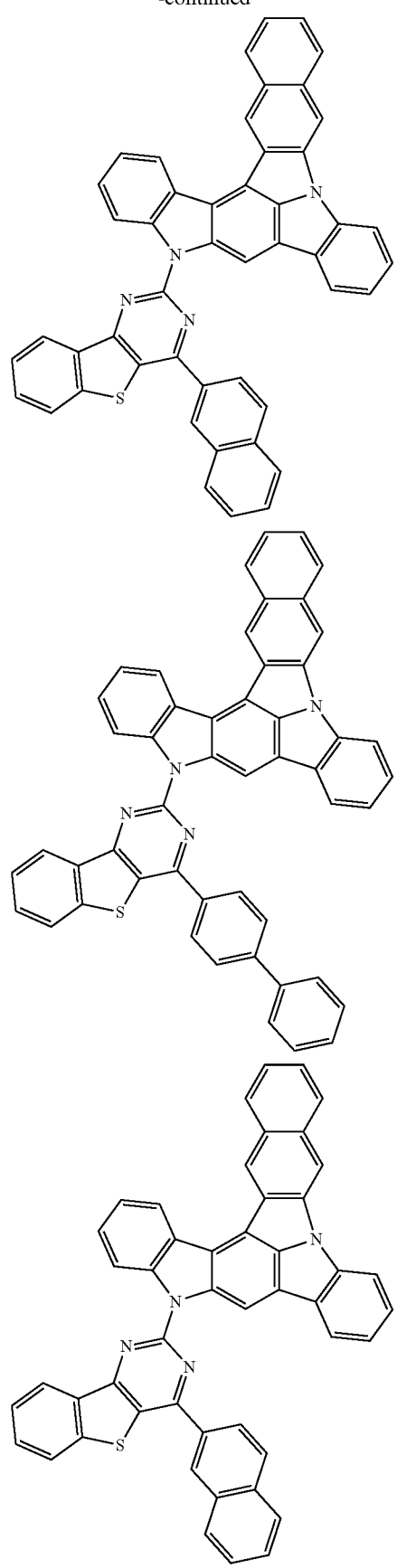

1239
-continued
1240
-continued
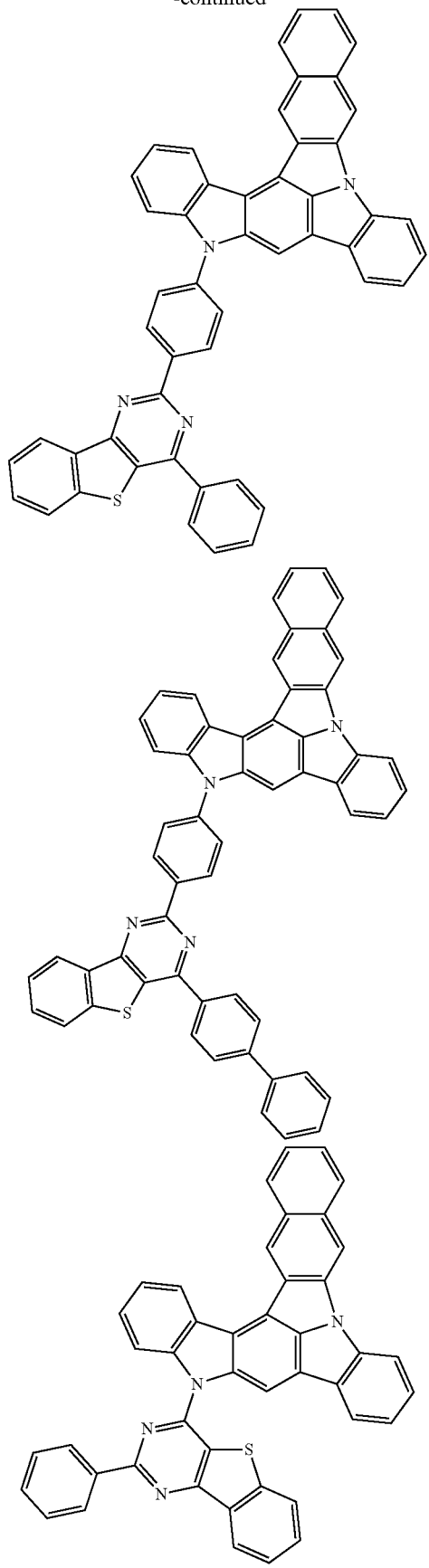
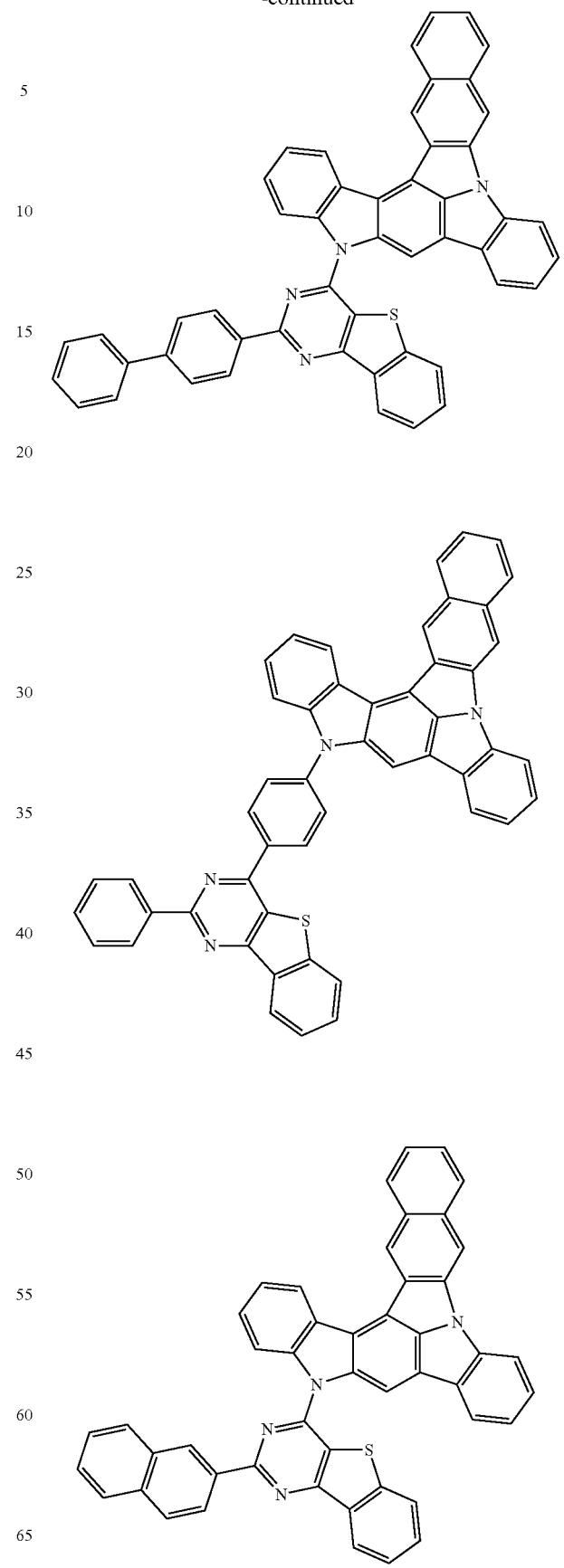

1241
-continued
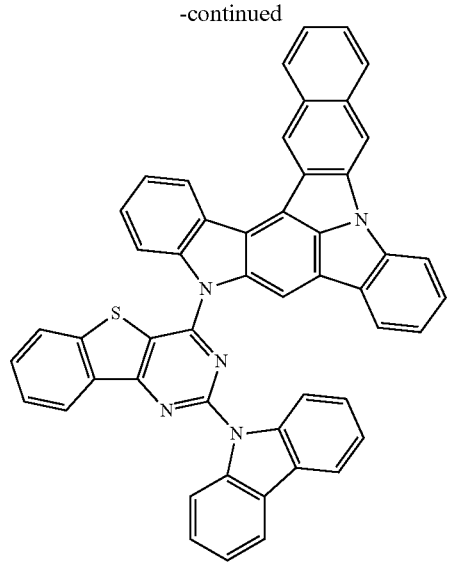
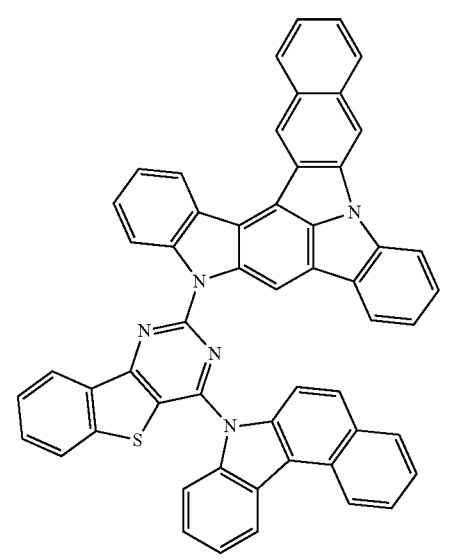
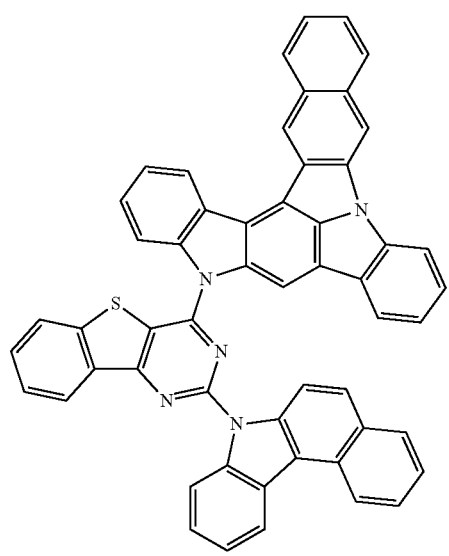
1242
-continued
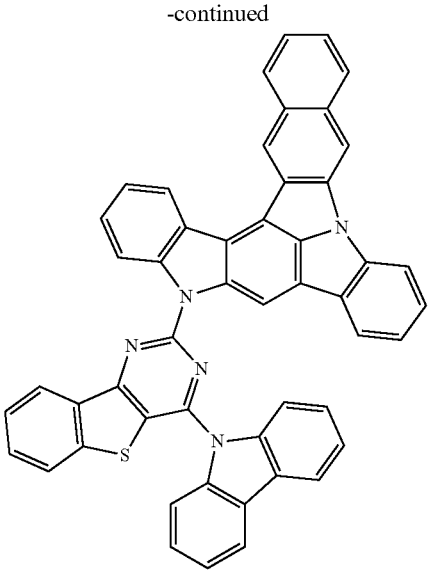
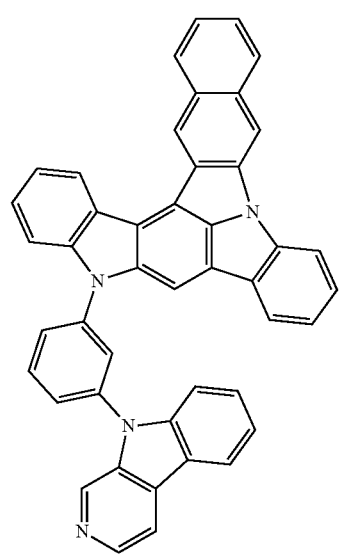
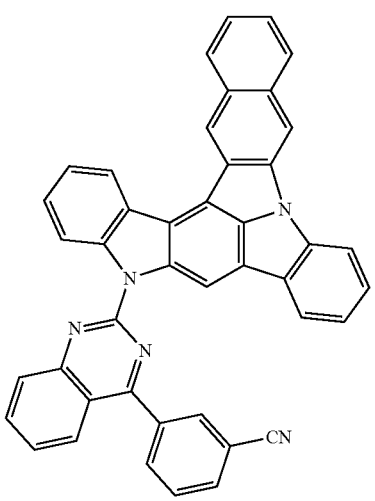

1243
-continued
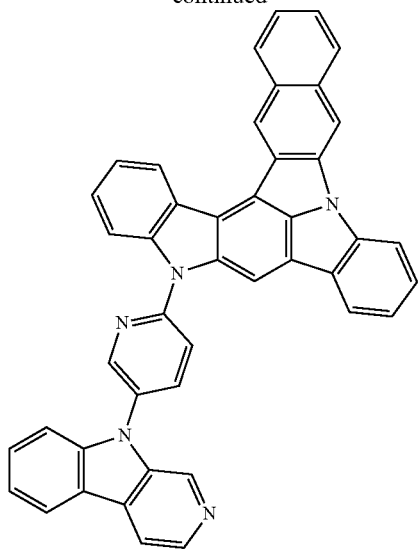
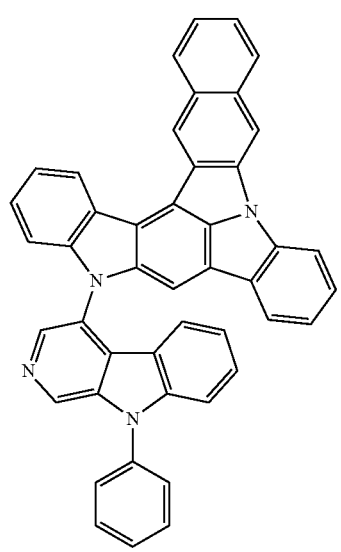
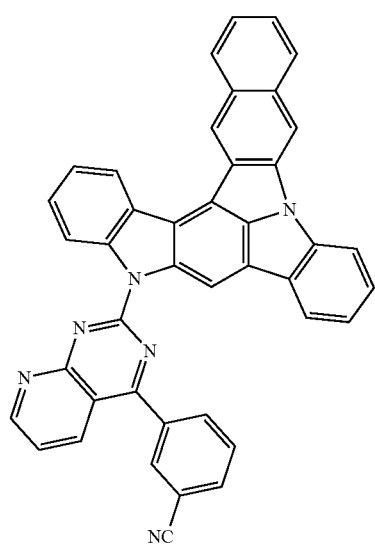
1244
-continued
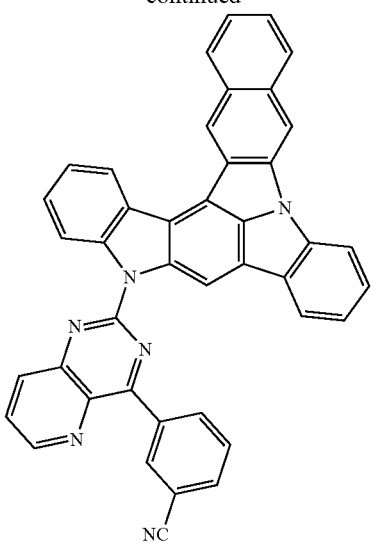
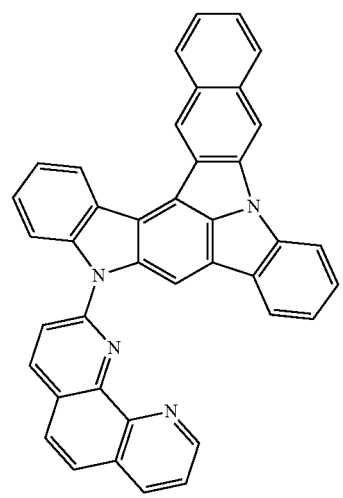
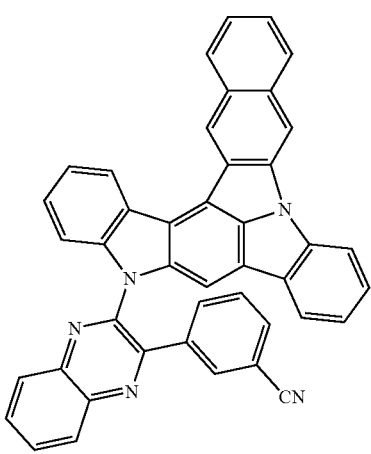

1245
-continued
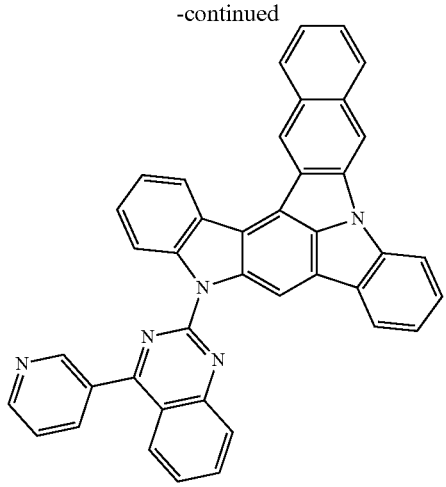
1246
-continued
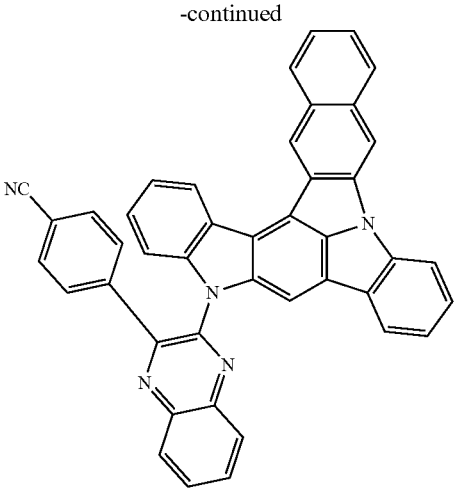
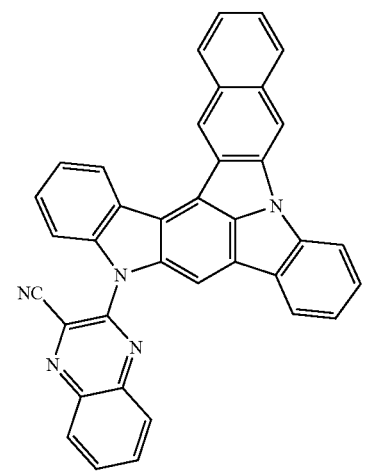
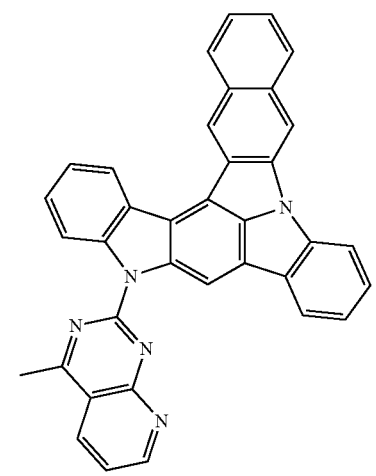

1247
-continued
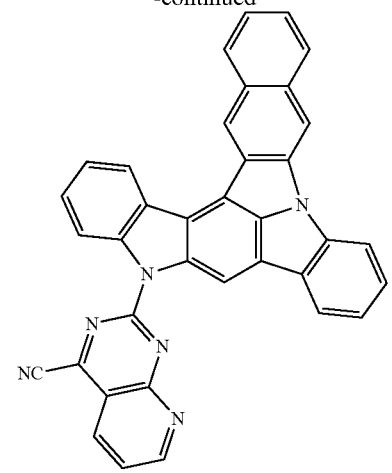
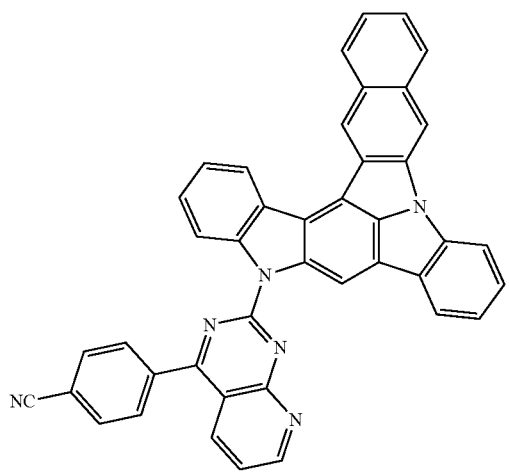
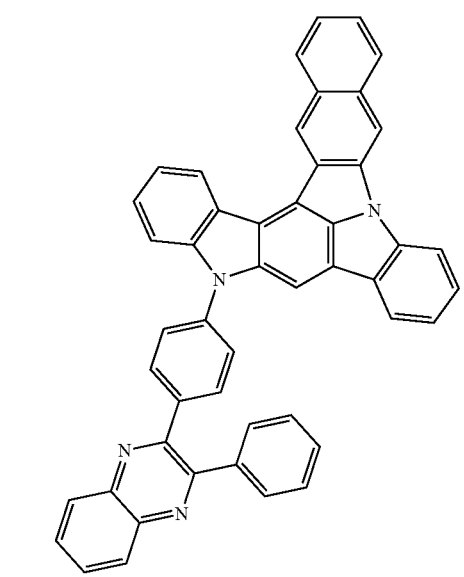
1248
-continued
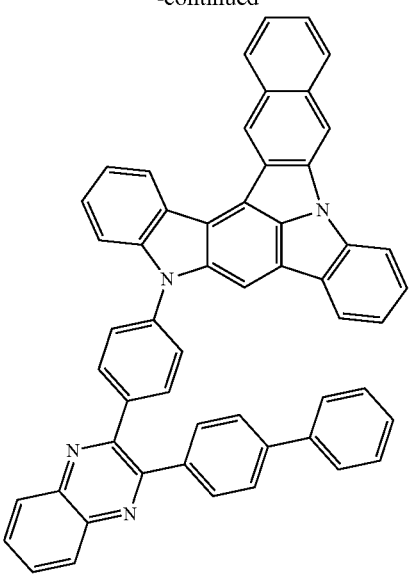
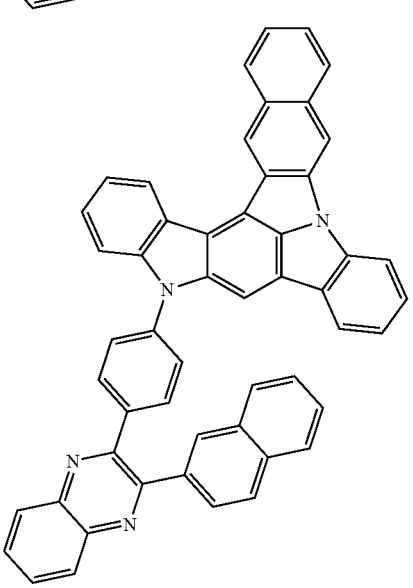
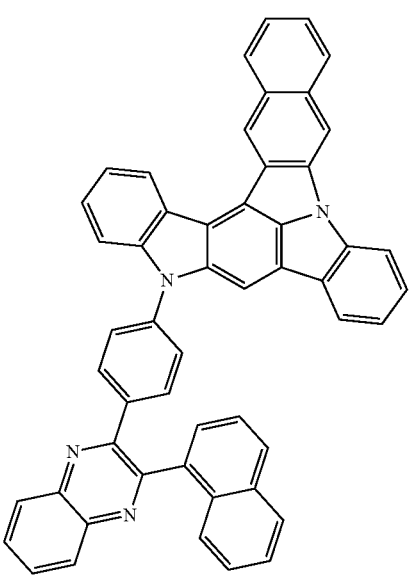

1249
-continued
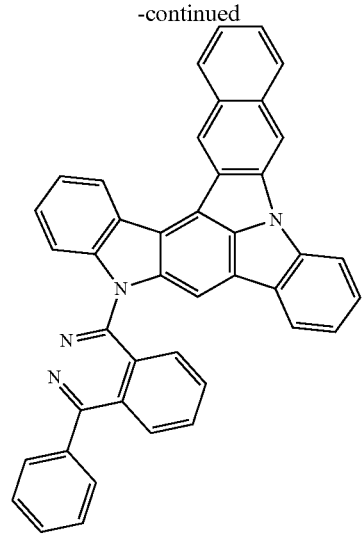
1250
-continued
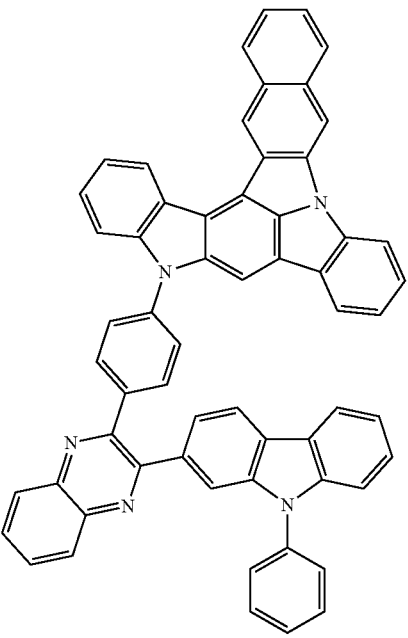
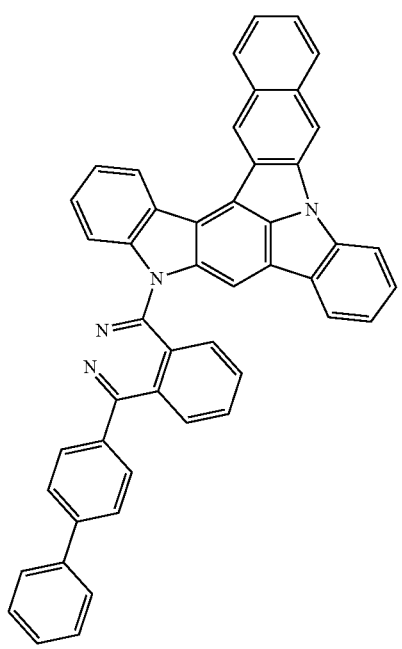
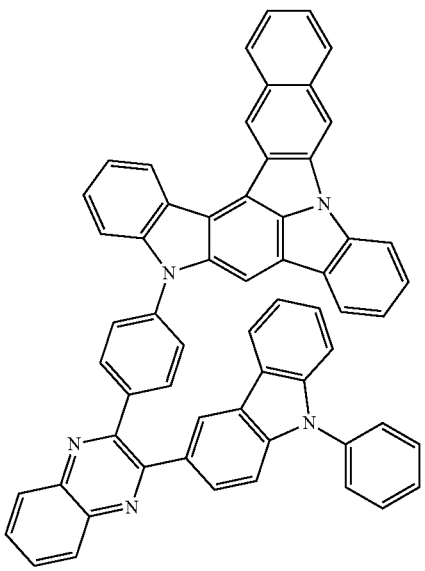

1251
-continued
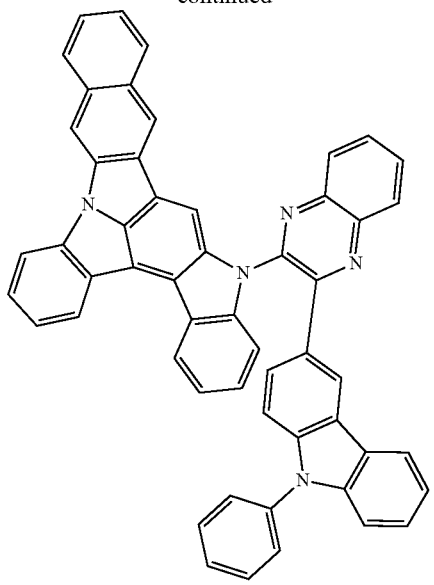
1252
-continued
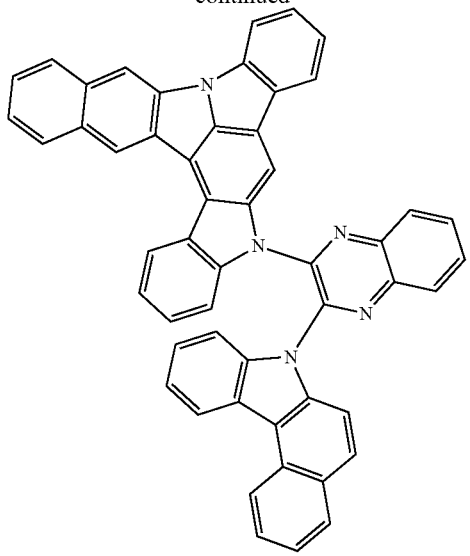
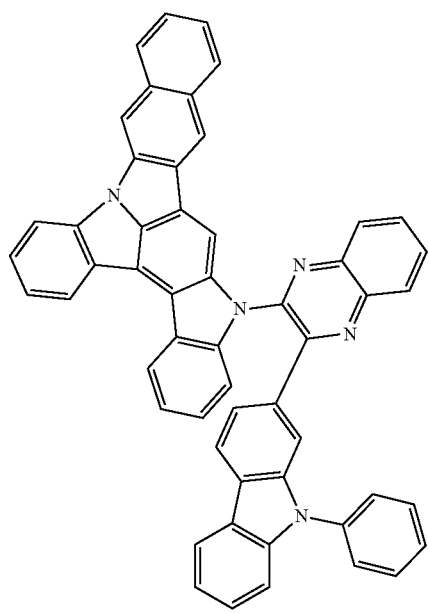
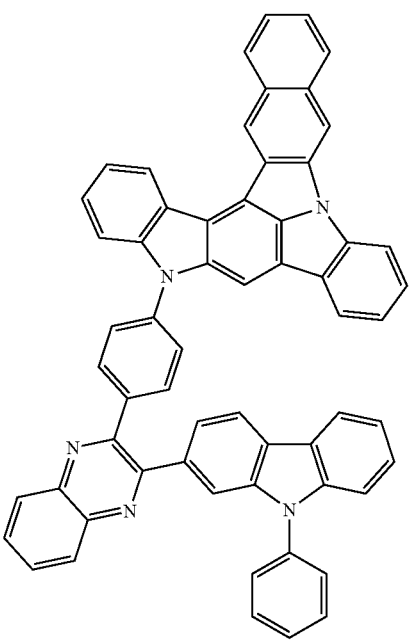

1253
-continued
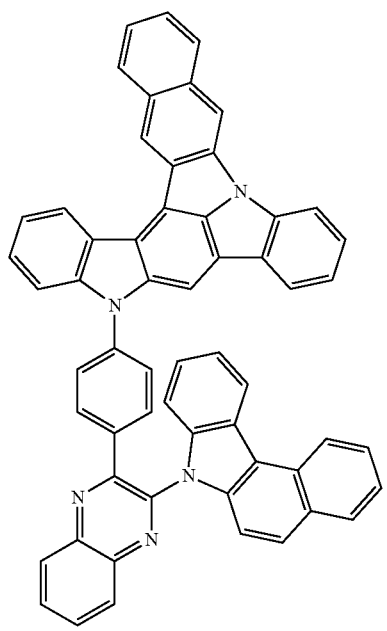
1254
-continued
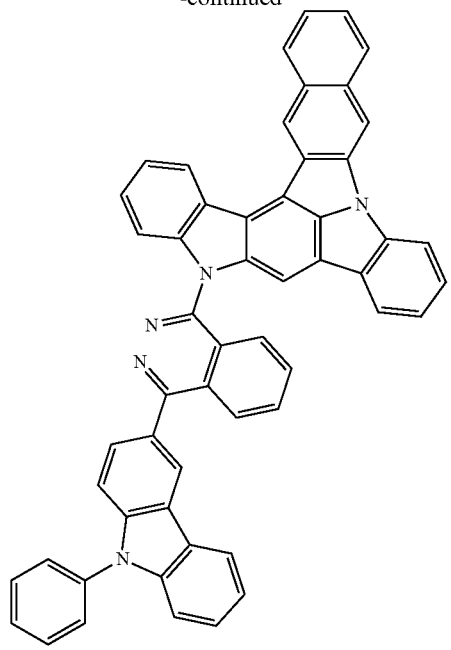
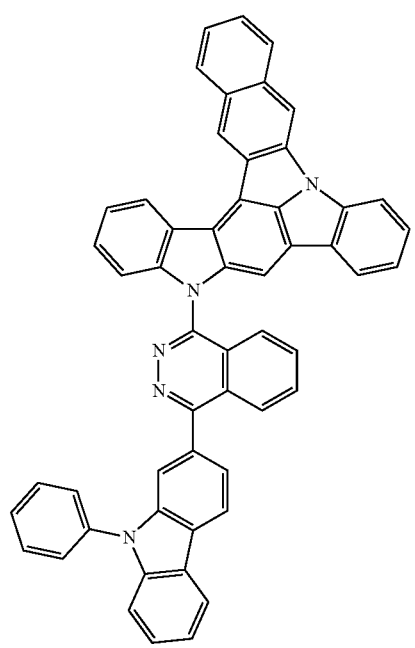
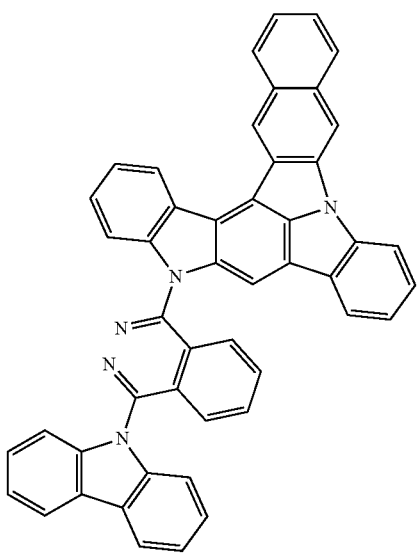

1255
-continued
1256
-continued
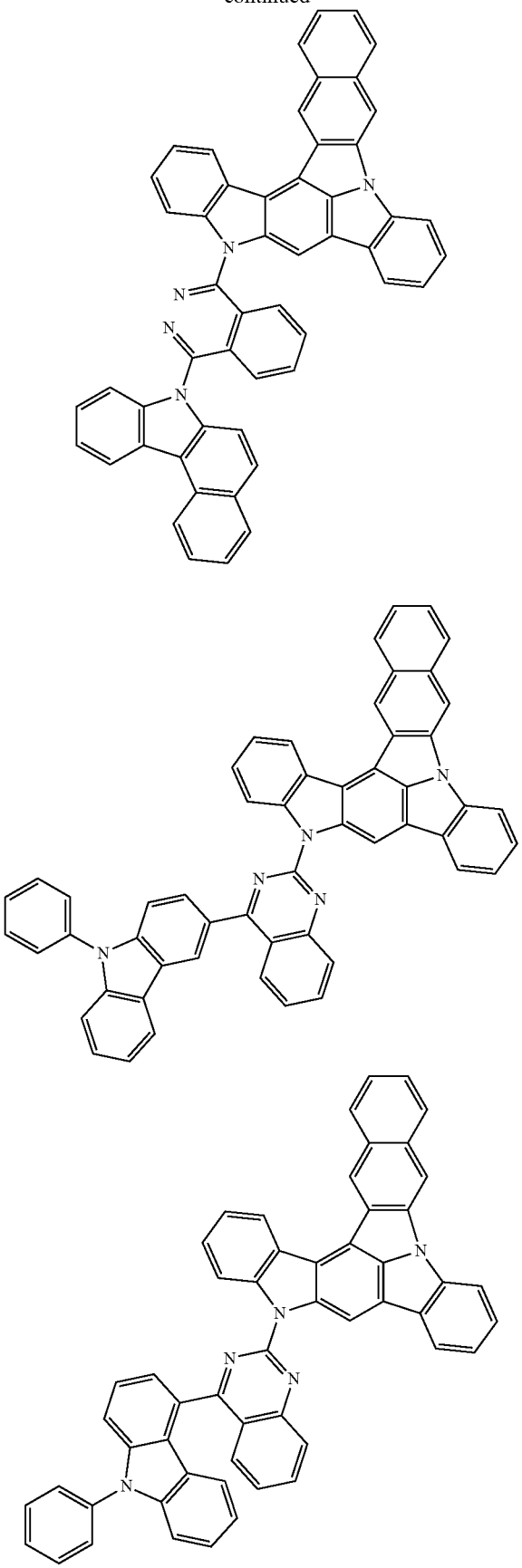
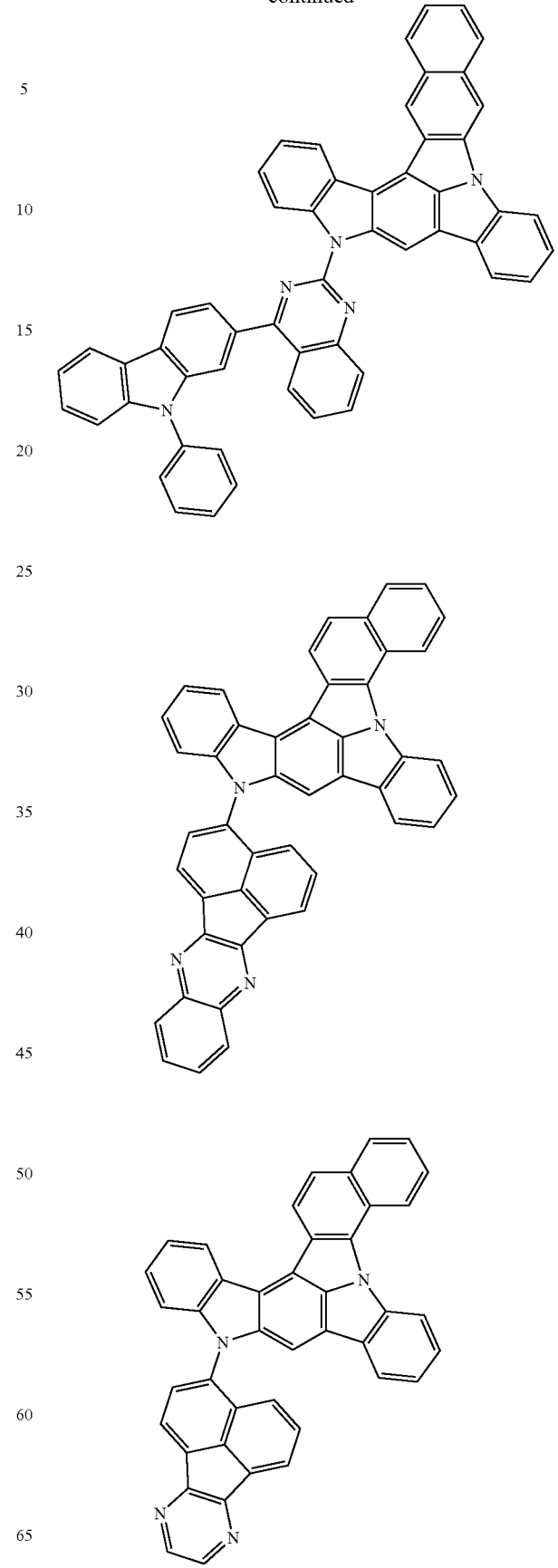

1257
-continued
1258
-continued
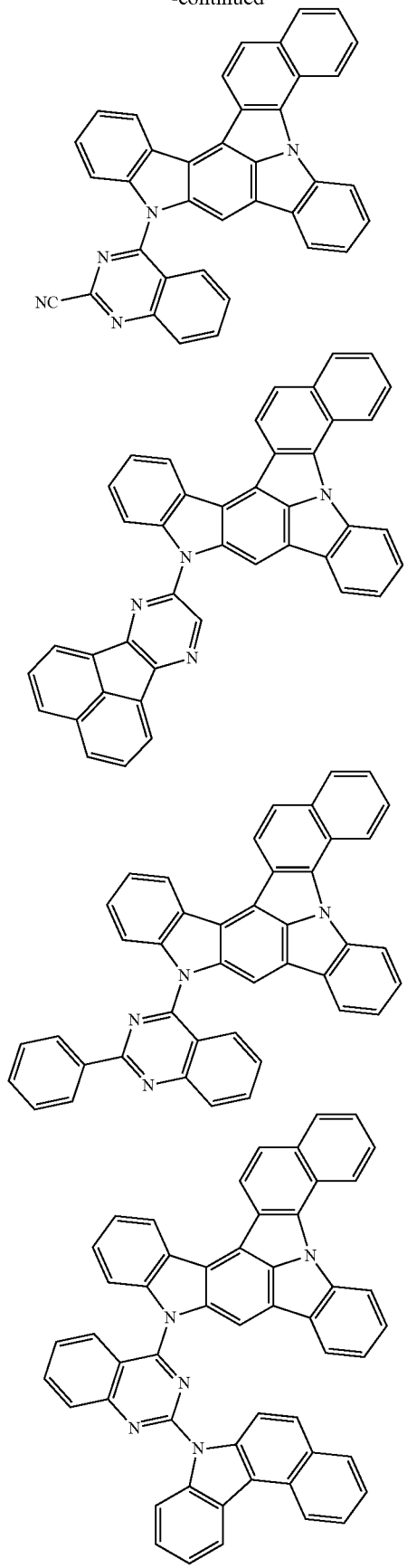
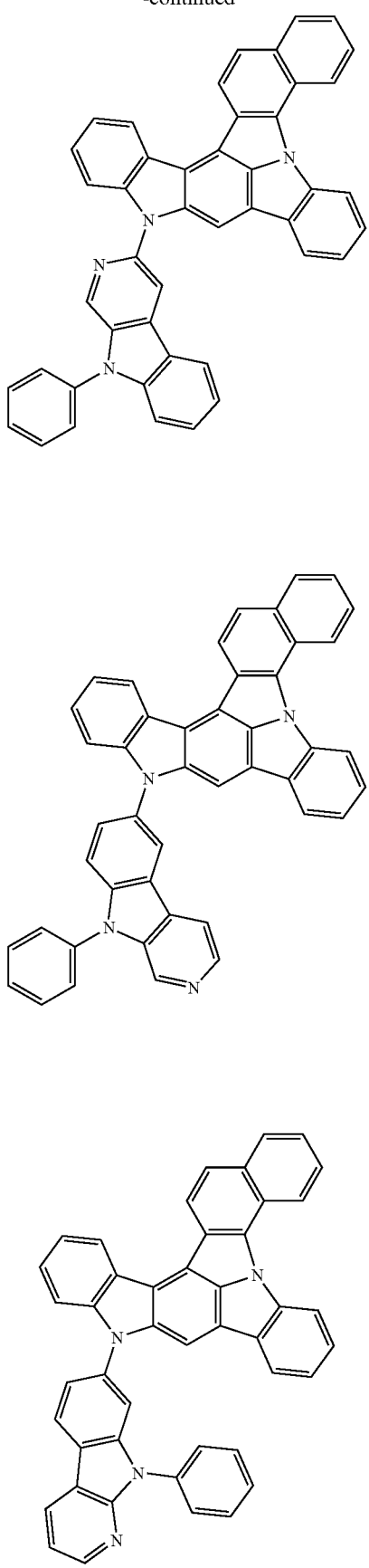

1259
-continued
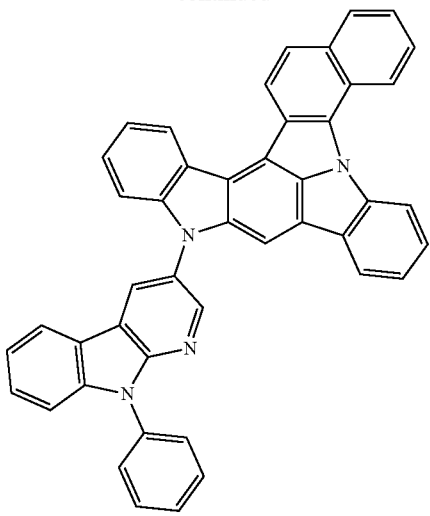
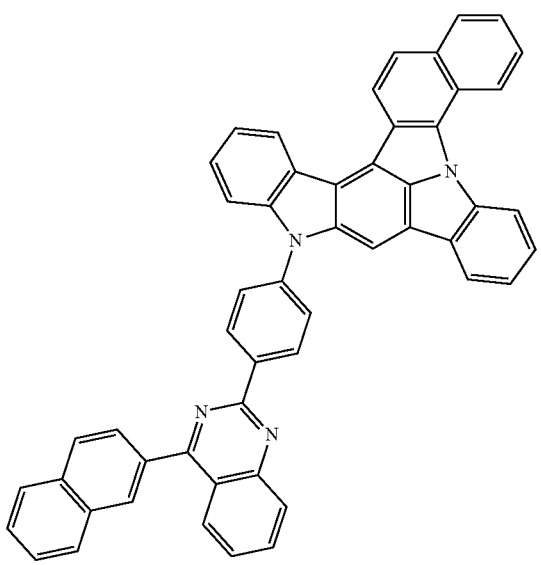
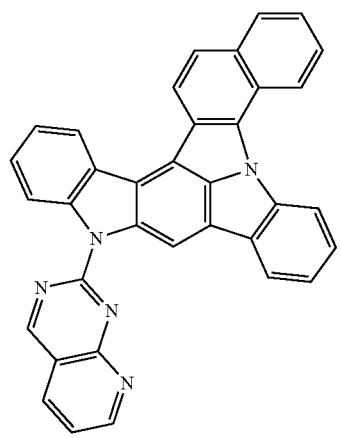
1260
-continued
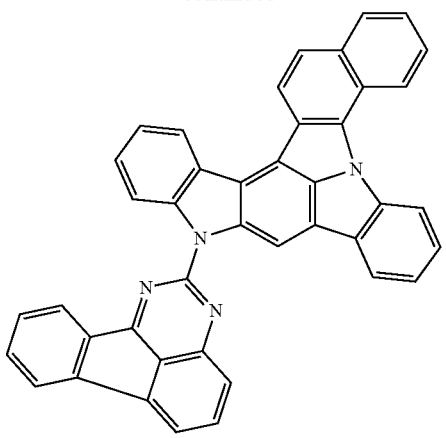
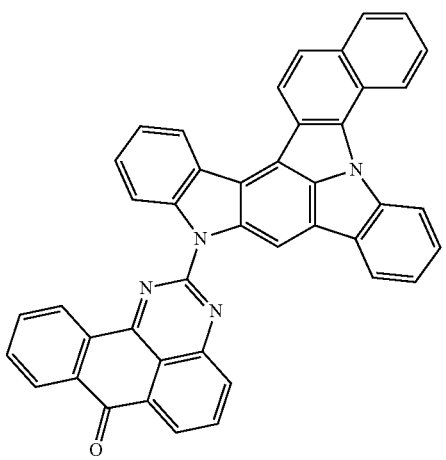
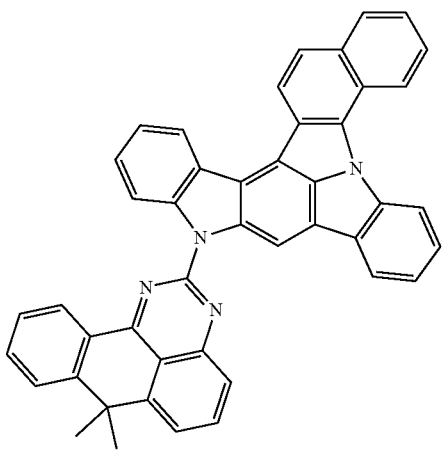

1261
-continued
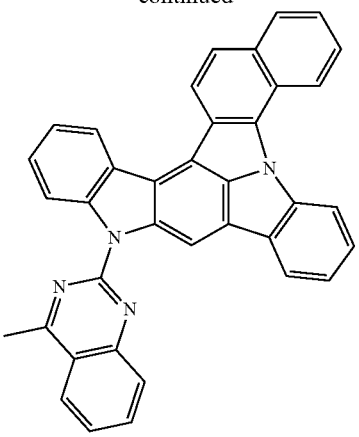
1262
-continued
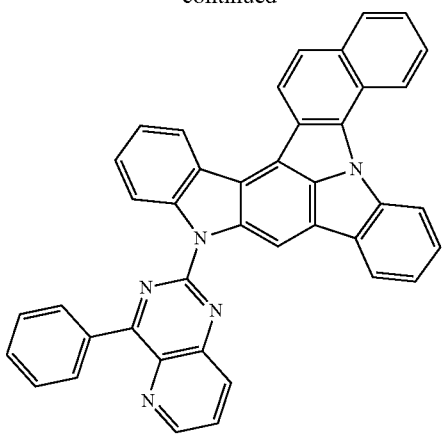
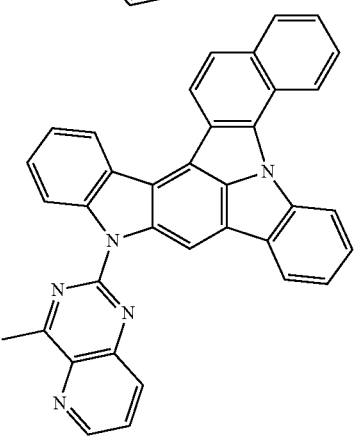
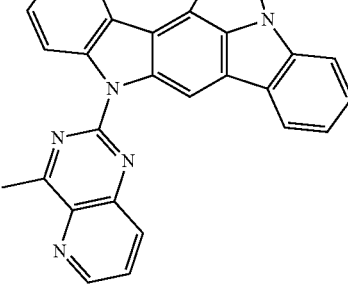
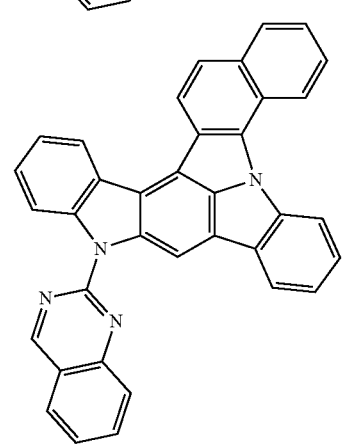
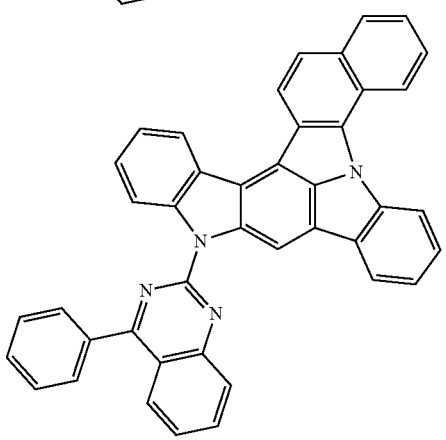

1263
-continued
1264
-continued
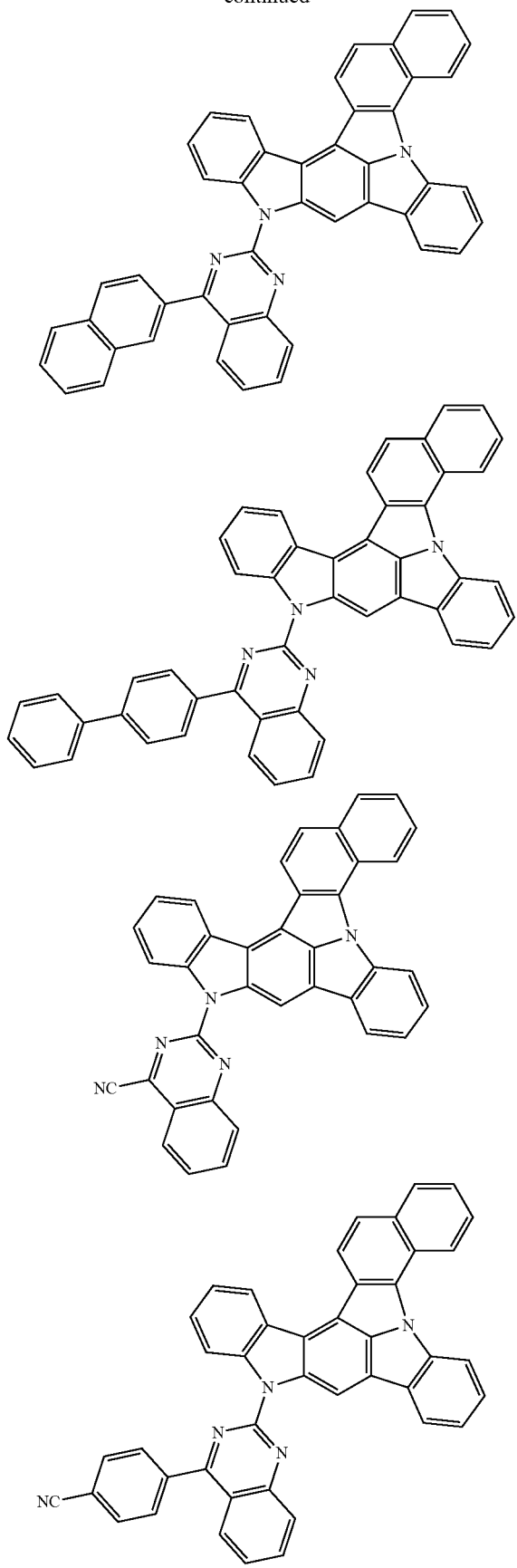
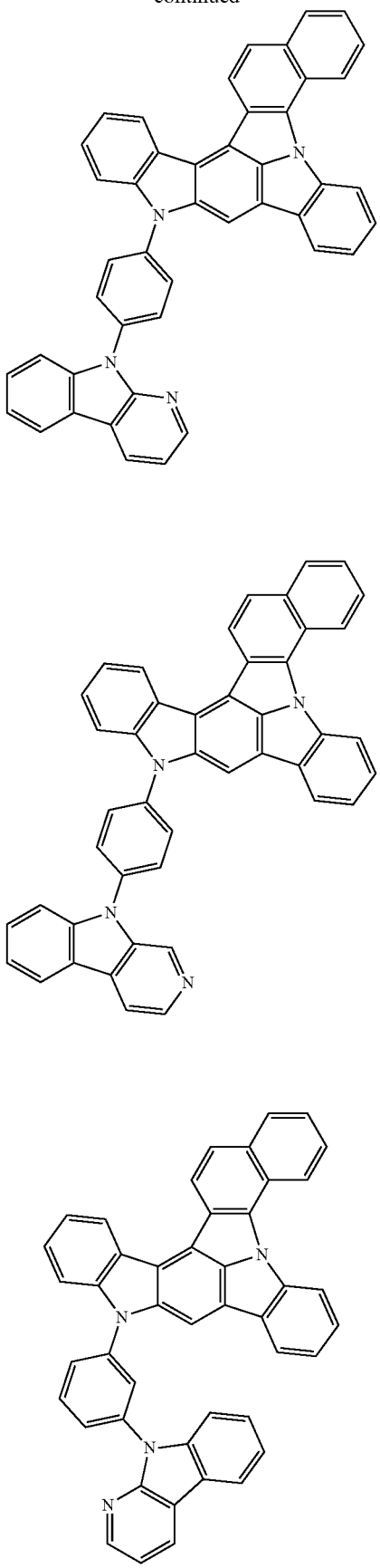

1265
-continued
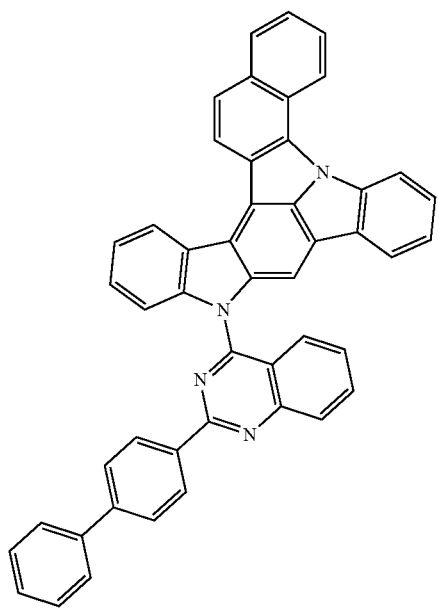
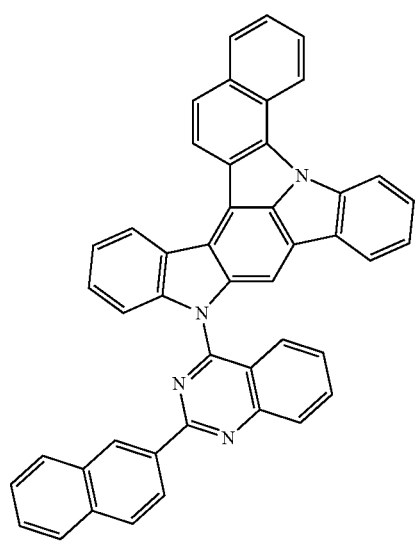
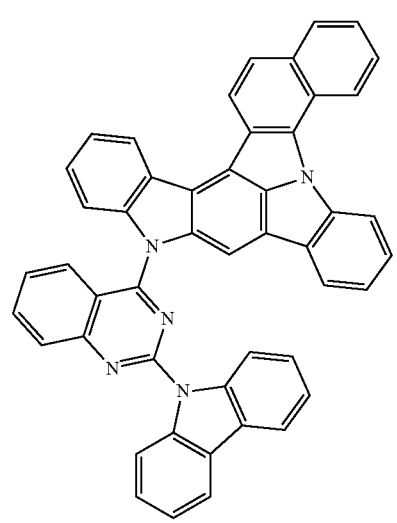
1266
-continued
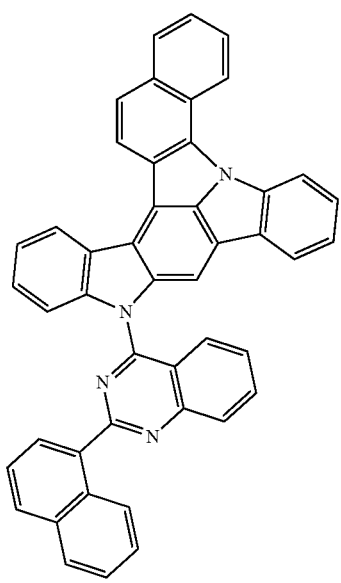
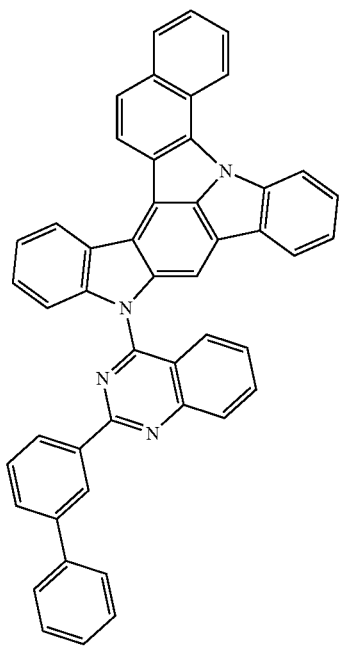

1267
-continued
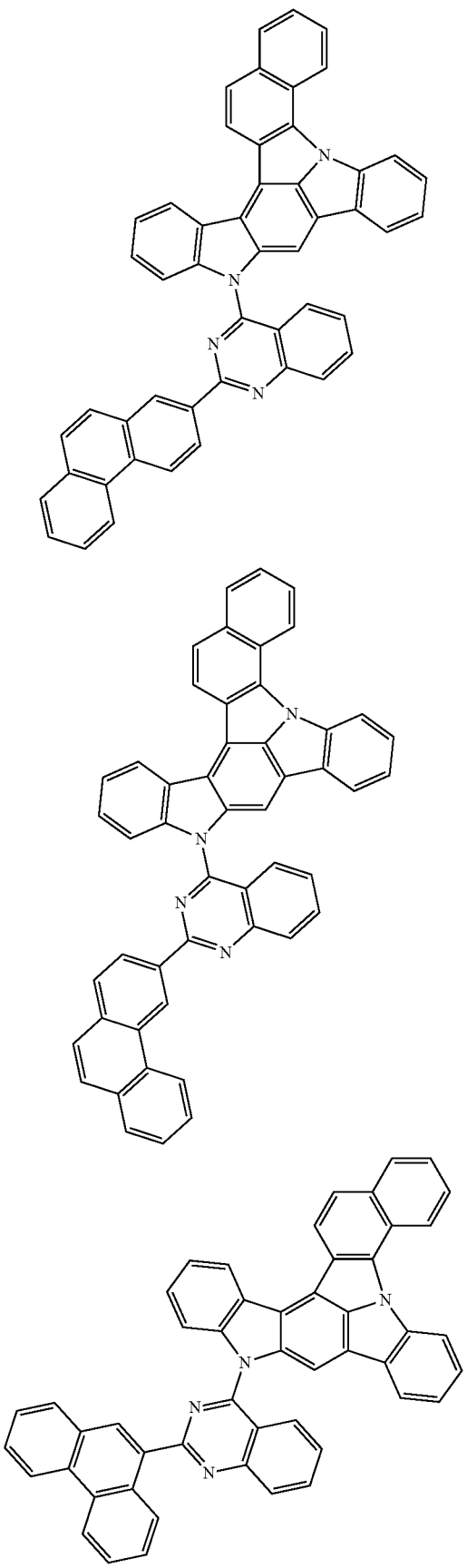
1268
-continued
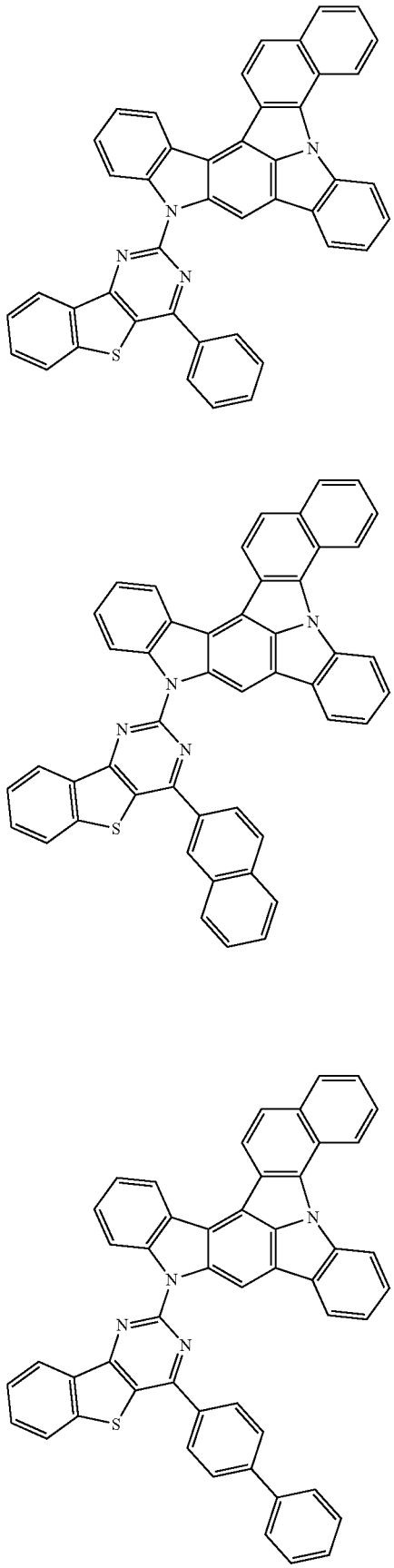

1269
-continued
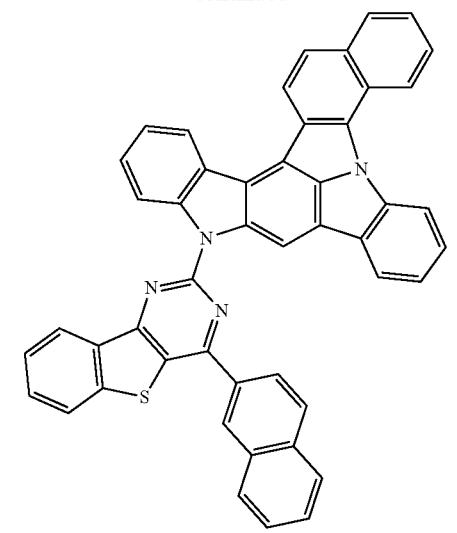 [SMILES: c1ccc2cc(-c3nc(-n4c5ccccc5c5c6c7ccc8ccccc8c7n7c8ccccc8c(cc54)c67)nc4c3sc3ccccc34)ccc2c1]
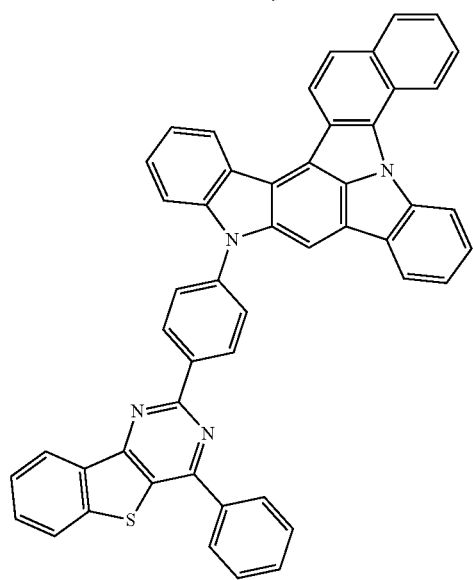
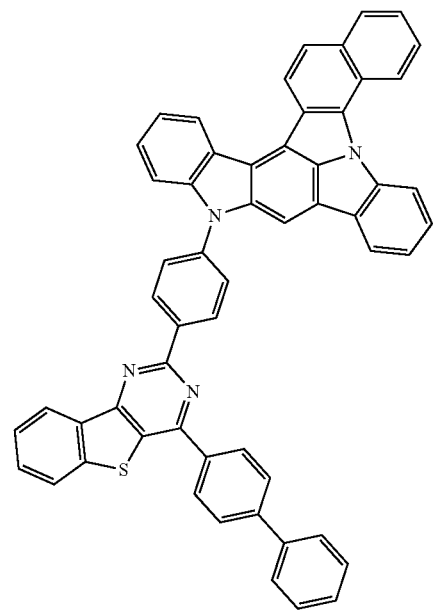
1270
-continued
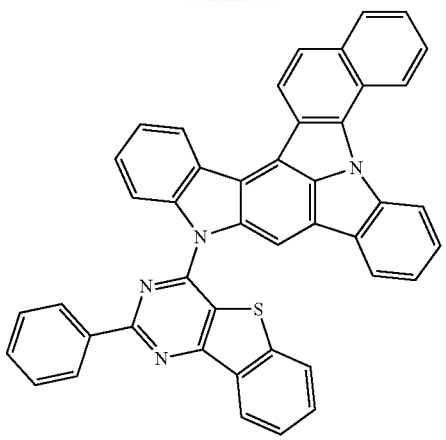
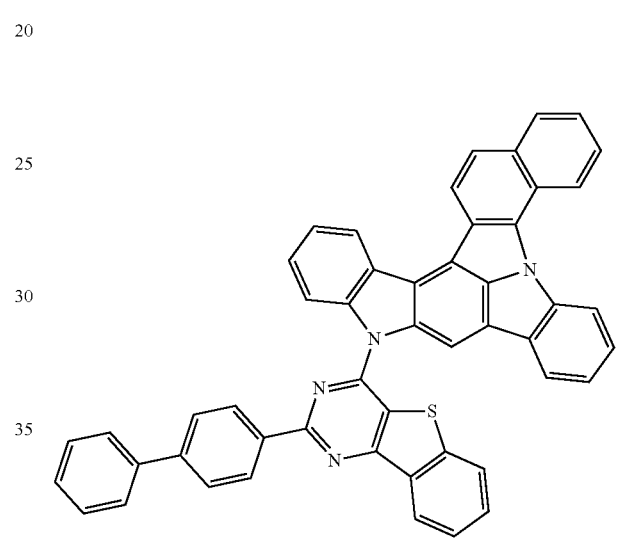
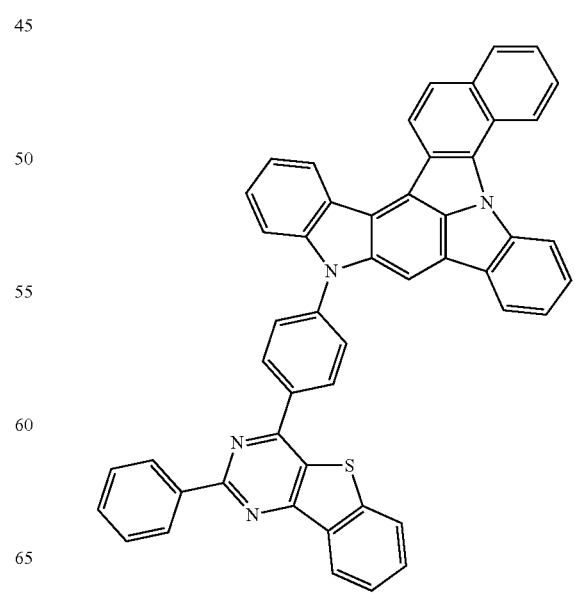

1271
-continued
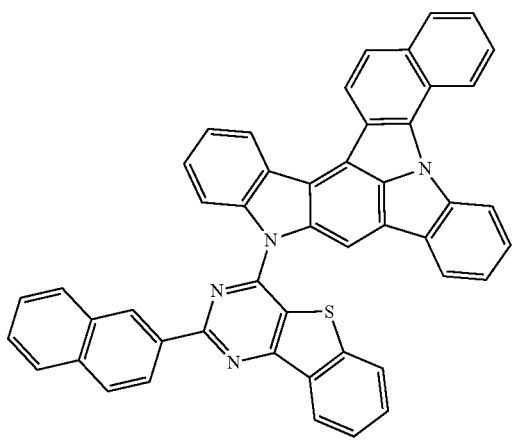
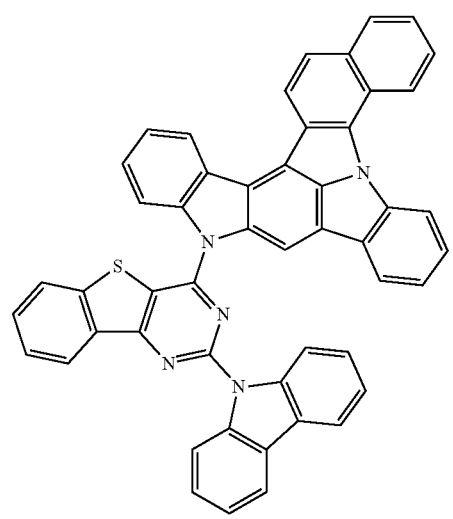
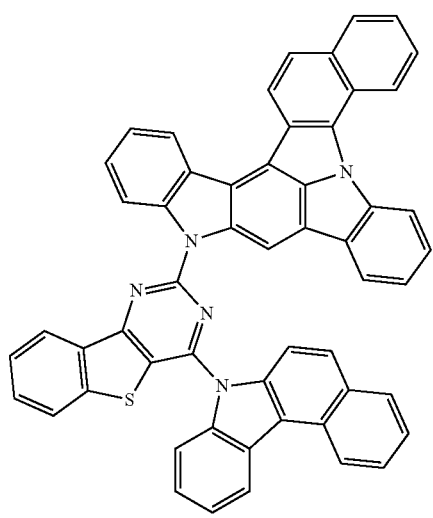
1272
-continued
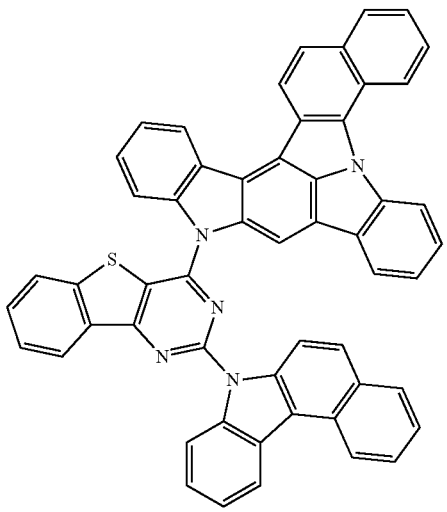
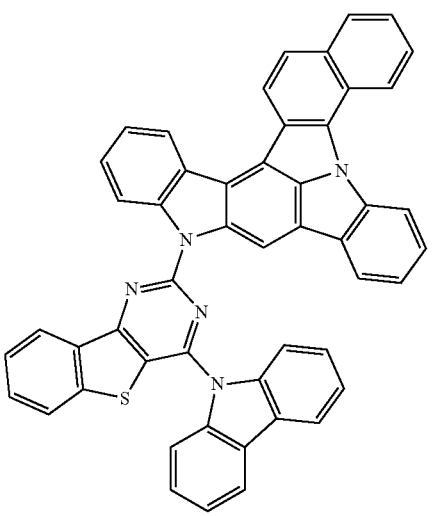
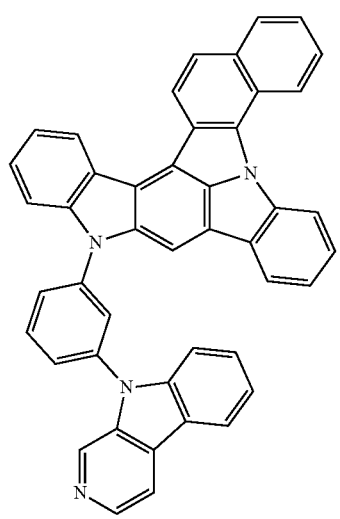

1273
-continued
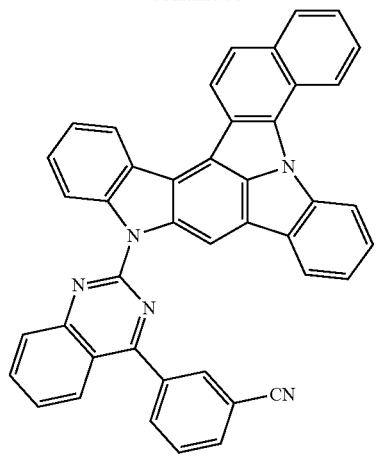
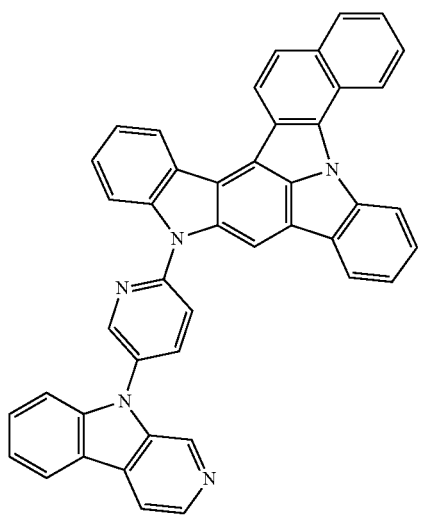
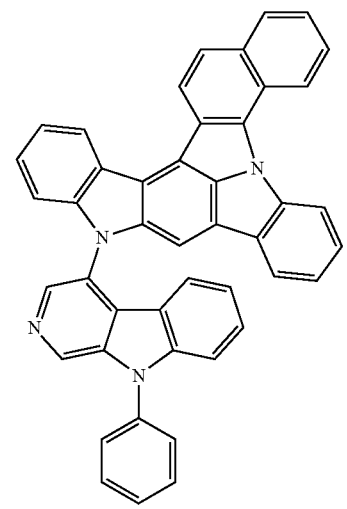
1274
-continued
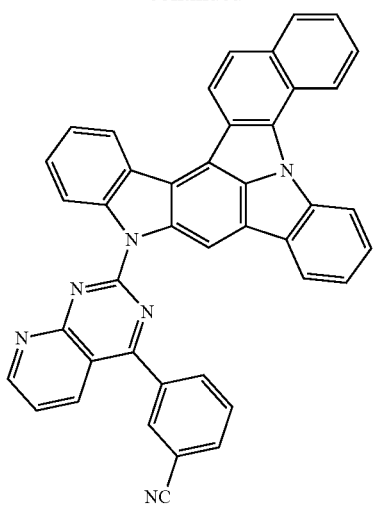
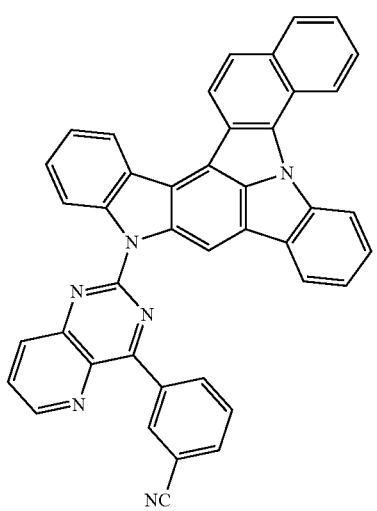
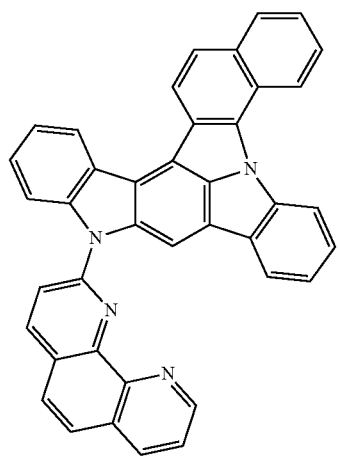

1275
-continued
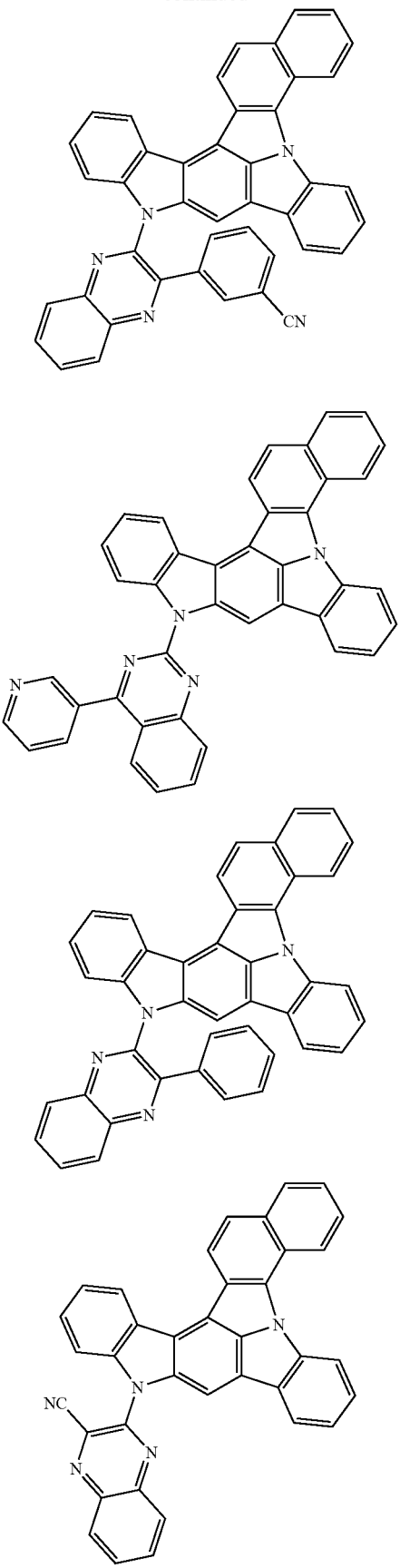
1276
-continued
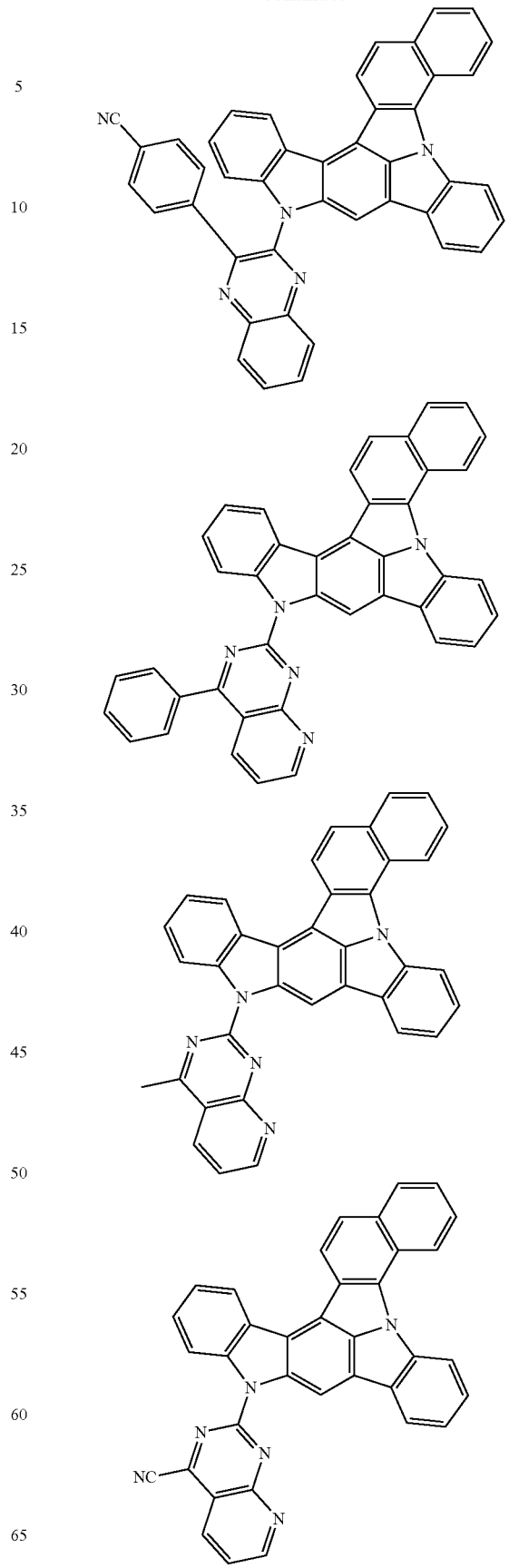

1277
-continued
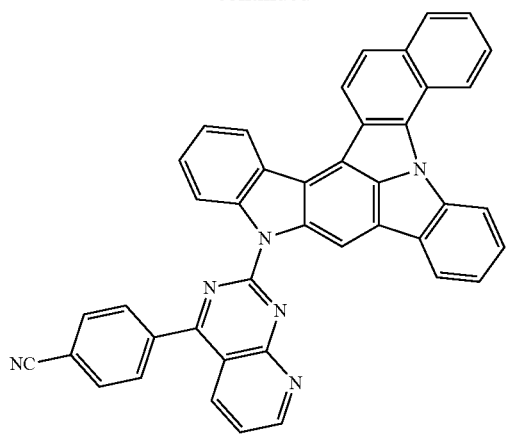
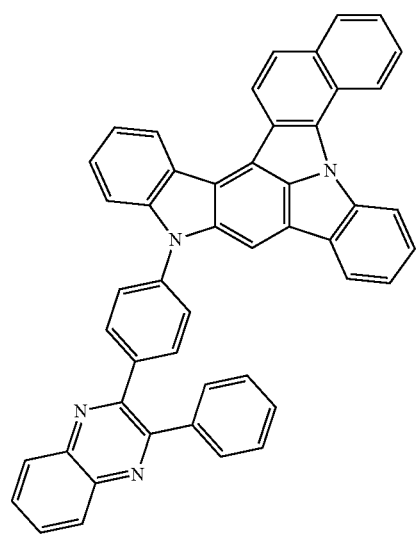
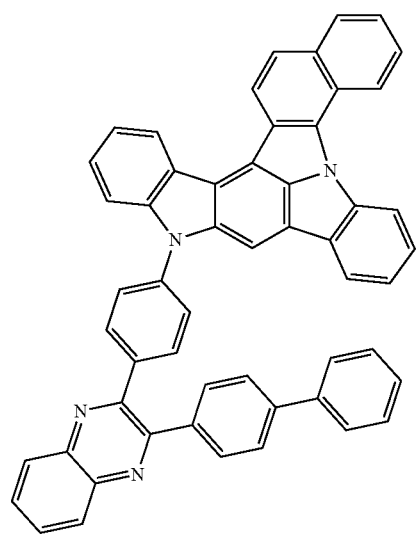
1278
-continued
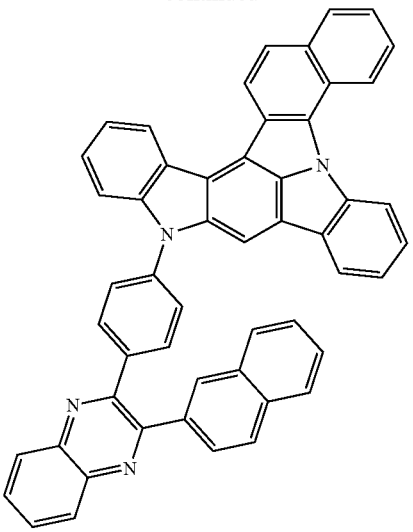
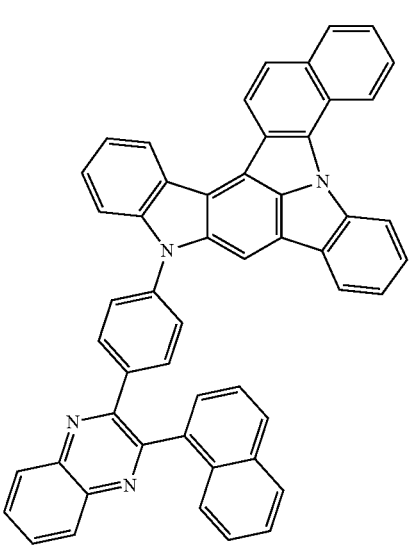
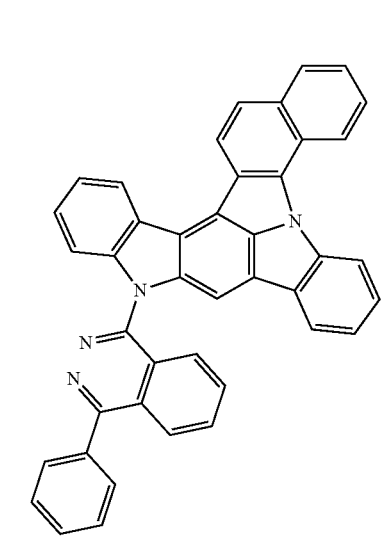

1279
-continued
1280
-continued
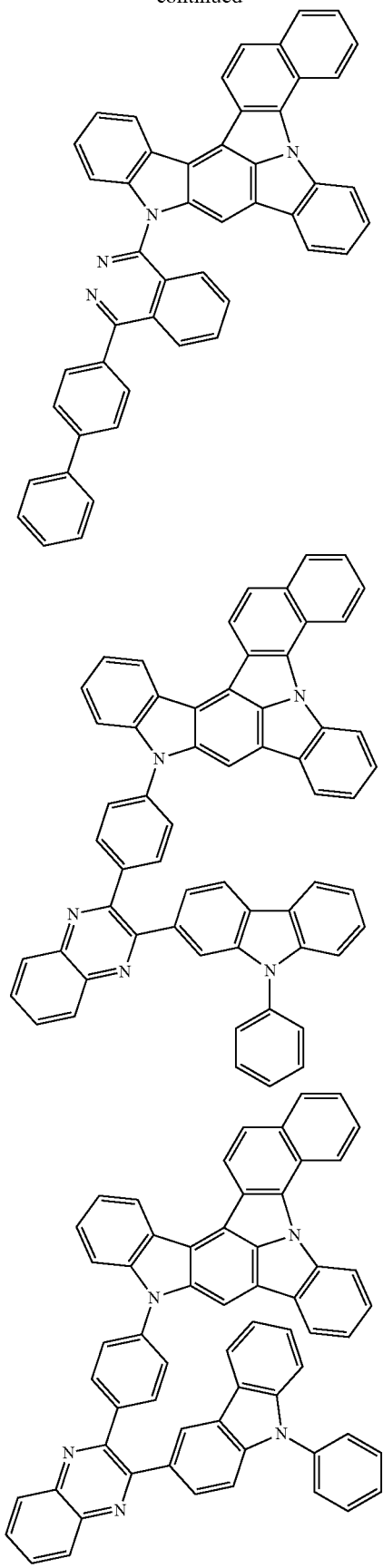
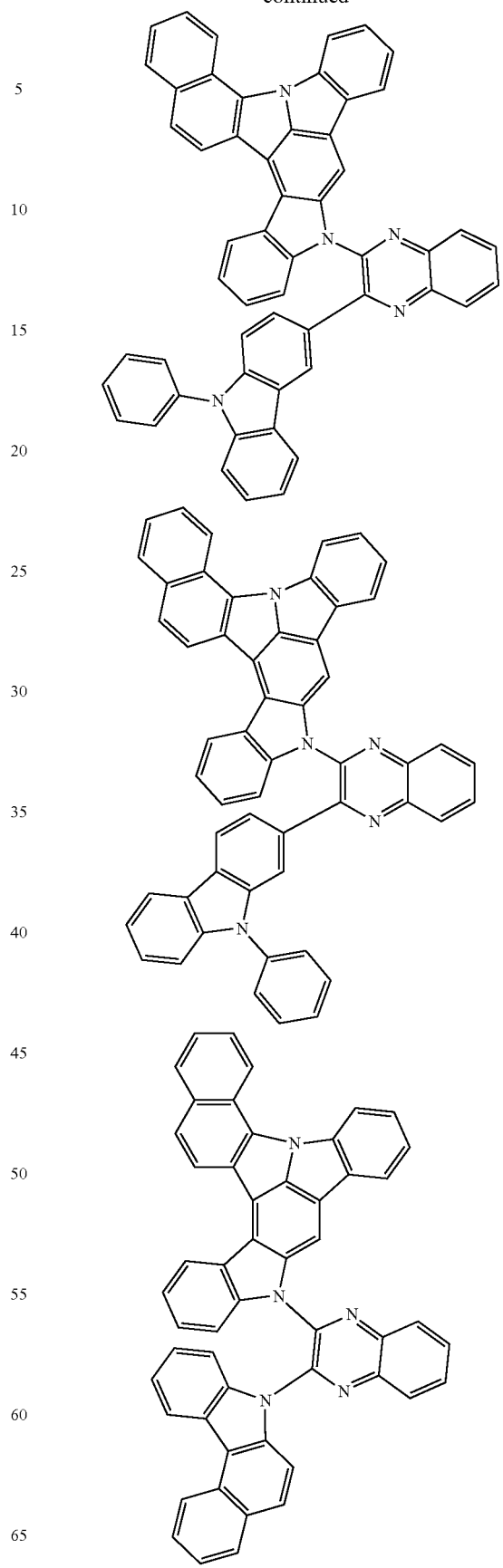

1281
-continued
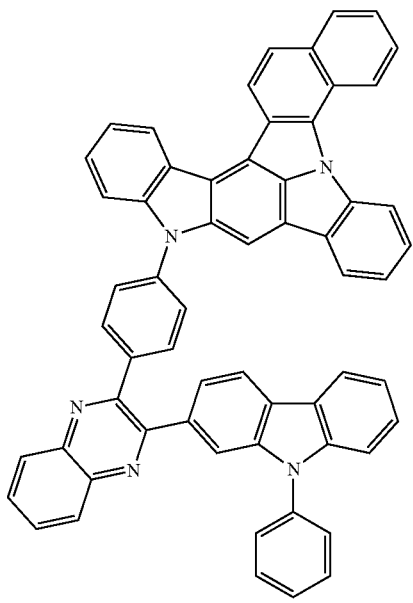
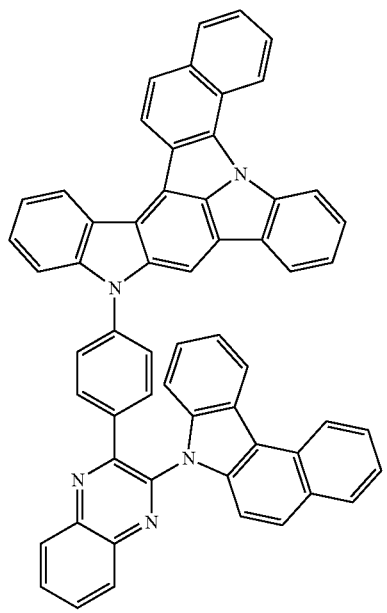
1282
-continued
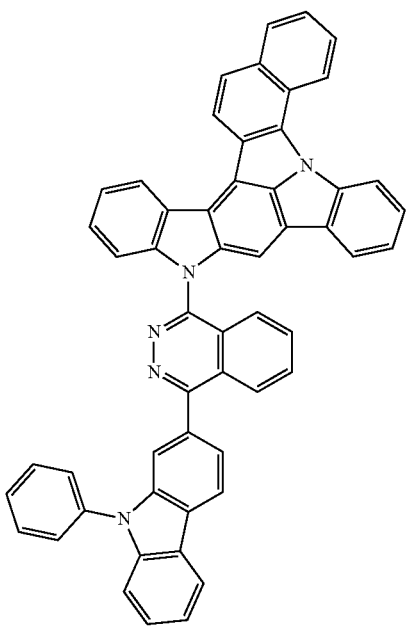
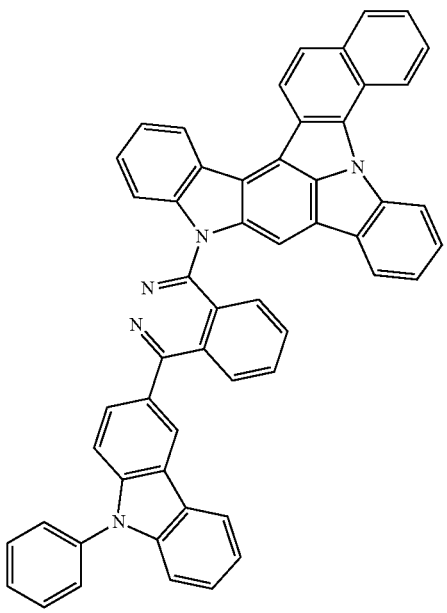

1283
-continued
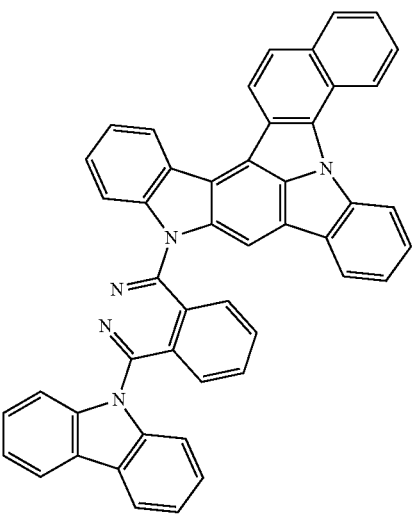
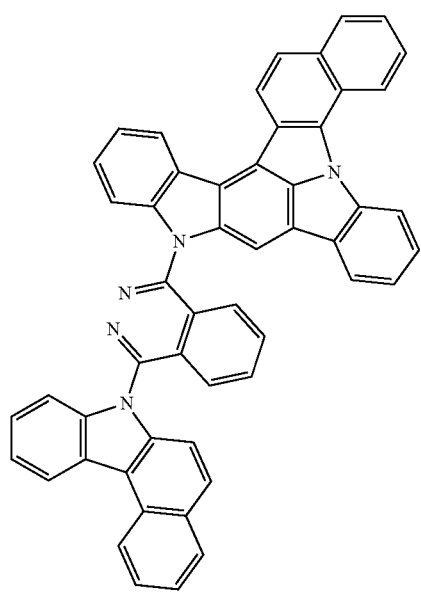
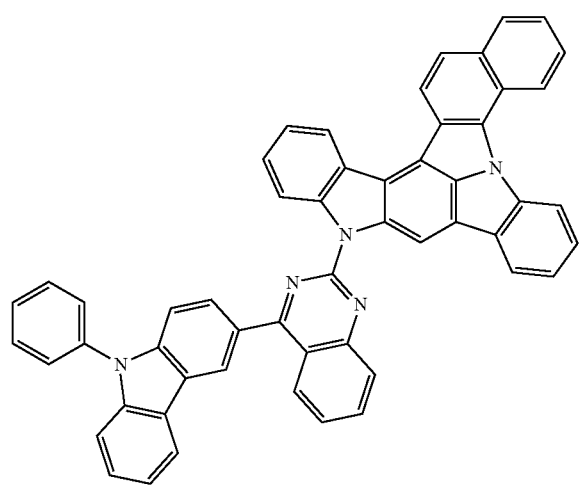
1284
-continued
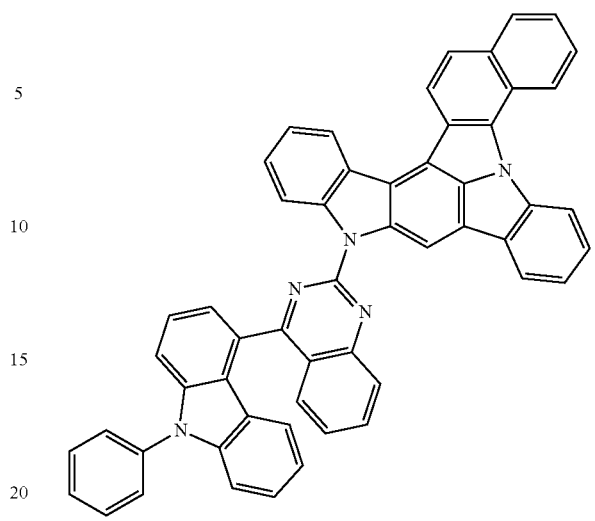
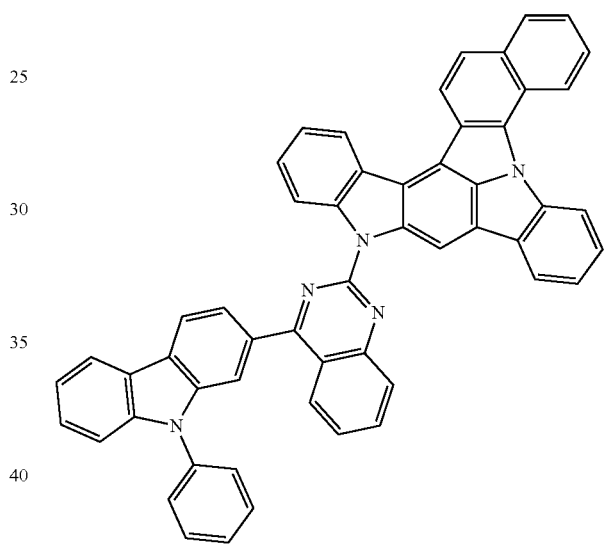
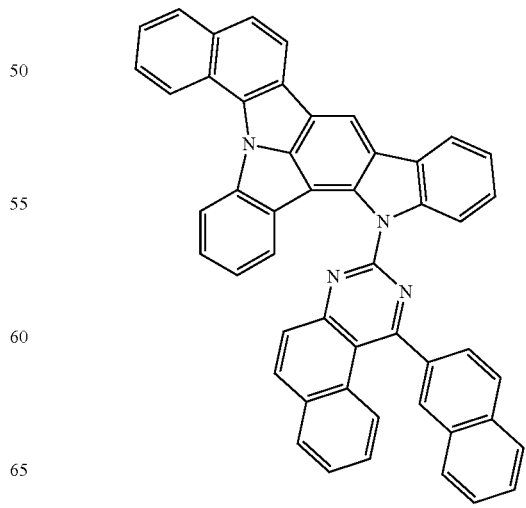

1285
-continued
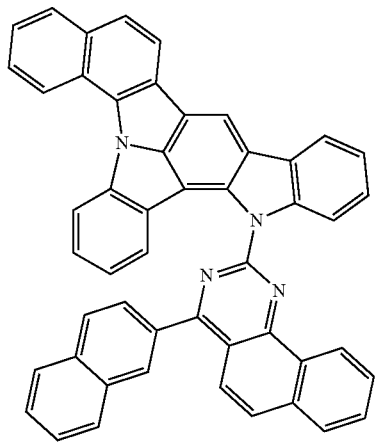
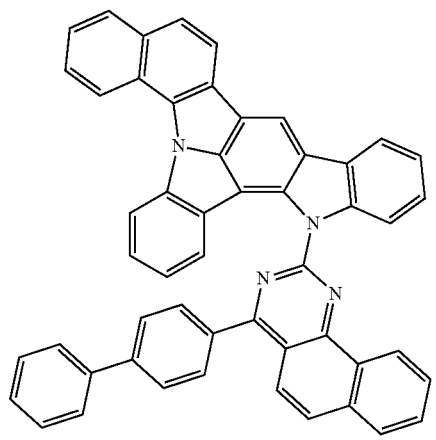
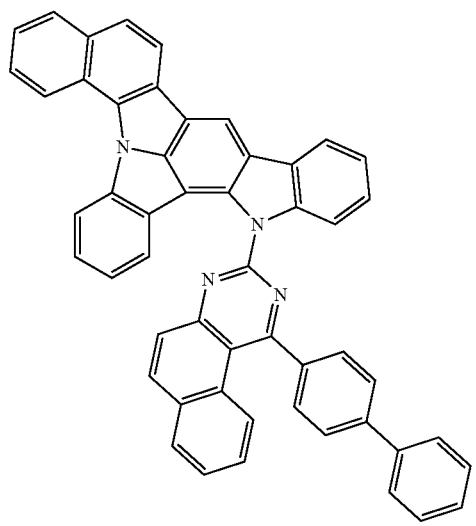
1286
-continued
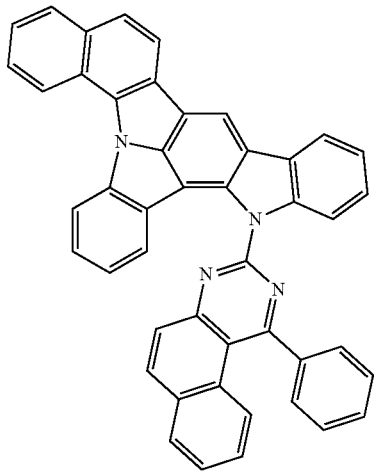
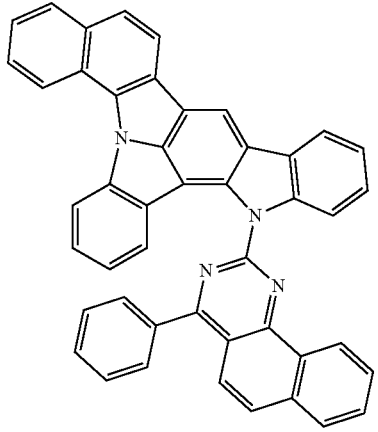
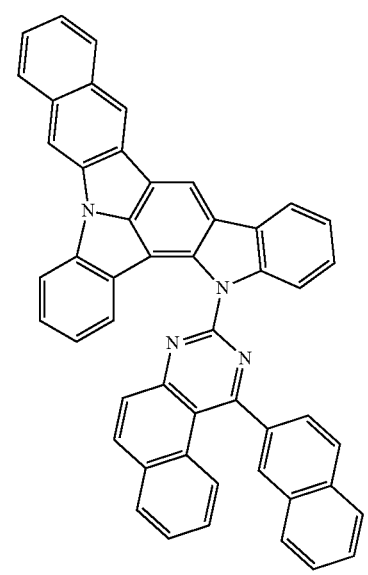

1287
-continued
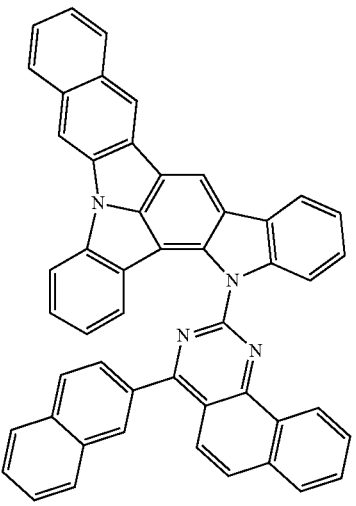
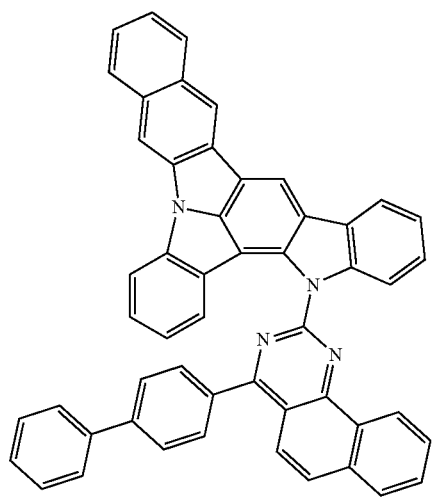
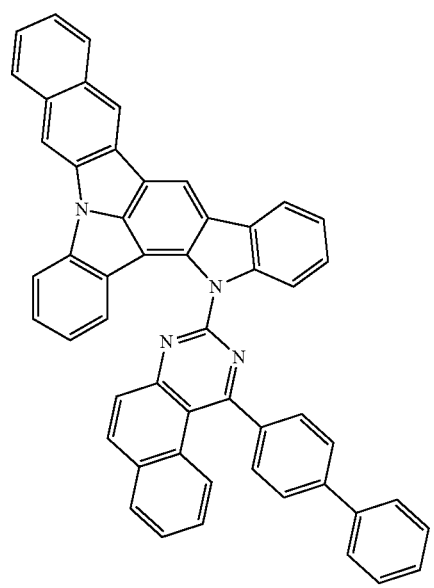
1288
-continued
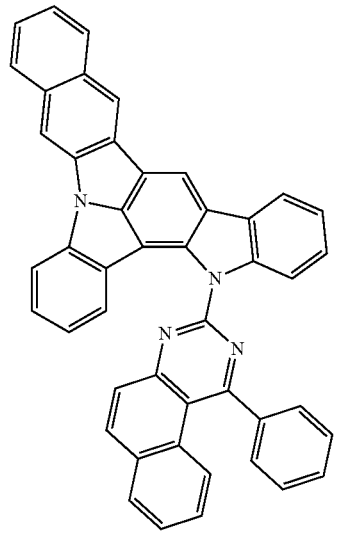
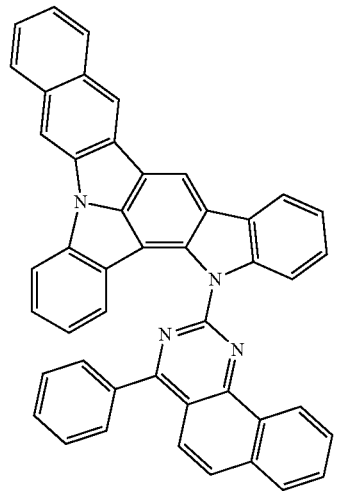
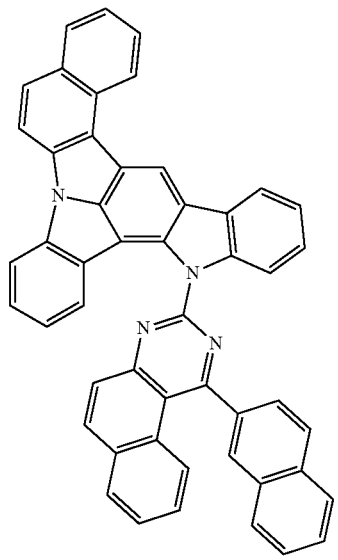

1289
-continued
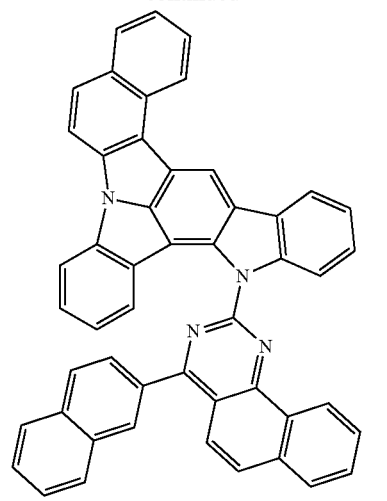
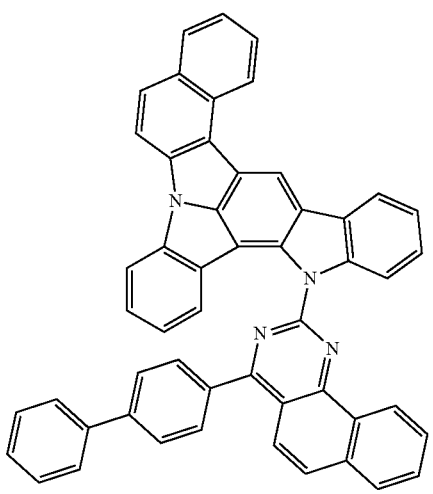
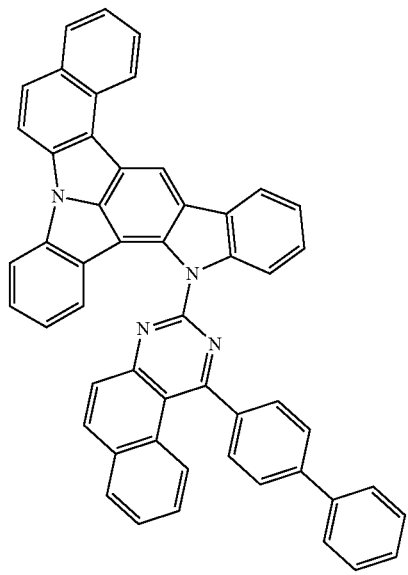
1290
-continued
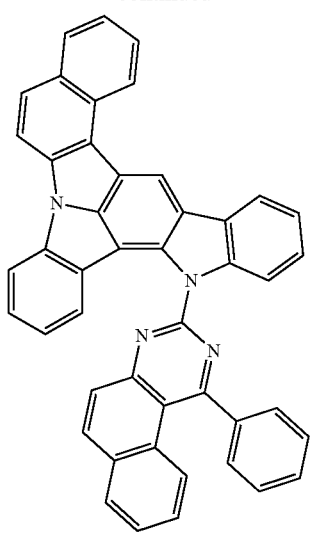
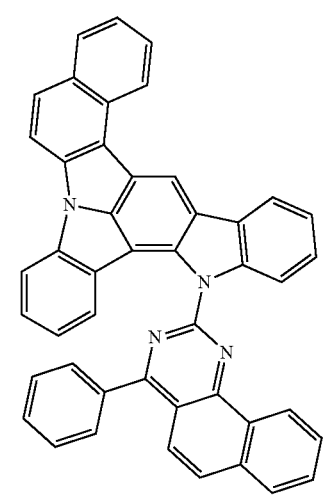

1291
-continued
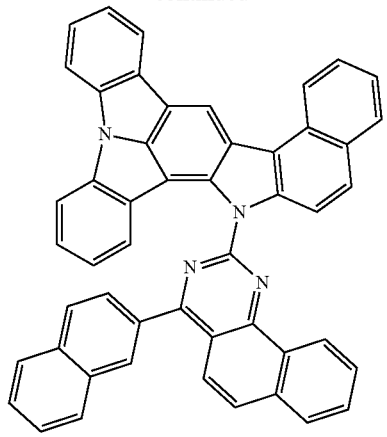
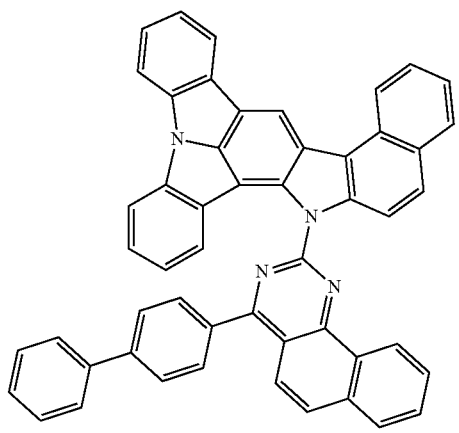
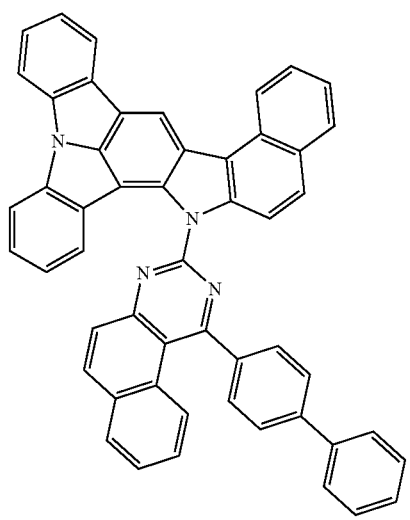
1292
-continued
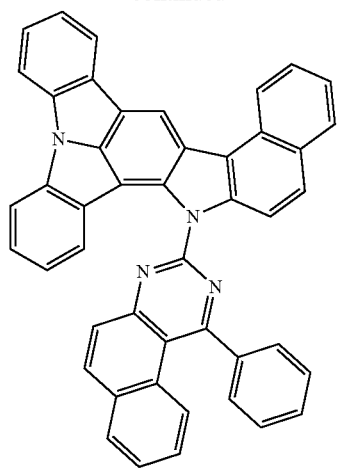
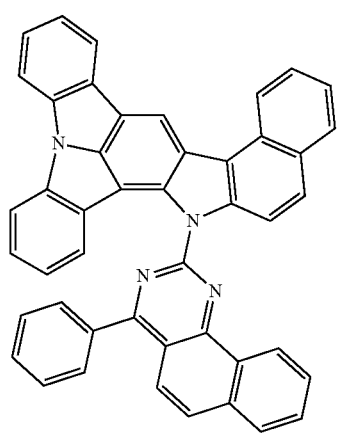
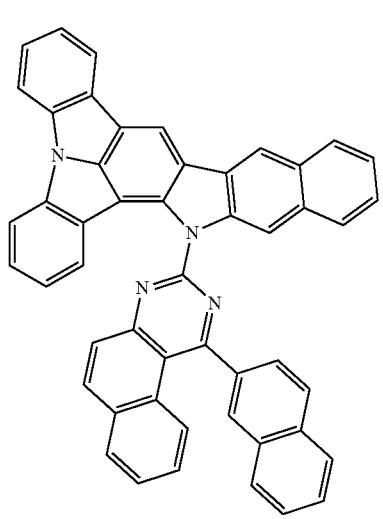

1293
-continued
1294
-continued
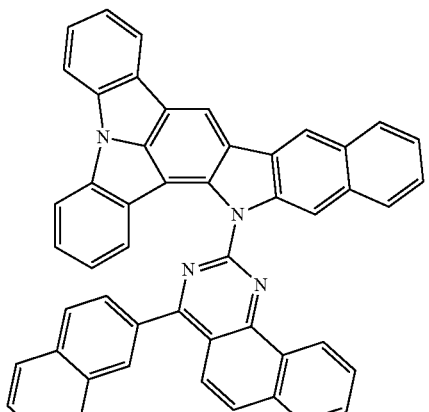
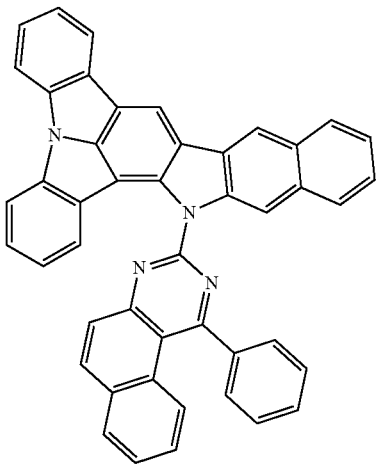
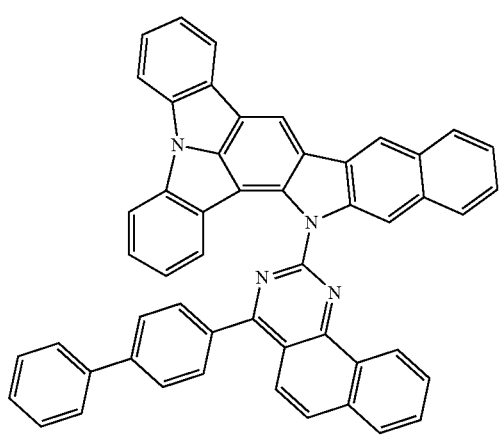
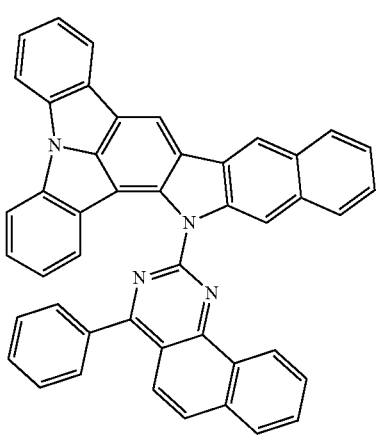
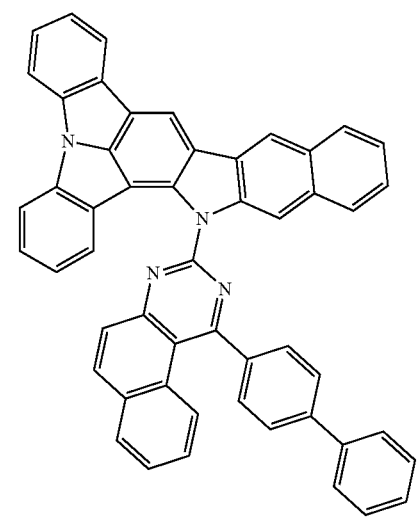
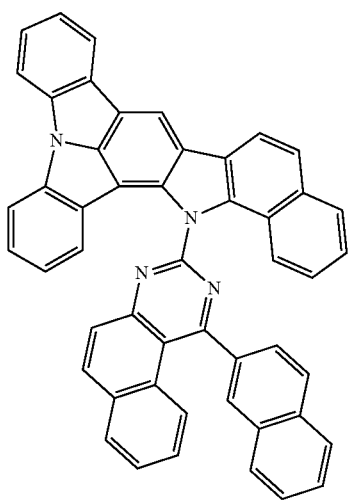

1295
-continued
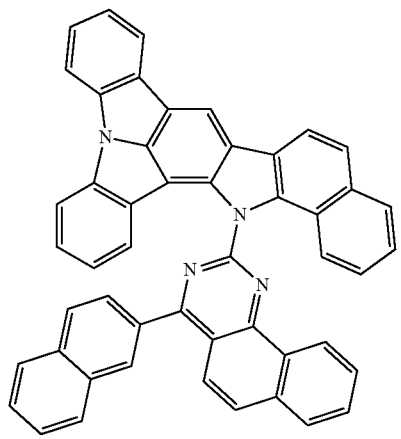
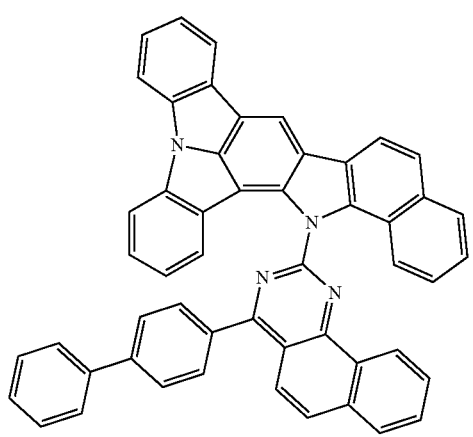
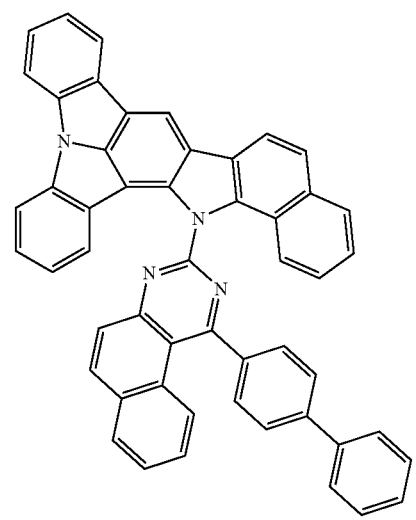
1296
-continued
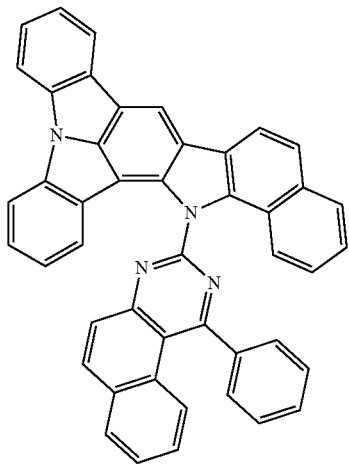
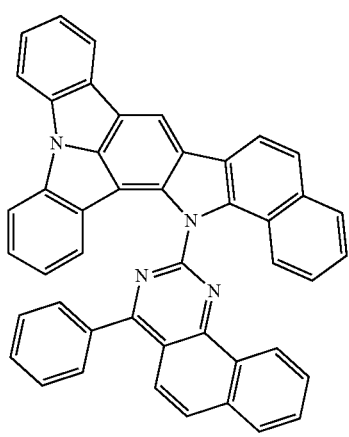
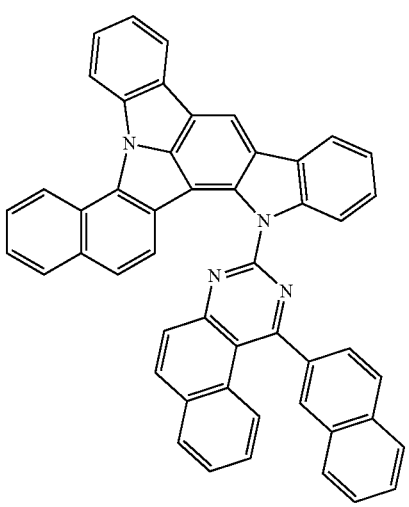

1297
-continued
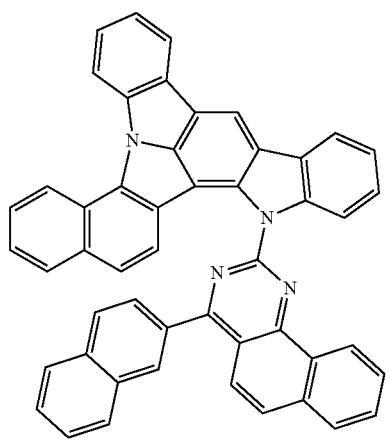
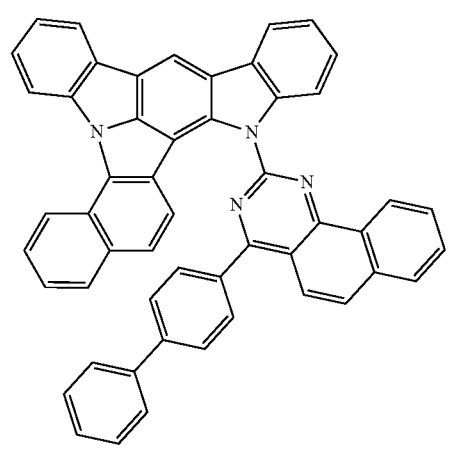
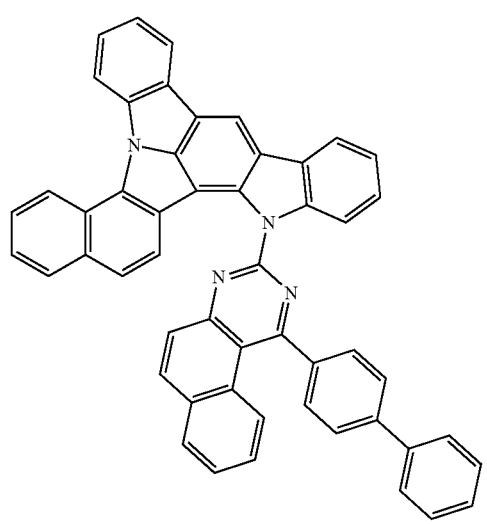
1298
-continued
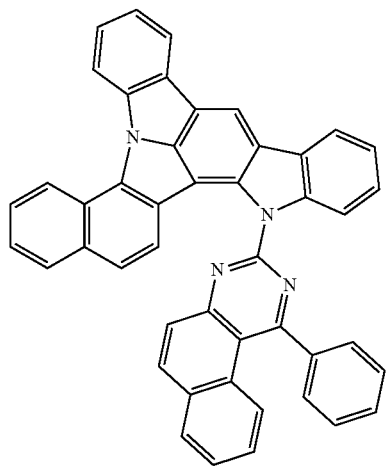
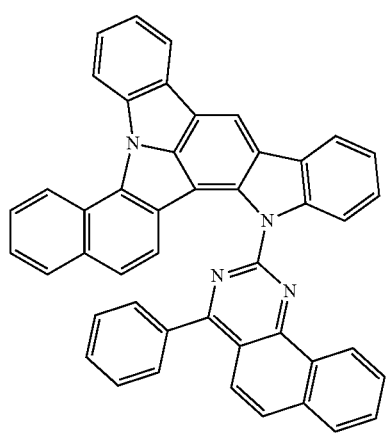
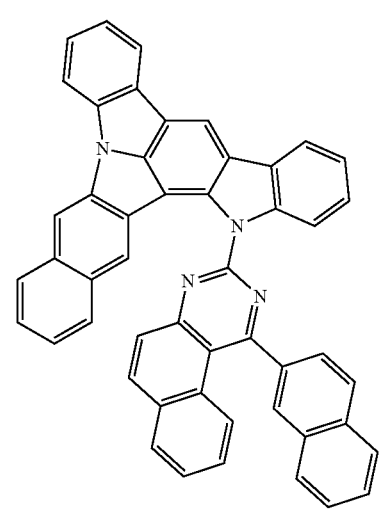

1299
-continued
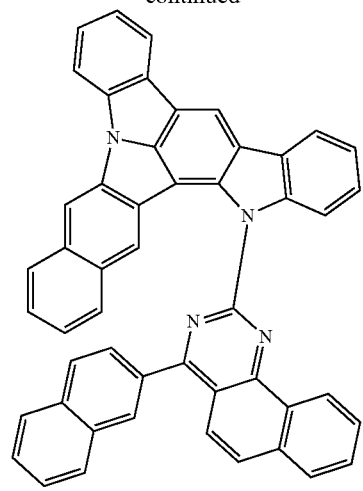
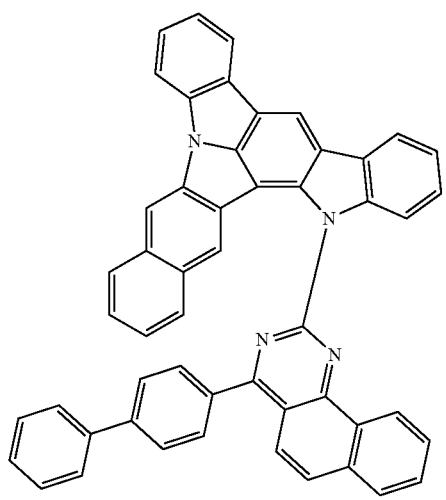
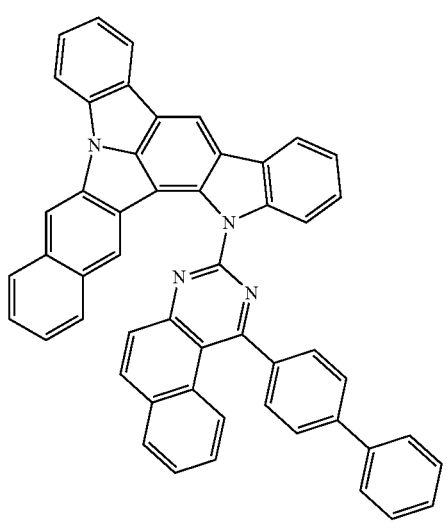
1300
-continued
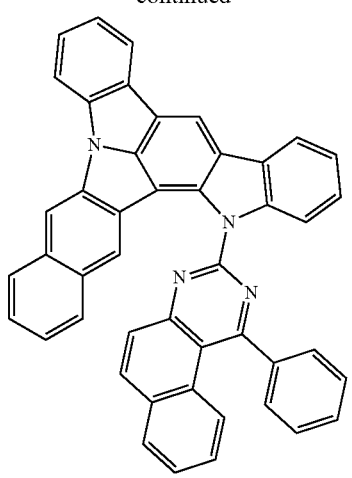
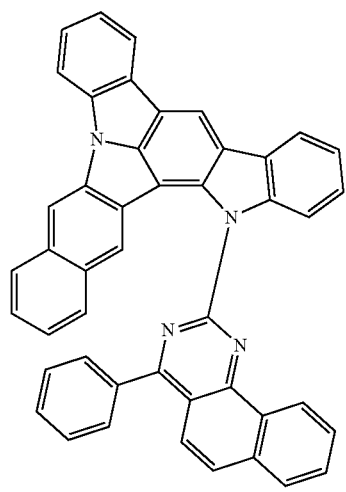
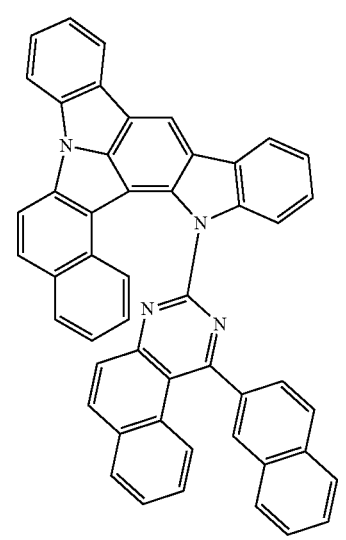

1301
-continued
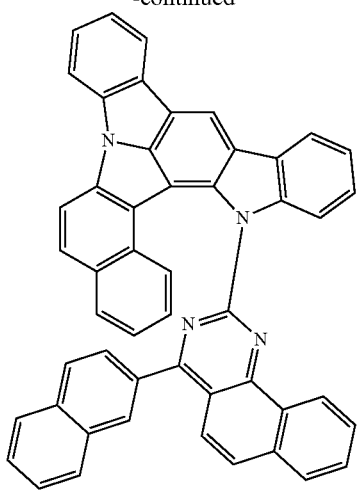
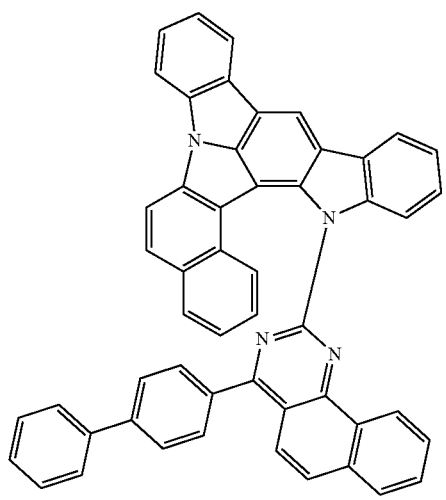
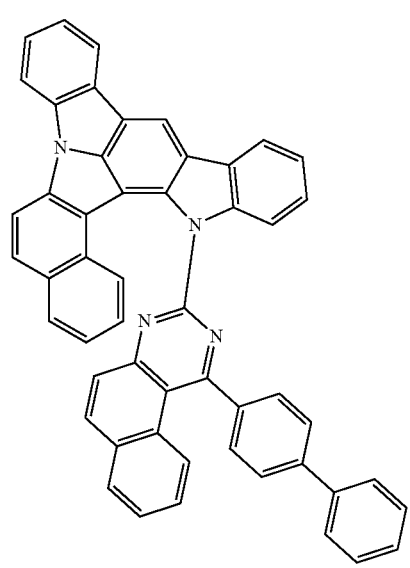
1302
-continued
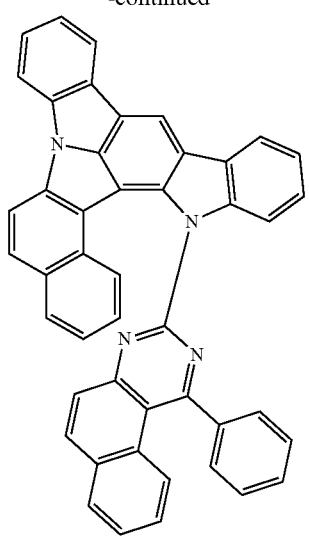
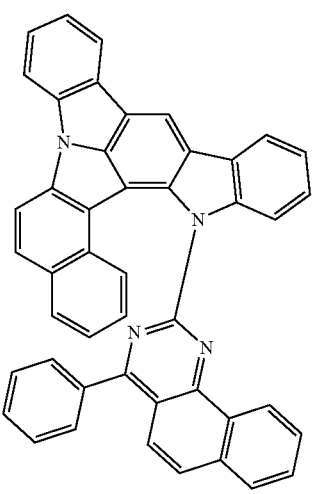
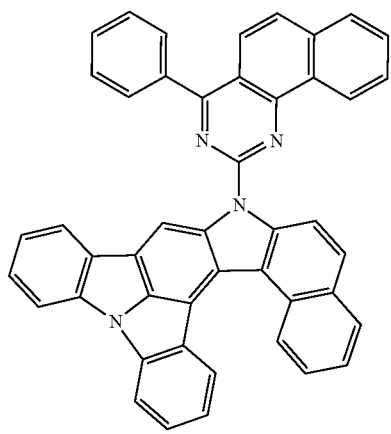

1303
-continued
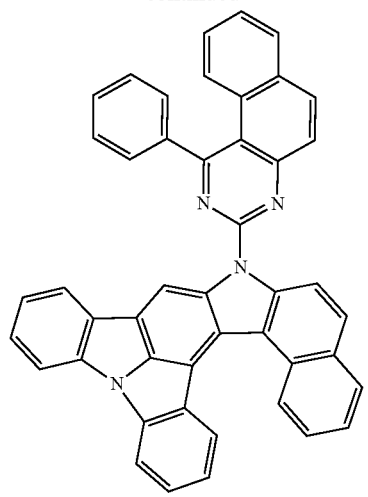
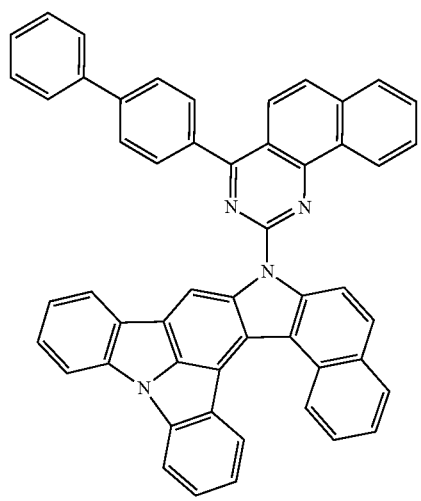
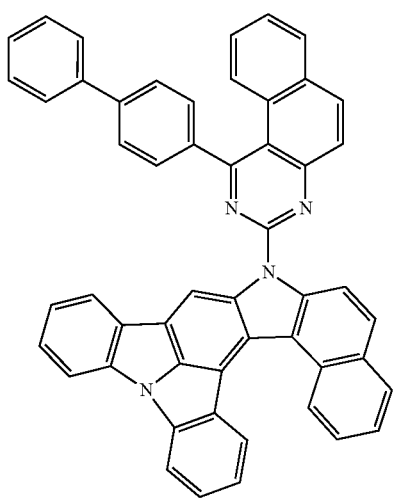
1304
-continued
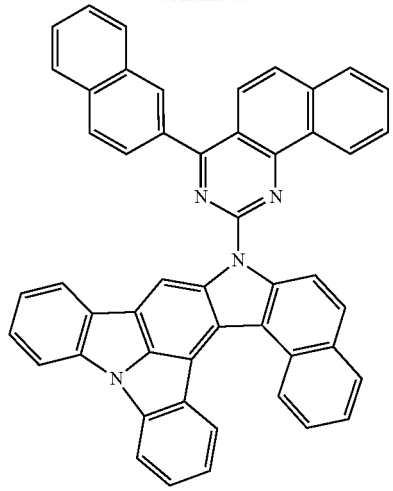
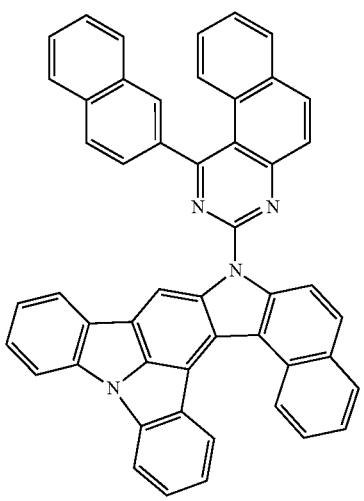
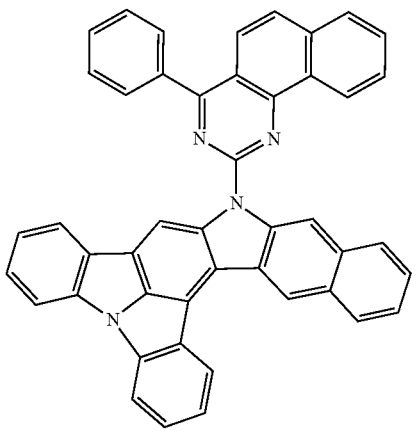

1305
-continued

1306
-continued

1307
-continued
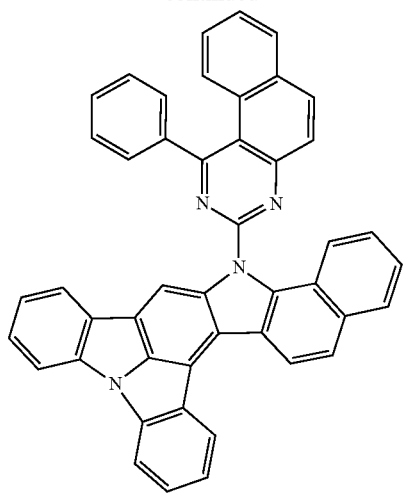
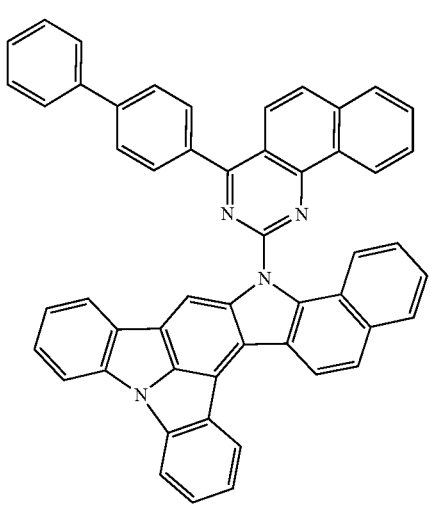
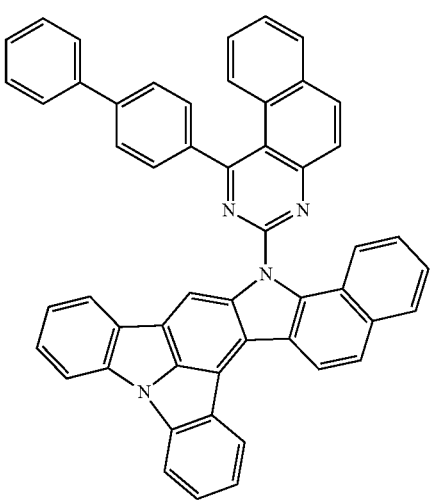
1308
-continued
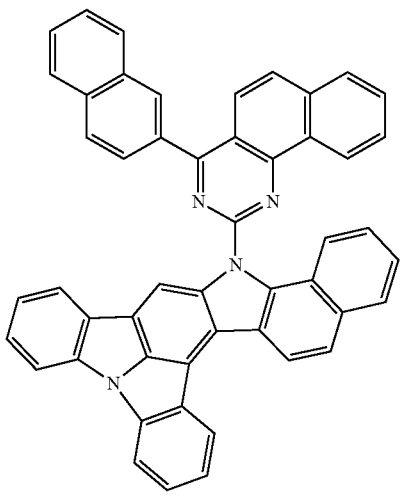
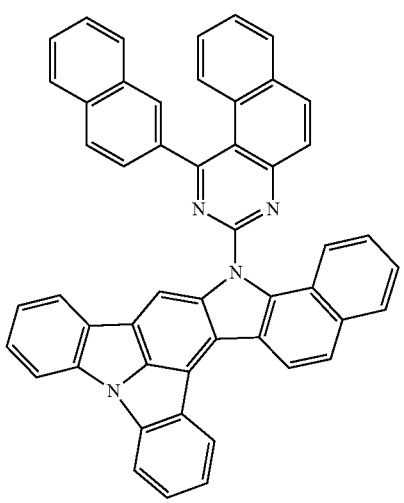
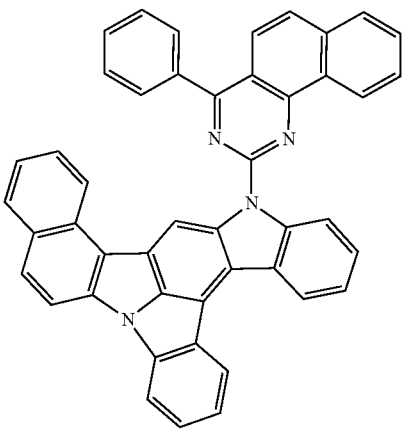

1309
-continued
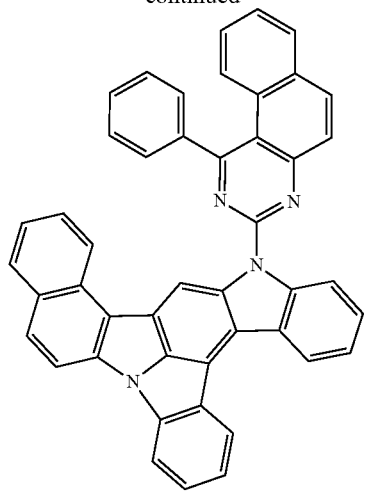
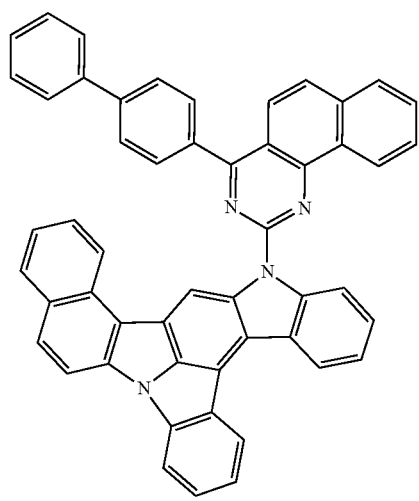
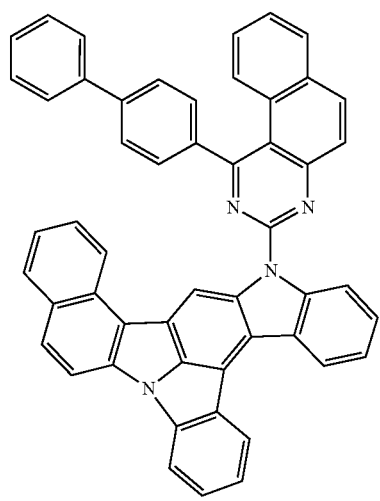
1310
-continued
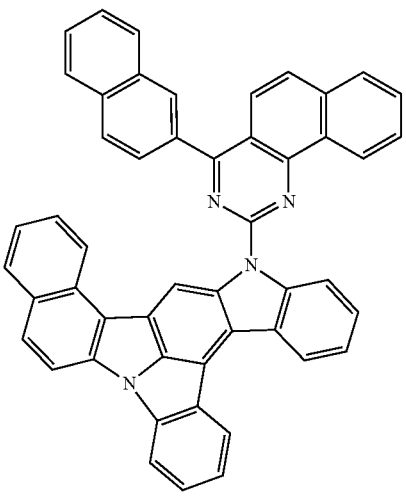
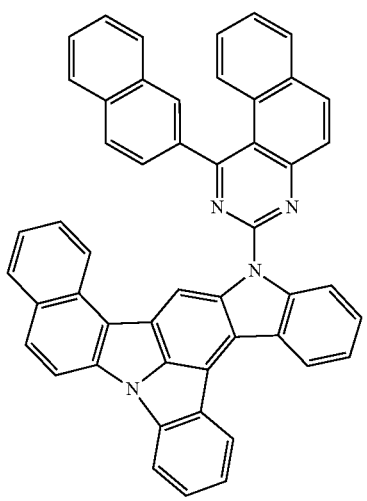
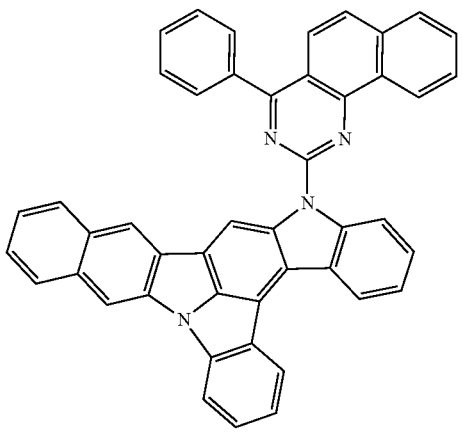

| 1311 -continued | 1312 -continued |
|---|---|
| 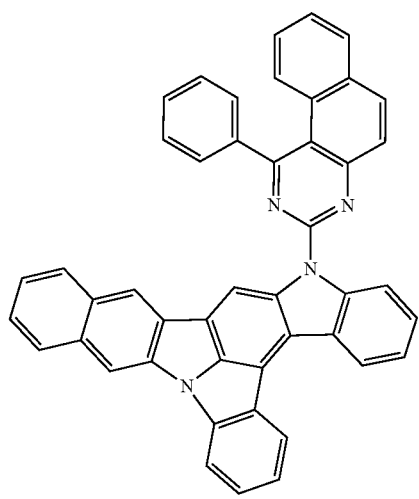 | 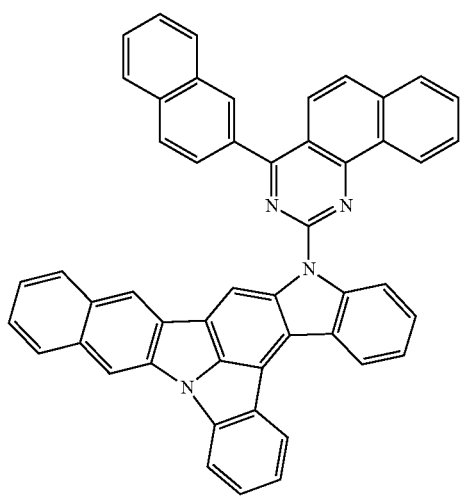 |
| 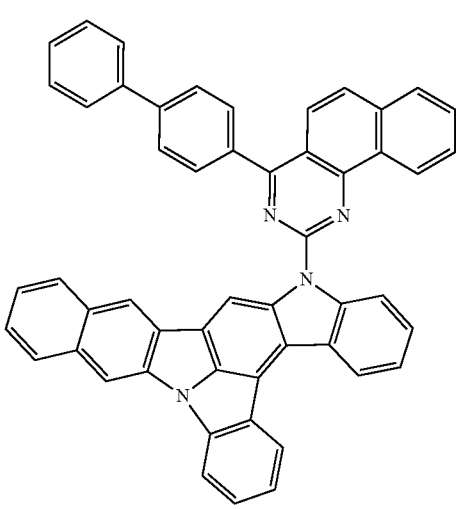 | 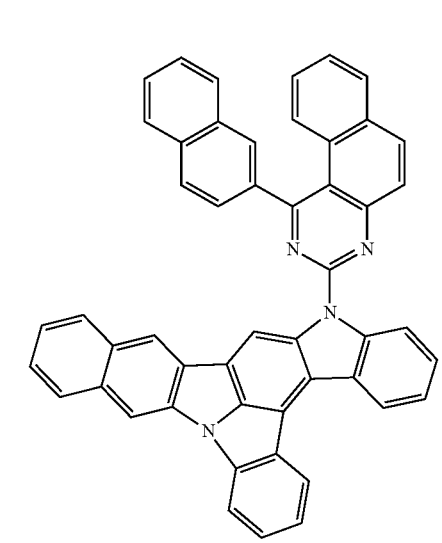 |
| 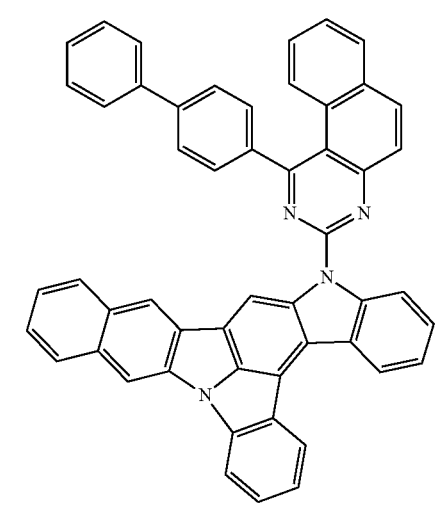 | 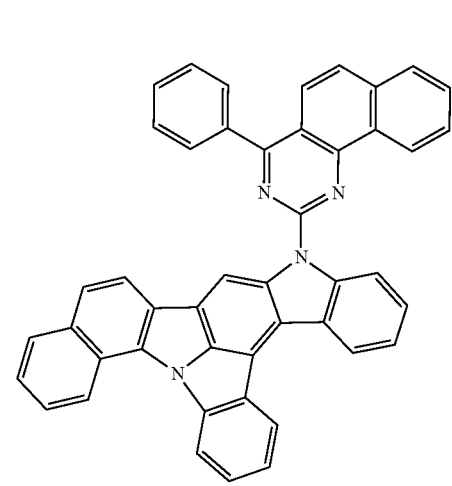 |

1313
-continued
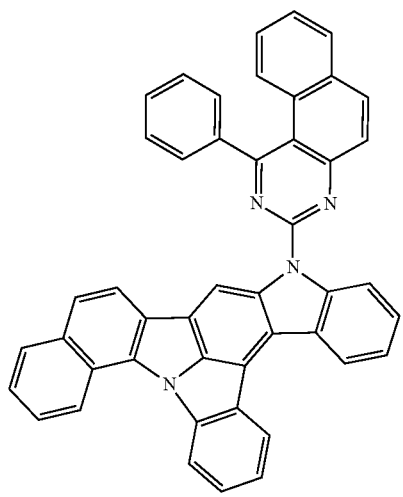
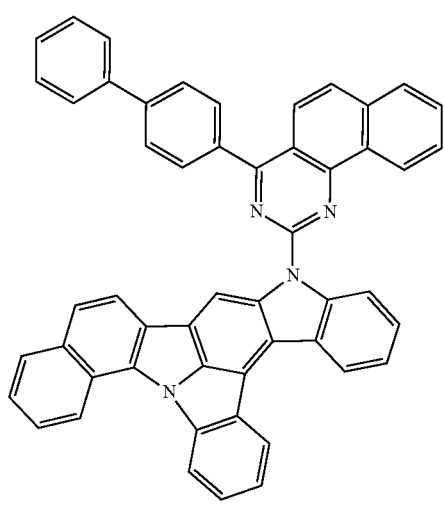
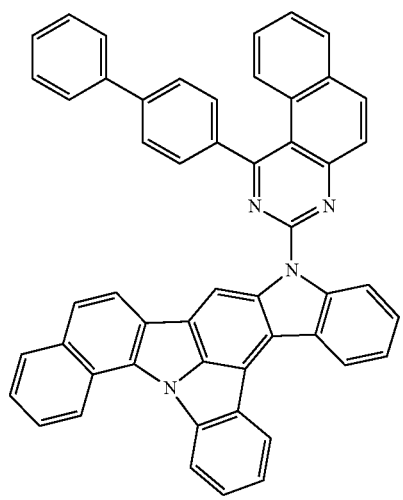
1314
-continued
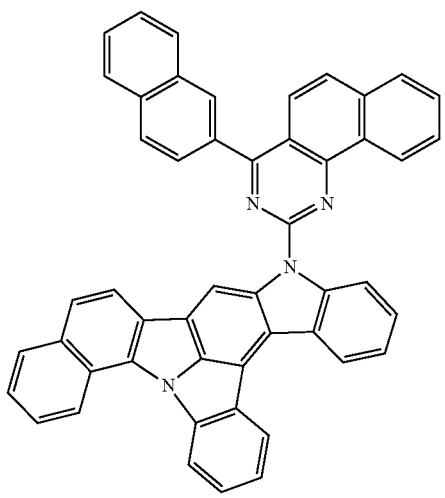
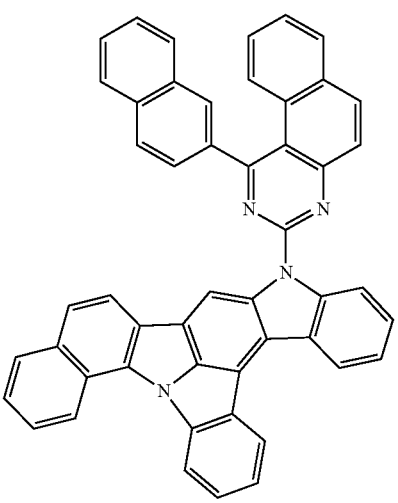
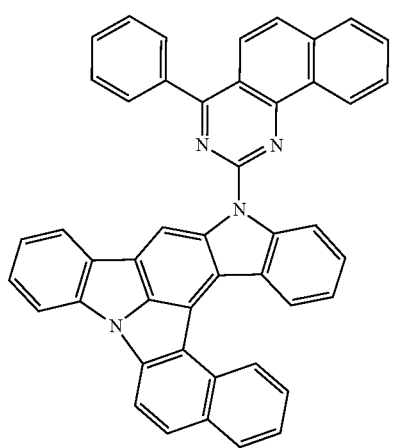

1315
-continued
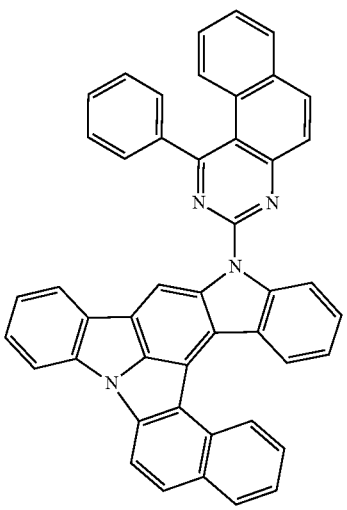
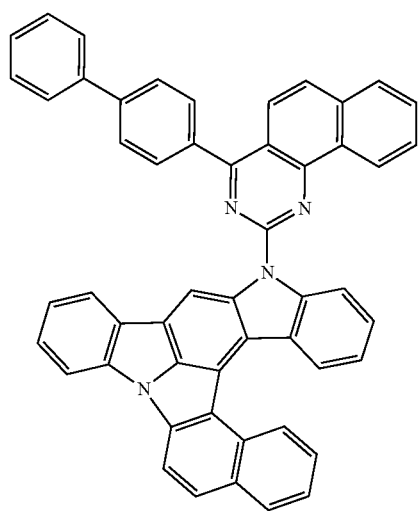
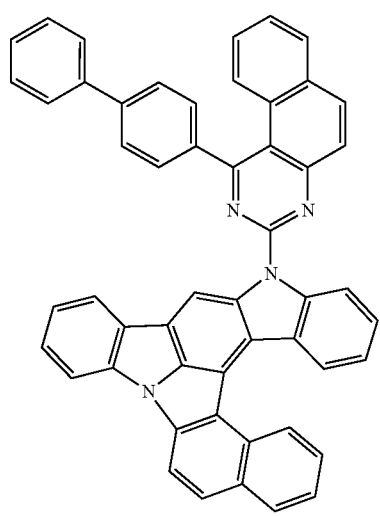
1316
-continued
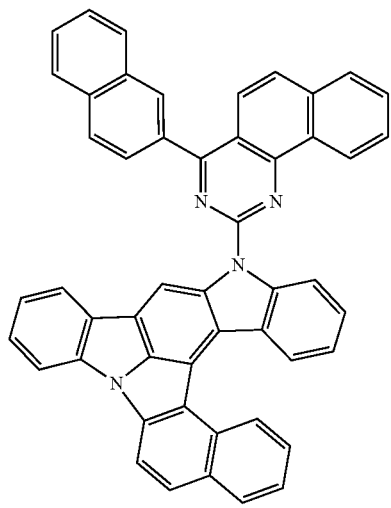
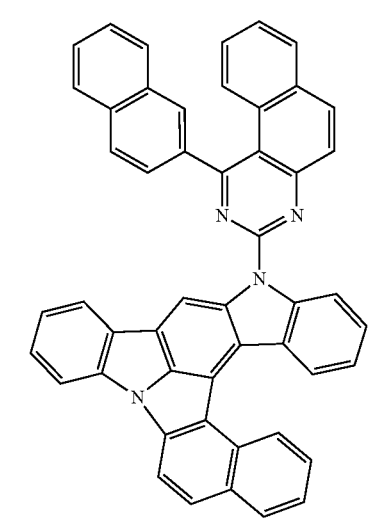
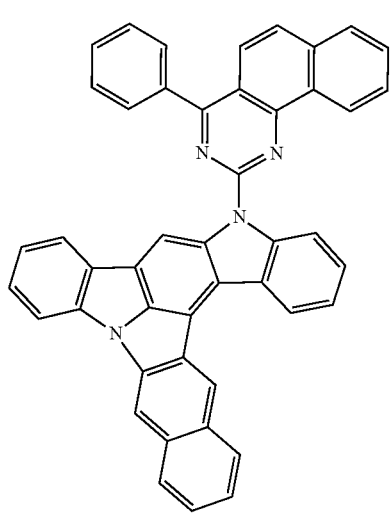

1317
-continued
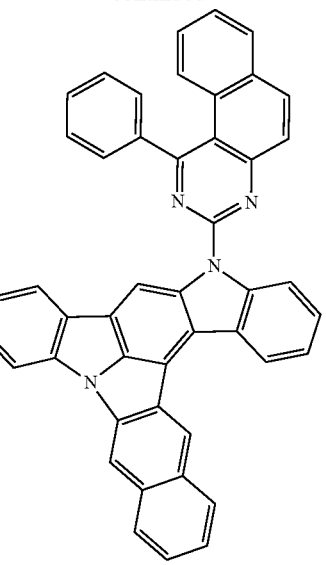
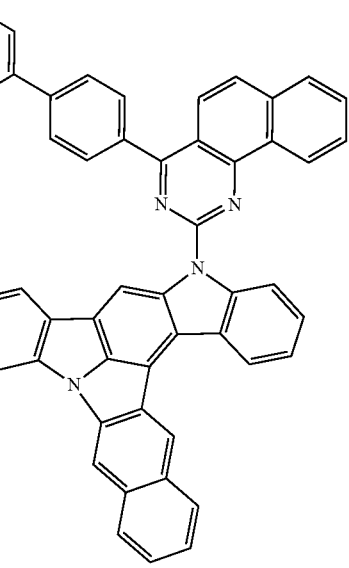
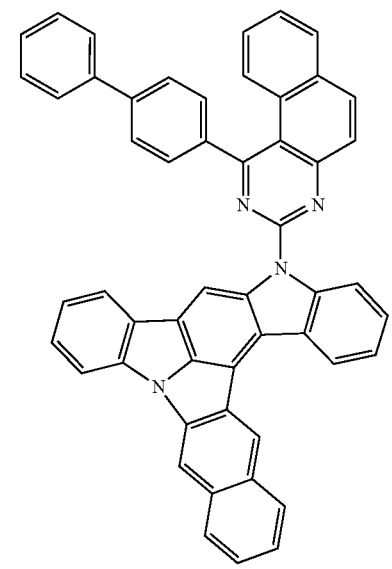
1318
-continued
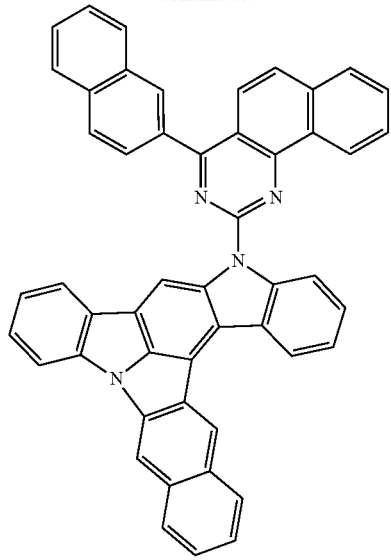
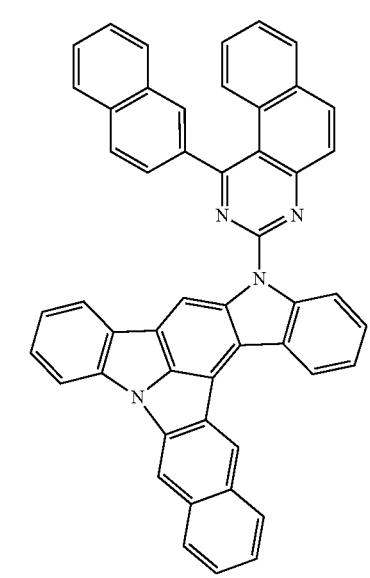
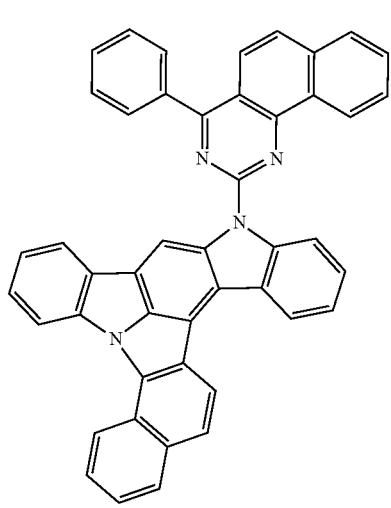

1319
-continued
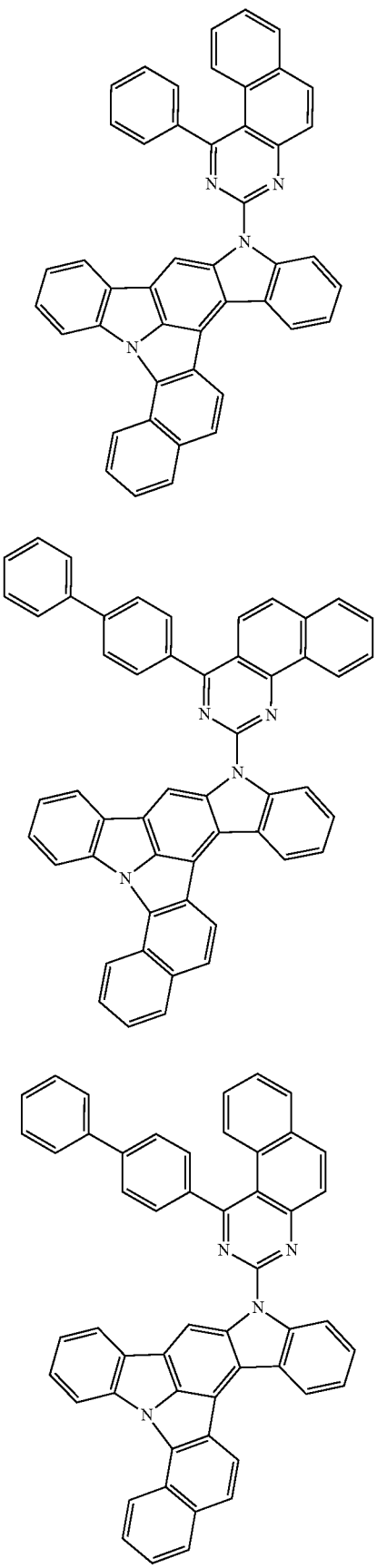
1320
-continued
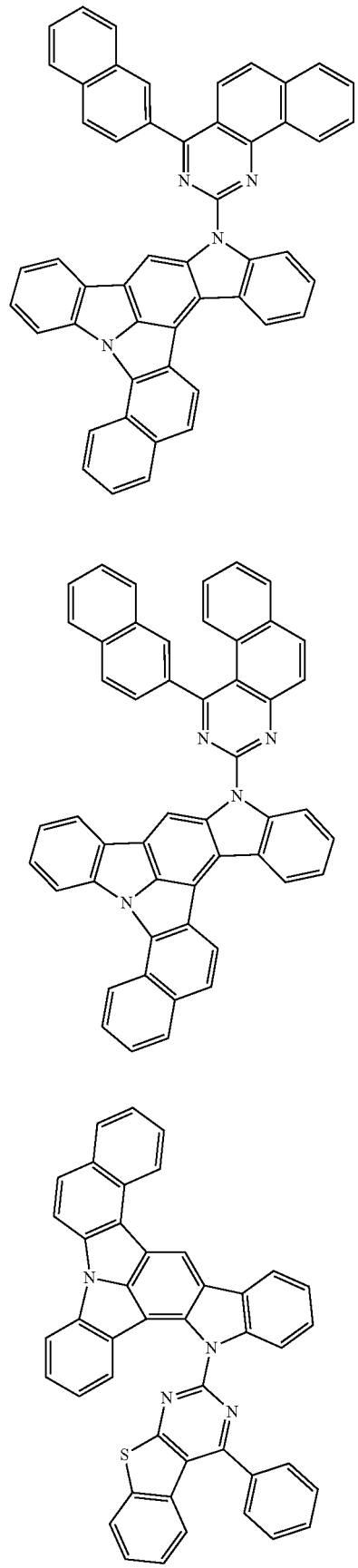

1321
-continued
1322
-continued
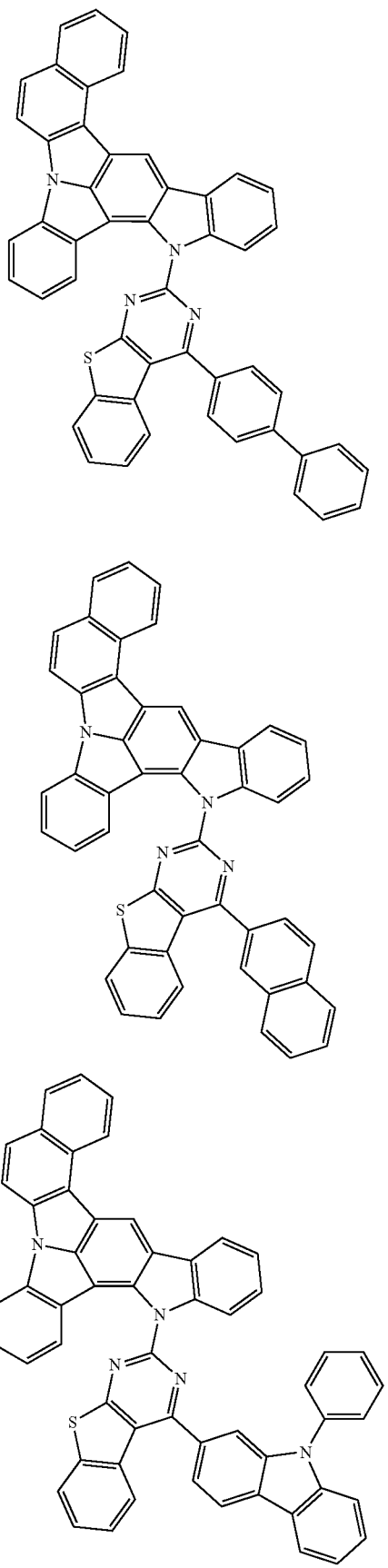
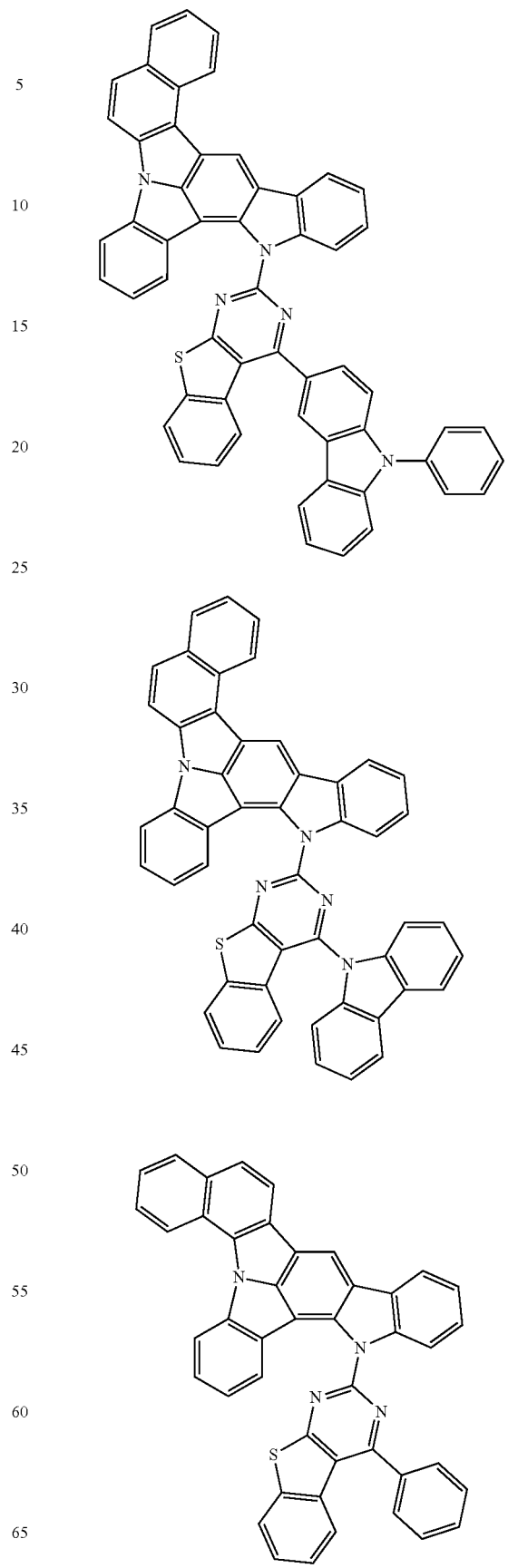

1323
-continued
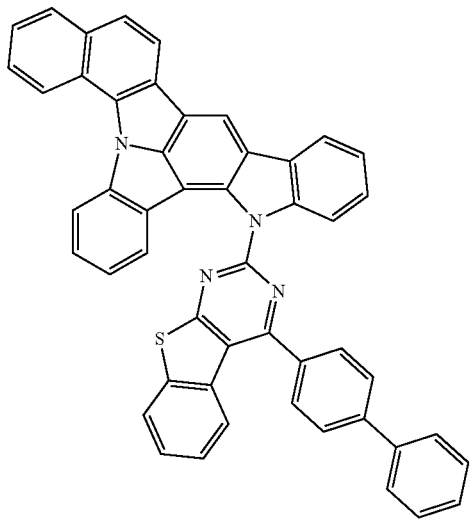
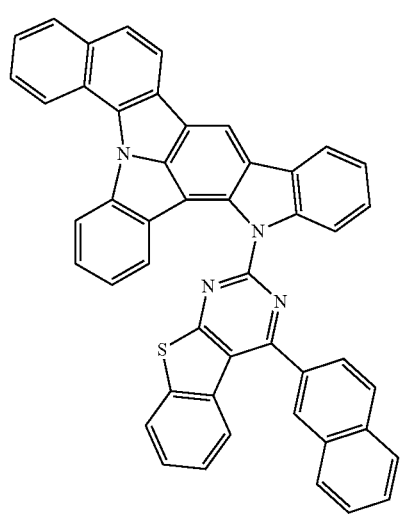
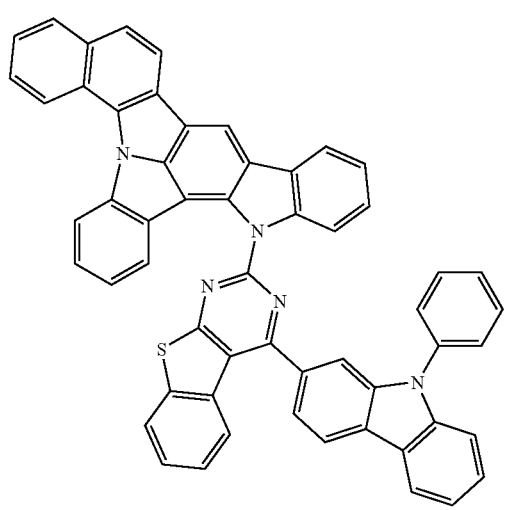
1324
-continued
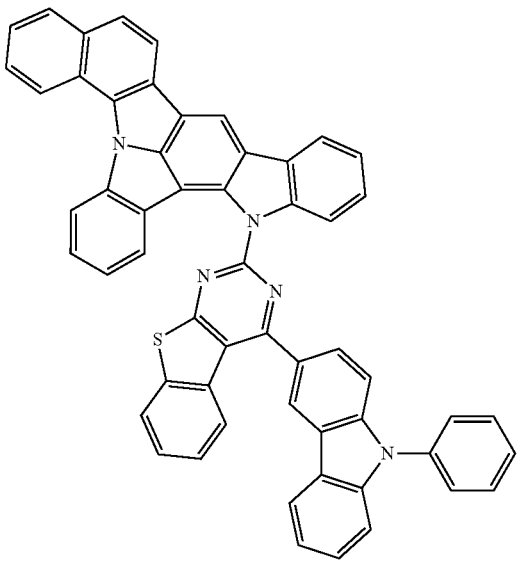
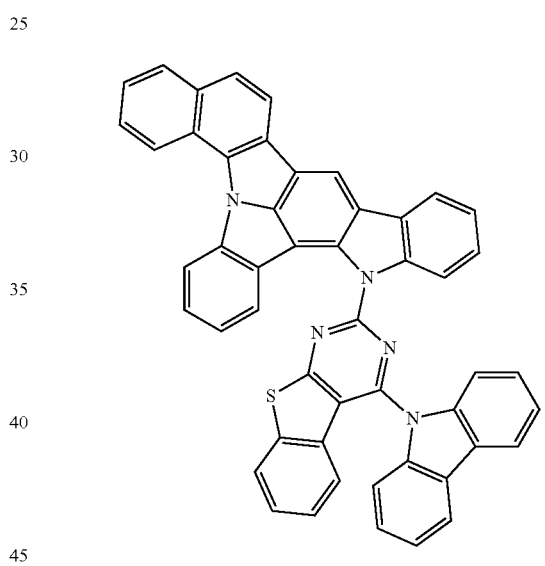
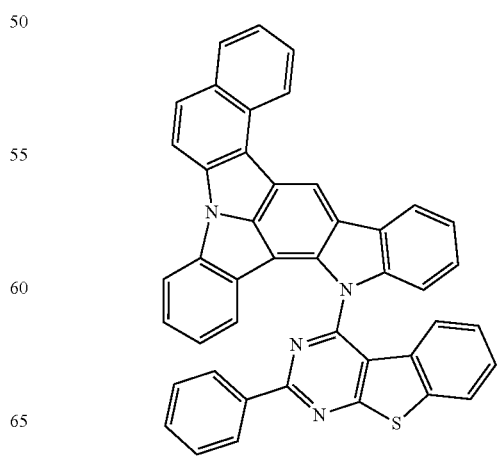

1325
-continued
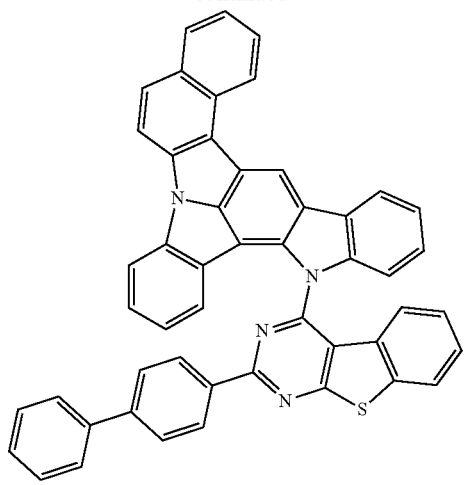
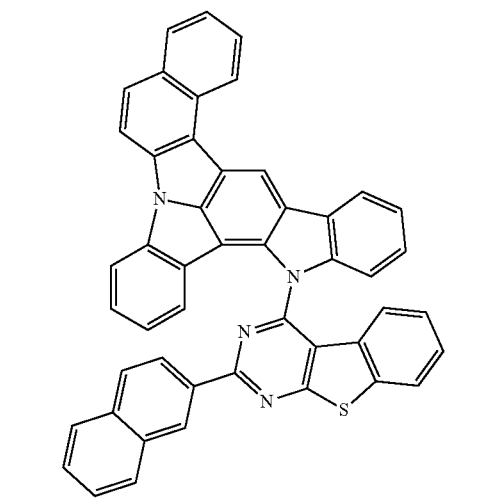
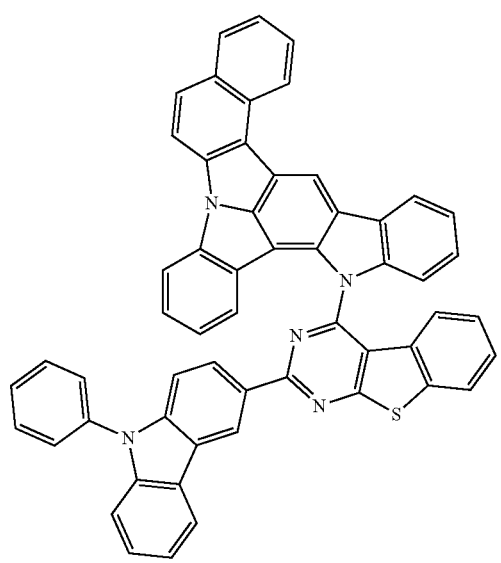
1326
-continued
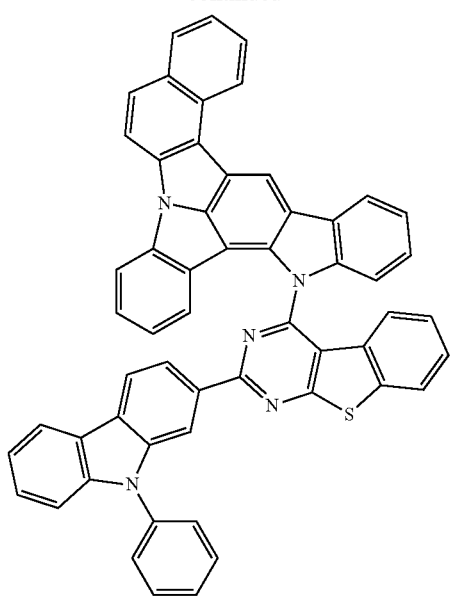
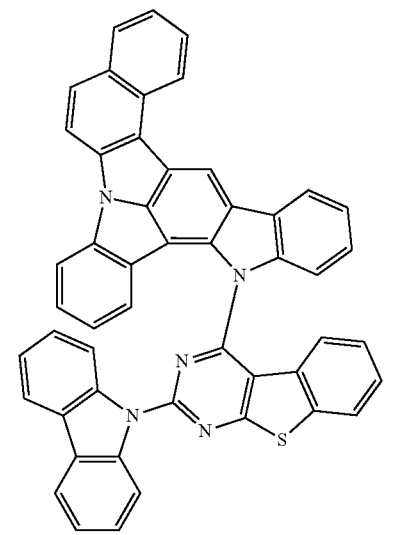
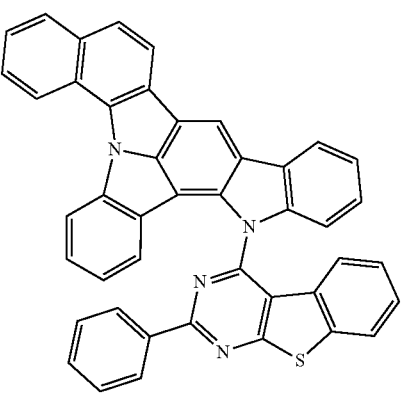

1327
-continued
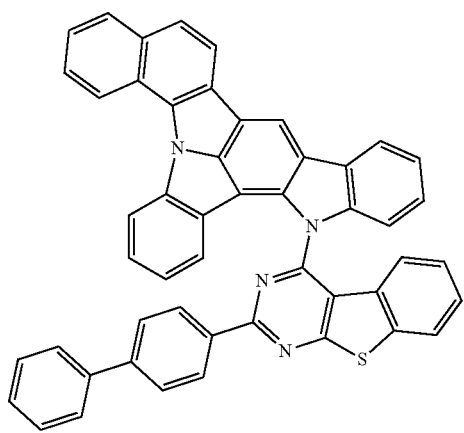
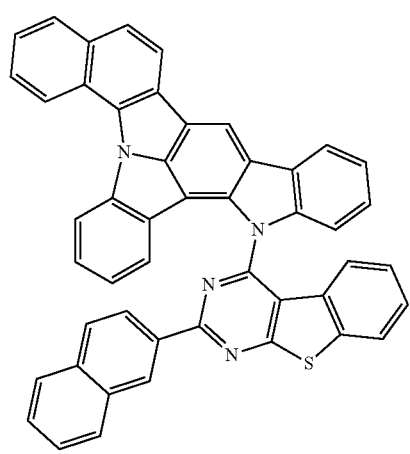
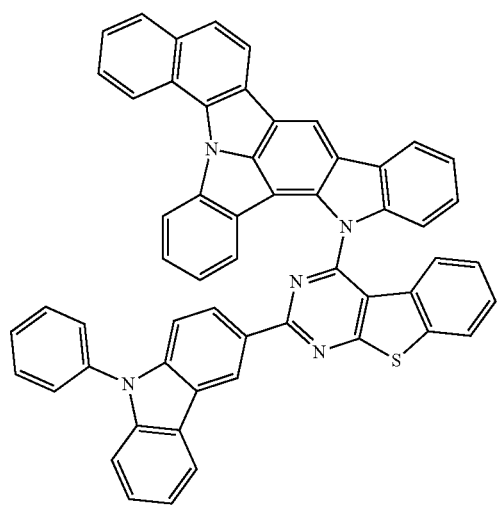
1328
-continued
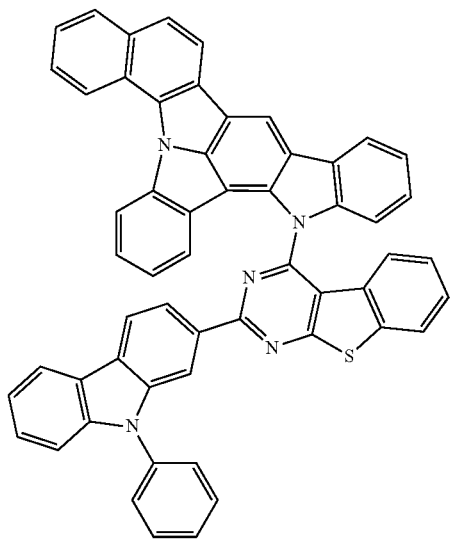
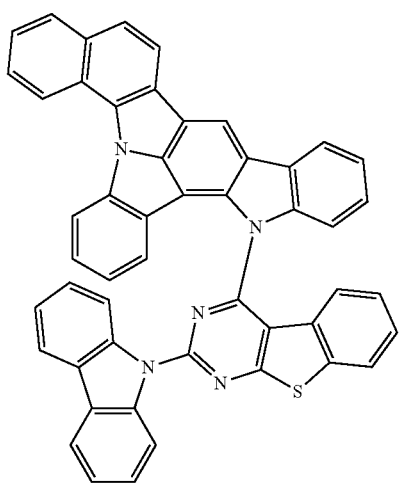
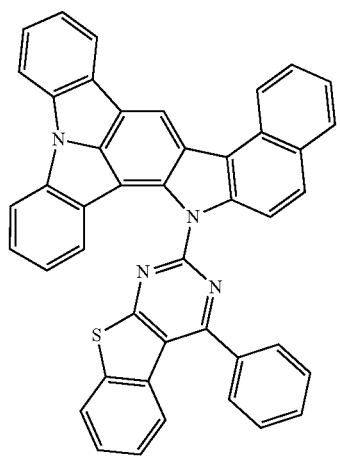

1329
-continued
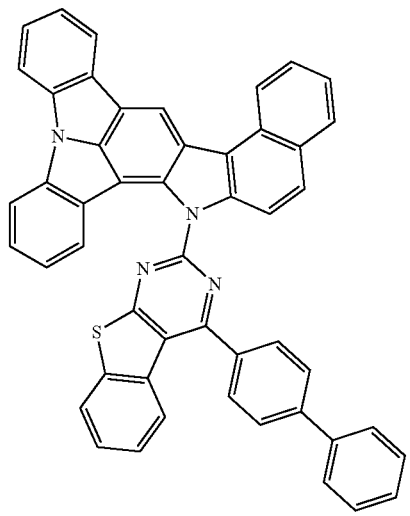
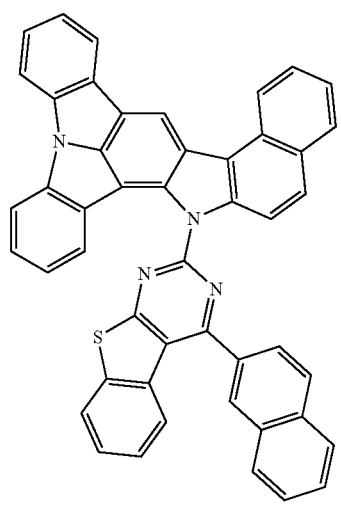
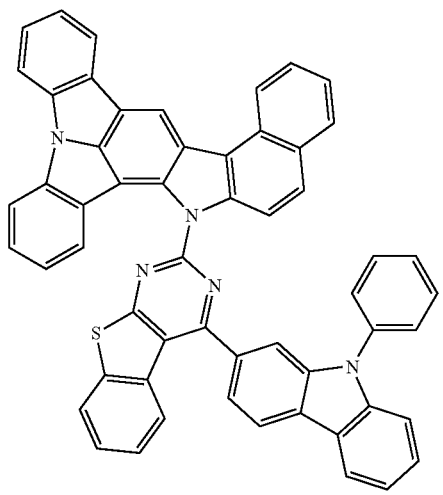
1330
-continued
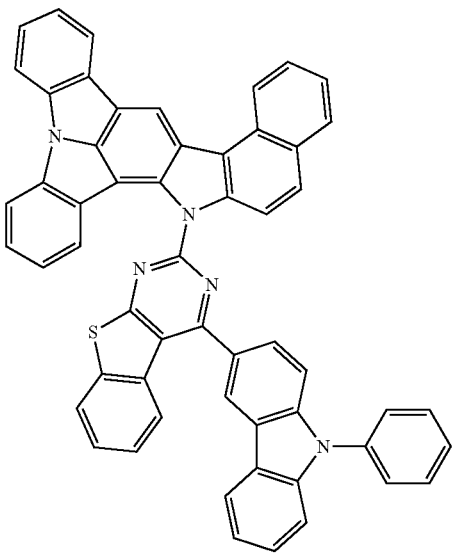
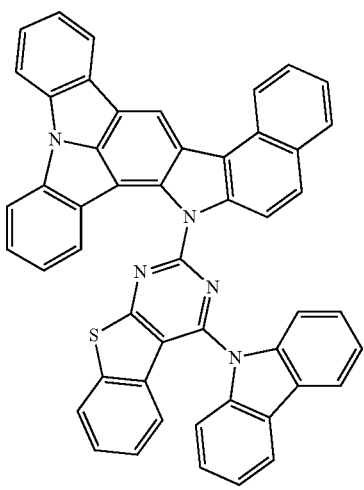
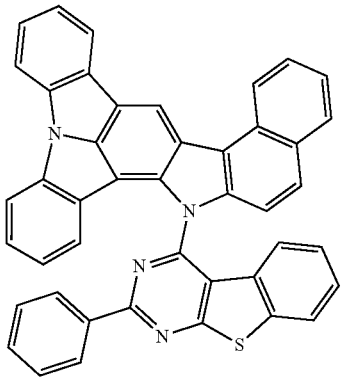

1331
-continued
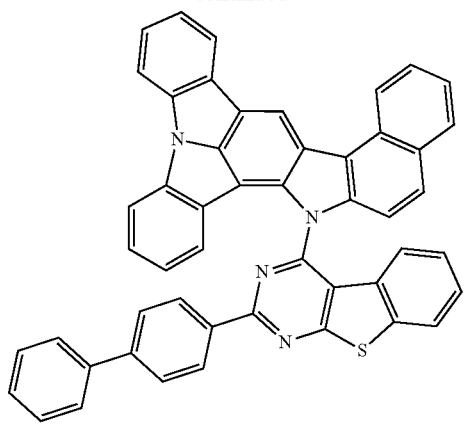
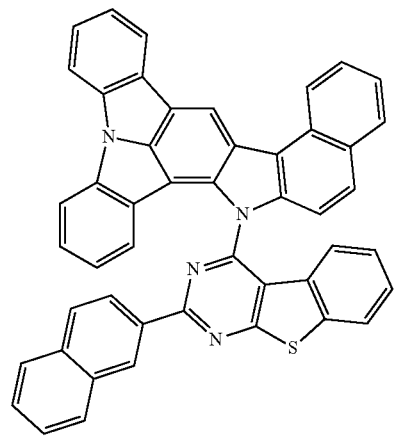
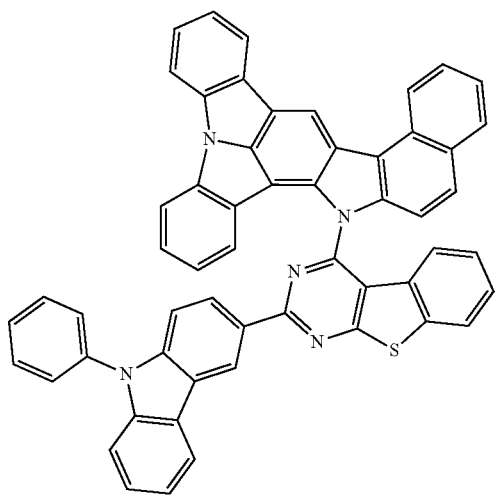
1332
-continued
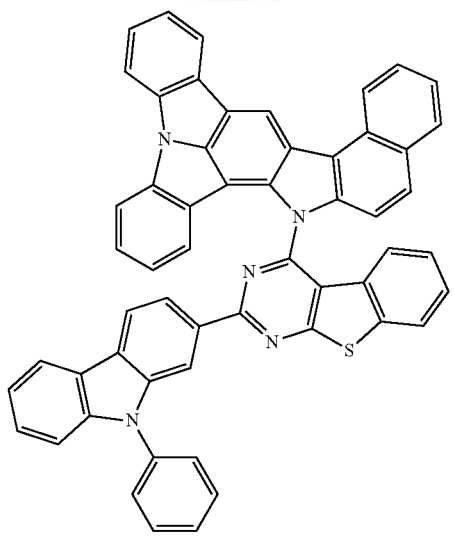
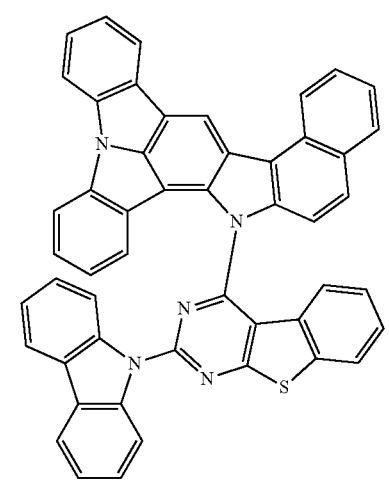
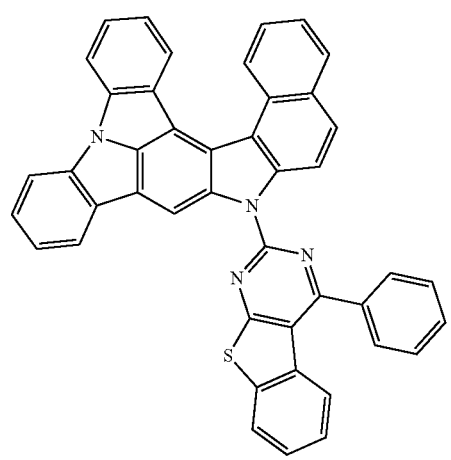

1333
-continued
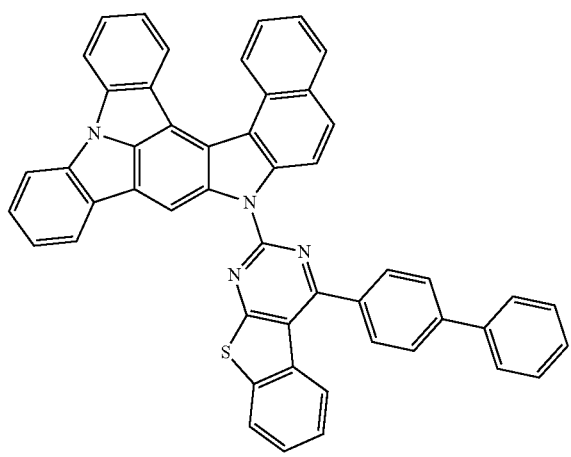
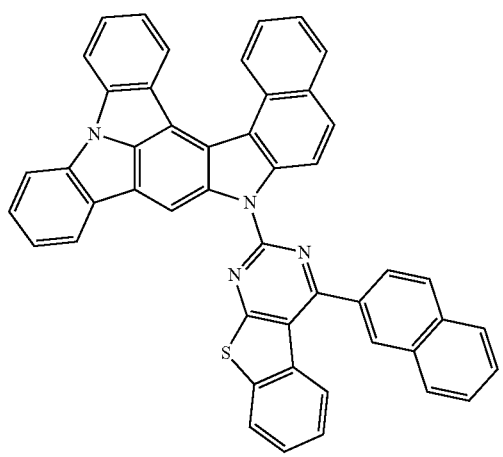
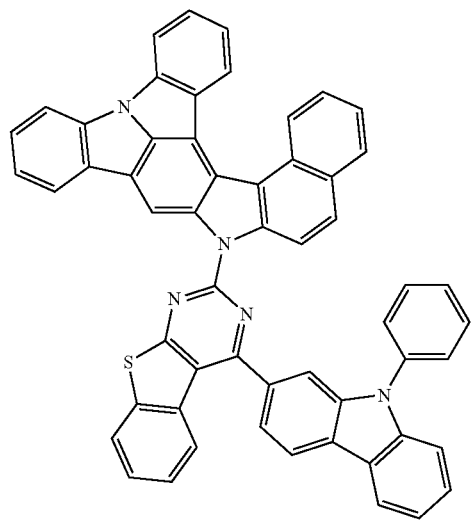
1334
-continued
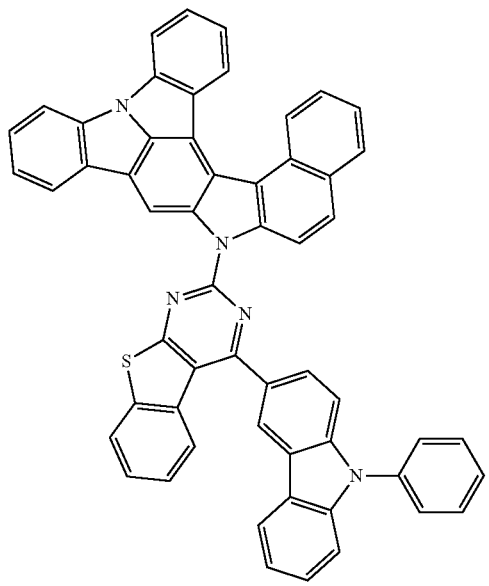
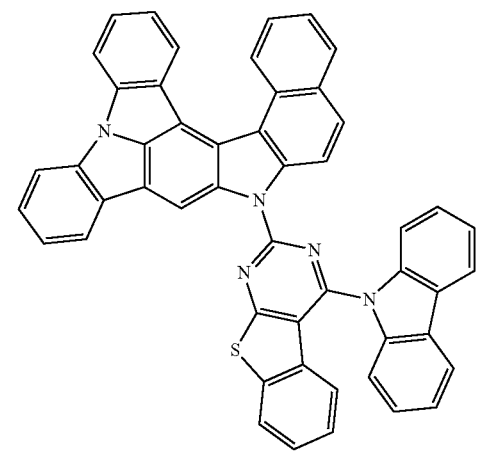
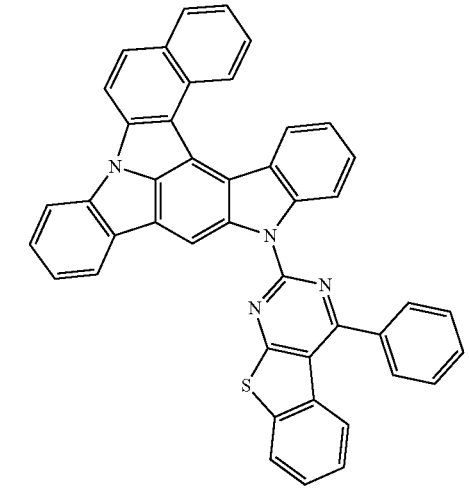

1335
-continued
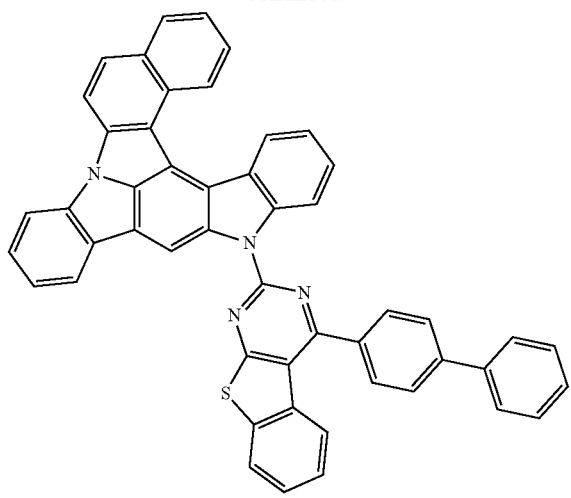
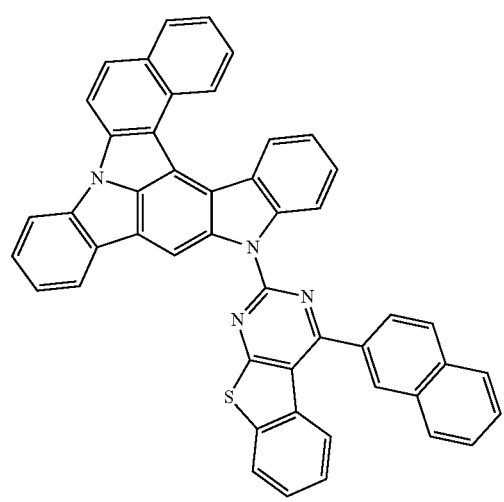
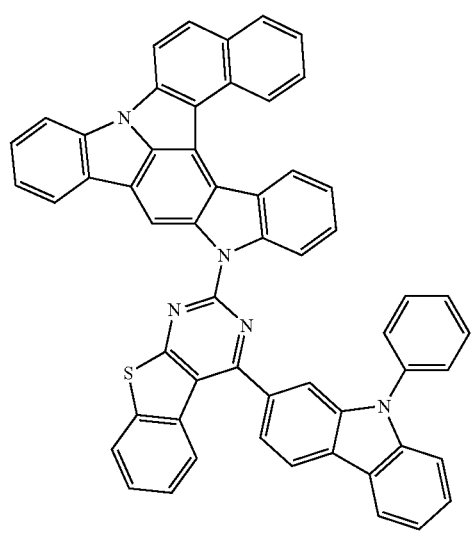
1336
-continued
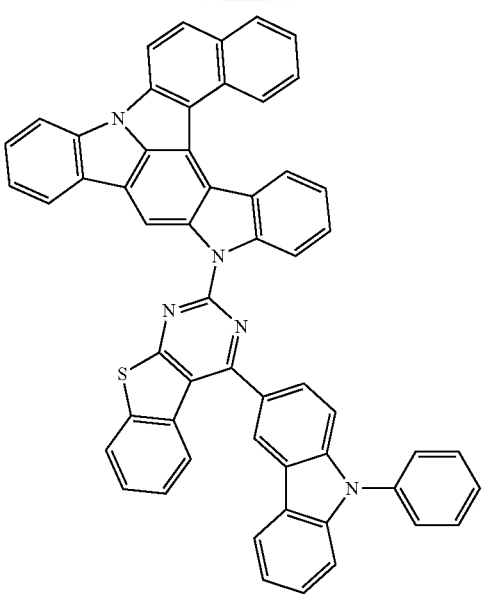
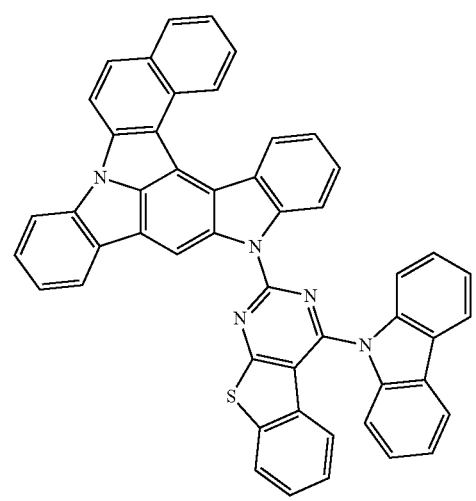
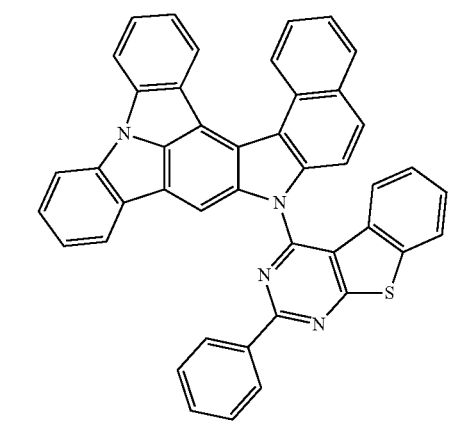

1337
-continued
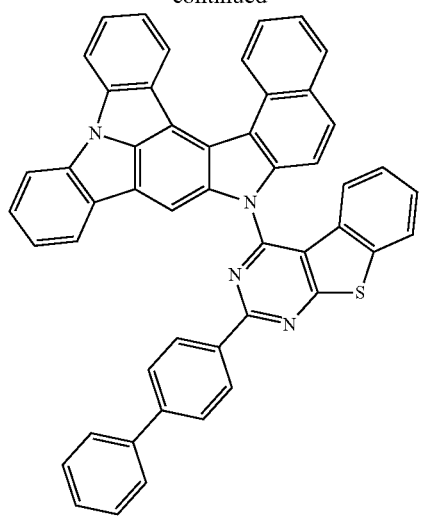
1338
-continued
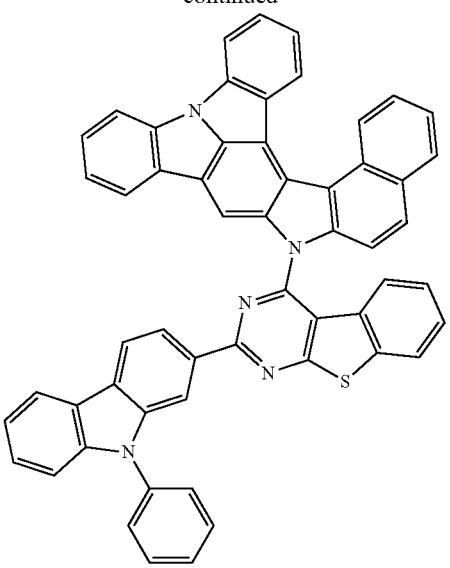
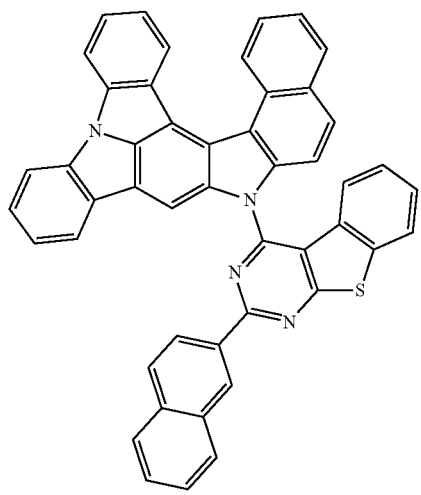
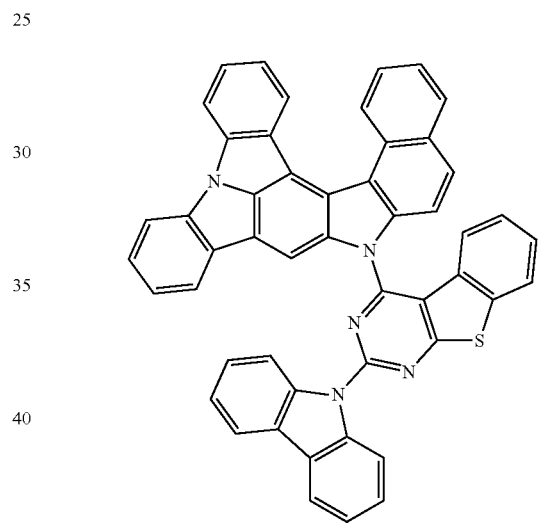
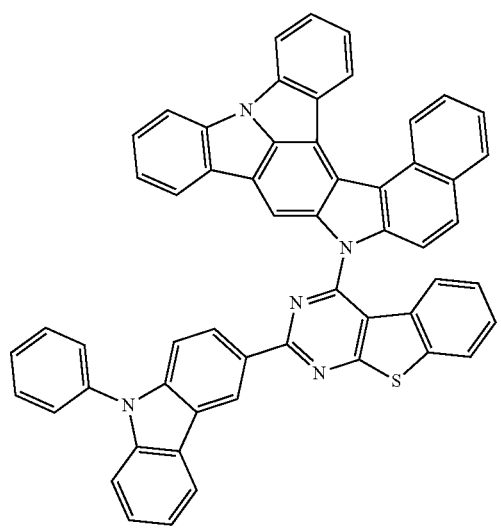
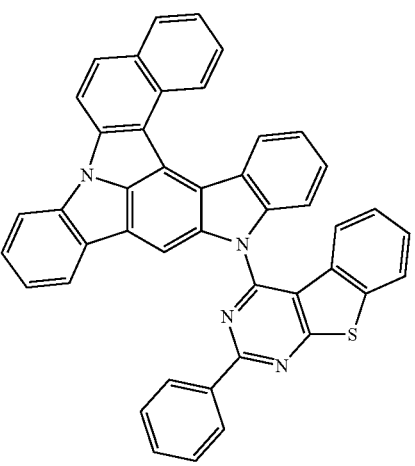

1339
-continued
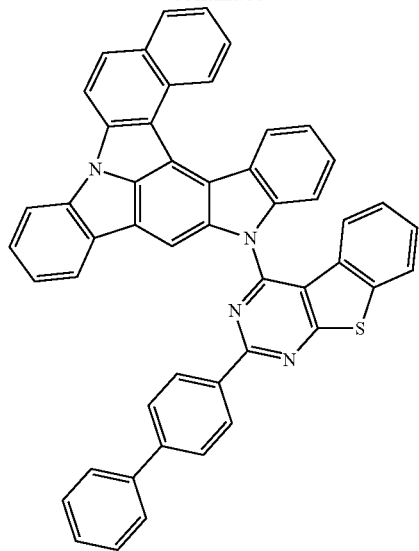
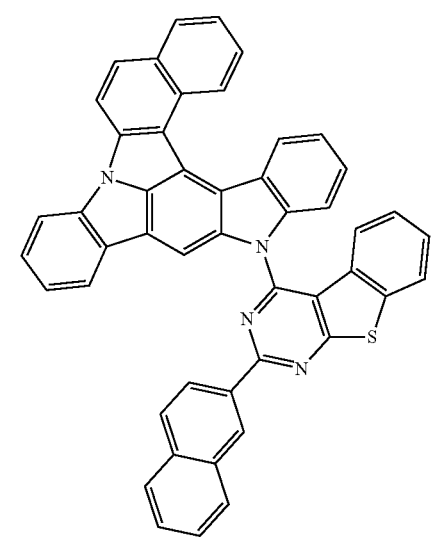
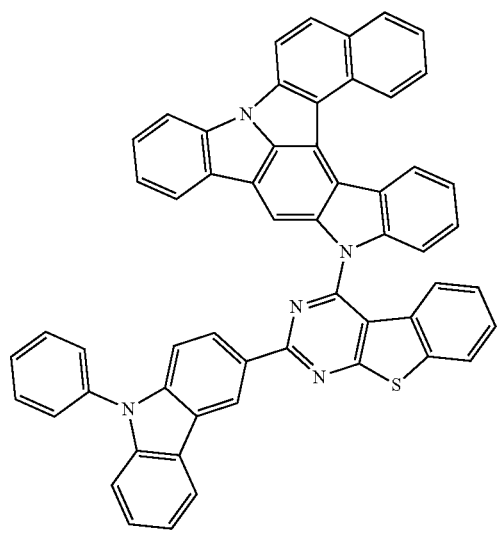
1340
-continued
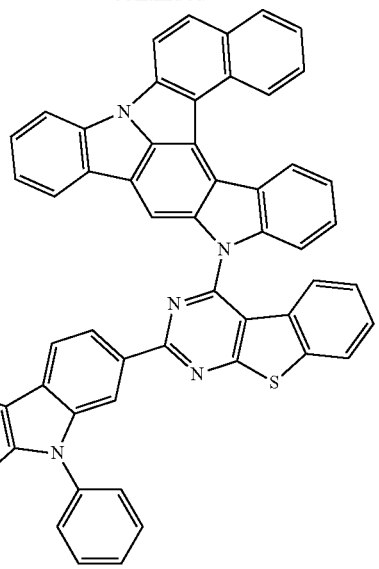
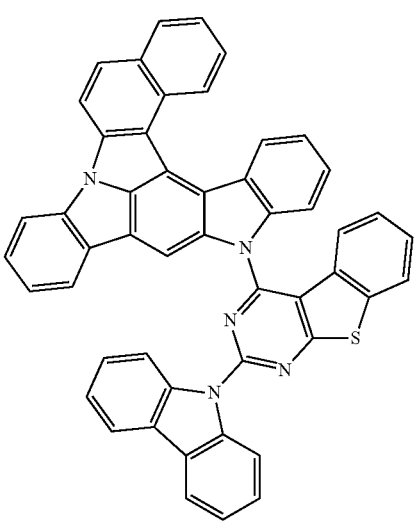
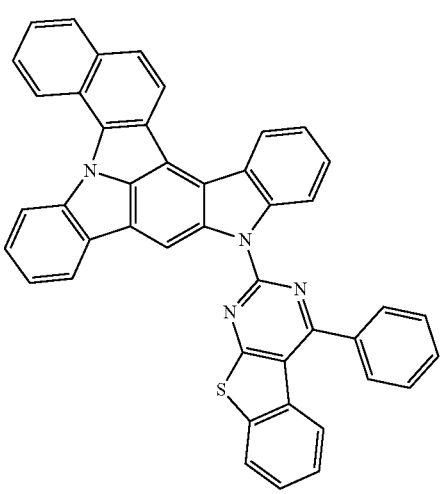

1341
-continued
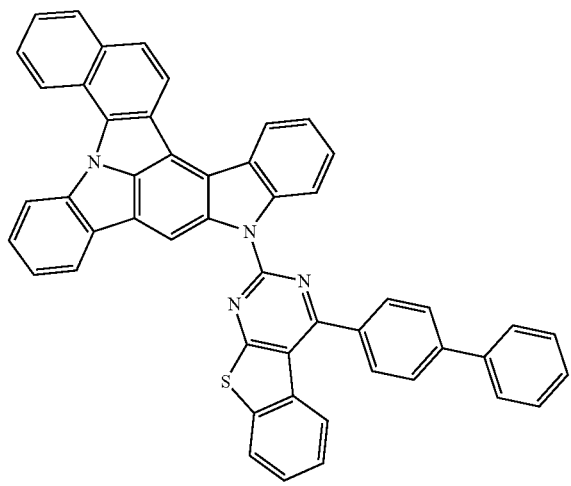
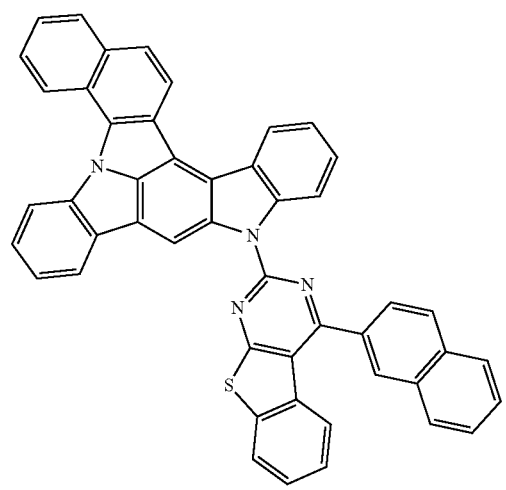
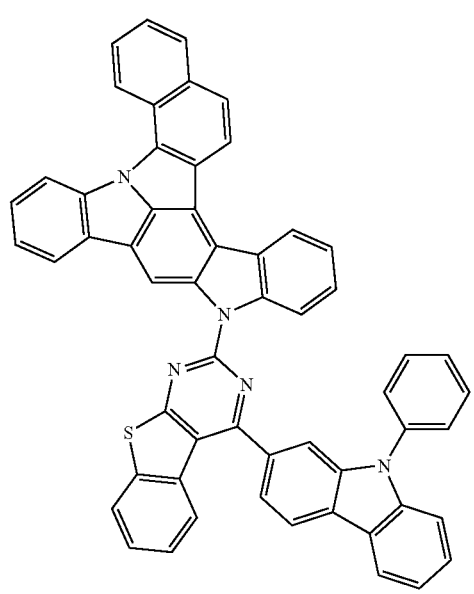
1342
-continued
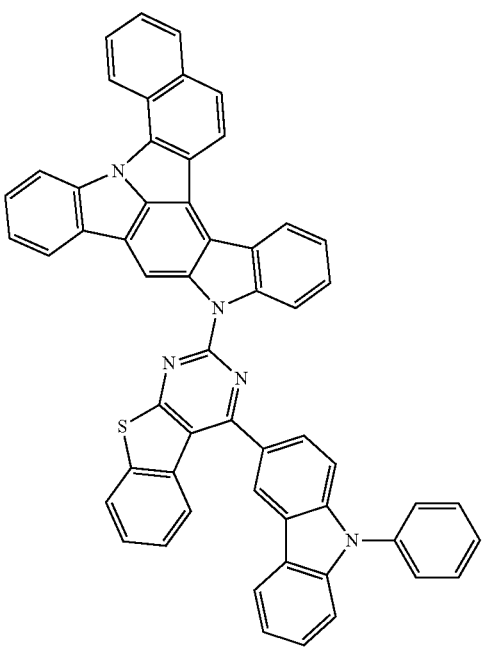
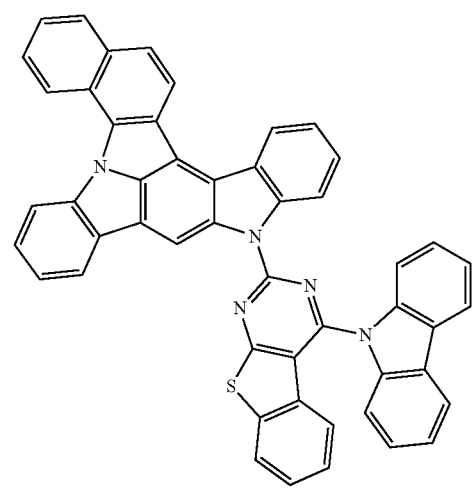
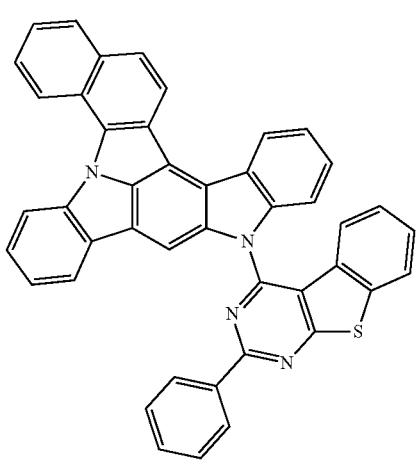

1343
-continued

1344
-continued

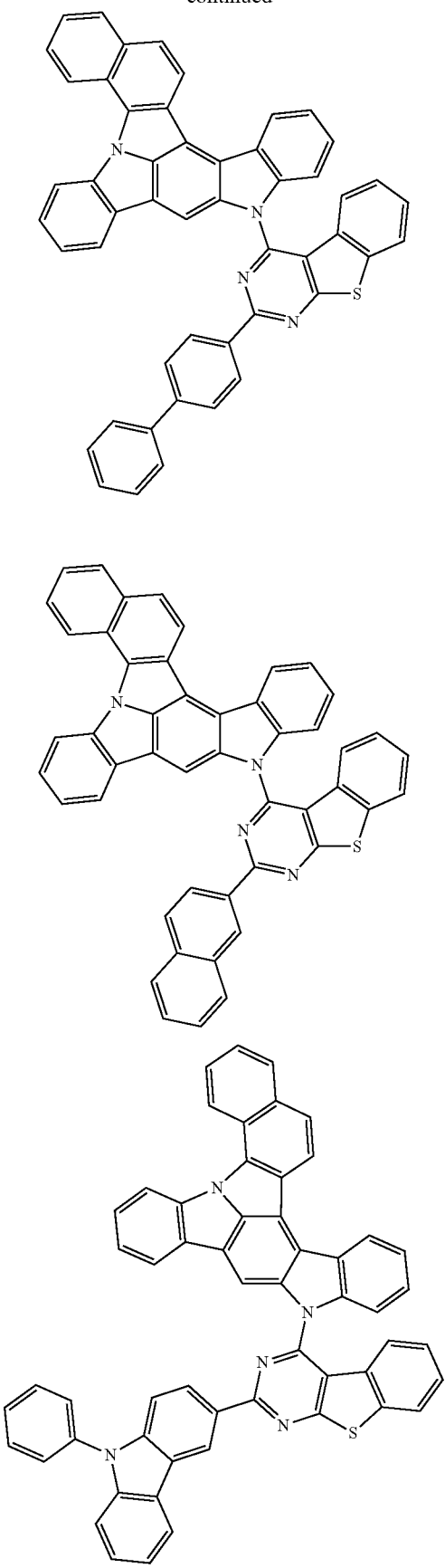

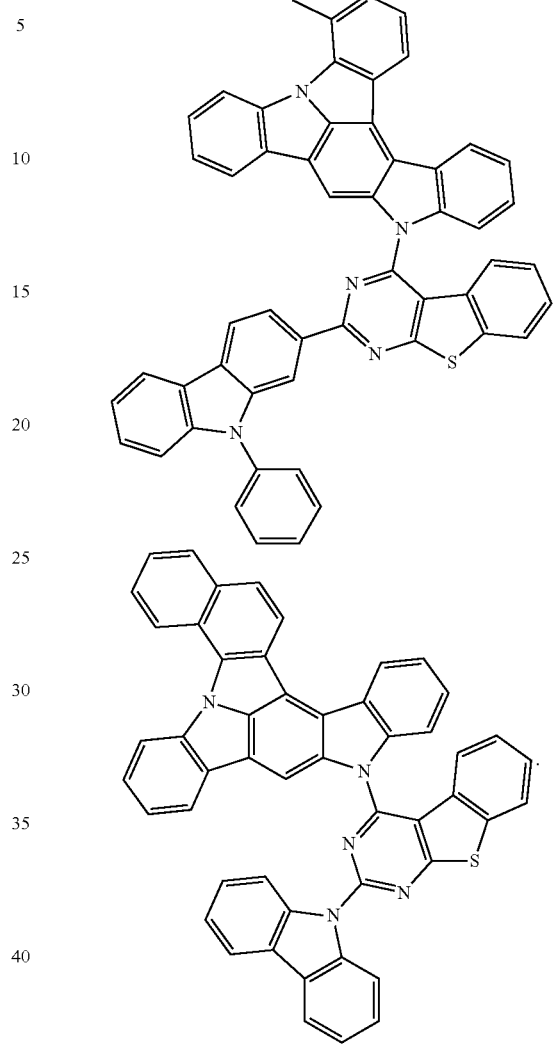

9. An organic light emitting device comprising:
   a first electrode;
   a second electrode provided to face the first electrode; and
   one or more organic material layers provided between the first electrode and the second electrode and comprising a light emitting layer,
   wherein one or more layers of the organic material layers comprise the compound of claim 1.

10. The organic light emitting device of claim 9, wherein the organic material layer comprises an electron transporting layer, an electron injection layer, a layer which simultaneously transports and injects electrons, a light emitting layer, a hole transporting layer, a hole injection layer, or a layer which simultaneously transports and injects holes, and the electron transporting layer, the electron injection layer, the layer which simultaneously transports and injects electrons, the light emitting layer, the hole transporting layer, the hole injection layer, or the layer which simultaneously transports and injects holes comprises the compound of Chemical Formula 1.

11. The organic light emitting device of claim 9, wherein the light emitting layer comprises the compound of Chemical Formula 1.

* * * * *